(12) United States Patent
Takahashi et al.

(10) Patent No.: US 10,202,379 B2
(45) Date of Patent: Feb. 12, 2019

(54) SUBSTITUTED POLYCYCLIC CARBAMOYL PYRIDONE DERIVATIVE PRODRUG

(71) Applicant: Shionogi & Co., Ltd., Osaka-shi, Osaka (JP)

(72) Inventors: Chika Takahashi, Osaka (JP); Hidenori Mikamiyama, Osaka (JP); Toshiyuki Akiyama, Osaka (JP); Kenji Tomita, Osaka (JP); Yoshiyuki Taoda, Osaka (JP); Makoto Kawai, Osaka (JP); Kosuke Anan, Osaka (JP); Masayoshi Miyagawa, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/676,540

(22) Filed: Aug. 14, 2017

(65) Prior Publication Data

US 2017/0349587 A1 Dec. 7, 2017

Related U.S. Application Data

(60) Continuation of application No. 14/562,117, filed on Dec. 5, 2014, now Pat. No. 9,758,515, which is a division of application No. 13/824,723, filed as application No. PCT/JP2011/071446 on Sep. 21, 2011, now Pat. No. 8,987,441.

(30) Foreign Application Priority Data

Sep. 24, 2010 (JP) ................................. 2010-213012

(51) Int. Cl.
| | |
|---|---|
| C07D 471/04 | (2006.01) |
| A61K 31/4738 | (2006.01) |
| C07F 9/6561 | (2006.01) |
| C07D 471/14 | (2006.01) |

(52) U.S. Cl.
CPC ........ *C07D 471/04* (2013.01); *A61K 31/4738* (2013.01); *C07D 471/14* (2013.01); *C07F 9/6561* (2013.01); *C07F 9/65616* (2013.01)

(58) Field of Classification Search
CPC .................................................. C07D 471/04
See application file for complete search history.

(56) References Cited

U.S. PATENT DOCUMENTS

| | | |
|---|---|---|
| 2006/0052361 A1 | 3/2006 | Miyazaki et al. |
| 2008/0161271 A1 | 7/2008 | Yoshida et al. |
| 2009/0143356 A1 | 6/2009 | Yoshida et al. |
| 2012/0184734 A1 | 7/2012 | Akiyama et al. |

FOREIGN PATENT DOCUMENTS

| | | |
|---|---|---|
| EP | 1 544 199 A1 | 6/2005 |
| EP | 1 852 434 A1 | 11/2007 |
| GB | 2 280 435 A | 2/1995 |
| WO | WO 2004/024078 A2 | 3/2004 |
| WO | WO 2005/016927 A1 | 2/2005 |
| WO | WO 2005/087766 A1 | 9/2005 |
| WO | WO 2005/092099 A1 | 10/2005 |
| WO | WO 2006/066414 A1 | 6/2006 |
| WO | WO 2006/088173 A1 | 8/2006 |
| WO | WO 2006/116764 A1 | 11/2006 |
| WO | WO 2007/049675 A1 | 5/2007 |
| WO | WO 2010/011812 A1 | 1/2010 |
| WO | WO 2010/011814 A1 | 1/2010 |
| WO | WO 2010/011815 A1 | 1/2010 |
| WO | WO 2010/011816 A1 | 1/2010 |
| WO | WO 2010/011818 A1 | 1/2010 |
| WO | WO 2010/011819 A1 | 1/2010 |
| WO | WO 2011/011483 A1 | 1/2011 |

OTHER PUBLICATIONS

Hastings, et al., "Anti-Influenza Virus Activities of 4-Substituted 2,4-Dioxobutanoic Acid Inhibitors," Antimicrobial Agents and Chemotherapy, vol. 40, No. 5, pp. 1304-1307 (May 1996).
Hensens, et al., "Isolation and Structure of Flutimide, a Novel Endonuclease Inhibitor of Influenza Virus," Tetrahedron Letters, vol. 36, No. 12, pp. 2005-2008 (1995).
International Search Report issued by the Japanese Patent Office in corresponding International Application No. PCT/JP2011/071446, dated Oct. 18, 2011 (4 pages).
Notification of Transmittal of Translation of the International Preliminary Report on Patentability International Preliminary Report on Patentability, and Translation of the Written Opinion of the International Searching Authority, for International Patent Application No. PCT/JP2011/071446, dated Apr. 25, 2013 (6 pages).
Tomassini et al., "Inhibition of Cap (rn GpppXm)-Dependent Endonuclease of Influenza Virus by 4-Substituted 2,4-Dioxobutanoic Acid Compounds," Antimicrobial Agents and Chemotherapy, vol. 38, No. 12, pp. 2827-2837 (Dec. 1994).
Parkers, et al., "Use of a Pharmacophore Model to Discover a New Class of Influenza Endonuclease Inhibitors," Journal of Medicinal Chemistry, vol. 46, No. 7, pp. 1153-1164 (2003).
Wai, et al., "Dihydroxypyridopyrazine-1,6-dione HIV-1 Integrase Inhibitors," Science Direct, Bioorganic & Medicinal Chemistry Letters 17, pp. 5595-5599 (2007).

*Primary Examiner* — Brian E McDowell
(74) *Attorney, Agent, or Firm* — Wenderoth, Lind & Ponack, L.L.P.

(57) ABSTRACT

The present invention provides a compound having antiviral effects, particularly having growth inhibitory activity on influenza viruses, a preferred example of the compound being a substituted 3-hydroxy-4-pyridone derivative prodrug having cap-dependent endonuclease inhibitory activity.

17 Claims, 2 Drawing Sheets

| Time (hr) | Transition of Reference example 301 concentration in plasma (ng/ml) | | | | |
|---|---|---|---|---|---|
| | 1 | 2 | 3 | Mean | SD |
| 0 | 0 | 0 | 0 | 0 | 0 |
| 0.25 | 3.0 | 2.5 | 4.2 | 3.2 | 0.9 |
| 0.5 | 5.1 | 3.6 | 7.4 | 5.3 | 1.9 |
| 1 | 5.5 | 4.4 | 5.9 | 5.2 | 0.8 |
| 2 | 3.3 | 2.1 | 3.7 | 3.0 | 0.8 |
| 4 | 0.9 | 1.1 | 1.6 | 1.2 | 0.3 |
| 6 | 1.1 | 1.1 | 2.8 | 1.7 | 1.0 |
| 8 | 1.0 | 2.2 | 3.5 | 2.2 | 1.2 |
| 24 | 0.3 | 0.2 | 0.2 | 0.2 | 0.1 |
| Cmax (ng/mL) | 5.5 | 4.4 | 7.4 | 5.8 | 1.5 |
| Tmax (hr) | 1.00 | 1.00 | 0.50 | 0.83 | 0.29 |
| AUCall (ng·hr/mL) | 24.7 | 32.6 | 54.1 | 37.2 | 15.2 |
| BA (%) | 4.51 | 5.95 | 9.87 | 6.78 | 2.77 |

| Time (hr) | Transition of Reference example 301 concentration in plasma (ng/ml) | | | | |
|---|---|---|---|---|---|
| | 1 | 2 | 3 | Mean | SD |
| 0 | 0 | 0 | 0 | 0 | 0 |
| 0.25 | 23.7 | 4.4 | 14.6 | 14.2 | 9.6 |
| 0.5 | 27.5 | 6.0 | 21.9 | 18.5 | 11.1 |
| 1 | 23.4 | 6.1 | 13.5 | 14.4 | 8.7 |
| 2 | 11.7 | 4.8 | 7.4 | 8.0 | 3.4 |
| 4 | 5.8 | 2.2 | 2.6 | 3.5 | 2.0 |
| 6 | 3.5 | 2.4 | 2.4 | 2.8 | 0.6 |
| 8 | 2.9 | 1.8 | 3.1 | 2.6 | 0.7 |
| 24 | 0.8 | 0 | 0 | 0.3 | 0.5 |
| Cmax (ng/mL) | 27.5 | 6.10 | 21.9 | 18.5 | 11.1 |
| Tmax (hr) | 0.50 | 1.0 | 0.50 | 0.67 | 0.29 |
| AUCall (ng·hr/mL) | 102 | 40.5 | 71.0 | 71.3 | 31.0 |
| BA (%) | 18.7 | 7.40 | 13.0 | 13.0 | 5.6 |

SUBSTITUTED POLYCYCLIC CARBAMOYL PYRIDONE DERIVATIVE PRODRUG

This application is a continuation of U.S. application Ser. No. 14/562,117, filed Dec. 5, 2017, which is a division of U.S. application Ser. No. 13/824,723, filed Mar. 18, 2013, which is the National Phase application based on PCT/JP2011/71446, filed Sep. 21, 2011, which claims the benefit of priority from Japanese Patent Application No. 2010-213012, filed Sep. 24, 2010, the content of each application being incorporated herein by reference.

TECHNICAL FIELD

This invention relates to substituted polycyclic carbamoylpyridone derivatives having cap-dependent endonuclease inhibitory activity, prodrugs thereof, and pharmaceutical compositions including thereof.

BACKGROUND ART

Influenza is an acute respiratory infectious disease caused by infection with an influenza virus. In Japan, there is a report of millions of influenza-like patients every winter, and influenza is accompanied with high morbidity and mortality. Influenza is a particularly important disease in a high risk population such as baby and elderly, a complication rate with pneumonia is high in elderly, and death with influenza is occupied with elderly in many cases.

As anti-influenza drugs, Symmetrel (trade name: Amantadine) and Flumadine (trade name: Rimantadine) which inhibit the denucleation process of a virus, and Oseltamivir (trade name: Tamiflu) and Zanamivir (trade name: Relenza) which are neuraminidase inhibitors suppressing virus budding and release from a cell are known. However, since problems of appearances of resistant strains and side effects, and worldwide epidemic of a new-type influenza virus having high pathogenicity and mortality are feared, development of an anti-influenza drug having a novel mechanism has been desired.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug. The cap-dependent endonuclease has a host mRNA precursor as a substrate, and has the endonuclease activity of producing a fragment of 9 to 13 bases including a cap structure (not including the number of bases of the cap structure). This fragment functions as a primer of a virus RNA polymerase, and is used in synthesizing mRNA encoding a virus protein. That is, it is believed that a substance which inhibits the cap-dependent endonuclease inhibits synthesis of a virus protein by inhibiting synthesis of virus mRNA and, as a result, inhibits virus proliferation.

As the substance which inhibits the cap-dependent endonuclease, flutimide (Patent Document 1 and Non-Patent Documents 1 and 2) and 4-substituted 2,4-dioxobutanoic acid (Non-Patent Documents 3 to 5) and the like have been reported, but they have not yet led to clinical use as anti-influenza drugs. In addition, Patent Documents 2 to 16 and Non-Patent Document 6 describe compounds having a similar structure to that of this invention as a compound having integrase inhibitory activity, however, the documents do not describe cap-dependent endonuclease. In addition, Patent Document 17 describes an invention relating to "substituted polycyclic carbamoylpyridone derivative" having cap-dependent endonuclease inhibitory activity, that has been filed by the applicants, but does not describe the prodrug relating to the present invention.

PRIOR ART DOCUMENTS

Patent Documents

[Patent Document 1] GB No. 2280435 specification
[Patent Document 2] International Publication No. 2007/049675 pamphlet
[Patent Document 3] International Publication No. 2006/088173 pamphlet
[Patent Document 4] International Publication No. 2006/066414 pamphlet
[Patent Document 5] International Publication No. 2005/092099 pamphlet
[Patent Document 6] International Publication No. 2005/087766 pamphlet
[Patent Document 7] International Publication No. 2005/016927 pamphlet
[Patent Document 8] International Publication No. 2004/024078 pamphlet
[Patent Document 9] International Publication No. 2006/116764 pamphlet
[Patent Document 10] International Publication No. 2010/011818 pamphlet
[Patent Document 11] International Publication No. 2010/011816 pamphlet
[Patent Document 12] International Publication No. 2010/011819 pamphlet
[Patent Document 13] International Publication No. 2010/011815 pamphlet
[Patent Document 14] International Publication No. 2010/011814 pamphlet
[Patent Document 15] International Publication No. 2010/011812 pamphlet
[Patent Document 16] International Publication No. 2011/011483 pamphlet
[Patent Document 17] International Publication No. 2010/147068 pamphlet

Non-Patent Documents

[NON-PATENT DOCUMENT 1] Tetrahedron Lett 1995, 36 (12), 2005
[NON-PATENT DOCUMENT 2] Tetrahedron Lett 1995, 36 (12), 2009
[NON-PATENT DOCUMENT 3] Antimicrobial Agents And Chemotherapy, December 1994, p. 2827-2837
[NON-PATENT DOCUMENT 4] Antimicrobial Agents And Chemotherapy, May 1996, p. 1304-1307
[NON-PATENT DOCUMENT 5] J. Med. Chem. 2003, 46, 1153-1164
[NON-PATENT DOCUMENT 6] Bioorganic & Medicinal Chemistry Letters 17 (2007) 5595-5599

SUMMARY OF THE INVENTION

Problems to be Solved by the Invention

An object of the present invention is to provide compounds having antiviral activities, especially inhibiting growth activity of influenza virus. Another object of the present invention is to provide compounds being efficiently absorbed into the body after administration and showing high pharmacological effect by converting into a prodrug a compound used for in vivo administration (for example, oral administration). More preferably, this invention provides compounds and medicament containing the same which inhibit increase of influenza virus by exhibiting cap-dependent endonuclease inhibitory activity after in vivo administration.

Means for Solving the Problems

The present invention provides inventions shown below.
(Item 1)
A compound represented by formula (I):

[Chemical formula 1]

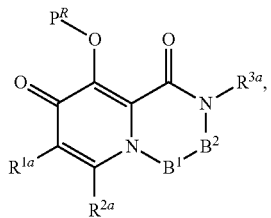

a pharmaceutically acceptable salt, or a solvate thereof:
(wherein $P^R$ is a group to form a prodrug (preferably, except for a benzyl group and methoxy group);
$R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy optionally substituted by substituent group C, heterocycleoxycarbonyl optionally substituted by substituent group C,
—Z—N($R^{A1}$)($R^{A2}$),
—Z—N($R^{A3}$)—SO$_2$—($R^{A4}$),
—Z—C(=O)—N($R^{A5}$)—SO$_2$—($R^{A6}$),
—Z—N($R^{A7}$)—C(=O)—$R^{A8}$,
—Z—S—$R^{A9}$,
—Z—SO$_2$—$R^{A10}$,
—Z—S(=O)—$R^{A11}$,
—Z—N($R^{A12}$)—C(=O)—O—$R^{A13}$,
—Z—N($R^{A14}$)—C(=O)—N($R^{A15}$)($R^{A16}$),
—Z—C(=O)—N($R^{A17}$)—C(=O)—N($R^{A18}$)($R^{A19}$),
—Z—N($R^{A20}$)—C(O)—C(=O)—$R^{A21}$, or
—Z—B(—O$R^{A22}$)(—O$R^{A23}$)
(wherein $R^{A1}$, $R^{A2}$, $R^{A3}$, $R^{A5}$, $R^{A7}$, $R^{A8}$, $R^{A9}$, $R^{A12}$, $R^{A13}$, $R^{A14}$, $R^{A15}$, $R^{A16}$, $R^{A17}$, $R^{A18}$, $R^{A19}$, $R^{A20}$, and $R^{A21}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{A4}$, $R^{A6}$, $R^{A10}$, and $R^{A11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{A1}$ and $R^{A2}$, $R^{A15}$ and $R^{A16}$, and $R^{A18}$ and $R^{A19}$, each may be taken together with an adjacent atom to form heterocycle, $R^{A22}$ and $R^{A23}$ are each independently an hydrogen atom, lower alkyl optionally substituted by substituent group C, or $R^{A22}$ and $R^{A23}$ may be taken together with an adjacent atom to form heterocycle, and Z is a single bond or straight or branched lower alkylene);
$R^{2a}$ is hydrogen, halogen, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—N($R^{B1}$)—SO$_2$—$R^{B2}$,
—Z—N($R^{B3}$)—C(=O)—$R^{B4}$,
—Z—N($R^{B5}$)—C(=O)—O—$R^{B6}$,
—Z—C(=O)—N($R^{B7}$)($R^{B8}$),
—Z—N($R^{B9}$)($R^{B10}$), or
—Z—SO$_2$—$R^{B11}$
(wherein $R^{B1}$, $R^{B3}$, $R^{B4}$, $R^{B5}$, $R^{B6}$, $R^{B7}$, $R^{B8}$, $R^{B9}$, and $R^{B10}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B2}$ and $R^{B11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B7}$ and $R^{B8}$, and $R^{B9}$ and $R^{B10}$ may be taken together with an adjacent atom to form heterocycle and Z is a single bond or straight or branched lower alkylene);

$R^{3a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$),
—Z—N($R^{C9}$)($R^{C10}$),
—Z—SO$_2$—$R^{C11}$, or
—Z—N($R^{C12}$)—O—C(=O)—$R^{C13}$ (wherein $R^{C1}$, $R^{C3}$, $R^{C4}$, $R^{C5}$, $R^{C6}$, $R^{C7}$, $R^{C8}$, $R^{C9}$, $R^{C10}$, $R^{C12}$, and $R^{C13}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C2}$ and $R^{C11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C7}$ and $R^{C8}$, and $R^{C9}$ and $R^{C10}$ each may be taken together with an adjacent atom to form heterocycle, and Z is a single bond or straight or branched lower alkylene) and;

a) either $B^1$ or $B^2$ is $CR^{5a}R^{6a}$, and the other is $NR^{7a}$, or
b) $B^1$ is $CR^{8a}R^{9a}$, and $B^2$ is $CR^{10a}R^{11a}$, $R^{5a}$, $R^{6a}$, $R^{7a}$, $R^{8a}$, $R^{9a}$, $R^{10a}$, and $R^{11a}$ are each independently selected from a substituent group consisting of hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C, —Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$),
—Z—C($R^{D7}$)($R^{D8}$)($R^{D9}$),
—Z—CH$_2$—$R^{D10}$,
—Z—N($R^{D11}$)—C(=O)—O—$R^{D12}$, or
—Z—N($R^{D13}$)—C(=O)—$R^{D14}$, or $R^{5a}$ and $R^{6a}$ may be taken together to form heterocyclic group optionally substituted by substituent group C (wherein $R^{D1}$, $R^{D4}$, $R^{D5}$, $R^{D6}$, $R^{D9}$, $R^{D11}$, $R^{D12}$, $R^{D13}$, and $R^{D14}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D2}$ and $R^{D3}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D7}$, $R^{D8}$, and $R^{D10}$ are each independently carbocyclic group optionally substituted by substituent group C, or heterocyclic group optionally substituted by substituent group C, $R^{D5}$ and $R^{D6}$ may be taken together with an adjacent atom to form heterocycle, Y is straight or branched lower alkylene, and Z is a single bond or straight or branched lower alkylene), and $R^{D5}$ and $R^{D6}$ may be taken together with an adjacent atom to form carbocycle;

1) when $B^1$ is $CR^{5a}R^{6a}$ and $B^2$ is $NR^{7a}$, $R^{3a}$ and $R^{7a}$ may be taken together with an adjacent atom to form heterocycle optionally substituted by substituent group D, 2) when $B^1$ is $NR^{7a}$ and $B^2$ is $CR^{5a}R^{6a}$ $R^{3a}$ and $R^{6a}$ may be taken together with an adjacent atom to form heterocycle optionally substituted by substituent group D, or 3) when $B^1$ is $CR^{8a}R^{9a}$, and $B^2$ is $CR^{10a}R^{11a}$,
$R^{8a}$ and $R^{10a}$ may be taken together with an adjacent atom to form carbocycle or heterocycle optionally substituted by substituent group D, or
$R^{3a}$ and $R^{11a}$ may be taken together with an adjacent atom to form heterocycle optionally substituted by substituent group D;
wherein
when $B^1$ is $CR^{8a}R^{9a}$, and $B^2$ is $CR^{10a}R^{11a}$, and $R^{9a}$ is hydrogen, and $R^{11a}$ is hydrogen,
i) either $R^{8a}$ or $R^{10a}$ is
—Z—C($R^{E1}$)($R^{E2}$)($R^{E3}$),
—Y—S—$R^{E4}$,
—Z—CH$_2$—$R^{E5}$, or
a group shown below:

[Chemical formula 2]

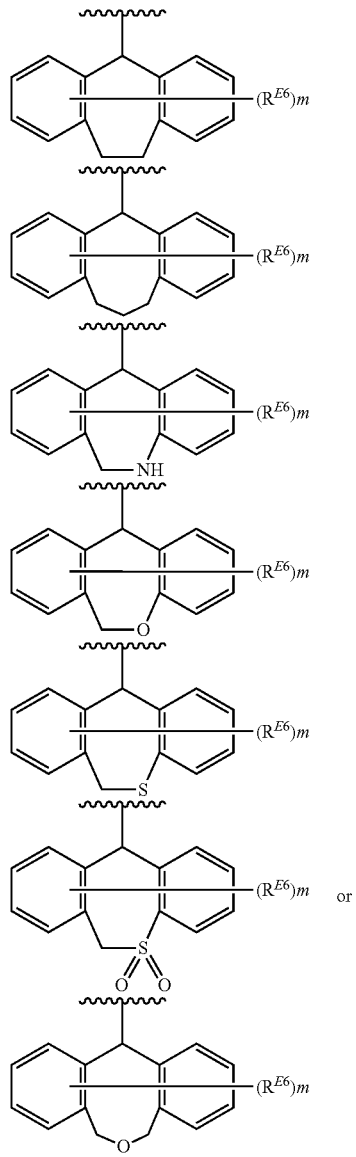

or (wherein $R^{E1}$ and $R^{E2}$ are each independently, selected from a substituent group consisting of carbocyclic group optionally substituted by substituent group C, and heterocyclic group optionally substituted by substituent group C, $R^{E3}$ is selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{E4}$ is selected from a substituent group consisting of carbocycle lower alkyl optionally substituted by substituent group C, and heterocycle lower alkyl optionally substituted by substituent group C, $R^{E5}$ is aromatic heterocyclic group optionally substituted by substituent group C, $R^{E6}$ is selected from a substituent group C, m is an integer of 0 or 1 or more, provided that m of $R^{E6}$s is same or different groups selected from substituent group C, Y is straight or branched lower alkylene, and Z is a single bond or straight or branched lower alkylene); and ii) the other of $R^{8a}$ or $R^{10a}$ is
hydrogen, carboxy, cyano, lower alkyl optionally substituted by substituent group C, lower alkenyl optionally substituted by substituent group C, lower alkynyl optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C,
—Y—S—$R^{F1}$,
—C(=O)—C(=O)—$R^{F2}$, or
—C(=O)—N($R^{F3}$)($R^{F4}$)
(wherein $R^{F1}$, $R^{F2}$, $R^{F3}$, and $R^{F4}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, and Y is straight or branched lower alkylene);
with a proviso that the following c) and d) are excluded
c) $R^{5a}$, $R^{6a}$, and $R^{7a}$ are all hydrogens.
d) $R^{8a}$, $R^{9a}$, $R^{10a}$, and $R^{11a}$ are all hydrogens.

Substituent group C: halogen, cyano, hydroxy, carboxy, formyl, amino, oxo, nitro, lower alkyl, lower alkenyl, lower alkynyl, halogeno lower alkyl, lower alkyloxy, lower alkynyloxy, lower alkylthio, hydroxy lower alkyl, carbocyclic group, heterocyclic group, heterocyclic group substituted by oxo, carbocycle lower alkyloxy, carbocycleoxy lower alkyl, carbocycle lower alkyloxy lower alkyl, heterocycle lower alkyloxy, heterocycleoxy lower alkyl, heterocycle lower alkyloxy lower alkyl, halogeno lower alkyloxy, lower alkyloxy lower alkyl, lower alkyloxy lower alkyloxy, lower alkylcarbonyl, lower alkylcarbonyloxy, lower alkyloxycarbonyl, lower alkylamino, lower alkylcarbonylamino, halogeno lower alkyl carbonylamino, lower alkylaminocarbonyl, lower alkylsulfonyl, lower alkylsulfinyl, and lower alkylsulfonylamino;

Substituent group D: halogen, cyano, hydroxy, carboxy, formyl, amino, oxo, nitro, lower alkyl, halogeno lower alkyl, lower alkyloxy, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, lower alkylsulfonylamino, carbocyclic group optionally substituted by substituent group C, heterocyclic group optionally substituted by substituent group C, carbocycle lower alkyl optionally substituted by substituent group C, and heterocycle lower alkyl optionally substituted by substituent group C).

(Item 2)

The compound according to item 1, or the pharmaceutically acceptable salt thereof or the solvate thereof, wherein $R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy optionally substituted by substituent group C, heterocycleoxycarbonyl optionally substituted by substituent group C, —Z—N($R^{41}$)($R^{42}$),
—Z—N($R^{43}$)—SO$_2$—($R^{44}$),
—Z—N($R^{47}$)—C(=O)—$R^{48}$,
—Z—S—$R^{49}$,
—Z—SO$_2$—$R^{410}$,
—Z—N($R^{412}$)—C(=O)—O—$R^{413}$,
—Z—N($R^{420}$)—C(=O)—C(=O)—$R^{421}$, or
—Z—B(—O$R^{422}$)(—O$R^{423}$)

(substituent group C, $R^{41}$, $R^{42}$, $R^{43}$, $R^{44}$, $R^{47}$, $R^{48}$, $R^{49}$, $R^{410}$, $R^{412}$, $R^{413}$, $R^{420}$, $R^{421}$, $R^{422}$, $R^{423}$, and Z are same as those of item 1).

(Item 3)

The compound according to item 1, or the pharmaceutically acceptable salt thereof or the solvate thereof, wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, —Z—N($R^{41}$)($R^{42}$),
—Z—N($R^{47}$)—C(=O)—$R^{48}$,
—Z—N($R^{412}$)—C(=O)—O—$R^{413}$, or
—Z—B(—O$R^{422}$)(—O$R^{423}$)

(substituent group C, $R^{41}$, $R^{42}$, $R^{47}$, $R^{48}$, $R^{412}$, $R^{413}$, $R^{422}$, $R^{423}$, and Z are same as those of item 1).

(Item 4)

The compound according to item 1, or the pharmaceutically acceptable salt thereof or the solvate thereof, wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, or

—Z—N($R^{41}$)($R^{42}$)

(substituent group C, $R^{41}$, $R^{42}$, and Z are same as those of item 1).

(Item 5)

The compound according to item 1, or the pharmaceutically acceptable salt thereof or the solvate thereof, wherein $R^{1a}$ is hydrogen, or carboxy.

(Item 6)

The compound according to any one of items 1 to 5, or the pharmaceutically acceptable salt thereof or the solvate thereof, wherein $R^{2a}$ is hydrogen, lower alkyl optionally substituted by substituent group C, carbocycle lower alkyl optionally substituted by substituent group C, heterocycle lower alkyl optionally substituted by substituent group C, or

—Z—N($R^{B9}$)($R^{B10}$)

(substituent group C, $R^{B9}$, $R^{10}$, and Z are same as those of item 1).

(Item 7)

The compound according to any one of items 1 to 5, or the pharmaceutically acceptable salt thereof or the solvate thereof, wherein $R^{2a}$ is hydrogen or lower alkyl optionally substituted by substituent group C (substituent group C is same as that of item 1).

(Item 8)

The compound according to any one of items 1 to 7, or the pharmaceutically acceptable salt thereof or the solvate thereof, wherein $R^{3a}$ is hydrogen, lower alkyl optionally substituted by substituent group C, lower alkenyl optionally substituted by substituent group C, lower alkynyl optionally substituted by substituent group C, carbocyclic group optionally substituted by substituent group C, carbocycle lower alkyl optionally substituted by substituent group C, carbocycleoxy lower alkyl optionally substituted by substituent group C, heterocycle lower alkyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$), or
—Z—N($R^{C9}$)($R^{C10}$)

(substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, and Z are same as those of item 1).

(Item 9)

The compound according to any one of items 1 to 7, or the pharmaceutically acceptable salt thereof or the solvate thereof, wherein $R^{3a}$ is hydrogen, lower alkyl optionally substituted by substituent group C, carbocyclic group optionally substituted by substituent group C, heterocyclic group optionally substituted by substituent group C, carbocycle lower alkyl optionally substituted by substituent group C, (substituent group C is same as that of item 1).

(Item 10)

The compound according to any one of items 1 to 9, or the pharmaceutically acceptable salt thereof or the solvate thereof, wherein $B^1$ is $NR^{7a}$, and $B^2$ is $CR^{5a}R^{6a}$, and $R^{5a}$, $R^{6a}$ and $R^{7a}$ are each independently hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C, —Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$),
—Z—C($R^{D7}$)($R^{D8}$)($R^{D9}$),
—Z—N($R^{D11}$)—C(=O)—O—$R^{D12}$, or
—Z—N($R^{D13}$)—C(=O)—$R^{D14}$ (substituent group C, $R^{D1}$, $R^{D2}$, $R^{D3}$, $R^{D4}$, $R^{D5}$, $R^{D6}$, $R^{D7}$, $R^{D8}$, $R^{D9}$, $R^{D11}$, $R^{D12}$, $R^{D13}$, $R^{D14}$, Y, and Z are same as those of item 1).

(Item 11)

The compound according to any one of items 1 to 9, or the pharmaceutically acceptable salt thereof or the solvate thereof, wherein $B^1$ is $NR^{7a}$, and $B^2$ is $CR^{5a}R^{6a}$, $R^{5a}$ is hydrogen, $R^{6a}$ is hydrogen, or lower alkyl optionally substituted by substituent group C, and $R^{7a}$ is lower alkyl optionally substituted by substituent group C, carbocyclic group optionally substituted by substituent group C, carbocycleoxy lower alkyl optionally substituted by substituent group C, heterocyclic group optionally substituted by substituent group C, carbocycle lower alkyl optionally substituted by substituent group C, heterocycle lower alkyl optionally substituted by substituent group C, or

—Z—C($R^{D7}$)($R^{D8}$)($R^{D9}$)

(substituent group C, $R^{D7}$, $R^{D8}$, $R^{D9}$, and Z are same as those of item 1).

(Item 12)

The compound according to any one of items 1 to 9, or the pharmaceutically acceptable salt thereof or the solvate thereof, wherein $B^1$ is $CR^{5a}R^{6a}$, and $B^2$ is $NR^{7a}$, $R^{5a}$ is hydrogen, $R^{6a}$ is hydrogen, or lower alkyl optionally substituted by substituent group C, and $R^{7a}$ is lower alkyl optionally substituted by substituent group C, carbocyclic group optionally substituted by substituent group C, carbocycleoxy lower alkyl optionally substituted by substituent group C, heterocyclic group optionally substituted by substituent group C, carbocycle lower alkyl optionally substituted by substituent group C, heterocycle lower alkyl optionally substituted by substituent group C, or

—Z—C($R^{D7}$)($R^{D8}$)($R^{D9}$)

(substituent group C, $R^{D7}$, $R^{D8}$, $R^{D9}$, and Z are same as those of item 1).

(Item 13)

The compound according to items 11 or 12, or the pharmaceutically acceptable salt thereof or the solvate thereof, wherein $R^{7a}$ is a group shown below:

[Chemical formula 3]

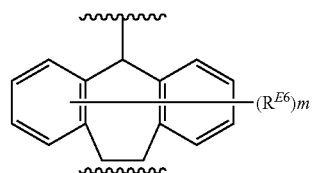

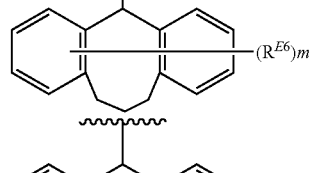

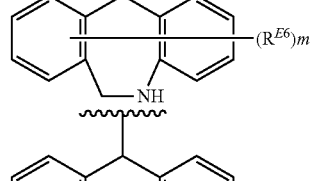

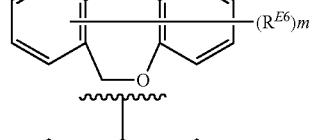

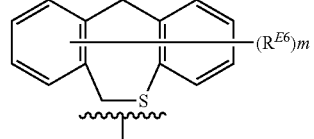

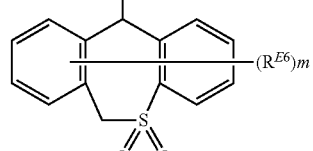

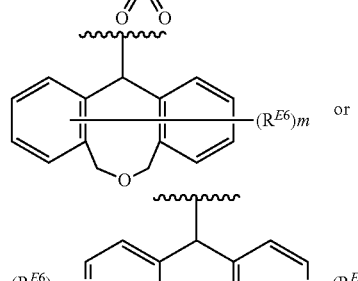

(wherein $R^{E6}$ and m are same as those of item 1).

(Item 14)

The compound according to item 1, or the pharmaceutically acceptable salt thereof or the solvate thereof,
wherein $R^{1a}$ is hydrogen, or carboxy,
$R^{2a}$ is hydrogen,
$R^{3a}$ is lower alkyl optionally substituted by substituent group C,
$B^1$ is $NR^{7a}$, and $B^2$ is $CH_2$, and
$R^{7a}$ is a group shown below:

[Chemical formula 4]

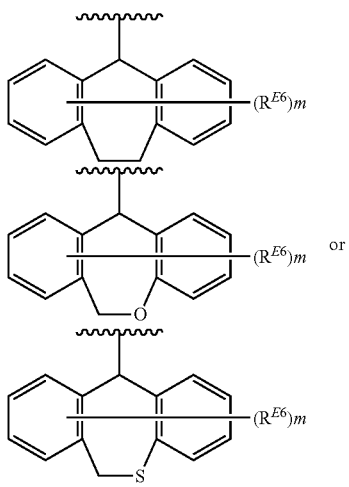

(wherein substituent group C, $R^{E6}$, and m are same as those of item 1).

(Item 15)

The compound according to any one of items 1 to 9, or the pharmaceutically acceptable salt thereof or the solvate thereof,
wherein $B^1$ is $CR^{8a}R^{9a}$, and $B^2$ is $CR^{10a}R^{11a}$,
$R^{9a}$ is hydrogen, and $R^{11a}$ is hydrogen, and
i) either $R^{8a}$ or $R^{10a}$ is
a group shown below:

[Chemical formula 5]

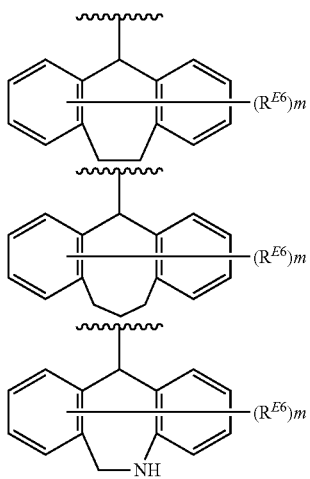

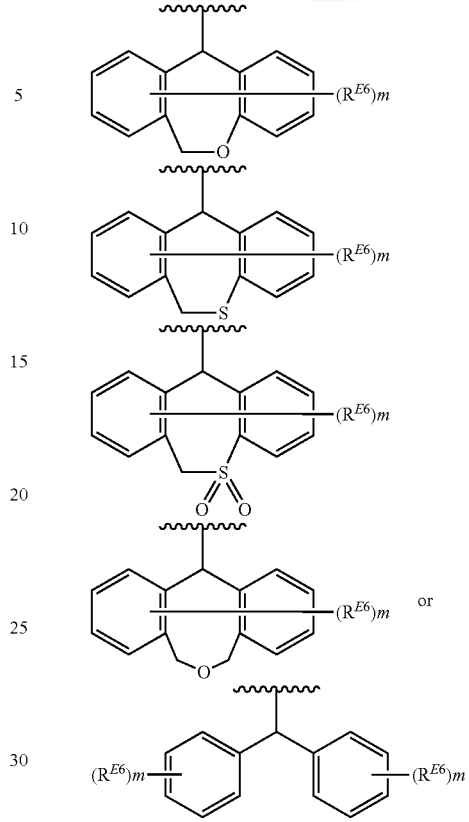

(wherein $R^{E6}$ and m are same as those of item 1); and
ii) the other of $R^{8a}$ or $R^{10a}$ is
hydrogen, or lower alkyl optionally substituted by substituent group C
(substituent group C is same as that of item 1).

(Item 16)

The compound according to any one of items 1 to 7, or the pharmaceutically acceptable salt thereof or the solvate thereof,
wherein $B^1$ is $CR^{5a}R^{6a}$, and $B^2$ is $NR^{7a}$,
$R^{6a}$ is hydrogen,
$R^{3a}$ and $R^{7a}$ are taken together with an adjacent atom to form heterocycle optionally substituted by substituent group D, and
$R^{5a}$ is hydrogen, lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C,
—Y—S—$R^{D1}$,
—C(=O)—C(=O)—$R^{D2}$, or
—C(=O)—N($R^{D3}$)($R^{D4}$)
(wherein $R^{D1}$, $R^{D2}$, $R^{D3}$, $R^{D4}$, Y, substituent group C and substituent group D are same as those of item 1).

(Item 17)

The compound according to item 16, or the pharmaceutically acceptable salt thereof or the solvate thereof,
wherein $R^{5a}$ is hydrogen, carbocyclic group optionally substituted by substituent group C, carbocycle lower alkyl optionally substituted by substituent group C, heterocyclic group optionally substituted by substituent group C, or heterocycle lower alkyl optionally substituted by substituent group C (wherein substituent group C is same as that of item 1).
(Item 18)

The compound according to any one of items 1 to 7, or the pharmaceutically acceptable salt thereof or the solvate thereof, wherein $B^1$ is $CR^{8a}R^{9a}$, and $B^2$ is $CR^{10a}R^{11a}$, $R^{9a}$ is hydrogen, and $R^{10a}$ is hydrogen, $R^{3a}$ and $R^{11a}$ are taken together with an adjacent atom to form heterocycle optionally substituted by substituent group D, and $R^{8a}$ is hydrogen, lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C, —Y—S—$R^{D1}$,
—C(=O)—C(=O)—$R^{D2}$, or
—C(=O)—N($R^{D3}$)($R^{D4}$)

(wherein $R^{D1}$, $R^{D2}$, $R^{D3}$, $R^{D4}$, Y, substituent group C and substituent group D are same as those of item 1).
(Item 19)

The compound according to item 18, or the pharmaceutically acceptable salt thereof or the solvate thereof, wherein $R^{8a}$ is hydrogen, carbocyclic group optionally substituted by substituent group C, carbocycle lower alkyl optionally substituted by substituent group C, heterocyclic group optionally substituted by substituent group C, or heterocycle lower alkyl optionally substituted by substituent group C (wherein substituent group C is same as that of item 1).
(Item 20)

The compound according to any one of items 16 to 19, or the pharmaceutically acceptable salt thereof or the solvate thereof, wherein substituent group D is carbocyclic group optionally substituted by substituent group C, heterocyclic group optionally substituted by substituent group C, carbocycle lower alkyl optionally substituted by substituent group C, or heterocycle lower alkyl optionally substituted by substituent group C (wherein substituent group C is same as that of item 1).
(Item 21)

The compound according to any one of items 1 to 20, or the pharmaceutically acceptable salt thereof or the solvate thereof, wherein $P^R$ is a group selected from the following formulae a) to y):

a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N($P^{R2}$)$_2$,
i) —C(=O)—O-L-O—$P^{R2}$,
j) —CH$_2$—O—$P^{R3}$,
k) —CH$_2$—O-L-O—$P^{R3}$,
l) —CH$_2$—O—C(=O)—$P^{R3}$,
m) —CH$_2$—O—C(=O)—O—$P^{R3}$,
n) —CH(—CH$_3$)—O—C(=O)—O—$P^{R3}$,
o) —CH$_2$—O—C(=O)—N(—K)—$P^{R3}$,
p) —CH$_2$—O—C(=O)—O-L-O—$P^{R3}$,
q) —CH$_2$—O—C(=O)—O-L-N($P^{R3}$)$_2$,
r) —CH$_2$—O—C(=O)—N(—K)-L-O—$P^{R3}$,
s) —CH$_2$—O—C(=O)—N(—K)-L-N($P^{R3}$)$_2$,
t) —CH$_2$—O—C(=O)—O-L-O-L-O—$P^{R3}$,
u) —CH$_2$—O—C(=O)—O-L-N(—K)—C(=O)—$P^{R3}$,
v) —CH$_2$—O—P(=O)(—OH)$_2$,
w) —CH$_2$—O—P(=O)(—OBn)$_2$,
x) —CH$_2$—$P^{R4}$ (except for a benzyl group)
y) —C(=N$^+$$P^{R5}$$_2$)(—N$P^{R5}$$_2$)

(wherein L is straight or branched lower alkylene, or straight or branched lower alkenylene, K is hydrogen, or straight or branched lower alkylene, $P^{R0}$ is lower alkyl optionally substituted by substituent group F, or lower alkenyl optionally substituted by substituent group F, $P^{R1}$ is carbocyclic group optionally substituted by substituent group F, heterocyclic group optionally substituted by substituent group F, lower alkyl amino optionally substituted by substituent group F, or lower alkylthio optionally substituted by substituent group F, $P^{R2}$ is lower alkyl optionally substituted by substituent group F, carbocyclic group optionally substituted by substituent group F, or heterocyclic group optionally substituted by substituent group F, $P^{R3}$ is lower alkyl optionally substituted by substituent group F, carbocyclic group optionally substituted by substituent group F, heterocyclic group optionally substituted by substituent group F, lower alkyl amino optionally substituted by substituent group F, carbocycle lower alkyl optionally substituted by substituent group F, heterocycle lower alkyl optionally substituted by substituent group F, or lower alkylsilyl, $P^{R4}$ is carbocyclic group optionally substituted by substituent group F, or heterocyclic group optionally substituted by substituent group F, and $P^{R5}$ is lower alkyl optionally substituted by substituent group F.

Substituent group F; oxo, lower alkyl, hydroxy lower alkyl, amino, lower alkylamino, carbocycle lower alkyl, lower alkylcarbonyl, halogen, hydroxy, carboxy, lower alkylcarbonylamino, lower alkylcarbonyloxy, lower alkyloxycarbonyl, lower alkyloxy, cyano, and nitro).
(Item 22)

A pharmaceutical composition containing a compound according to any one of items 1 to 21, or a pharmaceutically acceptable salt thereof or a solvate thereof.
(Item 23)

The pharmaceutical composition according to item 22 which exhibits anti influenza activity.
(Item 24)

The pharmaceutical composition according to item 22 which exhibits cap-dependent endonuclease inhibitory activity.
(Item 25)

The pharmaceutical composition according to item 22 for treating and/or preventing influenza infectious disease.
(Item 26)

A cap-dependent endonuclease inhibitor containing a compound according to any one of items 1 to 21, or a pharmaceutically acceptable salt thereof or a solvate thereof.

The present invention further provides a method for treating or preventing influenza infectious disease using the prodrug compound and the compound which exhibits anti influenza activity. The present invention further provides a parent compound of the prodrug compound. The parent compound is effective as an anti-influenza agent or an intermediate of the prodrug compound.

Effect of the Invention

The compound according to the present invention has an inhibitory activity on cap-dependent endonuclease. More preferred compound is a prodrug, and the prodrug becomes a parent compound having an inhibitory activity on cap-dependent endonuclease in vivo after administration, thus is effective as a therapeutic agent and/or preventive agent for influenza infectious disease.

BEST MODE FOR CARRYING OUT THE INVENTION

Figures 1, 2:
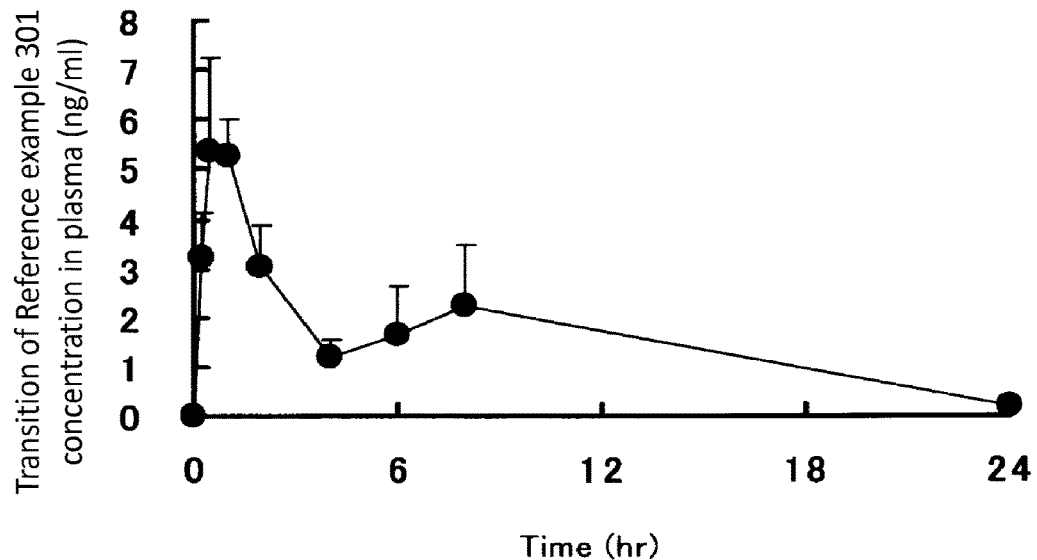
FIG. 1 is a result of measuring changes in the plasma concentration of Reference example 301, for compound of Example 114 obtained by converting into a prodrug compound of Reference example 301 that is a parent compound, after oral administration to rat under non-fasting conditions.
FIG. 2 is a graph showing an average of the changes in the plasma concentration when the measurement shown in FIG. 1 is performed three times.

The meaning of each term used in the present description is explained below. Each term is used in a unified sense, and is used in the same sense when used alone, or when used in combination of other term.

"Optionally substituted by substituent group C" means that an arbitrary position may be substituted by one, two or more same or different substituents selected from substituent group C.

"Optionally substituted by substituent group D", and "optionally substituted by substituent group F" are also as described above.

"Prodrug" in the present description refers to a compound represented by formula (I) in the following reaction formula:

[Chemical formula 6]

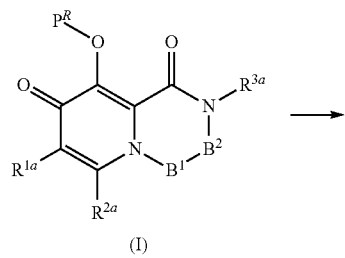

(I)

-continued

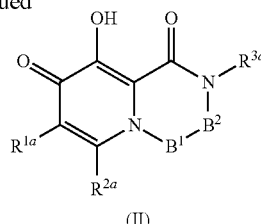

(II)

(wherein each symbol is same as that of item 1)
or a pharmaceutically acceptable salt thereof or a solvate thereof, and means a compound showing cap-dependant endonuclease (CEN) inhibitory activity and/or CPE inhibitory effect by being converted into a compound represented by formula (II) by a decomposition reaction caused by drug-metabolizing enzymes, hydrolases, gastric acids, enterobacteria, etc. under physiological conditions in vivo.

The prodrug more preferably means a compound in which bioavailability and/or AUC (area under the blood concentration curve) in in vivo administration is improved more than those of the compound represented by formula (II).

Therefore, the prodrug is efficiently absorbed into the body in the stomach and/or intestines after in vivo administration (for example, oral administration), then converted into the compound represented by formula (II). Thus, the prodrug preferably shows an effect of treating and/or preventing influenza higher than the compound represented by formula (II).

"Group to form a prodrug" in the present description refers to a "$P^R$" group in the formula (I), in the following reaction formula:

[Chemical formula 7]

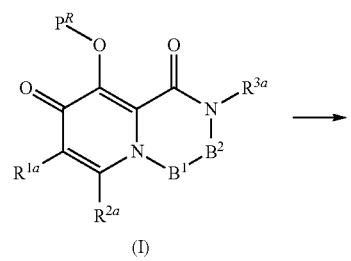

(I)

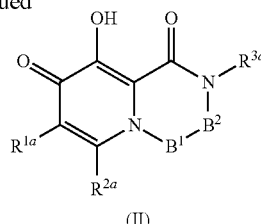

(II)

(wherein each symbol is same as that of item 1)
and —$OP^R$ group is converted into —OH group in the formula (II) by a decomposition reaction caused by drug-metabolizing enzymes, hydrolases, gastric acids, enterobacteria, etc. under physiological conditions in vivo. The "group to form a prodrug" more preferably means a group that improves bioavailability and/or AUC (area under the blood concentration curve) of the compound represented by formula (II) by being added to the compound represented by formula (II).

Examples of the group to form a prodrug include the groups described in Prog. Med. 5: 2157-2161 (1985) and Supplied by The British Library—"The world's Knowledge".

The "$P^R$" group in —$OP^R$ group in the formula (I) may be a group converted into —OH group in vivo. Preferably the groups selected from various substituted carbonyl groups, substituted lower alkyl oxy groups (e.g., substituted oxymethyl), optionally substituted cyclic group lower alkyl (e.g., optionally substituted cyclic methyl group), and optionally substituted imino lower alkyl (e.g., optionally substituted imino methyl) are exemplified, and examples preferably include a group selected from the following formulae a) to y).

a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N($P^{R2}$)$_2$,
i) —C(=O)—O-L-O—$P^{R2}$,
j) —CH$_2$—O—$P^{R3}$,
k) —CH$_2$—O-L-O—$P^{R3}$,
l) —CH$_2$—O—C(=O)—$P^{R3}$,
m) —CH$_2$—O—C(=O)—O—$P^{R3}$,
n) —CH(—CH$_3$)—O—C(=O)—O—$P^{R3}$,
o) —CH$_2$—O—C(=O)—N(—K)—$P^{R3}$,
p) —CH$_2$—O—C(=O)—O-L-O—$P^{R3}$,
q) —CH$_2$—O—C(=O)—O-L-N($P^{R3}$)$_2$,
r) —CH$_2$—O—C(=O)—N(—K)-L-O—$P^{R3}$,
s) —CH$_2$—O—C(=O)—N(—K)-L-N($P^{R3}$)$_2$,
t) —CH$_2$—O—C(=O)—O-L-O-L-O—$P^{R3}$,
u) —CH$_2$—O—C(=O)—O-L-N(—K)—C(=O)—$P^{R3}$,
v) —CH$_2$—O—P(=O)(—OH)$_2$,
w) —CH$_2$—O—P(=O)(—OBn)$_2$,
x) —CH$_2$—$P^{R4}$,
y) —C(=N$^+P^{R5}_2$)(—N$P^{R5}_2$)

(wherein L is straight or branched lower alkylene,
K is hydrogen, or straight or branched lower alkylene, or straight or branched lower alkenylene, $P^{R0}$ is lower alkyl optionally substituted by substituent group F, or lower alkenyl optionally substituted by substituent group F, $P^{R1}$ is carbocyclic group optionally substituted by substituent group F, heterocyclic group optionally substituted by substituent group F, lower alkyl amino optionally substituted by substituent group F, or lower alkylthio optionally substituted by substituent group F, $P^{R2}$ is lower alkyl optionally substituted by substituent group F, carbocyclic group optionally substituted by substituent group F, or heterocyclic group optionally substituted by substituent group F, $P^{R3}$ is lower alkyl optionally substituted by substituent group F, carbocyclic group optionally substituted by substituent group F, heterocyclic group optionally substituted by substituent group F, lower alkyl amino optionally substituted by substituent group F, carbocycle lower alkyl optionally substituted by substituent group F, heterocycle lower alkyl optionally substituted by substituent group F, or lower alkylsilyl, $P^{R4}$ is carbocyclic group optionally substituted by substituent group F, or heterocyclic group optionally substituted by substituent group F, and $P^{R5}$ is lower alkyl optionally substituted by substituent group F.

Substituent group F; oxo, lower alkyl, hydroxy lower alkyl, amino, lower alkylamino, carbocycle lower alkyl, lower alkylcarbonyl, halogen, hydroxy, carboxy, lower alkylcarbonylamino, lower alkylcarbonyloxy, lower alkyloxycarbonyl, lower alkyloxy, cyano, and nitro)

As the group to form a prodrug, the "$P^R$" group in —$OP^R$ group in the formula (I) is preferably a group selected from the following b), k), l), and m).

b) —C(=O)—$P^{R1}$,
l) —CH$_2$—O—C(=O)—$P^{R3}$,
m) —CH$_2$—O—C(=O)—O—$P^{R3}$,
n) —CH(—CH$_3$)—O—C(=O)—O—$P^{R3}$, (wherein each symbol is same as above)

"Converted into a prodrug" in the present description means that, as shown in the following reaction formula:

[Chemical formula 8]

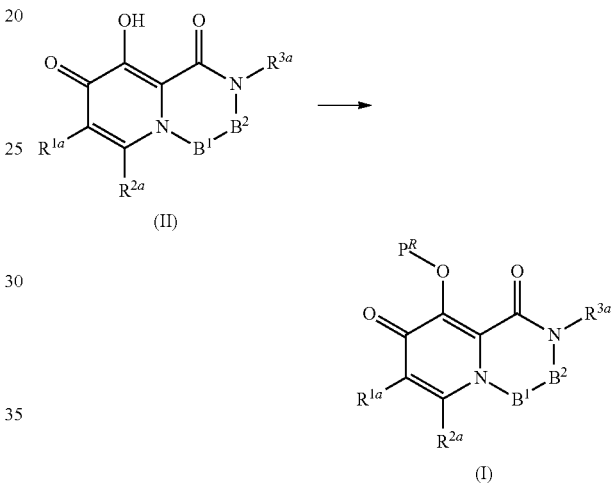

(wherein each symbol is same as that of item 1)

a hydroxy group in the formula (II) or pharmaceutically acceptable salt thereof or a solvate thereof is converted into —$OP^R$ group.

"Parent compound" in the present description means a compound to be a source before synthesizing the "prodrug" and/or a compound released from the "prodrug" by the reaction by enzymes, a gastric acid, and the like under physiological conditions in vivo, and specifically means a compound shown by the formula (II), or pharmaceutically acceptable salt thereof or a solvate thereof.

"Halogen" includes fluorine, chlorine, bromine and iodine. Preferable is fluorine, chlorine and bromine.

"Lower alkyl" includes straight or branched alkyl of a carbon number of 1 to 15, preferably a carbon number of 1 to 10, more preferably a carbon number of 1 to 6, further preferably a carbon number of 1 to 4, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl etc. Examples of a preferable embodiment of "lower alkyl" include methyl, ethyl, n-propyl, isopropyl, n-butyl, isobutyl, sec-butyl, tert-butyl, and n-pentyl. Examples of a further preferable embodiment include methyl, ethyl, n-propyl, isopropyl, and tert-butyl.

"Lower alkenyl" includes straight or branched alkenyl of a carbon number of 2 to 15, preferably a carbon number of 2 to 10, more preferably a carbon number of 2 to 6, further preferably a carbon number of 2 to 4, having one or more double bonds at an arbitrary position. Specifically, lower alkenyl includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl etc. Examples of a preferable embodiment of "lower alkenyl" include vinyl, allyl, propenyl, isopropenyl, and butenyl.

"Lower alkynyl" includes straight or branched alkynyl of a carbon number of 2 to 10, preferably a carbon number of 2 to 8, further preferably a carbon number of 3 to 6, having one or more triple bonds at an arbitrary position. Specifically, lower alkynyl includes ethynyl, propynyl, butynyl, pentynyl, hexynyl, heptynyl, octynyl, nonynyl, decynyl etc. These may further have a double bond at an arbitrary position. Examples of a preferable embodiment of "lower alkynyl" include ethynyl, propynyl, butynyl, and pentynyl.

A lower alkyl part of "lower alkyloxy", "lower alkylcarbonyl", "lower alkyloxycarbonyl", "carbocycle lower alkyl", "heterocycle lower alkyl", "carbocycleoxy lower alkyl", "heterocycleoxy lower alkyl", "halogeno lower alkyl", "carbocycle lower alkyloxy", "heterocycle lower alkyloxy", "halogeno lower alkyloxy", "lower alkyloxy lower alkyl", "lower alkyloxy lower alkyloxy", "lower alkylcarbonyl", "lower alkyloxycarbonyl", "lower alkylamino", "lower alkylcarbonylamino", "lower alkylaminocarbonyl", "lower alkylsulfonyl", "lower alkylsulfonylamino", "lower alkylthio", "hydroxy lower alkyl", "carbocycle lower alkyloxy lower alkyl", "heterocycle lower alkyloxy lower alkyl", "lower alkylcarbonyloxy", "halogeno lower alkylcarbonylamino", and "lower alkylsulfinyl" is the same as the "lower alkyl" as described above.

A lower alkenyl part of "lower alkenyloxy" is the same as the "lower alkenyl" as described above.

A halogen part of "halogeno lower alkyl", "halogeno lower alkyloxy", and "halogeno lower alkylcarbonylamino" is the same as the "halogen". Herein, an arbitrary position on an alkyl group of "lower alkyl", "lower alkyloxy", and "lower alkylcarbonylamino" may be substituted by same or different one or plural halogen atoms, respectively.

"Carbocyclic group" or "carbocycle" means carbocyclic group of a carbon number of 3 to 20, preferably a carbon number of 3 to 16, more preferably a carbon number of 4 to 12, and includes cycloalkyl, cycloalkenyl, aryl and a non-aromatic condensed carbocyclic group, etc.

Specifically, "cycloalkyl" is carbocyclic group of a carbon number of 3 to 16, preferably a carbon number of 3 to 12, more preferably a carbon number of 4 to 8, and examples include cyclopropyl, cyclobutyl, cyclopentyl, cyclohexyl, cycloheptyl, cyclooctyl, cyclononyl and cyclodecyl, etc.

Specifically, "cycloalkenyl" includes cycloalkenyl having one or more double bonds at an arbitrary position in the cycloalkyl ring, and examples include cyclopropenyl, cyclobutenyl, cyclopentenyl, cyclohexenyl, cycloheptynyl, cyclooctynyl and cyclohexadienyl, etc.

Specifically, "aryl" means an aromatic carbocyclic group, and includes phenyl, naphthyl, anthryl and phenanthryl, etc. and, particularly, phenyl is preferable.

Specifically, "non-aromatic condensed carbocyclic group" includes a group in which two or more cyclic groups selected from the "cycloalkyl", the "cycloalkenyl" and the "aryl" are condensed, and examples include indanyl, indenyl, tetrahydronaphthyl, fluorenyl, adamantyl, and groups shown below

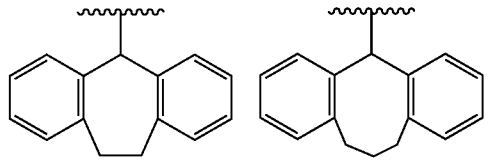

[Chemical formula 9]

etc.

Examples of a preferable embodiment of "carbocyclic group" or "carbocycle" include cycloalkyl, aryl and a non-aromatic condensed carbocyclic group, specifically examples include cyclopropyl, cyclobutyl, cyclopentyl, cyclohexyl, cycloheptyl, phenyl, naphthyl, and groups shown below

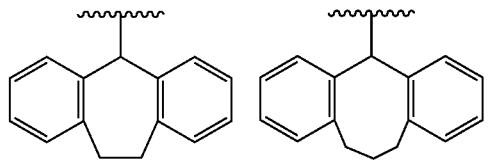

[Chemical formula 10]

etc.

A carbocyclic part of "carbocycle lower alkyl", "carbocycle lower alkyloxy", "carbocycleoxy lower alkyl", "carbocyclecarbonyl", "carbocycleoxy", "carbocycleoxycarbonyl" and "carbocycle lower alkyloxy lower alkyl" is the same as the "carbocyclic group" or the "carbocycle" as described above.

"Heterocyclic group" or "heterocycle" includes heterocyclic group such as heteroaryl, a non-aromatic heterocyclic group, a bicyclic condensed heterocyclic group, a tricyclic condensed heterocyclic group, a tetracyclic condensed heterocyclic group, etc., having one or more same or different hetero atoms arbitrarily selected from O, S and N in a ring.

Specifically, "heteroaryl" includes a 5- to 6-membered aromatic cyclic group such as pyrrolyl, imidazolyl, pyrazolyl, pyridyl, pyridazinyl, pyrimidinyl, pyrazinyl, triazolyl, triazinyl, tetrazolyl, furyl, thienyl, isooxazolyl, oxazolyl, oxadiazolyl, isothiazolyl, thiazolyl, thiadiazolyl, etc.

Specifically, "non-aromatic heterocyclic group" includes a 4- to 8-membered non-aromatic heterocyclic group such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxolyl, oxabicycloheptanyl, etc.

Specifically, "bicyclic condensed heterocyclic group" includes a cyclic group including at least one 4- to 8-membered aromatic or non-aromatic heterocyclic group such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisooxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotrianizyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzooxezinyl, dihydrobenzodioxepinyl, dihydrothienodioxynyl, etc.

Specifically, "tricyclic condensed heterocyclic group" includes a cyclic group including at least one 4- to 8-membered aromatic or non-aromatic heterocyclic group such as carbazolyl, acridinyl, xanthenyl, phenothiazinyl, phenoxathiinyl, phenoxazinyl, dibenzofuryl, imidazoquinolyl, tetrahydrocarbazolyl, and groups shown below

[Chemical formula 11]

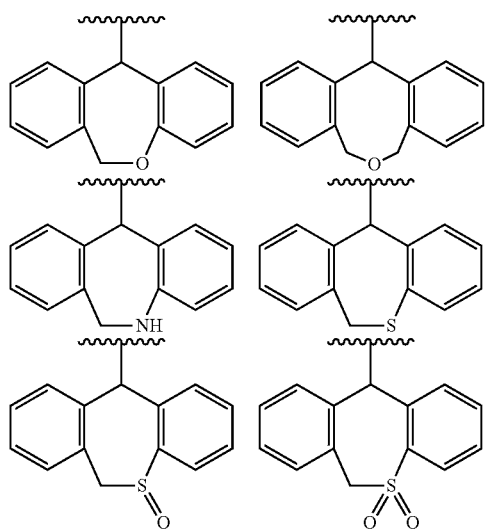

etc.

Examples of a preferable embodiment of "heterocyclic group" include 5- to 6-membered heteroaryl, a non-aromatic heterocyclic group and a tricyclic condensed heterocyclic group.

A heterocyclic part of "heterocycle lower alkyl", "heterocycle lower alkyloxy", "carbocycleoxy lower alkyl", "heterocyclecarbonyl", "heterocycleoxy", "heterocycleoxycarbonyl", and "heterocycle lower alkyloxy lower alkyl" is the same as the "heterocyclic group" or the "heterocycle" as described above.

"Heterocyclic group substituted by oxo" means the "heterocyclic group" as described above, substituted by oxo as shown below. Groups shown below

[Chemical formula 12]

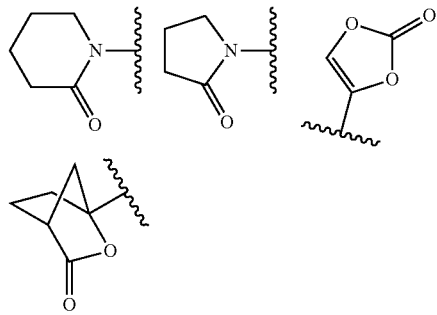

are exemplified.

"Straight or branched lower alkylene" is divalent "lower alkyl" as described above, and includes, for example, methylene, ethylene, propylene, butylene, isobutylene, pentylene, heptylene, dimethylmethylene, ethylmethylmethylene, 1,2-dimethylethylene, etc.

Examples of "lower alkyloxy" include methoxy, ethoxy, propyloxy, isopropyloxy, tert-butyloxy, isobutyloxy, sec-butyloxy, pentyloxy, isopentyloxy, hexyloxy, etc. Examples of a preferable embodiment include methoxy, ethoxy, propyloxy, isopropyloxy, and tert-butyloxy.

Examples of "lower alkylcarbonyl" include methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl, etc. Examples of a preferable embodiment include methylcarbonyl, ethylcarbonyl, and propylcarbonyl.

Examples of "lower alkyloxycarbonyl" include methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl, etc. Examples of a preferable embodiment include methyloxycarbonyl, ethyloxycarbonyl, and propyloxycarbonyl.

"Carbocycle lower alkyl" represents lower alkyl substituted by one, two or more carbocyclic groups, and examples of "carbocycle lower alkyl" include benzyl, phenethyl, phenylpropynyl, benzhydryl, trityl, cyclopropylmethyl, cyclobutylmethyl, cyclopentylmethyl, cyclohexylmethyl, naphthylmethyl, a group shown below

[Chemical formula 13]

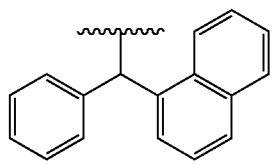

etc.

Examples of a preferable embodiment include benzyl, phenethyl, and benzhydryl.

"Heterocycle lower alkyl" represents lower alkyl substituted by one, two or more heterocyclic groups, and also includes heterocycle lower alkyl in which an alkyl part is substituted by carbocyclic group. Examples of "heterocycle lower alkyl" include pyridylmethyl, tetrahydropyranylmethyl, furanylmethyl, morpholinylethyl, imidazolylmethyl, indolylmethyl, benzothiophenylmethyl, oxazolylmethyl, isooxazolylmethyl, thiazolylmethyl, isothiazolylmethyl, pyrazolylmethyl, isopyrazolylmethyl, pyrrolidinylmethyl, benzoxazolylmethyl, piperidinylmethyl, piperazinylmethyl, groups shown below

[Chemical formula 14]

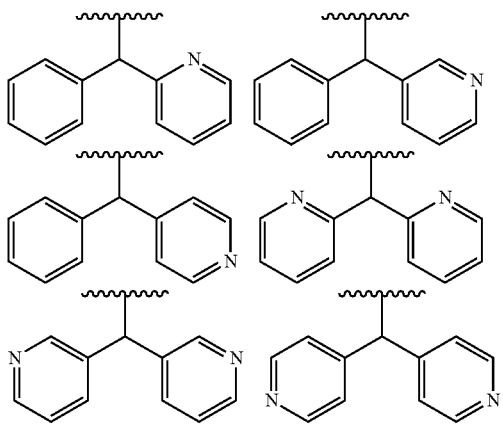

etc.

Examples of a preferable embodiment include pyridylmethyl, tetrahydropyranylmethyl, furanylmethyl, and morpholinylethyl.

Examples of "carbocycleoxy lower alkyl" include phenyloxymethyl, phenyloxyethyl, cyclopropyloxymethyl, cyclopropyloxyethyl, cyclobutyloxymethyl, cyclobutyloxyethyl, cyclohexyloxymethyl, cyclohexyloxyethyl, etc. Examples of a preferable embodiment include phenyloxymethyl, and phenyloxyethyl.

Examples of "heterocycleoxy lower alkyl" include pyridyloxymethyl, pyridyloxyethyl, morpholinyloxymethyl, morpholinyloxyethyl, benzoxazolyloxymethyl, etc. Examples of a preferable embodiment include pyridyloxymethyl, morpholinyloxymethyl, etc.

"Carbocycle lower alkyloxy" represents lower alkyloxy in which an alkyl part is substituted by one, two or more carbocyclic groups, and examples of "carbocycle lower alkyloxy" include phenylmethyloxy, phenylethyloxy, cyclopropylmethyloxy, cyclobutylmethyloxy, cyclopentylmethyloxy, cyclohexylmethyloxy, etc. Examples of a preferable embodiment include phenylmethyloxy, cyclopropylmethyloxy, etc.

"Heterocycle lower alkyloxy" represents lower alkyloxy in which an alkyl part is substituted by one, two or more heterocyclic groups, and also includes heterocycle lower alkyloxy in which an alkyl part is substituted by carbocyclic group. Examples of "heterocycle lower alkyloxy" include pyridylmethyloxy, pyridylethyloxy, imidazolylmethyloxy, imidazolylethyloxy, benzoxazolylmethyloxy, benzoxazolylethyloxy, etc.

Examples of "lower alkyloxy lower alkyl" include methoxymethyl, methoxyethyl, ethoxymethyl, ethoxyethyl, methoxypropyl, methoxybutyl, ethoxypropyl, ethoxybutyl, isopropyloxymethyl, tert-butyloxymethyl, etc. Examples of a preferable embodiment include methoxymethyl, methoxyethyl, ethoxymethyl, and ethoxyethyl.

Examples of "lower alkyloxy lower alkyloxy" include methoxymethoxy, methoxyethoxy, ethoxymethoxy, ethoxyethoxy, methoxypropyloxy, methoxybutyloxy, ethoxypropyloxy, ethoxybutyloxy, isopropyloxymethyloxy, tert-butyloxymethyloxy, etc. Examples of a preferable embodiment include methoxymethoxy, methoxyethoxy, ethoxymethoxy, and ethoxyethoxy.

Examples of "lower alkylamino" include methylamino, dimethylamino, ethylamino, diethylamino, isopropylamino, N,N-diisopropylamino, N-methyl-N-ethylamino, N-isopropyl-N-ethylamino, etc. Examples of a preferable embodiment include methylamino, dimethylamino, ethylamino, and diethylamino.

Examples of "lower alkylcarbonylamino" include methylcarbonylamino, ethylcarbonylamino, propylcarbonylamino, isopropylcarbonylamino, tert-butylcarbonylamino, isobutylcarbonylamino, sec-butylcarbonylamino, etc. Examples of a preferable embodiment include methylcarbonylamino, and ethylcarbonylamino.

Examples of "lower alkylaminocarbonyl" include methylaminocarbonyl, dimethylaminocarbonyl, ethylaminocarbonyl, diethylaminocarbonyl, isopropylaminocarbonyl, N,N-diisopropylaminocarbonyl, N-methyl-N-ethylaminocarbonyl, N-isopropyl-N-ethylaminocarbonyl, etc. Examples of a preferable embodiment include methylaminocarbonyl, dimethylaminocarbonyl, ethylaminocarbonyl, and diethylaminocarbonyl.

Examples of "lower alkylsulfonyl" include methylsulfonyl, ethylsulfonyl, propylsulfonyl, isopropylsulfonyl, tert-butylsulfonyl, isobutylsulfonyl, sec-butylsulfonyl, etc. Examples of a preferable embodiment include methylsulfonyl, and ethylsulfonyl.

Examples of "lower alkylsulfonylamino" include methylsulfonylamino, ethylsulfonylamino, propylsulfonylamino, isopropylsulfonylamino, tert-butylsulfonylamino, isobutylsulfonylamino, sec-butylsulfonylamino, etc. Examples of a preferable embodiment include methylsulfonylamino, and ethylsulfonylamino.

Examples of "lower alkenyloxy" include ethylenyloxy, 1-propylenyloxy, 2-propylenyloxy, 1-butylenyloxy, 2-butylenyloxy, 3-butylenyloxy, etc.

Examples of "halogeno lower alkyl" include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl, etc. Examples of a preferable embodiment include trifluoromethyl, trichloromethyl, 1,1,1-trifluoropropan-2-yl.

Examples of "halogeno lower alkyloxy" include monofluoromethoxy, monofluoroethoxy, trifluoromethoxy, trichloromethoxy, trifluoroethoxy, trichloroethoxy, etc. Examples of a preferable embodiment include trifluoromethoxy, and trichloromethoxy.

Examples of "lower alkylthio" include methylthio, ethylthio, propylthio, etc.

Examples of "hydroxy lower alkyl" include hydroxymethyl, hydroxyethyl, hydroxypropyl, etc.

Examples of "carbocycle lower alkyloxy lower alkyl" include benzyloxymethyl, benzyloxyethyl, benzhydryloxymethyl, etc.

Examples of "heterocycle lower alkyloxy lower alkyl" include pyridylmethyloxymethyl, pyridylmethyloxyethyl, etc.

Examples of "lower alkylcarbonyloxy" include methylcarbonyloxy, ethylcarbonyloxy, etc.

Examples of "halogeno lower alkylcarbonylamino" include trifluoromethylcarbonylamino, 2,2,3,3,3-pentafluoropropylcarbonylamino, etc.

Examples of "lower alkylsulfinyl" include methylsulfinyl, ethylsulfinyl, etc.

Examples of "carbocyclecarbonyl" include phenylcarbonyl, naphthylcarbonyl, cyclopropylcarbonyl, cyclobutylcarbonyl, cyclopentylcarbonyl, cyclohexylcarbonyl, etc.

Examples of "carbocycleoxy" include phenyloxy, naphthyloxy, cyclopropyloxy, cyclobutyloxy, cyclopentyloxy, cyclohexyloxy, etc.

Examples of "carbocycleoxycarbonyl" include phenyloxycarbonyl, naphthyloxycarbonyl, cyclopropyloxycarbonyl, cyclobutyloxycarbonyl, cyclopentyloxycarbonyl, cyclohexyloxycarbonyl, etc.

Examples of "heterocyclecarbonyl" include pyridylcarbonyl, benzoxazolylcarbonyl, morpholinylcarbonyl, tetrahydropyranylcarbonyl, etc.

Examples of "heterocycleoxy" include pyridyloxy, benzoxazolyloxy, morpholinyloxy, tetrahydropyranyloxy, etc.

Examples of "heterocycleoxycarbonyl" include pyridyloxycarbonyl, benzoxazolyloxycarbonyl, morpholinyloxycarbonyl, tetrahydropyranyloxycarbonyl, etc.

The terms:
"$R^{A1}$ and $R^{A2}$, $R^{A15}$ and $R^{A16}$, as well as $R^{A19}$ and $R^{A20}$, each may be taken together with an adjacent atom to form a heterocycle", "$R^{B7}$ and $R^{B8}$, as well as $R^{B9}$ and $R^{B10}$, each may be taken together with an adjacent atom to form a heterocycle", "$R^{C7}$ and $R^{C8}$, as well as $R^{C9}$ and $R^{C10}$, each may be taken together with an adjacent atom to form a heterocycle", and "$R^{D5}$ and $R^{D6}$ may be taken together with an adjacent atom to form a heterocycle" in item 1 mean a heterocycle having N atom, and include, for example, groups shown below

[Chemical formula 15]

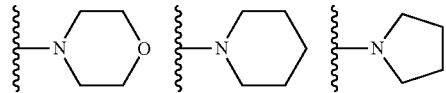

etc.

In the present description, $(R^{E6})m$ in the formulae shown below

[Chemical formula 16]

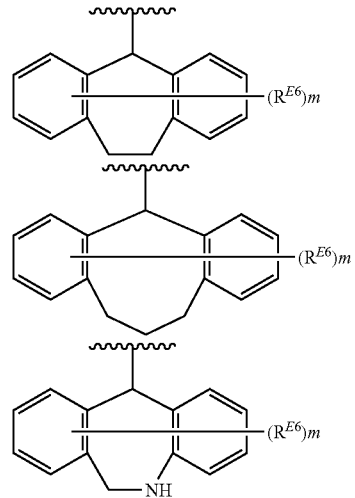

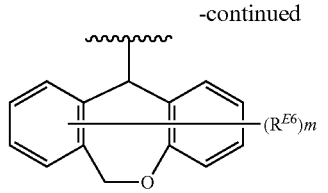

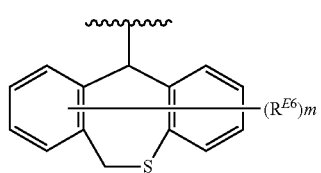

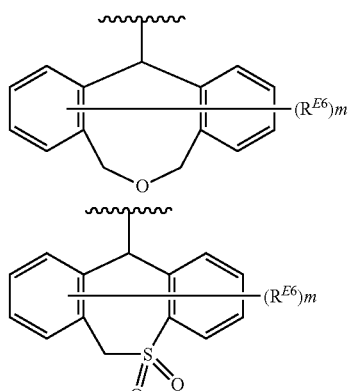

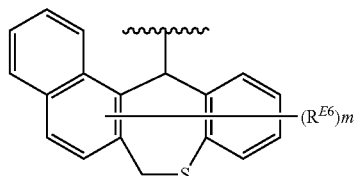

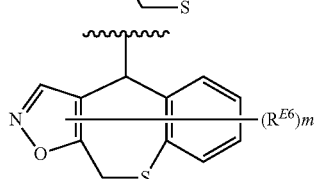

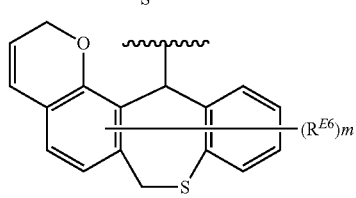

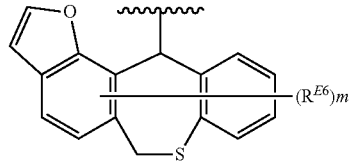

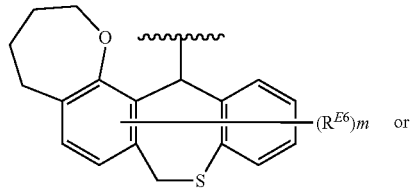 or

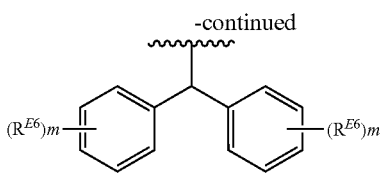

means that an arbitrary carbon atom or nitrogen atom which can chemically have a substituent on a ring is substituted by m of $R^{E6}$s which are same or different.

For example, in the formula below

[Chemical formula 17]

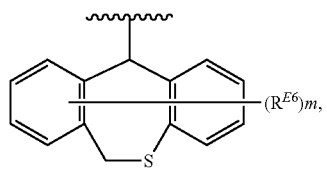

as shown by a substituent below

[Chemical formula 18]

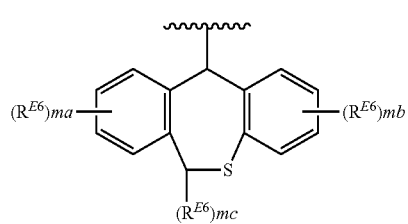

(wherein ma+mb+mc=m, and $R^{E6}$ is same as above), it is meant that any hydrogen atom on two benzene rings and a 7-membered ring containing a sulfur atom may be substituted by $R^{E6}$, and respective $R^{E6}$s may be the same or different.

And, ma is preferably an integer of 0 to 3, mb is preferably an integer of 0 to 3, and mc is preferably an integer of 0 or 1. And, ma is more preferably an integer of 0 or 1, mb is more preferably an integer of 0 or 1, and mc is more preferably 0.

For example, in the formula below

[Chemical formula 19]

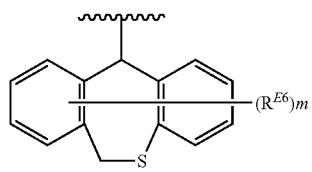

substituents shown below

[Chemical formula 20]

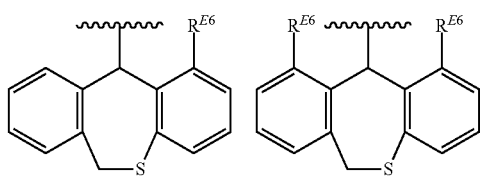

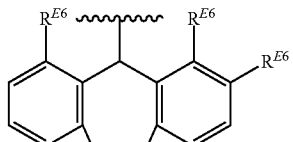


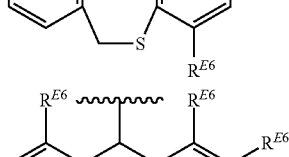

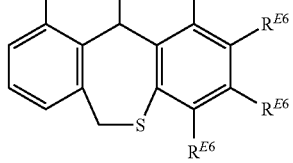


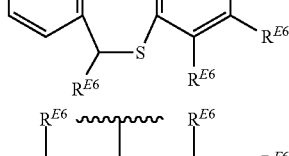

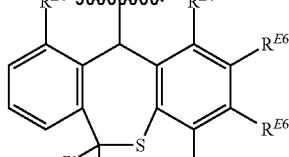

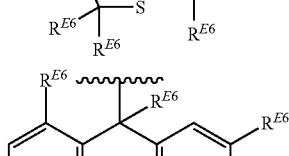

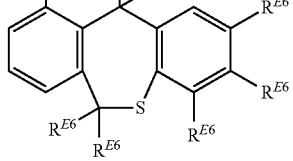

(wherein $R^{E6}$, and m are same as those of item 1)

etc. are included.

"$B^1$ is $CR^{5a}R^{6a}$, and $B^2$ is $NR^{7a}$, $R^{3a}$ and $R^{7a}$ may be taken together with an adjacent atom to form a heterocycle optionally substituted by substituent group D" in the formula (I) in item 1 represents the formula (I') shown below:

[Chemical formula 21]

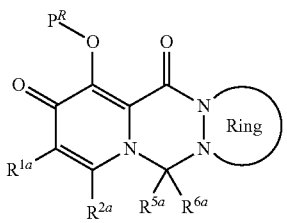

(I')

(wherein $P^R$, $R^{1a}$, $R^{2a}$, $R^{5a}$ and $R^{6a}$ are same as those of item 1), and indicates that a part of a ring may be substituted by one, two or more same or different substituents selected from substituent group D at an arbitrary position. The heterocycle is preferably a 5- to 7-membered ring. In addition, "the heterocycle may form a condensed ring" indicates that the ring in the formula (I') may be further condensed with a ring, and indicates that substituent group D may be bound to any of the ring in the formula (I') or the ring which is condensed with a ring.

Examples of the formula (I') include compounds shown by the following formulae

[Chemical formula 22]

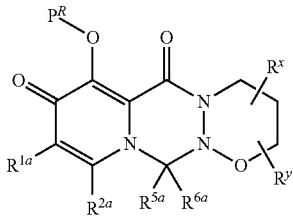

(wherein $R^x$, and $R^y$ are a substituent selected from substituent group D, and $P^R$, $R^{1a}$, $R^{2a}$, $R^{5a}$, and $R^{6a}$ are same as those of item 1) etc.

"When form a heterocycle" in "$B^1$ is $NR^{7a}$, and $B^2$ is $CR^{5a}R^{6a}$, $R^{3a}$ and $R^{6a}$ may be taken together with an adjacent atom to form a heterocycle optionally substituted by substituent group D" in the formula (I) in item 1 represents the formula (I") shown below:

[Chemical formula 23]

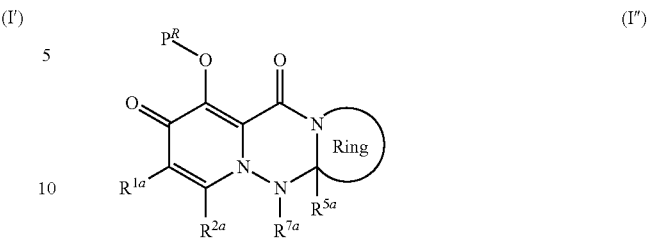

(I")

(wherein $P^R$, $R^{1a}$, $R^{2a}$, $R^{5a}$ and $R^{7a}$ are same as those of item 1), and indicates that "Ring" may be substituted by one, two or more same or different substituents selected from substituent group D at an arbitrary position. The heterocycle is preferably a 5- to 7-membered ring. In addition, "the heterocycle may form a condensed ring" indicates that the ring in the formula (I") may be further condensed with a ring, and indicates that one, two or more of substituent group D may be bound to any of the ring in the formula (I") or the ring which is condensed with a ring. Examples of the formula (I") include compounds shown by the following formulae

[Chemical formula 24]

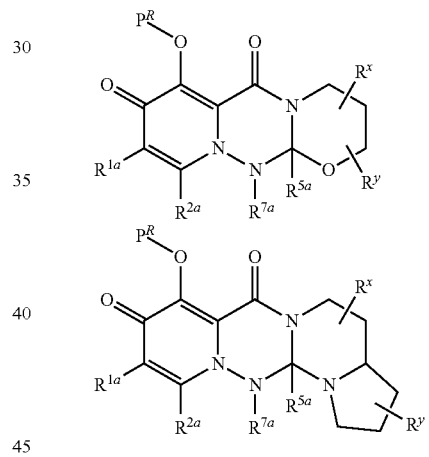

(wherein $R^x$, and $R^y$ are a substituent selected from substituent group D, and $P^R$, $R^{1a}$, $R^{2a}$, $R^{5a}$, and $R^{7a}$ are same as those of item 1) etc.

"When form a carbocycle or heterocyle" in "$R^{8a}$ and $R^{10a}$ may be taken together with an adjacent atom to form a carbocycle or heterocycle optionally substituted by substituent group D" in the formula (I) in item 1 represents the formula (I''') shown below:

[Chemical formula 25]

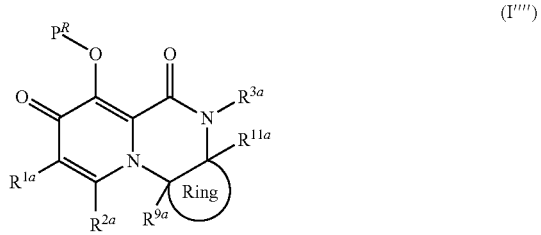

(I''')

(wherein $P^R$, $R^{1a}$, $R^{2a}$, $R^{3a}$, $R^{9a}$, and $R^{11a}$ are same as those of item 1), and indicates that "Ring" may be substituted by one, two or more same or different substituents selected from substituent group D at an arbitrary position. The carbocycle or the heterocycle is preferably a 5- to 7-membered ring. Examples of the formula (I'''') include compounds shown by the following formula

[Chemical formula 26]

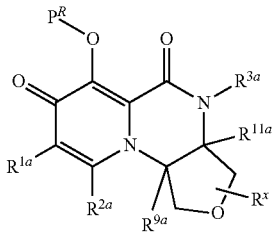

(wherein $R^x$ is a substituent selected from substituent group D, and $P^R$, $R^{1a}$, $R^{2a}$, $R^{3a}$, $R^{9a}$, and $R^{11a}$ are same as those of item 1) etc.

Further, "$R^{3a}$ and $R^{11a}$ may be taken together with an adjacent atom to form a heterocycle optionally substituted by substituent group D, and the heterocycle may form a condensed ring" represents the formula (I''''') shown below:

[Chemical formula 27]

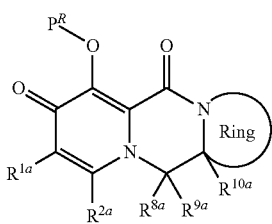

(I''''')

(wherein $P^R$, $R^{1a}$, $R^{2a}$, $R^{8a}$, $R^{9a}$, and $R^{10a}$ are same as those of item 1), and indicates that "Ring" may further form a condensed ring, and the same or different substituents selected from substituent group D may be bound to any of the ring in the formula (I''''') or the ring which is condensed with a ring at an arbitrary position. The heterocycle is preferably a 5- to 7-membered ring. Examples of the formula (I''''') include compounds shown by the following formulae

[Chemical formula 28]

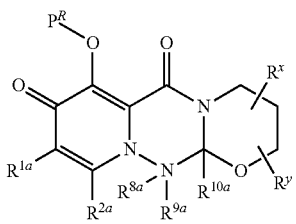

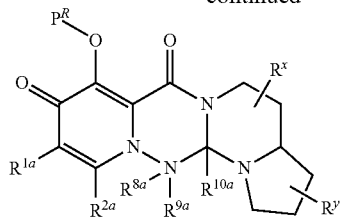

(wherein $R^x$, and $R^y$ are a substituent selected from substituent group D, and $P^R$, $R^{1a}$, $R^{2a}$, $R^{8a}$, $R^{9a}$, and $R^{10a}$ are same as those of item 1) etc.

"Solvate" includes, for example, a solvate with an organic solvent, a hydrate, etc. Preferred embodiment is a hydrate or alcoholate, and more preferred embodiment is a hydrate. When a hydrate is formed, the compound may be coordinated with an arbitrary number of water molecules. Examples include hemihydrate (1 water molecule is coordinated to 2 molecules of the present compound), monohydrate (1 water molecule is coordinated to 1 molecule of the present compound), dihydrate (2 water molecules are coordinated to 1 molecule of the present compound), trihydrate (3 water molecules are coordinated to 1 molecule of the present compound), etc. The same shall apply when an alcoholate is formed. Examples of alcohol when an alcoholate is formed include methanol, ethanol, isopropanol, etc.

The compound of the present invention includes a pharmaceutically acceptable salt. Examples include salts with an alkali metal (lithium, sodium or potassium, etc.), an alkaline earth metal (magnesium or calcium, etc.), ammonium, an organic base and an amino acid, or salts with an inorganic acid (hydrochloric acid, sulfuric acid, nitric acid, hydrobromic acid, phosphoric acid or hydroiodic acid, etc.), and an organic acid (acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzenesulfonic acid, p-toluenesulfonic acid, methanesulfonic acid or ethanesulfonic acid, etc.). These salts can be formed by the method which is usually performed.

Examples of preferred salt of the formula (I) in the present invention include hydrochloride, hydrobromate, acetate, sulfate, etc.

In addition, the compound of the present invention is not limited to a particular isomer, but includes all possible isomers (keto-enol isomer, imine-enamine isomer, diastereoisomer, optical isomer and rotation isomer, etc.) and racemic bodies.

The formula (I) in the present invention is not limited to a particular isomer, but includes all possible isomers and racemic bodies. For example, they also contain a tautomer and a steric isomer as shown below.

[Chemical formula 29]

(I)

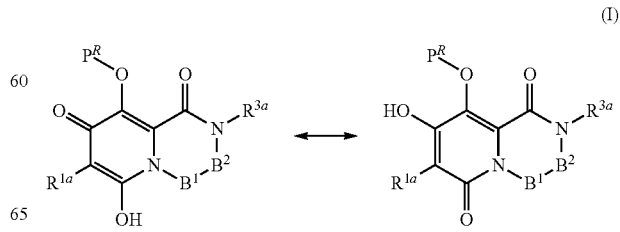

(wherein each symbol is same as above)

[Chemical formula 30]

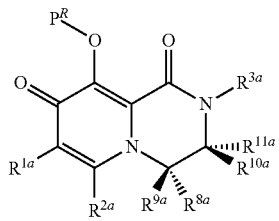
(Ia)-1

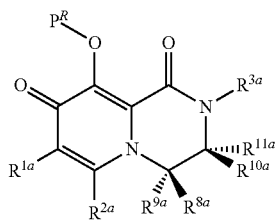
(Ia)-2

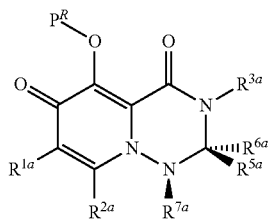
(Ib)-1

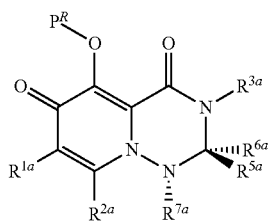
(Ib)-2

(wherein each symbol is same as above)

Further, one or more hydrogen atoms, carbon atoms or other atoms of the compound of the formula (I) can be substituted by an isotope of a hydrogen atom, a carbon atom or other atoms, respectively.

In addition, the compound of the formula (I) includes all radioactive labeled bodies thereof. Such the "radioactive labeling" and "radioactive labeled form" of the compound of the formula (I) are included in the present invention, respectively, and are useful as a study and/or diagnostic tool in metabolized drug dynamic state study and binding assay.

Examples of an isotope which can be incorporated into the compound of the formula (I) of the present invention include a hydrogen atom, a carbon atom, a nitrogen atom, an oxygen atom, a phosphorus atom, a sulfur atom, a fluorine atom and a chlorine atom, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$.

A particularly preferable example of an isotope which can be incorporated into the compound of the formula (I) of the present invention is $^2H$ (i.e. heavy hydrogen atom), and can be prepared by the method shown in Reference examples of the present description, or the method well-known in the art. In addition, a heavy hydrogen atom is expressed as "D" in Reference examples of the present description. Compound of the formula (I) of the present invention in which a hydrogen atom has been converted into a heavy hydrogen atom are excellent in respect of bioavailability, metabolism safety, drug efficacy, and toxicity as compared with unconverted forms, in some cases, and can be useful as medicaments.

Examples of "lower alkyl optionally substituted by substituent group C" include methyl, ethyl, propyl, isopropyl, butyl, tert-butyl, sec-butyl, pentan-2-yl, hydroxymethyl, hydroxyethyl, carboxymethyl, carboxyethyl, carboxypropyl, ethoxycarbonylpropyl, cyanomethyl, cyanoethyl, fluoromethyl, fluoroethyl, fluoropropyl, difluoromethyl, trifluoromethyl, chloromethyl, dichloromethyl, trichloromethyl, ethyloxycarbonylethyl, methoxymethyl, dimethoxymethyl, methoxyethyl, methoxypropyl, ethoxyethyl, 1-methyl-1-methoxymethyl, propyloxymethyl, aminopropyl, dimethylaminomethyl, aminomethyl, aminoethyl, dimethylaminoethyl, diethylaminomethyl, diethylaminoethyl, dimethylaminopropyl, cyclopropylmethyloxymethyl, methylsulfonylaminomethyl, methylaminocarbonylethyl, 1,1,1-trifluoropropan-2-yl, 1,1-difluoroethyl, 1,1,1-trifluoroethyl, 1,1,1-trifluoropropyl, trifluoromethyloxyethyl, trifluoromethylcarbonylaminomethyl, methylsulfonylethyl, methylcarbonyloxyethyl, and groups shown below

[Chemical formula 31]

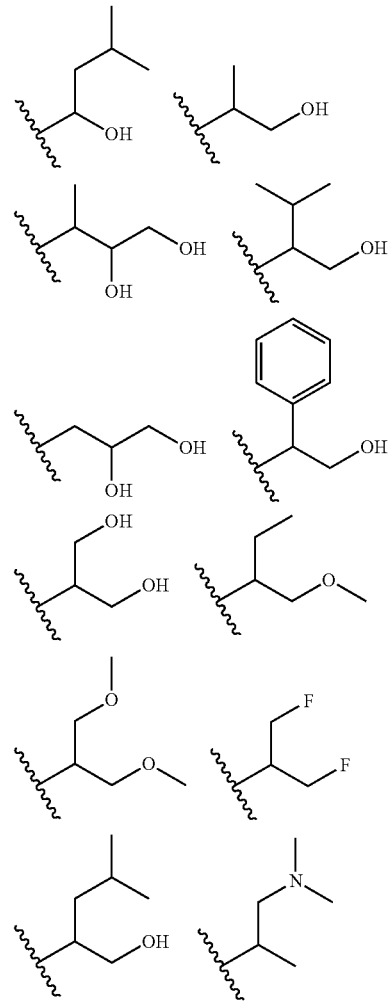

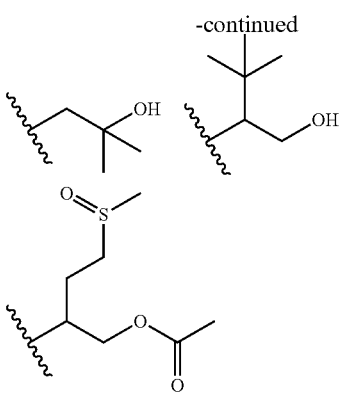

etc.

Examples of "lower alkyl optionally substituted by substituent group F" include hydroxyethyl, methyl, ethyl, propyl, isopropyl, butyl, tert-butyl, iso-butyl, sec-butyl, pentan-2-yl, hydroxymethyl, hydroxyethyl, carboxymethyl, carboxyethyl, carboxypropyl, ethoxycarbonylpropyl, and groups shown below

[Chemical formula 32]

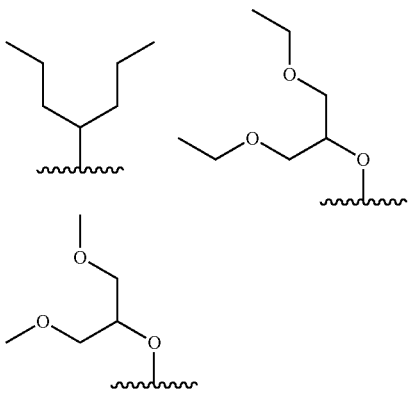

etc.

Examples of "lower alkenyl optionally substituted by substituent group C" include ethylenyl, 3-methylbuten-2-yl, carboxyethylenyl, hydroxyethylenyl, difluoroethylenyl, 1-propen-2-yl, etc.

Examples of "lower alkynyl optionally substituted by substituent group C" include 1-propynyl, 1-butynyl, 3,3,3-trifluoromethylpropynyl, 3-hydroxy-propynyl, etc.

Examples of "lower alkyloxy optionally substituted by substituent group C" include methyloxy, ethyloxy, trifluoromethyloxy, trichloromethyloxy, hydroxymethyloxy, hydroxyethyloxy, carboxymethyloxy, carboxyethyloxy, etc.

Examples of "lower alkenyloxy optionally substituted by substituent group C" include 3-fluoro-1-propenyloxy, ethylenyl, carboxyethylenyl, hydroxyethylenyloxy, difluoroethylenyloxy, etc.

Examples of "lower alkylcarbonyl optionally substituted by substituent group C" include methylcarbonyl, ethylcarbonyl, propylcarbonyl, isopropylcarbonyl, hydroxymethylcarbonyl, hydroxyethylcarbonyl, trifluoromethylcarbonyl, 2,2,2-trifluoromethylcarbonyl, carboxymethylcarbonyl, etc.

Examples of "lower alkyloxycarbonyl optionally substituted by substituent group C" include methyloxycarbonyl, ethyloxycarbonyl, trifluoromethyl oxycarbonyl, trichloromethyloxycarbonyl, hydroxymethyloxycarbonyl, hydroxyethyloxycarbonyl, carboxymethyloxycarbonyl, etc.

Examples of "carbocyclic group optionally substituted by substituent group C" include phenyl, naphthyl, anthracenyl, phenanthracenyl, adamantyl, 1-hydroxyadamantyl, 2-hydroxyadamantyl, 3-methylphenyl, 4-methylphenyl, 3-methoxyphenyl, 4-methoxyphenyl, 3-hydroxyphenyl, 4-hydroxyphenyl, 4-chlorophenyl, 4-fluorophenyl, 2-cyanophenyl, 3-cyanophenyl, 4-cyanophenyl, fluorocyclopropyl, difluorocyclobutanyl, difluorocyclohexyl, and groups shown below

[Chemical formula 33]

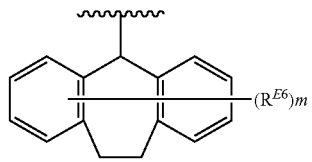

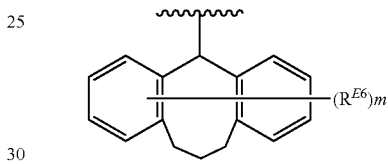

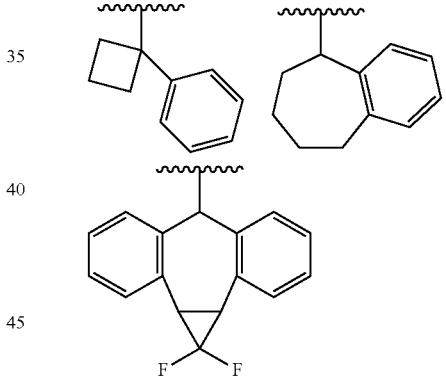

(wherein $R^{E6}$ represents a group selected from substituent group C, and m of $R^{E6}$s may be the same or different) etc.

Examples of "carbocyclic group optionally substituted by substituent group F" include phenyl, naphthyl, 3-methylphenyl, 4-methylphenyl, 3-methoxyphenyl, 4-methoxyphenyl, 3-hydroxyphenyl, 4-hydroxyphenyl, 4-chlorophenyl, 4-fluorophenyl, 1,5-difluorophenyl, etc.

Examples of "carbocycle lower alkyl optionally substituted by substituent group C" include cyclopropylmethyl, 4-hydroxybenzyl, cyclopentylmethyl, benzyl, 2-aminobenzyl, 2-cyanobenzyl, 2-fluorobenzyl, 4-fluorobenzyl, 2-trifluoromethylbenzyl, 1,3,5-trifluorobenzyl, 3,4,5-trifluorobenzyl, 4-methoxybenzyl, 2,4-difluorobenzyl, 2-fluoro-3-chlorobenzyl, benzhydryl, 4-phenylbenzyl, phenethyl, phenylpropyl, 4-methylcarbonylaminobenzyl, 3,4-dichlorobenzyl, 4-chloro-2-fluorobenzyl, 3,5-dihydroxybenzyl, and groups shown below

[Chemical formula 34]
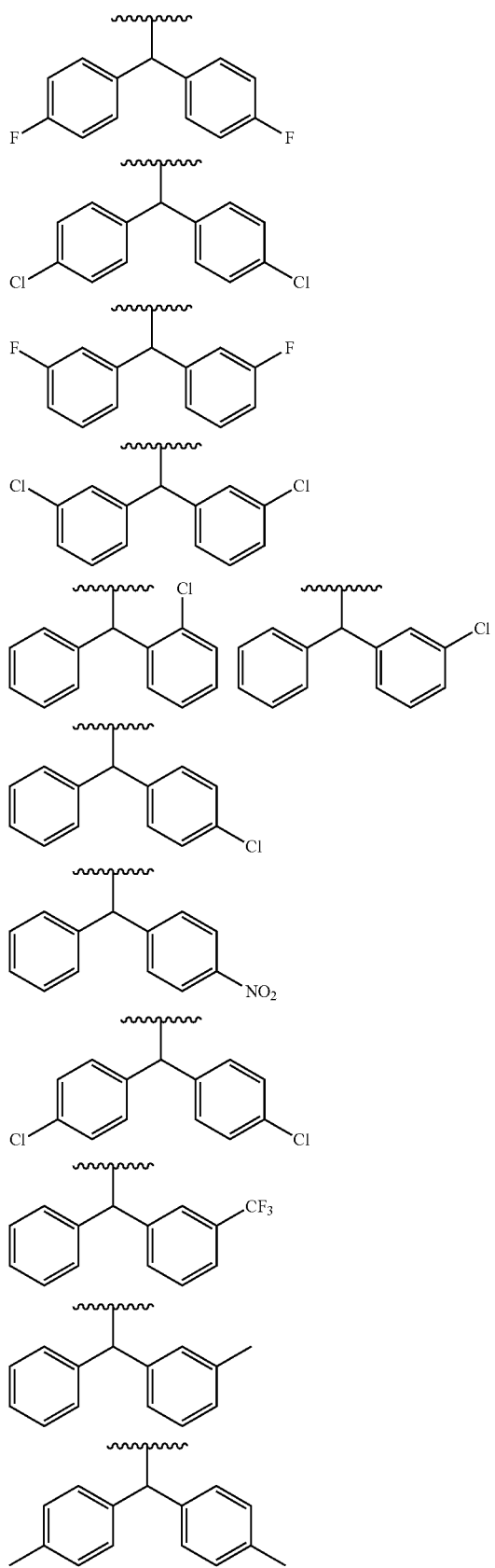
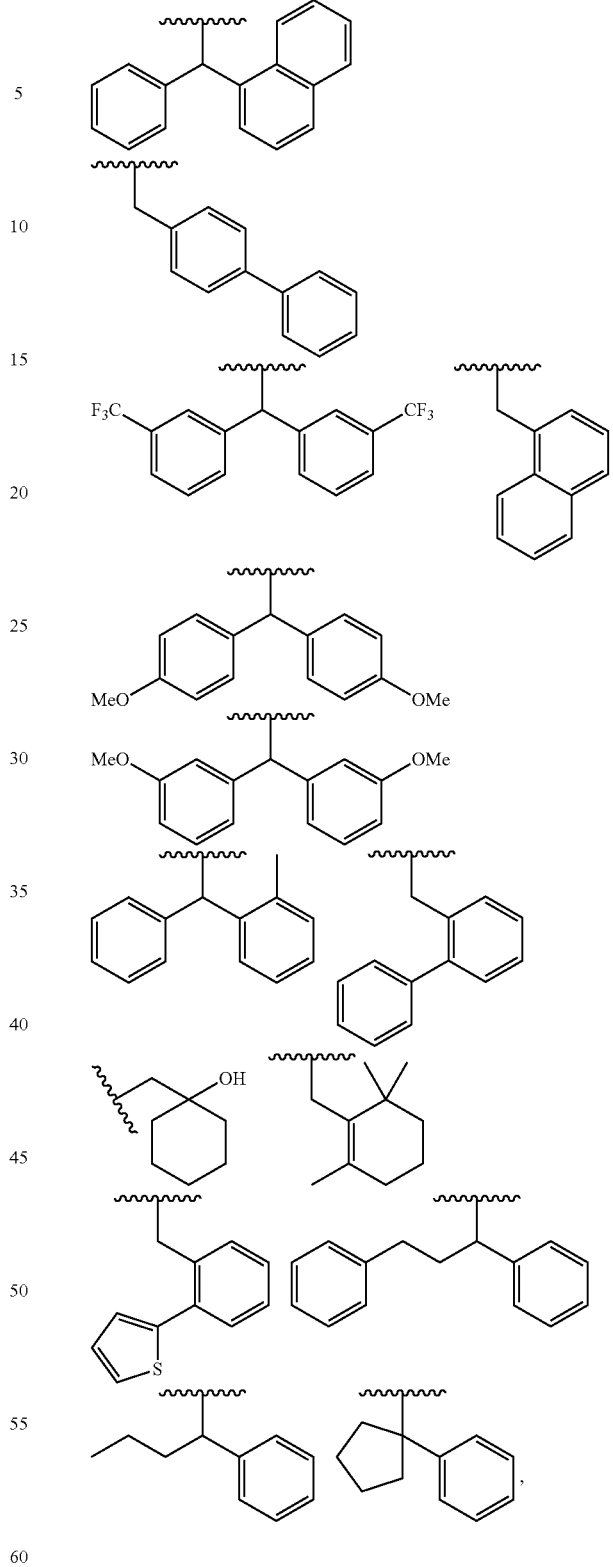
etc.
Examples of "carbocycle lower alkyl optionally substituted by substituent group F" include cyclopropylmethyl, 4-hydroxybenzyl, cyclopentylmethyl, benzyl, 2-aminobenzyl, 2-cyanobenzyl, 2-fluorobenzyl, 4-fluorobenzyl, 2-trifluoromethylbenzyl, 1,3,5-trifluorobenzyl, 3,4,5-trifluorobenzyl, 4-methoxybenzyl, 2,4-difluorobenzyl, 2-fluoro-3- chlorobenzyl, benzhydryl, 4-phenylbenzyl, phenethyl, phenylpropyl, 4-methylcarbonylaminobenzyl, 3,4-dichlorobenzyl, 4-chloro-2-fluorobenzyl, 3,5-dihydroxybenzyl, etc.

Examples of "carbocycleoxy lower alkyl optionally substituted by substituent group C" include 4-hydroxyphenyloxymethyl, 4-hydroxyphenyloxyethyl, cyclopropyloxymethyl, cyclopentyloxymethyl, 4-fluorophenyloxymethyl, 4-fluorophenyloxyethyl, 4-trifluoromethylphenyloxymethyl, 4-trifluoromethylphenyloxyethyl, 4-methoxyphenyloxymethyl, 4-methoxyphenyloxyethyl, etc.

Examples of "carbocyclecarbonyl optionally substituted by substituent group C" include phenylcarbonyl, 4-fluorophenylcarbonyl, 4-trifluoromethylphenylcarbonyl, 4-methoxyphenylcarbonyl, cyclopropylcarbonyl, etc.

Examples of "carbocycleoxy optionally substituted by substituent group C" include phenyloxy, cyclopropyloxy, cyclopentyloxy, 4-fluorophenyloxy, 4-trifluoromethylphenyloxy, 4-methoxyphenyloxy, etc.

Examples of "carbocycleoxycarbonyl optionally substituted by substituent group C" include phenyloxycarbonyl, cyclopropyloxycarbonyl, cyclopentyloxycarbonyl, 4-fluorophenyloxycarbonyl, 4-trifluoromethylphenyloxycarbonyl, 4-methoxyphenyloxycarbonyl, etc.

Examples of "heterocyclic group optionally substituted by substituent group C" include pyrimidinyl, pyridyl, benzoxazolyl, morpholinyl, tetrahydropyranyl, furyl, thiophenyl, oxazolyl, thiazolyl, pyrazolyl, methylpyrrolidinyl, isopropylpyrrolidinyl, methylsulfonylpyrrolidinyl, hydroxyethylpyrrolidinyl, methylpiperidinyl, methylpiperazinyl, tetrahydrofuryl, and groups shown below

[Chemical formula 35]

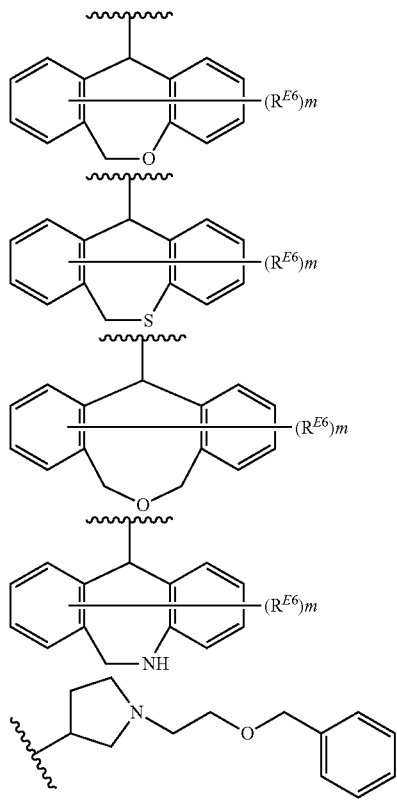

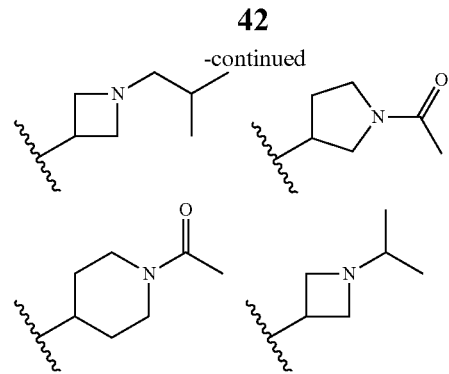

(wherein $R^{E6}$ represents a group selected from substituent group C, and m of $R^{E6}$s may be the same or different) etc.

Examples of "heterocyclic group optionally substituted by substituent group F" include morpholinyl, pyridyl, methyl-1,3-dioxol-2-one, trimethyl-2-oxabicyclo[2.2.1]heptan-3-one, pyrrolidinyl, methyl-pyrrolidine-2-carboxylate, tetrahydropyranyl, hydroxymethylpyrrolidinyl, etc.

Examples of "heterocycle lower alkyl optionally substituted by substituent group C" include tetrahydropyranylmethyl, pyridylmethyl, isoxazolylmethyl, 5-methyl-isoxazolylmethyl, 3-methyl-oxadiazolylmethyl, indolylmethyl, benzothiophenylmethyl, 5-chlorobenzothiophenylmethyl, thiazolylmethyl, 2-methylthiazolylmethyl, pyrazolylmethyl, 2-methylpyrazolylmethyl, dithiophenylmethyl, tetrazolylmethyl, quinazolylmethyl, morpholinylmethyl, and groups shown below

[Chemical formula 36]

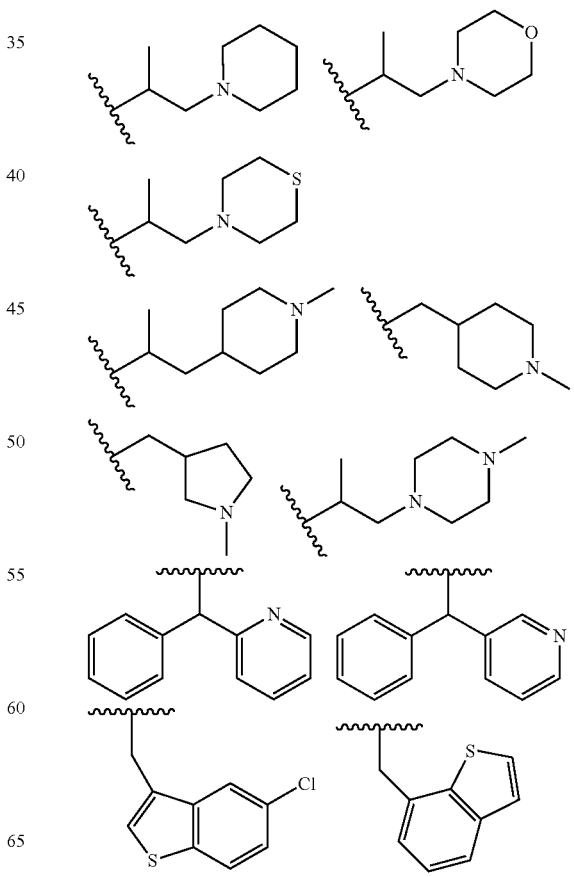

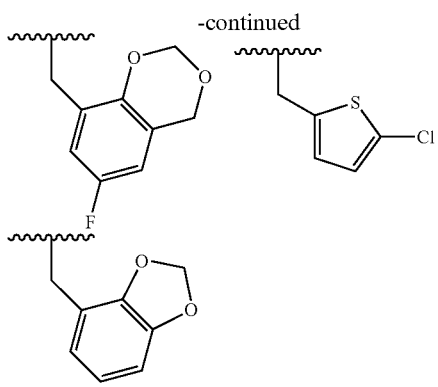

etc.

Examples of "heterocycle lower alkyl optionally substituted by substituent group F" include tetrahydropyranylmethyl, pyridylmethyl, isoxazolylmethyl, 5-methyl-isoxazolylmethyl, 3-methyl-oxadiazolylmethyl, indolylmethyl, benzothiophenylmethyl, 5-chlorobenzothiophenylmethyl, thiazolylmethyl, 2-methylthiazolylmethyl, pyrazolylmethyl, 2-methylpyrazolylmethyl, dithiophenylmethyl, tetrazolylmethyl, quinazolinylmethyl, morpholinylmethyl, etc.

Examples of "heterocycleoxy lower alkyl optionally substituted by a substituent group C" include tetrahydropyranyloxymethyl, pyridyloxymethyl, isoxazolyloxymethyl, 5-methyl-isoxazolyloxymethyl, indolyloxymethyl, benzothiophenyloxymethyl, 5-chlorobenzothiophenyloxymethyl, thiazolyloxymethyl, 2-methylthiazolyloxymethyl, pyrazolyloxymethyl, 2-methylpyrazolyloxymethyl, etc.

Examples of "heterocyclecarbonyl optionally substituted by substituent group C" include tetrahydropyranylcarbonyl, pyridylcarbonyl, isoxazolylcarbonyl, 5-methyl-isoxazolylcarbonyl, indolylcarbonyl, benzothiophenylcarbonyl, 5-chlorobenzothiophenylcarbonyl, thiazolylcarbonyl, 2-methylthiazolylcarbonyl, pyrazolylcarbonyl, 2-methylpyrazolylcarbonyl, etc.

Examples of "heterocycleoxy optionally substituted by substituent C" include tetrahydropyranyloxy, pyridyloxy, isoxazolyloxy, 5-methyl-isoxazolyloxy, indolyloxy, benzothiophenyloxy, 5-chlorobenzothiophenyloxy, thiazolyloxy, 2-methylthiazolyloxy, pyrazolyloxy, 2-methylpyrazolyloxy, etc.

Examples of "heterocycleoxycarbonyl optionally substituted by substituent group C" include tetrahydropyranyloxycarbonyl, pyridyloxycarbonyl, isoxazolyloxycarbonyl, 5-methyl-isoxazolyloxycarbonyl, indolyloxycarbonyl, benzothiophenyloxycarbonyl, 5-chlorobenzothiophenyloxycarbonyl, thiazolyloxycarbonyl, 2-methylthiazolyloxycarbonyl, pyrazolyloxycarbonyl, 2-methylpyrazolyloxycarbonyl, etc.

Examples of "lower alkylamino optionally substituted by substituent group F" include methylamino, dimethylamino, ethylamino, diethylamino, etc.

Examples of "lower alkylthio optionally substituted by substituent group F" include methylthio, ethylthio, etc.

Examples of "lower alkylsilyl optionally substituted by substituent group F" include trimethylsilyl, triethylsilyl, tert-butyldimethylsilyl, etc.

$P^R$ in —$OP^R$ group is preferably a group converted into —OH group by action of drug-metabolizing enzymes, hydrolases, gastric acids, and/or enterobacteria, after in vivo administration (for example, oral administration).

Examples of more preferred embodiment of $P^R$ include a group selected from the following formulae b) to x).

b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N($P^{R2}$)$_2$,
i) —C(=O)—O-L-O—$P^{R2}$,
j) —CH$_2$—O—$P^{R3}$,
k) —CH$_2$—O-L-O—$P^{R3}$,
l) —CH$_2$—O—C(=O)—$P^{R3}$,
m) —CH$_2$—O—C(=O)—O—$P^{R3}$,
n) —CH(—CH$_3$)—O—C(=O)—O—$P^{R3}$,
o) —CH$_2$—O—C(=O)—N(—K)—$P^{R3}$,
p) —CH$_2$—O—C(=O)—O-L-O—$P^{R3}$,
q) —CH$_2$—O—C(=O)—O-L-N($P^{R3}$)$_2$,
r) —CH$_2$—O—C(=O)—N(—K)-L-O—$P^{R3}$,
s) —CH$_2$—O—C(=O)—N(—K)-L-N($P^{R3}$)$_2$,
t) —CH$_2$—O—C(=O)—O-L-O-L-O—$P^{R3}$,
u) —CH$_2$—O—C(=O)—O-L-N(—K)—C(=O)—$P^{R3}$,
v) —CH$_2$—O—P(=O)(—OH)$_2$,
w) —CH$_2$—O—P(=O)(—OBn)$_2$,
x) —CH$_2$—$P^{R4}$ (wherein L is straight or branched lower alkylene, K is hydrogen, or straight or branched lower alkylene, or straight or branched lower alkenylene, $P^{R1}$ is carbocyclic group optionally substituted by substituent group F, heterocyclic group optionally substituted by substituent group F, lower alkyl amino optionally substituted by substituent group F, or lower alkylthio optionally substituted by substituent group F, $P^{R2}$ is lower alkyl optionally substituted by substituent group F, carbocyclic group optionally substituted by substituent group F, or heterocyclic group optionally substituted by substituent group F, $P^{R3}$ is lower alkyl optionally substituted by substituent group F, carbocyclic group optionally substituted by substituent group F, heterocyclic group optionally substituted by substituent group F, lower alkyl amino optionally substituted by substituent group F, carbocycle lower alkyl optionally substituted by substituent group F, heterocycle lower alkyl optionally substituted by substituent group F, or lower alkylsilyl, $P^{R4}$ is carbocyclic group optionally substituted by substituent group F, or heterocyclic group optionally substituted by substituent group F, and substituent group F; oxo, lower alkyl, hydroxy lower alkyl, amino, lower alkylamino, carbocycle lower alkyl, lower alkylcarbonyl, halogen, hydroxy, carboxy, lower alkylcarbonylamino, lower alkylcarbonyloxy, lower alkyloxycarbonyl, lower alkyloxy, cyano, and nitro)

Examples of further preferred embodiment of $P^R$ include following b), k), l), and m).

b) —C(=O)—$P^{R1}$,
l) —CH$_2$—O—C(=O)—$P^{R3}$,
n) —CH$_2$—O—C(=O)—O—$P^{R3}$,
n) —CH(—CH$_3$)—O—C(=O)—O—$P^{R3}$,
(wherein each symbol is same as above)

Examples of another embodiment of a preferable substituent of $P^R$ include groups of P-1 to P-83 in the following Tables 1 to 9.

TABLE 1
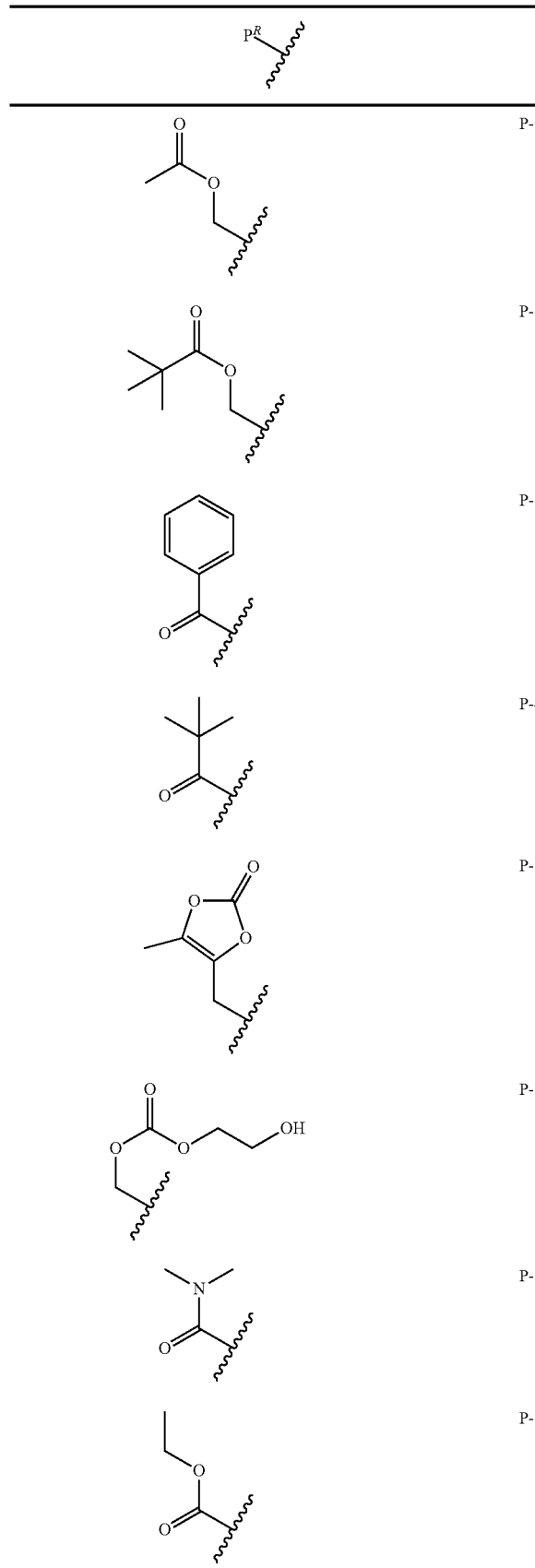
TABLE 1-continued
TABLE 2
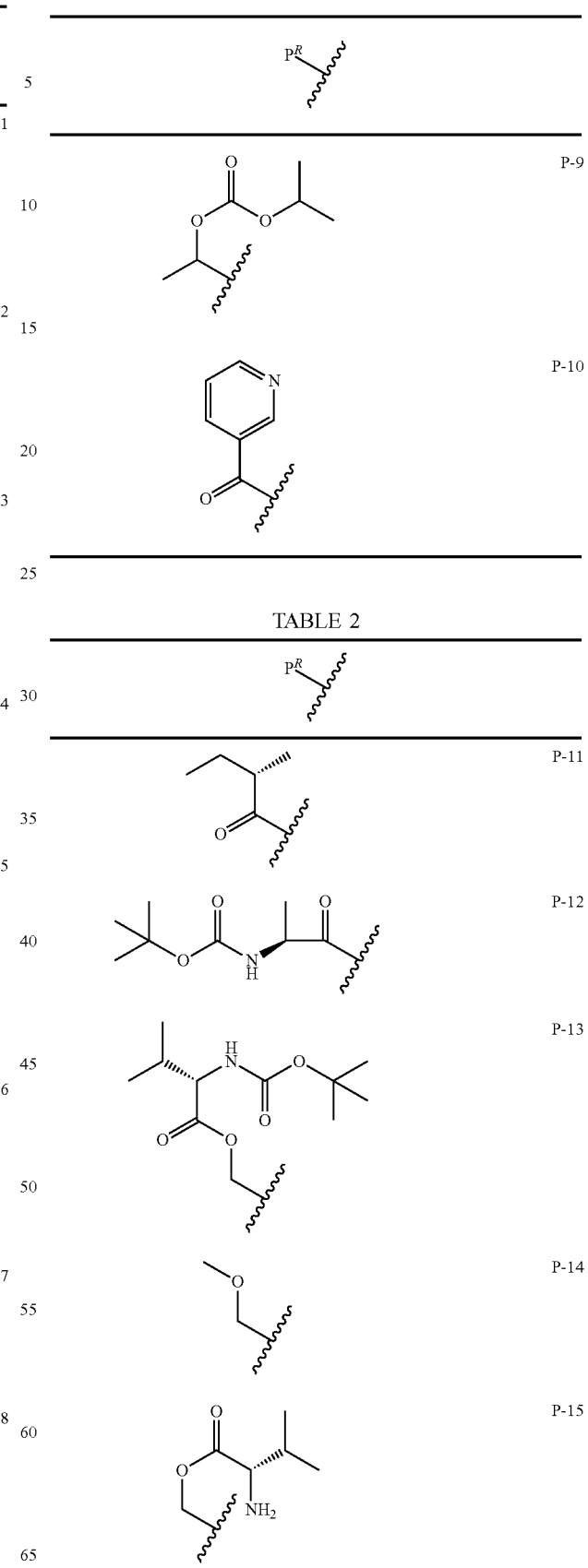

TABLE 2-continued
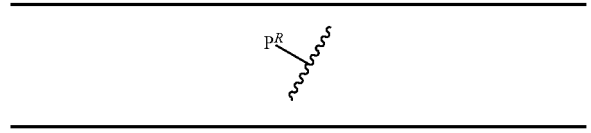
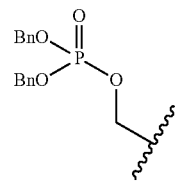 [SMILES: *COP(=O)(OCc1ccccc1)OCc1ccccc1] P-16
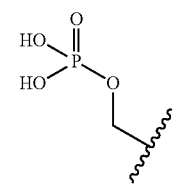 [SMILES: *COP(=O)(O)O] P-17
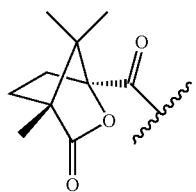 [SMILES: *C(=O)[C@@]12CC[C@@](C)(C(=O)O1)C2(C)C] P-18
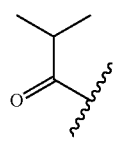 P-19
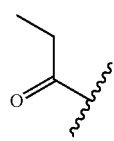 [SMILES: *C(=O)CC] P-20
TABLE 3
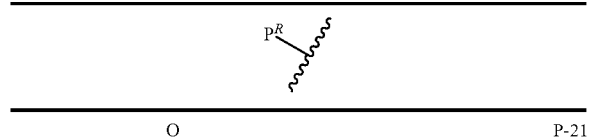
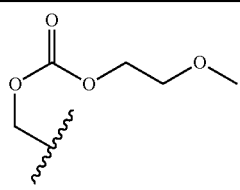 P-21
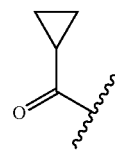 [SMILES: *C(=O)C1CC1] P-22
TABLE 3-continued
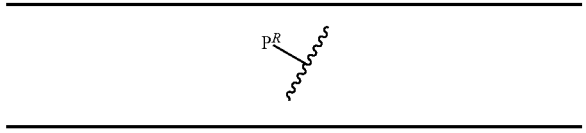
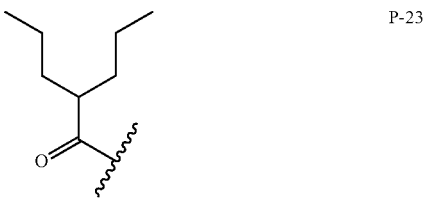 P-23
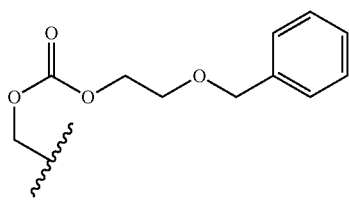 [SMILES: *COC(=O)OCCOCc1ccccc1] P-24
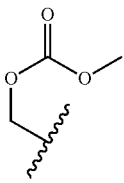 [SMILES: *COC(=O)OC] P-25
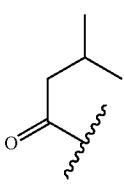 [SMILES: *C(=O)CC(C)C] P-26
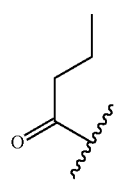 [SMILES: *C(=O)CCC] P-27
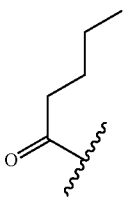 [SMILES: *C(=O)CCCC] P-28
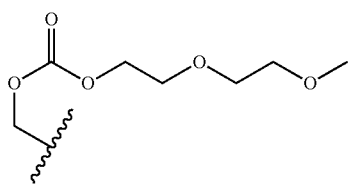 [SMILES: *COC(=O)OCCOCCOC] P-29

TABLE 3-continued
| $P^R$ | |
|---|---|
| 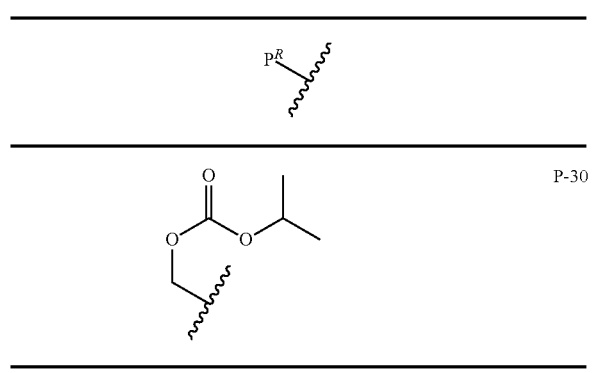 | P-30 |
TABLE 4
| $P^R$ | |
|---|---|
| 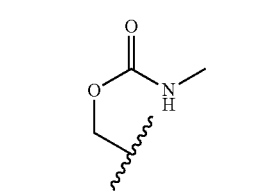 | P-31 |
| 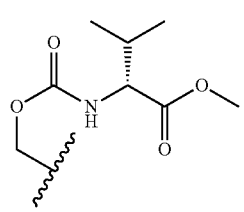 [SMILES: *COC(=O)N[C@@H](C(=O)OC)C(C)C] | P-32 |
| 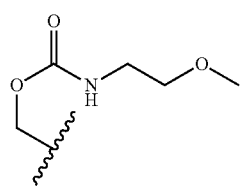 [SMILES: *COC(=O)NCCOC] | P-33 |
| | P-34 |
| | P-35 |
TABLE 4-continued
| $P^R$ | |
|---|---|
| 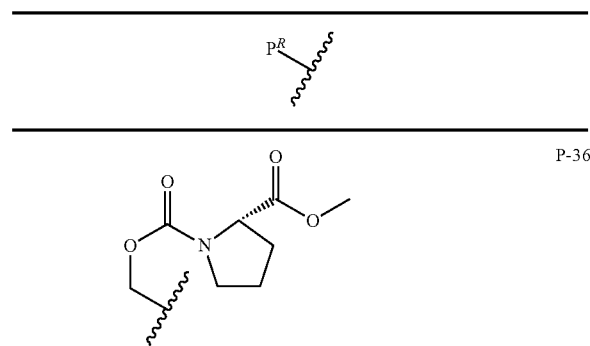 | P-36 |
| 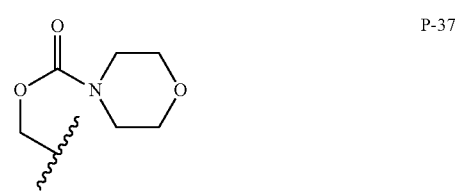 | P-37 |
| 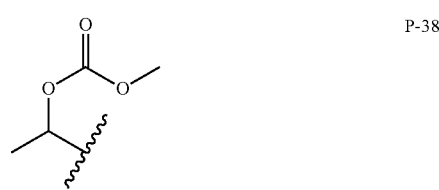 | P-38 |
| 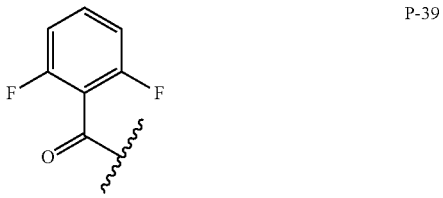 | P-39 |
| 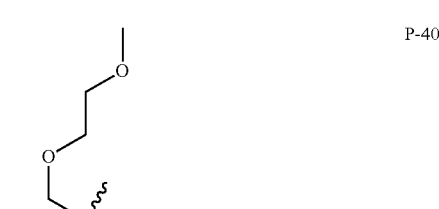 | P-40 |
TABLE 5
| $P^R$ | |
|---|---|
| 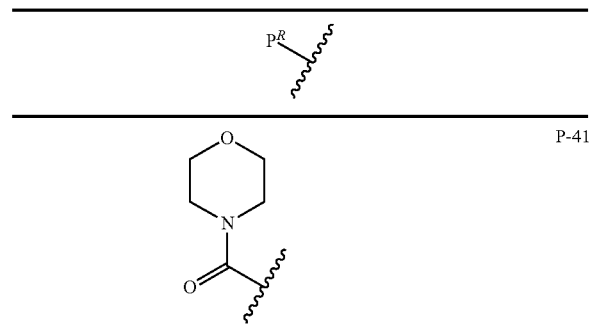 | P-41 |
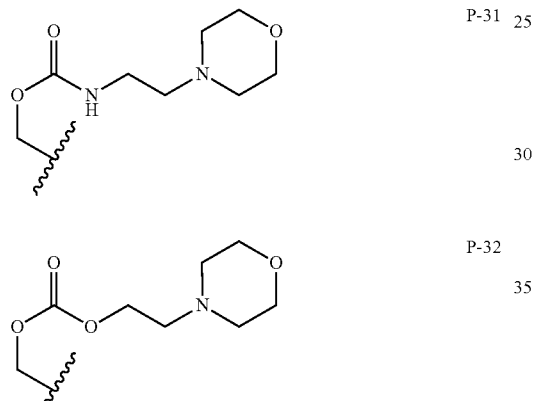

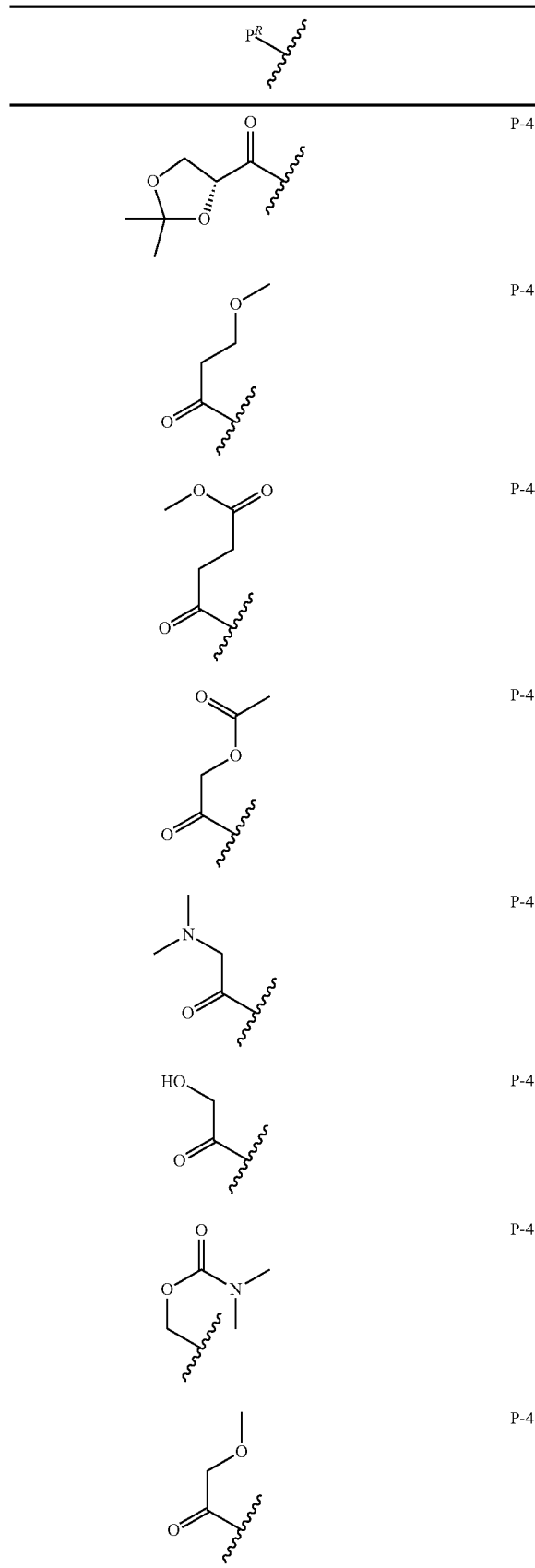
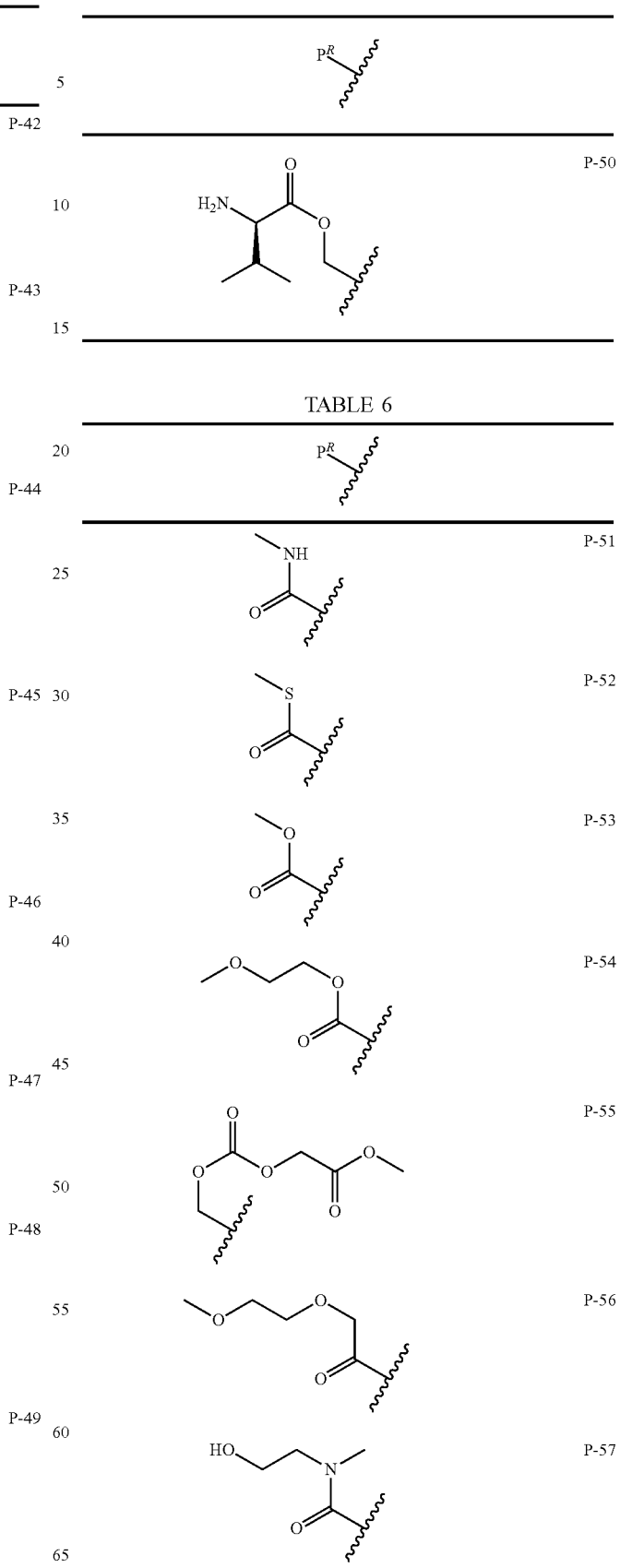

TABLE 6-continued
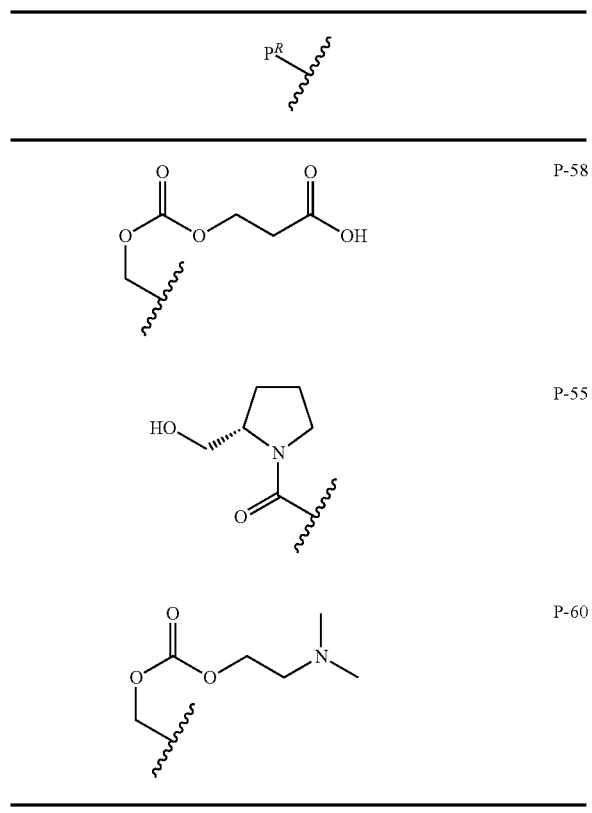
TABLE 7
TABLE 7-continued
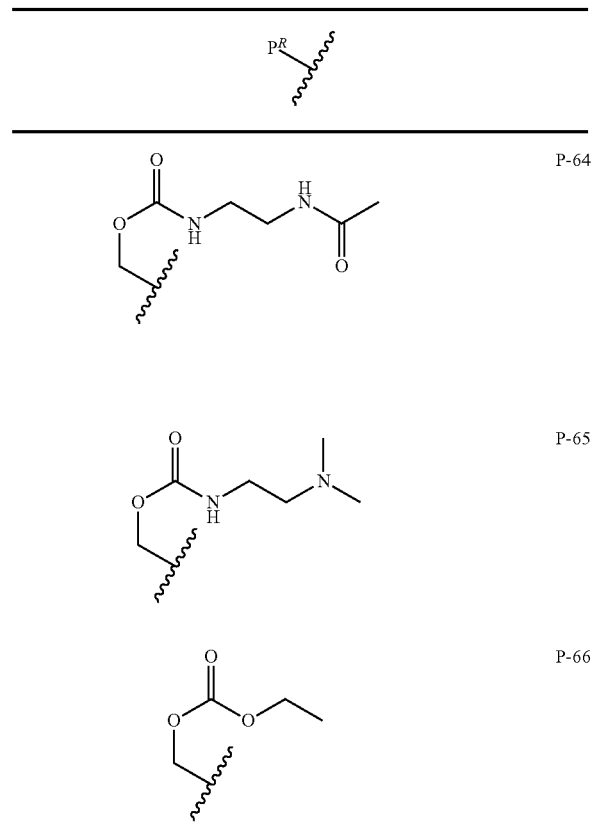
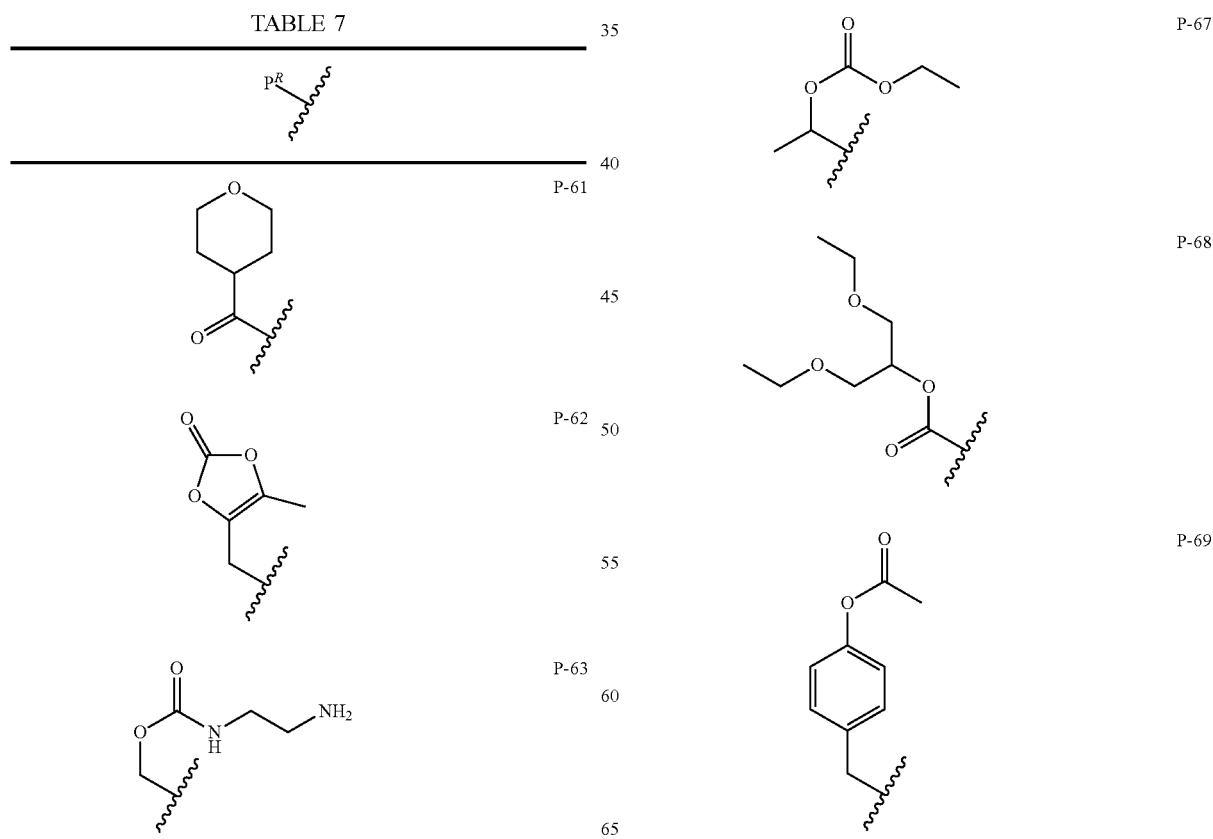

TABLE 7-continued
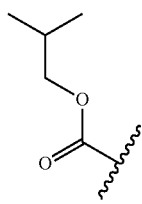 [SMILES: *C(=O)OCC(C)C] P-70
TABLE 8
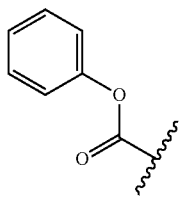 [SMILES: *C(=O)Oc1ccccc1] P-71
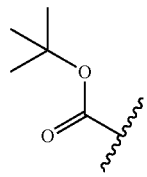 [SMILES: *C(=O)OC(C)(C)C] P-72
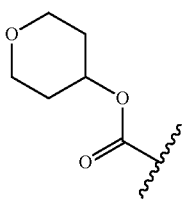 [SMILES: *C(=O)OC1CCOCC1] P-73
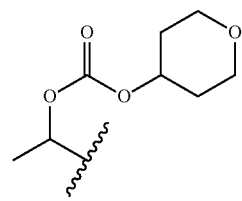 [SMILES: *C(C)OC(=O)OC1CCOCC1] P-74
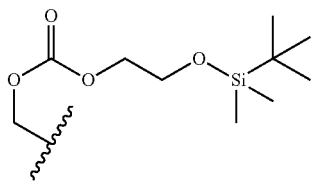 [SMILES: *COC(=O)OCCO[Si](C)(C)C(C)(C)C] P-75
TABLE 8-continued
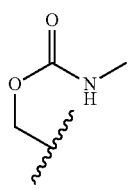 [SMILES: *COC(=O)NC] P-76
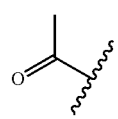 [SMILES: *C(C)=O] P-77
TABLE 9
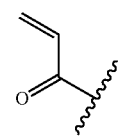 [SMILES: *C(=O)C=C] P-78
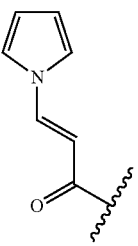 [SMILES: *C(=O)/C=C/n1cccc1] P-79
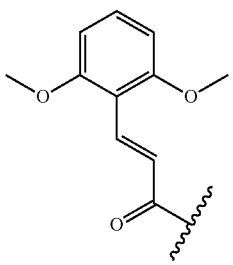 P-80
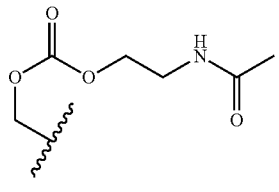 [SMILES: *COC(=O)OCCNC(C)=O] P-81

TABLE 9-continued

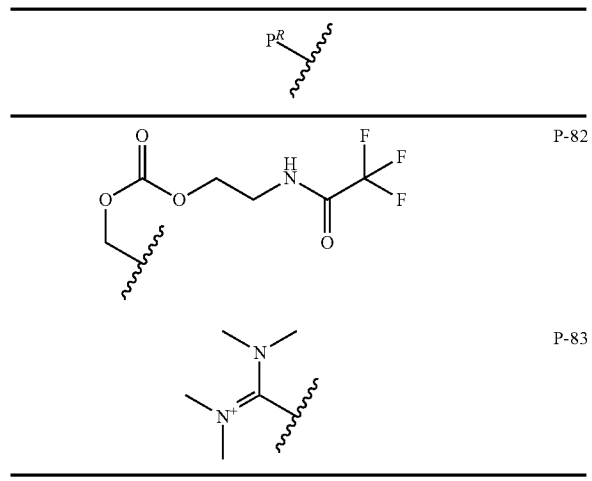

P-82

P-83

Examples of another embodiment of a particularly preferable substituent of $P^R$ include following groups.

[Chemical formula 37]

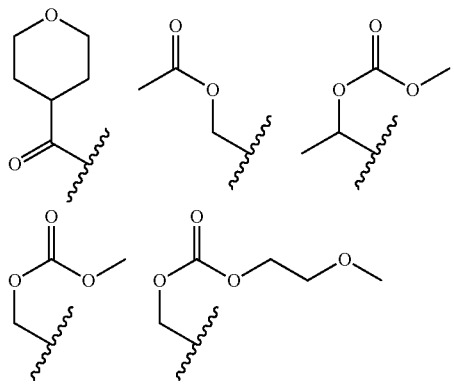

Examples of a preferable substituent in $R^{1a}$ include hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—N($R^{A1}$)($R^{A2}$),
—Z—N($R^{A3}$)—SO$_2$—($R^{A4}$),
—Z—C(=O)—N($R^{A5}$)—SO$_2$—($R^{A6}$),
—Z—N($R^{A7}$)—C(=O)—$R^{A8}$,
—Z—S—$R^{A9}$,
—Z—SO$_2$—$R^{A10}$,
—Z—S(=O)—$R^{A11}$,
—Z—N($R^{A12}$)—C(=O)—O—$R^{A13}$,
—Z—N($R^{A14}$)—C(=O)—N($R^{A15}$)($R^{A6}$),
—Z—C(=O)—N($R^{A17}$)—C(=O)—N($R^{A18}$)($R^{A19}$),
—Z—N($R^{A20}$)—C(=O)C(O)—C(=O)—$R^{A21}$, or
—Z—B(—O$R^{A22}$)(—O$R^{A23}$)
(substituent group C, $R^{A1}$, $R^{A2}$, $R^{A3}$, $R^{A5}$, $R^{A7}$, $R^{A8}$, $R^{A9}$, $R^{A10}$, $R^{A11}$, $R^{A12}$, $R^{A13}$, $R^{A14}$, $R^{A15}$, $R^{A16}$, $R^{A17}$, $R^{A18}$, $R^{A19}$, $R^{A20}$, $R^{A21}$, $R^{A22}$, $R^{A23}$, and Z are same as those of item 1).

Examples of a more preferable substituent in $R^{1a}$ include hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C,
—Z—N($R^{A1}$)($R^{A2}$),
—Z—N($R^{A7}$)—C(=O)—$R^{A8}$,
—Z—N($R^{A12}$)—C(=O)—O—$R^{A13}$, or
—Z—B(—O$R^{A22}$)(—O$R^{A23}$)
(substituent group C, $R^{A1}$, $R^{A2}$, $R^{A7}$, $R^{A8}$, $R^{A12}$, $R^{A13}$, $R^{A22}$, $R^{A23}$, and Z are same as those of item 1).

Examples of a preferable substituent in $R^{1a}$ include hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, or
—Z—N($R^{A1}$)($R^{A2}$)
(substituent group C, $R^{A1}$, $R^{A2}$, and Z are same as those of item 1).

Examples of another embodiment of a preferable substituent in $R^{1a}$ include hydrogen, carboxy, hydroxymethyl, methoxy, chlorine atom, bromine atom, ethoxymethyl, dimethylamino, hydroxy, —C(=O)—NH—S(=O)$_2$-Me, amino, methylamino, methylaminomethyl, —NH—C(=O)—CF$_3$, pyrazolyl, —NH—C(=O)-Me, —C(=O)N-Me$_2$, tetrazolyl, —NH—C(=O)-Ph, —C(=O)NH-Me, —C(=O)NH-Et, —C(=O)NH-cyclopropyl, methoxycarbonyl, methyl, propenyl, propyl, isopropyl, fluoromethyl, difluoromethyl, cyano, —C(=O)-Me, —CH(—OH)-Me, —B(—OH)$_2$,

[Chemical formula 38]

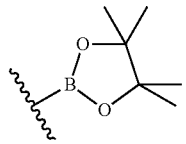

(Me represents a methyl group, Ph represents a phenyl group, and Et represents an ethyl group) etc.

Examples of another embodiment of a more preferable substituent in $R^{1a}$ include hydrogen, carboxy, hydroxymethyl, methoxy, bromine atom, ethoxymethyl, dimethylamino, hydroxy, —C(=O)—NH—S(=O)₂-Me, amino, methylamino, methyl, propenyl, —C(=O)-Me, —B(—OH)₂
(Me represents a methyl group) etc.

Examples of another embodiment of a further preferable substituent in $R^{1a}$ include hydrogen, carboxy, and —C(=O)-Me.

Examples of a most preferable substituent in $R^{1a}$ include hydrogen.

Examples of a preferable substituent in $R^{2a}$ is hydrogen, halogen, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—N($R^{B1}$)—SO₂—$R^{B2}$,
—Z—N($R^{B3}$)—C(=O)—$R^{B4}$,
—Z—N($R^{B5}$)—C(=O)—O—$R^{B6}$,
—Z—C(=O)—N($R^{B7}$)($R^{B8}$),
—Z—N($R^{B9}$)($R^{B10}$), or
—Z—SO₂—$R^{B11}$
(substituent group C, $R^{B1}$, $R^{B2}$, $R^{B3}$, $R^{B4}$, $R^{B5}$, $R^{B6}$, $R^{B7}$, $R^{B8}$, $R^{B9}$, $R^{B10}$, $R^{B11}$, and Z are same as those of item 1).

Examples of a more preferable substituent in $R^{2a}$ is hydrogen, lower alkyl optionally substituted by substituent group C, carbocycle lower alkyl optionally substituted by substituent group C, heterocycle lower alkyl optionally substituted by substituent group C, or
—Z—N($R^{B9}$)($R^{B10}$)
(substituent group C, $R^{B9}$, $R^{B10}$, and Z are same as those of item 1).

Examples of a further preferable substituent in $R^{2a}$ include hydrogen, or lower alkyl optionally substituted by substituent group C, heterocycle lower alkyl optionally substituted by substituent group C
(substituent group C is same as that of item 1).

Examples of another embodiment of a preferable substituent in $R^{2a}$ include hydrogen, hydroxymethyl, amino, methoxymethyl, methoxymethylcyclopropylmethyloxymethyl, cyanomethyl, aminomethyl, propyloxymethyl, —CH₂—NH—C(=O)-Me, methylaminomethyl, imidazolyl, dimethylaminomethyl, pyrrolidinyl, fluoromethyl, —CH₂—NH—C(=O)H (Me represents a methyl group) etc.

Examples of another embodiment of a more preferable substituent in $R^{2a}$ include hydrogen, hydroxymethyl, methoxymethylcyclopropylmethyloxymethyl, aminomethyl, propyloxymethyl, etc.

Examples of another embodiment of a further preferable substituent in $R^{2a}$ include hydrogen.

Examples of a preferable substituent in $R^{3a}$ include hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—N($R^{C1}$)—SO₂—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$),
—Z—N($R^{C9}$)($R^{C10}$), or
—Z—SO₂—$R^{C11}$
(substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, $R^{C11}$, and Z are same as those of item 1).

Examples of a more preferable substituent in $R^{3a}$ is hydrogen, lower alkyl optionally substituted by substituent group C, lower alkenyl optionally substituted by substituent group C, lower alkynyl optionally substituted by substituent group C, carbocyclic group optionally substituted by substituent group C, carbocycle lower alkyl optionally substituted by substituent group C, carbocycleoxy lower alkyl optionally substituted by substituent group C,
—Z—N($R^{C1}$)—SO₂—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$), or
—Z—N($R^{C9}$)($R^{C10}$)
(substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, and Z are same as those of item 1).

Examples of a further preferable substituent in $R^{3a}$ include hydrogen, lower alkyl optionally substituted by substituent group C, lower alkynyl optionally substituted by substituent group C, carbocyclic group optionally substituted by substituent group C, or carbocycle lower alkyl optionally substituted by substituent group C (substituent group C is same as that of item 1).

Examples of another embodiment of a preferable substituent in $R^{3a}$ include hydrogen, ethoxyethyl, methyl, ethyl, propyl, 2,4-difluorobenzyl, methoxyethyl, cyanomethyl, cyanoethyl, 3-chloro-2-fluorobenzyl, 1-methoxypropyl, pyridylmethyl, isopropyl, tetrahydropyranylmethyl, cyclopropylmethyl, benzyl, methylisoxazolylmethyl, methyloxadiazolyl, isopropyloxyethyl, hydroxyethyl, 4-fluorobenzyl, cyclopropyl, ethoxycarbonylethyl, —CH(Me)CH₂OMe, carboxyethyl, —CH₂CH₂C(=O)—N(Me)₂, —CH₂CH₂N(Me)-S(=O)₂-Ph, —CH₂CH₂—N(Me)-S(=O)₂-Me, —CH₂CH₂—NHC(=O)-Ph, —CH(Me)-CH₂—OMe, —CH₂CH₂—NH—S(=O)₂-Ph, —CH₂CH₂—NH—C(=O)—O—CH(Me)₂, —CH₂CH₂—C(=O)—NH-Ph, —CH₂CH₂—N(Me)C(=O)-Ph, —CH₂CH₂—NH—C (=O)-Me, —CH₂CH₂—NH—S(=O)₂-Me, aminoethyl, —CH₂CH₂—N(Me)-C(=O)-Me, —CH₂CH₂—C(=O)—N(Me)-Ph, —CH₂CH₂—NH—C(=O)—O-tBu, piperidinylcarbonylethyl, dimethylaminoethyl, cyclopropylmethyl, methylaminoethyl, furanylmethyl, morpholinylcarbonylethyl, sec-butyl, pentan-2-yl, carboxypropyl, ethoxycarbonylpropyl, phenylpropyl, propyloxyethyl, aminopropyl, dimethylaminomethyl, dimethylaminoethyl, diethylaminomethyl, diethylaminoethyl, dimethylaminopropyl, methylaminocarbonylethyl, 1,1,1-trifluoropropan-2-yl, 1,1-difluoroethyl, 1,1,1-trifluoroethyl, 1,1,1-trifluoropropyl, trifluoromethyloxyethyl, trifluoromethylcarbonylaminomethyl, methylsulfonylethyl, methylcarbonyloxyethyl, methylcarbonyloxypropyl, 1-fluoropropyl, fluorocyclopropyl, difluorocyclopropyl, 3,3-dimethylbutan-2-yl, 1-fluoroethyl, 1-methoxypropan-2-yl, amino, thiazolylmethyl, methylsulfonylethyl, 4-fluorophenyloxyethyl, pyridyl, pentan-2-yl, butan-2-yl, 3-methylbuten-2-yl, as well as groups shown below

[Chemical formula 39]

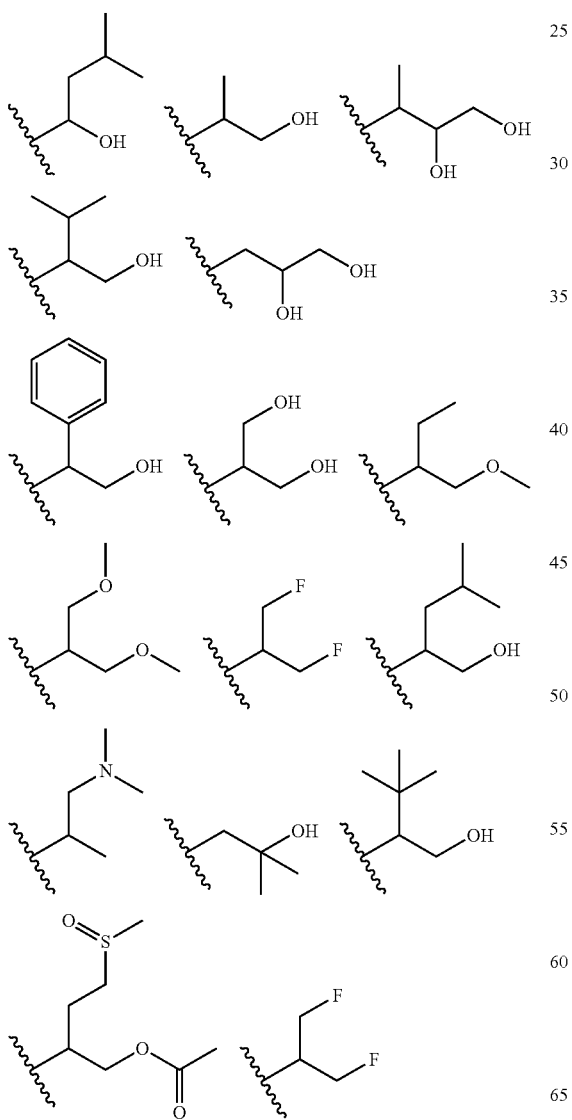

[Chemical formula 40]

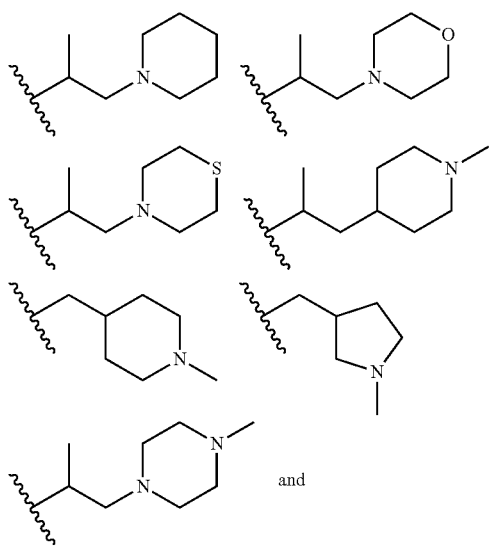

and

[Chemical formula 41]

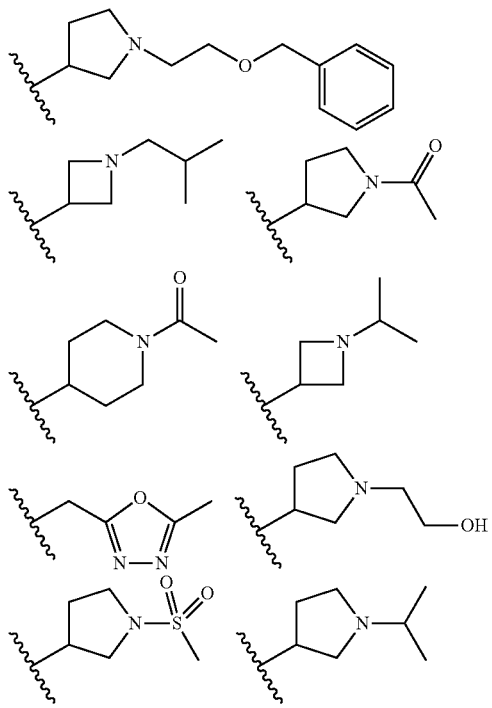

(Me represents a methyl group, Ph represents a phenyl group, and tBu represents a tert-butyl group) etc.

Examples of another embodiment of a more preferable substituent in $R^{3a}$ include ethoxyethyl, methyl, ethyl, 2,4-difluorobenzyl, methoxyethyl, cyanomethyl, 3-chloro-2-fluorobenzyl, methoxypropyl, pyridylmethyl, isopropyl, tetrahydropyranylmethyl, cyclopropylmethyl, benzyl, methylisoxazolylmethyl, 4-fluorobenzyl, cyclopropyl, ethoxycarbonylethyl, —CH(Me)CH₂OMe, carboxyethyl, —CH₂CH₂C(=O)—N(Me)₂, —CH₂CH₂N(Me)-S(=O)₂-Ph, —CH₂CH₂—N(Me)-S(=O)₂-Me, —CH₂CH₂—NHC(=O)-Ph, —CH(Me)-CH₂—OMe, —CH₂CH₂—NH—S(=O)₂-Ph, —CH₂CH₂—NH—C(=O)—O—CH(Me)₂, —CH₂CH₂—C(=O)—NH-Ph, —CH₂CH₂—N(Me)C (=O)-Ph, —CH₂CH₂—NH—C(=O)-Me, —CH₂CH₂—NH—S(=O)₂-Me, aminoethyl, 1,1,1-trifluoropropan-2-yl, propyl, methylthiomethyl, hydrogen, fluorocyclopropyl, trifluoromethoxyethyl, 1-fluoropropyl, 1-fluoroethyl, methylcarbonyloxymethyl, 1,1-difluoromethyl, and groups shown below

[Chemical formula 42]

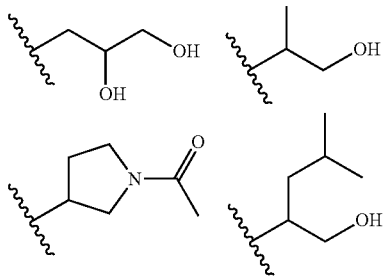

(Me represents methyl group, and Ph represents phenyl group) etc.

Examples of another embodiment of a further preferable substituent in R$^{3a}$ include ethoxyethyl, methyl, ethyl, 2,4-difluorobenzyl, methoxyethyl, cyanomethyl, 3-chloro-2-fluorobenzyl, methoxypropyl, pyridylmethyl, isopropyl, tetrahydropyranylmethyl, cyclopropylmethyl, benzyl, 4-fluorobenzyl, cyclopropyl, ethoxycarbonylethyl, —CH(Me)CH₂OMe, carboxyethyl, 1,1,1-trifluoropropan-2-yl, hydroxyethyl, 1-fluoroethyl
(Me represents methyl group) etc.

Examples of another embodiment of a most preferable substituent in R$^{3a}$ include 1,1,1-trifluoropropan-2-yl.

Examples of a preferable substituent in R$^{5a}$, R$^{6a}$, R$^{7a}$, R$^{8a}$, R$^{9a}$, R$^{10a}$, and R$^{11a}$ include hydrogen, carboxy, cyano, lower alkyl optionally substituted by substituent group C, lower alkenyl optionally substituted by substituent group C, lower alkynyl optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C,
—Y—S—R$^{D1}$,
—Z—S(=O)—R$^{D2}$,
—Z—SO₂—R$^{D3}$,
—C(=O)—C(=O)—R$^{D4}$,
—C(=O)—N(R$^{D5}$)(R$^{D6}$),
—Z—C(R$^{D7}$)(R$^{D8}$)(R$^{D9}$), or
—Z—CH₂—R$^{D10}$
(substituent group C, R$^{D1}$, R$^{D2}$, R$^{D3}$, R$^{D4}$, R$^{D5}$, R$^{D6}$, R$^{D7}$, R$^{D8}$, R$^{D9}$, R$^{D10}$, and Z are same as those of item 1).

Examples of a more preferable substituent in R$^{5a}$, R$^{6a}$, R$^{7a}$, R$^{8a}$, R$^{9a}$, R$^{10a}$, and R$^{11a}$ include hydrogen, lower alkyl optionally substituted by substituent group C, carbocyclic group optionally substituted by substituent group C, carbocycleoxy lower alkyl optionally substituted by substituent group C, heterocyclic group optionally substituted by substituent group C, tricyclic condensed heterocyclic group optionally substituted by substituent group C, heterocycleoxy lower alkyl optionally substituted by substituent group C,
—Y—S—R$^{D1}$, or
—Z—C(R$^{D7}$)(R$^{D8}$)(R$^{D9}$)
(substituent group C, R$^{D1}$, R$^{D7}$, R$^{D8}$, R$^{D9}$, Y, and Z are same as those of item 1).

Examples of another embodiment of a preferable substituent in R$^{5a}$, R$^{6a}$, R$^{7a}$, R$^{8a}$, R$^{9a}$, R$^{10a}$, and R$^{11a}$ include hydrogen, benzhydryl, benzyl, indolylmethyl, cyclohexylmethyl, phenethyl, benzylthiomethyl, 3,5-dimethylisoxazolyl, 5-chloro-3-ethylbenzothiophenyl, 4-fluorobenzyl, methylthiazolylmethyl, cyclopentylmethyl, 4-methoxybenzyl, 3-fluorobenzyl, naphthylmethyl, methyl, 3-trifluoromethylbenzyl, pyridylmethyl, 4-methylcarbonylaminobenzyl, pyrimidinyl, isobutyl, phenoxyethyl, methoxypropyl, phenylpropyl, as well as tricyclic or tetracyclic condensed heterocyclic group optionally substituted by substituent group C such as the following groups

[Chemical formula 43]

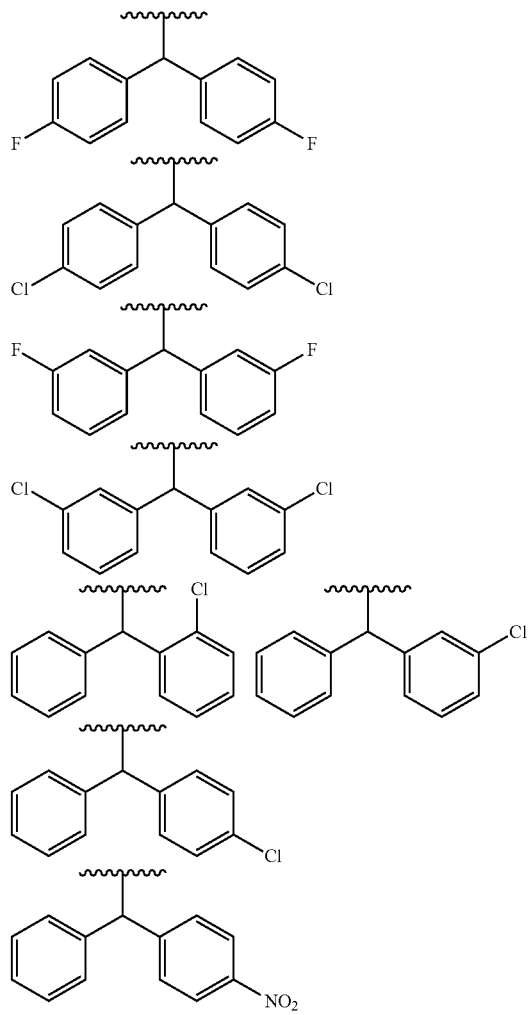

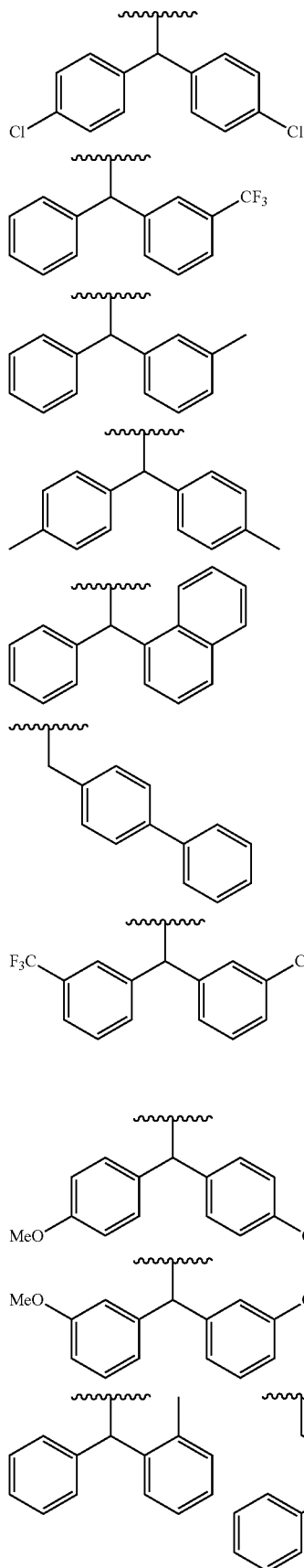
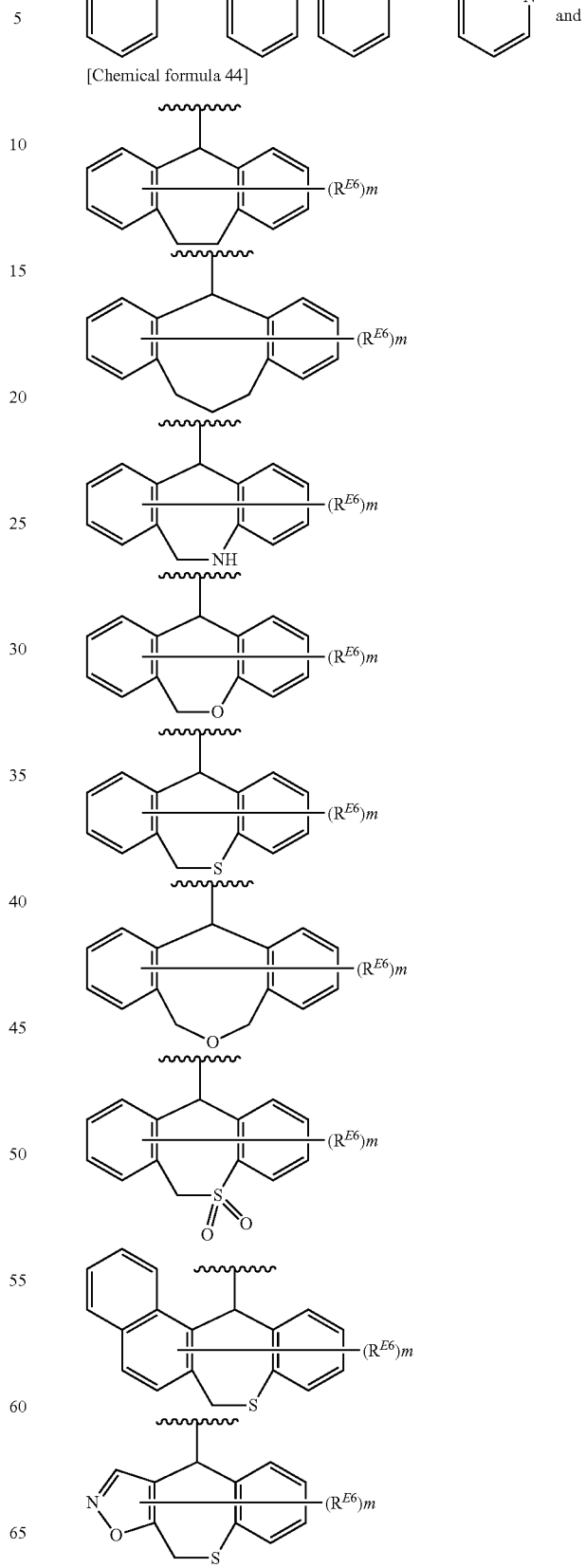

-continued

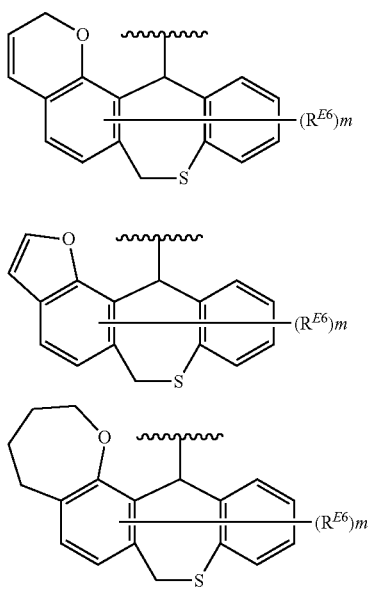

(wherein $R^{E6}$ represents a group selected from substituent group C, and m of $R^{E6}$s may be the same or different) etc.

Examples of another embodiment of a more preferable substituent in $R^{5a}$, $R^{6a}$, $R^{7a}$, $R^{8a}$, $R^{9a}$, $R^{10a}$, and $R^{11a}$ include hydrogen, benzhydryl, benzyl, indolylmethyl, cyclohexylmethyl, phenethyl, 3,5-dimethylisoxazolyl, 5-chloro-3-ethylbenzothiophenyl, biphenylmethyl, 4-fluorobenzyl, methylthiazolylmethyl, cyclopentylmethyl, 4-methoxybenzyl, 3-fluorobenzyl, naphthylmethyl, methyl, 3-trifluoromethylbenzyl, pyridylmethyl, 4-methylcarbonylaminobenzyl, pyrimidinyl, and the following groups

[Chemical formula 45]

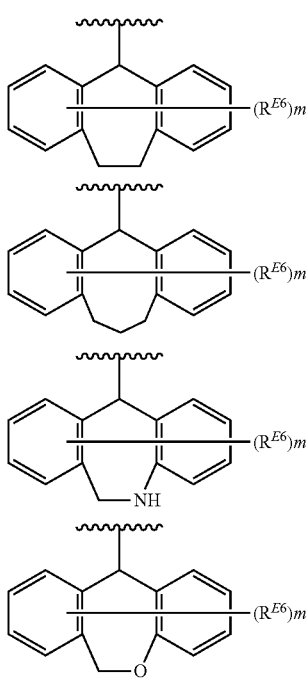

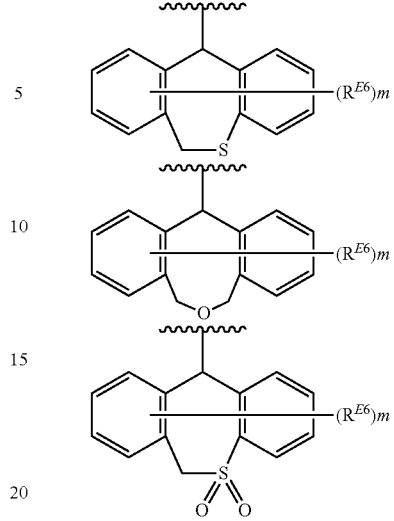

(wherein $R^{E6}$ represents a group selected from substituent group C, and m of $R^{E6}$s may be the same or different), etc.

1) Examples of a preferable embodiment when $B^1$ is $CR^{5a}R^{6a}$, and $B^2$ is $NR^{7a}$ include
the case where $R^{3a}$ and $R^{7a}$ are taken together with an adjacent atom to form a heterocycle optionally substituted by substituent group D.

2) Examples of a preferable embodiment when $B^1$ is $NR^{7a}$, and $B^2$ is $CR^{5a}R^{6a}$ include
the case where $R^{3a}$ and $R^{6a}$ are taken together with an adjacent atom to form a heterocycle optionally substituted by substituent group D.

3) Examples of a preferable embodiment when $B^1$ is $CR^{8a}R^{9a}$, and $B^2$ is $CR^{10a}R^{11a}$ include
the case where $R^{8a}$ and $R^{10a}$ are taken together with an adjacent atom to form a carbocycle or a heterocycle optionally substituted by substituent group D.

4) Examples of another preferable embodiment when $B^1$ is $CR^{8a}R^{9a}$, and $B^2$ is $CR^{10a}R^{11a}$ include
the case where $R^{3a}$ and $R^{11a}$ are taken together with an adjacent atom to form a heterocycle optionally substituted by substituent group D.

When one of $B^1$ and $B^2$ is $CR^{5a}R^{6a}$ and the other is $NR^{7a}$, the case where $B^1$ is $NR^{7a}$ and $B^2$ is $CR^{5a}R^{6a}$ is more preferable.

When one of $B^1$ and $B^2$ is $CR^{5a}R^{6a}$ and the other is $NR^{7a}$, it is preferable that at least one of $R^{5a}$ or $R^{6a}$ is hydrogen. A more preferable embodiment is such that $R^{5a}$ is hydrogen and $R^{6a}$ is hydrogen. In this case, $R^{7a}$ is not a hydrogen atom.

A particularly preferable embodiment of $B^1$ and $B^2$ is such that $B^1$ is $NR^{7a}$ and $B^2$ is $CR^{5a}R^{6a}$.

A most preferable embodiment of $B^1$ and $B^2$ is such that $B^1$ is $NR^{7a}$ and $B^2$ is $CH_2$.

A preferable embodiment of $R^{7a}$ is carbocyclic group optionally substituted by substituent group C, carbocycle lower alkyl optionally substituted by substituent group C, heterocyclic group optionally substituted by substituent group C, and hetereocycle lower alkyl optionally substituted by substituent group C.

A more preferable embodiment of $R^{7a}$ is cycloalkyl, cycloalkenyl, aryl, non-aromatic condensed carbocyclic group, heteroaryl, non-aromatic heterocyclic group, bicyclic condensed heterocyclic group, tricyclic condensed heterocyclic group, lower alkyl substituted by one or two carbocyclic groups, and lower alkyl substituted by one or two heterocyclic groups.

A further preferable embodiment of $R^{7a}$ is benzyl, benzhydryl, 4-fluorobenzyl, p-methoxybenzyl, and the following groups

[Chemical formula 46]

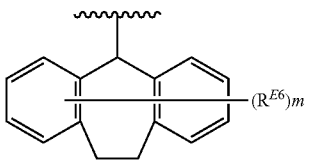
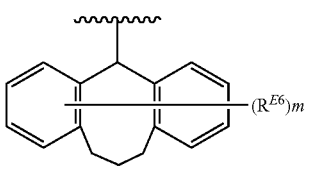
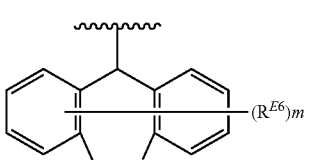
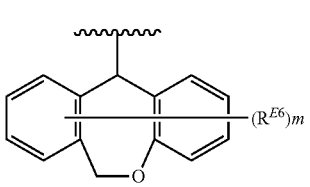
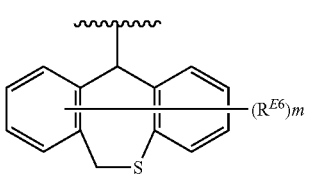
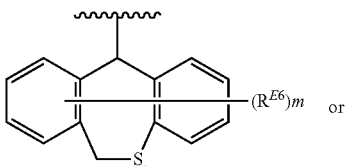
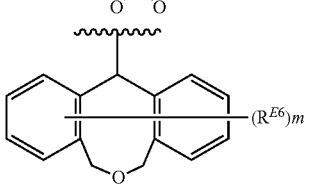

(wherein $R^{E6}$, and m are same as those of item 1).

A particularly preferable embodiment of $R^{7a}$ is the following groups

[Chemical formula 47]

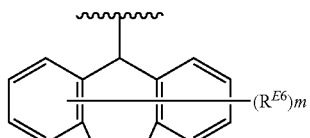

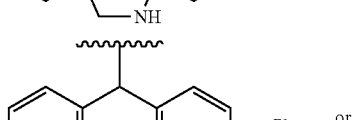
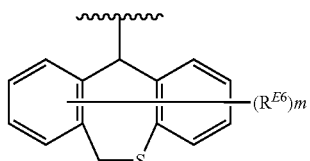

or (wherein $R^{E6}$, and m are same as those of item 1).

A most preferable embodiment of $R^{7a}$ is the following groups

[Chemical formula 48]

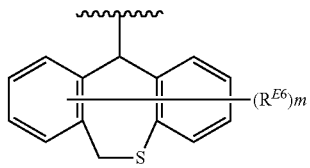

(wherein $R^{E6}$, and m are same as those of item 1).

When $B^1$ is $CR^{8a}R^{9a}$, and $B^2$ is $CR^{10a}R^{11a}$, it is preferable that $R^{9a}$ and $R^{11a}$ are hydrogen. A preferable embodiment of $R^{8a}$ and $R^{10a}$ is such that any one of them is hydrogen.

When $R^{9a}$ and $R^{11a}$ are hydrogen, and any one of $R^{8a}$ and $R^{10a}$ is hydrogen, a preferable embodiment of the other of $R^{8a}$ and $R^{10a}$ is the following groups

—Z—C($R^{E1}$)($R^{E2}$)($R^{E3}$)

or

[Chemical formula 49]

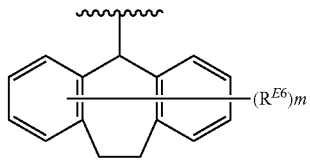

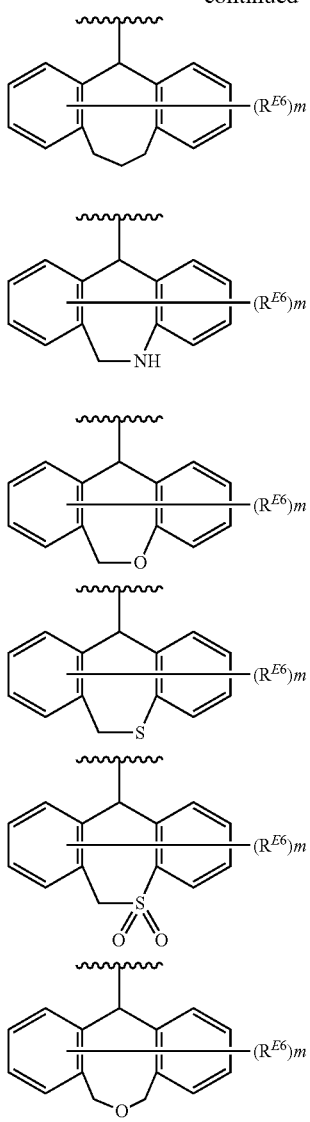

(wherein Z, $R^{E1}$, $R^{E2}$, $R^{E3}$, $R^{E6}$, and m are same as those of item 1).

When $R^{9a}$ and $R^{11a}$ are hydrogen, and any one of $R^{8a}$ and $R^{10a}$ is hydrogen, a further preferable embodiment of the other of $R^{8a}$ and $R^{10a}$ is the following groups

[Chemical formula 50]

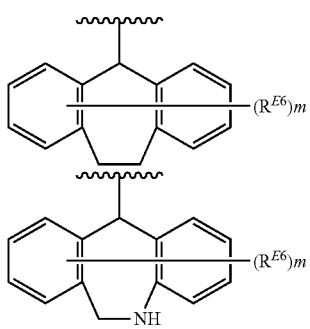

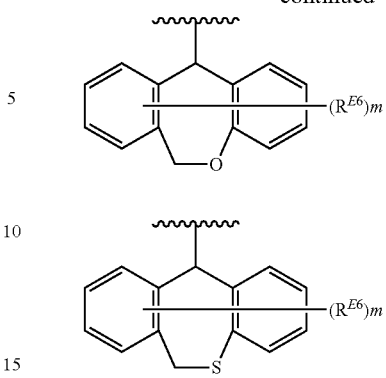

(wherein $R^{E6}$, and m are same as those of item 1).

When $R^{9a}$ and $R^{11a}$ are hydrogen, and any one of $R^{8a}$ and $R^{10a}$ is hydrogen, a most preferable embodiment of the other of $R^{8a}$ and $R^{10a}$ is the following groups

[Chemical formula 51]

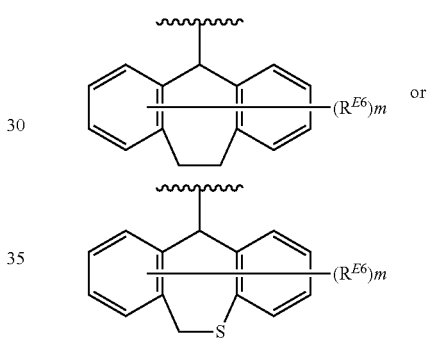

(wherein $R^{E6}$, and m are same as those of item 1).

Examples of a preferable substituent in substituent group D include carbocyclic group optionally substituted by substituent group C, heterocyclic group optionally substituted by substituent group C, carbocycle lower alkyl optionally substituted by substituent group C, and heterocycle lower alkyl optionally substituted by substituent group C.

Examples of another embodiment of a preferable substituent in substituent group D include benzyl, benzhydryl, 4-fluorobenzyl, p-methoxybenzyl,

[Chemical formula 52]

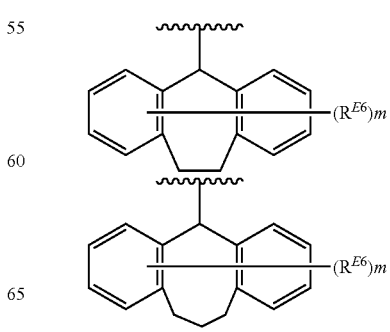

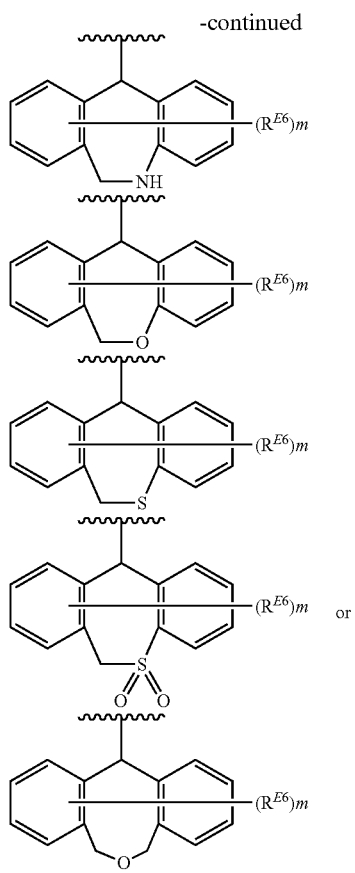

(wherein $R^{E6}$ represents a group selected from substituent group C, and m of $R^{E6}$s may be the same or different) etc.

Examples of a preferable substituent of $R^{E6}$ include halogen, cyano, hydroxy, carboxy, formyl, amino, oxo, nitro, lower alkyl, lower alkynyl, halogeno lower alkyl, lower alkyloxy, lower alkyl amino, halogeno lower alkyloxy, carbocyclic group, etc.

Examples of a more preferable substituent of $R^{E6}$ include fluorine atom, chlorine atom, bromine atom, cyano, hydroxy, methyl, ethyl, ethynyl, hydroxymethyl, isopropyl, methoxy, ethoxy, methoxymethyl, cyclopropyl, dimethylamino, trifluoromethyl, oxo, carboxy, etc.

Examples of a particularly preferable substituent of $R^{E6}$ include fluorine atom, chlorine atom, bromine atom, methyl, methoxy, and trifluoromethyl.

A preferable embodiment of m is an integer of 0 to 6, further preferably an integer of 0 to 3, and most preferably an integer of 0 to 2.

One of characteristics of the compound in the present invention is in that a prodrug of a polycyclic carbamoylpyridone derivative, in which two or more rings are condensed, such as shown in the formula (I) in item 1 and/or a composition including them, has high inhibitory activity on cap-dependent endonuclease, and has an effect of treating and/or preventing influenza infectious disease.

The characteristic of the compound in the present invention is that cap-dependent endonuclease inhibitory activity was improved, by applying a functional group as shown below to $R^{1a}$ in the formula (I).

Functional group: hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{A1}$)($R^{A2}$),
—Z—N($R^{A3}$)—SO$_2$—($R^{A4}$),
—Z—C(=O)—N($R^{A5}$)—SO$_2$—($R^{A6}$),
—Z—N($R^{A7}$)—C(=O)—$R^{A8}$,
—Z—S—$R^{A9}$,
—Z—SO$_2$—$R^{A10}$,
—Z—S(=O)—$R^{A11}$,
—Z—N($R^{A12}$)—C(=O)—O—$R^{A13}$,
—Z—N($R^{A14}$)—C(=O)—N($R^{A15}$)($R^{A16}$),
—Z—C(=O)—N($R^{A17}$)—C(=O)—N($R^{A18}$)($R^{A19}$), or
—Z—N($R^{A20}$)—C(=O)—C(=O)—$R^{A21}$ (substituent group C, $R^{A1}$, $R^{A2}$, $R^{A3}$, $R^{A5}$, $R^{A7}$, $R^{A8}$, $R^{A9}$, $R^{A12}$, $R^{A13}$, $R^{A14}$, $R^{A15}$, $R^{A16}$, $R^{A17}$, $R^{A18}$, $R^{A19}$, $R^{A20}$, and $R^{A21}$ are same as those of item 1)

The characteristic of a more preferable compound in the present invention is that cap-dependent endonuclease inhibitory activity was improved, by applying a functional group as shown below to $R^{1a}$ in the formula (I).

Functional group: hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, —Z—N($R^{A1}$)($R^{A2}$),
—Z—N($R^{A7}$)—C(=O)—$R^{A8}$, or
—Z—N($R^{A12}$)—C(=O)—O—$R^{A13}$ (substituent group C, $R^{A1}$, $R^{A2}$, $R^{A7}$, $R^{A8}$, $R^{A12}$, $R^{A13}$, and Z are same as those of item 1).

The characteristic of a further preferable compound in the present invention is that cap-dependent endonuclease inhibitory activity was improved, by applying a functional group as shown below to $R^{1a}$ in the formula (I).

Functional group: hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, or

—Z—N($R^{A1}$)($R^{A2}$)

(substituent group C, $R^{A1}$, $R^{A2}$, and Z are same as those of item 1).

The characteristic of a particularly preferable compound in the present invention is that cap-dependent endonuclease inhibitory activity was improved, by applying a functional group as shown below to $R^{1a}$ in the formula (I). Functional group: hydrogen, acetyl, or carboxy Another characteristic of the compound in the present invention is that cap-dependent endonuclease inhibitory activity was improved, by introducing one, two or more of lipid-soluble functional groups shown below on carbon atom or on nitrogen atom of $B^1$ and/or $B^2$ in the formula (I).

Lipid-soluble functional group: carbocyclic group optionally substituted by substituent group C, carbocycle lower alkyl optionally substituted by substituent group C, carbocycleoxy lower alkyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocycleoxycarbonyl optionally substituted by substituent group C (substituent group C is same as that of item 1).

Another characteristic of a more preferable compound in the present invention is that cap-dependent endonuclease inhibitory activity is improved, by introducing one lipid-soluble functional group shown below on carbon atom or on nitrogen atom of $B^1$ or $B^2$ in the formula (I).

Lipid-soluble functional group: carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C (substituent group C is same as that of item 1).

Another characteristic of a particularly preferable compound in the present invention is that cap-dependent endonuclease inhibitory activity is improved, by introducing one lipid-soluble functional group shown below on carbon atom or on nitrogen atom of $B^1$ or $B^2$ in the formula (I).

Lipid-soluble functional group: carbocyclic group optionally substituted by substituent group C, heterocyclic group optionally substituted by substituent group C (substituent group C is same as that of item 1).

Other characteristic of a preferable compound in the present invention is that the compound is efficiently absorbed into the body after in vivo administration (for example, oral administration) and shows high drug efficacy by introducing a group to form a prodrug into a $P^R$ part in the formula (I).

Other characteristic of a more preferable compound in the present invention is that the compound is efficiently absorbed into the body after administration and shows high drug efficacy by introducing a group selected from the following formulae a) to v) into a $P^R$ part in the formula (I).

a) —C(=O)—$P^{R0}$,
b) —C(=O)—$P^{R1}$,
c) —C(=O)-L-O—$P^{R1}$,
d) —C(=O)-L-O-L-O—$P^{R1}$,
e) —C(=O)-L-O—C(=O)—$P^{R1}$,
f) —C(=O)—O—$P^{R2}$,
g) —C(=O)—N($P^{R2}$)$_2$,
h) —C(O)—O-L-O—$P^{R2}$,
i) —CH$_2$—O—$P^{R3}$,
j) —CH$_2$—O-L-O—$P^{R3}$,
k) —CH$_2$—O—C(=O)—$P^{R3}$,
l) —CH$_2$—O—C(=O)—O—$P^{R3}$,
m) —CH(—CH$_3$)—O—C(=O)—O—$P^{R3}$,
n) —CH$_2$—O—C(=O)—N(—K)—$P^{R3}$,
o) —CH$_2$—O—C(=O)—O-L-O—$P^{R3}$,
p) —CH$_2$—O—C(=O)—O-L-N($P^{R3}$)$_2$,
q) —CH$_2$—O—C(=O)—N(—K)-L-O—$P^{R3}$,
r) —CH$_2$—O—C(=O)—N(—K)-L-N($P^{R3}$)$_2$,
s) —CH$_2$—O—C(=O)—O-L-O-L-O—$P^{R3}$,
t) —CH$_2$—O—P(=O)(—OH)$_2$,
u) —CH$_2$—O—P(=O)(—OBn)$_2$,
v) —CH$_2$—$P^{R4}$ (wherein L is straight or branched lower alkylene, K is hydrogen, or straight or branched lower alkylene, $P^{R0}$ is lower alkyl optionally substituted by substituent group F, $P^{R1}$ is carbocyclic group optionally substituted by substituent group F, heterocyclic group optionally substituted by substituent group F, lower alkyl amino optionally substituted by substituent group F, or lower alkylthio optionally substituted by substituent group F, $P^{R2}$ is lower alkyl optionally substituted by substituent group F, carbocyclic group optionally substituted by substituent group F, or heterocyclic group optionally substituted by substituent group F, $P^{R3}$ is lower alkyl optionally substituted by substituent group F, carbocyclic group optionally substituted by substituent group F, heterocyclic group optionally substituted by substituent group F, lower alkyl amino optionally substituted by substituent group F, carbocycle lower alkyl optionally substituted by substituent group F, heterocycle lower alkyl optionally substituted by substituent group F, or lower alkylsilyl, $P^{R4}$ is carbocyclic group optionally substituted by substituent group F, or heterocyclic group optionally substituted by substituent group F.

Substituent group F; oxo, lower alkyl, hydroxyl lower alkyl, amino, lower alkylamino, carbocycle lower alkyl, lower alkylcarbonyl, halogen, hydroxy, carboxy, lower alkylcarbonylamino, lower alkylcarbonyloxy, lower alkyloxycarbonyl, lower alkyloxy, cyano, and nitro)

Other characteristic of a more preferable compound in the present invention is that the compound is efficiently absorbed into the body after administration and shows high drug efficacy by introducing groups of P-1 to P-77 in Tables 1 to 8 into a $P^R$ part in the formula (I).

A preferable embodiment of the present invention will be exemplified below. In the formula (III), the formula (III'), the formula (III''), the formula (III'''), the formula (III''''), the formula (III'''''):

[Chemical formula 53]

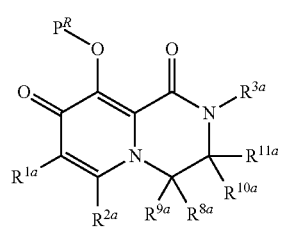

(III)

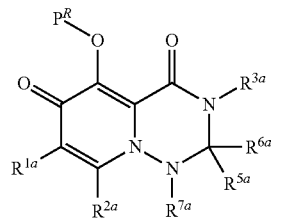

(III')

-continued

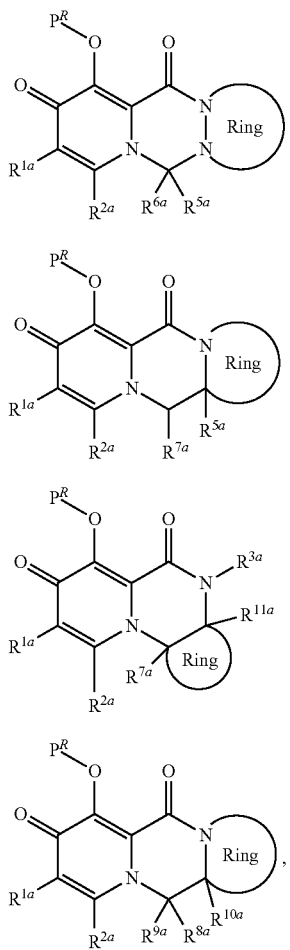

1)
a compound in which $R^{1a}$ is hydrogen (hereinafter, $R^{1a}$ is R1-1),
a compound in which $R^{1a}$ is carboxy (hereinafter, $R^{1a}$ is R1-2),
a compound in which $R^{1a}$ is halogen (hereinafter $R^{1a}$ is R1-3),
a compound in which $R^{1a}$ is hydroxy (hereinafter, $R^{1a}$ is R1-4),
a compound in which $R^{1a}$ is lower alkyl optionally substituted by substituent group C (hereinafter, $R^{1a}$ is R1-5),
a compound in which $R^{1a}$ is lower alkylcarbonyl optionally substituted by substituent group C (hereinafter, $R^{1a}$ is R1-6),
a compound in which $R^{1a}$ is lower alkyloxycarbonyl optionally substituted by substituent group C (hereinafter, $R^{1a}$ is R1-7),
a compound in which $R^{1a}$ is amino (hereinafter, $R^{1a}$ is R1-8),
2)
a compound in which $R^{2a}$ is hydrogen (hereinafter, $R^{2a}$ is R2-1),
a compound in which $R^{2a}$ is lower alkyl optionally substituted by substituent group C (hereinafter, $R^{2a}$ is R2-2),
3)
a compound in which $R^{3a}$ is lower alkyl optionally substituted by substituent group C (hereinafter, $R^{3a}$ is R3-1),
a compound in which $R^{3a}$ is carbocycle lower alkyl optionally substituted by substituent group C (hereinafter, $R^{3a}$ is R3-2),
a compound in which $R^{3a}$ is heterocycle lower alkyl optionally substituted by substituent group C (hereinafter, $R^{3a}$ is R3-3),
a compound in which $R^{3a}$ is carbocyclic group optionally substituted by substituent group C (hereinafter, $R^{3a}$ is R3-4),
a compound in which $R^{3a}$ is heterocyclic group optionally substituted by substituent group C (hereinafter, $R^{3a}$ is R3-5),
4)
a compound in which $P^R$ is —C(=O)—$P^{R1}$ (hereinafter, $P^R$ is Pr-1),
a compound in which $P^R$ is —CH$_2$—O—C(=O)—$P^{R3}$ (hereinafter, $P^R$ is Pr-2),
a compound in which $P^R$ is —CH$_2$—O—C(=O)—O—$P^{R3}$ (hereinafter, $P^R$ is Pr-3),
a compound in which $P^R$ is —CH(—CH$_3$)—O—C(=O)—O—$P^{R3}$ (hereinafter, $P^R$ is Pr-4),
(wherein each symbol is same as above)
in the formula (III'),
a compound in which $R^{7a}$ is carbocyclic group optionally substituted by substituent group C, and $R^{5a}$ and $R^{6a}$ are hydrogen (hereinafter, R7-1),
a compound in which $R^{7a}$ is heterocyclic group optionally substituted by substituent group C, and $R^{5a}$ and $R^{6a}$ are hydrogen (hereinafter, R7-2),
a compound in which $R^{7a}$ is carbocycle lower alkyl optionally substituted by substituent group C, and $R^{5a}$ and $R^{6a}$ are hydrogen (hereinafter, R7-3),
in the formula (III),
a compound in which $R^{9a}$ is carbocyclic group optionally substituted by substituent group C, and $R^{8a}$, $R^{10a}$ and $R^{11a}$ are hydrogen (hereinafter, R9-1),
a compound in which $R^{9a}$ is heterocyclic group optionally substituted by substituent group C, and $R^{8a}$, $R^{10a}$ and $R^{11a}$ are hydrogen (hereinafter, R9-2),
a compound in which $R^{9a}$ is carbocycle lower alkyl optionally substituted by substituent group C, and $R^{8a}$, $R^{10a}$, and $R^{11a}$ are hydrogen (hereinafter, R9-3)
Herein, the substituent group C is at least one selected from a substituent group consisting of halogen, cyano, hydroxy, carboxy, formyl, amino, oxo, nitro, lower alkyl, halogeno lower alkyl, lower alkyloxy, carbocyclic group, heterocyclic group, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, and lower alkylsulfonylamino.
Compounds in which, in the formula (III'), a combination of $R^{1a}$, $R^{2a}$, $R^{3a}$, $P^R$, as well as ($R^{5a}$, $R^{6a}$, and $R^{7a}$) is as follows.
(R1-1, R2-1, R3-1, Pr-1, R7-1), (R1-1, R2-1, R3-1, Pr-1, R7-2), (R1-1, R2-1, R3-1, Pr-1, R7-3), (R1-1, R2-1, R3-1, Pr-2, R7-1), (R1-1, R2-1, R3-1, Pr-2, R7-2), (R1-1, R2-1, R3-1, Pr-2, R7-3), (R1-1, R2-1, R3-1, Pr-3, R7-1), (R1-1, R2-1, R3-1, Pr-3, R7-2), (R1-1, R2-1, R3-1, Pr-3, R7-3), (R1-1, R2-1, R3-1, Pr-4, R7-1), (R1-1, R2-1, R3-1, Pr-4, R7-2), (R1-1, R2-1, R3-1, Pr-4, R7-3), (R1-1, R2-1, R3-2, Pr-1, R7-1), (R1-1, R2-1, R3-2, Pr-1, R7-2), (R1-1, R2-1, R3-2, Pr-1, R7-3), (R1-1, R2-1, R3-2, Pr-2, R7-1), (R1-1, R2-1, R3-2, Pr-2, R7-2), (R1-1, R2-1, R3-2, Pr-2, R7-3), (R1-1, R2-1, R3-2, Pr-3, R7-1), (R1-1, R2-1, R3-2, Pr-3, R7-2), (R1-1, R2-1, R3-2, Pr-3, R7-3), (R1-1, R2-1, R3-2, Pr-4, R7-1), (R1-1, R2-1, R3-2, Pr-4, R7-2), (R1-1, R2-1, R3-2, Pr-4, R7-3), (R1-1, R2-1, R3-3, Pr-1, R7-1), (R1-1, R2-1, R3-3, Pr-1, R7-2), (R1-1, R2-1, R3-3, Pr-1, R7-3), (R1-1, R2-1, R3-3, Pr-2, R7-1), (R1-1, R2-1, R3-3, Pr-2, R7-2), (R1-1, R2-1, R3-3, Pr-2, R7-3), (R1-1, R2-1, R3-3, Pr-3, R7-1), (R1-1, R2-1, R3-3, Pr-3, R7-2), (R1-1, R2-1, R3-3, Pr-3, R7-3), (R1-1, R2-1, R3-3, Pr-4, R7-1), (R1-1, R2-1, R3-3, Pr-4, R7-2), (R1-1, R2-1, R3-3, Pr-4, R7-3), (R1-1, R2-1, R3-4, Pr-1, R7-1), (R1-1, R2-1, R3-4, Pr-1, R7-2), (R1-1, R2-1, R3-4, Pr-1, R7-3), (R1-1, R2-1, R3-4, Pr-2, R7-1), (R1-1, R2-1, R3-4, Pr-2, R7-2), (R1-1, R2-1, R3-4, Pr-2, R7-3), (R1-1, R2-1, R3-4, Pr-3, R7-1), (R1-1, R2-1, R3-4, Pr-3, R7-2), (R1-1, R2-1, R3-4, Pr-3, R7-3), (R1-1, R2-1, R3-4, Pr-4, R7-1), (R1-1, R2-1, R3-4, Pr-4, R7-2), (R1-1, R2-1, R3-4, Pr-4, R7-3), (R1-1, R2-1, R3-5, Pr-1, R7-1), (R1-1, R2-1, R3-5, Pr-1, R7-2), (R1-1, R2-1, R3-5, Pr-1, R7-3), (R1-1, R2-1, R3-5, Pr-2, R7-1), (R1-1, R2-1, R3-5, Pr-2, R7-2), (R1-1, R2-1, R3-5, Pr-2, R7-3), (R1-1, R2-1, R3-5, Pr-3, R7-1), (R1-1, R2-1, R3-5, Pr-3, R7-2), (R1-1, R2-1, R3-5, Pr-3, R7-3), (R1-1, R2-1, R3-5, Pr-4, R7-1), (R1-1, R2-1, R3-5, Pr-4, R7-2), (R1-1, R2-1, R3-5, Pr-4, R7-3), (R1-1, R2-2, R3-1, Pr-1, R7-1), (R1-1, R2-2, R3-1, Pr-1, R7-2), (R1-1, R2-2, R3-1, Pr-1, R7-3), (R1-1, R2-2, R3-1, Pr-2, R7-1), (R1-1, R2-2, R3-1, Pr-2, R7-2), (R1-1, R2-2, R3-1, Pr-2, R7-3), (R1-1, R2-2, R3-1, Pr-3, R7-1), (R1-1, R2-2, R3-1, Pr-3, R7-2), (R1-1, R2-2, R3-1, Pr-3, R7-3), (R1-1, R2-2, R3-1, Pr-4, R7-1), (R1-1, R2-2, R3-1, Pr-4, R7-2), (R1-1, R2-2, R3-1, Pr-4, R7-3), (R1-1, R2-2, R3-2, Pr-1, R7-1), (R1-1, R2-2, R3-2, Pr-1, R7-2), (R1-1, R2-2, R3-2, Pr-1, R7-3), (R1-1, R2-2, R3-2, Pr-2, R7-1), (R1-1, R2-2, R3-2, Pr-2, R7-2), (R1-1, R2-2, R3-2, Pr-2, R7-3), (R1-1, R2-2, R3-2, Pr-3, R7-1), (R1-1, R2-2, R3-2, Pr-3, R7-2), (R1-1, R2-2, R3-2, Pr-3, R7-3), (R1-1, R2-2, R3-2, Pr-4, R7-1), (R1-1, R2-2, R3-2, Pr-4, R7-2), (R1-1, R2-2, R3-2, Pr-4, R7-3), (R1-1, R2-2, R3-3, Pr-1, R7-1), (R1-1, R2-2, R3-3, Pr-1, R7-2), (R1-1, R2-2, R3-3, Pr-1, R7-3), (R1-1, R2-2, R3-3, Pr-2, R7-1), (R1-1, R2-2, R3-3, Pr-2, R7-2), (R1-1, R2-2, R3-3, Pr-2, R7-3), (R1-1, R2-2, R3-3, Pr-3, R7-1), (R1-1, R2-2, R3-3, Pr-3, R7-2), (R1-1, R2-2, R3-3, Pr-3, R7-3), (R1-1, R2-2, R3-3, Pr-4, R7-1), (R1-1, R2-2, R3-3, Pr-4, R7-2), (R1-1, R2-2, R3-3, Pr-4, R7-3), (R1-1, R2-2, R3-4, Pr-1, R7-1), (R1-1, R2-2, R3-4, Pr-1, R7-2), (R1-1, R2-2, R3-4, Pr-1, R7-3), (R1-1, R2-2, R3-4, Pr-2, R7-1), (R1-1, R2-2, R3-4, Pr-2, R7-2), (R1-1, R2-2, R3-4, Pr-2, R7-3), (R1-1, R2-2, R3-4, Pr-3, R7-1) (R1-1, R2-2, R3-4, Pr-3, R7-2), (R1-1, R2-2, R3-4, Pr-3, R7-3), (R1-1, R2-2, R3-4, Pr-4, R7-1), (R1-1, R2-2, R3-4, Pr-4, R7-2), (R1-1, R2-2, R3-4, Pr-4, R7-3), (R1-1, R2-2, R3-5, Pr-1, R7-1), (R1-1, R2-2, R3-5, Pr-1, R7-2), (R1-1, R2-2, R3-5, Pr-1, R7-3), (R1-1, R2-2, R3-5, Pr-2, R7-1), (R1-1, R2-2, R3-5, Pr-2, R7-2), (R1-1, R2-2, R3-5, Pr-2, R7-3), (R1-1, R2-2, R3-5, Pr-3, R7-1), (R1-1, R2-2, R3-5, Pr-3, R7-2), (R1-1, R2-2, R3-5, Pr-3, R7-3), (R1-1, R2-2, R3-5, Pr-4, R7-1), (R1-1, R2-2, R3-5, Pr-4, R7-2), (R1-1, R2-2, R3-5, Pr-4, R7-3), (R1-2, R2-1, R3-1, Pr-1, R7-1), (R1-2, R2-1, R3-1, Pr-1, R7-2), (R1-2, R2-1, R3-1, Pr-1, R7-3), (R1-2, R2-1, R3-1, Pr-2, R7-1), (R1-2, R2-1, R3-1, Pr-2, R7-2), (R1-2, R2-1, R3-1, Pr-2, R7-3), (R1-2, R2-1, R3-1, Pr-3, R7-1), (R1-2, R2-1, R3-1, Pr-3, R7- 2), (R1-2, R2-1, R3-1, Pr-3, R7-3), (R1-2, R2-1, R3-1, Pr-4, R7-1), (R1-2, R2-1, R3-1, Pr-4, R7-2), (R1-2, R2-1, R3-1, Pr-4, R7-3), (R1-2, R2-1, R3-2, Pr-1, R7-1), (R1-2, R2-1, R3-2, Pr-1, R7-2), (R1-2, R2-1, R3-2, Pr-1, R7-3), (R1-2, R2-1, R3-2, Pr-2, R7-1), (R1-2, R2-1, R3-2, Pr-2, R7-2), (R1-2, R2-1, R3-2, Pr-2, R7-3), (R1-2, R2-1, R3-2, Pr-3, R7-1), (R1-2, R2-1, R3-2, Pr-3, R7-2), (R1-2, R2-1, R3-2, Pr-3, R7-3), (R1-2, R2-1, R3-2, Pr-4, R7-1), (R1-2, R2-1, R3-2, Pr-4, R7-2), (R1-2, R2-1, R3-2, Pr-4, R7-3), (R1-2, R2-1, R3-3, Pr-1, R7-1), (R1-2, R2-1, R3-1, Pr-1, R7-2), (R1-2, R2-1, R3-1, Pr-1, R7-3), (R1-2, R2-1, R3-1, Pr-2, R7-1), (R1-2, R2-1, R3-1, Pr-2, R7-2), (R1-2, R2-1, R3-1, Pr-2, R7-3), (R1-2, R2-1, R3-1, Pr-3, R7-1), (R1-2, R2-1, R3-1, Pr-3, R7- 2), (R1-2, R2-1, R3-1, Pr-3, R7-3), (R1-2, R2-1, R3-1, Pr-4, R7-1), (R1-2, R2-1, R3-1, Pr-4, R7-2), (R1-2, R2-1, R3-1, Pr-4, R7-3), (R1-2, R2-1, R3-2, Pr-1, R7-1), (R1-2, R2-1, R3-2, Pr-1, R7-2), (R1-2, R2-1, R3-2, Pr-1, R7-3), (R1-2, R2-1, R3-2, Pr-2, R7-1), (R1-2, R2-1, R3-2, Pr-2, R7-2), (R1-2, R2-1, R3-2, Pr-2, R7-3), (R1-2, R2-1, R3-2, Pr-3, R7-1), (R1-2, R2-1, R3-2, Pr-3, R7-2), (R1-2, R2-1, R3-2, Pr-3, R7-3), (R1-2, R2-1, R3-2, Pr-4, R7-1), (R1-2, R2-1, R3-2, Pr-4, R7-2), (R1-2, R2-1, R3-2, Pr-4, R7-3), (R1-2, R2-1, R3-3, Pr-1, R7-1), (R1-2, R2-1, R3-3, Pr-1, R7-2), (R1-2, R2-1, R3-3, Pr-1, R7-3), (R1-2, R2-1, R3-3, Pr-2, R7-1), (R1-2, R2-1, R3-3, Pr-2, R7-2), (R1-2, R2-1, R3-3, Pr-2, R7-3), (R1-2, R2-1, R3-3, Pr-3, R7-1), (R1-2, R2-1, R3-3, Pr-3, R7-2), (R1-2, R2-1, R3-3, Pr-3, R7-3), (R1-2, R2-1, R3-3, Pr-4, R7-1), (R1-2, R2-1, R3-3, Pr-4, R7-2), (R1-2, R2-1, R3-3, Pr-4, R7-3), (R1-2, R2-1, R3-4, Pr-1, R7-1), (R1-2, R2-1, R3-4, Pr-1, R7-2), (R1-2, R2-1, R3-4, Pr-1, R7-3), (R1-2, R2-1, R3-4, Pr-2, R7-1), (R1-2, R2-1, R3-4, Pr-2, R7-2), (R1-2, R2-1, R3-4, Pr-2, R7-3), (R1-2, R2-1, R3-4, Pr-3, R7-1), (R1-2, R2-1, R3-4, Pr-3, R7-2), (R1-2, R2-1, R3-4, Pr-3, R7-3), (R1-2, R2-1, R3-4, Pr-4, R7-1), (R1-2, R2-1, R3-4, Pr-4, R7-2), (R1-2, R2-1, R3-4, Pr-4, R7-3), (R1-2, R2-1, R3-5, Pr-1, R7-1), (R1-2, R2-1, R3-5, Pr-1, R7-2), (R1-2, R2-1, R3-5, Pr-1, R7-3), (R1-2, R2-1, R3-5, Pr-2, R7-1), (R1-2, R2-1, R3-5, Pr-2, R7-2), (R1-2, R2-1, R3-5, Pr-2, R7-3), (R1-2, R2-1, R3-5, Pr-3, R7-1), (R1-2, R2-1, R3-5, Pr-3, R7-2), (R1-2, R2-1, R3-5, Pr-3, R7-3), (R1-2, R2-1, R3-5, Pr-4, R7-1), (R1-2, R2-1, R3-5, Pr-4, R7-2), (R1-2, R2-1, R3-5, Pr-4, R7-3), (R1-2, R2-2, R3-1, Pr-1, R7-1), (R1-2, R2-2, R3-1, Pr-1, R7-2), (R1-2, R2-2, R3-1, Pr-1, R7-3), (R1-2, R2-2, R3-1, Pr-2, R7-1), (R1-2, R2-2, R3-1, Pr-2, R7-2), (R1-2, R2-2, R3-1, Pr-2, R7-3), (R1-2, R2-2, R3-1, Pr-3, R7-1), (R1-2, R2-2, R3-1, Pr-3, R7-2), (R1-2, R2-2, R3-1, Pr-3, R7-3), (R1-2, R2-2, R3-1, Pr-4, R7-1), (R1-2, R2-2, R3-1, Pr-4, R7-2), (R1-2, R2-2, R3-1, Pr-4, R7-3), (R1-2, R2-2, R3-2, Pr-1, R7-1), (R1-2, R2-2, R3-2, Pr-1, R7-2), (R1-2, R2-2, R3-2, Pr-1, R7-3), (R1-2, R2-2, R3-2, Pr-2, R7-1), (R1-2, R2-2, R3-2, Pr-2, R7-2), (R1-2, R2-2, R3-2, Pr-2, R7-3), (R1-2, R2-2, R3-2, Pr-3, R7-1), (R1-2, R2-2, R3-2, Pr-3, R7-2), (R1-2, R2-2, R3-2, Pr-3, R7-3), (R1-2, R2-2, R3-2, Pr-4, R7-1), (R1-2, R2-2, R3-2, Pr-4, R7-2), (R1-2, R2-2, R3-2, Pr-4, R7-3), (R1-2, R2-2, R3-3, Pr-1, R7-1), (R1-2, R2-2, R3-3, Pr-1, R7-2), (R1-2, R2-2, R3-3, Pr-1, R7-3), (R1-2, R2-2, R3-3, Pr-2, R7-1), (R1-2, R2-2, R3-3, Pr-2, R7-2), (R1-2, R2-2, R3-3, Pr-2, R7-3), (R1-2, R2-2, R3-3, Pr-3, R7-1), (R1-2, R2-2, R3-3, Pr-3, R7-2), (R1-2, R2-2, R3-3, Pr-3, R7-3), (R1-2, R2-2, R3-3, Pr-4, R7-1), (R1-2, R2-2, R3-3, Pr-4, R7-2), (R1-2, R2-2, R3-3, Pr-4, R7-3), (R1-2, R2-2, R3-4, Pr-1, R7-1), (R1-2, R2-2, R3-4, Pr-1, R7-2), (R1-2, R2-2, R3-4, Pr-1, R7-3), (R1-2, R2-2, R3-4, Pr-2, R7-1), (R1-2, R2-2, R3-4, Pr-2, R7-2), (R1-2, R2-2, R3-4, Pr-2, R7-3), (R1-2, R2-2, R3-4, Pr-3, R7-1), (R1-2, R2-2, R3-4, Pr-3, R7-2), (R1-2, R2-2, R3-4, Pr-3, R7-3), (R1-2, R2-2, R3-4, Pr-4, R7-1), (R1-2, R2-2, R3-4, Pr-4, R7-2), (R1-2, R2-2, R3-4, Pr-4, R7-3), (R1-2, R2-2, R3-5, Pr-1, R7-1), (R1-2, R2-2, R3-5, Pr-1, R7-2), (R1-2, R2-2, R3-5, Pr-1, R7-3), (R1-2, R2-2, R3-5, Pr-2, R7-1), (R1-2, R2-2, R3-5, Pr-2, R7-2), (R1-2, R2-2, R3-5, Pr-2, R7-3), (R1-2, R2-2, R3-5, Pr-3, R7-1), (R1-2, R2-2, R3-5, Pr-3, R7-2), (R1-2, R2-2, R3-5, Pr-3, R7-3), (R1-2, R2-2, R3-5, Pr-4, R7-1), (R1-2, R2-2, R3-5, Pr-4, R7-2), (R1-2, R2-2, R3-5, Pr-4, R7-3), (R1-3, R2-1, R3-1, Pr-1, R7-1), (R1-3, R2-1, R3-1, Pr-1, R7-2), (R1-3, R2-1, R3-1, Pr-1, R7-3), (R1-3, R2-1, R3-1, Pr-2, R7-1), (R1-3, R2-1, R3-1, Pr-2, R7-2), (R1-3, R2-1, R3-1, Pr-2, R7-3), (R1-3, R2-1, R3-1, Pr-3, R7-1), (R1-3, R2-1, R3-1, Pr-3, R7-2), (R1-3, R2-1, R3-1, Pr-3, R7-3), (R1-3, R2-1, R3-1, Pr-4, R7-1), (R1-3, R2-1, R3-1, Pr-4, R7-2), (R1-3, R2-1, R3-1, Pr-4, R7-3), (R1-3, R2-1, R3-2, Pr-1, R7-1), (R1-3, R2-1, R3-2, Pr-1, R7-2), (R1-3, R2-1, R3-2, Pr-1, R7-3), (R1-3, R2-1, R3-2, Pr-2, R7-1), (R1-3, R2-1, R3-2, Pr-2, R7-2), (R1-3, R2-1, R3-2, Pr-2, R7-3), (R1-3, R2-1, R3-2, Pr-3, R7-1), (R1-3, R2-1, R3-2, Pr-3, R7-2), (R1-3, R2-1, R3-2, Pr-3, R7-3), (R1-3, R2-1, R3-2, Pr-4, R7-1), (R1-3, R2-1, R3-2, Pr-4, R7-2), (R1-3, R2-1, R3-2, Pr-4, R7-3), (R1-3, R2-1, R3-3, Pr-1, R7-1), (R1-3, R2-1, R3-3, Pr-1, R7-2), (R1-3, R2-1, R3-3, Pr-1, R7-3), (R1-3, R2-1, R3-3, Pr-2, R7-1), (R1-3, R2-1, R3-3, Pr-2, R7-2), (R1-3, R2-1, R3-3, Pr-2, R7-3), (R1-3, R2-1, R3-3, Pr-3, R7-1), (R1-3, R2-1, R3-3, Pr-3, R7-2), (R1-3, R2-1, R3-3, Pr-3, R7-3), (R1-3, R2-1, R3-3, Pr-4, R7-1), (R1-3, R2-1, R3-3, Pr-4, R7-2), (R1-3, R2-1, R3-3, Pr-4, R7-3), (R1-3, R2-1, R3-4, Pr-1, R7-1), (R1-3, R2-1, R3-4, Pr-1, R7-2), (R1-3, R2-1, R3-4, Pr-1, R7-3), (R1-3, R2-1, R3-4, Pr-2, R7-1), (R1-3, R2-1, R3-4, Pr-2, R7-2), (R1-3, R2-1, R3-4, Pr-2, R7-3), (R1-3, R2-1, R3-4, Pr-3, R7-1), (R1-3, R2-1, R3-4, Pr-3, R7-2), (R1-3, R2-1, R3-4, Pr-3, R7-3), (R1-3, R2-1, R3-4, Pr-4, R7-1), (R1-3, R2-1, R3-4, Pr-4, R7-2), (R1-3, R2-1, R3-4, Pr-4, R7-3), (R1-3, R2-1, R3-5, Pr-1, R7-1), (R1-3, R2-1, R3-5, Pr-1, R7-2), (R1-3, R2-1, R3-5, Pr-1, R7-3), (R1-3, R2-1, R3-5, Pr-2, R7-1), (R1-3, R2-1, R3-5, Pr-2, R7-2), (R1-3, R2-1, R3-5, Pr-2, R7-3), (R1-3, R2-1, R3-5, Pr-3, R7-1), (R1-3, R2-1, R3-5, Pr-3, R7-2), (R1-3, R2-1, R3-5, Pr-3, R7-3), (R1-3, R2-1, R3-5, Pr-4, R7-1), (R1-3, R2-1, R3-5, Pr-4, R7-2), (R1-3, R2-1, R3-5, Pr-4, R7-3), (R1-3, R2-2, R3-1, Pr-1, R7-1), (R1-3, R2-2, R3-1, Pr-1, R7-2), (R1-3, R2-2, R3-1, Pr-1, R7-3), (R1-3, R2-2, R3-1, Pr-2, R7-1), (R1-3, R2-2, R3-1, Pr-2, R7-2), (R1-3, R2-2, R3-1, Pr-2, R7-3), (R1-3, R2-2, R3-1, Pr-3, R7-1), (R1-3, R2-2, R3-1, Pr-3, R7-2), (R1-3, R2-2, R3-1, Pr-3, R7-3), (R1-3, R2-2, R3-1, Pr-4, R7-1), (R1-3, R2-2, R3-1, Pr-4, R7-2), (R1-3, R2-2, R3-1, Pr-4, R7-3), (R1-3, R2-2, R3-2, Pr-1, R7-1), (R1-3, R2-2, R3-2, Pr-1, R7-2), (R1-3, R2-2, R3-2, Pr-1, R7-3), (R1-3, R2-2, R3-2, Pr-2, R7-1), (R1-3, R2-2, R3-2, Pr-2, R7-2), (R1-3, R2-2, R3-2, Pr-2, R7-3), (R1-3, R2-2, R3-2, Pr-3, R7-1), (R1-3, R2-2, R3-2, Pr-3, R7-2), (R1-3, R2-2, R3-2, Pr-3, R7-3), (R1-3, R2-2, R3-2, Pr-4, R7-1), (R1-3, R2-2, R3-2, Pr-4, R7-2), (R1-3, R2-2, R3-2, Pr-4, R7-3), (R1-3, R2-2, R3-3, Pr-1, R7-1), (R1-3, R2-2, R3-3, Pr-1, R7-2), (R1-3, R2-2, R3-3, Pr-1, R7-3), (R1-3, R2-2, R3-3, Pr-2, R7-1), (R1-3, R2-2, R3-3, Pr-2, R7-2), (R1-3, R2-2, R3-3, Pr-2, R7-3), (R1-3, R2-2, R3-3, Pr-3, R7-1), (R1-3, R2-2, R3-3, Pr-3, R7-2), (R1-3, R2-2, R3-3, Pr-3, R7-3), (R1-3, R2-2, R3-3, Pr-4, R7-1), (R1-3, R2-2, R3-3, Pr-4, R7-2), (R1-3, R2-2, R3-3, Pr-4, R7-3), (R1-3, R2-2, R3-4, Pr-1, R7-1), (R1-3, R2-2, R3-4, Pr-1, R7-2), (R1-3, R2-2, R3-4, Pr-1, R7-3), (R1-3, R2-2, R3-4, Pr-2, R7-1), (R1-3, R2-2, R3-4, Pr-2, R7-2), (R1-3, R2-2, R3-4, Pr-2, R7-3), (R1-3, R2-2, R3-4, Pr-3, R7-1), (R1-3, R2-2, R3-4, Pr-3, R7-2), (R1-3, R2-2, R3-4, Pr-3, R7-3), (R1-3, R2-2, R3-4, Pr-4, R7-1), (R1-3, R2-2, R3-4, Pr-4, R7-2), (R1-3, R2-2, R3-4, Pr-4, R7-3), (R1-3, R2-2, R3-5, Pr-1, R7-1), (R1-3, R2-2, R3-5, Pr-1, R7-2), (R1-3, R2-2, R3-5, Pr-1, R7-3), (R1-3, R2-2, R3-5, Pr-2, R7-1), (R1-3, R2-2, R3-5, Pr-2, R7-2), (R1-3, R2-2, R3-5, Pr-2, R7-3), (R1-3, R2-2, R3-5, Pr-3, R7-1), (R1-3, R2-2, R3-5, Pr-3, R7-2), (R1-3, R2-2, R3-5, Pr-3, R7-3), (R1-3, R2-2, R3-5, Pr-4, R7-1), (R1-3, R2-2, R3-5, Pr-4, R7-2), (R1-3, R2-2, R3-5, Pr-4, R7-3), (R1-4, R2-1, R3-1, Pr-1, R7-1), (R1-4, R2-1, R3-1, Pr-1, R7-2), (R1-4, R2-1, R3-1, Pr-1, R7-3), (R1-4, R2-1, R3-1, Pr-2, R7-1), (R1-4, R2-1, R3-1, Pr-2, R7-2), (R1-4, R2-1, R3-1, Pr-2, R7-3), (R1-4, R2-1, R3-1, Pr-3, R7-1), (R1-4, R2-1, R3-1, Pr-3, R7- 2), (R1-4, R2-1, R3-1, Pr-3, R7-3), (R1-4, R2-1, R3-1, Pr-4, R7-1), (R1-4, R2-1, R3-1, Pr-4, R7-2), (R1-4, R2-1, R3-1, Pr-4, R7-3), (R1-4, R2-1, R3-2, Pr-1, R7-1), (R1-4, R2-1, R3-2, Pr-1, R7-2), (R1-4, R2-1, R3-2, Pr-1, R7-3), (R1-4, R2-1, R3-2, Pr-2, R7-1), (R1-4, R2-1, R3-2, Pr-2, R7-2), (R1-4, R2-1, R3-2, Pr-2, R7-3), (R1-4, R2-1, R3-2, Pr-3, R7-1), (R1-4, R2-1, R3-2, Pr-3, R7-2), (R1-4, R2-1, R3-2, Pr-3, R7-3), (R1-4, R2-1, R3-2, Pr-4, R7-1), (R1-4, R2-1, R3-2, Pr-4, R7-2), (R1-4, R2-1, R3-2, Pr-4, R7-3), (R1-4, R2-1, R3-3, Pr-1, R7-1), (R1-4, R2-1, R3-3, Pr-1, R7-2), (R1-4, R2-1, R3-3, Pr-1, R7-3), (R1-4, R2-1, R3-3, Pr-2, R7-1), (R1-4, R2-1, R3-3, Pr-2, R7-2), (R1-4, R2-1, R3-3, Pr-2, R7-3), (R1-4, R2-1, R3-3, Pr-3, R7-1), (R1-4, R2-1, R3-3, Pr-3, R7-2), (R1-4, R2-1, R3-3, Pr-3, R7-3), (R1-4, R2-1, R3-3, Pr-4, R7-1), (R1-4, R2-1, R3-3, Pr-4, R7-2), (R1-4, R2-1, R3-3, Pr-4, R7-3), (R1-4, R2-1, R3-4, Pr-1, R7-1), (R1-4, R2-1, R3-4, Pr-1, R7-2), (R1-4, R2-1, R3-4, Pr-1, R7-3), (R1-4, R2-1, R3-4, Pr-2, R7-1), (R1-4, R2-1, R3-4, Pr-2, R7-2), (R1-4, R2-1, R3-4, Pr-2, R7-3), (R1-4, R2-1, R3-4, Pr-3, R7-1), (R1-4, R2-1, R3-4, Pr-3, R7-2), (R1-4, R2-1, R3-4, Pr-3, R7-3), (R1-4, R2-1, R3-4, Pr-4, R7-1), (R1-4, R2-1, R3-4, Pr-4, R7-2), (R1-4, R2-1, R3-4, Pr-4, R7-3), (R1-4, R2-1, R3-5, Pr-1, R7-1), (R1-4, R2-1, R3-5, Pr-1, R7-2), (R1-4, R2-1, R3-5, Pr-1, R7-3), (R1-4, R2-1, R3-5, Pr-2, R7-1), (R1-4, R2-1, R3-5, Pr-2, R7-2), (R1-4, R2-1, R3-5, Pr-2, R7-3), (R1-4, R2-1, R3-5, Pr-3, R7-1), (R1-4, R2-1, R3-5, Pr-3, R7-2), (R1-4, R2-1, R3-5, Pr-3, R7-3), (R1-4, R2-1, R3-5, Pr-4, R7-1), (R1-4, R2-1, R3-5, Pr-4, R7-2), (R1-4, R2-1, R3-5, Pr-4, R7-3), (R1-4, R2-2, R3-1, Pr-1, R7-1), (R1-4, R2-2, R3-1, Pr-1, R7-2), (R1-4, R2-2, R3-1, Pr-1, R7-3), (R1-4, R2-2, R3-1, Pr-2, R7-1), (R1-4, R2-2, R3-1, Pr-2, R7-2), (R1-4, R2-2, R3-1, Pr-2, R7-3), (R1-4, R2-2, R3-1, Pr-3, R7-1), (R1-4, R2-2, R3-1, Pr-3, R7-2), (R1-4, R2-2, R3-1, Pr-3, R7-3), (R1-4, R2-2, R3-1, Pr-4, R7-1), (R1-4, R2-2, R3-1, Pr-4, R7-2), (R1-4, R2-2, R3-1, Pr-4, R7-3), (R1-4, R2-2, R3-2, Pr-1, R7-1), (R1-4, R2-2, R3-2, Pr-1, R7-2), (R1-4, R2-2, R3-2, Pr-1, R7-3), (R1-4, R2-2, R3-2, Pr-2, R7-1), (R1-4, R2-2, R3-2, Pr-2, R7-2), (R1-4, R2-2, R3-2, Pr-2, R7-3), (R1-4, R2-2, R3-2, Pr-3, R7-1), (R1-4, R2-2, R3-2, Pr-3, R7-2), (R1-4, R2-2, R3-2, Pr-3, R7-3), (R1-4, R2-2, R3-2, Pr-4, R7-1), (R1-4, R2-2, R3-2, Pr-4, R7-2), (R1-4, R2-2, R3-2, Pr-4, R7-3), (R1-4, R2-2, R3-3, Pr-1, R7-1), (R1-4, R2-2, R3-3, Pr-1, R7-2), (R1-4, R2-2, R3-3, Pr-1, R7-3), (R1-4, R2-2, R3-3, Pr-2, R7-1), (R1-4, R2-2, R3-3, Pr-2, R7-2), (R1-4, R2-2, R3-3, Pr-2, R7-3), (R1-4, R2-2, R3-3, Pr-3, R7-1), (R1-4, R2-2, R3-3, Pr-3, R7-2), (R1-4, R2-2, R3-3, Pr-3, R7-3), (R1-4, R2-2, R3-3, Pr-4, R7-1), (R1-4, R2-2, R3-3, Pr-4, R7-2), (R1-4, R2-2, R3-3, Pr-4, R7-3), (R1-4, R2-2, R3-4, Pr-1, R7-1), (R1-4, R2-2, R3-4, Pr-1, R7-2), (R1-4, R2-2, R3-4, Pr-1, R7-3), (R1-4, R2-2, R3-4, Pr-2, R7-1), (R1-4, R2-2, R3-4, Pr-2, R7-2), (R1-4, R2-2, R3-4, Pr-2, R7-3), (R1-4, R2-2, R3-4, Pr-3, R7-1), (R1-4, R2-2, R3-4, Pr-3, R7-2), (R1-4, R2-2, R3-4, Pr-3, R7-3), (R1-4, R2-2, R3-4, Pr-4, R7-1), (R1-4, R2-2, R3-4, Pr-4, R7-2), (R1-4, R2-2, R3-4, Pr-4, R7-3), (R1-4, R2-2, R3-5, Pr-1, R7-1), (R1-4, R2-2, R3-5, Pr-1, R7-2), (R1-4, R2-2, R3-5, Pr-1, R7-3), (R1-4, R2-2, R3-5, Pr-2, R7-1), (R1-4, R2-2, R3-5, Pr-2, R7-2), (R1-4, R2-2, R3-5, Pr-2, R7-3), (R1-4, R2-2, R3-5, Pr-3, R7-1), (R1-4, R2-2, R3-5, Pr-3, R7-2), (R1-4, R2-2, R3-5, Pr-3, R7-3), (R1-4, R2-2, R3-5, Pr-4, R7-1), (R1-4, R2-2, R3-5, Pr-4, R7-2), (R1-4, R2-2, R3-5, Pr-4, R7-3), (R1-5, R2-1, R3-1, Pr-1, R7-1), (R1-5, R2-1, R3-1, Pr-1, R7-2), (R1-5, R2-1, R3-1, Pr-1, R7-3), (R1-5, R2-1, R3-1, Pr-2, R7-1), (R1-5, R2-1, R3-1, Pr-2, R7-2), (R1-5, R2-1, R3-1, Pr-2, R7-3), (R1-5, R2-1, R3-1, Pr-3, R7-1), (R1-5, R2-1, R3-1, Pr-3, R7-2), (R1-5, R2-1, R3-1, Pr-3, R7-3), (R1-5, R2-1, R3-1, Pr-4, R7-1), (R1-5, R2-1, R3-1, Pr-4, R7-2), (R1-5, R2-1, R3-1, Pr-4, R7-3), (R1-5, R2-1, R3-2, Pr-1, R7-1), (R1-5, R2-1, R3-2, Pr-1, R7-2), (R1-5, R2-1, R3-2, Pr-1, R7-3), (R1-5, R2-1, R3-2, Pr-2, R7-1), (R1-5, R2-1, R3-2, Pr-2, R7-2), (R1-5, R2-1, R3-2, Pr-2, R7-3), (R1-5, R2-1, R3-2, Pr-3, R7-1), (R1-5, R2-1, R3-2, Pr-3, R7-2), (R1-5, R2-1, R3-2, Pr-3, R7-3), (R1-5, R2-1, R3-2, Pr-4, R7-1), (R1-5, R2-1, R3-2, Pr-4, R7-2), (R1-5, R2-1, R3-2, Pr-4, R7-3), (R1-5, R2-1, R3-3, Pr-1, R7-1), (R1-5, R2-1, R3-3, Pr-1, R7-2), (R1-5, R2-1, R3-3, Pr-1, R7-3), (R1-5, R2-1, R3-3, Pr-2, R7-1), (R1-5, R2-1, R3-3, Pr-2, R7-2), (R1-5, R2-1, R3-3, Pr-2, R7-3), (R1-5, R2-1, R3-3, Pr-3, R7-1), (R1-5, R2-1, R3-3, Pr-3, R7-2), (R1-5, R2-1, R3-3, Pr-3, R7-3), (R1-5, R2-1, R3-3, Pr-4, R7-1), (R1-5, R2-1, R3-3, Pr-4, R7-2), (R1-5, R2-1, R3-3, Pr-4, R7-3), (R1-5, R2-1, R3-4, Pr-1, R7-1), (R1-5, R2-1, R3-4, Pr-1, R7-2), (R1-5, R2-1, R3-4, Pr-1, R7-3), (R1-5, R2-1, R3-4, Pr-2, R7-1), (R1-5, R2-1, R3-4, Pr-2, R7-2), (R1-5, R2-1, R3-4, Pr-2, R7-3), (R1-5, R2-1, R3-4, Pr-3, R7-1), (R1-5, R2-1, R3-4, Pr-3, R7-2), (R1-5, R2-1, R3-4, Pr-3, R7-3), (R1-5, R2-1, R3-4, Pr-4, R7-1), (R1-5, R2-1, R3-4, Pr-4, R7-2), (R1-5, R2-1, R3-4, Pr-4, R7-3), (R1-5, R2-1, R3-5, Pr-1, R7-1), (R1-5, R2-1, R3-5, Pr-1, R7-2), (R1-5, R2-1, R3-5, Pr-1, R7-3), (R1-5, R2-1, R3-5, Pr-2, R7-1), (R1-5, R2-1, R3-5, Pr-2, R7-2), (R1-5, R2-1, R3-5, Pr-2, R7-3), (R1-5, R2-1, R3-5, Pr-3, R7-1), (R1-5, R2-1, R3-5, Pr-3, R7-2), (R1-5, R2-1, R3-5, Pr-3, R7-3), (R1-5, R2-1, R3-5, Pr-4, R7-1), (R1-5, R2-1, R3-5, Pr-4, R7-2), (R1-5, R2-1, R3-5, Pr-4, R7-3), (R1-5, R2-2, R3-1, Pr-1, R7-1), (R1-5, R2-2, R3-1, Pr-1, R7-2), (R1-5, R2-2, R3-1, Pr-1, R7-3), (R1-5, R2-2, R3-1, Pr-2, R7-1), (R1-5, R2-2, R3-1, Pr-2, R7-2), (R1-5, R2-2, R3-1, Pr-2, R7-3), (R1-5, R2-2, R3-1, Pr-3, R7-1), (R1-5, R2-2, R3-1, Pr-3, R7-2), (R1-5, R2-2, R3-1, Pr-3, R7-3), (R1-5, R2-2, R3-1, Pr-4, R7-1), (R1-5, R2-2, R3-1, Pr-4, R7-2), (R1-5, R2-2, R3-1, Pr-4, R7-3), (R1-5, R2-2, R3-2, Pr-1, R7-1), (R1-5, R2-2, R3-2, Pr-1, R7-2), (R1-5, R2-2, R3-2, Pr-1, R7-3), (R1-5, R2-2, R3-2, Pr-2, R7-1), (R1-5, R2-2, R3-2, Pr-2, R7-2), (R1-5, R2-2, R3-2, Pr-2, R7-3), (R1-5, R2-2, R3-2, Pr-3, R7-1), (R1-5, R2-2, R3-2, Pr-3, R7-2), (R1-5, R2-2, R3-2, Pr-3, R7-3), (R1-5, R2-2, R3-2, Pr-4, R7-1), (R1-5, R2-2, R3-2, Pr-4, R7-2), (R1-5, R2-2, R3-2, Pr-4, R7-3), (R1-5, R2-2, R3-3, Pr-1, R7-1), (R1-5, R2-2, R3-3, Pr-1, R7-2), (R1-5, R2-2, R3-3, Pr-1, R7-3), (R1-5, R2-2, R3-3, Pr-2, R7-1), (R1-5, R2-2, R3-3, Pr-2, R7-2), (R1-5, R2-2, R3-3, Pr-2, R7-3), (R1-5, R2-2, R3-3, Pr-3, R7-1), (R1-5, R2-2, R3-3, Pr-3, R7-2), (R1-5, R2-2, R3-3, Pr-3, R7-3), (R1-5, R2-2, R3-3, Pr-4, R7-1), (R1-5, R2-2, R3-3, Pr-4, R7-2), (R1-5, R2-2, R3-3, Pr-4, R7-3), (R1-5, R2-2, R3-4, Pr-1, R7-1), (R1-5, R2-2, R3-4, Pr-1, R7-2), (R1-5, R2-2, R3-4, Pr-1, R7-3), (R1-5, R2-2, R3-4, Pr-2, R7-1), (R1-5, R2-2, R3-4, Pr-2, R7-2), (R1-5, R2-2, R3-4, Pr-2, R7-3), (R1-5, R2-2, R3-4, Pr-3, R7-1), (R1-5, R2-2, R3-4, Pr-3, R7-2), (R1-5, R2-2, R3-4, Pr-3, R7-3), (R1-5, R2-2, R3-4, Pr-4, R7-1), (R1-5, R2-2, R3-4, Pr-4, R7-2), (R1-5, R2-2, R3-4, Pr-4, R7-3), (R1-5, R2-2, R3-5, Pr-1, R7-1), (R1-5, R2-2, R3-5, Pr-1, R7-2), (R1-5, R2-2, R3-5, Pr-1, R7-3), (R1-5, R2-2, R3-5, Pr-2, R7-1), (R1-5, R2-2, R3-5, Pr-2, R7-2), (R1-5, R2-2, R3-5, Pr-2, R7-3), (R1-5, R2-2, R3-5, Pr-3, R7-1), (R1-5, R2-2, R3-5, Pr-3, R7-2), (R1-5, R2-2, R3-5, Pr-3, R7-3), (R1-5, R2-2, R3-5, Pr-4, R7-1), (R1-5, R2-2, R3-5, Pr-4, R7-2), (R1-5, R2-2, R3-5, Pr-4, R7-3), (R1-6, R2-1, R3-1, Pr-1, R7-1), (R1-6, R2-1, R3-1, Pr-1, R7-2), (R1-6, R2-1, R3-1, Pr-1, R7-3), (R1-6, R2-1, R3-1, Pr-2, R7-1), (R1-6, R2-1, R3-1, Pr-2, R7-2), (R1-6, R2-1, R3-1, Pr-2, R7-3), (R1-6, R2-1, R3-1, Pr-3, R7-1), (R1-6, R2-1, R3-1, Pr-3, R7- 2), (R1-6, R2-1, R3-1, Pr-3, R7-3), (R1-6, R2-1, R3-1, Pr-4, R7-1), (R1-6, R2-1, R3-1, Pr-4, R7-2), (R1-6, R2-1, R3-1, Pr-4, R7-3), (R1-6, R2-1, R3-2, Pr-1, R7-1), (R1-6, R2-1, R3-2, Pr-1, R7-2), (R1-6, R2-1, R3-2, Pr-1, R7-3), (R1-6, R2-1, R3-2, Pr-2, R7-1), (R1-6, R2-1, R3-2, Pr-2, R7-2), (R1-6, R2-1, R3-2, Pr-2, R7-3), (R1-6, R2-1, R3-2, Pr-3, R7-1), (R1-6, R2-1, R3-2, Pr-3, R7-2), (R1-6, R2-1, R3-2, Pr-3, R7-3), (R1-6, R2-1, R3-2, Pr-4, R7-1), (R1-6, R2-1, R3-2, Pr-4, R7-2), (R1-6, R2-1, R3-2, Pr-4, R7-3), (R1-6, R2-1, R3-3, Pr-1, R7-1), (R1-6, R2-1, R3-3, Pr-1, R7-2), (R1-6, R2-1, R3-3, Pr-1, R7-3), (R1-6, R2-1, R3-3, Pr-2, R7-1), (R1-6, R2-1, R3-3, Pr-2, R7-2), (R1-6, R2-1, R3-3, Pr-2, R7-3), (R1-6, R2-1, R3-3, Pr-3, R7-1), (R1-6, R2-1, R3-3, Pr-3, R7-2), (R1-6, R2-1, R3-3, Pr-3, R7-3), (R1-6, R2-1, R3-3, Pr-4, R7-1), (R1-6, R2-1, R3-3, Pr-4, R7-2), (R1-6, R2-1, R3-3, Pr-4, R7-3), (R1-6, R2-1, R3-4, Pr-1, R7-1), (R1-6, R2-1, R3-4, Pr-1, R7-2), (R1-6, R2-1, R3-4, Pr-1, R7-3), (R1-6, R2-1, R3-4, Pr-2, R7-1), (R1-6, R2-1, R3-4, Pr-2, R7-2), (R1-6, R2-1, R3-4, Pr-2, R7-3), (R1-6, R2-1, R3-4, Pr-3, R7-1), (R1-6, R2-1, R3-4, Pr-3, R7-2), (R1-6, R2-1, R3-4, Pr-3, R7-3), (R1-6, R2-1, R3-4, Pr-4, R7-1), (R1-6, R2-1, R3-4, Pr-4, R7-2), (R1-6, R2-1, R3-4, Pr-4, R7-3), (R1-6, R2-1, R3-5, Pr-1, R7-1), (R1-6, R2-1, R3-5, Pr-1, R7-2), (R1-6, R2-1, R3-5, Pr-1, R7-3), (R1-6, R2-1, R3-5, Pr-2, R7-1), (R1-6, R2-1, R3-5, Pr-2, R7-2), (R1-6, R2-1, R3-5, Pr-2, R7-3), (R1-6, R2-1, R3-5, Pr-3, R7-1), (R1-6, R2-1, R3-5, Pr-3, R7-2), (R1-6, R2-1, R3-5, Pr-3, R7-3), (R1-6, R2-1, R3-5, Pr-4, R7-1), (R1-6, R2-1, R3-5, Pr-4, R7-2), (R1-6, R2-1, R3-5, Pr-4, R7-3), (R1-6, R2-2, R3-1, Pr-1, R7-1), (R1-6, R2-2, R3-1, Pr-1, R7-2), (R1-6, R2-2, R3-1, Pr-1, R7-3), (R1-6, R2-2, R3-1, Pr-2, R7-1), (R1-6, R2-2, R3-1, Pr-2, R7-2), (R1-6, R2-2, R3-1, Pr-2, R7-3), (R1-6, R2-2, R3-1, Pr-3, R7-1), (R1-6, R2-2, R3-1, Pr-3, R7-2), (R1-6, R2-2, R3-1, Pr-3, R7-3), (R1-6, R2-2, R3-1, Pr-4, R7-1), (R1-6, R2-2, R3-1, Pr-4, R7-2), (R1-6, R2-2, R3-1, Pr-4, R7-3), (R1-6, R2-2, R3-2, Pr-1, R7-1), (R1-6, R2-2, R3-2, Pr-1, R7-2), (R1-6, R2-2, R3-2, Pr-1, R7-3), (R1-6, R2-2, R3-2, Pr-2, R7-1), (R1-6, R2-2, R3-2, Pr-2, R7-2), (R1-6, R2-2, R3-2, Pr-2, R7-3), (R1-6, R2-2, R3-2, Pr-3, R7-1), (R1-6, R2-2, R3-2, Pr-3, R7-2), (R1-6, R2-2, R3-2, Pr-3, R7-3), (R1-6, R2-2, R3-2, Pr-4, R7-1), (R1-6, R2-2, R3-2, Pr-4, R7-2), (R1-6, R2-2, R3-2, Pr-4, R7-3), (R1-6, R2-2, R3-3, Pr-1, R7-1), (R1-6, R2-2, R3-3, Pr-1, R7-2), (R1-6, R2-2, R3-3, Pr-1, R7-3), (R1-6, R2-2, R3-3, Pr-2, R7-1), (R1-6, R2-2, R3-3, Pr-2, R7-2), (R1-6, R2-2, R3-3, Pr-2, R7-3), (R1-6, R2-2, R3-3, Pr-3, R7-1), (R1-6, R2-2, R3-3, Pr-3, R7-2), (R1-6, R2-2, R3-3, Pr-3, R7-3), (R1-6, R2-2, R3-3, Pr-4, R7-1), (R1-6, R2-2, R3-3, Pr-4, R7-2), (R1-6, R2-2, R3-3, Pr-4, R7-3), (R1-6, R2-2, R3-4, Pr-1, R7-1), (R1-6, R2-2, R3-4, Pr-1, R7-2), (R1-6, R2-2, R3-4, Pr-1, R7-3), (R1-6, R2-2, R3-4, Pr-2, R7-1), (R1-6, R2-2, R3-4, Pr-2, R7-2), (R1-6, R2-2, R3-4, Pr-2, R7-3), (R1-6, R2-2, R3-4, Pr-3, R7-1), (R1-6, R2-2, R3-4, Pr-3, R7-2), (R1-6, R2-2, R3-4, Pr-3, R7-3), (R1-6, R2-2, R3-4, Pr-4, R7-1), (R1-6, R2-2, R3-4, Pr-4, R7-2), (R1-6, R2-2, R3-4, Pr-4, R7-3), (R1-6, R2-2, R3-5, Pr-1, R7-1), (R1-6, R2-2, R3-5, Pr-1, R7-2), (R1-6, R2-2, R3-5, Pr-1, R7-3), (R1-6, R2-2, R3-5, Pr-2, R7-1), (R1-6, R2-2, R3-5, Pr-2, R7-2), (R1-6, R2-2, R3-5, Pr-2, R7-3), (R1-6, R2-2, R3-5, Pr-3, R7-1), (R1-6, R2-2, R3-5, Pr-3, R7-2), (R1-6, R2-2, R3-5, Pr-3, R7-3), (R1-6, R2-2, R3-5, Pr-4, R7-1), (R1-6, R2-2, R3-5, Pr-4, R7-2), (R1-6, R2-2, R3-5, Pr-4, R7-3)

(R1-7, R2-1, R3-1, Pr-1, R7-1), (R1-7, R2-1, R3-1, Pr-1, R7-2), (R1-7, R2-1, R3-1, Pr-1, R7-3), (R1-7, R2-1, R3-1, Pr-2, R7-1), (R1-7, R2-1, R3-1, Pr-2, R7-2), (R1-7, R2-1, R3-1, Pr-2, R7-3), (R1-7, R2-1, R3-1, Pr-3, R7-1), (R1-7, R2-1, R3-1, Pr-3, R7-2), (R1-7, R2-1, R3-1, Pr-3, R7-3), (R1-7, R2-1, R3-1, Pr-4, R7-1), (R1-7, R2-1, R3-1, Pr-4, R7-2), (R1-7, R2-1, R3-1, Pr-4, R7-3), (R1-7, R2-1, R3-2, Pr-1, R7-1), (R1-7, R2-1, R3-2, Pr-1, R7-2), (R1-7, R2-1, R3-2, Pr-1, R7-3), (R1-7, R2-1, R3-2, Pr-2, R7-1), (R1-7, R2-1, R3-2, Pr-2, R7-2), (R1-7, R2-1, R3-2, Pr-2, R7-3), (R1-7, R2-1, R3-2, Pr-3, R7-1), (R1-7, R2-1, R3-2, Pr-3, R7-2), (R1-7, R2-1, R3-2, Pr-3, R7-3), (R1-7, R2-1, R3-2, Pr-4, R7-1), (R1-7, R2-1, R3-2, Pr-4, R7-2), (R1-7, R2-1, R3-2, Pr-4, R7-3), (R1-7, R2-1, R3-3, Pr-1, R7-1), (R1-7, R2-1, R3-3, Pr-1, R7-2), (R1-7, R2-1, R3-3, Pr-1, R7-3), (R1-7, R2-1, R3-3, Pr-2, R7-1), (R1-7, R2-1, R3-3, Pr-2, R7-2), (R1-7, R2-1, R3-3, Pr-2, R7-3), (R1-7, R2-1, R3-3, Pr-3, R7-1), (R1-7, R2-1, R3-3, Pr-3, R7-2), (R1-7, R2-1, R3-3, Pr-3, R7-3), (R1-7, R2-1, R3-3, Pr-4, R7-1), (R1-7, R2-1, R3-3, Pr-4, R7-2), (R1-7, R2-1, R3-3, Pr-4, R7-3), (R1-7, R2-1, R3-4, Pr-1, R7-1), (R1-7, R2-1, R3-4, Pr-1, R7-2), (R1-7, R2-1, R3-4, Pr-1, R7-3), (R1-7, R2-1, R3-4, Pr-2, R7-1), (R1-7, R2-1, R3-4, Pr-2, R7-2), (R1-7, R2-1, R3-4, Pr-2, R7-3), (R1-7, R2-1, R3-4, Pr-3, R7-1), (R1-7, R2-1, R3-4, Pr-3, R7-2), (R1-7, R2-1, R3-4, Pr-3, R7-3), (R1-7, R2-1, R3-4, Pr-4, R7-1), (R1-7, R2-1, R3-4, Pr-4, R7-2), (R1-7, R2-1, R3-4, Pr-4, R7-3), (R1-7, R2-1, R3-5, Pr-1, R7-1), (R1-7, R2-1, R3-5, Pr-1, R7-2), (R1-7, R2-1, R3-5, Pr-1, R7-3), (R1-7, R2-1, R3-5, Pr-2, R7-1), (R1-7, R2-1, R3-5, Pr-2, R7-2), (R1-7, R2-1, R3-5, Pr-2, R7-3), (R1-7, R2-1, R3-5, Pr-3, R7-1), (R1-7, R2-1, R3-5, Pr-3, R7-2), (R1-7, R2-1, R3-5, Pr-3, R7-3), (R1-7, R2-1, R3-5, Pr-4, R7-1), (R1-7, R2-1, R3-5, Pr-4, R7-2), (R1-7, R2-1, R3-5, Pr-4, R7-3), (R1-7, R2-2, R3-1, Pr-1, R7-1), (R1-7, R2-2, R3-1, Pr-1, R7-2), (R1-7, R2-2, R3-1, Pr-1, R7-3), (R1-7, R2-2, R3-1, Pr-2, R7-1), (R1-7, R2-2, R3-1, Pr-2, R7-2), (R1-7, R2-2, R3-1, Pr-2, R7-3), (R1-7, R2-2, R3-1, Pr-3, R7-1), (R1-7, R2-2, R3-1, Pr-3, R7-2), (R1-7, R2-2, R3-1, Pr-3, R7-3), (R1-7, R2-2, R3-1, Pr-4, R7-1), (R1-7, R2-2, R3-1, Pr-4, R7-2), (R1-7, R2-2, R3-1, Pr-4, R7-3), (R1-7, R2-2, R3-2, Pr-1, R7-1), (R1-7, R2-2, R3-2, Pr-1, R7-2), (R1-7, R2-2, R3-2, Pr-1, R7-3), (R1-7, R2-2, R3-2, Pr-2, R7-1), (R1-7, R2-2, R3-2, Pr-2, R7-2), (R1-7, R2-2, R3-2, Pr-2, R7-3), (R1-7, R2-2, R3-2, Pr-3, R7-1), (R1-7, R2-2, R3-2, Pr-3, R7-2), (R1-7, R2-2, R3-2, Pr-3, R7-3), (R1-7, R2-2, R3-2, Pr-4, R7-1), (R1-7, R2-2, R3-2, Pr-4, R7-2), (R1-7, R2-2, R3-2, Pr-4, R7-3), (R1-7, R2-2, R3-3, Pr-1, R7-1), (R1-7, R2-2, R3-3, Pr-1, R7-2), (R1-7, R2-2, R3-3, Pr-1, R7-3), (R1-7, R2-2, R3-3, Pr-2, R7-1), (R1-7, R2-2, R3-3, Pr-2, R7-2), (R1-7, R2-2, R3-3, Pr-2, R7-3), (R1-7, R2-2, R3-3, Pr-3, R7-1), (R1-7, R2-2, R3-3, Pr-3, R7-2), (R1-7, R2-2, R3-3, Pr-3, R7-3), (R1-7, R2-2, R3-3, Pr-4, R7-1), (R1-7, R2-2, R3-3, Pr-4, R7-2), (R1-7, R2-2, R3-3, Pr-4, R7-3), (R1-7, R2-2, R3-4, Pr-1, R7-1), (R1-7, R2-2, R3-4, Pr-1, R7-2), (R1-7, R2-2, R3-4, Pr-1, R7-3), (R1-7, R2-2, R3-4, Pr-2, R7-1), (R1-7, R2-2, R3-4, Pr-2, R7-2), (R1-7, R2-2, R3-4, Pr-2, R7-3), (R1-7, R2-2, R3-4, Pr-3, R7-1), (R1-7, R2-2, R3-4, Pr-3, R7-2), (R1-7, R2-2, R3-4, Pr-3, R7-3), (R1-7, R2-2, R3-4, Pr-4, R7-1), (R1-7, R2-2, R3-4, Pr-4, R7-2), (R1-7, R2-2, R3-4, Pr-4, R7-3), (R1-7, R2-2, R3-5, Pr-1, R7-1), (R1-7, R2-2, R3-5, Pr-1, R7-2), (R1-7, R2-2, R3-5, Pr-1, R7-3), (R1-7, R2-2, R3-5, Pr-2, R7-1), (R1-7, R2-2, R3-5, Pr-2, R7-2), (R1-7, R2-2, R3-5, Pr-2, R7-3), (R1-7, R2-2, R3-5, Pr-3, R7-1), (R1-7, R2-2, R3-5, Pr-3, R7-2), (R1-7, R2-2, R3-5, Pr-3, R7-3), (R1-7, R2-2, R3-5, Pr-4, R7-1), (R1-7, R2-2, R3-5, Pr-4, R7-2), (R1-7, R2-2, R3-5, Pr-4, R7-3), (R1-8, R2-1, R3-1, Pr-1, R7-1), (R1-8, R2-1, R3-1, Pr-1, R7-2), (R1-8, R2-1, R3-1, Pr-1, R7-3), (R1-8, R2-1, R3-1, Pr-2, R7-1), (R1-8, R2-1, R3-1, Pr-2, R7-2), (R1-8, R2-1, R3-1, Pr-2, R7-3), (R1-8, R2-1, R3-1, Pr-3, R7-1), (R1-8, R2-1, R3-1, Pr-3, R7-2), (R1-8, R2-1, R3-1, Pr-3, R7-3), (R1-8, R2-1, R3-1, Pr-4, R7-1), (R1-8, R2-1, R3-1, Pr-4, R7-2), (R1-8, R2-1, R3-1, Pr-4, R7-3), (R1-8, R2-1, R3-2, Pr-1, R7-1), (R1-8, R2-1, R3-2, Pr-1, R7-2), (R1-8, R2-1, R3-2, Pr-1, R7-3), (R1-8, R2-1, R3-2, Pr-2, R7-1), (R1-8, R2-1, R3-2, Pr-2, R7-2), (R1-8, R2-1, R3-2, Pr-2, R7-3), (R1-8, R2-1, R3-2, Pr-3, R7-1), (R1-8, R2-1, R3-2, Pr-3, R7-2), (R1-8, R2-1, R3-2, Pr-3, R7-3), (R1-8, R2-1, R3-2, Pr-4, R7-1), (R1-8, R2-1, R3-2, Pr-4, R7-2), (R1-8, R2-1, R3-2, Pr-4, R7-3), (R1-8, R2-1, R3-3, Pr-1, R7-1), (R1-8, R2-1, R3-3, Pr-1, R7-2), (R1-8, R2-1, R3-3, Pr-1, R7-3), (R1-8, R2-1, R3-3, Pr-2, R7-1), (R1-8, R2-1, R3-3, Pr-2, R7-2), (R1-8, R2-1, R3-3, Pr-2, R7-3), (R1-8, R2-1, R3-3, Pr-3, R7-1), (R1-8, R2-1, R3-3, Pr-3, R7-2), (R1-8, R2-1, R3-3, Pr-3, R7-3), (R1-8, R2-1, R3-3, Pr-4, R7-1), (R1-8, R2-1, R3-3, Pr-4, R7-2), (R1-8, R2-1, R3-3, Pr-4, R7-3), (R1-8, R2-1, R3-4, Pr-1, R7-1), (R1-8, R2-1, R3-4, Pr-1, R7-2), (R1-8, R2-1, R3-4, Pr-1, R7-3), (R1-8, R2-1, R3-4, Pr-2, R7-1), (R1-8, R2-1, R3-4, Pr-2, R7-2), (R1-8, R2-1, R3-4, Pr-2, R7-3), (R1-8, R2-1, R3-4, Pr-3, R7-1), (R1-8, R2-1, R3-4, Pr-3, R7-2), (R1-8, R2-1, R3-4, Pr-3, R7-3), (R1-8, R2-1, R3-4, Pr-4, R7-1), (R1-8, R2-1, R3-4, Pr-4, R7-2), (R1-8, R2-1, R3-4, Pr-4, R7-3), (R1-8, R2-1, R3-5, Pr-1, R7-1), (R1-8, R2-1, R3-5, Pr-1, R7-2), (R1-8, R2-1, R3-5, Pr-1, R7-3), (R1-8, R2-1, R3-5, Pr-2, R7-1), (R1-8, R2-1, R3-5, Pr-2, R7-2), (R1-8, R2-1, R3-5, Pr-2, R7-3), (R1-8, R2-1, R3-5, Pr-3, R7-1), (R1-8, R2-1, R3-5, Pr-3, R7-2), (R1-8, R2-1, R3-5, Pr-3, R7-3), (R1-8, R2-1, R3-5, Pr-4, R7-1), (R1-8, R2-1, R3-5, Pr-4, R7-2), (R1-8, R2-1, R3-5, Pr-4, R7-3), (R1-8, R2-2, R3-1, Pr-1, R7-1), (R1-8, R2-2, R3-1, Pr-1, R7-2), (R1-8, R2-2, R3-1, Pr-1, R7-3), (R1-8, R2-2, R3-1, Pr-2, R7-1), (R1-8, R2-2, R3-1, Pr-2, R7-2), (R1-8, R2-2, R3-1, Pr-2, R7-3), (R1-8, R2-2, R3-1, Pr-3, R7-1), (R1-8, R2-2, R3-1, Pr-3, R7-2), (R1-8, R2-2, R3-1, Pr-3, R7-3), (R1-8, R2-2, R3-1, Pr-4, R7-1), (R1-8, R2-2, R3-1, Pr-4, R7-2), (R1-8, R2-2, R3-1, Pr-4, R7-3), (R1-8, R2-2, R3-2, Pr-1, R7-1), (R1-8, R2-2, R3-2, Pr-1, R7-2), (R1-8, R2-2, R3-2, Pr-1, R7-3), (R1-8, R2-2, R3-2, Pr-2, R7-1), (R1-8, R2-2, R3-2, Pr-2, R7-2), (R1-8, R2-2, R3-2, Pr-2, R7-3), (R1-8, R2-2, R3-2, Pr-3, R7-1), (R1-8, R2-2, R3-2, Pr-3, R7-2), (R1-8, R2-2, R3-2, Pr-3, R7-3), (R1-8, R2-2, R3-2, Pr-4, R7-1), (R1-8, R2-2, R3-2, Pr-4, R7-2), (R1-8, R2-2, R3-2, Pr-4, R7-3), (R1-8, R2-2, R3-3, Pr-1, R7-1), (R1-8, R2-2, R3-3, Pr-1, R7-2), (R1-8, R2-2, R3-3, Pr-1, R7-3), (R1-8, R2-2, R3-3, Pr-2, R7-1), (R1-8, R2-2, R3-3, Pr-2, R7-2), (R1-8, R2-2, R3-3, Pr-2, R7-3), (R1-8, R2-2, R3-3, Pr-3, R7-1), (R1-8, R2-2, R3-3, Pr-3, R7-2), (R1-8, R2-2, R3-3, Pr-3, R7-3), (R1-8, R2-2, R3-3, Pr-4, R7-1), (R1-8, R2-2, R3-3, Pr-4, R7-2), (R1-8, R2-2, R3-3, Pr-4, R7-3), (R1-8, R2-2, R3-4, Pr-1, R7-1), (R1-8, R2-2, R3-4, Pr-1, R7-2), (R1-8, R2-2, R3-4, Pr-1, R7-3), (R1-8, R2-2, R3-4, Pr-2, R7-1), (R1-8, R2-2, R3-4, Pr-2, R7-2), (R1-8, R2-2, R3-4, Pr-2, R7-3), (R1-8, R2-2, R3-4, Pr-3, R7-1), (R1-8, R2-2, R3-4, Pr-3, R7-2), (R1-8, R2-2, R3-4, Pr-3, R7-3), (R1-8, R2-2, R3-4, Pr-4, R7-1), (R1-8, R2-2, R3-4, Pr-4, R7-2), (R1-8, R2-2, R3-4, Pr-4, R7-3), (R1-8, R2-2, R3-5, Pr-1, R7-1), (R1-8, R2-2, R3-5, Pr-1, R7-2), (R1-8, R2-2, R3-5, Pr-1, R7-3), (R1-8, R2-2, R3-5, Pr-2, R7-1), (R1-8, R2-2, R3-5, Pr-2, R7-2), (R1-8, R2-2, R3-5, Pr-2, R7-3), (R1-8, R2-2, R3-5, Pr-3, R7-1), (R1-8, R2-2, R3-5, Pr-3, R7-2), (R1-8, R2-2, R3-5, Pr-3, R7-3), (R1-8, R2-2, R3-5, Pr-4, R7-1), (R1-8, R2-2, R3-5, Pr-4, R7-2), (R1-8, R2-2, R3-5, Pr-4, R7-3).

Compounds in which, in the formula (III), a combination of $R^{1a}$, $R^{2a}$, $R^{3a}$, $P^R$, as well as ($R^{8a}$, $R^{9a}$, $R^{10a}$, and $R^{11a}$) is as follows.

(R1-1, R2-1, R3-1, Pr-1, R9-1), (R1-1, R2-1, R3-1, Pr-1, R9-2), (R1-1, R2-1, R3-1, Pr-1, R9-3), (R1-1, R2-1, R3-1, Pr-2, R9-1), (R1-1, R2-1, R3-1, Pr-2, R9-2), (R1-1, R2-1, R3-1, Pr-2, R9-3), (R1-1, R2-1, R3-1, Pr-3, R9-1), (R1-1, R2-1, R3-1, Pr-3, R9-2), (R1-1, R2-1, R3-1, Pr-3, R9-3), (R1-1, R2-1, R3-1, Pr-4, R9-1), (R1-1, R2-1, R3-1, Pr-4, R9-2), (R1-1, R2-1, R3-1, Pr-4, R9-3), (R1-1, R2-1, R3-2, Pr-1, R9-1), (R1-1, R2-1, R3-2, Pr-1, R9-2), (R1-1, R2-1, R3-2, Pr-1, R9-3), (R1-1, R2-1, R3-2, Pr-2, R9-1), (R1-1, R2-1, R3-2, Pr-2, R9-2), (R1-1, R2-1, R3-2, Pr-2, R9-3), (R1-1, R2-1, R3-2, Pr-3, R9-1), (R1-1, R2-1, R3-2, Pr-3, R9-2), (R1-1, R2-1, R3-2, Pr-3, R9-3), (R1-1, R2-1, R3-2, Pr-4, R9-1), (R1-1, R2-1, R3-2, Pr-4, R9-2), (R1-1, R2-1, R3-2, Pr-4, R9-3), (R1-1, R2-1, R3-3, Pr-1, R9-1), (R1-1, R2-1, R3-3, Pr-1, R9-2), (R1-1, R2-1, R3-3, Pr-1, R9-3), (R1-1, R2-1, R3-3, Pr-2, R9-1), (R1-1, R2-1, R3-3, Pr-2, R9-2), (R1-1, R2-1, R3-3, Pr-2, R9-3), (R1-1, R2-1, R3-3, Pr-3, R9-1), (R1-1, R2-1, R3-3, Pr-3, R9-2), (R1-1, R2-1, R3-3, Pr-3, R9-3), (R1-1, R2-1, R3-3, Pr-4, R9-1), (R1-1, R2-1, R3-3, Pr-4, R9-2), (R1-1, R2-1, R3-3, Pr-4, R9-3), (R1-1, R2-1, R3-4, Pr-1, R9-1), (R1-1, R2-1, R3-4, Pr-1, R9-2), (R1-1, R2-1, R3-4, Pr-1, R9-3), (R1-1, R2-1, R3-4, Pr-2, R9-1), (R1-1, R2-1, R3-4, Pr-2, R9-2), (R1-1, R2-1, R3-4, Pr-2, R9-3), (R1-1, R2-1, R3-4, Pr-3, R9-1), (R1-1, R2-1, R3-4, Pr-3, R9-2), (R1-1, R2-1, R3-4, Pr-3, R9-3), (R1-1, R2-1, R3-4, Pr-4, R9-1), (R1-1, R2-1, R3-4, Pr-4, R9-2), (R1-1, R2-1, R3-4, Pr-4, R9-3), (R1-1, R2-1, R3-5, Pr-1, R9-1), (R1-1, R2-1, R3-5, Pr-1, R9-2), (R1-1, R2-1, R3-5, Pr-1, R9-3), (R1-1, R2-1, R3-5, Pr-2, R9-1), (R1-1, R2-1, R3-5, Pr-2, R9-2), (R1-1, R2-1, R3-5, Pr-2, R9-3), (R1-1, R2-1, R3-5, Pr-3, R9-1), (R1-1, R2-1, R3-5, Pr-3, R9-2), (R1-1, R2-1, R3-5, Pr-3, R9-3), (R1-1, R2-1, R3-5, Pr-4, R9-1), (R1-1, R2-1, R3-5, Pr-4, R9-2), (R1-1, R2-1, R3-5, Pr-4, R9-3), (R1-1, R2-2, R3-1, Pr-1, R9-1), (R1-1, R2-2, R3-1, Pr-1, R9-2), (R1-1, R2-2, R3-1, Pr-1, R9-3), (R1-1, R2-2, R3-1, Pr-2, R9-1), (R1-1, R2-2, R3-1, Pr-2, R9-2), (R1-1, R2-2, R3-1, Pr-2, R9-3), (R1-1, R2-2, R3-1, Pr-3, R9-1), (R1-1, R2-2, R3-1, Pr-3, R9-2), (R1-1, R2-2, R3-1, Pr-3, R9-3), (R1-1, R2-2, R3-1, Pr-4, R9-1), (R1-1, R2-2, R3-1, Pr-4, R9-2), (R1-1, R2-2, R3-1, Pr-4, R9-3), (R1-1, R2-2, R3-2, Pr-1, R9-1), (R1-1, R2-2, R3-2, Pr-1, R9-2), (R1-1, R2-2, R3-2, Pr-1, R9-3), (R1-1, R2-2, R3-2, Pr-2, R9-1), (R1-1, R2-2, R3-2, Pr-2, R9-2), (R1-1, R2-2, R3-2, Pr-2, R9-3), (R1-1, R2-2, R3-2, Pr-3, R9-1), (R1-1, R2-2, R3-2, Pr-3, R9-2), (R1-1, R2-2, R3-2, Pr-3, R9-3), (R1-1, R2-2, R3-2, Pr-4, R9-1), (R1-1, R2-2, R3-2, Pr-4, R9-2), (R1-1, R2-2, R3-2, Pr-4, R9-3), (R1-1, R2-2, R3-3, Pr-1, R9-1), (R1-1, R2-2, R3-3, Pr-1, R9-2), (R1-1, R2-2, R3-3, Pr-1, R9-3), (R1-1, R2-2, R3-3, Pr-2, R9-1), (R1-1, R2-2, R3-3, Pr-2, R9-2), (R1-1, R2-2, R3-3, Pr-2, R9-3), (R1-1, R2-2, R3-3, Pr-3, R9-1), (R1-1, R2-2, R3-3, Pr-3, R9-2), (R1-1, R2-2, R3-3, Pr-3, R9-3), (R1-1, R2-2, R3-3, Pr-4, R9-1), (R1-1, R2-2, R3-3, Pr-4, R9-2), (R1-1, R2-2, R3-3, Pr-4, R9-3), (R1-1, R2-2, R3-4, Pr-1, R9-1), (R1-1, R2-2, R3-4, Pr-1, R9-2), (R1-1, R2-2, R3-4, Pr-1, R9-3), (R1-1, R2-2, R3-4, Pr-2, R9-1), (R1-1, R2-2, R3-4, Pr-2, R9-2), (R1-1, R2-2, R3-4, Pr-2, R9-3), (R1-1, R2-2, R3-4, Pr-3, R9-1), (R1-1, R2-2, R3-4, Pr-3, R9-2), (R1-1, R2-2, R3-4, Pr-3, R9-3), (R1-1, R2-2, R3-4, Pr-4, R9-1), (R1-1, R2-2, R3-4, Pr-4, R9-2), (R1-1, R2-2, R3-4, Pr-4, R9-3), (R1-1, R2-2, R3-5, Pr-1, R9-1), (R1-1, R2-2, R3-5, Pr-1, R9-2), (R1-1, R2-2, R3-5, Pr-1, R9-3), (R1-1, R2-2, R3-5, Pr-2, R9-1), (R1-1, R2-2, R3-5, Pr-2, R9-2), (R1-1, R2-2, R3-5, Pr-2, R9-3), (R1-1, R2-2, R3-5, Pr-3, R9-1), (R1-1, R2-2, R3-5, Pr-3, R9-2), (R1-1, R2-2, R3-5, Pr-3, R9-3), (R1-1, R2-2, R3-5, Pr-4, R9-1), (R1-1, R2-2, R3-5, Pr-4, R9-2), (R1-1, R2-2, R3-5, Pr-4, R9-3), (R1-2, R2-1, R3-1, Pr-1, R9-1), (R1-2, R2-1, R3-1, Pr-1, R9-2), (R1-2, R2-1, R3-1, Pr-1, R9-3), (R1-2, R2-1, R3-1, Pr-2, R9-1), (R1-2, R2-1, R3-1, Pr-2, R9-2), (R1-2, R2-1, R3-1, Pr-2, R9-3), (R1-2, R2-1, R3-1, Pr-3, R9-1), (R1-2, R2-1, R3-1, Pr-3, R9- 2), (R1-2, R2-1, R3-1, Pr-3, R9-3), (R1-2, R2-1, R3-1, Pr-4, R9-1), (R1-2, R2-1, R3-1, Pr-4, R9-2), (R1-2, R2-1, R3-1, Pr-4, R9-3), (R1-2, R2-1, R3-2, Pr-1, R9-1), (R1-2, R2-1, R3-2, Pr-1, R9-2), (R1-2, R2-1, R3-2, Pr-1, R9-3), (R1-2, R2-1, R3-2, Pr-2, R9-1), (R1-2, R2-1, R3-2, Pr-2, R9-2), (R1-2, R2-1, R3-2, Pr-2, R9-3), (R1-2, R2-1, R3-2, Pr-3, R9-1), (R1-2, R2-1, R3-2, Pr-3, R9-2), (R1-2, R2-1, R3-2, Pr-3, R9-3), (R1-2, R2-1, R3-2, Pr-4, R9-1), (R1-2, R2-1, R3-2, Pr-4, R9-2), (R1-2, R2-1, R3-2, Pr-4, R9-3), (R1-2, R2-1, R3-3, Pr-1, R9-1), (R1-2, R2-1, R3-3, Pr-1, R9-2), (R1-2, R2-1, R3-3, Pr-1, R9-3), (R1-2, R2-1, R3-3, Pr-2, R9-1), (R1-2, R2-1, R3-3, Pr-2, R9-2), (R1-2, R2-1, R3-3, Pr-2, R9-3), (R1-2, R2-1, R3-3, Pr-3, R9-1), (R1-2, R2-1, R3-3, Pr-3, R9-2), (R1-2, R2-1, R3-3, Pr-3, R9-3), (R1-2, R2-1, R3-3, Pr-4, R9-1), (R1-2, R2-1, R3-3, Pr-4, R9-2), (R1-2, R2-1, R3-3, Pr-4, R9-3), (R1-2, R2-1, R3-4, Pr-1, R9-1), (R1-2, R2-1, R3-4, Pr-1, R9-2), (R1-2, R2-1, R3-4, Pr-1, R9-3), (R1-2, R2-1, R3-4, Pr-2, R9-1), (R1-2, R2-1, R3-4, Pr-2, R9-2), (R1-2, R2-1, R3-4, Pr-2, R9-3), (R1-2, R2-1, R3-4, Pr-3, R9-1), (R1-2, R2-1, R3-4, Pr-3, R9-2), (R1-2, R2-1, R3-4, Pr-3, R9-3), (R1-2, R2-1, R3-4, Pr-4, R9-1), (R1-2, R2-1, R3-4, Pr-4, R9-2), (R1-2, R2-1, R3-4, Pr-4, R9-3), (R1-2, R2-1, R3-5, Pr-1, R9-1), (R1-2, R2-1, R3-5, Pr-1, R9-2), (R1-2, R2-1, R3-5, Pr-1, R9-3), (R1-2, R2-1, R3-5, Pr-2, R9-1), (R1-2, R2-1, R3-5, Pr-2, R9-2), (R1-2, R2-1, R3-5, Pr-2, R9-3), (R1-2, R2-1, R3-5, Pr-3, R9-1), (R1-2, R2-1, R3-5, Pr-3, R9-2), (R1-2, R2-1, R3-5, Pr-3, R9-3), (R1-2, R2-1, R3-5, Pr-4, R9-1), (R1-2, R2-1, R3-5, Pr-4, R9-2), (R1-2, R2-1, R3-5, Pr-4, R9-3), (R1-2, R2-2, R3-1, Pr-1, R9-1), (R1-2, R2-2, R3-1, Pr-1, R9-2), (R1-2, R2-2, R3-1, Pr-1, R9-3), (R1-2, R2-2, R3-1, Pr-2, R9-1), (R1-2, R2-2, R3-1, Pr-2, R9-2), (R1-2, R2-2, R3-1, Pr-2, R9-3), (R1-2, R2-2, R3-1, Pr-3, R9-1), (R1-2, R2-2, R3-1, Pr-3, R9-2), (R1-2, R2-2, R3-1, Pr-3, R9-3), (R1-2, R2-2, R3-1, Pr-4, R9-1), (R1-2, R2-2, R3-1, Pr-4, R9-2), (R1-2, R2-2, R3-1, Pr-4, R9-3), (R1-2, R2-2, R3-2, Pr-1, R9-1), (R1-2, R2-2, R3-2, Pr-1, R9-2), (R1-2, R2-2, R3-2, Pr-1, R9-3), (R1-2, R2-2, R3-2, Pr-2, R9-1), (R1-2, R2-2, R3-2, Pr-2, R9-2), (R1-2, R2-2, R3-2, Pr-2, R9-3), (R1-2, R2-2, R3-2, Pr-3, R9-1), (R1-2, R2-2, R3-2, Pr-3, R9-2), (R1-2, R2-2, R3-2, Pr-3, R9-3), (R1-2, R2-2, R3-2, Pr-4, R9-1), (R1-2, R2-2, R3-2, Pr-4, R9-2), (R1-2, R2-2, R3-2, Pr-4, R9-3), (R1-2, R2-2, R3-3, Pr-1, R9-1), (R1-2, R2-2, R3-3, Pr-1, R9-2), (R1-2, R2-2, R3-3, Pr-1, R9-3), (R1-2, R2-2, R3-3, Pr-2, R9-1), (R1-2, R2-2, R3-3, Pr-2, R9-2), (R1-2, R2-2, R3-3, Pr-2, R9-3), (R1-2, R2-2, R3-3, Pr-3, R9-1), (R1-2, R2-2, R3-3, Pr-3, R9-2), (R1-2, R2-2, R3-3, Pr-3, R9-3), (R1-2, R2-2, R3-3, Pr-4, R9-1), (R1-2, R2-2, R3-3, Pr-4, R9-2), (R1-2, R2-2, R3-3, Pr-4, R9-3), (R1-2, R2-2, R3-4, Pr-1, R9-1), (R1-2, R2-2, R3-4, Pr-1, R9-2), (R1-2, R2-2, R3-4, Pr-1, R9-3), (R1-2, R2-2, R3-4, Pr-2, R9-1), (R1-2, R2-2, R3-4, Pr-2, R9-2), (R1-2, R2-2, R3-4, Pr-2, R9-3), (R1-2, R2-2, R3-4, Pr-3, R9-1), (R1-2, R2-2, R3-4, Pr-3, R9-2), (R1-2, R2-2, R3-4, Pr-3, R9-3), (R1-2, R2-2, R3-4, Pr-4, R9-1), (R1-2, R2-2, R3-4, Pr-4, R9-2), (R1-2, R2-2, R3-4, Pr-4, R9-3), (R1-2, R2-2, R3-5, Pr-1, R9-1), (R1-2, R2-2, R3-5, Pr-1, R9-2), (R1-2, R2-2, R3-5, Pr-1, R9-3), (R1-2, R2-2, R3-5, Pr-2, R9-1), (R1-2, R2-2, R3-5, Pr-2, R9-2), (R1-2, R2-2, R3-5, Pr-2, R9-3), (R1-2, R2-2,

R3-5, Pr-3, R9-1), (R1-2, R2-2, R3-5, Pr-3, R9-2), (R1-2, R2-2, R3-5, Pr-3, R9-3), (R1-2, R2-2, R3-5, Pr-4, R9-1), (R1-2, R2-2, R3-5, Pr-4, R9-2), (R1-2, R2-2, R3-5, Pr-4, R9-3), (R1-3, R2-1, R3-1, Pr-1, R9-1), (R1-3, R2-1, R3-1, Pr-1, R9-2), (R1-3, R2-1, R3-1, Pr-1, R9-3), (R1-3, R2-1, R3-1, Pr-2, R9-1), (R1-3, R2-1, R3-1, Pr-2, R9-2), (R1-3, R2-1, R3-1, Pr-2, R9-3), (R1-3, R2-1, R3-1, Pr-3, R9-1), (R1-3, R2-1, R3-1, Pr-3, R9-2), (R1-3, R2-1, R3-1, Pr-3, R9-3), (R1-3, R2-1, R3-1, Pr-4, R9-1), (R1-3, R2-1, R3-1, Pr-4, R9-2), (R1-3, R2-1, R3-1, Pr-4, R9-3), (R1-3, R2-1, R3-2, Pr-1, R9-1), (R1-3, R2-1, R3-2, Pr-1, R9-2), (R1-3, R2-1, R3-2, Pr-1, R9-3), (R1-3, R2-1, R3-2, Pr-2, R9-1), (R1-3, R2-1, R3-2, Pr-2, R9-2), (R1-3, R2-1, R3-2, Pr-2, R9-3), (R1-3, R2-1, R3-2, Pr-3, R9-1), (R1-3, R2-1, R3-2, Pr-3, R9-2), (R1-3, R2-1, R3-2, Pr-3, R9-3), (R1-3, R2-1, R3-2, Pr-4, R9-1), (R1-3, R2-1, R3-2, Pr-4, R9-2), (R1-3, R2-1, R3-2, Pr-4, R9-3), (R1-3, R2-1, R3-3, Pr-1, R9-1), (R1-3, R2-1, R3-3, Pr-1, R9-2), (R1-3, R2-1, R3-3, Pr-1, R9-3), (R1-3, R2-1, R3-3, Pr-2, R9-1), (R1-3, R2-1, R3-3, Pr-2, R9-2), (R1-3, R2-1, R3-3, Pr-2, R9-3), (R1-3, R2-1, R3-3, Pr-3, R9-1), (R1-3, R2-1, R3-3, Pr-3, R9-2), (R1-3, R2-1, R3-3, Pr-3, R9-3), (R1-3, R2-1, R3-3, Pr-4, R9-1), (R1-3, R2-1, R3-3, Pr-4, R9-2), (R1-3, R2-1, R3-3, Pr-4, R9-3), (R1-3, R2-1, R3-4, Pr-1, R9-1), (R1-3, R2-1, R3-4, Pr-1, R9-2), (R1-3, R2-1, R3-4, Pr-1, R9-3), (R1-3, R2-1, R3-4, Pr-2, R9-1), (R1-3, R2-1, R3-4, Pr-2, R9-2), (R1-3, R2-1, R3-4, Pr-2, R9-3), (R1-3, R2-1, R3-4, Pr-3, R9-1), (R1-3, R2-1, R3-4, Pr-3, R9-2), (R1-3, R2-1, R3-4, Pr-3, R9-3), (R1-3, R2-1, R3-4, Pr-4, R9-1), (R1-3, R2-1, R3-4, Pr-4, R9-2), (R1-3, R2-1, R3-4, Pr-4, R9-3), (R1-3, R2-1, R3-5, Pr-1, R9-1), (R1-3, R2-1, R3-5, Pr-1, R9-2), (R1-3, R2-1, R3-5, Pr-1, R9-3), (R1-3, R2-1, R3-5, Pr-2, R9-1), (R1-3, R2-1, R3-5, Pr-2, R9-2), (R1-3, R2-1, R3-5, Pr-2, R9-3), (R1-3, R2-1, R3-5, Pr-3, R9-1), (R1-3, R2-1, R3-5, Pr-3, R9-2), (R1-3, R2-1, R3-5, Pr-3, R9-3), (R1-3, R2-1, R3-5, Pr-4, R9-1), (R1-3, R2-1, R3-5, Pr-4, R9-2), (R1-3, R2-1, R3-5, Pr-4, R9-3), (R1-3, R2-2, R3-1, Pr-1, R9-1), (R1-3, R2-2, R3-1, Pr-1, R9-2), (R1-3, R2-2, R3-1, Pr-1, R9-3), (R1-3, R2-2, R3-1, Pr-2, R9-1), (R1-3, R2-2, R3-1, Pr-2, R9-2), (R1-3, R2-2, R3-1, Pr-2, R9-3), (R1-3, R2-2, R3-1, Pr-3, R9-1), (R1-3, R2-2, R3-1, Pr-3, R9-2), (R1-3, R2-2, R3-1, Pr-3, R9-3), (R1-3, R2-2, R3-1, Pr-4, R9-1), (R1-3, R2-2, R3-1, Pr-4, R9-2), (R1-3, R2-2, R3-1, Pr-4, R9-3), (R1-3, R2-2, R3-2, Pr-1, R9-1), (R1-3, R2-2, R3-2, Pr-1, R9-2), (R1-3, R2-2, R3-2, Pr-1, R9-3), (R1-3, R2-2, R3-2, Pr-2, R9-1), (R1-3, R2-2, R3-2, Pr-2, R9-2), (R1-3, R2-2, R3-2, Pr-2, R9-3), (R1-3, R2-2, R3-2, Pr-3, R9-1), (R1-3, R2-2, R3-2, Pr-3, R9-2), (R1-3, R2-2, R3-2, Pr-3, R9-3), (R1-3, R2-2, R3-2, Pr-4, R9-1), (R1-3, R2-2, R3-2, Pr-4, R9-2), (R1-3, R2-2, R3-2, Pr-4, R9-3), (R1-3, R2-2, R3-3, Pr-1, R9-1), (R1-3, R2-2, R3-3, Pr-1, R9-2), (R1-3, R2-2, R3-3, Pr-1, R9-3), (R1-3, R2-2, R3-3, Pr-2, R9-1), (R1-3, R2-2, R3-3, Pr-2, R9-2), (R1-3, R2-2, R3-3, Pr-2, R9-3), (R1-3, R2-2, R3-3, Pr-3, R9-1), (R1-3, R2-2, R3-3, Pr-3, R9-2), (R1-3, R2-2, R3-3, Pr-3, R9-3), (R1-3, R2-2, R3-3, Pr-4, R9-1), (R1-3, R2-2, R3-3, Pr-4, R9-2), (R1-3, R2-2, R3-3, Pr-4, R9-3), (R1-3, R2-2, R3-4, Pr-1, R9-1), (R1-3, R2-2, R3-4, Pr-1, R9-2), (R1-3, R2-2, R3-4, Pr-1, R9-3), (R1-3, R2-2, R3-4, Pr-2, R9-1), (R1-3, R2-2, R3-4, Pr-2, R9-2), (R1-3, R2-2, R3-4, Pr-2, R9-3), (R1-3, R2-2, R3-4, Pr-3, R9-1), (R1-3, R2-2, R3-4, Pr-3, R9-2), (R1-3, R2-2, R3-4, Pr-3, R9-3), (R1-3, R2-2, R3-4, Pr-4, R9-1), (R1-3, R2-2, R3-4, Pr-4, R9-2), (R1-3, R2-2, R3-4, Pr-4, R9-3), (R1-3, R2-2, R3-5, Pr-1, R9-1), (R1-3, R2-2, R3-5, Pr-1, R9-2), (R1-3, R2-2, R3-5, Pr-1, R9-3), (R1-3, R2-2, R3-5, Pr-2, R9-1), (R1-3, R2-2, R3-5, Pr-2, R9-2), (R1-3, R2-2, R3-5, Pr-2, R9-3), (R1-3, R2-2, R3-5, Pr-3, R9-1), (R1-3, R2-2, R3-5, Pr-3, R9-2), (R1-3, R2-2, R3-5, Pr-3, R9-3), (R1-3, R2-2, R3-5, Pr-4, R9-1), (R1-3, R2-2, R3-5, Pr-4, R9-2), (R1-3, R2-2, R3-5, Pr-4, R9-3), (R1-4, R2-1, R3-1, Pr-1, R9-1), (R1-4, R2-1, R3-1, Pr-1, R9-2), (R1-4, R2-1, R3-1, Pr-1, R9-3), (R1-4, R2-1, R3-1, Pr-2, R9-1), (R1-4, R2-1, R3-1, Pr-2, R9-2), (R1-4, R2-1, R3-1, Pr-2, R9-3), (R1-4, R2-1, R3-1, Pr-3, R9-1), (R1-4, R2-1, R3-1, Pr-3, R9- 2), (R1-4, R2-1, R3-1, Pr-3, R9-3), (R1-4, R2-1, R3-1, Pr-4, R9-1), (R1-4, R2-1, R3-1, Pr-4, R9-2), (R1-4, R2-1, R3-1, Pr-4, R9-3), (R1-4, R2-1, R3-2, Pr-1, R9-1), (R1-4, R2-1, R3-2, Pr-1, R9-2), (R1-4, R2-1, R3-2, Pr-1, R9-3), (R1-4, R2-1, R3-2, Pr-2, R9-1), (R1-4, R2-1, R3-2, Pr-2, R9-2), (R1-4, R2-1, R3-2, Pr-2, R9-3), (R1-4, R2-1, R3-2, Pr-3, R9-1), (R1-4, R2-1, R3-2, Pr-3, R9-2), (R1-4, R2-1, R3-2, Pr-3, R9-3), (R1-4, R2-1, R3-2, Pr-4, R9-1), (R1-4, R2-1, R3-2, Pr-4, R9-2), (R1-4, R2-1, R3-2, Pr-4, R9-3), (R1-4, R2-1, R3-3, Pr-1, R9-1), (R1-4, R2-1, R3-3, Pr-1, R9-2), (R1-4, R2-1, R3-3, Pr-1, R9-3), (R1-4, R2-1, R3-3, Pr-2, R9-1), (R1-4, R2-1, R3-3, Pr-2, R9-2), (R1-4, R2-1, R3-3, Pr-2, R9-3), (R1-4, R2-1, R3-3, Pr-3, R9-1), (R1-4, R2-1, R3-3, Pr-3, R9-2), (R1-4, R2-1, R3-3, Pr-3, R9-3), (R1-4, R2-1, R3-3, Pr-4, R9-1), (R1-4, R2-1, R3-3, Pr-4, R9-2), (R1-4, R2-1, R3-3, Pr-4, R9-3), (R1-4, R2-1, R3-4, Pr-1, R9-1), (R1-4, R2-1, R3-4, Pr-1, R9-2), (R1-4, R2-1, R3-4, Pr-1, R9-3), (R1-4, R2-1, R3-4, Pr-2, R9-1), (R1-4, R2-1, R3-4, Pr-2, R9-2), (R1-4, R2-1, R3-4, Pr-2, R9-3), (R1-4, R2-1, R3-4, Pr-3, R9-1), (R1-4, R2-1, R3-4, Pr-3, R9-2), (R1-4, R2-1, R3-4, Pr-3, R9-3), (R1-4, R2-1, R3-4, Pr-4, R9-1), (R1-4, R2-1, R3-4, Pr-4, R9-2), (R1-4, R2-1, R3-4, Pr-4, R9-3), (R1-4, R2-1, R3-5, Pr-1, R9-1), (R1-4, R2-1, R3-5, Pr-1, R9-2), (R1-4, R2-1, R3-5, Pr-1, R9-3), (R1-4, R2-1, R3-5, Pr-2, R9-1), (R1-4, R2-1, R3-5, Pr-2, R9-2), (R1-4, R2-1, R3-5, Pr-2, R9-3), (R1-4, R2-1, R3-5, Pr-3, R9-1), (R1-4, R2-1, R3-5, Pr-3, R9-2), (R1-4, R2-1, R3-5, Pr-3, R9-3), (R1-4, R2-1, R3-5, Pr-4, R9-1), (R1-4, R2-1, R3-5, Pr-4, R9-2), (R1-4, R2-1, R3-5, Pr-4, R9-3), (R1-4, R2-2, R3-1, Pr-1, R9-1), (R1-4, R2-2, R3-1, Pr-1, R9-2), (R1-4, R2-2, R3-1, Pr-1, R9-3), (R1-4, R2-2, R3-1, Pr-2, R9-1), (R1-4, R2-2, R3-1, Pr-2, R9-2), (R1-4, R2-2, R3-1, Pr-2, R9-3), (R1-4, R2-2, R3-1, Pr-3, R9-1), (R1-4, R2-2, R3-1, Pr-3, R9-2), (R1-4, R2-2, R3-1, Pr-3, R9-3), (R1-4, R2-2, R3-1, Pr-4, R9-1), (R1-4, R2-2, R3-1, Pr-4, R9-2), (R1-4, R2-2, R3-1, Pr-4, R9-3), (R1-4, R2-2, R3-2, Pr-1, R9-1), (R1-4, R2-2, R3-2, Pr-1, R9-2), (R1-4, R2-2, R3-2, Pr-1, R9-3), (R1-4, R2-2, R3-2, Pr-2, R9-1), (R1-4, R2-2, R3-2, Pr-2, R9-2), (R1-4, R2-2, R3-2, Pr-2, R9-3), (R1-4, R2-2, R3-2, Pr-3, R9-1), (R1-4, R2-2, R3-2, Pr-3, R9-2), (R1-4, R2-2, R3-2, Pr-3, R9-3), (R1-4, R2-2, R3-2, Pr-4, R9-1), (R1-4, R2-2, R3-2, Pr-4, R9-2), (R1-4, R2-2, R3-2, Pr-4, R9-3), (R1-4, R2-2, R3-3, Pr-1, R9-1), (R1-4, R2-2, R3-3, Pr-1, R9-2), (R1-4, R2-2, R3-3, Pr-1, R9-3), (R1-4, R2-2, R3-3, Pr-2, R9-1), (R1-4, R2-2, R3-3, Pr-2, R9-2), (R1-4, R2-2, R3-3, Pr-2, R9-3), (R1-4, R2-2, R3-3, Pr-3, R9-1), (R1-4, R2-2, R3-3, Pr-3, R9-2), (R1-4, R2-2, R3-3, Pr-3, R9-3), (R1-4, R2-2, R3-3, Pr-4, R9-1), (R1-4, R2-2, R3-3, Pr-4, R9-2), (R1-4, R2-2, R3-3, Pr-4, R9-3), (R1-4, R2-2, R3-4, Pr-1, R9-1), (R1-4, R2-2, R3-4, Pr-1, R9-2), (R1-4, R2-2, R3-4, Pr-1, R9-3), (R1-4, R2-2, R3-4, Pr-2, R9-1), (R1-4, R2-2, R3-4, Pr-2, R9-2), (R1-4, R2-2, R3-4, Pr-2, R9-3), (R1-4, R2-2, R3-4, Pr-3, R9-1), (R1-4, R2-2, R3-4, Pr-3, R9-2), (R1-4, R2-2, R3-4, Pr-3, R9-3), (R1-4, R2-2, R3-4, Pr-4, R9-1), (R1-4, R2-2, R3-4, Pr-4, R9-2), (R1-4, R2-2, R3-4, Pr-4, R9-3), (R1-4, R2-2, R3-5, Pr-1, R9-1), (R1-4, R2-2, R3-5, Pr-1, R9-2), (R1-4, R2-2, R3-5, Pr-1, R9-3), (R1-4, R2-2, R3-5, Pr-2, R9-1), (R1-4, R2-2, R3-5, Pr-2, R9-2), (R1-4, R2-2,

R3-5, Pr-2, R9-3), (R1-4, R2-2, R3-5, Pr-3, R9-1), (R1-4, R2-2, R3-5, Pr-3, R9-2), (R1-4, R2-2, R3-5, Pr-3, R9-3), (R1-4, R2-2, R3-5, Pr-4, R9-1), (R1-4, R2-2, R3-5, Pr-4, R9-2), (R1-4, R2-2, R3-5, Pr-4, R9-3),
(R1-5, R2-1, R3-1, Pr-1, R9-1), (R1-5, R2-1, R3-1, Pr-1, R9-2), (R1-5, R2-1, R3-1, Pr-1, R9-3), (R1-5, R2-1, R3-1, Pr-2, R9-1), (R1-5, R2-1, R3-1, Pr-2, R9-2), (R1-5, R2-1, R3-1, Pr-2, R9-3), (R1-5, R2-1, R3-1, Pr-3, R9-1), (R1-5, R2-1, R3-1, Pr-3, R9-2), (R1-5, R2-1, R3-1, Pr-3, R9-3), (R1-5, R2-1, R3-1, Pr-4, R9-1), (R1-5, R2-1, R3-1, Pr-4, R9-2), (R1-5, R2-1, R3-1, Pr-4, R9-3), (R1-5, R2-1, R3-2, Pr-1, R9-1), (R1-5, R2-1, R3-2, Pr-1, R9-2), (R1-5, R2-1, R3-2, Pr-1, R9-3), (R1-5, R2-1, R3-2, Pr-2, R9-1), (R1-5, R2-1, R3-2, Pr-2, R9-2), (R1-5, R2-1, R3-2, Pr-2, R9-3), (R1-5, R2-1, R3-2, Pr-3, R9-1), (R1-5, R2-1, R3-2, Pr-3, R9-2), (R1-5, R2-1, R3-2, Pr-3, R9-3), (R1-5, R2-1, R3-2, Pr-4, R9-1), (R1-5, R2-1, R3-2, Pr-4, R9-2), (R1-5, R2-1, R3-2, Pr-4, R9-3), (R1-5, R2-1, R3-3, Pr-1, R9-1), (R1-5, R2-1, R3-3, Pr-1, R9-2), (R1-5, R2-1, R3-3, Pr-1, R9-3), (R1-5, R2-1, R3-3, Pr-2, R9-1), (R1-5, R2-1, R3-3, Pr-2, R9-2), (R1-5, R2-1, R3-3, Pr-2, R9-3), (R1-5, R2-1, R3-3, Pr-3, R9-1), (R1-5, R2-1, R3-3, Pr-3, R9-2), (R1-5, R2-1, R3-3, Pr-3, R9-3), (R1-5, R2-1, R3-3, Pr-4, R9-1), (R1-5, R2-1, R3-3, Pr-4, R9-2), (R1-5, R2-1, R3-3, Pr-4, R9-3), (R1-5, R2-1, R3-4, Pr-1, R9-1), (R1-5, R2-1, R3-4, Pr-1, R9-2), (R1-5, R2-1, R3-4, Pr-1, R9-3), (R1-5, R2-1, R3-4, Pr-2, R9-1), (R1-5, R2-1, R3-4, Pr-2, R9-2), (R1-5, R2-1, R3-4, Pr-2, R9-3), (R1-5, R2-1, R3-4, Pr-3, R9-1), (R1-5, R2-1, R3-4, Pr-3, R9-2), (R1-5, R2-1, R3-4, Pr-3, R9-3), (R1-5, R2-1, R3-4, Pr-4, R9-1), (R1-5, R2-1, R3-4, Pr-4, R9-2), (R1-5, R2-1, R3-4, Pr-4, R9-3), (R1-5, R2-1, R3-5, Pr-1, R9-1), (R1-5, R2-1, R3-5, Pr-1, R9-2), (R1-5, R2-1, R3-5, Pr-1, R9-3), (R1-5, R2-1, R3-5, Pr-2, R9-1), (R1-5, R2-1, R3-5, Pr-2, R9-2), (R1-5, R2-1, R3-5, Pr-2, R9-3), (R1-5, R2-1, R3-5, Pr-3, R9-1), (R1-5, R2-1, R3-5, Pr-3, R9-2), (R1-5, R2-1, R3-5, Pr-3, R9-3), (R1-5, R2-1, R3-5, Pr-4, R9-1), (R1-5, R2-1, R3-5, Pr-4, R9-2), (R1-5, R2-1, R3-5, Pr-4, R9-3), (R1-5, R2-2, R3-1, Pr-1, R9-1), (R1-5, R2-2, R3-1, Pr-1, R9-2), (R1-5, R2-2, R3-1, Pr-1, R9-3), (R1-5, R2-2, R3-1, Pr-2, R9-1), (R1-5, R2-2, R3-1, Pr-2, R9-2), (R1-5, R2-2, R3-1, Pr-2, R9-3), (R1-5, R2-2, R3-1, Pr-3, R9-1), (R1-5, R2-2, R3-1, Pr-3, R9-2), (R1-5, R2-2, R3-1, Pr-3, R9-3), (R1-5, R2-2, R3-1, Pr-4, R9-1), (R1-5, R2-2, R3-1, Pr-4, R9-2), (R1-5, R2-2, R3-1, Pr-4, R9-3), (R1-5, R2-2, R3-2, Pr-1, R9-1), (R1-5, R2-2, R3-2, Pr-1, R9-2), (R1-5, R2-2, R3-2, Pr-1, R9-3), (R1-5, R2-2, R3-2, Pr-2, R9-1), (R1-5, R2-2, R3-2, Pr-2, R9-2), (R1-5, R2-2, R3-2, Pr-2, R9-3), (R1-5, R2-2, R3-2, Pr-3, R9-1), (R1-5, R2-2, R3-2, Pr-3, R9-2), (R1-5, R2-2, R3-2, Pr-3, R9-3), (R1-5, R2-2, R3-2, Pr-4, R9-1), (R1-5, R2-2, R3-2, Pr-4, R9-2), (R1-5, R2-2, R3-2, Pr-4, R9-3), (R1-5, R2-2, R3-3, Pr-1, R9-1), (R1-5, R2-2, R3-3, Pr-1, R9-2), (R1-5, R2-2, R3-3, Pr-1, R9-3), (R1-5, R2-2, R3-3, Pr-2, R9-1), (R1-5, R2-2, R3-3, Pr-2, R9-2), (R1-5, R2-2, R3-3, Pr-2, R9-3), (R1-5, R2-2, R3-3, Pr-3, R9-1), (R1-5, R2-2, R3-3, Pr-3, R9-2), (R1-5, R2-2, R3-3, Pr-3, R9-3), (R1-5, R2-2, R3-3, Pr-4, R9-1), (R1-5, R2-2, R3-3, Pr-4, R9-2), (R1-5, R2-2, R3-3, Pr-4, R9-3), (R1-5, R2-2, R3-4, Pr-1, R9-1), (R1-5, R2-2, R3-4, Pr-1, R9-2), (R1-5, R2-2, R3-4, Pr-1, R9-3), (R1-5, R2-2, R3-4, Pr-2, R9-1), (R1-5, R2-2, R3-4, Pr-2, R9-2), (R1-5, R2-2, R3-4, Pr-2, R9-3), (R1-5, R2-2, R3-4, Pr-3, R9-1), (R1-5, R2-2, R3-4, Pr-3, R9-2), (R1-5, R2-2, R3-4, Pr-3, R9-3), (R1-5, R2-2, R3-4, Pr-4, R9-1), (R1-5, R2-2, R3-4, Pr-4, R9-2), (R1-5, R2-2, R3-4, Pr-4, R9-3), (R1-5, R2-2, R3-5, Pr-1, R9-1), (R1-5, R2-2, R3-5, Pr-1, R9-2), (R1-5, R2-2, R3-5, Pr-1, R9-3), (R1-5, R2-2, R3-5, Pr-2, R9-1), (R1-5, R2-2, R3-5, Pr-2, R9-2), (R1-5, R2-2, R3-5, Pr-2, R9-3), (R1-5, R2-2, R3-5, Pr-3, R9-1), (R1-5, R2-2, R3-5, Pr-3, R9-2), (R1-5, R2-2, R3-5, Pr-3, R9-3), (R1-5, R2-2, R3-5, Pr-4, R9-1), (R1-5, R2-2, R3-5, Pr-4, R9-2), (R1-5, R2-2, R3-5, Pr-4, R9-3),
(R1-6, R2-1, R3-1, Pr-1, R9-1), (R1-6, R2-1, R3-1, Pr-1, R9-2), (R1-6, R2-1, R3-1, Pr-1, R9-3), (R1-6, R2-1, R3-1, Pr-2, R9-1), (R1-6, R2-1, R3-1, Pr-2, R9-2), (R1-6, R2-1, R3-1, Pr-2, R9-3), (R1-6, R2-1, R3-1, Pr-3, R9-1), (R1-6, R2-1, R3-1, Pr-3, R9- 2), (R1-6, R2-1, R3-1, Pr-3, R9-3), (R1-6, R2-1, R3-1, Pr-4, R9-1), (R1-6, R2-1, R3-1, Pr-4, R9-2), (R1-6, R2-1, R3-1, Pr-4, R9-3), (R1-6, R2-1, R3-2, Pr-1, R9-1), (R1-6, R2-1, R3-2, Pr-1, R9-2), (R1-6, R2-1, R3-2, Pr-1, R9-3), (R1-6, R2-1, R3-2, Pr-2, R9-1), (R1-6, R2-1, R3-2, Pr-2, R9-2), (R1-6, R2-1, R3-2, Pr-2, R9-3), (R1-6, R2-1, R3-2, Pr-3, R9-1), (R1-6, R2-1, R3-2, Pr-3, R9-2), (R1-6, R2-1, R3-2, Pr-3, R9-3), (R1-6, R2-1, R3-2, Pr-4, R9-1), (R1-6, R2-1, R3-2, Pr-4, R9-2), (R1-6, R2-1, R3-2, Pr-4, R9-3), (R1-6, R2-1, R3-3, Pr-1, R9-1), (R1-6, R2-1, R3-3, Pr-1, R9-2), (R1-6, R2-1, R3-3, Pr-1, R9-3), (R1-6, R2-1, R3-3, Pr-2, R9-1), (R1-6, R2-1, R3-3, Pr-2, R9-2), (R1-6, R2-1, R3-3, Pr-2, R9-3), (R1-6, R2-1, R3-3, Pr-3, R9-1), (R1-6, R2-1, R3-3, Pr-3, R9-2), (R1-6, R2-1, R3-3, Pr-3, R9-3), (R1-6, R2-1, R3-3, Pr-4, R9-1), (R1-6, R2-1, R3-3, Pr-4, R9-2), (R1-6, R2-1, R3-3, Pr-4, R9-3), (R1-6, R2-1, R3-4, Pr-1, R9-1), (R1-6, R2-1, R3-4, Pr-1, R9-2), (R1-6, R2-1, R3-4, Pr-1, R9-3), (R1-6, R2-1, R3-4, Pr-2, R9-1), (R1-6, R2-1, R3-4, Pr-2, R9-2), (R1-6, R2-1, R3-4, Pr-2, R9-3), (R1-6, R2-1, R3-4, Pr-3, R9-1), (R1-6, R2-1, R3-4, Pr-3, R9-2), (R1-6, R2-1, R3-4, Pr-3, R9-3), (R1-6, R2-1, R3-4, Pr-4, R9-1), (R1-6, R2-1, R3-4, Pr-4, R9-2), (R1-6, R2-1, R3-4, Pr-4, R9-3), (R1-6, R2-1, R3-5, Pr-1, R9-1), (R1-6, R2-1, R3-5, Pr-1, R9-2), (R1-6, R2-1, R3-5, Pr-1, R9-3), (R1-6, R2-1, R3-5, Pr-2, R9-1), (R1-6, R2-1, R3-5, Pr-2, R9-2), (R1-6, R2-1, R3-5, Pr-2, R9-3), (R1-6, R2-1, R3-5, Pr-3, R9-1), (R1-6, R2-1, R3-5, Pr-3, R9-2), (R1-6, R2-1, R3-5, Pr-3, R9-3), (R1-6, R2-1, R3-5, Pr-4, R9-1), (R1-6, R2-1, R3-5, Pr-4, R9-2), (R1-6, R2-1, R3-5, Pr-4, R9-3), (R1-6, R2-2, R3-1, Pr-1, R9-1), (R1-6, R2-2, R3-1, Pr-1, R9-2), (R1-6, R2-2, R3-1, Pr-1, R9-3), (R1-6, R2-2, R3-1, Pr-2, R9-1), (R1-6, R2-2, R3-1, Pr-2, R9-2), (R1-6, R2-2, R3-1, Pr-2, R9-3), (R1-6, R2-2, R3-1, Pr-3, R9-1), (R1-6, R2-2, R3-1, Pr-3, R9-2), (R1-6, R2-2, R3-1, Pr-3, R9-3), (R1-6, R2-2, R3-1, Pr-4, R9-1), (R1-6, R2-2, R3-1, Pr-4, R9-2), (R1-6, R2-2, R3-1, Pr-4, R9-3), (R1-6, R2-2, R3-2, Pr-1, R9-1), (R1-6, R2-2, R3-2, Pr-1, R9-2), (R1-6, R2-2, R3-2, Pr-1, R9-3), (R1-6, R2-2, R3-2, Pr-2, R9-1), (R1-6, R2-2, R3-2, Pr-2, R9-2), (R1-6, R2-2, R3-2, Pr-2, R9-3), (R1-6, R2-2, R3-2, Pr-3, R9-1), (R1-6, R2-2, R3-2, Pr-3, R9-2), (R1-6, R2-2, R3-2, Pr-3, R9-3), (R1-6, R2-2, R3-2, Pr-4, R9-1), (R1-6, R2-2, R3-2, Pr-4, R9-2), (R1-6, R2-2, R3-2, Pr-4, R9-3), (R1-6, R2-2, R3-3, Pr-1, R9-1), (R1-6, R2-2, R3-3, Pr-1, R9-2), (R1-6, R2-2, R3-3, Pr-1, R9-3), (R1-6, R2-2, R3-3, Pr-2, R9-1), (R1-6, R2-2, R3-3, Pr-2, R9-2), (R1-6, R2-2, R3-3, Pr-2, R9-3), (R1-6, R2-2, R3-3, Pr-3, R9-1), (R1-6, R2-2, R3-3, Pr-3, R9-2), (R1-6, R2-2, R3-3, Pr-3, R9-3), (R1-6, R2-2, R3-3, Pr-4, R9-1), (R1-6, R2-2, R3-3, Pr-4, R9-2), (R1-6, R2-2, R3-3, Pr-4, R9-3), (R1-6, R2-2, R3-4, Pr-1, R9-1), (R1-6, R2-2, R3-4, Pr-1, R9-2), (R1-6, R2-2, R3-4, Pr-1, R9-3), (R1-6, R2-2, R3-4, Pr-2, R9-1), (R1-6, R2-2, R3-4, Pr-2, R9-2), (R1-6, R2-2, R3-4, Pr-2, R9-3), (R1-6, R2-2, R3-4, Pr-3, R9-1), (R1-6, R2-2, R3-4, Pr-3, R9-2), (R1-6, R2-2, R3-4, Pr-3, R9-3), (R1-6, R2-2, R3-4, Pr-4, R9-1), (R1-6, R2-2, R3-4, Pr-4, R9-2), (R1-6, R2-2, R3-4, Pr-4, R9-3), (R1-6, R2-2, R3-5, Pr-1, R9-1), (R1-6, R2-2, R3-5, Pr-1, R9-2), (R1-6, R2-2, R3-5, Pr-1, R9-3), (R1-6, R2-2, R3-5, Pr-2, R9-1), (R1-6, R2-2, R3-5, Pr-2, R9-2), (R1-6, R2-2,

R3-5, Pr-2, R9-3), (R1-6, R2-2, R3-5, Pr-3, R9-1), (R1-6, R2-2, R3-5, Pr-3, R9-2), (R1-6, R2-2, R3-5, Pr-3, R9-3), (R1-6, R2-2, R3-5, Pr-4, R9-1), (R1-6, R2-2, R3-5, Pr-4, R9-2), (R1-6, R2-2, R3-5, Pr-4, R9-3),
(R1-7, R2-1, R3-1, Pr-1, R9-1), (R1-7, R2-1, R3-1, Pr-1, R9-2), (R1-7, R2-1, R3-1, Pr-1, R9-3), (R1-7, R2-1, R3-1, Pr-2, R9-1), (R1-7, R2-1, R3-1, Pr-2, R9-2), (R1-7, R2-1, R3-1, Pr-2, R9-3), (R1-7, R2-1, R3-1, Pr-3, R9-1), (R1-7, R2-1, R3-1, Pr-3, R9- 2), (R1-7, R2-1, R3-1, Pr-3, R9-3), (R1-7, R2-1, R3-1, Pr-4, R9-1), (R1-7, R2-1, R3-1, Pr-4, R9-2), (R1-7, R2-1, R3-1, Pr-4, R9-3), (R1-7, R2-1, R3-2, Pr-1, R9-1), (R1-7, R2-1, R3-2, Pr-1, R9-2), (R1-7, R2-1, R3-2, Pr-1, R9-3), (R1-7, R2-1, R3-2, Pr-2, R9-1), (R1-7, R2-1, R3-2, Pr-2, R9-2), (R1-7, R2-1, R3-2, Pr-2, R9-3), (R1-7, R2-1, R3-2, Pr-3, R9-1), (R1-7, R2-1, R3-2, Pr-3, R9-2), (R1-7, R2-1, R3-2, Pr-3, R9-3), (R1-7, R2-1, R3-2, Pr-4, R9-1), (R1-7, R2-1, R3-2, Pr-4, R9-2), (R1-7, R2-1, R3-2, Pr-4, R9-3), (R1-7, R2-1, R3-3, Pr-1, R9-1), (R1-7, R2-1, R3-3, Pr-1, R9-2), (R1-7, R2-1, R3-3, Pr-1, R9-3), (R1-7, R2-1, R3-3, Pr-2, R9-1), (R1-7, R2-1, R3-3, Pr-2, R9-2), (R1-7, R2-1, R3-3, Pr-2, R9-3), (R1-7, R2-1, R3-3, Pr-3, R9-1), (R1-7, R2-1, R3-3, Pr-3, R9-2), (R1-7, R2-1, R3-3, Pr-3, R9-3), (R1-7, R2-1, R3-3, Pr-4, R9-1), (R1-7, R2-1, R3-3, Pr-4, R9-2), (R1-7, R2-1, R3-3, Pr-4, R9-3), (R1-7, R2-1, R3-4, Pr-1, R9-1), (R1-7, R2-1, R3-4, Pr-1, R9-2), (R1-7, R2-1, R3-4, Pr-1, R9-3), (R1-7, R2-1, R3-4, Pr-2, R9-1), (R1-7, R2-1, R3-4, Pr-2, R9-2), (R1-7, R2-1, R3-4, Pr-2, R9-3), (R1-7, R2-1, R3-4, Pr-3, R9-1), (R1-7, R2-1, R3-4, Pr-3, R9-2), (R1-7, R2-1, R3-4, Pr-3, R9-3), (R1-7, R2-1, R3-4, Pr-4, R9-1), (R1-7, R2-1, R3-4, Pr-4, R9-2), (R1-7, R2-1, R3-4, Pr-4, R9-3), (R1-7, R2-1, R3-5, Pr-1, R9-1), (R1-7, R2-1, R3-5, Pr-1, R9-2), (R1-7, R2-1, R3-5, Pr-1, R9-3), (R1-7, R2-1, R3-5, Pr-2, R9-1), (R1-7, R2-1, R3-5, Pr-2, R9-2), (R1-7, R2-1, R3-5, Pr-2, R9-3), (R1-7, R2-1, R3-5, Pr-3, R9-1), (R1-7, R2-1, R3-5, Pr-3, R9-2), (R1-7, R2-1, R3-5, Pr-3, R9-3), (R1-7, R2-1, R3-5, Pr-4, R9-1), (R1-7, R2-1, R3-5, Pr-4, R9-2), (R1-7, R2-1, R3-5, Pr-4, R9-3), (R1-7, R2-2, R3-1, Pr-1, R9-1), (R1-7, R2-2, R3-1, Pr-1, R9-2), (R1-7, R2-2, R3-1, Pr-1, R9-3), (R1-7, R2-2, R3-1, Pr-2, R9-1), (R1-7, R2-2, R3-1, Pr-2, R9-2), (R1-7, R2-2, R3-1, Pr-2, R9-3), (R1-7, R2-2, R3-1, Pr-3, R9-1), (R1-7, R2-2, R3-1, Pr-3, R9-2), (R1-7, R2-2, R3-1, Pr-3, R9-3), (R1-7, R2-2, R3-1, Pr-4, R9-1), (R1-7, R2-2, R3-1, Pr-4, R9-2), (R1-7, R2-2, R3-1, Pr-4, R9-3), (R1-7, R2-2, R3-2, Pr-1, R9-1), (R1-7, R2-2, R3-2, Pr-1, R9-2), (R1-7, R2-2, R3-2, Pr-1, R9-3), (R1-7, R2-2, R3-2, Pr-2, R9-1), (R1-7, R2-2, R3-2, Pr-2, R9-2), (R1-7, R2-2, R3-2, Pr-2, R9-3), (R1-7, R2-2, R3-2, Pr-3, R9-1), (R1-7, R2-2, R3-2, Pr-3, R9-2), (R1-7, R2-2, R3-2, Pr-3, R9-3), (R1-7, R2-2, R3-2, Pr-4, R9-1), (R1-7, R2-2, R3-2, Pr-4, R9-2), (R1-7, R2-2, R3-2, Pr-4, R9-3), (R1-7, R2-2, R3-3, Pr-1, R9-1), (R1-7, R2-2, R3-3, Pr-1, R9-2), (R1-7, R2-2, R3-3, Pr-1, R9-3), (R1-7, R2-2, R3-3, Pr-2, R9-1), (R1-7, R2-2, R3-3, Pr-2, R9-2), (R1-7, R2-2, R3-3, Pr-2, R9-3), (R1-7, R2-2, R3-3, Pr-3, R9-1), (R1-7, R2-2, R3-3, Pr-3, R9-2), (R1-7, R2-2, R3-3, Pr-3, R9-3), (R1-7, R2-2, R3-3, Pr-4, R9-1), (R1-7, R2-2, R3-3, Pr-4, R9-2), (R1-7, R2-2, R3-3, Pr-4, R9-3), (R1-7, R2-2, R3-4, Pr-1, R9-1), (R1-7, R2-2, R3-4, Pr-1, R9-2), (R1-7, R2-2, R3-4, Pr-1, R9-3), (R1-7, R2-2, R3-4, Pr-2, R9-1), (R1-7, R2-2, R3-4, Pr-2, R9-2), (R1-7, R2-2, R3-4, Pr-2, R9-3), (R1-7, R2-2, R3-4, Pr-3, R9-1), (R1-7, R2-2, R3-4, Pr-3, R9-2), (R1-7, R2-2, R3-4, Pr-3, R9-3), (R1-7, R2-2, R3-4, Pr-4, R9-1), (R1-7, R2-2, R3-4, Pr-4, R9-2), (R1-7, R2-2, R3-4, Pr-4, R9-3), (R1-7, R2-2, R3-5, Pr-1, R9-1), (R1-7, R2-2, R3-5, Pr-1, R9-2), (R1-7, R2-2, R3-5, Pr-1, R9-3), (R1-7, R2-2, R3-5, Pr-2, R9-1), (R1-7, R2-2, R3-5, Pr-2, R9-2), (R1-7, R2-2, R3-5, Pr-2, R9-3), (R1-7, R2-2, R3-5, Pr-3, R9-1), (R1-7, R2-2, R3-5, Pr-3, R9-2), (R1-7, R2-2, R3-5, Pr-3, R9-3), (R1-7, R2-2, R3-5, Pr-4, R9-1), (R1-7, R2-2, R3-5, Pr-4, R9-2), (R1-7, R2-2, R3-5, Pr-4, R9-3),
(R1-8, R2-1, R3-1, Pr-1, R9-1), (R1-8, R2-1, R3-1, Pr-1, R9-2), (R1-8, R2-1, R3-1, Pr-1, R9-3), (R1-8, R2-1, R3-1, Pr-2, R9-1), (R1-8, R2-1, R3-1, Pr-2, R9-2), (R1-8, R2-1, R3-1, Pr-2, R9-3), (R1-8, R2-1, R3-1, Pr-3, R9-1), (R1-8, R2-1, R3-1, Pr-3, R9- 2), (R1-8, R2-1, R3-1, Pr-3, R9-3), (R1-8, R2-1, R3-1, Pr-4, R9-1), (R1-8, R2-1, R3-1, Pr-4, R9-2), (R1-8, R2-1, R3-1, Pr-4, R9-3), (R1-8, R2-1, R3-2, Pr-1, R9-1), (R1-8, R2-1, R3-2, Pr-1, R9-2), (R1-8, R2-1, R3-2, Pr-1, R9-3), (R1-8, R2-1, R3-2, Pr-2, R9-1), (R1-8, R2-1, R3-2, Pr-2, R9-2), (R1-8, R2-1, R3-2, Pr-2, R9-3), (R1-8, R2-1, R3-2, Pr-3, R9-1), (R1-8, R2-1, R3-2, Pr-3, R9-2), (R1-8, R2-1, R3-2, Pr-3, R9-3), (R1-8, R2-1, R3-2, Pr-4, R9-1), (R1-8, R2-1, R3-2, Pr-4, R9-2), (R1-8, R2-1, R3-2, Pr-4, R9-3), (R1-8, R2-1, R3-3, Pr-1, R9-1), (R1-8, R2-1, R3-3, Pr-1, R9-2), (R1-8, R2-1, R3-3, Pr-1, R9-3), (R1-8, R2-1, R3-3, Pr-2, R9-1), (R1-8, R2-1, R3-3, Pr-2, R9-2), (R1-8, R2-1, R3-3, Pr-2, R9-3), (R1-8, R2-1, R3-3, Pr-3, R9-1), (R1-8, R2-1, R3-3, Pr-3, R9-2), (R1-8, R2-1, R3-3, Pr-3, R9-3), (R1-8, R2-1, R3-3, Pr-4, R9-1), (R1-8, R2-1, R3-3, Pr-4, R9-2), (R1-8, R2-1, R3-3, Pr-4, R9-3), (R1-8, R2-1, R3-4, Pr-1, R9-1), (R1-8, R2-1, R3-4, Pr-1, R9-2), (R1-8, R2-1, R3-4, Pr-1, R9-3), (R1-8, R2-1, R3-4, Pr-2, R9-1), (R1-8, R2-1, R3-4, Pr-2, R9-2), (R1-8, R2-1, R3-4, Pr-2, R9-3), (R1-8, R2-1, R3-4, Pr-3, R9-1), (R1-8, R2-1, R3-4, Pr-3, R9-2), (R1-8, R2-1, R3-4, Pr-3, R9-3), (R1-8, R2-1, R3-4, Pr-4, R9-1), (R1-8, R2-1, R3-4, Pr-4, R9-2), (R1-8, R2-1, R3-4, Pr-4, R9-3), (R1-8, R2-1, R3-5, Pr-1, R9-1), (R1-8, R2-1, R3-5, Pr-1, R9-2), (R1-8, R2-1, R3-5, Pr-1, R9-3), (R1-8, R2-1, R3-5, Pr-2, R9-1), (R1-8, R2-1, R3-5, Pr-2, R9-2), (R1-8, R2-1, R3-5, Pr-2, R9-3), (R1-8, R2-1, R3-5, Pr-3, R9-1), (R1-8, R2-1, R3-5, Pr-3, R9-2), (R1-8, R2-1, R3-5, Pr-3, R9-3), (R1-8, R2-1, R3-5, Pr-4, R9-1), (R1-8, R2-1, R3-5, Pr-4, R9-2), (R1-8, R2-1, R3-5, Pr-4, R9-3), (R1-8, R2-2, R3-1, Pr-1, R9-1), (R1-8, R2-2, R3-1, Pr-1, R9-2), (R1-8, R2-2, R3-1, Pr-1, R9-3), (R1-8, R2-2, R3-1, Pr-2, R9-1), (R1-8, R2-2, R3-1, Pr-2, R9-2), (R1-8, R2-2, R3-1, Pr-2, R9-3), (R1-8, R2-2, R3-1, Pr-3, R9-1), (R1-8, R2-2, R3-1, Pr-3, R9-2), (R1-8, R2-2, R3-1, Pr-3, R9-3), (R1-8, R2-2, R3-1, Pr-4, R9-1), (R1-8, R2-2, R3-1, Pr-4, R9-2), (R1-8, R2-2, R3-1, Pr-4, R9-3), (R1-8, R2-2, R3-2, Pr-1, R9-1), (R1-8, R2-2, R3-2, Pr-1, R9-2), (R1-8, R2-2, R3-2, Pr-1, R9-3), (R1-8, R2-2, R3-2, Pr-2, R9-1), (R1-8, R2-2, R3-2, Pr-2, R9-2), (R1-8, R2-2, R3-2, Pr-2, R9-3), (R1-8, R2-2, R3-2, Pr-3, R9-1), (R1-8, R2-2, R3-2, Pr-3, R9-2), (R1-8, R2-2, R3-2, Pr-3, R9-3), (R1-8, R2-2, R3-2, Pr-4, R9-1), (R1-8, R2-2, R3-2, Pr-4, R9-2), (R1-8, R2-2, R3-2, Pr-4, R9-3), (R1-8, R2-2, R3-3, Pr-1, R9-1), (R1-8, R2-2, R3-3, Pr-1, R9-2), (R1-8, R2-2, R3-3, Pr-1, R9-3), (R1-8, R2-2, R3-3, Pr-2, R9-1), (R1-8, R2-2, R3-3, Pr-2, R9-2), (R1-8, R2-2, R3-3, Pr-2, R9-3), (R1-8, R2-2, R3-3, Pr-3, R9-1), (R1-8, R2-2, R3-3, Pr-3, R9-2), (R1-8, R2-2, R3-3, Pr-3, R9-3), (R1-8, R2-2, R3-3, Pr-4, R9-1), (R1-8, R2-2, R3-3, Pr-4, R9-2), (R1-8, R2-2, R3-3, Pr-4, R9-3), (R1-8, R2-2, R3-4, Pr-1, R9-1), (R1-8, R2-2, R3-4, Pr-1, R9-2), (R1-8, R2-2, R3-4, Pr-1, R9-3), (R1-8, R2-2, R3-4, Pr-2, R9-1), (R1-8, R2-2, R3-4, Pr-2, R9-2), (R1-8, R2-2, R3-4, Pr-2, R9-3), (R1-8, R2-2, R3-4, Pr-3, R9-1), (R1-8, R2-2, R3-4, Pr-3, R9-2), (R1-8, R2-2, R3-4, Pr-3, R9-3), (R1-8, R2-2, R3-4, Pr-4, R9-1), (R1-8, R2-2, R3-4, Pr-4, R9-2), (R1-8, R2-2, R3-4, Pr-4, R9-3), (R1-8, R2-2, R3-5, Pr-1, R9-1), (R1-8, R2-2, R3-5, Pr-1, R9-2), (R1-8, R2-2, R3-5, Pr-1, R9-3), (R1-8, R2-2, R3-5, Pr-2, R9-1), (R1-8, R2-2, R3-5, Pr-2, R9-2), (R1-8, R2-2,

R3-5, Pr-2, R9-3), (R1-8, R2-2, R3-5, Pr-3, R9-1), (R1-8, R2-2, R3-5, Pr-3, R9-2), (R1-8, R2-2, R3-5, Pr-3, R9-3), (R1-8, R2-2, R3-5, Pr-4, R9-1), (R1-8, R2-2, R3-5, Pr-4, R9-2), (R1-8, R2-2, R3-5, Pr-4, R9-3).

(Method for Producing Compound of the Present Invention)

A general method for producing the compound of the present invention will be exemplified below. And, as extraction and purification, treatment which is performed in a normal experiment of organic chemistry may be conducted.

Synthesis of the compound of the present invention can be carried out referring to the procedures known in the art.

As a raw material compound, commercially available compounds, compounds described in the present description, compounds described in the references cited in the present description, and other known compounds can be utilized.

Among the compounds of the present invention, there are compounds in which a tautomer can be present, and the present invention includes all possible isomers and a mixture thereof, including them.

When one wants to obtain a salt of the compound of the present invention, in the case where the compound of the present invention is obtained in a form of a salt, it may be purified as it is and, in the case where the compound of the present invention is obtained in a free form, a salt may be formed by a normal method by dissolving or suspending the compound in a suitable organic solvent, and adding an acid or a base.

In addition, the compound of the present invention and a pharmaceutically acceptable salt thereof are present in a form of adducts with water or various solvents (hydrate or solvate) in some cases, and these adducts are included in the present invention.

In a general synthesis method as well as Reference examples, Examples, and Intermediate Synthesis Examples, the meaning of each abbreviation is as follows.
DMF: N,N-dimethylformamide
DMA: N,N-dimethylacetamide,
NMP: N-methylpyrrolidone
DMI: dimethylimidazolidinone
THF: tetrahydrofuran
Ms: methanesulfonyl
Ts: paratoluenesulfonyl
Boc: tert-butoxycarbonyl
DIBALH: diisobutylaluminum hydride
WSC or EDCI: N-ethyl-N'-(3-dimethylaminopropyl)carbodiimide
HOBt: 1-hydroxybenzotriazole
HATU: O-(7-azabenzotriazol-1-yl)-N,N,N',N'-tetramethyluronium hexafluorophosphate
NBS: N-bromosuccinimide
NCS: N-chlorosuccinimide
TEMPO: 2,2,6,6-tetramethylpiperidine-1-oxyl radical
PDC: pyridinium dichromate
DEAD: diethyl azodicarboxylate
DIAD: diisopropyl azodicarboxylate
DMAP: 4-dimethylaminopyridine
mCPBA: m-chloroperbenzoic acid
DBU: 1,8-diazabicyclo[5.4.0]-7-undecene
DIPEA: diisopropylethylamine
TBAF: tetrabutylammonium fluoride
IBX: 2-iodoxybenzoic acid
DMSO: dimethyl sulfoxide
NaHMDS: sodium hexamethyldisilazide
TFA: trifluoroacetic acid
Ac: acetyl
TBS: tert-butyldimethylsilyl
PEPPSI™-IPr: (1,3-diisopropylimidazol-2-ylidene)(3-chloropyridyl)palladium(II) dichloride
BEMP: 2-tert-butylimino-2-diethylamino-1,3-dimethylperhydro-1,3,2-diazaphosphorine Synthesis of Compound aj of Reference Example (See: Reference Example 1)

[Chemical formula 54]

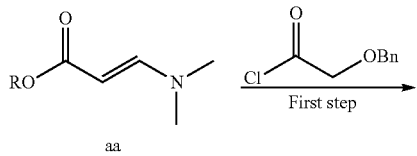

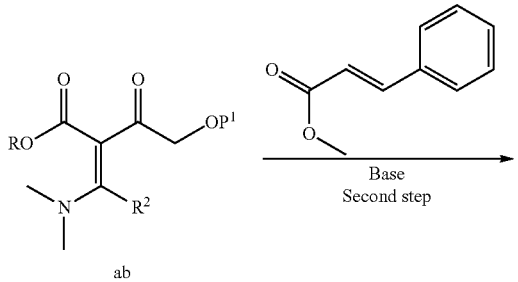

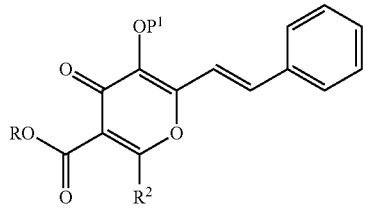

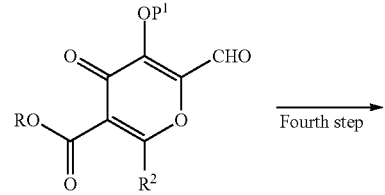

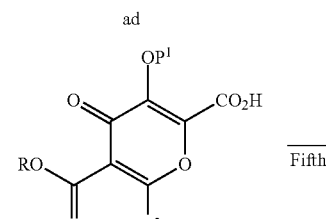

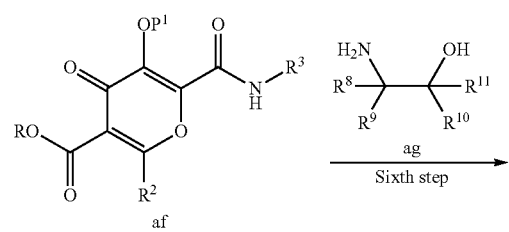

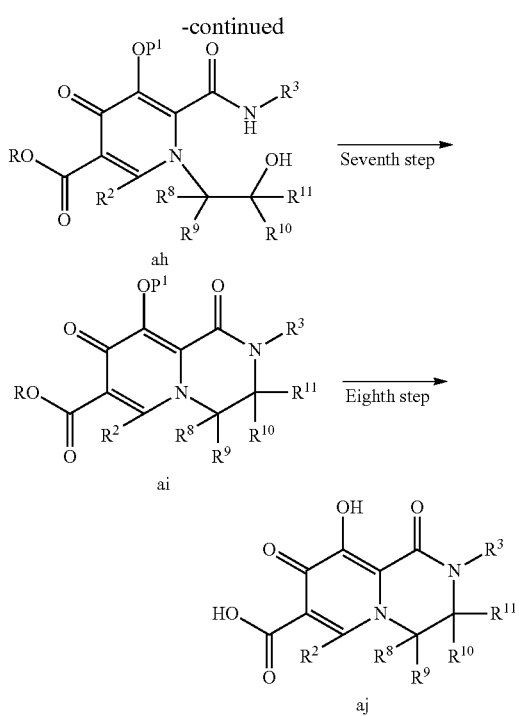

(wherein R is carboxy protective group, $P^1$ is hydroxyl protective group, $R^2$, $R^3$, $R^8$, $R^9$, $R^{10}$ and $R^{11}$ are same as $R^{2a}$, $R^{3a}$, $R^{8a}$, $R^{9a}$, $R^{10a}$ and $R^{11a}$ in item 1, respectively, R and $P^1$ may be a group which can be protected and/or deprotected by the method described in Protective Groups in Organic Synthesis, Theodora W Green (John Wiley & Sons) etc. and, for example, R is lower alkyl etc., and $P^1$ is arylalkyl etc.)

First Step

A compound ab can be obtained by reacting a compound aa which is commercially available or can be prepared by the known method at −20° C. to 30° C., preferably 0° C. to 20° C. for 0.1 hours to 24 hours, preferably 0.5 hours to 12 hours in a solvent such as dichloromethane, toluene, THF etc. or a mixed solvent thereof, by adding dropwise tertiary amine such as pyridine, trimethylamine, N-methylmorpholine, 4-dimethylaminopyridine etc. and benzyloxyacetyl chloride.

Second Step

A compound ac can be obtained by adding an organometallic base such as lithium hexamethyldisilazane, lithium diisopropylamide, butyllithium, tert-butyllithium etc. to the compound ab in a solvent such as ether, dichloromethane, THF etc. or a mixed solvent thereof, in the presence of cinnamoyl chloride, and performing a reaction at −80° C. to 0° C., preferably −80° C. to −40° C. for 1 minute to 2 hours, preferably 10 minutes to 1 hour.

Third Step

A compound ad can be obtained by adding a catalytic amount of an oxidizing agent such as ruthenium chloride and sodium periodate, TEMPO, manganese dioxide, as well as PDC etc. to the compound ac in a solvent such as ether, dichloromethane, THF, acetonitrile etc. or a mixed solvent thereof, and performing a reaction at −40° C. to 80° C., preferably 0° C. to 40° C. for 0.1 hours to 24 hours, preferably 0.2 hours to 3 hours.

Fourth Step

Concentrated sulfuric acid and an aqueous solution of amidosululic acid are added to the compound ad at 0° C. to 60° C., preferably 10° C. to 40° C. in the presence of a solvent such as ether, dichloromethane, THF, acetonitrile, acetone, water etc. or in a mixed solvent thereof. An aqueous sodium chlorite solution is added dropwise thereto at the same temperature to perform a reaction for 1 minute to 3 hours, preferably 5 minutes to 1 hour, thereby, a compound ae can be obtained.

Fifth Step

A compound af can be obtained by adding a compound $R^3$—$NH_2$ having a substituent corresponding to an objective compound to the compound ae in a solvent such as DMF, THF, dichloromethane, acetonitrile etc. in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5,-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU etc., and performing a reaction at −20° C. to 60° C., preferably −10° C. to 40° C. for 0.1 hours to 24 hours, preferably 1 hour to 12 hours.

Sixth Step

A compound ah can be obtained by adding a compound ag in the presence of a solvent such as toluene, xylene, THF, dioxane etc. or in a mixed solvent thereof, and performing a reaction for 0.1 hours to 12 hours, preferably 0.2 hours to 6 hours under the heat-refluxing condition.

Seventh Step

A compound ai can be obtained by adding triphenylphosphine and a condensation agent such as DEAD, DIAD etc. to the compound ah in the presence of a solvent such as THF, dioxane, ethyl acetate, acetonitrile etc. or in a mixed solvent thereof, and performing a reaction at 0° C. to 60° C., preferably 10° C. to 40° C. for 0.1 hours to 12 hours, preferably 0.2 hours to 6 hours.

Eighth Step

By subjecting the compound ai to the known general deprotecting reaction of a carboxyl protective group and a hydroxyl protective group, a compound aj can be obtained.

Synthesis of Compound bk of Reference Example (See: Reference Example 12)

[Chemical formula 55]

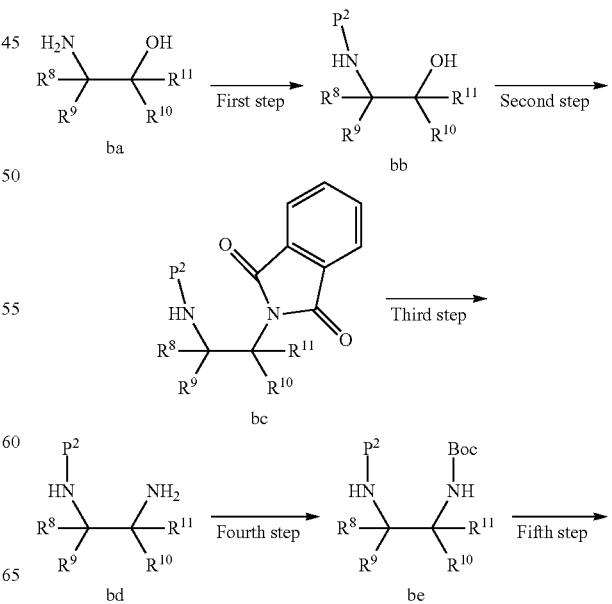

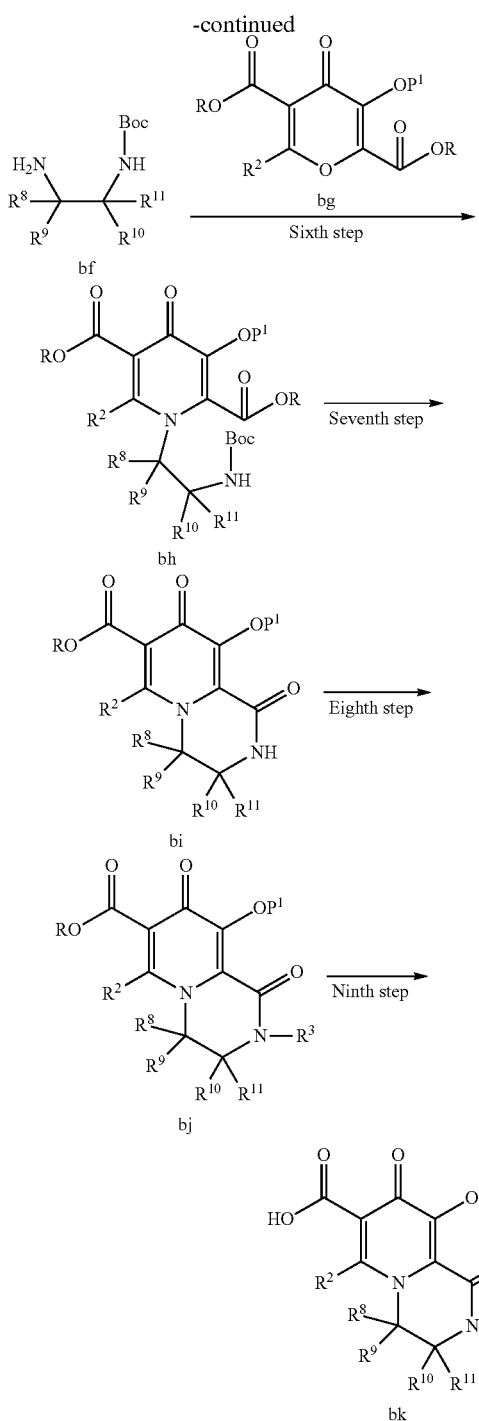

(wherein P² is amino protective group, P² may be a group which can be protected and/or deprotected by the method described in Protective Groups in Organic Synthesis, Theodora W Green (John Wiley & Sons) etc. and, for example, P² is arylalkyloxycarbonyl, lower alkyloxycarbonyl, etc. Other each symbol is same as above.)

First Step

A compound bb can be obtained by adding a base such as potassium carbonate, sodium carbonate, cesium carbonate etc. and a compound P²-L (wherein L is a leaving group such as halogen, OMs etc.) having a substituent corresponding to an objective compound to a compound ba in the presence of a solvent such as DMF, THF, dioxane, acetonitrile etc. or in a mixed solvent thereof, and performing a reaction at −20° C. to 80° C., preferably 0° C. to 50° C. for 0.1 hours to 6 hours, preferably 0.2 hours to 6 hours.

Second Step

A compound bc can be obtained by adding triphenylphosphine and phthalimide to the compound bb in the presence of a solvent such as DMF, THF, dioxane, acetonitrile etc. or in a mixed solvent thereof, adding a dehydration-condensation reagent such as DIAD, DEAD etc., and performing a reaction at −10° C. to 60° C., preferably 0° C. to 50° C. for 0.1 hours to 24 hours, preferably 0.2 hours to 12 hours.

Third Step

A compound bd can be obtained by adding hydrazine hydrate or methylhydrazine to the compound bc in the presence of a solvent such as methanol, THF, dioxane, acetonitrile, etc. or in a mixed solvent thereof, and performing a reaction at −10° C. to 80° C., preferably 10° C. to 60° C. for 0.5 hours to 24 hours, preferably 1 to 12 hours.

Fourth Step

A compound be can be obtained by adding Boc₂O to the compound bd in the presence of a solvent such as THF, dioxane, acetonitrile etc. or in a mixed solvent thereof, and performing a reaction at −10° C. to 80° C., preferably 10° C. to 60° C. for 0.5 hours to 24 hours, preferably 1 to 12 hours.

Fifth Step

A compound bf can be obtained by subjecting the compound be to the known general deprotecting reaction of an amino protective group.

Sixth Step

A compound bh can be obtained by adding a compound bg to the compound bf in the presence of a solvent such as toluene, THF, dioxane, acetonitrile etc. or in a mixed solvent thereof, and performing a reaction at 20° C. to 110° C., preferably 40° C. to under heat-refluxing for 0.5 hours to 24 hours, preferably 1 hour to 12 hours.

Seventh Step

HCl-ethyl acetate, HCl-dioxane, formic acid etc. is added to the compound bh, and they are reacted at 0° C. to 40° C., preferably 0° C. to 20° C. for 0.5 hours to 12 hours, preferably 1 hour to 6 hours. After the solvent is distilled off under reduced pressure, an aqueous saturated sodium bicarbonate solution is added, and the mixture is stirred, thereby, a compound bi can be obtained.

Eighth Step

A compound bj can be obtained by adding a base such as potassium carbonate, sodium carbonate, lithium carbonate, cesium carbonate etc. and a compound R³-L (L is a leaving group such as halogen, OMs etc.) to the compound bi in the presence of a solvent such as DMF, THF, DMA, NMP etc. or in a mixed solvent thereof, and performing a reaction at 0° C. to 60° C., preferably 10° C. to 30° C. for 0.5 hours to 12 hours, preferably 1 hour to 6 hours.

Ninth Step

A compound bk can be obtained by subjecting the compound bj to the known general deprotecting reaction of a carboxyl protective group and a hydroxyl protective group.

Synthesis of Compound cd of Reference Example (See: Reference Examples 28 and 43)

[Chemical formula 56]

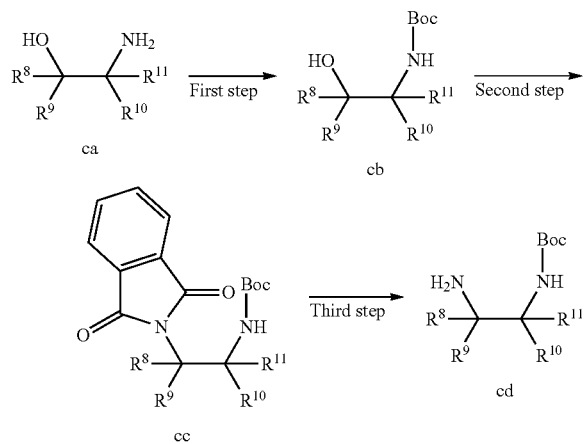

(wherein each symbol is same as above)

First Step

A compound cb can be obtained by adding tertiary amine such as triethylamine, DMAP, morpholine etc. or a base such as sodium carbonate, sodium bicarbonate etc. to a compound ca in the presence of a solvent such as THF, dioxane, acetonitrile, water etc. or in a mixed solvent thereof, adding $Boc_2O$, and performing a reaction at −10° C. to 80° C., preferably 10° C. to 60° C. for 0.5 hours to 24 hours, preferably 1 to 12 hours.

Second Step

A compound cc can be obtained by adding triphenylphosphine and phthalimide to the compound cb in the presence of a solvent such as DMF, THF, dioxane, acetonitrile etc. or in a mixed solvent thereof, adding a dehydration-condensation reagent such as DIAD, DEAD etc., and performing a reaction at −10° C. to 60° C., preferably 0° C. to 50° C. for 0.1 hours to 24 hours, preferably 0.2 hours to 12 hours.

Third Step

A compound cd can be obtained by adding hydrazine hydrate to the compound cc in the presence of a solvent such as methanol, THF, dioxane, acetonitrile etc. or in a mixed solvent thereof, and performing a reaction at −10° C. to 80° C., preferably 10° C. to 60° C. for 0.5 hours to 24 hours, preferably 1 to 12 hours.

Synthesis of Compound dg of Reference Example (See: Reference Examples 36, 41, and 46)

[Chemical formula 57]

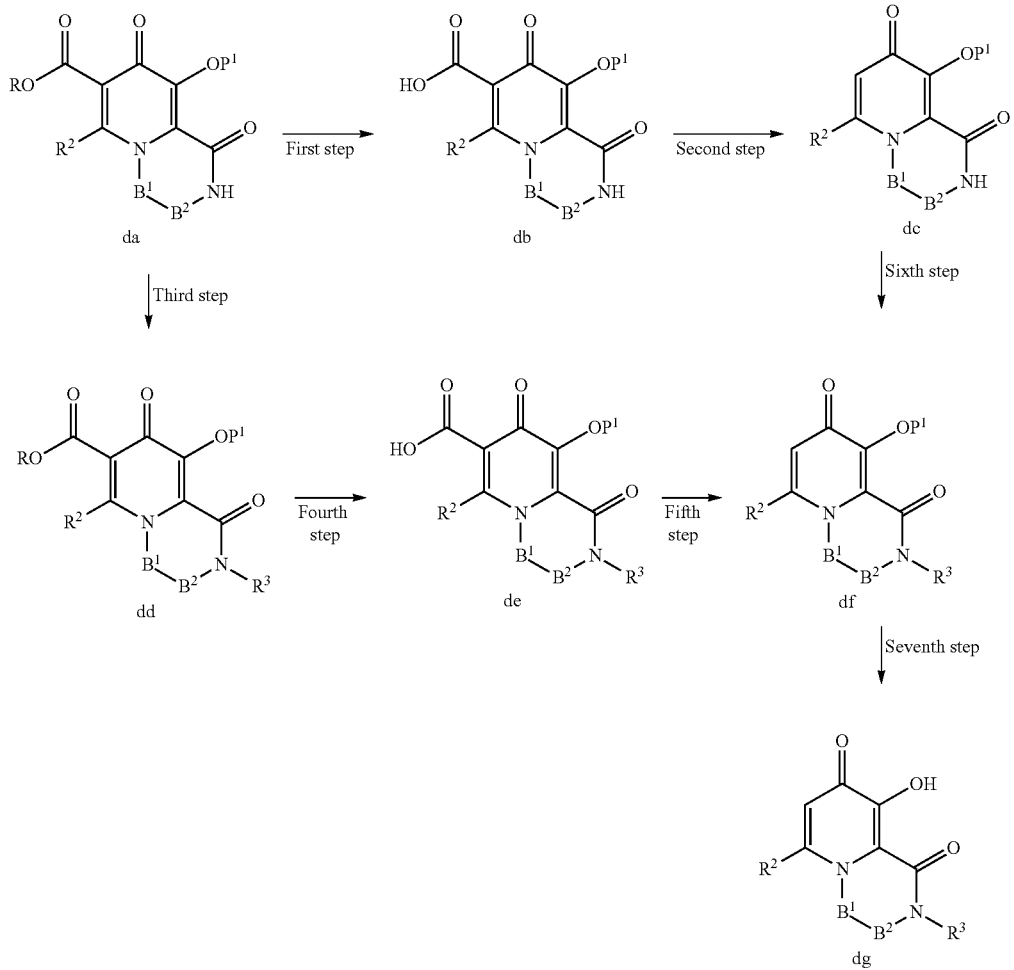

(wherein B¹ and B² are same as those of item 1, and other each symbol is same as above).

First Step

A compound db can be obtained by subjecting the compound da obtained by the same method as the synthesis method of bi to the known general carboxyl deprotecting reaction.

Second Step

A decarbonized compound dc can be obtained by reacting the compound db for 1 minute to 2 hours under microwave irradiation in a solvent such as diphenyl ether etc. And, a decarbonized compound d can be obtained by adding copper in a quinoline solvent, and performing a reaction at 180° C. for 2 to 48 hours.

Third Step

A compound bd can be obtained by adding a base such as potassium carbonate, sodium carbonate, lithium carbonate, cesium carbonate etc. and a compound R³-L (L is a leaving group such as halogen, OMs etc.) to the compound da obtained by the method described in Reference example 12 in the presence of a solvent such as DMF, THF, DMA, NMP etc. or in a mixed solvent thereof, and performing a reaction at 0° C. to 60° C., preferably 10° C. to 30° C. for 0.5 hours to 12 hours, preferably 1 hour to 6 hours.

Fourth Step

A compound de can be obtained by the same method as that of the first step.

Fifth Step

A compound df can be obtained by the same method as that of the second step.

Sixth Step

A compound df can be obtained by the same method as that of the third step.

Seventh Step

A compound dg can be obtained by subjecting the compound df to the known general hydroxyl group deprotecting reaction.

Synthesis of Compound ec of Reference Example (see: Reference Example 48)

[Chemical formula 58]

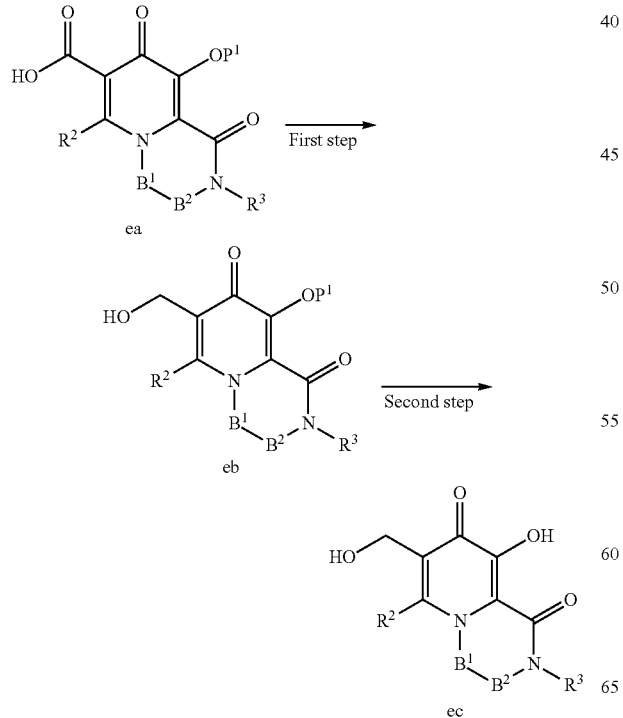

(wherein each symbol is same as above)

First Step

A base such as triethylamine, N-methylmorpholine, diisopropylethylamine etc. and ethyl chloroformate are added to a compound ea in the presence of a solvent such as THF, dioxane, dichloromethane, toluene etc. or in a mixed solvent thereof. A reducing agent having a low reducing power such as sodium borohydride etc. is added thereto, and a reaction is performed at −20° C. to 60° C., preferably −10° C. to 20° C. for 0.2 hours to 12 hours, preferably 0.5 hours to 6 hours, thereby, a compound eb can be obtained.

Second Step

A compound ec can be obtained by subjecting the compound eb to the known general hydroxyl group deprotecting reaction.

Synthesis of Compound fh of Reference Example (see: Reference Example 50)

[Chemical formula 59]

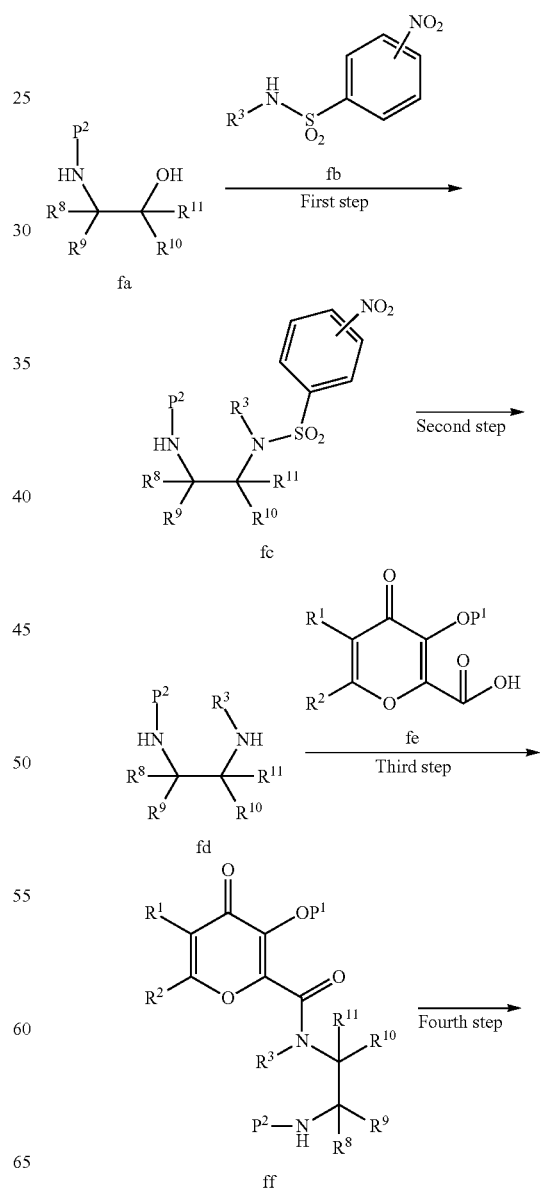

-continued

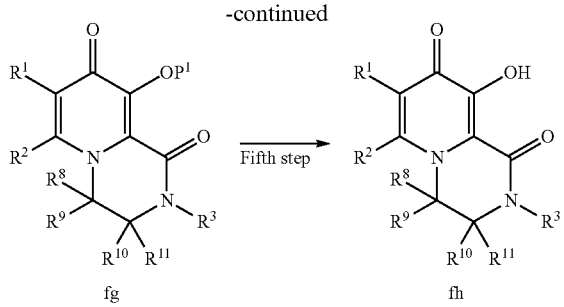

(wherein R¹ is a group corresponding to $R^{1a}$ in item 1, and other each symbol is same as above)

First Step

A compound fb and triphenylphosphine are added to a compound fa in the presence of a solvent such as THF, dichloromethane, dioxane, acetonitrile etc. or in a mixed solvent thereof. DIAD is added thereto, and a reaction is performed at 0° C. to 60° C., preferably 10° C. to 30° C. for 0.5 hours to 12 hours, preferably 1 hour to 12 hours, thereby, a compound fc can be obtained.

Second Step

A compound fd can be obtained by adding a base such as potassium carbonate, sodium carbonate, lithium carbonate, cesium carbonate etc. and thiol such as benzenethiol etc. to the compound fc in the presence of a solvent such as THF, dioxane, acetonitrile etc. or in a mixed solvent thereof, and performing a reaction at 0° C. to 60° C., preferably 10° C. to 30° C. for 0.5 hours to 12 hours, preferably 1 hour to 12 hours.

Third Step

A compound ff can be obtained by adding a compound fe having a substituent corresponding to an objective compound to the compound fd in a solvent such as DMF, THF, dichloromethane, acetonitrile etc. in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl etc., and performing a reaction at 0° C. to 60° C., preferably 10° C. to 40° C. for 1 hour to 48 hours, preferably 2 hours to 24 hours.

Fourth Step

A compound fd can be obtained by subjecting the compound ff to the known general deprotecting reaction concerning a P² group on an amino group, subsequently, adding a base such as an aqueous sodium carbonate solution, an aqueous potassium carbonate solution etc. in a solvent such as water, ethanol, methanol, acetonitrile etc. or in a mixed solvent thereof, and performing a reaction at 20° C. to 80° C., preferably 20° C. to 70° C. for 0.5 hours to 24 hours, preferably 1 hour to 6 hours.

Fifth Step

A compound fh can be obtained by subjecting the compound fg to the known general hydroxyl group deprotecting reaction.

Synthesis of Compound ga of Reference Example (See: Reference Example 51)

[Chemical formula 60]

(wherein each symbol is same as above)

First Step

A compound ga can be obtained by subjecting a compound dd to the known general hydroxyl group deprotecting reaction.

Synthesis of Compound hh of Reference Example (see: Reference Example 52)

[Chemical formula 61]

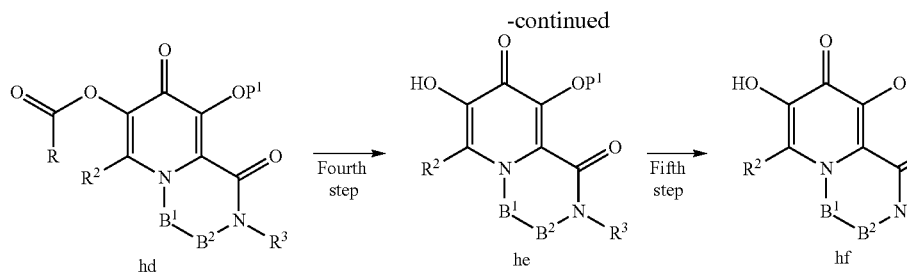

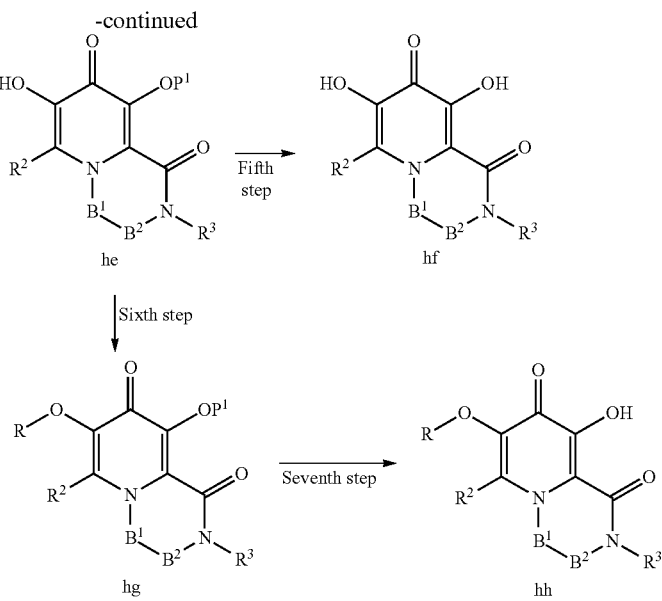

(wherein each symbol is same as above)

First Step

A compound hb can be obtained by adding O,N-dimethylhydroxylamine hydrochloride to a compound ha in a solvent such as DMF, THF, dichloromethane, acetonitrile etc. in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU etc., adding a tertiary base such as triethylamine, diisopropylethylamine, N-methylmorpholine etc., and performing a reaction at 0° C. to 60° C., preferably 10° C. to 40° C. for 1 hour to 24 hours, preferably 1 hour to 12 hours.

Second Step

A compound hc can be obtained by adding a Grignard reagent (R-MgBr) to the compound hb at −80° C. to −40° C. in the presence of a solvent such as THF, ether, dichloromethane, dioxane etc. or in a mixed solvent thereof, and performing a reaction at −80° C. to 0° C., preferably −60° C. to −20° C. for 0.5 hours to 24 hours, preferably 0.5 hours to 6 hours.

Third Step

A compound hd can be obtained by adding mCPBA to the compound hc in the presence of a solvent such as chloroform and dichloromethane, and performing a reaction at −20° C. to 30° C., preferably 10° C. to 30° C. for 0.1 hours to 12 hours, preferably 0.5 hours to 6 hours.

Fourth Step

A compound he can be obtained by adding an aqueous sodium hydroxide solution to the compound hd in the presence of a solvent such as ethanol etc., and performing a reaction at 0° C. to 120° C., preferably 30° C. to 90° C. for 1 minute to 10 hours, preferably 30 minutes to 120 minutes.

Fifth Step

A compound hf can be obtained by subjecting the compound he to the known general hydroxyl group deprotecting reaction.

Sixth Step

A compound hg can be obtained by adding a compound R—Br etc. corresponding to an objective compound to a compound he in the presence of a solvent such as chloroform, dichloromethane, THF, toluene etc. or in a mixed solvent thereof, adding a metal base such as sodium hydride, sodium methylate, n-butyllithium etc., and performing a reaction at −20° C. to 120° C., preferably 0° C. to 30° C. for 0.5 hours to 12 hours, preferably 1 hour to 6 hours.

Seventh Step

A compound hh can be obtained by subjecting the compound hg to the known general hydroxyl group deprotecting reaction.

Synthesis of Compound ic of Reference Example (see: Reference Example 53)

[Chemical formula 62]

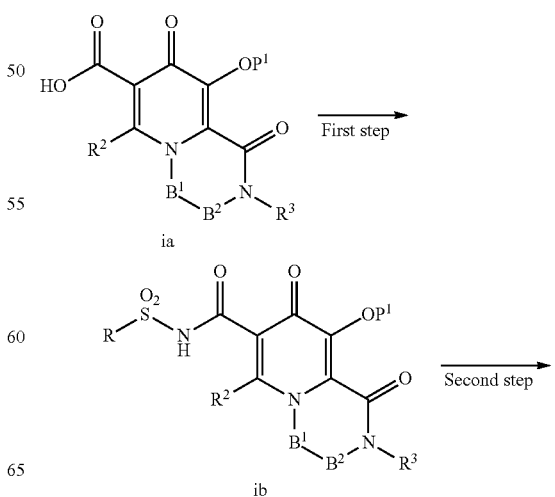

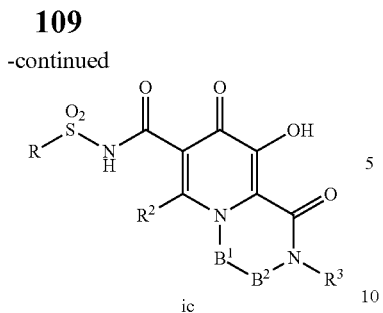

ic (wherein each symbol is same as above)

First Step

Tertiary amine such as triethylamine, diisopropylethylamine, N-methylmorpholine etc., and a chlorinating reagent such as ethyl chlorocarbonate, and ethyl chloroformate are added to a compound ia in the presence of a solvent such as DMF, DMA, NMP, THF etc. or in a mixed solvent thereof, and the mixture is stirred at 0° C. to 30° C. for 0.1 hours to 1 hour. A compound R—$SO_2$—$NH_2$ (e.g.: methanesulfonylamide) corresponding to an objective substance and DMAP are added thereto, and a reaction is performed at 40° C. to 100° C., preferably 40° C. to 80° C. for 0.5 hours to 12 hours, preferably 1 hour to 6 hours, thereby, a compound ib can be obtained.

Second Step

A compound ic can be obtained by subjecting the compound ib to the known general hydroxyl group deprotecting reaction.

Synthesis of Compound je of Reference Example (see: Reference Example 54)

[Chemical formula 63]

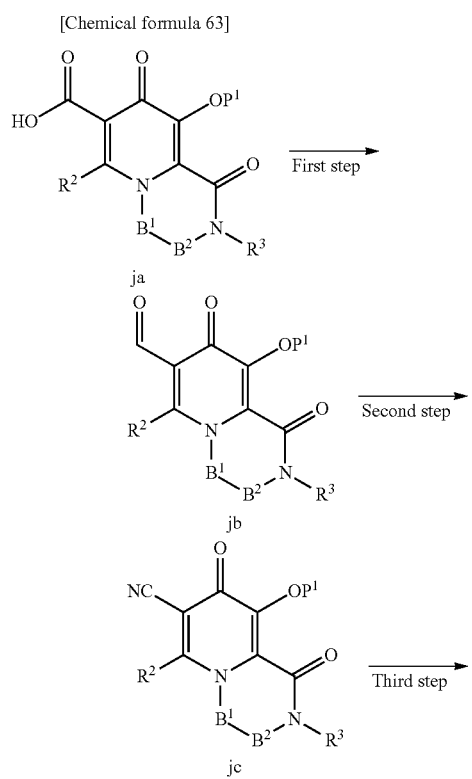

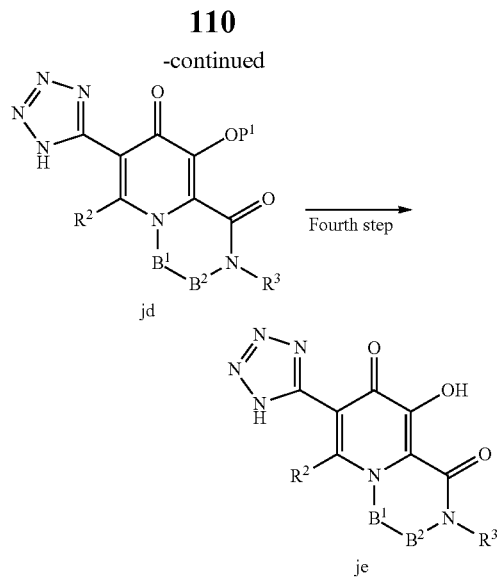

(wherein each symbol is same as above)

First Step

Tertiary amine such as triethylamine, N-methylmorpholine, diisopropylethylamine etc. and ethyl chloroformate or ethyl chlorocarbonate are added to a compound ja in the presence of a solvent such as THF, dioxane, dichloromethane, toluene, DMF etc. or in a mixed solvent thereof. A reducing agent having low reactivity such as sodium borohydride etc. is added thereto, and a reaction is performed at −20° C. to 40° C., preferably −10° C. to 20° C. for 0.2 hours to 12 hours, preferably 0.5 hours to 6 hours to obtain an alcohol intermediate. This intermediate is dissolved in dichloromethane, chloroform, etc., an oxidizing agent such as TEMPO, manganese dioxide, PDC etc. is added, and a reaction is performed at −40° C. to 30° C., preferably 0° C. to 30° C. for 0.1 hours to 24 hours, preferably 0.5 hours to 12 hours, thereby, a compound jb can be obtained.

Second Step

A compound jc can be obtained by adding 28% aqueous ammonia and iodine to the compound jb in the presence of a solvent such as THF, dioxane, dichloromethane etc., and performing a reaction at 0° C. to 40° C., preferably 10° C. to 30° C. for 0.5 hours to 24 hours, preferably 1 hour to 6 hours.

Third Step

A compound jd can be obtained by adding sodium azide, and tertiary amine such as triethylamine, diisopropylethylamine, N-methylmorpholine etc. to the compound jc in the presence of a solvent such as toluene, xylene, THF, dioxane etc. or in a mixed solvent thereof, and performing a reaction at 0° C. to 60° C., preferably 10° C. to 40° C. for 0.5 hours to 24 hours, preferably 1 hour to 12 hours.

Fourth Step

A compound je can be obtained by subjecting the compound jd to the known general hydroxyl group deprotecting reaction.

Synthesis of Compounds kd and kf of Reference Example (see: Reference Example 56 and Derivative Thereof)

[Chemical formula 64]

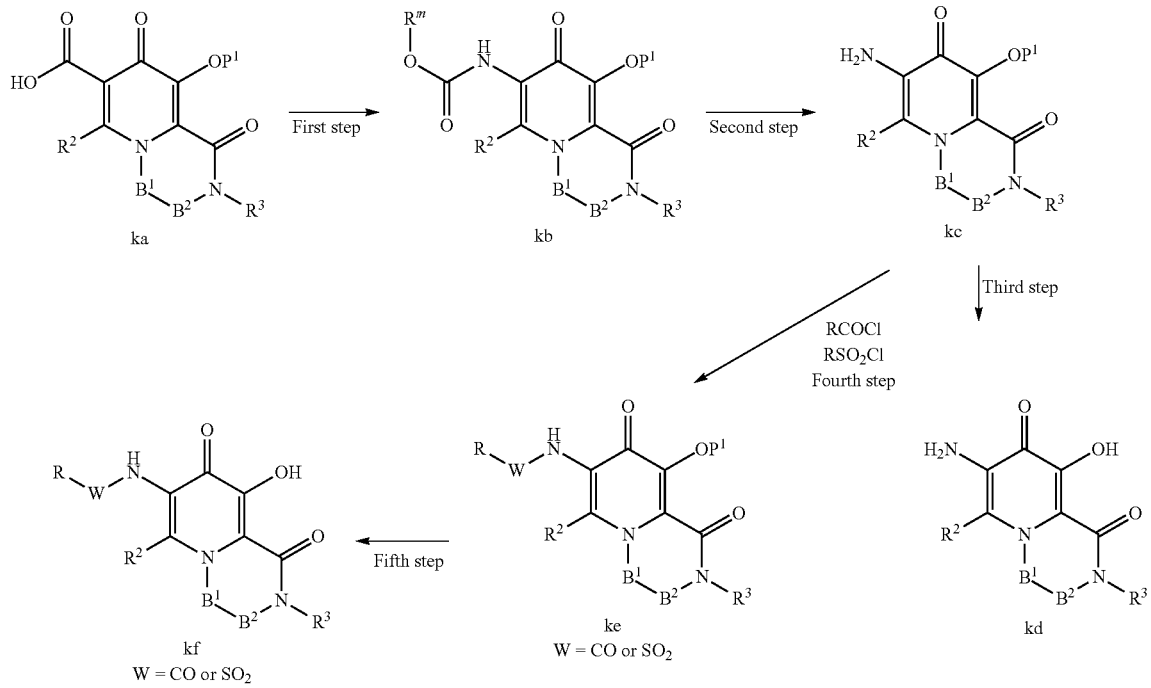

(wherein $R^m$ is lower alkyl, R is a substituent corresponding to an objective compound, W is —C(=O)— or —SO$_2$—, and other each symbol is same as above)

First Step

Tertiary amine such as triethylamine, N-methylmorpholine, diisopropylethylamine etc. and ethyl chloroformate or ethyl chlorocarbonate are added to a compound ka in the presence of a solvent such as THF, dioxane, dichloromethane, toluene, DMF etc. or in a mixed solvent thereof. Sodium azide is added thereto to perform a reaction at 0° C. to 40° C., preferably 10° C. to 30° C. for 0.5 hours to 24 hours, preferably 1 hour to 12 hours. Thereafter, an alcohol ($R^m$—OH) is added, and a reaction is performed at 20° C. to 60° C., preferably 20° C. to 50° C. for 0.5 hours to 24 hours, preferably 1 hour to 12 hours, thereby, a compound kb can be obtained.

Second Step

A compound kc can be obtained by adding a base such as an aqueous sodium hydroxide solution, an aqueous potassium hydroxide solution etc. to the compound kb in a solvent such as ethanol, methanol, water etc. or in a mixed solvent thereof, and performing a reaction at 20° C. to 80° C., preferably 40° C. to 60° C. for 0.5 hours to 24 hours, preferably 1 hour to 12 hours.

Third Step

A compound kd can be obtained by subjecting the compound kc to the known general hydroxyl group deprotecting reaction.

Fourth Step

A compound ke can be obtained by adding acid chloride (R—CO—Cl) or sulfonyl chloride (R—SO$_2$—Cl) corresponding to an objective substance to a compound kc in a solvent such as THF, dioxane, toluene, dichloromethane etc., adding tertiary amine such as pyridine, triethylamine, N-methylmorpholine etc. as necessary, and performing a reaction at −20° C. to 40° C., preferably 0° C. to 30° C. for 0.1 hours to 12 hours, preferably 0.2 hours to 6 hours.

Fifth Step

A compound kf can be obtained by subjecting the compound ke to the known general hydroxyl group deprotecting reaction.

Synthesis of Compound lc of Reference Example (see: Reference Example 60)

[Chemical formula 65]

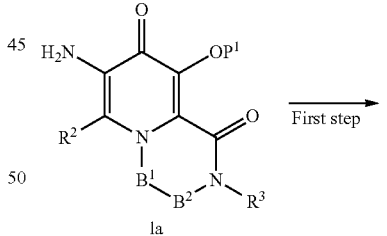

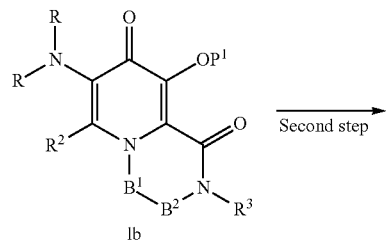

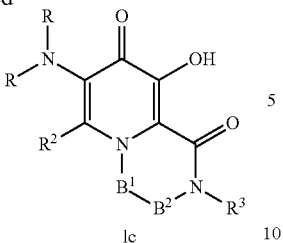

Ic

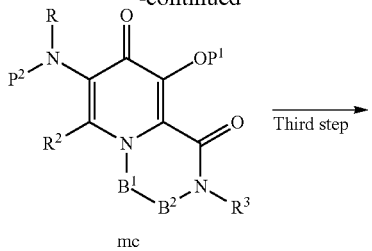

mc

Third step →

(wherein R is a substituent corresponding to an objective compound, and other each symbol is same as above)

First Step

Sodium hydride is added to a compound Ia in a solvent such as THF, dichloromethane, DMF etc. R-L (L is a leaving group such as halogen, OMs etc.) corresponding to an objective substance is added thereto, and a reaction is performed at −20° C. to 40° C., preferably 0° C. to 30° C. for 0.1 hours to 12 hours, preferably 0.2 hours to 6 hours, thereby, a compound Ib can be obtained.

Alternatively, a compound Ib can be obtained by adding formaldehyde to a compound Ia in a solvent of formic acid, and performing a reaction at 70° C. to 110° C. for 0.5 hours to 24 hours, preferably 1 hour to 12 hours.

Second Step

A compound Ic can be obtained by subjecting the compound Ib to the known general hydroxyl group deprotecting reaction.

Synthesis of Compound md of Reference Example (see: Reference Example 61)

[Chemical formula 66]

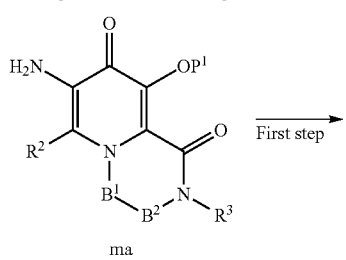

ma

First step →

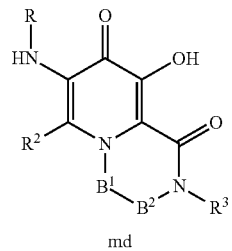

md (wherein R is a substituent corresponding to an objective compound, and other each symbol is same as above)

First Step

An amino-protected body mb can be obtained by adding $Boc_2O$ etc. to a compound ma in a solvent such as THF, dioxane, acetonitrile, water etc. or in a mixed solvent thereof, and subjecting this to an amine protecting reaction.

Second Step

Sodium hydride is added to a compound mb in a solvent such as THF, dichloromethane, DMF etc. R-L (L is a leaving group such as halogen, OMs etc.) corresponding to an objective substance is added thereto, and a reaction is performed at −20° C. to 40° C., preferably 0° C. to 30° C. for 0.1 hours to 12 hours, preferably 0.2 hours to 6 hours, thereby, a compound mc can be obtained.

Third Step

A compound md can be obtained by subjecting the compound mc to the known general amino group and hydroxyl group deprotecting reaction.

Synthesis of Compound nc and Compound ne of Reference Example (see: Reference Examples 63 and 64)

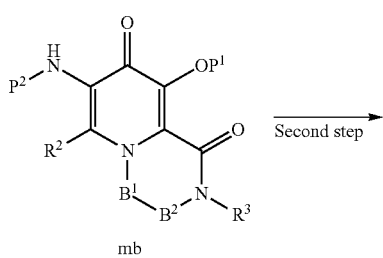

mb

Second step →

[Chemical formula 67]

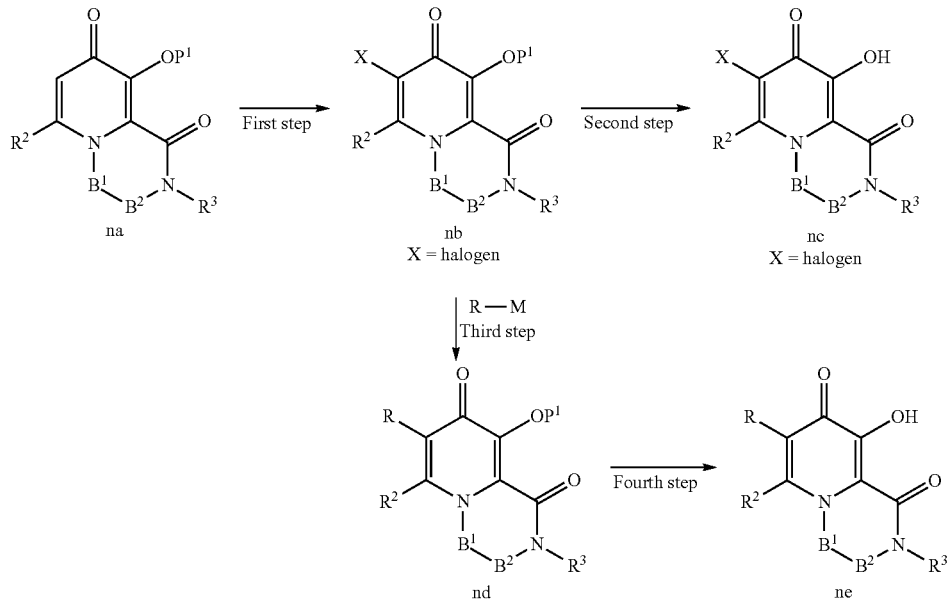

(wherein X is halogen, M is boronic acid ester such as B(O-phenyl)$_3$ etc., and other each symbol is same as above)

First Step

A compound nb can be obtained by adding a halogenating reagent (e.g. NBS, NCS, bromine etc.) to a compound na in a solvent such as dichloromethane, toluene, THF, dioxane etc., and performing a reaction for 0.1 hours to 12 hours, preferably 0.2 hours to 6 hours under the overheating refluxing condition.

Second Step

A compound nc can be obtained by subjecting the compound nb to the known general hydroxyl group deprotecting reaction.

Third Step

Boronic acid ester (R-M) corresponding to an objective substance is added to a compound nb in a solvent such as toluene, THF, DMF etc. or in a mixed solvent thereof, and a base such as potassium carbonate, sodium carbonate, sodium hydroxide etc. is added. A 0-valent palladium catalyst (e.g.: Pd(PPh$_3$)$_4$) is added thereto under nitrogen stream, and a reaction is performed at 60° C. to 120° C., preferably 80° C. to 110° C. for 1 hour to 48 hours, preferably 2 hours to 24 hours, thereby, a compound nd can be obtained.

Fourth Step

A compound ne can be obtained by subjecting the compound nd to the known general hydroxyl group deprotecting reaction.

Synthesis of Compound oh of Reference Example (see: Reference Example 65)

[Chemical formula 68]

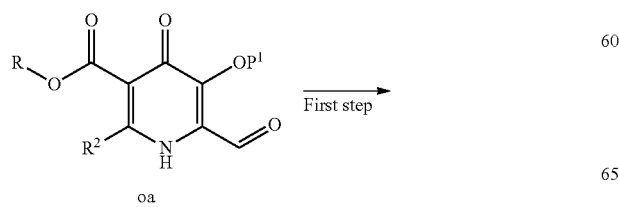

-continued

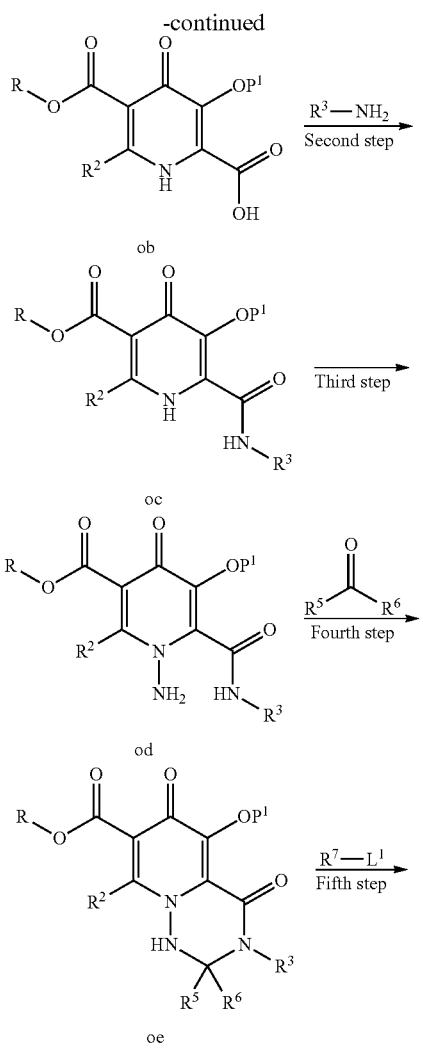

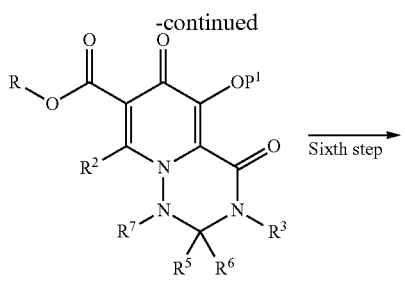

of

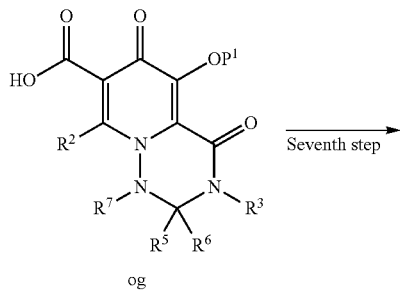

og

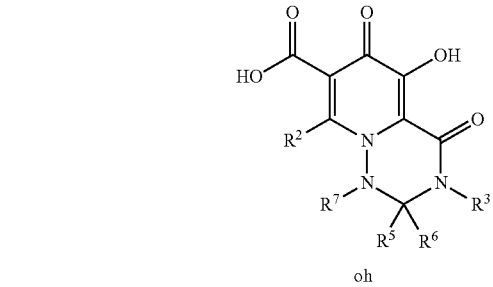

oh (wherein R is a carboxyl protective group such as lower alkyl etc., $R^7$ is same as $R^{7a}$ in item 1, $L^1$ is a leaving group such as halogen, OMs, OTs etc., and other symbol is same as above)

First Step

A compound ob can be obtained by adding sodium chlorite and amidosulfuric acid to a compound oa in the presence of a solvent such as THF, dioxane, dichloromethane, acetonitrile etc., and performing a reaction at 0° C. to 40° C., preferably 0° C. to 30° C. for 0.1 hours to 24 hours, preferably 1 hour to 12 hours.

Second Step

A compound oc can be obtained by adding a condensation agent such as HATU, WSC.HCl etc. to the compound ob in the presence of a solvent such as DMF, DMA, NMP, THF etc., adding amine ($R^3$—$NH_2$) corresponding to an objective substance, and tertiary amine such as triethylamine, N-methylmorpholine, pyridine etc., and performing a reaction at 10° C. to 60° C., preferably 20° C. to 40° C. for 0.1 hours to 24 hours, preferably 1 hour to 12 hours.

Third Step

A compound od can be obtained by adding potassium carbonate, sodium carbonate, and O-(2,4-dinitrophenyl)hydroxylamine to the compound oc in the presence of a solvent such as DMF, DMA, NMP, THF etc., and performing a reaction at 10° C. to 60° C., preferably 20° C. to 40° C. for 0.1 hours to 24 hours, preferably 1 hour to 12 hours.

Fourth Step

A compound oe can be obtained by adding $R^5$—C(=O)—$R^6$ and acetic acid to the compound od in the presence of a solvent such as toluene, DMF, DMA, NMP, THF etc., and performing a reaction at 60° C. to 120° C., preferably 80° C. to 110° C. for 0.1 hours to 24 hours, preferably 1 hour to 12 hours.

Fifth Step

A compound of can be obtained by adding a compound $R^7$-$L^1$ corresponding to an objective substance, and a base such as sodium carbonate, potassium carbonate, cesium carbonate etc. to the compound oe in the presence of a solvent such as DMF, DMA, NMP, THF etc., and performing a reaction at 0° C. to 60° C., preferably 10° C. to 40° C. for 0.1 hours to 24 hours, preferably 1 hour to 12 hours.

Sixth Step

A compound og can be obtained by subjecting the compound of to the known general carboxyl group deprotecting reaction.

Seventh Step

A compound oh can be obtained by subjecting the compound og to the known general hydroxyl group deprotecting reaction.

Synthesis of Compound pg of Reference Example (see: Reference Example 95)

[Chemical formula 69]

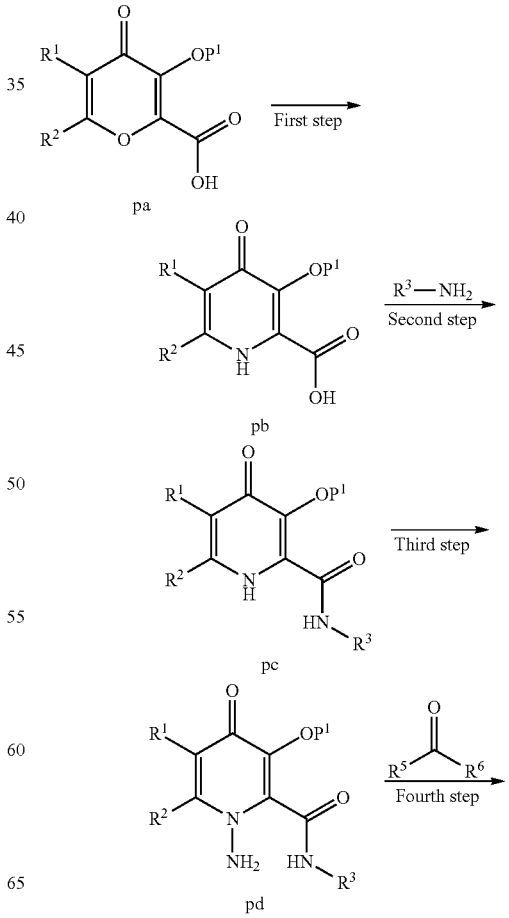

-continued

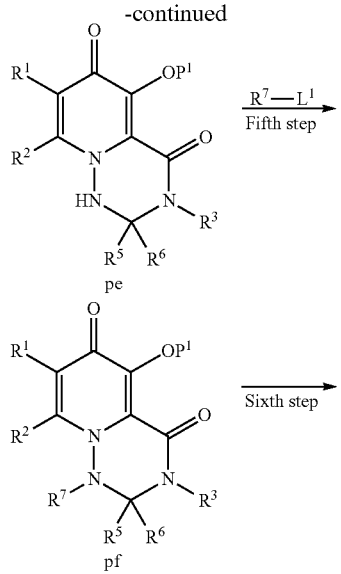

(wherein each symbol is same as above)

First Step

A compound pb can be obtained by adding aqueous ammonia to a compound pa, and performing a reaction at 0° C. to 30° C., preferably 10° C. to 30° C. for 0.5 hours to 48 hours, preferably 1 hour to 24 hours.

Second Step

A compound pc can be obtained by adding a condensation agent such as HATU, WSC.HCl etc. to the compound pb in the presence of a solvent such as DMF, DMA, NMP, THF etc. or in a mixed solvent thereof, adding amine ($R^3$—$NH_2$) corresponding to an objective substance and, if necessary, tertiary amine such as triethylamine, N-methylmorpholine etc., and performing a reaction at 10° C. to 60° C., preferably 20° C. to 40° C. for 0.1 hours to 24 hours, preferably 1 hour to 12 hours.

Third Step

A compound pd can be obtained by adding potassium carbonate, sodium carbonate, and O-(2,4-dinitrophenyl)hydroxylamine to the compound pc in the presence of a solvent such as DMF, DMA, NMP, THF etc., and performing a reaction at 10° C. to 60° C., preferably 20° C. to 40° C. for 0.1 hours to 24 hours, preferably 1 hour to 12 hours.

Fourth Step

A compound pe can be obtained by adding $R^5$—C(=O)—$R^6$ and acetic acid to the compound pd in the presence of a solvent such as toluene, DMF, DMA, NMP, THF etc., and performing a reaction at 60° C. to 120° C., preferably 80° C. to 110° C. for 0.1 hours to 12 hours, preferably 0.2 hours to 6 hours.

Fifth Step

A compound pf can be obtained by adding a compound $R^7$-$L^1$ corresponding to an objective substance, and a base such as sodium carbonate, potassium carbonate, cesium carbonate etc. to the compound pe in the presence of a solvent such as DMF, DMA, NMP, THF etc., and performing a reaction at 0° C. to 60° C., preferably 10° C. to 40° C. for 0.1 hours to 24 hours, preferably 1 hour to 12 hours.

Sixth Step

A compound pg can be obtained by subjecting the compound pf to the known general hydroxyl group deprotecting reaction.

Synthesis of Compound qg, Compound qi, and Compound qk of Reference Example (see: Reference Example 128)

[Chemical formula 70]

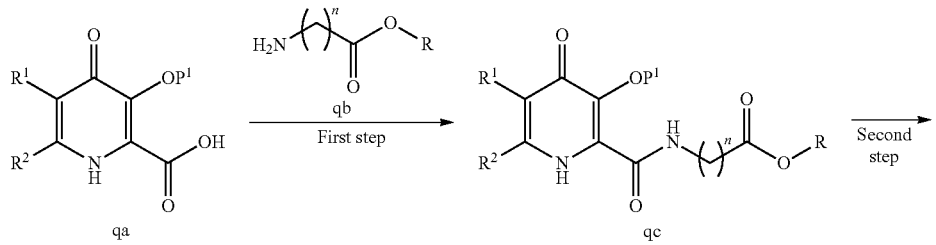

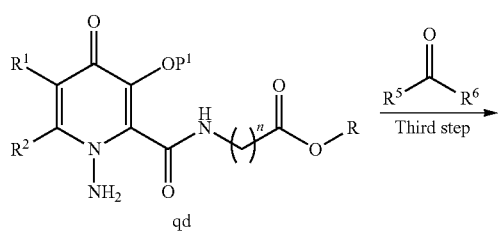

121

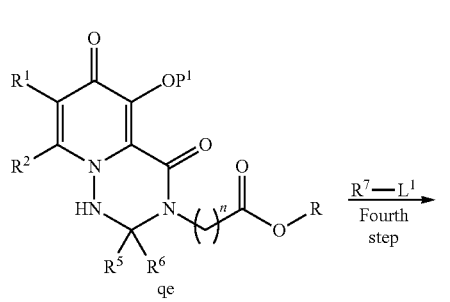
qe

-continued

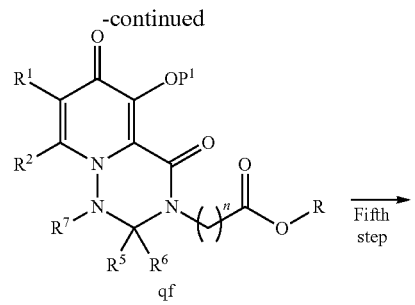
qf

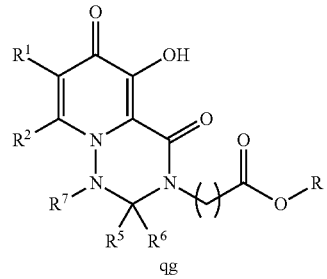
qg

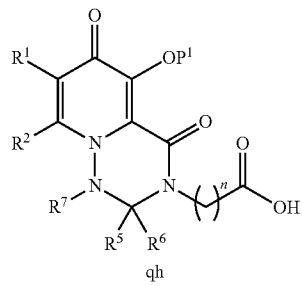
qh

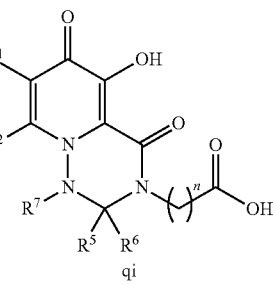
qi

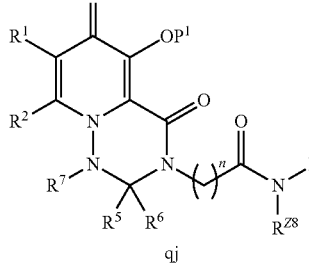
qj

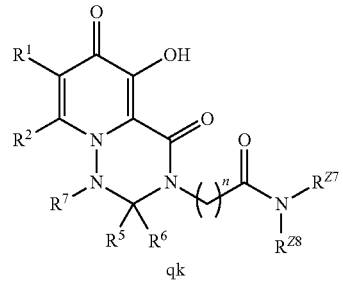
qk (wherein R represents a carboxyl protective group, n represents an integer of 0 to 6, $R^{Z7}$ and $R^{Z8}$ are same as $R^{C7}$ and $R^{C8}$ in item 1, and other each symbol is same as above)

First Step

A compound qc can be obtained by adding a condensation agent such as HATU, WSC.HCl etc. to a compound qa in the presence of a solvent such as pyridine, DMF, DMA, NMP, THF etc. or in a mixed solvent thereof, adding a compound qb and, if necessary, tertiary amine such as triethylamine, N-methylmorpholine etc., and performing a reaction at 10° C. to 60° C., preferably 20° C. to 40° C. for 0.1 hours to 24 hours, preferably 1 hour to 12 hours.

Second Step

A compound qd can be obtained by adding potassium carbonate, sodium carbonate, and O-(2,4-dinitrophenyl)hydroxylamine to the compound qc in the presence of a solvent such as DMF, DMA, NMP, THF etc. or in a mixed solvent thereof, and performing a reaction at 10° C. to 60° C., preferably 20° C. to 40° C. for 0.1 hours to 48 hours, preferably 1 hour to 24 hours.

Third Step

A compound pe can be obtained by adding $R^5$—C(=O)—$R^6$ and acetic acid to the compound qd in the presence of a solvent such as toluene, DMF, DMA, NMP, THF etc. or in a mixed solvent thereof, and performing a reaction at 60° C. to 120° C., preferably 80° C. to 110° C. for 0.1 hours to 12 hours, preferably 0.2 hours to 6 hours. Alternatively, a compound qe can be obtained by performing a reaction at 100° C. to 200° C. for 5 minutes to 1 hour under microwave irradiation condition in a solvent such as ethanol, isopropyl alcohol etc.

Fourth Step

A compound qf can be obtained by adding a compound $R^7$-$L^1$ corresponding to an objective substance, and a base such as sodium carbonate, potassium carbonate, cesium carbonate etc. to the compound qe in the presence of a solvent such as DMF, DMA, NMP etc. or in a mixed solvent thereof, and performing a reaction at 0° C. to 60° C., preferably 10° C. to 40° C. for 0.1 hours to 48 hours, preferably 1 hour to 24 hours.

Fifth Step

A compound qg can be obtained by subjecting the compound qf to the known general hydroxyl group deprotecting reaction.

Sixth Step

A compound qh can be obtained by subjecting the compound qf to the known general carboxyl group deprotecting reaction.

Seventh Step

A compound qi can be obtained by subjecting the compound qh to the known general hydroxyl group deprotecting reaction.

Eighth Step

A compound qj can be obtained by adding a condensation agent such as HATU, WSC.HCl etc. to a compound qh in the presence of a solvent such as pyridine, DMF, DMA, NMP, THF etc. or in a mixed solvent thereof, adding a compound $HNR^{Z7}R^{Z8}$ and, if necessary, tertiary amine such as triethylamine, diisopropylethylamine, N-methylmorpholine etc., and performing a reaction at 10° C. to 60° C., preferably 20° C. to 40° C. for 0.1 hours to 24 hours, preferably 1 hour to 12 hours.

Ninth Step

A compound qk can be obtained by subjecting the compound qj to the known general hydroxyl group deprotecting reaction.

Synthesis of Compound qq of Reference example, Compound qs of Reference Example, Compound qu of Reference Example, and Compound qw of Reference Example (See: Reference Example 128)

[Chemical formula 71]

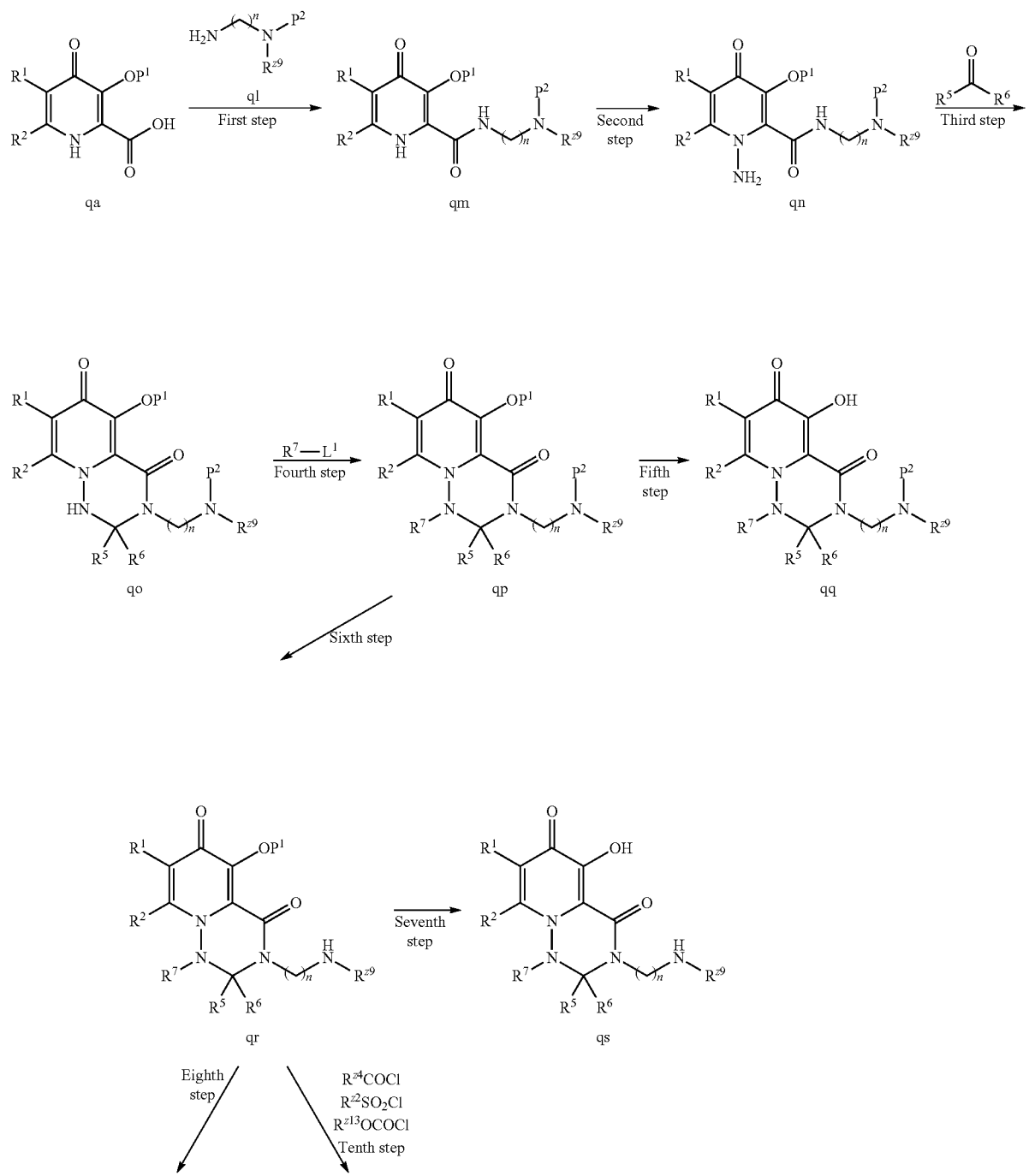

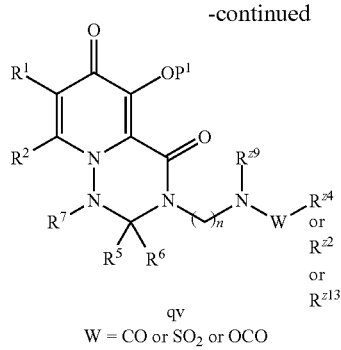
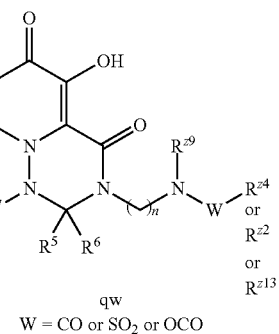

qv
W = CO or SO₂ or OCO qw
W = CO or SO₂ or OCO

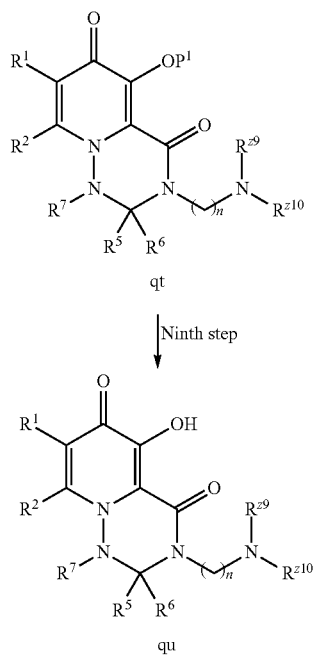

(wherein $R^{Z2}$, $R^{Z4}$, $R^{Z9}$, $R^{Z10}$, and $R^{Z13}$ are same as $R^{C2}$, $R^{C4}$, $R^{C9}$, $R^{C10}$, and $R^{C13}$ in item 1, and other each symbol is same as above)

First Step

A compound qm can be obtained by adding a condensation agent such as HATU, WSC.HCl, etc. to a compound qa in the presence of a solvent such as pyridine, DMF, DMA, NMP etc. or in a mixed solvent thereof, adding a compound ql and, if necessary, tertiary amine such as triethylamine, diisopropylethylamine, N-methylmorpholine, etc., and performing a reaction at 10° C. to 60° C., preferably 20° C. to 40° C. for 0.1 hours to 24 hours, preferably 1 hour to 12 hours.

Second Step

A compound qn can be obtained by adding potassium carbonate, sodium carbonate, and O-(2,4-dinitrophenyl)hydroxylamine to the compound qm in the presence of a solvent such as DMF, DMA, NMP, THF etc., and performing a reaction at 10° C. to 60° C., preferably 20° C. to 40° C. for 0.1 hours to 48 hours, preferably 1 hour to 24 hours.

Third Step

A compound pe can be obtained by adding $R^5$—C(=O)—$R^6$ and acetic acid to the compound qn in the presence of a solvent such as toluene, DMF, DMA, NMP, THF etc. or in a mixed solvent thereof, and performing a reaction at 60° C. to 120° C., preferably 80° C. to 110° C. for 0.1 hours to 12 hours, preferably 0.2 hours to 6 hours. Alternatively, a compound qo can be obtained by performing a reaction at 100° C. to 200° C. for 5 minutes to 1 hour under microwave irradiation condition in a solvent such as ethanol etc.

Fourth Step

A compound qp can be obtained by adding a compound $R^7$-$L^1$ corresponding to an objective substance, and a base such as sodium carbonate, potassium carbonate, cesium carbonate, etc. to the compound qo in the presence of a solvent such as DMF, DMA, NMP, THF, etc. or in a mixed solvent thereof, and performing a reaction at 0° C. to 60° C., preferably 10° C. to 40° C. for 0.1 hours to 48 hours, preferably 1 hour to 24 hours.

Fifth Step

A compound qq can be obtained by subjecting the compound qp to the known general hydroxyl group deprotecting reaction.

Sixth Step

A compound qr can be obtained by subjecting the compound qp to the known general amino group deprotecting reaction.

Seventh Step

A compound qs can be obtained by subjecting the compound qr to the known general hydroxyl group deprotecting reaction.

Eighth Step

A compound qt can be obtained by adding a compound $R^{Z10}$-$L^1$ corresponding to an objective substance, and a base such as sodium carbonate, potassium carbonate, cesium carbonate, etc. to the compound qr in the presence of a solvent such as DMF, DMA, NMP, THF, etc. or in a mixed solvent thereof, and performing a reaction at 0° C. to 60° C., preferably 10° C. to 40° C. for 0.1 hours to 48 hours, preferably 1 hour to 24 hours.

Ninth Step

A compound qu can be obtained by subjecting the compound qt to the known general hydroxyl group deprotecing reaction.

Tenth Step

A base such as sodium carbonate, potassium carbonate, cesium carbonate etc. is added to the compound qr in the presence of a solvent such as THF, dioxane, dichloromethane, acetonitrile, etc. A compound ($R^{Z4}$COCl, $R^{Z2}$SO₂Cl, or $R^{Z13}$OCOCl) corresponding to an objective substance is slowly added thereto, and a reaction is performed at −20° C. to 60° C., preferably 0° C. to 30° C. for 0.1 hours to 48 hours, preferably 1 hour to 24 hours, thereby, a compound qv can be obtained.

Eleventh Step

A compound qw can be obtained by subjecting the compound qv to the known general hydroxyl group deprotecting reaction.

Synthesis of Compound rb of Reference Example (see: Reference Example 155)

[Chemical formula 72]

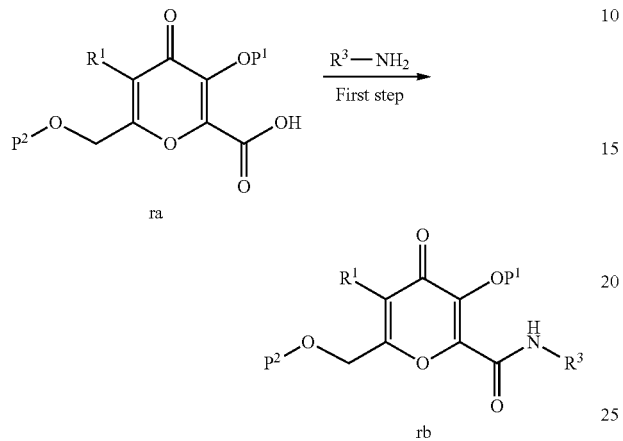

(wherein each symbol is same as above)

A compound rb can be obtained by adding a compound $R^3NH_2$ having a substituent corresponding to an objective compound to a compound ra in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU, etc. in a solvent such as DMF, THF, dichloromethane, acetonitrile, etc. or in a mixed solvent thereof, and performing a reaction at −20° C. to 60° C., preferably −10° C. to 40° C. for 0.1 hours to 24 hours, preferably 1 hour to 12 hours.

Alternatively, a compound rb can be obtained by adding an acylating reagent such as diphenylchlorophosphate, thionyl chloride, oxalyl chloride, etc. to a compound ra in the presence or absence of a base such as pyridine, triethylamine, diisopropylethylamine, 1-methylimidazole, etc. in the presence of a solvent such as THF, dioxane, dichloromethane, DMF, etc. to generate acid chloride, adding a compound $R^3$—$NH_2$ having a substituent corresponding to an objective compound, and performing a reaction at −20° C. to 60° C., preferably −10° C. to 40° C. for 0.1 hours to 24 hours, preferably 0.5 hours to 12 hours.

Synthesis of Compound sl of Reference Example (see: Reference Example 49)

[Chemical formula 73]

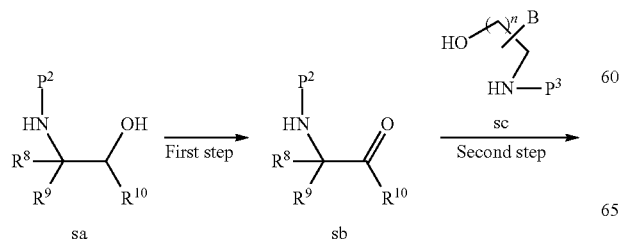

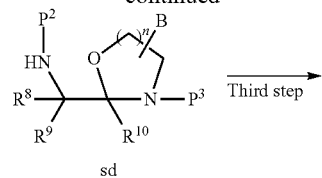

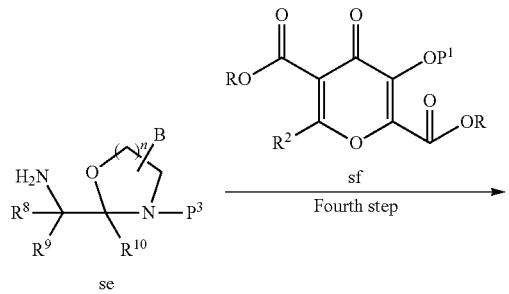

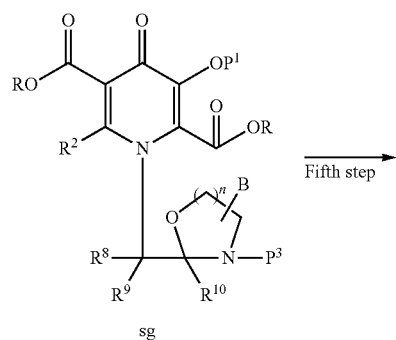

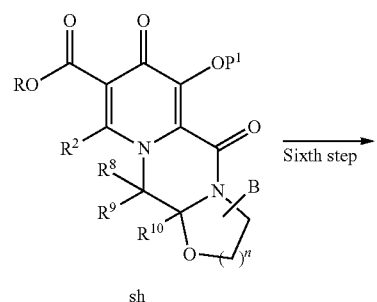

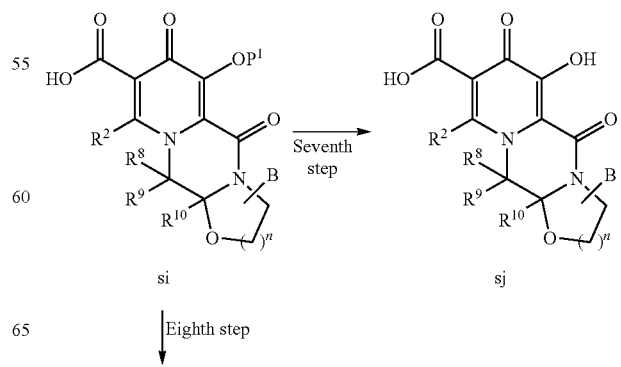

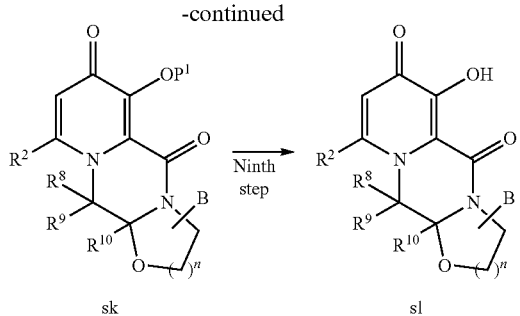

(wherein P³ is an amino protective group, and may be a group which can be protected and/or deprotected by the method described in Protective Groups in Organic Synthesis, Theodora W Green (John Wiley & Sons) etc. and, for example, P³ is aryl lower alkyloxycarbonyl, lower alkylcarbonyl, etc. B is same as substituent group D in item 1, and other each symbol is same as above)

First Step

A compound sb can be obtained by adding an oxidizing reagent such as Dess Martin Periodinane, manganese dioxide, PDC, etc, to a compound sa in the presence of a solvent such as dichloromethane, THF, dioxane, toluene etc., and performing a reaction at −20° C. to 60° C., preferably 0° C. to 40° C. for 0.1 hours to 24 hours, preferably 0.5 hours to 12 hours.

Second Step

A compound sd can be obtained by adding sodium sulfate and an aminoalcohol sc corresponding to an objective substance to the compound sb in the presence or absence of a solvent such as toluene, THF etc., and performing a reaction at 0° C. to 80° C., preferably 20° C. to 60° C. for 0.1 hours to 24 hours, preferably 0.5 hours to 12 hours.

Third Step

A compound se can be obtained by subjecting the compound sd to the known general amino group deprotecting reaction.

Fourth Step

A compound sg can be obtained by adding a compound sf to the compound se in the presence of a solvent such as toluene, THF, dioxane etc., and performing a reaction at 40° C. to 110° C., preferably 60° C. to 100° C. for 0.5 hours to 24 hours, preferably 1 hour to 12 hours.

Fifth Step

A compound sh can be obtained by subjecting the compound sg to the known general amino group deprotecting reaction and, thereafter, performing a reaction at 40° C. to 110° C., preferably 60° C. to 100° C. for 0.1 hours to 12 hours, preferably 0.2 hours to 6 hours in the presence of a solvent such as toluene, THF, dioxane, etc.

Sixth Step

A compound si can be obtained by subjecting the compound sh to the known general carboxyl group deprotecting reaction.

Seventh Step

A compound sj can be obtained by subjecting the compound si to the known general hydroxyl group deprotecting reaction.

Eighth Step

A decarbonized compound sk can be obtained by reacting the compound si for 1 minute to 2 hours under microwave irradiation in a solvent such as diphenyl ether etc.

Ninth Step

A compound sl can be obtained by subjecting the compound sk to the known general hydroxyl group deprotecting reaction.

Synthesis of Compound un of Reference Example (see: Reference Example 177)

[Chemical formula 74]

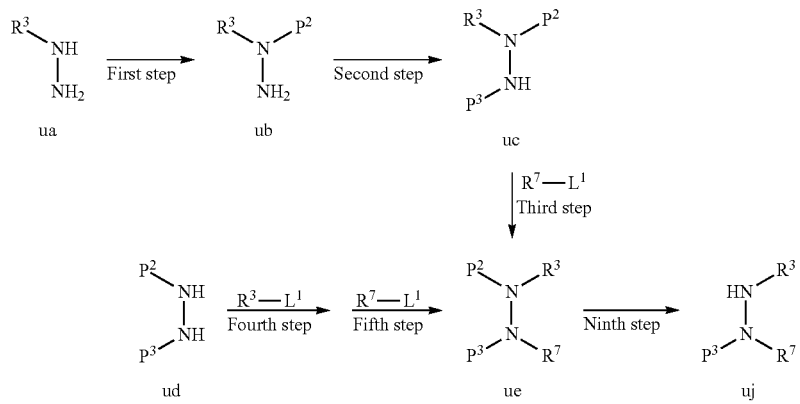

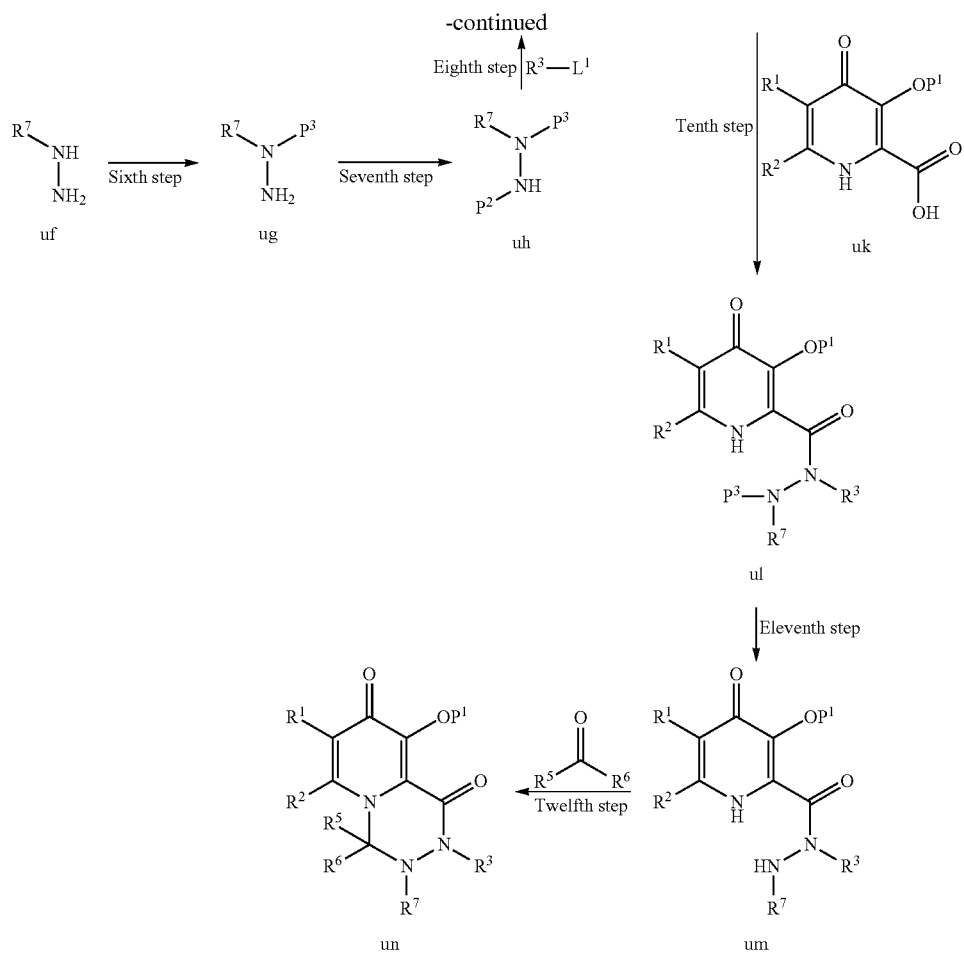

(wherein $L^1$ represents a leaving group such as halogen, OMs, OTs etc., and other each symbol is same as above)

First Step

A compound ub can be obtained by subjecting a compound ua to a secondary amino group protecting reaction.

Second Step

A compound uc can be obtained by subjecting the compound ub to a general amino group protecting reaction.

Third Step

A compound ue can be obtained by adding a compound $R^7$-$L^1$ corresponding to an objective compound to the compound uc in the presence of a solvent such as DMF, DMA, NMP, etc. and a base such as NaH etc., and performing a reaction at 0° C. to 80° C., preferably 20° C. to 60° C. for 0.5 hours to 12 hours, preferably 1 hour to 6 hours.

Fourth Step, Fifth Step (wherein $R^3$ and $R^7$ may be bound adjacently and, in this case, a fourth step and a fifth step are performed simultaneously)

A compound ue can be obtained by reacting a compound ud sequentially with compounds corresponding to an objective compound, $R^3$-$L^1$ and $R^7$-$L^1$ in the presence of a solvent such as DMF, DMA, NMP etc. and a base such as NaH etc.

Sixth Step

A compound ug can be obtained by subjecting a compound uf to a secondary amino group protecting reaction.

Seventh Step

A compound uh can be obtained by subjecting the compound ug to a secondary amino group protecting reaction.

Eighth Step

A compound ue can be obtained by adding a base such as NaH etc. to the compound uh in the presence of a solvent such as DMF, DMA, NMP, acetonitrile etc. or in a mixed solvent thereof, and performing a reaction with a compound $R^3$-$L^1$ corresponding to an objective compound.

Ninth Step

A compound uj can be obtained by subjecting the compound ue to a general secondary amine deprotecting reaction.

Tenth Step

A compound ul can be obtained by adding a condensation agent such as HATU, WSC.HCl etc. to a compound uk in the presence of a solvent such as DMF, DMA, THF, etc., adding amine uj corresponding to an objective substance, and tertiary amine such as pyridine, triethylamine, N-methylmorpholine etc., and performing a reaction at 10° C. to 60° C., preferably 20° C. to 40° C. for 0.1 hours to 24 hours, preferably 1 hour to 12 hours.

Eleventh Step

A compound um can be obtained by subjecting the compound ul to a general amino group protecting reaction.

Twelfth Step

A compound un can be obtained by adding $R^5$—C(=O)—$R^6$, tertiary amine such as, triethylamine, diisopropylethylamine, N-methylmorpholine, etc. and acetic acid, to the compound um in the presence of a solvent such as toluene, DMF, DMA, NMP etc., and performing a reaction at 60° C. to 120° C., preferably 80° C. to 100° C. for 0.1 hours to 24 hours, preferably 1 hour to 12 hours.

Synthesis of Compound te of Reference Example

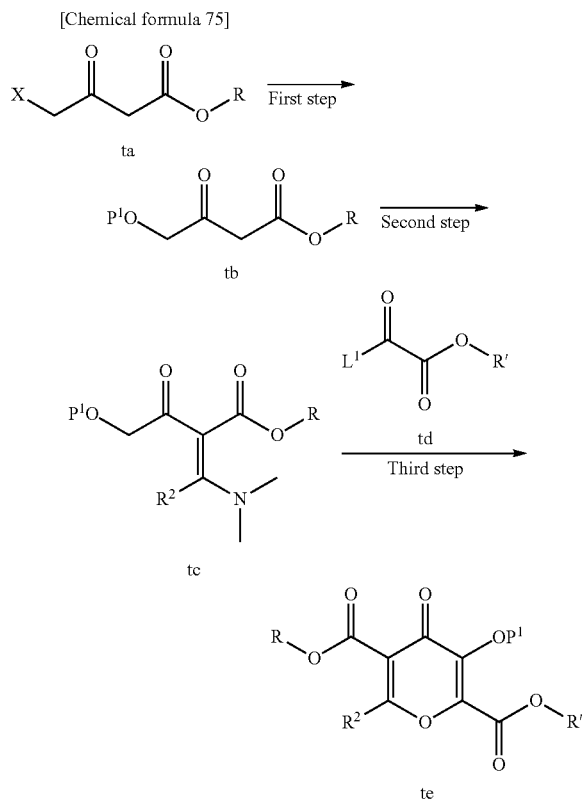

(wherein R' may be a group which can be protected and/or deprotected by the method described in Protective Groups in Organic Synthesis, Theodora W Green (John Wiley & Sons) etc. and, for example, R' is lower alkyl etc. X is halogen, and other each symbol is same as above)

First Step

An alcohol ($P^1$—OH) corresponding to an objective substance is added to an organometallic base such as sodium tert-pentoxide, n-butyllithium, tert-butyllithium etc. in a solvent such as THF, ether, dichloromethane, DMI, DMF, DMA, etc. or in a mixed solution thereof. A solution of a compound ta is added dropwise thereto, and a reaction is performed at −20° C. to 40° C., preferably 0° C. to 30° C. for 0.1 hours to 12 hours, preferably 0.5 hours to 6 hours, thereby, a compound tb can be obtained.

Second Step

A compound tc can be obtained by adding N,N-dimethylformamidodimethylacetal to the compound tb in a solvent such as THF, dioxane, toluene, ethyl acetate etc. or in a mixed solvent thereof, or without a solvent, and performing a reaction at 0° C. to 80° C., preferably 20° C. to 40° C. for 0.5 hours to 24 hours, preferably 1 hour to 12 hours.

Third Step

A compound td corresponding to an objective substance is added to an organometallic base such as sodium tert-pentoxide, n-butyllithium, tert-butyllithium, sodium metoxide, sodium ethoxide, sodium tert-butoxide, potassium tert-butoxide etc. in a solvent such as THF, ether, DMI, methanol, ethanol, etc. or in a mixed solvent thereof. A solution of the compound tc is added dropwise thereto, a reaction is performed at −20° C. to 60° C., preferably 0° C. to 30° C. for 0.5 hours to 24 hours, preferably 1 hour to 12 hours and, thereafter, an acid such as hydrochloric acid, sulfuric acid etc. is added to perform a reaction at −20° C. to 60° C., preferably 0° C. to 30° C. for 0.5 hours to 24 hours, preferably 1 hour to 12 hours, thereby, a compound te can be obtained.

Synthesis of Compound tm of Reference Example and Compound tp of Reference Example (See: Reference Examples 165, and 169)

[Chemical formula 76]

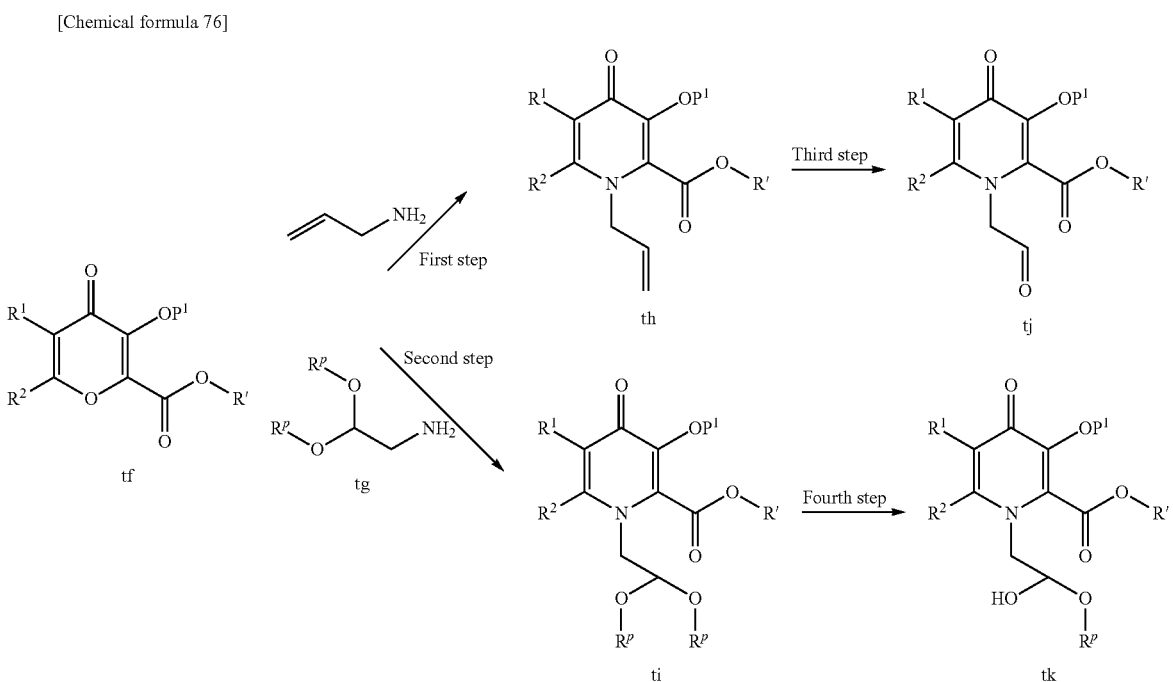

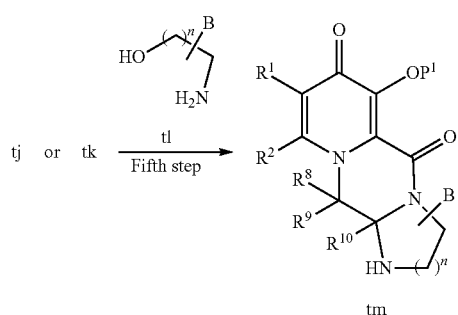

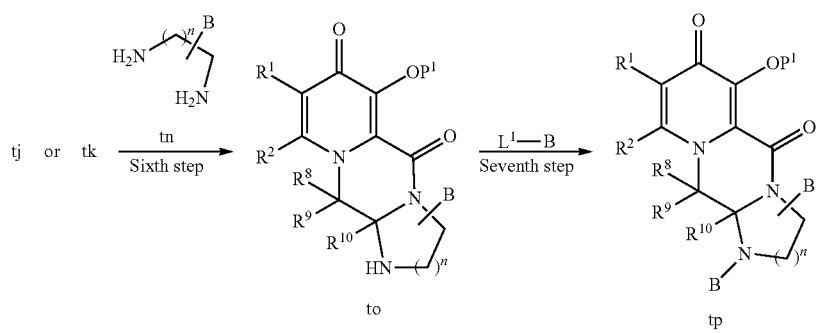

(wherein $R^P$ may be an acetal protective group which can protect and/or can be deprotected by the method described in Protective Groups in Organic Synthesis, Theodora W Green (John Wiley & Sons) etc. and, for example, $R^P$ is lower alkyl etc. Other each symbol is same as above)

First Step

A compound th can be obtained by adding allylamine to a compound tf which can be synthesized by the same method as that of a compound te in the presence of a solvent such as ethanol, THF, dioxane, acetonitrile, etc. or in a mixed solvent thereof, and performing a reaction at 0° C. to 80° C., preferably 20° C. to 60° C. for 0.5 hours to 48 hours, preferably 1 hour to 24 hours.

Second Step

A compound ti can be obtained by adding a compound tg to a compound tf in the presence of a solvent such as ethanol, THF, dioxane, acetonitrile etc. or in a mixed solvent thereof, and performing a reaction at 0° C. to 80° C., preferably 20° C. to 60° C. for 0.5 hours to 48 hours, preferably 1 hour to 24 hours.

Third Step

A compound tj can be obtained by adding potassium osmate dihydrate, sodium periodate, and water to the compound th in the presence of a solvent such as THF, ethyl acetate, dioxane, etc. or in a mixed solvent thereof, and performing a reaction at 0° C. to 60° C., preferably 10° C. to 40° C. for 0.5 hours to 24 hours, preferably 1 hour to 12 hours.

Alternatively, a compound tj can be obtained by introducing ozone into the compound th at −10° C. to 20° C. in the presence of a solvent such as THF, ethyl acetate, dioxane etc. or in a mixed solvent thereof and, subsequent to completion of the reaction, adding zinc-acetic acid, $(EtO)_3P$, or dimethyl sulfide.

Fourth Step

A compound tk can be obtained by adding an acid such as formic acid, trifluoroacetic acid, paratoluenesulfonic acid, etc. to the compound ti in a solvent such as acetone, acetonitrile, ethanol, water, etc. or in a mixed solvent thereof, or adding sulfuric acid in a formic acid solvent, and performing a reaction at 0° C. to 90° C., preferably 20° C. to 80° C. for 0.5 hours to 24 hours, preferably 1 hour to 12 hours.

Fifth Step

A compound tm can be obtained by adding a compound tl and acetic acid to the compound tj or the compound tk in the presence of a solvent such as chloroform, dichloromethane, THF, etc., and performing a reaction at 0° C. to 40° C., preferably 10° C. to 30° C. for 0.5 hours to 24 hours, preferably 1 hour to 12 hours.

Sixth Step

A compound to can be obtained by adding a compound tn and acetic acid to the compound tj or the compound tk in the presence of a solvent such as chloroform, dichloromethane, THF, etc., and performing a reaction at 0° C. to 40° C., preferably 10° C. to 30° C. for 0.5 hours to 24 hours, preferably 1 hour to 12 hours.

Seventh Step

A compound tp can be obtained by adding a compound $B-L^1$ corresponding to an objective compound to the compound to in the presence of a solvent such as DMF, DMA, NMP, THF, etc. or in a mixed solvent thereof, and performing a reaction at 0° C. to 80° C., preferably 20° C. to 60° C. for 0.5 hours to 12 hours, preferably 1 hour to 6 hours.

Synthesis of Compound vf of Reference Example (See: Reference Examples 583, and 584)

[Chemical formula 77]

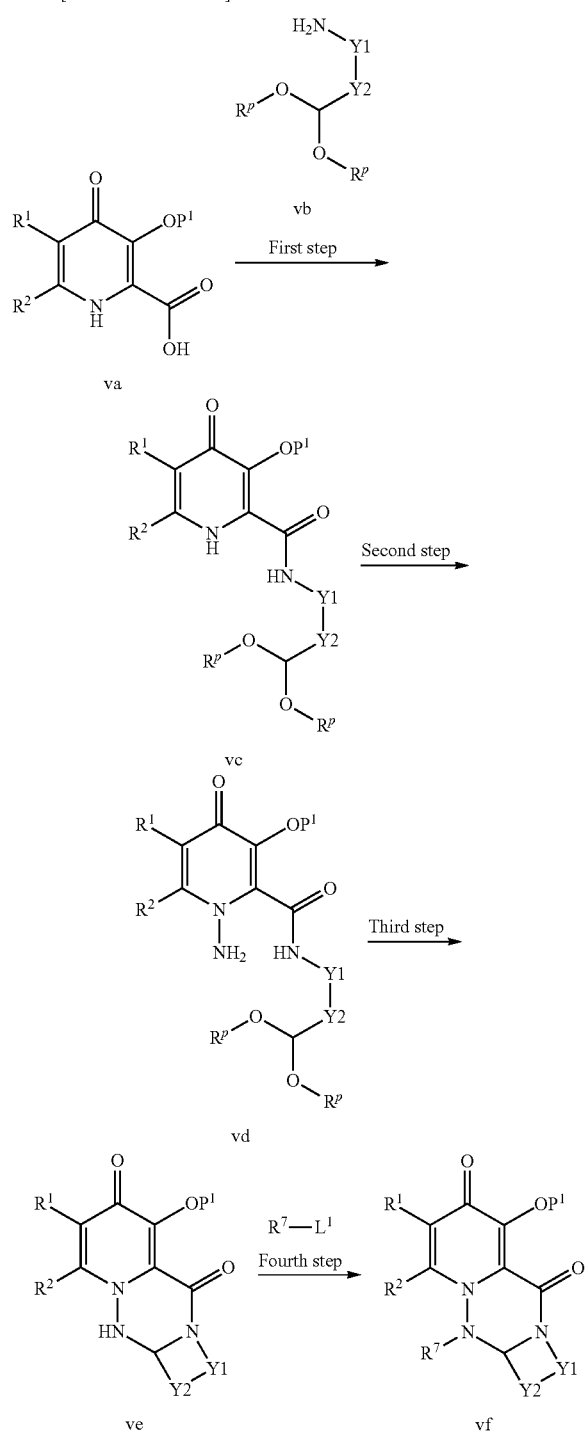

(wherein Y1 is a substituent corresponding to $R^{3a}$, and Y2 is a substituent corresponding to $R^{11a}$. Other each symbol is same as above)

First Step

A compound vc can be obtained by adding a compound vb having a substituent corresponding to an objective compound to a compound va in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU, etc. in a solvent such as DMF, THF, dichloromethane, acetonitrile etc. or in a mixed solvent thereof, and performing a reaction at −20° C. to 60° C., preferably −10° C. to 40° C. for 0.1 hours to 24 hours, preferably 1 hour to 12 hours.

Alternatively, a compound vc can be obtained by adding an acylating reagent such as diphenylchlorophosphate, thionyl chloride, oxalyl chloride etc. to a compound va in the presence or absence of a base such as pyridine, triethylamine, diisopropylethylamine, 1-methylimidazole, etc. in the presence of a solvent such as THF, dioxane, dichloromethane, DMF etc., thereby, generating acid chloride, and adding a compound vb having a substituent corresponding to an objective compound, and performing a reaction at −20° C. to 60° C., preferably −10° C. to 40° C. for 0.1 hours to 24 hours, preferably 0.5 hours to 12 hours.

Second Step

A compound vd can be obtained by adding potassium carbonate, sodium carbonate, and O-(2,4-dinitrophenyl)hydroxylamine to the compound vc in the presence of a solvent such as DMF, DMA, NMP, THF, etc., and performing a reaction at 10° C. to 60° C., preferably 20° C. to 40° C. for 0.1 hours to 48 hours, preferably 1 hour to 24 hours.

Third Step

A deprotecting reaction of an acetal protective group of the compound vd can be performed by the general method described in Protective Groups in Organic Synthesis, Theodora W Green (John Wiley & Sons) etc. Thereafter, a generated aldehyde group is subjected to an intramolecular reaction, thereby, a compound ve can be obtained.

For example, a compound ve can be obtained by adding acetic acid and/or paratoluenesulfonic acid to the compound vd in the presence of a solvent such as DMF, toluene, THF, etc., and performing a reaction at 10° C. to 80° C., preferably 30° C. to 60° C. for 0.5 hours to 12 hours, preferably 1 hour to 6 hours.

Fourth Step

A compound vf can be obtained by adding a compound $R^7$-$L^1$ corresponding to an objective substance, and a base such as sodium carbonate, potassium carbonate, cesium carbonate, etc. to the compound ve in the presence of a solvent such as DMF, DMA, NMP, THF, etc. or in a mixed solvent thereof, and performing a reaction at 0° C. to 60° C., preferably 10° C. to 40° C. for 0.1 hours to 48 hours, preferably 1 hour to 24 hours.

Synthesis of Compound wd of Reference Example (see: Reference Example 592, etc.)

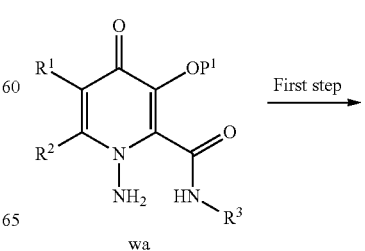

-continued

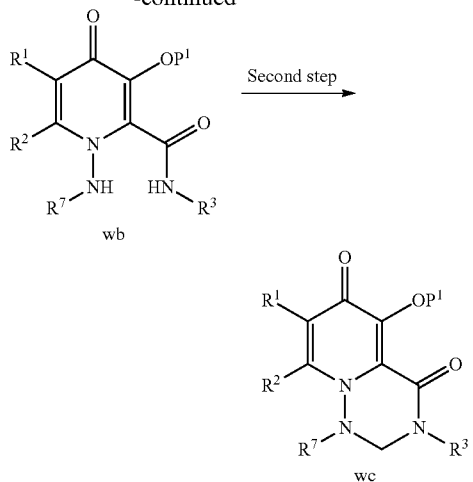

wb

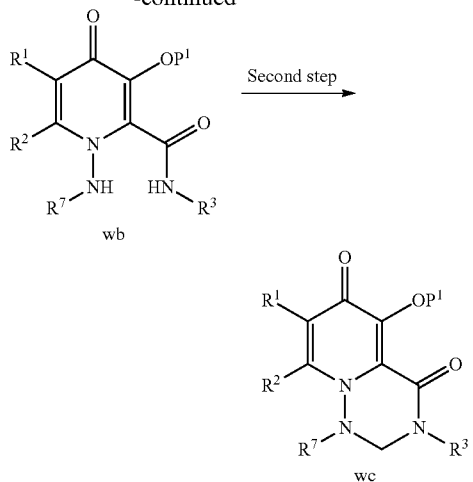

wc (wherein each symbol is same as above, and P¹ may be a group which can be protected and/or deprotected by the method described in Protective Groups in Organic Synthesis, Theodora W Green (John Wiley & Sons) etc. and, for example, P¹ is arylalkyl, etc.)

First Step

A compound wb can be obtained by adding a cation-forming reagent (e.g.: dichloroacetic acid) to the compound wa in the presence of a solvent such as 1,2-dichloroethane, THF, dioxane, chloroform, etc. and adding a reagent, $R^7$—OH corresponding to an objective substance, and performing a reaction at 10° C. to 60° C., preferably 20° C. to 40° C. for 0.1 hours to 24 hours, preferably 0.5 hours to 12 hours.

Second Step

Abase (e.g.: 2-tert-butylimino2-diethylamino-1,3-dimethylperhydro-1,3,2-diazaphosphorine) is added to the compound wb in the presence of a solvent such as DMF, DMA, NMP, THF, etc., paraformaldehyde is added, and they are reacted at 0° C. to 60° C., preferably 10° C. to 40° C. for 0.1 hours to 24 hours, preferably 0.5 hours to 12 hours. Next, a compound we can be obtained by adding a detachment reagent (e.g.: p-toluenesulfonyl chloride), and performing a reaction at 0° C. to 60° C., preferably 10° C. to 40° C. for 0.1 hours to 24 hours, preferably 0.5 hours to 12 hours.

Synthesis of Compound of Example (Prodrug: Formula (I)) from Compound of Reference Example (Parent Compound: Formula (II)) (See: Examples 1, 98, 105, 106, 106, 107, 108, 111, 112, 113, 122, 151, 152, 163, 177, 178, 186, 190, 192, 194, 196, 197, 199, 200, 201, and 203)

[Chemical formula 78]

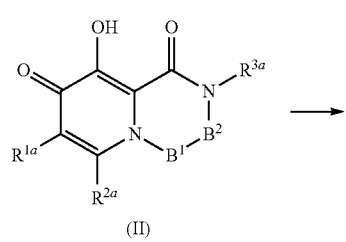

(II)

-continued

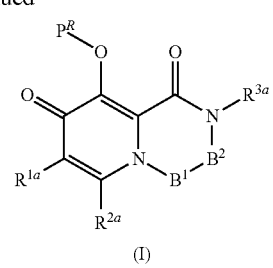

(I)

(wherein each substituent is same as in item 1)

A compound of Example can be obtained by the general method including converting a hydroxyl group into an ester group or ether group, using a compound shown in Reference example as a source.

For example, the method described in Protective Groups in Organic Synthesis, Theodora W Green (John Wiley & Sons), Prog. Med. 5: 2157-2161 (1985), and Supplied by The British Library—"The world's Knowledge", etc. can be utilized.

The present invention will be explained in more detail below by way of Examples, Reference examples, Intermediate Synthesis Examples, as well as Test Examples of the present invention, but the present invention is not limited by them.

Hereinbelow, structural formulae of compounds of Reference examples 1 to 775 that are parent compounds, and Synthesis Examples are shown.

REFERENCE EXAMPLE 1

[Chemical formula 79]

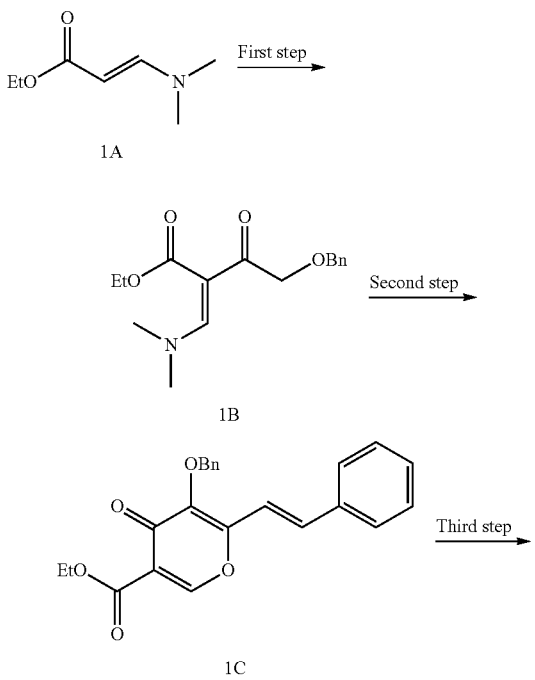

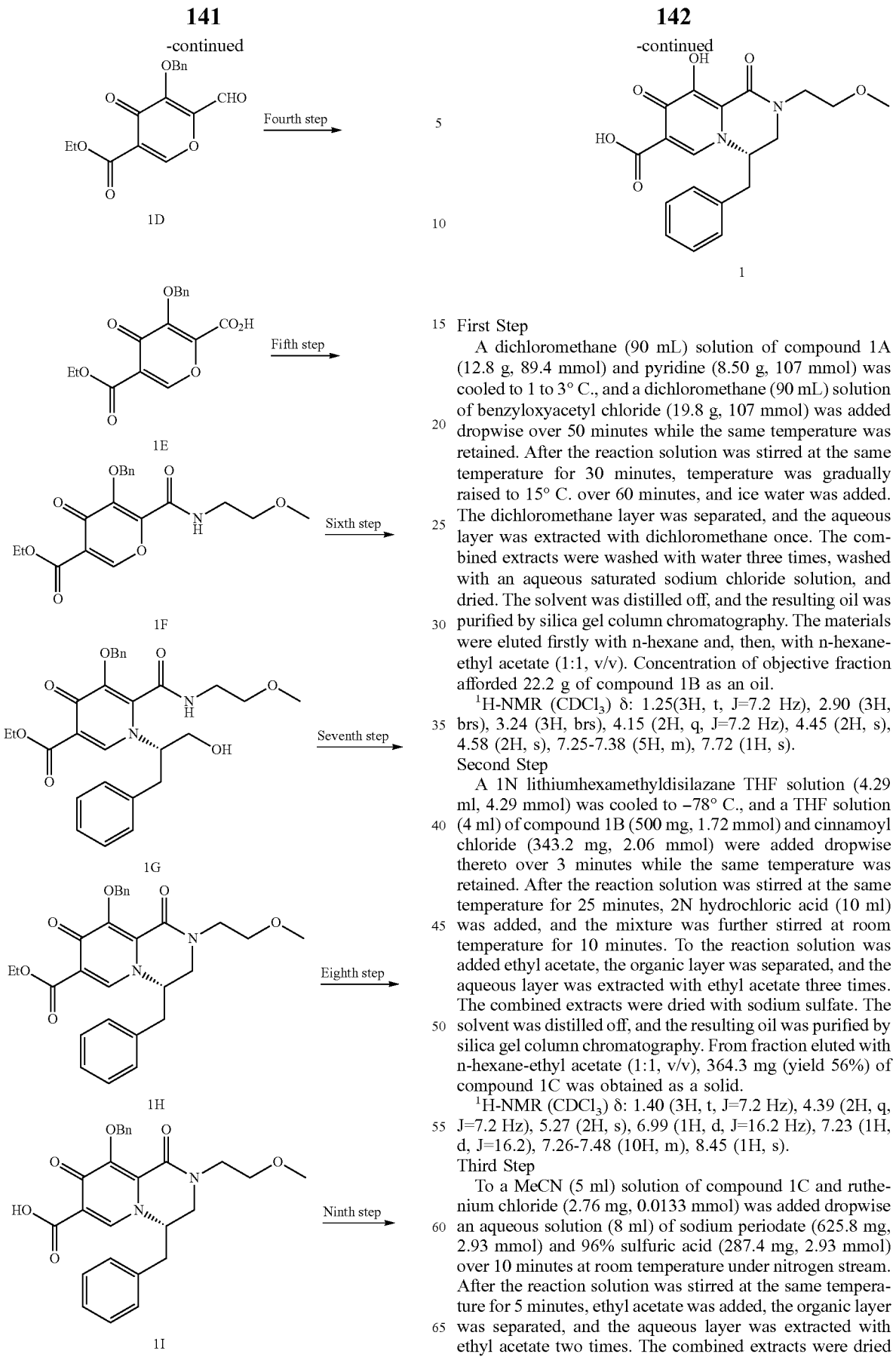

First Step

A dichloromethane (90 mL) solution of compound 1A (12.8 g, 89.4 mmol) and pyridine (8.50 g, 107 mmol) was cooled to 1 to 3° C., and a dichloromethane (90 mL) solution of benzyloxyacetyl chloride (19.8 g, 107 mmol) was added dropwise over 50 minutes while the same temperature was retained. After the reaction solution was stirred at the same temperature for 30 minutes, temperature was gradually raised to 15° C. over 60 minutes, and ice water was added. The dichloromethane layer was separated, and the aqueous layer was extracted with dichloromethane once. The combined extracts were washed with water three times, washed with an aqueous saturated sodium chloride solution, and dried. The solvent was distilled off, and the resulting oil was purified by silica gel column chromatography. The materials were eluted firstly with n-hexane and, then, with n-hexane-ethyl acetate (1:1, v/v). Concentration of objective fraction afforded 22.2 g of compound 1B as an oil.

$^1$H-NMR (CDCl$_3$) δ: 1.25(3H, t, J=7.2 Hz), 2.90 (3H, brs), 3.24 (3H, brs), 4.15 (2H, q, J=7.2 Hz), 4.45 (2H, s), 4.58 (2H, s), 7.25-7.38 (5H, m), 7.72 (1H, s).

Second Step

A 1N lithiumhexamethyldisilazane THF solution (4.29 ml, 4.29 mmol) was cooled to −78° C., and a THF solution (4 ml) of compound 1B (500 mg, 1.72 mmol) and cinnamoyl chloride (343.2 mg, 2.06 mmol) were added dropwise thereto over 3 minutes while the same temperature was retained. After the reaction solution was stirred at the same temperature for 25 minutes, 2N hydrochloric acid (10 ml) was added, and the mixture was further stirred at room temperature for 10 minutes. To the reaction solution was added ethyl acetate, the organic layer was separated, and the aqueous layer was extracted with ethyl acetate three times. The combined extracts were dried with sodium sulfate. The solvent was distilled off, and the resulting oil was purified by silica gel column chromatography. From fraction eluted with n-hexane-ethyl acetate (1:1, v/v), 364.3 mg (yield 56%) of compound 1C was obtained as a solid.

$^1$H-NMR (CDCl$_3$) δ: 1.40 (3H, t, J=7.2 Hz), 4.39 (2H, q, J=7.2 Hz), 5.27 (2H, s), 6.99 (1H, d, J=16.2 Hz), 7.23 (1H, d, J=16.2), 7.26-7.48 (10H, m), 8.45 (1H, s).

Third Step

To a MeCN (5 ml) solution of compound 1C and ruthenium chloride (2.76 mg, 0.0133 mmol) was added dropwise an aqueous solution (8 ml) of sodium periodate (625.8 mg, 2.93 mmol) and 96% sulfuric acid (287.4 mg, 2.93 mmol) over 10 minutes at room temperature under nitrogen stream. After the reaction solution was stirred at the same temperature for 5 minutes, ethyl acetate was added, the organic layer was separated, and the aqueous layer was extracted with ethyl acetate two times. The combined extracts were dried with sodium sulfate. The solvent was distilled off, and the resulting oil was purified by silica gel column chromatography. From fraction eluted with n-hexane-ethyl acetate (1:1, v/v), 303.2 mg (yield 75%) of compound 1D was obtained as an oil.

$^1$H-NMR (CDCl$_3$) δ: 1.39 (3H, t, J=6.9 Hz), 4.40 (2H, q, J=6.9 Hz), 5.54 (2H, s), 7.37 (5H, s), 8.48 (1H, s), 9.85 (1H, s).

Fourth Step

To a MeCN (15 ml) solution of compound 1D (1.00 g, 3.31 mmol) was added an aqueous solution (10 ml) of 96% sulfuric acid (421.7 mg, 4.30 mmol) and amidosululic acid (642.7 mg, 6.62 mmol) at room temperature, the mixture was stirred, and an aqueous solution (10 ml) of sodium chlorite (388.9 mg, 4.30 mmol) was added dropwise over 5 minutes while the same temperature was retained. After the reaction solution was stirred at the same temperature for 5 minutes, an aqueous saturated sodium chloride solution was added, and the mixture was extracted with ethyl acetate three times. The combined extracts were dried with sodium sulfate. The solvent was distilled off, and the resulting oil was purified by silica gel column chromatography. The materials were eluted firstly with chloroform and, then, with chloroform-MeOH (7:3, v/v). Concentration of objective fraction afforded 748.8 mg (yield 71%) of compound 1E as an oil.

$^1$H-NMR (CDCl$_3$) δ: 1.40 (3H, t, J=7.2 Hz), 3.93 (1H, brs), 4.40 (2H, q, J=7.2 Hz), 5.61 (2H, s), 7.38-7.44 (10H, m), 8.52 (1H, s).

Fifth Step

To a DMF (10 ml) solution of compound 1E (1.00 g, 3.14 mmol) were added WSC HCl (1.20 g, 6.28 mmol) and HOBt (551.6 mg, 4.08 mmol) at room temperature, and the mixture was stirred at the same temperature for 90 minutes. The reaction solution was cooled to 0° C., and a DMF (2 ml) solution of 2-methoxyethanamine (236.0 mg, 3.14 mmol) was added dropwise over 3 minutes. The reaction solution was stirred at the same temperature for 1 hour, water was added, and the mixture was extracted with ethyl acetate three times. The extract was washed with water three times, and dried with sodium sulfate. The solvent was distilled off, and the resulting oil was purified by silica gel chromatography. The materials were eluted firstly with n-hexane-ethyl acetate (1:1, v/v) and, then, with n-hexane-ethyl acetate (1:9, v/v). Concentration of objective fraction afforded 928.5 mg (yield 79%) of compound 1F as an oil.

$^1$H-NMR (CDCl$_3$) δ: 1.39 (3H, t, J=7.2 Hz), 3.29 (3H, s), 3.41 (2H, t, J=5.4 Hz), 3.47-3.53 (2H, m), 4.39 (2H, q, J=7.2 Hz), 5.44 (2H, s), 7.36 (3H, m), 7.44-7.47 (2H, m), 8.07 (1H, brs), 8.54 (1H, s).

Sixth Step

A xylene (2 ml) solution of compound 1F (500 mg, 1.33 mmol) and (S)-2-amino-3-phenylpropan-1-ol (604.2 mg, 4.0 mmol) was heated to 120° C., and stirred for 30 minutes. After the reaction solution was cooled to room temperature, and the solvent was distilled off, the resulting oil was purified by silica gel chromatography. The materials were eluted firstly with chloroform and, then, with chloroform-MeOH (9:1, v/v). Concentration of objective fraction afforded 487 mg (yield 72%) of compound 1G as an oil.

$^1$H-NMR (CDCl$_3$) δ: 1.41 (3H, t, J=6.9 Hz), 2.24-2.34 (1H, m), 2.24-3.00 (1H, m), 3.03-3.16 (1H, m), 3.05 (3H, m), 3.25-3.32 (2H, m), 4.13-4.19 (1H, m), 4.17-4.30 (1H, m), 4.36-4.47 (1H, m), 4.51-4.54 (1H, m), 4.55 (1H, d, J=10.5 Hz), 5.78 (1H, t, J=6.9 Hz), 7.17-7.26 (4H, m), 7.28-7.35 (5H, m), 7.49 (1H, t, J=5.4 Hz), 6.32 (1H, s).

Seventh Step

To a THF (6 ml) solution of compound 1G (2.86 g, 5.63 mmol) and triphenylphosphine (2.21 g, 8.45 mmol) was added dropwise a DEAD 40 wt % toluene solution (3.68 g, 8.45 mmol) at room temperature over 3 minutes. The reaction solution was stirred at the same temperature for 30 minutes, the solvent was distilled off, and the resulting oil was purified by silica gel chromatography. From a fraction eluted with ethyl acetate-MeOH (9:1, v/v), 1.37 g (yield 50%) of compound 1H was obtained as an oil.

$^1$H-NMR (CDCl$_3$) δ: 1.31 (3H, t, J=7.2 Hz), 3.07 (2H, d, J=6.9 Hz), 3.33 (3H, s), 3.57-3.80 (4H, m), 3.95 (1H, dd, J=3.0 Hz, 6.6 Hz), 4.01-4.14 (1H, m), 4.16-4.34 (2H, m), 5.24 (1H, d, J=9.9 Hz), 5.51 (1H, d, J=9.9 Hz), 7.01-7.03 (2H, m), 7.21-7.37 (5H, m), 7.41-7.58 (1H, m), 7.64-7.69 (2H, m).

Eighth Step

To an EtOH (6 ml) solution of compound 1H (1.0 g, 2.04 mmol) was added a 2N aqueous sodium hydroxide solution (6 ml), and the mixture was stirred at room temperature for 30 minutes. The reaction solution was neutralized with 2N hydrochloric acid, and the precipitated solid was filtered, and dried to obtain 754 mg (yield 80%) of compound 1I.

$^1$H-NMR (CDCl$_3$) δ: 3.10 (2H, d, J=7.8 Hz), 3.33 (3H, s), 3.57-3.69 (4H, m), 3.82-3.90 (1H, m), 3.95 (1H, dd, J=3.3 Hz, 13.8 Hz), 4.36 (1H, dd, J=6.3 Hz, 7.5 Hz), 5.36 (1H, d, J=10.2 Hz), 5.45 (1H, d, J=10.2 Hz), 6.98-7.01 (2H, m), 7.28-7.39 (6H, m), 7.59 (2H, dd, J=1.8 Hz, 8.1 Hz), 7.87 (1H, s).

Ninth Step

Compound 1I (1.0 g, 2.16 mmol) was dissolved in THF (10 ml), 10% Pd—C (200 mg) was added, and the mixture was subjected to a catalytic reduction reaction under hydrogen stream. The catalyst was removed by filtration, and the filtrate was concentrated. The resulting residue was washed with ether to obtain 512 mg (yield 64%) of compound 1.

$^1$H-NMR (CDCl$_3$) δ: 6.24 (2H, d, J=6.3 Hz), 3.36 (3H, s), 3.60-3.86 (5H, m), 4.14 (1H, d, J=12.9 Hz), 4.47 (1H, s), 7.03-7.05 (2H, m), 7.30-7.35 (3H, m), 7.88 (1H, s), 12.68 (1H, s), 14.83 (1H, s).

REFERENCE EXAMPLE 2

[Chemical formula 80]

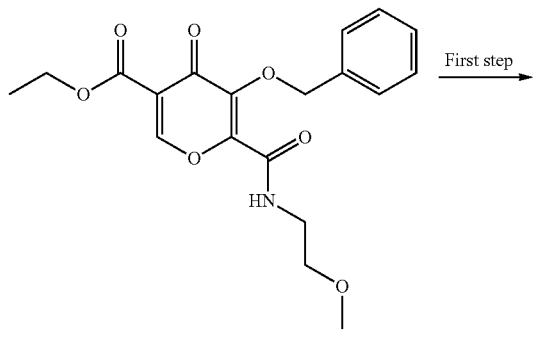

1F

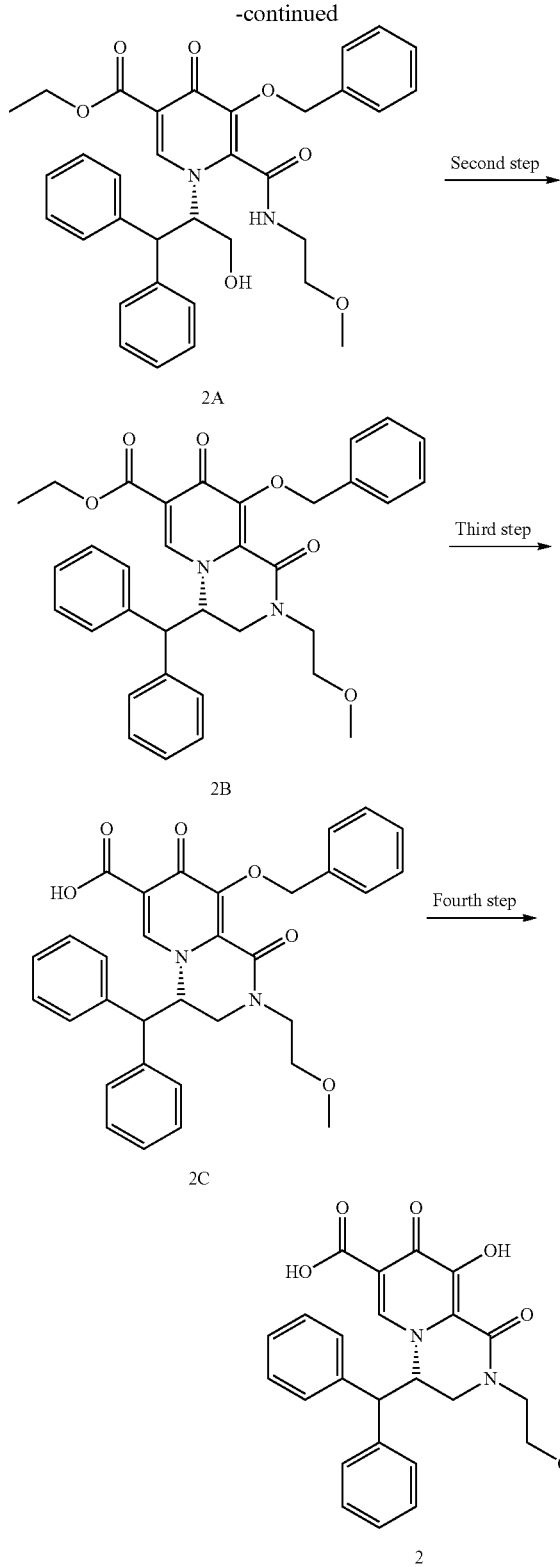

2A

2B

2C

2

First Step

To (S)-tert-butyl 3-hydroxy-1,1-diphenylpropan-2-ylcarbamate (5.00 g, 15.3 mmol) was added trifluoroacetic acid (40 ml), and the mixture was stirred for 1 hour under ice-cooling. After trifluoroacetic acid was distilled off, toluene was added, and distilled off again under reduced pressure to obtain crude (S)-2-amino-3,3-diphenylpropan-1-ol. To the resulting (S)-2-amino-3,3-diphenylpropan-1-ol were added compound 1F (5.73 g, 15.3 mmol), toluene (50 ml), and triethylamine (6.4 ml, 45.8 mmol), the mixture was stirred at 90° C. for 1 hour, and cooled to room temperature and, thereafter, the solvent was distilled off. To the resulting residue was added dichloromethane, and the mixture was washed with 2N aqueous hydrochloric acid solution, an aqueous saturated sodium bicarbonate solution, and an aqueous saturated sodium chloride solution. After separation of the organic layer, after magnesium sulfate was added, the mixture was filtered with celite, and the filtrate was distilled off to obtain candy-like compound 2A (9.12 g).

MS: m/z=585.2 [M+H]$^+$.

Second Step

The compound 2A (8.60 g, 14.7 mmol) and triphenylphosphine (7.72 g, 29.4 mmol) were dissolved in tetrahydrofuran (90 ml), and a 2.2M toluene solution of diethyl azodicarboxylate (10.0 ml, 22.0 mmol) was added dropwise under ice-cooling. After the mixture was stirred for 2 hours under ice-cooling, and for 18 hours under room temperature, the solvent was distilled off. The resulting residue was purified by silica gel column chromatography to obtain foamy compound 2B (3.88 g, 6.85 mmol).

$^1$H-NMR (DMSO-d$_6$) δ: 1.18 (3H, m), 3.11 (3H, s), 3.16 (1H, m), 3.28 (1H, m), 3.76 (1H, m), 3.97-4.13 (3H, m), 4.31 (1H, d, J=11.3 Hz), 5.08 (2H, s), 5.52 (1H, d, J=12.0 Hz), 7.18-7.25 (6H, m), 7.25-7.45 (6H, m), 7.55-7.66 (6H, m).

MS: m/z=567.7 [M+H]$^+$.

Third Step

To compound 2B (3.4 g, 6.0 mmol) were added ethanol (36 ml), water (12 ml), and a 2N aqueous sodium hydroxide solution (4.5 ml, 9.0 mmol), and the mixture was stirred at room temperature for 40 minutes, thereafter, ethanol (10 ml) and water (10 ml) were added, and the mixture was further stirred for 30 minutes. Ethanol was distilled off, ethyl acetate and water were added, and the mixture was stirred vigorously and, thereafter, layers were separated. The ethyl acetate layer was washed with 2N sodium hydroxide three times, and the aqueous layers were combined into one aqueous layer. To the aqueous layer was added ethyl acetate, the mixture was neutralized using 2N hydrochloric acid, then the mixture was stirred vigorously and, thereafter, the ethyl acetate layer was separated. To the ethyl acetate layer was added magnesium sulfate, the mixture was filtered with celite, and the filtrate was distilled off. The resulting residue was dissolved in MeOH, and the solvent was distilled off to obtain a solid of compound 2C (3.0 g, 5.64 mmol).

$^1$H-NMR (DMSO-d$_6$) δ: 3.11 (3H, s), 3.16 (1H, m), 3.25 (1H, m), 3.75 (1H, m), 4.11 (1H, m), 4.36 (1H, d, J=11.6 Hz), 5.18 (2H, dd, J=15.7 Hz, 10.4 Hz), 5.71 (1H, d, J=11.6 Hz), 7.08-7.20 (5H, m), 7.29-7.45 (6H, m), 7.55 (2H, d, J=6.7 Hz), 7.61 (2H, d, J=7.5 Hz), 7.98 (1H, s).

MS: m/z=539.4 [M+H]$^+$.

Fourth Step

To compound 2C (1.50 g, 2.79 mmol) were added methanol (22 ml), and 10% palladium carbon-50% wet (150 mg), and the mixture was stirred for 1 hour under hydrogen atmosphere. Ethyl acetate (44 ml) was added, the mixture was filtered with celite, and the filtrate was distilled off. The resulting residue was dissolved in methanol (20 ml), water (10 ml) was added, and methanol was distilled off. The precipitate was filtered, and dried to obtain compound 2 (1.15 g, 2.56 mmol).

$^1$H-NMR (DMSO-d$_6$) δ: 3.15 (3H, s), 3.50-3.70 (5H, m), 4.19 (1H, dd, J=13.8 Hz, 3.1 Hz), 4.49 (1H, d, J=11.6 Hz), 5.78 (1H, d, J=9.6 Hz), 7.10-7.27 (6H, m), 7.34 (1H, m), 7.46 (2H, t, J=7.5 Hz), 7.63 (2H, t, J=7.7 Hz), 7.94 (1H, s), 12.94 (1H, s), 15.08 (1H, s).

MS: m/z=449.4 [M+H]$^+$.

REFERENCE EXAMPLE 3

[Chemical formula 81]

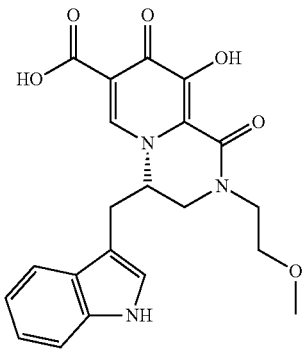

3

According to Reference example 2, compound 3 was synthesized by the same procedure.

$^1$H-NMR (DMSO-d$_6$) δ: 3.15 (1H, m), 3.26 (3H, s), 3.52-3.70 (4H, m), 3.70-3.80 (2H, m), 4.10 (1H, d, J=12.9 Hz), 4.92 (1H, brs), 6.98 (1H, t, J=7.4 Hz), 7.03 (1H, brs), 7.08 (1H, t, 7.6 Hz), 7.34 (1H, d, J=7.8 Hz), 7.47 (1H, d, J=7.3 Hz), 7.80 (1H, s), 10.94 (1H, brs), 15.38 (1H, brs).

MS: m/z=412.4 [M+H]$^+$.

REFERENCE EXAMPLE 4

[Chemical formula 82]

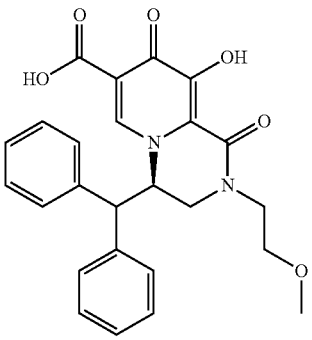

4

According to Reference example 2, compound 4 was synthesized by the same procedure.

$^1$H-NMR (DMSO-d$_6$) δ: 3.13 (3H, s), 3.46-3.72 (5H, m), 4.16 (1H, d, J=12.6 Hz), 4.48 (1H, d, J=10.9 Hz), 5.77 (1H, d, J=11.6 Hz), 7.10-7.27 (6H, m), 7.32 (1H, m), 7.44 (2H, m), 7.61 (2H, m), 7.93 (1H, s), 15.04 (1H, s).

MS: m/z=449.3 [M+H]$^+$.

REFERENCE EXAMPLE 5

[Chemical formula 83]

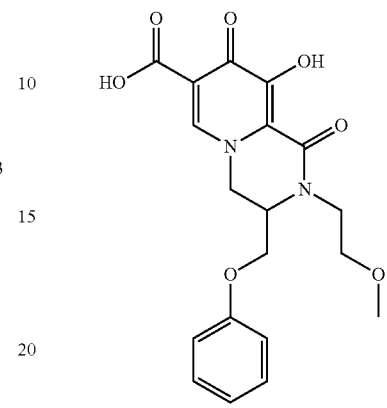

5

According to Reference example 2, compound 5 was synthesized by the same procedure.

$^1$H-NMR (DMSO-d$_6$) δ: 3.28 (3H, s), 3.52-3.68 (4H, m), 4.06 (1H, m), 4.25 (2H, m), 4.41 (1H, brs), 4.56 (1H, d, J=13.6 Hz), 4.82 (1H, d, J=13.9 Hz), 6.74 (2H, d, J=7.6 Hz), 6.92 (1H, t, J=7.20 Hz), 7.25 (2H, t, J=7.8 Hz), 8.58 (1H, s), 12.48 (1H, brs), 15.55 (1H, brs).

MS: m/z=389.4 [M+H]$^+$.

REFERENCE EXAMPLE 6

[Chemical formula 84]

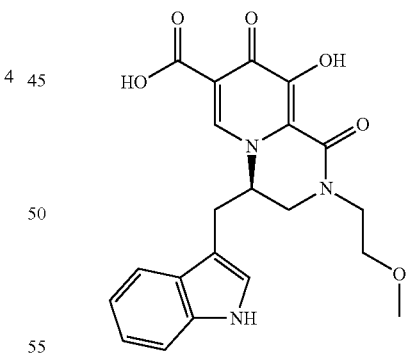

6

According to Reference example 2, compound 6 was synthesized by the same procedure.

$^1$H-NMR (DMSO-d$_6$) δ: 3.16 (1H, m), 3.26 (3H, s), 3.50-3.70 (4H, m), 3.70-3.80 (2H, m), 4.10 (1H, d, J=13.4 Hz), 4.92 (1H, brs), 6.98 (1H, t, J=7.1 Hz), 7.03 (1H, brs), 7.08 (1H, t, J=7.3 Hz), 7.34 (1H, d, J=7.8 Hz), 7.48 (1H, d, J=7.3 Hz), 7.81 (1H, s), 12.91 (1H, s), 15.36 (1H, s).

MS: m/z=412.4 [M+H]$^+$.

REFERENCE EXAMPLE 7

[Chemical formula 85]

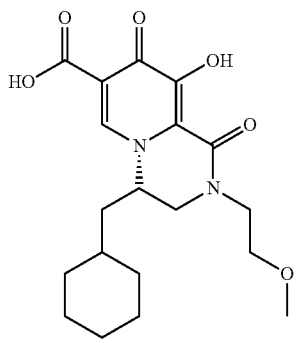

According to Reference example 2, compound 7 was synthesized by the same procedure.

$^1$H-NMR (DMSO-$d_6$) δ: 0.85-0.95 (2H, m), 1.05-1.25 (5H, m), 1.45-1.80 (8H, m), 3.28 (3H, s), 3.46 (1H, m), 3.58 (1H, m), 3.72 (1H, d, J=13.9 Hz), 3.93 (1H, m), 4.04 (1H, d, J=13.1 Hz), 4.88 (1H, s), 8.56 (1H, s), 12.80 (1H, s), 15.51 (1H, s).

MS: m/z=379.3 [M+H]$^+$.

REFERENCE EXAMPLE 8

[Chemical formula 86]

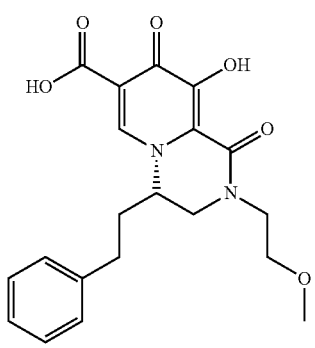

According to Reference example 2, compound 8 was synthesized by the same procedure.

$^1$H-NMR (DMSO-$d_6$) δ: 2.07 (2H, m), 2.55 (1H, m), 2.74 (1H, m), 3.17 (1H, s), 3.23 (3H, s), 3.48-3.65 (4H, m), 3.79 (1H, d, J=13.6 Hz), 3.87 (1H, m), 4.09 (1H, d, J=13.6 Hz), 4.80 (1H, s), 7.10-7.29 (5H, m), 8.59 (1H, s), 12.77 (1H, s), 15.49 (1H, s).

MS: m/z=387.3 [M+H]$^+$.

REFERENCE EXAMPLE 9

[Chemical formula 87]


According to Reference example 2, compound 9 was synthesized by the same procedure.

$^1$H-NMR (DMSO-$d_6$) δ: 2.80 (1H, dd, J=14.5 Hz, J2=8.5 Hz), 2.93 (1H, dd, J=14.4 Hz, 5.6 Hz), 3.21 (3H, s), 3.40-3.55 (4H, m), 3.77 (2H, s), 3.82 (1H, d, J=13.1 Hz), 3.88 (1H, m), 4.13 (1H, d, J=13.6 Hz), 4.85 (1H, s), 7.20-7.35 (5H, m), 8.61 (1H, s), 12.79 (1H, s), 15.43 (1H, s).

MS: m/z=419.3 [M+H]$^+$.

REFERENCE EXAMPLE 10

[Chemical formula 88]

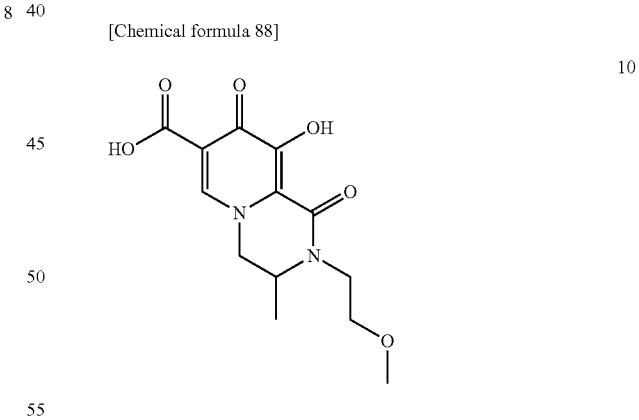

According to Reference example 2, compound 10 was synthesized by the same procedure.

$^1$H-NMR (DMSO-$d_6$) δ: 1.22 (3H, d, J=6.2 Hz), 3.29 (3H, s), 3.43 (1H, m), 3.58 (2H, m), 3.94 (1H, m), 4.12 (1H, brs), 4.41 (1H, d, J=13.6 Hz), 4.49 (1H, d, J=13.1 Hz), 8.59 (1H, s), 12.65 (1H, s), 15.53 (1H, s).

MS: m/z=297.2 [M+H]$^+$.

REFERENCE EXAMPLE 11

[Chemical formula 89]

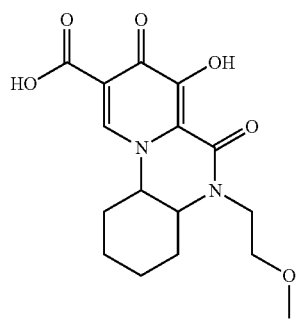

11

According to Reference example 2, compound 11 was synthesized by the same procedure.

$^1$H-NMR (DMSO-$d_6$) δ: 1.46 (4H, brs), 1.76-1.90 (2H, m), 2.22 (1H, brs), 3.27 (3H, s), 3.57 (1H, d, J=5.3 Hz), 4.07 (1H, m), 4.69 (1H, m), 8.47 (1H, s), 13.04 (1H, s), 15.52 (1H, s).

MS: m/z=337.2 [M+H]$^+$.

REFERENCE EXAMPLE 12

[Chemical formula 90]

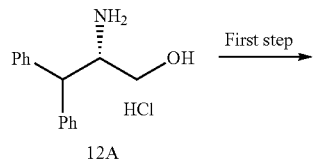
12A → First step

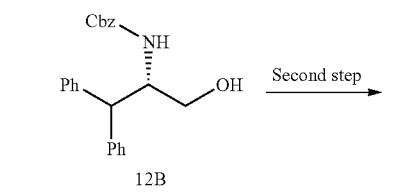
12B → Second step

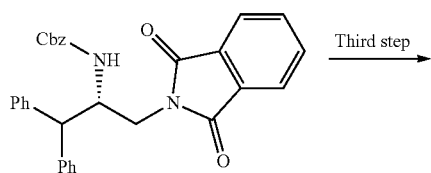
12C → Third step

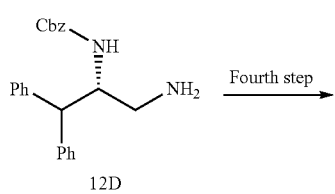
12D → Fourth step

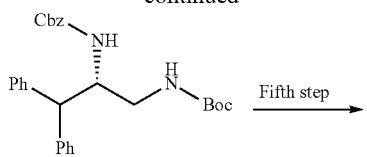
12E → Fifth step

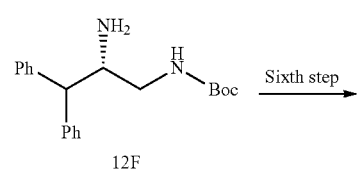
12F → Sixth step

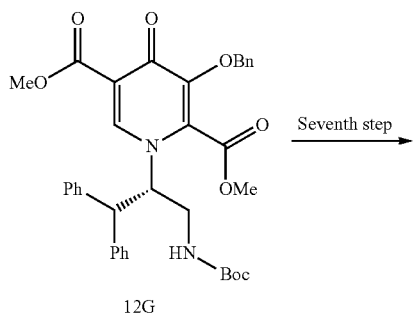
12G → Seventh step

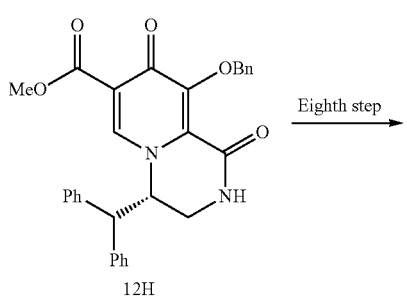
12H → Eighth step

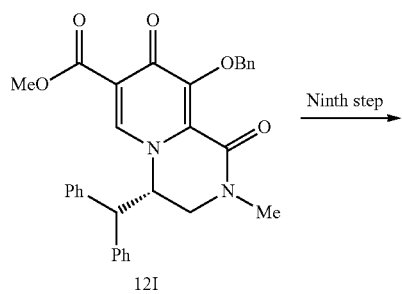
12I → Ninth step

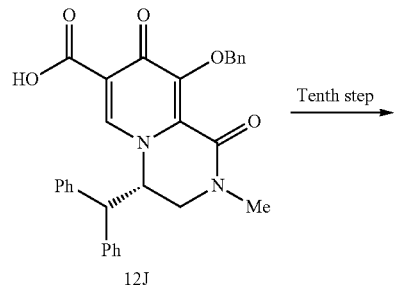
12J → Tenth step

153

-continued

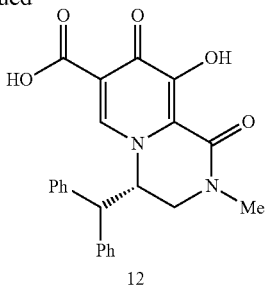

12

First Step

Compound 12A (1.53 g, 5.80 mmol) were dissolved in THF (6 ml) and water (6 ml), potassium carbonate (2.41 g, 17.4 mmol) was added, the mixture was stirred, and benzyl chloroformate (1.09 g, 6.38 mmol) was added dropwise at 0° C. After stirring at 0° C. for 10 minutes, the mixture was stirred at room temperature for 2 hours. The reaction solution was poured into sodium bicarbonate water, and the mixture was extracted with ethyl acetate. The extract was washed with 1N hydrochloric acid and an aqueous saturated sodium chloride solution, and dried with sodium sulfate. The solvent was distilled off to obtain 2.32 g of compound 12B as a colorless gummy substance.

$^1$H-NMR (CDCl$_3$) δ: 1.98 (1H, brs), 3.55 (1H, m), 3.75 (1H, m), 4.20 (1H, d, J=10.5 Hz), 4.58 (1H, m), 4.83 (1H, brs), 5.07 (2H, s), 7.16-7.39 (15H, m).

Second Step

The compound 12B (1.94 g, 5.37 mmol), triphenylphosphine (2.11 g, 8.05 mmol) and phthalimide (948 mg, 6.44 mmol) were added to THF (20 ml), and diisopropyl azodicarboxylate (2.2M in toluene, 3.66 ml, 8.05 mmol) was added dropwise at room temperature. After stirring at room temperature for 4 hours, the solvent was distilled off under reduced pressure. The resulting crude product was purified by silica gel column chromatography (n-hexane-ethyl acetate, 1:1, v/v) to obtain 2.39 g of compound 12C as a colorless solid.

$^1$H-NMR (CDCl$_3$) δ: 3.73 (2H, m), 4.05 (1H, d, J=10.1 Hz), 4.70 (1H, d, J=9.6 Hz), 4.77 (2H, d, J=7.2 Hz) 5.02 (1H, m), 7.03-7.42 (15H, m), 7.68 (2H, dd, J=5.7, 2.1 Hz), 7.78 (2H, dd, J=5.7, 2.1 Hz).

Third Step

The compound 12C (2.39 g, 4.87 mmol) was added to THF (20 ml) and methanol (20 ml), hydrazine hydrate (4.88 g, 97.4 mmol) was added, and the mixture was stirred at 50° C. for 4 hours. The white precipitate was removed by filtration, and washed with methanol. After the filtrate was distilled off under reduced pressure, the resulting crude product was purified by amino column chromatography (chloroform-methanol, 99:1, v/v) to obtain 1.41 g of compound 12D as a colorless solid.

$^1$H-NMR (CDCl$_3$) δ: 2.63 (1H, dd, J=13.2, 5.8 Hz), 2.86 (1H, d, J=9.9 Hz), 4.07 (1H, d, J=10.4 Hz), 4.53 (1H, m), 4.81 (1H, m), 5.00 (2H, d, J=8.4 Hz), 7.20-7.36 (10H, m).

Fourth Step

Compound 12D (1.41 g, 3.91 mmol) was dissolved in THF (15 ml), and Boc2O (896 mg, 4.11 mmol) was added at room temperature. After stirring for 1.5 hours, the solvent was concentrated under reduced pressure. The resulting crude product was purified by silica gel column chromatography (n-hexane-ethyl acetate, 1:1, v/v) to obtain 1.77 g of compound 12E as a colorless solid.

154

$^1$H-NMR (CDCl$_3$) δ: 1.41 (9H, s), 3.23 (2H, brm), 3.97 (1H, d, J=9.8 Hz), 4.58-4.80 (3H, m), 5.00 (2H, d, J=9.8 Hz), 7.15-7.29 (10H, m).

Fifth Step

Compound 12E (1.73 g, 3.76 mmol) and palladium-active carbon (10%, wet, 200 mg) were added to methanol (20 ml), and the mixture was stirred at room temperature for 1 hour under hydrogen atmosphere. After filtration with celite, the solvent was concentrated under reduced pressure to obtain 1.01 g of a colorless oily substance 12F.

$^1$H-NMR (CDCl$_3$) δ: 1.44 (9H, s), 2.82 (1H, m), 3.31 (1H, m), 3.73 (2H, d, J=6.9 Hz), 4.98 (1H, s), 7.18-7.39 (10H, m).

Sixth Step

Dimethyl 3-(benzyloxy)-4-oxo-4H-pyran-2,5-dicarboxylate (974 mg, 3.06 mmol) obtained by the method shown in Intermediate Synthesis Example 1, and 12F (999 mg, 3.06 mmol) were added to toluene (10 ml), and the mixture was stirred at 110° C. for 5 hours. After the solvent was distilled off under reduced pressure, the resulting crude product was purified by silica gel column chromatography (chloroform-methanol, 98:2, v/v) to obtain 1.51 g of compound 12G as a pale yellow solid.

$^1$H-NMR (CDCl$_3$) δ: 1.36 (9H, s), 3.40 (1H, m), 3.53 (1H, m), 3.82 (3H, s), 3.91 (3H, s), 4.29 (1H, d, J=11.3 Hz), 4.78 (1H, m), 4.82 (1H, m), 5.11 (1.9H, d, J=7.5 Hz), 7.10-7.38 (10H, m), 8.27 (1H, s).

Seventh Step

To compound 12G (1.45 g, 2.31 mmol) was added 4N HCl (ethyl acetate solution, 20 ml), and the mixture was stirred at room temperature for 1.5 hours. After the solvent was distilled off under reduced pressure, sodium bicarbonate water was added, and the mixture was stirred at room temperature for 1.5 hours. This was extracted with chloroform, and dried with sodium sulfate. After the solvent was distilled off under reduced pressure, the resulting crude product was purified by silica gel column chromatography (chloroform-methanol, 95:5, v/v) to obtain 1.01 g of compound 12H as a colorless solid.

$^1$H-NMR (CDCl$_3$) δ: 3.40 (1H, dd, J=13.6, 6.6 Hz), 3.78 (3H, s), 3.80 (1H, m), 4.37 (1H, d, J=11.6 Hz), 4.59 (1H, d, J=11.0 Hz), 5.43 (2H, d, J=10.2 Hz), 5.93 (1H, d, J=5.8 Hz), 7.03-7.21 (5H, m), 7.37 (9H, m), 7.63 (2H, m).

Eighth Step

Compound 12H (50 mg, 0.10 mmol) was dissolved in DMF (1 ml), and cesium carbonate (165 mg, 0.50 mmol) was added. After stirring at room temperature for 30 minutes, iodomethane (0.032 ml, 0.50 mmol) was added, and the mixture was stirred at room temperature for 3.5 hours. The reaction solution was poured into water, and the mixture was extracted with ethyl acetate, and dried with sodium sulfate. After the solvent was distilled off under reduced pressure, the resulting crude product was purified by silica gel column chromatography (chloroform-methanol, 95:5, v/v) to obtain 49 mg of compound 121 as a colorless solid.

Ninth Step

Compound 121 (49 mg, 0.096 mmol) was dissolved in THF (0.5 ml) and methanol (0.5 ml), a 2N aqueous sodium hydroxide solution (0.24 ml, 0.48 mmol) was added at room temperature, and the mixture was stirred for 1.5 hours. After 1N hydrochloric acid was added, and the mixture was extracted with ethyl acetate, the extract was dried with sodium sulfate. After the solvent was distilled off under reduced pressure, 54 mg of compound 12J was obtained as a colorless solid.

MS: m/z=481 [M+H]$^+$.

Tenth Step

To compound 12J obtained in the ninth step was added trifluoroacetic acid (1 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-methanol-ethyl ether were added, and the precipitated solid was filtered to obtain 26 mg of compound 12 as a colorless solid.

$^1$H-NMR (DMSO-$d_6$) δ: 3.01 (3H, s), 3.26 (1H, t, J=14.4 Hz), 4.23 (1H, dd, J=13.5, 3.8 Hz), 4.57 (1H, d, J=11.6 Hz), 5.78 (1H, d, J=11.3 Hz), 7.16-7.70 (10H, m), 8.00 (1H, s), 13.00 (1H, s), 15.10 (1H, s).

MS: m/z=405 [M+H]$^+$.

REFERENCE EXAMPLE 13

[Chemical formula 91]

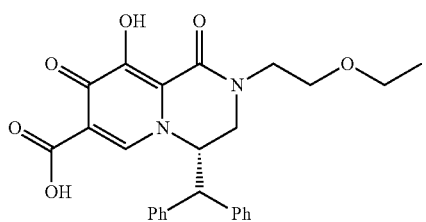

According to Reference example 12, compound 13 was synthesized by the same procedure.

$^1$H-NMR (DMSO-$d_6$) δ: 1.05 (3H, t, J=6.9 Hz), 3.43-3.65 (3H, m), 4.22 (1H, d, J=10.6 Hz), 4.55 (1H, d, J=11.6 Hz), 5.81 (1H, d, J=10.1 Hz), 7.15-7.68 (10H, m), 7.97 (1H, s), 12.96 (1H, s), 15.07 (1H, s).

MS: m/z=463 [M+H]$^+$.

REFERENCE EXAMPLE 14

[Chemical formula 92]

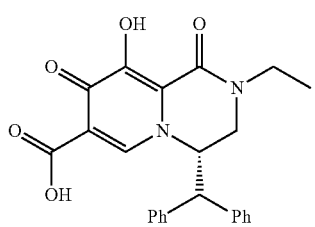

According to Reference example 12, compound 14 was synthesized by the same procedure.

$^1$H-NMR (DMSO-$d_6$) δ: 0.98 (3H, t, J=7.17 Hz), 3.44-3.64 (3H, m), 4.15 (1H, dd, J=13.7, 3.5 Hz), 4.45 (1H, d, J=11.6 Hz), 5.79 (1H, d, J=12.2 Hz), 7.08-7.63 (10H, m), 7.89 (1H, s), 13.01 (1H, s), 15.06 (1H, s).

MS: m/z=419 [M+H]$^+$.

REFERENCE EXAMPLE 15

[Chemical formula 93]

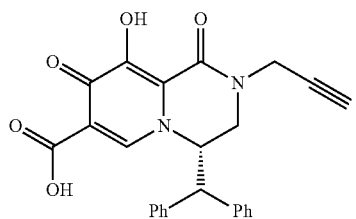

According to Reference example 12, compound 15 was synthesized by the same procedure.

$^1$H-NMR (DMSO-$d_6$) δ: 3.22 (1H, s), 3.47 (1H, d, J=13.3 Hz), 4.17 (2H, m), 4.44 (2H, dd, J=16.7, 3.0 Hz), 5.79 (1H, d, J=12.2 Hz), 7.10-7.64 (10H, m), 7.98 (1H, s), 12.56 (1H, s), 15.05 (1H, brs).

REFERENCE EXAMPLE 16

[Chemical formula 94]

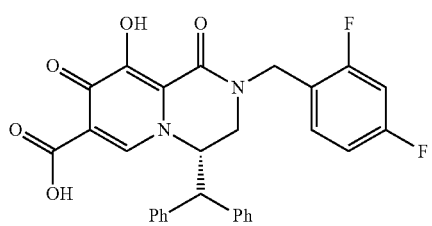

According to Reference example 12, compound 16 was synthesized by the same procedure.

$^1$H-NMR (DMSO-$d_6$) δ: 3.24 (1H, d, J=13.2 Hz), 4.23 (1H, m), 4.25 (1H, d, J=14.7 Hz), 4.40 (1H, d, J=14.8 Hz), 4.92 (1H, d, J=15.4 Hz), 5.79 (1H, m), 7.03-7.48 (10H, m), 7.93 (1H, s), 12.82 (1H, s), 15.06 (1H, s).

REFERENCE EXAMPLE 17

[Chemical formula 95]

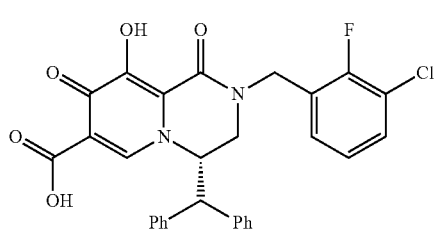

According to Reference example 12, compound 17 was synthesized by the same procedure.

$^1$H-NMR (DMSO-$d_6$) δ: 3.23 (1H, d, J=13.4 Hz), 4.22 (1H, m), 4.25 (1H, d, J=12.0 Hz), 4.45 (1H, d, J=14.9 Hz), 4.93 (1H, d, J=15.3 Hz), 5.77 (1H, d, J=11.6 Hz), 7.09-7.56 (10H, m), 7.92 (1H, s), 12.74 (1H, s), 15.06 (1H, s).

REFERENCE EXAMPLE 18

[Chemical formula 96]

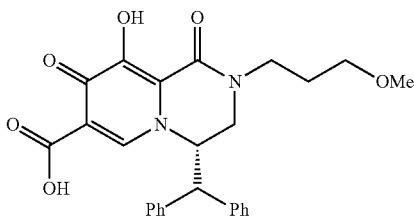

18

According to Reference example 12, compound 18 was synthesized by the same procedure.
$^1$H-NMR (DMSO-d$_6$) δ: 1.63 (2H, m), 3.20 (3H, s), 3.44 (5H, m), 4.19 (1H, d, J=10.2 Hz), 4.51 (1H, d, J=11.8 Hz), 5.80 (1H, d, J=11.0 Hz), 7.13-7.65 (10H, m), 7.93 (1H, s), 13.02 (1H, s).
MS: m/z=463 [M+H]$^+$.

REFERENCE EXAMPLE 19

[Chemical formula 97]

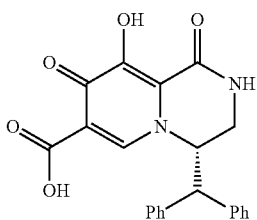

19

According to Reference example 12, compound 19 was synthesized by the same procedure.
$^1$H-NMR (DMSO-d$_6$) δ: 3.15 (1H, d, J=9.5 Hz), 3.95 (1H, dd, J=13.5, 3.4 Hz), 4.51 (1H, d, J=11.6 Hz), 5.74 (1H, d, J=11.1 Hz), 7.11-7.62 (10H, m), 7.93 (1H, s), 9.34 (1H, s), 12.97 (1H, s), 15.07 (1H, brs).
MS: m/z=391 [M+H]$^+$.

REFERENCE EXAMPLE 20

[Chemical formula 98]

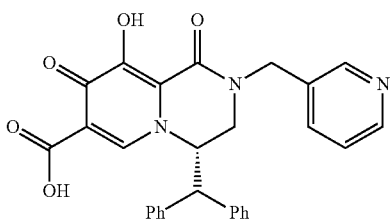

20

According to Reference example 12, compound 20 was synthesized by the same procedure.
$^1$H-NMR (DMSO-d$_6$) δ: 3.26 (1H, m), 4.24 (1H, m), 4.27 (1H, d, J=12.0 Hz), 4.41 (1H, d, J=14.8 Hz), 4.87 (1H, d, J=14.9 Hz), 5.75 (1H, d, J=7.6 Hz), 7.09-7.77 (12H, m), 7.93 (1H, s), 8.52 (2H, m), 12.79 (1H, s), 15.07 (1H, brs).
MS: m/z=482 [M+H]$^+$.

REFERENCE EXAMPLE 21

[Chemical formula 99]

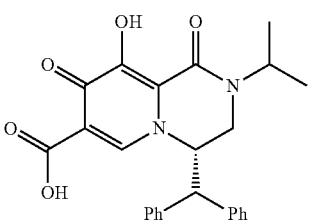

21

According to Reference example 12, compound 21 was synthesized by the same procedure.
$^1$H-NMR (DMSO-d$_6$) δ: 0.62 (3H, d, J=6.9 Hz), 0.82 (3H, d, J=6.6 Hz), 3.18 (1H, m), 3.75 (1H, d, J=10.2 Hz), 4.25 (1H, d, J=11.8 Hz), 4.58 (1H, m), 5.65 (1H, d, J=11.3 Hz), 6.89-7.43 (10H, m), 7.67 (1H, s), 12.94 (1H, s).
MS: m/z=433 [M+H]$^+$.

REFERENCE EXAMPLE 22

[Chemical formula 100]

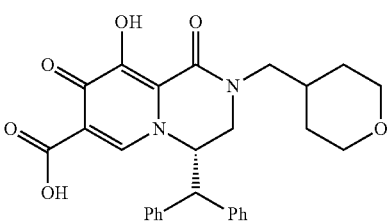

22

According to Reference example 12, compound 22 was synthesized by the same procedure.
$^1$H-NMR (DMSO-d$_6$) δ: 1.07-1.70 (5H, m), 3.04-3.34 (5H, m), 3.82 (2H, dm), 4.18 (1H, d, J=10.2 Hz), 4.42 (1H, d, J=12.0 Hz), 5.81 (1H, d, J=11.7 Hz), 7.11-7.59 (10H, m), 7.86 (1H, s), 12.96 (1H, s), 15.07 (1H, brs).
MS: m/z=489 [M+H]$^+$.

REFERENCE EXAMPLE 23

[Chemical formula 101]

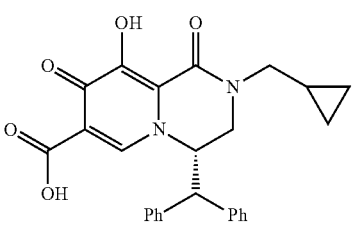

23

According to Reference example 12, compound 23 was synthesized by the same procedure.

$^1$H-NMR (DMSO-$d_6$) δ: 0.01-0.79 (5H, m), 3.05 (1H, dd, J=14.1, 7.5 Hz), 3.49-3.59 (2H, m), 4.16 (1H, dd, J=14.0, 3.3 Hz), 4.50 (1H, d, J=11.9 Hz), 5.82 (1H, d, J=11.1 Hz), 7.11-7.62 (10H, m), 7.89 (1H, s), 12.99 (1H, s), 15.07 (1H, brs).

MS: m/z=445 [M+H]$^+$.

REFERENCE EXAMPLE 24

[Chemical formula 102]

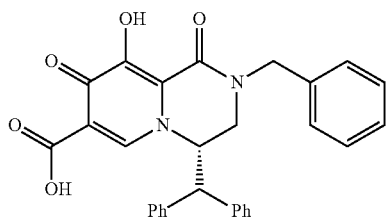

24

According to Reference example 12, compound 24 was synthesized by the same procedure.

$^1$H-NMR (DMSO-$d_6$) δ: 3.23 (1H, d, J=13.7 Hz), 4.16 (1H, dd, J=13.2, 3.3 Hz), 4.19 (2H, d, J=12.0 Hz), 4.38 (1H, d, J=14.6 Hz), 4.84 (1H, d, J=14.6 Hz), 5.72 (1H, d, J=11.4 Hz), 7.08-7.33 (15H, m), 7.98 (1H, s), 12.88 (1H, s), 15.07 (1H, s).

MS: m/z=481 [M+H]$^+$.

REFERENCE EXAMPLE 25

[Chemical formula 103]

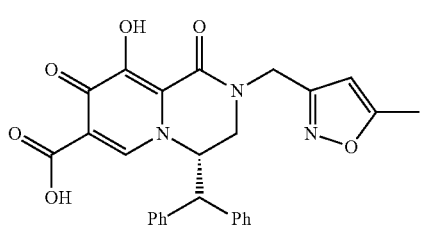

25

According to Reference example 12, compound 25 was synthesized by the same procedure.

$^1$H-NMR (DMSO-$d_6$) δ: 2.39 (3H, s), 3.37 (1H, m), 4.21 (1H, dd, J=14.4, 3.9 Hz), 4.40 (1H, dd, J=11.7 Hz), 4.45 (1H, d, J=15.3 Hz), 4.81 (1H, d, J=15.4 Hz), 5.78 (1H, d, J=12.0 Hz), 6.30 (1H, s), 7.09-7.42 (10H, m), 7.95 (1H, s), 12.65 (1H, s), 15.07 (1H, s).

MS: m/z=486 [M+H]$^+$.

REFERENCE EXAMPLE 26

[Chemical formula 104]

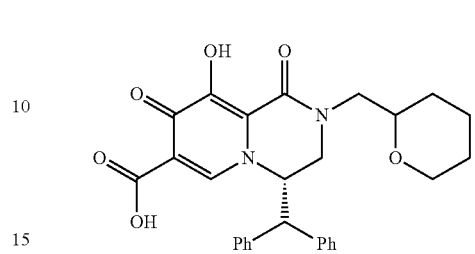

26

According to Reference example 12, compound 26 was synthesized by the same procedure.

$^1$H-NMR (DMSO-$d_6$) δ: 1.20-1.77 (6H, m), 3.11-3.61 (6H, m), 4.21 (1H, d, J=9.9 Hz), 4.53 (1H, d, J=11.7 Hz), 5.80 (1H, d, J=11.8 Hz), 7.14-7.65 (10H, m), 7.95 (1H, s), 12.95 (1H, brs), 15.06 (1H, brs).

MS: m/z=489 [M+H]$^+$.

REFERENCE EXAMPLE 27

[Chemical formula 105]

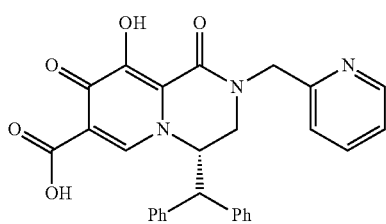

27

According to Reference example 12, compound 27 was synthesized by the same procedure.

$^1$H-NMR (DMSO-$d_6$) δ: 3.36 (1H, m), 4.28 (1H, d, J=12.0 Hz), 4.54 (1H, d, J=11.4 Hz), 4.62 (1H, d, J=15.3 Hz), 4.79 (1H, d, J=15.4 Hz), 5.77 (1H, d, J=9.9 Hz), 7.09-7.79 (13H, m), 7.98 (1H, s), 8.46 (1H, d, J=4.6 Hz), 12.82 (1H, brs), 15.06 (1H, brs).

MS: m/z=482 [M+H]$^+$.

REFERENCE EXAMPLE 28

[Chemical formula 106]

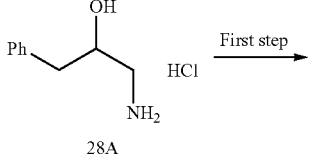

28A

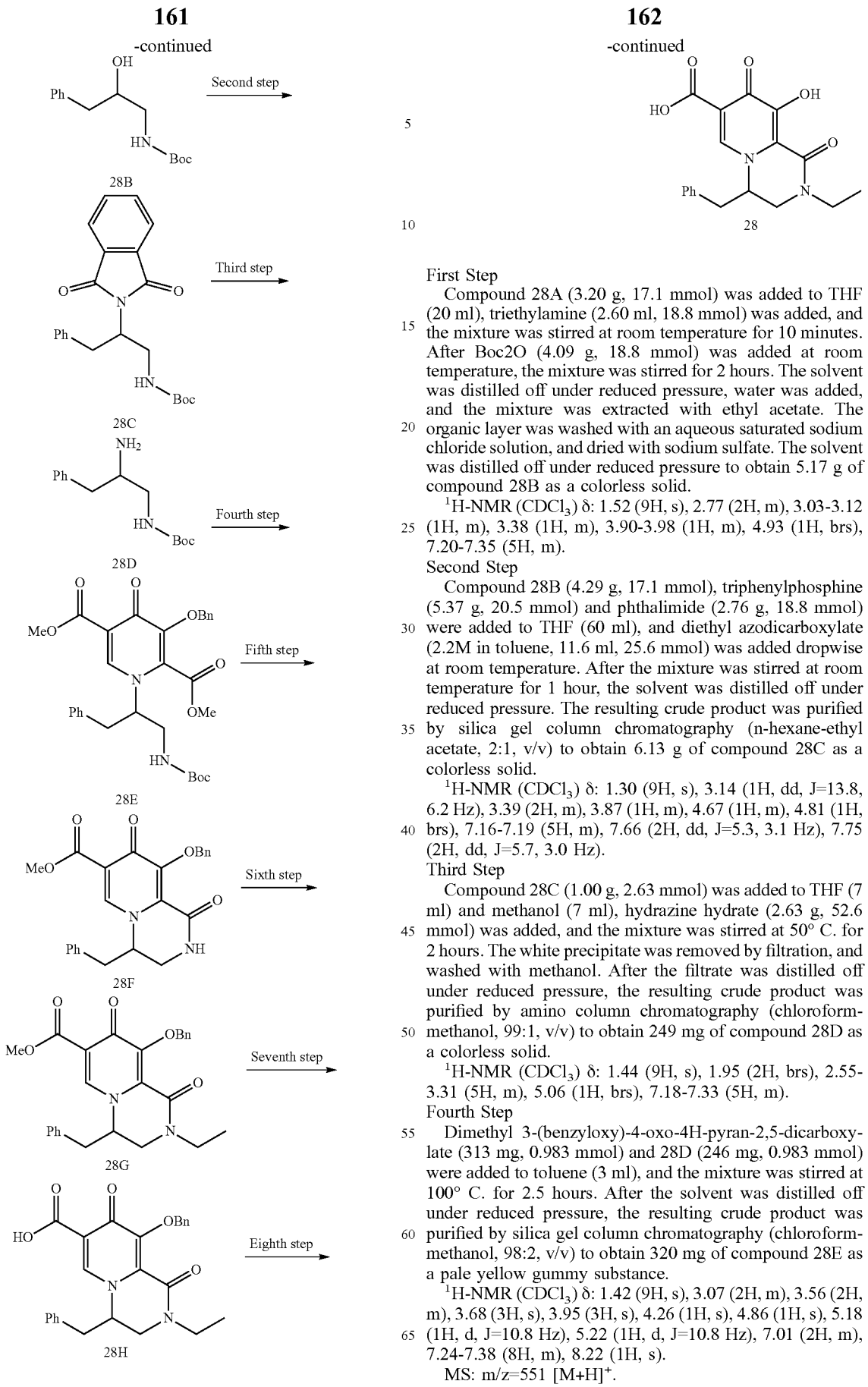

First Step

Compound 28A (3.20 g, 17.1 mmol) was added to THF (20 ml), triethylamine (2.60 ml, 18.8 mmol) was added, and the mixture was stirred at room temperature for 10 minutes. After Boc2O (4.09 g, 18.8 mmol) was added at room temperature, the mixture was stirred for 2 hours. The solvent was distilled off under reduced pressure, water was added, and the mixture was extracted with ethyl acetate. The organic layer was washed with an aqueous saturated sodium chloride solution, and dried with sodium sulfate. The solvent was distilled off under reduced pressure to obtain 5.17 g of compound 28B as a colorless solid.

$^1$H-NMR (CDCl$_3$) δ: 1.52 (9H, s), 2.77 (2H, m), 3.03-3.12 (1H, m), 3.38 (1H, m), 3.90-3.98 (1H, m), 4.93 (1H, brs), 7.20-7.35 (5H, m).

Second Step

Compound 28B (4.29 g, 17.1 mmol), triphenylphosphine (5.37 g, 20.5 mmol) and phthalimide (2.76 g, 18.8 mmol) were added to THF (60 ml), and diethyl azodicarboxylate (2.2M in toluene, 11.6 ml, 25.6 mmol) was added dropwise at room temperature. After the mixture was stirred at room temperature for 1 hour, the solvent was distilled off under reduced pressure. The resulting crude product was purified by silica gel column chromatography (n-hexane-ethyl acetate, 2:1, v/v) to obtain 6.13 g of compound 28C as a colorless solid.

$^1$H-NMR (CDCl$_3$) δ: 1.30 (9H, s), 3.14 (1H, dd, J=13.8, 6.2 Hz), 3.39 (2H, m), 3.87 (1H, m), 4.67 (1H, m), 4.81 (1H, brs), 7.16-7.19 (5H, m), 7.66 (2H, dd, J=5.3, 3.1 Hz), 7.75 (2H, dd, J=5.7, 3.0 Hz).

Third Step

Compound 28C (1.00 g, 2.63 mmol) was added to THF (7 ml) and methanol (7 ml), hydrazine hydrate (2.63 g, 52.6 mmol) was added, and the mixture was stirred at 50° C. for 2 hours. The white precipitate was removed by filtration, and washed with methanol. After the filtrate was distilled off under reduced pressure, the resulting crude product was purified by amino column chromatography (chloroform-methanol, 99:1, v/v) to obtain 249 mg of compound 28D as a colorless solid.

$^1$H-NMR (CDCl$_3$) δ: 1.44 (9H, s), 1.95 (2H, brs), 2.55-3.31 (5H, m), 5.06 (1H, brs), 7.18-7.33 (5H, m).

Fourth Step

Dimethyl 3-(benzyloxy)-4-oxo-4H-pyran-2,5-dicarboxylate (313 mg, 0.983 mmol) and 28D (246 mg, 0.983 mmol) were added to toluene (3 ml), and the mixture was stirred at 100° C. for 2.5 hours. After the solvent was distilled off under reduced pressure, the resulting crude product was purified by silica gel column chromatography (chloroform-methanol, 98:2, v/v) to obtain 320 mg of compound 28E as a pale yellow gummy substance.

$^1$H-NMR (CDCl$_3$) δ: 1.42 (9H, s), 3.07 (2H, m), 3.56 (2H, m), 3.68 (3H, s), 3.95 (3H, s), 4.26 (1H, s), 4.86 (1H, s), 5.18 (1H, d, J=10.8 Hz), 5.22 (1H, d, J=10.8 Hz), 7.01 (2H, m), 7.24-7.38 (8H, m), 8.22 (1H, s).

MS: m/z=551 [M+H]$^+$.

Fifth Step

To compound 28E (315 mg, 0.572 mmol) was added 4N HCl (ethyl acetate solution, 5 ml), and the mixture was stirred at room temperature for 30 minutes. After the solvent was distilled off under reduced pressure, aqueous sodium bicarbonate water was added, and the mixture was extracted with chloroform, and dried with sodium sulfate. After the solvent was distilled off under reduced pressure, the resulting crude product was purified by silica gel column chromatography (chloroform-methanol, 95:5, v/v) to obtain 210 mg of compound 28F as a colorless solid.

$^1$H-NMR (CDCl$_3$) δ: 3.07-3.15 (2H, m), 3.34 (1H, dd, J=13.2, 6.0 Hz), 3.74 (2H, m), 3.86 (3H, s), 4.12 (1H, m), 5.27 (1H, d, J=10.1 Hz), 5.47 (1H, d, J=10.1 Hz), 6.76 (1H, d, J=6.4 Hz), 7.04 (2H, m), 7.32 (6H, m), 7.62 (2H, dd, J=7.7, 1.4 Hz), 7.70 (1H, s).

MS: m/z=419 [M+H]$^+$.

Sixth Step

Compound 28F (50 mg, 0.12 mmol) was dissolved in DMF (1 ml), and cesium carbonate (195 mg, 0.597 mmol) was added. After the mixture was stirred at room temperature for 30 minutes, iodoethane (0.048 ml, 0.60 mmol) was added, and the mixture was stirred at room temperature for 3.5 hours. The reaction solution was poured into water, and the mixture was extracted with ethyl acetate, and dried with sodium sulfate. After the solvent was distilled off under reduced pressure, the resulting crude product was purified by silica gel column chromatography (chloroform-methanol, 95:5, v/v) to obtain 47 mg of compound 28G as a colorless solid.

$^1$H-NMR (CDCl$_3$) δ: 1.22 (3H, t, J=7.2 Hz), 3.00-3.15 (2H, m), 3.28 (1H, dd, J=13.6, 1.6 Hz), 3.48 (1H, m), 3.75 (1H, m), 3.85 (3H, s), 3.88 (1H, dd, J=13.3, 3.2 Hz), 4.15 (1H, m), 5.25 (1H, d, J=9.9 Hz), 5.50 (1H, d, J=9.9 Hz), 7.04 (2H, m), 7.29-7.38 (6H, m), 7.60 (1H, s), 7.68 (2H, m).

MS: m/z=447 [M+H]$^+$.

Seventh Step

Compound 28G (47 mg, 0.11 mmol) was dissolved in THF (0.5 ml) and methanol (0.5 ml), a 2N aqueous sodium hydroxide solution (0.26 ml, 0.53 mmol) was added at room temperature, and the mixture was stirred for 1 hour. After 1N hydrochloric acid was added, and the mixture was extracted with ethyl acetate, the extract was dried with sodium sulfate. After the solvent was distilled off under reduced pressure, 40 mg of compound 28H was obtained as a colorless solid.

MS: m/z=433 [M+H]$^+$.

Eighth Step

To compound 28H obtained in the seventh step was added trifluoroaceteic acid (1 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-methanol-ethyl ether were added, and the precipitated solid was filtered to obtain 17 mg of compound 28 as a colorless solid.

$^1$H-NMR (DMSO-d$_6$) δ: 1.17 (3H, t, J=7.2 Hz), 3.08 (2H, m), 3.51-3.63 (3H, m), 4.08 (1H, dd, J=13.6, 3.9 Hz), 5.03 (1H, brs), 7.21 (5H, m), 8.07 (1H, s), 12.98 (1H, s), 15.07 (1H, brs).

MS: m/z=343 [M+H]$^+$.

REFERENCE EXAMPLE 29

[Chemical formula 107]

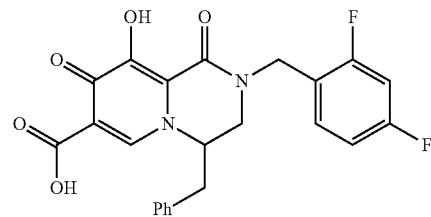

29

According to Reference example 28, compound 29 was synthesized by the same procedure.

$^1$H-NMR (DMSO-d$_6$) δ: 2.96 (2H, d, J=7.6 Hz), 3.46 (1H, d, J=13.3 Hz), 4.06 (1H, dd, J=13.6, 3.8 Hz), 4.64 (1H, d, J=14.9 Hz), 4.89 (1H, d, J=14.6 Hz), 4.98 (1H, m), 6.97 (2H, m), 7.10-7.37 (5H, m), 7.57 (1H, m), 8.12 (1H, s), 12.75 (1H, s), 15.07 (1H, brs).

REFERENCE EXAMPLE 30

[Chemical formula 108]

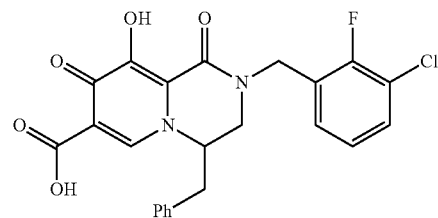

30

According to Reference example 28, compound 30 was synthesized by the same procedure.

$^1$H-NMR (DMSO-d$_6$) δ: 2.99 (2H, dd, J=7.5, 3.6 Hz), 3.48 (1H, d, J=13.4 Hz), 4.09 (1H, dd, J=13.4, 4.0 Hz), 4.73 (1H, d, J=15.1 Hz), 4.92 (1H, d, J=15.1 Hz), 4.99 (1H, m), 6.97 (2H, m), 7.18-7.29 (4H, m), 7.49 (1H, m), 7.61 (1H, m), 8.15 (1H, s), 12.69 (1H, s), 15.06 (1H, brs).

REFERENCE EXAMPLE 31

[Chemical formula 109]

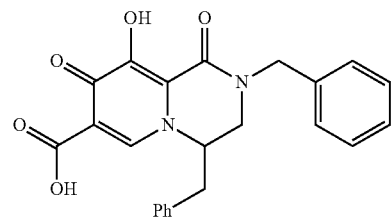

31

According to Reference example 28, compound 31 was synthesized by the same procedure.

$^1$H-NMR (DMSO-d$_6$) δ: 2.91 (2H, m), 3.45 (1H, d, J=13.1 Hz), 4.02 (1H, dd, J=13.6, 4.0 Hz), 4.57 (1H, d, J=14.6 Hz), 4.91 (1H, d, J=14.6 Hz), 4.93 (1H, m), 6.89 (2H, m), 7.18 (3H, m), 7.40 (5H, m), 8.16 (1H, s), 12.86 (1H, brs), 15.06 (1H, brs).

MS: m/z=405 [M+H]⁺.

REFERENCE EXAMPLE 32

[Chemical formula 110]

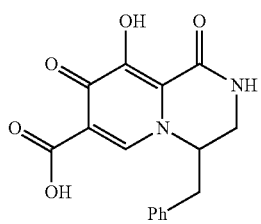

32

According to Reference example 28, compound 32 was synthesized by the same procedure.

¹H-NMR (DMSO-d₆) δ: 3.10 (2H, m), 3.39 (1H, d, J=13.6 Hz), 3.84 (1H, dd, J=13.6, 4.0 Hz), 4.94 (1H, m), 7.23 (5H, m), 8.19 (1H, s), 9.44 (1H, brs), 12.97 (1H, s), 15.06 (1H, brs).

MS: m/z=315 [M+H]⁺.

REFERENCE EXAMPLE 33

[Chemical formula 111]

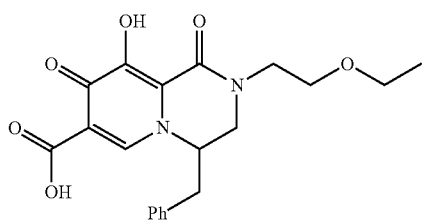

33

According to Reference example 28, compound 33 was synthesized by the same procedure.

¹H-NMR (DMSO-d₆) δ: 1.09 (3H, t, J=6.9 Hz), 3.10 (2H, m), 3.42-3.50 (2H, m), 3.71 (5H, m), 4.11 (1H, dd, J=13.6, 3.8 Hz), 4.99 (1H, brs), 7.11-7.29 (5H, m), 7.99 (1H, s), 12.88 (1H, s), 15.06 (1H, brs).

MS: m/z=387 [M+H]⁺.

REFERENCE EXAMPLE 34

[Chemical formula 112]

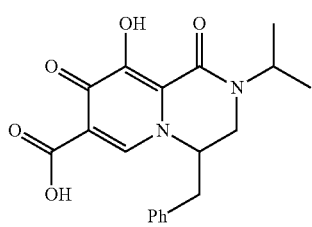

34

According to Reference example 28, compound 34 was synthesized by the same procedure.

¹H-NMR (DMSO-d₆) δ: 1.16 (3H, d, J=6.9 Hz), 1.21 (3H, d, J=6.9 Hz), 2.98 (1H, dd, J=13.6, 9.8 Hz), 3.13 (1H, dd, J=13.7, 5.8 Hz), 3.68 (1H, d, J=12.8 Hz), 3.87 (1H, dd, J=13.6, 3.7 Hz), 4.83 (1H, quin, J=6.8 Hz), 5.07 (1H, brs), 7.19 (5H, m), 7.90 (1H, s), 13.09 (1H, s), 15.08 (1H, brs).

MS: m/z=357 [M+H]⁺.

REFERENCE EXAMPLE 35

[Chemical formula 113]

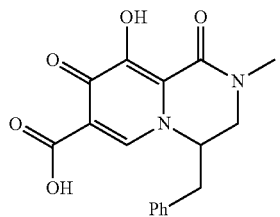

35

According to Reference example 28, compound 35 was synthesized by the same procedure.

¹H-NMR (DMSO-d₆) δ: 3.07 (3H, s), 3.14 (2H, m), 3.49 (1H, d, J=13.3 Hz), 4.08 (1H, dd, J=13.7, 4.0 Hz), 4.99 (1H, m), 7.13-7.31 (5H, m), 8.18 (1H, s), 12.95 (1H, s), 15.06 (1H, brs).

MS: m/z=329 [M+H]⁺.

REFERENCE EXAMPLE 36

[Chemical formula 114]

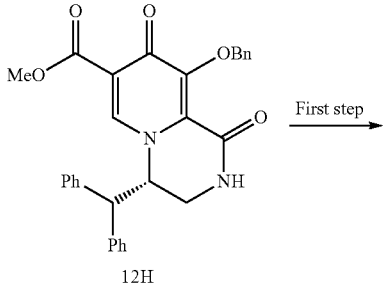

12H

First step →

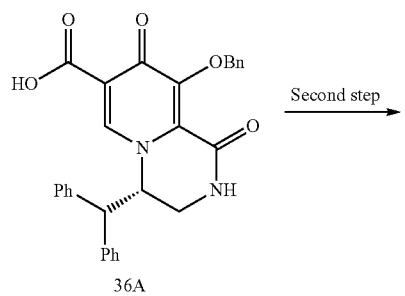

36A

Second step →

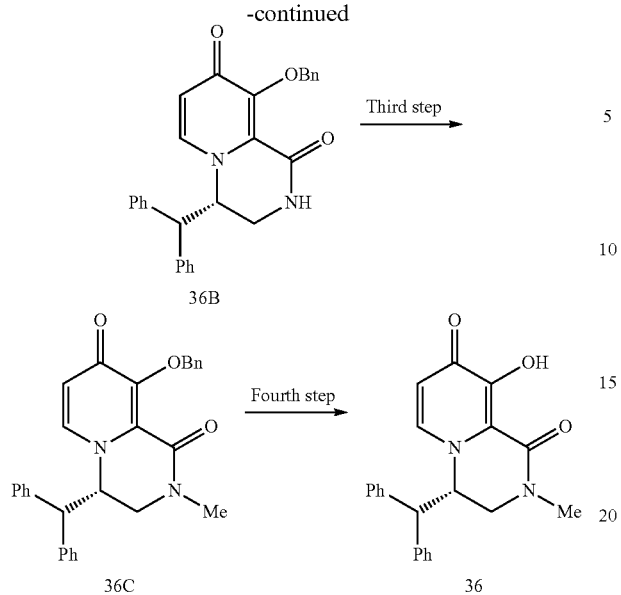

First Step

Compound 12H (460 mg, 0.930 mmol) was dissolved in THF (2.5 ml) and methanol (2.5 ml), a 2N aqueous sodium hydroxide solution (2.33 ml, 4.65 mmol) was added at room temperature, and the mixture was stirred for 1.5 hours. After 1N hydrochloric acid was added, and the mixture was extracted with ethyl acetate, the extract was dried with sodium sulfate. After the solvent was distilled off under reduced pressure, 405 mg of compound 36A was obtained as a colorless solid.

$^1$H-NMR (CDCl$_3$) δ: 3.45 (1H, ddd, J=13.8, 6.9, 1.3 Hz), 3.80 (1H, dd, J=13.5, 2.1 Hz), 4.35 (1H, d, J=11.6 Hz), 4.77 (1H, d, J=11.3 Hz), 5.46 (1H, d, J=10.5 Hz), 5.52 (1H, d, J=10.5 Hz), 6.11 (1H, d, J=5.8 Hz), 6.94-6.98 (2H, m), 7.17 (3H, m), 7.31-7.46 (8H, m), 7.58 (3H, m).

Second Step

Compound 36A (402 mg, 0.837 mmol) was added to diphenyl ether (5 ml), and the mixture was stirred at 245° C. for 1 hour under microwave irradiation. The reaction solution was poured into n-hexane, and the precipitated solid was filtered. The resulting crude product was purified by amino column chromatography (chloroform-methanol, 99:1, v/v) to obtain 164 mg of compound 36B as a colorless solid.

$^1$H-NMR (CDCl$_3$) δ: 3.36 (1H, dd, J=13.0, 7.0 Hz), 3.72 (1H, d, J=11.1 Hz), 4.35 (1H, d, J=11.4 Hz), 4.49 (1H, d, J=10.2 Hz), 5.38 (1H, d, J=10.5 Hz), 5.43 (1H, d, J=10.4 Hz), 5.94 (1H, d, J=7.2 Hz), 6.29 (1H, d, J=6.6 Hz), 6.38 (1H, d, J=7.5 Hz), 6.99 (2H, m), 7.17 (3H, m), 7.36 (8H, m), 7.60 (2H, m).

Third Step

Compound 36B (40 mg, 0.092 mmol) was dissolved in DMF (1 ml), and cesium carbonate (179 mg, 0.55 mmol) was added. After stirring at room temperature for 30 minutes, iodomethane (0.029 ml, 0.46 mmol) was added, and the mixture was stirred at room temperature for 3.5 hours. The reaction solution was poured into water, and the mixture was extracted with ethyl acetate, and dried with sodium sulfate. After the solvent was distilled off under reduced pressure, the resulting crude product was purified by silica gel column chromatography (chloroform-methanol, 95:5, v/v) to obtain 44 mg of compound 36C as a colorless gummy substance.

Fourth Step

To compound 36C obtained in the third step was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, chloroform-ethyl ether were added, and the precipitated solid was filtered to obtain 24 mg of compound 36 as a colorless solid.

$^1$H-NMR (DMSO-d$_6$) δ: 2.93 (3H, s), 3.17 (1H, d, J=13.0 Hz), 4.13 (1H, dd, J=13.6, 3.4 Hz), 4.47 (1H, d, J=11.4 Hz), 5.52 (1H, dd, J=9.3, 3.4 Hz), 5.99 (1H, d, J=7.3 Hz), 7.18 (4H, m), 7.30 (3H, m), 7.41 (2H, t, J=7.5 Hz), 7.60 (2H, d, J=7.2 Hz).

MS: m/z=361 [M+H]$^+$.

REFERENCE EXAMPLE 37

[Chemical formula 115]

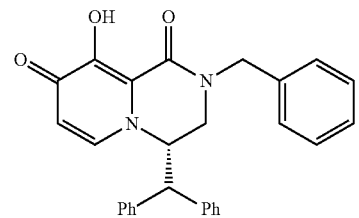

37

According to Reference example 36, compound 37 was synthesized by the same procedure.

$^1$H-NMR (DMSO-d$_6$) δ: 3.16 (2H, d, J=13.3 Hz), 4.05 (1H, d, J=10.5 Hz), 4.15 (1H, d, J=11.7 Hz), 4.38 (1H, d, J=14.9 Hz), 4.74 (1H, d, J=14.5 Hz), 5.35 (1H, d, J=11.4 Hz), 5.65 (1H, d, J=7.3 Hz), 6.99 (1H, d, J=7.5 Hz), 7.21 (15H, m).

MS: m/z=437 [M+H]$^+$.

REFERENCE EXAMPLE 38

[Chemical formula 116]

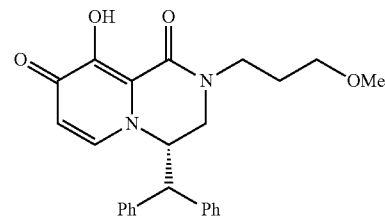

38

According to Reference example 36, compound 38 was synthesized by the same procedure.

$^1$H-NMR (DMSO-d$_6$) δ: 1.57 (2H, m), 3.17 (3H, s), 3.21-3.31 (5H, m), 4.07 (1H, dd, J=13.5, 3.7 Hz), 4.36 (1H, d, J=11.6 Hz), 5.42 (1H, d, J=9.2 Hz), 5.61 (1H, d, J=7.3 Hz), 6.89 (1H, d, J=7.5 Hz), 7.13-7.31 (6H, m), 7.40 (2H, t, J=6.3 Hz), 7.57 (2H, d, J=7.3 Hz), 12.31 (1H, brs).

MS: m/z=419 [M+H]$^+$.

REFERENCE EXAMPLE 39

[Chemical formula 117]

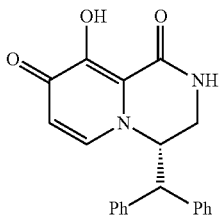

39

According to Reference example 36, compound 39 was synthesized by the same procedure.

$^1$H-NMR (DMSO-$d_6$) δ: 3.12 (1H, dd, J=13.6, 5.5 Hz), 3.87 (1H, d, J=9.5 Hz), 4.44 (1H, d, J=11.7 Hz), 5.45 (1H, d, J=10.4 Hz), 5.83 (1H, d, J=7.5 Hz), 7.04 (1H, d, J=7.2 Hz), 7.14-7.31 (6H, m), 7.40 (2H, t, J=7.5 Hz), 7.58 (2H, d, J=7.5 Hz), 9.09 (1H, d, J=5.2 Hz).

MS: m/z=347 [M+H]$^+$.

REFERENCE EXAMPLE 40

[Chemical formula 118]

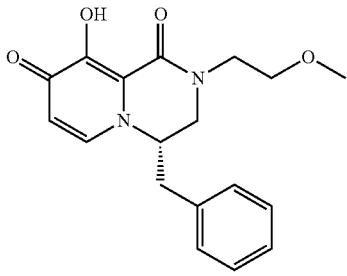

40

According to Reference example 36, compound 40 was synthesized by the same procedure.

$^1$H-NMR (DMSO-$d_6$) δ: 2.88-3.15 (2H, m), 3.27 (3H, s), 3.53-3.73 (5H, m), 3.99 (1H, dd, J=13.27, 3.97 Hz), 4.56-4.60 (1H, m), 5.89 (1H, d, J=7.32 Hz), 7.08-7.30 (6H, m).

REFERENCE EXAMPLE 41

[Chemical formula 119]

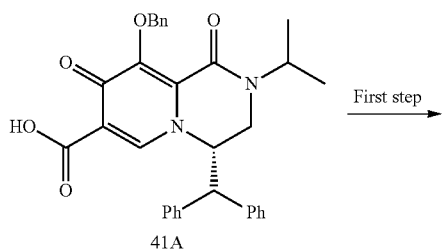

41A

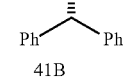 First step

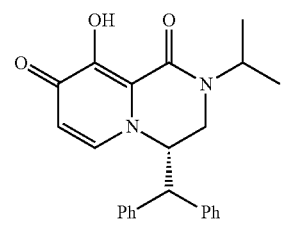

41B

-continued

Second step →

(compound 41 structure)

41

First Step

Compound 41A (290 mg, 0.555 mmol) synthesized according to Reference example 12 was added to diphenyl ether (5 ml), and the mixture was stirred at 245° C. for 1 hour under microwave irradiation. The reaction solution was poured into n-hexane, and the precipitated solid was filtered. The resulting crude product was purified by amino column chromatography (chloroform-methanol, 99:1→97:3, v/v) to obtain 86 mg of compound 41B as a colorless solid.

$^1$H-NMR (CDCl$_3$) δ: 0.76 (3H, d, J=6.7 Hz), 0.98 (3H, d, J=6.9 Hz), 3.43-3.52 (2H, m), 3.62 (1H, dd, J=13.6, 3.5 Hz), 4.22 (1H, d, J=11.6 Hz), 4.52 (1H, d, J=11.6 Hz), 4.86-4.95 (1H, m), 5.37 (1H, d, J=10.2 Hz), 5.45 (1H, d, J=10.2 Hz), 5.90 (1H, d, J=7.5 Hz), 6.22 (1H, d, J=7.5 Hz), 6.89 (2H, m), 7.15 (3H, m), 7.36 (8H, m), 7.67 (2H, m).

Second Step

To compound 41B obtained in the first step was added trifluoroacetic acid (2 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 45 mg of compound 41 as a colorless solid.

$^1$H-NMR (DMSO-$d_6$) δ: 0.82 (3H, d, J=6.7 Hz), 1.05 (3H, d, J=6.7 Hz), 3.90 (1H, dd, J=13.6, 3.4 Hz), 4.39 (1H, d, J=11.9 Hz), 4.77-4.86 (1H, m), 5.50 (1H, d, J=8.6 Hz), 5.69 (1H, d, J=7.4 Hz), 6.92 (1H, d, J=7.4 Hz), 7.15-7.48 (8H, m), 7.63 (2H, d, J=7.7 Hz) 12.51 (1H, Brs).

MS: m/z=389 [M+H]$^+$.

REFERENCE EXAMPLE 42

[Chemical formula 120]

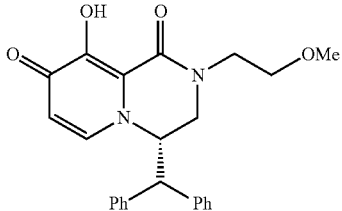

42

According to Reference example 41, compound 42 was synthesized by the same procedure.

$^1$H-NMR (DMSO-$d_6$) δ: 3.12 (3H, s), 3.51 (5H, m), 4.05 (1H, dd, J=13.9, 3.5 Hz), 4.37 (1H, d, J=11.4 Hz), 5.38 (1H, d, J=11.6 Hz), 5.60 (1H, d, J=7.3 Hz), 6.90 (1H, d, J=7.5 Hz), 7.22 (6H, m), 7.40 (2H, t, J=7.5 Hz), 7.56 (2H, d, J=7.2 Hz).

MS: m/z=405 [M+H]$^+$.

REFERENCE EXAMPLE 43

[Chemical formula 121]

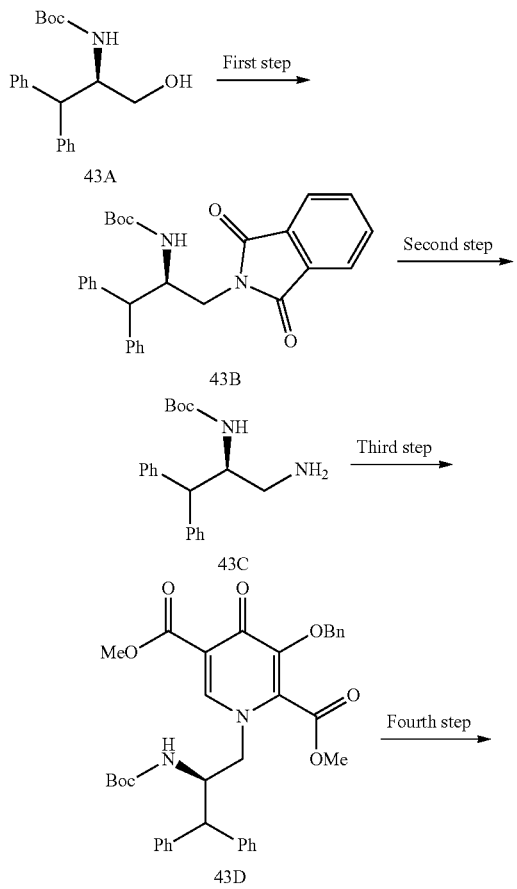

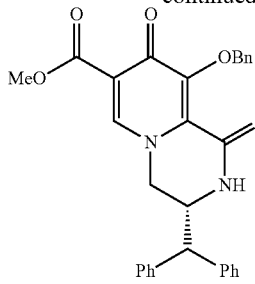

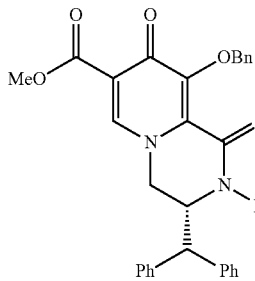

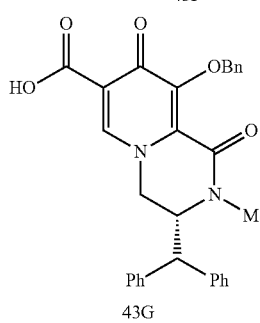

First Step

Compound 43A (2.00 g, 6.11 mmol), triphenylphosphine (2.40 g, 9.16 mmol) and phthalimide (1.08 g, 7.33 mmol) were added to THF (20 ml), and diethyl azodicarboxylate (2.2M in toluene, 4.16 ml, 9.16 mmol) was added dropwise at room temperature. After stirring at room temperature for 3 hours, the solvent was distilled off under reduced pressure. The resulting crude product was purified by silica gel column chromatography (n-hexane-ethyl acetate, 1:1, v/v) to obtain 2.39 g of compound 43B as a colorless solid.

$^1$H-NMR (DMSO-$d_6$) δ: 1.00 (9H, s), 3.30 (1H, m), 3.61 (1H, dd, J=13.4, 10.2 Hz), 4.15 (1H, d, J=12.2 Hz), 4.75 (1H, m), 6.79 (1H, d, J=9.5 Hz), 7.25 (15H, m), 7.76-7.89 (4H, m).

Second Step

Compound 43B (2.06 g, 4.51 mmol) was added to THF (20 ml) and methanol (20 ml), hydrazine hydrate (4.52 g, 90.2 mmol) was added, and the mixture was stirred at 60° C. for 5 hours. The white precipitate was removed by filtration, and washed with methanol. After the filtrate was distilled off under reduced pressure, the resulting crude product was purified by amino column chromatography (chloroform-methanol, 99:1, v/v), n-hexane was added, and the precipitated solid was filtered to obtain 1.25 g of compound 43C as a colorless solid.

$^1$H-NMR (CDCl$_3$) δ: 1.32 (9H, s), 2.55 (1H, dd, J=13.3, 6.0 Hz), 2.80 (1H, dd, J=13.3, 3.5 Hz), 3.99 (1H, d, J=10.1 Hz), 4.47 (2H, m), 7.13-7.33 (10H, m).

Third Step

Dimethyl 3-(benzyloxy)-4-oxo-4H-pyran-2,5-dicarboxylate (488 mg, 1.53 mmol) and 43C (500 mg, 1.53 mmol) were added to toluene (8 ml), and the mixture was stirred at 110° C. for 1 hour. After the solvent was distilled off under reduced pressure, the resulting crude product was purified by silica gel column chromatography (chloroform-methanol, 97:3→96:4→94:6, v/v) to obtain 667 mg of compound 43D as a pale yellow gummy substance.

$^1$H-NMR (CDCl$_3$) δ: 1.28 (9H, s), 3.63 (3H, s), 3.80 (1H, m), 3.87 (3H, s), 4.02 (1H, dd, J=14.5, 10.1 Hz), 4.21 (1H, d, J=10.4 Hz), 4.47 (2H, m), 5.20 (1H, d, J=10.8 Hz), 5.26 (1H, d, J=10.7 Hz), 7.30 (15H, m), 8.05 (1H, s).

MS: m/z=627 [M+H]$^+$.

Fourth Step

To compound 43D (664 mg, 1.06 mmol) was added 4N HCl (ethyl acetate solution, 10 ml), and the mixture was stirred at room temperature for 1 hour. After the solvent was distilled off under reduced pressure, THF and saturated sodium bicarbonate water were added, and the mixture was stirred for 2.5 hours. This was extracted with chloroform, and dried with sodium sulfate. After the solvent was distilled off under reduced pressure, methylene chloride-ethyl ether were added, and the precipitated solid was filtered to obtain 458 mg of compound 43E as a colorless solid.

$^1$H-NMR (CDCl$_3$) δ: 3.86 (3H, m), 3.92 (3H, s), 4.41-4.48 (1H, m), 5.32 (1H, d, J=10.8 Hz), 5.42 (1H, d, J=10.1 Hz), 5.92 (1H, s), 7.21-7.39 (13H, m), 7.59 (2H, m), 7.89 (1H, s).

MS: m/z=495 [M+H]$^+$.

Fifth Step

Compound 43E (50 mg, 0.10 mmol) was dissolved in DMF (1 ml), and cesium carbonate (165 mg, 0.51 mmol) was added. After the mixture was stirred at room temperature for 30 minutes, iodomethane (0.025 ml, 0.40 mmol) was added, and the mixture was stirred at room temperature for 1 hour. The reaction solution was poured into water, and the mixture was extracted with ethyl acetate, and dried with sodium sulfate. After the solvent was distilled off under reduced pressure, the resulting crude product was purified by silica gel column chromatography (chloroform-methanol, 97:3 →95:5, v/v) to obtain 60 mg of compound 43F as a colorless solid.

$^1$H-NMR (CDCl$_3$) δ: 2.57 (3H, s), 3.75 (2H, d, J=11.3 Hz), 3.93 (3H, s), 4.20-4.29 (2H, m), 5.25 (1H, d, J=9.9 Hz), 5.57 (1H, d, J=9.9 Hz), 7.15-7.41 (13H, m), 7.63 (1H, s), 7.72-7.76 (2H, m).

Sixth Step

Compound 43F obtained in the fifth step was dissolved in THF (0.5 ml) and methanol (0.5 ml), a 2N aqueous sodium hydroxide solution (0.25 ml, 0.50 mmol) was added at room temperature, and the mixture was stirred for 1 hour. After 1N hydrochloric acid was added, and the mixture was extracted with ethyl acetate, the extract was dried with sodium sulfate. After the solvent was distilled off under reduced pressure, a colorless gummy compound 43G was obtained.

Seventh Step

To compound 43G obtained in the sixth step was added trifluoroacetic acid (2 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-ethyl ether were added, and the precipitated solid was filtered to obtain 27 mg of compound 43 as a colorless solid.

$^1$H-NMR (DMSO-d$_6$) δ: 2.53 (3H, s), 4.26 (1H, d, J=10.9 Hz), 4.35 (1H, d, J=13.3 Hz), 4.58 (1H, dd, J=13.8, 3.5 Hz), 5.06 (1H, d, J=10.9 Hz), 7.36 (10H, m), 8.36 (1H, s), 12.58 (1H, s), 15.62 (1H, s).

MS: m/z=405 [M+H]$^+$.

REFERENCE EXAMPLE 44

[Chemical formula 122]

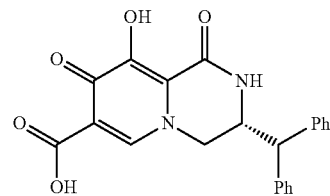

44

According to Reference example 43, compound 44 was synthesized by the same procedure.

$^1$H-NMR (DMSO-d$_6$) δ: 4.19 (2H, m), 4.42 (1H, dd, J=13.3, 3.8 Hz), 4.90 (1H, d, J=9.2 Hz), 7.17-7.41 (10H, m), 8.40 (1H, s), 9.66 (1H, s), 12.70 (1H, s), 15.60 (1H, s).

MS: m/z=391 [M+H]$^+$.

REFERENCE EXAMPLE 45

[Chemical formula 123]

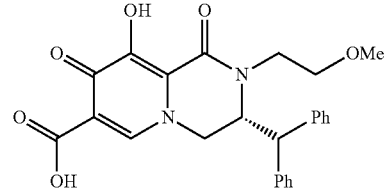

45

According to Reference example 43, compound 45 was synthesized by the same procedure.

$^1$H-NMR (DMSO-d$_6$) δ: 2.17-2.26 (1H, m), 3.22 (3H, s), 3.39 (2H, m), 3.58-3.67 (1H, m), 4.19 (1H, d, J=10.7 Hz), 4.38 (2H, m), 4.95 (1H, d, J=10.8 Hz), 7.20-7.44 (10H, m), 8.28 (1H, s), 12.40 (1H, s), 15.60 (1H, s).

MS: m/z=449 [M+H]$^+$.

REFERENCE EXAMPLE 46

[Chemical formula 124]

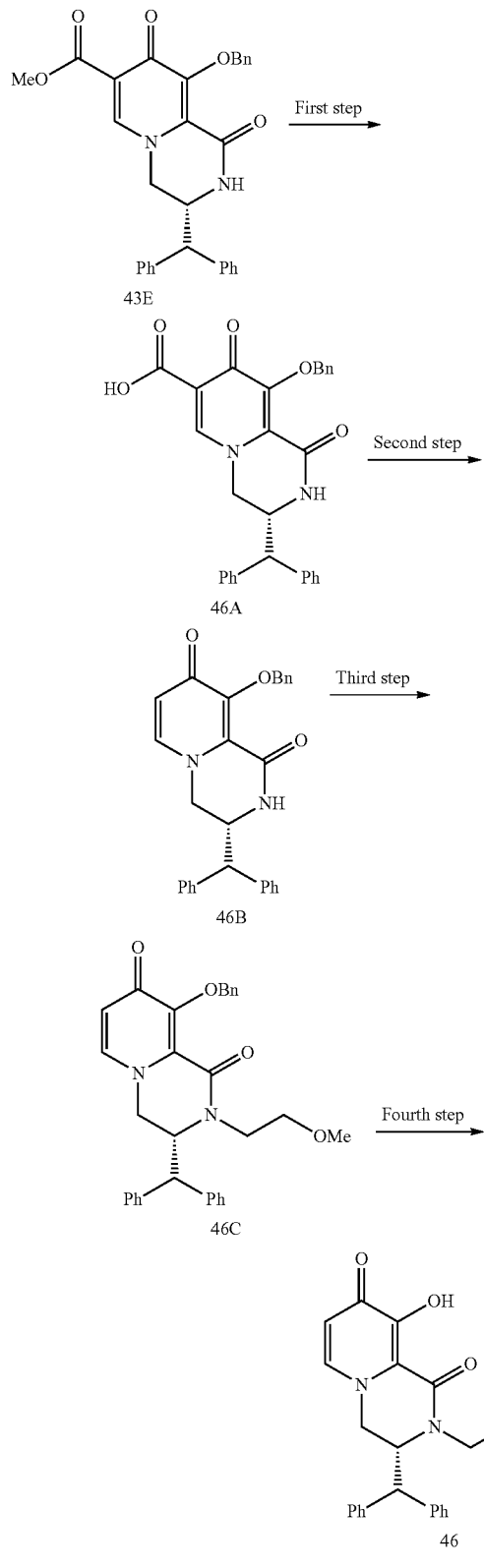

First Step

Compound 43E (289 mg, 0.584 mmol) obtained in Reference example 35 was dissolved in THF (3 ml) and methanol (3 ml), a 2N aqueous sodium hydroxide solution (1.46 ml, 2.92 mmol) was added at room temperature, and the mixture was stirred for 1.5 hours. After 1N hydrochloric acid was added, and the mixture was extracted with ethyl acetate, the extract was dried with sodium sulfate. After the solvent was distilled off under reduced pressure, 342 mg of compound 46A was obtained as a colorless solid.

$^1$H-NMR (CDCl$_3$) δ: 3.72-4.04 (3H, m), 4.46 (1H, m), 5.39 (1H, d, J=10.4 Hz), 5.44 (1H, d, J=10.4 Hz), 6.04 (1H, brs), 7.19-7.60 (15H, m), 8.10 (1H, s).

Second Step

Compound 46A (402 mg, 0.837 mmol) was added to diphenyl ether (5 ml), and the mixture was stirred at 245° C. for 1 hour under microwave irradiation. The reaction solution was poured into n-hexane, and the precipitated solid was filtered. The resulting crude product was purified by silica gel column chromatography (chloroform-methanol, 97:3→95:5→92:8, v/v) to obtain 85 mg of compound 46B as a colorless solid.

$^1$H-NMR (CDCl$_3$) δ: 3.86 (3H, m), 4.45 (1H, m), 5.35 (1H, d, J=10.5 Hz), 5.41 (1H, d, J=10.4 Hz), 5.94 (1H, brs), 6.48 (1H, d, J=7.4 Hz), 7.00 (1H, d, J=7.4 Hz), 7.25-7.44 (13H, m), 7.62 (2H, m).

Third Step

Compound 46B (39 mg, 0.089 mmol) was dissolved in DMF (1 ml), and cesium carbonate (145 mg, 0.445 mmol) was added. After stirring at room temperature for 30 minutes, 1-bromo-2-methoxyethane (0.033 ml, 0.36 mmol) was added, and the mixture was stirred at room temperature for 3.5 hours. The reaction solution was poured into water, and the mixture was extracted with ethyl acetate, and dried with sodium sulfate. After the solvent was distilled off under reduced pressure, the resulting crude product was purified by silica gel column chromatography (chloroform-methanol, 97:3→95:5→92:8, v/v) to obtain 66 mg of compound 46C as a colorless gummy substance.

Fourth Step

To compound 46C obtained in the third step was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 21 mg of compound 46 as a colorless solid.

$^1$H-NMR (DMSO-d$_6$) δ: 2.12-2.21 (1H, m), 3.20 (3H, s), 3.55-3.64 (3H, m), 3.81 (1H, d, J=13.0 Hz), 3.99 (1H, d, J=11.0 Hz), 4.22 (1H, dd, J=13.3, 3.1 Hz), 4.86 (1H, d, J=11.0 Hz), 6.11 (1H, d, J=7.2 Hz), 7.18-7.45 (11H, m).

MS: m/z=405 [M+H]$^+$.

REFERENCE EXAMPLE 47

[Chemical formula 125]

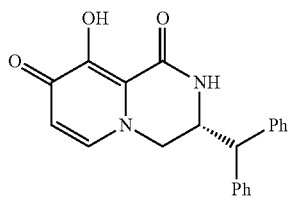

47

According to Reference example 46, compound 47 was synthesized by the same procedure.

$^1$H-NMR (DMSO-d$_6$) δ: 3.70 (1H, d, J=12.2 Hz), 4.02 (1H, d, J=10.7 Hz), 4.17 (1H, dd, J=13.2, 3.6 Hz), 4.79 (1H, t, J=3.4 Hz), 6.11 (1H, d, J=7.3 Hz), 7.18-7.44 (11H, m), 9.23 (1H, d, J=4.3 Hz).

MS: m/z=347 [M+H]$^+$.

REFERENCE EXAMPLE 48

[Chemical formula 126]

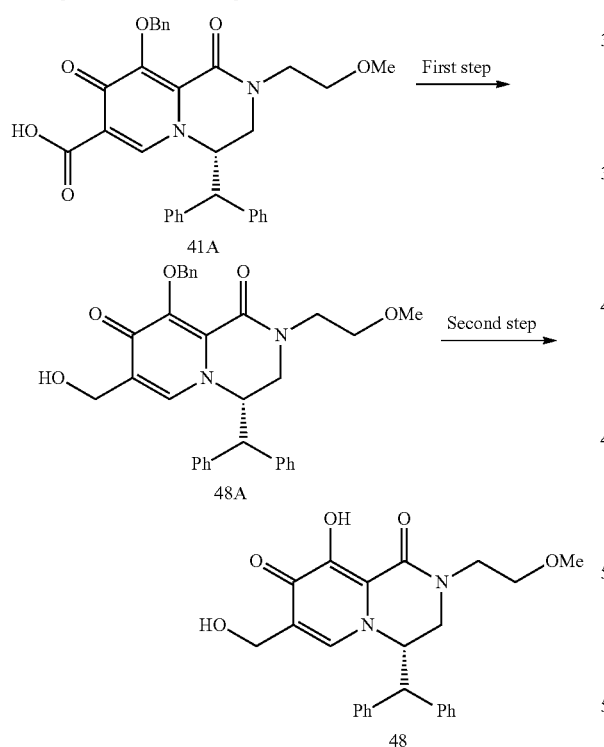

First Step

Compound 41A (400 mg, 0.743 mmol) was dissolved in DMF (5 ml), triethylamine (0.21 ml, 1.5 mmol) and ethyl chloroformate (0.143 ml, 1.49 mmol) were added at 0° C., and the mixture was stirred for 20 minutes. Sodium borohydride (70.2 mg, 1.86 mmol) was added at 0° C., and the mixture was stirred at room temperature for 30 minutes. Sodium borohydride (70.2 mg, 1.86 mmol) was further added at 0° C., and the mixture was stirred at room temperature for 2 hours. The reaction solution was poured into water, the mixture was extracted with ethyl acetate, and the extract was dried with sodium sulfate. After the solvent was distilled off under reduced pressure, the resulting crude product was purified by silica gel column chromatography (chloroform-methanol, 97:3, v/v) to obtain 160 mg of compound 48A as a colorless solid.

$^1$H-NMR (CDCl$_3$) δ: 3.19 (3H, s), 3.37-3.54 (3H, m), 3.65-3.73 (1H, m), 3.87 (1H, m), 4.06 (2H, d, J=13.9 Hz), 4.31 (1H, d, J=11.2 Hz), 4.39 (1H, d, J=13.8 Hz), 4.77 (1H, d, J=11.2 Hz), 5.36 (1H, d, J=10.1 Hz), 5.41 (1H, d, J=10.1 Hz), 6.65 (1H, brs), 7.00 (2H, m), 7.19 (3H, m), 7.33-7.49 (8H, m), 7.70 (2H, m).

Second Step

To compound 48A (50 mg, 0.095 mmol) was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. The solvent was distilled off under reduced pressure, chroloform-ethyl ether were added, and the precipitated solid was filtered to obtain 3.5 mg of compound 48 as a colorless solid.

$^1$H-NMR (DMSO-d$_6$) δ: 3.12 (3H, s), 3.51 (5H, m), 3.71 (1H, d, J=13.7 Hz), 4.02 (1H, d, J=9.9 Hz), 4.09 (1H, d, J=12.0 Hz), 4.36 (1H, d, J=11.6 Hz), 4.73 (1H, brs), 5.45 (1H, d, J=12.5 Hz), 7.00 (1H, s), 7.15 (5H, m), 7.28 (1H, t, J=7.2 Hz), 7.40 (2H, t, J=7.5 Hz), 7.59 (2H, d, J=7.6 Hz).

MS: m/z=435 [M+H]$^+$.

REFERENCE EXAMPLE 49

[Chemical formula 127]

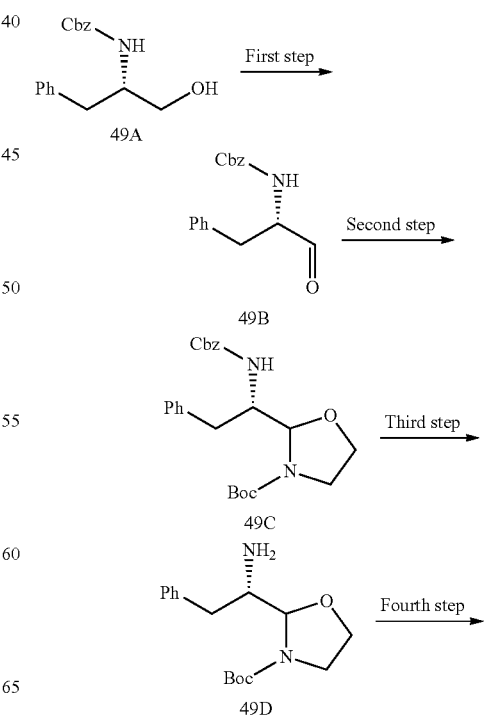

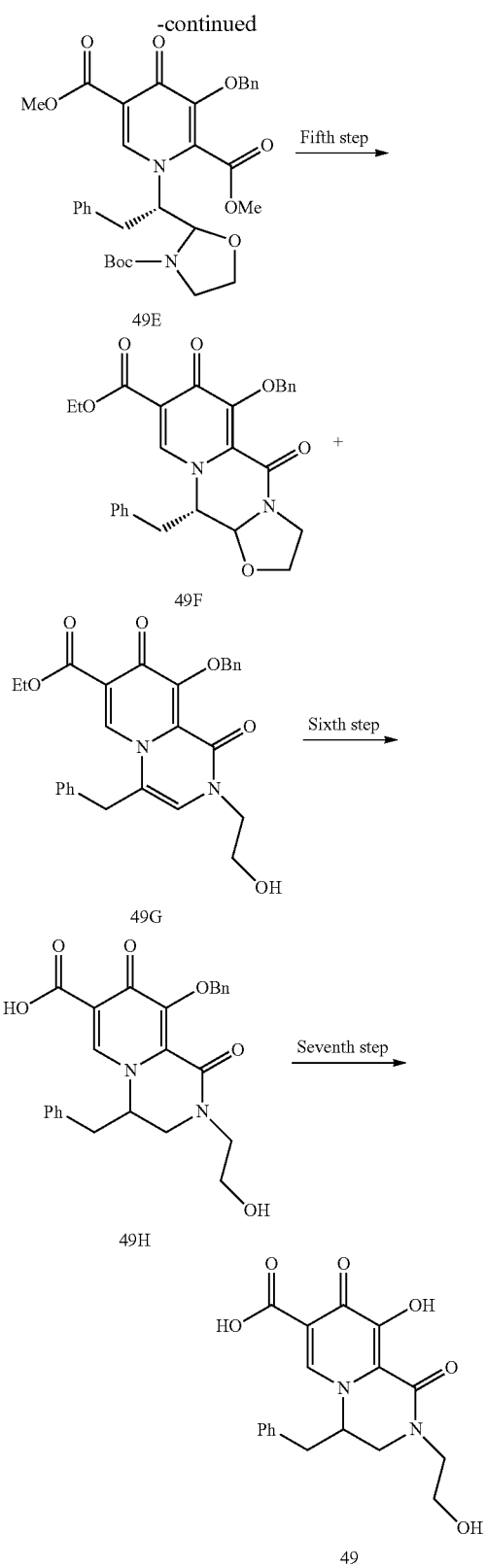

hours, the reaction mixture was poured into a 1N aqueous sodium hydroxide solution, and the mixture was extracted with ethyl ether. The organic layer was washed with a 1N aqueous sodium hydroxide solution and an aqueous saturated sodium chloride solution, and dried with magnesium sulfate. After the solvent was distilled off under reduced pressure, 2.08 g of compound 49B was obtained as a white solid.

$^1$H-NMR (CDCl$_3$) δ: 3.13 (2H, d, J=6.6 Hz), 4.53 (1H, q, J=6.7 Hz), 5.12 (2H, s), 5.28 (1H, brs), 7.26 (10H, m), 9.64 (1H, s).

Second Step

Compound 49B (700 mg, 2.47 mmol), 2-aminoethanol (166 mg, 2.72 mmol) and sodium sulfate (1.76 g, 12.4 mmol) were added to toluene (20 ml), and the mixture was stirred at room temperature for 1 hour. Boc2O (0.631 ml, 2.72 mmol) was added at room temperature, and the mixture was stirred for 18 hours. The reaction solution was filtered, and the filtrate was concentrated under reduced pressure. The resulting crude product was purified by silica gel column chromatography (n-hexane-ethyl acetate, 1:1, v/v) to obtain 893 mg of 49C as a colorless gummy substance.

Third Step

Compound 49C (890 mg, 2.09 mmol) and palladium-active carbon (10%, wet, 200 mg) were added to ethanol (20 ml), and the mixture was stirred at room temperature for 2 hours under hydrogen atmosphere. After filtration with celite, the solvent was concentrated under reduced pressure to obtain 656 mg of a colorless oily substance 49D.

$^1$H-NMR (CDCl$_3$) δ: 1.40 (9H, s), 2.65-2.86 (2H, m), 3.32 (2H, m), 3.80 (2H, m), 4.03-4.12 (1H, m), 4.86 (1H, brs), 7.22 (5H, m).

Fourth Step

Dimethyl 3-(benzyloxy)-4-oxo-4H-pyran-2,5-dicarboxylate (610 mg, 2.09 mmol) and 49D (664 mg, 2.09 mmol) were added to toluene (6 ml), and the mixture was stirred at 100° C. for 4 hours. After the solvent was distilled off under reduced pressure, the resulting crude product was purified by silica gel column chromatography (n-hexane-ethyl acetate, 1:1, v/v) to obtain 884 mg of compound 49E as a pale yellow gummy substance.

MS: m/z=593 [M+H]$^+$.

Fifth Step

To compound 49E (860 mg, 1.45 mmol) was added 4N HCl (ethyl acetate solution, 10 ml). After stirring at room temperature for 30 minutes, the solvent was distilled off under reduced pressure. Subsequently, toluene (10 ml) and 2-aminoethanol (0.175 ml, 2.90 mmol) were added, and the mixture was stirred at 80° C. for 30 minutes. After the solvent was distilled off under reduced pressure, the resulting crude product was purified by silica gel column chromatography (chloroform-methanol, 99:1→95:5→90:10, v/v) to obtain 157 mg of compound 49F as a colorless gummy substance and 217 mg of compound 49G as a yellow solid.

49F: $^1$H-NMR (CDCl$_3$) δ: 2.48 (1H, dd, J=14.0, 11.4 Hz), 3.22 (1H, dd, J=14.1, 3.3 Hz), 3.69 (1H, m), 3.77 (3H, s), 3.83-3.95 (1H, m), 4.08 (1H, m), 4.29 (1H, m), 4.41 (1H, m), 5.34 (2H, m), 5.48 (1H, d, J=10.1 Hz), 6.86 (2H, m), 7.20-7.39 (7H, m), 7.64 (2H, m)

49G: $^1$H-NMR (DMSO-d$_6$) δ: 3.70 (2H, t, J=5.3 Hz), 3.73 (3H, s), 3.86 (2H, t, J=5.3 Hz), 4.14 (2H, s), 4.98 (1H, t, J=5.0 Hz), 5.06 (2H, s), 6.98 (1H, s), 7.35 (8H, m), 7.62 (2H, d, J=7.1 Hz), 8.34 (1H, d, J=0.8 Hz).

Sixth Step

The compound 49G (214 mg, 0.465 mmol) was dissolved in THF (4 ml), ethanol (2 ml) and methylene chloride (2 ml), First Step To Dess-Martin Periodinane (0.3M, methylene chrolide solution, 52.0 ml, 15.6 mmol) was added dropwise a methylene chloride solution (20 ml) of compound 49A (2.97 g, 10.4 mmol) at 0° C. After stirring at room temperature for 3 a 2N aqueous sodium hydroxide solution (1.16 ml, 2.32 mmol) was added at room temperature, and the mixture was stirred for 2.5 hours. After 1N hydrochloric acid was added, and the mixture was extracted with chloroform, the extract was dried with sodium sulfate. After the solvent was distilled off under reduced pressure, 158 mg of compound 49H was obtained as a yellow solid.

$^1$H-NMR (DMSO-$d_6$) δ: 3.70 (2H, q, J=5.2 Hz), 3.89 (2H, t, J=5.3 Hz), 4.22 (2H, s), 4.97 (1H, t, J=5.6 Hz), 5.12 (2H, s), 7.23-7.41 (9H, m), 7.60 (2H, m), 8.54 (1H, s).

Seventh Step

Compound 49H (50.0 mg, 0.112 mmol) and palladium-active carbon (10%, wet, 12 mg) were added to methanol (1 ml) and DMF (3 ml), and the mixture was stirred at room temperature for 5 hours under hydrogen atmosphere. After filtration with celite, the solvent was concentrated under reduced pressure, chloroform-methanol-ethyl ether were added, and the precipitated solid was filtered to obtain 9.0 mg of compound 49 as a colorless solid.

$^1$H-NMR (DMSO-$d_6$) δ: 3.10 (2H, m), 3.51-3.69 (4H, m), 4.10 (1H, d, J=10.7 Hz), 4.94 (2H, m), 7.11-7.26 (5H, m), 8.03 (1H, s), 12.94 (1H, brs), 15.30 (1H, brs).

MS: m/z=359 [M+H]$^+$.

REFERENCE EXAMPLE 50

[Chemical formula 128]

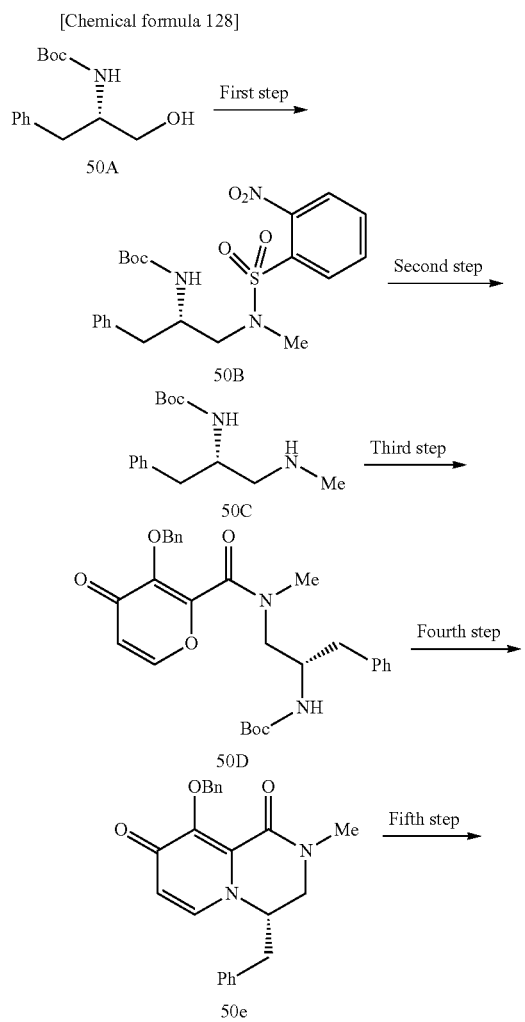

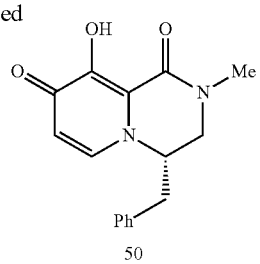

50

First Step

Compound 50A (1.00 g, 3.98 mmol), triphenylphosphine (1.15 g, 4.48 mmol) and N-methyl-2-nitrobenzenesulfonamide (860 mg, 3.98 mmol) were added to THF (10 ml), and diethyl azodicarboxylate (2.2M in toluene, 1.99 ml, 4.38 mmol) was added dropwise at room temperature. After stirring at room temperature for 3 hours, the solvent was distilled off under reduced pressure. The resulting crude product was purified by silica gel column chromatography (n-hexane-ethyl acetate, 1:1, v/v) to obtain 710 mg of compound 50B as a colorless gummy substance.

Second Step

Compound 50B (458 mg, 1.02 mmol) was dissolved in acetonitrile, potassium carbonate (422 mg, 3.06 mmol) and benzenethiol (0.126 ml, 1.22 mmol) were added, and the mixture was stirred at room temperature for 5 hours. The reaction solution was poured into a 1N aqueous sodium hydroxide solution, the mixture was extracted with methylene chloride, and the extract was dried with sodium sulfate. The resulting crude product was purified by amino column chromatography (chloroform-methanol, 95:5, v/v) to obtain 147 mg of compound 50C as a colorless oily substance.

$^1$H-NMR (CDCl$_3$) δ: 1.36 (9H, s), 2.40 (3H, s), 2.51-2.89 (4H, m), 3.90 (1H, s), 4.69 (1H, s), 7.17-7.31 (5H, m).

Third Step

Compound 50C (140 mg, 0.530 mmol) and 3-(benzyloxy)-4-oxo-4H-pyran-2-carboxylic acid (WO 2006/116764, 119 mg, 0.482 mmol) were added to THF (3 ml), 1-(3-dimethylaminopropyl)-3-ethylcarbodiimide hydrochloride (111 mg, 0.578 mmol) and 1-hydroxybenzotriazole (65.1 mg, 0.482 mmol) were added, and the mixture was stirred at room temperature for 18 hours. The reaction solution was poured into sodium bicarbonate water, the mixture was extracted with ethyl acetate, and the extract was dried with sodium sulfate. The resulting crude product was purified by silica gel column chromatography (chloroform-methanol, 97:3, v/v) to obtain 219 mg of compound 50D as a colorless solid.

MS: m/z=493 [M+H]$^+$.

Fourth Step

To compound 50D (216 mg, 0.439 mmol) was added 4N HCl (ethyl acetate solution, 3 ml). After the mixture was stirred at room temperature for 1 hour, the solvent was distilled off under reduced pressure. Subsequently, ethanol (4 ml) and an aqueous saturated sodium carbonate solution (3 ml) were added, and the mixture was stirred at 60° C. for 2 hours. After water was added, and the mixture was extracted with ethyl acetate, the extract was dried with sodium sulfate. The resulting crude product was purified by amino column chromatography (chloroform-methanol, 95:5, v/v) to obtain 108 mg of compound 50E as a pale yellow gummy substance.

$^1$H-NMR (CDCl$_3$) δ: 3.00 (2H, m), 3.13 (3H, s), 3.18 (1H, m), 3.88 (1H, dd, J=13.5, 3.4 Hz), 4.00-4.07 (1H, m), 5.26 (1H, d, J=10.2 Hz), 5.46 (1H, d, J=10.1 Hz), 6.25 (1H, d,

J=7.5 Hz), 6.73 (1H, d, J=7.5 Hz), 6.99-7.02 (2H, m), 7.28-7.37 (6H, m), 7.63-7.67 (2H, m).

Fifth Step

To compound 50E (105 mg, 0.280 mmol) was added trifluoroacetic acid (2 ml), and the mixture was stirred at room temperature for 30 minutes. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-methanol-ethyl ether were added, and the precipitated solid was filtered to obtain 29 mg of compound 50 as a colorless solid.

$^1$H-NMR (DMSO-$d_6$) δ: 2.99 (3H, s), 3.26-3.47 (3H, m), 4.07 (1H, d, J=11.1 Hz), 4.80 (1H, m), 6.43 (1H, d, J=6.9 Hz), 7.11-7.29 (5H, m), 7.50 (1H, d, J=6.9 Hz).

MS: m/z=285 [M+H]$^+$.

REFERENCE EXAMPLE 51

[Chemical formula 129]

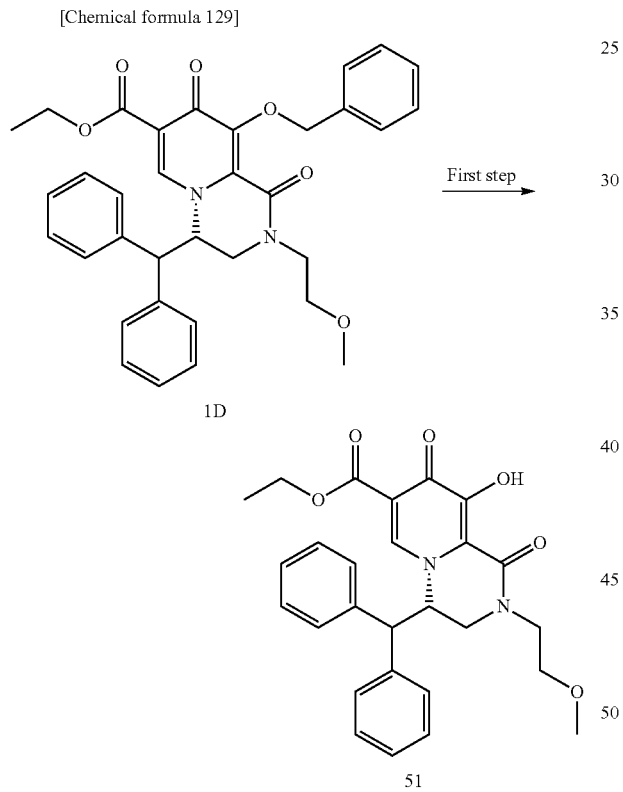

First Step

Compound 1D (60 mg, 0.11 mmol) was dissolved in trifluoroacetic acid (1 ml), and the mixture was stirred at room temperature for 1 hour. The reaction solution was distilled off, and the resulting residue was purified by LC/MS to obtain compound 51 (43 mg, 0.09 mmol).

$^1$H-NMR (DMSO-$d_6$) δ: 1.17 (3H, t, J=6.9 Hz), 3.11 (3H, s), 3.48-3.58 (2H, m), 3.95-4.12 (3H, m), 4.40 (1H, d, J=11.4 Hz), 5.59 (1H, d, J=11.4 Hz), 7.11 (1H, d, J=7.3 Hz), 7.17 (2H, t, J=7.2 Hz), 7.26 (2H, d, J=7.1 Hz), 7.30 (1H, t, J=7.3 Hz), 7.42 (2H, t, J=7.2 Hz), 7.60 (3H, m), 12.55 (1H, brs).

MS: m/z=477.2 [M+H]$^+$.

REFERENCE EXAMPLE 52

[Chemical formula 130]

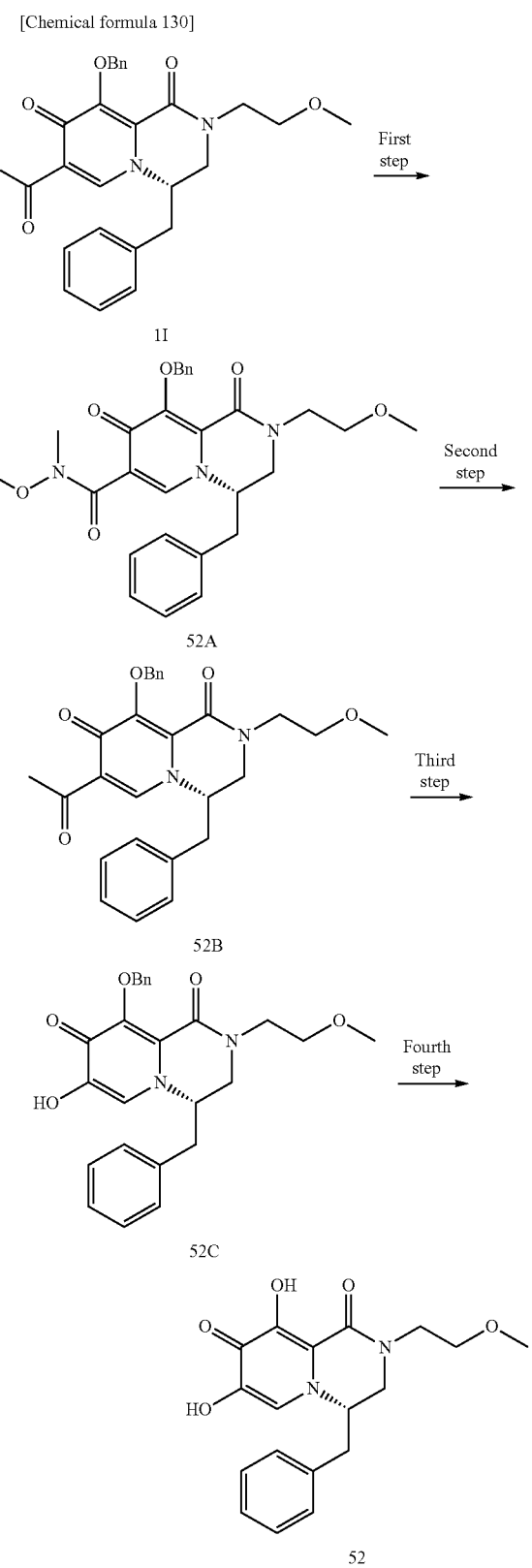

First Step

To a DMF (10 ml) solution of compound 1I (2.0 g, 4.32 mmol) were added WSC HCl (1.24 g, 6.49 mmol) and HOBt (876.9 mg, 6.49 mmol) at room temperature, and the mixture was stirred at the same temperature for 1 hour. To the reaction solution were added O,N-dimethylhydroxylamine hydrochloride (842.7 mg, 8.64 mmol) and triethylamine (2.19 g, 21.6 mmol), the mixture was stirred at the same temperature for 3 hours, thereafter, water was added, and the mixture was extracted with ethyl acetate three times. After the extract was washed with water three times, and dried with sodium sulfate, the solvent was distilled off, and the resulting oil was purified by silica gel chromatography. The materials were eluted firstly with n-hexane-ethyl acetate (7:3, v/v) and, then, with only ethyl acetate. Concentration of an objective fraction afforded 543 mg (yield 25%) of compound 52A as an oil.

MS: m/z=506 [M+H]$^+$.

Second Step

A THF (5 ml) solution of compound 52A (543 mg, 1.07 mmol) was cooled to −78° C., a methylmagnesium bromide 0.97M THF solution (1.66 ml, 1.61 mmol) was added, and temperature was raised up to −20° C. over 2 hours. To the reaction solution was added 1N hydrochloric acid, and the mixture was extracted with ethyl acetate three times. After the extract was dried with sodium sulfate, the solvent was distilled off, and the resulting oil was purified by silica gel chromatography. The materials were eluted firstly with n-hexane-ethyl acetate (7:3, v/v) and, then, with only ethyl acetate. Concentration of an objective fraction afforded 256.8 mg (yield 52%) of compound 52B as an oil.

$^1$H-NMR (CDCl$_3$) δ: 2.65 (3H, s), 3.08 (2H, d, J=7.5 Hz), 3.12 (3H, s), 3.53-3.68 (4H, m), 3.79-3.95 (1H, m), 3.92 (1H, dd, J=3.3 Hz, 13.5 Hz), 4.10-4.16 (1H, m), 5.30 (1H, d, J=10.2 hz), 5.45 (1H, d, J=10.2 Hz), 6.99-7.02 (2H, m), 7.25-7.38 (6H, m), 7.49 (1H, s), 7.63-7.66 (2H, m).

Third Step

To a dichloromethane (4 ml) solution of compound 52B (256 mg, 0.558 mmol) was added mCPBA (144.3 mg, 0.836 mmol) under ice-cooling, and the mixture was stirred at room temperature for 2 hours. To the reaction solution was added an aqueous sodium thiosulfate solution, and the mixture was extracted with ethyl acetate three times. After the extract was washed with saturated sodium bicarbonate water two times, and dried with sodium sulfate, the solvent was distilled off, the resulting oil was dissolved in ethanol (4 ml), and a 2N-aqueous sodium hydroxide solution (1 ml) was added, followed by refluxing for 1 hour. After the solvent was distilled off, the precipitated solid was washed with diisopropyl ether to obtain 242 mg (yield 100%) of compound 52C.

$^1$H-NMR (CDCl$_3$) δ: 3.09 (2H, d, J=6.9 Hz), 3.32 (3H, s), 3.54 (1H, d, J=14.1 Hz), 3.59-3.71 (2H, m), 3.76-3.85 (1H, m), 3.92 (1H, dd, J=3.6 Hz, 13.5 Hz), 4.03 (1H, brt), 5.28 (1H, d, J=10.2 Hz), 5.47 (1H, d, J=10.2 Hz), 6.68 (1H, s), 7.00-7.04 (2H, m), 7.23-7.37 (6H, m), 7.64 (2H, d, J=6.3 Hz).

Fourth Step

To a THF (3 ml) solution of compound 52C (242 mg, 0.558 mmol) was added 10% Pd-C (50 mg), and the mixture was subjected to a catalytic reduction reaction under hydrogen stream. The catalyst was removed by filtration, and the filtrate was concentrated. To the resulting residue was added diisopropyl ether, and the precipitated solid was filtered to obtain 60 mg (yield 31%) of compound 52.

$^1$H-NMR (CDCl$_3$) δ: 3.05 (2H, brs), 3.36 (3H, s), 3.58 (1H, d, J=12 Hz), 3.66-3.68 (2H, m), 3.74-3.75 (2H, m), 4.11-4.19 (2H, m), 6.80 (1H, brs), 6.90-7.04 (2H, m), 7.30 (3H, brs).

REFERENCE EXAMPLE 53

[Chemical formula 131]

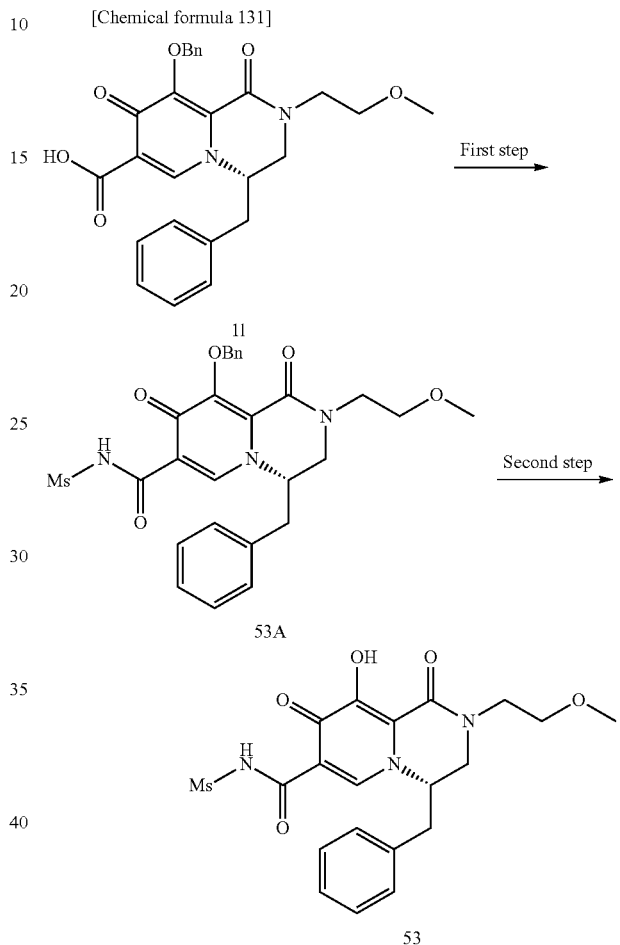

First Step

To a DMF (10 ml) solution of compound 1I (1.0 mg, 2.23 mmol) were added triethylamine (677 mg, 6.69 mmol) and ethyl chlorocarbonate (729 mg, 6.69 mmol) under ice-cooling, and the mixture was stirred at room temperature for 10 minutes. To the reaction solution were added methanesulfonamide (1.06 g, 11.15 mmol) and DMAP (272.4 mg, 2.23 mmol), and the mixture was heated to stir at 80° C. for 2 hours. To the reaction solution was added water, and the mixture was extracted with ethyl acetate three times. After the extract was washed with water three times, and dried with sodium sulfate, the solvent was distilled off, and the resulting oil was purified by silica gel chromatography. The materials were eluted firstly with only chloroform and, then, with chloroform-MeOH (9:1, v/v). Concentration of an objective fraction afforded 535 mg (yield 46%) of compound 53A as an oil.

MS: m/z=463 [M+H]$^+$.

Second Step

To a THF (5 ml) solution of compound 53A (535 mg, 0.991 mmol) was added 10% Pd-C (218 mg), and the mixture was subjected to a catalytic reduction reaction under hydrogen stream. The catalyst was removed by filtration, and the filtrate was concentrated. To the resulting residue was added diisopropyl ether, and the precipitated solid was filtered to obtain 235 mg (yield 53%) of compound 53.

$^1$H-NMR (DMSO-$d_6$) δ: 2.99-3.17 (2H, m), 3.27 (3H, s), 3.33 (3H, s), 3.53-3.76 (5H, m), 4.06 (1H, dd, J=3.6 Hz, 13.8 Hz), 4.98 (1H, brs), 7.14 (2H, d, J=6.6 Hz), 7.19-7.30 (3H, m), 8.07 (1H, s), 12.84 (1H, s), 13.24 (1H, s).

REFERENCE EXAMPLE 54

[Chemical formula 132]

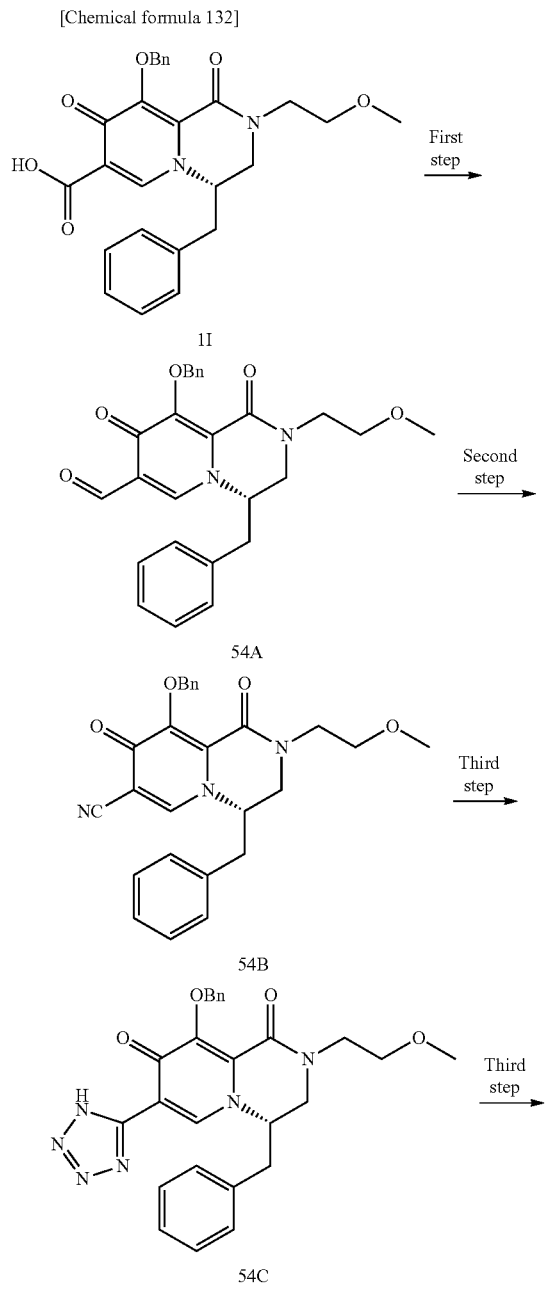

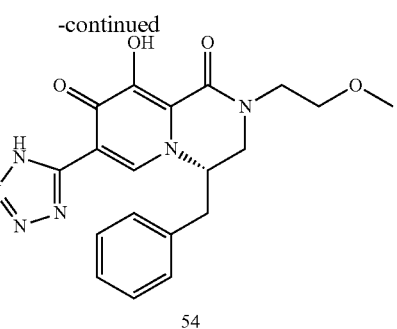

First Step

To a DMF (10 ml) solution of compound 1I (1.0 mg, 2.23 mmol) were added triethylamine (677 mg, 6.69 mmol) and ethyl chlorocarbonate (729 mg, 6.69 mmol) under ice-cooling, and the mixture was stirred at the same temperature for 10 minutes. The reaction solution was added dropwise to an ice-cooled solution of sodium borohydride (441 mg, 11.7 mmol) in water (5 ml), and the mixture was stirred at the same temperature for 2 hours. To the reaction solution was added 2N hydrochloric acid to stop the reaction, and the mixture was neutralized with a 2N aqueous sodium hydroxide solution, and extracted with ethyl acetate three times. After the extract was washed with water three times, and dried with sodium sulfate, the solvent was distilled off, and the resulting crude product was dissolved in dichloromethane (5 ml).

To the dichloromethane solution was added manganese dioxide (2.1 g, 24.15 mmol), and the mixture was stirred at room temperature for 6 hours. After the reaction solution was filtered, and the solvent was distilled off, the resulting oil was purified by silica gel chromatography. Elution with ethyl acetate-MeOH (9:1, v/v) and concentration of an objective fraction afforded 188 mg (yield 19%) of compound 54A.

MS: m/z=447 [M+H]$^+$.

Second Step

Compound 54A (188 mg, 0.422 mmol) was dissolved in THF (6 ml), 28% aqueous ammonia and iodine (117.7 mg, 0.464 mmol) were added at room temperature, and the mixture was stirred at the same temperature for 2 hours. To the reaction solution was added an aqueous sodium thiosulfate solution, and the mixture was extracted with ethyl acetate three times. After the extract was dried with sodium sulfate, the solvent was distilled off, and the resulting oil was purified by silica gel chromatography. Elution with ethyl acetate-MeOH (9:1, v/v) and concentration of an objective fraction afforded 54.7 mg (yield 29%) of compound 54B.

$^1$H-NMR (CDCl$_3$) δ: 3.05 (2H, d, J=7.5 Hz), 3.33 (3H, s), 3.56-3.79 (5H, m), 3.99 (1H, dd, J=3.6 Hz, 13.8 Hz), 4.08 (1H, brt), 5.33 (1H, d, J=10.2 Hz), 5.46 (1H, d, J=10.2 Hz), 6.83 (1H, s), 6.93-6.97 (2H, m), 7.25-7.37 (5H, m), 7.58-7.62 (2H, m).

Third Step

To a toluene (2 ml) solution of compound 54B (216 mg, 0.487 mmol) were added sodium azide (95 mg, 1.46 mmol) and triethylamine (201 mg, 1.46 mmol), and the mixture was stirred at room temperature for 6 hours. The reaction solution was extracted with a 2N aqueous sodium hydroxide solution two times, and the extract was neutralized with 2N hydrochloric acid, and extracted with ethyl acetate three times. After drying of the organic layer with sodium sulfate, the solvent was distilled off to obtain 65 mg (yield 27%) of compound 54C.

¹H-NMR (CDCl₃) δ: 3.08-3.21 (2H, m), 3.33 (3H, s), 3.55-3.70 (4H, m), 3.81-3.90 (1H, m), 3.96-4.01 (1H, m), 4.51 (1H, brt), 5.31 (1H, d, J=10.2 Hz), 5.42 (1H, d, J=10.2 Hz), 7.03-7.05 (2H, m), 7.18-7.37 (6H, m), 7.58-7.61 (2H, m), 8.33 (1H, s).

Fourth Step

To a THF (2 ml)-MeOH (2 ml) solution of compound 54C (500 mg, 1.03 mmol) was added 10% Pd-C (100 mg), and the mixture was subjected to a catalytic reduction reaction under hydrogen stream. The catalyst was removed by filtration, and the filtrate was concentrated. The resulting residue was dissolved in dichloromethane (10 ml), and the solution was extracted with a 2N aqueous sodium hydroxide solution two times. After the extract was neutralized with 2N hydrochloric acid, the mixture was extracted with ethyl acetate three times. The organic layer was dried with sodium sulfate, the solvent was distilled off, and the resulting solid was washed with diisopropyl ether, and filtered to obtain 55 mg (yield 14%) of compound 54.

¹H-NMR (DMSO-d₆) δ: 3.01-3.19 (2H, m), 3.28 (3H, s), 3.51-3.79 (5H, m), 4.09 (1H, dd, J=3.9 Hz, 13.5 Hz), 4.95 (1H, brs), 7.13-7.26 (5H, m), 8.20 (1H, s), 12.23 (1H, s).

REFERENCE EXAMPLE 55

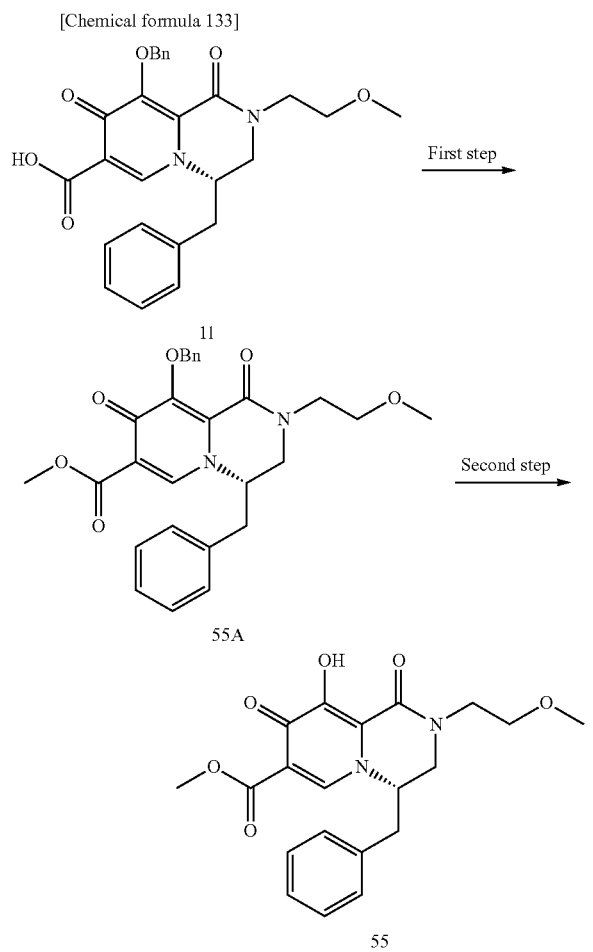

First Step

To a THF (5 ml) solution of compound 1I (500 mg, 1.08 mmol) was added a trimethylsilyldiazomethane 2M hexane solution (1 ml, 2.0 mmol) at room temperature, and the mixture was heated to 50° C., and stirred. After the solvent was distilled off, the resulting oil was purified by silica gel chromatography. Elution with n-hexane-ethyl acetate (1:1, v/v) and concentration of objective fraction afforded 115 mg (yield 22%) of compound 55A.

¹H-NMR (CDCl₃) δ: 3.06 (2H, d, J=7.5 Hz), 3.31 (3H, s), 3.51-3.72 (5H, m), 3.81 (3H, s), 3.98 (1H, dd, J=3.6 Hz, 13.5 Hz), 4.11 (1H, brt), 5.22 (1H, d, J=9.6 Hz), 5.46 (1H, d, J=9.6 Hz), 6.99-7.02 (2H, m), 7.26-7.37 (6H, m), 7.46 (1H, s), 7.65-7.69 (2H, m).

Second Step

Compound 55A (210 mg, 0.441 mmol) was dissolved in THF (2 ml), 10% Pd-C (85.7 mg) was added, and the mixture was subjected to a catalytic reduction reaction under hydrogen stream. The catalyst was removed by filtration, and the filtrate was concentrated. The resulting residue was washed with diisopropyl ether ether to obtain 50 mg (yield 23%) of compound 55.

¹H-NMR (CDCl₃) δ: 1.55 (2H, d, J=7.5 Hz), 3.37 (3H, s), 3.59-3.84 (5H, m), 4.23-4.32 (2H, m), 7.00 (2H, dd, J=1.5 Hz, 6.9 Hz), 7.23-7.32 (3H, m), 7.39 (1H, s), 12.31 (1H, brs).

REFERENCE EXAMPLE 56

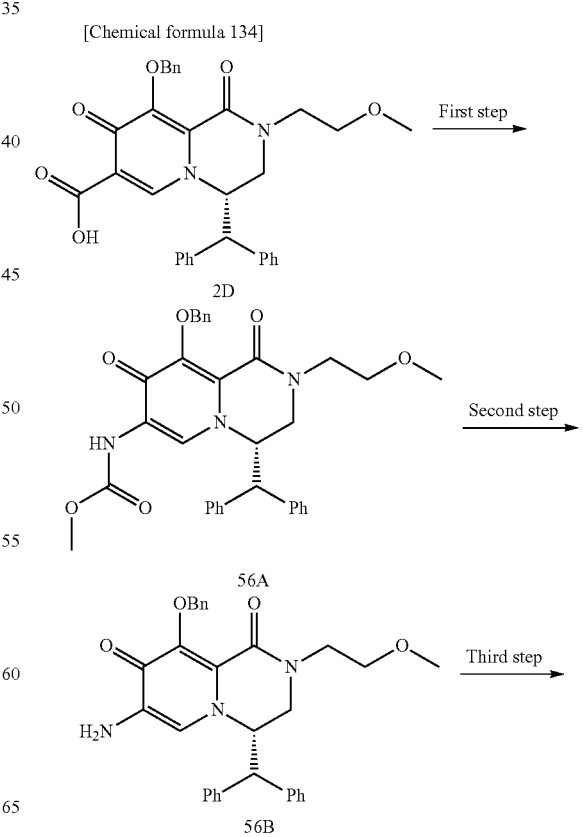

-continued

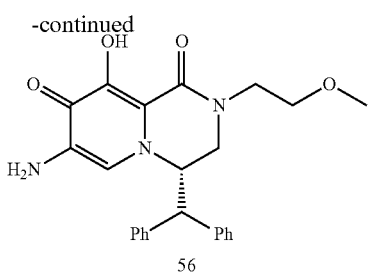

56

First Step

A DMF (5 ml) solution of compound 2D (424 mg, 0.787 mmol) was ice-cooled, and triethylamine (327 ul, 2.36 mmol) and, subsequently, ethyl chloroformate (150 ul, 1.57 mmol) were added. After the reaction solution was stirred at room temperature for 10 minutes, it was ice-cooled again, sodium azide (154 mg, 2.36 mmol) was added, and the mixture was stirred for 1 hour. To the reaction solution were added dichloromethane, water and a small amount of methanol, the dichloromethane layer was separated, and the aqueous layer was extracted with dichloromethane once. The combined extracts were concentrated, methanol (8 ml) was added to the resulting residue, the mixture was stirred at 50° C. for 3 hours, and the solvent was distilled off. The resulting oil was purified by silica gel column chromatography. The materials were eluted firstly with n-hexane-ethyl acetate (1:1, v/v) and, then, with only ethyl acetate. Concentration of objective fraction afforded 160 mg of compound 56A as a white solid.

$^1$H-NMR (CDCl$_3$) δ: 3.08-3.18 (4H, m), 3.35-3.49 (3H, m), 3.68 (3H, s), 3.98 (2H, dt, J=23.1, 5.6 Hz), 4.32 (1H, d, J=11.3 Hz), 4.59 (1H, d, J=11.3 Hz), 5.37 (2H, dd, J=12.0, 10.4 Hz), 6.98-7.70 (15H, m).

MS: m/z=568.25 [M+H]$^+$.

Second Step

Compound 56A (160 mg, 0.102 mmol) was dissolved in EtOH (10 mL), a 2N aqueous sodium hydroxide solution (14 ml) was added, and the mixture was stirred at 60° C. for 2 hours. After the reaction solution was concentrated under reduced pressure, the residue was distributed between dichloromethane and water. The dichloromethane layer was separated, and the aqueous layer was extracted with dichloromethane three times. The solvent was distilled off to obtain compound 56B.

$^1$H-NMR (CDCl$_3$) δ: 2.97-3.06 (1H, m), 3.15 (3H, s), 3.38-3.44 (3H, m), 3.71 (2H, s), 3.93-3.99 (2H, m), 4.35 (2H, dd, J=19.3, 11.1 Hz), 5.37 (2H, dd, J=31.6, 10.1 Hz), 6.04 (1H, s), 6.98 (2H, dd, J=6.4, 2.9 Hz), 7.17 (4H, t, J=3.3 Hz), 7.28-7.69 (12H, m).

MS: m/z=509.23 [M+H]$^+$.

Third Step

Compound 56B (56 mg, 0.11 mmol) was dissolved in TFA (3 mL), and the mixture was stirred at room temperature for 1 hour. The reaction mixture was subjected to toluene azeotropy, and the resulting residue was purified using an LCMS fractionating device. The eluted solvent was distilled off, isopropyl ether was added to the residue, and the precipitated solid was filtered. Washing with isopropyl ether and drying afforded 7 mg of compound 56.

MS: m/z=420.07 [M+H]$^+$.

REFERENCE EXAMPLE 57

[Chemical formula 135]

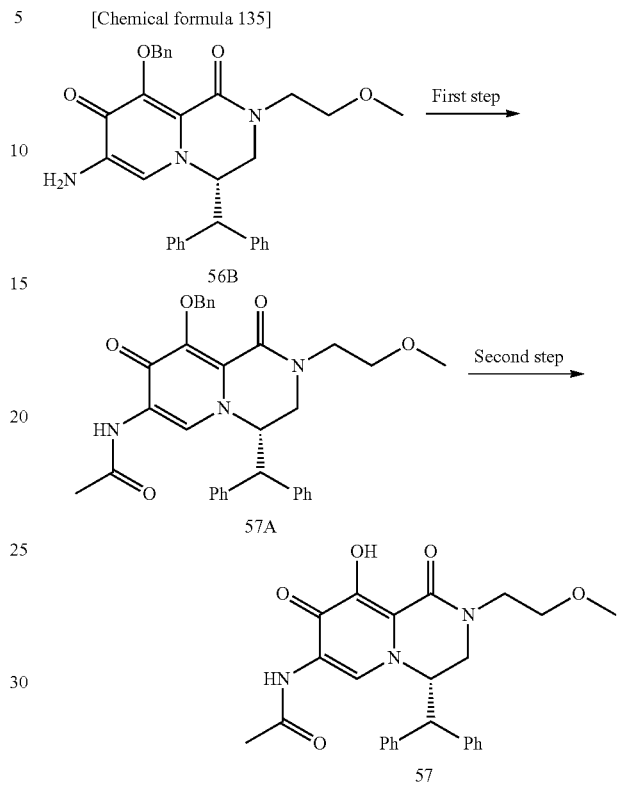

First Step

To a THF (1 mL) solution of compound 56B (25 mg, 0.049 mmol) were added triethylamine (20 uL, 0.15 mmol) and, subsequently, acetic acid anhydride (7.0 ul, 0.074 mmol) under ice-cooling, and the mixture was stirred at room temperature for 15 minutes. Then, 4-fluorobenzyl amine (330 mg, 1.75 mmol) was added, and the mixture was stirred for 7 hours. Further, triethylamine (20 uL, 0.15 mmol) and, subsequently, acetic acid anhydride (7.0 ul, 0.074 mmol) were added, and the mixture was stirred overnight. To the reaction solution were added water, ethyl acetate, and brine, the ethyl acetate layer was separated, and the aqueous layer was extracted with ethyl acetate. To the combined extracts was added sodium sulfate, and filtration and concentration afforded 18 mg of compound 57A as a white solid.

$^1$H-NMR (CDCl$_3$) δ: 2.05 (3H, s), 3.09-3.14 (4H, m), 3.41-3.45 (3H, m), 3.95-4.02 (2H, m), 4.31 (1H, d, J=11.4 Hz), 4.59 (1H, d, J=12.4 Hz), 5.36 (2H, s), 7.00 (2H, d, J=4.0 Hz), 7.11-7.16 (3H, m), 7.36 (7H, tt, J=14.5, 5.1 Hz), 7.62 (2H, t, J=7.3 Hz), 8.02 (1H, s), 8.18 (1H, s).

MS: m/z=552.20 [M+H]$^+$.

Second Step

Compound 57A (21 mg, 0.038 mmol) was dissolved in TFA (3 mL), and the mixture was stirred at room temperature for 3.5 hours. The reaction mixture was subjected to toluene azeotropy, isopropyl ether was added to the resulting residue, and the precipitated solid was filtered. Washing with isopropyl ether, and drying afforded 10 mg of compound 57.

$^1$H-NMR (CDCl$_3$) δ: 2.12 (3H, s), 3.20 (3H, s), 3.39-3.60 (4H, m), 3.76-3.86 (1H, m), 4.08 (1H, dd, J=13.7, 3.7 Hz), 4.31 (1H, d, J=11.5 Hz), 4.68 (1H, dd, J=8.5, 4.3 Hz), 6.96-7.19 (4H, m), 7.30-7.44 (6H, m), 8.11 (1H, s).

MS: m/z=462.20 [M+H]⁺.

REFERENCE EXAMPLE 58

[Chemical formula 136]

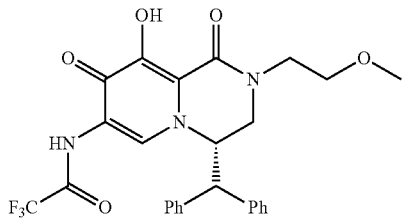

58

According to Reference example 57, compound 58 was synthesized by the same procedure.

¹H-NMR (CDCl₃) δ: 3.20 (3H, s), 3.41-3.54 (3H, m), 3.60-3.68 (2H, m), 3.73-3.85 (1H, m), 4.12 (1H, dt, J=14.0, 3.5 Hz), 4.31 (1H, d, J=11.4 Hz), 4.68 (1H, dd, J=11.4, 2.6 Hz), 6.95-7.21 (5H, m), 7.39 (5H, dt, J=26.9, 7.6 Hz), 7.94 (1H, s), 8.88 (1H, s).

MS: m/z=516.10 [M+H]⁺.

REFERENCE EXAMPLE 59

[Chemical formula 137]

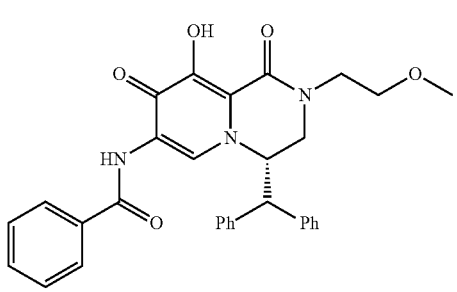

59

According to Reference example 57, compound 59 was synthesized by the same procedure.

¹H-NMR (CDCl₃) δ: 3.21 (3H, s), 3.43-3.63 (4H, m), 3.82 (1H, d, J=14.0 Hz), 4.12 (1H, dd, J=8.3, 4.2 Hz), 4.35 (1H, d, J=11.2 Hz), 4.74 (1H, d, J=8.3 Hz), 6.90-7.18 (5H, m), 7.34-7.60 (8H, m), 7.82 (2H, d, J=6.8 Hz), 8.34 (1H, s), 8.89 (1H, s).

MS: m/z=523.21 [M+H]⁺.

REFERENCE EXAMPLE 60

[Chemical formula 138]

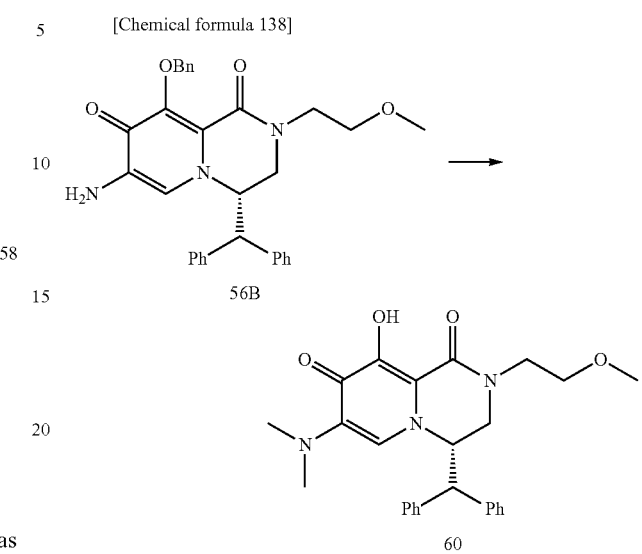

To compound 56B (30 mg, 0.059 mmol) were added formic acid (1.0 mL, 26 mmol) and, subsequently, a 37% formaldehyde solution (0.5 mL, 6.7 mmol), and the mixture was stirred at 100° C. for 7 hours. The reaction solution was subjected to toluene azeotropy, DMSO was added, insolubles were filtered and, thereafter, purification was performed using an LCMS fractionating device. The eluted solvent was distilled off, isopropyl ether was added to the residue, and the precipitated solid was filtered. Washing with isopropyl ether, and drying afforded 3 mg of compound 60.

¹H-NMR (CDCl₃) δ: 2.37 (6H, s), 3.18 (3H, s), 3.29-3.66 (4H, m), 3.82 (1H, d, J=12.5 Hz), 4.06-4.15 (1H, m), 4.31 (1H, d, J=11.7 Hz), 4.54 (1H, d, J=8.1 Hz), 5.97 (1H, s), 7.01 (2H, dd, J=6.4, 2.8 Hz), 7.17 (3H, t, J=2.9 Hz), 7.32-7.45 (6H, m).

MS: m/z=448.15 [M+H]⁺.

REFERENCE EXAMPLE 61

[Chemical formula 139]

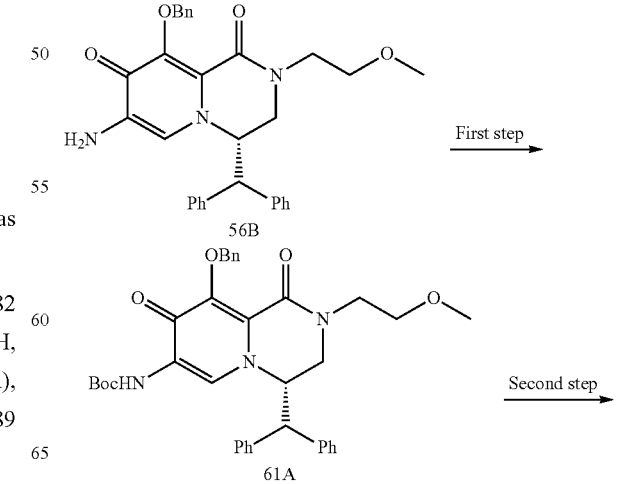

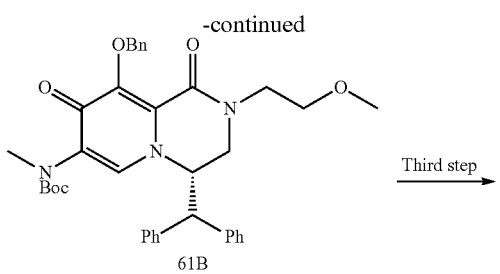

61B

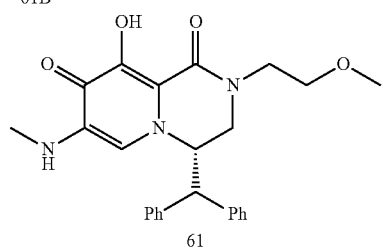

61

First Step

Compound 56B (50 mg, 0.098 mmol) was dissolved in THF (1 mL), Boc2O (0.068 mL, 0.29 mmol) and, subsequently, DMAP (6.0 mg, 0.049 mmol) were added, and the mixture was stirred at room temperature for 5 hours. To the reaction solution were added water and ethyl acetate, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 20 mg of compound 61A as a colorless transparent oil.

MS: m/z=610.50 [M+H]$^+$.

Second Step

Compound 61A (20 mg, 0.033 mmol) was dissolved in DMF (1 mL), sodium hydride (2.6 mg, 0.066 mmol) was added under ice-cooling, the mixture was stirred for 10 minutes, methyl iodide (4.1 uL, 0.066 mmol) was added, and the mixture was stirred at room temperature for 1.5 hours. Ice water, ethyl acetate and brine were added, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 13 mg of compound 61B as a white solid.

MS: m/z=624.25 [M+H]$^+$.

Third Step

Compound 61B (13 mg, 0.021 mmol) was dissolved in TFA (3 mL), and the mixture was stirred at room temperature for 3 hours. The reaction mixture was subjected to toluene azeotropy, and the resulting residue was purified using an LCMS fractionating device. The eluted solvent was distilled off, isopropyl ether-hexane were added to the residue, and the precipitated solid was filtered. Washing with isopropyl ether, and drying afforded 7.5 mg of compound 61.

$^1$H-NMR (CDCl$_3$) δ: 2.19 (3H, s), 3.26 (3H, s), 3.46-3.70 (4H, m), 4.23 (1H, d, J=11.0 Hz), 4.58-4.60 (1H, brm), 5.41-5.44 (1H, brm), 6.28 (1H, brs), 6.99 (2H, brs), 7.13 (3H, brs), 7.31-7.46 (6H, m).

MS: m/z=434.10 [M+H]$^+$.

REFERENCE EXAMPLE 62

[Chemical formula 140]

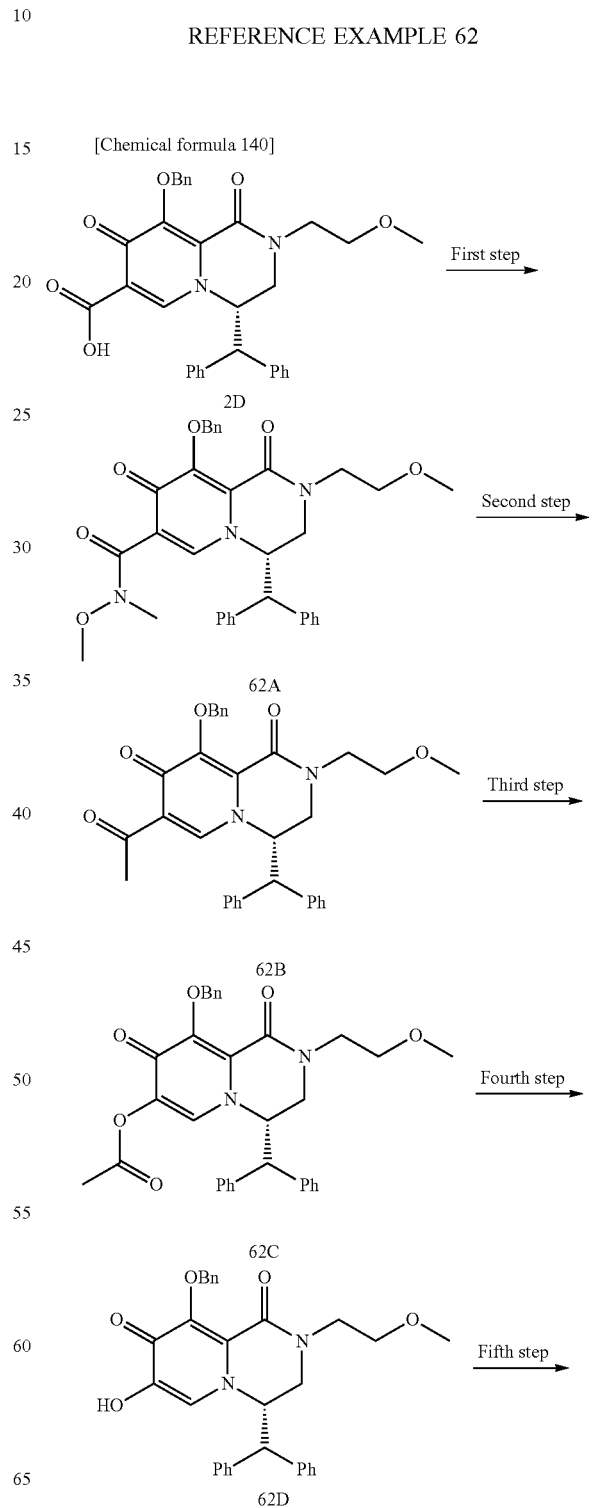

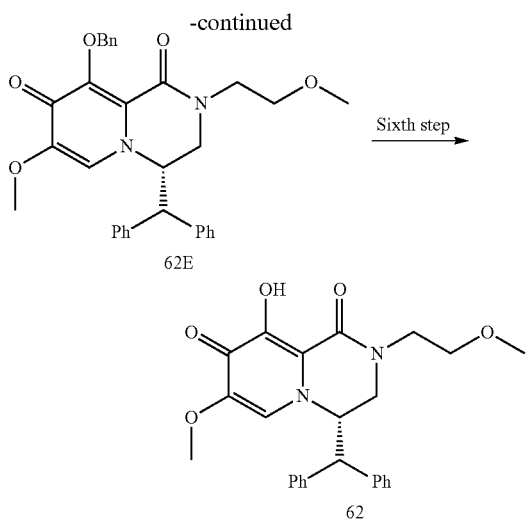

First Step

Compound 2D (112 mg, 0.208 mmol) was dissolved in DMF (2 mL), triethylamine (0.144 ml, 1.04 mmol) and, subsequently, ethyl chloroformate (0.040 mL, 0.42 mmol) were added under ice-cooling, the mixture was stirred at room temperature for 10 minutes, thereafter, N,O-dimethylhydroxyamine hydrochloride (41 mg, 0.42 mmol) and, subsequently, DMAP (3 mg, 0.02 mmol) were added, and the mixture was stirred at room temperature for 1 hour. To the reaction solution were added water and ethyl acetate, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 127 mg of crude purified product 62A as a yellow oil.

MS: m/z=582.20 $[M+H]^+$.

Second Step

Compound 62A (137 mg, 0.236 mmol) was dissolved in THF (8 mL), a 2M THF solution of methylmagnesium bromide (0.444 ml, 0.471 mmol) was added at −78° C. under nitrogen stream, and the mixture was stirred for 30 minutes while temperature was raised to −50° C. To the reaction solution was added 1M hydrochloric acid (4 ml), the mixture was stirred at 0° C. for 20 minutes, ethyl acetate was added, the ethyl acetate layer was separated, and the aqueous layer was extracted with ethyl acetate. The combined extracts were neutralized with an aqueous saturated sodium bicarbonate solution, sodium sulfate was added to the organic layer, the mixture was filtered, and the solvent was distilled off. The resulting residue was purified by silica gel column chromatography. Concentration of an objective fraction afforded 67 mg of compound 62B as a yellow oil.

$^1$H-NMR (CDCl$_3$) δ: 2.55 (3H, s), 3.01-3.14 (1H, m), 3.16 (3H, s), 3.37-3.54 (3H, m), 3.91-4.07 (2H, m), 4.28 (1H, d, J=11.3 Hz), 4.50-4.60 (1H, m), 5.42 (2H, d, J=1.2 Hz), 6.97-6.99 (2H, m), 7.14-7.17 (4H, m), 7.31-7.45 (8H, m), 7.65 (2H, d, J=6.5 Hz).

MS: m/z=537.20 $[M+H]^+$.

Third Step

Compound 62B (67 mg, 0.13 mmol) was dissolved in dichloromethane (4 mL), mCPBA (32 mg, 0.19 mmol) was added at 0° C. under nitrogen stream, and the mixture was stirred at room temperature for 3 hours. The reaction solution was ice-cooled, an aqueous sodium thiosulfate solution, and ethyl acetate were added, the ethyl acetate layer was separated, and the aqueous layer was extracted with ethyl acetate. The combined extracts were neutralized with an aqueous saturated sodium bicarbonate solution, sodium sulfate was added to the organic layer, the mixture was filtered, and the solvent was distilled off to obtain 64 mg of compound 62C.

MS: m/z=553.23 $[M+H]^+$.

Fourth Step

Compound 62C (64 mg, 0.12 mmol) was dissolved in ethanol (8 mL), and the solution was heated to reflux for 4 hours. The reaction solution was concentrated, and the resulting residue was purified by silica gel column chromatography. Concentration of an objective fraction afforded 42 mg of compound 62D.

$^1$H-NMR (CDCl$_3$) δ: 2.93-3.09 (1H, m), 3.16 (3H, s), 3.33-3.53 (4H, m), 3.90-4.07 (2H, m), 4.29-4.47 (2H, m), 5.41 (2H, q, J=10.4 Hz), 6.34 (1H, s), 6.95-6.99 (2H, m), 7.12-7.21 (4H, m), 7.33-7.42 (8H, m), 7.64 (2H, d, J=6.9 Hz).

MS: m/z=511.21 $[M+H]^+$.

Fifth Step

Compound 62D (41 mg, 0.080 mmol) was dissolved in DMF (1 mL), sodium hydride (6.4 mg, 0.16 mmol) was added under ice-cooling, the mixture was stirred for 10 minutes, methyl iodide (0.010 ml, 0.16 mmol) was added, and the mixture was stirred at room temperature for 1.5 hours. To the reaction solution were added ice water and ethyl acetate, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 41 mg of compound 62E as a white solid.

$^1$H-NMR (CDCl$_3$) δ: 2.99-3.09 (1H, m), 3.16 (3H, s), 3.25 (3H, s), 3.32-3.38 (1H, m), 3.42-3.50 (2H, m), 3.94-4.03 (2H, m), 4.28 (1H, d, J=11.3 Hz), 4.43 (1H, brs), 5.40 (2H, dd, J=28.3, 10.2 Hz), 6.01 (1H, s), 6.90-7.19 (5H, m), 7.28-7.44 (8H, m), 7.66 (2H, d, J=6.4 Hz).

MS: m/z=525.21 $[M+H]^+$.

Sixth Step

Compound 62E (40 mg, 0.076 mmol) was dissolved in TFA (3 mL), and the mixture was stirred at room temperature for 30 minutes. The reaction mixture was subjected to toluene azeotropy, and the resulting residue was purified using an LCMS fractionating device. The eluted solvent was distilled off, ethyl acetate-isopropyl ether-hexane were added to the residue, and the precipitated solid was filtered. Washing with isopropyl ether, and drying afforded 7.1 mg of compound 62 as a pink solid.

$^1$H-NMR (CDCl$_3$) δ: 3.17 (3H, s), 3.22 (3H, s), 3.40-3.53 (4H, m), 3.63-3.71 (1H, m), 4.24 (1H, d, J=11.5 Hz), 4.45 (1H, d, J=13.3 Hz), 4.60 (1H, d, J=11.2 Hz), 6.08 (1H, d, J=11.7 Hz), 6.96-6.99 (2H, brm), 7.13-7.17 (3H, m), 7.30-7.43 (5H, m).

MS: m/z=435.15 $[M+H]^+$.

REFERENCE EXAMPLE 63

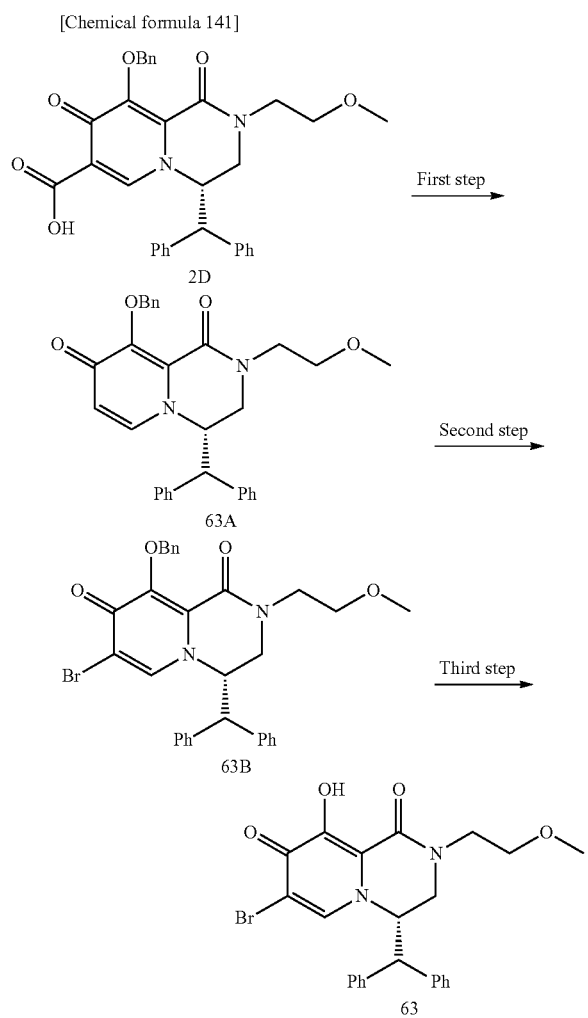

First Step

Compound 2D (164 mg, 0.304 mmol) was dissolved in diphenyl ether (1 mL), the mixture was stirred at 245° C. for 1 hour using a microwave apparatus and, thereafter, the reaction solution was purified by silica gel column chromatography. Concentration of an objective fraction afforded 72 mg of compound 63A as a brown solid.

$^1$H-NMR (CDCl$_3$) δ: 2.92-3.01 (1H, m), 3.16 (3H, s), 3.32-3.50 (3H, m), 3.90-4.46 (4H, m), 5.42 (2H, dd, J=26.1, 10.3 Hz), 5.94 (1H, d, J=7.4 Hz), 6.28 (1H, d, J=7.5 Hz), 6.96-6.99 (2H, m), 7.15-7.19 (3H, m), 7.28-7.44 (8H, m), 7.62-7.65 (2H, m).

MS: m/z=495.21 [M+H]$^+$.

Second Step

To a dichloromethane (4 mL) solution of compound 63A (21 mg, 0.042 mmol) was added NBS (11 mg, 0.062 mmol), and the mixture was heated to reflux for 1 hour. The reaction solution was allowed to cool, and purified by silica gel column chromatography. Concentration of an objective fraction afforded 26 mg of compound 63B as a white solid.

$^1$H-NMR (CDCl$_3$) δ: 3.01-3.09 (1H, m), 3.16 (3H, s), 3.35-3.53 (3H, m), 3.92-4.47 (4H, m), 5.41 (2H, dd, J=32.6, 10.0 Hz), 6.72 (1H, s), 6.97-7.00 (2H, brm), 7.20-7.22 (3H, m), 7.30-7.46 (8H, m), 7.66-7.70 (2H, m).

MS: m/z=573.20 [M+H]$^+$.

Third Step

Compound 63B (10 mg, 0.017 mmol) was dissolved in TFA (3 mL), and the mixture was stirred at room temperature for 50 minutes. The reaction mixture was subjected to toluene azeotropy, isopropyl ether was added to the resulting residue, and the precipitated solid was filtered. Washing with isopropyl ether, and drying afforded 1.4 mg of compound 63 as an orange solid.

MS: m/z=483.15 [M+H]$^+$.

REFERENCE EXAMPLE 64

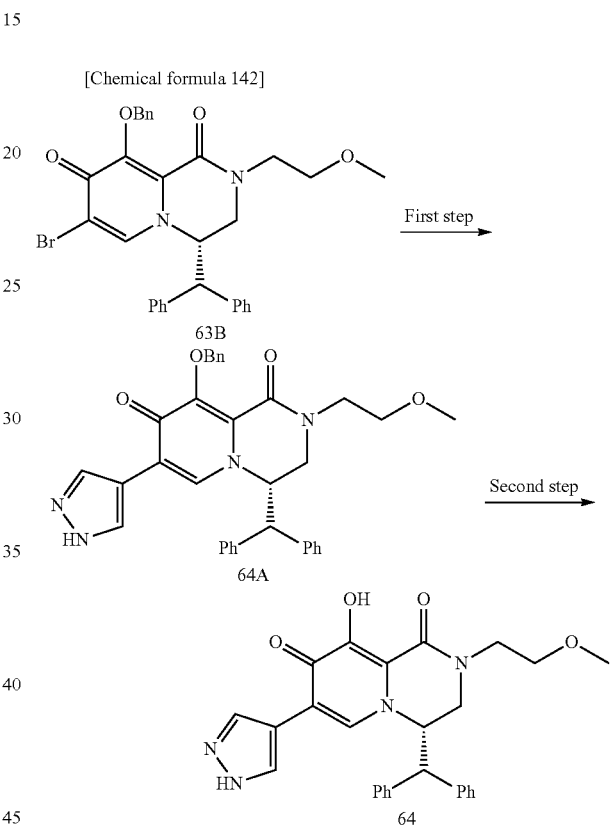

First Step

To a DMF solution (2 mL) of compound 63B (20 mg, 0.035 mmol) were added pyrazole-4-boronic acid pinacol ester (36 mg, 0.19 mmol) and, subsequently, potassium carbonate (29 mg, 0.21 mmol) and, thereafter, tetrakistriphenylphosphinepalladium (24 mg, 0.021 mmol) was added under nitrogen atmosphere, and the mixture was stirred at 110° C. for 8.5 hours. After the reaction solution was concentrated, ethyl acetate and methanol were added, and insolubles were removed. The filtrate was concentrated, and the resulting residue was purified by silica gel column chromatography. Concentration of an objective fraction afforded 18 mg of compound 64A as a white solid.

MS: m/z=561.30 [M+H]$^+$.

Second Step

Compound 64A (14 mg, 0.025 mmol) was dissolved in TFA (2 mL), and the mixture was stirred at room temperature for 30 minutes. The reaction mixture was subjected to toluene azeotropy, and the resulting residue was purified using an LCMS fractionating device. The eluted solvent was distilled off, isopropyl ether was added to the residue, and the precipitated solid was filtered. Washing with isopropyl ether, and drying afforded 1.1 mg of compound 64 as an orange solid.

MS: m/z=471.20 [M+H]+.

REFERENCE EXAMPLE 65

[Chemical formula 143]

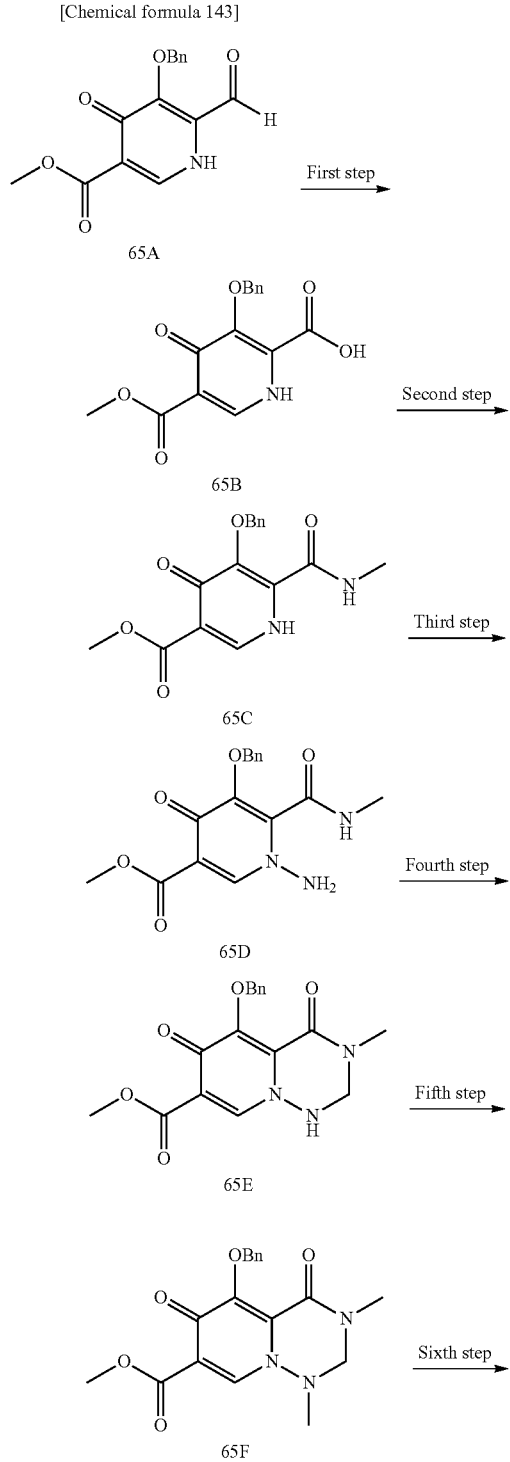

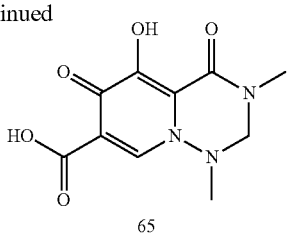

First Step

A THF (1.1 L) solution of compound 65A (WO 2006/088173, 20.0 g, 69.6 mmol) was retained at 25° C. on a water bath, an aqueous (378 mL) solution of sodium chlorite (25.2 g, 278 mmol) and amidosulfuric acid (27.0 g, 278 mmol) was added dropwise over 30 minutes. The reaction solution was stirred at the same temperature for 1 hour, and concentrated under reduced pressure. To the residue were added ice water (100 mL) and diethyl ether (100 mL), and the precipitated solid was filtered. The resulting crude purified product was washed with water and diethyl ether to obtain 20.3 g of compound 65B as a white solid.

$^1$H-NMR (DMSO-$d_6$) δ: 3.74 (3H, s), 5.11 (2H, s), 7.31-7.38 (3H, m), 7.48 (2H, d, J=7.2 Hz), 8.11 (1H, s), 12.07 (1H, brs).

Second Step

Compound 65B (2.0 g, 6.59 mmol) was dissolved in DMF (340 mL), HATU (2.76 g, 7.25 mmol), methylamine (2 mol/L THF solution, 3.63 mL, 7.25 mmol) and triethylamine (9.89 mmol) were added, and the mixture was stirred at room temperature for 5 hours. The reaction solution was distributed between ethyl acetate and water. The ethyl acetate layer was separated, and the aqueous layer was extracted with ethyl acetate once. The combined extracts were washed with water and an aqueous saturated sodium chloride solution, and dried. The solvent was distilled off to obtain 1.66 g of a crude purified product of compound 65C as a white solid.

$^1$H-NMR (DMSO-$d_6$) δ: 3.38 (3H, brs), 3.75 (3H, s), 5.37 (2H, s), 7.34-7.44 (5H, m), 8.10 (1H, s), 8.38 (1H, s), 11.84 (1H, brs).

Third Step

To a DMF (20 mL) solution of compound 65C (1.2 g, 3.79 mmol) were added potassium carbonate (1.04 g, 7.59 mmol) and O-(2,4-dinitrophenyl)hydroxylamine (831 mg, 4.17 mmol), and the mixture was stirred at room temperature for 3 hours. To the reaction solution was added water, and the precipitated solid was filtered, and washed with water to obtain 1.0 g of a crude purified product of compound 65D.

$^1$H-NMR (DMSO-$d_6$) δ: 3.74 (3H, s), 3.83 (3H, brs), 5.05 (2H, s), 6.46 (2H, brs), 7.31-7.38 (5H, m), 8.20 (1H, s), 8.52 (1H, brs).

Fourth Step

To a DMF (10 mL) solution of compound 65D (1.0 g, 3.02 mmol) were added paraformaldehyde (109 mg, 3.62 mmol) and acetic acid (0.017 ml, 0.302 mmol) at room temperature, and the mixture was stirred at 105° C. for 2 hours. The reaction solution was cooled to 0° C., cesium carbonate (3.44 g, 10.6 mmol) was added, and the mixture was stirred at room temperature for 1 hour. To the reaction solution was added water, and the mixture was distributed between ethyl acetate and water. The organic layer was washed with an aqueous saturated sodium chloride solution, and dried. The solvent was distilled off to obtain 120 mg of compound 65E.

MS: m/z=344 [M+H]+.

Fifth Step

To a DMF (1 mL) solution of compound 65E (17.0 mg, 0.05 mmol) were added cesium carbonate (81.4 mg, 0.25 mmol) and methylamine (2 mol/L THF solution, 0.125 ml, 0.25 mmol), and the mixture was stirred at room temperature for 5 hours. The reaction solution was filtered, and the filtrate was fractionated and purified by LCMS to obtain compound 65F.

MS: m/z=358 [M+H]$^+$.

Sixth Step

To a DMF (0.5 mL) solution of compound 65F was added a 2N aqueous sodium hydroxide solution (0.2 mL), and the mixture was stirred at room temperature for 2 hours. To the reaction solution was added ion-exchange resin DOWEX (50W-X8), and the mixture was filtered, and washed with DMF. After concentration of the filtrate, trifluoroacetic acid (0.5 mL) was added, and the mixture was stirred at 80° C. for 4 hours. After concentration of the reaction solution, water and chloroform were added, and the organic layer was separated. The organic layer was concentrated, and fractionation-purified by LCMS to obtain 6.47 mg of compound 65.

MS: m/z=254 [M+H]$^+$.

According to Reference example 65, compounds of Reference examples 66 to 92 shown in Tables 10 to 14 below were synthesized by the same procedure.

TABLE 10

| Reference example | Structure | MS |
|---|---|---|
| Reference example 66 | 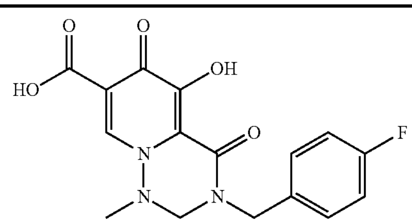 | 348 |
| Reference example 67 | 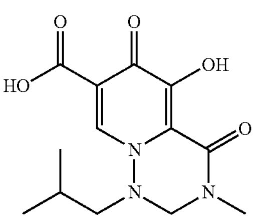 [SMILES: CC(C)CN1CN(C)C(=O)c2c(O)c(=O)c(C(=O)O)cn21] | 296 |
| Reference example 68 | 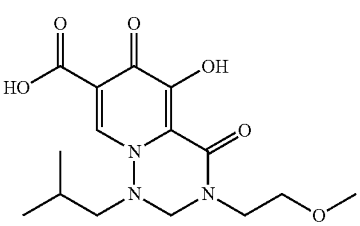 [SMILES: COCCN1CN(CC(C)C)n2cc(C(=O)O)c(=O)c(O)c2C1=O] | 340 |
| Reference example 69 | 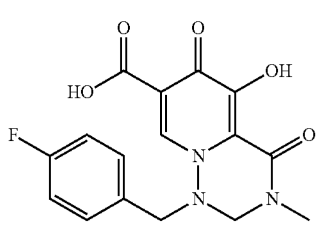 [SMILES: CN1CN(Cc2ccc(F)cc2)n2cc(C(=O)O)c(=O)c(O)c2C1=O] | 348 |

TABLE 10-continued

| Reference example | Structure | MS |
|---|---|---|
| Reference example 70 | 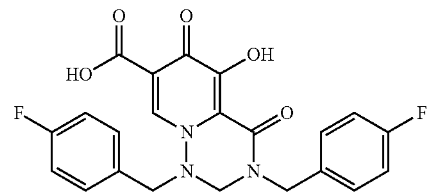 [SMILES: O=C(O)c1cn2c(c(O)c1=O)C(=O)N(Cc1ccc(F)cc1)CN2Cc1ccc(F)cc1] | 442 |
| Reference example 71 | 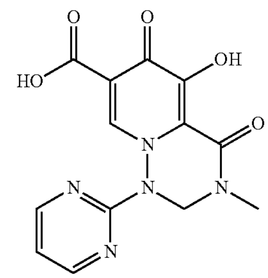 [SMILES: CN1CN(c2ncccn2)n2cc(C(=O)O)c(=O)c(O)c2C1=O] | 318 |

TABLE 11

| Reference example | Structure | MS |
|---|---|---|
| Reference example 72 | 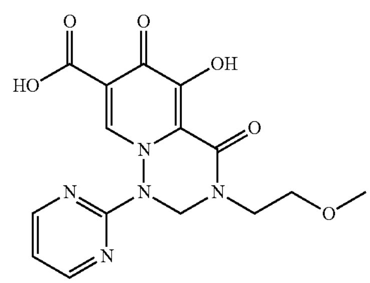 [SMILES: COCCN1CN(c2ncccn2)n2cc(C(=O)O)c(=O)c(O)c2C1=O] | 362 |
| Reference example 73 | 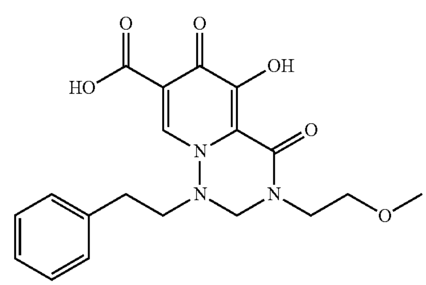 [SMILES: COCCN1CN(CCc2ccccc2)n2cc(C(=O)O)c(=O)c(O)c2C1=O] | 388 |
| Reference example 74 | 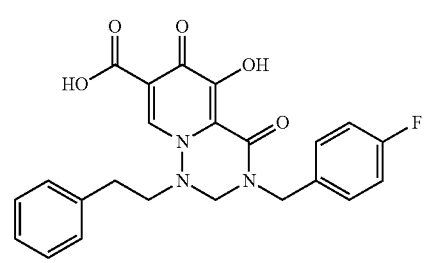 [SMILES: O=C(O)c1cn2c(c(O)c1=O)C(=O)N(Cc1ccc(F)cc1)CN2CCc1ccccc1] | 438 |

TABLE 11-continued
| Reference example | Structure | MS |
|---|---|---|
| Reference example 75 | 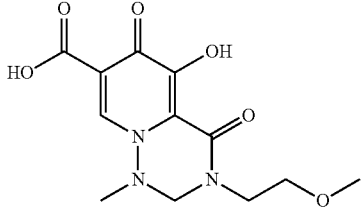 [SMILES: COCCN1CN(C)n2cc(C(=O)O)c(=O)c(O)c2C1=O] | 298 |
| Reference example 76 | 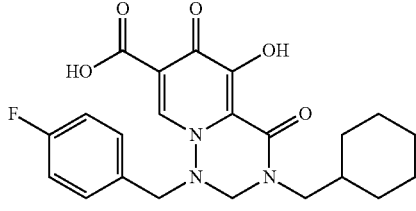 [SMILES: O=C(O)c1cn2c(c(O)c1=O)C(=O)N(CC1CCCCC1)CN2Cc1ccc(F)cc1] | 430 |
| Reference example 77 | 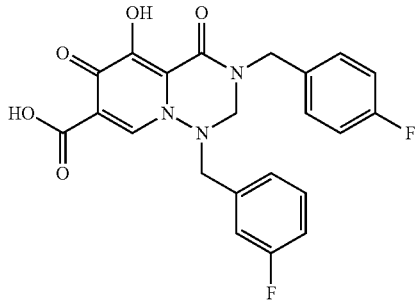 [SMILES: O=C(O)c1cn2c(c(O)c1=O)C(=O)N(Cc1ccc(F)cc1)CN2Cc1cccc(F)c1] | 442 |
TABLE 12
| Reference example | Structure | MS |
|---|---|---|
| Reference example 78 | 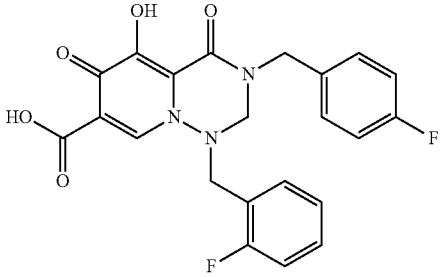 [SMILES: O=C(O)c1cn2c(c(O)c1=O)C(=O)N(Cc1ccc(F)cc1)CN2Cc1ccccc1F] | 442 |
| Reference example 79 | 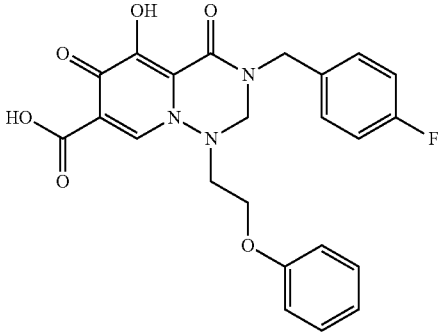 [SMILES: O=C(O)c1cn2c(c(O)c1=O)C(=O)N(Cc1ccc(F)cc1)CN2CCOc1ccccc1] | 454 |
TABLE 12-continued
| Reference example | Structure | MS |
|---|---|---|
| Reference example 80 | 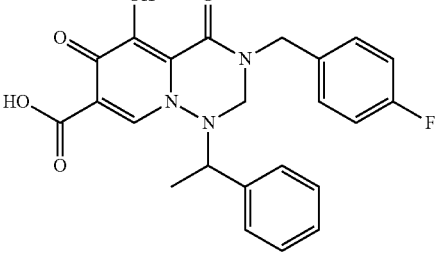 | 438 |
| Reference example 81 | 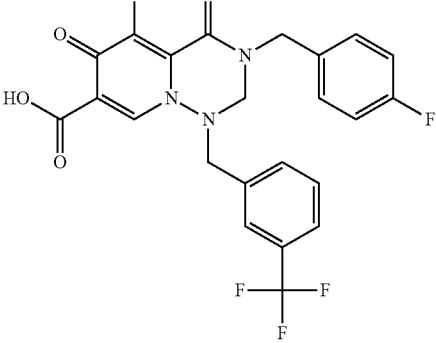 | 492 |
| Reference example 82 | 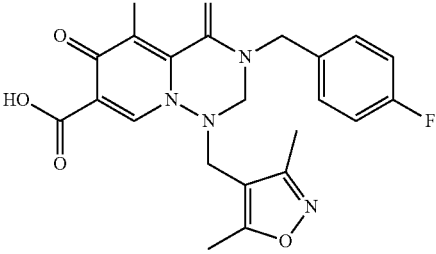 | 443 |
TABLE 13
| Reference example | Structure | MS |
|---|---|---|
| Reference example 83 | 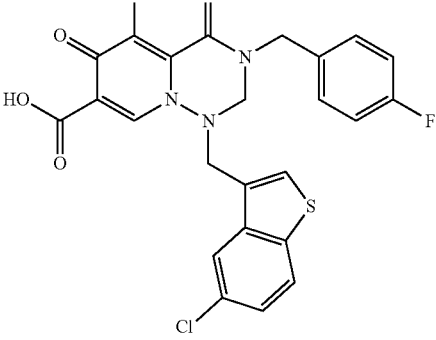 | 513 |

TABLE 13-continued

| Reference example | Structure | MS |
|---|---|---|
| Reference example 84 | (structure) | 500 |
| Reference example 85 | (structure) | 454 |
| Reference example 86 | (structure) | 452 |
| Reference example 87 | (structure) | 480 |

TABLE 14

| Reference example | Structure | MS |
|---|---|---|
| Reference example 88 | (structure) | 406 |
| Reference example 89 | (structure) | 445 |
| Reference example 90 | (structure) | 500 |
| Reference example 91 | (structure) | 416 |

TABLE 14-continued

| Reference example | Structure | MS |
|---|---|---|
| Reference example 92 | 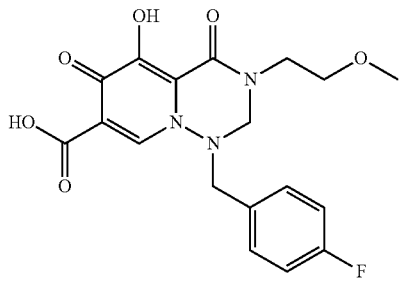 | 450 |

REFERENCE EXAMPLE 93

[Chemical formula 144]

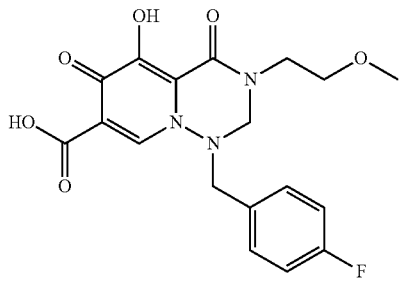

According to Reference example 65, compound 93 was synthesized by the same procedure.

$^1$H-NMR (CDCl$_3$) δ: 3.34 (3H, s), 3.57-3.68 (2H, m), 3.73 (2H, brs), 4.18 (2H, s), 4.75 (2H, brs), 7.06-7.12 (2H, m), 7.21-7.24 (2H, m), 8.10 (1H, s), 11.96 (1H, brs), 14.52 (1H, brs).

REFERENCE EXAMPLE 94

[Chemical formula 145]

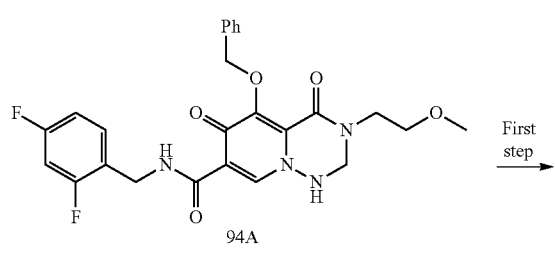

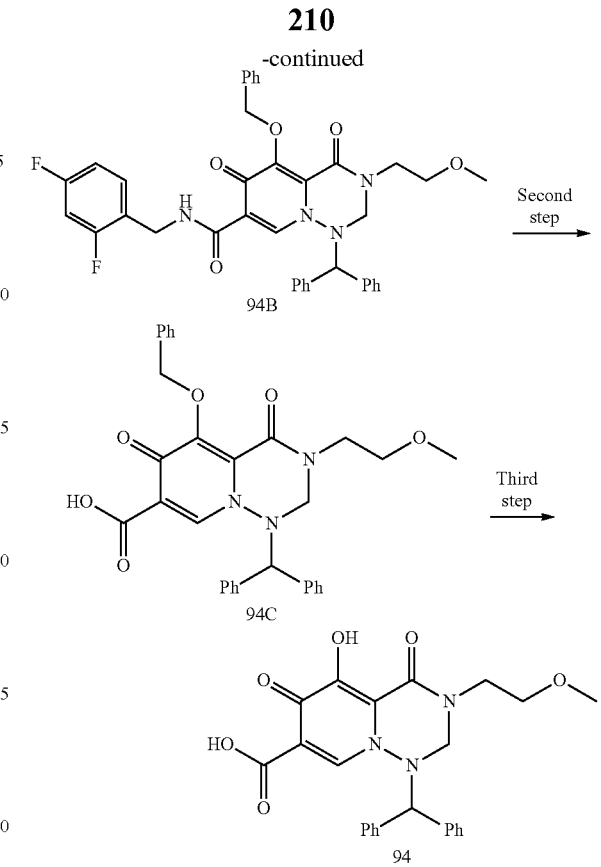

First Step

Using compound 94A (WO 2007/049675), and according to the same procedure as that of the fifth step of Reference example 65, compound 94B was synthesized.

$^1$H-NMR (CDCl$_3$) δ: 3.00-3.09 (1H, m), 3.18 (3H, s), 3.44 (2H, dd, J=7.55, 2.82 Hz), 4.02-4.08 (1H, m), 4.44-4.59 (3H, m), 4.86 (1H, d, J=13.57 Hz), 5.25 (1H, s), 5.36 (2H, dd, J=14.87, 9.99 Hz), 6.74-6.84 (2H, m), 7.09-7.60 (16H, m), 7.90 (1H, s), 10.07 (1H, t, J=5.87 Hz).

Second Step

To a MeCN (20 ml) solution of compound 94B (1.1 g, 1.655 mmol) were added DMAP (202 mg, 1.655 mmol) and Boc2O (20 ml, 86 mmol) at room temperature under nitrogen stream, and the mixture was heated to reflux for 5 hours. Further, Boc2O (20 ml, 86 mmol) was added, and the mixture was heated to reflux for 5 hours. After concentration under reduced pressure, to the residue were added ethanol (20.00 ml) and an aqueous sodium hydroxide solution (40%, 25 ml), and the mixture was stirred at room temperature for 5 hours. To the reaction mixture were added ethyl acetate-water to make the aqueous layer acidic. After extraction with ethyl acetate (2×200 mL), the organic layer was washed with an aqueous saturated sodium chloride solution. After drying with magnesium sulfate, the solvent was distilled off under reduced pressure. The crude product was purified by silica gel column chromatography (CHCl3/MeOH 20:1) to obtain compound 94C. (750 mg, 63%)

$^1$H-NMR (DMSO-d$_6$) δ: 3.13 (3H, s), 3.25-3.34 (3H, m), 3.79 (1H, d, J=13.73 Hz), 4.42 (1H, d, J=14.03 Hz), 5.11-5.27 (3H, m), 5.48 (1H, s), 7.18-7.21 (5H, m), 7.33-7.49 (6H, m), 7.56-7.58 (2H, m), 7.74 (2H, d, J=7.32 Hz), 8.01 (1H, s).

Third Step

Using compound 94C, and according to the same procedure as that of the tenth step of Reference example 12, compound 94 was synthesized.

$^1$H-NMR (DMSO-$d_6$) δ: 3.13 (3H, s), 3.41-3.56 (4H, m), 4.50 (1H, d, J=13.57 Hz), 5.21 (1H, d, J=13.42 Hz), 5.58 (1H, s), 7.16-7.50 (8H, m), 7.72 (2H, d, J=7.32 Hz), 7.93 (1H, s), 12.12 (1H, s).

REFERENCE EXAMPLE 95

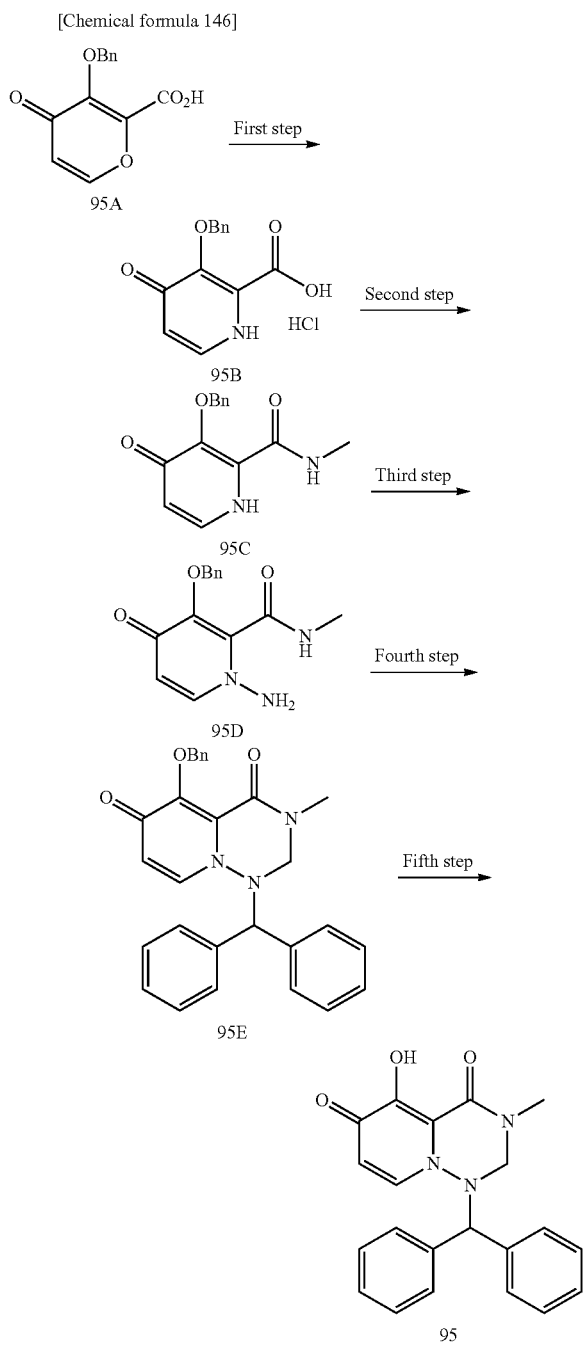

[Chemical formula 146]

First Step

Compound 95A (WO 2006/116764, 1 g, 4.06 mmol) was dissolved in 28% aqueous ammonia, and the solution was stirred at room temperature for 12 hours. After concentration of the reaction solution, the resulting residue was neutralized with 2N hydrochloric acid, and the precipitated solid was suspended in ethyl acetate, filtered, and dried to obtain 1.14 g (yield 100%) of compound 95B.

$^1$H-NMR (DMSO-$d_6$) δ: 5.14 (2H, s), 7.31 (1H, d, J=6.6 Hz), 7.34-7.41 (3H, m), 7.45-7.51 (2H, m), 8.17 (1H, d, J=6.6 Hz).

Second Step

To a DMF (10 ml) solution of the compound 95B (3.00 g, 10.65 mmol) were added WSC HCl (3.06 g, 15.98 mmol) and HOBt (1.58 g, 11.7 mmol) at room temperature, the mixture was stirred for 10 minutes, and a methylamine 33 wt % ethanol solution (1.50 g, 15.98 mmol) was added dropwise. After the reaction solution was stirred at the same temperature for 2 hours, water was added, and the mixture was extracted with chloroform five times. The extract was dried with sodium sulfate, the solvent was distilled off, and the resulting oil was purified by silica gel chromatography. From a fraction eluted with ethyl acetate-MeOH (6:4, v/v), 2.62 g (yield 95%) of compound 95C was obtained as a solid.

$^1$H-NMR (CDCl$_3$) δ: 2.77 (3H, d, J=4.8 Hz), 5.49 (2H, s), 6.57 (1H, d, J=6.9 Hz), 7.25-7.43 (5H, m), 7.48 (1H, t, J=6.0 Hz), 8.23 (1H, brs), 9.77 (1H, brs).

Third Step

To a DMF (10 ml) solution of the compound 95C (2.62 g, 10.14 mmol) was suspended potassium carbonate (4.20 g, 30.42 mmol) at room temperature, the suspension was stirred for 5 minutes, O-(2,4-dinitrophenyl)hydroxylamine (3.03 g, 15.21 mmol) was added, and the mixture was stirred at the same temperature for 3 hours. To the reaction solution was added water, the mixture was extracted with chloroform five times, and the extract was dried with sodium sulfate. After the solvent was distilled off, the resulting oil was purified by silica gel chromatography. From a fraction eluted with ethyl acetate-MeOH (6:4, v/v), 1.41 g (yield 51%) of compound 95D was obtained as a solid.

$^1$H-NMR (CDCl$_3$) δ: 2.62 (3H, d, J=5.1 Hz), 5.06 (2H, s), 5.22 (2H, s), 6.18 (1H, d, J=7.8 Hz), 7.25-7.36 (5H, m), 5.89 (1H, d, J=7.8 Hz), 7.57 (1H, q, J=5.1 Hz).

Fourth Step

A toluene (10 ml) solution of the compound 95D (1.0 g, 3.66 mmol) were added paraformaldehyde (109.9 mg, 3.66 mmol) and acetic acid (22 mg, 0.37 mmol), and the mixture was heated to stir at 100° C. for 40 minutes. After cooling, the solvent was distilled off, the residue was dissolved in DMF (10 ml) without purification, cesium carbonate (3.58 g, 10.98 mmol) was added under ice-cooling, and the mixture was stirred for 10 minutes. To the reaction solution was added benzohydryl bromide (1.36 g, 5.49 mmol), the mixture was stirred at room temperature for 3 hours, water was added, and the mixture was extracted with ethyl acetate three times. The extract was washed with water three times, and dried with sodium sulfate. The solvent was distilled off, and the resulting oil was purified by silica gel chromatography. From a fraction eluted with ethyl acetate-MeOH (9:1, v/v), 1.26 g (yield 71%) of compound 95E was obtained as a solid.

$^1$H-NMR (CDCl$_3$) δ: 2.91 (3H, s), 4.26 (1H, d, J=13.2 Hz), 4.77 (1H, d, J=13.2 Hz), 5.12 (1H, s), 5.42 (1H, J=13.2 Hz), 5.45 (1H, d, J=13.2 Hz), 5.82 (1H, J=7.5 Hz), 6.71 (1H, d, J=7.5 Hz), 7.10-7.23 (5H, m), 7.27-7.46 (6H, m), 7.52 (2H, d, J=6.9 Hz), 7.60-7.64 (2H, m).

Fifth Step

Compound 95E (100 mg, 0.221 mmol) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 50 mg (yield 63%) of compound 95.

$^1$H-NMR (CDCl$_3$) δ: 2.95 (3H, s), 4.36 (1H, d, J=13.2 Hz), 4.95 (1H, d, J=13.2 Hz), 5.22 (1H, s), 5.71 (1H, d, J=7.8 Hz), 6.75 (1H, d, J=7.8 Hz), 7.21 (5H, brs), 7.33-7.47 (4H, m), 7.55 (2H, d, J=6.6 Hz).

According to Reference example 95, the following compounds were synthesized by the same procedure.

REFERENCE EXAMPLE 96

[Chemical formula 147]

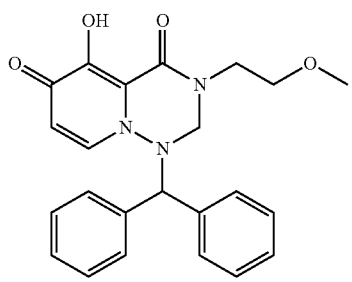

96

$^1$H-NMR (CDCl$_3$) δ: 3.12-3.18 (1H, m), 3.21 (3H, s), 3.38-3.52 (2H, m), 3.81 (1H, ddd, J=3.3 Hz, 4.2 Hz, 14.1 Hz), 4.52 (1H, d, J=13.2 Hz), 5.00 (1H, d, J=13.2 Hz), 5.28 (1H, s), 5.71 (1H, d, J=7.8 Hz), 6.74 (1H, d, J=7.8 Hz), 7.14-7.21 (5H, m), 7.32-7.46 (3H, m), 7.53 (2H, d, J=7.5 Hz).

REFERENCE EXAMPLE 97

[Chemical formula 148]

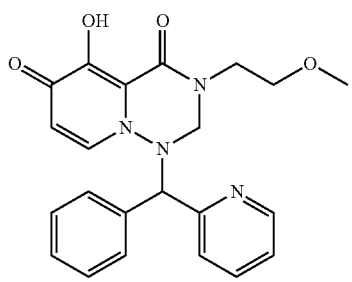

97

$^1$H-NMR (CDCl$_3$) δ: 2.99-3.06 (0.54H, m), 3.18-3.23 (3.9H, m), 3.42-3.54 (2.5H, m), 3.86-3.91 (0.42H, m), 4.03-4.08 (0.58H, m), 4.37 (0.58H, d, J=13.5 Hz), 4.54 (0.42H, d, J=13.8 Hz), 4.98 (0.58H, d, J=13.5 Hz), 5.08 (0.42H, d, J=13.8 Hz), 5.36 (0.58H, s), 5.43 (0.42H, s), 5.70-5.77 (1H, m), 6.77 (0.42H, d, J=7.5 Hz), 6.94 (0.58H, d, J=7.8 Hz), 7.08-7.53 (6H, m), 7.60-7.78 (2H, m), 8.55 (0.58H, d, J=4.2 Hz), 8.72 (0.42H, d, J=3.9 Hz).

REFERENCE EXAMPLE 98

[Chemical formula 149]

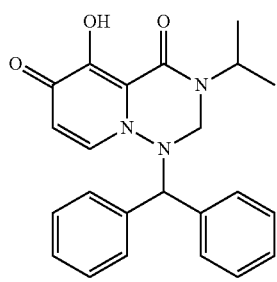

98

$^1$H-NMR (CDCl$_3$) δ: 0.930 (3H, d, J=6.9 Hz), 1.09 (3H, d, J=6.9 Hz), 4.58 (1H, d, J=12.6 Hz), 4.79 (1H, d, J=12.6 Hz), 4.83-4.90 (1H, m), 5.20 (1H, s), 5.67 (1H, d, J=7.5 Hz), 6.66 (1H, d, J=7.5 Hz), 7.07-7.09 (2H, m), 7.13-7.19 (3H, m), 7.34-7.46 (3H, m), 7.52 (1H, d, J=7.5 Hz).

REFERENCE EXAMPLE 99

[Chemical formula 150]

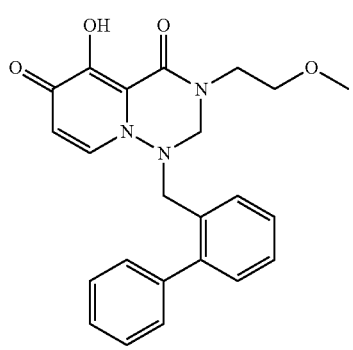

99

$^1$H-NMR (CDCl$_3$) δ: 3.30 (3H, s), 3.49 (1H, brs), 3.54-3.56 (2H, m), 3.73 (1H, brs), 4.11 (2H, brs), 4.25 (1H, brs), 4.78 (1H, brs), 6.00 (1H, d, J=7.5 Hz), 8.33 (1H, d, J=7.5 Hz), 7.19-7.24 (3H, m), 7.34-7.37 (2H, m), 7.38-7.48 (4H, m).

REFERENCE EXAMPLE 100

[Chemical formula 151]

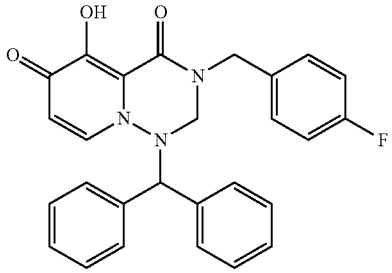

$^1$H-NMR (CDCl$_3$) δ: 4.32 (1H, d, J=14.7 Hz), 4.41 (1H, d, J=12.9 Hz), 4.69 (1H, d, J=14.7 Hz), 4.88 (1H, d, J=12.9 Hz), 4.97 (1H, s), 5.68 (1H, d, J=7.5 Hz), 6.70 (1H, d, J=7.5 Hz), 6.91-6.98 (2H, m), 7.05-7.08 (2H, m), 7.12-7.20 (7H, m), 7.30-7.32 (4H, m).

REFERENCE EXAMPLE 101

[Chemical formula 152]

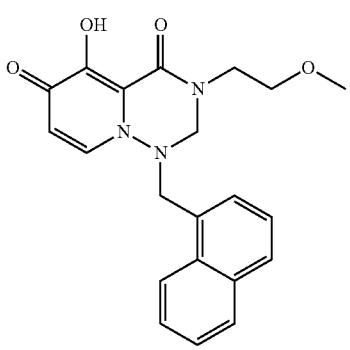

$^1$H-NMR (CDCl$_3$) δ: 3.35 (3H, s), 3.66-3.69 (3H, m), 3.89 (1H, brs), 4.51 (1H, brs), 4.64 (2H, brs), 5.05 (1H, brs), 5.89 (1H, d, J=7.5 Hz), 6.58 (1H, d, J=7.5H), 7.11 (1H, d, J=7.2 Hz), 7.26-7.40 (1H, m), 7.54-7.62 (2H, m), 7.86-7.93 (2H, m), 8.13 (1H, d, J=8.4 Hz).

REFERENCE EXAMPLE 102

[Chemical formula 153]

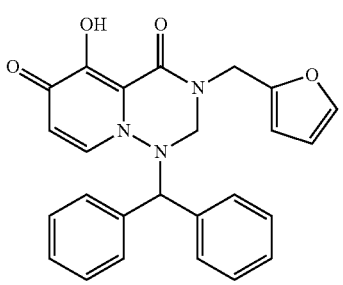

$^1$H-NMR (CDCl$_3$) δ: 4.54 (1H, d, J=12.9 Hz), 4.56 (2H, s), 4.94 (1H, d, J=12.9 Hz), 5.14 (1H, s), 5.68 (1H, d, J=7.8 Hz), 6.20 (1H, d, J=3.0 Hz), 6.25-6.27 (1H, m), 6.72 (1H, d, J=7.8 Hz), 7.10-7.37 (11H, m).

REFERENCE EXAMPLE 103

[Chemical formula 154]

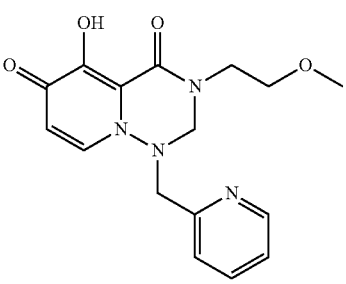

$^1$H-NMR (CDCl$_3$) δ: 3.33 (3H, s), 3.63-3.66 (2H, m), 3.75 (2H, brs), 4.27 (2H, brs), 4.67 (1H, brs), 5.00 (1H, brs), 6.09 (1H, d, J=7.8 Hz), 6.99 (1H, d, J=7.8 Hz), 7.18 (1H, d, J=7.8 Hz), 7.27-7.32 (1H, m), 7.66-7.71 (1H, m), 8.63-8.65 (1H, m).

REFERENCE EXAMPLE 104

[Chemical formula 155]

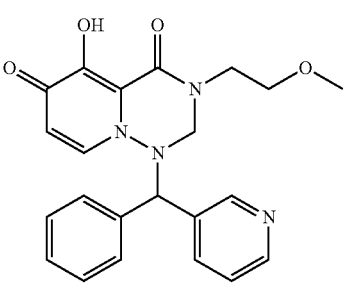

$^1$H-NMR (CDCl$_3$) δ: 3.12-3.22 (1H, m), 3.21 (3H, m), 3.38-3.55 (3H, m), 3.74-3.80 (0.55H, m), 3.87-3.94 (0.44H, m), 4.46-4.54 (1H, m), 5.00-5.07 (1H, m), 5.30-5.39 (1H, m), 5.70 (0.55H, d, J=7.5 Hz), 5.77 (0.45H, d, J=7.5 Hz), 6.74 (0.55H, d, J=7.8 Hz), 6.81 (0.45H, d, J=7.8 Hz), 7.11-7.54 (7.45H, m), 7.90 (0.55H, d, J=7.8 Hz), 8.459-8.783 (2H, m).

REFERENCE EXAMPLE 105

[Chemical formula 156]

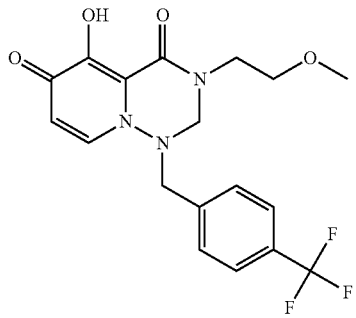

¹H-NMR (CDCl₃) δ: 3.34 (3H, s), 3.65-3.70 (4H, m), 4.18 (1H, brs), 4.21 (1H, brs), 4.48 (1H, brs), 4.98 (1H, brs), 6.12 (1H, d, J=7.8 Hz), 6.97 (1H, d, J=7.8 Hz), 7.36 (1H, d, J=7.5 Hz), 7.49 (1H, t, J=7.8 Hz), 7.61-7.66 (2H, m).

REFERENCE EXAMPLE 106

[Chemical formula 157]

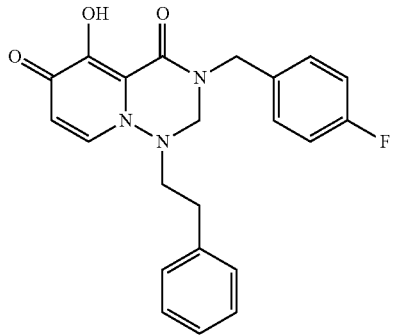

¹H-NMR (CDCl₃) δ: 2.54 (2H, t, J=7.5 Hz), 3.01 (2H, t, J=7.5 Hz), 4.38 (2H, brs), 4.77 (2H, brs), 6.27 (1H, d, J=7.5 Hz), 6.96-7.00 (2H, m), 7.04-7.09 (3H, m), 7.19-7.33 (5H, m).

REFERENCE EXAMPLE 107

[Chemical formula 158]

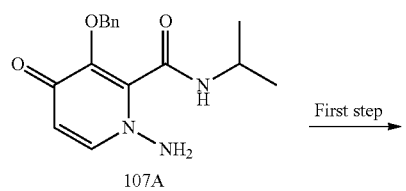

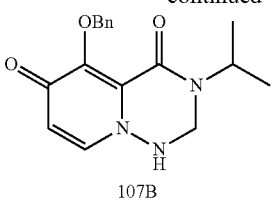

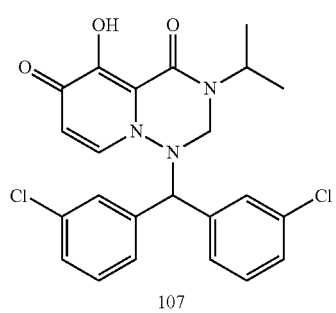

First Step

To a DMF (30 ml) solution of compound 107A (3.0 g, 9.96 mmol) synthesized according to the method of synthesizing compound 95D were added paraformaldehyde (299 mg, 9.96 mmol) and acetic acid (1 ml), and the mixture was heated to stir at 120° C. for 4 hours. After the solvent was distilled off, to the residue were added ethyl acetate-diisopropyl ether, and the precipitated solid was filtered to obtain 2.85 g (yield 91%) of compound 107B.

¹H-NMR (CDCl₃) δ: 1.19 (6H, J=6.6 Hz), 4.34 (2H, J=7.5 Hz), 4.72-4.86 (1H, m), 5.30 (2H, s), 5.49 (1H, t, J=7.5 Hz), 6.36 (1H, d, J=7.8 Hz), 7.26-7.35 (4H, m), 7.37 (1H, d, J=7.8 Hz), 7.55-7.58 (2H, m).

Second Step

To an acetic acid (2 ml) solution of compound 107B (100 mg, 0.319 mmol) were added 96% sulfuric acid (0.5 ml) and bis(3-chlorophenyl)methanol (242.3 mg, 0.957 mmol) at room temperature, and the mixture was stirred at 80° C. for 2 hours. After the reaction solution was cooled to room temperature, water was added, and the mixture was extracted with ethyl acetate three times. The organic layer was washed with water once, and dried with sodium sulfate. After the solvent was distilled off, to the residue was added diisopropyl ether, and the precipitated solid was filtered to obtain 42 mg (yield 29%) of compound 107.

¹H-NMR (CDCl₃) δ: 0.953 (3H, d, J=3.9 Hz), 1.12 (3H, d, J=4.2 Hz), 4.51 (1H, 13.5 Hz), 4.83 (1H, d, J=13.5 Hz), 4.83-4.92 (1H, m), 5.18 (1H, s), 5.74 (1H, d, J=7.8 Hz), 6.73 (1H, d, J=7.8 Hz), 6.90 (1H, d, J=7.5 Hz), 7.12 (2H, dd, J=7.2 Hz, 8.1 Hz), 7.19-7.22 (1H, m), 7.37-7.41 (3H, m), 7.55 (1H, s).

According to Reference example 107, the following compounds were synthesized by the same procedure.

REFERENCE EXAMPLE 108

[Chemical formula 159]

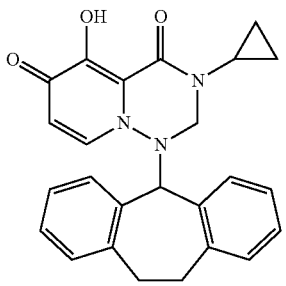

108

¹H-NMR (CDCl₃) δ: 0.465-0.549 (1H, m), 0.642-0.738 (1H, m), 0.754-0.907 (2H, m), 2.71-2.79 (1H, m), 2.86 (1H, ddd, J=4.8 Hz, 5.7 Hz, 14.7 Hz), 3.01 (2H, ddd, J=4.2 Hz, 16.0 Hz, 16.8 Hz), 3.88 (1H, ddd, J=4.8 Hz, 5.1 Hz, 16.8 Hz), 4.08-4.14 (1H, m), 4.16 (1H, d, J=12.9 Hz), 4.70 (1H, d, J=12.9 Hz), 4.96 (1H, s), 5.75 (1H, d, J=7.8 Hz), 6.58 (1H, d, J=7.8 Hz), 6.61 (1H, d, J=7.5 Hz), 6.92 (1H, dd, J=6.0 Hz, 7.5 Hz), 7.11-7.80 (6H, m).

REFERENCE EXAMPLE 109

[Chemical formula 160]

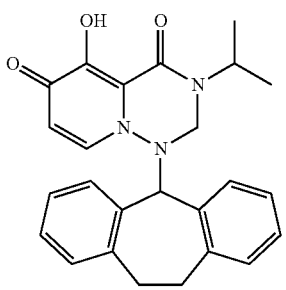

109

¹H-NMR (CDCl₃) δ: 1.14 (3H, d, J=6.9 Hz), 1.18 (3H, d, J=6.9 Hz), 2.82 (1H, ddd, J=4.5 Hz, 4.8 Hz, 14.1 Hz), 3.08 (1H, ddd, J=4.2 Hz, 13.2 Hz, 17.7 Hz), 3.53 (1H, ddd, J=4.2 Hz, 4.5 Hz, 17.7 Hz), 4.27 (1H, d, J=12.9 Hz), 4.26-4.37 (1H, m), 4.62-4.71 (1H, m), 4.68 (1H, d, J=12.9 Hz), 5.05 (1H, s), 5.71 (1H, d, J=7.5 Hz), 6.63 (2H, d, J=7.2 Hz), 6.90 (1H, t, J=7.5 Hz), 7.08-7.63 (6H, m).

REFERENCE EXAMPLE 110

[Chemical formula 161]

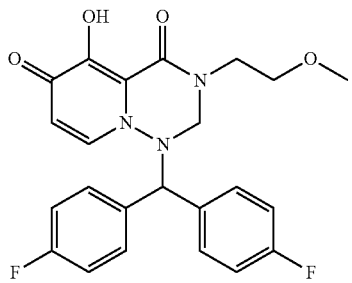

110

¹H-NMR (CDCl₃) δ: 3.16-3.28 (1H, m), 3.22 (3H, s), 3.46-3.50 (2H, m), 3.86 (1H, ddd, J=3.6 Hz, 3.6 Hz, 14.4 Hz), 4.47 (1H, d, J=13.2 Hz), 5.01 (1H, d, J=13.2 Hz), 5.30 (1H, s), 5.76 (1H, d, J=7.5 Hz), 6.72 (1H, d, J=7.5 Hz), 6.90 (2H, t, J=8.4 Hz), 7.06-7.18 (4H, m), 7.51 (2H, dd, J=5.4 Hz, 8.7 Hz).

REFERENCE EXAMPLE 111

[Chemical formula 162]

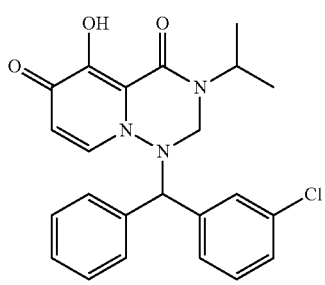

111

¹H-NMR (CDCl₃) δ: 0.903 (1.3H, d, J=6.9 Hz), 0.982 (1.5H, d, J=6.6 Hz), 1.08-1.14 (3.2H, m), 4.55 (1H, dd, J=13.2 Hz, 16.5 Hz), 4.78-4.93 (2H, m), 5.20 (1H, s), 5.66 (0.58H, d, J=7.5 Hz), 5.75 (0.42H, d, J=7.5 Hz), 6.67 (0.55H, d, J=7.5 Hz), 6.73 (0.45H, d, J=7.5 Hz), 6.92 (0.45H, d, J=7.2 Hz), 7.04-7.59 (8.6H, m).

REFERENCE EXAMPLE 112

[Chemical formula 163]

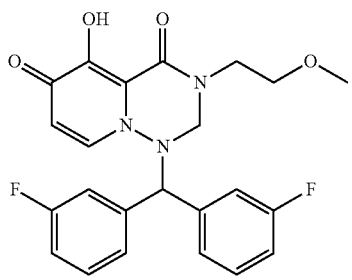

112

¹H-NMR (CDCl₃) δ: 3.22 (3H, s), 3.24-3.32 (1H, m), 3.47-3.50 (2H, m), 3.84 (1H, ddd, J=3.3 Hz, 3.9 Hz, 14.4 Hz), 4.51 (1H, d, J=13.5 Hz), 5.03 (1H, d, J=13.5 Hz), 5.32 (1H, s), 5.77 (1H, d, J=7.8 Hz), 6.80 (1H, d, J=7.8 Hz), 6.84 (1H, d, J=7.8 Hz), 6.93 (2H, t, J=8.4 Hz), 7.06-7.20 (2H, m), 7.25-7.29 (2H, m), 7.39-7.47 (1H, m).

REFERENCE EXAMPLE 113

[Chemical formula 164]

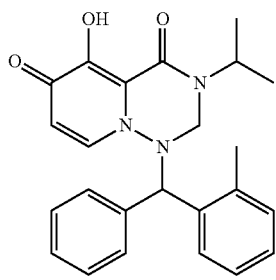

113

¹H-NMR (CDCl₃) δ: 0.88 (3H, d, J=6.9 Hz), 1.10 (3H, d, J=6.6 Hz), 2.10 (3H, s), 4.62-4.69 (1H, m), 4.79-4.92 (2H, m), 5.32 (1H, s), 5.64 (0.74H, 7.5 Hz), 5.72 (0.26H, d, J=7.5 Hz), 6.61 (0.74H, d, J=7.8 Hz), 6.82 (0.26H, d, J=7.8 Hz), 6.96-7.52 (8.26H, m), 7.48 (0.74H, d, J=7.5 Hz).

REFERENCE EXAMPLE 114

[Chemical formula 165]

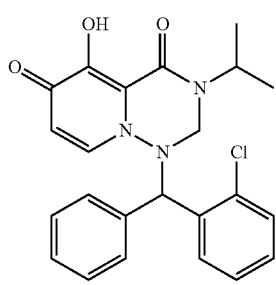

114

¹H-NMR (CDCl₃) δ: 0.976 (2H, d, J=6.9 Hz), 1.09-1.14 (3H, m), 5.63 (0.74H, d, J=7.8 Hz), 5.65 (0.74H, s), 5.73 (0.26H, d, J=7.8 Hz), 6.20 (0.26H, s), 6.65 (0.74H, d, J=7.8 Hz), 6.79 (0.26H, d, J=7.8 Hz), 7.05-7.24 (4.26H, m), 7.31-7.56 (4H, m), 8.02 (0.74H, d, J=6.3 Hz).

REFERENCE EXAMPLE 115

[Chemical formula 166]

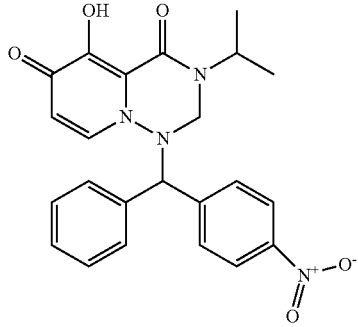

115

¹H-NMR (CDCl₃) δ: 0.893 (1.2H, d, J=6.6 Hz), 0.958 (1.8H, d, J=6.9 Hz), 1.09-1.13 (3H, m), 4.44 (0.56H, d, J=13.2 Hz), 4.63 (0.44H, d, J=13.5 Hz), 4.81-4.93 (2H, m), 5.35 (1H, m), 5.67 (0.56H, d, J=7.8 Hz), 5.72 (0.44H, d, J=7.8 Hz), 6.67-6.73 (1H, m), 7.03 (1H, d, J=6.6 Hz), 7.20-7.51 (5H, m), 7.75 (1H, d, 0.8.4 Hz), 8.06 (0.88H, d, J=8.7 Hz), 8.33 (1.1H, d, J=8.7 Hz).

REFERENCE EXAMPLE 116

[Chemical formula 167]

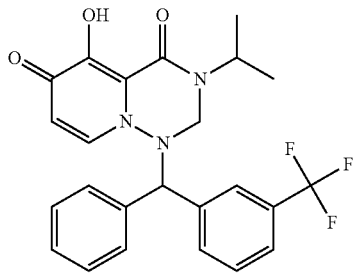

116

¹H-NMR (CDCl₃) δ: 0.91-0.0.948 (3H, m), 1.10-1.14 (3H, m), 3.61-3.68 (1H, m), 4.44 (0.56H, d, J=12.9 Hz), 4.59 (0.44H, d, J=12.9 Hz), 4.79-4.91 (2H, m), 5.29 (1H, s), 5.67-5.69 (1H, m), 6.63-6.70 (2H, m), 6.90-7.81 (8H, m).

REFERENCE EXAMPLE 117

[Chemical formula 168]

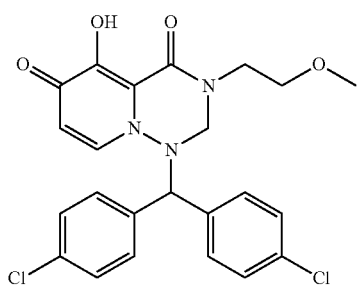

117

$^1$H-NMR (CDCl$_3$) δ: 3.19-3.28 (1H, m), 3.22 (3H, s), 3.46-3.50 (2H, m), 3.85 (1H, ddd, J=3 Hz, 4.2 Hz, 14.4 Hz), 4.47 (1H, d, J=13.2 Hz), 5.01 (1H, d, J=13.2 Hz), 5.28 (1H, s), 5.78 (1H, d, J=7.8 Hz), 6.73 (1H, d, J-=7.8 Hz), 7.04 (2H, d, J=8.4 Hz), 7.19 (2H, d, 8.4 Hz), 7.36-7.50 (4H, m).

REFERENCE EXAMPLE 118

[Chemical formula 169]

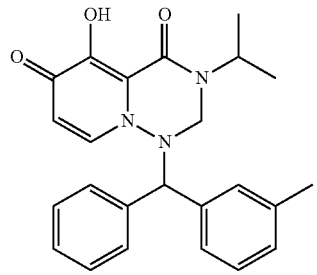

118

$^1$H-NMR (CDCl$_3$) δ: 0.914-0.957 (3H, m), 1.08-1.14 (3H, m), 2.20 (1.4H, s). 2.39 (1.6H, s), 4.56 (0.48H, d, J=4.5 Hz), 4.60 (0.52H, d, J=4.2 Hz), 4.77-4.89 (2H, m), 5.16 (1H, s), 5.66-5.70 (1H, m), 6.65-6.69 (1H, m), 6.85-6.91 (1H, m), 6.98-7.10 (2H, m), 7.14-7.19 (2H, m), 7.30-7.39 (2H, m), 7.44 (1H, t, J=6.9 Hz), 7.51 (1H, d, J=6.9 Hz).

REFERENCE EXAMPLE 119

[Chemical formula 170]

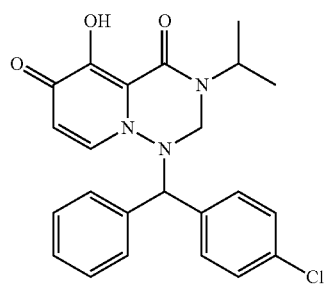

119

$^1$H-NMR (CDCl$_3$) δ: 0.893-0.982 (3H, m), 1.08-1.14 (3H, m), 4.49-4.60 (1H, m), 4.78-4.90 (2H, m), 5.20 (1H, s), 5.65 (0.57H, J=7.5 Hz), 5.76 (0.43H, d, J=7.8 Hz), 6.64-6.70 (1H, m), 7.03 (2H, d, J=8.1 Hz), 7.10-7.20 (3H, m), 7.28-7.51 (4H, m).

REFERENCE EXAMPLE 120

[Chemical formula 171]

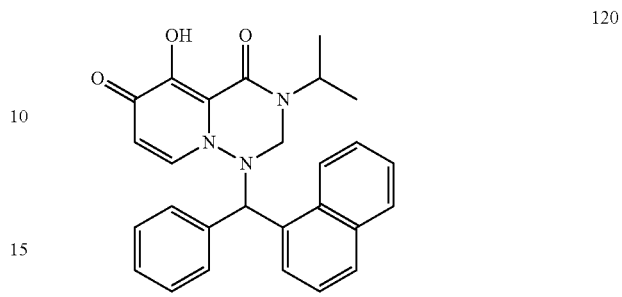

120

$^1$H-NMR (CDCl$_3$) δ: 0.526 (3H, d, J=6.9 Hz), 1.01 (3H, d, J=6.6 Hz), 4.69 (1H, d, J=13.8 Hz), 4.75-4.83 (1H, m), 4.86 (1H, d, J=13.8 Hz), 5.69 (1H, d, J=7.8 Hz), 6.03 (1H, s), 6.70 (1H, d, J=7.8 Hz), 7.16 (5H, s), 7.40-7.48 (2H, m), 7.67 (1H, t, J=7.8 Hz), 7.81-7.91 (3H, m), 8.16 (1H, d, J=7.2 Hz).

REFERENCE EXAMPLE 121

[Chemical formula 172]


121

$^1$H-NMR (CDCl$_3$) δ: 0.947 (3H, d, J=6.9 Hz), 1.09 (3H, d, J=7.2 Hz), 2.22 (3H, s), 2.37 (3H, s), 4.58 (1H, d, J=12.9 Ha), 4.76 (1H, d, J=12.9 Hz), 4.78-4.88 (1H, m), 5.13 (1H, s), 5.72 (1H, d, J=7.8 Hz), 6.67 (1H, d, J=7.8 Hz), 6.72 (1H, s), 6.90-6.98 (4H, m), 7.22 (2H, d, J=7.8 Hz), 7.38 (2H, d, J=7.8 Hz).

REFERENCE EXAMPLE 122

[Chemical formula 173]

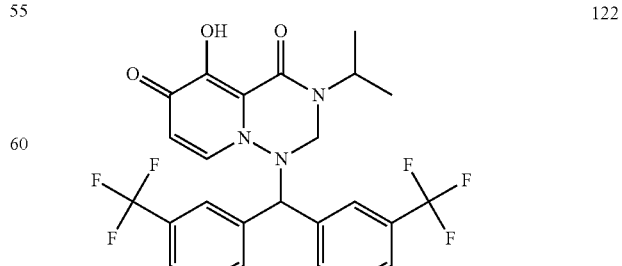

122

¹H-NMR (CDCl₃) δ: 0.932 (3H, d, J=6.6 Hz), 1.12 (3H, d, J=6.9 Hz), 4.44 (1H, d, J=13.2 Hz), 4.86 (1H, d, J=13.2 Hz), 4.87-4.93 (1H, m), 5.38 (1H, s), 5.67 (1H, d, J=7.8 Hz), 6.67 (1H, d, J=7.8 Hz), 7.21-7.24 (1H, m), 7.32-7.40 (2H, m), 7.52 (1H, d, J=7.5 Hz), 7.60-7.72 (2H, m), 7.77-7.79 (2H, m).

REFERENCE EXAMPLE 123

[Chemical formula 174]

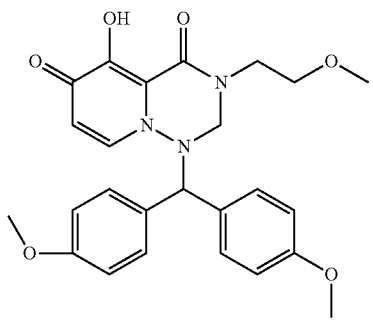

123

¹H-NMR (CDCl₃) δ: 3.08-3.17 (1H, m), 3.23 (3H, s), 3.40-3.54 (2H, m), 3.71 (3H, s), 3.82 (3H, s), 3.95 (1H, ddd, J=3.3 Hz, 3.9 Hz, 14.4 Hz), 4.48 (1H, d, J=13.5 Hz), 4.96 (1H, d, J=13.5 Hz), 5.16 (1H, s), 5.76 (1H, d, J=7.5 Hz), 6.70 (2H, d, J=9.0 Hz), 6.73 (1H, d, J=7.5 Hz), 6.94 (2H, d, J=8.7 Hz), 7.03 (2H, d, J=8.7 Hz), 7.42 (2H, d, J=8.7 Hz).

REFERENCE EXAMPLE 124

[Chemical formula 175]

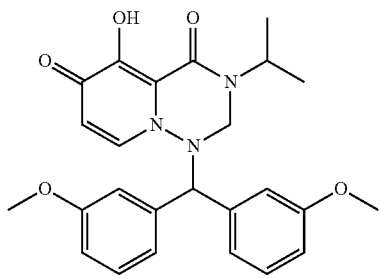

124

¹H-NMR (CDCl₃) δ: 0.966 (3H, d, J=6.9 Hz), 1.10 (3H, d, J=6.9 Hz), 3.67 (3H, s), 3.83 (3H, s), 4.60 (1H, d, J=12.9 Hz), 4.78 (1H, d, J=12.9 Hz), 4.80-4.90 (1H, m), 5.13 (1H, m), 5.23 (1H, d, J=7.8 Hz), 6.66 (2H, d, J=7.2 Hz), 6.72-6.87 (2H, m), 6.87-6.90 (1H, m), 7.06-7.11 (3H, m), 7.34 (1H, t, J=8.1 Hz).

REFERENCE EXAMPLE 125

[Chemical formula 176]

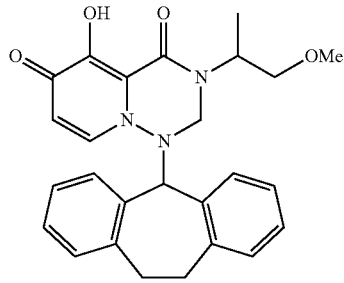

125

¹H-NMR (DMSO-d₆) δ: 1.05 (2H, d, J=7.0 Hz), 1.15 (1H, d, J=7.5 Hz), 2.73-3.63 (8H, m), 4.20-4.93 (4H, m), 5.25 (0.4H, s), 5.30 (0.6H, s), 5.46 (1H, d, J=7.8 Hz), 6.68-7.46 (11H, m).
MS: m/z=446 [M+H]⁺.

REFERENCE EXAMPLE 126

[Chemical formula 177]

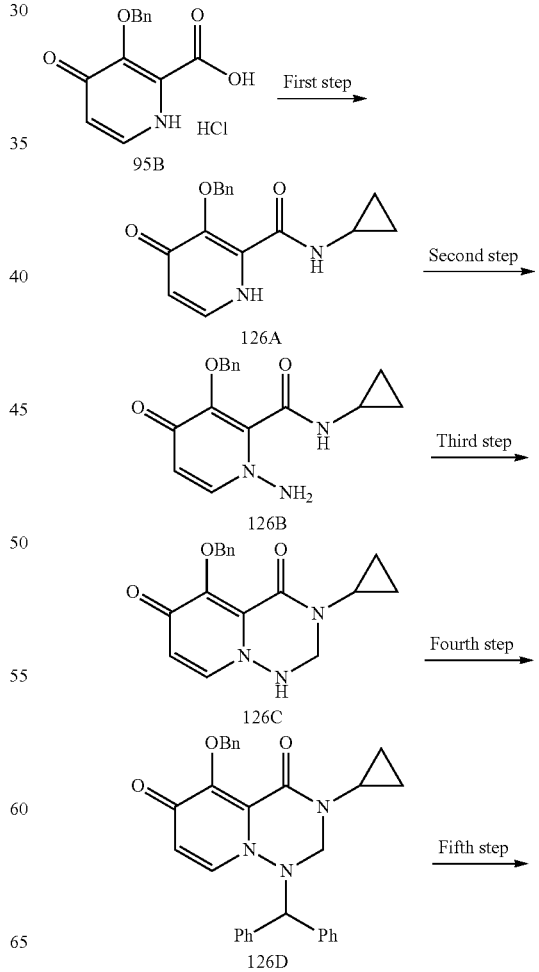

-continued

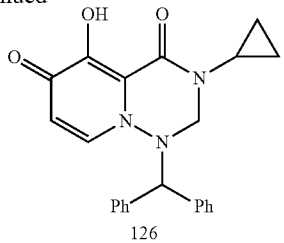

126

First Step

Compound 95B (1.00 g, 3.55 mmol) and cyclopropanamine (0.492 ml, 7.10 mmol) were added to pyridine (20 ml), 1-hydroxybenzotriazole (544 mg, 3.55 mmol) and 1-(3-dimethylaminopropyl)-3-ethylcarbodiimide hydrochloride (1.36 g, 7.10 mmol) were sequentially added, and the mixture was stirred at room temperature for 18 hours. After the solvent was distilled off under reduced pressure, the resulting crude product was purified by silica gel column chromatography (chloroform-methanol, 95:5, v/v) and, subsequently, amino column chromatography (chloroform-methanol, 99:1, v/v) to obtain 1.19 g of compound 126A as a colorless solid.

$^1$H-NMR (CDCl$_3$) δ: 0.22 (1H, m), 0.70 (2H, m), 2.76-2.83 (1H, m), 5.50 (2H, s), 6.59 (1H, dd, J=7.0, 1.9 Hz), 7.44 (5H, d, J=0.7 Hz), 7.53 (1H, dd, J=6.9, 6.2 Hz), 8.30 (1H, brs), 9.71 (1H, brs).

Second Step

Compound 126A (1.19 g, 4.19 mmol) was dissolved in DMF (15 ml), potassium carbonate (2.90 g, 20.1 mmol) was added, and the mixture was stirred at room temperature for 30 minutes. O-(2,4-dinitrophenyl)hydroxylamine (1.67 g, 8.38 mmol) was added, and the mixture was stirred at room temperature for 18 hours. To the reaction solution was added chloroform, the precipitated yellow precipitate was removed by filtration, and the filtrate was concentrated under reduced pressure. The resulting crude product was purified by amino column chromatography (chloroform-methanol, 97:3→95:5, v/v) to obtain 851 mg of compound 126B as a yellow solid.

$^1$H-NMR (CDCl$_3$) δ: 0.41-0.46 (2H, m), 0.76 (2H, m), 2.73-2.81 (1H, m), 5.19 (2H, s), 5.61 (2H, s), 6.26 (1H, d, J=7.2 Hz), 7.38 (5H, s), 7.44 (1H, d, J=7.8 Hz), 7.70 (1H, s).

Third Step

Compound 126B (847 mg, 2.83 mmol) and paraformaldehyde (255 mg, 8.49 mmol) were added to ethanol (12 ml), and the mixture was stirred at 140° C. for 30 minutes under microwave irradiation. The reaction solution was concentrated under reduced pressure, the resulting crude product was purified by silica gel column chromatography (chloroform-methanol, 97:3→95:5→90:10, v/v) and, subsequently, amino column chromatography (chloroform-methanol, 97:3, v/v), methylene chloride-ethyl ether were added, and the precipitated solid was filtered to obtain 665 mg of compound 126C as a colorless solid.

$^1$H-NMR (CDCl$_3$) δ: 0.61-0.66 (2H, m), 0.87 (2H, m), 2.68-2.76 (1H, m), 4.32 (2H, d, J=7.9 Hz), 5.28 (2H, s), 6.33 (1H, d, J=7.7 Hz), 6.45 (1H, t, J=7.7 Hz), 7.33 (3H, m), 7.38 (1H, d, J=7.7 Hz), 7.52 (2H, m).

Fourth Step

Compound 126C (100 mg, 0.321 mmol) was dissolved in DMF (0.5 ml), cesium carbonate (314 mg, 0.964 mmol) and (bromomethylene)dibenzene (119 mg, 0.482 mmol) were added at 0° C., and the mixture was stirred at room temperature for 2 hours. The reaction solution was poured into water, the mixture was extracted with ethyl acetate, and the organic layer was washed with water, and dried with sodium sulfate. The solvent was distilled off under reduced pressure, and the resulting crude product was purified by silica gel column chromatography (chloroform-methanol, 97:3→95:5, v/v) to obtain 124 mg of compound 126D as a colorless gummy substance.

$^1$H-NMR (CDCl$_3$) δ: 0.37-0.47 (2H, m), 0.74 (2H, m), 2.63-2.68 (1H, m), 4.35 (1H, d, J=13.4 Hz), 4.65 (1H, d, J=13.4 Hz), 5.07 (1H, s), 5.40 (1H, d, J=10.7 Hz), 5.47 (1H, d, J=10.5 Hz), 5.79 (1H, d, J=7.6 Hz), 6.67 (1H, d, J=7.8 Hz), 7.04-7.62 (15H, m).

Fifth Step

To compound 126D obtained in the fourth step was added trifluoroacetic acid (2 ml), and the mixture was stirred at room temperature for 1.5 hours. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 52 mg of compound 126 as a colorless solid.

$^1$H-NMR (DMSO-d$_6$) δ: −0.19−−0.06 (1H, m), 0.44-0.54 (1H, m), 0.82 (2H, m), 2.62-2.69 (1H, m), 4.21 (1H, d, J=13.3 Hz), 5.11 (1H, d, J=13.1 Hz), 5.32 (1H, s), 5.47 (1H, t, J=11.1 Hz), 7.13 (1H, d, J=7.6 Hz), 7.23 (3H, m), 7.28-7.47 (8H, m), 7.69 (2H, t, J=8.5 Hz).

MS: m/z=388 [M+H]$^+$.

REFERENCE EXAMPLE 127

[Chemical formula 178]

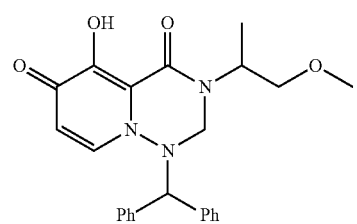

127

According to Reference example 126, compound 127 was synthesized by the same procedure.

$^1$H-NMR (DMSO-d$_6$) δ: 0.86 (1.5H, d, J=7.0 Hz), 1.04 (1.5H, d, J=7.2 Hz), 3.08 (1.5H, s), 3.16 (1.5H, s), 4.52-5.05 (3H, m), 5.48 (2H, m), 7.31-7.47 (9H, m), 7.66 (2H, t, J=8.4 Hz).

MS: m/z=420 [M+H]$^+$.

REFERENCE EXAMPLE 128

[Chemical formula 179]

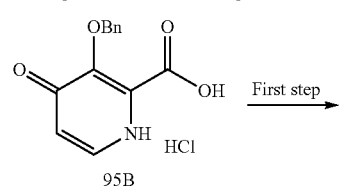

95B

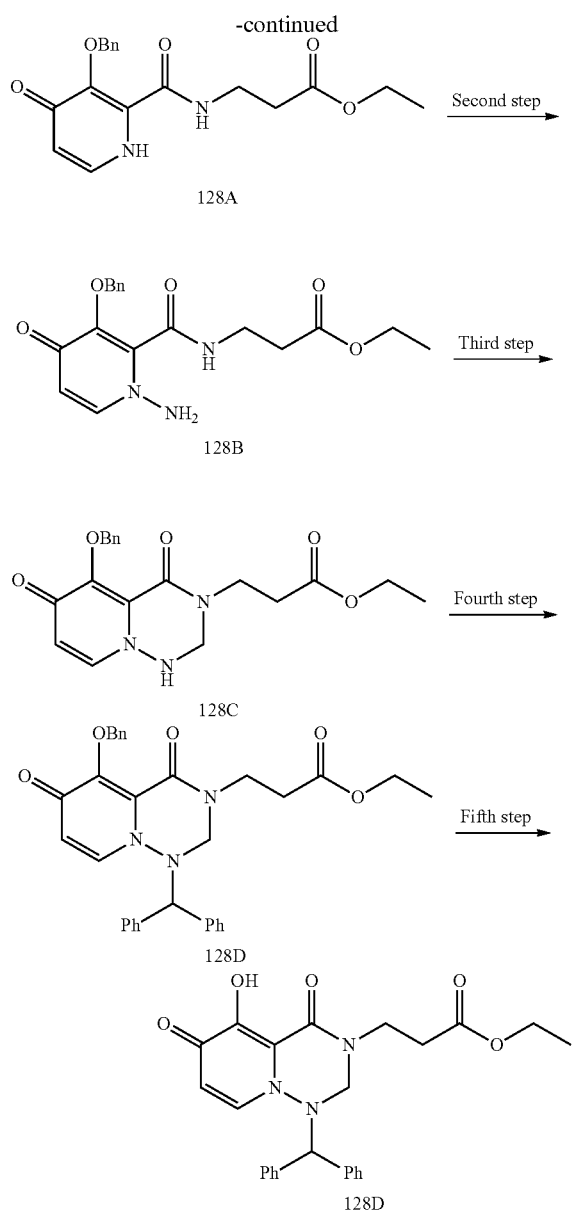

128A

128B

128C

128D

128D

First Step

Compound 95B (2.40 g, 8.52 mmol) and ethyl 3-aminopropanoate hydrochloride (2.62 g, 17.0 mmol) were added to pyridine (30 ml), 1-hydroxybenzotriazole (1.31 g, 8.52 mmol) and 1-(3-dimethylaminopropyl)-3-ethylcarbodiimide hydrochloride (3.27 g, 17.0 mmol) were sequentially added, and the mixture was stirred at room temperature for 2 hours. The solvent was distilled off under reduced pressure, and the resulting crude product was purified by amino column chromatography (chloroform-methanol, 95:5, v/v) to obtain 1.90 g of compound 128A as a colorless solid.

$^1$H-NMR (CDCl$_3$) δ: 1.29 (3H, t, J=7.1 Hz), 2.48 (2H, t, J=6.4 Hz), 3.58 (2H, q, J=6.3 Hz), 4.17 (2H, q, J=7.1 Hz), 5.59 (2H, s), 6.57 (1H, dd, J=7.1, 1.6 Hz), 7.37-7.52 (6H, m), 8.73 (1H, brs), 9.72 (1H, brs).

Second Step

Compound 128A (2.58 g, 7.49 mmol) was dissolved in DMF (30 ml), potassium carbonate (5.18 g, 37.5 mmol) was added, and the mixture was stirred at room temperature for 30 minutes. O-(2,4-dinitrophenyl)hydroxylamine (2.98 g, 15.0 mmol) was added, and the mixture was stirred at room temperature for 20 hours. To the reaction solution was added chloroform, the precipitated yellow precipitate was removed by filtration, and the filtrate was concentrated under reduced pressure. The resulting crude product was purified by amino column chromatography (chloroform-methanol, 97:3→95:5, v/v) and, subsequently, silica gel column chromatography (chloroform-methanol, 95:5→92:8, v/v) to obtain 1.67 g of compound 128B as a yellow solid.

$^1$H-NMR (CDCl$_3$) δ: 1.26 (3H, t, J=7.2 Hz), 2.42 (2H, t, J=6.6 Hz), 3.43 (2H, q, J=6.4 Hz), 4.12 (2H, q, J=7.1 Hz), 5.13 (2H, s), 5.53 (2H, s), 6.21 (1H, d, J=7.6 Hz), 7.33 (5H, s), 7.39 (1H, d, J=7.6 Hz), 7.85 (1H, t, J=5.6 Hz).

Third Step

Compound 128B (1.66 g, 4.62 mmol) and paraformaldehyde (416 mg, 13.9 mmol) were added to ethanol (20 ml), and the mixture was stirred at 140° C. for 30 minutes under microwave irradiation. The reaction solution was concentrated under reduced pressure, the resulting crude product was purified by amino column chromatography (chloroform-methanol, 99:1→95:5, v/v) to obtain 1.57 g of compound 128C as a colorless solid.

$^1$H-NMR (CDCl$_3$) δ: 1.27 (3H, t, J=7.2 Hz), 2.70 (2H, t, J=5.7 Hz), 3.57 (2H, t, J=5.8 Hz), 4.13 (2H, q, J=7.1 Hz), 4.50 (2H, d, J=7.9 Hz), 5.27 (2H, s), 5.87 (1H, t, J=7.8 Hz), 6.32 (1H, d, J=7.6 Hz), 7.31 (4H, m), 7.54 (2H, m).

Fourth Step

Compound 128C (1.00 g, 2.69 mmol) was dissolved in DMF (10 ml), cesium carbonate (2.63 g, 8.08 mmol) and (bromomethylene)dibenzene (998 mg, 4.04 mmol) were added at 0° C., and the mixture was stirred at room temperature for 18 hours. The reaction solution was poured into water, the mixture was extracted with ethyl acetate, and the organic layer was washed with water, and dried with sodium sulfate. The solvent was distilled off under reduced pressure, and the resulting crude product was purified by silica gel column chromatography (chloroform/methanol, 98:2, v/v) to obtain 500 mg of compound 128D as a colorless gummy substance.

$^1$H-NMR (CDCl$_3$) δ: 1.25 (3H, t, J=7.3 Hz), 2.46 (1H, m), 2.70-2.80 (1H, m), 2.87-2.96 (1H, m), 4.11 (2H, q, J=7.3 Hz), 4.12 (1H, m), 4.48 (1H, d, J=13.7 Hz), 4.85 (1H, d, J=13.7 Hz), 5.10 (1H, s), 5.47 (2H, s), 5.83 (1H, d, J=8.0 Hz), 6.73 (1H, d, J=8.0 Hz), 7.37 (15H, m).

Fifth Step

To compound 128D (40 mg, 0.074 mmol) was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 20 mg of compound 128 as a colorless solid.

$^1$H-NMR (DMSO-d$_6$) δ: 1.16 (3H, t, J=7.1 Hz), 2.45-2.58 (3H, m), 3.70 (1H, m), 4.02 (2H, q, J=7.1 Hz), 4.39 (1H, d, J=13.4 Hz), 5.09 (1H, d, J=13.3 Hz), 5.48 (1H, d, J=3.2 Hz), 5.51 (1H, s), 7.19-7.38 (7H, m), 7.45 (2H, t, J=7.3 Hz), 7.69 (2H, d, J=7.2 Hz).

MS: m/z=448 [M+H]$^+$.

REFERENCE EXAMPLE 129

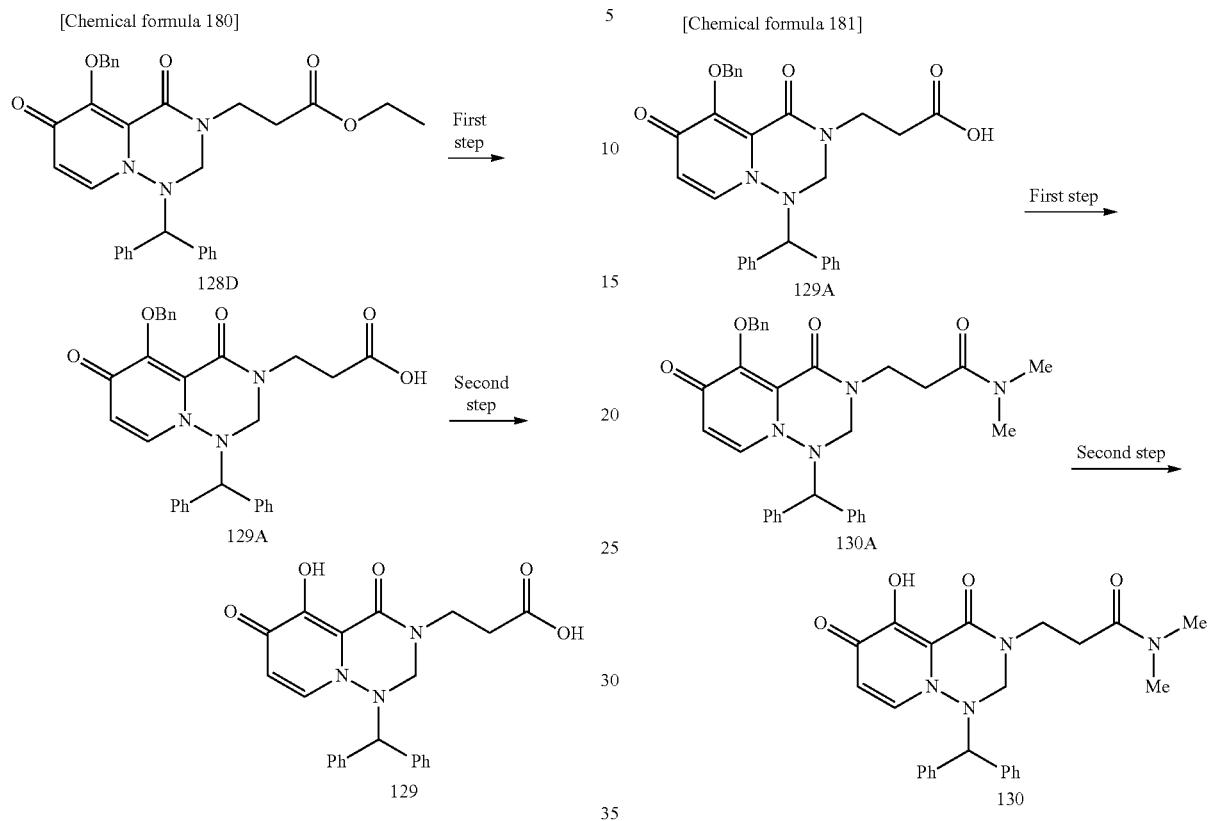

First Step

Compound 128D (426 mg, 0.792 mmol) was dissolved in ethanol (3 ml) and THF (3 ml), a 2N aqueous sodium hydroxide solution (1.19 ml, 2.38 mmol) was added, and the mixture was stirred at room temperature for 1.5 hours. To the reaction solution was added 2N hydrochloric acid, and the mixture was extracted with chloroform, and dried with sodium sulfate. To the resulting crude product were added methylene chloride-ethyl ether, and the precipitated solid was filtered to obtain 359 mg of compound 129A as a colorless solid.

Second Step

To compound 129A (40 mg, 0.079 mmol) was added trifluoroacetic acid (1 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-methanol-ethyl ether were added, and the precipitated solid was filtered to obtain 25 mg of compound 129 as a colorless solid.

$^1$H-NMR (DMSO-d$_6$) δ: 2.31-2.41 (1H, m), 2.57 (1H, m), 3.63-3.72 (1H, m), 4.37 (1H, d, J=13.3 Hz), 5.09 (1H, d, J=13.3 Hz), 5.47 (1H, s), 5.50 (1H, d, J=7.8 Hz), 7.28 (7H, m), 7.44 (2H, t, J=7.5 Hz), 7.69 (2H, d, J=7.2 Hz), 12.40 (1H, brs).

MS: m/z=420 [M+H]$^+$.

REFERENCE EXAMPLE 130

First Step

Compound 129A (50 mg, 0.098 mmol) was added to DMF (1 ml), 1-hydroxybenzotriazole (14 mg, 0.098 mmol), dimethylamine hydrochloride (24 mg, 0.29 mmol), triethylamine (0.048 ml, 0.34 mmol), and 1-(3-dimethylaminopropyl)-3-ethylcarbodiimide hydrochloride (28 mg, 0.15 mmol) were added, and the mixture was stirred at room temperature for 1.5 hours. The reaction solution was poured into water, and the mixture was extracted with ethyl acetate, washed with sodium bicarbonate water, and dried with sodium sulfate. The solvent was distilled off under reduced pressure to obtain compound 130A as a colorless gummy substance.

Second Step

To compound 130A obtained in the first step was added trifluoroacetic acid (1 ml), and the mixture was stirred at room temperature for 2 hours. After concentration under reduced pressure, pH was adjusted to 6 with sodium bicarbonate water and an aqueous ammonium chloride solution, and the mixture was extracted with chloroform, and dried with sodium sulfate. The solvent was distilled off under reduced pressure, chloroform-ethyl ether were added, and the precipitated solid was filtered to obtain 25 mg of compound 130 as a colorless solid.

$^1$H-NMR (DMSO-d$_6$) δ: 2.33-2.43 (1H, m), 2.66 (1H, m), 2.78 (3H, s), 2.89 (3H, s), 3.56 (2H, m), 4.45 (1H, d, J=13.6 Hz), 5.05 (1H, d, J=13.6 Hz), 5.47 (s, 1H), 5.49 (1H, d, J=7.5 Hz), 7.27 (7H, m), 7.44 (2H, t, J=7.3 Hz), 7.69 (2H, d, J=7.3 Hz).

REFERENCE EXAMPLE 131

[Chemical formula 182]

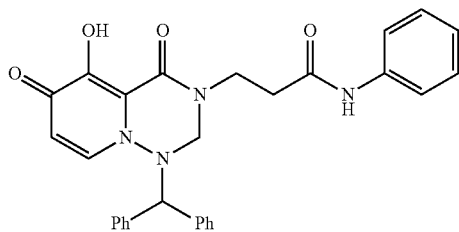

131

According to Reference example 130, compound 131 was synthesized by the same procedure.

$^1$H-NMR (DMSO-$d_6$) δ: 2.60-2.77 (3H, m), 3.94 (1H, m), 4.42 (1H, d, J=13.4 Hz), 5.15 (1H, d, J=13.4 Hz), 5.49 (1H, s), 5.55 (1H, d, J=7.2 Hz), 7.07 (1H, t, J=7.3 Hz), 7.12-7.49 (13H, m), 7.73 (2H, d, J=7.2 Hz), 10.01 (1H, s).

MS: m/z=495 [M+H]$^+$.

REFERENCE EXAMPLE 132

[Chemical formula 183]

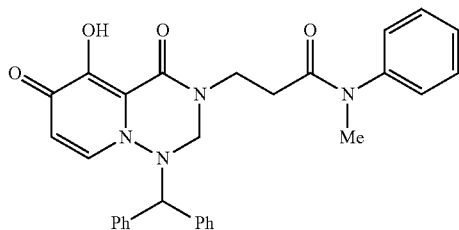

132

According to Reference example 130, compound 132 was synthesized by the same procedure.

$^1$H-NMR (DMSO-$d_6$) δ: 3.14 (3H, s), 3.65 (4H, m), 4.34 (1H, d, J=13.6 Hz), 5.06 (1H, d, J=13.6 Hz), 5.42 (1H, s), 5.53 (1H, d, J=7.5 Hz), 7.42-7.58 (16H, m).

MS: m/z=509 [M+H]$^+$.

REFERENCE EXAMPLE 133

[Chemical formula 184]

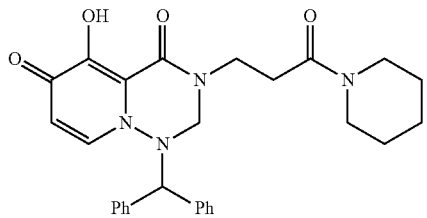

133

According to Reference example 130, compound 133 was synthesized by the same procedure.

$^1$H-NMR (DMSO-$d_6$) δ: 1.08-1.55 (8H, m), 2.33 (1H, m), 2.68 (1H, m), 4.45 (1H, d, J=13.6 Hz), 5.05 (1H, d, J=13.6 Hz), 5.50 (2H, brs), 7.46-7.68 (11H, m).

MS: m/z=487 [M+H]$^+$.

REFERENCE EXAMPLE 134

[Chemical formula 185]

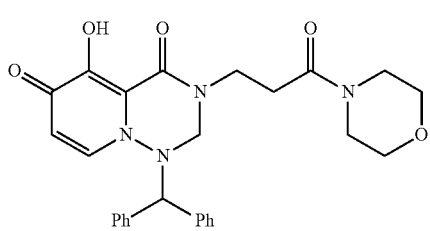

134

According to Reference example 130, compound 134 was synthesized by the same procedure.

$^1$H-NMR (DMSO-$d_6$) δ: 2.34-2.40 (1H, m), 2.61-2.77 (1H, m), 3.51-3.69 (10H, m), 4.44 (1H, d, J=13.4 Hz), 5.03-5.11 (1H, d, J=13.4 Hz), 5.51 (2H, s), 7.18-7.52 (9H, m), 7.69-7.75 (2H, m).

REFERENCE EXAMPLE 135

[Chemical formula 186]

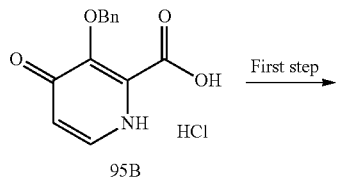

95B

First step →

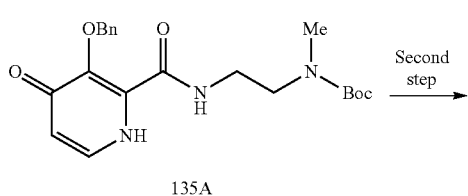

135A

Second step →

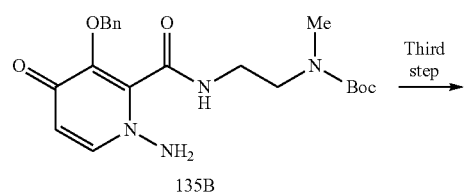

135B

Third step →

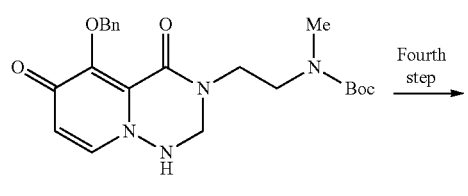

135C

Fourth step →

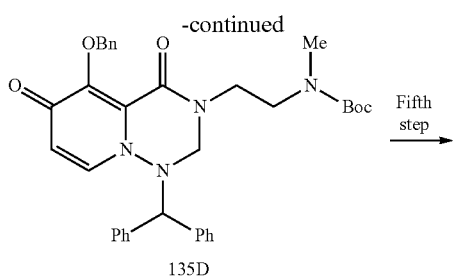

135D

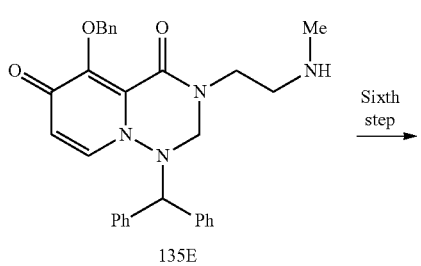

135E

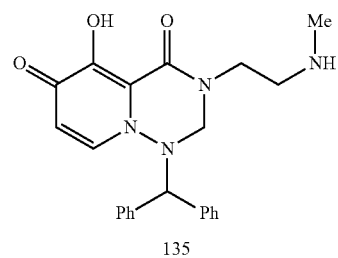

135

First Step

Compound 95B (1.50 g, 5.32 mmol) and tert-butyl 2-aminoethyl(methyl)carbamate (1.86 g, 10.7 mmol) were added to pyridine (20 ml), 1-hydroxybenzotriazole (815 mg, 5.32 mmol) and 1-(3-dimethylaminopropyl)-3-ethylcarbodiimide hydrochloride (2.04 g, 10.7 mmol) were sequentially added, and the mixture was stirred at room temperature for 2 hours. The reaction solution was poured into 1N hydrochloric acid, and the mixture was extracted with ethyl acetate, and dried with sodium sulfate. The solvent was distilled off under reduced pressure, and the resulting crude product was purified by amino column chromatography (chloroform-methanol, 95:5, v/v) and, subsequently, silica gel column chromatography (chloroform-methanol, 95:5, v/v) to obtain 1.63 g of compound 135A as a colorless gummy substance.

$^1$H-NMR (CDCl$_3$) δ: 1.44 (9H, s), 2.82 (3H, s), 3.28 (4H, m), 5.59 (2H, s), 6.57 (1H, d, J=6.0 Hz), 7.46 (6H, m), 8.46 (1H, m), 9.68 (1H, brs).

Second Step

Compound 135A (1.05 g, 2.62 mmol) was dissolved in DMF (15 ml), potassium carbonate (1.81 g, 13.1 mmol) was added, and the mixture was stirred at room temperature for 30 minutes. O-(2,4-dinitrophenyl)hydroxylamine (1.04 g, 5.23 mmol) was added, and the mixture was stirred at room temperature for 18 hours. To the reaction solution was added chloroform, the precipitated yellow precipitate was removed by filtration, and the filtrate was concentrated under reduced pressure. The resulting crude product was purified by amino column chromatography (chloroform-methanol, 97:3→95:5, v/v) to obtain 887 mg of compound 135B as a pale yellow solid.

$^1$H-NMR (CDCl$_3$) δ: 1.44 (9H, s), 2.84 (3H, s), 3.38 (4H, m), 5.33 (2H, s), 5.68 (1H, brs), 5.80 (1H, brs), 6.35 (1H, d, J=7.6 Hz), 6.74 (1H, brs), 7.39 (5H, brm), 7.52 (1H, t, J=9.5 Hz).

Third Step

Compound 135B (880 mg, 2.11 mmol) and paraformaldehyde (190 mg, 6.34 mmol) were added to ethanol (18 ml), and the mixture was stirred at 140° C. for 30 minutes under microwave irradiation. The reaction solution was concentrated under reduced pressure, and the resulting crude product was purified by silica gel column chromatography (chloroform-methanol, 97:3→95:5→90:10 v/v) and, subsequently, amino column chromatography (chloroform-methanol, 97:3, v/v) to obtain 721 mg of compound 135C as a colorless solid.

$^1$H-NMR (CDCl$_3$) δ: 1.29 (9H, s), 2.95 (3H, s), 4.38 (2H, brs), 5.33 (2H, brs), 6.36 (1H, d, J=7.6 Hz), 6.85 (1H, t, J=7.4 Hz), 7.33 (4H, m), 7.55 (2H, m).

MS: m/z=429 [M+H]$^+$.

Fourth Step

Compound 135C (720 mg, 1.68 mmol) was dissolved in DMF (3.5 ml), cesium carbonate (1.64 g, 5.04 mmol) and (bromomethylene)dibenzene (623 mg, 2.52 mmol) were added at 0° C., and the mixture was stirred at room temperature for 18 hours. The reaction solution was poured into water, the mixture was extracted with ethyl acetate, and the organic layer was washed with water, and dried with sodium sulfate. The solvent was distilled off under reduced pressure, and the resulting crude product was purified by silica gel column chromatography (chloroform-methanol, 97:3→95:5 v/v) to obtain 732 mg of compound 135D.

Fifth Step

To compound 135D (727 mg, 1.22 mmol) was added 4N HCl (ethyl acetate solution, 10 ml). After the mixture was stirred at room temperature for 1 hour, the solvent was distilled off under reduced pressure. Saturated sodium bicarbonate water was added, the mixture was extracted with chloroform, and the extract was dried with sodium sulfate. The solvent was distilled off under reduced pressure, to the resulting crude product were added methylene chloride-ethyl ether, and the precipitated solid was filtered to obtain 575 mg of compound 135E as a colorless solid.

Sixth Step

To compound 135E (50 mg, 0.10 mmol) was added trifluoroacetic acid (2 ml), and the mixture was stirred at room temperature for 1.5 hours. After concentration under reduced pressure, pH was adjusted to 6 with sodium bicarbonate water and an aqueous ammonium chloride solution, and the mixture was extracted with chloroform, and dried with sodium sulfate. After the solvent was distilled off under reduced pressure, methylene chloride-ethyl ether were added, and the precipitated solid was filtered to obtain 15 mg of compound 135 as a colorless solid.

$^1$H-NMR (DMSO-d$_6$) δ: 2.40 (3H, s), 2.80 (1H, s), 3.12 (3H, m), 3.87 (1H, m), 4.37 (1H, d, J=13.6 Hz), 5.10 (1H, d, J=13.4 Hz), 5.52 (1H, s), 5.53 (1H, d, J=5.5 Hz), 7.15-7.70 (11H, m).

MS: m/z=405 [M+H]$^+$.

REFERENCE EXAMPLE 136

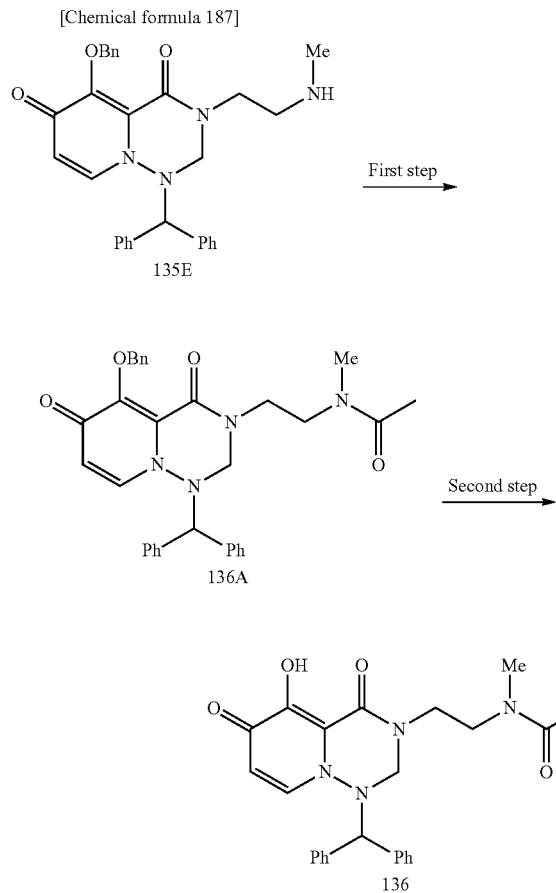

First Step

Compound 135E (50 mg, 0.10 mmol) was dissolved in methylene chloride (1 ml), triethylamine (0.042 ml, 0.30 mmol) and acetyl chloride (0.011 ml, 0.15 mmol) were added, and the mixture was stirred at room temperature for 1 hour. The solvent was distilled off under reduced pressure, and the resulting crude product was purified by silica gel column chromatography (chloroform-methanol, 97:3→95:5, v/v) and, subsequently, amino column chromatography (chloroform-methanol, 97:3, v/v) to obtain 72 mg of compound 136A as a colorless solid.

Second Step

To compound 136A obtained in the first step was added trifluoroacetic acid (2 ml), and the mixture was stirred at room temperature for 1.5 hours. After concentration under reduced pressure, pH was adjusted to 6 with sodium bicarbonate water and an aqueous ammonium chloride solution, and the mixture was extracted with chloroform, and dried with sodium sulfate. After the solvent was distilled off under reduced pressure, methylene chloride-ethyl ether were added, and the precipitated solid was filtered to obtain 23 mg of compound 136 as a colorless solid.

$^1$H-NMR (DMSO-$d_6$) δ: 1.89 (2H, s), 1.92 (1H, s), 2.73 (1H, s), 2.95 (2H, s), 3.00-3.06 (1H, m), 3.43 (2H, m), 3.80 (1H, m), 4.34 (0.7H, d, J=13.3 Hz), 4.45 (0.3H, d, J=13.1 Hz), 5.11 (1H, m), 5.49 (2H, s), 7.20-7.73 (11H, m).

REFERENCE EXAMPLE 137

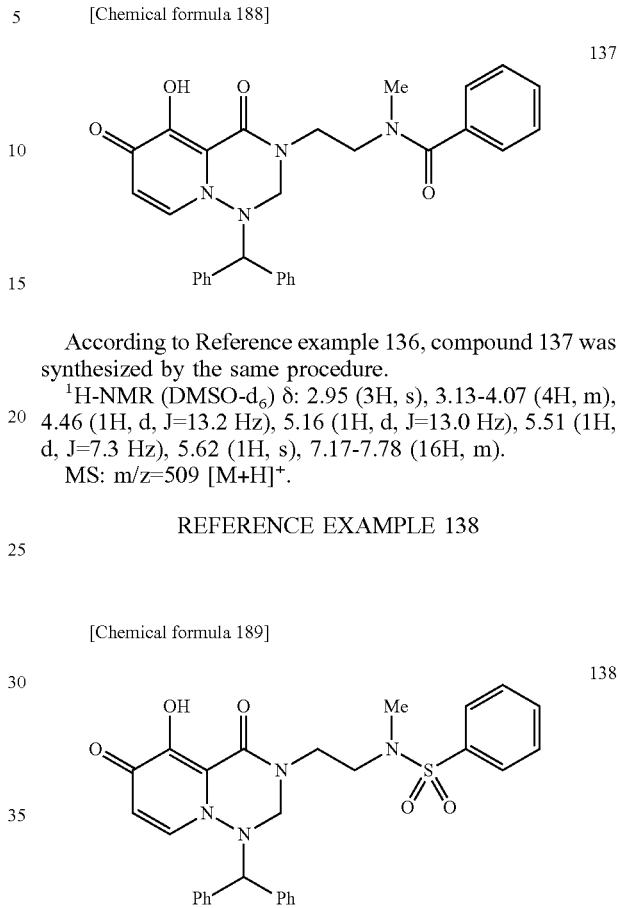

According to Reference example 136, compound 137 was synthesized by the same procedure.

$^1$H-NMR (DMSO-$d_6$) δ: 2.95 (3H, s), 3.13-4.07 (4H, m), 4.46 (1H, d, J=13.2 Hz), 5.16 (1H, d, J=13.0 Hz), 5.51 (1H, d, J=7.3 Hz), 5.62 (1H, s), 7.17-7.78 (16H, m).

MS: m/z=509 [M+H]$^+$.

REFERENCE EXAMPLE 138

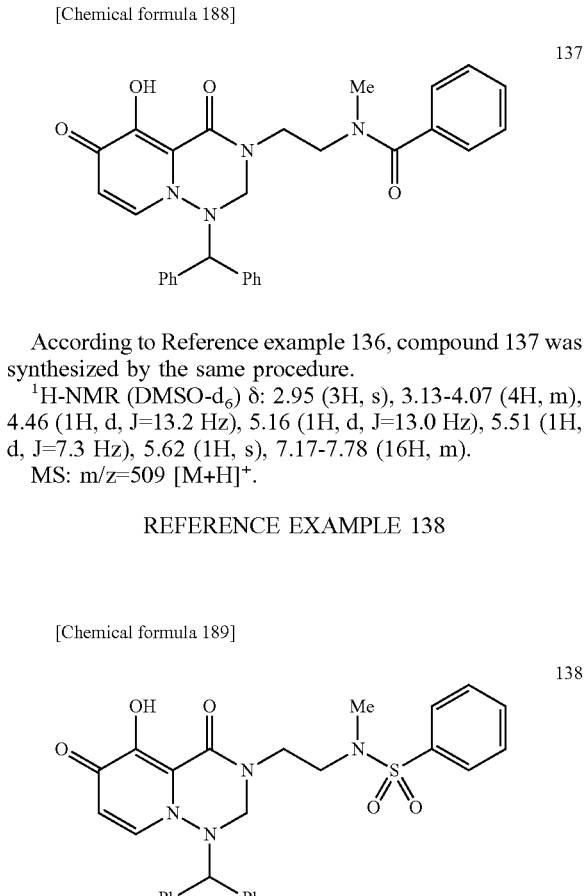

According to Reference example 136, compound 138 was synthesized by the same procedure.

$^1$H-NMR (DMSO-$d_6$) δ: 2.62 (3H, s), 3.03-3.22 (4H, m), 3.72 (2H, d, J=13.3 Hz), 4.39 (1H, d, J=13.3 Hz), 5.08 (1H, d, J=13.3 Hz), 5.53 (1H, d, J=7.8 Hz), 5.55 (1H, s), 7.19-7.79 (16H, m).

MS: m/z=545 [M+H]$^+$.

REFERENCE EXAMPLE 139

[Chemical formula 190]

According to Reference example 136, compound 139 was synthesized by the same procedure.

$^1$H-NMR (DMSO-$d_6$) δ: 2.72 (3H, s), 2.88 (3H, s), 3.12-3.24 (3H, m), 3.75-3.80 (1H, m), 4.37 (1H, d, J=13.0

Hz), 5.10 (1H, d, J=13.4 Hz), 5.51 (1H, d, J=7.6 Hz), 5.54 (1H, s), 7.19-7.46 (19H, m), 7.72 (2H, d, J=7.0 Hz).
MS: m/z=483 [M+H]⁺.

REFERENCE EXAMPLE 140

[Chemical formula 191]

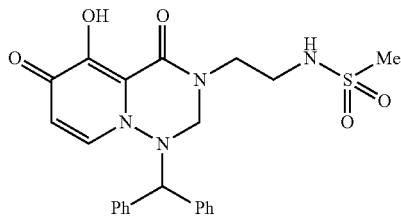

140

According to Reference example 136, compound 140 was synthesized by the same procedure.
¹H-NMR (DMSO-d₆) δ: 2.88 (3H, s), 2.98-3.12 (3H, m), 3.77 (1H, m), 4.31 (1H, d, J=13.3 Hz), 5.13 (1H, d, J=13.3 Hz), 5.51 (1H, s), 5.52 (1H, d, J=7.6 Hz), 7.13-7.46 (9H, m), 7.71 (2H, d, J=7.2 Hz).
MS: m/z=469 [M+H]⁺.

REFERENCE EXAMPLE 141

[Chemical formula 192]

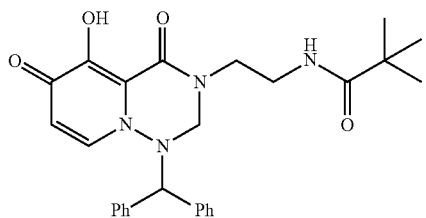

141

According to Reference example 136, compound 141 was synthesized by the same procedure.
¹H-NMR (DMSO-d₆) δ: 1.07 (9H, s), 2.84 (1H, m), 3.19 (2H, d, J=3.9 Hz), 3.96 (1H, d, m), 4.28 (1H, d, J=13.1 Hz), 5.21 (1H, d, J=13.1 Hz), 5.52 (1H, s), 5.56 (1H, t, J=4.2 Hz), 7.25-7.59 (10H, m), 7.75 (2H, d, J=7.7 Hz).
MS: m/z=475 [M+H]⁺.

REFERENCE EXAMPLE 142

[Chemical formula 193]

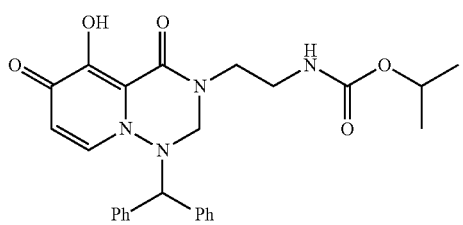

142

According to Reference example 136, compound 142 was synthesized by the same procedure.
¹H-NMR (DMSO-d₆) δ: 1.10 (6H, m), 2.98 (3H, m), 3.78 (1H, m), 4.27 (1H, d, J=13.6 Hz), 4.68 (1H, m), 5.11 (1H, d, J=12.8 Hz), 5.51 (2H, m), 7.07-7.46 (10H, m), 7.70 (2H, d, J=7.2 Hz).
MS: m/z=477 [M+H]⁺.

REFERENCE EXAMPLE 143

[Chemical formula 194]

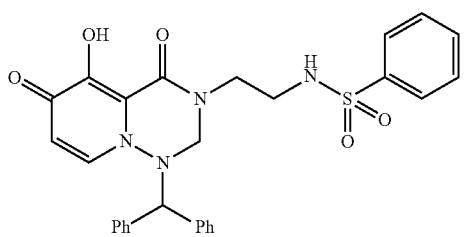

143

According to Reference example 136, compound 143 was synthesized by the same procedure.
¹H-NMR (DMSO-d₆) δ: 2.89 (3H, m), 3.62 (1H, m), 4.17 (1H, d, J=13.1 Hz), 4.99 (1H, d, J=13.1 Hz), 5.45 (1H, s), 5.51 (1H, d, J=7.8 Hz), 7.18-7.77 (17H, m).
MS: m/z=531 [M+H]⁺.

REFERENCE EXAMPLE 144

[Chemical formula 195]

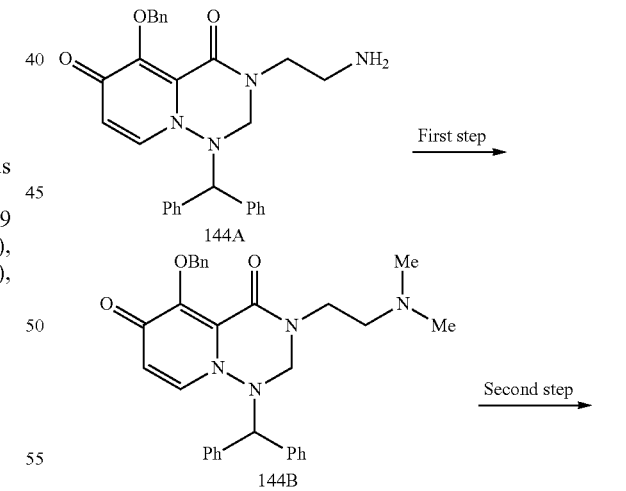

First Step

To compound 144A synthesized according to the first to fifth steps of Reference example 135 were added formic acid and formalin, and the mixture was stirred at 80° C. for 1.5 hours. The solvent was distilled off under reduced pressure, saturated sodium bicarbonate water was added, then the mixture was extracted with chloroform, and the extract was dried with sodium sulfate. The solvent was concentrated under reduced pressure, and the resulting crude product was purified by silica gel column chromatography (chloroform-methanol, 95:5→92:8, v/v) to obtain 26 mg of compound 144B.

$^1$H-NMR (CDCl$_3$) δ: 2.06 (6H, s), 2.18-2.26 (1H, m), 2.36-2.45 (1H, m), 2.89-2.98 (1H, m), 3.91 (1H, dt, J=14.1, 5.9 Hz), 4.43 (1H, d, J=13.6 Hz), 4.82 (1H, d, J=13.4 Hz), 5.20 (1H, s), 5.41 (1H, d, J=10.8 Hz), 5.46 (1H, d, J=10.7 Hz), 5.80 (1H, d, J=7.8 Hz), 6.69 (1H, d, J=7.8 Hz), 7.05-7.64 (15H, m).

Second Step

To compound 144B obtained in the first step was added trifluoroacetic acid (1 ml), and the mixture was stirred at room temperature for 1 hour. After concentration under reduced pressure, pH was adjusted to 6 with sodium bicarbonate water and an aqueous ammonium chloride solution, and the mixture was extracted with chloroform, and dried with sodium sulfate. After the solvent was distilled off under reduced pressure, methylene chloride-ethyl ether were added, and the precipitated solid was filtered to obtain 13 mg of compound 144 as a colorless solid.

$^1$H-NMR (DMSO-d$_6$) δ: 2.17 (6H, s), 2.38-2.46 (3H, m), 3.59 (1H, m), 4.41 (1H, d, J=13.1 Hz), 5.09 (1H, d, J=13.3 Hz), 5.50 (1H, d, J=6.4 Hz), 5.51 (1H, s), 7.19-7.47 (9H, m), 7.66 (2H, d, J=7.3 Hz).

MS: m/z=419 [M+H]$^+$.

REFERENCE EXAMPLE 145

[Chemical formula 196]

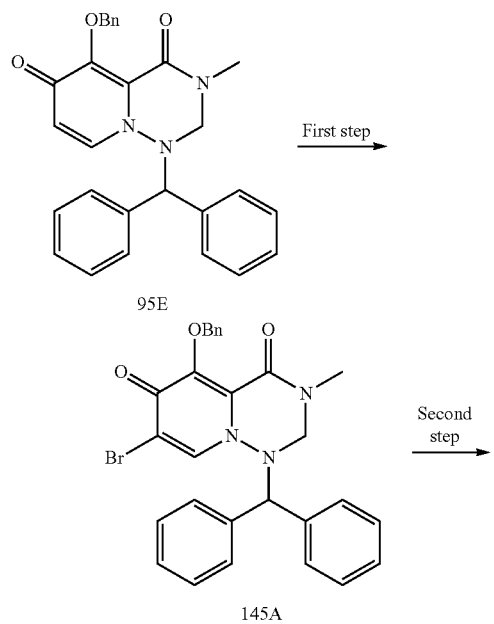

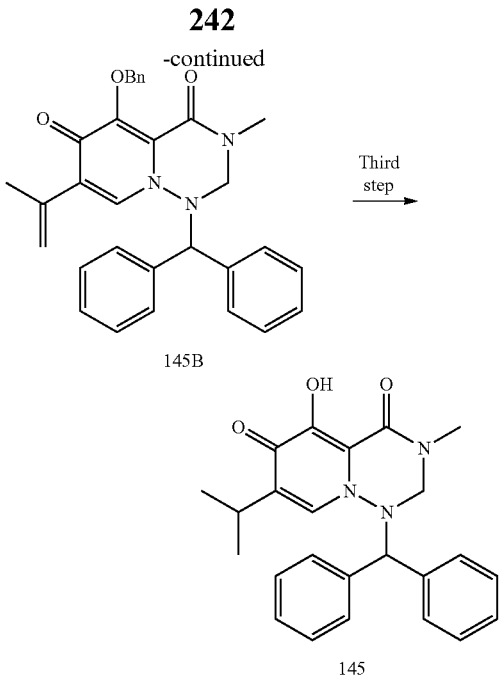

First Step

To a dichloromethane (5 ml) solution of compound 95E (300 mg, 0.664 mmol) was added NBS (130 mg, 0.731 mmol) under ice-cooling, temperature was raised to room temperature and, thereafter, the mixture was refluxed for 1 hour. After the solvent was distilled off, the resulting residue was purified by silica gel chromatography. The materials were eluted firstly with n-hexane-ethyl acetate (1:1, v/v) and, then, with ethyl acetate. Concentration of an objective fraction afforded 326.7 mg (yield 93%) of compound 145A as a solid.

$^1$H-NMR (CDCl$_3$) δ: 2.93 (3H, s), 4.27 (1H, d, J=13.5 Hz), 4.82 (1H, d, J=13.5 Hz), 5.13 (1H, s), 5.41 (2H, s), 5.41-7.12 (2H, m), 7.15 (1H, s), 7.17-7.28 (3H, m), 7.31-7.47 (6H, m), 7.52 (2H, d, J=6.6 Hz), 7.63-7.67 (2H, m).

Second Step

To a DMF (3 ml) solution of compound 145A (100 mg, 0.189 mmol) were added a solution of potassium carbonate (78.4 mg, 0.567 mmol) in water (0.5 ml), 4,4,5,5-tetramethyl-2-(prop-1-en-2-yl)-1,3,2-dioxaborolane (47.6 mg, 0.284 mmol) and tetakistriphenylphosphinepalladium (21.8 mg, 0.0189 mmol), and the mixture was heated to stir at 80° C. for 4 hours. After the reaction solution was cooled to room temperature, water was added, and the mixture was extracted with ethyl acetate three times. The extract was washed with water three times, and dried with sodium sulfate and, thereafter, the resulting oil was purified by silica gel chromatography. Elution with only ethyl acetate, and concentration of an objective fraction afforded 42.0 mg (yield 45%) of compound 145B as an oil.

$^1$H-NMR (CDCl$_3$) δ: 1.73 (3H, s), 2.92 (3H, s), 4.29 (1H, d, J=13.5 Hz), 4.83 (1H, d, J=13.5 Hz), 4.96-4.97 (1H, m), 5.15 (1H, s), 5.21-5.21 (1H, m), 5.37 (1H, d, J=10.8 Hz), 5.40 (1H, d, J=10.8 Hz), 6.82 (1H, s), 7.15-7.21 (5H, m), 7.27-7.47 (6H, m), 7.54 (2H, d, J=6.9 Hz), 7.64-7.69 (2H, m).

Third Step

To a THF (2 ml) solution of compound 145B (40 mg, 0.081 mmol) was added 10% Pd-C (8 mg), and the mixture was subjected to a catalytic reduction reaction under hydrogen stream. The catalyst was removed by filtration, and the filtrate was concentrated. The resulting residue was washed with ether to obtain 6.8 mg (yield 21%) of compound 145.

$^1$H-NMR (CDCl$_3$) δ: 0.629 (3H, d, J=6.9 Hz), 0.900 (3H, d, J=6.9 Hz), 2.87-3.00 (1H, m), 2.94 (3H, s), 4.37 (1H, d, J=13.2 Hz), 4.93 (1H, d, J=13.2 Hz), 5.21 (1H, s), 6.69 (1H, s), 7.21 (5H, s), 7.35-7.47 (3H, m), 7.57 (2H, d, J=7.5 Hz).

REFERENCE EXAMPLE 146

[Chemical formula 197]

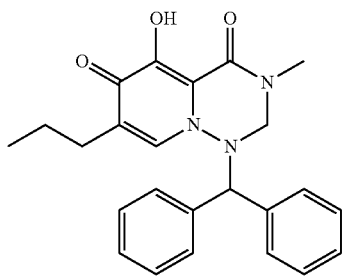

146

According to Reference example 145, compound 146 was synthesized by the same procedure.

$^1$H-NMR (CDCl$_3$) δ: 0.738 (3H, t, J=7.2 Hz), 1.05-1.18 (2H, m), 2.01-2.18 (2H, m), 2.94 (3H, s), 4.35 (1H, d, J=13.2 Hz), 4.95 (1H, d, J=13.2 Hz), 5.22 (1H, s), 6.71 (1H, s), 7.20 (5H, s), 7.35-7.47 (3H, m), 7.55 (2H, d, J=6.9 Hz).

REFERENCE EXAMPLE 147

[Chemical formula 198]

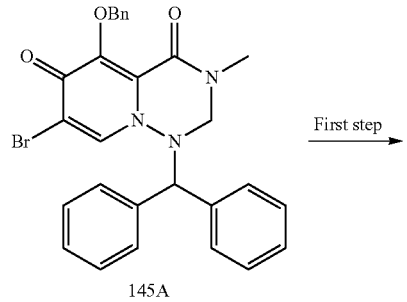

145A

First step →

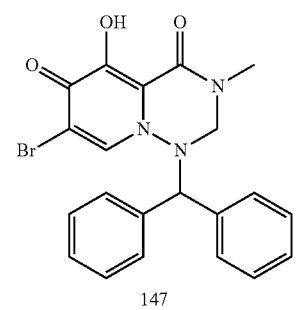

147

First Step

Compound 145A (60 mg, 0.113 mg) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 30 mg (yield 60%) of compound 147.

$^1$H-NMR (CDCl$_3$) δ: 2.97 (3H, s), 4.36 (1H, d, J=13.2 Hz), 5.01 (1H, d, J=13.2 Hz), 5.21 (1H, s), 7.14 (1H, s), 7.17-7.25 (5H, m), 7.36-7.48 (3H, m), 7.54 (2H, d, J=7.2 Hz).

REFERENCE EXAMPLE 148

[Chemical formula 199]

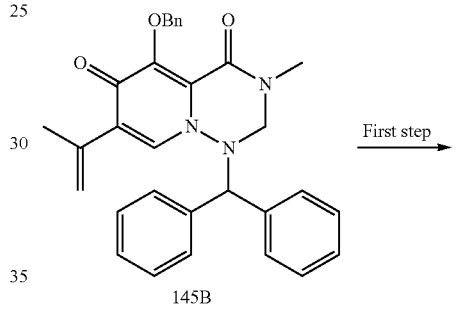

145B

First step →

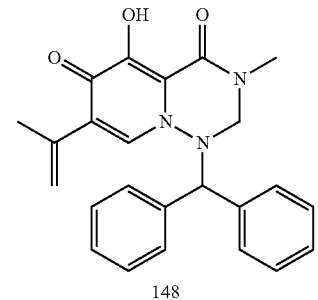

148

Compound 145B (41 mg, 0.083 mg) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 12 mg (yield 36%) of compound 148.

$^1$H-NMR (CDCl$_3$) δ: 1.70 (3H, s), 2.95 (3H, s), 4.36 (1H, d, J=12.9 Hz), 4.95 (1H, d, J=12.9 Hz), 4.96-4.98 (1H, m), 5.23 (1H, s), 5.32-5.33 (1H, m), 6.86 (1H, s), 7.21 (5H, s), 7.35-7.48 (3H, m), 7.56 (2H, d, J=7.2 Hz).

REFERENCE EXAMPLE 149

[Chemical formula 200]

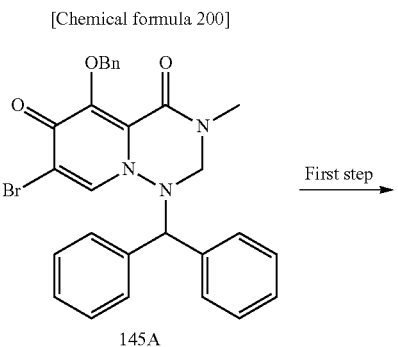

145A

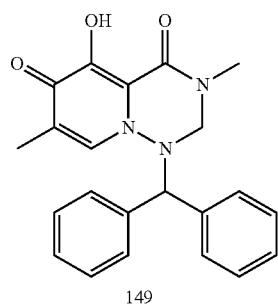

149

To a THF (2 ml) solution of compound 145A (100 mg, 0.189 mg) were added a 2N methylzinc chloride THF solution (0.377 ml, 0.754 mmol) and tetrakistriphenylphosphinepalladium (10.9 mg, 0.0945 mmol) at room temperature, and the mixture was heated to stir at 60° C. for 4 hours. After the reaction solution was cooled to room temperature, water was added, and the mixture was extracted with chloroform three times. After the extract was dried with sodium sulfate, the solvent was distilled off, and the resulting oil was purified by a MS trigger reverse layer column to obtain 9.6 mg (yield 14%) of compound 149.

$^1$H-NMR (CDCl$_3$) δ: 1.63 (3H, s), 2.95 (3H, s), 4.34 (1H, d, J=12.9 Hz), 4.68 (1H, d, J=12.9 Hz), 5.21 (1H, s), 6.70 (1H, s), 7.18 (5H, s), 7.37-7.47 (3H, m), 7.54 (2H, d, J=6.9 Hz).

REFERENCE EXAMPLE 150

[Chemical formula 201]

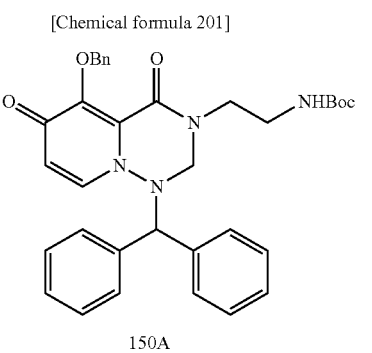

150A

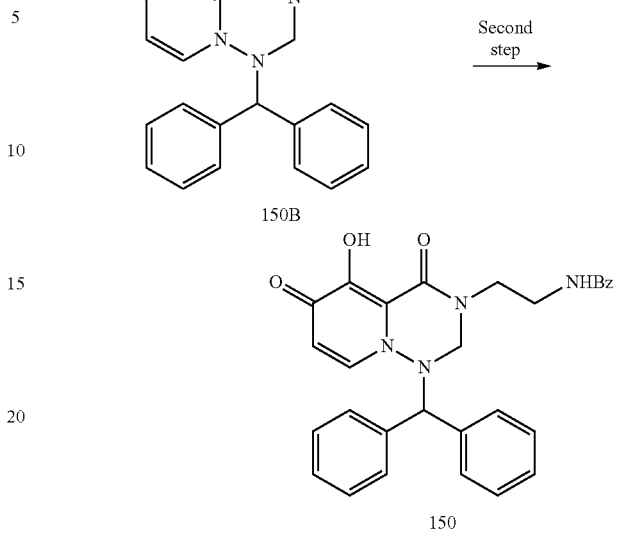

150B

150

First Step

Reference compound 150A (465 mg, 0.801 mmol) synthesized according to the first to fourth step of Reference example 135 was dissolved in a 4N hydrochloric acid dioxane solution (5 ml), and the mixture was stirred at room temperature for 2 hours. The reaction solution was neutralized with saturated sodium bicarbonate water, and was extracted with dichloromethane three times. After the extract was dried with sodium sulfate, the solvent was distilled off, and 100 mg of the resulting oil was dissolved in dichloromethane (2 ml). To the dichloromethane solution were added triethylamine (63.2 mg, 0.624 mmol) and benzoyl chloride (31.9 mg, 0.312 mmol) under ice-cooling, and the mixture was stirred at room temperature for 1 hour. To the reaction solution was added water, and the mixture was extracted with dichloromethane three times. After the extract was dried with sodium sulfate, the solvent was distilled off, and the resulting residue was washed with diethyl ether to obtain 68 mg (yield 56%) of compound 150B.

$^1$H-NMR (CDCl$_3$) δ: 3.05-3.12 (1H, m), 3.38-3.45 (1H, m), 3.64-3.70 (1H, m), 3.93-3.99 (1H, m), 4.22 (1H, d, J=13.2 Hz), 5.04 (1H, s), 5.07 (1H, d, J=13.2 Hz), 5.22 (1H, d, J=10.2 Hz), 5.31 (1H, d, J=10.2 Hz), 5.70 (1H, d, J=7.8 Hz), 6.55 (1H, d, J=7.8 Hz), 6.98 (2H, d, J=6.6 Hz), 7.08-7.19 (4H, m), 7.29-7.46 (5H, m), 7.49-7.53 (2H, m), 7.87 (2H, d, J=7.2 Hz), 8.06 (1H, brs).

Second Step

Compound 150B (30 mg, 0.051 mg) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 15 mg (yield 59%) of compound 150.

$^1$H-NMR (CDCl$_3$) δ: 2.91-2.98 (1H, m), 3.54-3.66 (1H, m), 3.76-3.84 (1H, m), 4.13-4.18 (1H, m), 4.28 (1H, d, J=12.9 Hz), 5.11 (1H, s), 5.43 (1H, d, J=12.9 Hz), 5.45 (1H, d, J=7.5 Hz), 6.68 (1H, d, J=7.5 Hz), 7.10-7.18 (4H, m), 7.35-7.47 (8H, m), 7.89 (2H, d, J=7.2 Hz), 8.41 (1H, s).

REFERENCE EXAMPLE 151

[Chemical formula 202]

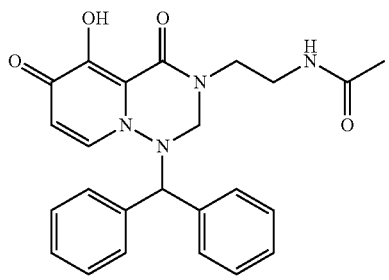

151

According to Reference example 150, compound 151 was synthesized by the same procedure.

$^1$H-NMR (CDCl$_3$) δ: 2.02 (3H, s), 2.69 (1H, brt, J=10.8 Hz), 3.40-3.49 (1H, m), 3.06-3.74 (1H, m), 4.12-4.22 (1H, m), 4.20 (1H, d, J=12.9 Hz), 5.08 (1H, s), 5.47 (1H, d, J=7.8 Hz), 5.50 (1H, d, J=12.9 Hz), 6.67 (1H, d, J=7.8 Hz), 7.12-7.21 (5H, m), 7.28-7.46 (5H, m), 8.31 (1H, brs).

REFERENCE EXAMPLE 152

[Chemical formula 203]

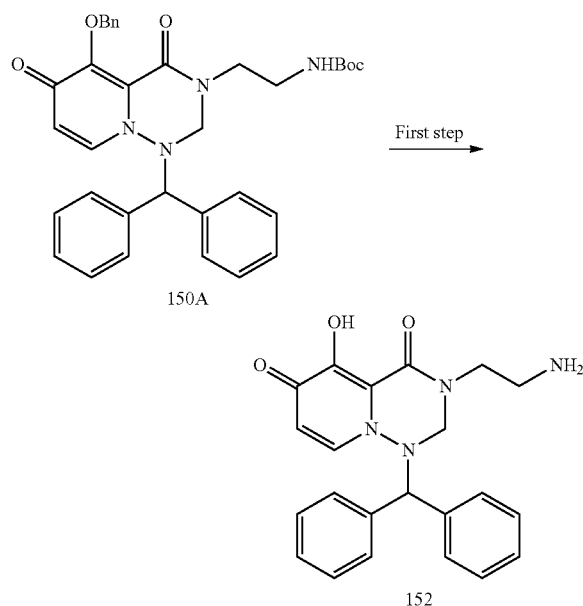

First Step

Compound 150A (50 mg, 0.801 mmol) was dissolved in a 4N hydrochloric acid dioxane solution (5 ml), and the mixture was stirred at room temperature for 2 hours. The reaction solution was neutralized with saturated sodium bicarbonate water, and was extracted with dichloromethane three times. After the extract was dried with sodium sulfate, the solvent was distilled off, and 50 mg of the resulting oil was dissolved in methanol (2 ml). To the methanol solution was added 10% Pd-C (10 mg), and the mixture was subjected to a catalytic reduction reaction under hydrogen stream. The catalyst was removed by filtration, and the filtrate was concentrated. To the resulting residue was added diisopropyl ether, and the precipitated solid was filtered to obtain 10 mg (yield 25%) of compound 152.

$^1$H-NMR (DMSO-d$_6$) δ: 2.74-2.78 (2H, m), 3.00-3.07 (1H, m), 3.78-3.85 (1H, m), 4.34 (1H, d, J=13.5 Hz), 5.13 (1H, d, J=13.5 Hz), 5.48-5.54 (1H, m), 5.10 (1H, s), 7.20-7.47 (9H, m), 7.63-7.71 (2H, m).

REFERENCE EXAMPLE 153

[Chemical formula 204]

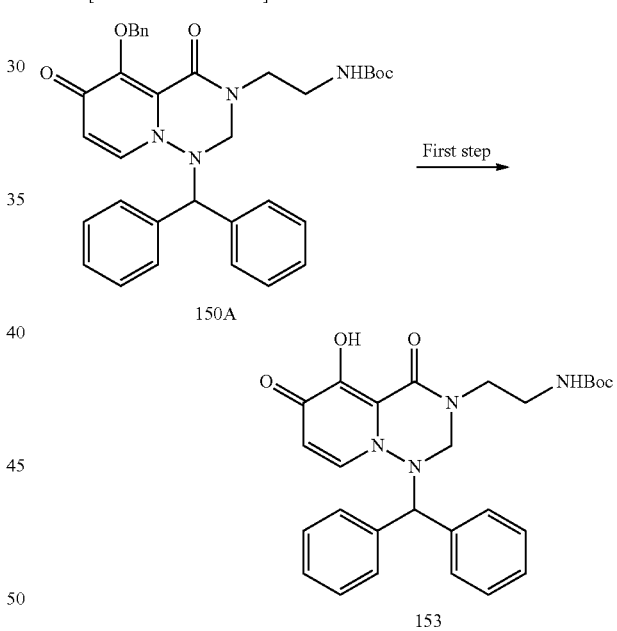

First Step

To a THF (3 ml) solution of compound 150A (30 mg, 0.052 mmol) was added 10% Pd—C (10 mg), and the mixture was subjected to a catalytic reduction reaction under hydrogen stream. The catalyst was removed by filtration, and the filtrate was concentrated. To the resulting residue was added diisopropyl ether, and the precipitated solid was filtered to obtain 20 mg (yield 79%) of compound 153.

$^1$H-NMR (CDCl$_3$) δ: 1.34 (9H, s), 2.84-2.91 (1H, m), 3.18-3.25 (2H, m), 4.03-4.11 (1H, m), 4.35 (1H, d, J-=13.2 Hz), 5.20 (1H, s), 5.24 (1H, d, J=13.2 Hz), 5.49 (1H, brs), 5.70 (1H, d, J=7.8 Hz), 6.73 (1H, d, J=7.8 Hz), 7.16-7.20 (5H, m), 7.32-7.46 (3H, m), 7.53 (2H, d, J=7.2 Hz).

REFERENCE EXAMPLE 154

[Chemical formula 205]

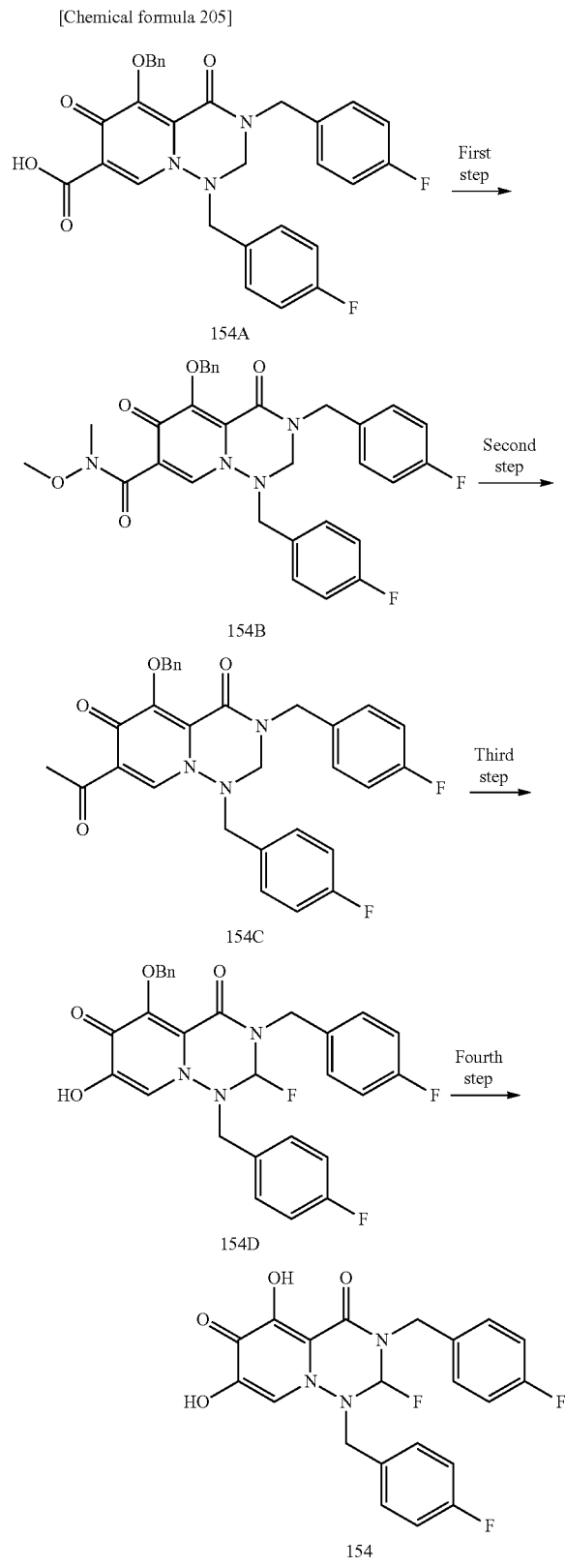

First Step

To a DMF (10 ml) solution of compound 154A (539 mg, 1.01 mmol) synthesized according to the synthesis method of Reference example 65 were added triethylamine (615.7 mg, 6.08 mmol) and ethyl chlorocarbonate (328.8 mg, 3.03 mmol) under ice-cooling, and the mixture was stirred at room temperature for 10 minutes. To the reaction solution were added O,N-dimethylhydroxylamine hydrochloride (295.0 mg, 3.03 mmol) and DMAP (12.3 mg, 0.101 mmol), the mixture was stirred at the same temperature for 2 hours, water was added, and was extracted with ethyl acetate three times. After the extract was washed with water three times, and dried with sodium sulfate, the solvent was distilled off, and the resulting oil was purified by silica gel chromatography. The materials were eluted firstly with n-hexane-ethyl acetate (7:3, v/v) and, then, with only ethyl acetate. Concentration of an objective fraction afforded 445.4 mg (yield 76%) of compound 154B as an oil.

$^1$H-NMR (DMSO-d$_6$) δ: 3.09 (3H, s), 3.52 (3H, s), 3.94 (2H, s), 4.40 (1H, brs), 4.64 (2H, s), 4.96 (1H, brs), 5.15 (2H, s), 7.06-7.15 (4H, m), 7.21 (2H, t, J=8.7 Hz), 7.28-7.38 (3H, m), 7.43 (2H, dd, J=5.7 Hz, 8.4 Hz), 7.52-7.54 (2H, m), 7.66 (1H, s).

Second Step

A THF (5 ml) solution of compound 154B (250 mg, 0.435 mmol) was cooled to −78° C., a methylmagnesium bromide 0.97M THF solution (0.673 ml, 0.653 mmol) was added, and temperature was raised to −20° C. over 2 hours. To the reaction solution was added 1N hydrochloric acid, and the mixture was extracted with ethyl acetate three times. After the extract was dried with sodium sulfate, the solvent was distilled off, and the resulting oil was purified by silica gel chromatography. The materials were eluted firstly with only chloroform and, then, with chloroform-methanol (7:3, v/v). Concentration of an objective fraction afforded 117.0 mg (yield 51%) of compound 154C as an oil.

$^1$H-NMR (CDCl$_3$) δ: 2.68 (3H, s), 3.80 (2H, brs), 4.29 (2H, brs), 4.71 (2H, brs), 5.45 (2H, brs), 6.83 (2H, m), 6.92-6.98 (2H, m), 7.03-7.10 (2H, m), 7.28-7.39 (5H, m), 7.90 (1H, s).

Third Step

To a dichloromethane (2 ml) solution of compound 154C (117 mg, 0.221 mmol) was added mCPBA (52.7 mg, 0.332 mmol) under ice-cooling, and the mixture was stirred at room temperature for 2 hours. To the reaction solution was added an aqueous sodium thiosulfate solution, and the mixture was extracted with ethyl acetate three times. After the extract was washed with saturated sodium bicarbonate water two times, and dried with sodium sulfate, the solvent was distilled off, the resulting oil was dissolved in ethanol (2 ml), and the solution was refluxed for 1 hour. After the solvent was distilled off, the precipitated solid was washed with diisopropyl ether to obtain 54 mg (yield 49%) of compound 154D.

$^1$H-NMR (CDCl$_3$) δ: 3.74 (1H, brs), 3.85 (1H, brs), 4.20 (2H, brs), 4.61 (1H, brs), 4.93 (1H, brs), 5.41 (2H, brs), 6.79-6.86 (2H, m), 6.91-6.96 (2H, m), 7.02-7.09 (2H, m), 7.15-7.16 (1H, m), 7.26-7.34 (5H, m), 7.56-7.65 (2H, m).

Fourth Step

To a THF (3 ml) solution of compound 154D (54 mg, 0.107 mmol) was added 10% Pd—C (20 mg), and the mixture was subjected to a catalytic reduction reaction under hydrogen stream. The catalyst was removed by filtration, and the filtrate was concentrated. To the resulting residue was added diisopropyl ether, and the precipitated solid was filtered to obtain 21 mg (yield 47%) of compound 154.

¹H-NMR (DMSO-d₆) δ: 3.90 (2H, brs), 3.95 (2H, s), 4.66 (2H, brs), 7.07-7.12 (4H, m), 7.22 (2H, t, J=8.7 Hz), 7.29 (1H, s), 7.43-7.47 (2H, m).

REFERENCE EXAMPLE 155

[Chemical formula 206]

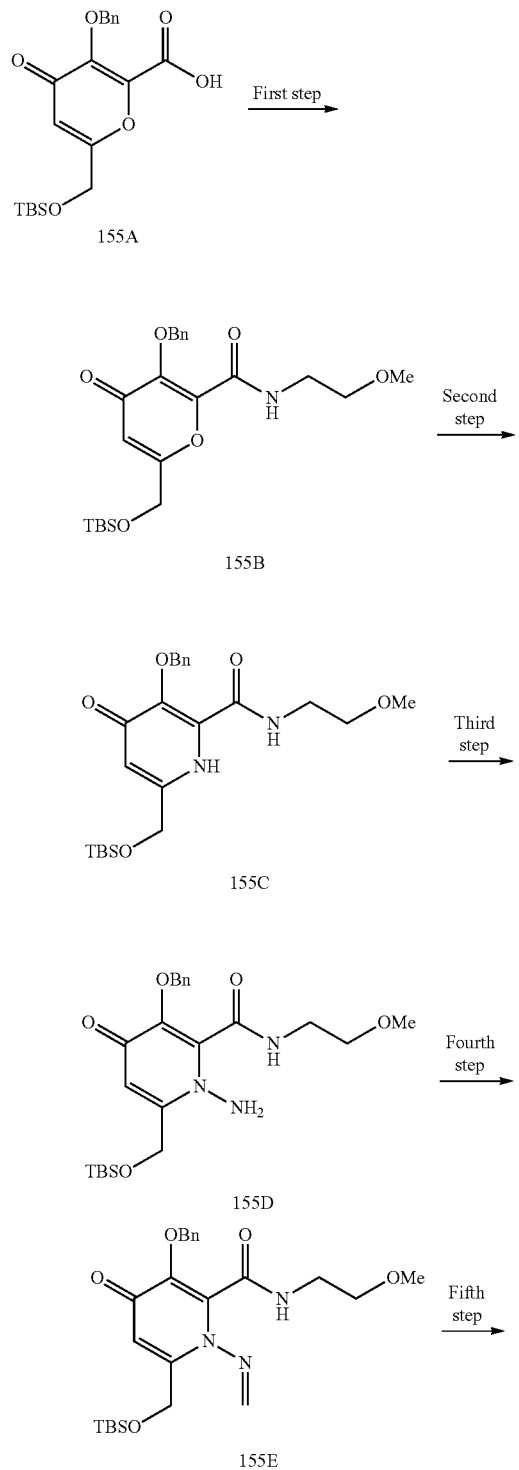

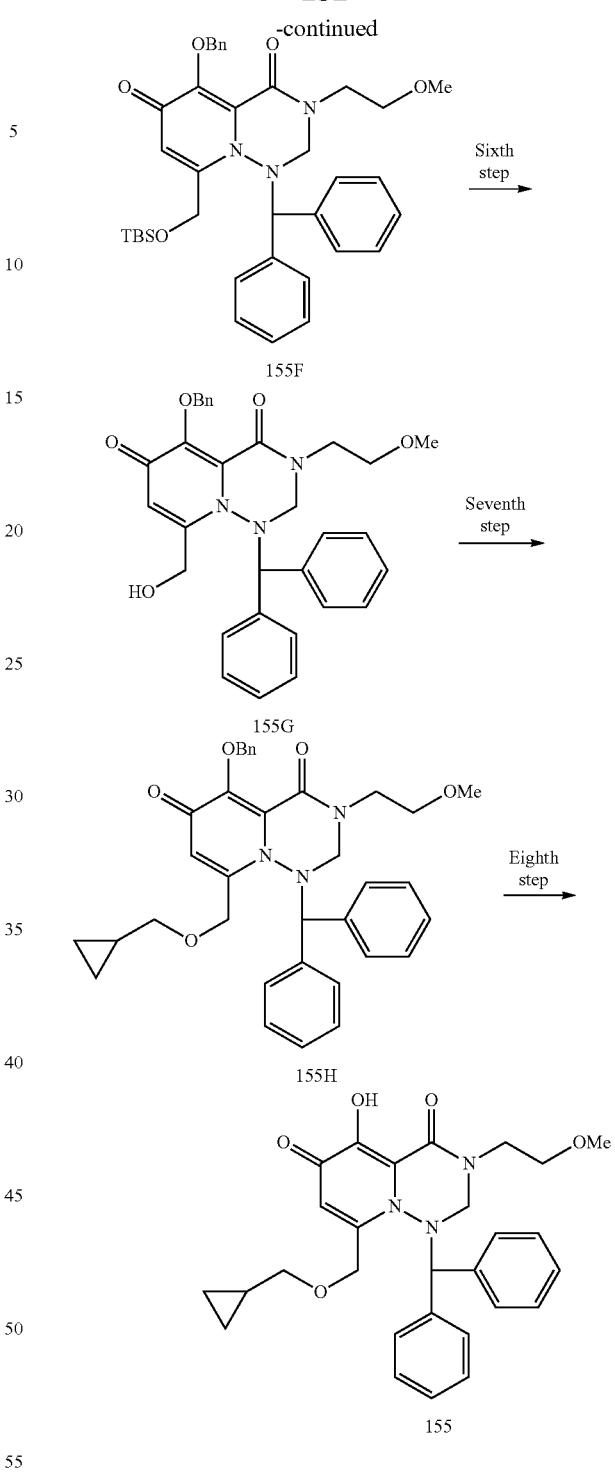

First Step

To a toluene (150 mL) solution of compound 155A (WO 2006/066414, 15.0 g, 38.4 mmol) were sequentially added N,N-diisopropylethylamine (16.1 mL, 92.0 mmol), 1-methylimidazole (3.70 mL, 46.4 mmol) and 2-methoxyethylamine (4.05 mL, 46.4 mmol) under ice-cooling and, thereafter, diphenyl chlorophosphate (9.60 mL, 46.1 mmol) was further added dropwise over 10 minutes. After the reaction solution was stirred for 20 minutes under ice-cooling, acetonitrile (50 mL) was added, and the mixture was further stirred for 2 hours. To the reaction solution was added an aqueous acetic acid solution (10%, 100 mL) under ice-cooling and, thereafter, the mixture was extracted with ethyl acetate. The extract was sequentially washed with water (100 mL), saturated sodium bicarbonate water (150 mL) and an aqueous saturated sodium chloride solution (100 mL) and, thereafter, dried with sodium sulfate. The solvent was distilled off under reduced pressure, and the resulting residue was purified by silica gel column chromatography (ethyl acetate/n-hexane=25%→50%) to obtain compound 155B (7.86 g, 46%) as a colorless oil.

$^1$H-NMR (CDCl$_3$) δ: 0.10 (6H, s), 0.93 (9H, s), 3.29 (3H, s), 3.39 (2H, m), 3.47 (2H, m), 4.56 (2H, d, J=1.2 Hz), 5.41 (2H, s), 6.60 (1H, s), 7.35-7.42 (5H, m), 8.11 (1H, brt).

Second Step

To an ethanol (80 mL) solution of compound 155B (7.70 g, 17.2 mmol) was added aqueous ammonia (40 mL) at room temperature, and the mixture was stirred for 18 hours. The solvent was distilled off under reduced pressure, and the resulting residue was purified by silica gel column chromatography (ethyl acetate/n-hexane=75%→100%) to obtain compound 155C (7.15 g, 93%) as a colorless oil.

$^1$H-NMR (CDCl$_3$) δ: 0.14 (6H, s), 0.97 (9H, s), 3.28 (3H, s), 3.38 (2H, m), 3.49 (2H, m), 4.64 (2H, s), 5.53 (2H, s), 6.31 (1H, s), 7.34-7.49 (5H, m), 8.61 (1H, brs), 9.94 (1H, brs).

Third Step

To a DMF (125 mL) solution of compound 155C (7.15 g, 16.0 mmol) and potassium carbonate (6.64 g, 48.0 mmol) was added O-(2,4-dinitrophenyl)hydroxylamine (7.97 g, 40.0 mmol) at room temperature, and the mixture was stirred for 2 days. To the reaction solution was added water (250 mL) under ice-cooling and, thereafter, the mixture was extracted with ethyl acetate (300 mL×2). After the extract was sequentially washed with water (300 mL), saturated sodium bicarbonate water (300 mL×2) and an aqueous saturated sodium chloride solution (150 mL), the mixture was dried with sodium sulfate. The solvent was distilled off under reduced pressure, and the resulting residue was purified by silica gel column chromatography (methanol/chloroform=0%→10%) to obtain compound 155D (6.47 g, 88%) as a pale yellow solid.

$^1$H-NMR (CDCl$_3$) δ: 0.11 (6H, s), 0.94 (9H, s), 3.26 (3H, s), 3.35 (4H, m), 4.66 (2H, s), 5.16 (2H, s), 5.24 (2H, s), 6.43 (1H, s), 7.31-7.40 (5H, m), 7.59 (1H, brs).

Fourth Step

To a toluene (100 mL) solution of compound 155D (6.47 g, 14.0 mmol) and acetic acid (0.080 mL, 1.4 mmol) was added paraformaldehyde (0.422 g, 14.1 mmol) at room temperature, and the mixture was stirred at 80° C. for 2 hours. The solvent was distilled off under reduced pressure, and the resulting crude product of compound 155E was utilized in a next step without purification.

Fifth Step

To a DMF (100 mL) solution of the crude product of compound 155E obtained in the fourth step was added cesium carbonate (22.7 g, 69.8 mmol) under ice-cooling, and the mixture was stirred for 1 hour. Under ice-cooling, bromodiphenylmethane (5.20 g, 21.0 mmol) was added, and the mixture was stirred at room temperature for 19 hours. To the reaction solution was added water (200 mL) under ice-cooling and, thereafter, the mixture was extracted with ethyl acetate (200 mL×3). The extract was sequentially washed with water (200 mL×2) and an aqueous saturated sodium chloride solution (100 mL), and dried with sodium sulfate. The solvent was distilled off under reduced pressure, and the resulting crude product of compound 155F was utilized in a next step without purification.

MS: m/z=640 [M+H]$^+$.

Sixth Step

To a methanol (100 mL) solution of the crude product of compound 155F obtained in the fifth step was added hydrogen chloride (4N ethyl acetate solution, 40 mL) at room temperature, and the mixture was stirred for 2.5 hours. To the reaction solution was added an aqueous sodium hydroxide solution (2N, 75 mL) to perform neutralization (pH=6) under ice-cooling, and the mixture was extracted with chloroform (200 mL×3). The extract was dried with sodium sulfate, the solvent was distilled off under reduced pressure, and the resulting residue was purified by silica gel column chromatography (methanol/chloroform=5%→40%) to obtain compound 155G (5.18 g, 3 step 70%) as an orange oil.

$^1$H-NMR (CDCl$_3$) δ: 3.16 (3H, s), 3.18-3.43 (3H, m), 3.60-3.74 (2H, m), 4.06 (1H, d, J=13.5 Hz), 4.19 (1H, brs), 4.58 (1H, d, J=14.7 Hz), 5.00 (1H, d, J=13.5 Hz), 5.24 (1H, s), 5.27 (2H, s), 5.96 (1H, s), 6.78 (2H, m), 6.98-7.10 (3H, m), 7.30-7.42 (8H, m), 7.72 (2H, m).

Seventh Step

To a THF (2 mL) solution of compound 155G (100 mg, 0.190 mmol), (bromomethyl)cyclopropane (0.110 mL, 1.12 mmol) and sodium iodide (5.0 mg, 0.033 mmol) was added potassium tert-butoxide (78.0 mg, 0.695 mmol) at room temperature, the mixture was stirred at room temperature for 22 hours and, thereafter, the mixture was stirred at 100° C. for 10 minutes under microwave irradiation. To the reaction solution were added water and hydrochloric acid (2N) (pH=1), the mixture was extracted with chloroform, and the extract was dried with sodium sulfate. The solvent was distilled off under reduced pressure, and the resulting crude product of compound 155H was utilized in a next step without purification.

MS: m/z=580 [M+H]$^+$.

Eighth Step

To a DMF (2 mL) solution of the crude product of compound 155H obtained in the seventh step was added lithium chloride (35.0 mg, 0.826 mmol) at room temperature, and the mixture was stirred at 150° C. for 15 minutes under microwave irradiation. The reaction solution was purified by preparative LCMS to obtain compound 155 (4.3 mg, 2 step 5%) as a white solid.

$^1$H-NMR (CDCl$_3$) δ: 0.16 (2H, m), 0.52 (2H, m), 0.98 (1H, m), 3.08 (3H, m), 3.20 (3H, s), 3.46 (2H, m), 3.68 (1H, dd, J=0.6, 14.1 Hz), 3.90 (1H, m), 4.52 (1H, d, J=13.2 Hz), 4.58 (1H, d, J=14.1 Hz), 4.93 (1H, d, J=13.2 Hz), 5.38 (1H, s), 6.01 (1H, s), 6.98 (2H, m), 7.11-7.48 (8H, m).

MS: m/z=490 [M+H]$^+$.

REFERENCE EXAMPLE 156

[Chemical formula 207]

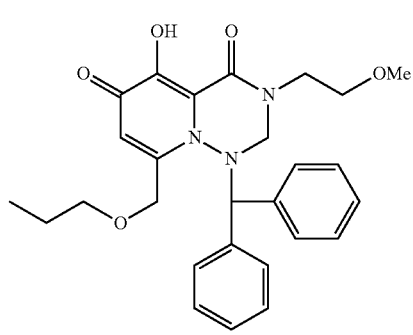

156

According to Reference example 155, compound 156 was synthesized by the same procedure.

$^1$H-NMR (CDCl$_3$) δ: 0.88 (3H, t, J=7.4 Hz), 1.51 (2H, m), 3.15-3.23 (6H, m), 3.46 (2H, m), 3.69 (1H, dd, J=0.6, 14.1 Hz), 3.88 (1H, m), 4.54 (2H, d, J=14.1 Hz), 4.58 (1H, d, J=14.1 Hz), 4.93 (1H, d, J=13.5 Hz), 5.39 (1H, s), 6.12 (1H, s), 6.97 (2H, m), 7.12-7.47 (8H, m).

MS: m/z=478 [M+H]$^+$.

REFERENCE EXAMPLE 157

[Chemical formula 208]

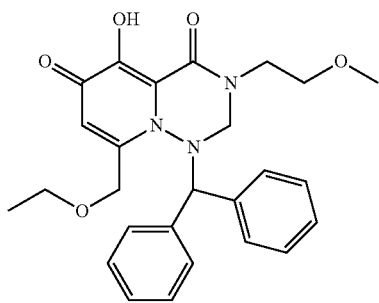

157

According to Reference example 155, compound 157 was synthesized by the same procedure.

$^1$H-NMR (CDCl$_3$) δ: 3.13-3.22 (1H, m), 3.18 (3H, s), 3.20 (3H, s), 3.41-3.51 (2H, m), 3.60 (1H, d, J=13.8 Hz), 3.89 (1H, ddd, J=3.3 Hz, 4.2 Hz, 14.4 Hz), 4.52 (1H, d, J=13.2 Hz), 4.53 (1H, d, J=13.8 Hz), 4.92 (1H, d, J=13.2 Hz), 5.38 (1H, s), 5.98 (1H, s), 6.98 (2H, d, J=8.4 Hz), 7.11-7.22 (3H, m), 7.36-7.48 (5H, m).

REFERENCE EXAMPLE 158

[Chemical formula 209]

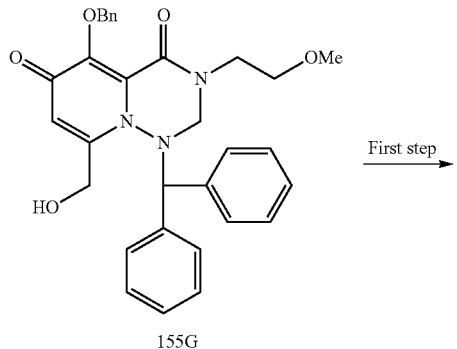

155G

First step →

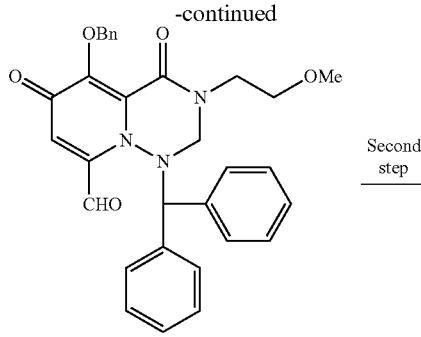

158A

Second step →

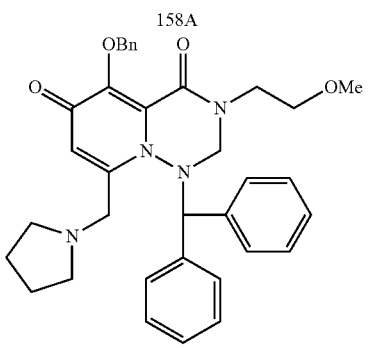

158B

Third step →

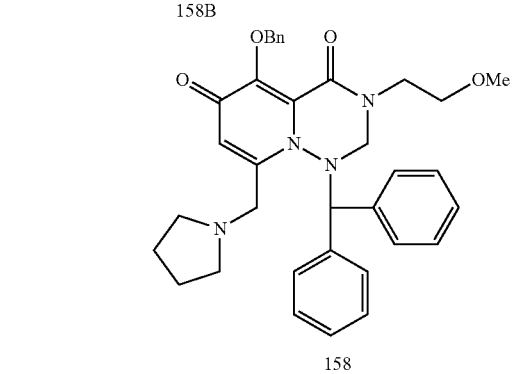

158

First Step

To a THF (100 mL) solution of compound 155G (960 mg, 1.83 mmol) was added manganese dioxide (2.06 g, 92.0 mmol) at room temperature, and the mixture was stirred for 2 days. After the reaction solution was filtered, the filtrate was distilled off under reduced pressure, and the resulting residue was purified by silica gel column chromatography (ethyl acetate/n-hexane=60%→100%) to obtain compound 158A (554 mg, 58%) as a pale yellow foam.

$^1$H-NMR (CDCl$_3$) δ: 2.96 (1H, m), 3.18 (3H, s), 3.44 (2H, m), 4.18 (1H, m), 4.56 (1H, d, J=13.8 Hz), 4.98 (1H, d, J=13.8 Hz), 5.28 (1H, s), 5.54 (1H, d, J=10.5 Hz), 5.64 (1H, d, J=10.5 Hz), 6.35 (1H, s), 6.85 (2H, m), 7.03 (2H, m), 7.18 (1H, m), 7.26-7.48 (8H, m), 7.64 (2H, m), 10.10 (1H, s).

Second Step

To a methylene chloride (4 mL) solution of compound 158A (83.0 mg, 0.159 mmol), pyrrolidine (0.0400 mL, 0.484 mmol) and acetic acid (0.100 mL) was added sodium triacetoxyborohydride (136 mg, 0.642 mmol) at room temperature, and the mixture was stirred for 28 hours. To the reaction solution was added water, the mixture was extracted with chloroform, and the extract was dried with sodium sulfate. The solvent was distilled off under reduced pressure, and the resulting crude product of compound 158B was utilized in a next step without purification.

MS: m/z=579 [M+H]$^+$.

Third Step

To a DMF (2 mL) solution of the crude product of compound 158B obtained in the second step was added lithium chloride (39.2 mg, 0.925 mmol) at room temperature, and the mixture was stirred at 150° C. for 15 minutes under microwave irradiation. The reaction solution was distilled off under reduced pressure, and the resulting residue was purified by preparative LCMS to obtain compound 158 (8.8 mg, 2 step 11%) as a yellow oil.

$^1$H-NMR (CDCl$_3$) δ: 1.84 (4H, m), 2.70-2.85 (5H, m), 3.19 (3H, s), 3.20-3.47 (3H, m), 3.80 (1H, m), 4.25 (1H, d, J=14.7 Hz), 4.57 (1H, d, J=13.5 Hz), 5.07 (1H, d, J=13.5 Hz), 5.39 (1H, s), 6.06 (1H, s), 6.97 (2H, m), 7.12-7.54 (8H, m), 8.29 (1H, s).

MS: m/z=489 [M+H]$^+$.

REFERENCE EXAMPLE 159

[Chemical formula 210]

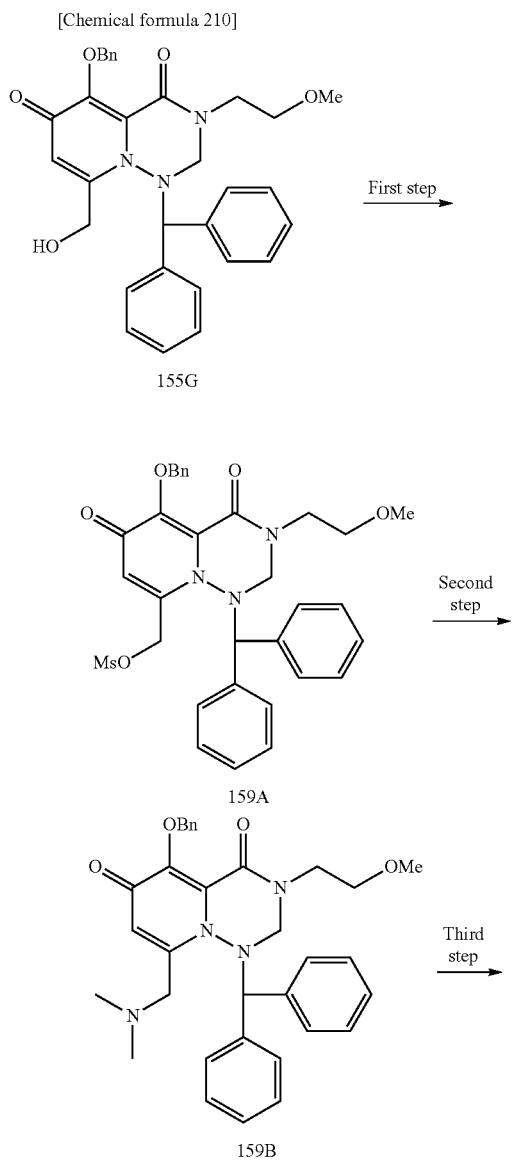

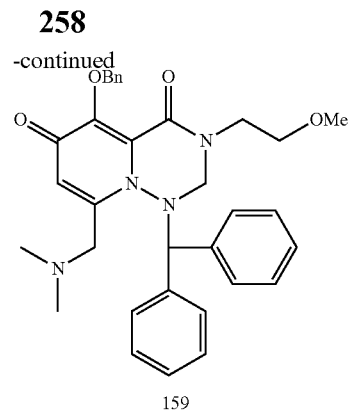

First Step

To a methylene chloride (20 mL) solution of compound 155G (950 mg, 1.81 mmol) and N,N-diisopropylethylamine (0.380 mL, 2.18 mmol) was added dropwise methanesulfonyl chloride (0.148 mL, 1.90 mmol) under ice-cooling, and the mixture was stirred for 90 minutes. To the reaction solution was added water (20 mL), the mixture was extracted with chloroform (50 mL), and the extract was dried with sodium sulfate. The solvent was distilled off under reduced pressure, and the resulting crude product (1.06 g) of compound 159A was utilized in a next step without purification.

MS: m/z=604 [M+H]$^+$.

Second Step

To the crude product (161 mg) of compound 159A obtained in the first step was added dimethylamine (2M THF solution, 2.00 mL, 4.00 mmol) at room temperature, and the mixture was stirred for 3 days. To the reaction solution was added an aqueous saturated sodium chloride solution (2 mL), the mixture was extracted with ethyl acetate, and the extract was dried with sodium sulfate. The solvent was distilled off under reduced pressure, and the resulting crude product of compound 159B was utilized in a next step without purification.

MS: m/z=553 [M+H]$^+$.

Third Step

To a DMF (2 mL) solution of the crude product of compound 159B obtained in the second step was added lithium chloride (56.0 mg, 1.32 mmol) at room temperature, and the mixture was stirred at 150° C. for 30 minutes under microwave irradiation. The reaction solution was distilled off under reduced pressure, and the resulting residue was purified by preparative LCMS to obtain compound 159 (33.6 mg, 3 step 27%) as a white solid.

$^1$H-NMR (CDCl$_3$) δ: 2.37 (6H, s), 2.69 (1H, d, J=14.4 Hz), 3.19 (3H, s), 3.30-3.46 (3H, m), 3.76 (1H, m), 4.00 (1H, d, J=14.4 Hz), 4.60 (1H, d, J=13.5 Hz), 5.20 (1H, d, J=13.5 Hz), 5.40 (1H, s), 6.01 (1H, s), 6.97 (2H, m), 7.11-7.42 (8H, m).

MS: m/z=463 [M+H]$^+$.

REFERENCE EXAMPLE 160

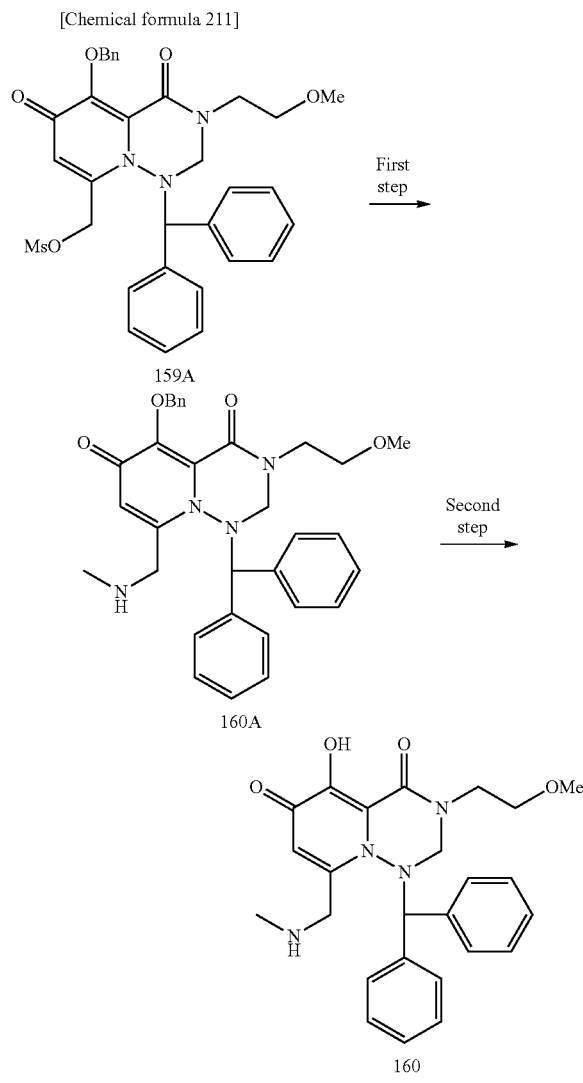

First Step

To a crude product (95.8 mg) of compound 159A was added methylamine (2M THF solution, 2.00 mL, 4.00 mmol) at room temperature, and the mixture was stirred for 3 days. The reaction solution was filtered, the solvent was distilled off under reduced pressure, and the resulting crude product of compound 160A was utilized in a next step without purification.

MS: m/z=539 [M+H]$^+$.

Second Step

To an acetonitrile (3 mL) suspension of the crude product of compound 160A and sodium iodide (100 mg, 0.667 mmol) was added chlorotrimethylsilane (0.0850 mL, 0.665 mmol) at room temperature, and the mixture was stirred for 5 hours. To the reaction solution was added water (1 mL), the solvent was distilled off under reduced pressure, and the resulting residue was purified by preparative LCMS to obtain compound 160 (59.8 mg, 3 step 84%) as a white solid.

$^1$H-NMR (CDCl$_3$) δ: 2.75 (3H, s), 3.08 (1H, d, J=13.5 Hz), 3.24 (3H, s), 3.30-3.40 (3H, m), 3.75 (1H, m), 4.32 (1H, d, J=13.8 Hz), 4.66 (1H, d, J=13.8 Hz), 5.33 (1H, s), 5.58 (1H, d, J=13.5 Hz), 6.40 (1H, s), 6.98 (2H, m), 7.12-7.25 (3H, m), 7.40-7.51 (2H, m), 7.60 (2H, m).

MS: m/z=449 [M+H]$^+$.

REFERENCE EXAMPLE 161

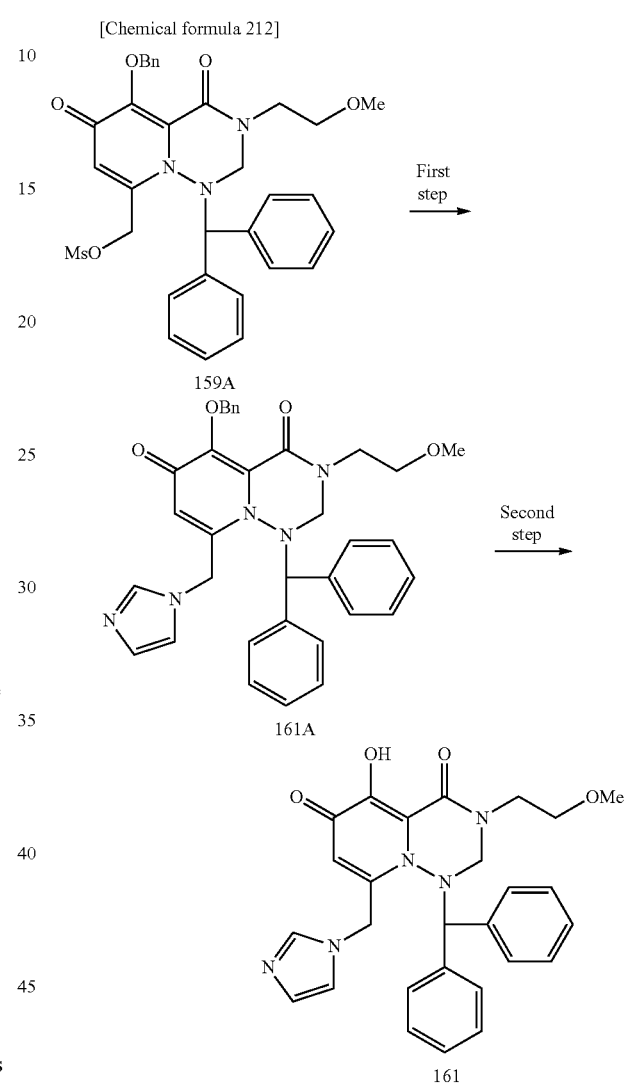

First Step

After a DMF (2 mL) suspension of a crude product (156 mg) of compound 159A, imidazole (19.5 mg, 0.286 mmol) and potassium carbonate (37.7 mg, 0.273 mmol) was stirred at room temperature for 4 hours, sodium hydride (60%, 11.7 mg, 0.293 mmol) was added, and the mixture was stirred for 3 days. To the reaction solution was added an aqueous acetic acid solution (10%), the mixture was extracted with chloroform, and the extract was dried with sodium sulfate. The solvent was distilled off under reduced pressure, and the resulting crude product of compound 161A was utilized in a next step without purification.

MS: m/z=576 [M+H]$^+$.

Second Step

To the crude product of compound 161A was added trifluoroacetic acid (1 mL) at room temperature, and the mixture was stirred for 18 hours and, thereafter, the mixture was stirred at 60° C. for 3 hours. The reaction solution was distilled off under reduced pressure, and the resulting residue was purified by preparative LCMS to obtain compound 161 (19.8 mg, 3 step 16%) as a pale orange amorphous substance.

¹H-NMR (CDCl₃) δ: 3.17-3.25 (1H, m), 3.21 (3H, s), 3.38-3.47 (2H, m), 3.82 (1H, m), 4.40 (1H, d, J=16.5 Hz), 4.54 (1H, d, J=13.5 Hz), 5.02 (1H, d, J=13.5 Hz), 5.09 (1H, s), 5.32 (1H, d, J=16.5 Hz), 5.40 (1H, s), 6.65 (1H, brs), 7.03 (2H, m), 7.15-7.49 (8H, m), 8.08 (1H, brs).

MS: m/z=486 [M+H]⁺.

REFERENCE EXAMPLE 162

[Chemical formula 213]

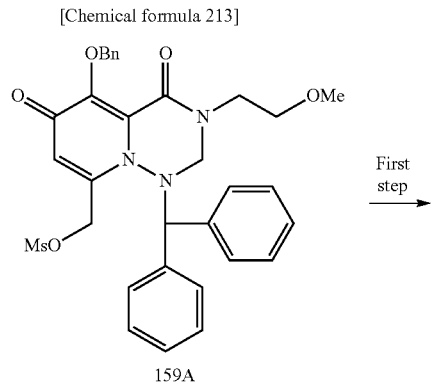

159A

First step →

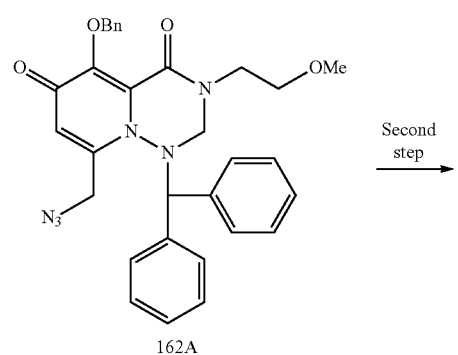

162A

Second step →

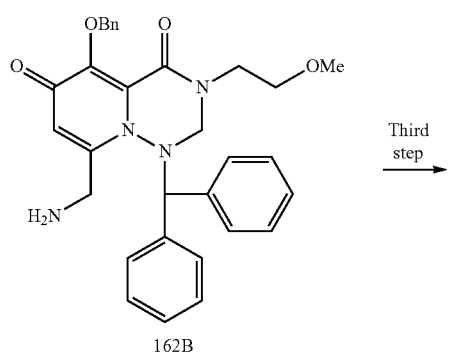

162B

Third step →

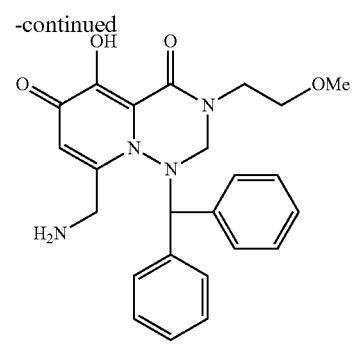

162

First Step

To a DMF (2 mL) solution of a crude product (192 mg) of compound 159A was added sodium azide (24.2 mg, 0.372 mmol) at room temperature, and the mixture was stirred at 60° C. for 2 hours. The reaction solution was distilled off under reduced pressure, and the resulting crude product of compound 162A was utilized in a next step without purification.

MS: m/z=551 [M+H]⁺.

Second Step

To a THF (4 mL) solution of the crude product of compound 162A were sequentially added water (0.200 mL) and triphenylphosphine (83.0 mg, 0.316 mmol) at room temperature, and the mixture was stirred at 60° C. for 1 hour. The reaction solution was distilled off under reduced pressure, and the resulting residue was purified by preparative LCMS to obtain compound 162B (110 mg, 3 step 66%) as a colorless oil.

MS: m/z=525 [M+H]⁺.

Third Step

To an acetonitrile (1 mL) suspension of compound 162B (50.0 mg, 0.0950 mmol) and sodium iodide (56.2 mg, 0.375 mmol) was added chlorotrimethylsilane (0.0490 mL, 0.381 mmol) at room temperature, and the mixture was stirred for 6 hours. To the reaction solution was added water (0.5 mL), the solvent was distilled off under reduced pressure, and the resulting residue was purified by preparative LCMS to obtain compound 162 (25.9 mg, 63%) as a pale orange solid.

¹H-NMR (CDCl₃) δ: 3.12 (1H, d, J=14.7 Hz), 3.27 (3H, s), 3.35-3.48 (3H, m), 3.81 (1H, m), 4.65 (1H, d, J=13.5 Hz), 5.31 (1H, s), 5.59 (1H, d, J=13.5 Hz), 6.40 (1H, s), 6.98 (2H, m), 7.19 (3H, m), 7.40 (1H, m), 7.50 (2H, m), 7.62 (2H, m), 8.11 (1H, s).

MS: m/z=435 [M+H]⁺.

REFERENCE EXAMPLE 163

[Chemical formula 214]

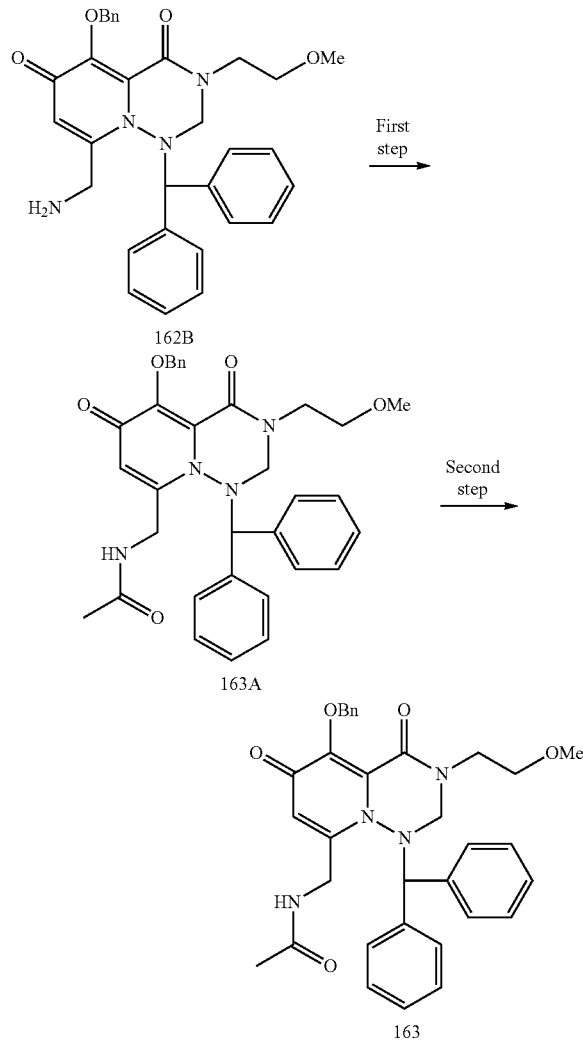

First Step

To an acetonitrile (3 mL) solution of compound 162B (50.0 mg, 0.0950 mmol) and N,N-diisopropylethylamine (0.0366 mL, 0.210 mmol) was added acetic anhydride (0.0100 mL, 0.106 mmol) at room temperature, and the mixture was stirred for 6 hours. The reaction solution was distilled off under reduced pressure, and the resulting crude product of compound 163A was utilized in a next step without purification.

MS: m/z=567 $[M+H]^+$.

Second Step

To an acetonitrile (5 mL) suspension of the crude product of compound 163A and sodium iodide (59.2 mg, 0.395 mmol) was added chlorotrimethylsilane (0.0487 mL, 0.381 mmol) at room temperature, and the mixture was stirred for 16 hours. To the reaction solution was added water (0.5 mL), the solvent was distilled off under reduced pressure, and the resulting residue was purified by preparative LCMS to obtain compound 163 (28.1 mg, 2 step 62%) as a pale orange foam.

$^1$H-NMR (CDCl$_3$) δ: 2.07 (3H, s), 3.24 (3H, s), 3.27-3.52 (4H, m), 3.67 (1H, m), 4.54 (1H, d, J=13.5 Hz), 4.78 (1H, dd, J=6.5, 14.9 Hz), 5.17 (1H, d, J=13.5 Hz), 5.28 (1H, s), 5.61 (1H, s), 7.01 (2H, m), 7.01-7.58 (9H, m).

MS: m/z=477 $[M+H]^+$.

REFERENCE EXAMPLE 164

[Chemical formula 215]

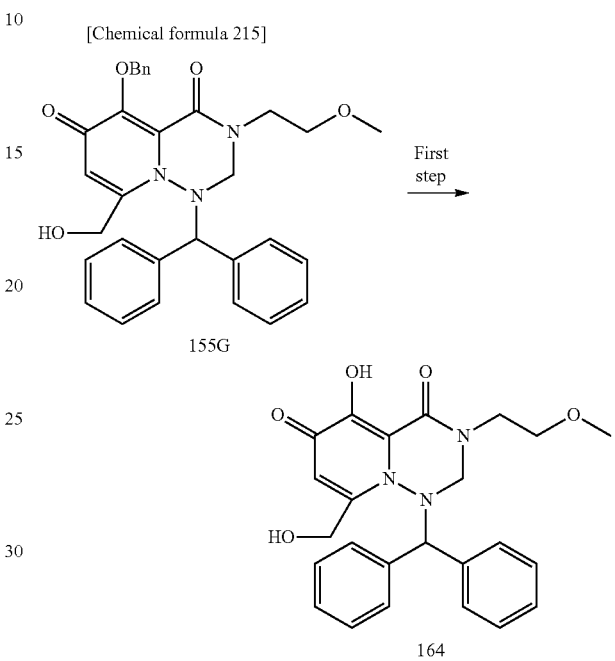

First Step

Compound 155G (43.3 mg, 0.221 mmol) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 22 mg (yield 61%) of compound 164.

$^1$H-NMR (CDCl$_3$) δ: 1.13 (6H, d, J=6.0 Hz), 3.18-3.77 (7H, m), 3.26 (3H, s), 4.49 (1H, d, J=12.3 Hz), 4.76 (1H, d, J=12.3 Hz), 5.27 (2H, brs), 5.89 (1H, s), 6.90 (2H, d, J=7.2 Hz), 6.98-7.14 (3H, m), 7.315-7.50 (5H, m).

REFERENCE EXAMPLE 165

[Chemical formula 216]

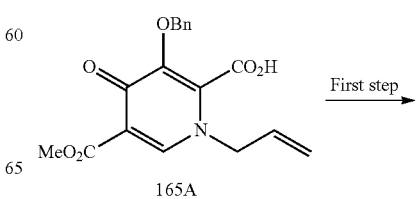

165A

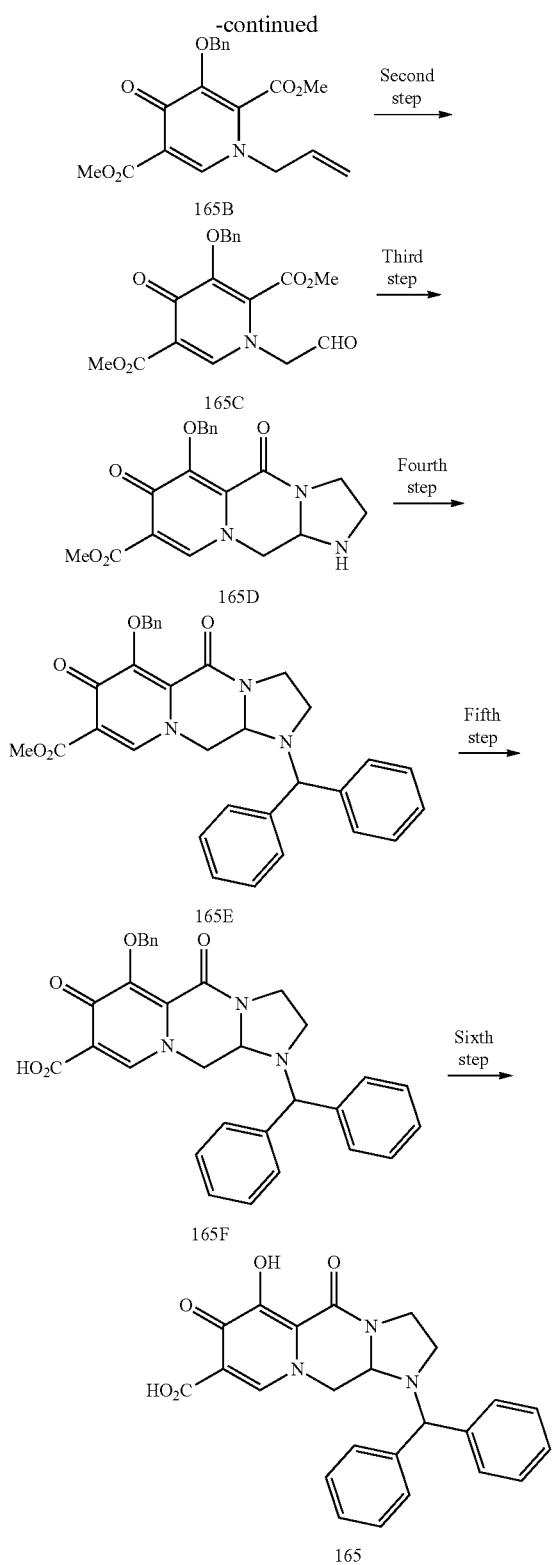

First Step

To a DMF (370 mL) solution of compound 165A (WO 2006/088173, 37.0 g, 108 mmol) were sequentially added potassium carbonate (17.9 g, 129 mmol) and methyl iodide (8.03 mL, 129 mmol) at room temperature, and the mixture was stirred for 1.5 hours. The reaction solution was added to a solution of ammonium chloride (20.8 g, 390 mmol) in water (1110 mL) under ice-cooling, and the precipitated solid was filtered, and washed with water to obtain a crude product (33 g). In addition, the aqueous layer was salted out with sodium chloride, and the mixture was extracted with ethyl acetate, and dried with sodium sulfate. The solvent was distilled off under reduced pressure, and a crude product (9 g) was obtained from the resulting residue. The crude products were combined and purified by silica gel column chromatography (ethyl acetate/n-hexane=50%→100%) to obtain compound 165B (36.5 g, 95%) as a white solid.

Second Step

To a 1,4-dioxane (548 mL) solution of compound 165B (36.5 g, 102 mmol) were sequentially added potassium osmate dihydrate (1.13 g, 3.06 mmol), sodium periodate (87.3 g, 408 mmol) and water (365 mmol) at room temperature, and the mixture was stirred for 6 hours. The reaction solution was extracted with methylene chloride, and the extract was dried with sodium sulfate. The solvent was distilled off under reduced pressure, and the resulting residue was purified by silica gel column chromatography (ethyl acetate/n-hexane=50%→100%) to obtain compound 165C (33.0 g, 90%) as a bronzed foam.

Third Step

To a toluene (25 mL) suspension of compound 165C (1.38 g, 3.66 mmol) were sequentially added ethylenediamine (0.247 mL, 3.66 mmol) and acetic acid (0.0210 mL, 0.366 mmol) at room temperature and, thereafter, the mixture was stirred for 1 hour, and further stirred at 50° C. for 17 hours. The precipitated solid was filtered, and washed with ether to obtain compound 165D (1.11 g, 100%) as a pale yellow solid.

$^1$HNMR (DMSO-$d_6$) δ: 3.05 (2H, m), 3.26 (1H, m), 3.63 (2H, m), 3.75 (3H, s), 3.87 (1H, m), 4.52 (1H, dd, J=3.3, 12.6 Hz), 4.69 (1H, m), 4.99 (1H, d, J=10.4 Hz), 5.15 (1H, d, J=10.4 Hz), 7.35 (3H, m), 7.54 (2H, m), 8.41 (1H, s).

Fourth Step

To an acetonitrile (30 mL) suspension of compound 165D (2.77 g, 7.50 mmol), potassium carbonate (2.23 g, 16.1 mmol) and sodium iodide (102 mg, 0.680 mmol) was added bromodiphenylmethane (2.26 g, 9.14 mmol) at room temperature, and the mixture was stirred at 90° C. for 7 hours. The reaction solution was poured into hydrochloric acid (2N, 10 mL) and an ice (20 g), the mixture was extracted with chloroform (100 mL×2), and the extract was dried with sodium sulfate. The solvent was distilled off under reduced pressure, and the resulting residue was purified by silica gel column chromatography (chloroform/methanol=0%→5%) to obtain compound 165E (2.72 g, 68%) as a pale yellow solid.

Fifth Step

To an ethanol (30 mL) solution of compound 165E (2.72 g, 5.08 mmol) was added an aqueous sodium hydroxide solution (2N, 10 mL) at room temperature, and the mixture was stirred for 3 days. To the reaction solution was added hydrochloric acid (1N, 20 mL) (pH=1) at room temperature, the mixture was extracted with chloroform (100 mL×2), and the extract was dried with sodium sulfate. The solvent was distilled off under reduced pressure, and the resulting residue was purified by silica gel column chromatography (chloroform/methanol=0%→10%) to obtain compound 165F (1.77 g, 67%) as a pale yellow solid.

$^1$HNMR (DMSO-$d_6$) δ: 2.63 (1H, m), 3.16 (1H, m), 3.49 (1H, m), 3.73 (1H, m), 4.12 (2H, m), 4.56 (1H, m), 5.04 (1H, s), 5.09 (1H, d, J=10.7 Hz), 5.19 (1H, d, J=10.7 Hz), 7.28-7.53 (15H, m), 8.32 (1H, s), 8.39 (1H, s).

Sixth Step

A N,N'-dimethylimidazolidinone (20 mL) solution of compound 165F (1.77 g, 3.39 mmol) and lithium chloride (0.515 g, 12.2 mmol) was stirred at 90° C. for 1 hour. To the reaction solution were sequentially added water (10 mL), hydrochloric acid (2N, 10 mL) and water (10 mL) at room temperature. The precipitated solid was filtered, and washed with ether, DMF-water were added, and the precipitated solid was filtered to obtain compound 165 (599 mg, 41%) as a white solid.

$^1$HNMR (DMSO-$d_6$) δ: 2.60 (1H, m), 3.20 (1H, m), 3.64 (2H, m), 4.00 (2H, m), 4.55 (1H, m), 5.01 (1H, s), 7.28-7.47 (10H, m), 8.16 (1H, s), 11.97 (1H, brs).

MS: m/z=432 [M+H]$^+$.

REFERENCE EXAMPLE 166

[Chemical formula 217]

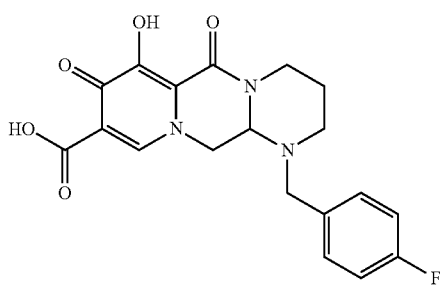

166

According to Reference example 165, following compound 166 was synthesized by the same procedure.

$^1$HNMR (DMSO-$d_6$) δ: 1.54 (1H, d, J=12.6H), 1.66-1.78 (1H, m), 2.60 (1H, t, J=9.9 Hz), 2.83 (1H, d, J=11.7 Hz), 3.01 (1H, t, J=11.7 Hz), 3.34-3.38 (1H, m), 3.94 (1H, d, J=13.8 Hz), 4.44-4.59 (3H, m), 4.82 (1H, d, J=14.7 Hz), 7.06 (2H, t, J=8.7 Hz), 7.18-7.23 (2H, m), 8.27 (1H, s), 12.84 (1H, brs).

REFERENCE EXAMPLE 167

[Chemical formula 218]

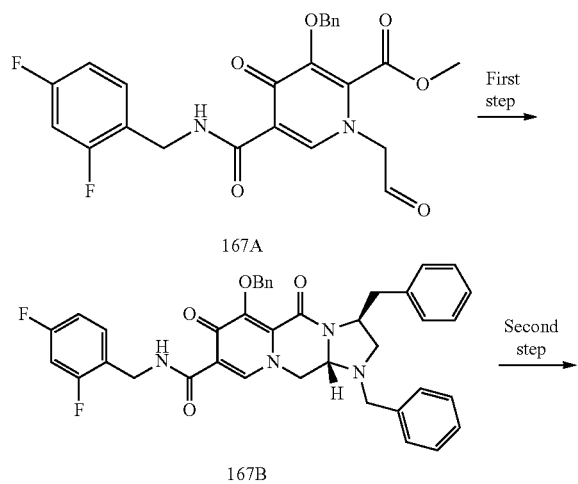

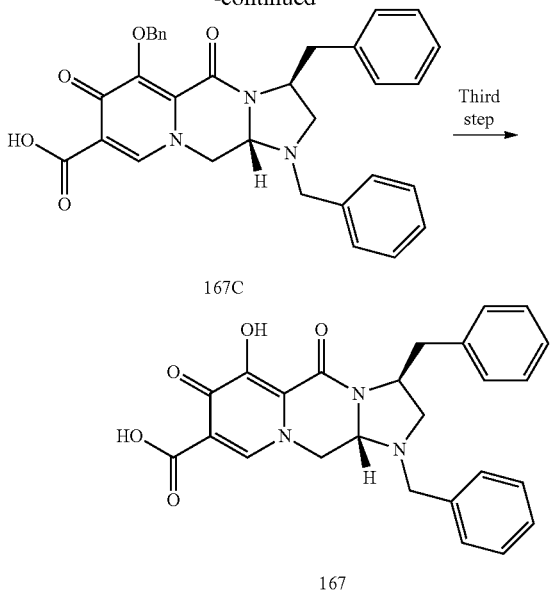

First Step

To a xylene (30 ml) solution of compound 167A (WO 2006/11674, 3.58 g, 7.61 mmol) were added (S)—N1-benzyl-3-phenylpropane-1,2-diamine (Journal of the American Chemical Society; English; 127; 30; 2005; 10504, 1.83 g, 7.61 mmol) and acetic acid (0.5 ml), and the mixture was refluxed for 2 hours. After cooling to room temperature, the solvent was distilled off, and the resulting oil was purified by silica gel chromatography. The materials were eluted firstly with n-hexane-ethyl acetate (9:1, v/v) and, then, with n-hexane-ethyl acetate (1:1, v/v). Concentration of an objective fraction afforded 349 mg (yield 7%) of compound 167B as an oil.

$^1$HNMR (CDCl$_3$) δ: 2.54 (1H, t, J=9.6 Hz), 2.77 (1H, dd, J=9.0 Hz, 13.2 Hz), 3.31 (1H, dd, J=6.9 Hz, 9.6 Hz), 3.43-3.78 (5H, m), 4.04-4.15 (1H, m), 4.42-4.48 (1H, m), 4.62 (2H, d, J=6.0 Hz), 5.29 (1H, d, J=10.5 Hz), 5.43 (1H, d, J=10.5 Hz), 6.77-6.85 (2H, m), 7.19-7.39 (14H, m), 7.60 (2H, d, J=6.3 Hz), 8.05 (1H, s).

Second Step

To a MeCN (10 ml) solution of compound 167B (968 mg, 1.47 mmol) were added Boc2O (3 ml) and DMAP (180 mg, 1.47 mmol), and the mixture was heated to reflux for 5 hours. To the reaction solution was added a 2N aqueous sodium hydroxide solution to stop the reaction, the reaction solution was neutralized using 2N hydrochloric acid and, thereafter, the mixture was extracted with ethyl acetate three times. After the extract was washed with an aqueous saturated sodium chloride solution, the solvent was distilled off, and the resulting oil was purified by silica gel chromatography. The materials were eluted firstly with n-hexane-ethyl acetate (6:4, v/v) and, then, only with ethyl acetate. Concentration of an objective fraction afforded 349 mg (yield 45%) of compound 167C.

$^1$HNMR (CDCl$_3$) δ: 2.54 (1H, t=9.0 Hz), 2.76 (1H, dd, J=9.3 Hz, 16.5 Hz), 3.31 (1H, dd, J=6.9 Hz, 9.6 Hz), 3.45 (1H, dd, J=3.3 Hz, 12.6 Hz), 3.51-3.78 (4H, m), 4.04-4.13 (1H, m), 4.42-4.52 (1H, m), 4.61 (2H, d, J=6.0 Hz), 2.79 (1H, d, J=10.2 Hz), 5.29 (1H, d, J=10.2 Hz), 5.43 (1H, d, J=10.2 Hz), 6.76-7.39 (11H, m), 7.60 (2H, d, J=6.6 Hz), 8.05 (1H, s), 10.42 (1H, t, J=5.7 Hz).

Third Step

The compound 167C (150 mg, 0.280 mmol) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 71 mg (yield 57%) of compound 167.

$^1$HNMR (CDCl$_3$) δ: 2.65 (1H, dd, J=8.4 Hz, 9.6 Hz), 2.97 (1H, dd, J=9 Hz, 13.5 Hz), 3.43 (1J, dd, J=7.2 Hz, 9.6 Hz), 3.55 (1H, dd, J=3.0 Hz, 13.2 Hz), 3.61-3.80 (4H, m), 4.15 (1H, dd, J=4.2 Hz, 9.9 Hz), 4.51-4.60 (1H, m), 7.15-7.18 (2H, m), 7.28-7.38 (8H, m), 8.02 (1H, s), 12.04 (1H, s).

REFERENCE EXAMPLE 168

[Chemical formula 219]

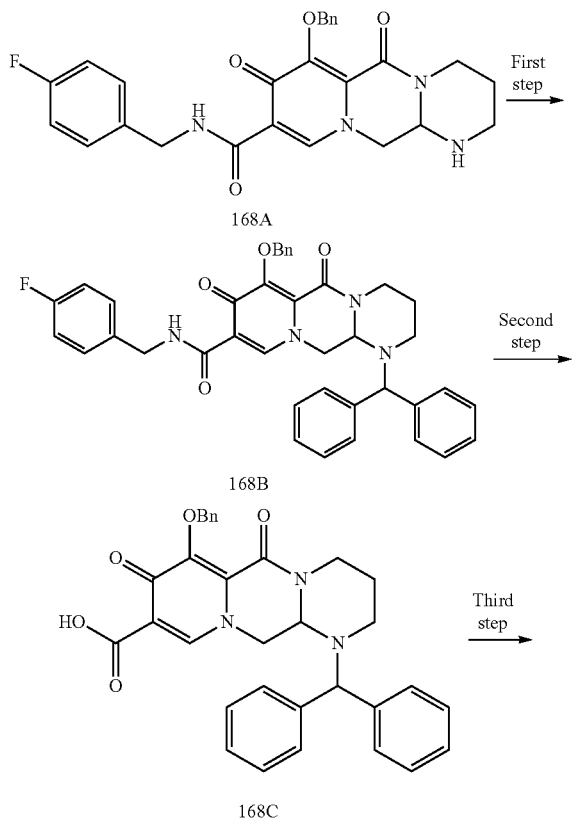

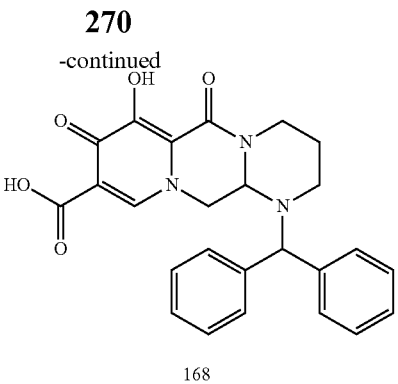

168

First Step

To a DMF (3 mL) solution of compound 168A (WO 2006/116764, 400 mg, 0.840 mmol) were added cesium carbonate (821 mg, 2.52 mmol) and, subsequently, bromomethylenedibenzene (311 mg, 1.26 mmol), and the mixture was stirred at 100° C. for 5 hours. To the reaction solution were added 2N aqueous hydrochloric acid solution, water and ethyl acetate, the ethyl acetate layer was separated, and the aqueous layer was extracted with ethyl acetate once. The combined extracts were washed with an aqueous saturated sodium bicarbonate solution and brine, dried with magnesium sulfate, filtered and concentrated. The resulting residue was purified by silica gel column chromatography. Concentration of an objective fraction afforded 100 mg of compound 168B as a yellow oil.

$^1$H-NMR (CDCl$_3$) δ: 1.79-1.84 (2H, m), 2.67-2.77 (1H, m), 2.84-3.05 (2H, m), 4.03 (1H, dd, J=13.0, 4.2 Hz), 4.28 (1H, dd, J=13.6, 6.5 Hz), 4.49 (1H, dd, J=6.4, 3.8 Hz), 4.57 (2H, d, J=5.7 Hz), 4.78 (1H, dd, J=13.4, 5.7 Hz), 4.93 (1H, s), 5.27 (2H, s), 7.00 (2H, t, J=8.8 Hz), 7.15-7.37 (14H, m), 7.57-7.63 (2H, m), 7.76 (1H, s), 10.44 (1H, t, J=5.9 Hz).

MS: m/z=643.20 [M+H]$^+$.

Second Step

Compound 168B (100 mg, 0.156 mmol) was dissolved in acetonitrile (3 mL), Boc2O (4.0 mL, 17.3 mmol) and, subsequently, DMAP (84 mg, 0.69 mmol) were added, and the mixture was stirred at 80° C. for 6 hours. The reaction solution was allowed to cool, a 2N aqueous sodium hydroxide solution (8 mL) and, subsequently, ethanol (3 mL) were added, and the mixture was stirred at 60° C. for 2 hours. To the reaction solution were added 2N aqueous hydrochloric acid solution and ethyl acetate, the ethyl acetate layer was separated, and the aqueous layer was extracted with ethyl acetate. The solvent was distilled off, and the resulting residue was purified by silica gel chromatography. Elution with ethyl acetate-methanol, and concentration of an objective fraction afforded 84 mg of compound 168C.

MS: m/z=536.25 [M+H]$^+$.

Third Step

To a DMI (2 mL) solution of compound 168C (80 mg, 0.15 mmol) was added lithium chloride (19 mg, 0.45 mmol), and the mixture was stirred at 90° C. for 2 hours. To the reaction mixture were added water and 2N aqueous hydrochloric acid solution, the precipitated solid was filtered, and the resulting solid was purified using an LCMS fractionating device. The eluted solvent was distilled off, isopropyl ether was added to the residue, and the precipitated solid was filtered. Washing with isopropyl ether and drying afforded 12 mg of compound 168.

MS: m/z=446.05 [M+H]$^+$.

REFERENCE EXAMPLE 169

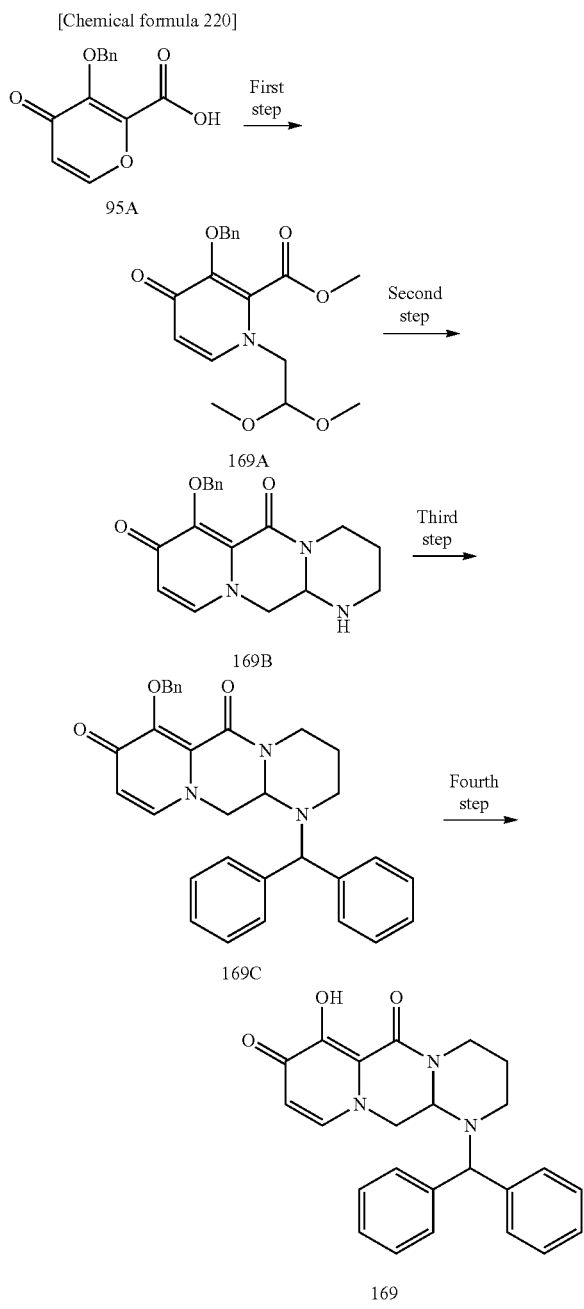

First Step

To an ethanol (5 mL) solution of compound 95A (WO 2006/116764, 500 mg, 2.03 mmol) was added 2,2-dimethoxyethanamine (0.49 ml, 4.47 mmol), and the mixture was stirred at 80° C. for 3 hours. After the reaction solution was allowed to cool, acetic acid (0.27 ml, 4.69 mmol) was added at room temperature, and the mixture was concentrated under reduced pressure. The resulting residue was dissolved in DMF (5 mL), DBU (0.66 mL, 4.4 mmol) and, subsequently, methyl iodide (1.02 mL, 16.2 mmol) were added under nitrogen atmosphere, and the mixture was stirred at room temperature for 3 hours. To the reaction solution were added an aqueous saturated sodium bicarbonate solution and ethyl acetate, the ethyl acetate layer was separated, and the aqueous layer was extracted with ethyl acetate. To the combined extracts was added sodium sulfate, the mixture was filtered and concentrated, and the resulting residue was purified by silica gel chromatography. Elution with chloroform-methanol (9:1) and concentration of an objective fraction afforded 258 mg of compound 169A as a brown oil.

$^1$H-NMR (CDCl$_3$) δ: 3.37 (6H, s), 3.80 (3H, s), 3.87 (2H, d, J=4.8 Hz), 4.46 (1H, t, J=4.8 Hz), 5.30 (2H, s), 6.75 (1H, d, J=6.0 Hz), 7.30-7.41 (6H, m).

Second Step

To compound 169A (1.00 g, 2.88 mmol) were added formic acid (31 mL) and, subsequently, water (5 mL), and the mixture was stirred at 70° C. for 6.5 hours. To the reaction mixture were added water and ethyl acetate, the ethyl acetate layer was separated, and the aqueous layer was extracted with ethyl acetate. After the combined extracts were washed with an aqueous saturated sodium bicarbonate solution, and sodium sulfate was added, then the mixture was filtered and concentrated, and the resulting residue was purified by silica gel chromatography. Elution with ethyl acetate-methanol, and concentration of an objective fraction afforded a mixture of aldehyde hydride and methylacetal as a colorless transparent oil. The resulting oil was dissolved in dichloromethane (5 mL), 1,3-diaminopropane dihydrochloride (354 mg, 2.41 mmol) and, subsequently, acetic acid (0.069 ml, 1.2 mmol) were added, and the mixture was stirred at room temperature for 6 hours. The reaction solution was diluted with dichloromethane, insolubles were filtered and, thereafter, the mixture was concentrated under reduced pressure to obtain a crude purified product of compound 169B.

MS: m/z=326.20 [M+H]$^+$.

Third Step

To an acetonitrile (4 mL) solution of compound 169B (391 mg, 1.20 mmol) were added potassium carbonate (498 mg, 3.61 mmol) and, subsequently, bromomethylenedibenzene (890 mg, 3.61 mmol). After the reaction solution was stirred at 90° C. for 2 hours, to the reaction solution were added water, ethyl acetate and brine, the ethyl acetate layer was separated, and the aqueous layer was extracted with ethyl acetate once. After the combined extracts were dried with magnesium sulfate, then the mixture was filtered and concentrated. The resulting residue was purified by silica gel column chromatography. Elution with ethyl acetate-methanol, and concentration of an objective fraction afforded 106 mg of compound 169C as an orange solid.

MS: m/z=492.15 [M+H]$^+$.

Fourth Step

To a DMI (2 mL) solution of compound 169C (105 mg, 0.214 mmol) was added lithium chloride (27.2 mg, 0.641 mmol), and the mixture was stirred at 90° C. for 3 hours. Further, lithium chloride (27.2 mg, 0.641 mmol) was added, and the mixture was stirred at 90° C. for 1 hour. The reaction solution was concentrated under reduced pressure, and the resulting residue was purified using an LCMS fractionating device. The eluted solvent was distilled off, to the residue was added diethyl ether, and the precipitated solid was filtered. Washing with diethyl ether, and drying afforded 27 mg of compound 169.

$^1$H-NMR (CD$_3$OD) δ: 1.63 (1H, dd, J=13.4, 2.8 Hz), 1.84 (1H, brs), 2.55-2.64 (1H, m), 2.90-3.10 (2H, m), 4.30 (1H, dd, J=14.5, 4.0 Hz), 4.52 (4H, dd, J=14.5, 3.8 Hz), 4.63-4.75 (4H, m), 5.16 (1H, s), 6.16 (1H, d, J=7.2 Hz), 6.78 (1H, d, J=7.2 Hz), 7.16-7.32 (10H, m).

MS: m/z=402.10 [M+H]$^+$.

REFERENCE EXAMPLE 170

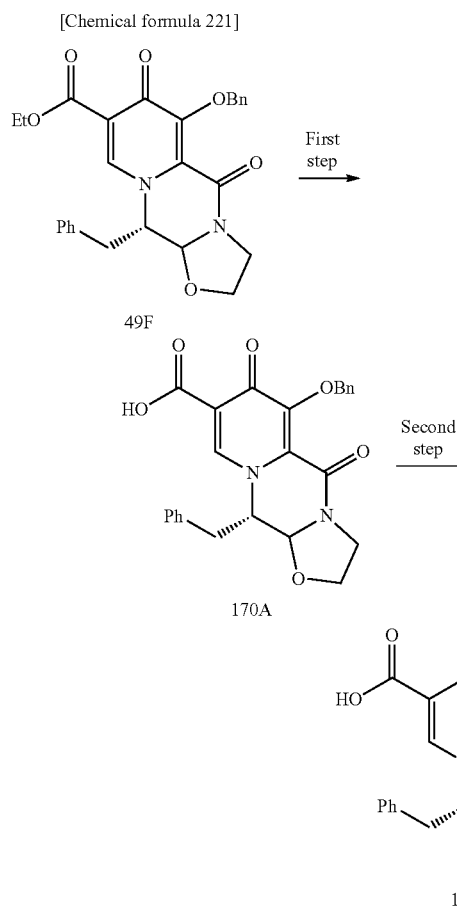

First Step

Compound 49F (87 mg, 0.19 mmol) was dissolved in ethanol (1 ml) and THF (1 ml), a 2N aqueous sodium hydroxide solution (0.47 ml, 0.95 mmol) was added, and the mixture was stirred at room temperature for 1.5 hours. To the reaction solution was added 2N hydrochloric acid, the mixture was extracted with ethyl acetate, and the extract was dried with sodium sulfate. The resulting crude product was purified by silica gel column chromatography (chloroform-methanol 95:5→90:10, v/v) to obtain 60 mg of compound 170A.

$^1$H-NMR (CDCl$_3$) δ: 2.48 (1H, dd, J=13.8, 11.8 Hz), 3.27 (1H, dd, J=14.2, 3.4 Hz), 3.73-3.80 (1H, m), 3.92 (1H, m), 4.16 (1H, m), 4.45 (2H, m), 5.34 (1H, d, J=3.5 Hz), 5.47 (1H, d, J=10.4 Hz), 5.52 (1H, d, J=10.7 Hz), 6.73 (2H, d, J=6.9 Hz), 7.18-7.42 (7H, m), 7.60 (2H, d, J=6.9 Hz), 14.63 (1H, s).

Second Step

To compound 170A (57 mg, 0.13 mmol) was added trifluoroacetic acid (1 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-ethyl ether were added, and the precipitated solid was filtered to obtain 19 mg of compound 170 as a colorless solid.

$^1$H-NMR (DMSO-d$_6$) δ: 2.74 (1H, t, J=12.1 Hz), 3.10-3.22 (1H, m), 3.76 (2H, m), 4.12 (1H, q, J=8.0 Hz), 4.44 (1H, m), 5.35 (1H, m), 5.49 (1H, d, J=3.4 Hz), 7.05 (5H, m), 7.77 (1H, s), 12.05 (1H, brs).

REFERENCE EXAMPLE 171

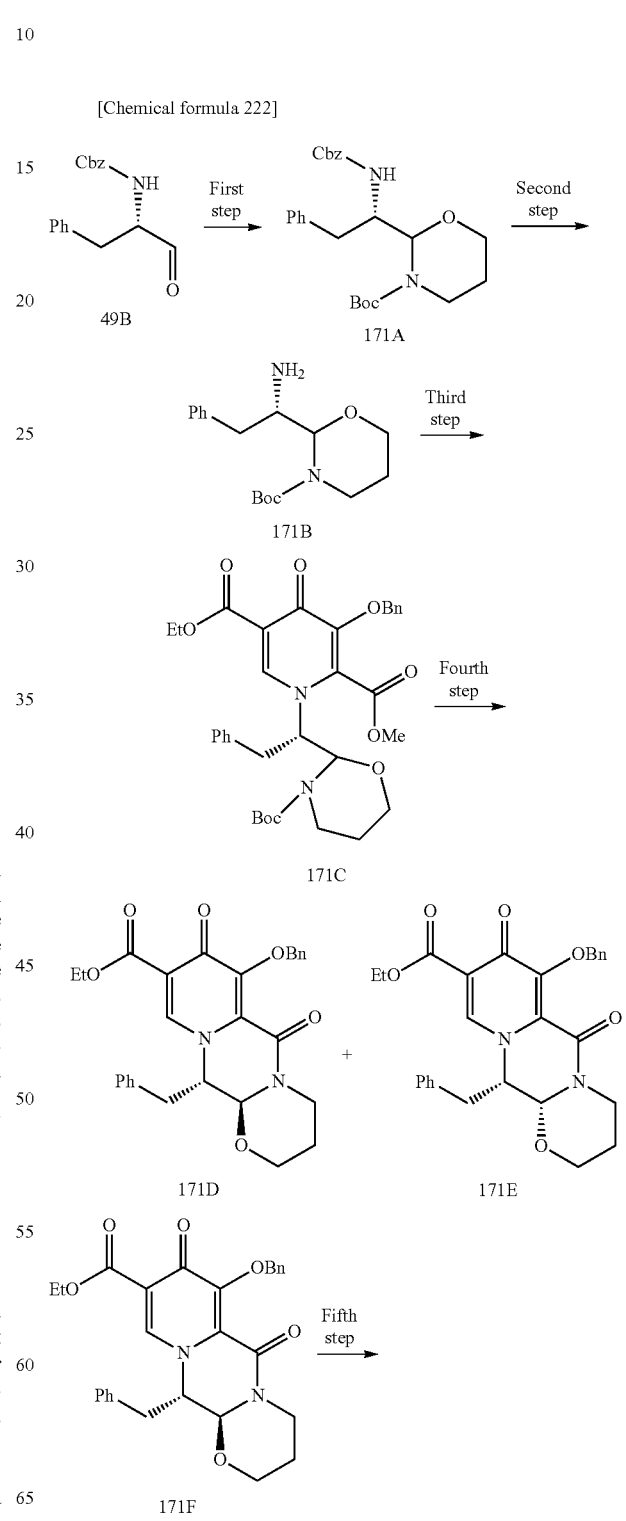

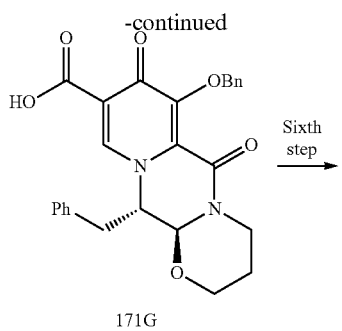

171G

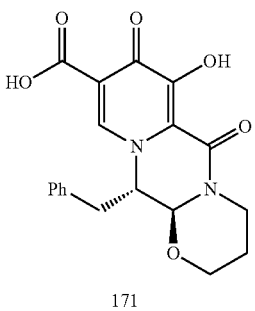 [SMILES: O=C(O)c1cn2c(c(O)c1=O)C(=O)N1CCCO[C@H]1[C@@H]2Cc1ccccc1]

171

First Step

Compound 49B (950 mg, 3.35 mmol), 3-aminopropan-1-ol (277 mg, 3.69 mmol) and sodium sulfate (1.91 g, 13.4 mmol) were added to toluene (25 ml), and the mixture was stirred at room temperature for 1 hour. Boc2O (0.856 ml, 3.69 mmol) was added at room temperature, and the mixture was stirred for 18 hours. Further, Boc2O (0.400 ml, 1.72 mmol) was added at room temperature, and the mixture was stirred for 60 hours. The reaction solution was filtered, and the filtrate was concentrated under reduced pressure. The resulting crude product was purified by silica gel column chromatography (n-hexane-ethyl acetate, 1:1, v/v) to obtain 1.02 g of compound 171A as a colorless gummy substance.

Second Step

Compound 171A (1.01 g, 2.29 mmol) and palladium-active carbon (10%, wet, 200 mg) were added to ethanol (20 ml), and the mixture was stirred at room temperature for 1.5 hours under hydrogen atmosphere. After filtration with celite, the solvent was concentrated under reduced pressure to obtain 755 mg of a colorless oily substance 171B.

$^1$H-NMR (CDCl$_3$) δ: 1.42 (5H, s), 1.49 (4H, s), 1.56-1.92 (2H, m), 2.49 (0.4H, dd, J=13.6, 9.8 Hz), 2.62 (0.6H, dd, J=13.6, 8.5 Hz), 2.81 (0.4H, dd, J=13.5, 3.6 Hz), 3.16 (1.6H, m), 3.60-4.14 (4H, m), 5.13 (0.6H, d, J=8.8 Hz), 5.19 (0.4H, d, J=8.5 Hz), 7.22-7.37 (5H, m).

Third Step

Dimethyl 3-(benzyloxy)-4-oxo-4H-pyran-2,5-dicarboxylate (660 mg, 1.99 mmol) and compound 171B (609 mg, 1.99 mmol) were added to toluene (8 ml), and the mixture was stirred at 100° C. for 1.5 hours. After the solvent was distilled off under reduced pressure, the resulting crude product was purified by silica gel column chromatography (chloroform-methanol, 99:1, v/v) to obtain 1.02 g of compound 171C as a pale yellow gummy substance.

Fourth Step

To compound 171C (991 mg, 1.60 mmol) was added 4N HCl (ethyl acetate solution, 12 ml). After the mixture was stirred at room temperature for 1 hour, the solvent was distilled off under reduced pressure. Subsequently, toluene (12 ml) and 3-aminopropan-1-ol (0.244 ml, 3.19 mmol) were added, the mixture was stirred at 80° C. for 10 minutes. After the solvent was distilled off under reduced pressure, the resulting crude product was purified by silica gel column chromatography (chloroform-methanol, 99:1→95:5→90:10, v/v) to obtain 341 mg of compound 171D as a yellow gummy substance and 338 mg of compound 171E as a colorless solid.

171D: $^1$H-NMR (CDCl$_3$) δ: 1.29 (3H, t, J=7.1 Hz), 1.51 (1H, d, J=13.7 Hz), 1.97 (1H, m), 2.91 (1H, dd, J=13.8, 9.8 Hz), 2.99-3.10 (2H, m), 3.90 (1H, td, J=12.1, 2.5 Hz), 4.12 (2H, m), 4.25 (2H, m), 4.83 (2H, m), 5.33 (1H, d, J=10.1 Hz), 5.51 (1H, d, J=10.1 Hz), 6.88 (2H, m), 7.23-7.40 (7H, m), 7.68 (2H, m)

171E: $^1$H-NMR (CDCl$_3$) δ: 1.19 (3H, t, J=7.2 Hz), 1.82-1.99 (2H, m), 2.73 (1H, dd, J=14.0, 11.3 Hz), 3.13 (1H, m), 3.35 (1H, dd, J=14.0, 3.4 Hz), 3.63 (1H, m), 3.90-4.26 (4H, m), 4.43 (1H, d, J=13.6 Hz), 5.27 (1H, t, J=3.5 Hz), 5.31 (2H, s), 6.78 (2H, dd, J=6.3, 3.2 Hz), 7.01 (1H, d, J=7.0 Hz), 7.18 (3H, t, J=3.1 Hz), 7.28-7.39 (3H, m), 7.67 (2H, m).

Fifth Step

Compound 171D (329 mg, 0.673 mmol) was dissolved in ethanol (2 ml) and THF (4 ml), a 2N aqueous sodium hydroxide solution (1.69 ml, 3.38 mmol) was added, and the mixture was stirred at room temperature for 1 hour. To the reaction solution was added 2N hydrochloric acid, the mixture was extracted with ethyl acetate, and the extract was dried with sodium sulfate. The solvent was concentrated under reduced pressure to obtain 215 mg of compound 171F as a colorless solid.

MS: m/z=461 [M+H]$^+$.

Sixth Step

To compound 171F (50 mg, 0.11 mmol) was added trifluoroacetic acid (2 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, chloroform-methanol-ethyl ether were added, and the precipitated solid was filtered to obtain 24 mg of compound 171 as a colorless solid.

$^1$H-NMR (DMSO-d$_6$) δ: 1.63 (1H, d, J=12.6 Hz), 1.83 (1H, m), 2.96-3.29 (3H, m), 4.05 (2H, m), 4.55 (1H, dd, J=13.2, 4.4 Hz), 5.08 (1H, dd, J=9.2, 5.4 Hz), 5.30 (1H, s), 7.19 (5H, m), 8.09 (1H, s), 12.84 (1H, brs).

MS: m/z=371 [M+H]$^+$.

REFERENCE EXAMPLE 172

[Chemical formula 223]

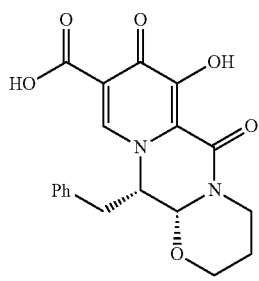

172

According to Reference example 171, using compound 171E, compound 172 was synthesized by the same procedure.

¹H-NMR (DMSO-d₆) δ: 1.91 (2H, m), 2.94 (1H, dd, J=14.0, 10.8 Hz), 3.11-3.21 (3H, m), 3.71 (1H, m), 4.19 (1H, m), 4.29-4.35 (1H, m), 5.08-5.14 (1H, m), 5.47 (1H, d, J=4.0 Hz), 6.92-7.22 (5H, m), 7.71 (1H, s), 12.80 (1H, brs), 15.06 (1H, brs).

MS: m/z=371 [M+H]⁺.

REFERENCE EXAMPLE 173

[Chemical formula 224]

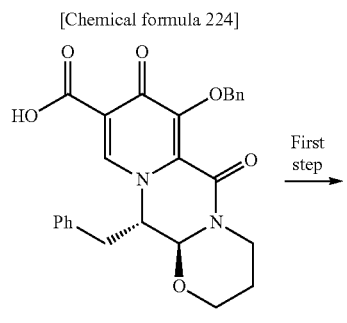

171F

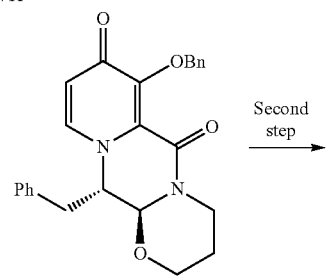

173A

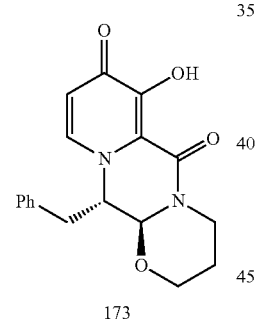

173

First Step

Compound 171F (159 mg, 0.345 mmol) was added to diphenyl ether (2.5 ml), and the mixture was stirred at 245° C. for 1 hour under microwave irradiation. The reaction solution was poured into n-hexane, and the precipitated solid was filtered. The resulting crude product was purified by silica gel column chromatography (chloroform-methanol, 95:5→90:10, v/v) to obtain compound 173A.

Second Step

To compound 173A obtained in the first step was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 10 mg of compound 173 as a colorless solid.

¹H-NMR (DMSO-d₆) δ: 1.55-1.86 (2H, m), 2.84-3.26 (3H, m), 3.92-4.09 (2H, m), 4.55 (2H, m), 5.15 (1H, s), 5.89 (1H, d, J=7.5 Hz), 7.17 (6H, m), 12.11 (1H, brs)

MS: m/z=327 [M+H]⁺.

REFERENCE EXAMPLE 174

[Chemical formula 225]

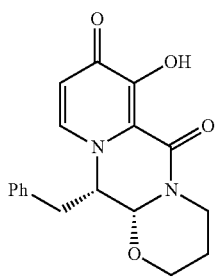

174

According to Reference example 173, compound 174 was synthesized by the same procedure.

¹H-NMR (DMSO-d₆) δ: 1.86 (2H, m), 2.87 (1H, t, J=12.3 Hz), 3.18 (2H, m), 3.68 (1H, t, J=10.4 Hz), 4.16 (1H, d, J=10.1 Hz), 4.29 (1H, d, J=12.4 Hz), 4.71 (1H, d, J=9.2 Hz), 5.37 (1H, d, J=3.5 Hz), 5.75 (1H, d, J=7.5 Hz), 7.00 (6H, m), 12.51 (1H, brs).

MS: m/z=327 [M+H]⁺.

REFERENCE EXAMPLE 175

[Chemical formula 226]

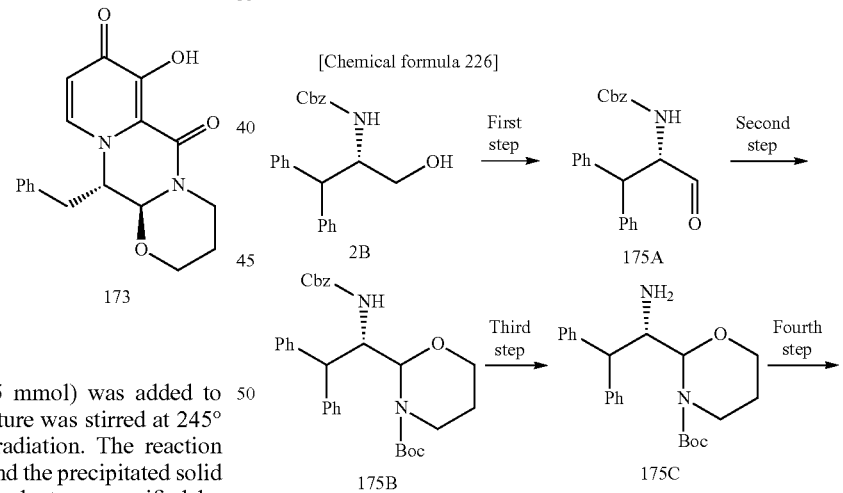

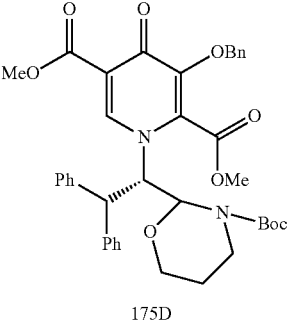

175D

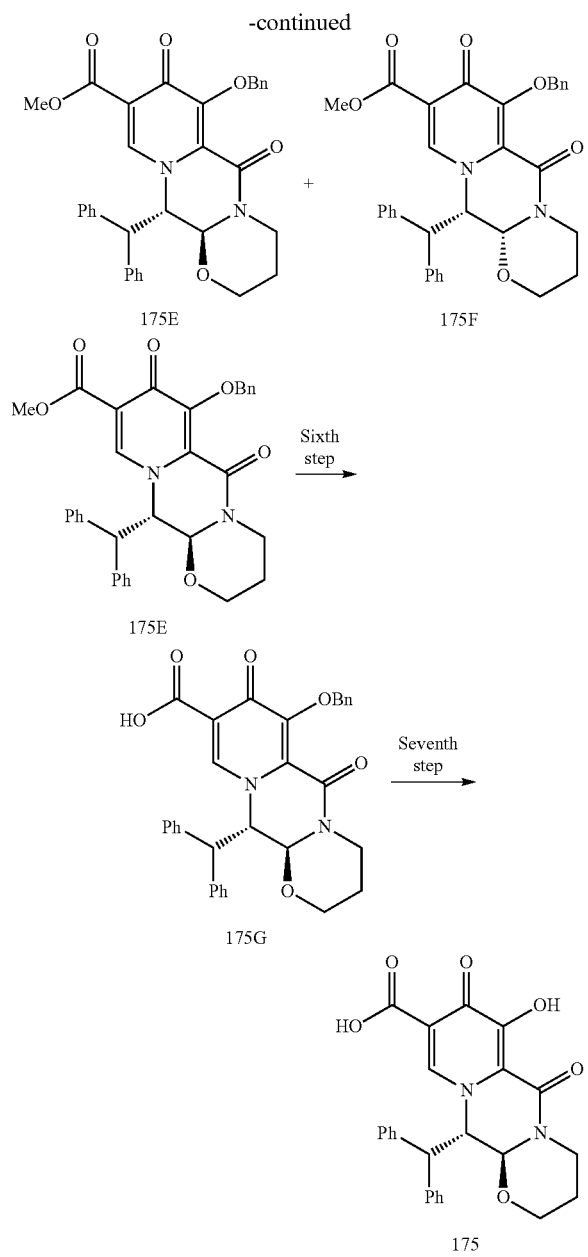

First Step

To Dess-Martin Periodinane (0.3M, methylene chloride solution, 25.0 ml, 7.50 mmol) was added dropwise a methylene chloride solution (10 ml) of compound 2B (1.98 g, 5.48 mmol) at 0° C. After stirring at room temperature for 3 hours, the reaction mixture was poured into a 1N aqueous sodium hydroxide solution, and the mixture was extracted with ethyl ether. The organic layer was washed with a 1N aqueous sodium hydroxide solution and an aqueous saturated sodium chloride solution, and dried with magnesium sulfate. After the solvent was distilled off under reduced pressure, purification was performed by silica gel column chromatography (n-hexane-ethyl acetate, 2:1, v/v) to obtain 1.73 g of compound 175A as a white solid.

$^1$H-NMR (CDCl$_3$) δ: 4.55 (1H, d, J=7.3 Hz), 5.09 (2H, s), 5.14 (2H, m), 7.22-7.35 (15H, m), 9.62 (1H, s).

Second Step

Compound 175A (1.30 g, 4.59 mmol), 3-aminopropan-1-ol (379 mg, 5.05 mmol) and sodium sulfate (3.26 g, 22.4 mmol) were added to toluene (40 ml), and the mixture was stirred at room temperature for 1 hour. Boc2O (1.17 ml, 5.05 mmol) was added at room temperature, and the mixture was stirred for 18 hours. Boc2O (1.17 ml, 5.05 mmol) and sodium sulfate (3.26 g, 22.4 mmol) were added, and the mixture was stirred for 60 hours. The reaction solution was filtered, and the filtrate was concentrated under reduced pressure. The resulting crude product was purified by silica gel column chromatography (n-hexane-ethyl acetate, 1:1, v/v) to obtain 635 mg of compound 175B as a colorless solid.

Third Step

Compound 175B (632 mg, 1.22 mmol) and palladium-active carbon (10%, wet, 100 mg) were added to ethanol (10 ml) and THF (5 ml), and the mixture was stirred at room temperature for 3 hours under hydrogen atmosphere. After filtration with celite, the solvent was concentrated under reduced pressure to obtain 502 mg of a colorless oily substance 175C.

$^1$H-NMR (CDCl$_3$) δ: 1.45 (9H, s), 1.77 (2H, m), 3.18-3.27 (1H, m), 3.43-3.51 (1H, m), 4.04 (4H, m), 4.92 (1H, d, J=4.7 Hz), 7.28 (10H, m).

Fourth Step

Dimethyl 3-(benzyloxy)-4-oxo-4H-pyran-2,5-dicarboxylate (390 mg, 1.22 mmol) and compound 175C (468 mg, 1.22 mmol) were added to toluene (5 ml), and the mixture was stirred at 100° C. for 2 hours. After the solvent was distilled off under reduced pressure, the resulting crude product was purified by silica gel column chromatography (n-hexane-ethyl acetate, 1:1, v/v) to obtain 391 mg of compound 175D as a pale yellow gummy substance.

Fifth Step

To compound 175D (388 mg, 0.568 mmol) was added 4N HCl (ethyl acetate solution, 4 ml). After the mixture was stirred at room temperature for 1 hour, the solvent was distilled off under reduced pressure. Subsequently, toluene (4 ml) and 3-aminopropan-1-ol (0.0870 ml, 1.14 mmol) were added, and the mixture was stirred at 80° C. for 5 hours. After the solvent was distilled off under reduced pressure, the resulting crude product was purified by silica gel column chromatography (chloroform-methanol, 98:2, v/v) to obtain 57 mg of compound 175E as a yellow gummy substance and 44 mg of compound 175F as a brown gummy substance.

175E: $^1$H-NMR (CDCl$_3$) δ: 1.91-2.00 (2H, m), 2.87 (1H, m), 3.78 (3H, s), 3.87-4.15 (3H, m), 4.61 (1H, d, J=12.1 Hz), 4.78 (2H, m), 5.33 (1H, d, J=10.2 Hz), 5.63 (1H, d, J=10.2 Hz), 6.95 (2H, m), 7.13-7.53 (12H, m), 7.76 (2H, m)

175F: $^1$H-NMR (CDCl$_3$) δ: 1.83-1.97 (2H, m), 3.12-3.22 (1H, m), 3.50 (1H, m), 3.85 (3H, s), 3.90 (1H, m), 4.34-4.40 (1H, m), 4.74 (1H, d, J=8.6 Hz), 4.84-4.89 (1H, m), 5.09 (1H, d, J=3.3 Hz), 5.15 (1H, d, J=9.9 Hz), 5.26 (1H, d, J=9.6 Hz), 7.08-7.50 (13H, m), 7.65-7.77 (3H, m).

Sixth Step

Compound 175E (57 mg, 0.10 mmol) was dissolved in THF (0.5 ml) and ethanol (0.5 ml), a 2N aqueous sodium hydroxide solution (0.25 ml, 0.50 mmol) was added at room temperature, and the mixture was stirred for 1 hour. After 1N hydrochloric acid was added, and the mixture was extracted with chloroform, the extract was dried with sodium sulfate. The solvent was distilled off under reduced pressure, the resulting crude product was purified by silica gel column chromatography (chloroform-methanol, 98:2, v/v) to obtain compound 175G.

Seventh Step

To compound 175G obtained in the sixth step was added trifluoroacetic acid (1 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-methanol-ethyl ether were added, and the precipitated solid was filtered to obtain 11 mg of compound 175 as a colorless solid.

$^1$H-NMR (DMSO-$d_6$) δ: 1.50 (1H, d, J=13.1 Hz), 1.79 (1H, m), 3.17 (1H, m), 3.86 (1H, t, J=11.0 Hz), 4.03 (1H, dd, J=10.8, 4.1 Hz), 4.46 (1H, d, J=12.0 Hz), 4.53 (1H, dd, J=12.7, 4.2 Hz), 4.84 (1H, s), 5.85 (1H, d, J=11.7 Hz), 7.22 (7H, m), 7.44 (2H, t, J=7.6 Hz), 7.65 (2H, d, J=7.3 Hz), 8.14 (1H, s), 12.75 (1H, s), 15.33 (1H, brs).

MS: m/z=447 [M+H]$^+$.

REFERENCE EXAMPLE 176

[Chemical formula 227]

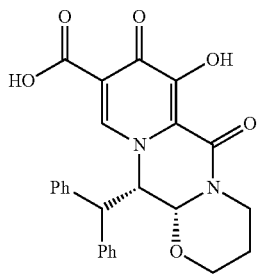

176

According to Reference example 175, using compound 175F, compound 176 was synthesized by the same procedure.

$^1$H-NMR (DMSO-$d_6$) δ: 1.75 (2H, m), 3.17 (2H, m), 3.43 (1H, m), 3.60 (1H, d, J=10.7 Hz), 4.31 (1H, d, J=12.7 Hz), 4.73 (1H, d, J=9.8 Hz), 5.52 (1H, d, J=3.4 Hz), 5.87 (1H, dd, J=9.9, 3.4 Hz), 7.10 (7H, m), 7.29 (2H, t, J=7.5 Hz), 7.58 (2H, d, J=7.3 Hz), 8.37 (1H, s), 12.65 (1H, brs).

MS: m/z=447 [M+H]$^+$.

REFERENCE EXAMPLE 177

[Chemical formula 228]

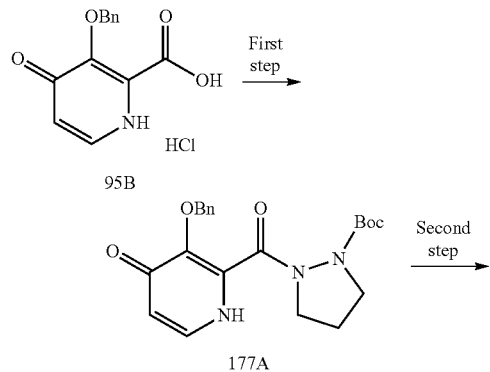

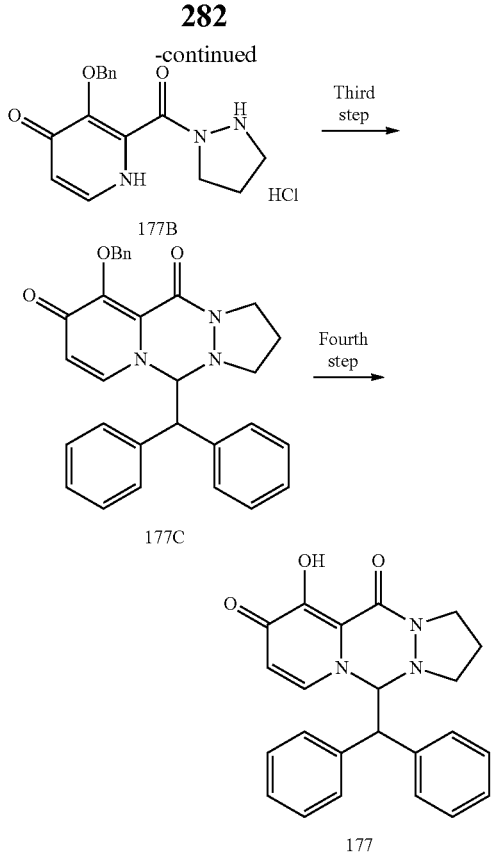

First Step

Tert-butyl pyrazolidine-1-carboxylate (275 mg, 1.60 mmol) synthesized according to the method of the reference (Journal of the Chemical Society, Perkin Transactions 1: Organic and Bio-Organic Chemistry (1972-1999), 1975, p. 1712), and compound 95B (409 mg, 1.45 mmol) were dissolved in pyridine (5 ml), HATU (607 mg, 1.60 mmol) was added at room temperature, and the mixture was stirred for 18 hours. The reaction solution was poured into 1N hydrochloric acid, and the mixture was extracted with ethyl acetate, and dried with sodium sulfate. The solvent was distilled off under reduced pressure, and the resulting crude product was purified by silica gel column chromatography (chloroform-methanol, 97:3→95:5, v/v) to obtain 529 mg of compound 177A as a yellow solid.

$^1$H-NMR (CDCl$_3$) δ: 1.35 (9H, s), 1.88-2.10 (2H, m), 3.04 (1H, s), 3.31 (1H, s), 3.86 (2H, m), 4.96 (1H, d, J=9.3 Hz), 5.45 (1H, d, J=11.0 Hz), 6.56 (1H, d, J=6.7 Hz), 7.29-7.43 (6H, m).

Second Step

To compound 177A (525 mg, 1.31 mmol) was added 4N HCl (dioxane solution, 6 ml). After the mixture was stirred at room temperature for 1.5 hours, the solvent was distilled off under reduced pressure to obtain 413 mg of compound 177B as a colorless solid.

$^1$H-NMR (DMSO-$d_6$) δ: 1.95-2.05 (2H, m), 2.78 (2H, t, J=6.6 Hz), 3.41-3.54 (2H, m), 5.11 (2H, s), 7.38 (5H, m), 7.46 (1H, d, J=6.6 Hz), 8.36 (1H, d, J=6.7 Hz).

Third Step

Compound 177B (100 mg, 0.298 mmol) was added to ethanol (2 ml), 2,2-diphenylacetaldehyde (58 mg, 0.30 mmol), triethylamine (0.083 ml, 0.596 mmol) and acetic acid (0.051 ml, 0.89 mmol) were added, and the mixture was stirred at 80° C. for 3 hours. The reaction solution was poured into water, the mixture was extracted with chloroform, and the extract was dried with sodium sulfate. The solvent was distilled off under reduced pressure, and the resulting crude product was purified by silica gel column chromatography (chloroform-methanol, 97:3→95:5→93:7→90:10, v/v) to obtain 106 mg of compound 177C as a yellow gummy substance.

MS: m/z=478 [M+H]$^+$.

Fourth Step

To compound 177C obtained in the third step was added trifluoroacetic acid (2 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 7 mg of compound 177 as a colorless solid.

$^1$H-NMR (DMSO-d$_6$) δ: 1.95 (2H, m), 2.76 (1H, m), 2.96-3.17 (2H, m), 4.04 (1H, m), 4.68 (1H, d, J=10.4 Hz), 5.66 (1H, d, J=7.3 Hz), 6.56 (1H, d, J=10.5 Hz), 7.03 (1H, d, J=7.2 Hz), 7.17 (6H, m), 7.34 (2H, t, J=7.3 Hz), 7.55 (2H, d, J=7.5 Hz).

MS: m/z=388 [M+H]$^+$.

REFERENCE EXAMPLE 178

[Chemical formula 229]

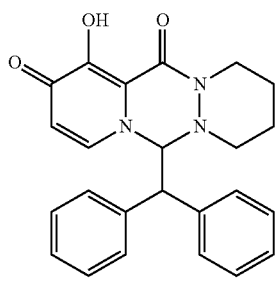

178

According to Reference example 177, compound 178 was synthesized by the same procedure.

$^1$H-NMR (DMSO-d$_6$) δ: 1.55 (4H, m), 2.35-7.49 (1H, m), 2.39 (1H, t, J=12.6 Hz), 2.77 (1H, t, J=10.0 Hz), 3.09 (1H, d, J=11.4 Hz), 4.34 (1H, d, J=12.8 Hz), 4.55 (1H, d, J=10.8 Hz), 5.71 (1H, d, J=7.0 Hz), 6.17 (1H, d, J=10.8 Hz), 6.82 (1H, d, J=7.3 Hz), 7.13-7.40 (8H, m), 7.48 (2H, d, J=7.3 Hz).

MS: m/z=402 [M+H]$^+$.

REFERENCE EXAMPLE 179

[Chemical formula 230]

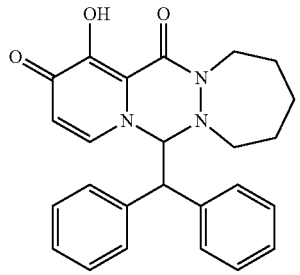

179

According to Reference example 177, compound 179 was synthesized by the same procedure.

$^1$H-NMR (DMSO-d$_6$) δ: 1.31 (6H, m), 2.68 (2H, m), 3.21 (1H, m), 4.04 (1H, m), 4.40 (1H, d, J=10.8 Hz), 5.77 (1H, t, J=5.2 Hz), 6.26 (1H, d, J=10.8 Hz), 6.78 (1H, d, J=7.3 Hz), 7.27 (8H, m), 7.53 (2H, d, J=7.2 Hz).

MS: m/z=416 [M+H]$^+$.

REFERENCE EXAMPLE 180

[Chemical formula 231]

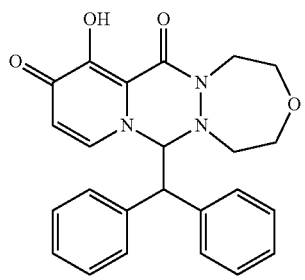

180

According to Reference example 177, compound 180 was synthesized by the same procedure.

$^1$H-NMR (DMSO-d$_6$) δ: 2.78-3.74 (7H, m), 4.17 (1H, m), 4.49 (1H, d, J=10.8 Hz), 5.79 (1H, d, J=7.2 Hz), 6.32 (1H, d, J=10.8 Hz), 6.79 (1H, d, J=7.2 Hz), 7.28 (8H, m), 7.55 (2H, d, J=7.6 Hz).

MS: m/z=418 [M+H]$^+$.

Using amines which are commercially available or known in the references and halides which are commercially available or known in the references, and according to the method of Reference example 12, Reference examples 181 to 187 were synthesized.

REFERENCE EXAMPLE 181
[Chemical formula 232]
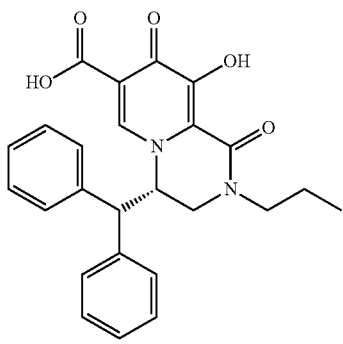
MS: m/z=433 [M+H]⁺.
REFERENCE EXAMPLE 182
[Chemical formula 233]
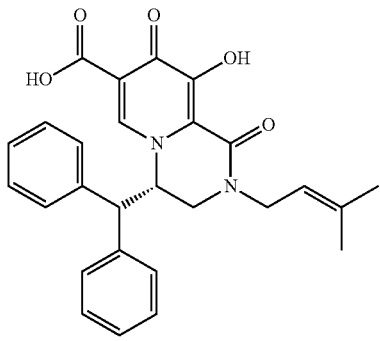
MS: m/z=459 [M+H]⁺.
REFERENCE EXAMPLE 183
[Chemical formula 234]
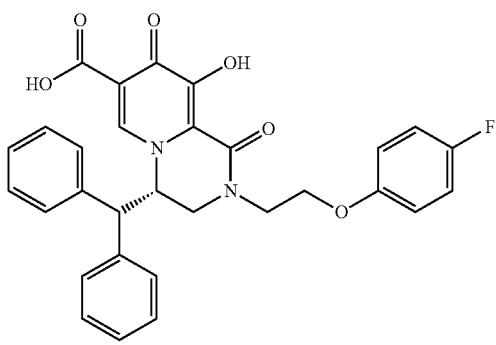
MS: m/z=529 [M+H]⁺.
REFERENCE EXAMPLE 184
[Chemical formula 235]
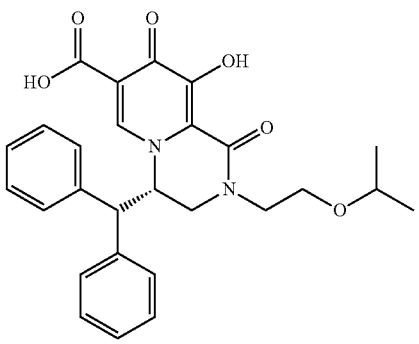
MS: m/z=477 [M+H]⁺.
REFERENCE EXAMPLE 185
[Chemical formula 236]
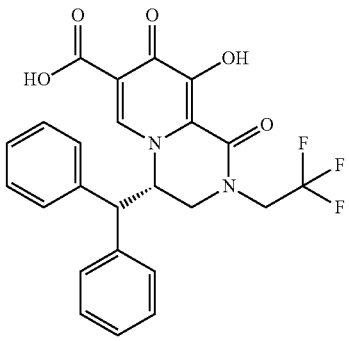
MS: m/z=473 [M+H]⁺.
REFERENCE EXAMPLE 186
[Chemical formula 237]
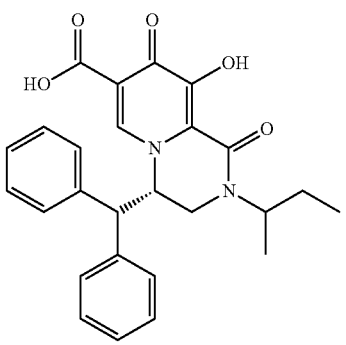
MS: m/z=447 [M+H]⁺.

REFERENCE EXAMPLE 187

[Chemical formula 238]

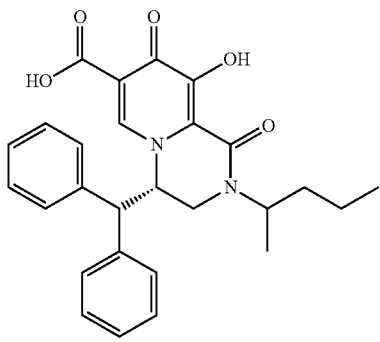

MS: m/z=461 [M+H]$^+$

REFERENCE EXAMPLE 188

[Chemical formula 239]

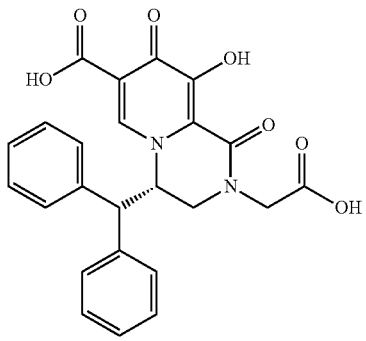

According to Reference example 12 and Reference example 129, Compound 188 was synthesized by the same procedure.

MS: m/z=449 [M+H]$^+$.

Using amines which are commercially available or known in the references and halides which are commercially available or known in the references, and according to Reference example 95, Compounds 189-229 were synthesized by the same procedure.

REFERENCE EXAMPLE 189

[Chemical formula 240]

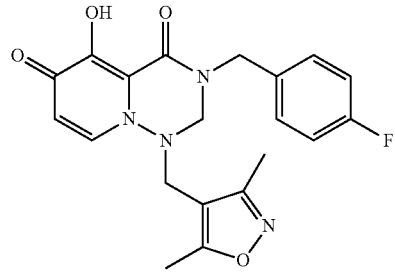

MS: m/z=399 [M+H]$^+$

REFERENCE EXAMPLE 190

[Chemical formula 241]

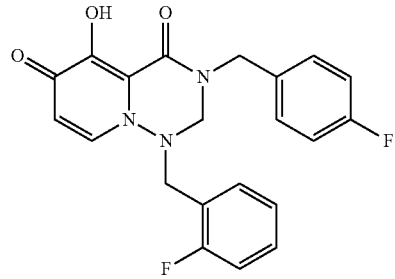

MS: m/z=488 [M+H]$^+$

REFERENCE EXAMPLE 191

[Chemical formula 242]

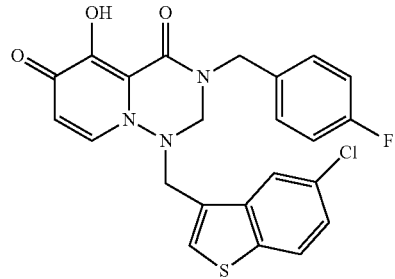

MS: m/z=470 [M+H]$^+$

REFERENCE EXAMPLE 192
[Chemical formula 243]
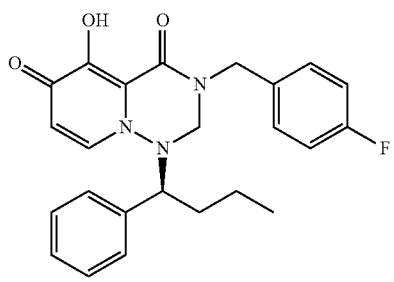
MS: m/z=422 [M+H]+.
REFERENCE EXAMPLE 193
[Chemical formula 244]
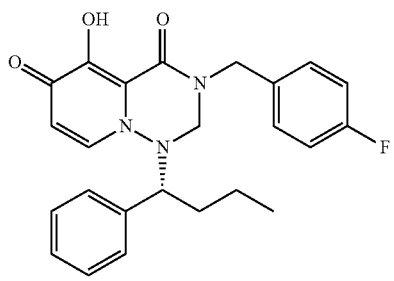
MS: m/z=422 [M+H]+
REFERENCE EXAMPLE 194
[Chemical formula 245]
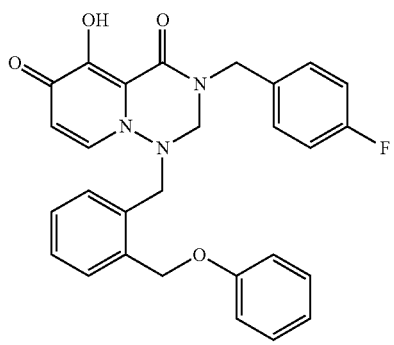
MS: m/z=486 [M+H]+
REFERENCE EXAMPLE 195
[Chemical formula 246]
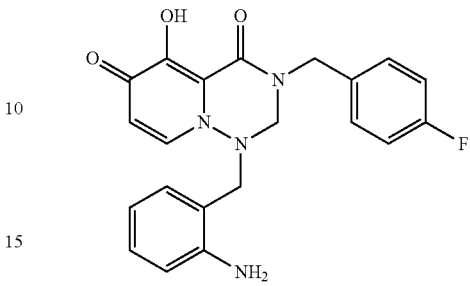
MS: m/z=365 [M+H]+
REFERENCE EXAMPLE 196
[Chemical formula 247]
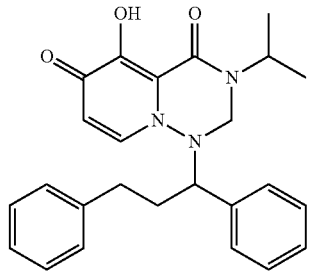
MS: m/z=418 [M+H]+
REFERENCE EXAMPLE 197
[Chemical formula 248]
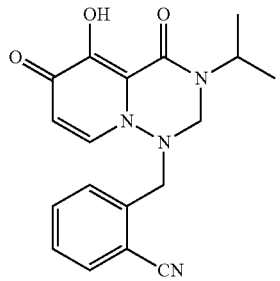
MS: m/z=339 [M+H]+

REFERENCE EXAMPLE 198
[Chemical formula 249]
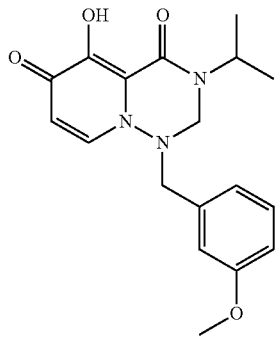
MS: m/z=344 [M+H]+
REFERENCE EXAMPLE 199
[Chemical formula 250]
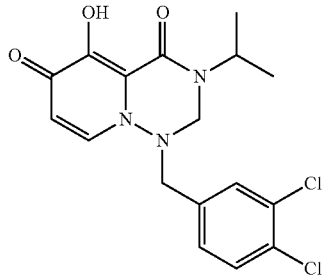
MS: m/z=383 [M+H]+
REFERENCE EXAMPLE 200
[Chemical formula 251]
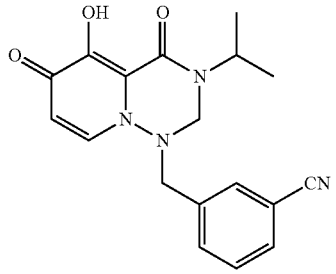
MS: m/z=339 [M+H]+
REFERENCE EXAMPLE 201
[Chemical formula 252]
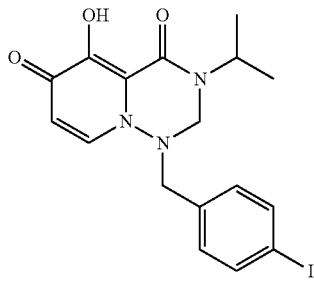
MS: m/z=440 [M+H]+
REFERENCE EXAMPLE 202
[Chemical formula 253]
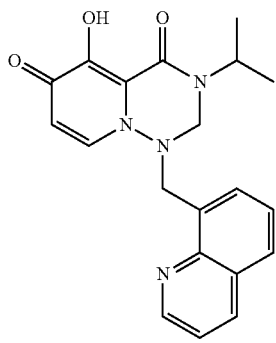
MS: m/z=365 [M+H]+
REFERENCE EXAMPLE 203
[Chemical formula 254]
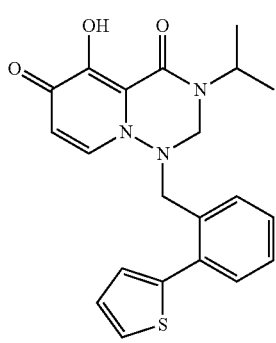
MS: m/z=396 [M+H]+

REFERENCE EXAMPLE 204
[Chemical formula 255]
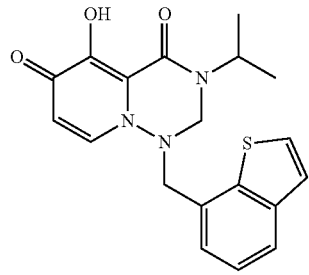
MS: m/z=370 [M+H]$^+$
REFERENCE EXAMPLE 205
[Chemical formula 256]
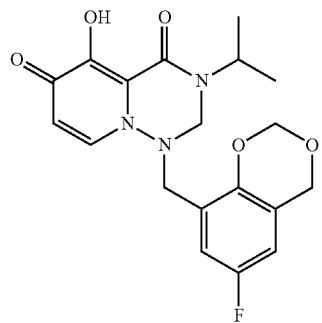
MS: m/z=390 [M+H]$^+$
REFERENCE EXAMPLE 206
[Chemical formula 257]
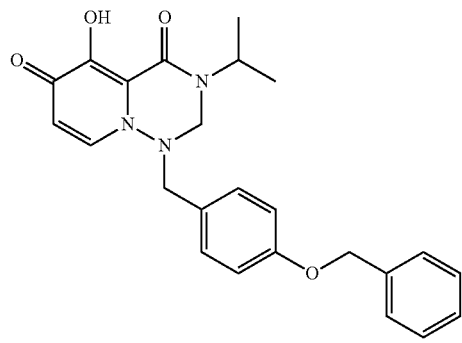
MS: m/z=420 [M+H]$^+$
REFERENCE EXAMPLE 207
[Chemical formula 258]
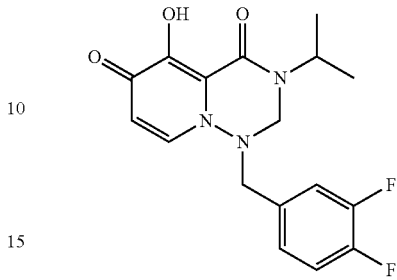
MS: m/z=350 [M+H]$^+$
REFERENCE EXAMPLE 208
[Chemical formula 259]
MS: m/z=428 [M+H]$^+$
REFERENCE EXAMPLE 209
[Chemical formula 260]
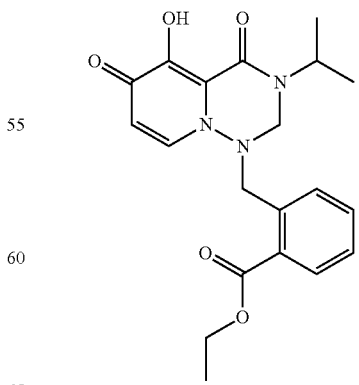
MS: m/z=386 [M+H]$^+$ REFERENCE EXAMPLE 210
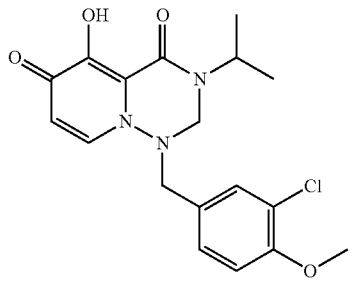
MS: m/z=378 [M+H]+
REFERENCE EXAMPLE 211
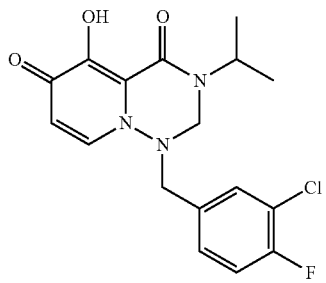
MS: m/z=366 [M+H]+
REFERENCE EXAMPLE 212
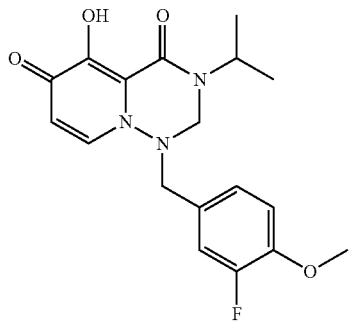
MS: m/z=362 [M+H]+
REFERENCE EXAMPLE 213
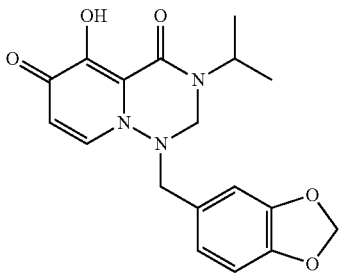
MS: m/z=358 [M+H]+
REFERENCE EXAMPLE 214
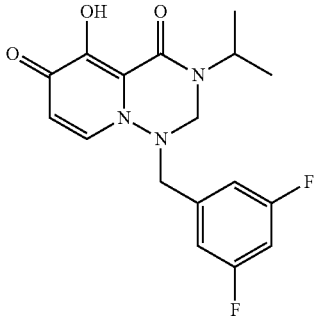
MS: m/z=350 [M+H]+
REFERENCE EXAMPLE 215
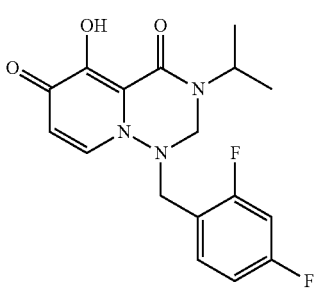
MS: m/z=350 [M+H]+

REFERENCE EXAMPLE 216
[Chemical formula 267]
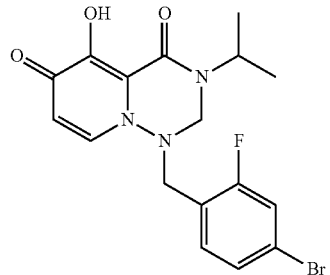
MS: m/z=411 [M+H]+
REFERENCE EXAMPLE 217
[Chemical formula 268]
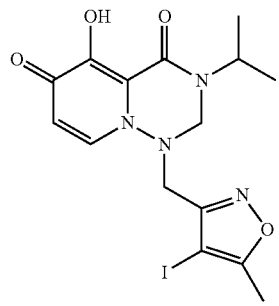
MS: m/z=445 [M+H]+
REFERENCE EXAMPLE 218
[Chemical formula 269]
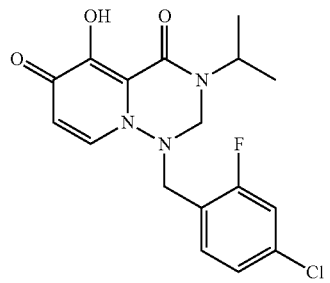
MS: m/z=366 [M+H]+
REFERENCE EXAMPLE 219
[Chemical formula 270]
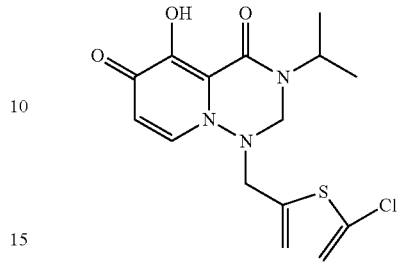
MS: m/z=354 [M+H]+
REFERENCE EXAMPLE 220
[Chemical formula 271]
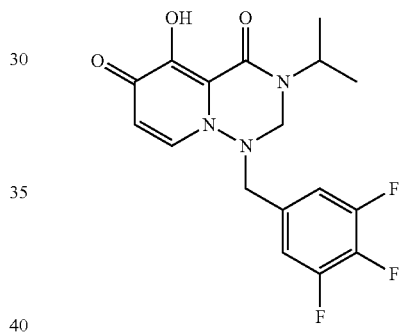
MS: m/z=368 [M+H]+
REFERENCE EXAMPLE 221
[Chemical formula 272]
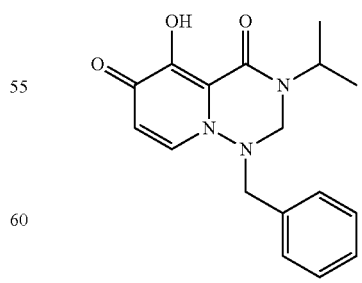
MS: m/z=314 [M+H]+

REFERENCE EXAMPLE 222
[Chemical formula 273]
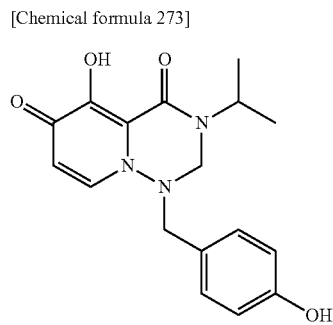 [SMILES: CC(C)N1CN(Cc2ccc(O)cc2)n2ccc(=O)c(O)c2C1=O]
MS: m/z=330 [M+H]+
REFERENCE EXAMPLE 223
[Chemical formula 274]
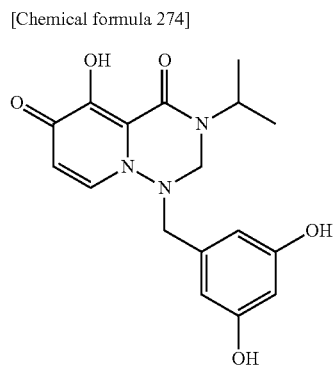 [SMILES: CC(C)N1CN(Cc2cc(O)cc(O)c2)n2ccc(=O)c(O)c2C1=O]
MS: m/z=346 [M+H]+
REFERENCE EXAMPLE 224
[Chemical formula 275]
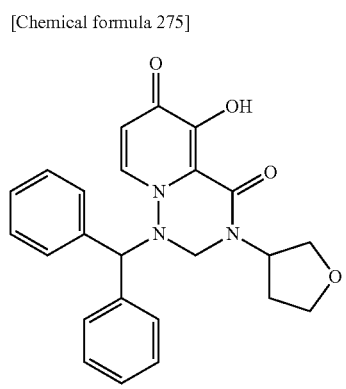 [SMILES: O=C1c2c(O)c(=O)ccn2N(C(c2ccccc2)c2ccccc2)CN1C1CCOC1]
MS: m/z=418 [M+H]+.
REFERENCE EXAMPLE 225
[Chemical formula 276]
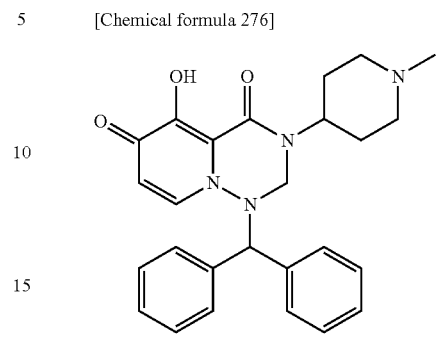
MS: m/z=445 [M+H]+.
REFERENCE EXAMPLE 226
[Chemical formula 277]
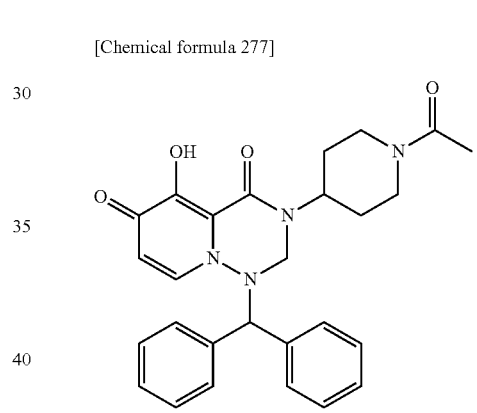
MS: m/z=473 [M+H]+.
REFERENCE EXAMPLE 227
[Chemical formula 278]
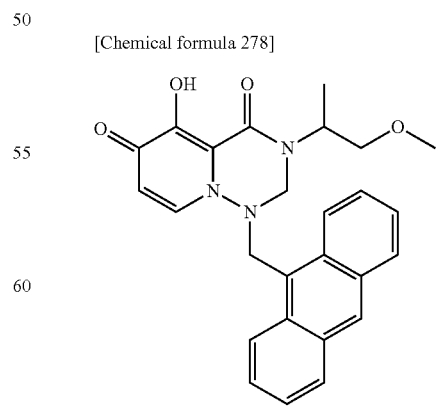
MS: m/z=444 [M+H]+.

REFERENCE EXAMPLE 228

[Chemical formula 279]

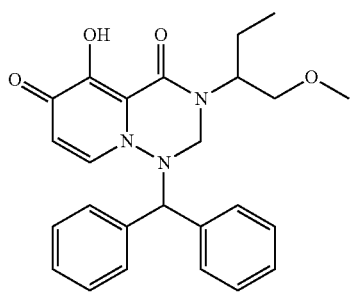

MS: m/z=434 [M+H]⁺.

REFERENCE EXAMPLE 229

[Chemical formula 280]

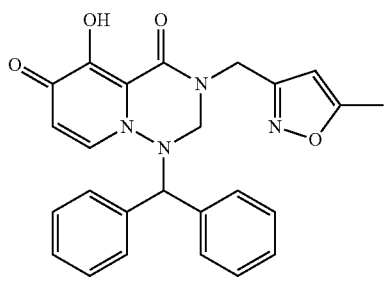

MS: m/z=443 [M+H]⁺.

REFERENCE EXAMPLE 230

[Chemical formula 281]

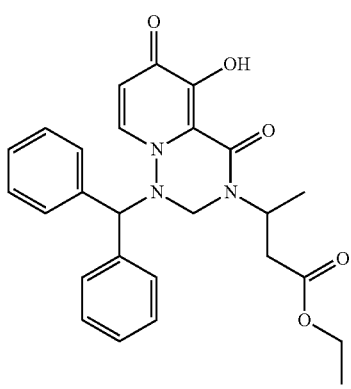

According to Reference example 128, compound 230 was synthesized by the same procedure.
MS: m/z=461 [M+H]⁺.

REFERENCE EXAMPLE 231

[Chemical formula 282]

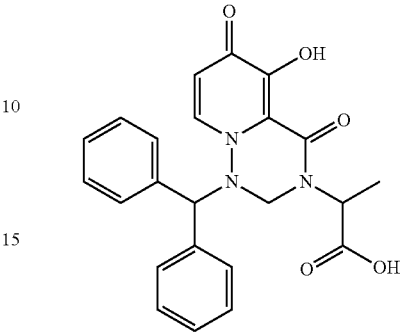

According to Reference example 129, compound 231 was synthesized by the same procedure.
MS: m/z=420 [M+H]⁺.

REFERENCE EXAMPLE 232

[Chemical formula 283]

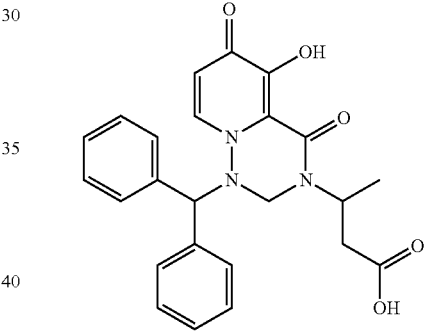

According to Reference example 129, compound 232 was synthesized by the same procedure.
MS: m/z=434 [M+H]⁺.

REFERENCE EXAMPLE 233

[Chemical formula 284]

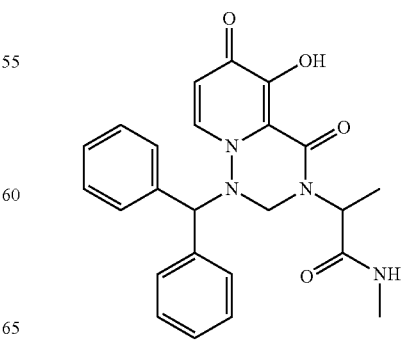

According to Reference example 130, compound 233 was synthesized by the same procedure.

MS: m/z=433 [M+H]$^+$.

REFERENCE EXAMPLE 234

[Chemical formula 285]

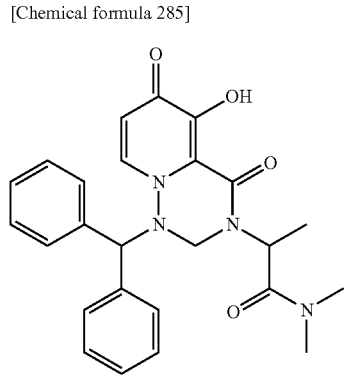 [SMILES: CC(C(=O)N(C)C)N1CN(C(c2ccccc2)c2ccccc2)n2ccc(=O)c(O)c2C1=O]

According to Reference example 130, compound 234 was synthesized by the same procedure.

MS: m/z=447 [M+H]$^+$.

REFERENCE EXAMPLE 235

[Chemical formula 286]

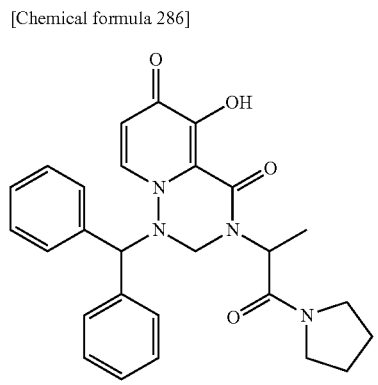 [SMILES: CC(C(=O)N1CCCC1)N1CN(C(c2ccccc2)c2ccccc2)n2ccc(=O)c(O)c2C1=O]

According to Reference example 130, compound 235 was synthesized by the same procedure.

MS: m/z=473 [M+H]$^+$.

REFERENCE EXAMPLE 236

[Chemical formula 287]

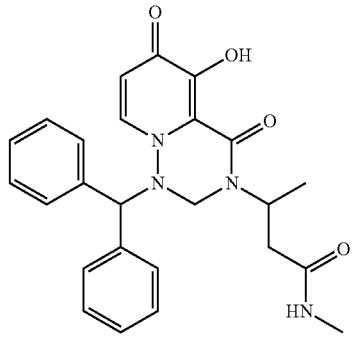

According to Reference example 130, compound 236 was synthesized by the same procedure.

MS: m/z=447 [M+H]$^+$.

REFERENCE EXAMPLE 237

[Chemical formula 288]

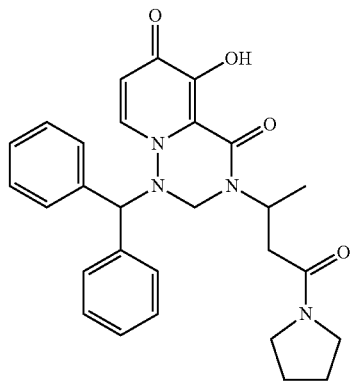

According to Reference example 130, compound 237 was synthesized by the same procedure.

MS: m/z=487 [M+H]$^+$.

REFERENCE EXAMPLE 238

[Chemical formula 289]

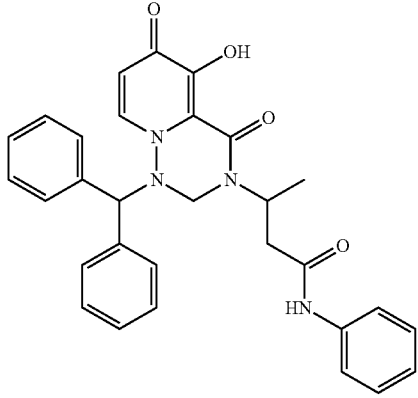

According to Reference example 130, compound 238 was synthesized by the same procedure.
MS: m/z=509 [M+H]⁺.

REFERENCE EXAMPLE 239

[Chemical formula 290]

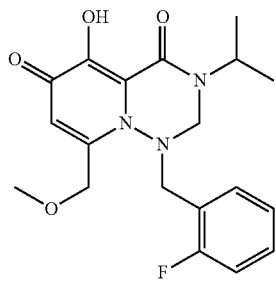

MS: m/z=376 [M+H]⁺.
According to Reference example 157, compound 239 was synthesized by the same procedure.
Using amines which are commercially available or known in the references and alcohols which are commercially available or known in the references, and according to the method of Reference example 107, Examples 240 to 245 were synthesized.

REFERENCE EXAMPLE 240

[Chemical formula 291]

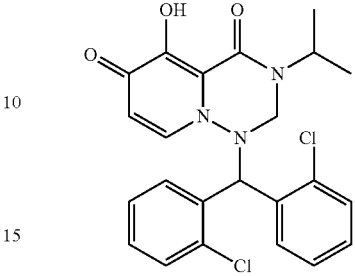

$^1$H-NMR (CDCl$_3$) δ: 1.05 (3H, d, J=6.9 Hz), 1.04-1.14 (4H, m), 4.49 (1H, d, J=13.2 Hz), 4.83 (1H, d, J=13.2 Hz), 4.91-4.99 (1H. m), 5.73 (1H, d, J=7.8 Hz), 6.50 (1H, s), 6.70 (1H, d, J=7.8 Hz), 7.12-7.30 (4H, m), 7.33-7.43 (2H, m), 7.46-7.54 (1H, m), 8.06 (1H, d, J=7.5 Hz).

REFERENCE EXAMPLE 241

[Chemical formula 292]

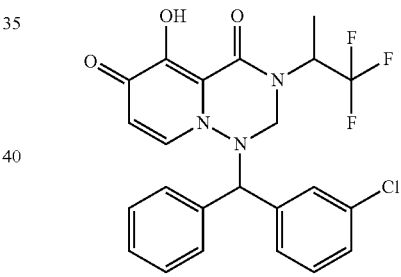

MS: m/z=478 [M+H]⁺

REFERENCE EXAMPLE 242

[Chemical formula 293]

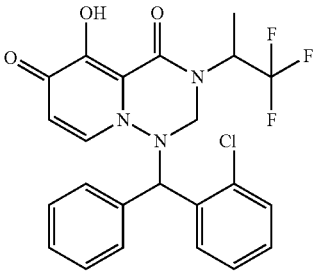

MS: m/z=478 [M+H]⁺

REFERENCE EXAMPLE 243
[Chemical formula 294]
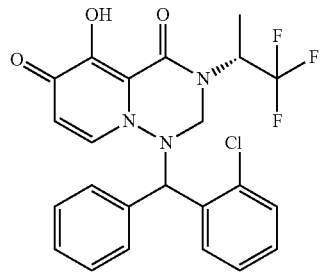
MS: m/z=478 [M+H]+
REFERENCE EXAMPLE 244
[Chemical formula 295]
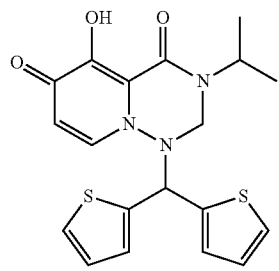
¹H-NMR (CDCl₃) δ: 1.14 (6H, d, J=6.9 Hz), 4.59 (1H, d, J=12.6 Hz), 4.77 (1H, d, J=12.6 Hz), 4.81-4.91 (1H, m), 5.82 (1H, d, J=7.5 Hz), 5.82 (1H, s), 6.71 (1H, brs), 6.78 (1H, brs), 6.87 (1H, d, J=7.5 Hz), 7.05 (1H, brs), 7.16 (1H, brs), 7.25 (1H, brs), 7.41 (1H, brs).
REFERENCE EXAMPLE 245
[Chemical formula 296]
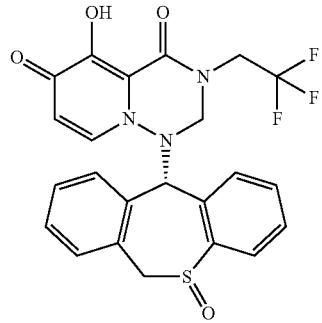
MS: m/z=490 [M+H]+.
REFERENCE EXAMPLE 246
[Chemical formula 297]
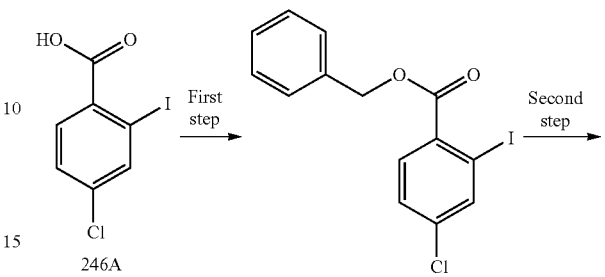
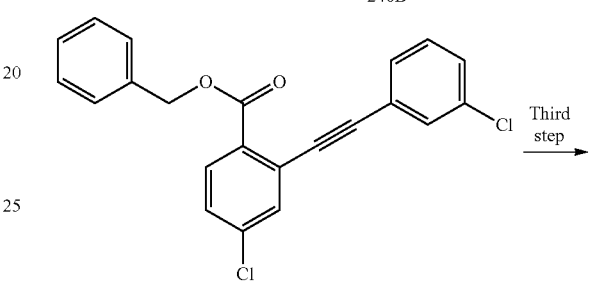
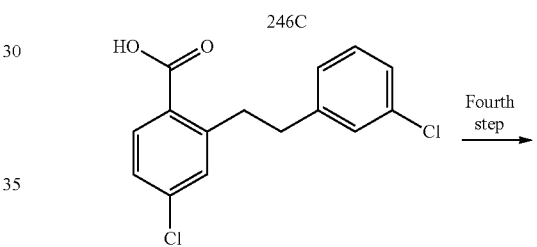
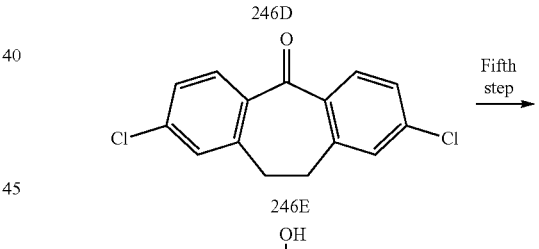
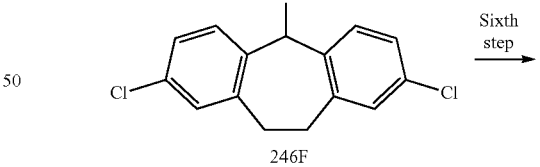
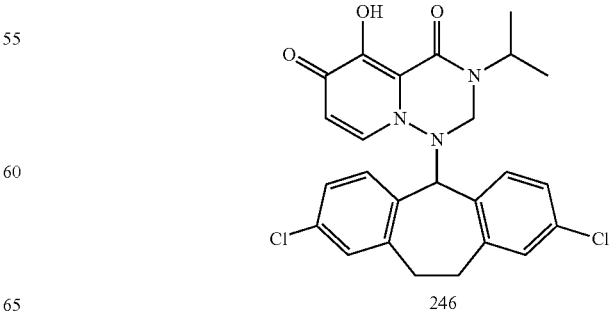

First Step

To a dimethylformamide (20 ml) solution of compound 246A (5.30 g, 18.76 mmol) and potassium carbonate (5.19 g, 27.53 mmol) was added benzyl bromide (3.21 g, 18.76 mmol), and the mixture was stirred at room temperature for 1 hour. To the reaction solution was added ethyl acetate (80 ml), insolubles were filtered off, and 1N hydrochloric acid was added. The organic layer was separated, and the aqueous layer was extracted with ethyl acetate two times. The combined organic layers were washed with water once and, further, washed with sodium bicarbonate water once, and with an aqueous saturated sodium chloride solution once. The resulting solution was dried with sodium sulfate, and the solvent was distilled off to obtain 6.98 g of compound 246B as an oil.

$^1$H-NMR (CDCl$_3$) δ: 5.36 (2H, s), 7.35-7.47 (6H, m), 7.78 (1H, d, J=8.4 Hz), 8.01 (1H, d, J=2.1 Hz).

Second Step

To a dimethylformamide (15 ml) solution of compound 246B (3 g, 8.05 mmol) and 1-chloro-3-ethynylbenzene (1.32 g, 9.66 mmol) and triethylamine (4.07 g, 40.25 mmol) were added copper chloride (76.6 mg, 0.403 mmol) and dichlorobis(triphenylphosphine)palladium (282.5 mg, 0.403 mmol) under nitrogen atmosphere, and the mixture was stirred at room temperature for 5 hours. The reaction solution was diluted with water, and the mixture was extracted with ethyl acetate three times. The combined extracts were washed with water three times, and dried with sodium sulfate, then the solvent was distilled off. The resulting oil was purified by silica gel column chromatography. The materials were eluted firstly with hexane and, then, with hexane-ethyl acetate (7:3, v/v). Concentration of an objective fraction afforded 3.10 g of compound 246C as an oil.

$^1$H-NMR (CDCl$_3$) δ: 5.39 (2H, s), 7.21-7.46 (9H, m), 7.62 (1H, d, J=2.1 Hz), 7.98 (1H, d, J=8.4 Hz).

Third Step

To a methanol (30 ml) solution of compound 246C (3.10 g, 8.05 mmol) was added 10% palladium carbon (620 mg, 20 wt %), and the mixture was stirred at room temperature under 1 atm hydrogen atmosphere. The reaction solution was filtered with celite, the solvent was distilled off, to the resulting crude product were added ethyl acetate-diisopropyl ether, and the precipitated residue was filtered to obtain 618 mg of compound 246D as a solid.

$^1$H-NMR (CDCl$_3$) δ: 2.90 (2H, dd, J=7.8 Hz, 10.8 Hz), 3.29 (2H, dd, J=7.5 Hz, 10.5 Hz), 7.06-7.09 (1H, m), 7.18-7.25 (4H, m), 7.31 (1H, dd, J=2.1 Hz, 8.7 Hz), 8.05 (1H, d, J=8.4 Hz).

Fourth Step

To compound 246D (2.20 g, 7.45 mmol) was added polyphosphoric acid (20 g), and the mixture was stirred at 200° C. for 1 hour. After cooled to room temperature, water was added, and the mixture was extracted with ethyl acetate three times. The combined extracts were washed with saturated sodium bicarbonate water once, and dried with sodium sulfate and, thereafter, the solvent was distilled off. The resulting oil was purified by silica gel column chromatography. The materials were eluted firstly with hexane and, then, with hexane-ethyl acetate (7:3, v/v). Concentration of an objective fraction afforded 1.05 g of compound 246E as an oil.

$^1$H-NMR (CDCl$_3$) δ: 3.17 (4H, s), 7.24 (2H, d, J=2.1 Hz), 7.32 (2H, dd, J=2.1 Hz, 8.4 Hz), 8.00 (2H, d, J=8.4 Hz).

Fifth Step

A methanol (10 ml) suspension of sodium borohydride (409 mg, 10.82 mmol) was cooled to 1 to 3° C., and compound 246E (1.0 g, 3.61 mmol) was added while the same temperature was retained. After the reaction solution was stirred at the same temperature for 30 minutes, water was added. The precipitated solid was filtered to obtain 968 mg of compound 246F.

$^1$H-NMR (CDCl$_3$) δ: 2.25 (1H, d, J=3.0 Hz), 3.05-3.16 (2H, m), 3.27-3.38 (2H, m), 5.95 (1H, d, J=3.0 Hz), 7.14-7.17 (4H, m), 7.39 (2H, d, J=8.1 Hz).

Sixth Step

According to Reference example 107, compound 246 was synthesized by the same procedure.

$^1$H-NMR (CDCl$_3$) δ: 1.14 (3H, d, J=6.9 Hz), 1.20 (3H, d, J=6.9 Hz), 2.79 (1H, ddd, J=4.5 Hz, 4.5 Hz, 14.4 Hz), 2.99-3.11 (1H, m), 3.50 (1H, ddd, J=4.8 Hz, 4.8 Hz, 17.7 Hz), 4.21-4.33 (1H, m), 4.23 (1H, d, J=12.9 Hz), 4.62-4.74 (2H, m), 5.04 (1H, s), 5.84 (1H, d, J=7.8 Hz), 6.57 (1H, d, J=8.1 Hz), 6.65-6.72 (2H, m), 6.89-6.92 (1H, m), 7.11-7.30 (4H, m).

Using amines which are commercially available or known in the references and intermediates corresponding to compound 246A to compound 246F which are commercially available or known in the references, and according to the method of Reference example 246, compounds 247 to 284 were synthesized.

REFERENCE EXAMPLE 247

[Chemical formula 298]

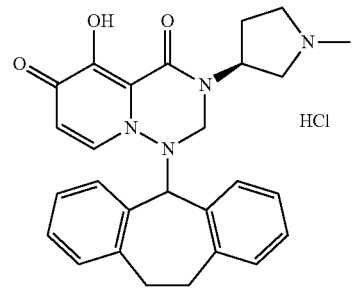

MS: m/z=457 [M+H]$^+$.

REFERENCE EXAMPLE 248

[Chemical formula 299]

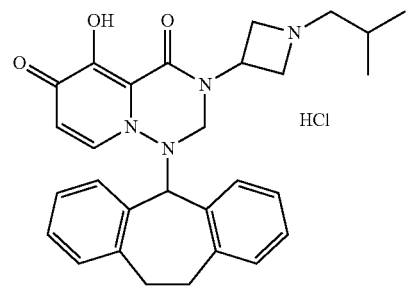

MS: m/z=485 [M+H]$^+$.

REFERENCE EXAMPLE 249
[Chemical formula 300]
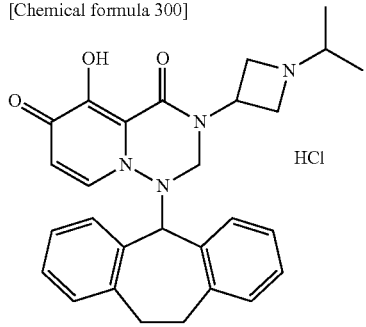 [SMILES: CC(C)N1CC(N2CN(C3c4ccccc4CCc4ccccc43)n3ccc(=O)c(O)c3C2=O)C1 ; Cl]
MS: m/z=471 [M+H]+.
REFERENCE EXAMPLE 250
[Chemical formula 301]
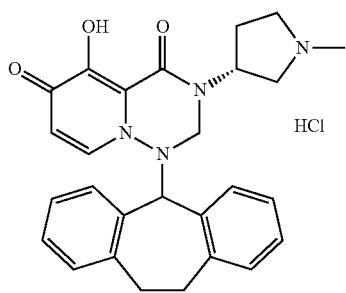
MS: m/z=457 [M+H]+.
REFERENCE EXAMPLE 251
[Chemical formula 302]
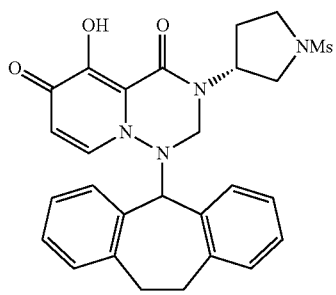
MS: m/z=521 [M+H]+.
REFERENCE EXAMPLE 252
[Chemical formula 303]
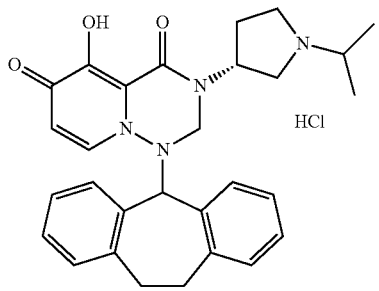
MS: m/z=485 [M+H]+.
REFERENCE EXAMPLE 253
[Chemical formula 304]
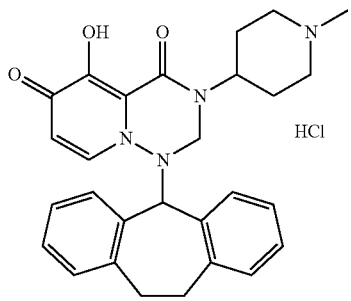
MS: m/z=471 [M+H]+.
REFERENCE EXAMPLE 254
[Chemical formula 305]
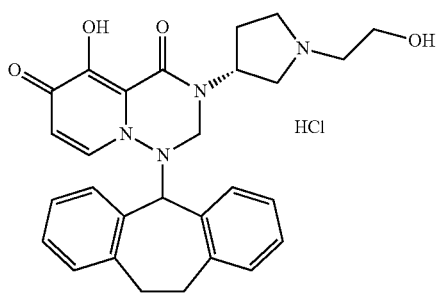
MS: m/z=487 [M+H]+.

REFERENCE EXAMPLE 255

[Chemical formula 306]

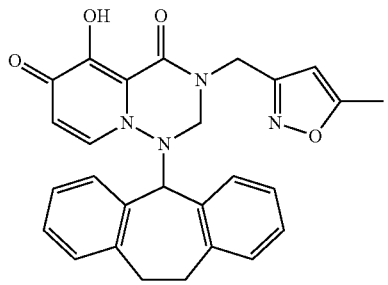

MS: m/z=469 [M+H]⁺.

REFERENCE EXAMPLE 256

[Chemical formula 307]

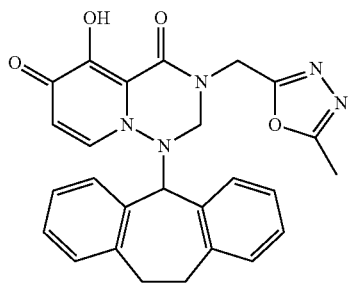

MS: m/z=470 [M+H]⁺.

REFERENCE EXAMPLE 257

[Chemical formula 308]

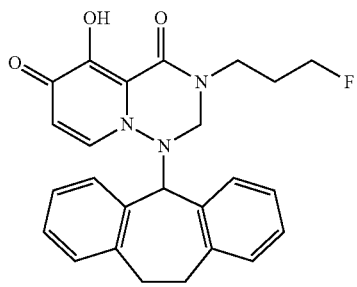

MS: m/z=434 [M+H]⁺.

REFERENCE EXAMPLE 258

[Chemical formula 309]

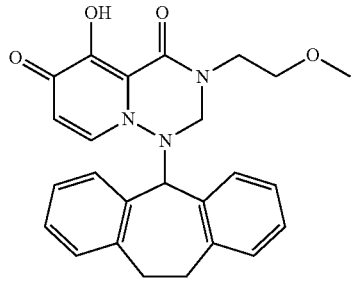

$^1$H-NMR (DMSO-$d_6$) δ: 2.88 (3H, m), 3.43 (2H, m), 3.69 (1H, dt, J=16.9, 5.1 Hz), 4.01 (1H, d, J=13.4 Hz), 4.07-4.17 (2H, m), 4.97 (1H, d, J=13.4 Hz), 5.24 (1H, s), 5.50 (1H, d, J=7.6 Hz), 6.73 (1H, d, J=7.2 Hz), 6.85-6.94 (2H, m), 7.14-7.41 (6H, m), 11.73 (1H, s).
MS: m/z=432 [M+H]⁺.

REFERENCE EXAMPLE 259

[Chemical formula 310]

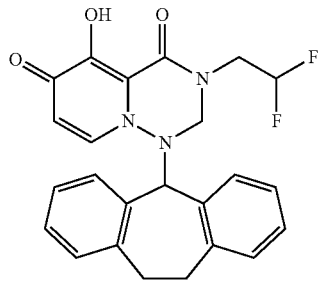

$^1$H-NMR (DMSO-$d_6$) δ: 2.80 (1H, td, J=9.6, 4.5 Hz), 2.86-2.99 (1H, m), 3.00-3.18 (1H, m), 3.67 (1H, dt, J=17.1, 5.0 Hz), 4.03-4.19 (2H, m), 4.32-4.52 (1H, m), 5.05 (1H, d, J=13.3 Hz), 5.26 (1H, s), 5.53 (1H, d, J=7.6 Hz), 6.17 (1H, tt, J=55.0, 3.5 Hz), 6.72 (1H, d, J=7.5 Hz), 6.87-6.94 (2H, m), 7.12-7.27 (3H, m), 7.30-7.43 (3H, m).
MS: m/z=438 [M+H]⁺.

REFERENCE EXAMPLE 260

[Chemical formula 311]

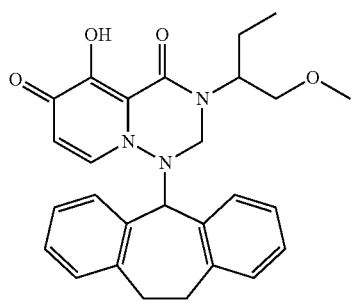

MS: m/z=460 [M+H]⁺.

REFERENCE EXAMPLE 261

[Chemical formula 312]

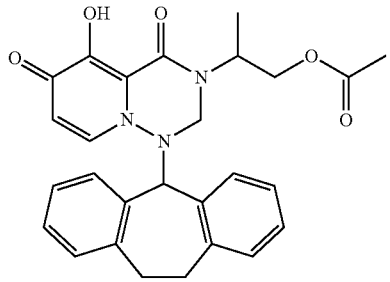

MS: m/z=474 [M+H]⁺.

REFERENCE EXAMPLE 262

[Chemical formula 313]

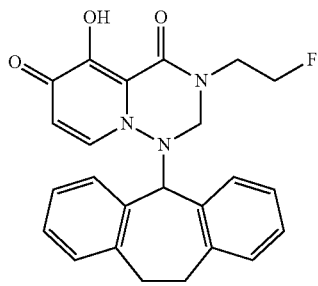

¹H-NMR (DMSO-d$_6$) δ: 2.80 (1H, dt, J=14.2, 5.1 Hz), 2.86-2.99 (1H, m), 3.00-3.18 (1H, m), 3.68 (1H, dt, J=16.9, 5.3 Hz), 4.05 (1H, d, J=13.3 Hz), 4.07-4.32 (2H, m), 4.37-4.52 (1H, m), 4.53-4.67 (1H, m), 5.02 (1H, d, J=13.0 Hz), 5.26 (1H, s), 5.50 (1H, d, J=7.8 Hz), 6.73 (1H, d, J=7.6 Hz), 6.85-6.94 (2H, m), 7.12-7.27 (3H, m), 7.30-7.43 (3H, m).
MS: m/z=420 [M+H]⁺.

REFERENCE EXAMPLE 263

[Chemical formula 314]

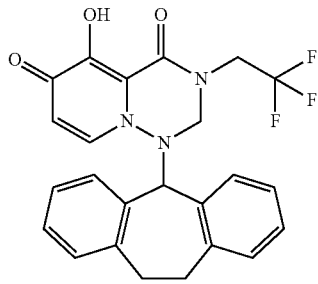

¹H-NMR (DMSO-d$_6$) δ: 2.76-3.00 (2H, m), 3.46-3.73 (2H, m), 4.06-4.22 (2H, m), 4.77-4.91 (1H, m), 5.15 (1H, d, J=12.9 Hz), 5.24 (1H, s), 5.56 (1H, d, J=7.7 Hz), 6.72 (1H, d, J=7.1 Hz), 6.88-6.95 (1H, m), 6.96 (1H, d, J=7.7 Hz), 7.09-7.41 (7H, m).

MS: m/z=456 [M+H]⁺

REFERENCE EXAMPLE 264

[Chemical formula 315]

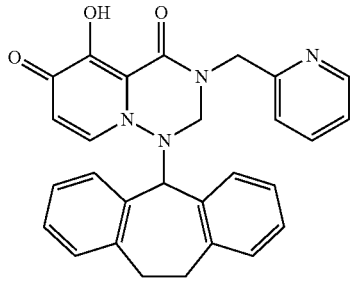

¹H-NMR (DMSO-d$_6$) δ: 2.74-2.99 (2H, m), 3.62-3.73 (1H, m), 4.01-4.20 (3H, m), 5.12 (1H, d, J=13.2 Hz), 5.15 (1H, d, J=15.7 Hz), 5.34 (1H, s), 5.52 (1H, d, J=7.7 Hz), 6.78 (1H, d, J=8.0 Hz), 6.89-6.96 (2H, m), 7.10-7.23 (5H, m), 7.27-7.35 (3H, m), 7.43 (1H, d, J=7.7 Hz), 7.79 (1H, td, J=7.6, 1.8 Hz), 8.45-8.50 (1H, m).

MS: m/z=465 [M+H]⁺.

REFERENCE EXAMPLE 265

[Chemical formula 316]

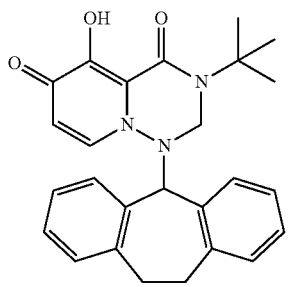

¹H-NMR (DMSO-d$_6$) δ: 1.32 (9H, s), 2.76-2.86 (1H, m), 2.87-3.01 (1H, m), 3.59-3.70 (1H, m), 4.12-4.25 (1H, m), 4.29 (1H, d, J=13.5 Hz), 4.90 (1H, d, J=13.2 Hz), 5.20 (1H, s), 5.49 (1H, d, J=7.4 Hz), 6.75 (1H, d, J=8.0 Hz), 6.81 (1H, d, J=7.4 Hz), 6.91 (1H, t, J=6.6 Hz), 7.12-7.21 (2H, m), 7.22-7.30 (1H, m), 7.33-7.38 (2H, m), 7.46 (1H, d, J=7.4 Hz).

MS: m/z=430 [M+H]⁺.

REFERENCE EXAMPLE 266

[Chemical formula 317]

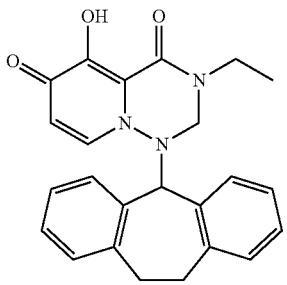

$^1$H-NMR (DMSO-d$_6$) δ: 1.05 (3H, t, J=7.2 Hz), 2.80 (1H, dt, J=14.4, 5.1 Hz), 2.85-2.99 (2H, m), 3.68 (1H, dt, J=16.8, 5.0 Hz), 3.74-3.87 (1H, m), 4.02 (1H, d, J=13.3 Hz), 4.06-4.19 (1H, m), 4.98 (1H, d, J=13.1 Hz), 5.22 (1H, s), 5.48 (1H, d, J=7.6 Hz), 6.73 (1H, d, J=7.5 Hz), 6.83-6.94 (2H, m), 7.12-7.40 (6H, m).
MS: m/z=402 [M+H]$^+$.

REFERENCE EXAMPLE 267

[Chemical formula 318]

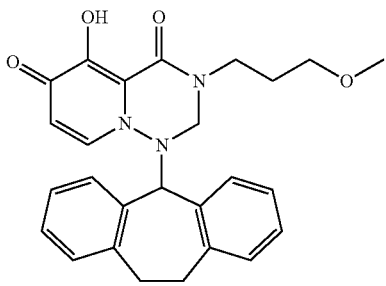

$^1$H-NMR (CDCl$_3$) δ: 1.74-1.86 (2H, m), 2.71-2.82 (1H, m), 2.83-2.93 (1H, m), 2.98-3.11 (1H, m), 3.25 (3H, s), 3.39 (2H, t, J=5.4 Hz), 3.62-3.74 (1H, m), 4.02-4.14 (2H, m), 4.16-4.28 (1H, m), 4.82 (1H, d, J=13.2 Hz), 5.03 (1H, s), 5.76 (1H, d, J=7.7 Hz), 6.58 (1H, d, J=7.7 Hz), 6.64 (1H, d, J=7.4 Hz), 6.89-6.97 (1H, m), 7.12-7.39 (6H, m).
MS: m/z=446 [M+H]$^+$.

REFERENCE EXAMPLE 268

[Chemical formula 319]

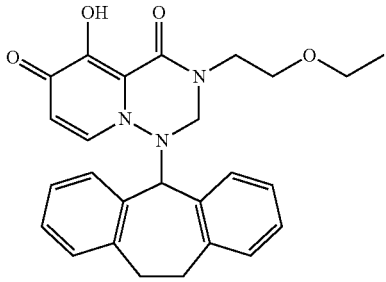

$^1$H-NMR (CDCl$_3$) δ: 1.09 (3H, t, J=7.0 Hz), 2.65-2.77 (1H, m), 2.83-2.94 (1H, m), 2.97-3.10 (1H, m), 3.40 (2H, q, J=7.0 Hz), 3.45-3.52 (1H, m), 3.55-3.64 (1H, m), 3.65-3.76 (1H, m), 4.00-4.15 (2H, m), 4.36-4.45 (1H, m), 4.90 (1H, d, J=13.5 Hz), 5.02 (1H, s), 5.79 (1H, d, J=7.7 Hz), 6.59 (1H, d, J=7.7 Hz), 6.63 (1H, d, J=7.4 Hz), 6.90-6.97 (1H, m), 7.13-7.39 (6H, m).
MS: m/z=446 [M+H]$^+$.

REFERENCE EXAMPLE 269

[Chemical formula 320]

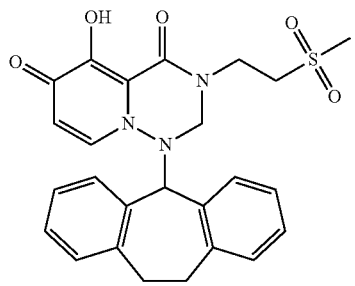

MS: m/z=480 [M+H]$^+$.

REFERENCE EXAMPLE 270

[Chemical formula 321]

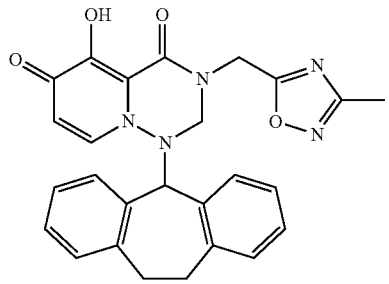

$^1$H-NMR (DMSO-d$_6$) δ: 2.33 (3H, s), 2.85 (2H, m), 3.68 (1H, m), 4.16 (1H, m), 4.29 (1H, d, J=13.3 Hz), 4.45 (1H, d, J=17.1 Hz), 5.12 (1H, d, J=13.1 Hz), 5.26 (1H, d, J=17.4 Hz), 5.36 (1H, s), 5.55 (1H, d, J=7.6 Hz), 6.74 (1H, d, J=7.6 Hz), 6.89-7.38 (8H, m).
MS: m/z=470 [M+H]$^+$.

REFERENCE EXAMPLE 271

[Chemical formula 322]

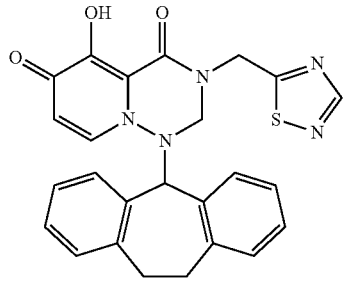

¹H-NMR (DMSO-d₆) δ: 2.87 (2H, m), 3.61-3.69 (1H, m), 4.15 (1H, m), 4.18 (1H, d, J=13.2 Hz), 4.51 (1H, d, J=15.9 Hz), 5.08 (1H, d, J=13.1 Hz), 5.21 (1H, s), 5.22 (1H, d, J=15.6 Hz), 5.52 (1H, d, J=7.6 Hz), 6.72 (1H, d, J=7.5 Hz), 6.89-7.32 (8H, m), 7.76 (2H, s).
MS: m/z=471 [M+H]⁺.

REFERENCE EXAMPLE 272

[Chemical formula 323]

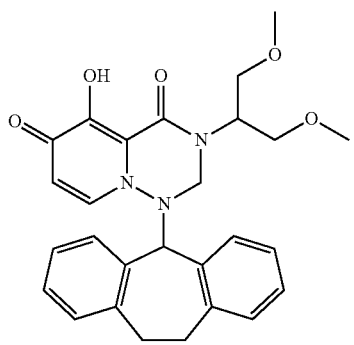

MS: m/z=476 [M+H]⁺

REFERENCE EXAMPLE 273

[Chemical formula 324]

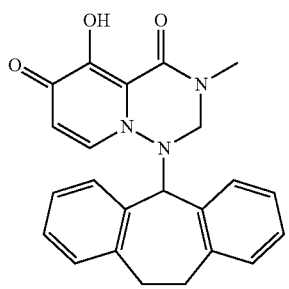

¹H-NMR (CDCl₃) δ: 2.84-2.93 (1H, m), 2.98 (3H, s), 2.98-3.09 (1H, m), 3.66-3.75 (1H, m), 3.99-4.15 (1H, m), 4.06 (1H, d, J=12.9 Hz), 4.80 (1H, d, J=13.2 Hz), 5.03 (1H, s), 5.74 (1H, d, J=7.5 Hz), 6.56 (1H, d, J=7.5 Hz), 6.63 (1H, d, J=6.6 Hz), 6.90-6.96 (1H, m), 7.14-7.37 (6H, m).

REFERENCE EXAMPLE 274

[Chemical formula 325]

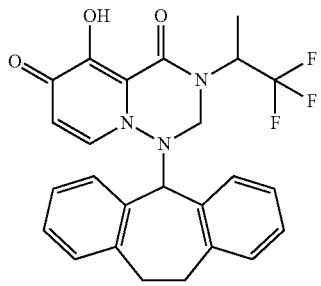

MS: m/z=470 [M+H]⁺.

REFERENCE EXAMPLE 275

[Chemical formula 326]

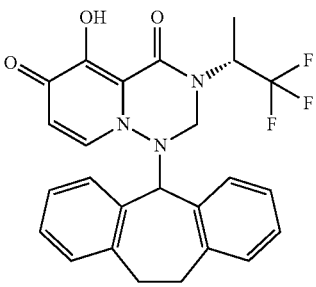

MS: m/z=470 [M+H]⁺.

REFERENCE EXAMPLE 276

[Chemical formula 327]

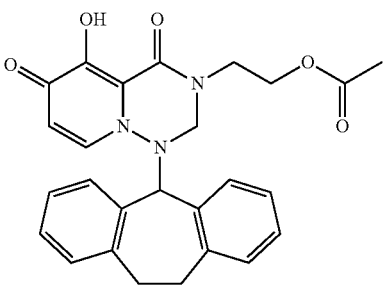

MS: m/z=460 [M+H]⁺

REFERENCE EXAMPLE 277

[Chemical formula 328]

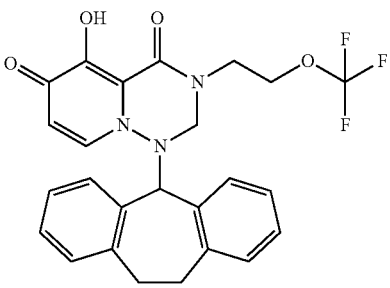

MS: m/z=486 [M+H]⁺.

REFERENCE EXAMPLE 278

[Chemical formula 329]

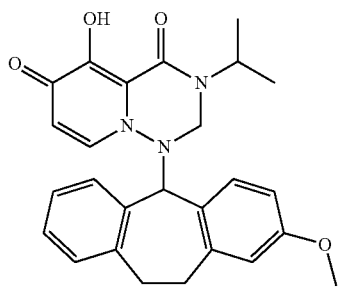

MS: m/z=446 [M+H]⁺

REFERENCE EXAMPLE 279

[Chemical formula 330]

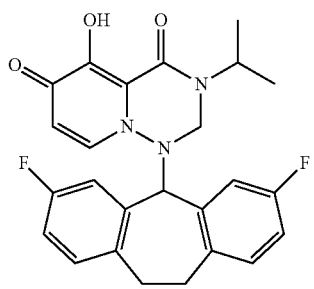

¹H-NMR (CDCl₃) δ: 1.08-1.21 (6H, m), 2.84 (1H, ddd, J=4.8 Hz, 4.8 Hz, 14.4 Hz), 2.97-3.08 (1H, m), 3.54 (1H, ddd, J=4.8 Hz, 6.6 Hz, 17.1 Hz), 4.09-4.26 (1H, m), 4.24 (1H, d, J=13.2 Hz), 4.64-4.74 (m, 1H), 4.70 (1H, d, J=13.2 Hz), 4.94 (1H, s), 5.81 (1H, d, J=7.8 Hz), 6.42 (1H, dd, J=2.7 Hz, 9.0 Hz), 6.67 (1H, d, J=7.8 Hz), 6.89-7.12 (4H, m), 7.19-7.36 (1H, m).

REFERENCE EXAMPLE 280

[Chemical formula 331]

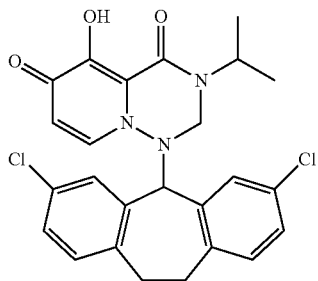

¹H-NMR (CDCl₃) δ: 1.15 (3H, d, J=6.9 Hz), 1.20 (3H, d, J=6.9 Hz), 2.84 (1H, ddd, J=4.8 Hz, 5.1 Hz, 14.4 Hz), 2.96-3.07 (1H, m), 3.55 (1H, ddd, J=4.8 Hz, 5.1 Hz, 17.4 Hz), 4.11-4.23 (1H, m), 4.21 (1H, d, J=12.9 Hz), 4.65-4.74 (1H, m), 4.70 (1H, d, J=12.9 Hz), 4.95 (1H, s), 5.78 (1H, d, J=7.8 Hz), 6.63 (1H, d, J=7.8 Hz), 6.69 (1H, d, J=2.1 Hz), 7.06 (1H, d, J=8.4 Hz), 7.18 (1H, dd, J=2.1 Hz, 8.4 Hz), 7.23-7.26 (2H, m), 7.24 (1H, dd, J=2.1 Hz, 8.1 Hz).

REFERENCE EXAMPLE 281

[Chemical formula 332]

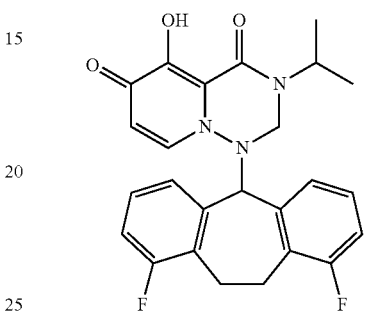

¹H-NMR (CDCl₃) δ: 1.13 (3H, d, J=6.6 Hz), 1.20 (3H, d, J=6.9 Hz), 2.90-3.32 (1H, m), 3.36 (1H, ddd, J=4.5 Hz, 4.5 Hz, 9.6 Hz), 3.42-3.51 (1H, m), 3.95-4.02 (1H, m), 4.28 (1H, d, J=12.9 Hz), 4.64-4.75 (1H, m), 1.89 (1H, d, J=12.9 Hz), 5.15 (1H, s), 5.80 (1H, d, J=7.5 Hz), 6.46-6.49 (1H, m), 6.70 (1H, d, J=7.8 Hz), 6.88-7.00 (2H, m), 7.03-7.06 (1H, m), 7.11-7.22 (2H, m).

REFERENCE EXAMPLE 282

[Chemical formula 333]

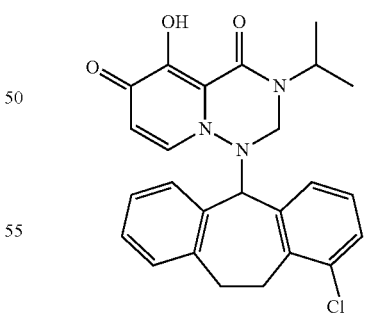

¹H-NMR (CDCl₃) δ: 1.09-1.19 (6H, m), 2.80-3.10 (2H, m), 3.40-3.60 (1H, m), 4.16-4.41 (2H, m), 4.61-4.47 (2H, m), 5.06-5.10 (1H, m), 5.71 (0.45H, d, J=7.5 Hz), 5.74 (0.55H, d, J=7.8 Hz), 6.60-6.72 (2H, m), 6.86-6.94 (1H, m), 7.10-7.46 (6H, m).

REFERENCE EXAMPLE 283

[Chemical formula 334]

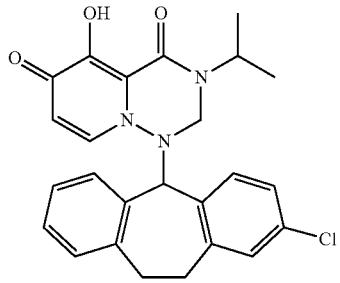

$^1$H-NMR (CDCl$_3$) δ: 1.10-1.21 (6H, m), 2.75-2.86 (1H, m), 2.99-3.14 (1H, m), 4.23-4.37 (2H, m), 4.59-4.74 (2H, m), 5.04 (1H, s), 5.67-5.80 (1H, m), 6.58-6.67 (2H, m), 6.88-7.08 (1H, m), 7.11-7.38 (5H, m).

REFERENCE EXAMPLE 284

[Chemical formula 335]

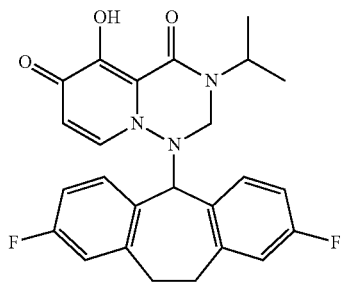

$^1$H-NMR (CDCl$_3$) δ: 1.15 (3H, d, J=6.9 Hz), 1.20 (3H, d, J=6.9 Hz), 2.80 (1H, ddd, J=4.5 Hz, 4.5 Hz, 9.9 Hz), 3.07 (1H, t, J=3.9 Hz, 13.2 Hz, 13.2 Hz), 3.50 (1H, ddd, J=4.2 Hz, 4.2 Hz, 18.0 Hz), 4.24 (1H, 6.9 Hz), 4.34 (1H, ddd, J=4.2 Hz, 13.5 Hz, 13.5 Hz), 4.63-4.74 (2H, m), 5.06 (1H, s), 5.81 (1H, d, J=7.8 Hz), 6.57-6.64 (2H, m), 6.65 (1H, d, J=7.5 Hz), 6.82 (1H, d, J=9.3 Hz), 6.90 (1H, ddd, J=2.7 Hz, 8.4 Hz, 8.4 Hz), 7.02 (1H, dd, J=2.7 Hz, 9.0 Hz), 7.19-7.26 (2H, m).

REFERENCE EXAMPLE 285

[Chemical formula 336]

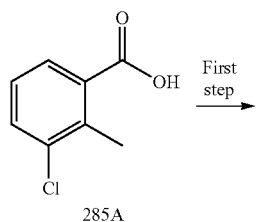
285A
First step →

-continued

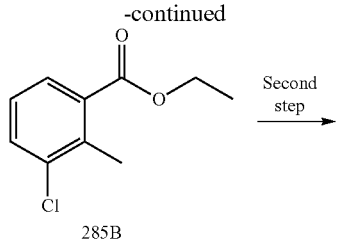
285B
Second step →

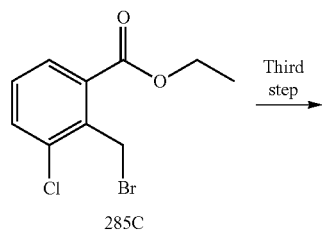
285C
Third step →

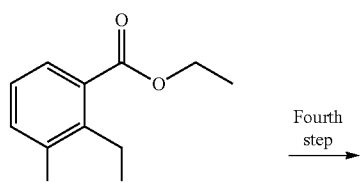
285D
Fourth step →

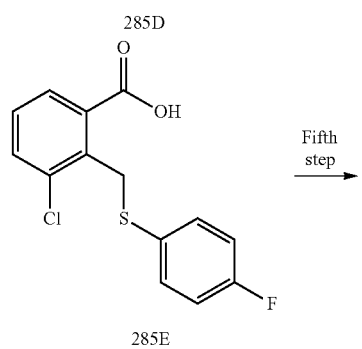
285E
Fifth step →

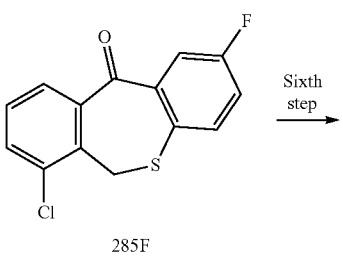
285F
Sixth step →

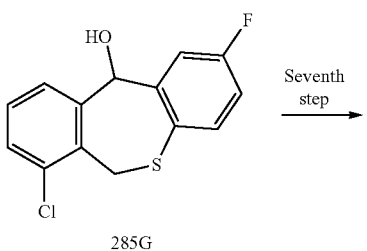
285G
Seventh step →

-continued

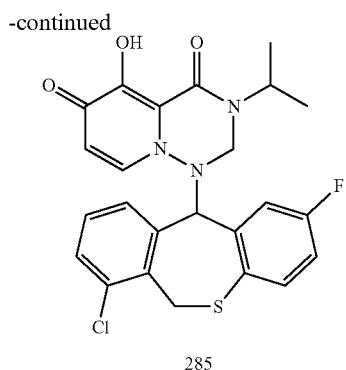

285

First Step

Compound 285A (5.00 g, 29.3 mmol) was dissolved in dimethylformamide (150 ml), potassium carbonate (14.2 mmol) and iodoethane (7.11 ml, 88.0 mmol) were added, and the mixture was stirred at room temperature for 2 hours. To the reaction solution was added hexane, and the mixture was washed with water and an aqueous saturated sodium chloride solution. The organic layer was dried with sodium sulfate, and the solvent was distilled off under reduced pressure to obtain a colorless oily substance 285B.

$^1$H-NMR (CDCl$_3$) δ: 1.40 (3H, t, J=7.2 Hz), 2.60 (3H, s), 4.37 (2H, q, J=7.1 Hz), 7.17 (1H, td, J=7.9, 0.6 Hz), 7.49 (1H, ddd, J=8.0, 1.4, 0.4 Hz), 7.68 (1H, ddd, J=7.8, 1.4, 0.3 Hz).

Second Step

Compound 285B (5.63 g, 28.3 mmol) obtained in the first step was dissolved in carbon tetrachloride (150 ml), N-bromosuccinimide (5.55 g, 31.2 mmol) was added, and the mixture was stirred at 100° C. for 18 hours. The reaction solution was cooled to room temperature, and washed with water and an aqueous saturated sodium chloride solution. The organic layer was dried with sodium sulfate, and the solvent was distilled off under reduced pressure to obtain 8.08 g of an orange oily substance 285C.

$^1$H-NMR (CDCl$_3$) δ: 1.43 (3H, t, J=7.6 Hz), 4.42 (2H, q, J=7.1 Hz), 5.10 (2H, s), 7.31 (1H, t, J=8.6 Hz), 7.57 (1H, d, J=8.1 Hz), 7.84 (1H, d, J=8.1 Hz).

Third Step

Compound 285C (2.17 g, 7.8 mmol) obtained in the second step was dissolved in acetone (25 ml), 4-fluorobenzenethiol (1.00 g, 7.80 mmol) and potassium carbonate (1.62 g, 11.7 mmol) were added, and the mixture was stirred at 80° C. for 18 hours. After cooled to room temperature, the reaction solution was poured into water, the mixture was extracted with ethyl acetate, the extract was washed with an aqueous saturated sodium chloride solution, and the organic layer was dried with sodium sulfate. The solvent was distilled off under reduced pressure, and the resulting crude product was purified by silica gel column chromatography and eluted with n-hexane-ethyl acetate (4:1, v/v) to obtain 2.20 g of a colorless oily substance 285D.

$^1$H-NMR (CDCl$_3$) δ: 1.35 (3H, t, J=7.2 Hz), 4.25 (2H, d, J=7.5 Hz), 4.65 (2H, s), 6.91 (2H, t, J=8.8 Hz), 7.19-7.31 (3H, m), 7.48 (1H, dd, J=8.2, 1.4 Hz), 7.70 (1H, dd, J=7.6, 1.5 Hz).

Fourth Step

Compound 285D (2.20 g, 6.77 mmol) obtained in the third step was dissolved in ethanol (20 ml), a 2N aqueous sodium hydroxide solution (16.9 ml, 33.8 mmol) was added, and the mixture was stirred at room temperature for 3 hours. To the reaction solution was added water, the mixture was made acidic with dilute hydrochloric acid, and extracted with ethyl acetate. The organic layer was washed with an aqueous saturated sodium chloride solution, and dried with sodium sulfate, and the solvent was distilled off under reduced pressure. To the resulting compound was added n-hexane, and the precipitated residue was filtered to obtain 1.81 g of a white solid 285E.

$^1$H-NMR (CDCl$_3$) δ: 4.74 (2H, s), 6.95 (2H, t, J=8.8 Hz), 7.34 (3H, m), 7.59 (1H, dd, J=7.9, 1.5 Hz), 7.92 (1H, dd, J=7.9, 1.3 Hz).

Fifth Step

To compound 285E (1.81 g, 6.10 mmol) obtained in the fourth step was added polyphosphoric acid (10.0 g), and the mixture was stirred at 120° C. for 5 hours. After cooled to room temperature, water was added, and the mixture was extracted with ethyl acetate. The organic layer was dried with sodium sulfate, the solvent was concentrated under reduced pressure, to the resulting compound were added n-hexane-ethyl acetate, and the precipitated residue was filtered to obtain 1.18 g of a white solid 285F.

$^1$H-NMR (CDCl$_3$) δ: 4.28 (2H, s), 7.18 (1H, ddd, J=9.3, 6.6, 2.3 Hz), 7.33 (2H, m), 7.46 (1H, dd, J=7.7, 1.5 Hz), 7.59 (1H, dd, J=7.9, 1.3 Hz), 7.91 (1H, dd, J=10.1, 2.9 Hz).

Sixth Step

To compound 285F (1.17 g, 4.20 mmol) was added methanol (15 ml), sodium borohydride (191 mg, 5.04 mmol) was added at 0° C., and the mixture was stirred at room temperature for 2 hours. The reaction solution was poured into water, the mixture was extracted with dichloromethane, the organic layer was dried with sodium sulfate, and the solvent was distilled off. To the resulting compound were added n-hexane-dichloromethane, and the precipitated residue was filtered to obtain 945 mg of a white solid 285G.

$^1$H-NMR (CDCl$_3$) δ: 2.58 (1H, d, J=3.2 Hz), 4.46 (1H, d, J=14.3 Hz), 4.58 (1H, d, J=14.6 Hz), 6.33 (1H, d, J=3.7 Hz), 6.82 (1H, td, J=8.3, 2.9 Hz), 7.07 (1H, dd, J=8.5, 5.4 Hz), 7.20 (1H, t, J=7.9 Hz), 7.33 (2H, m), 7.44 (1H, d, J=6.9 Hz).

Seventh Step

According to the same procedure as that of Reference example 107, compound 285 was synthesized.

MS: m/z=486 [M+H]$^+$

Using amines which are commercially available or known in the references and intermediates corresponding to compound 285A to compound 285G which are commercially available or known in the references, and according to the method of Reference example 285, compounds 286 to compound 359 were synthesized.

REFERENCE EXAMPLE 286

[Chemical formula 337]

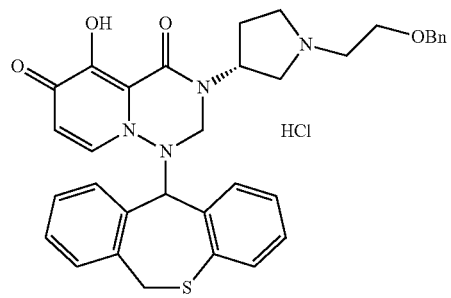

MS: m/z=595 [M+H]$^+$.

REFERENCE EXAMPLE 287

[Chemical formula 338]

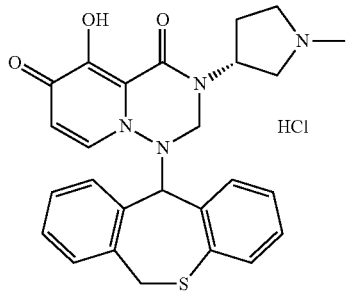

MS: m/z=475 [M+H]+.

REFERENCE EXAMPLE 288

[Chemical formula 339]

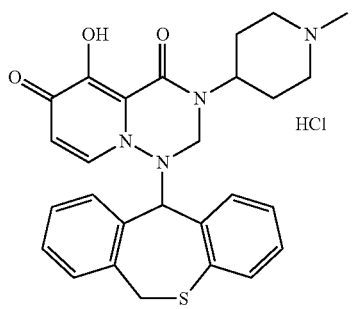

¹H-NMR (DMSO-d₆) δ: 1.57 (1H, brs), 1.84-1.99 (2H, m), 2.68 (3H, d, J=4.6 Hz), 3.08-3.17 (2H, m), 3.39 (3H, brs), 3.89 (1H, d, J=13.4 Hz), 4.16 (1H, d, J=13.3 Hz), 4.54 (1H, brs), 5.10 (1H, d, J=12.7 Hz), 5.50 (1H, s), 5.63 (1H, d, J=13.4 Hz), 5.73 (1H, d, J=7.8 Hz), 6.82-7.94 (9H, m).

MS: m/z=489 [M+H]+.

REFERENCE EXAMPLE 289

[Chemical formula 340]

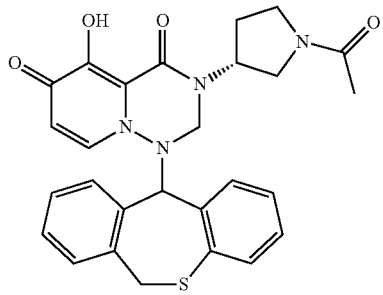

MS: m/z=503 [M+H]+.

REFERENCE EXAMPLE 290

[Chemical formula 341]

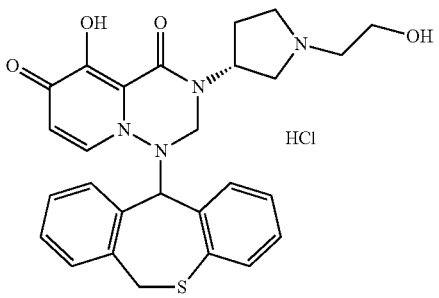

MS: m/z=505 [M+H]+.

REFERENCE EXAMPLE 291

[Chemical formula 342]

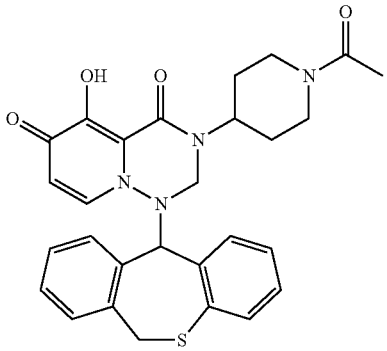

MS: m/z=517 [M+H]+.

REFERENCE EXAMPLE 292

[Chemical formula 343]

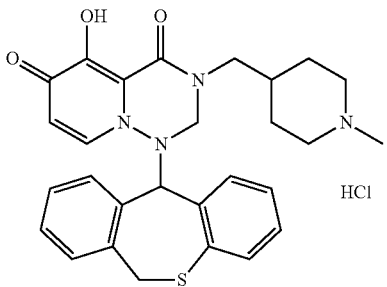

MS: m/z=503 [M+H]+.

REFERENCE EXAMPLE 293

[Chemical formula 344]

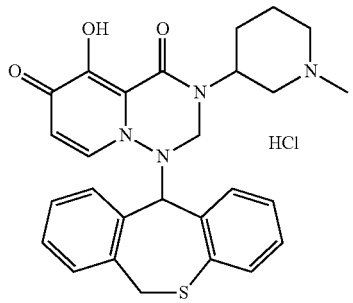

HCl

MS: m/z=489 [M+H]$^+$.

REFERENCE EXAMPLE 294

[Chemical formula 345]

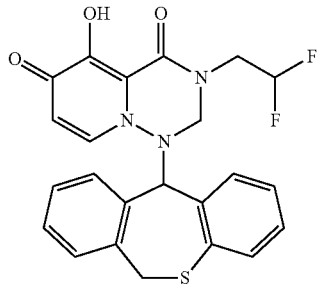

MS: m/z=456 [M+H]$^+$.

REFERENCE EXAMPLE 295

[Chemical formula 346]

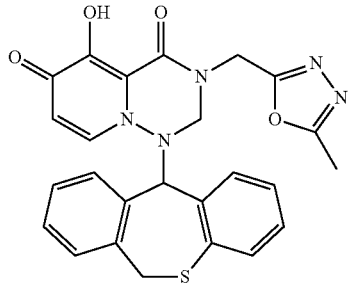

MS: m/z=488 [M+H]$^+$.

REFERENCE EXAMPLE 296

[Chemical formula 347]

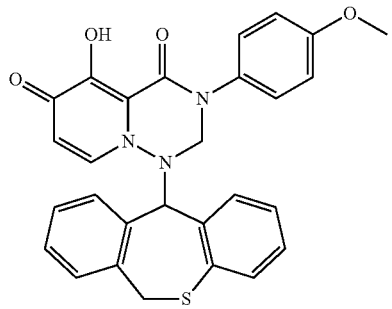

MS: m/z=498 [M+H]$^+$

REFERENCE EXAMPLE 297

[Chemical formula 348]

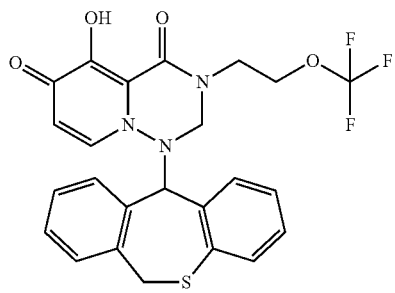

$^1$H-NMR (DMSO-d$_6$) δ: 3.21 (1H, m), 3.85 (1H, d, J=13.4 Hz), 4.08-4.18 (3H, m), 4.28 (1H, d, J=13.4 Hz), 5.10 (1H, d, J=13.7 Hz), 5.45 (1H, s), 5.57-5.64 (2H, m), 6.82-7.50 (10H, m).
MS: m/z=504 [M+H]$^+$.

REFERENCE EXAMPLE 298

[Chemical formula 349]

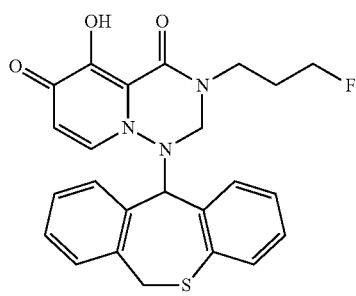

According to Reference example 107, compound 298 was synthesized by the same procedure.
MS: m/z=452 [M+H]$^+$.

REFERENCE EXAMPLE 299

[Chemical formula 350]

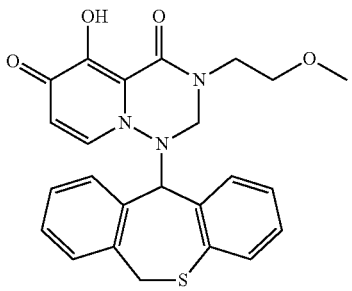

MS: m/z=450 [M+H]⁺.

REFERENCE EXAMPLE 300

[Chemical formula 351]

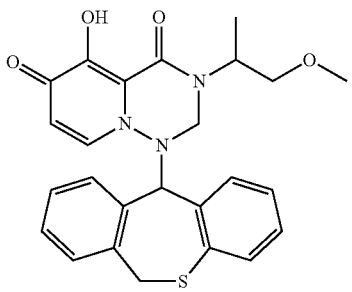

MS: m/z=464 [M+H]⁺.

REFERENCE EXAMPLE 301

[Chemical formula 352]

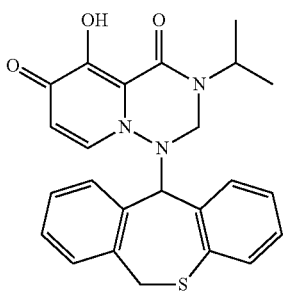

$^1$H-NMR (DMSO-$d_6$) δ: 1.00(3H, d, J=6.9 Hz), 1.06 (3H, d, J=6.9 Hz), 3.88 (1H, d, J=13.4 Hz), 4.32 (1H, d, J=13.3 Hz), 4.67 (1H, m), 4.97 (1H, d, J=13.4 Hz), 5.43 (1H, s), 5.59 (2H, m), 6.84-7.45 (9H, m), 11.90 (1H, brs).
MS: m/z=434 [M+H]⁺.

REFERENCE EXAMPLE 302

[Chemical formula 353]

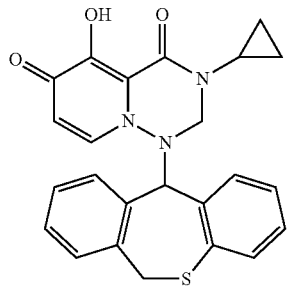

$^1$H-NMR (DMSO-$d_6$) δ: 0.11 (1H, m), 0.54-0.92 (3H, m), 2.71 (1H, m), 3.85 (1H, d, J=13.7 Hz), 4.06 (1H, d, J=13.1 Hz), 5.06 (1H, d, J=13.1 Hz), 5.35 (1H, s), 5.57 (2H, m), 7.15 (9H, m), 11.66 (1H, brs).
MS: m/z=432 [M+H]⁺.

REFERENCE EXAMPLE 303

[Chemical formula 354]

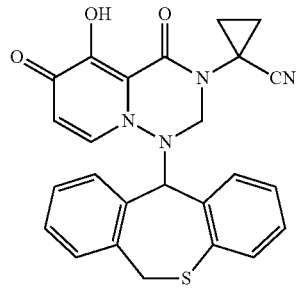

$^1$HNMR (CDCl$_3$) δ: 1.14 (1H, m), 1.54 (2H, m), 1.67 (1H, m), 3.60 (1H, d, J=13.5 Hz), 4.39 (1H, d, J=12.6 Hz), 5.02 (1H, s), 5.07 (1H, d, J=12.6 Hz), 5.60 (1H, d. J=13.5 Hz), 5.77 (1H, d, J=7.7 Hz), 6.69 (1H, d, J=7.7 Hz), 7.07-7.13 (3H, m), 7.25-7.44 (4H, m).
MS: m/z=457.10 [M+H]⁺.

REFERENCE EXAMPLE 304

[Chemical formula 355]

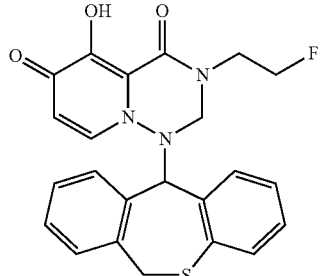

¹H-NMR (DMSO-d₆) δ: 3.33-3.42 (1H, m), 3.84 (1H, d, J=13.1 Hz), 3.90-4.10 (1H, m), 4.24 (1H, d, J=13.4 Hz), 4.35-4.66 (2H, m), 5.13 (1H, d, J=13.4 Hz), 5.43 (1H, s), 5.54-5.64 (2H, m), 6.80-6.95 (2H, m), 7.04-7.50 (8H, m).
MS: m/z=438 [M+H]⁺.

REFERENCE EXAMPLE 305

[Chemical formula 356]

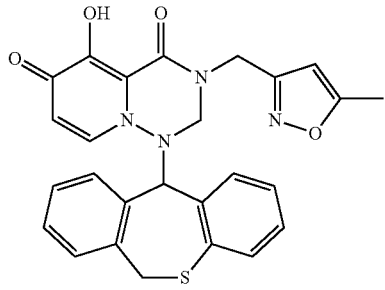

MS: m/z=487 [M+H]⁺.

REFERENCE EXAMPLE 306

[Chemical formula 357]

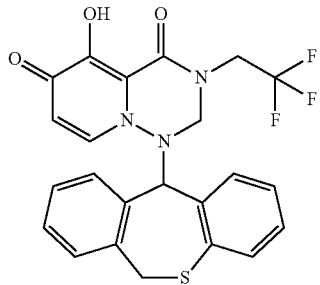

¹H-NMR (DMSO-d₆) δ: 3.69-3.82 (1H, m), 3.89 (1H, d, J=13.6 Hz), 4.40 (1H, d, J=12.9 Hz), 4.60-4.77 (1H, m), 5.27 (1H, d, J=13.3 Hz), 5.43 (1H, s), 5.60 (1H, d, J=13.6 Hz), 5.70 (1H, d, J=7.7 Hz), 6.84-6.95 (1H, m), 7.08-7.55 (9H, m).
MS: m/z=474 [M+H]⁺.

REFERENCE EXAMPLE 307

[Chemical formula 358]

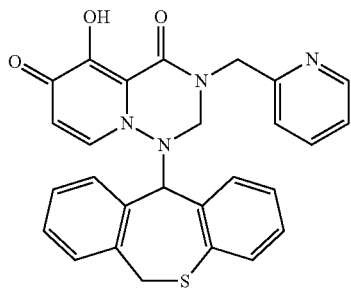

¹H-NMR (DMSO-d₆) δ: 3.81 (1H, d, J=13.5 Hz), 4.29 (1H, d, J=13.5 Hz), 4.33 (1H, d, J=16.2 Hz), 4.96 (1H, d, J=16.2 Hz), 5.23 (1H, d, J=13.5 Hz), 5.49 (1H, s), 5.59 (1H, d, J=13.2 Hz), 5.64 (1H, d, J=7.7 Hz), 6.82-6.97 (2H, m), 7.05-7.41 (10H, m), 7.80 (1H, td, J=7.6, 1.7 Hz), 8.47 (1H, d, J=4.9 Hz).
MS: m/z=483 [M+H]⁺.

REFERENCE EXAMPLE 308

[Chemical formula 359]

¹H-NMR (DMSO-d₆) δ: 1.28 (9H, s), 3.86 (1H, d, J=13.6 Hz), 4.42 (1H, d, J=13.3 Hz), 4.99 (1H, d, J=13.4 Hz), 5.32 (1H, s), 5.53 (1H, d, J=13.3 Hz), 5.60 (1H, d, J=7.6 Hz), 6.81-7.63 (10H, m).
MS: m/z=448 [M+H]⁺.

REFERENCE EXAMPLE 309

[Chemical formula 360]

¹H-NMR (DMSO-d₆) δ: 1.03 (3H, t, J=7.4 Hz), 3.12-3.26 (1H, m), 3.43-3.58 (1H, m), 3.85 (1H, d, J=13.6 Hz), 4.21 (1H, d, J=13.4 Hz), 5.07 (1H, d, J=13.4 Hz), 5.40 (1H, s), 5.57 (1H, d, J=13.1 Hz), 5.59 (1H, d, J=7.3 Hz), 6.80-6.88 (1H, m), 6.91 (1H, d, J=7.9 Hz), 7.03-7.55 (8H, m).
MS: m/z=420 [M+H]⁺.

REFERENCE EXAMPLE 310

[Chemical formula 361]

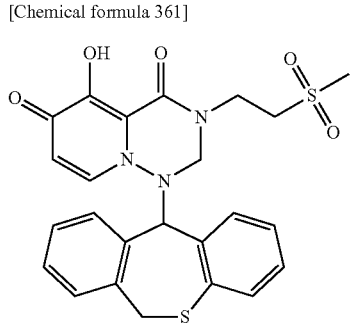 [SMILES: CS(=O)(=O)CCN1CN(C2c3ccccc3CSc3ccccc32)n2ccc(=O)c(O)c2C1=O]

MS: m/z=498 [M+H]⁺.

REFERENCE EXAMPLE 311

[Chemical formula 362]

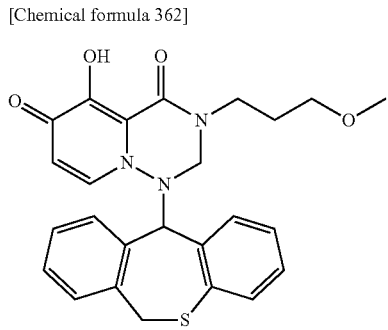 [SMILES: COCCCN1CN(C2c3ccccc3CSc3ccccc32)n2ccc(=O)c(O)c2C1=O]

¹H-NMR (CDCl₃) δ: 1.73-1.85 (2H, m), 2.96-3.07 (1H, m), 3.27 (3H, s), 3.42 (2H, t, J=5.6 Hz), 3.56 (1H, d, J=13.5 Hz), 3.93-4.04 (1H, m), 4.25 (1H, d, J=13.2 Hz), 4.95 (1H, d, J=12.9 Hz), 5.13 (1H, s), 5.65 (1H, d, J=13.2 Hz), 5.82 (1H, d, J=7.7 Hz), 6.69 (1H, d, J=7.7 Hz), 6.78-6.86 (1H, m), 7.03-7.15 (3H, m), 7.17-7.47 (5H, m).
MS: m/z=464 [M+H]⁺.

REFERENCE EXAMPLE 312

[Chemical formula 363]

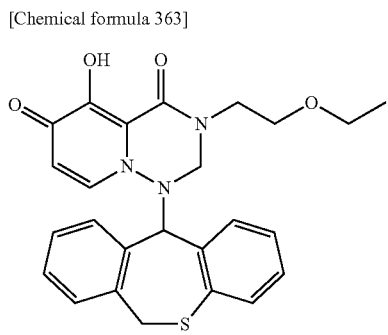 [SMILES: CCOCCN1CN(C2c3ccccc3CSc3ccccc32)n2ccc(=O)c(O)c2C1=O]

¹H-NMR (CDCl₃) δ: 1.10 (3H, t, J=6.9 Hz), 2.79-2.91 (1H, m), 3.41 (2H, q, J=7.1 Hz), 3.46-3.69 (3H, m), 4.30 (1H, d, J=13.5 Hz), 5.01 (1H, d, J=13.5 Hz), 5.12 (1H, s), 5.65 (1H, d, J=13.5 Hz), 5.83 (1H, d, J=7.7 Hz), 6.68 (1H, d, J=7.7 Hz), 6.77-6.86 (1H, m), 7.03-7.12 (3H, m), 7.16-7.46 (5H, m).
MS: m/z=464 [M+H]⁺.

REFERENCE EXAMPLE 313

[Chemical formula 364]

¹H-NMR (CDCl₃) δ: 1.30-1.47 (1H, m), 1.49-1.67 (1H, m), 1.73-2.02 (4H, m), 2.09-2.23 (2H, m), 3.60 (1H, d, J=13.5 Hz), 4.39 (1H, d, J=12.9 Hz), 4.45-4.64 (1H, m), 4.93 (1H, d, J=12.6 Hz), 5.10 (1H, s), 5.65 (1H, d, J=13.5 Hz), 5.87 (1H, d, J=7.4 Hz), 6.67 (1H, d, J=8.0 Hz), 6.76-6.85 (1H, m), 7.08 (2H, d, J=3.8 Hz), 7.16 (2H, d, J=7.7 Hz), 7.23-7.31 (1H, m), 7.34-7.48 (2H, m).
MS: m/z=510 [M+H]⁺.

REFERENCE EXAMPLE 314

[Chemical formula 365]

MS: m/z=476 [M+H]⁺.

REFERENCE EXAMPLE 315

[Chemical formula 366]

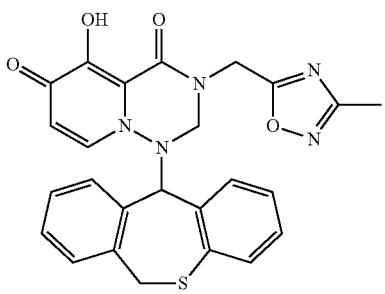

MS: m/z=488 [M+H]+.

REFERENCE EXAMPLE 316

[Chemical formula 367]

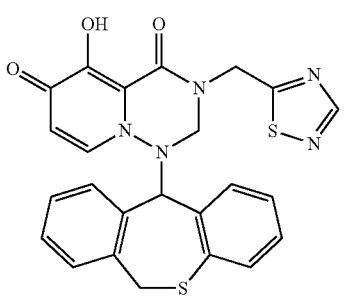

¹H-NMR (DMSO-d₆) δ: 3.83 (1H, d, J=13.4 Hz), 4.34 (1H, d, J=13.1 Hz), 4.67 (1H, d, J=15.9 Hz), 5.05 (1H, d, J=15.9 Hz), 5.20 (1H, d, J=13.4 Hz), 5.33 (1H, s), 5.60 (1H, d, J=13.8 Hz), 5.64 (1H, d, J=7.8 Hz), 6.87 (3H, m), 7.05-7.19 (4H, m), 7.35-7.44 (2H, m), 7.74 (1H, d, 3.3 Hz), 7.77 (1H, d, 3.3 Hz).

REFERENCE EXAMPLE 317

[Chemical formula 368]

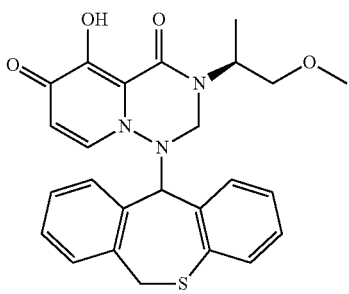

MS: m/z=464 [M+H]+.

REFERENCE EXAMPLE 318

[Chemical formula 369]

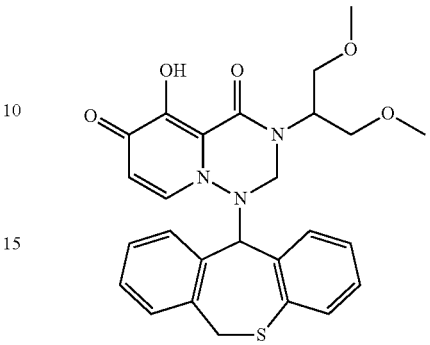

MS: m/z=494 [M+H]+

REFERENCE EXAMPLE 319

[Chemical formula 370]

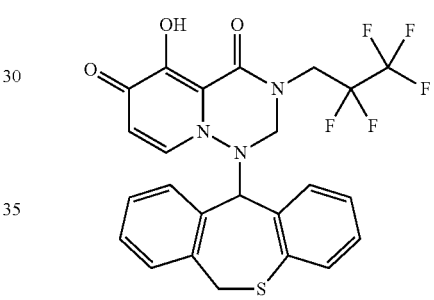

¹H-NMR (CDCl₃) δ: 3.18-3.35 (1H, m), 3.60 (1H, d, J=13.7 Hz), 4.37 (1H, d, J=13.2 Hz), 4.75-4.95 (1H, m), 5.07-5.15 (2H, m), 5.60 (1H, d, J=13.7 Hz), 5.85 (1H, d, J=7.7 Hz), 6.68 (1H, d, J=7.7 Hz), 6.79-6.88 (1H, m), 7.09-7.14 (3H, m), 7.16 (1H, d, J=7.7 Hz), 7.29-7.36 (1H, m), 7.36-7.41 (1H, m), 7.42-7.50 (1H, m).
MS: m/z=524 [M+H]+.

REFERENCE EXAMPLE 320

[Chemical formula 371]

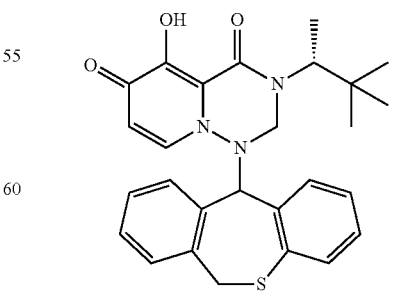

¹H-NMR (CDCl₃) δ: 0.89 (9H, s), 0.97 (3H, d, J=7.1 Hz), 3.61 (1H, d, J=13.2 Hz), 4.43 (1H, d, J=13.2 Hz), 4.84-4.92

(2H, m), 5.11 (1H, s), 5.70 (1H, d, J=13.2 Hz), 5.83 (1H, d, J=7.7 Hz), 6.72 (1H, d, J=7.4 Hz), 6.79-6.85 (1H, m), 7.03-7.09 (2H, m), 7.16-7.24 (3H, m), 7.29-7.44 (2H, m).

MS: m/z=476 [M+H]⁺.

REFERENCE EXAMPLE 321

[Chemical formula 372]

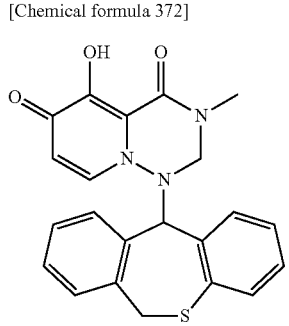 [SMILES: CN1CN(C2c3ccccc3CSc3ccccc32)n2ccc(=O)c(O)c2C1=O]

$^1$H-NMR (CDCl$_3$) δ: 2.87 (0.75 H, s), 3.01 (2.25H, s), 3.55 (1.5H, d, J=10.2 Hz), 3.62 (0.5H, 13.5 Hz), 4.17 (0.5H, d, J=13.2 Hz), 4.22 (1.5 Hz, J=12.9 Hz), 4.97 (1H, d, J=12.9 Hz), 5.02 (0.25H, s), 5.11 (0.75H, s), 5.63 (0.75H, d, J=13.5 Hz), 5.77-5.83 (1.25H, m), 6.64-6.68 (1H, m), 6.76-6.85 (1H, m), 7.01 (1H, d, J=7.5 Hz), 7.05-7.13 (2H, m), 7.17-7.45 (3H, m).

REFERENCE EXAMPLE 322

[Chemical formula 373]

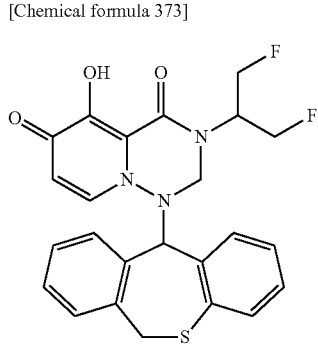 [SMILES: O=C1c2c(O)c(=O)ccn2N(C2c3ccccc3CSc3ccccc32)CN1C(CF)CF]

$^1$H-NMR (CDCl$_3$) δ: 3.63 (1H, d, J=13.4 Hz), 4.51-4.59 (2H, m), 4.68-4.98 (4H, m), 5.13 (1H, d, J=12.9 Hz), 5.28 (1H, s), 5.71 (1H, d, J=13.3 Hz), 5.85 (1H, d, J=7.7 Hz), 6.77 (1H, d, J=7.4 Hz), 6.82-6.89 (1H, m), 7.12 (2H, d, J=3.5 Hz), 7.24 (1H, d, J=7.6 Hz), 7.33 (2H, d, J=4.4 Hz), 7.39 (1H, d, J=7.1 Hz), 7.42-7.50 (1H, m).

MS: m/z=470 [M+H]⁺.

REFERENCE EXAMPLE 323

[Chemical formula 374]

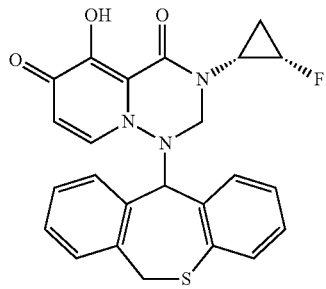

MS: m/z=450 [M+H]⁺

REFERENCE EXAMPLE 324

[Chemical formula 375]

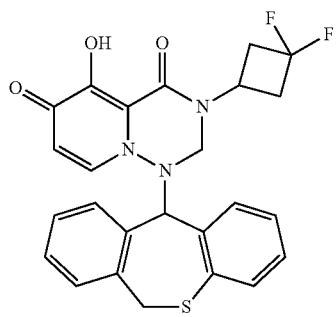

MS: m/z=482 [M+H]⁺

REFERENCE EXAMPLE 325

[Chemical formula 376]

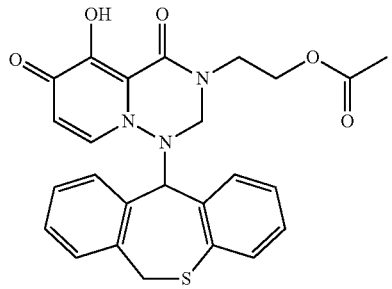

$^1$H-NMR (DMSO-d$_6$) δ: 1.93 (3H, s), 3.13 (1H, m), 3.86 (1H, d, J=13.6 Hz), 4.06 (3H, m), 4.26 (1H, d, J=13.3 Hz), 5.14 (1H, d, J=13.6 Hz), 5.44 (1H, s), 5.60 (2H, m), 6.82-7.49 (10H, m).

MS: m/z=478 [M+H]⁺.

REFERENCE EXAMPLE 326

[Chemical formula 377]

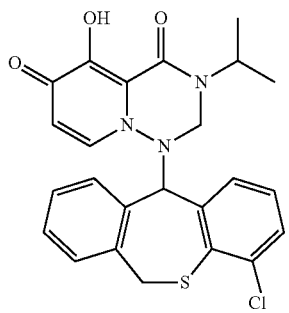

$^1$H-NMR (CDCl$_3$) δ: 1.07 (3H, d, J=6.6 Hz), 1.10 (3H, d, J=6.9 Hz), 3.70 (1H, d, J=13.5 Hz), 4.37 (1H, d, J=12.9 Hz), 4.75-4.85 (2H, m), 5.18 (1H, s), 5.76 (1H, d, J=13.2 Hz), 5.82 (1H, d, J=7.8 Hz), 6.67 (1H, dd, J=1.2 Hz, 7.8 Hz), 6.77 (1H, t, J=7.8 Hz), 7.07 (1H, d, J=7.5 Hz), 7.18-7.30 (3H, m), 7.35-7.46 (2H, m).

REFERENCE EXAMPLE 327

[Chemical formula 378]

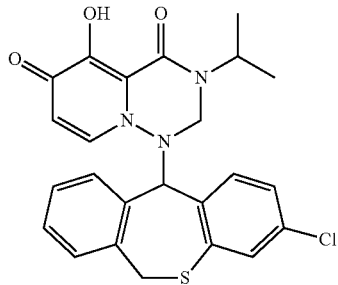

$^1$H-NMR (CDCl$_3$) δ: 1.06 (3H, d, J=6.9 Hz), 1.15 (3H, d, J=7.2 Hz), 3.60 (H, d, J=13.5 Hz), 4.36 (1H, d, J=12.9 Hz), 4.75-4.83 (2H, m), 5.10 (1H, s), 5.67 (1H, d, J=13.2 Hz), 5.86 (1H, d, J=7.5 Hz), 6.65 (1H, d, J=8.1 Hz), 6.78 (1H, dd, J=1.8 Hz, 8.1 Hz), 7.08-7.18 (2H, m), 7.13 (1H, d, J=8.1 Hz), 7.24-7.30 (1H, m), 7.33-7.36 (1H, m), 7.39-7.45 (1H, m).

REFERENCE EXAMPLE 328

[Chemical formula 379]

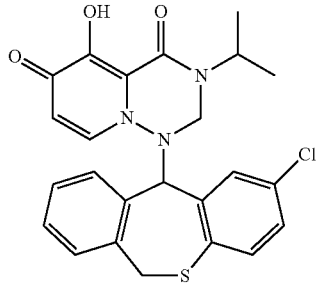

$^1$H-NMR (CDCl$_3$) δ: 0.98 (0.4H, d, J=7.2 Hz), 1.07 (2.6H, d, J=6.6 Hz), 1.15 (2.6H, d, J=6.9 Hz), 1.27 (0.4H, d, J=0.6 Hz), 3.62 (0.9H, d, J=13.2 Hz), 3.73 (0.1H, d, J=13.8 Hz), 4.36 (1H, d, J=12.9 Hz), 4.77-4.88 (1H, m), 4.83 (1H, d, J=12.9 Hz), 5.07 (1H, s), 5.62 (1H, d, J=13.2 Hz), 5.77 (0.1H, d, J=7.5 Hz), 5.85 (0.9H, d, J=7.8 Hz), 6.69-6.83 (1H, m), 6.98-7.07 (2H, m), 7.18 (2H, d, J=7.8 Hz), 7.25-7.35 (2H, m), 7.40-7.45 (1H, m).

REFERENCE EXAMPLE 329

[Chemical formula 380]

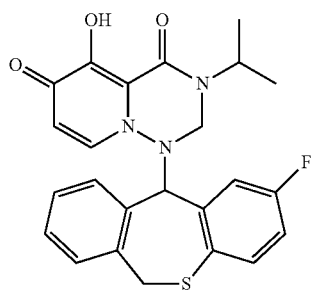

$^1$H-NMR (CDCl$_3$) δ: 1.07 (3H, d, J=6.6 Hz), 1.15 (3H, d, J=6.9 Hz), 3.63 (1H, d, J=13.2 Hz), 4.37 (1H, d, J=12.9 Hz), 4.77-4.8 (1H, m), 4.82 (1H, d, J=12.6 Hz), 5.06 (1H, s), 5.60 (1H, d, J=12.9 Hz), 5.85 (1H, d, J=7.8 Hz), 6.53 (1H, dd, J=3.0 Hz, 9.0 Hz), 6.80-6.86 (1H, m), 7.03 (1H, dd, J=4.2 Hz, 9.0 Hz), 7.16-7.30 (3H, m), 7.35 (1H, d, J=6.3 Hz), 7.40-7.45 (1H, m).

REFERENCE EXAMPLE 330

[Chemical formula 381]

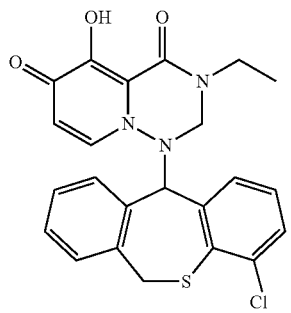

$^1$H-NMR (DMSO-d$_6$) δ: 1.02 (3H, t, J=7.2 Hz), 3.07-3.22 (1H, m), 3.44-3.59 (1H, m), 4.00 (1H, d, J=13.4 Hz), 4.21 (1H, d, J=13.4 Hz), 5.06 (1H, d, J=13.3 Hz), 5.47-5.76 (3H, m), 6.84-6.92 (1H, m), 6.92-6.99 (1H, m), 7.04 (1H, d, J=7.6 Hz), 7.10-7.52 (6H, m).

MS: m/z=454 [M+H]$^+$.

REFERENCE EXAMPLE 331

[Chemical formula 382]

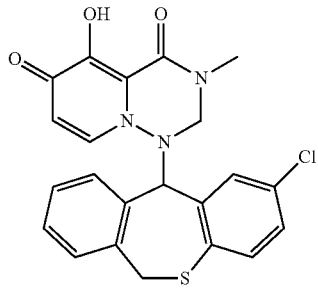

¹H-NMR (CDCl₃) δ: 2.96 (0.79H, s), 3.00 (2.2H, s), 3.59 (0.75H, d, J=13.2 Hz), 3.62 (0.25H, d, J=13.8 Hz), 4.15 (0.25H, d, J=13.2 Hz), 4.21 (0.75H, d, J=12.9 Hz), 4.95-5.01 (2H, m), 5.07 (1H, s), 5.56 (1H, d, J=13.5 Hz), 5.75-5.79 (1H, m), 5.88 (1H, d, J=7.8 Hz), 6.63 (0.36H, d, J=7.8 Hz), 6.73 (1H, d, J=1.8 Hz), 6.83 (0.39H, d, J=7.2 Hz), 7.01-7.46 (7.25H, m).

REFERENCE EXAMPLE 332

[Chemical formula 383]

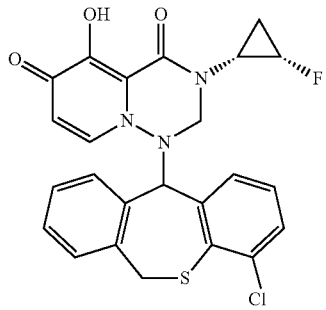

MS: m/z=484 [M+H]⁺

REFERENCE EXAMPLE 333

[Chemical formula 384]

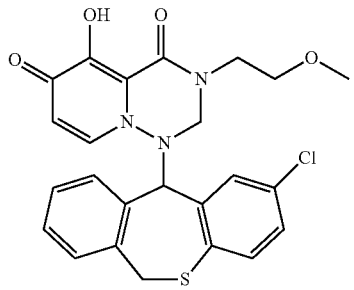

MS: m/z=484 [M+H]⁺.

REFERENCE EXAMPLE 334

[Chemical formula 385]

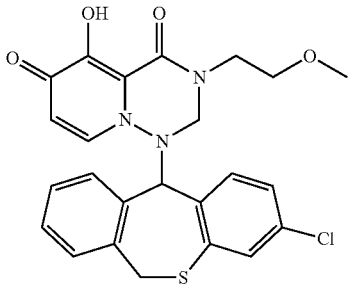

¹H-NMR (DMSO-d₆) δ: 3.01-3.10 (1H, m), 3.16 (3H, s), 3.40 (2H, m), 3.89 (2H, d, J=13.4 Hz), 4.19 (1H, d, J=13.4 Hz), 5.06 (1H, d, J=13.6 Hz), 5.49 (1H, s), 5.58 (1H, d, J=13.4 Hz), 5.70 (1H, d, J=7.8 Hz), 6.89-7.48 (8H, m), 11.36 (1H, s).

REFERENCE EXAMPLE 335

[Chemical formula 386]

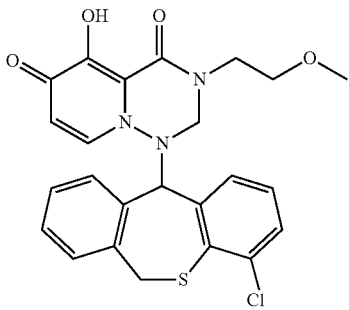

¹H-NMR (DMSO-d₆) δ: 3.00-3.09 (1H, m), 3.15 (3H, s), 3.39 (2H, m), 3.94 (1H, m), 4.00 (1H, d, J=13.2 Hz), 4.20 (1H, d, J=13.4 Hz), 5.06 (1H, d, J=13.4 Hz), 5.54 (1H, s), 5.65 (2H, m), 6.86-7.50 (8H, m), 11.54 (1H, brs).

REFERENCE EXAMPLE 336

[Chemical formula 387]

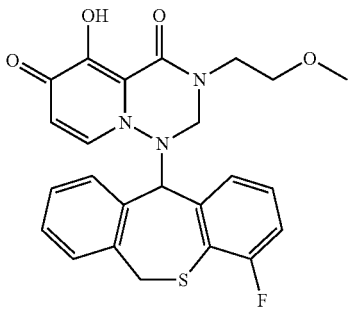

¹H-NMR (DMSO-d₆) δ: 3.01-3.09 (1H, m), 3.15 (3H, s), 3.40 (2H, m), 3.87-3.94 (1H, m), 3.98 (1H, d, J=13.6 Hz), 4.20 (1H, d, J=13.6 Hz), 5.06 (1H, d, J=13.4 Hz), 5.54 (1H, s), 5.62 (1H, d, J=13.6 Hz), 5.67 (1H, d, J=7.6 Hz), 6.78-7.50 (8H, m).
MS: m/z=468 [M+H]+

REFERENCE EXAMPLE 337

[Chemical formula 388]

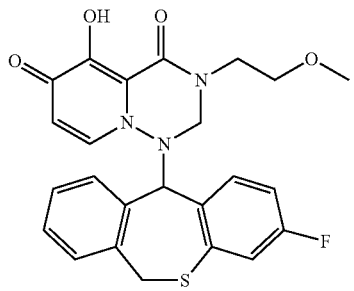

¹H-NMR (DMSO-d₆) δ: 3.07 (1H, m), 3.16 (3H, s), 3.41 (2H, s), 3.89 (1H, d, J=13.7 Hz), 3.91 (1H, m), 4.19 (1H, d, J=13.6 Hz), 5.06 (1H, d, J=13.6 Hz), 5.48 (1H, s), 5.61 (1H, d, J=13.3 Hz), 5.69 (1H, d, J=7.6 Hz), 6.70-7.48 (9H, m).
MS: m/z=468 [M+H]+

REFERENCE EXAMPLE 338

[Chemical formula 389]

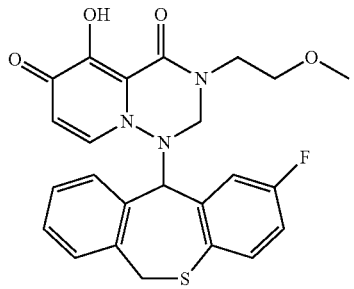

MS: m/z=468 [M+H]+

REFERENCE EXAMPLE 339

[Chemical formula 390]

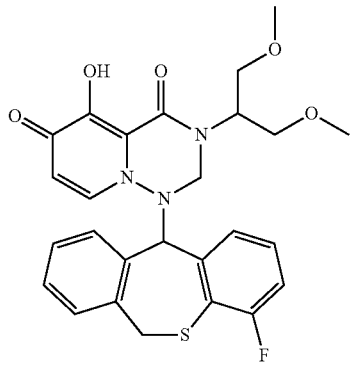

¹H-NMR (DMSO-d₆) δ: 3.14 (3H, s), 3.18 (s, 3H), 3.50 (4H, m), 4.00 (1H, d, J=13.1 Hz), 4.49 (1H, d, J=13.3 Hz), 4.77 (1H, m), 4.95 (1H, d, J=13.3 Hz), 5.56 (1H, s), 5.68 (2H, m), 7.14 (8H, m).
MS: m/z=512 [M+H]+

REFERENCE EXAMPLE 340

[Chemical formula 391]

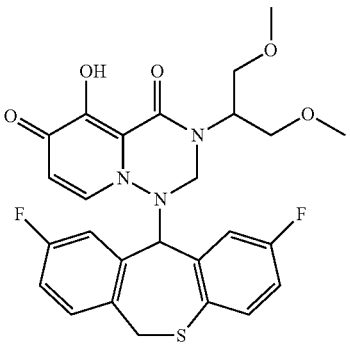

¹H-NMR (DMSO-d₆) δ: 3.12 (3H, s), 3.20 (3H, s), 3.51 (4H, m), 3.96 (1H, d, J=13.3 Hz), 4.53 (1H, d, J=13.4 Hz), 4.75 (1H, m), 4.97 (1H, d, J=13.1 Hz), 5.50 (1H, d, J=13.3 Hz), 5.54 (1H, s), 5.67 (1H, d, J=7.8 Hz), 6.87-7.54 (8H, m).
MS: m/z=530 [M+H]+

REFERENCE EXAMPLE 341

[Chemical formula 392]

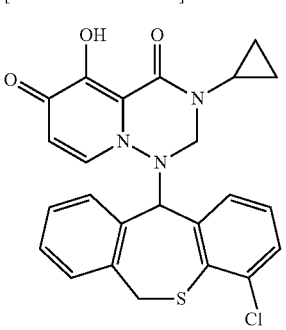

MS: m/z=466 [M+H]+

REFERENCE EXAMPLE 342
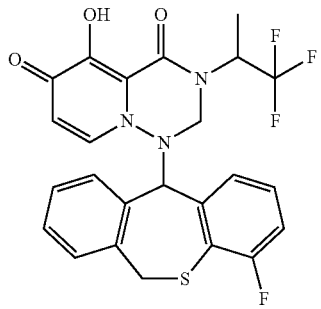
MS: m/z=506 [M+H]+
REFERENCE EXAMPLE 343
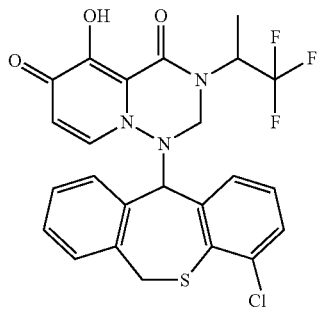
MS: m/z=522 [M+H]+
REFERENCE EXAMPLE 344
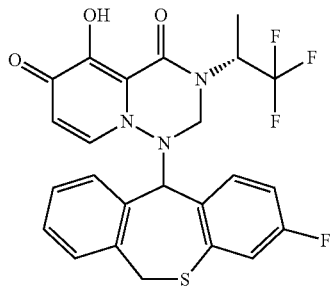
MS: m/z=506 [M+H]+
REFERENCE EXAMPLE 345
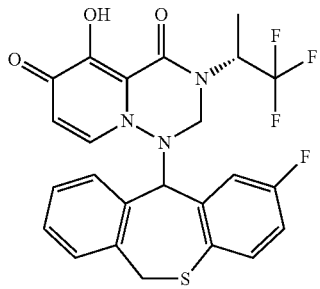
MS: m/z=506 [M+H]+
REFERENCE EXAMPLE 346
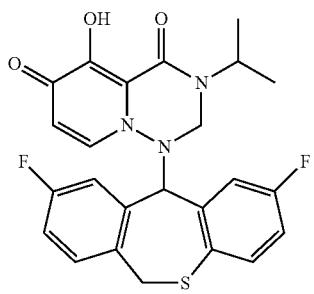
MS: m/z=470 [M+H]+
REFERENCE EXAMPLE 347
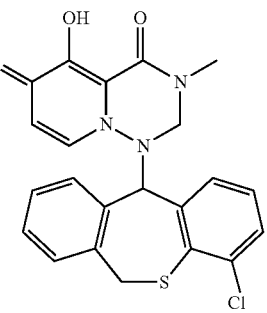
$^1$H-NMR (CDCl$_3$) δ: 2.88 (0.60H, s), 2.99 (2.40H, s), 3.67 (0.80H, d, J=13.8 Hz), 3.73 (0.20H, d, J=14.1 Hz), 4.16 (0.20H, d, J=11.1 Hz), 4.20 (0.80H, d, J=12.9 Hz), 4.97 (0.80H, d, J=12.9 Hz), 4.99 (0.20H, d, J=15 Hz), 5.10 (0.20H, s), 5.18 (0.80H, s), 5.69 (0.80H, d, J=13.5 Hz), 5.79 (0.20H, d, J=7.8 Hz), 5.85 (0.80H, d, J=7.5 Hz), 5.88 (0.20H, J=13.5 Hz), 6.62-6.66 (1H, m), 6.75-6.85 (1H, m), 6.98 (1H, d, J=7.5 Hz), 7.03-7.16 (0.5H, m), 7.19 (1H, d, J=6.9 Hz), 7.24-7.39 (2.5H, m), 7.43-7.48 (1H, m).

REFERENCE EXAMPLE 348

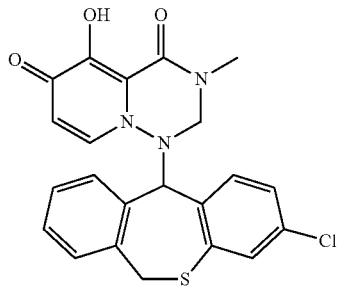

[Chemical formula 399]

¹H-NMR (CDCl₃) δ: 2.91 (0.75H, s), 2.99 (2.25H, s), 3.57 (0.75H, d, J=13.8 Hz), 3.63 (0.25H, d, 13.8 Hz), 4.17 (0.25H, d, J=12.9 Hz), 4.10 (0.75H, d, J=12.9 Hz), 4.99 (0.75H, d, J=12.9 Hz), 5.00 (0.25H, s), 5.01 (0.25H, d, J=12.3 Hz), 5.10 (0.75H, s), 5.61 (0.75H, d, J=13.5 Hz), 5.78 (0.25H, J=7.5 Hz), 5.80 (0.25H, J=15 Hz), 5.89 (0.75H, d, J=7.5 Hz), 6.60 (0.75H, d, J=8.4 Hz), 6.64 (0.25H, d, J=7.8 Hz), 6.78 (1H, dd, J=2.1 Hz, 8.1 Hz), 7.03 (1H, d, J=7.8 Hz), 7.04-7.21 (2H, m), 7.26-7.36 (2H, m), 7.41-7.47 (1H, m).

REFERENCE EXAMPLE 349

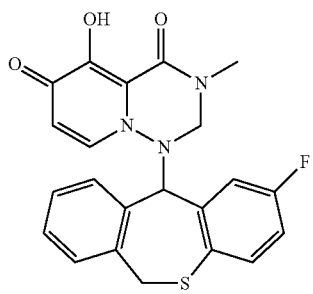

[Chemical formula 400]

¹H-NMR (CDCl₃) δ: 2.94 (0.66H, s), 3.00 (2.34H, s), 3.60 (0.78H, d, J=13.5 Hz), 3.65 (0.22H, d, J=3.8 Hz), 4.22 (1H, d, J=12.9 Hz), 4.94-5.00 (1H, m), 5.06 (1H, s), 5.54 (0.78H, d, J=13.2 Hz), 5.71 (0.22H, d, J=13.8 Hz), 5.78 (0.22H, d, J=7.5 Hz), 5.88 (0.78H, d, J=7.8 Hz), 6.49 (1H, dd, J=3.0 Hz, 9.0 Hz), 6.66 (0.22H, d, J=7.8 Hz), 6.82-6.88 (1H, m), 6.97-7.13 (2H, m), 7.16-7.21 (1H, m), 7.29-7.36 (2H, m), 7.41-7.46 (1H, m).

REFERENCE EXAMPLE 350

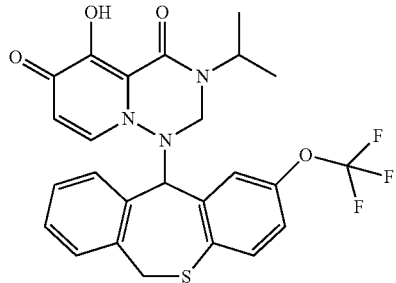

[Chemical formula 401]

¹H-NMR (CDCl₃) δ: 1.08 (3H, d, J=6.9 Hz), 1.16 (3H, d, J=6.9 Hz), 3.63 (1H, d, J=13.2 Hz), 4.37 (1H, d, J=12.6 Hz), 4.78-4.87 (1H, m), 5.10 (1H, s), 5.67 (1H, d, J=13.2 Hz), 5.82 (1H, d, J=7.8 Hz), 6.65 (1H, d, J=2.1 Hz), 6.96-6.99 (1H, m), 7.08-7.12 (2H, m), 7.17 (1H, d, J=13.5 Hz), 7.25-7.32 (1H, m), 7.35-7.37 (1H, m), 7.42-7.47 (1H, m).

REFERENCE EXAMPLE 351

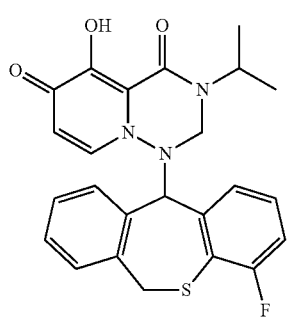

[Chemical formula 402]

¹H-NMR (CDCl₃) δ: 1.08 (3H, d, J=6.9 Hz), 1.16 (3H, d, J=6.9 Hz), 3.68 (1H, d, J=13.2 Hz), 4.37 (1H, d, J=12.9 Hz), 4.76-4.84 (2H, m), 5.18 (1H, s), 5.72 (1H, d, J=13.5 Hz), 5.81 (1H, dd, J=0.9 Hz, 7.5 Hz), 6.56 (1H, d, J=7.2 Hz), 6.76-6.83 (1H, m), 6.90 (1H, t, J=9.0 Hz), 7.07-7.11 (1H, m), 7.19 (1H, d, J=7.5 Hz), 7.25-7.30 (1H, m), 7.35-7.45 (2H, m).

REFERENCE EXAMPLE 352

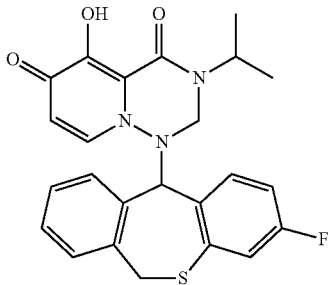

¹H-NMR (CDCl₃) δ: 1.07 (3H, d, J=6.9 Hz), 1.15 (3H, d, J=7.1 Hz), 3.59 (1H, d, J=13.2 Hz), 4.36 (1H, d, J=9.9 Hz), 4.75-4.85 (2H, m), 5.11 (1H, s), 5.70 (1H, d, J=13.2 Hz), 5.84 (1H, d, J=7.8 Hz), 6.48-6.55 (1H, m), 6.71 (1H, dd, J=5.4 Hz, 8.4 Hz), 6.80 (1H, dd, J=2.4 Hz, 9.3 Hz), 7.11 (1H, d, J=7.8 Hz), 7.18 (1H, dd, J=0.9 Hz), 7.5 Hz), 7.25-7.30 (1H, m), 7.32-7.36 (1H, m), 7.39-7.45 (1H, m).

REFERENCE EXAMPLE 353

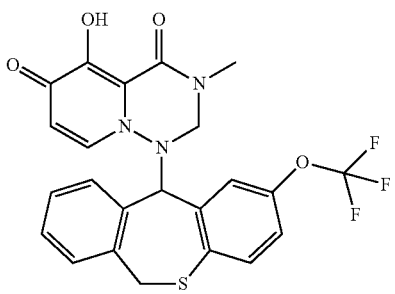

¹H-NMR (CDCl₃) δ: 2.92 (0.66H, s), 3.01 (2.34H, s), 3.59 (0.78H, d, J=13.5 Hz), 3.67 (0.22H, d, J=13.8 Hz), 4.18 (0.22H, d, J=13.2 Hz), 4.21 (0.78H, d, J=12.9 Hz), 5.03 (1H, J=12.9 Hz), 5.05 (0.22H, s), 5.10 (0.78H, s), 5.62 (0.78H, d, J=13.5 Hz), 5.76-5.82 (0.44H, m), 5.87 (0.78H, d, J=7.8 Hz), 6.62 (0.78H, brs), 6.68 (0.22H, d, J=8.1 Hz), 6.85 (0.22H, d, J=7.8 Hz), 6.98-7.04 (1.56H, m), 7.11-7.39 (3H, m), 7.44-7.49 (1H, m).

REFERENCE EXAMPLE 354

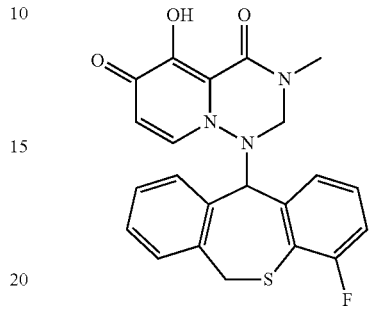

¹H-NMR (CDCl₃) δ: 2.89 (0.48H, s), 3.00 (2.52H, s), 3.64 (0.84H, d, J=13.5 Hz), 3.71 (0.16H, d, J=13.8 Hz), 4.21 (1H, d, J=12.9 Hz), 4.94 (0.84H, d, J=12.9 Hz), 4.98 (0.16H, d, J=12.9 Hz), 5.10 (0.16H, s), 5.19 (0.84H, s), 5.65 (0.84H, d, J=7.5 Hz), 5.77-5.85 (1.32H, m), 6.52 (0.84H, d, J=7.8 Hz), 6.64 (0.16H, d, J=7.8 Hz), 6.77-6.84 (1H, m), 6.89-6.95 (1H, m), 6.99 (1H, d, J=7.8 Hz), 7.07-7.25 (1H, m), 7.29-7.38 (2H, m), 7.42-7.47 (1H, m).

REFERENCE EXAMPLE 355

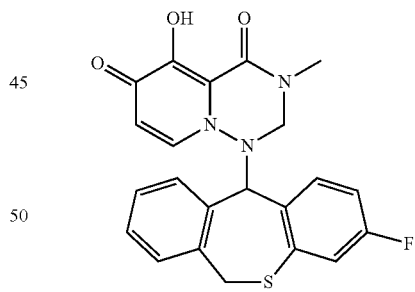

¹H-NMR (CDCl₃) δ: 2.91 (0.48H, s), 3.00 (2.52H, s), 3.56 (d, J=13.8 Hz), 3.62 (0.16H, d, J=13.8 Hz), 4.18 (0.16H, d, J=12.9 Hz), 4.20 (0.84H, d, J=12.9 Hz), 4.96 (0.84H, d, J=12.9 Hz), 4.98 (0.16H, d, J=13.8 Hz), 5.03 (0.16H, s), 5.12 (0.84H, s), 5.64 (0.84H, d, J=13.5 Hz), 5.78-5.87 (0.32H, m), 5.89 (0.84H, d, J=7.8 Hz), 6.50-6.56 (0.84H, m), 6.63-6.69 (1.16H, m), 6.84 (1H, dd, J=2.4 Hz, 9.3 Hz), 6.94-6.97 (0.16H, m), 7.02 (0.84H, d, J=7.5 Hz), 7.13-7.23 (1H, m), 7.33-7.38 (2H, m), 7.42-7.47 (1H, m).

REFERENCE EXAMPLE 356

[Chemical formula 407]

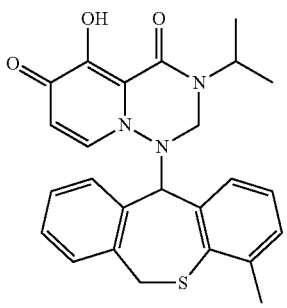

¹H-NMR (CDCl₃) δ: 1.08 (3H, d, J=6.9 Hz), 1.15 (3H, d, J=6.9 Hz), 2.24 (3H, s), 3.68 (1H, d, J=13.2 Hz), 4.38 (1H, d, J=13.2 Hz), 4.76-4.85 (1H, m), 4.80 (1H, d, J=12.6 Hz), 5.14 (1H, s), 5.72 (1H, d, J=12.9 Hz), 5.76 (1H, d, J=7.8 Hz), 6.59 (1H, d, J=7.5 Hz), 6.72 (1H, t, J=7.5 Hz), 6.99 (1H, d, J=6.9 Hz), 7.07 (1H, d, J=7.8 Hz), 7.17-7.27 (2H, m), 7.33-7.42 (2H, m).

REFERENCE EXAMPLE 357

[Chemical formula 408]

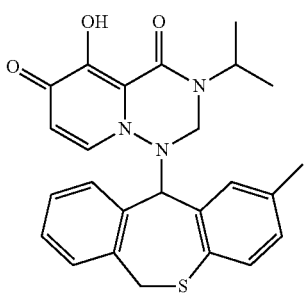

¹H-NMR (CDCl₃) δ: 1.10 (3H, d, J=6.9 Hz), 1.16 (3H, d, J=6.9 Hz), 3.58 (1H, d, J=13.2 Hz), 4.37 (1H, d, J=12.9 Hz), 4.76-4.87 (1H, m), 4.85 (1H, d, J=12.6 Hz), 5.06 (1H, s), 5.65 (1H, d, J=13.2 Hz), 5.79 (1H, d, J=7.5 Hz), 6.54 (1H, s), 6.89 (1H, dd, J=1.5 Hz, 8.4 Hz), 6.95 (1H, d, J=7.8 Hz), 7.14-7.19 (1H, m), 7.22-7.28 (1H, m), 7.33-7.43 (2H, m).

REFERENCE EXAMPLE 358

[Chemical formula 409]

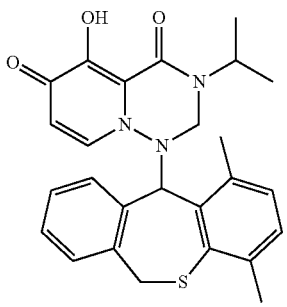

¹H-NMR (CDCl₃) δ: 1.07 (3H, d, J=6.9 Hz), 1.16 (3H, d, J=6.9 Hz), 2.20 (3H, s), 2.23 (3H, s), 3.77 (1H, d, J=12.6 Hz), 4.47 (1H, d, J=12.9 Hz), 4.78-4.86 (1H, m), 4.88 (1H, 12.9 Hz), 5.49 (1H, d, J=12.9 Hz), 5.83 (1H, d, J=11.1 Hz), 5.85 (1H, d, J=9.0 Hz), 6.64 (1H, d, J=7.8 Hz), 6.86 (1H, J=7.8 Hz), 7.16-7.40 (5H, m).

REFERENCE EXAMPLE 359

[Chemical formula 410]

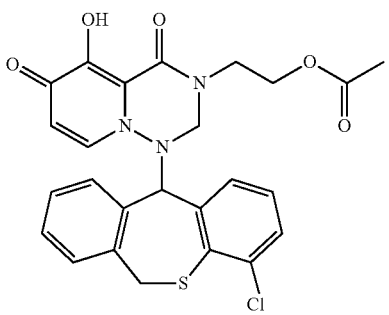

¹H-NMR (DMSO-d₆) δ: 1.94 (3H, s), 3.07 (1H, m), 3.98-4.12 (4H, m), 4.25 (2H, d, J=13.4 Hz), 5.13 (2H, d, J=13.3 Hz), 5.56 (1H, s), 5.66 (1H, d, J=13.5 Hz), 5.68 (1H, t, J=7.8 Hz), 6.87-7.51 (8H, m).

REFERENCE EXAMPLE 360

[Chemical formula 411]

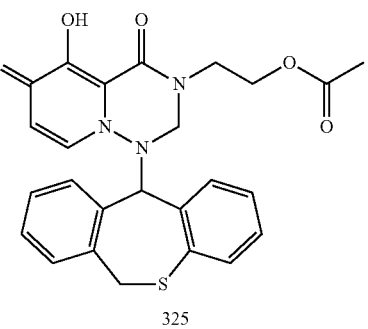

325

→

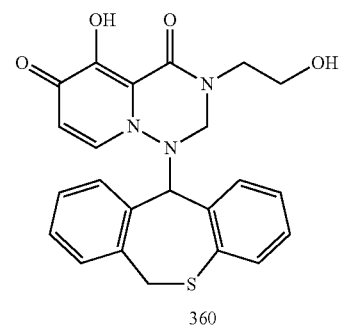

360

Compound 325 (46.0 mg, 0.0960 mmol) was dissolved in methanol (0.5 ml) and tetrahydrofuran (0.5 ml), a 2N aqueous sodium hydroxide solution (0.241 ml, 0.482 mmol) was added, and the mixture was stirred for 30 minutes. To the reaction solution was added dilute hydrochloric acid to make the solution acidic, and the mixture was extracted with chloroform. The organic layer was dried with sodium sulfate, and the reaction solution was concentrated under reduced pressure. To the resulting compound 360 were added n-hexane-diethyl ether, and the precipitated residue was filtered to obtain 33 mg of a white solid.

$^1$H-NMR (DMSO-$d_6$) δ: 2.85-2.94 (1H, m), 3.52 (2H, m), 3.89 (1H, d, J=13.4 Hz), 3.98 (1H, td, J=9.1, 4.5 Hz), 4.24 (1H, d, J=13.6 Hz), 4.84 (1H, brs), 5.16 (1H, d, J=13.6 Hz), 5.48 (1H, s), 5.65 (2H, m), 6.86-7.55 (9H, m).

MS: m/z=436 [M+H]$^+$

Using ester bodies synthesized according to Reference examples 107, 246 and 285, and according to the method of Reference example 320, compounds 361 to 382 were synthesized.

REFERENCE EXAMPLE 361

[Chemical formula 412]

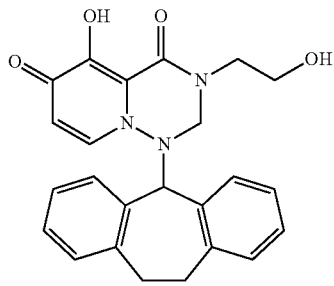

$^1$H-NMR (DMSO-$d_6$) δ: 2.82 (3H, m), 3.49 (1H, brs), 3.71 (1H, dt, J=16.7, 5.0 Hz), 4.03 (1H, t, J=7.8 Hz), 4.08-4.15 (2H, m), 4.79 (1H, brs), 5.01 (1H, d, J=13.4 Hz), 5.25 (1H, s), 5.51 (1H, d, J=7.6 Hz), 6.72-7.41 (9H, m).

REFERENCE EXAMPLE 362

[Chemical formula 413]

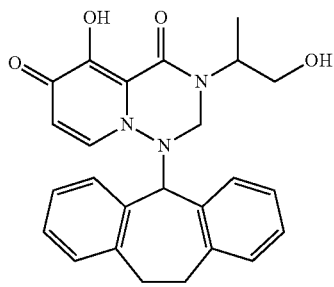

MS: m/z=432 [M+H]$^+$.

REFERENCE EXAMPLE 363

[Chemical formula 414]

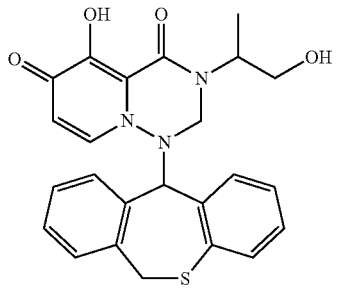

MS: m/z=450 [M+H]$^+$.

REFERENCE EXAMPLE 364

[Chemical formula 415]

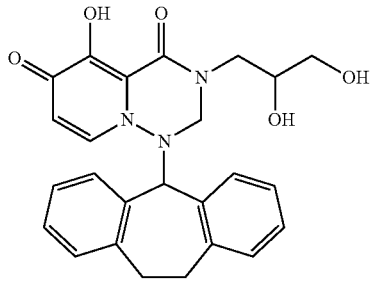

MS: m/z=448 [M+H]$^+$.

REFERENCE EXAMPLE 365

[Chemical formula 416]

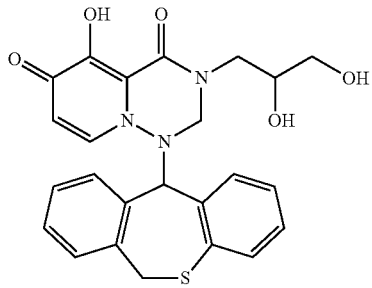

MS: m/z=466 [M+H]$^+$.

REFERENCE EXAMPLE 366

[Chemical formula 417]

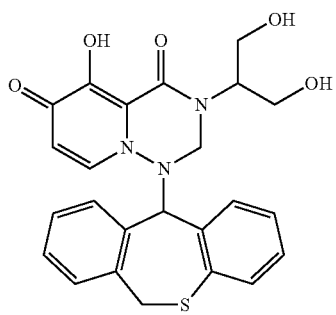

MS: m/z=466 [M+H]⁺.

REFERENCE EXAMPLE 367

[Chemical formula 418]

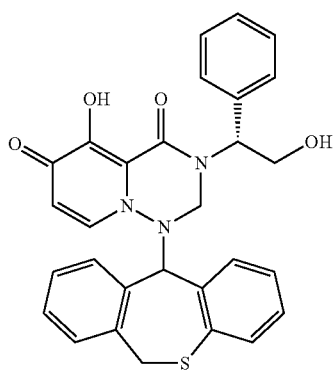

MS: m/z=512 [M+H]⁺.

REFERENCE EXAMPLE 368

[Chemical formula 419]

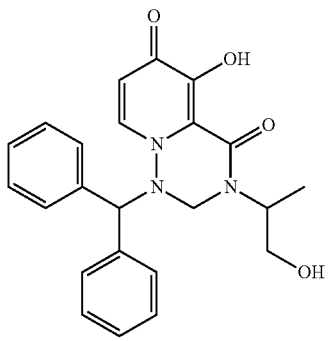

MS: m/z=406 [M+H]⁺.

REFERENCE EXAMPLE 369

[Chemical formula 420]

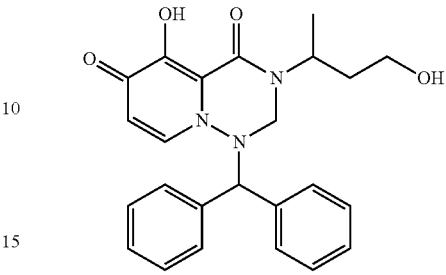

MS: m/z=420 [M+H]⁺.

REFERENCE EXAMPLE 370

[Chemical formula 421]

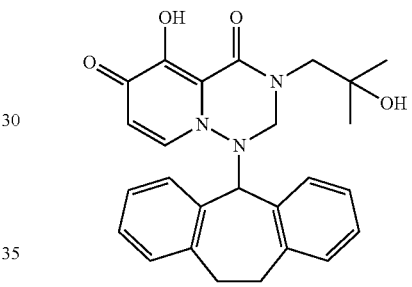

$^1$H-NMR (CDCl$_3$) δ: 1.23 (3H, s), 1.24 (3H, s), 2.43 (1H, d, J=13.7 Hz), 2.81-2.91 (1H, m), 2.96-3.10 (1H, m), 3.61-3.72 (1H, m), 4.02-4.14 (1H, m), 4.15 (1H, d, J=13.7 Hz), 4.42 (1H, d, J=14.0 Hz), 4.95 (1H, s), 5.15 (1H, d, J=13.5 Hz), 5.74 (1H, d, J=7.7 Hz), 6.54-6.61 (2H, m), 6.86-6.94 (1H, m), 7.11-7.39 (8H, m).
MS: m/z=446 [M+H]⁺.

REFERENCE EXAMPLE 371

[Chemical formula 422]

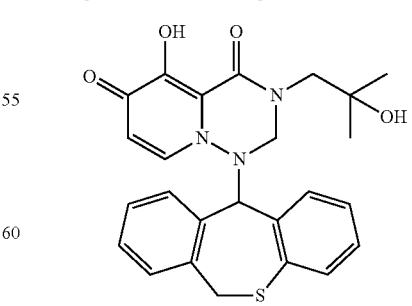

$^1$H-NMR (CDCl$_3$) δ: 1.24 (3H, s), 1.26 (3H, s), 2.52 (1H, d, J=14.0 Hz), 3.56 (1H, d, J=13.7 Hz), 4.34 (1H, d, J=13.5 Hz), 4.36 (1H, d, J=13.5 Hz), 5.04 (1H, s), 5.23 (1H, d,

J=13.7 Hz), 5.63 (1H, d, J=13.5 Hz), 5.84 (1H, d, J=7.7 Hz), 6.65 (1H, d, J=7.7 Hz), 6.76-6.84 (1H, m), 7.03-7.18 (5H, m), 7.27-7.47 (4H, m).

MS: m/z=464 [M+H]$^+$.

REFERENCE EXAMPLE 372

[Chemical formula 423]

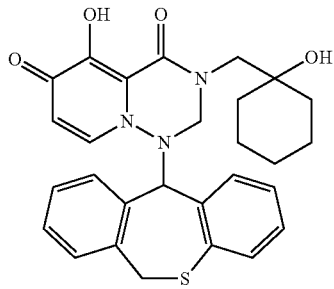

$^1$H-NMR (CDCl$_3$) δ: 1.21-1.68 (10H, m), 2.47 (1H, d, J=13.7 Hz), 3.55 (1H, d, J=13.5 Hz), 4.34 (1H, d, J=13.6 Hz), 4.35 (1H, d, J=13.6 Hz), 5.03 (1H, s), 5.25 (1H, d, J=13.5 Hz), 5.63 (1H, d, J=13.5 Hz), 5.79 (1H, d, J=7.7 Hz), 6.64 (1H, d, J=7.4 Hz), 6.76-6.84 (1H, m), 7.03 (1H, d, J=7.7 Hz), 7.06-7.10 (2H, m), 7.15 (1H, d, J=7.1 Hz), 7.28-7.37 (2H, m), 7.37-7.46 (1H, m).

MS: m/z=504 [M+H]$^+$.

REFERENCE EXAMPLE 373

[Chemical formula 424]

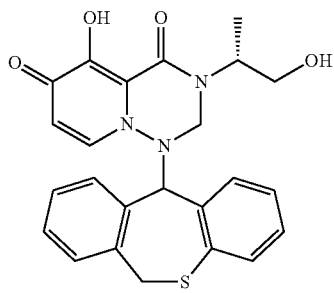

MS: m/z=450 [M+H]$^+$.

REFERENCE EXAMPLE 374

[Chemical formula 425]

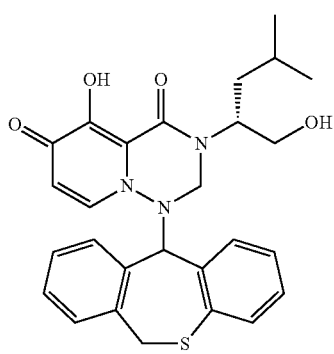

MS: m/z=492 [M+H]$^+$.

REFERENCE EXAMPLE 375

[Chemical formula 426]

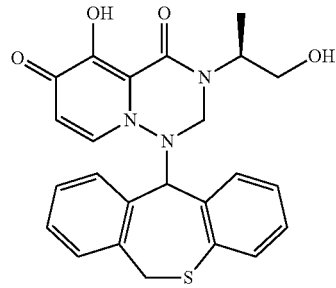

MS: m/z=445 [M+H]$^+$.

REFERENCE EXAMPLE 376

[Chemical formula 427]

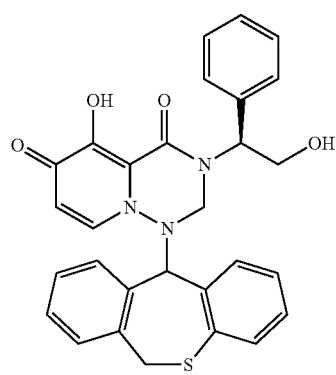

MS: m/z=512 [M+H]$^+$.

REFERENCE EXAMPLE 377

[Chemical formula 428]

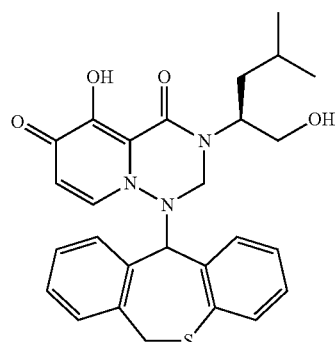

MS: m/z=492 [M+H]$^+$.

REFERENCE EXAMPLE 378
[Chemical formula 429]
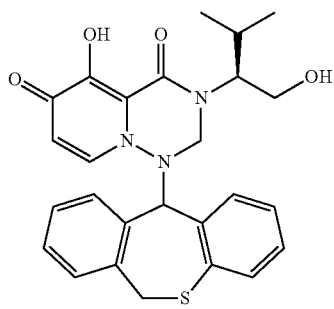
MS: m/z=478 [M+H]+
REFERENCE EXAMPLE 379
[Chemical formula 430]
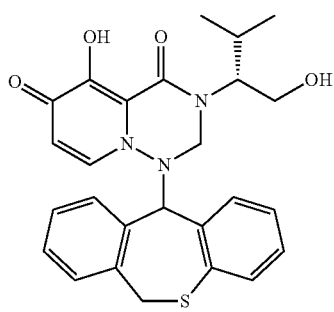
MS: m/z=478 [M+H]+
REFERENCE EXAMPLE 380
[Chemical formula 431]
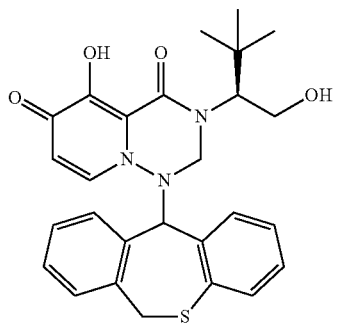
MS: m/z=492 [M+H]+
REFERENCE EXAMPLE 381
[Chemical formula 432]
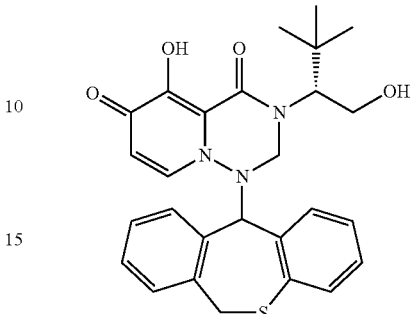
MS: m/z=492 [M+H]+
REFERENCE EXAMPLE 382
[Chemical formula 433]
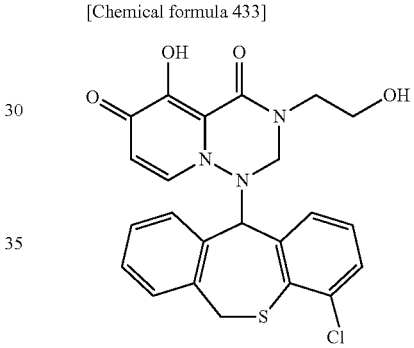
$^1$H-NMR (DMSO-$d_6$) δ: 2.76-2.85 (1H, m), 3.58 (2H, m), 3.92 (1H, m), 3.98 (1H, d, J=13.5 Hz), 4.18 (1H, d, J=13.6 Hz), 4.80 (1H, brs), 5.10 (1H, t, J=8.8 Hz), 5.50-5.68 (3H, m), 6.87-7.52 (8H, m).
REFERENCE EXAMPLE 383
[Chemical formula 434]
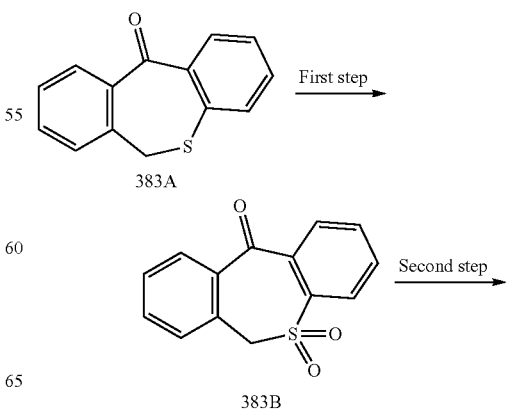

363

-continued

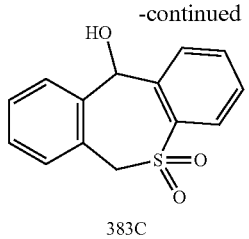

383C

Third step →

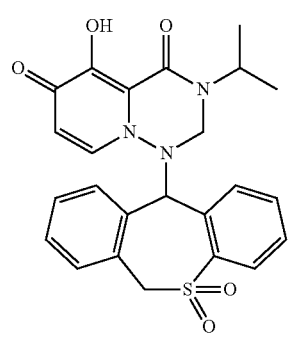

383

First Step

Compound 383A (1.00 g, 4.42 mmol) was dissolved in dichloromethane (50 ml), mCPBA (2.67 g, 15.5 mmol) was added at 0° C., and the mixture was stirred at room temperature for 4 hours. To the reaction solution was added an aqueous sodium sulfite solution, and the mixture was extracted with dichloromethane. The organic layer was washed with an aqueous sodium bicarbonate solution, and dried with sodium sulfate, and the solvent was distilled off. To the resulting compound were added n-hexane-dichloromethane, and the precipitated residue was filtered to obtain 1.06 g of a white solid 383B.

$^1$H-NMR (CDCl$_3$) δ: 4.81 (2H, s), 7.29-8.12 (6H, m).

Second Step

To compound 383B (1.05 g, 4.07 mmol) was added methanol (11 ml), sodium borohydride (185 mg, 4.88 mmol) was added at 0° C., and the mixture was stirred at room temperature for 30 minutes. The reaction solution was poured into water, the mixture was extracted with dichloromethane, the organic layer was dried with sodium sulfate, and the solvent was distilled off. To the resulting compound were added n-hexane-dichloromethane, and the precipitated residue was filtered to obtain 1.01 g of a white solid 383C.

$^1$H-NMR (CDCl$_3$) δ: 2.84 (1H, d, J=3.7 Hz), 4.76 (1H, d, J=14.6 Hz), 5.25 (1H, d, J=14.6 Hz), 6.23 (1H, d, J=3.7 Hz), 7.28-7.96 (8H, m).

Third Step

According to Reference example 107, compound 383 was synthesized by the same procedure.

MS: m/z=466 [M+H]$^+$.

Using intermediates corresponding to 383A to 383C which are commercially available or known in the references, and according to the method of Reference example 383, compounds 384 to 389 were synthesized.

364

REFERENCE EXAMPLE 384

[Chemical formula 435]

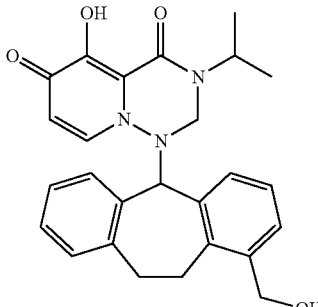

$^1$H-NMR (CDCl$_3$) δ: 1.12-1.25 (6H, m), 2.87-3.26 (3H, m), 3.42-3.67 (1H, m), 4.00-4.08 (1H, m), 4.28-4.35 (1H, m), 4.56-4.83 (3H, m), 5.10-5.30 (1H, m), 5.89-6.11 (1H, m), 6.55-6.63 (0.5H, m), 6.71-6.75 (0.5H, m), 6.84-6.94 (1H, m), 7.03-7.47 (4H, m), 8.18-8.20(0.5H, m), 8.48-8.49 (0.5H, m).

REFERENCE EXAMPLE 385

[Chemical formula 436]

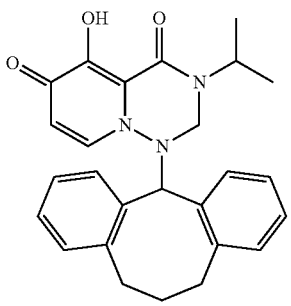

$^1$H-NMR (CDCl$_3$) δ: 0.59 (3H, d, J=6.6 Hz), 1.07-1.14 (4H, m), 1.19-1.28 (1H, m), 2.22-2.32 (1H, m), 2.73-3.12 (3H, m), 4.71-4.81 (1H, m), 4.83 (1H, d, J=12.9 Hz), 4.96 (1H, d, J=12.9 Hz), 5.88 (1H, d, J=7.5 Hz), 5.89 (1H, s), 6.89 (1H, m), 7.00-7.04 (2H, m), 7.08-7.18 (2H, m), 7.22-7.27 (1H, m), 7.38 (1H, d, J=7.5 Hz), 7.58-7.61 (1H, m), 7.79 (1H, d, J=7.5 Hz).

REFERENCE EXAMPLE 386

[Chemical formula 437]

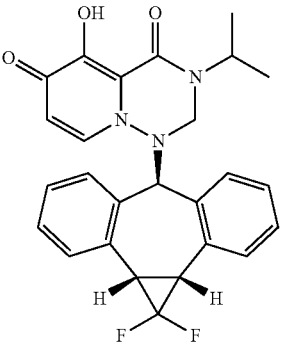

¹H-NMR (CDCl₃) δ: 0.95 (3H, d, J=6.9 Hz), 1.17 (3H, d, 6.9 Hz), 3.34(2H, d, J=12.3 Hz), 4.39 (1H, d, J=12.9 Hz), 4.56-4.65 (1H, m), 4.85 (1H, d, J=12.9 Hz), 4.93 (1H, m), 5.77 (1H, d, J=7.5 Hz), 6.77-6.81 (1H, m), 6.79 (1H, d, J=7.5 Hz), 7.00-7.05 (1H, m), 7.21-7.29 (2H, m), 7.32-7.42 (3H, m).

REFERENCE EXAMPLE 387

[Chemical formula 438]

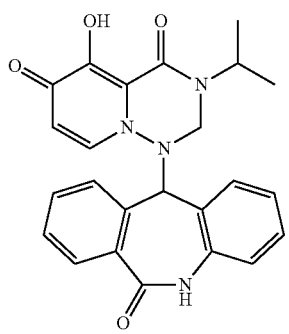

¹H-NMR (CDCl₃) δ: 1.06-1.17 (6H, m), 4.02-4.17 (1H, m), 4.61-4.78 (2H, m), 5.16 (1H, d, J=5.1 Hz), 5.72 (1H, t, J=8.1 Hz), 6.54 (0.5H, d, J=7.8 Hz), 6.84 (0.5H, d, J=7.8 Hz), 6.91-7.08 (2H, m), 7.16-7.47 (4H, m), 7.56-7.59 (1H, m), 8.00 (0.5H, J=6.3 Hz), 8.09-8.12 (0.5H, m), 8.51 (0.5H, s), 8.68 (0.5H, s).

REFERENCE EXAMPLE 388

[Chemical formula 439]

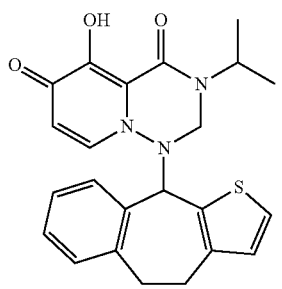

¹H-NMR (CDCl₃) δ: 1.19 (3H, d, J=6.9 Hz), 1.25 (3H, d, J=6.9 Hz), 2.76-2.91 (2H, m), 3.23-3.31 (1H, m), 4.17-4.33 (2H, m), 4.54-4.84 (2H, m), 5.18 (1H, s), 5.87 (1H, d, J=7.8 Hz), 6.70 (1H, d, J=5.1 Hz), 6.86 (1H, d, J=7.8 Hz), 7.04 (1H, d, J=5.1 Hz), 7.19-7.25 (2H, m), 7.32-7.38 (2H, m).

REFERENCE EXAMPLE 389

[Chemical formula 440]

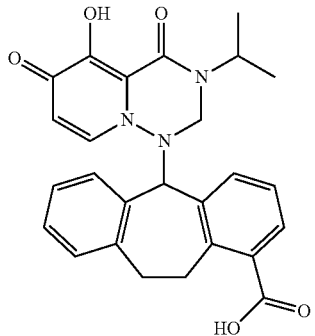

¹H-NMR (DMSO-d₆) δ: 1.04-1.20 (6H, m), 2.83-3.02 (1H, m), 3.46-3.57 (1H, m), 3.75-3.85 (1H, m), 4.13-4.26 (1H, m), 4.32-4.50 (1H, m), 4.56-4.62 (1H, m), 4.89 (1H, d, J=13.2 Hz), 5.36 (1H, s), 5.44-5.50 (1H, m), 6.73 (1H, d, J=7.8 Hz), 6.86 (1H, t, J=7.5 Hz), 6.95-6.98 (1H, m), 7.09-6.54 (5H, m).

REFERENCE EXAMPLE 390

[Chemical formula 441]

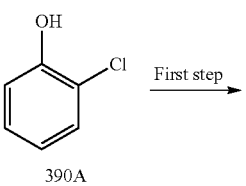

390A

First step →

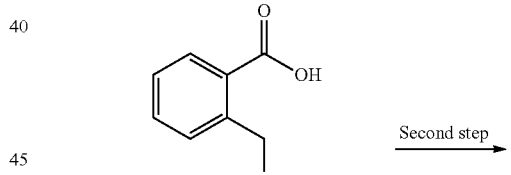

390B

Second step →

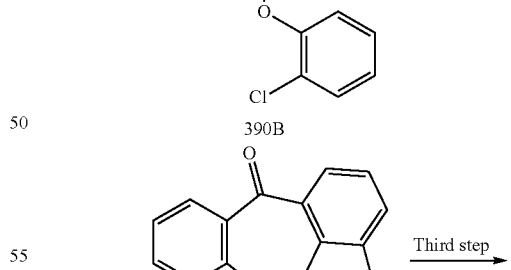

390C

Third step →

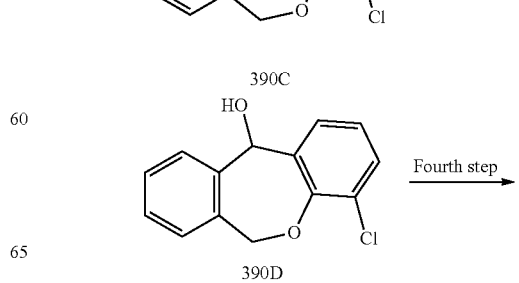

390D

Fourth step →

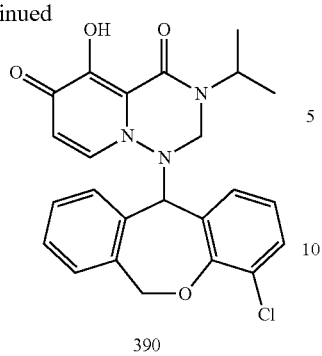

390

First Step

Compound 390A (14.8 g, 115 mmol) was added to methanol (200 ml), sodium methoxide (28% methanol solution, 22.2 g, 115 mmol) was added at room temperature, and the mixture was stirred for 1 hour. The solvent was distilled off under reduced pressure to obtain 17.3 g of a white solid. To 5.61 g of it was added phthalide (5.00 g, 37.3 mmol), and the mixture was stirred at 200° C. for 1 hour. The reaction solution was poured into water, the mixture was made acidic with hydrochloric acid, and the generated white precipitate was filtered. This was dissolved in chloroform, the solution was dried with sodium sulfate, and the solvent was distilled off. To the resulting compound were added n-hexane-chloroform-diisopropyl ether, and the precipitated residue was filtered to obtain 2.44 g of a pale brown solid 390B.

$^1$H-NMR (CDCl$_3$) δ: 5.61 (2H, s), 6.92 (1H, td, J=7.6, 1.4 Hz), 7.01 (1H, dd, J=8.3, 1.3 Hz), 7.21 (1H, ddd, J=8.7, 7.0, 1.2 Hz), 7.32-7.54 (2H, m), 7.66 (1H, td, J=7.6, 1.4 Hz), 7.92-7.99 (1H, m), 8.17 (1H, dd, J=7.9, 1.3 Hz).

Second Step

Compound 390B (2.44 g, 9.29 mmol) was dissolved in dichloromethane (30 ml), trifluoroacetic anhydride (1.44 ml, 10.2 mmol) and boron trifluoride etherate (0.235 ml, 1.86 mmol) were added, and the mixture was stirred at room temperature for 3 hours. The reaction solution was poured into water, the mixture was extracted with dichloromethane, the organic layer was washed with 1N hydrochloric acid and an aqueous saturated sodium chloride solution, and the solvent was distilled off. The resulting crude product was purified by silica gel column chromatography, and eluted with n-hexane-ethyl acetate (4:1, v/v) to obtain 1.76 g of a pale yellow solid 390C.

$^1$H-NMR (CDCl$_3$) δ: 5.36 (2H, s), 7.11 (1H, t, J=8.0 Hz), 7.43-7.66 (4H, m), 7.93 (1H, d, J=6.5 Hz), 8.19 (1H, dd, J=8.1, 1.8 Hz).

Third Step

To compound 390C (1.76 g, 7.19 mmol) was added methanol (20 ml), sodium borohydride (327 mg, 8.63 mmol) was added at 0° C., and the mixture was stirred at room temperature for 30 minutes. The reaction solution was poured into water, the mixture was extracted with dichloromethane, the organic layer was dried with sodium sulfate, and the solvent was distilled off. To the resulting compound were added n-hexane-dichloromethane, and the precipitated residue was filtered to obtain 1.44 g of a white solid 390D.

$^1$H-NMR (CDCl$_3$) δ: 2.75 (1H, d, J=5.0 Hz), 5.18 (1H, d, J=13.6 Hz), 5.69 (1H, d, J=5.0 Hz), 5.89 (1H, d, J=13.6 Hz), 6.93 (1H, t, J=7.9 Hz), 7.19-7.43 (6H, m).

Fourth Step

According to the same procedure as that of Reference example 107, compound 390 was synthesized.

MS: m/z=452 [M+H]$^+$

Using amines which are commercially available or known in the references and intermediates corresponding to 390A to 390D which are commercially available or known in the references, and according to the method of Reference example 390, compounds 391 to 412 were synthesized.

REFERENCE EXAMPLE 391

[Chemical formula 442]

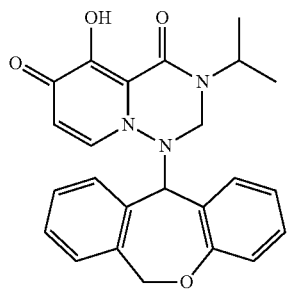

MS: m/z=418 [M+H]$^+$.

REFERENCE EXAMPLE 392

[Chemical formula 443]

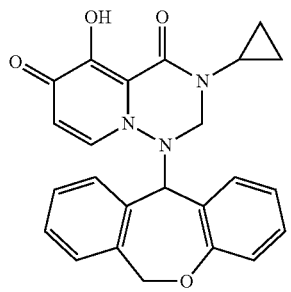

MS: m/z=416 [M+H]$^+$.

REFERENCE EXAMPLE 393

[Chemical formula 444]

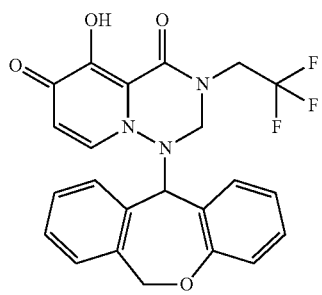

MS: m/z=458 [M+H]$^+$.

REFERENCE EXAMPLE 394

[Chemical formula 445]

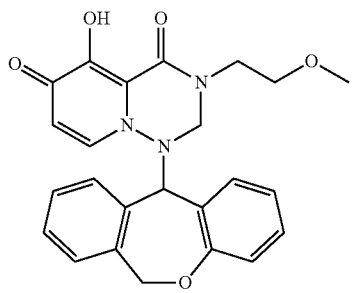

MS: m/z=434 [M+H]+.

REFERENCE EXAMPLE 395

[Chemical formula 446]

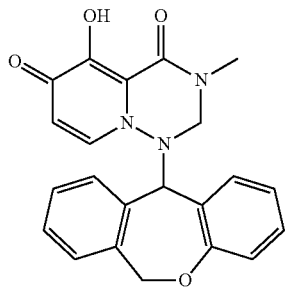

MS: m/z=390 [M+H]+.

REFERENCE EXAMPLE 396

[Chemical formula 447]

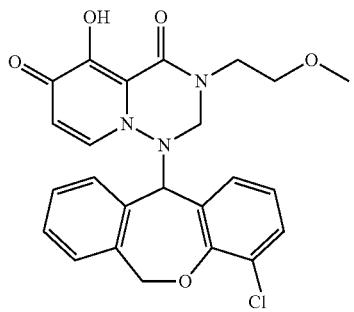

MS: m/z=468 [M+H]+

REFERENCE EXAMPLE 397

[Chemical formula 448]

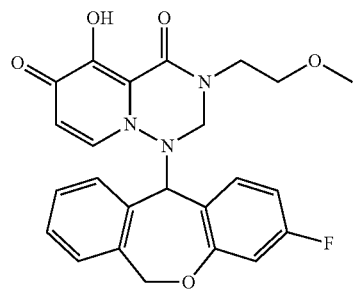

MS: m/z=452 [M+H]+.

REFERENCE EXAMPLE 398

[Chemical formula 449]

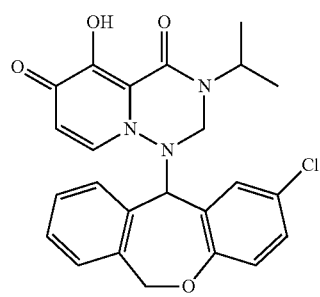

$^1$H-NMR (CDCl$_3$) δ: 1.12-1.32 (6H, m), 4.25 (0.52H, d, J=12.9 Hz), 4.41 (0.48H, d, J=13.2 Hz), 4.58-4.79 (2H, m), 4.92-5.03 (2H, m), 5.73 (0.48H, d, J=7.8 Hz), 5.89 (0.52H, d, J=7.8 Hz), 6.12 (0.48H, d, J=12 Hz), 6.46-6.58 (1.52H, m), 6.74-6.78 (1H, m), 6.98 (1H, t, J=7.5 Hz), 7.10-7.14 (1H, m), 7.20-7.50 (4H, m).

REFERENCE EXAMPLE 399

[Chemical formula 450]

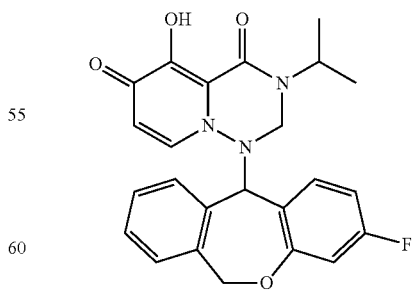

$^1$H-NMR (CDCl$_3$) δ: 1.12-1.31 (6H, m), 4.25 (0.75H, d, J=12.9 Hz), 4.43 (0.25H, d, J=12.9 Hz), 4.53-4.60 (0.50H, m), 4.67-4.78 (1.5H, m), 4.90-5.05 (2H, m), 5.70 (0.25H, d, J=7.8 Hz), 5.86 (0.75H, d, J=7.5 Hz), 6.18 (0.25H, d, J=13.5

Hz), 6.36-6.42 (0.75H, m), 6.49-6.56 (2H, m), 6.69-6.80 (1H, m), 6.94 (1H, d, J=7.8 Hz), 7.10-7.19 (0.25H, m), 7.21-7.50 (3.75H, m).
REFERENCE EXAMPLE 400
[Chemical formula 451]
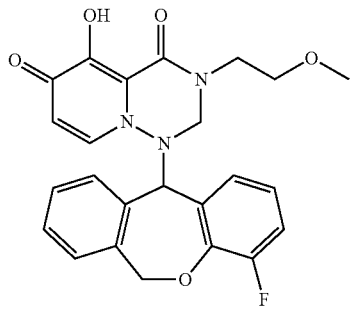
MS: m/z=452 [M+H]$^+$
REFERENCE EXAMPLE 401
[Chemical formula 452]
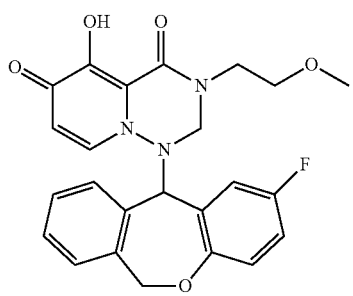
MS: m/z=452 [M+H]$^+$
REFERENCE EXAMPLE 402
[Chemical formula 453]
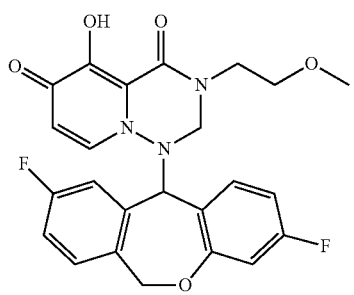
MS: m/z=470 [M+H]$^+$
REFERENCE EXAMPLE 403
[Chemical formula 454]
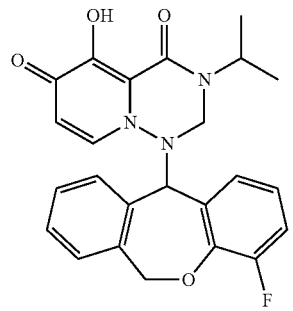
MS: m/z=436 [M+H]$^+$
REFERENCE EXAMPLE 404
[Chemical formula 455]
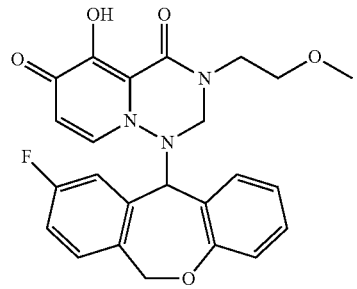
MS: m/z=452 [M+H]$^+$
REFERENCE EXAMPLE 405
[Chemical formula 456]
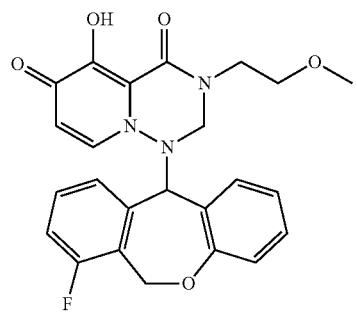
MS: m/z=452 [M+H]$^+$ REFERENCE EXAMPLE 406
[Chemical formula 457]
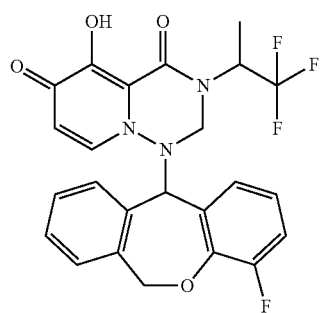
MS: m/z=490 [M+H]+
REFERENCE EXAMPLE 407
[Chemical formula 458]
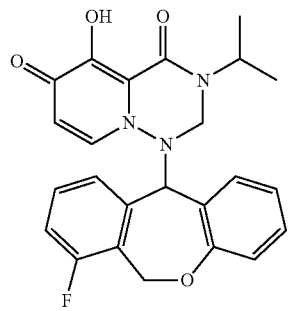
MS: m/z=436 [M+H]+
REFERENCE EXAMPLE 408
[Chemical formula 459]
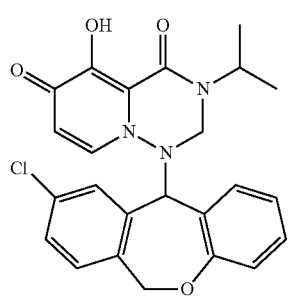
MS: m/z=452 [M+H]+
REFERENCE EXAMPLE 409
[Chemical formula 460]
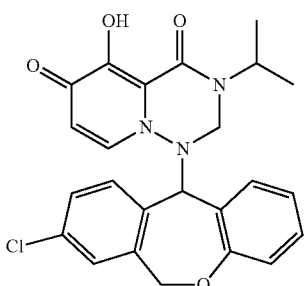
MS: m/z=452 [M+H]+
REFERENCE EXAMPLE 410
[Chemical formula 461]
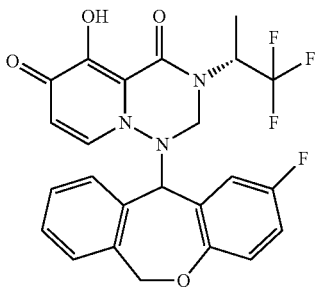
MS: m/z=490 [M+H]+
REFERENCE EXAMPLE 411
[Chemical formula 462]
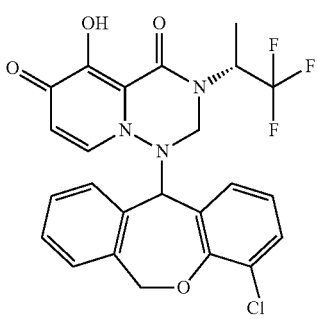
MS: m/z=506 [M+H]+

REFERENCE EXAMPLE 412

[Chemical formula 463]

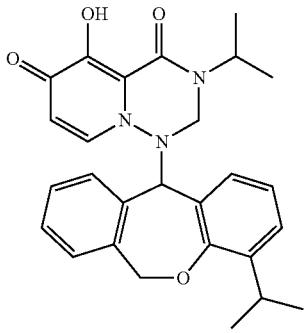

¹H-NMR (CDCl₃) δ: 1.13-1.31 (12H, m), 3.28-3.37 (0.50H, m), 3.44-3.53 (0.50H, m), 4.29-4.36 (1H, m), 4.65-4.76 (2H, m), 4.98-5.05 (2H, m), 6.37 (0.5H, d, J=12.9 Hz), 6.45 (0.5H, d, J=7.5 Hz), 6.67 (0.5H, t, J=7.8 Hz), 6.81 (0.5H, 7.8 Hz), 6.98-7.08 (2H, m), 7.14 (0.5Hm d, J=7.8 Hz), 7.22-7.45 (2.5H, m).

REFERENCE EXAMPLE 413, REFERENCE EXAMPLE 414

[Chemical formula 464]

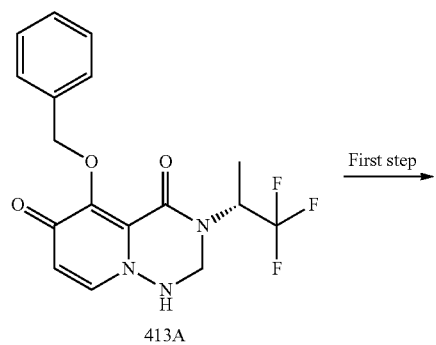
413A

First step →

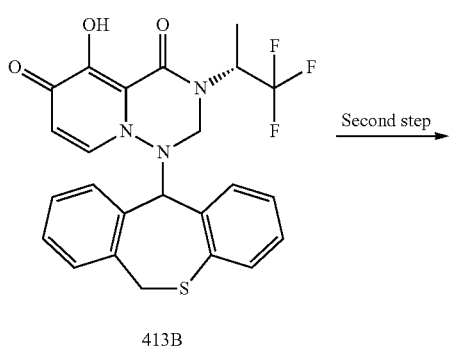
413B

Second step →

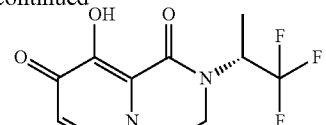
413

+

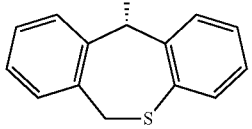
414

First Step

Compound 413A (200 mg, 0.544 mmol) obtained by the same procedure as that of Reference example 95, and 6,11-dihydrodibenzo[b,e]thiepin-11-ol (124 mg, 0.554 mmol) were dissolved in acetic acid (8 ml), and concentrated sulfuric acid (2 ml) was added dropwise under water-cooling. After the mixture was stirred at room temperature for 30 minutes, water was added, and the mixture was extracted with ethyl acetate. The organic layer was dried with sodium sulfate, and the solvent was distilled off under reduced pressure to obtain a crude product of 413B.

Second Step

Compound 413B obtained in the first step was dissolved in dichloromethane (2 ml), acetic acid anhydride (0.154 ml, 1.63 mmol), triethylamine (0.226 ml, 1.63 mmol) and 4-(dimethylamino)pyridine (cat.) were added, and the mixture was stirred at room temperature for 30 minutes. The solvent was distilled off, the resulting crude product was purified by silica gel column chromatography, and eluted with chloroform-methanol (97:3, v/v), and diastereomers were resolved. They were dissolved in methanol (1 ml) and tetrahydrofuran (1 ml), respectively, a 2N aqueous sodium hydroxide solution (0.198 ml, 0.397 mmol) was added, and the mixture was stirred at room temperature for 30 minutes. The reaction solution was poured into water, and the mixture was made acidic with hydrochloric acid, and extracted with ethyl acetate. The organic layer was dried with sodium sulfate, and the solvent was distilled off under reduced pressure. To the resulting compound were added ethyl acetate-diethyl ether, and the fractionation-precipitated residue was filtered to obtain compound 413 (22 mg) and compound 414 (20 mg), respectively.

REFERENCE EXAMPLE 413

¹H-NMR (DMSO-d₆) δ: 1.20 (3H, d, J=7.4 Hz), 3.92 (1H, d, J=13.6 Hz), 4.45 (1H, d, J=13.4 Hz), 5.12 (1H, d, J=12.8 Hz), 5.60 (4H, m), 6.87-7.60 (9H, m).

MS: m/z=488 [M+H]⁺

REFERENCE EXAMPLE 414

MS: m/z=488 [M+H]⁺

According to Reference example 413, compounds 414 to 475 were synthesized using the same procedure.

REFERENCE EXAMPLE 415

[Chemical formula 465]

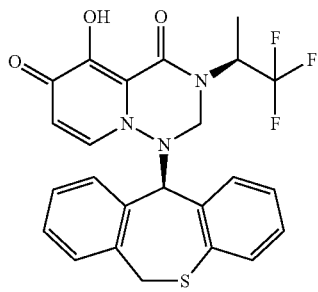

¹H-NMR (DMSO-d₆) δ: 1.16 (3H, d, J=7.3 Hz), 3.88 (1H, d, J=13.3 Hz), 4.41 (1H, d, J=13.3 Hz), 5.07 (1H, d, J=13.0 Hz), 5.42-5.52 (1H, m), 5.62 (3H, m), 6.82-7.56 (9H, m).
MS: m/z=488 [M+H]⁺

REFERENCE EXAMPLE 416

[Chemical formula 466]

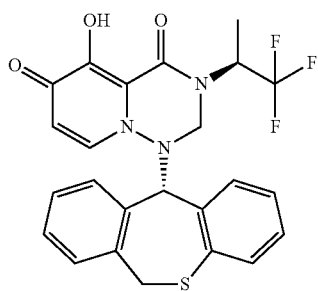

¹H-NMR (DMSO-d₆) δ: 1.35 (3H, d, J=7.3 Hz), 3.88 (1H, d, J=13.3 Hz), 4.44 (1H, d, J=12.7 Hz), 5.15 (1H, d, J=12.5 Hz), 5.16 (1H, m), 5.29 (1H, s), 5.57 (1H, d, J=13.4 Hz), 5.64 (1H, d, J=7.8 Hz), 6.81-7.45 (9H, m).
MS: m/z=488 [M+H]⁺

REFERENCE EXAMPLE 417

[Chemical formula 467]

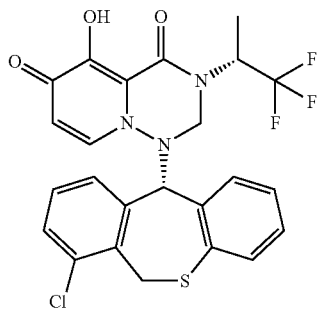

¹H-NMR (CDCl₃) δ: 1.22 (3H, d, J=7.2 Hz), 4.32 (1H, d, J=13.9 Hz), 4.49 (1H, d, J=13.1 Hz), 4.90 (1H, d, J=13.3 Hz), 5.15 (1H, s), 5.47-5.65 (2H, m), 5.83 (1H, d, J=8.1 Hz), 6.69 (1H, d, J=6.5 Hz), 6.80-6.87 (1H, m), 7.07-7.24 (5H, m), 7.54 (1H, d, J=7.9 Hz).
MS: m/z=522 [M+H]⁺.

REFERENCE EXAMPLE 418

[Chemical formula 468]

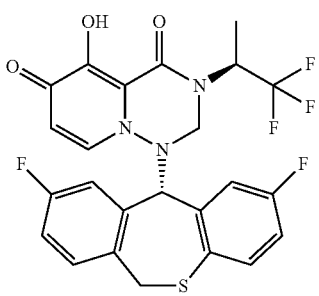

¹H-NMR (CDCl₃) δ: 1.48 (3H, d, J=7.1 Hz), 3.63 (1H, d, J=13.2 Hz), 4.49 (1H, d, J=12.6 Hz), 5.03 (1H, s), 5.28-5.45 (2H, m), 5.53 (1H, d, J=13.5 Hz), 5.73 (1H, d, J=7.7 Hz), 6.50 (1H, dd, J=8.7, 2.6 Hz), 6.79-6.86 (1H, m), 6.90 (1H, d, J=9.1 Hz), 7.02 (1H, dd, J=8.8, 5.2 Hz), 7.10 (1H, ddd, J=8.1, 2.5, 1.2 Hz), 7.25 (1H, d, J=7.7 Hz), 7.30 (1H, dd, J=8.5, 5.5 Hz).
MS: m/z=524 [M+H]⁺.

REFERENCE EXAMPLE 419

[Chemical formula 469]

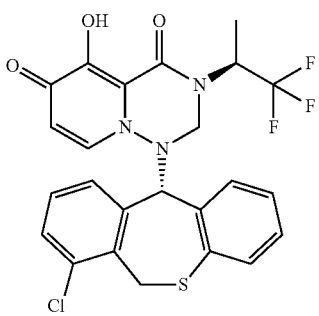

¹H-NMR (CDCl₃) δ: 1.50 (3H, d, J=7.1 Hz), 4.28 (1H, d, J=13.7 Hz), 4.50 (1H, d, J=12.4 Hz), 5.17 (1H, s), 5.26-5.44 (2H, m), 5.60-5.69 (2H, m), 6.65 (1H, d, J=7.4 Hz), 6.73-6.80 (1H, m), 7.01-7.21 (5H, m), 7.48 (1H, d, J=8.0 Hz).
MS: m/z=522 [M+H]⁺.

REFERENCE EXAMPLE 420

[Chemical formula 470]

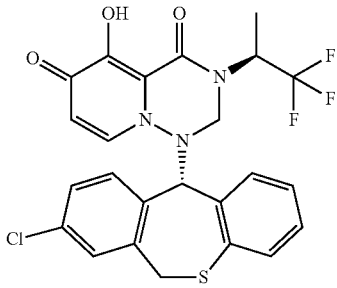

¹H-NMR (CDCl₃) δ: 1.49 (3H, d, J=7.4 Hz), 3.51 (1H, d, J=13.5 Hz), 4.48 (1H, d, J=12.6 Hz), 5.12 (1H, s), 5.28-5.44 (2H, m), 5.60-5.70 (2H, m), 6.65 (1H, d, J=7.4 Hz), 6.73-6.80 (1H, m), 7.00-7.06 (2H, m), 7.10 (1H, d, J=8.5 Hz), 7.14 (1H, d, J=8.0 Hz), 7.23 (1H, dd, J=8.2, 2.2 Hz), 7.31 (1H, d, J=1.9 Hz).
MS: m/z=522 [M+H]⁺.

REFERENCE EXAMPLE 421

[Chemical formula 471]

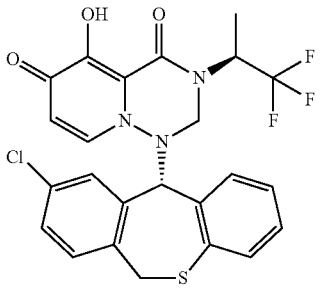

¹H-NMR (CDCl₃) δ: 1.53 (3H, d, J=7.4 Hz), 3.59 (1H, d, J=13.4 Hz), 4.51 (1H, d, J=12.6 Hz), 5.12 (1H, s), 5.30-5.48 (2H, m), 5.62-5.70 (2H, m), 6.71 (1H, d, J=7.7 Hz), 6.80-6.83 (1H, m), 7.07-7.11 (2H, m), 7.18 (1H, d, J=7.7 Hz), 7.22 (1H, s), 7.28 (1H, d, J=8.4 Hz), 7.39 (1H, d, J=8.1 Hz).
MS: m/z=522 [M+H]⁺.

REFERENCE EXAMPLE 422

[Chemical formula 472]

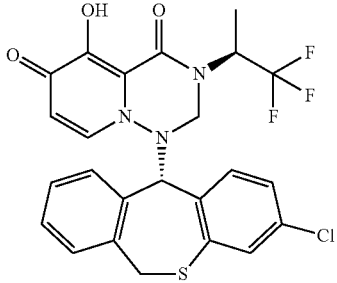

¹H-NMR (CDCl₃) δ: 1.49 (3H, d, J=7.4 Hz), 3.59 (1H, d, J=13.5 Hz), 4.48 (1H, d, J=12.4 Hz), 5.12 (1H, s), 5.29-5.39 (2H, m), 5.66 (1H, d, J=13.5 Hz), 5.73 (1H, d, J=7.7 Hz), 6.61 (1H, d, J=8.2 Hz), 6.73 (1H, dd, J=8.2, 2.2 Hz), 7.04 (1H, d, J=2.2 Hz), 7.12-7.20 (2H, m), 7.23-7.27 (1H, m), 7.31 (1H, d, J=6.3 Hz), 7.36-7.44 (1H, m).
MS: m/z=522 [M+H]⁺.

REFERENCE EXAMPLE 423

[Chemical formula 473]

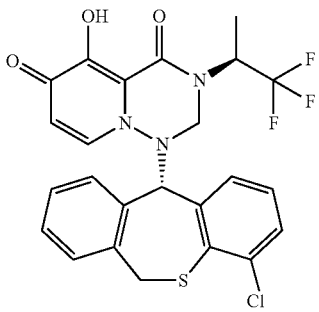

¹H-NMR (CDCl₃) δ: 1.47 (3H, d, J=7.1 Hz), 3.69 (1H, d, J=13.5 Hz), 4.49 (1H, d, J=12.6 Hz), 5.21 (1H, s), 5.27 (1H, d, J=12.6 Hz), 5.30-5.40 (1H, m), 5.70 (1H, d, J=7.7 Hz), 5.75 (1H, d, J=13.5 Hz), 6.65 (1H, dd, J=7.8, 1.5 Hz), 6.73 (1H, t, J=7.7 Hz), 7.13 (1H, d, J=7.7 Hz), 7.15-7.22 (2H, m), 7.25-7.29 (1H, m), 7.32 (1H, d, J=8.0 Hz), 7.37-7.45 (1H, m).
MS: m/z=522 [M+H]⁺.

REFERENCE EXAMPLE 424

[Chemical formula 474]

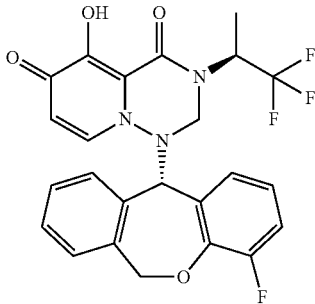

MS: m/z=490 [M+H]⁺.

REFERENCE EXAMPLE 425

[Chemical formula 475]

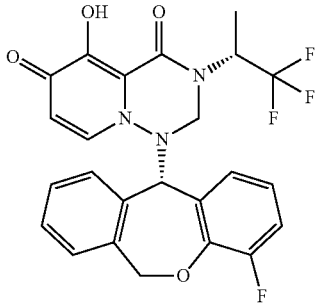

MS: m/z=490 [M+H]+.

REFERENCE EXAMPLE 426

[Chemical formula 476]

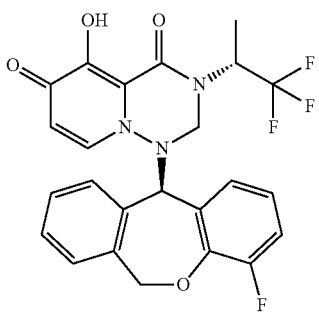

MS: m/z=490 [M+H]+.

REFERENCE EXAMPLE 427

[Chemical formula 477]

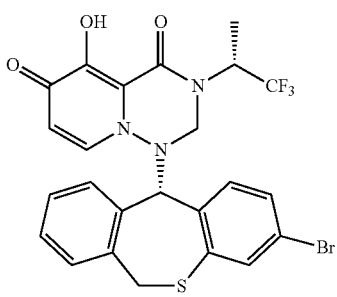

¹HNMR (CDCl$_3$) δ: 1.14 (3H, d, J=6.9 Hz), 3.64 (1H, d, J=13.5 Hz), 4.48 (1H, d, J=12.8 Hz), 4.88 (1H, d, J=12.8 Hz), 5.08 (1H, s), 5.51 (1H, m), 5.60 (1H, d, J=13.5 Hz), 5.93 (1H, d, J=8.1 Hz), 6.58 (1H, d, J=8.1 Hz), 6.95 (1H, dd, J=2.0, 8.1 Hz), 7.18 (2H, m), 7.29 (1H, m), 7.37-7.45 (2H, m).

REFERENCE EXAMPLE 428

[Chemical formula 478]

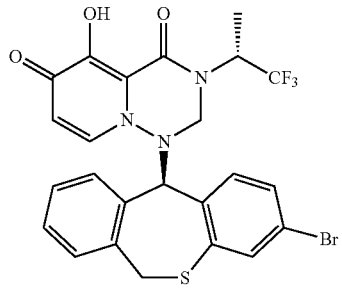

¹HNMR (CDCl$_3$) δ: 1.41 (3H, d, J=7.5 Hz), 3.61 (1H, d, J=13.4 Hz), 4.55 (1H, d, J=12.5 Hz), 5.06 (1H, d, J=12.5 Hz), 5.16 (1H, s), 5.34 (1H, m), 5.63 (1H, d, J=13.4 Hz), 5.87 (1H, d, J=8.1 Hz), 6.61 (1H, d, J=8.1 Hz), 6.93 (1H, dd, J=1.8, 8.1 Hz), 7.16-7.41 (5H, m).

REFERENCE EXAMPLE 429

[Chemical formula 479]

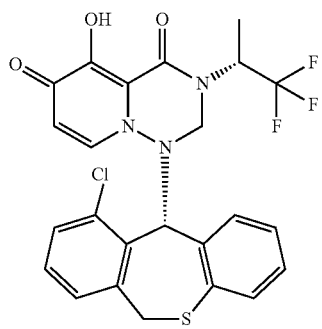

¹H-NMR (CDCl$_3$) δ: 1.15 (3H, d, J=7.4 Hz), 3.64 (1H, d, J=13.5 Hz), 4.44 (1H, d, J=13.2 Hz), 4.87 (1H, d, J=13.2 Hz), 5.44-5.57 (1H, m), 5.68 (1H, d, J=13.2 Hz), 5.83 (1H, d, J=7.7 Hz), 5.94 (1H, s), 6.78-6.91 (2H, m), 7.08-7.18 (3H, m), 7.28-7.38 (3H, m).

MS: m/z=522 [M+H]+.

REFERENCE EXAMPLE 430

[Chemical formula 480]

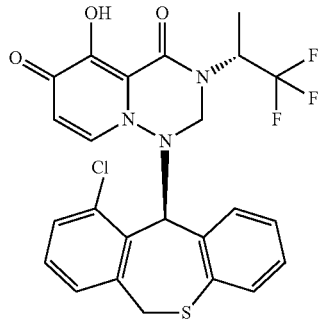

MS: m/z=522 [M+H]+.

REFERENCE EXAMPLE 431

[Chemical formula 481]

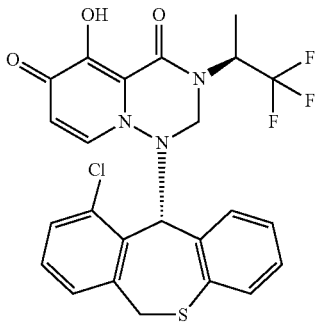

MS: m/z=522 [M+H]⁺.

REFERENCE EXAMPLE 432

[Chemical formula 482]

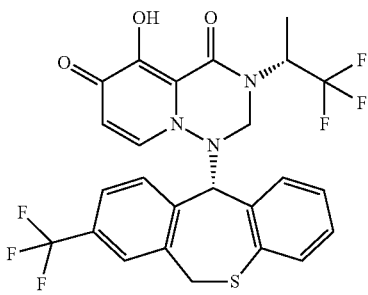

¹H-NMR (CDCl₃) δ: 1.21 (3H, d, J=7.4 Hz), 3.70 (1H, d, J=13.5 Hz), 4.43 (1H, d, J=13.2 Hz), 4.93 (1H, d, J=13.2 Hz), 5.21 (1H, s), 5.46-5.60 (1H, m), 5.70 (1H, d, J=13.5 Hz), 5.84 (1H, d, J=7.7 Hz), 6.73 (1H, d, J=7.1 Hz), 6.82-6.89 (1H, m), 7.08-7.17 (2H, m), 7.22 (1H, d, J=7.7 Hz), 7.35 (1H, d, J=8.0 Hz), 7.55 (1H, d, J=8.0 Hz), 7.67 (1H, s).
MS: m/z=071 [M+H]⁺.

REFERENCE EXAMPLE 433

[Chemical formula 483]

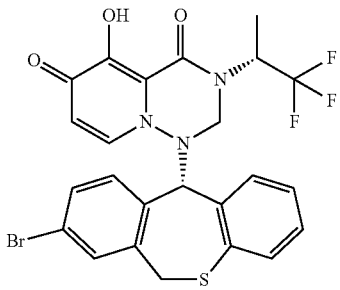

¹H-NMR (CDCl₃) δ: 1.22 (3H, d, J=7.1 Hz), 3.56 (1H, d, J=13.5 Hz), 4.48 (1H, d, J=13.2 Hz), 4.90 (1H, d, J=13.2 Hz), 5.09 (1H, s), 5.46-5.60 (1H, m), 5.62 (1H, d, J=13.2 Hz), 5.82 (1H, d, J=7.7 Hz), 6.69 (1H, d, J=7.4 Hz), 6.84 (1H, dt, J=10.0, 3.5 Hz), 7.04-7.14 (3H, m), 7.17 (1H, d, J=7.7 Hz), 7.42 (1H, dd, J=8.0, 1.6 Hz), 7.55 (1H, d, J=1.9 Hz).
MS: m/z=433 [M+H]⁺.

REFERENCE EXAMPLE 434

[Chemical formula 484]

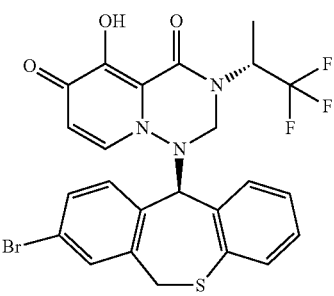

¹H-NMR (CDCl₃) δ: 1.44 (3H, d, J=7.3 Hz), 3.54 (1H, d, J=13.4 Hz), 4.54 (1H, d, J=12.5 Hz), 5.10 (1H, d, J=12.5 Hz), 5.16 (1H, s), 5.31-5.45 (1H, m), 5.65 (1H, d, J=13.3 Hz), 5.73 (1H, d, J=7.8 Hz), 6.71 (1H, d, J=7.8 Hz), 6.77-6.84 (1H, m), 7.03-7.11 (3H, m), 7.22 (1H, d, J=7.6 Hz), 7.40 (1H, dd, J=8.2, 2.0 Hz), 7.48 (1H, d, J=2.0 Hz).
MS: m/z=433 [M+H]⁺.

REFERENCE EXAMPLE 435

[Chemical formula 485]

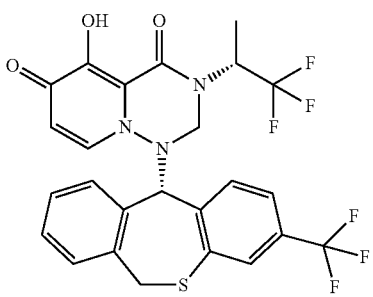

¹H-NMR (CDCl₃) δ: 1.14 (3H, d, J=7.3 Hz), 3.70 (1H, d, J=13.4 Hz), 4.51 (1H, d, J=13.1 Hz), 4.90 (1H, d, J=12.8 Hz), 5.19 (1H, s), 5.44-5.58 (1H, m), 5.62 (1H, d, J=13.3 Hz), 5.87 (1H, d, J=7.6 Hz), 6.86 (1H, d, J=7.9 Hz), 7.07 (1H, dd, J=8.2, 1.4 Hz), 7.15-7.22 (2H, m), 7.27-7.51 (4H, m).
MS: m/z=433 [M+H]⁺.

REFERENCE EXAMPLE 436

[Chemical formula 486]

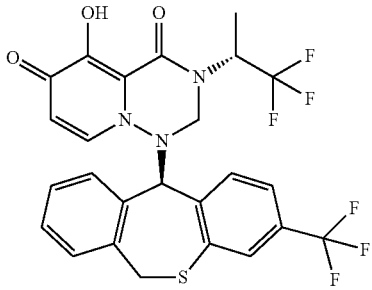

¹H-NMR (CDCl₃) δ: 1.48 (3H, d, J=7.4 Hz), 3.71 (1H, d, J=13.3 Hz), 4.60 (1H, d, J=12.6 Hz), 5.21 (1H, d, J=12.6 Hz), 5.29 (1H, s), 5.32-5.46 (1H, m), 5.70 (1H, d, J=13.3 Hz), 5.80 (1H, d, J=7.7 Hz), 6.91 (1H, d, J=7.9 Hz), 7.08 (1H, d, J=7.4 Hz), 7.20-7.29 (2H, m), 7.33-7.51 (4H, m).
MS: m/z=433 [M+H]⁺.

REFERENCE EXAMPLE 437

[Chemical formula 487]

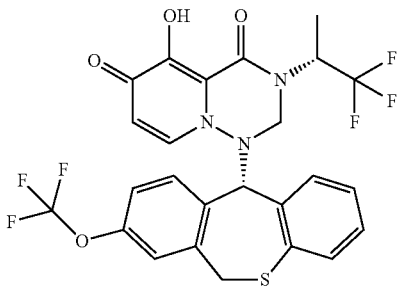

¹H-NMR (CDCl₃) δ: 1.21 (3H, d, J=7.3 Hz), 3.60 (1H, d, J=13.6 Hz), 4.46 (1H, d, J=13.1 Hz), 4.90 (1H, d, J=12.8 Hz), 5.15 (1H, s), 5.47-5.59 (1H, m), 5.68 (1H, d, J=13.4 Hz), 5.83 (1H, d, J=7.6 Hz), 6.70 (1H, d, J=7.3 Hz), 6.80-6.88 (1H, m), 7.07-7.26 (6H, m).
MS: m/z=433 [M+H]⁺.

REFERENCE EXAMPLE 438

[Chemical formula 488]

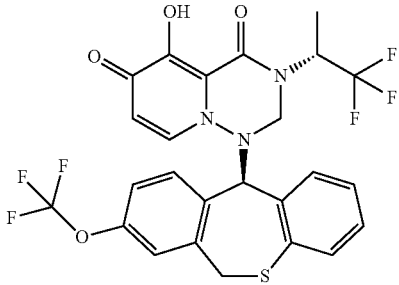

¹H-NMR (CDCl₃) δ: 1.42 (3H, d, J=7.3 Hz), 3.57 (1H, d, J=13.3 Hz), 4.55 (1H, d, J=12.5 Hz), 5.05 (1H, d, J=12.5 Hz), 5.23 (1H, s), 5.32-5.47 (1H, m), 5.70 (1H, d, J=13.4 Hz), 5.77 (1H, d, J=7.6 Hz), 6.74 (1H, d, J=7.8 Hz), 6.79-6.87 (1H, m), 7.04-7.26 (6H, m).
MS: m/z=433 [M+H]⁺.

REFERENCE EXAMPLE 439

[Chemical formula 489]

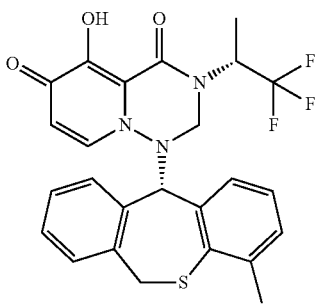

¹H-NMR (CDCl₃) δ: 1.20 (3H, d, J=7.2 Hz), 2.29 (3H, s), 3.76 (1H, d, J=13.3 Hz), 4.54 (1H, d, J=13.1 Hz), 4.92 (1H, d, J=13.1 Hz), 5.18 (1H, s), 5.50-5.62 (1H, m), 5.71 (1H, d, J=13.4 Hz), 5.84 (1H, d, J=7.7 Hz), 6.63 (1H, d, J=7.4 Hz), 6.78 (1H, t, J=7.6 Hz), 7.06 (1H, d, J=7.6 Hz), 7.17 (1H, d, J=7.7 Hz), 7.23 (1H, d, J=7.6 Hz), 7.28-7.34 (1H, m), 7.39-7.51 (2H, m).
MS: m/z=433 [M+H]⁺.

REFERENCE EXAMPLE 440

[Chemical formula 490]

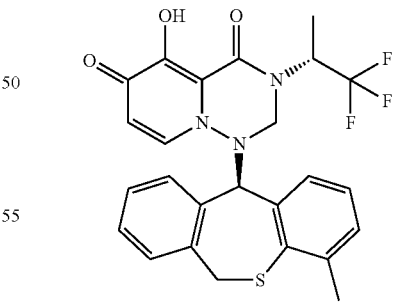

¹H-NMR (CDCl₃) δ: 1.45 (3H, d, J=7.2 Hz), 2.27 (3H, s), 3.74 (1H, d, J=13.3 Hz), 4.61 (1H, d, J=12.4 Hz), 5.07 (1H, d, J=12.4 Hz), 5.27 (1H, s), 5.31-5.44 (1H, m), 5.75 (1H, d, J=13.3 Hz), 5.80 (1H, d, J=7.7 Hz), 6.67 (1H, d, J=7.1 Hz), 6.77 (1H, t, J=7.6 Hz), 7.04 (1H, d, J=7.1 Hz), 7.21-7.47 (5H, m).
MS: m/z=433 [M+H]⁺.

REFERENCE EXAMPLE 441

[Chemical formula 491]

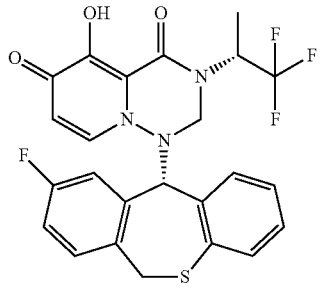

$^1$H-NMR (DMSO-$d_6$) δ: 1.22 (3H, d, J=7.2 Hz), 3.94 (1H, d, J=13.3 Hz), 4.45 (1H, d, J=13.4 Hz), 5.08 (1H, d, J=12.8 Hz), 5.56 (4H, dm), 6.84-7.54 (8H, m).

REFERENCE EXAMPLE 442

[Chemical formula 492]

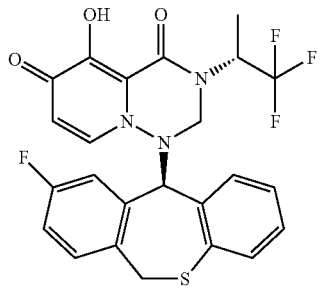

$^1$H-NMR (DMSO-$d_6$) δ: 1.37 (3H, d, J=7.2 Hz), 3.98 (1H, d, J=13.4 Hz), 4.48 (1H, d, J=13.1 Hz), 5.21 (1H, d, J=12.9 Hz), 5.22 (1H, m), 5.38 (1H, s), 5.52 (1H, d, J=13.4 Hz), 5.67 (1H, d, J=7.6 Hz), 6.87-7.57 (8H, m).

REFERENCE EXAMPLE 443

[Chemical formula 493]

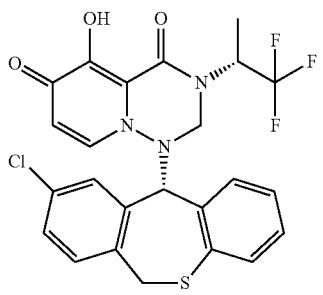

$^1$H-NMR (DMSO-$d_6$) δ: 1.19 (3H, d, J=7.2 Hz), 3.92 (1H, d, J=13.4 Hz), 4.43 (1H, d, J=13.1 Hz), 5.05 (1H, d, J=13.0 Hz), 5.54 (4H, m), 7.29 (8H, m).
MS: m/z=522 [M+H]$^+$

REFERENCE EXAMPLE 444

[Chemical formula 494]

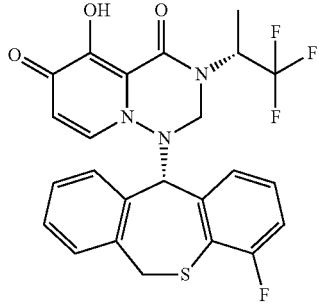

$^1$H-NMR (DMSO-$d_6$) δ: 1.13 (3H, d, J=7.0 Hz), 4.00 (1H, d, J=14.2 Hz), 4.40 (1H, d, J=13.3 Hz), 5.05 (1H, d, J=13.3 Hz), 5.44 (1H, m), 5.62-5.71 (3H, m), 6.82-7.56 (8H, m).
MS: m/z=506 [M+H]$^+$

REFERENCE EXAMPLE 445

[Chemical formula 495]

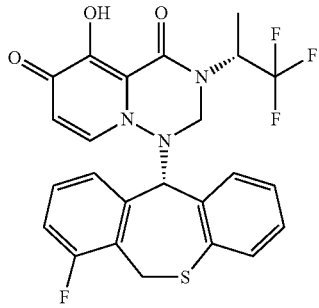

$^1$H-NMR (DMSO-$d_6$) δ: 1.23 (3H, d, J=7.2 Hz), 4.14 (1H, d, J=13.8 Hz), 4.60 (1H, d, J=13.6 Hz), 5.10 (1H, d, J=13.3 Hz), 5.48 (1H, d, J=15.6 Hz) 5.49 (1H, m), 5.69 (1H, d, J=7.9 Hz), 5.70 (1H, s), 6.89-7.47 (8H, m).
MS: m/z=506 [M+H]$^+$

REFERENCE EXAMPLE 446

[Chemical formula 496]

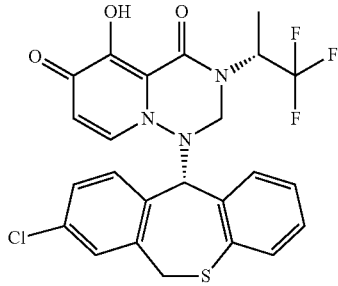

¹H-NMR (DMSO-d₆) δ: 1.22 (3H, d, J=6.9 Hz), 3.93 (1H, d, J=13.1 Hz), 4.49 (1H, d, J=13.4 Hz), 5.05 (1H, d, J=13.7 Hz), 5.57 (4H, m), 6.87-7.61 (8H, m).
MS: m/z=522 [M+H]⁺

REFERENCE EXAMPLE 447

[Chemical formula 497]

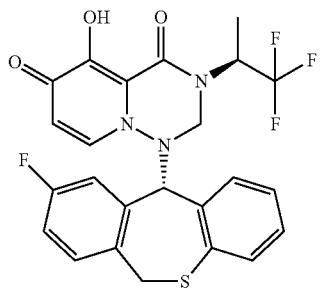

¹H-NMR (DMSO-d₆) δ: 1.41 (3H, d, J=7.2 Hz), 3.98 (1H, d, J=13.3 Hz), 4.48 (1H, d, J=12.9 Hz), 5.21 (1H, d, J=14.4 Hz), 5.22 (1H, m), 5.39 (1H, s), 5.52 (1H, d, J=13.6 Hz), 5.67 (1H, d, J=7.6 Hz), 6.88-7.57 (8H, m).
MS: m/z=506 [M+H]⁺

REFERENCE EXAMPLE 448

[Chemical formula 498]

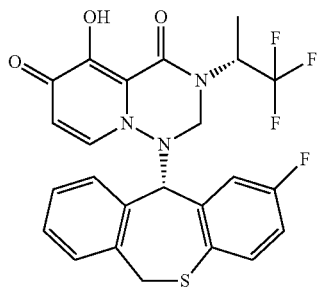

¹H-NMR (DMSO-d₆) δ: 1.19 (3H, d, J=7.2 Hz), 3.94 (1H, d, J=13.3 Hz), 4.44 (1H, d, J=13.3 Hz), 5.12 (1H, d, J=13.1 Hz), 5.46-5.68 (3H, m), 5.76 (1H, d, J=7.6 Hz), 7.27 (8H, m).
MS: m/z=506 [M+H]⁺

REFERENCE EXAMPLE 449

[Chemical formula 499]

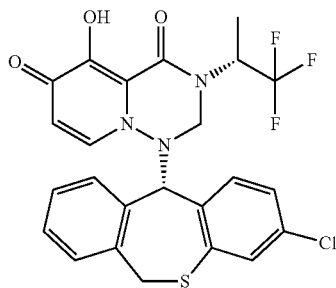

¹H-NMR (DMSO-d₆) δ: 1.14 (3H, d, J=7.2 Hz), 3.93 (1H, d, J=13.3 Hz), 4.40 (1H, d, J=13.1 Hz), 5.07 (1H, d, J=13.0 Hz), 5.46 (1H, m), 5.62 (1H, d, J=15.6 Hz), 5.64 (1H, s), 5.75 (1H, d, J=7.6 Hz), 6.94-7.55 (8H, m).
MS: m/z=522 [M+H]⁺

REFERENCE EXAMPLE 450

[Chemical formula 500]

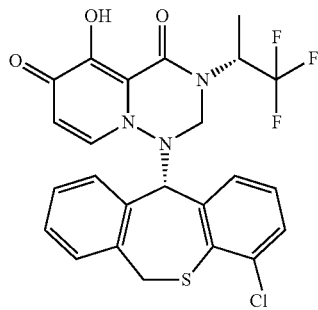

¹H-NMR (DMSO-d₆) δ: 1.14 (3H, d, J=7.2 Hz), 4.03 (1H, d, J=13.3 Hz), 4.41 (1H, d, J=13.3 Hz), 5.06 (1H, d, J=13.0 Hz), 5.46 (1H, m), 5.69 (3H, m), 6.88-7.57 (8H, m).
MS: m/z=522 [M+H]⁺

REFERENCE EXAMPLE 451

[Chemical formula 501]

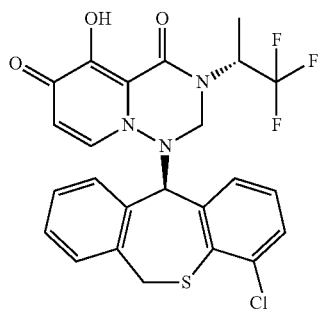

¹H-NMR (DMSO-d₆) δ: 1.35 (3H, d, J=7.2 Hz), 4.03 (1H, d, J=13.3 Hz), 4.43 (1H, d, J=13.0 Hz), 5.14 (1H, t, J=12.6 Hz), 5.15 (1H, m), 5.42 (1H, s), 5.63 (1H, d, J=13.5 Hz), 5.65 (1H, d, J=7.8 Hz), 6.88-7.44 (8H, m).
MS: m/z=522 [M+H]⁺

REFERENCE EXAMPLE 452

[Chemical formula 502]

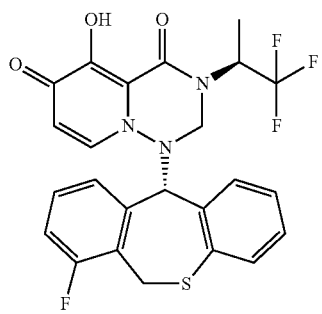

¹H-NMR (DMSO-d₆) δ: 1.42 (3H, d, J=7.2 Hz), 4.14 (1H, d, J=13.9 Hz), 4.57 (1H, d, J=13.1 Hz), 5.14 (1H, d, J=13.0

Hz), 5.15 (1H, m), 5.30 (1H, d, J=13.0 Hz), 5.40 (1H, s), 5.68 (1H, d, J=7.7 Hz), 6.89-7.38 (8H, m).
MS: m/z=506 [M+H]⁺

REFERENCE EXAMPLE 453

[Chemical formula 503]

¹H-NMR (DMSO-d₆) δ: 1.40 (3H, d, J=7.4 Hz), 4.05 (1H, d, J=13.4 Hz), 4.47 (1H, d, J=13.1 Hz), 5.18 (1H, m), 5.19 (1H, d, J=13.2 Hz), 5.46 (1H, s), 5.65 (1H, d, J=13.4 Hz), 5.74 (1H, d, J=7.6 Hz), 6.89-7.52 (8H, m).
MS: m/z=506 [M+H]⁺

REFERENCE EXAMPLE 454

[Chemical formula 504]

¹H-NMR (DMSO-d₆) δ: 1.20 (3H, d, J=7.2 Hz), 3.89 (1H, d, J=13.4 Hz), 4.46 (1H, d, J=13.4 Hz), 5.05 (1H, d, J=13.4 Hz), 5.44-5.66 (4H, m), 6.83-7.63 (8H, m).
MS: m/z=506 [M+H]⁺

REFERENCE EXAMPLE 455

[Chemical formula 505]

¹H-NMR (DMSO-d₆) δ: 1.16 (3H, d, J=7.3 Hz), 3.92 (1H, d, J=13.3 Hz), 4.39 (1H, d, J=13.1 Hz), 5.07 (1H, d, J=13.3 Hz), 5.47 (1H, m), 5.60 (1H, d, J=13.3 Hz), 5.68 (1H, s), 5.72 (1H, d, J=7.6 Hz), 7.07-7.54 (8H, m).
MS: m/z=522 [M+H]⁺

REFERENCE EXAMPLE 456

[Chemical formula 506]

¹H-NMR (DMSO-d₆) δ: 1.13 (5H, d, J=6.3 Hz), 4.00 (1H, d, J=13.4 Hz), 4.52 (1H, d, J=13.6 Hz), 5.09 (1H, d, J=13.3 Hz), 5.49-5.69 (4H, m), 6.84-7.51 (8H, m).
MS: m/z=506 [M+H]⁺

REFERENCE EXAMPLE 457

[Chemical formula 507]

¹H-NMR (DMSO-d₆) δ: 1.40 (3H, d, J=7.2 Hz), 4.02 (1H, d, J=13.1 Hz), 4.53 (1H, d, J=13.3 Hz), 5.20 (1H, d, J=12.9 Hz), 5.26 (1H, m), 5.67 (3H, m), 7.18 (8H, m).
MS: m/z=506 [M+H]⁺

REFERENCE EXAMPLE 458

[Chemical formula 508]

¹H-NMR (DMSO-d₆) δ: 1.15 (3H, d, J=7.3 Hz), 3.91 (1H, d, J=13.4 Hz), 4.39 (1H, d, J=13.3 Hz), 5.06 (1H, d, J=13.3

Hz), 5.45 (1H, m), 5.62 (1H, s), 5.63 (1H, t, J=13.5 Hz), 5.74 (1H, d, J=7.6 Hz), 6.71-7.55 (8H, m).
MS: m/z=506 [M+H]+

REFERENCE EXAMPLE 459

[Chemical formula 509]

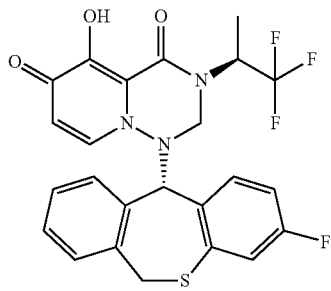

¹H-NMR (DMSO-d₆) δ: 1.39 (3H, d, J=7.4 Hz), 3.95 (1H, d, J=13.4 Hz), 4.46 (1H, d, J=12.9 Hz), 5.19 (1H, d, J=13.1 Hz), 5.20 (1H, m), 5.41 (1H, s), 5.62 (1H, d, J=13.4 Hz), 5.76 (1H, d, J=7.7 Hz), 6.72-7.50 (8H, m).
MS: m/z=506 [M+H]+

REFERENCE EXAMPLE 460

[Chemical formula 510]

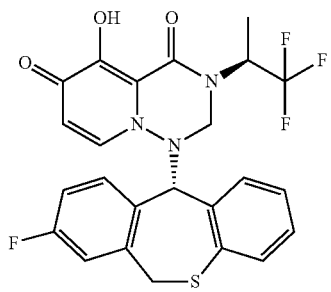

¹H-NMR (DMSO-d₆) δ: 1.42 (3H, d, J=7.2 Hz), 3.94 (1H, d, J=13.3 Hz), 4.50 (1H, d, J=13.1 Hz), 5.17 (1H, d, J=12.4 Hz), 5.18 (1H, m), 5.39 (1H, s), 5.60-5.69 (2H, m), 6.87-7.42 (8H, m).
MS: m/z=506 [M+H]+

REFERENCE EXAMPLE 461

[Chemical formula 511]

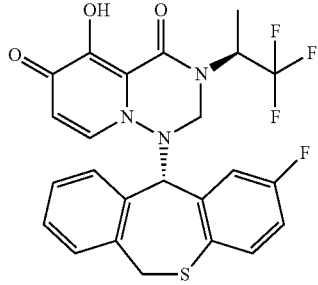

¹H-NMR (DMSO-d₆) δ: 1.35 (3H, d, J=7.2 Hz), 3.91 (1H, d, J=13.0 Hz), 4.43 (1H, d, J=13.1 Hz), 5.15 (1H, d, J=12.8

Hz), 5.16 (1H, m), 5.41 (1H, s), 5.47 (1H, d, J=13.0 Hz), 5.69 (1H, d, J=7.6 Hz), 7.00-7.45 (8H, m).
MS: m/z=506 [M+H]+

REFERENCE EXAMPLE 462

[Chemical formula 512]

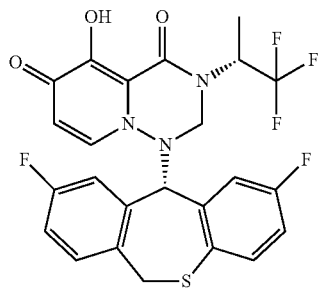

¹H-NMR (DMSO-d₆) δ: 1.21 (3H, d, J=7.3 Hz), 3.97 (1H, d, J=13.3 Hz), 4.46 (1H, d, J=13.1 Hz), 5.09 (1H, d, J=13.6 Hz), 5.50 (1H, m), 5.51 (1H, d, J=12.8 Hz), 5.65 (1H, s), 5.72 (1H, d, J=7.6 Hz), 6.85-7.55 (7H, m).
MS: m/z=524 [M+H]+

REFERENCE EXAMPLE 463

[Chemical formula 513]

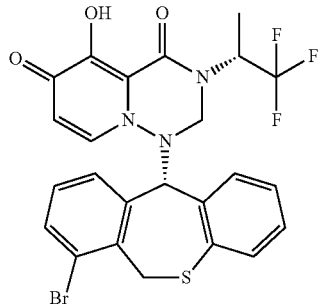

MS: m/z=568 [M+H]+

REFERENCE EXAMPLE 464

[Chemical formula 514]

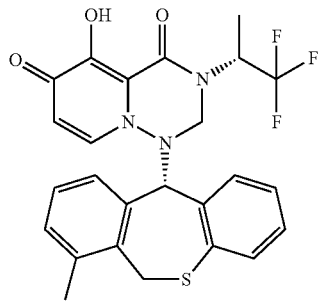

MS: m/z=502 [M+H]+

REFERENCE EXAMPLE 465

[Chemical formula 515]

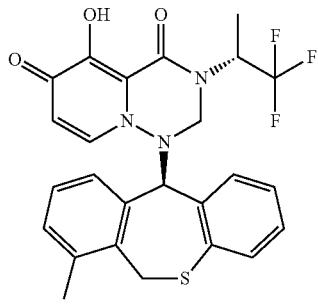

MS: m/z=502 [M+H]⁺

REFERENCE EXAMPLE 466

[Chemical formula 516]

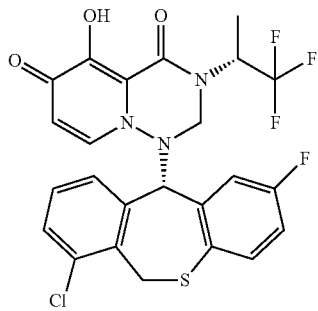

MS: m/z=540 [M+H]⁺

REFERENCE EXAMPLE 467

[Chemical formula 517]

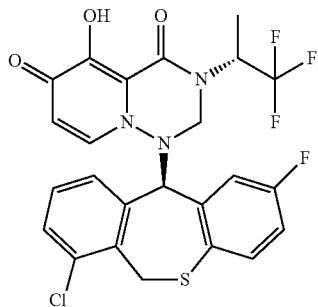

MS: m/z=540 [M+H]⁺

REFERENCE EXAMPLE 468

[Chemical formula 518]

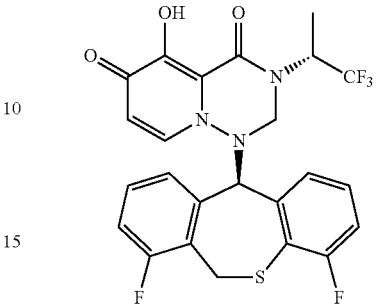

$^1$HNMR (CDCl$_3$) δ: 1.13 (3H, d, J=5.8 Hz), 4.20 (1H, d, J=13.6 Hz), 4.58 (1H, d, J=12.7 Hz), 4.99 (1H, d, J=12.7 Hz), 5.29-5.42 (3H, m), 5.84 (1H, d, J=7.8 Hz), 6.60 (1H, m), 6.79-7.01 (3H, m), 7.19-7.28 (4H, m).
MS: m/z=524 [M+H]⁺.

REFERENCE EXAMPLE 469

[Chemical formula 519]

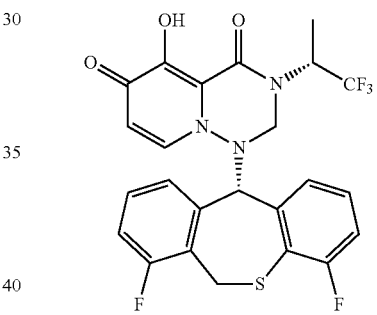

$^1$HNMR (CDCl$_3$) δ: 1.19 (3H, d, J=7.6 Hz), 4.21 (1H, d, J=13.9 Hz), 4.48 (1H, d, J=13.3 Hz), 4.89 (1H, d, J=13.3 Hz), 5.22 (1H, s), 5.37 (1H, dd, J=2.1, 13.9 Hz), 5.52 (1H, m), 5.86 (1H, d, J=7.6), 6.55 (1H, m), 6.83 (1H, m), 6.96 (1H, m), 7.14 (1H, d, J=7.6 Hz), 7.19-7.30 (4H, m).
MS: m/z=524 [M+H]⁺.

REFERENCE EXAMPLE 470

[Chemical formula 520]

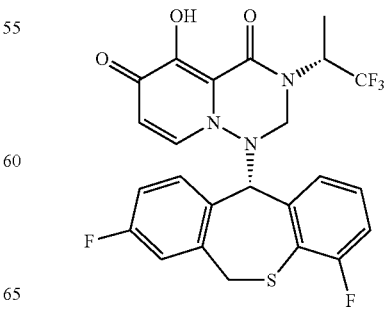

$^1$HNMR (CDCl$_3$) δ: 1.19 (3H, d, J=7.3 Hz), 3.65 (1H, d, J=13.5 Hz), 4.47 (1H, d, J=13.0 Hz), 4.87 (1H, d, J=13.0 Hz), 5.18 (1H, s), 5.50 (1H, m), 5.69 (1H, d, J=13.5 Hz), 5.85 (1H, d, J=7.8 Hz), 6.53 (1H, m), 6.83 (1H, m), 6.91-7.01 (2H, m), 7.11 (1H, d, J=7.6 Hz), 7.10-7.20 (3H, m).

MS: m/z=524 [M+H]$^+$.

REFERENCE EXAMPLE 471

[Chemical formula 521]

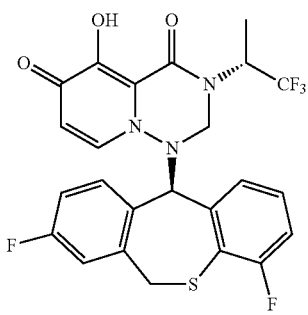

$^1$HNMR (CDCl$_3$) δ: 1.13 (3H, d, J=6.1 Hz), 3.63 (1H, d, J=13.5 Hz), 4.56 (1H, d, J=12.5 Hz), 5.02 (1H, d, J=12.5 Hz), 5.26 (1H, s), 5.38 (1H, m), 5.71 (1H, d, J=13.5 Hz), 5.81 (1H, d, J=7.8 Hz), 6.57 (1H, m), 6.81 (1H, m), 6.91 (1H, m), 6.99 (1H, dd, J=2.6, 8.2 Hz), 7.05 (1H, dd, J=2.6, 8.7 Hz), 7.17 (2H, m), 7.19 (1H, d, J=7.6 Hz).

MS: m/z=524 [M+H]$^+$.

REFERENCE EXAMPLE 472

[Chemical formula 522]

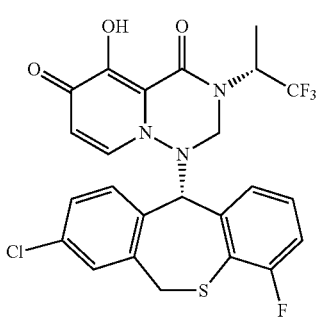

$^1$HNMR (CDCl$_3$) δ: 1.21 (3H, d, J=7.4 Hz), 3.66 (1H, d, J=13.5 Hz), 4.47 (1H, d, J=13.3 Hz), 4.88 (1H, d, J=13.3 Hz), 5.17 (1H, s), 5.52 (1H, m), 5.66 (1H, d, J=13.5 Hz), 5.85 (1H, d, J=7.7 Hz), 6.54 (1H, m), 6.83 (1H, m), 6.95 (1H, m), 7.11-7.14 (2H, m), 7.23-7.29 (2H, m), 7.41 (1H, d, J=2.0 Hz).

MS: m/z=540 [M+H]$^+$.

REFERENCE EXAMPLE 473

[Chemical formula 523]

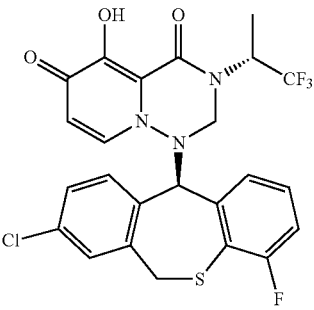

$^1$HNMR (CDCl$_3$) δ: 1.13 (3H, d, J=6.2 Hz), 3.63 (1H, d, J=13.5 Hz), 4.55 (1H, d, J=12.6 Hz), 5.04 (1H, d, J=12.6 Hz), 5.25 (1H, s), 5.38 (1H, m), 5.69 (1H, d, J=13.5 Hz), 5.80 (1H, d, J=7.7 Hz), 6.58 (1H, m), 6.82 (1H, m), 6.92 (1H, m), 7.13 (1H, m), 7.19 (1H, d, J=7.7 Hz), 7.24-7.29 (2H, m), 7.34 (1H, d, J=2.2 Hz).

MS: m/z=540 [M+H]$^+$.

REFERENCE EXAMPLE 474

[Chemical formula 524]

$^1$HNMR (CDCl$_3$) δ: 1.19 (3H, d, J=7.3 Hz), 4.40 (1H, d, J=13.9 Hz), 4.59 (1H, d, J=13.0 Hz), 5.02 (1H, d, J=13.0 Hz), 5.31 (1H, s), 5.39 (1H, m), 5.66 (1H, d, J=13.9 Hz), 5.84 (1H, d, J=7.8 Hz), 6.58 (1H, m), 6.82 (1H, m), 6.92 (1H, m), 7.10 (1H, m), 7.19 (1H, dd, J=3.7, 7.9 Hz), 7.20-7.26 (2H, m), 7.51 (1H, m).

MS: m/z=540 [M+H]$^+$.

REFERENCE EXAMPLE 475

[Chemical formula 525]

MS: m/z=522 [M+H]$^+$.

REFERENCE EXAMPLE 476

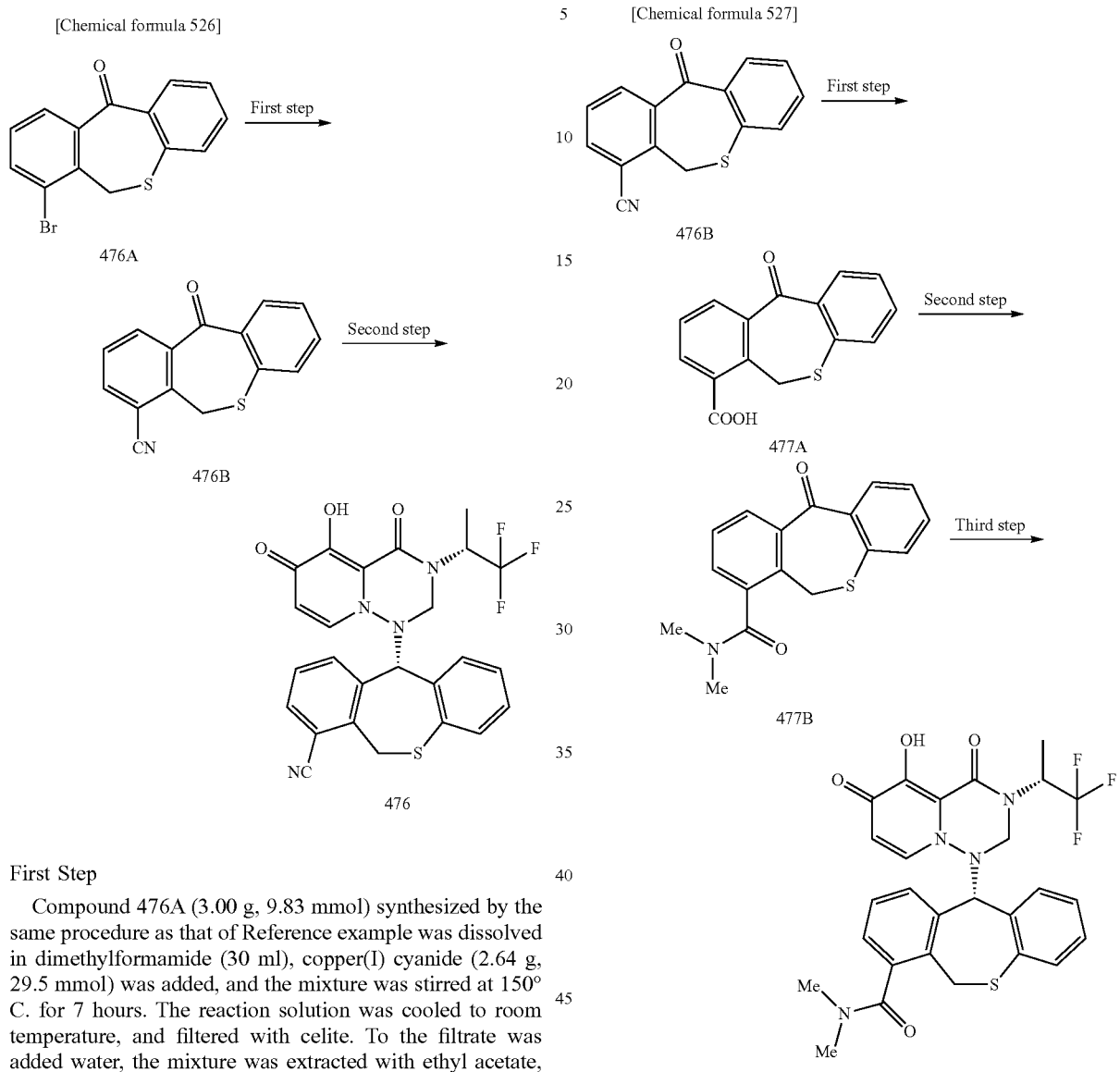

REFERENCE EXAMPLE 477

First Step

Compound 476A (3.00 g, 9.83 mmol) synthesized by the same procedure as that of Reference example was dissolved in dimethylformamide (30 ml), copper(I) cyanide (2.64 g, 29.5 mmol) was added, and the mixture was stirred at 150° C. for 7 hours. The reaction solution was cooled to room temperature, and filtered with celite. To the filtrate was added water, the mixture was extracted with ethyl acetate, and the organic layer was washed with water. The solvent was distilled off under reduced pressure, and the resulting crude product was purified by silica gel column chromatography, and eluted with n-hexane-ethyl acetate (1:1, v/v). To the resulting compound was added n-hexane, and the precipitated residue was filtered to obtain 1.81 g of a white solid 476B.

$^1$H-NMR (CDCl$_3$) δ: 4.29 (2H, s), 7.28-7.48 (4H, m), 7.78 (2H, t, J=7.5 Hz), 8.20 (1H, dd, J=8.1, 1.5 Hz).

Second Step

According to the same procedure as that of Reference example 107, compound 476 was synthesized.

$^1$H-NMR (DMSO-d$_6$) δ: 1.16 (3H, d, J=7.0 Hz), 4.01 (1H, d, J=14.0 Hz), 4.65 (1H, d, J=13.7 Hz), 5.04 (1H, d, J=13.3 Hz), 5.45 (1H, t, J=8.1 Hz), 5.66 (1H, d, J=7.6 Hz), 5.74 (1H, s), 5.84 (1H, d, J=14.0 Hz), 6.87-7.93 (7H, m).

MS: m/z=513 [M+H]$^+$

First Step

To compound 476B (859 mg, 3.42 mmol) was added concentrated sulfuric acid (13 ml), and the mixture was stirred at room temperature for 18 hours, and at 60° C. for 2 hours. The reaction solution was added to water, the mixture was extracted with ethyl acetate, and the organic layer was dried with sodium sulfate. The solvent was concentrated under reduced pressure to obtain 387 mg of a pale yellow solid. To the resulting compound was added methanol (10 ml), a 10N aqueous sodium hydroxide solution (6 ml) was added, and the mixture was stirred at 90° C. for 5 hours. The reaction solution was cooled to room temperature, water was added, and the mixture was washed with dichloromethane. To the aqueous layer was added dilute hydrochloric acid, the mixture was extracted with ethyl acetate, and the organic layer was dried with sodium sulfate. The solvent was concentrated under reduced pressure to obtain 296 mg of a yellow solid 477A.

Second Step

Compound 477A (179 mg, 0.662 mmol) obtained in the first step was dissolved in dichloromethane (4 ml), dimethylamine hydrochloride (108 mg, 1.32 mmol), EDCI (190 mg, 0.993 mmol), 1H-benzo[d][1,2,3]triazol-1-ol (89.0 mg, 0.662 mmol) and triethylamine (0.3 ml) were added, and the mixture was stirred at room temperature for 2 hours. To the reaction solution was added water, the mixture was extracted with ethyl acetate, and the organic layer was washed with an aqueous sodium bicarbonate solution, and dried with sodium sulfate. The solvent was distilled off under reduced pressure, and the resulting crude product was purified by silica gel column chromatography, and eluted with n-hexane-ethyl acetate (1:1, v/v), to obtain 170 mg of a colorless gummy substance 477B.

$^1$H-NMR (CDCl3) δ: 2.99 (3H, s), 3.23 (3H, s), 4.08 (2H, s), 7.28-7.44 (5H, m), 7.58 (1H, t, J=4.4 Hz), 8.22 (1H, dd, J=8.1, 1.5 Hz).

Third Step

According to the same procedure as that of Reference example 107, compound 477 was synthesized.

MS: m/z=559 [M+H]$^+$

REFERENCE EXAMPLE 478

[Chemical formula 528]

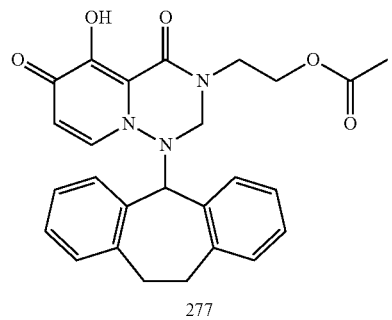

277

First step →

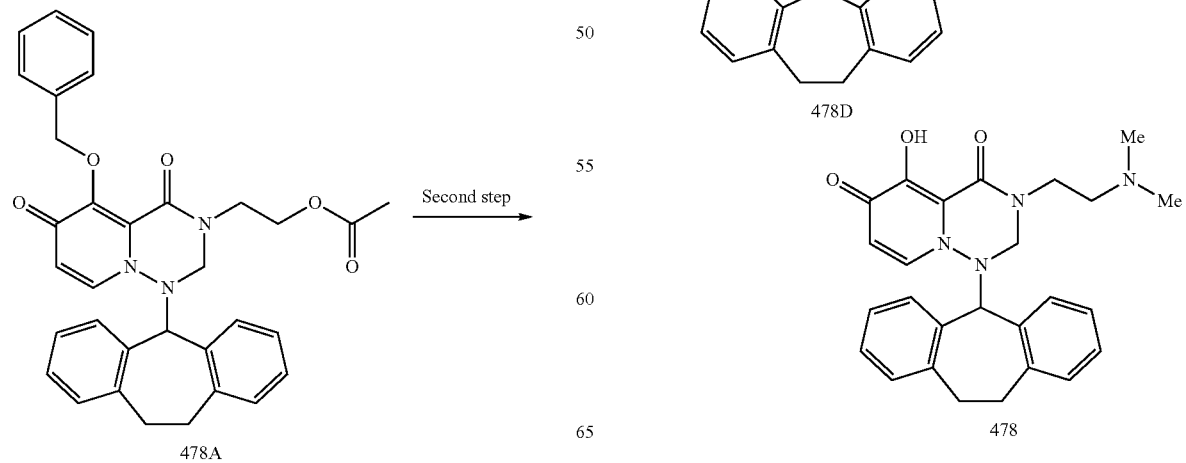

478A

Second step →

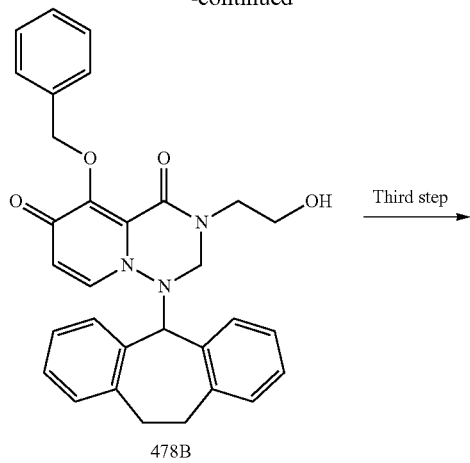

478B

Third step →

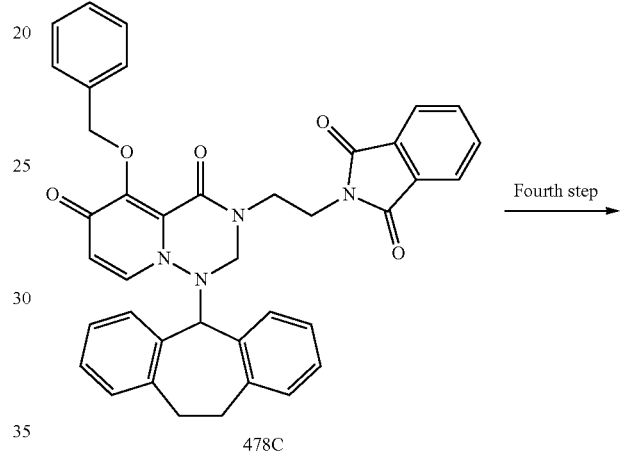

478C

Fourth step →

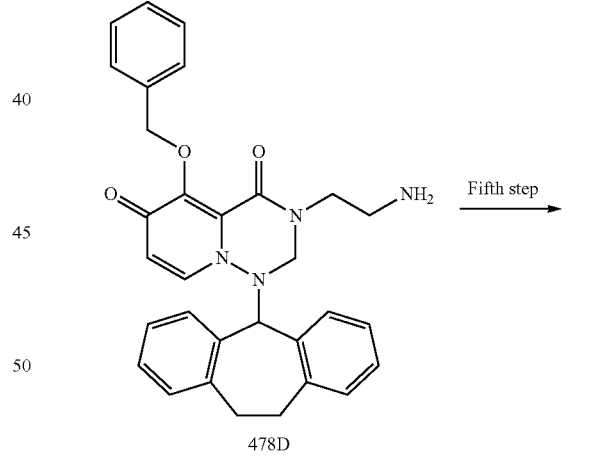

478D

Fifth step →

478

First Step

Compound 277 (971 mg, 2.11 mmol) was dissolved in dimethylformamide (10 ml), cesium carbonate (2.75 g, 8.45 mmol) and benzyl bromide (0.753 ml, 6.34 mmol) were added, and the mixture was stirred at room temperature for 4 hours. The reaction solution was poured into water, then extracted with ethyl acetate, and the organic layer was washed with water, and dried with sodium sulfate. The solvent was distilled off under reduced pressure, to the resulting compound were added dichloromethane-diethyl ether, and the precipitated residue was filtered to obtain 740 mg of a white solid 478A.

Second Step

Compound 478A (740 mg, 1.35 mmol) was dissolved in tetrahydrofuran (7 ml) and methanol (7 ml), a 2N aqueous sodium hydroxide solution (3.37 ml, 6.73 mmol) was added, and the mixture was stirred at room temperature for 30 minutes. To the reaction solution was added dilute hydrochloric acid to make the solution acidic, the mixture was extracted with chloroform, and the organic layer was dried with sodium sulfate. The solvent was concentrated under reduced pressure to obtain 618 mg of a white solid 478B.

MS: m/z=508 [M+H]$^+$

Third Step

Compound 478B (505 mg, 0.995 mmol) was dissolved in tetrahydrofuran (10 ml), triphenylphosphine (391 mg, 1.49 mmol), phthalimide (220 mg, 1.49 mmol) and azodicarboxylic acid diisopropyl ester (0.290 ml, 1.49 mmol) were added, and the mixture was stirred at room temperature for 1 hour. The reaction solution was concentrated under reduced pressure, and the resulting crude product was purified by silica gel column chromatography, and eluted with chloroform-methanol (97:3, v/v). To the resulting compound were added dichloromethane-diethyl ether, and the precipitated residue was filtered to obtain 578 mg of a white solid 478C.

MS: m/z=637 [M+H]$^+$

Fourth Step

To compound 478C (667 mg, 1.05 mmol) was added ethanol (10 ml), hydrazine hydrate (0.254 ml, 5.24 mmol) was added, and the mixture was stirred at 90° C. for 2 hours. The reaction solution was cooled to room temperature, chloroform was added, insolubles were removed by filtration, and the filtrate was concentrated under reduced pressure. The resulting crude product was purified by amino column chromatography, and eluted with chloroform-methanol (97:3, v/v). To the resulting compound were added dichloromethane-diethyl ether, and the precipitated residue was filtered to obtain 462 mg of a white solid 478D.

MS: m/z=507 [M+H]$^+$

Fifth Step

To compound 478D (100 mg, 0.197 mmol) were added formic acid (1.0 ml) and an aqueous formalin solution (1.0 ml), and the mixture was stirred at 80° C. for 1 hour. To the reaction solution was added a 1N aqueous sodium hydroxide solution, the mixture was extracted with dichloromethane, and the organic layer was dried with sodium sulfate. The resulting crude product was purified by amino column chromatography, and eluted with chloroform-methanol (97:3, v/v), to obtain 56 mg of a colorless oily substance. This compound was dissolved in acetic acid (2.0 ml), concentrated sulfuric acid (0.5 ml) was added dropwise, and the mixture was stirred at room temperature for 30 minutes. The reaction solution was poured into an aqueous sodium bicarbonate solution, and was extracted with chloroform, and the organic layer was dried with sodium sulfate. The solvent was distilled off under reduced pressure, to the resulting crude product were added dichloromethane-ethyl acetate-diethyl ether, and the precipitated residue was filtered to obtain 12 mg of a white solid 478.

MS: m/z=445 [M+H]$^+$

REFERENCE EXAMPLE 479

[Chemical formula 529]

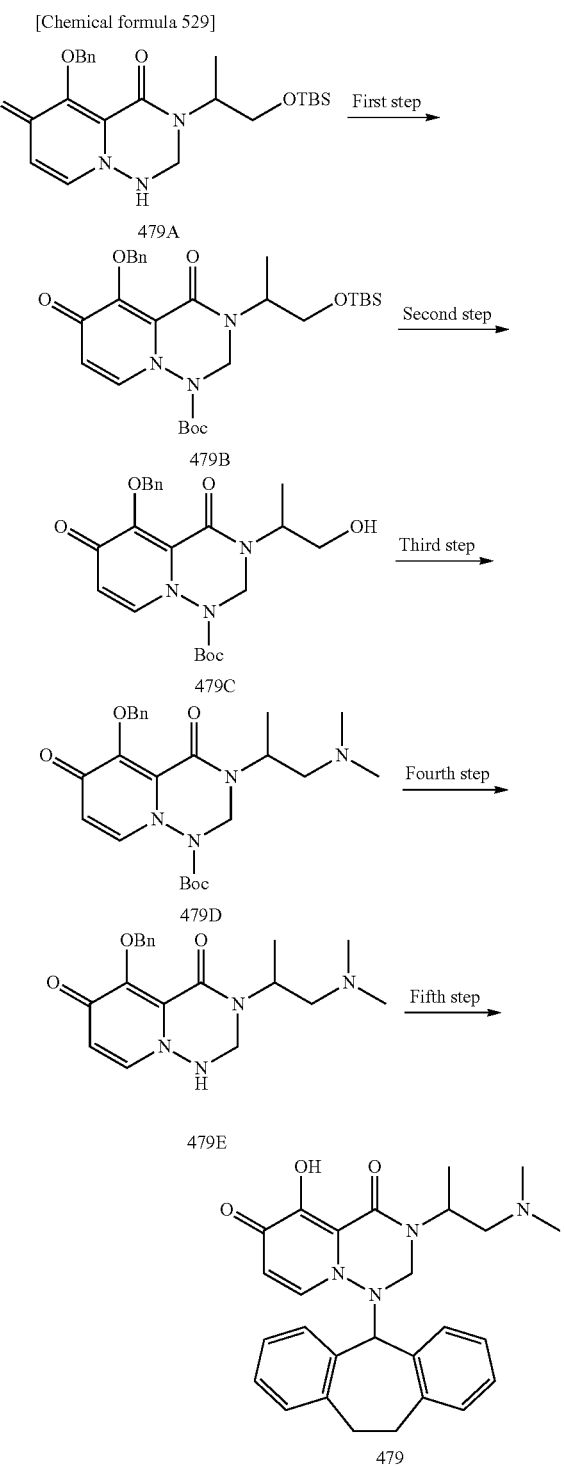

First Step

To a dichloromethane (50 ml) solution of compound 479A (5.25 g, 11.8 mmol) synthesized according to Reference example 95, DIPEA (6.20 mL, 35.5 mmol) and Boc2O (5.17 g, 23.7 mmol) was added DMAP (434 mg, 3.55 mmol), and the mixture was stirred at room temperature for 4 hours. After the reaction solution was concentrated under reduced pressure, the residue was dissolved in ethyl acetate. The solution was sequentially washed with 0.5N aqueous hydrochloric acid solution and an aqueous saturated sodium chloride solution, and dried with sodium sulfate. The solvent was distilled off, and the resulting oil was purified by silica gel chromatography. The materials were eluted firstly with chloroform and, then, with chloroform-methanol (97:3, v/v). Concentration of an objective fraction afforded 5.22 g of compound 479B as an oil.

MS: m/z=544 [M+H]$^+$.

Second Step

To a THF (340 mL) solution of compound 479B (29.7 g, 102 mmol) and acetic acid (29.7 g, 102 mmol) was added TBAF (1M THF solution, 23.6 g, 310 mmol) under ice-cooling, and the mixture was stirred at room temperature for 16 hours. To the reaction solution were added ethyl acetate and water, and the ethyl acetate layer was separated, washed with water, and dried with sodium sulfate. The solvent was distilled off, and the resulting oil was solidified by adding dichloromethane-ether, to obtain 2.76 g of compound 479C.

MS: m/z=430 [M+H]$^+$.

Third Step

To an ethyl acetate (20 mL) suspension of compound 479C (500 mg, 1.16 mmol) was added IBX (652 mg, 2.33 mmol), and the mixture was heated to stir for 3 hours. After the reaction solution was diluted with ethyl acetate, insolubles were filtered, and the resulting filtrate was sequentially washed with a 1N aqueous sodium hydroxide solution and water, and dried with sodium sulfate. After the solvent was distilled off, and the resulting oil was dissolved in THF (5 mL), dimethylamine (2M THF solution, 0.873 mL, 1.75 mmol) and NaBH(OAc)3 (370 mg, 1.75 mmol) were added under ice-cooling, and the mixture was stirred at room temperature for 1.5 hours. After 2N aqueous hydrochloric acid solution was added to the reaction solution under ice-cooling, the mixture was made basic with an aqueous sodium bicarbonate solution. This was extracted with chloroform, and dried with sodium sulfate. The solvent was distilled off, and the resulting oil was purified by silica gel chromatography. The materials were eluted firstly with chloroform and, then, with chloroform-methanol (93:7, v/v). Concentration of an objective fraction afforded 437 mg of compound 479D as an amorphous substance.

MS: m/z=457 [M+H]$^+$.

Fourth Step

Compound 479D (430 mg, 0.942 mmol) was dissolved in acetic acid (10 mL), and the solution was heated to stir for 1 hour. The solvent was distilled off, and the resulting oil was purified by silica gel chromatography. The materials were eluted firstly with chloroform and, then, with chloroform-methanol (95:5, v/v).

Concentration of an objective fraction afforded 330 mg of compound 479E as an oil.

MS: m/z=357 [M+H]$^+$.

Fifth Step

To an acetic acid (2 mL) solution of compound 479E (50 mg, 0.140 mmol) and dibenzosuberol (29.5 mg, 0.140 mmol) was added dropwise sulfuric acid (0.5 mL), and the mixture was stirred for 30 minutes. To the reaction solution were added ethyl acetate and water, thereafter, the aqueous layer was separated, and neutralized with an aqueous sodium bicarbonate solution. Extraction was performed using the ethyl acetate layer, and the extract was washed with water, and dried with sodium sulfate. The solvent was distilled off, and the resulting oil was solidified by adding ether, to obtain 17.0 mg of compound 479.

MS: m/z=354 [M+H]$^+$.

According to Reference example 478 or Reference example 479, compounds were synthesized as compounds of Reference examples 480 to 490 using the same procedure.

REFERENCE EXAMPLE 480

[Chemical formula 530]

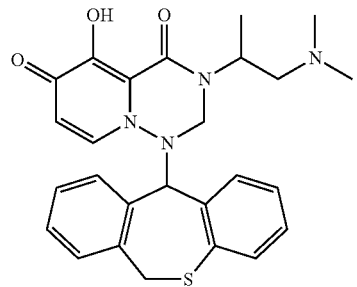

MS: m/z=477 [M+H]$^+$.

REFERENCE EXAMPLE 481

[Chemical formula 531]

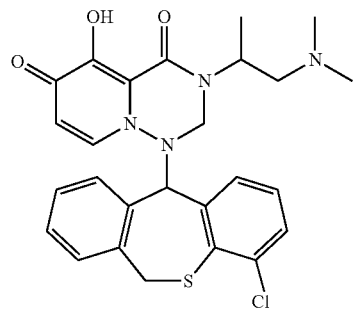

MS: m/z=512 [M+H]$^+$.

REFERENCE EXAMPLE 482

[Chemical formula 532]

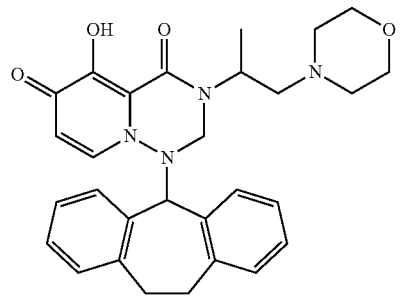

MS: m/z=501 [M+H]$^+$.

REFERENCE EXAMPLE 483
[Chemical formula 533]
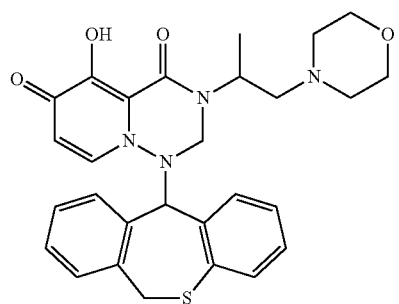
MS: m/z=519 [M+H]+.
REFERENCE EXAMPLE 484
[Chemical formula 534]
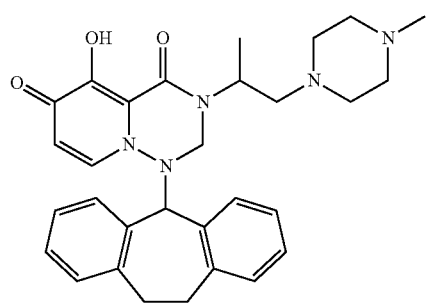
MS: m/z=514 [M+H]+.
REFERENCE EXAMPLE 485
[Chemical formula 535]
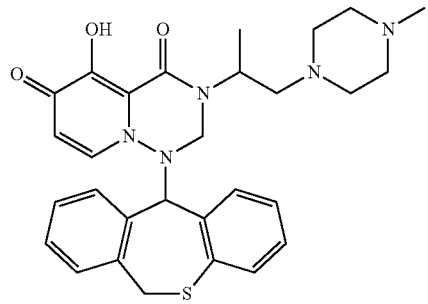
MS: m/z=532 [M+H]+
REFERENCE EXAMPLE 486
[Chemical formula 536]
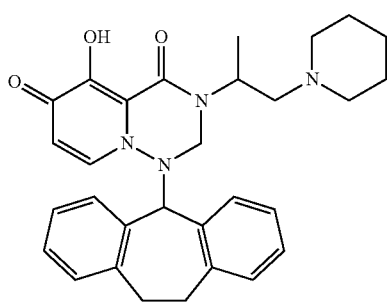
MS: m/z=499 [M+H]+.
REFERENCE EXAMPLE 487
[Chemical formula 537]
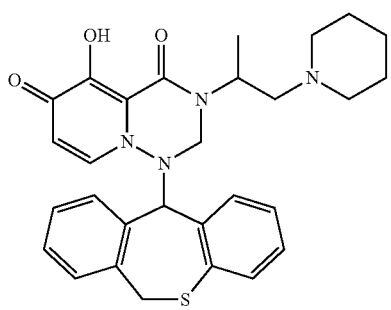
MS: m/z=517 [M+H]+.
REFERENCE EXAMPLE 488
[Chemical formula 538]
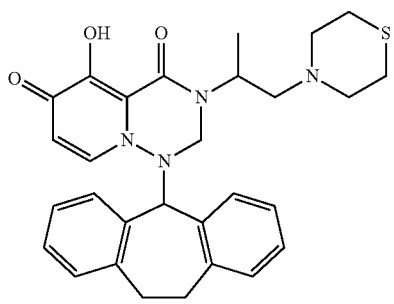
MS: m/z=517 [M+H]+.

REFERENCE EXAMPLE 489

[Chemical formula 539]

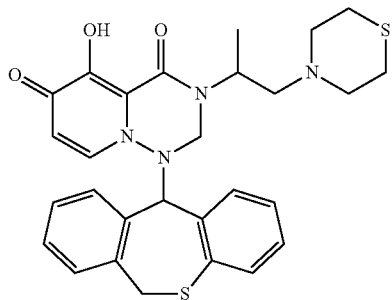

MS: m/z=535 [M+H]+.

REFERENCE EXAMPLE 490

[Chemical formula 540]

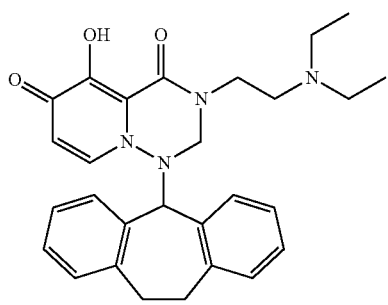

MS: m/z=473 [M+H]+

REFERENCE EXAMPLE 491

[Chemical formula 541]

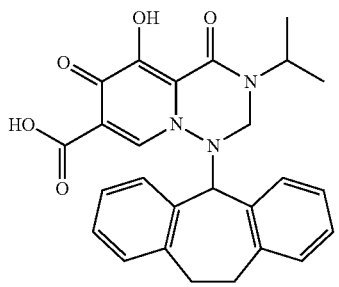

According to Reference example 65 and Reference example 107, compound 491 was synthesized by the same procedure.

$^1$H-NMR (DMSO-$d_6$) δ: 1.10 (3H, d, J=4.0 Hz), 1.12 (3H, d, J=4.6 Hz), 2.82-3.06 (2H, m), 3.56 (1H, d, J=17.8 Hz), 4.26 (1H, d, J=13.2 Hz), 4.31 (1H, m), 4.51-4.60 (1H, m), 4.97 (1H, d, J=13.1 Hz), 5.39 (1H, s), 6.74-7.52 (8H, m).

MS: m/z=460 [M+H]+

REFERENCE EXAMPLE 492

[Chemical formula 542]

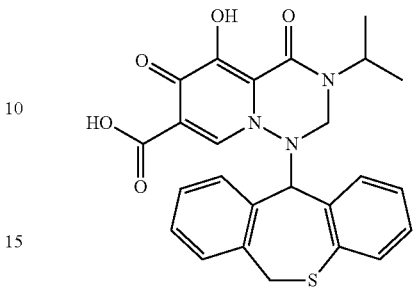

According to Reference example 65 and Reference example 107, compound 492 was synthesized by the same procedure.

MS: m/z=478 [M+H]+

REFERENCE EXAMPLE 493

[Chemical formula 543]

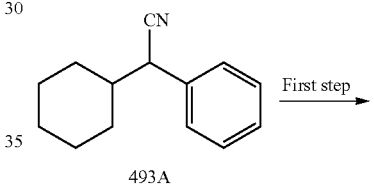

493A

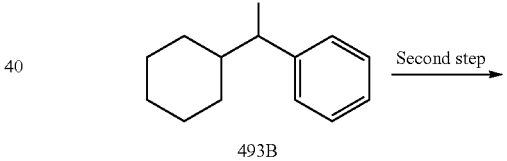

493B

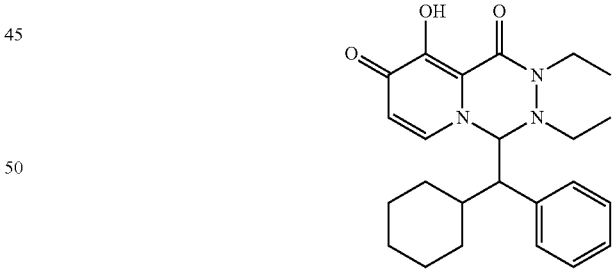

493

First Step

A dichloromethane (5 mL) solution of compound 493A (258 mg, 1.30 mmol) was cooled to −50C, and a toluene solution (1M, 1.96 mL) of DIBAL-H was added dropwise over 5 minutes while the same temperature was retained. After the reaction solution was stirred at the same temperature for 1 hour, temperature was raised to room temperature, and the mixture was stirred for 2.5 hours. To the reaction solution was added an aqueous saturated ammonium chloride solution, thereafter, the mixture was stirred at room temperature for 1 hour, and insolubles were removed by filtration. The dichloromethane layer was separated, and the aqueous layer was extracted with dichloromethane once. The combined extracts were washed with water three times, washed with an aqueous saturated sodium chloride solution, and dried. The solvent was distilled off, and the resulting oil was subjected to silica gel column chromatography, and eluted with n-hexane-ethyl acetate. Concentration of an objective fraction afforded 148 mg of compound 493B as an oil.

$^1$HNMR (CDCl$_3$) δ: 1.03-1.44 (5H, m), 1.63-1.83 (5H, m), 2.05-2.13 (1H, m), 3.25 (1H, dd, J=9.5 Hz, 3.4 Hz), 7.16-7.19 (2H, ms), 7.27-7.38 (3H, m), 9.69 (1H, d, J=3.5 Hz).

Second Step

According to Reference example 177, compound 493 was synthesized by the same procedure.

MS: m/z=410 [M+H]$^+$

Using aldehydes which are commercially available or known in the references and hydrazines which are commercially available or known in the references, and according to Reference example 493, compounds 494 to 505 were synthesized.

REFERENCE EXAMPLE 494

[Chemical formula 544]

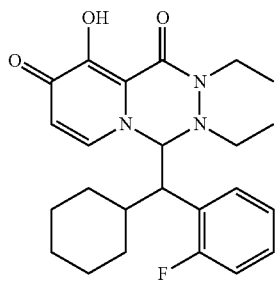

MS: m/z=428 [M+H]$^+$

REFERENCE EXAMPLE 495

[Chemical formula 545]

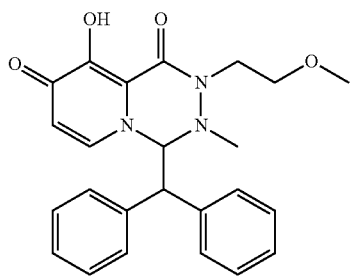

MS: m/z=420 [M+H]$^+$.

REFERENCE EXAMPLE 496

[Chemical formula 546]

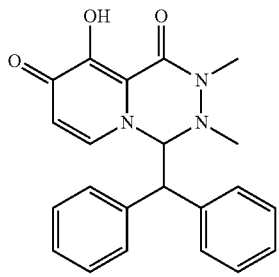

MS: m/z=376 [M+H]$^+$.

REFERENCE EXAMPLE 497

[Chemical formula 547]

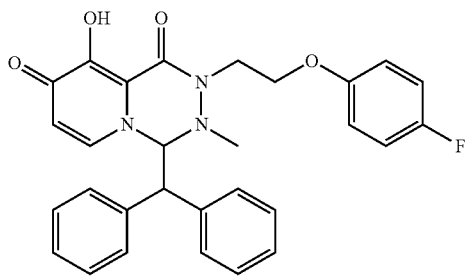

MS: m/z=500 [M+H]$^+$.

REFERENCE EXAMPLE 498

[Chemical formula 548]

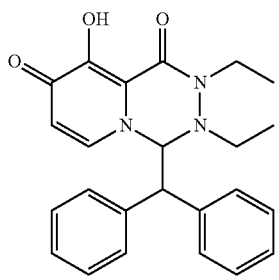

MS: m/z=404 [M+H]$^+$.

REFERENCE EXAMPLE 499

[Chemical formula 549]

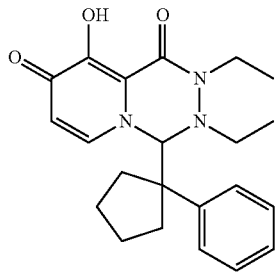

MS: m/z=382 [M+H]⁺.

REFERENCE EXAMPLE 500

[Chemical formula 550]

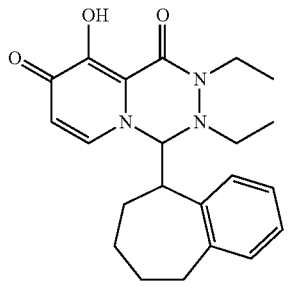

MS: m/z=382 [M+H]⁺.

REFERENCE EXAMPLE 501

[Chemical formula 551]

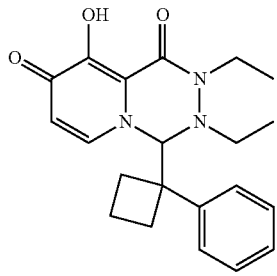

MS: m/z=368 [M+H]⁺.

REFERENCE EXAMPLE 502

[Chemical formula 552]

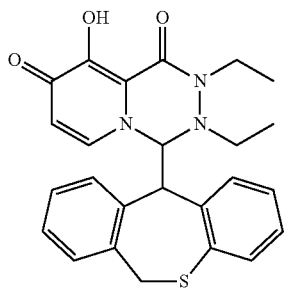

$^1$H-NMR (CDCl$_3$) δ: 0.94 (3H, t, J=7.2 Hz), 1.26 (3H, t, J=7.3 Hz), 2.87-2.94 (2H, m), 3.10-3.22 (1H, m), 3.79-3.89 (1H, m), 3.98 (1H, d, J=16.9 Hz), 4.17 (1H, d, J=16.8 Hz), 4.28 (1H, d, J=9.8 Hz), 6.04 (1H, d, J=7.2 Hz), 6.54 (2H, t, J=8.1 Hz), 6.73 (1H, d, J=9.8 Hz), 6.95-7.33 (6H, m), 7.66 (1H, dd, J=5.3, 3.6 Hz).

MS: m/z=448 [M+H]⁺.

REFERENCE EXAMPLE 503

[Chemical formula 553]

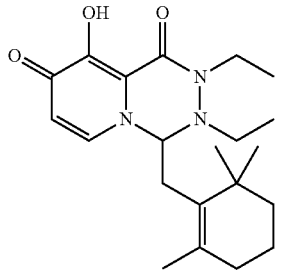

MS: m/z=374 [M+H]⁺.

REFERENCE EXAMPLE 504

[Chemical formula 554]

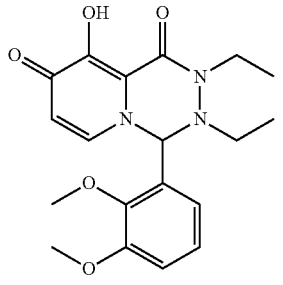

MS: m/z=374 [M+H]⁺.

REFERENCE EXAMPLE 505

[Chemical formula 555]

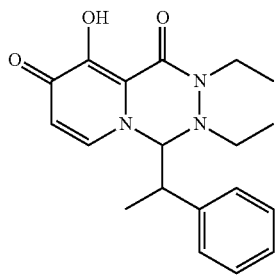

MS: m/z=342 [M+H]+.

REFERENCE EXAMPLE 506

[Chemical formula 556]

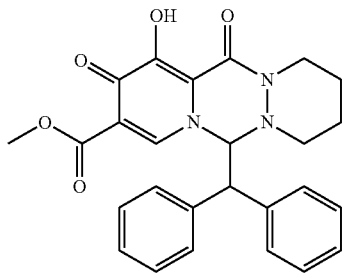

According to Reference example 177, using compound 65B, compound 506 was synthesized by the same procedure.
MS: m/z=470 [M+H]+.

REFERENCE EXAMPLE 507

[Chemical formula 557]

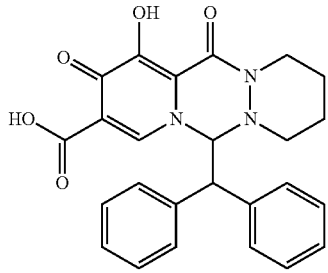

According to Reference example 65, using compound 506, compound 507 was synthesized by the same procedure.
MS: m/z=446 [M+H]+.

REFERENCE EXAMPLE 508

[Chemical formula 558]

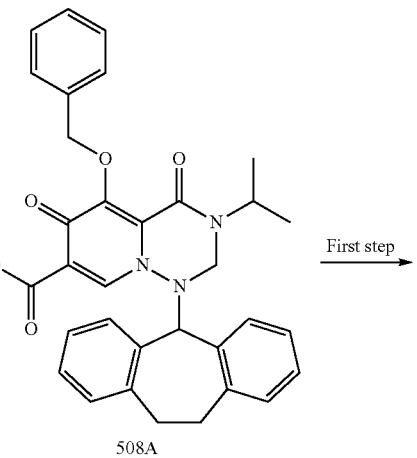

508A

First step →

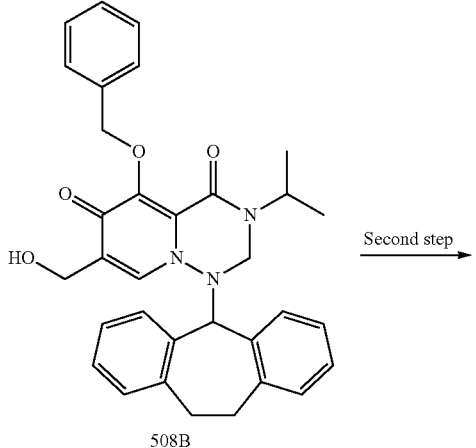

508B

Second step →

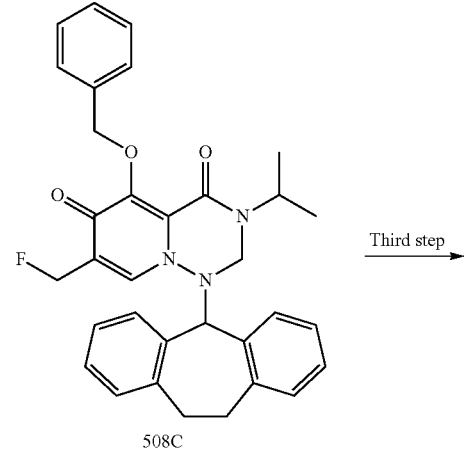

508C

Third step →

417
-continued

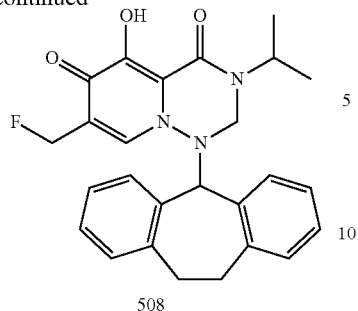

508

First Step

Compound 508A (261 mg, 0.475 mmol) which is a synthetic intermediate of Reference example 491 was dissolved in dimethyformamide (3 ml), triethylamine (0.132 ml, 0.950 mmol) and ethyl chloroformate (0.0910 ml, 0.950 mmol) were added at 0° C., and the mixture was stirred at room temperature for 20 minutes. An aqueous solution (0.5 ml) of sodium borohydride (71.9 mg, 1.90 mmol) was added at 0° C., and the mixture was stirred for 30 minutes. The reaction solution was poured into water, the mixture was extracted with ethyl acetate, and the organic layer was dried with sodium sulfate. The solvent was distilled off under reduced pressure, and the resulting crude product was purified by silica gel column chromatography, and eluted with chloroform-methanol (97:3, v/v). Diethyl ether was added, and the precipitated residue was filtered to obtain 107 mg of a white solid 508B.

MS: m/z=536 [M+H]$^+$

Second Step

Compound 508B (100 mg, 0.187 mmol) obtained in the first step was dissolved in dichloromethane (1 ml), DAST (33.1 mg, 0.205 mmol) was added at 0° C., and the mixture was stirred for 30 minutes. The reaction solution was poured into water, the mixture was extracted with chloroform, and the organic layer was dried with sodium sulfate. The solvent was distilled off under reduced pressure, and the resulting crude product was purified by silica gel column chromatography, and eluted with chloroform-methanol (97:3, v/v), to obtain 28 mg of a pale yellow gummy substance 508C.

MS: m/z=538 [M+H]$^+$

Third Step

To compound 508C obtained in the second step were added acetic acid (2 ml) and concentrated sulfuric acid (0.5 ml), and the mixture was stirred at room temperature for 20 minutes. The reaction solution was poured into water, the mixture was extracted with ethyl acetate, and the organic layer was dried with sodium sulfate. Diethyl ether was added, and the precipitated residue was filtered to obtain 4.5 mg of a white solid 508.

MS: m/z=448 [M+H]$^+$

418
REFERENCE EXAMPLE 509

[Chemical formula 559]

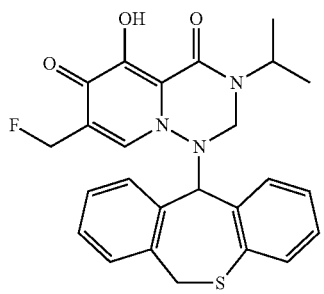

According to Reference example 508, compound 509 was synthesized by the same procedure.

MS: m/z=466 [M+H]$^+$

REFERENCE EXAMPLE 510

[Chemical formula 560]

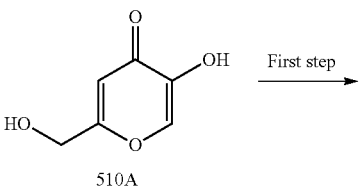

510A

First step

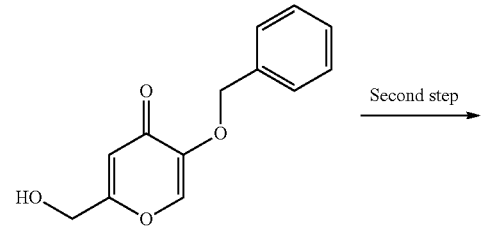

510B

Second step

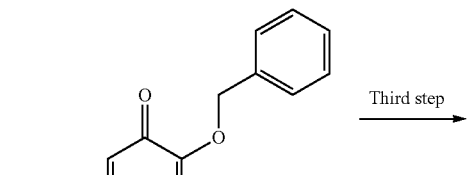

510C

Third step

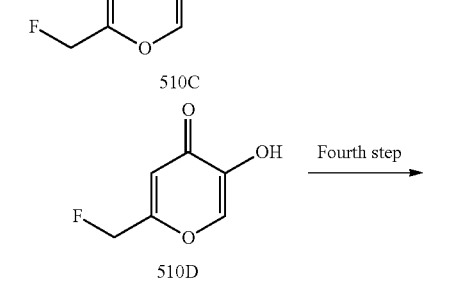

510D

Fourth step

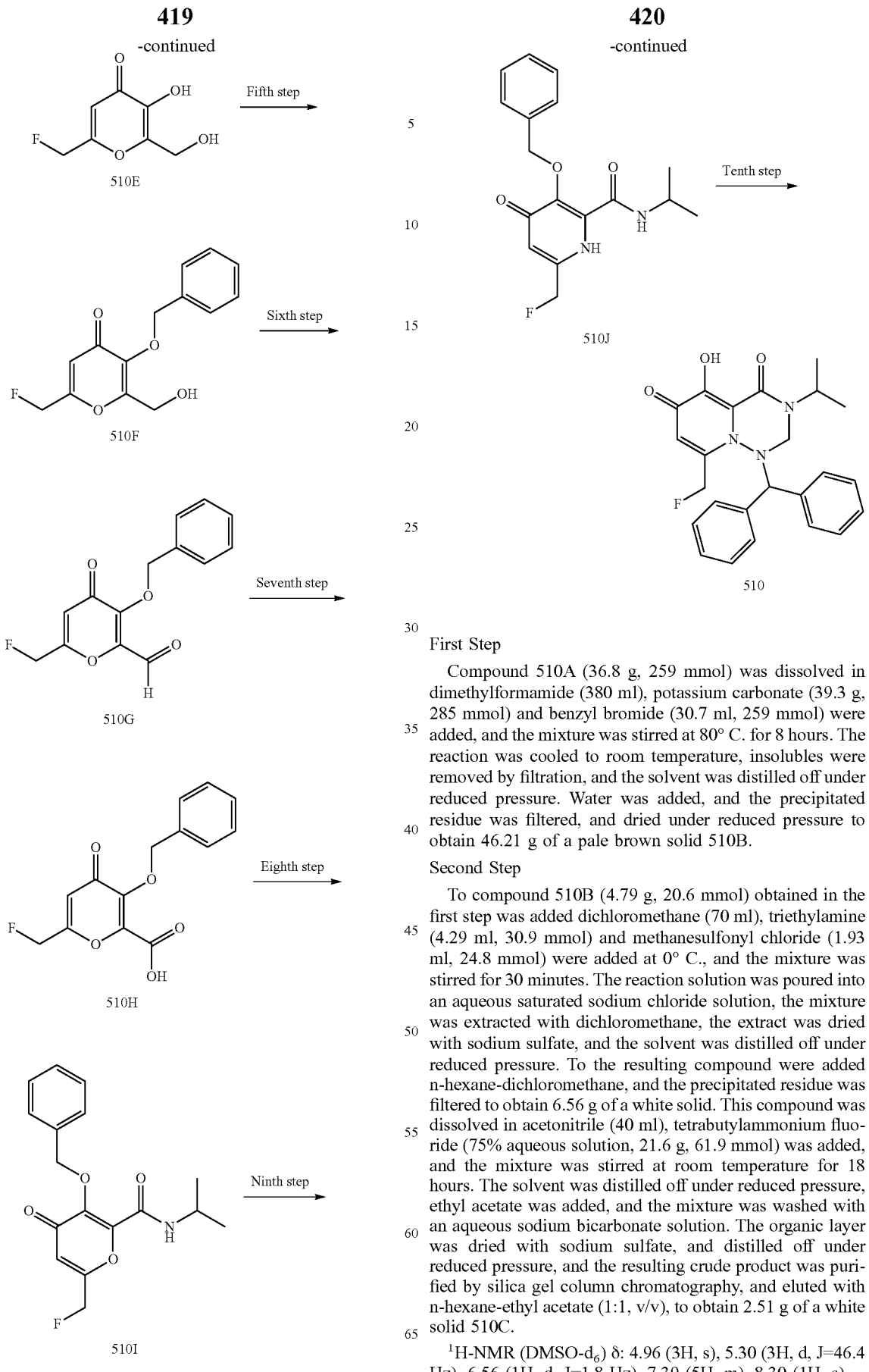

First Step

Compound 510A (36.8 g, 259 mmol) was dissolved in dimethylformamide (380 ml), potassium carbonate (39.3 g, 285 mmol) and benzyl bromide (30.7 ml, 259 mmol) were added, and the mixture was stirred at 80° C. for 8 hours. The reaction was cooled to room temperature, insolubles were removed by filtration, and the solvent was distilled off under reduced pressure. Water was added, and the precipitated residue was filtered, and dried under reduced pressure to obtain 46.21 g of a pale brown solid 510B.

Second Step

To compound 510B (4.79 g, 20.6 mmol) obtained in the first step was added dichloromethane (70 ml), triethylamine (4.29 ml, 30.9 mmol) and methanesulfonyl chloride (1.93 ml, 24.8 mmol) were added at 0° C., and the mixture was stirred for 30 minutes. The reaction solution was poured into an aqueous saturated sodium chloride solution, the mixture was extracted with dichloromethane, the extract was dried with sodium sulfate, and the solvent was distilled off under reduced pressure. To the resulting compound were added n-hexane-dichloromethane, and the precipitated residue was filtered to obtain 6.56 g of a white solid. This compound was dissolved in acetonitrile (40 ml), tetrabutylammonium fluoride (75% aqueous solution, 21.6 g, 61.9 mmol) was added, and the mixture was stirred at room temperature for 18 hours. The solvent was distilled off under reduced pressure, ethyl acetate was added, and the mixture was washed with an aqueous sodium bicarbonate solution. The organic layer was dried with sodium sulfate, and distilled off under reduced pressure, and the resulting crude product was purified by silica gel column chromatography, and eluted with n-hexane-ethyl acetate (1:1, v/v), to obtain 2.51 g of a white solid 510C.

$^1$H-NMR (DMSO-$d_6$) δ: 4.96 (3H, s), 5.30 (3H, d, J=46.4 Hz), 6.56 (1H, d, J=1.8 Hz), 7.39 (5H, m), 8.30 (1H, s).

Third Step

Compound 510C (2.40 g, 10.3 mmol) obtained in the second step was dissolved in dichloromethane (40 ml), boron tribromide (1M dichloromethane solution, 10.3 ml, 10.3 mmol) was added dropwise at 0° C., and the mixture was stirred for 30 minutes. Methanol was added, the solvent was distilled off under reduced pressure, ethyl acetate was added, and the mixture was washed with an aqueous saturated sodium chloride solution. The organic layer was dried with sodium sulfate, the solvent was distilled off under reduced pressure, and the resulting solid was washed with diethyl ether to obtain 940 mg of 510D.

$^1$H-NMR (CDCl$_3$) δ: 5.20 (2H, d, J=46.3 Hz), 6.40 (1H, s), 6.62 (1H, s), 7.91 (1H, s).

Fourth Step

Compound 510D (940 mg, 6.52 mmol) obtained in the third step was dissolved in methanol (8 ml), a 2N aqueous sodium hydroxide solution (3.26 ml, 6.52 mmol) and a 37% aqueous formaldehyde solution (1.46 ml, 19.6 mmol) were added at 0° C., and the mixture was stirred at room temperature for 20 hours. To the reaction solution was added an aqueous saturated ammonium chloride solution, and the solvent was distilled off under reduced pressure. Hydrochloric acid was added, the mixture was extracted with chloroform, and the organic layer was dried with sodium sulfate. The solvent was distilled off under reduced pressure, to the resulting compound were added n-hexane-dichloromethane-ethyl acetate, and the precipitated residue was filtered to obtain 858 mg of a pale yellow solid 510E.

$^1$H-NMR (CDCl$_3$) δ: 4.73 (2H, s), 5.19 (2H, d, J=46.1 Hz), 6.55 (1H, s).

Fifth Step

Compound 510E (855 mg, 4.91 mmol) obtained in the fourth step was dissolved in dimethylformamide (10 ml), potassium carbonate (746 mg, 5.40 mmol) and benzyl bromide (0.583 ml, 4.91 mmol) were added, and the mixture was stirred at 80° C. for 5 hours. Insolubles were removed by filtration, and the filtrate was distilled off under reduced pressure. The resulting crude product was purified by silica gel column chromatography, and eluted with chloroform-methanol (97:3, v/v), to obtain 887 mg of a pale orange solid 510F.

$^1$H-NMR (CDCl$_3$) δ: 1.39 (1H, t, J=7.1 Hz), 4.31 (2H, d, J=7.2 Hz), 5.12 (2H, dd, J=46.3, 0.7 Hz), 5.23 (2H, s), 6.50 (1H, s), 7.33-7.43 (5H, m).

Sixth Step

Compound 510F (887 mg, 3.36 mmol) obtained in the fifth step was dissolved in chloroform, manganese dioxide (2.00 g, 23.0 mmol) was added, and the mixture was stirred at 80° C. for 2 hours. After cooled to room temperature, the mixture was filtered with celite, and the solvent was distilled off under reduced pressure to obtain 812 mg of a white solid 510G.

$^1$H-NMR (CDCl$_3$) δ: 5.18 (2H, dd, J=45.8, 0.8 Hz), 5.52 (2H, s), 6.60 (1H, d, J=0.8 Hz), 7.32-7.38 (5H, m), 9.86 (1H, s).

Seventh Step

To compound 510G (884 mg, 3.37 mmol) obtained in the sixth step were added acetonitrile and water, monosodium dihydrogen phosphate (809 mg, 6.74 mmol) and sodium hypochlorite (1.01 g, 11.1 mmol) were added, and the mixture was stirred at room temperature for 1 hour. The reaction solution was concentrated, pH was adjusted to 3 with hydrochloric acid, the mixture was extracted with chloroform, and the extract was dried with sodium sulfate. The solvent was distilled off under reduced pressure to obtain 404 mg of a white solid 510H.

$^1$H-NMR (DMSO-d$_6$) δ: 5.17 (2H, s), 5.38 (2H, d, J=46.2 Hz), 6.73 (1H, d, J=1.5 Hz), 7.34-7.51 (5H, m).

Eighth Step

Compound 510H (402 mg, 1.45 mmol) obtained in the seventh step was dissolved in dimethylformamide, N1-((ethylimino)methylene)-N3,N3-dimethylpropane-1,3-diamine hydrochloride (554 mg, 2.89 mmol) and 1H-benzo[d][1,2,3]triazol-1-ol (195 mg, 1.45 mmol) were added, and the mixture was stirred at room temperature for 5 minutes. After propan-2-amine (0.149 ml, 1.73 mmol) was added, the mixture was stirred at room temperature for 1 hour. The reaction solution was concentrated under reduced pressure, water was added, the mixture was extracted with ethyl acetate, and the organic layer was washed with an aqueous sodium bicarbonate solution, and dried with sodium sulfate. The reaction solution was distilled off under reduced pressure, to the resulting compound was added n-hexane, and the precipitated residue was filtered to obtain 3.56 g of a white solid 510I.

$^1$H-NMR (CDCl$_3$) δ: 0.98 (6H, d, J=6.6 Hz), 4.05 (1H, m), 5.24 (2H, dd, J=45.9, 0.9 Hz), 5.41 (2H, s), 6.59 (1H, q, J=0.9 Hz), 7.40 (5H, m), 7.56 (1H, brs).

Ninth Step

Compound 510I (392 mg, 1.23 mmol) obtained in the eighth step was dissolved in ethanol (6 ml), aqueous ammonia (4 ml) was added, and the mixture was stirred at room temperature for 15 hours. The reaction solution was concentrated under reduced pressure, and the resulting crude product was purified by silica gel column chromatography, and eluted with chloroform-methanol (97:3, v/v), to obtain 333 mg of a white solid 510J.

MS: m/z=319 [M+H]$^+$

Tenth Step

Compound 510 was synthesized by the same procedure as that of Reference example 95.

MS: m/z=422 [M+H]$^+$

REFERENCE EXAMPLE 511

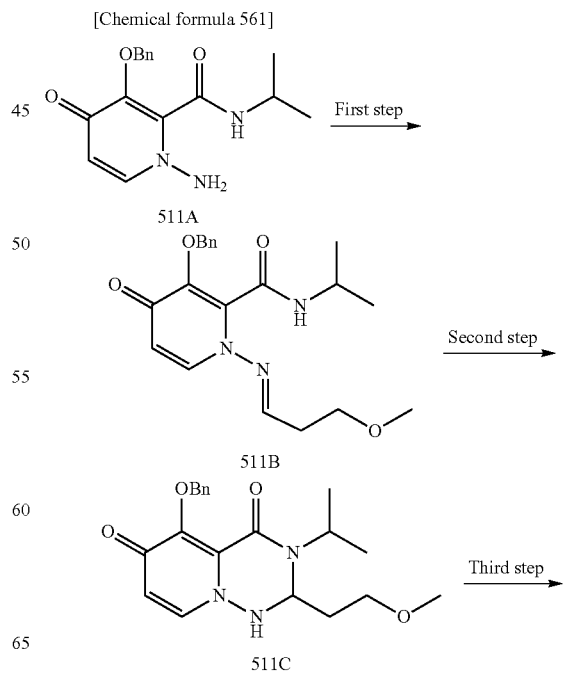

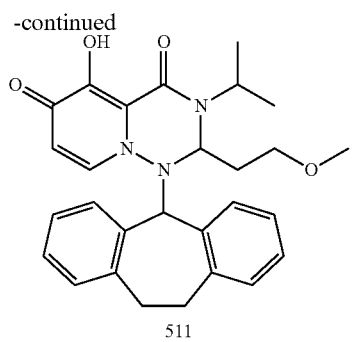

511

First Step

A dichloromethane (90 mL) solution of compound 511A (200 mg, 0.664 mmol) and 1,1,3-trimethoxypropane (178.2 mg, 1.33 mmol) was cooled to 1 to 3° C., and a boron trifluoride diethyl ether complex (113 mg, 0.797 mmol) was added dropwise while the same temperature was retained. After the reaction solution was stirred at the same temperature for 30 minutes, saturated sodium bicarbonate water was added. The dichloromethane layer was separated, and the aqueous layer was extracted with dichloromethane three times. After the combined extracts were dried with sodium sulfate, the solvent was distilled off, and the resulting oil was purified by silica gel column chromatography. The materials were eluted firstly with ethyl acetate and, then, with ethyl acetate-methanol (3:2, v/v). Concentration of an objective fraction afforded 179.2 mg of compound 511B as an oil.

$^1$H-NMR (CDCl$_3$) δ: 1.14 (6H, d, J=6.3 Hz), 2.71 (2H, dd, J=6.0 Hz), 3.34 (3H, s), 3.64 (2H, t, J=6.0 Hz), 4.06-4.17 (1H, m), 5.23 (2H, s), 6.34 (1H, brs), 6.37 (1H, d, J=7.8 Hz), 7.26-7.43 (6H, m), 7.90 (1H, t, J=5.4 Hz).

Second Step

A dimethylformamide (3 ml) solution of compound 511B (179.2 mg, 0.482 mmol) was cooled to 1 to 3° C., cesium carbonate (786 mg, 2.41 mmol) was added while the same temperature was retained, and the mixture was stirred at the same temperature for 15 minutes. The reaction solution was diluted with water, and extracted with chloroform three times. After the combined extracts were dried with sodium sulfate, the solvent was distilled off to obtain 130 mg of compound 511C as a solid.

$^1$H-NMR (CDCl$_3$) δ: 1.22 (3H, d, J=6.9 Hz), 1.28 (3H, d, J=6.9 Hz), 1.59 (2H, brs), 3.22-3.41 (2H, m), 3.12 (3H, s), 4.57-4.70 (2H, m), 5.19 (1H, d, J=10.5 Hz), 5.38 (1H, brs), 5.54 (1H, d, J=10.5 Hz), 6.34 (1H, d, J=7.8 Hz), 7.26-7.32 (4H, m), 7.49-7.52 (2H, m).

Third Step

To an acetic acid (2 ml) solution of compound 511C (130 mg, 0.350 mmol) and dibenzosuberol (368 mg, 1.75 mmol) was added dropwise sulfuric acid (0.4 ml) at room temperature, and the mixture was stirred at the same temperature for 30 minutes. The reaction solution was diluted with water, and the mixture was extracted with ethyl acetate three times. The extract was washed with water once, and dried with sodium sulfate, thereafter, the solvent was distilled off, and the resulting solid was washed with diisopropyl ether to obtain 65 mg of compound 511 as a solid.

$^1$H-NMR (CDCl$_3$) δ: 1.27 (3H, d, J=6.9 Hz), 1.49 (3H, d, J=6.6 Hz), 1.64-1.74 (1H, m), 1.88-1.99 (1H, m), 2.83 (1H, d, J=4.5 Hz, 4.5 Hz, 13.2 Hz), 3.06 (1H, ddd, J=5.6 Hz, 13.2 Hz, 13.2 Hz), 3.19 (3H, s), 3.30-3.44 (1H, m), 3.50-3.57 (1H, m), 3.78-3.92 (1H, m), 4.28 (1H, ddd, J=4.2 Hz, 13.5 Hz, 13.5 Hz), 4.53 (1H, dd, J=3.3 Hz, 10.8 Hz), 4.96 (1H, s), 5.73 (1H, d, J=7.5 Hz), 6.61 (1H, d, J=7.5 Hz), 6.65 (1H, d, J=7.5 Hz), 6.89-6.93 (1H, m), 7.08-7.36 (6H, m).

Using amines which are commercially available or known in the references and acetals which are commercially available or known in the references, and according to Reference example 511, compounds 512 to 515 were synthesized.

REFERENCE EXAMPLE 512

[Chemical formula 562]

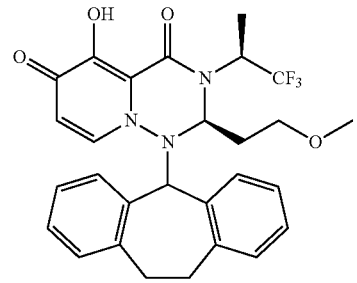

MS: m/z=528 [M+H]$^+$

REFERENCE EXAMPLE 513

[Chemical formula 563]

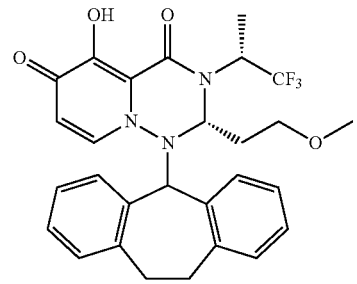

MS: m/z=528 [M+H]$^+$

REFERENCE EXAMPLE 514

[Chemical formula 564]

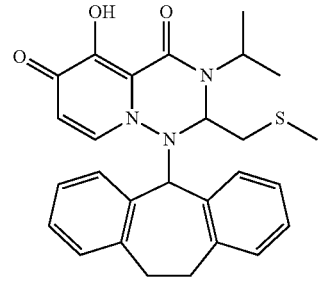

$^1$H-NMR (CDCl$_3$) δ: 1.27 (1H, 3H, d, J=6.9 Hz), 1.48 (3H, d, J=6.6 Hz), 1.95 (3H, s), 2.63-2.68 (2H, m), 2.84 (1H, ddd, J=4.8 Hz, 9.3 Hz, 9.3 Hz), 3.05 (1H, ddd, J=4.2 Hz, 13.2 Hz, 13.2 Hz), 3.60 (1H, ddd, J=4.8 Hz, 4.8 Hz, 17.4 Hz), 3.87-3.98 (1H, m), 4.42 (1H, dd, J=6.6 Hz, 8.1 Hz), 4.59 (1H, ddd, J=4.2 Hz, 13.5 Hz, 13.5 Hz), 4.93 (1H, s), 5.77 (1H, d, J=7.8 Hz), 6.64 (1H, d, J=6.9 Hz), 6.69 (1H, d, J=7.8 Hz), 6.91 (1H, t, J=6.0 Hz), 7.09-7.38 (6H, m).

REFERENCE EXAMPLE 515

[Chemical formula 565]

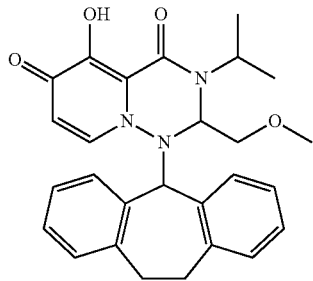

$^1$H-NMR (CDCl$_3$) δ: 1.20 (3H, d, J=6.9 Hz), 1.44 (3H, d, J=6.9 Hz), 2.80 (1H, ddd, J=4.5 Hz, 4.5 Hz, 9.3 Hz), 3.07 (1H, ddd, J=4.5 Hz, 13.5 Hz, 13.5 Hz), 3.25 (3H, s), 3.22-3.43 (2H, m), 3.55 (1H, ddd, J=4.2 Hz, 4.2 Hz, 8.7 Hz), 3.85-3.94 (1H, m), 4.36 (1H, dd, J=5.1 Hz, 14.1 Hz), 4.42-4.48 (1H, m), 4.92 (1H, s), 5.78 (1H, d, J=7.5 Hz), 6.59 (1H, d, J=7.8 Hz), 6.64 (1H, d, J=7.5 Hz), 6.91 (1H, t, J=6.9 Hz), 7.09-7.36 (6H, m).

REFERENCE EXAMPLE 516

[Chemical formula 566]

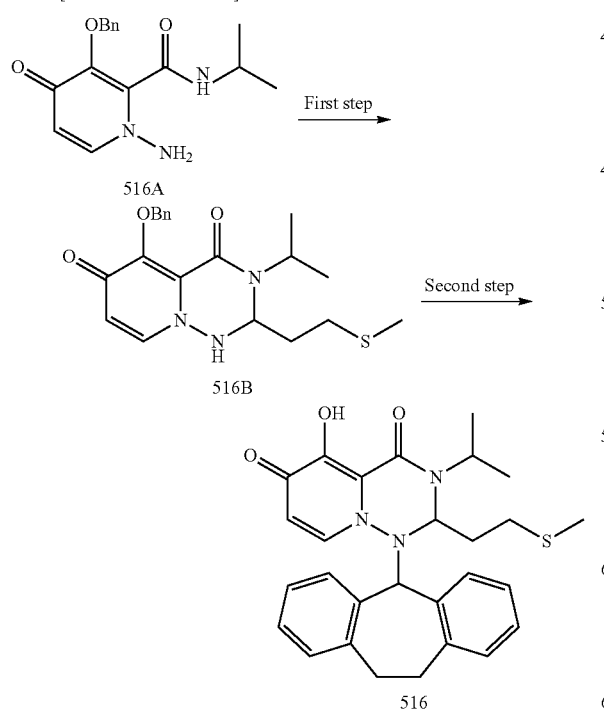

First Step

To a toluene (3 ml) solution of compound 516A (100 mg, 0.332 mmol) and 3-(methylthio)propanal (52 mg, 0.498 mmol) was added acetic acid (30 mg, 0.500 mmol), and the mixture was refluxed for 30 minutes. After cooled to room temperature, the solvent was distilled off, and the resulting crude product was dissolved in dimethylformamide (3 ml). The solution was cooled to 1 to 3° C., cesium carbonate (541 mg, 1.66 mmol) was added while the same temperature was retained, and the mixture was stirred at the same temperature for 30 minutes. The reaction solution was diluted with water, and the mixture was extracted with ethyl acetate three times. The combined extracts were washed with water three times, and dried with sodium sulfate, and the solvent was distilled off. The resulting oil was purified by silica gel column chromatography. The materials were eluted firstly with ethyl acetate and, then, with ethyl acetate-methanol (7:3, v/v). Concentration of an objective fraction afforded 84.7 mg of compound 516B as an oil.

$^1$H-NMR (CDCl$_3$) δ: 1.21 (3H, J=6.9 Hz), 1.28 (3H, d, J=6.9 Hz), 1.31-1.56 (2H, m), 2.05 (3H, s), 2.46 (2H, dd, J=5.4 Hz, 7.8 Hz), 4.57-4.71 (2H, m), 5.18 (1H, d, J=10.5 Hz), 5.51 (1H, d, J=10.5 Hz), 5.66 (1H, brs), 6.33 (1H, d, J=7.8 Hz), 7.19-7.35 (4H, m), 7.46-7.49 (2H, m).

Second Step

Compound 516 was synthesized by the same procedure as that of Reference example 511.

$^1$H-NMR (CDCl$_3$) δ: 1.29 (3H, d, J=6.9 Hz), 1.49 (3H, d, J=6.6 Hz), 1.82-1.89 (2H, m), 1.99 (3H, s), 2.41-2.58 (2H, m), 2.86 (1H, ddd, J=4.5 Hz, 4.5 Hz, 14.1 Hz), 2.99-3.11 (1H, m), 3.53 (1H, ddd, J=4.5 Hz, 4.5 Hz, 17.7 Hz), 4.87-3.96 (1H, m), 4.21 (1H, ddd, J=3.9 Hz, 12.9 Hz, 12.9 Hz), 4.53 (1H, dd, J=5.1 Hz, 8.7 Hz), 4.96 (1H, s), 5.74 (1H, d, J=7.5 Hz), 6.62 (1H, d, J=7.5 Hz), 6.64 (1H, d, J=9.0 Hz), 6.89-6.94 (1H, m), 7.07-7.37 (6H, m).

Using amines which are commercially available or known in the references and aldehydes which are commercially available or known in the references, and according to Reference example 516, compounds 517 to 526 were synthesized.

REFERENCE EXAMPLE 517

[Chemical formula 567]

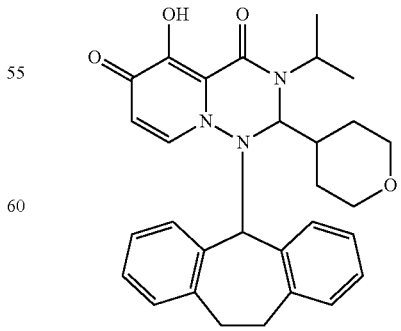

MS: m/z=500 [M+H]$^+$

REFERENCE EXAMPLE 518

[Chemical formula 568]

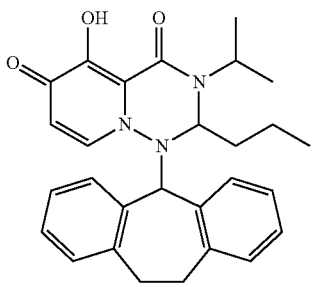

$^1$H-NMR (CDCl$_3$) δ: 1.78 (3H, t, J=6.9 Hz), 1.19-1.30 (1H, m), 1.29 (3H, d, J=6.9 Hz), 1.43-1.62 (3H, m), 1.50 (3H, d, J=6.9 Hz), 2.84 (1H, ddd, J=4.5 Hz, 4.5 Hz, 14.1 Hz), 3.00-3.11 (1H, ddd, J=3.9 Hz, 12.9 Hz, 12.9 Hz), 3.52 (1H, ddd, J=4.5 Hz, 4.5 Hz, 17.4 Hz), 3.79-3.88 (1H, m), 4.23-4.35 (2H, m), 4.96 (1H, s), 5.74 (1H, d, J=7.8 Hz), 6.61 (1H, d, J=7.5 Hz), 6.65 (1H, dd, J=1.2 Hz, 7.8 Hz), 6.91 (1H, ddd, J=1.5 Hz, 7.5 Hz, 7.5 Hz), 7.08-7.37 (6H, m).

REFERENCE EXAMPLE 519

[Chemical formula 569]

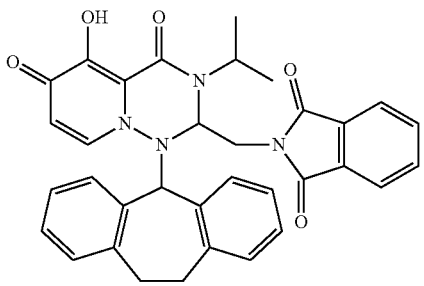

$^1$H-NMR (CDCl$_3$) δ: 1.44 (3H, d, J=6.9 Hz), 1.54 (3H, d, J=6.6 Hz), 1.88 (1H, ddd, J=3.9 Hz, 3.9 Hz, 14.4 Hz), 2.72 (1H, ddd, J=3.6 Hz, 14.1 Hz, 14.1 Hz), 3.15 (1H, ddd, J=4.2 Hz, 4.2 Hz, 16.5 Hz), 3.54 (1H, dd, J=3.0 Hz, 14.4 Hz), 3.66 (1H, ddd, J=3.9 Hz, 13.8 Hz, 13.8 Hz), 4.03 (1H, dd, J=10.5 Hz, 14.1 Hz), 4.27-4.26 (1H, m), 4.64 (1H, dd, J=2.7 Hz, 10.5 Hz), 4.92 (1H, s), 5.80 (1H, d, J=7.8 Hz), 6.62-6.70 (2H, m), 6.69 (1H, d, J=7.8 Hz), 6.89 (1H, t, J=7.5 Hz), 6.96 (1H, d, J=7.5 Hz), 7.09-7.25 (4H, m), 7.77-7.89 (4H, m).

REFERENCE EXAMPLE 520

[Chemical formula 570]

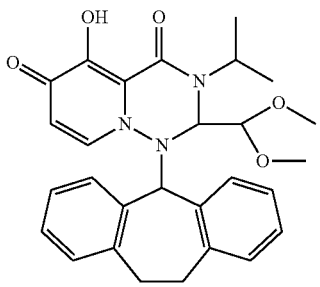

$^1$H-NMR (CDCl$_3$) δ: 1.30 (3H, d, J=6.6 Hz), 1.54 (3H, d, J=6.6 Hz), 2.83 (1H, ddd, J=4.8 Hz, 4.8 Hz, 14.1 Hz), 3.03-3.14 (1H, m), 3.21 (3H, s), 3.30 (3H, s), 3.53 (1H, ddd, J=4.5 Hz, 4.5 Hz, 17.7 Hz), 3.61-3.70 (1H, m), 4.18 (1H, d, J=5.4 Hz), 4.26 (1H, d, J=5.4 Hz), 4.45 (1H, ddd, J=4.5 Hz, 13.8 Hz, 13.8 Hz), 4.92 (1H, s), 5.72 (1H, d, J=7.8 Hz), 6.63 (1H, d, J=7.8 Hz), 6.65 (1H, d, J=6.6 Hz), 6.91 (1H, t, J=6.0 Hz), 7.08-7.36 (6H, m).

REFERENCE EXAMPLE 521

[Chemical formula 571]

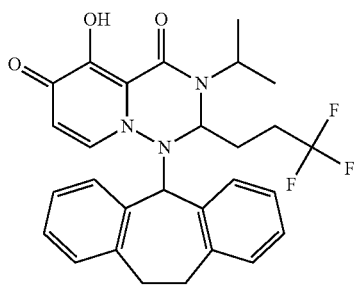

$^1$H-NMR (CDCl$_3$) δ: 1.30 (2.52H, d, J=6.9 Hz), 1.36 (0.48H, d, J=6.9 Hz), 1.42 (0.48H, d, J=6.9 Hz), 1.50 (2.52H, d, J=6.9 Hz), 1.74-1.98 (1H, m), 2.00-2.12 (1H, m), 2.16-2.35 (1H, m), 2.89 (1H, ddd, J=5.1 Hz, 5.1 Hz, 13.5 Hz), 3.06 (1H, ddd, J=3.9 Hz, 12.9 Hz, 12.9 H), 3.52 (1H, d, J=4.2 Hz, 4.2 Hz, 17.4 Hz), 3.86-3.96 (1H, m), 4.15 (1H, ddd, J=3.9 Hz, 13.5 Hz, 13.5 Hz), 4.32 (1H, dd, J=3.9 Hz, 10.8 Hz), 4.48-4.64 (1H, m), 4.97 (0.84H, s), 5.30 (0.16H, s), 5.73 (0.84H, d, J=7.8 Hz), 6.20 (0.16H, d, J=7.5 Hz), 6.45 (0.16H, brs), 6.61 (1H, d, J=7.5 Hz), 6.64 (0.84H, d, J=8.7 Hz), 6.92 (1H, t, J=6.3 Hz), 7.10 (1H, d, J=7.5 Hz), 7.15-7.39 (3H, m).

REFERENCE EXAMPLE 522

[Chemical formula 572]

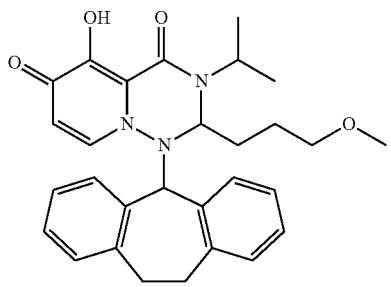

$^1$H-NMR (CDCl$_3$) δ: 1.28 (3H, d, J=6.9 Hz), 1.49 (3H, d, J=6.9 Hz), 1.54-1.79 (4H, m), 2.84 (1H, ddd, J=4.8 Hz, 4.8 Hz, 14.1 Hz), 3.05 (1H, ddd, J=4.2 Hz, 13.5 Hz, 13.5 Hz), 3.17 (3H, s), 3.17-3.21 (2H, m), 3.52 (1H, ddd, J=4.2 Hz, 4.2 Hz, 17.7 Hz), 3.83-3.92 (1H, m), 4.22-4.32 (2H, m), 4.96 (1H, s), 5.73 (1H, d, J=7.5 Hz), 6.62 (1H, d, J=7.8 Hz), 6.65 (1H, d, J=8.1 Hz), 6.92 (1H, t, J=7.2 Hz), 7.07-7.37 (6H, m).

REFERENCE EXAMPLE 523

[Chemical formula 573]

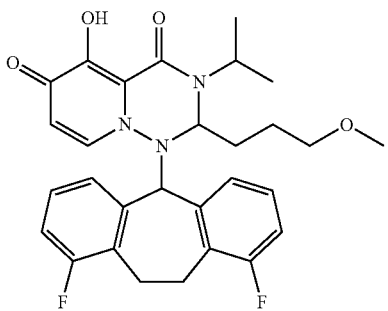

¹H-NMR (CDCl₃) δ: 1.19-1.28 (1H, m), 1.28 (3H, d, J=6.9 Hz), 1.40-1.82 (4H, m), 1.48 (3H, d, J=6.6 Hz), 2.89-3.00 z81H, m), 3.17 (3H, s), 3.20-3.27 (2H, m), 3.31-3.40 (1H, m), 3.44-3.53 (1H, m), 3.86-3.98 (2H, m), 4.38 (1H, dd, J=3.6 Hz, 10.5 Hz), 5.05 (1H, s), 5.84 (1H, d, 7.5 Hz), 6.48-6.50 (1H, m), 6.66-6.69 (1H, m), 6.89-7.00 (2H, m), 7.05 (1H, d, 7.2 Hz), 7.11-7.24 (2H, m).

REFERENCE EXAMPLE 524

[Chemical formula 574]

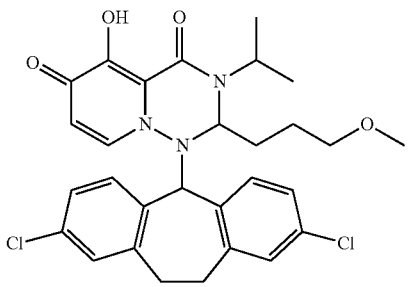

¹H-NMR (CDCl₃) δ: 1.29 (3H, d, J=6.9 Hz), 1.42-1.83 (4H, m), 1.48 (3H, d, J=6.6 Hz), 2.80 (1H, ddd, J=4.5 Hz, 4.5 Hz), 14.4 H), 2.94-3.11 (1H, m), 3.18 (3H, s), 3.21-3.26 (2H, m), 3.49 (1H, ddd, J=4.2 Hz, 4.2 Hz, 18.0 Hz), 3.82-3.91 (1H, m), 4.20-4.33 (2H, m), 5.83 (1H, s), 5.84 (1Hm d, J=7.8 Hz), 6.58-6.72 (2H, m), 6.91-6.94 (1H, m), 7.11-7.30 (4H, m).

REFERENCE EXAMPLE 525

[Chemical formula 575]

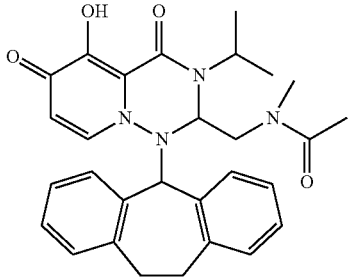

¹H-NMR (CDCl₃) δ: 1.29 (3H, d, J=6.9 Hz), 1.47 (3H, d, J=6.6 Hz), 2.10 (3H, s), 2.78 (1H, ddd, J=4.2 Hz, 4.2 Hz, 13.8 Hz), 2.97 (3H, s), 3.01-3.13 (2H, m), 3.47 (1H, ddd, J=4.2 Hz, 4.2 Hz, 17.7 Hz), 3.65 (1H, dd, J=3.3 Hz, 14.1 Hz), 3.99-4.23 (2H, m), 4.70 (1H, dd, J=3.3 Hz, 10.2 Hz), 4.95 (1H, s), 5.78 (1H, d, J=7.8 Hz), 6.61 (1H, d, J=7.8 Hz), 6.65 (1H, d, J=7.5 Hz), 6.93 (1H, t, J=6.6 Hz), 7.09 (1H, d, J=7.5 Hz), 7.15-7.27 (4H, m), 7.30-7.37 (1H, m).

REFERENCE EXAMPLE 526

[Chemical formula 576]

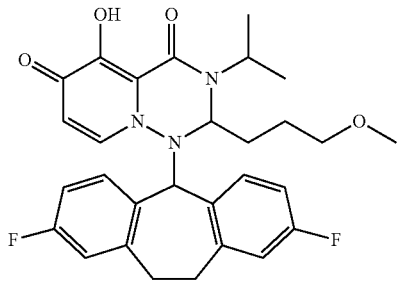

¹H-NMR (CDCl₃) δ: 1.57-1.34 (1H, m), 1.29 (3H, d, J=6.9 Hz), 1.41-1.52 (1H, m), 1.48 (3H, d, J=6.6 Hz), 1.59-1.81 (2H, m), 2.80 (1H, ddd, 4.5 Hz, 4.5 Hz, 14.4 Hz), 3.04 (1H, ddd, J=4.2 Hz, 13.2 Hz, 13.2 Hz), 3.14-3.26 (2H, m), 3.18 (3H, s), 3.49 (1H, ddd, J=4.8 Hz, 4.8 Hz, 17.7 Hz), 3.84-3.93 (1H, m), 4.23-4.34 (2H, m), 4.96 (1H, s), 5.81 (1H, d, J=7.5 Hz), 6.60-6.79 (3H, m), 6.81 (1Hm d, J=9.3 Hz), 6.92 (1H, ddd, J=2.7 Hz, 8.4 Hz, 8.4 Hz), 7.19-7.24 (1H, m).

REFERENCE EXAMPLE 527

[Chemical formula 577]

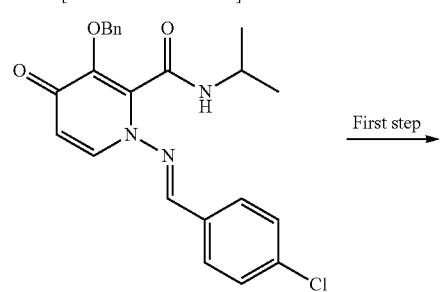

First step →

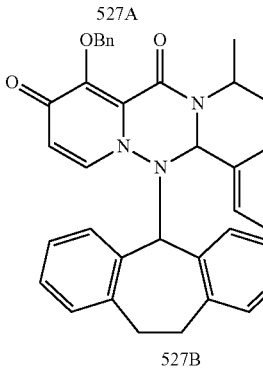

Second step →

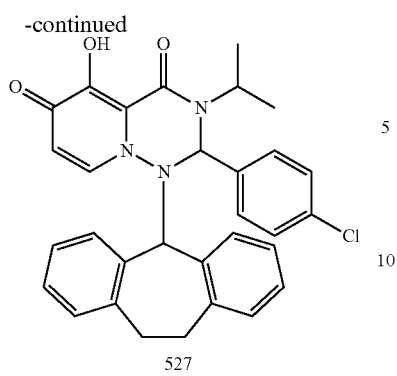

527

First Step

A DMF (0.2 mL) solution of compound 527A (36 mg, 0.09 mmol) synthesized according to the method of synthesizing compound 516 was cooled to 1 to 3° C., 5-chlorodibenzosuberane (97 mg, 0.43 mmol) and cesium carbonate (138 mg, 0.43 mmol) were added, and the mixture was stirred at room temperature overnight. To the reaction solution was added water, and the mixture was distributed between ethyl acetate and water. The organic layer was washed with an aqueous saturated sodium chloride solution, and dried. The solvent was distilled off, and the resulting oil was subjected to silica gel column chromatography, and eluted with chloroform-methanol. Concentration of an objective fraction afforded 19 mg of compound 527B as an oil.

MS: m/z=616 [M+H]$^+$.

Second Step

Compound 527B (19 mg, 0.03 mmol) was dissolved in MeOH (0.6 mL), 10% Pd—C (3 mg) was added, and the mixture was subjected to a catalytic reduction reaction under hydrogen stream. The catalyst was removed by filtration, and the filtrate was concentrated. The resulting oil was subjected to diol silica gel column chromatography, and eluted with chloroform-methanol. Concentration of an objective fraction afforded 7 mg of compound 527 as an oil.

MS: m/z=526 [M+H]$^+$.

Using halides which are commercially available or known in the references and aldehydes which are commercially available or known in the references, and according to the method of Reference example 527, compounds 528 to 531 were synthesized.

REFERENCE EXAMPLE 528

[Chemical formula 578]

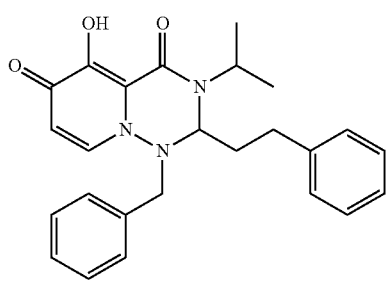

MS: m/z=418 [M+H]$^+$

REFERENCE EXAMPLE 529

[Chemical formula 579]

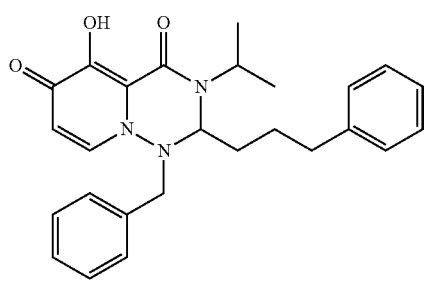

MS: m/z=432 [M+H]$^+$

REFERENCE EXAMPLE 530

[Chemical formula 580]

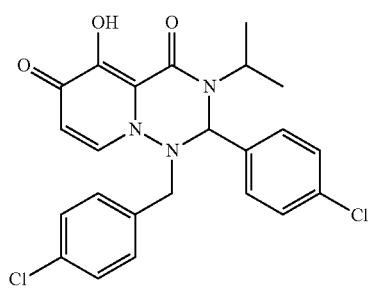

MS: m/z=459 [M+H]$^+$

REFERENCE EXAMPLE 531

[Chemical formula 581]

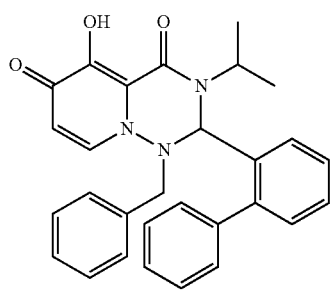

MS: m/z=466 [M+H]$^+$

REFERENCE EXAMPLE 532

[Chemical formula 582]

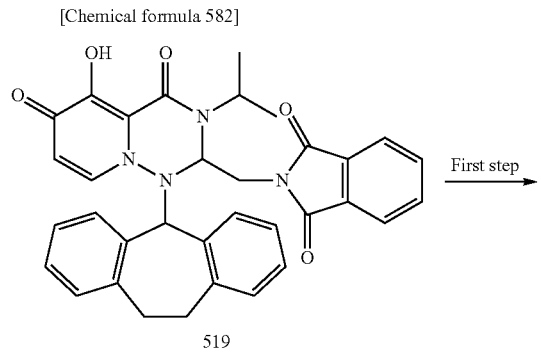

First step

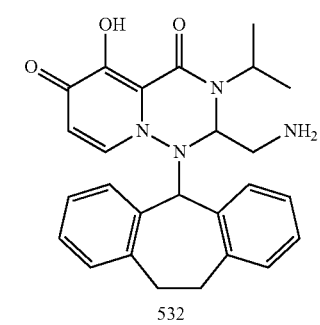

First Step

To a methanol (5 ml) solution of compound 519 (440 mg, 0.766 mmol) was added hydrazine hydrate (383 mg, 7.66 mmol), and the mixture was refluxed for 1 hour. After cooled to room temperature, the precipitated insolubles were filtered off. After the solvent was distilled off, the residue was suspended in ethyl acetate, the insolubles were filtered off, and the solvent was distilled off. The resulting crude product was suspended in chloroform, and insolubles were filtered off. The solvent was distilled off, and the resulting crude product was washed with ethyl acetate-diisopropyl ether to obtain 190 mg of compound 532 as a solid.

$^1$H-NMR (CDCl$_3$) δ: 1.24 (3H, d, J=6.9H), 1.46 (3H, d, J=6.6 Hz), 2.73-2.90 (3H, m), 3.08 (1H, ddd, J=4.2 Hz, 12.9 Hz, 12.9 Hz), 3.54 (1H, ddd, J=4.5 Hz, 4.5 Hz, 17.7 Hz), 3.85-3.94 (1H, m), 4.19 (1H, dd, J=7.2 Hz, 11.1 Hz), 4.35 (1H, ddd, J=4.5 Hz, 13.8 Hz, 13.8 Hz), 4.97 (1H, s), 5.74 (1H, d, J=7.5 Hz), 6.60 (1H, d, J=7.8 Hz), 6.65 (1H, d, J=7.2 Hz), 6.92 (1H, t, J=6.3 Hz), 7.09-7.45 (6H, m).

REFERENCE EXAMPLE 533

[Chemical formula 583]

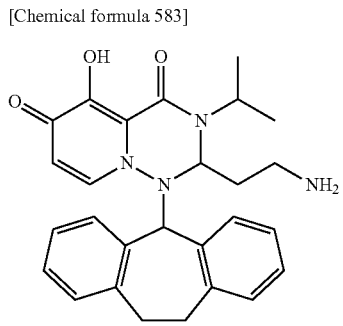 [SMILES: CC(C)N1C(=O)c2c(O)c(=O)ccn2N(C2c3ccccc3CCc3ccccc32)C1CCN]

Compound 533 was synthesized by the same procedure as that of Reference example 532.

$^1$H-NMR (DMSO-d$_6$) δ: 1.22 (3H, d, J=6.6 Hz), 1.40 (3H, d, J=6.6 Hz), 0.1.45-1.58 (1H, m), 1.62-1.75 (1H, m), 2.61-2.69 (1H, m), 2.71-2.84 (1H, m), 2.88-2.95 (1H, m), 3.16-3.34 (1H, m), 3.60-3.64 (1H, m), 3.92-4.00 (1H, m), 4.24-4.33 (1H, m), 4.42-4.46 (1H, dd, J=3.3 Hz, 10.8 Hz), 5.10 (1H, s), 5.47 (1H, d, J=7.5 Hz), 6.70 (1H, d, J=7.5 Hz), 6.88 (1H, t, J=7.5 Hz), 7.02 (1H, d, J=10.8 Hz), 7.09-7.16 (2H, m), 7.19-7.25 (1H, m), 7.33 (2H, d, J=4.2 Hz), 7.42 (1H, d, J=7.5 Hz).

REFERENCE EXAMPLE 534

[Chemical formula 584]

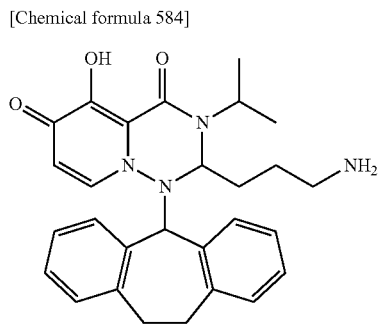 [SMILES: CC(C)N1C(=O)c2c(O)c(=O)ccn2N(C2c3ccccc3CCc3ccccc32)C1CCCN]

Compound 534 was synthesized by the same procedure as that of Reference example 532.

$^1$H-NMR (DMSO-d$_6$) δ: 1.25 (3H, d, J=6.9 Hz), 1.44 (3H, d, J=6.6 Hz), 1.32-1.58 (2H, m), 1.77-1.79 (2H, m), 2.64-2.73 (1H, m), 2.79-3.00 (2H, m), 3.88-3.97 (2H, m), 4.19-4.28 (2H, m), 5.15 (1H, s), 5.67 (1H, d, J=7.5 Hz), 5.73 (1H, d, J=7.5 Hz), 6.90 (1H, t, J=6.6 Hz), 7.03 (1H, d, J=7.5 Hz), 7.13-7.32 (3H, m), 7.36 (2H, d, J=4.2 Hz), 7.44 (1H, J=7.2 Hz), 7.75 (1H, brs).

REFERENCE EXAMPLE 535

[Chemical formula 585]

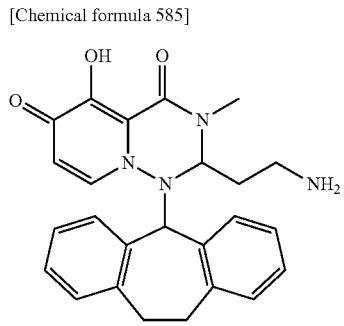 [SMILES: CN1C(=O)c2c(O)c(=O)ccn2N(C2c3ccccc3CCc3ccccc32)C1CCN]

Compound 535 was synthesized by the same procedure as that of Reference example 532.

$^1$H-NMR (DMSO-d$_6$) δ: 1.40-1.52 (1H, m), 1.61-1.72 (1H, m), 2.40-2.49 (1H, m), 2.58-2.62 (1H, m), 2.78-2.86 (1H, m), 2.89-2.95 (1H, m), 2.95 (3H, m), 3.66-3.74 (1H, m), 4.01-4.13 (1H, m), 4.28-4.32 (1H, m), 5.14 (1H, m), 5.51 (1H, d, J=7.8 Hz), 6.72 (1H, d, J=7.5 Hz), 6.91-6.94 (2H, m), 7.14-7.40 (6H, m).

REFERENCE EXAMPLE 536

[Chemical formula 586]

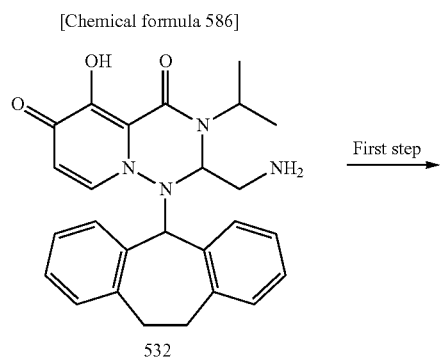

532

First step →

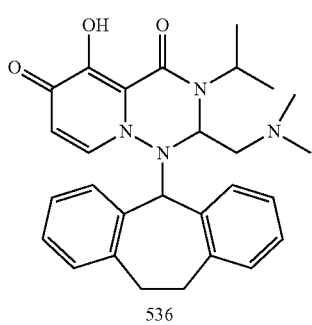

536

First Step

A dichloromethane (1 ml) solution of compound 532 (30 mg, 0.0675 mmol) and a 38% aqueous formalin solution (53.5 mg, 0.675 mmol) was cooled to 1 to 3° C., sodium triacetoxyhydroborate (42.9 mg, 0.293 mmol) and acetic acid (10 mg, 0.166 mmol) were added while the same temperature was retained. After the reaction solution was stirred at the same temperature for 30 minutes, saturated sodium bicarbonate water was added, and the mixture was extracted with ethyl acetate three times. The combined extracts were washed with water once, and dried with sodium sulfate, and the solvent was distilled off. The resulting crude product was washed with ethyl acetate-diisopropyl ether to obtain 20 mg of compound 536 as a solid.

$^1$H-NMR (CDCl$_3$) δ: 1.22 (3H, d, J=6.6 Hz), 1.44 (3H, d, J=6.9 Hz), 2.06 (6H, s), 2.29 (1H, dd, J=4.5 Hz, 13.2 Hz), 4.23 (1H, dd, J=8.4 Hz, 13.2 Hz), 2.78 (1H, ddd, J=4.5 Hz, 4.5 Hz, 14.1 Hz), 3.06 (1H, J=4.2 Hz, 13.5 Hz, 13.5 Hz), 3.55 (1H, ddd, J=4.2 Hz, 4.2 Hz, 17.7 Hz), 3.83-3.92 (1H, m), 4.34 (1H, dd, J=4.5 Hz, 8.4 Hz), 4.54 (1H, ddd, J=4.5 Hz, 13.8 Hz, 13.8 Hz), 4.91 (1H, s), 5.74 (1H, d, J=7.5 Hz), 6.63 (1H, d, J=7.8 Hz), 6.64 (1H, d, J=7.8 Hz), 6.88-6.93 (1H, m), 7.08-7.45 (6H, m).

REFERENCE EXAMPLE 537

[Chemical formula 587]

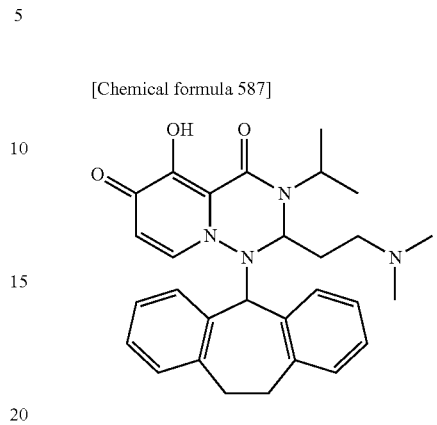

Compound 537 was synthesized by the same procedure as that of Reference example 536.

$^1$H-NMR (DMSO-d$_6$) δ: 1.25 (3H, d, J=6.6 Hz), 1.40 (3H, d, J=6.6 Hz), 1.46-1.57 (1H, m), 1.68-1.79 (1H, m), 1.98 (6H, s), 2.04-2.11 (1H, m), 2.27-2.41 (1H, m), 2.72-2.94 (2H, m), 3.55-3.64 (1H, m), 3.91-4.00 (1H, m), 4.29-4.44 (2H, m), 5.10 (1H, s), 5.48 (1H, d, J=7.8 Hz), 6.71 (1H, d, J=7.8 Hz), 6.86-6.90 (1H, m), 7.05-7.24 (4H, m), 7.33 (2H, d, J=4.2 Hz), 7.40 (1H, d, J=7.5 Hz).

REFERENCE EXAMPLE 538

[Chemical formula 588]

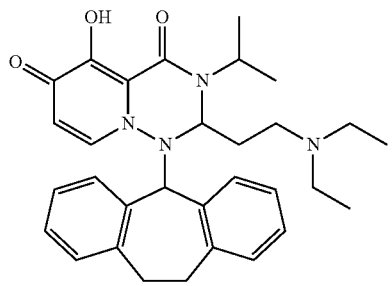

Compound 538 was synthesized by the same procedure as that of Reference example 536.

$^1$H-NMR (DMSO-d$_6$) δ: 0.75 (6H, t, J=6.6 Hz), 1.28 (3H, d, J=6.6 Hz), 1.41 (3H, d, J=6.6 Hz), 1.45-1.56 (1H, m), 1.67-1.78 (1H, m), 2.22-2.49 (4H, m), 2.74-2.97 (2H, m), 3.94-4.03 (1H, m), 4.29-4.41 (2H, m), 5.11 (1H, s), 5.48 (1H, d, J=7.8 Hz), 6.71 (1H, d, J=6.9 Hz), 6.87 (1H, t, J=7.2 Hz), 7.06-7.25 (4H, m), 7.33 (2H, d, J=7.2 Hz), 7.35 (1H, m).

REFERENCE EXAMPLE 539

[Chemical formula 589]

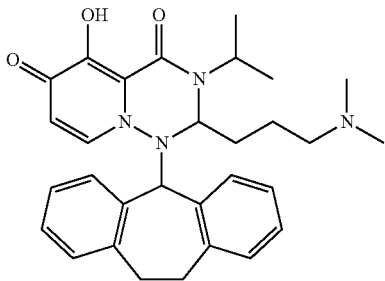

Compound 539 was synthesized by the same procedure as that of Reference example 536.

¹H-NMR (DMSO-d₆) δ: 1.25 (3H, d, J=6.6 Hz), 1.44 (3H, d, J=6.6 Hz), 1.42-1.51 (2H, m), 1.75-1.91 (2H, m), 2.62-2.67 (1H, m), 2.65 (6H, s), 2.74-2.97 (3H, m), 3.57-3.63 (1H, m), 3.91-3.26 (4H, m), 5.16 (1H, s), 5.73 (1H, d, J=7.5 Hz), 6.71 (1H, d, J=7.2 Hz), 6.89 (1H, t, J=6.9 Hz), 7.12-7.28 (4H, m), 7.33-7.45 (3H, m).

REFERENCE EXAMPLE 540

[Chemical formula 590]

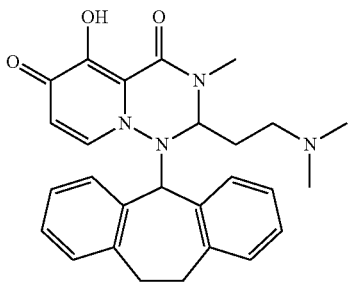

Compound 540 was synthesized by the same procedure as that of Reference example 536.

¹H-NMR (CDCl₃) δ: 1.58-1.78 (2H, m), 2.06 (6H, s), 2.15-2.35 (2H, m), 2.84-2.93 (1H, m), 2.96-3.11 (1H, m), 3.00 (3H, s), 3.65-3.74 (1H, m), 3.99-4.14 (1H, m), 4.28-4.33 (1H, m), 4.94 (1H, s), 5.78 (1H, d, J=7.5 Hz), 6.56 (1H, d, J=7.8 Hz), 8.66 (1H, d, J=7.2 Hz), 6.95 (t, J=7.2 Hz), 7.13-7.38 (6H, m).

REFERENCE EXAMPLE 541

[Chemical formula 591]

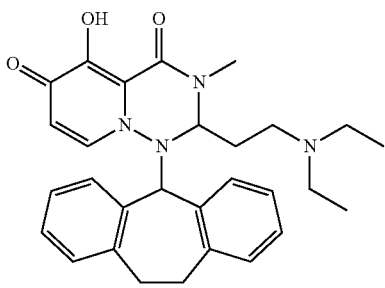

Compound 541 was synthesized by the same procedure as that of Reference example 536.

¹H-NMR (CDCl₃) δ: 0.846 (6H, t, J=7.2 Hz), 1.49-1.75 (2H, m), 2.30-2.41 (5H, m), 2.43-2.53 (1H, m), 2.85-2.93 (1H, m), 2.98-3.08 (1H, m), 3.01 (3H, s), 3.63-3.74 (1H, m), 3.97-4.07 (1H, m), 4.30 (1H, dd, J=5.1 Hz, 8.1 Hz), 4.95 (1H, s), 5.77 (1H, d, J=6.0 Hz), 6.56 (1H, d, J=7.8 Hz), 6.65 (1H, d, J=7.8 Hz), 6.95 (1H, t, J=6.3 Hz), 7.13-7.38 (6H, m).

REFERENCE EXAMPLE 542

[Chemical formula 592]

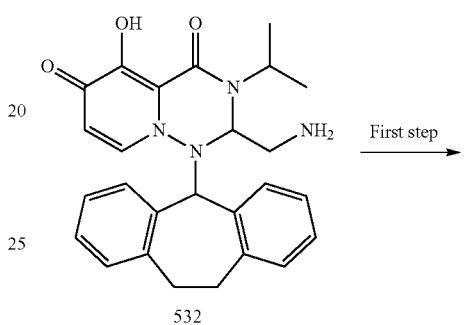

First Step

A dichloromethane (1 ml) solution of compound 532 (30 mg, 0.0675 mmol) and triethylamine (20.5 mg, 0.202 mmol) was cooled to 1 to 3° C., and acetic acid anhydride (10.3 mg, 0.101 mmol) was added while the same temperature was retained. After the reaction solution was stirred at the same temperature for 30 minutes, water was added, and the mixture was extracted with ethyl acetate three times. The combined extracts were washed with water once, and dried with sodium sulfate, and the solvent was distilled off. The resulting crude product was washed with ethyl acetate-diisopropyl ether to obtain 15 mg of compound 542 as a solid.

¹H-NMR (CDCl₃) δ: 1.30 (3H, d, J=6.9 Hz), 1.47 (3H, d, J=6.6 Hz), 2.00 (3H, s), 2.78-2.94 (2H, m), 3.04 (1H, ddd, J=4.2 Hz, 13.5 Hz, 13.5 Hz), 3.48-3.60 (1H, m), 3.98-3.07 (1H, m), 4.36 (1H, ddd, J=4.2 Hz, 13.5 Hz, 13.5 Hz), 4.64 (1H, dd, J=3.9 Hz, 9.3 Hz), 4.87 (1H, s), 5.43 (1H, d, J=7.5 Hz), 6.57 (1H, d, J=7.5 Hz), 6.68 (1H, d, J=7.5 Hz), 6.85 (1H, t, J=6.0 Hz), 7.09-7.36 (6H, m), 7.41 (1H, brs).

REFERENCE EXAMPLE 543

[Chemical formula 593]

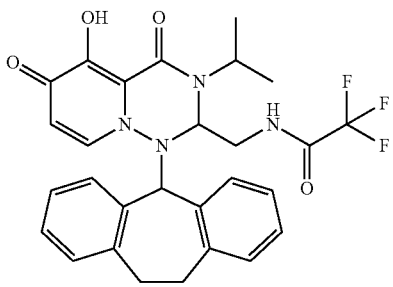

Compound 543 was synthesized by the same procedure as that of Reference example 542.

$^1$H-NMR (CDCl$_3$) δ: 1.32 (3H, d, J=6.9 Hz), 1.50 (3H, d, J=6.9 Hz), 2.79 (1H, ddd, J=4.2 Hz, 4.2 Hz, 14.4 Hz), 3.01 (1H, ddd, J=3.9 Hz, 13.5 Hz, 13.5 Hz), 3.18-3.28 (1H, m), 3.46-3.59 (2H, m), 4.04-4.18 (1H, m), 4.27 (1H, ddd, J=3.9 Hz, 13.5 Hz, 13.5 Hz), 4.69 (1H, dd, J=3.3 Hz, 9.9 Hz), 4.87 (0.9H, s), 5.17 (0.1H, s), 5.37 (0.9H, d, J=7.8 Hz), 4.50 (0.1H, d, J=7.8H), 6.32 (0.1H, d, J=7.8 Hz), 6.54 (1H, d, J=7.5 Hz), 6.78 (0.9H, d, J=7.5 Hz), 6.84 (1H, t, J=6.6 Hz), 6.91 (0.1H, d, J=6.0 Hz), 7.06-7.51 (6H, m), 9.29 (1H, brs).

REFERENCE EXAMPLE 544

[Chemical formula 594]

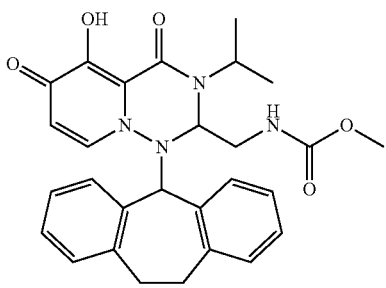

Compound 544 was synthesized by the same procedure as that of Reference example 542.

$^1$H-NMR (CDCl$_3$) δ: 1.29 (3H, d, J=6.9 Hz), 1.46 (3H, d, J=6.3 Hz), 2.78 (1H, ddd, J=4.5 Hz, 4.5 Hz, 15.9 Hz), 2.94-3.10 (2H, m), 3.19-3.54 (2H, m), 3.64 (3H, s), 3.96-3.11 (1H, m), 4.28 (1H, ddd, J=4.2 Hz, 13.5 Hz, 13.5 Hz), 4.57 (1H, dd, J=3.3 Hz, 9.9 Hz), 4.91 (1H, s), 5.57 (1H, brs), 5.70 (1H, d, J=7.5 Hz), 6.60 (1H, d, J=7.5 Hz), 6.66 (1H, d, J=7.8 Hz), 6.89 (1H, t, J=7.2 Hz), 7.08-7.47 (6H, m).

REFERENCE EXAMPLE 545

[Chemical formula 595]

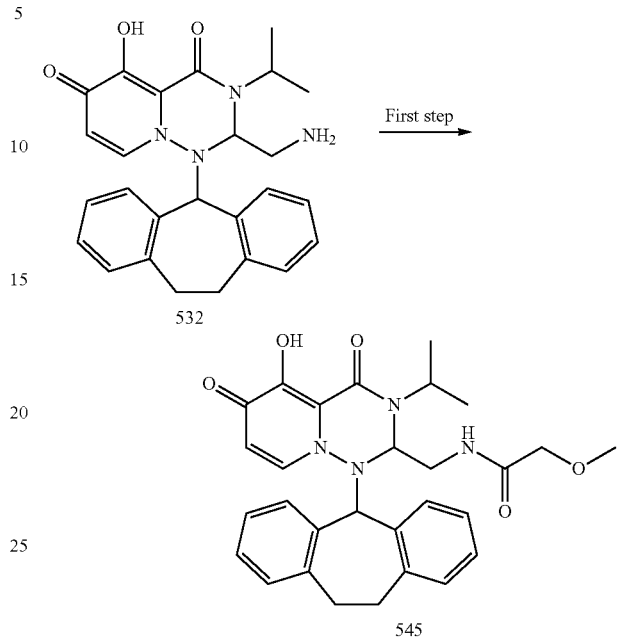

First Step

A dichloromethane (1 ml) solution of compound 532 (30 mg, 0.0675 mmol) and pyridine (16 mg, 0.203 mmol) was cooled to 1 to 3° C., and 2-methoxyacetyl chloride (11 mg, 0.101 mmol) was added while the same temperature was retained. After the reaction solution was stirred at the same temperature for 30 minutes, water was added, and the mixture was extracted with ethyl acetate three times. The combined extracts were washed with water once, and dried with sodium sulfate, and the solvent was distilled off. The resulting crude product was washed with ethyl acetate-diisopropyl ether to obtain 22 mg of compound 545 as a solid.

$^1$H-NMR (CDCl$_3$) δ: 1.31 (3H, d, J=6.9 Hz), 1.49 (3H, d, J=6.9 Hz), 2.77 (1H, ddd, J=4.8 Hz, 4.8 Hz, 14.1 Hz), 2.99-3.11 (2H, m), 3.47 (3H, s), 3.47-3.55 (1H, m), 3.64-3.72 (1H, m), 3.77-3.88 (2H, m), 4.02-4.11 (1H, m), 4.23 (1H, ddd, J=4.2 Hz, 13.8 Hz, 13.8 Hz), 4.47 (1H, dd, J=3.3 Hz, 9.9 Hz), 4.94 (1H, s), 5.75 (1H, d, J=7.8 Hz), 6.64 (1H, d, J=9.0 Hz), 6.67 (1H, 7.8 Hz), 6.80 (1H, brt), 6.91 (1H, t, J=7.5 Hz), 7.08-7.23 (5H, m), 7.29-7.36 (1H, m).

REFERENCE EXAMPLE 546

[Chemical formula 596]

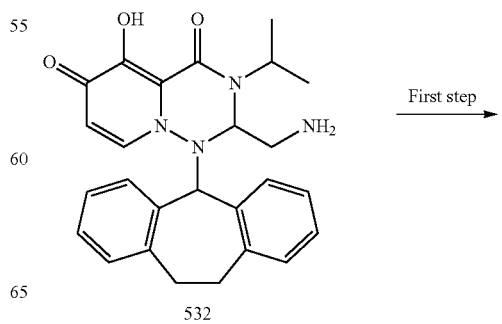

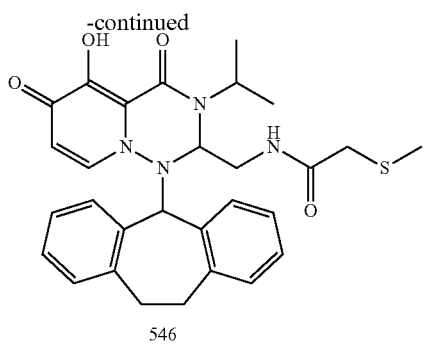

546

First Step

To a dimethylformamide (1 ml) solution of 2-(methylthio) acetic acid (15.7 mg, 0.148 mmol) were added EDCI (28.5 mg, 0.148 mmol) and 1-hydroxy benzotriazole (11.4 mg, 0.0742 mmol) at room temperature, the mixture was stirred at the same temperature for 5 minutes, and compound 532 was added. The reaction solution was stirred at room temperature for 1 hour, and diluted with methanol (3 ml). The solution was cooled to 1 to 3° C., a 2N aqueous sodium hydroxide solution (1 ml) was added, the mixture was stirred at the same temperature for 30 minutes, and the mixture was neutralized with 2N hydrochloric acid (1 ml). The reaction solution was extracted with ethyl acetate three times, the combined extracts were washed with water once, and dried with sodium sulfate, and the solvent was distilled off. The resulting crude product was washed with ethyl acetate-diisopropyl ether to obtain 15 mg of compound 546 as a solid.

$^1$H-NMR (CDCl$_3$) δ: 1.32 (3H, d, J=6.9 Hz), 1.50 (3H, J=6.6 Hz), 2.11 (3, s), 2.79 (1H, ddd, J=4.2 Hz, 4.2 Hz, 14.1 Hz), 2.99-3.16 (4H, m), 3.50 (1H, ddd, J=4.5 Hz, 4.5 Hz, 12.9 Hz), 3.68 (1H, d, J=10.2 Hz), 3.97-4.11 (1H, m), 4.26 (1H, ddd, J=4.5 Hz, 13.8 Hz, 13.8 Hz), 4.94 (3H, s), 5.69 (1H, d, J=7.5 Hz), 6.63 (1H, d, J=7.5 Hz), 6.70 (1H, d, J=7.8 Hz), 6.90 (1H, t, J=6.0 Hz), 7.09 (1H, d, J=7.5 Hz), 7.20-7.25 (3H, m), 7.29-7.36 (1H, m), 7.36-7.49 (1H, m).

REFERENCE EXAMPLE 547

[Chemical formula 597]

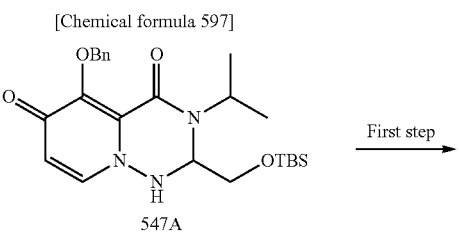

First Step

To an acetic acid (3 ml) solution of compound 547A (367 mg, 0.812 mmol) synthesized by the same procedure as that of Reference example 516 and dibenzosuberol (205 mg, 0.974 mmol) was added dropwise sulfuric acid (0.6 ml) at room temperature, and the mixture was stirred at the same temperature for 30 minutes. The reaction solution was diluted with water, and the mixture was extracted with ethyl acetate three times. The extract was washed with water once, and dried with sodium sulfate, and the solvent was distilled off. The resulting crude product was dissolved in methanol (3 ml), a 2N aqueous sodium hydroxide solution (1 ml) was added at room temperature, and the mixture was stirred for 30 minutes. The reaction solution was neutralized with 2N aqueous hydrochloric acid solution (1 ml), and extracted with ethyl acetate three times. The combined extracts were dried with sodium sulfate, and the solvent was distilled off. The resulting crude product was washed with ethyl acetate-diisopropyl ether to obtain 75 mg of compound 547 as a solid.

$^1$H-NMR (CDCl$_3$) δ: 1.22 (3H, d, J=6.9 Hz), 1.45 (3H, d, J=6.3 Hz), 2.80 (1H, ddd, J=4.5 Hz, 4.5 Hz, 14.1 Hz), 2.99-3.11 (1H, m), 3.53 (1H, ddd, J=3.9 Hz, 3.9 Hz, 17.7 Hz), 3.64 (1H, dd, J=6.9 Hz), 12.3 Hz), 3.82 (1H, dd, J=3.3 Hz, 12.3 Hz), 3.86-3.97 (1H, m), 4.34-4.44 (2H, m), 4.88 (1H, s), 5.35 (1H, d, J=7.5 Hz), 6.52-6.58 (2H, m), 6.82 (1H, dt, J=1.8 Hz, 7.2 Hz), 7.06-7.35 (6H, m).

REFERENCE EXAMPLE 548

[Chemical formula 598]

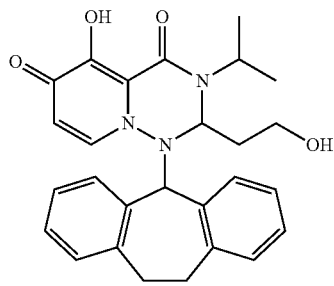

Compound 548 was synthesized by the same procedure as that of Reference example 547.

$^1$H-NMR (CDCl$_3$) δ: 1.29 (3H, d, J=6.6 Hz), 1.50 (3H, d, J=6.6 Hz), 1.70-1.81 (1H, m), 1.88-2.00 (1H, m), 2.85 (1H, ddd, J=4.5 Hz, 4.5 Hz, 14.1 Hz), 2.99-3.11 (1H, m), 3.48-3.57 (1H, m), 3.68-3.73 (2H, m), 3.83-3.92 (1H, m), 4.30 (1H, ddd, J=4.2 Hz, 13.8 Hz, 13.8 Hz), 4.54 (1H, dd, J=3.6 Hz, 11.1 Hz), 4.67 (1H, s), 5.69 (1H, d, J=7.8 Hz), 6.62 (1H, d, J=7.5 Hz), 6.64 (1H, d, J=5.7 Hz), 6.90 (1H, t, J=6.9 Hz), 7.07-7.36 (6H, m).

REFERENCE EXAMPLE 549

[Chemical formula 599]

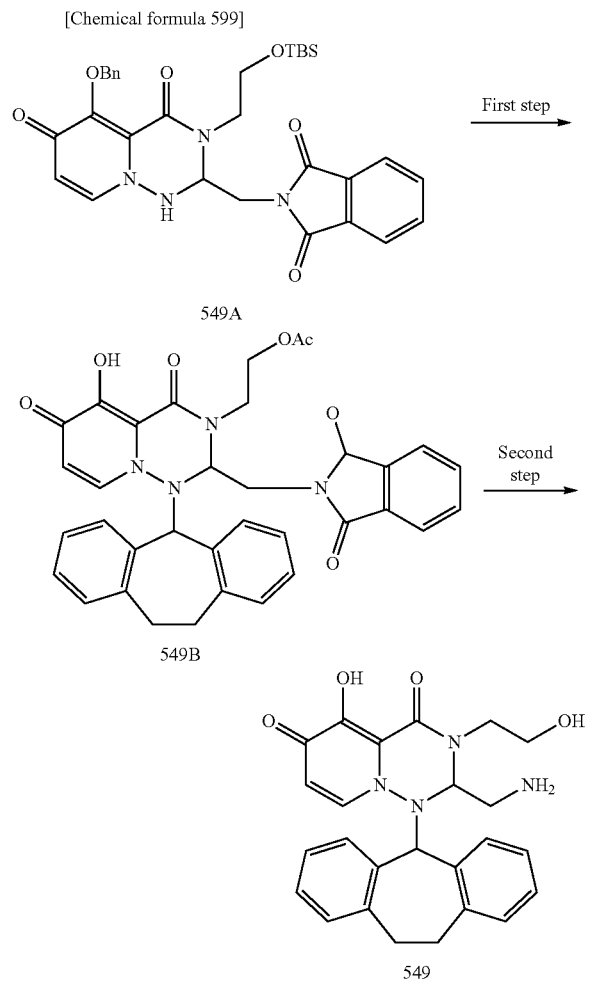

First Step

To an acetic acid (3 ml) solution of compound 549A (997 mg, 1.69 mmol) synthesized by the same procedure as that of Reference example 516 and dibenzosuberol (1.07 g, 5.08 mmol) was added dropwise sulfuric acid (0.6 ml) at room temperature, and the mixture was stirred at the same temperature for 30 minutes. The reaction solution was diluted with water, and the mixture was extracted with ethyl acetate three times. The extract was washed with water once, and dried with sodium sulfate, and the solvent was distilled off. The resulting crude product was washed with ethyl acetate-diisopropyl ether to obtain 513 mg of compound 549B.

$^1$H-NMR (CDCl$_3$) δ: 2.09 (3H, s), 2.71 (1H, ddd, J=3.6 Hz, 13.5 Hz, 13.5 Hz), 3.18-3.27 (1H, m), 3.42-3.56 (2H, m), 3.80 (1H, dd, J=2.7 Hz, 14.1 Hz), 4.03 (1H, dd, J=10.2 Hz, 14.1 Hz), 4.15 (1H, ddd, J=4.2 Hz, 4.2 Hz, 9.3 Hz), 4.32-4.40 (1H, m), 4.49-4.53 (2H, m), 4.94 (1H, s), 5/83 (1H, d, J=7.8 Hz), 6.63 (1H, d, J=7.5 Hz), 6.69 (1H, d, J=7.8 Hz), 6.76 (1H, d, J=6.6 Hz), 6.91 (1H, t, J=7.5 Hz), 7.00 (1H, d, J=8.1 Hz), 7.12-7.17 (2H, m), 7.20-7.32 (2H, m), 7.82-7.89 (4H, m).

Second Step

To a methanol (5 ml) solution of compound 549B (513 mg, 0.829 mmol) was added hydrazine hydrate (124.5 mg, 2.49 mmol), and the mixture was refluxed for 2 hours. After cooled to room temperature, to the reaction solution were added 2N hydrochloric acid (30 ml) and ethyl acetate (30 ml). After the layers were separated, the organic layer was extracted with 2N hydrochloric acid two times. The combined aqueous layers were neutralized with sodium bicarbonate water, and extracted with chloroform-methanol three times. The combined organic layers were dried with sodium sulfate, and the solvent was distilled off. The resulting crude product was washed with ethyl acetate-diisopropyl ether to obtain 135 mg of compound 549.

$^1$H-NMR (DMSO-d$_6$) δ: 2.40-2.50 (1H, m), 2.72-2.80 (1H, m), 2.83-2.98 (2H, m), 3.03-3.66 (4H, m), 3.79-3.87 (1H, m), 4.11 (1H, 4.2 Hz), 4.32-4.44 (1H, m), 5.12 (1H, s), 5.51 (1H, 7.5 Hz), 6.69 (d, J=7.5 Hz), 6.84-6.90 (1H, m), 7.07-7.24 (4H, m), 7.30-7.34 (2H, m), 7.39-7.42 (1H, m).

REFERENCE EXAMPLE 550

[Chemical formula 600]

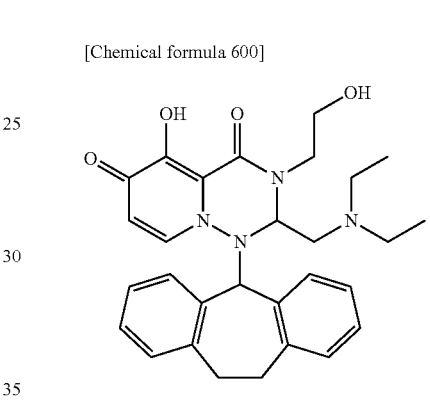

According to Reference example 536, compound 550 was synthesized from compound 549 by the same procedure.

$^1$H-NMR (DMSO-d$_6$) δ: 0.77 (6H, t, 6.9 Hz), 1.99-2.36 (3H, m), 2.38-2.56 (1H, m), 2.64 (1H, dd, J=3.9 Hz, 14.1 Hz), 2.75 z81H, ddd, J=4.5 Hz, 4.5 Hz, 14.4 Hz), 2.89-3.00 (1H, m), 3.09-3.68 (4H, m), 3.74-3.82 (1H, m), 4.09 (1H, brs), 4.17 (1H, dd, J=3.6 Hz, 8.4 Hz), 5.03 (1H, brs), 5.17 (1H, s), 5.53 (1H, d, J=7.5 Hz), 6.73 (1H, d, J=7.5 Hz), 6.84 (1H, d, J=7.8 Hz), 6.91 (1H, t, J=7.2 Hz), 7.12-7.26 (4H, m), 7.31-7.44 (4H, m), 7.45 (1H, d, J=7.2 Hz).

REFERENCE EXAMPLE 551

[Chemical formula 601]

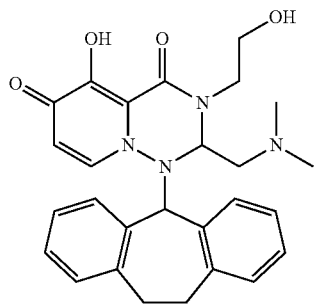

According to Reference example 536, compound 551 was synthesized from compound 549 by the same procedure.

$^1$H-NMR (DMSO-d$_6$) δ: 1.99 (6H, s), 2.27 (1H, brs), 2.51-2.27 (3H, m), 3.56-3.70 (4H, m), 4.03 (2H, brs), 4.36 (1H, brs), 4.94 (2H, brs), 5.29 (1H, brs), 6.54-6.83 (3H, m), 7.11-7.33 (6H, m).

REFERENCE EXAMPLE 552

[Chemical formula 602]

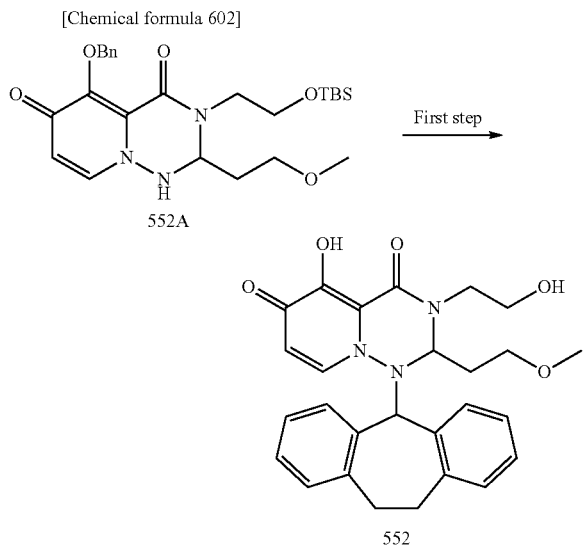

First Step

To an acetic acid (2 ml) solution of compound 552A (137 mg, 0.367 mmol) synthesized by the same procedure as that of Reference example 516 and dibenzosuberol (386 mg, 1.83 mmol) was added dropwise sulfuric acid (0.4 ml) at room temperature, and the mixture was stirred at the same temperature for 30 minutes. The reaction solution was diluted with water, and the mixture was extracted with ethyl acetate three times. The extract was washed with water once, and dried with sodium sulfate, and the solvent was distilled off. The resulting crude product was dissolved in methanol (5 ml), a 2N aqueous sodium hydroxide solution (2 ml) was added at room temperature, and the mixture was stirred for 30 minutes. The reaction solution was neutralized with 2N aqueous hydrochloric acid solution (2 ml), and extracted with ethyl acetate two times. The combined extracts were dried with sodium sulfate, and the solvent was distilled off. The resulting crude product was washed with ethyl acetate to obtain 62 mg of compound 552.

$^1$H-NMR (CDCl$_3$) δ: 1.71-1.82 (1H, m), 2.09-2.21 (1H, m), 2.82-2.90 (1H, m), 3.06 (1H, ddd, J=4.2 Hz, 13.2 Hz, 13.2 Hz), 3.19 (3H, s), 3.22-3.43 (3H, m), 3.60 (1H, ddd, J=10.5 Hz, 10.5 Hz, 17.4 Hz), 3.79-3.96 (3H, m), 4.12-4.21 (1H, m), 4.46 (1H, dd, J=3.3 Hz, 10.2 Hz), 4.98 (1H, s), 5.89 (1H, d, J=7.5 Hz), 6.62 (1H, d, J=6.9 Hz), 6.64 (1H, d, J=7.5 Hz), 6.88-6.93 (1H, m), 7.11-7.37 (6H, m).

REFERENCE EXAMPLE 553

[Chemical formula 603]

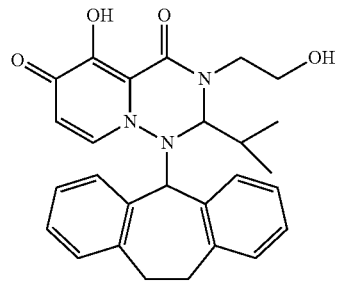

Compound 553 was synthesized by the same procedure as that of Reference example 552.

$^1$H-NMR (CDCl$_3$) δ: 0.80 (3H, d, J=6.6 Hz), 0.94 (3H, d, J=6.9 Hz), 1.94-2.00 (1H, m), 2.82-2.90 (1H, m), 3.00-3.11 (1H, m), 5.31-3.59 (2H, m), 3.64-3.74 (1H, m), 3.94-4.04 (3H, m), 4.25-4.36 (1H, m), 5.04 (1H, s), 5.87 (1H, d, J=7.2 Hz), 6.65 (1H, d, J=7.2 Hz), 7.12 (1H, d, J=7.5 Hz), 6.92 (1H, t, J=8.1 Hz), 7.10 (1H, d, J=7.2 Hz), 7.15-7.38 (5H, m).

REFERENCE EXAMPLE 554

[Chemical formula 604]

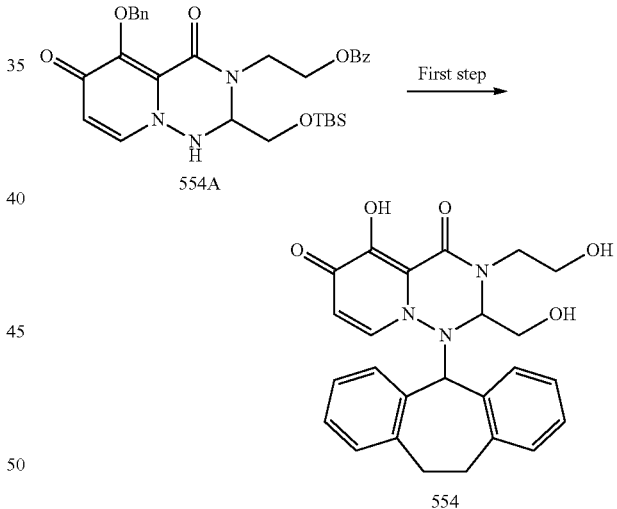

First Step

To an acetic acid (2 ml) solution of compound 554A (100 mg, 0.177 mmol) synthesized by the same procedure as that of Reference example 516 and dibenzosuberol (186 mg, 0.885 mmol) was added dropwise sulfuric acid (0.4 ml) at room temperature, and the mixture was stirred at the same temperature for 30 minutes. The reaction solution was diluted with water, and the mixture was extracted with ethyl acetate three times. The extract was washed with water once, and dried with sodium sulfate, and the solvent was distilled off. The resulting crude product was dissolved in methanol (5 ml), a 2N aqueous sodium hydroxide solution (2 ml) was added at room temperature, and the mixture was stirred for 30 minutes. The reaction solution was neutralized with an aqueous citric acid solution, and extracted with ethyl acetate two times. The combined extracts were washed with sodium bicarbonate water, and dried with sodium sulfate, and the solvent was distilled off. The resulting crude product was washed with ethyl acetate to obtain 24 mg of compound 554.

¹H-NMR (CDCl₃) δ: 2.81-2.91 (2H, m), 2.98-3.09 (1H, m), 3.60-3.75 (2H, m), 3.91-4.04 (2H, m), 4.08-4.17 (2H, m), 4.22-4.33 (2H, m), 4.80 (1H, s), 5.69 (1H, d, J=7.8 Hz), 6.48 (1H, d, J=7.5 Hz), 6.59 (1H, d, J=7.5 Hz), 6.80-6.85 (1H, m), 7.13-7.35 (6H, m).

REFERENCE EXAMPLE 555

[Chemical formula 605]

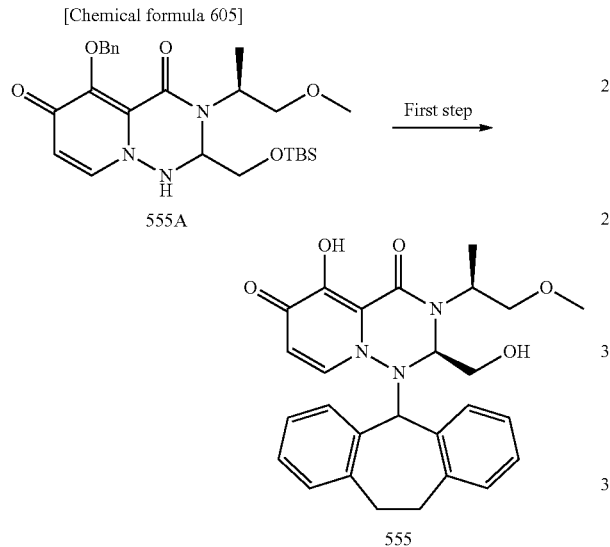

To an acetic acid (4 ml) solution of compound 555A (380 mg, 1.11 mmol) synthesized according to Reference example 516 and dibenzosuberol (1.16 g, 5.52 mmol) was added dropwise sulfuric acid (0.8 ml) at room temperature, and the mixture was stirred at the same temperature for 30 minutes. The reaction solution was diluted with water, and the mixture was extracted with ethyl acetate three times. The extract was washed with water once, and dried with sodium sulfate, and the solvent was distilled off. The resulting crude product was dissolved in methanol (5 ml), a 2N aqueous sodium hydroxide solution (2 ml) was added at room temperature, and the mixture was stirred for 30 minutes. The reaction solution was neutralized with an aqueous citric acid solution, and extracted with ethyl acetate three times. The combined extracts were dried with sodium sulfate, and the solvent was distilled off. To the resulting crude product were added ethyl acetate-diisopropyl ether, and the precipitated residue was filtered to obtain 22 mg of compound 555.

¹H-NMR (CDCl₃) δ: 1.62 (3H, d, J=6.9 Hz), 2.81 (1H, ddd, J=4.2 Hz, 4.2 Hz, 14.4 Hz), 3.09 (1H, ddd, J=4.5 Hz, 13.8 Hz, 13.8 Hz), 3.37 (3H, s), 3.37-3.53 (2H, m), 3.70 (1H, d, J=5.4 Hz), 4.23-4.30 (2H, m), 4.33-4.44 (1H, m), 4.94 (1H, s), 5.70 (1H, d, J=7.8 Hz), 6.59 (1H, d, J=7.5 Hz), 6.64 (1H, d, J=7.8 Hz), 6.88-6.92 (1H, m), 7.08-7.37 (6H, m).

REFERENCE EXAMPLE 556

[Chemical formula 606]

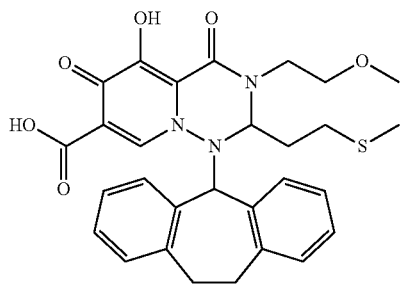

According to Reference example 65 and Reference example 516, compound 556 was synthesized by the same procedure.

¹H-NMR (CDCl₃) δ: 1.66-1.78 (2H, m), 1.97 (3H, s), 2.19-2.31 (1H, m), 2.35-2.44 (1H, m), 2.49-2.57 (1H, m), 2.85-2.93 (1H, m), 3.06 (1H, J=3.9 Hz, 12.9 Hz, 12.9 Hz), 3.27-3.39 (2H, m), 3.34 (3H, s), 3.58-3.73 (3H, m), 3.96-4.04 (1H, m), 4.08-4.18 (1H, m), 4.60 (1H, dd, J=3.0 Hz, 11.1 Hz), 4.96 (1H, s), 6.52 (1H, d, J=7.5 Hz), 6.87-6.92 (1H, m), 7.18-7.28 (4H, m), 7.31-7.40 (2H, m), 7.65 (1H, s), 12.04 (1H, s), 14.33 (1H, s).

REFERENCE EXAMPLE 557

[Chemical formula 607]

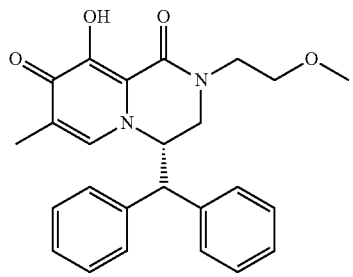

Compound 557 was synthesized by the same procedure as that of Reference example 149.
MS: m/z=419 [M+H]⁺.

REFERENCE EXAMPLE 558

[Chemical formula 608]

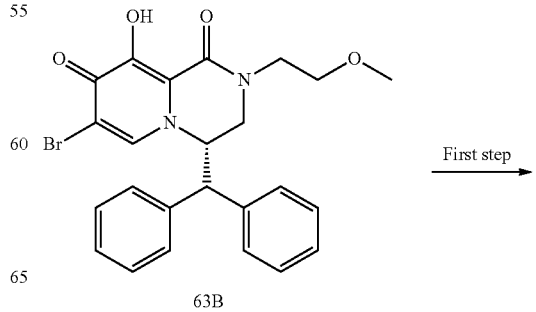

-continued

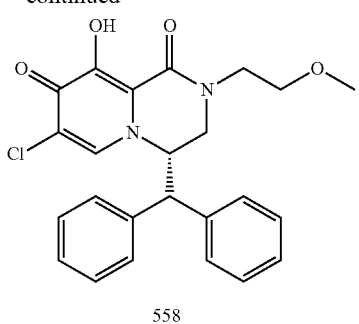

558

To a DMSO (2 mL) solution of compound 63B (68.8 mg, 0.120 mmol) was added copper chloride (39.2 mg, 0.396 mmol), and the mixture was stirred at 110° C. for 2 hours and, further, at 120° C. for 1 hour. Thereafter, copper chloride (50.0 mg, 0.505 mmol) was added, and the mixture was stirred at 200° C. for 1 hour. The reaction solution was purified using an LCMS fractionating device, the eluted solvent was distilled off, to the concentrated residue was added diethyl ether, and the precipitated white solid was filtered. Washing with diethyl ether, and drying afforded 20.9 mg of compound 558.

MS: m/z=439 [M+H]$^+$.

REFERENCE EXAMPLE 559

[Chemical formula 609]

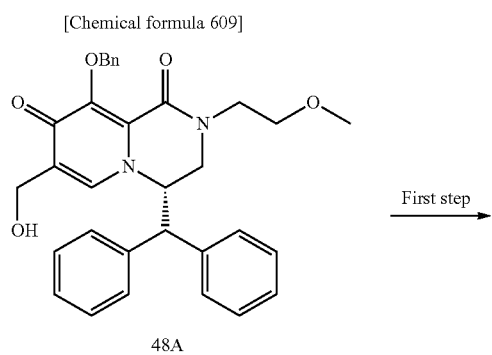

48A

First step

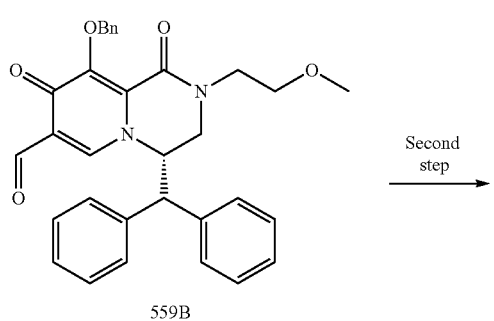

559B

Second step

-continued

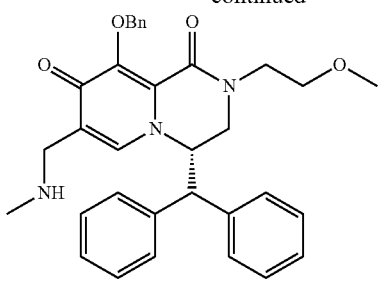

559C

Third step

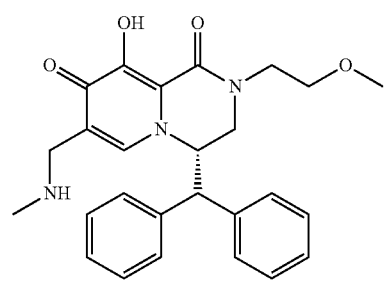

559

First Step

Compound 48A (43 mg, 0.083 mmol) was dissolved in dichloromethane (6.0 mL), manganese dioxide (120 mg, 1.38 mmol) was added, and the mixture was stirred at room temperature for 3 hours. After the reaction solution was filtered with celite, the filtrate was concentrated to obtain 22.3 mg of compound 559B as a pale yellow solid.

$^1$HNMR (CDCl$_3$) δ: 3.17 (3H, s), 3.41-3.55 (4H, m), 3.95-4.07 (2H, m), 4.28 (1H, d, J=16.1 Hz), 4.53 (1H, d, J=11.8 Hz), 5.49 (2H, d, J=2.0 Hz), 6.97-7.66 (16H, m), 10.07 (1H, s).

Second Step

Compound 559B (22 mg, 0.043 mmol) was dissolved in THF (6.0 mL), a 40% methanamine methanol solution (6.5 ul, 0.064 mmol) and acetic acid (3.7 ul, 0.064 mmol) were added, and the mixture was stirred at room temperature for 5 minutes. The reaction solution was ice-cooled, NaBH(OAc)$_3$ (14 mg, 0.064 mmol) was added, and the mixture was stirred at room temperature overnight. To the reaction solution were added water and chloroform, and the chloroform layer was separated. The aqueous layer was extracted with chloroform, and sodium sulfate was added to the combined extracts to dry them. The solvent was distilled off to obtain 24 mg of compound 559C as a pale yellow solid.

MS: m/z=538 [M+H]$^+$.

Third Step

Compound 559 was synthesized by the same procedure as that of Reference example 1.

MS: m/z=448 [M+H]$^+$.

REFERENCE EXAMPLE 560
[Chemical formula 610]
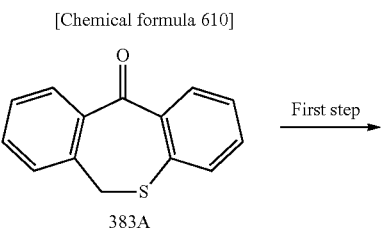
383A
First step →
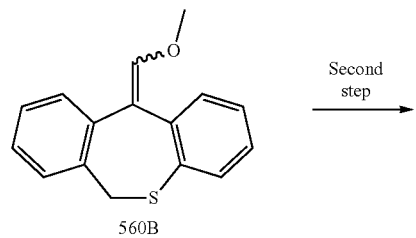
560B
Second step →
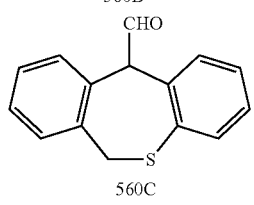
560C
Third step →
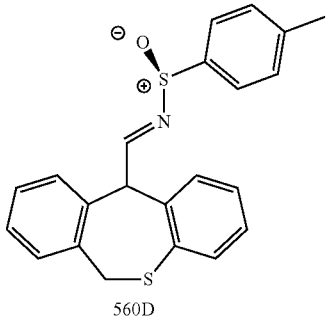
560D
Fourth step →
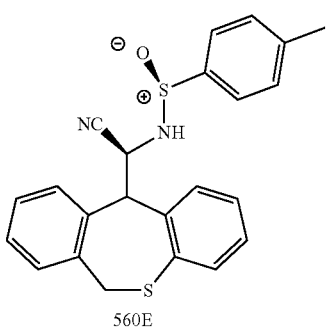
560E
Fifth step →
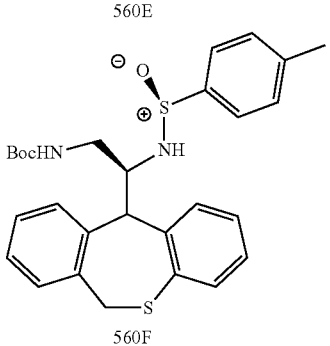
560F
Sixth step →
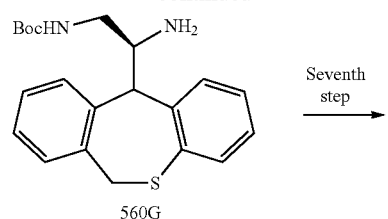
560G
Seventh step →
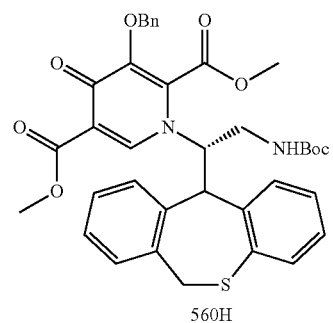
560H
Eighth step →
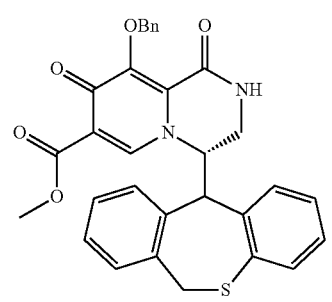
560I
Ninth step →
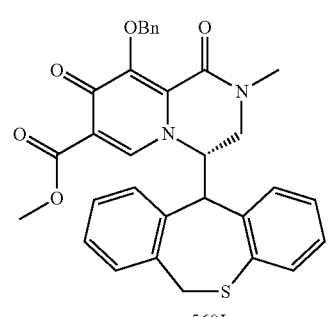
560J
Tenth step →
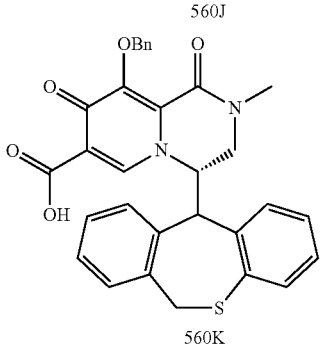
560K
Eleventh step →

-continued

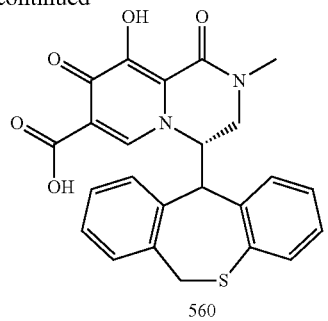

560

First Step

A dioxane (20 mL) mixed solution of (methoxymethyl) triphenylphosphonium chloride (6.73 g, 19.0 mmol) was cooled to 0° C., and a 1.06M NaHMDS toluene solution (18.0 ml, 19.0 mmol) was added dropwise while the same temperature was retained. After the reaction solution was stirred at the same temperature for 30 minutes, compound 383A was added, and the mixture was refluxed for 1 hour and 30 minutes. The reaction solution was returned to room temperature, and water and ethyl acetate were added. The ethyl acetate layer was separated, and the aqueous layer was extracted with ethyl acetate. To the combined extracts was added sodium sulfate to dry them. The solvent was distilled off, and the resulting oil was purified by silica gel column chromatography, and eluted with n-hexane-ethyl acetate (95:5, v/v). Concentration of an objective fraction afforded 2.22 g of compound 560B as an oil.

$^1$H-NMR (CDCl$_3$) δ: 3.68 (3H, s), 3.73 (3H, s), 4.20 (4H, brs), 6.17 (1H, s), 6.39 (1H, s), 6.96-7.07 (6H, m), 7.18-7.32 (9H, m), 7.32-7.46 (1H, m).

Second Step

Compound 560B (1.98 g, 7.78 mmol) was dissolved in dichloromethane (30 mL), a 70% aqueous perchloric acid solution (8.0 ml, 93 mmol) was added, and the mixture was stirred at room temperature overnight. To the reaction solution was added an aqueous saturated sodium carbonate solution, and the dichloromethane layer was separated. The aqueous layer was extracted with dichloromethane, and magnesium sulfate was added to the combined extracts to dry them. The solvent was distilled off, and the resulting oil was purified by silica gel column chromatography, and eluted with n-hexane-ethyl acetate (90:10, v/v). Concentration of an objective fraction afforded 1.80 g of compound 560C as an oil.

$^1$H-NMR (CDCl$_3$) δ: 3.93 (1H, d, J=16.1 Hz), 4.06 (1H, d, J=16.1 Hz), 4.53 (1H, s), 7.11-7.50 (8H, m), 9.89 (1H, s).

MS: m/z=241 [M+H]$^+$.

Third Step

To a dichloromethane (30 mL) solution of compound 560C (2.87 g, 11.9 mmol) were added tetraisopropoxytitanium (17.5 mL, 59.7 mmol) and (S)-4-methylbenzenesulfinamide (2.27 g, 14.3 mmol) at room temperature, then the mixture was refluxed for 3 hours and 30 minutes. The reaction solution was ice-cooled, ice water (30 ml) was added, the mixture was stirred for 1 hour while temperature was retained at the same temperature, and the precipitated solid was filtered using celite. The resulting filtrate was extracted with dichloromethane, and magnesium sulfate was added to the combined extracts to dry them. The solvent was distilled off, and the resulting oil was purified by silica gel column chromatography, and eluted with n-hexane-ethyl acetate (70:30, v/v). Concentration of an objective fraction afforded 3.16 g of compound 560D as a yellow solid.

$^1$H-NMR (CDCl$_3$) δ: 2.39 (6H, s), 3.60 (1H, d, J=15.2 Hz), 3.68 (1H, d, J=14.9 Hz), 3.97 (1H, d, J=15.0 Hz), 4.07 (1H, d, J=15.0 Hz), 4.90 (1H, d, J=2.7 Hz), 4.92 (1H, d, J=2.9 Hz), 7.08-7.26 (20H, m), 7.46-7.51 (4H, m), 8.62 (1H, d, J=2.8 Hz), 8.65 (1H, d, J=2.7 Hz).

MS: m/z=378 [M+H]$^+$.

Fourth Step

A THF (30 mL) suspension of a 1M cyanodiethylaluminum toluene solution (16.7 mL, 16.7 mmol) was cooled to 0° C., 2-propanol (1.29 mL, 16.7 mmol) was added and, thereafter, the mixture was stirred for 1 hour while temperature was retained at the same temperature. Thereafter, the reaction solution was cooled to −60° C., a THF (12 mL) solution of compound 560D (3.16 g, 8.37 mmol) was added dropwise, the mixture was stirred for 15 minutes while temperature was retained at the same temperature, thereafter, temperature was raised to room temperature, and the mixture was stirred overnight. The reaction solution was ice-cooled, an aqueous saturated ammonium chloride solution was added, the mixture was stirred at room temperature for 1 hour and 30 minutes and, thereafter, the precipitated solid was filtered using celite, and washed with dichloromethane. The dichloromethane layer of the filtrate was separated, and the aqueous layer was extracted with dichloromethane and, thereafter, sodium sulfate was added to the combined extracts to dry them. The solvent was distilled off, and the resulting oil was purified by silica gel column chromatography, and eluted with chloroform-methanol (97:3, v/v). Concentration of an objective fraction afforded 1.88 g of compound 560E as a white solid.

MS: m/z=427 [M+Na]$^+$.

Fifth Step

A methanol (4 mL) solution of compound 560E (235 mg, 0.581 mmol) was cooled to 0° C., cobalt(II) chloride hexahydrate (55.3 mg, 0.232 mmol) was added, and the mixture was stirred at room temperature for 30 minutes. Thereafter, the reaction solution was ice-cooled, a DMF (4 mL) solution of sodium borohydride (88 mg, 2.3 mmol) was added dropwise, and the mixture was stirred at the same temperature for 5 minutes, and at room temperature for 1 hour. Then, Boc$_2$O (0.674 mL, 2.90 mmol) was added, and the mixture was stirred for 30 minutes. To the reaction solution was added water, the mixture was extracted with ethyl acetate, and sodium sulfate was added to the combined extracts to dry them. The solvent was distilled off, and the resulting oil was subjected to silica gel column chromatography, and eluted with chloroform-methanol (98:2, v/v). Concentration of an objective fraction afforded a crude product (211 mg) of compound 560F.

MS: m/z=509 [M+Na]$^+$.

Sixth Step

To a methanol (6 mL) solution of the crude product (211 mg) of compound 560F was added TFA (0.128 mL, 1.66 mmol), and the mixture was stirred at room temperature for 2.5 hours. To the reaction solution was added triethylamine (0.230 mL, 1.66 mmol), the solvent was distilled off, and the resulting crude product of compound 560G was used in a next reaction without purification.

MS: m/z=371 [M+H]$^+$.

Seventh Step

To a toluene (4 mL) solution of the crude product of compound 560G was added dimethyl 3-(benzyloxy)-4-oxo-4H-pyran-2,5-dicarboxylate (132 mg, 0.416 mmol), and the mixture was refluxed for 1 hour and 30 minutes. The reaction solution was subjected to silica gel column chromatography, and eluted with chloroform-methanol (100:0→90:10, v/v). Concentration of an objective fraction afforded a crude product (287 mg) of compound 560H.

MS: m/z=671 [M+H]$^+$.

Eighth Step

To the crude product of compound 560H obtained in the seventh step was added a 4N hydrochloric acid ethyl acetate solution (3 mL), and the mixture was stirred at room temperature for 30 minutes. The solvent was distilled off, to the resulting concentrated residue were added THF (2 mL) and an aqueous saturated sodium bicarbonate solution (2 mL), and the mixture was stirred at room temperature for 45 minutes. To the reaction solution was added water, the mixture was extracted with chloroform, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded 27 mg of compound 560I as a yellow solid.

MS: m/z=539 [M+H]$^+$.

Ninth Step

Compound 560I (27 mg, 0.050 mmol) was dissolved in DMF (2 mL), cesium carbonate (82 mg, 0.25 mmol) and methyl iodide (0.010 mL, 0.16 mmol) were added, and the mixture was stirred at room temperature for 1 hour and 30 minutes. To the reaction solution was added water, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded a crude product of compound 560J.

MS: m/z=553 [M+H]$^+$.

Tenth Step

To an EtOH (2 mL) solution of the crude product of compound 560J obtained in the ninth step was added 2N NaOH (1 mL), and the mixture was stirred at room temperature for 40 minutes. To the reaction solution was added a 2N aqueous HCl solution, the mixture was extracted with ethyl acetate, and sodium sulfate was added to the combined extracts to dry them. The solvent was distilled off to obtain 17 mg of compound 560K as a white oil.

MS: m/z=539 [M+H]$^+$.

Eleventh Step

To compound 560K (17 mg, 0.032 mmol) was added TFA (2.0 mL), and the mixture was stirred at room temperature for 35 minutes. The reaction solution was subjected to toluene azeotropy, to the resulting concentrated residue was added isopropyl ether, and the precipitated solid was filtered and washed to obtain 7.1 mg of compound 560 as a pink solid.

MS: m/z=449 [M+H]$^+$.

REFERENCE EXAMPLE 561

[Chemical formula 611]

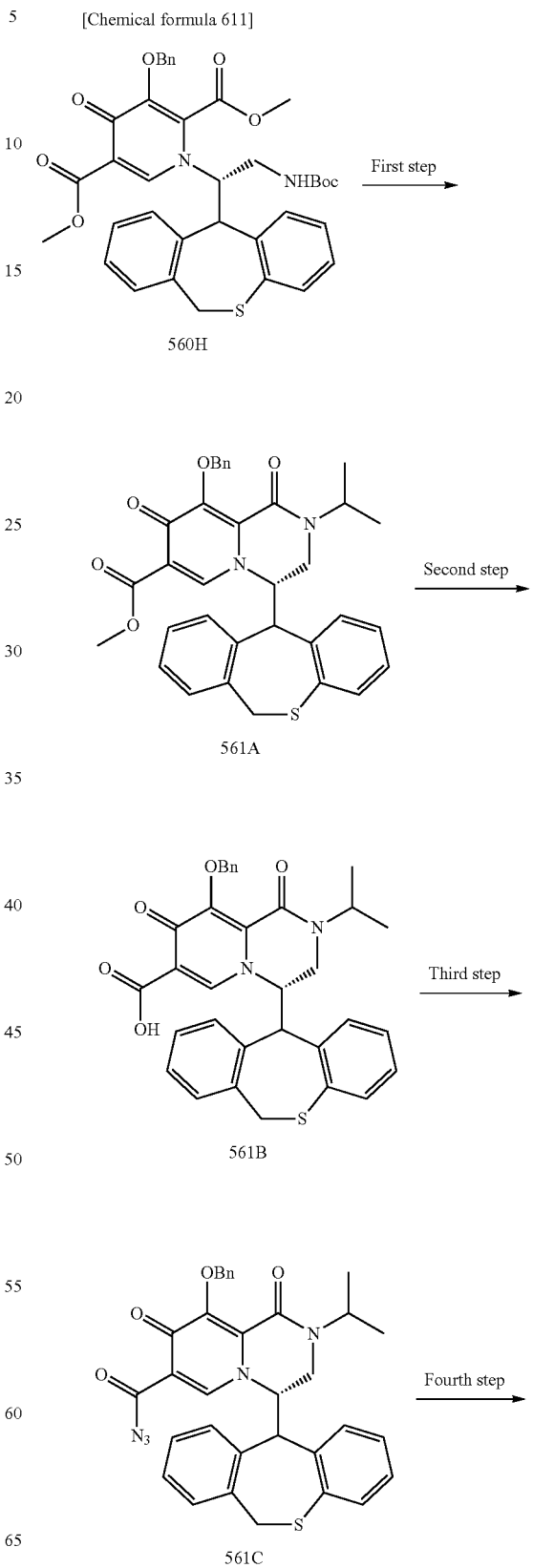

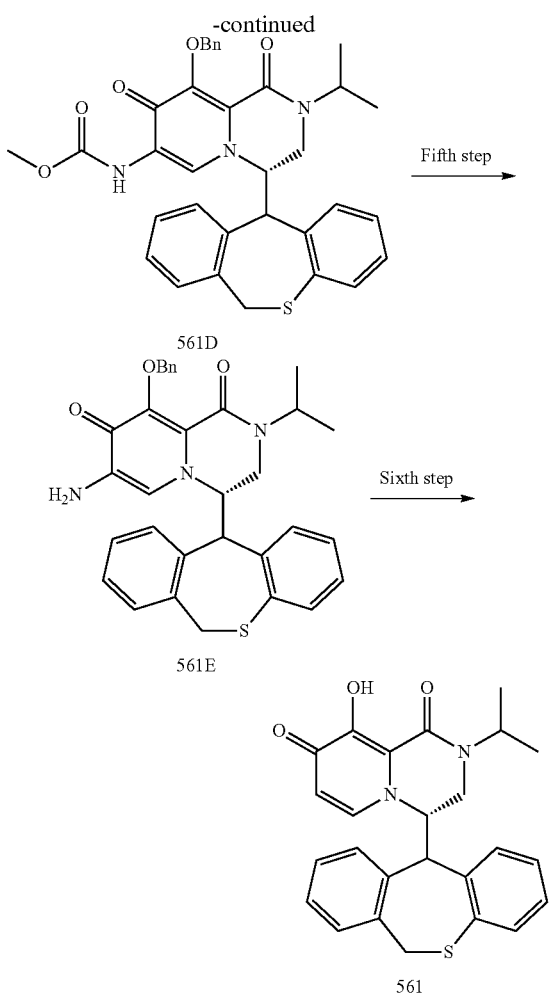

561D

561E

561

First Step

To a crude product (433 mg) of compound 560H was added a 4N hydrochloric acid ethyl acetate solution (3 mL), and the mixture was stirred at room temperature for 1 hour. The solvent was distilled off, to a THF (2 mL) solution of the resulting residue was added acetone (2 mL), the mixture was stirred at room temperature for 20 minutes, NaBH(OAc)$_3$ (70 mg, 0.32 mmol) was added, and the mixture was stirred at room temperature for 1 hour and 30 minutes. Thereafter, to the reaction solution was added an aqueous saturated sodium bicarbonate solution (3 mL), and the mixture was stirred at room temperature overnight. To the reaction solution was added water, the mixture was extracted with chloroform, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded a crude product (79 mg) of compound 561A.

MS: m/z=581 [M+H]$^+$.

Second Step

To an EtOH (4 mL) solution of the crude product (79 mg) of compound 561A was added 2N NaOH (2 mL), and the mixture was stirred at room temperature for 1 hour. To the reaction solution was added a 2N aqueous HCl solution, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded compound 561B (53 mg).

MS: m/z=567 [M+H]$^+$.

Third Step

A DMF (2 mL) solution of compound 561B (53 mg, 0.093 mmol) was cooled to 0° C., triethylamine (0.039 mL, 0.28 mmol) and ethyl chloroformate (0.018 mL, 0.187 mmol) were added, and the mixture was stirred at room temperature for 10 minutes. Thereafter, the reaction solution was cooled to 0° C., sodium azide (18 mg, 0.28 mmol) was added, and the mixture was stirred for 50 minutes while temperature was retained at the same temperature. To the reaction solution was added water, the mixture was extracted with dichloromethane, and the combined extracts were concentrated to obtain a crude product of compound 561C.

MS: m/z=592 [M+H]$^+$.

Fourth Step

The crude product (55 mg) of compound 561C was dissolved in methanol (2 mL), and the mixture was stirred at 50° C. for 1 hour. The reaction solution was subjected to silica gel column chromatography, and eluted with chloroform-methanol (100:0→94:6, v/v). Concentration of an objective fraction afforded a crude product (43 mg) of compound 561D.

MS: m/z=596 [M+H]$^+$.

Fifth Step

To an EtOH (2 mL) solution of the crude product (43 mg) of compound 561D was added 2N NaOH (4 mL), and the mixture was stirred at 60° C. for 1 hour. The solvent was distilled off, water was added, the mixture was extracted with ethyl acetate and, thereafter, sodium sulfate was added to the combined extracts to dry them. The solvent was distilled off, the resulting oil was subjected to amino column chromatography, and eluted with chloroform-methanol (100:0→80:20, v/v). Concentration of an objective fraction afforded 16 mg of compound 561E as a pale yellow solid.

MS: m/z=538 [M+H]$^+$.

Sixth Step

Compound 561E (16 mg, 0.029 mmol) was dissolved in EtOH (1 mL) and a 48% aqueous tetrafluoroboric acid (1 mL), the reaction solution was cooled to 0° C., sodium nitrite (15 mg, 0.22 mmol) was added, and the mixture was stirred for 1 hour and 30 minutes while temperature was retained at the same temperature and, further, at room temperature for 2 hours and 30 minutes. To the reaction solution was added water, the mixture was extracted with chloroform, and sodium sulfate was added to the combined extracts to dry them. The solvent was distilled off, to the resulting concentrated residue were added ethyl acetate and isopropyl ether, and the precipitated solid was filtered and washed to obtain 5 mg of compound 561 as a white solid.

$^1$H-NMR (CDCl$_3$) δ: 0.96 (3H, d, J=6.9 Hz), 1.17 (3H, d, J=6.8 Hz), 3.37 (1H, d, J=13.3 Hz), 3.88 (1H, dd, J=13.4, 4.3 Hz), 3.99 (1H, d, J=14.9 Hz), 4.08 (1H, d, J=11.3 Hz), 4.52 (1H, d, J=14.9 Hz), 4.81-4.90 (1H, m), 5.67 (1H, dd, J=11.3, 3.1 Hz), 5.94 (1H, d, J=7.4 Hz), 6.59 (1H, d, J=6.4 Hz), 6.72 (1H, d, J=7.3 Hz), 6.86 (1H, t, J=7.1 Hz), 7.09 (1H, t, J=7.6 Hz), 7.16-7.31 (5H, m).

REFERENCE EXAMPLE 562
[Chemical formula 612]
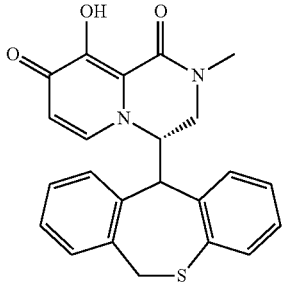
Compound 562 was synthesized by the same procedure as that of Reference example 561.
$^1$H-NMR (CDCl$_3$) δ: 3.07 (3H, s), 3.21 (1H, d, J=12.3 Hz), 4.00-4.31 (4H, m), 5.78 (1H, d, J=10.5 Hz), 5.94 (1H, d, J=7.4 Hz), 6.54 (1H, d, J=7.3 Hz), 6.69 (1H, d, J=7.5 Hz), 6.98 (1H, t, J=7.6 Hz), 7.14-7.41 (6H, m).
MS: m/z=405 [M+H]$^+$.
REFERENCE EXAMPLE 563
[Chemical formula 613]
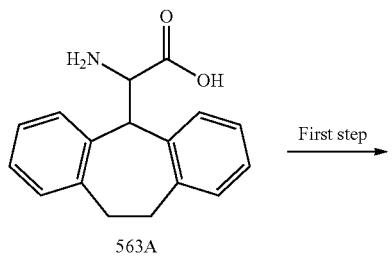
563A
→ First step
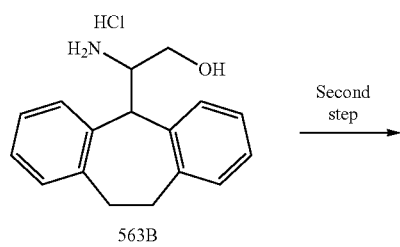
563B
→ Second step
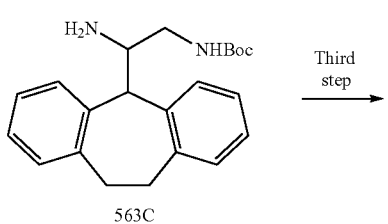
563C
→ Third step
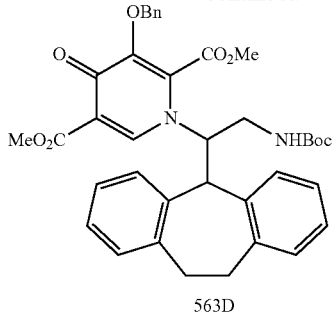
563D
→ Fourth step
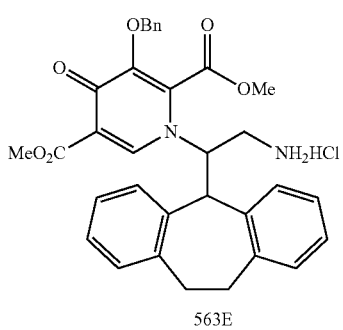
563E
→ Fifth step
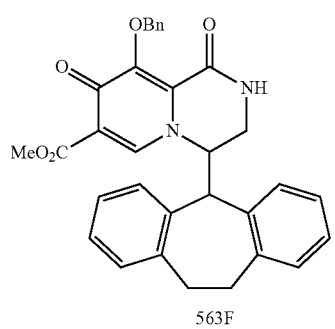
563F
→ Sixth step
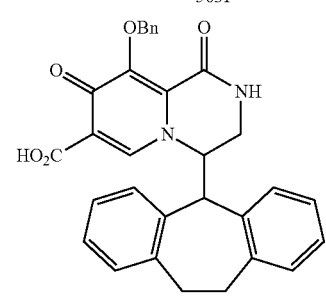
563G
→ Seventh step
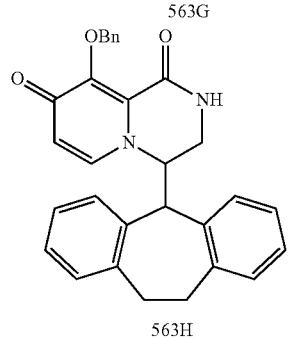
563H
→ Eighth step

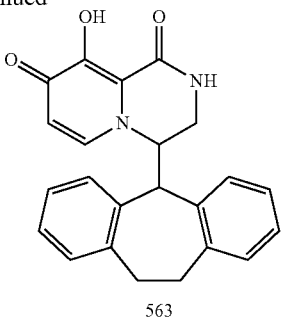

563

First Step

Compound 563A (Tetrahedron Letters, 34, 953-956, 1993, 41.1 g, 154 mmol) was dissolved in THF (300 mL), 1M $BH_3$-THF (770 mL) was slowly added at room temperature, and the mixture was stirred for 18 hours. 3N aqueous hydrochloric acid solution (513 mL) was slowly added, and the mixture was refluxed for 1 hour, and was progressed to a next step without purification.

LC-MS: m/z=254 $[M+H]^+$.

Second Step

Using a solution containing compound 563B, according to Reference example 12, compound 563C was synthesized.

LC-MS: m/z=353 $[M+H]^+$.

$^1$H-NMR (DMSO-$d_6$): 1.40 (9H, s), 2.65-2.72 (1H, m), 2.86-2.92 (3H, m), 3.47-3.56 (3H, m), 3.56-3.69 (1H, m), 6.63 (1H, s), 7.11-7.26 (8H, m).

Third Step

A toluene (30 mL) solution of compound 563C (2.16 g, 6.79 mmol) and dimethyl 3-(benzyloxy)-4-oxo-4H-pyran-2,5-dicarboxylate (2.38 g, 6.75 mmol) was stirred at 100° C. for 4 hours. The reaction solution was distilled off under reduced pressure, and the resulting crude product of compound 563D was used in a next reaction without purification.

MS: m/z=653.05 $[M+H]^+$.

Fourth Step

To an ethyl acetate (20 mL) solution of the crude product of compound 563D was added hydrogen chloride (4N ethyl acetate solution, 20 mL) at room temperature, and the mixture was stirred for 30 minutes. The reaction solution was distilled off under reduced pressure, and the resulting crude product of compound 563E was used in a next reaction without purification.

MS: m/z=553.05 $[M+H]^+$.

Fifth Step

To a tetrahydrofuran (40 mL) solution of the crude product of compound 563E was added saturated sodium bicarbonate water (5 mL) at room temperature, and the mixture was stirred for 16 hours. To the reaction solution was added water (50 mL), the mixture was extracted with chloroform three times, and the extracts were combined, and dried with sodium sulfate. The solvent was distilled off under reduced pressure, and diethyl ether and chloroform were added to the resulting residue to covert them into a powder, to obtain compound 563F (2.90 g, 70.2%) as a white solid.

MS: m/z=521.05 $[M+H]^+$.

Sixth Step

To a methanol (7.5 mL) suspension of compound 563F (523 mg, 1.01 mmol) was added an aqueous sodium hydroxide solution (2M, 1.5 mL) at room temperature, and the mixture was stirred for 3 hours. To the reaction solution were added hydrochloric acid (2N, 1.5 mL) and water (3 mL) at room temperature and, thereafter, the mixture was stirred at 0° C. for 15 minutes. The precipitated solid was filtered, and washed with water and diethyl ether to obtain compound 563G (418 mg, 82.0%) as a white solid.

MS: m/z=507.00 $[M+H]^+$.

Seventh Step

A diphenyl ether (5 mL) suspension of compound 563G (107 mg, 0.211 mmol) was stirred at 240° C. for 1 hour under microwave irradiation. The reaction solution was purified by silica gel column chromatography (methanol/chloroform=0%→5%) to obtain compound 563H (64.4 mg, 65.9%) as a white solid.

MS: m/z=463.05 $[M+H]^+$.

Eighth Step

A methanol (30 mL) solution of compound 563H (64.4 mg, 0.139 mmol) was hydrogenated by passing through 10% Pd—C CatCart (H-cube, Full-$H_2$ mode, 25° C.) for 3 hours. The reaction solution was distilled off under reduced pressure, and ethyl acetate and methanol were added to the resulting residue to convert it into a powder, to obtain compound 563 (31.1 mg, 60.0%) as a gray white solid.

$^1$HNMR (DMSO-$d_6$) δ: 2.50-3.03 (3H, m), 3.50-3.72 (3H, m), 4.29 (1H, d, J=11.4 Hz), 5.12 (1H, m), 5.69 (1H, d, J=7.2 Hz), 6.50 (1H, d, J=7.7 Hz), 6.75 (1H, d, J=7.7 Hz), 6.84 (1H, m), 7.14-7.30 (6H, m), 9.16 (1H, d, J=4.8 Hz).

MS: m/z=372.90 $[M+H]^+$.

REFERENCE EXAMPLE 564

[Chemical formula 614]

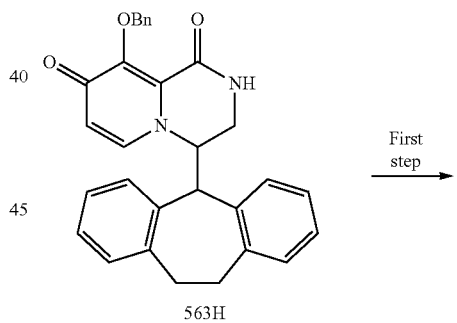

563H

First step

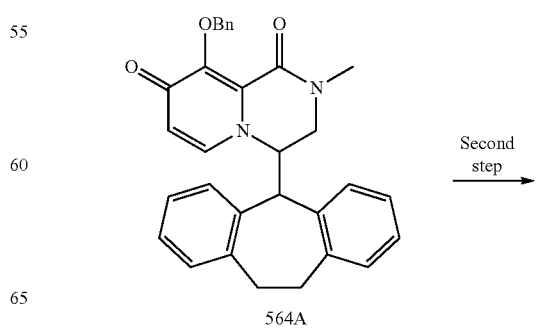

564A

Second step

-continued

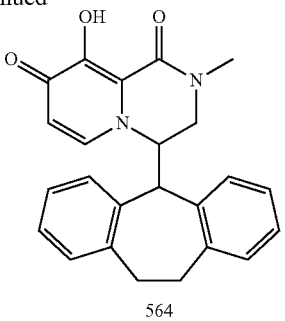

564

First Step

To a dimethylformamide (2 mL) suspension of compound 563H (64.2 mg, 0.139 mmol) and cesium carbonate (220 mg, 0.675 mmol) was added methyl iodide (0.0430 mL, 0.688 mmol) at room temperature, and the mixture was stirred for 3 hours. To the reaction solution was added water (10 mL) at room temperature, and the mixture was extracted with ethyl acetate (30 mL). The organic layer was washed with water (10 mL) and an aqueous saturated sodium chloride solution (10 mL), and dried with sodium sulfate. The solvent was distilled off under reduced pressure, and the residue was purified by silica gel column chromatography (methanol/chloroform=2.5%→10%) to obtain compound 564A (56.0 mg, 85.0%) as a colorless gummy substance.

MS: m/z=477.00 [M+H]$^+$.

Second Step

A solution of compound 564A (56.0 mg, 0.118 mmol) in methanol (10 mL), ethyl acetate (5 mL) and tetrahydrofuran (5 mL) was hydrogenated by passing through 10% Pd—C CatCart (H-cube, Full-H$_2$ mode, 25° C.) for 75 minutes. The reaction solution was distilled off under reduced pressure, and ethyl acetate and methanol were added to the resulting residue to convert it into a powder, to obtain compound 564 (22.0 mg, 48.4%) as a gray white solid.

$^1$HNMR (DMSO-d$_6$) δ: 2.86-2.98 (6H, m), 3.51-3.58 (2H, m), 3.94 (1H, m), 4.30 (1H, d, J=11.1 Hz), 5.19 (1H, d, J=10.2 Hz), 5.79 (1H, d, J=6.9 Hz), 6.49 (1H, d, J=7.4 Hz), 6.74 (1H, d, J=7.4 Hz), 6.85 (1H, m), 7.14 (2H, m), 7.25 (4H, m), 12.50 (1H, brs).

MS: m/z=387.05 [M+H]$^+$.

REFERENCE EXAMPLE 565

[Chemical formula 615]

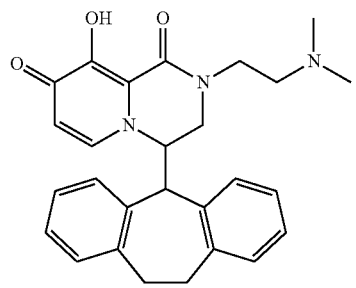

Compound 565 was synthesized by the same procedure as that of Reference example 564.

MS: m/z=443.95 [M+H]$^+$.

REFERENCE EXAMPLE 566

[Chemical formula 616]

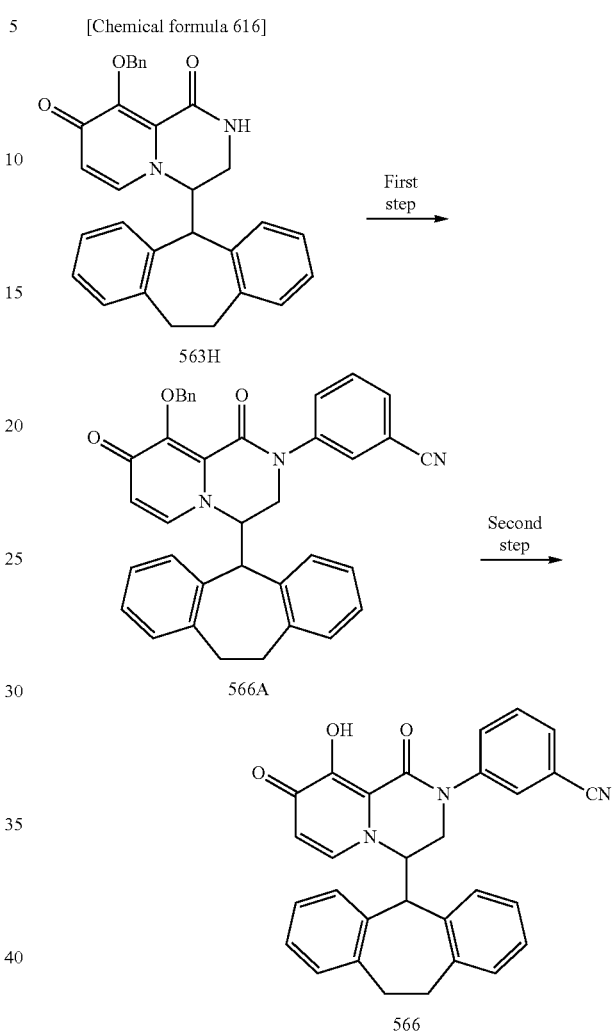

First Step

A dimethylformamide (2 mL) suspension of compound 563H (75.4 mg, 0.163 mmol), 3-iodobenzonitrile (124 mg, 0.541 mmol), copper(I) iodide (33.2 mg, 0.174 mmol), potassium carbonate (74.7 mg, 0.540 mmol) and N,N'-dimethylethylenediamine (0.0200 ml, 0.186 mmol) was stirred at 140° C. for 2 hours under microwave irradiation. To the reaction solution were added water (10 mL) and hydrochloric acid (2M, 2 mL) at room temperature, and the mixture was extracted with ethyl acetate. The extract was filtered with celite, and the filtrate was washed with water (10 mL×2) and an aqueous saturated sodium chloride solution (10 mL), and dried with sodium sulfate. The solvent was distilled off under reduced pressure, and the resulting crude product of compound 566A was used in a next reaction without purification.

MS: m/z=564.05 [M+H]$^+$.

Second Step

To a methylene chloride (10 mL) solution of the crude product of compound 566A obtained in the first step was added trifluoroacetic acid (2 mL) at room temperature, and the mixture was stirred for 1 hour. The reaction solution was concentrated under reduced pressure, and the resulting residue was purified by preparative LCMS to obtain compound 566 (30.3 mg, 39.3%) as a yellow solid.

$^1$HNMR (DMSO-$d_6$) δ: 2.81-2.94 (2H, m), 3.38-3.58 (2H, m), 4.54 (1H, d, J=10.5 Hz), 4.64 (1H, d, J=10.5 Hz), 5.35 (1H, d, J=10.5 Hz), 5.76 (1H, m), 6.66-6.71 (3H, m), 6.90 (1H, m), 7.06-7.15 (6H, m), 7.76 (2H, m), 7.90 (2H, m).

MS: m/z=473.90 [M+H]$^+$.

REFERENCE EXAMPLE 567

[Chemical formula 617]

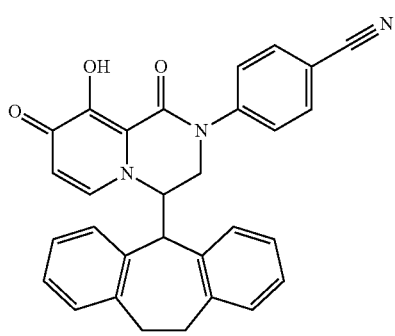

Compound 567 was synthesized by the same procedure as that of Reference example 566.

$^1$HNMR (DMSO-$d_6$) δ: 2.80-3.00 (2H, m), 3.40-3.70 (2H, m), 4.52 (1H, m), 4.64 (1H, m), 5.38 (1H, m), 5.76 (1H, m), 6.60-7.20 (10H, m), 7.60-7.90 (3H, m), 8.11 (1H, m).

MS: m/z=474.00 [M+H]$^+$.

REFERENCE EXAMPLE 568

[Chemical formula 618]

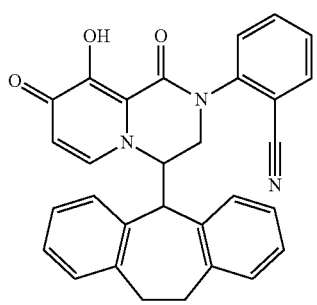

Compound 568 was synthesized by the same procedure as that of Reference example 566.

$^1$HNMR (DMSO-$d_6$) δ: 2.87-2.96 (2H, m), 3.34-3.73 (2H, m), 4.64 (2H, m), 5.33 (1H, m), 5.71 (1H, d, J=7.2 Hz), 6.61 (1H, d, J=7.8 Hz), 6.87-6.95 (3H, m), 7.00-7.27 (6H, m), 7.62 (2H, m), 7.86 (1H, m), 8.07 (1H, m).

MS: m/z=474.00 [M+H]$^+$.

REFERENCE EXAMPLE 569

[Chemical formula 619]

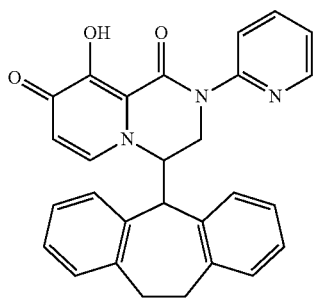

Compound 569 was synthesized by the same procedure as that of Reference example 566.

MS: m/z=449.95 [M+H]$^+$.

REFERENCE EXAMPLE 570

[Chemical formula 620]

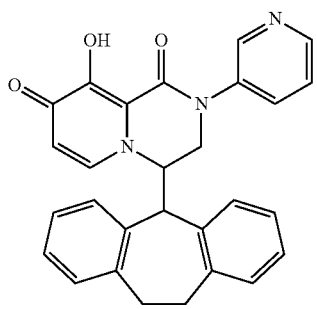

Compound 570 was synthesized by the same procedure as that of Reference example 566.

$^1$HNMR (DMSO-$d_6$) δ: 2.83-2.97 (3H, m), 3.16-3.62 (2H, m), 3.56 (1H, m), 3.66 (1H, d, J=11.1 Hz), 5.35 (1H, d, J=11.1 Hz), 5.73 (1H, d, J=7.4 Hz), 6.68 (1H, d, J=7.4 Hz), 6.92 (1H, m), 7.06-7.21 (5H, m), 7.49 (1H, m), 7.97 (1H, d, J=8.4 Hz), 8.14 (1H, s), 8.50 (1H, d, J=3.6 Hz), 8.81 (1H, d, J=2.1 Hz).

MS: m/z=449.95 [M+H]$^+$.

REFERENCE EXAMPLE 571

[Chemical formula 621]

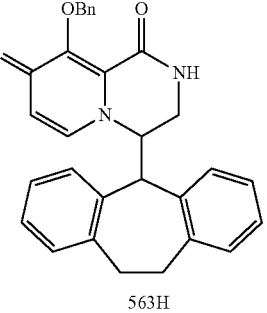

First step →

563H

-continued

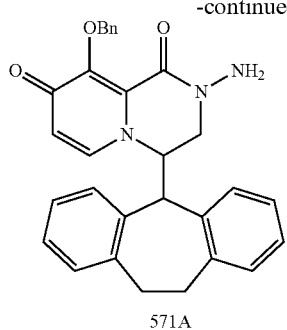
571A

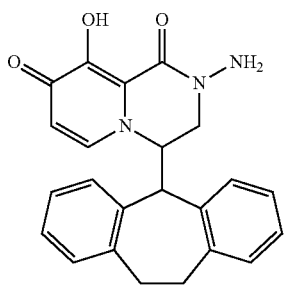
571

First Step

To a DMF (1 mL) solution of compound 563H (50.0 mg, 0.108 mmol) was added cesium carbonate (176 mg, 0.540 mmol), and the mixture was stirred at room temperature for 10 minutes. To the reaction solution was added O-(2,4-dinitrophenyl)hydroxylamine (64.6 mg, 0.324 mmol), and the mixture was stirred at room temperature for 9 hours. To the reaction solution was added chloroform, and the mixture was washed with water, and dried with sodium sulfate. The solvent was distilled off, and the resulting oil was purified by silica gel column chromatography. The materials were eluted firstly with chloroform and, then, with chloroform-methanol (98:2, v/v). Concentration of an objective fraction afforded 28.3 mg of compound 571A as an amorphous substance.

MS: m/z=478 [M+H]$^+$.

Second Step

Compound 571A (27.0 g, 0.057 mmol) was dissolved in a THF-methanol (1 mL, 1:1, v/v) solution, 10% palladium carbon (15.0 mg) was added, and the mixture was stirred at room temperature for 2 hours under hydrogen atmosphere. After dilution with chloroform, insolubles were removed by celite filtration. After the filtrate was concentrated under reduced pressure, the residue was solidified with dichloromethane-ether to obtain 12.0 mg of compound 571.

MS: m/z=388 [M+H]$^+$.

REFERENCE EXAMPLE 572

[Chemical formula 622]

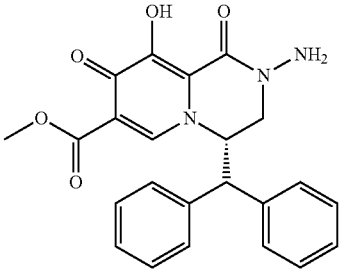

Using compound 12H, and according to Reference example 571, compound 572 was synthesized by the same procedure.

MS: m/z=420 [M+H]$^+$.

REFERENCE EXAMPLE 573

[Chemical formula 623]

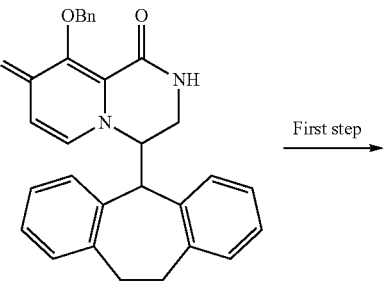
563H

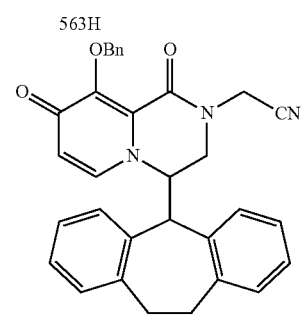
573A

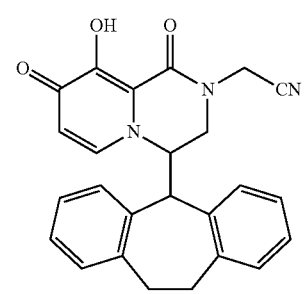
573

469

First Step

To a dimethylformamide (1.5 mL) solution of compound 563H (83.2 mg, 0.160 mmol) was added sodium hydride (60%, 13.2 mg, 0.330 mmol) under ice-cooling, the mixture was stirred for 30 minutes, thereafter, bromoacetonitrile (0.0190 mL, 0.270 mmol) was added, and the mixture was stirred at room temperature for 1 hour. To the reaction solution was added an aqueous ammonium chloride solution (10%, 3 mL), and the mixture was extracted with ethyl acetate. The organic layer was washed with water (10 mL) and an aqueous saturated sodium chloride solution (10 mL), and dried with sodium sulfate. The solvent was distilled off under reduced pressure, and the resulting crude product of compound 573A was used in a next reaction without purification.

MS: m/z=502.00 [M+H]$^+$.

Second Step

To an acetonitrile (4 mL) suspension of the crude product of compound 573A obtained in the first step and sodium iodide (111 mg, 0.741 mmol) was added chlorotrimethylsilane (0.0920 mL, 0.720 mmol) at room temperature, and the mixture was stirred for 24 hours. To the reaction solution was added an aqueous sodium hydrogen sulfite solution (10%, 10 mL) and, thereafter, the mixture was extracted with chloroform. After the extracts were combined, and dried with sodium sulfate, the solvent was concentrated under reduced pressure, and the resulting residue was purified by preparative LCMS to obtain compound 573 (22.0 mg, 29.7%) as a gray white solid.

$^1$H-NMR (DMSO-d$_6$) δ: 2.86-2.95 (2H, m), 3.45-3.63 (2H, m), 4.01 (1H, m), 4.30 (1H, d, J=10.8 Hz), 4.35 (1H, d, J=17.4 Hz), 4.74 (1H, d, J=17.4 Hz), 5.20 (1H, m), 5.66 (1H, d, J=7.5 Hz), 6.52 (1H, d, J=7.8 Hz), 6.73 (1H, d, J=7.5 Hz), 6.83 (1H, m), 7.11-7.28 (6H, m).

MS: m/z=502.00 [M+H]$^+$.

REFERENCE EXAMPLE 574

[Chemical formula 624]

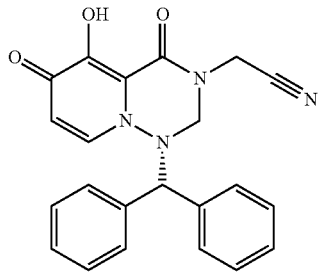

Compound 574 was synthesized by the same procedure as that of Reference example 573.

$^1$H-NMR (DMSO-d$_6$) δ: 4.16 (1H, dd, J=13.26, 3.53 Hz), 4.36 (1H, d, J=11.58 Hz), 4.52 (2H, dd, J=20.73, 17.54 Hz), 5.44 (1H, d, J=11.41 Hz), 5.65 (1H, d, J=7.39 Hz), 6.99 (1H, d, J=7.55 Hz), 7.11-7.32 (6H, m), 7.36-7.45 (2H, m), 7.58 (2H, d, J=7.39 Hz).

REFERENCE EXAMPLE 575

[Chemical formula 625]

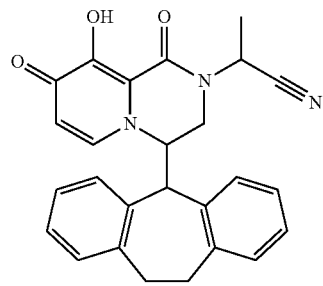

Compound 575 was synthesized by the same procedure as that of Reference example 573.

MS: m/z=425.95 [M+H]$^+$.

REFERENCE EXAMPLE 576

[Chemical formula 626]

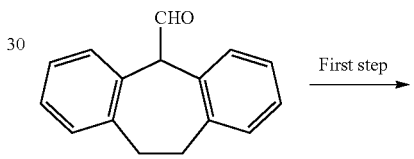

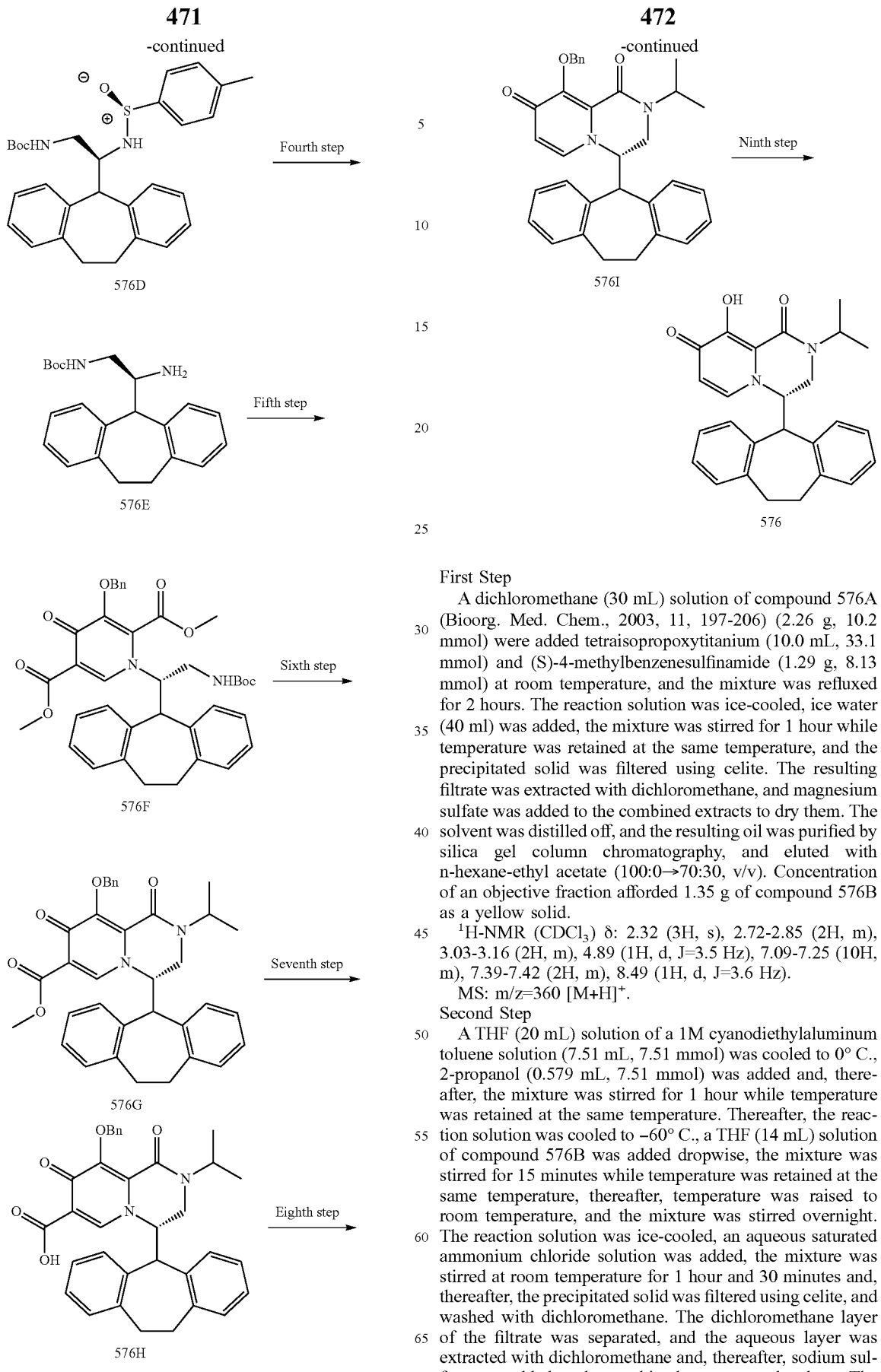

First Step

A dichloromethane (30 mL) solution of compound 576A (Bioorg. Med. Chem., 2003, 11, 197-206) (2.26 g, 10.2 mmol) were added tetraisopropoxytitanium (10.0 mL, 33.1 mmol) and (S)-4-methylbenzenesulfinamide (1.29 g, 8.13 mmol) at room temperature, and the mixture was refluxed for 2 hours. The reaction solution was ice-cooled, ice water (40 ml) was added, the mixture was stirred for 1 hour while temperature was retained at the same temperature, and the precipitated solid was filtered using celite. The resulting filtrate was extracted with dichloromethane, and magnesium sulfate was added to the combined extracts to dry them. The solvent was distilled off, and the resulting oil was purified by silica gel column chromatography, and eluted with n-hexane-ethyl acetate (100:0→70:30, v/v). Concentration of an objective fraction afforded 1.35 g of compound 576B as a yellow solid.

$^1$H-NMR (CDCl$_3$) δ: 2.32 (3H, s), 2.72-2.85 (2H, m), 3.03-3.16 (2H, m), 4.89 (1H, d, J=3.5 Hz), 7.09-7.25 (10H, m), 7.39-7.42 (2H, m), 8.49 (1H, d, J=3.6 Hz).

MS: m/z=360 [M+H]$^+$.

Second Step

A THF (20 mL) solution of a 1M cyanodiethylaluminum toluene solution (7.51 mL, 7.51 mmol) was cooled to 0° C., 2-propanol (0.579 mL, 7.51 mmol) was added and, thereafter, the mixture was stirred for 1 hour while temperature was retained at the same temperature. Thereafter, the reaction solution was cooled to −60° C., a THF (14 mL) solution of compound 576B was added dropwise, the mixture was stirred for 15 minutes while temperature was retained at the same temperature, thereafter, temperature was raised to room temperature, and the mixture was stirred overnight. The reaction solution was ice-cooled, an aqueous saturated ammonium chloride solution was added, the mixture was stirred at room temperature for 1 hour and 30 minutes and, thereafter, the precipitated solid was filtered using celite, and washed with dichloromethane. The dichloromethane layer of the filtrate was separated, and the aqueous layer was extracted with dichloromethane and, thereafter, sodium sulfate was added to the combined extracts to dry them. The solvent was distilled off, to the resulting oil were added ethyl acetate and hexane, and the precipitated solid was filtered and washed to obtain 976 mg of compound 576C as a white solid.

$^1$H-NMR (CDCl$_3$) δ: 2.38 (3H, s), 2.92-3.055 (2H, m), 3.41-3.52 (2H, m), 4.25 (1H, d, J=10.8 Hz), 4.28 (1H, d, J=5.6 Hz), 4.94 (1H, dd, J=10.6, 5.7 Hz), 7.14-7.41 (12H, m).

Third Step

A methanol (8 mL) suspension of compound 576C (500 mg, 1.29 mmol) was cooled to 0° C., cobalt(II) chloride hexahydrate (123 mg, 0.517 mmol) was added, and the mixture was stirred at room temperature for 30 minutes. To the reaction solution was added chloroform (5 mL), thereafter, the mixture was ice-cooled, a DMF (4 mL) solution of sodium borohydride (196 mg, 5.17 mmol) was added dropwise, and the mixture was stirred at the same temperature for 5 minutes, and at room temperature for 2 hours. Then, Boc$_2$O (1.0 mL, 4.3 mmol) was added, and the mixture was stirred at room temperature overnight. To the reaction solution was added water, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→98:2, v/v). Concentration of an objective fraction afforded a crude product (200 mg) of compound 576D.

MS: m/z=491 [M+Na]$^+$.

Fourth Step

To a methanol (6 mL) solution of the crude product (200 mg) of compound 576D obtained in the third step was added TFA (0.188 mL, 2.45 mmol), and the mixture was stirred at room temperature for 2.5 hours. To the reaction solution was added triethylamine (0.399 mL, 2.45 mmol), the solvent was distilled off, and the resulting crude product of compound 576E was used in a next reaction without purification.

MS: m/z=353 [M+H]$^+$.

Fifth Step

To a toluene (4 mL) solution of the crude product of compound 576E obtained in the fourth step was added dimethyl 3-(benzyloxy)-4-oxo-4H-pyran-2,5-dicarboxylate (130 mg, 0.409 mmol), and the mixture was refluxed for 2 hours. The reaction solution was subjected to silica gel column chromatography, and eluted with chloroform-methanol (100:0→90:10, v/v). Concentration of an objective fraction afforded a crude product (268 mg) of compound 576F.

MS: m/z=653 [M+H]$^+$.

Sixth Step

To the crude product (263 mg) of compound 576F obtained in the fifth Step was added a 4N hydrochloric acid ethyl acetate solution (3 mL), and the mixture was stirred at room temperature for 1 hour and 30 minutes. The solvent was distilled off, to a THF (4 mL) solution of the resulting concentrated residue was added acetone (1 mL), the mixture was stirred at room temperature for 25 minutes, thereafter, NaBH(OAc)$_3$ (180 mg, 0.807 mmol) was added, and the mixture was stirred at room temperature for 1 hour and 15 minutes. Thereafter, to the reaction solution was added an aqueous saturated sodium bicarbonate solution (7 mL), and the mixture was stirred at room temperature overnight. To the reaction solution was added water, the mixture was extracted with chloroform, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded a crude product (160 mg) of compound 576G.

MS: m/z=563 [M+H]$^+$.

Seventh Step

To an EtOH (4 mL) solution of the crude product (160 mg) of compound 576G obtained in the sixth step was added 2N NaOH (2 mL), and the mixture was stirred at room temperature for 3 hours. To the reaction solution was added a 2N aqueous HCl solution, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded 78 mg of compound 576H as a yellow solid.

MS: m/z=549 [M+H]$^+$.

Eighth Step

To compound 576H (78 mg, 0.14 mmol) was added diphenyl ether (3 mL), and the mixture was stirred at 245° C. for 1 hour under microwave irradiation. The reaction solution was subjected to silica gel column chromatography, and eluted with chloroform-methanol (100:0→90:10, v/v). Concentration of an objective fraction afforded 43 mg of compound 576I as a bronzed oil.

MS: m/z=505 [M+H]$^+$.

Ninth Step

To compound 576I (42 mg, 0.083 mmol) was added TFA (1.0 mL), and the mixture was stirred at room temperature for 35 minutes. The reaction solution was subjected to toluene azeotropy, to the resulting concentrated residue was added an aqueous saturated sodium bicarbonate solution, and the mixture was extracted with ethyl acetate. To the combined extracts was added sodium sulfate to dry them. The solvent was distilled off, to the resulting oil were added ethyl acetate and isopropyl ether, and the precipitated solid was filtered and washed to obtain 14 mg of compound 576 as a pale brown solid.

$^1$H-NMR (CDCl$_3$) δ: 1.13 (3H, d, J=6.7 Hz), 1.20 (3H, d, J=6.7 Hz), 2.95-3.13 (2H, m), 3.28 (1H, d, J=13.1 Hz), 3.37-3.59 (2H, m), 3.75 (1H, d, J=10.3 Hz), 4.10 (1H, d, J=10.8 Hz), 4.80-4.87 (2H, m), 5.91 (1H, d, J=5.8 Hz), 6.41 (2H, t, J=6.5 Hz), 6.85 (1H, t, J=6.4 Hz), 7.05-7.35 (6H, m).

MS: m/z=415 [M+H]$^+$.

REFERENCE EXAMPLE 577

[Chemical formula 627]

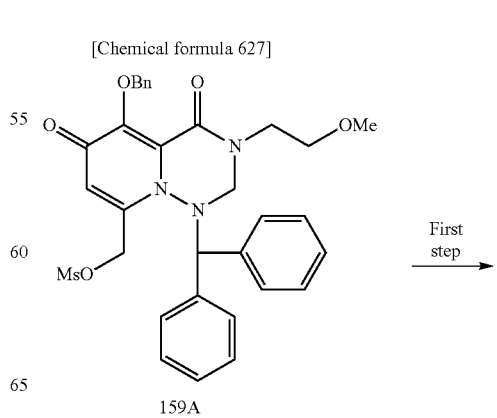

159A

First step →

REFERENCE EXAMPLE 578

[Chemical formula 628]

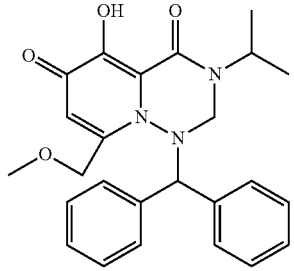

Compound 578 was synthesized by the same procedure as that of Reference example 157.

$^1$HNMR (CDCl$_3$) δ: 0.97 (3H, d, J=6.6 Hz), 1.19 (3H, d, J=6.9 Hz), 3.29 (3H, s), 3.97 (1H, d, J=16.1 Hz), 4.56 (1H, d, J=13.7 Hz), 4.82 (1H, m), 4.96 (1H, d, J=16.1 Hz), 5.34 (1H, s), 5.97 (1H, d, J=13.7 Hz), 6.78 (2H, m), 7.12 (2H, m), 7.44-7.51 (6H, m).

MS: m/z=434.10 [M+H]$^+$.

REFERENCE EXAMPLE 579

[Chemical formula 629]

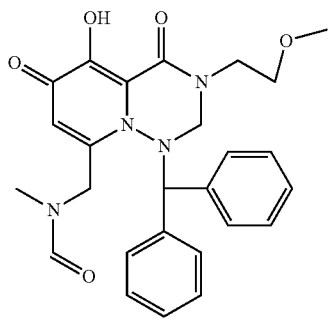

Compound 579 was synthesized by the same procedure as that of Reference example 163.

MS: m/z=477.25 [M+H]$^+$.

REFERENCE EXAMPLE 580

[Chemical formula 630]

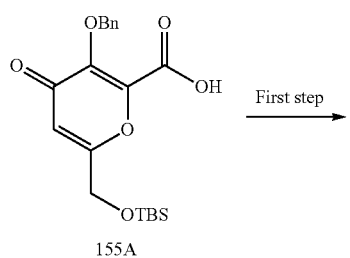

155A

First step

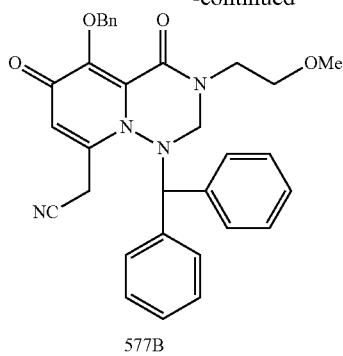

577B

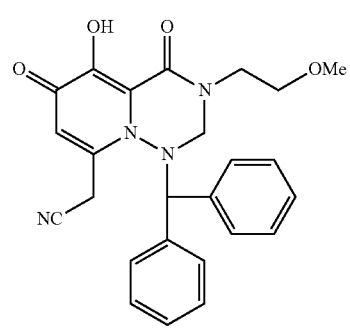

577

First Step

To a dimethylformamide (3 mL) solution of a crude product (140 mg) of compound 159A was added potassium cyanide (21.0 mg, 0.323 mmol) at room temperature, and the mixture was stirred at 80° C. for 30 minutes, and at 100° C. for 30 minutes. The reaction solution was concentrated under reduced pressure, and the resulting residue was purified by silica gel column chromatography (ethyl acetate/n-hexane=80%→100%) to obtain compound 577B (41.5 mg, 33.5%) as a pale orange foam.

MS: m/z=535.25 [M+H]$^+$.

Second Step

To an acetonitrile (4 mL) solution of compound 577B (41.5 mg, 0.078 mmol) and sodium iodide (45.5 mg, 0.304 mmol) was added chlorotrimethylsilane (0.0400 mL, 0.313 mmol) at room temperature, and the mixture was stirred for 2 hours. To the reaction solution was added water (1 mL), the reaction solution was concentrated under reduced pressure, and the resulting residue was purified by preparative LCMS. Diethyl ether was added to the resulting residue to convert it into a powder, to obtain compound 577 (20.7 mg, 60.0%) as a gray white solid.

$^1$HNMR (DMSO-d$_6$) δ: 3.10 (3H, s), 3.51 (2H, m), 3.70 (1H, d, J=18.9 Hz), 4.03 (1H, d, J=18.9 Hz), 4.46 (1H, d, J=13.4 Hz), 5.04 (1H, d, J=13.4 Hz), 5.56 (1H, s), 5.69 (1H, s), 7.09-7.21 (5H, m), 7.39-7.63 (3H, m), 7.64 (2H, m).

MS: m/z=445.20 [M+H]$^+$.

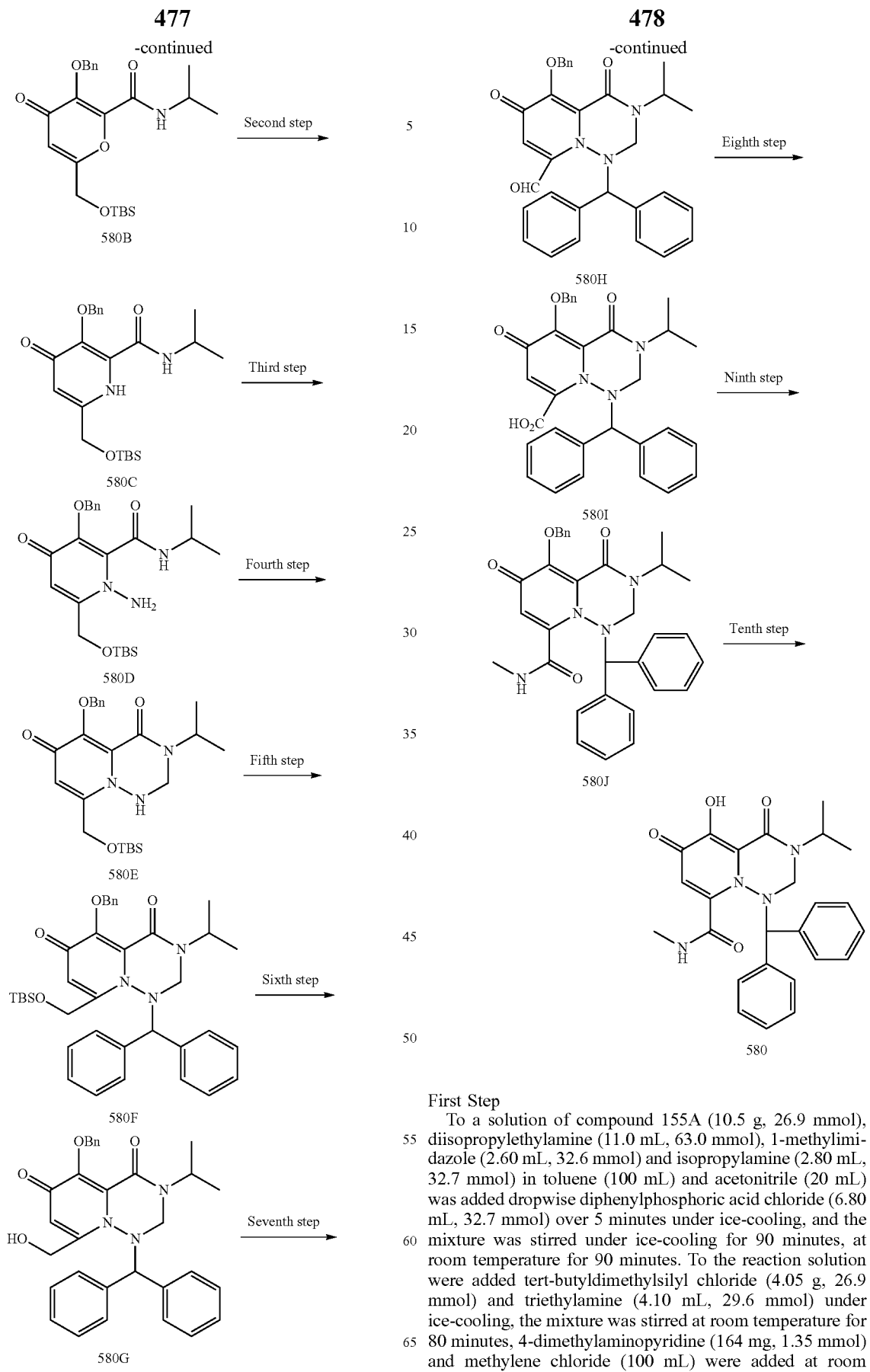

First Step

To a solution of compound 155A (10.5 g, 26.9 mmol), diisopropylethylamine (11.0 mL, 63.0 mmol), 1-methylimidazole (2.60 mL, 32.6 mmol) and isopropylamine (2.80 mL, 32.7 mmol) in toluene (100 mL) and acetonitrile (20 mL) was added dropwise diphenylphosphoric acid chloride (6.80 mL, 32.7 mmol) over 5 minutes under ice-cooling, and the mixture was stirred under ice-cooling for 90 minutes, at room temperature for 90 minutes. To the reaction solution were added tert-butyldimethylsilyl chloride (4.05 g, 26.9 mmol) and triethylamine (4.10 mL, 29.6 mmol) under ice-cooling, the mixture was stirred at room temperature for 80 minutes, 4-dimethylaminopyridine (164 mg, 1.35 mmol) and methylene chloride (100 mL) were added at room temperature, and the mixture was stirred for 15.5 hours. To the reaction solution was added tert-butyldimethylsilyl chloride (2.04 g, 26.9 mmol) at room temperature, and the mixture was stirred for 24 hours. To the reaction solution was added a 10% aqueous acetic acid solution (100 mL) at room temperature. The mixture was extracted with chloroform, the extracts were combined, washed with saturated sodium bicarbonate water (100 mL), and dried with sodium sulfate. The solvent was concentrated under reduced pressure, and the resulting residue was purified by silica gel column chromatography (ethyl acetate/n-hexane=15%→40%) to obtain compound 580B (6.96 g, 59.9%) as a pale yellow oil.

MS: m/z=432.25 [M+H]$^+$.

Second Step

To an ethanol (50 mL) solution of compound 580B (6.96 g, 16.1 mmol) was added aqueous ammonia (35 mL) at room temperature, and the mixture was stirred for 4 days. The reaction solution was concentrated under reduced pressure, and the resulting residue was purified by silica gel column chromatography (ethyl acetate/n-hexane=75%→100%, methanol/chloroform=0%→15%) to obtain compound 580C (4.50 g, 64.8%) as a pale orange gummy substance.

MS: m/z=431.25 [M+H]$^+$.

Third Step

To a dimethylformamide (90 mL) solution of compound 580C (4.50 g, 10.5 mmol) and potassium carbonate (7.27 g, 52.6 mmol) was added O-(2,4-dinitrophenyl)hydroxylamine (6.29 g, 31.6 mmol) at room temperature, and the mixture was stirred for 2 days. To the reaction solution was added chloroform (180 mL) at room temperature, the precipitated insolubles were filtered off, the filtrate was concentrated under reduced pressure, and the resulting residue was purified by silica gel column chromatography (methanol/chloroform=0%→10%) to obtain compound 580D (5.28 g, quant) as a yellow solid.

MS: m/z=446.25 [M+H]$^+$.

Fourth Step

To an ethanol (15 ml) solution of compound 580D (1.29 g, 2.89 mmol) was added paraformaldehyde (261 mg, 8.68 mmol) at room temperature, and the mixture was stirred at 140° C. for 3 hours under microwave irradiation. The reaction solution was concentrated under reduced pressure, and the resulting residue was purified by silica gel column chromatography (ethyl acetate/n-hexane=50%→100%) to obtain compound 580E (2.47 g, 93.0%) as a pale orange solid.

MS: m/z=458.20 [M+H]$^+$.

Fifth Step

To a DMF (25 mL) solution of compound 580E (2.47 g, 5.40 mmol) were added cesium carbonate (5.28 g, 16.2 mmol) and bromodiphenylmethane (4.02 g, 16.3 mmol) under ice-cooling, and the mixture was stirred at room temperature for 2 days. To the reaction solution was added water (50 mL) under ic e-cooling and, thereafter, the mixture was extracted with ethyl acetate (150 mL×2). The extracts were combined, sequentially washed with water (50 mL×2) and an aqueous saturated sodium chloride solution (50 mL), and dried with sodium sulfate. The solvent was concentrated under reduced pressure, and the resulting residue was purified by silica gel column chromatography (ethyl acetate/n-hexane=50%→100%, methanol/chloroform=10%→20%) to obtain compound 580F (1.60 g, 47.5%) as a yellow form.

MS: m/z=624.30 [M+H]$^+$.

Sixth Step

To a methanol (40 mL) solution of compound 580F (1.60 g, 2.56 mmol) was added hydrogen chloride (4N ethyl acetate solution, 20 mL) at room temperature, and the mixture was stirred for 2 hours. The reaction solution was concentrated under reduced pressure, to the resulting residue was added saturated sodium bicarbonate water (20 mL) at room temperature and, thereafter, the mixture was extracted with chloroform three times. The extracts were combined, and dried with sodium sulfate, the solvent was distilled off under reduced pressure, and the resulting residue was purified by silica gel column chromatography (ethyl acetate) to obtain compound 580G (920 mg, 70.4%) as a white foam.

MS: m/z=510.25 [M+H]$^+$.

Seventh Step

To a THF (80 mL) solution of compound 580G (816 mg, 1.60 mmol) was added manganese dioxide (2.39 g, 27.5 mmol) at room temperature, and the mixture was stirred for 19 hours. After the reaction solution was filtered, the filtrate was distilled off under reduced pressure, and the resulting crude product (785 mg) of compound 580H was used in a next reaction without purification.

MS: m/z=508.20 [M+H]$^+$.

Eighth Step

To a solution of the crude product (635 mg, 1.25 mmol) of compound 580H obtained in the seventh step and amidosulfuric acid (425 mg, 4.38 mmol) in methanol (30 mL) and water (10 mL) was added dropwise a solution of sodium chlorite (396 mg, 4.38 mmol) in water (4 mL) over 10 minutes under ice-cooling, the mixture was stirred at room temperature for 30 minutes, and a 5% aqueous sodium hydrogen sulfite solution (10 mL) was added. Methanol was distilled off under reduced pressure, and the resulting residue was extracted with ethyl acetate two times. The extracts were combined, washed with an aqueous saturated sodium chloride solution (10 mL), and dried with sodium sulfate. The filtrate was distilled off under reduced pressure, and the resulting crude product of compound 580I was used in a next reaction without purification.

MS: m/z=524.25 [M+H]$^+$.

Ninth Step

To a methylene chloride (20 mL) solution of the crude product (164 mg, 0.313 mmol) of compound 580I obtained in the eighth step, diisopropylethylamine (0.131 mL, 0.751 mmol), 1-methylimidazole (0.0300 mL, 0.376 mmol) and methylamine (2.0M tetrahydrofuran solution, 0.188 mL, 0.376 mmol) was added diphenylphosphoric acid chloride (0.0780 mL, 0.375 mmol) at room temperature, the mixture was stirred for 3.5 hours, methylamine hydrochloride (25.0 mg, 0.370 mmol) was added, and the mixture was stirred for 6 days. The reaction solution was distilled off under reduced pressure, and the resulting residue was purified by silica gel column chromatography (ethyl acetate/n-hexane=75%→100%) to obtain compound 580J (45.7 mg, 27.2%) as a white foam.

MS: m/z=537.30 [M+H]$^+$.

Tenth Step

To an acetonitrile (4 mL) solution of compound 580J (45.7 mg, 0.0850 mmol) and sodium iodide (103 mg, 0.687 mmol) was added chlorotrimethylsilane (0.0870 mL, 0.681 mmol) at room temperature, and the mixture was stirred for 20 hours. To the reaction solution was added a 5% aqueous sodium hydrogen sulfite solution (4 mL), and the mixture was extracted with chloroform two times. After the extracts were combined, and dried with sodium sulfate, the residue obtained by concentration under reduced pressure was purified by preparative LCMS. Diethyl ether and n-hexane were added to the resulting residue to convert it into a powder, to obtain compound 580 (17.1 mg, 45.0%) as a white solid.

$^1$HNMR (CDCl$_3$) δ: 0.93 (3H, d, J=6.9 Hz), 1.11 (3H, d, J=6.9 Hz), 2.83 (3H, d, J=4.8 Hz), 4.53 (1H, d, J=13.4 Hz), 4.85 (1H, m), 4.97 (1H, d, J=13.4 Hz), 5.07 (1H, brd), 5.25 (1H, s), 5.86 (1H, s), 6.97 (2H, m), 7.15-7.24 (2H, m), 7.38-7.46 (6H, m).
MS: m/z=447.20 [M+H]$^+$.

REFERENCE EXAMPLE 581

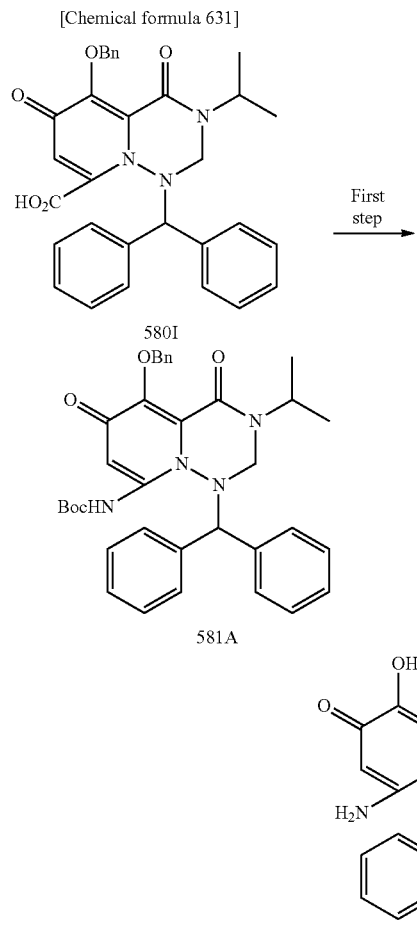

First Step
To a tert-butanol (4 mL) solution of compound 580I (398 mg, 0.760 mmol) were added triethylamine (0.158 mL, 1.14 mmol) and diphenylphosphoric acid azide (0.196 mL, 0.912 mmol) at room temperature, and the mixture was heated to reflux for 20 hours. To the reaction solution was added water (20 mL) at room temperature, and the mixture was extracted with chloroform three times. The extracts were combined, and dried with sodium sulfate. The solvent was distilled off under reduced pressure, and the resulting residue was purified by silica gel column chromatography (methanol/chloroform=0%→10%) to obtain compound 581A (167 mg, 36.9%) as a gray white solid.
MS: m/z=595.10 [M+H]$^+$.

Second Step
To a methylene chloride (2 mL) solution of compound 581A (167 mg, 0.281 mmol) was added trifluoroacetic acid (2 mL) at room temperature, and the mixture was stirred for 1.5 hours. The reaction solution was concentrated under reduced pressure, and the resulting residue was purified by preparative LCMS. Ethyl acetate, diethyl ether, and methanol were added to the resulting residue to convert it into a powder, to obtain compound 581 (29.4 mg, 25.9%) as a white solid.
$^1$HNMR (DMSO-d$_6$) δ: 0.81 (3H, d, J=6.5 Hz), 0.98 (3H, d, J=6.5 Hz), 4.35 (1H, d, J=12.6 Hz), 4.63 (1H, m), 4.68 (1H, d, J=12.6 Hz), 4.80 (1H, s), 5.28 (1H, s), 6.34 (2H, s), 7.10-7.43 (8H, m), 7.81-7.83 (2H, m).
MS: m/z=404.95 [M+H]$^+$.

REFERENCE EXAMPLE 582

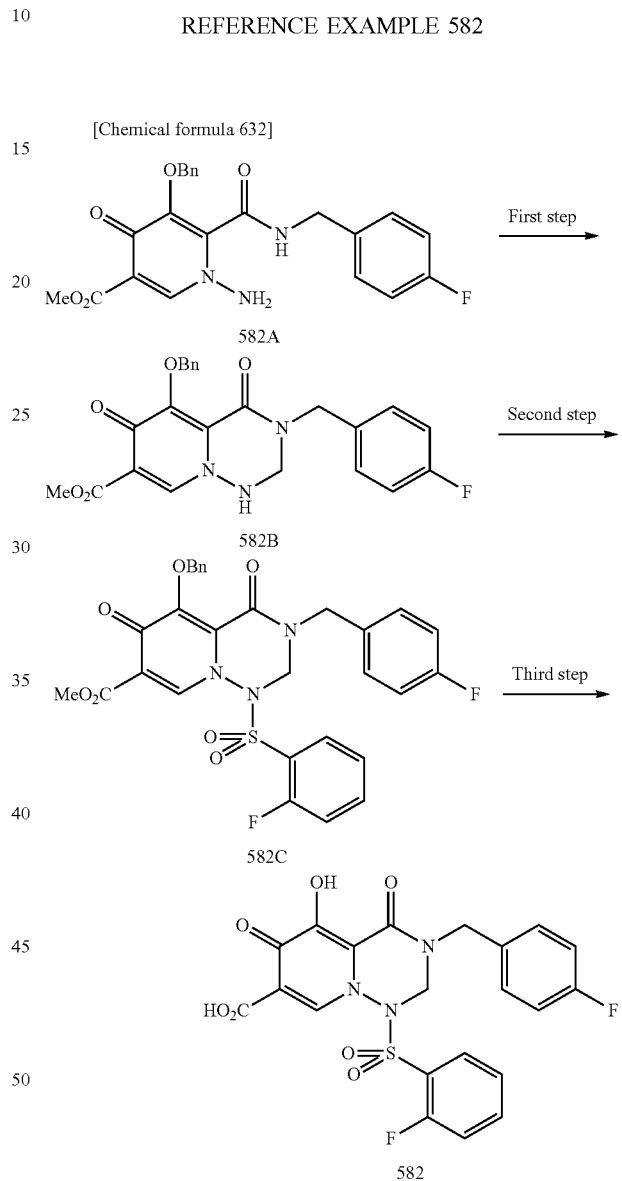

First Step
To an ethanol (4 mL) solution of compound 582A (200 mg, 0.470 mmol) synthesized according to the synthesis method of Reference example 65 was added paraformaldehyde (14.8 mg, 0.493 mmol) at room temperature, and the mixture was stirred at 140° C. for 45 minutes under microwave irradiation. The reaction solution was distilled off under reduced pressure, and the resulting residue was purified by silica gel column chromatography (ethyl acetate/n-hexane=90%→100%) to obtain compound 582B (173 mg, 84.0%) as a white solid.
MS: m/z=438.15 [M+H]$^+$.

483

Second Step

To a methylene chloride (4 mL) solution of compound 582B (173 mg, 0.396 mmol), 4-dimethylaminopyridine (5.6 mg, 0.046 mmol) and triethylamine (0.164 mL, 1.18 mmol) was added 2-fluorobenzenesulfonyl chloride (0.0790 mL, 0.597 mmol) at room temperature, and the mixture was stirred for 3 days. The reaction solution was distilled off under reduced pressure, and the resulting residue was purified by silica gel column chromatography (ethyl acetate/n-hexane=60%→80%) to obtain compound 582C (199 mg, 84.0%) as a white solid.

MS: m/z=596.15 [M+H]$^+$.

Third Step

To an acetic acid (2 mL) solution of compound 582C (162 mg, 0.272 mmol) was added 48% aqueous hydrogen bromide (2 mL) at room temperature, and the mixture was stirred at 100° C. for 20 minutes under microwave irradiation. The solvent was distilled off under reduced pressure, and diethyl ether and methanol were added to the resulting residue to convert it into a powder, to obtain compound 582 (160 mg, quant) as a yellow solid.

$^1$HNMR (DMSO-d$_6$) δ: 4.34 (1H, d, J=14.7 Hz), 4.59 (1H, d, J=14.7 Hz), 5.50 (1H, d, J=14.3 Hz), 5.81 (1H, d, J=14.3 Hz), 7.15-7.21 (2H, m), 7.35-7.40 (2H, m), 7.45-7.61 (2H, m), 7.78 (1H, m), 7.93 (1H, m), 8.42 (1H, s).

MS: m/z=492.10 [M+H]$^+$.

REFERENCE EXAMPLE 583, REFERENCE EXAMPLE 584

[Chemical formula 633]

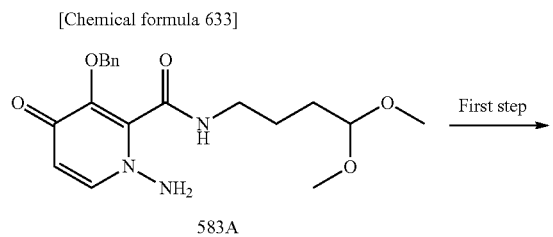

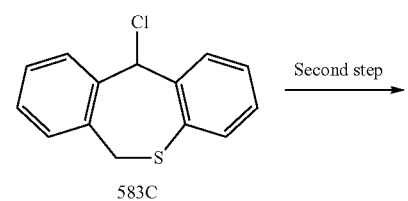

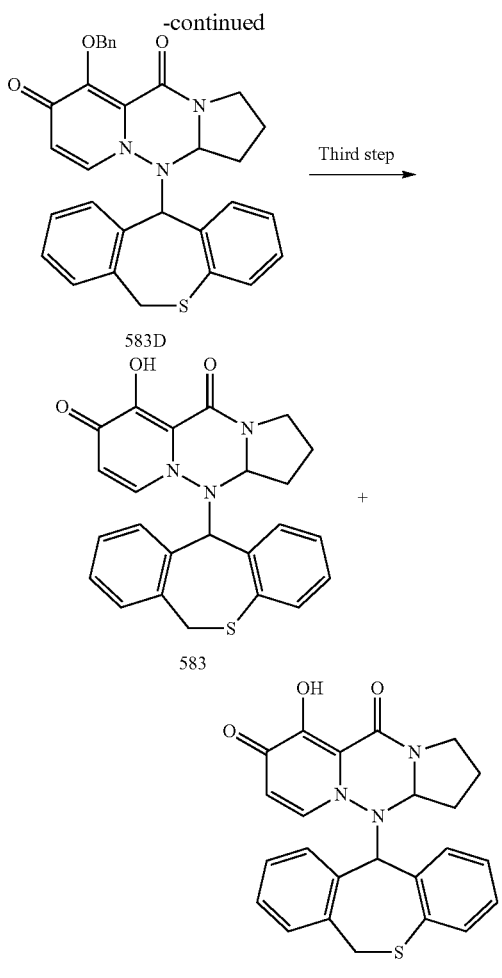

First Step

Compound 583A (3.0 g, 0.99 mmol) synthesized according to Reference example 95 was added to toluene (300 ml) and acetic acid (30.0 ml) to dissolve, and TsOH H2O (0.1 g, 0.526 mmol) was added at room temperature. The reaction mixture was stirred for 3 hours under heat-refluxing. After concentration under reduced pressure, the residue was purified by amino silica gel column chromatography (CHCl3/MeOH 50:1) to obtain compound 583B (1.8 g, 72.4%).

MS: m/z=312 [M+H]$^+$.

Second Step

Compound 583B (233 mg, 0.748 mmol) and compound 403C (197 mg, 0.8 mmol) were suspended in THF (7.5 ml), and NaHMDS (1.123 ml, 1.123 mmol, 1M-THF solution) was added at room temperature under nitrogen stream. After stirring at room temperature for 3 hours, water was added, and the mixture was extracted with ethyl acetate (2×30 mL). The ethyl acetate layer was washed with an aqueous saturated sodium chloride solution, and dried with sodium sulfate, and the solvent was distilled off under reduced pressure. The residue was purified by silica gel column chromatography (CHCl3/MeOH 20:1) to obtain compound 583D (90 mg, 23.1%).

MS: m/z=522 [M+H]$^+$.

Third Step

Compound 583D (90 mg, 0.173 mmol) was dissolved in a mixed solvent of MeOH (3 ml) and THF (3.00 ml), and 10% palladium-carbon (90 mg, 0.846 mmol) was added. The mixture was stirred for 24 hours under hydrogen (2 atm) stream, and insolubles were filtered. The residue was purified using HPLC (MeCN—H2O), and diastereomers were resolved.
First fraction (compound 583)
(15 mg, 20.1%)
MS: m/z=432 [M+H]$^+$.
Second fraction (compound 584)
(45 mg, 60.4%)
MS: m/z=432 [M+H]$^+$.

REFERENCE EXAMPLE 585

[Chemical formula 634]

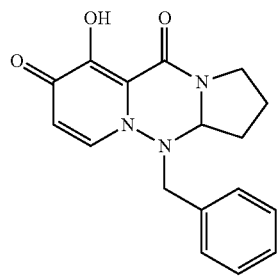

Compound 585 was synthesized by the same procedure as that of Reference example 403.

$^1$H-NMR (DMSO-d$_6$) δ: 1.87-2.28 (4H, m), 3.40-3.80 (3H, m), 4.32 (1H, d, J=12.96 Hz), 5.34 (1H, t, J=7.32 Hz), 5.65 (1H, d, J=7.63 Hz), 6.90 (1H, d, J=7.78 Hz), 7.10-7.35 (5H, m).
MS: m/z=312 [M+H]$^+$.

REFERENCE EXAMPLE 586

[Chemical formula 635]

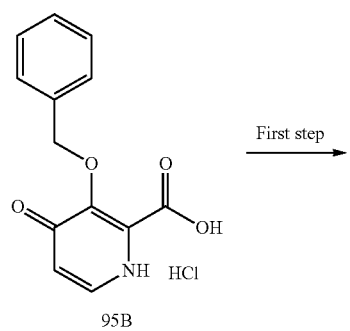
95B

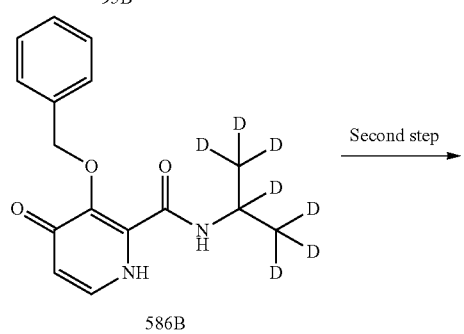
586B

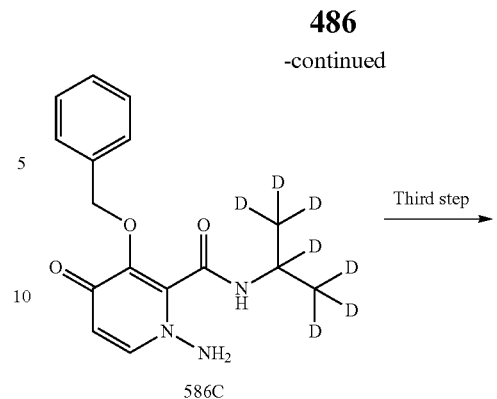
586C

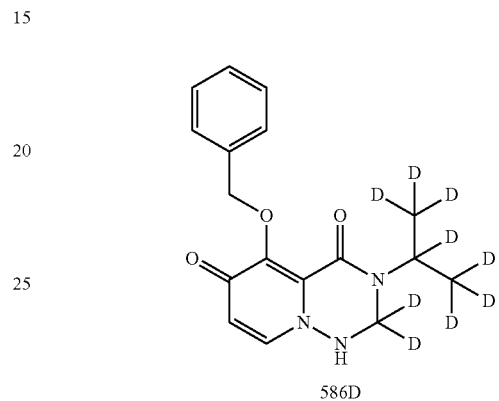
586D

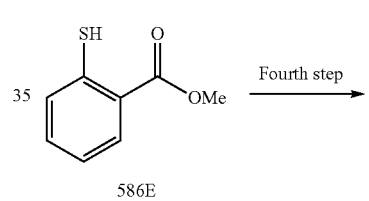
586E

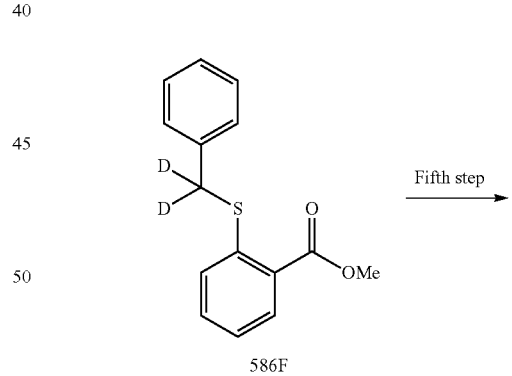
586F

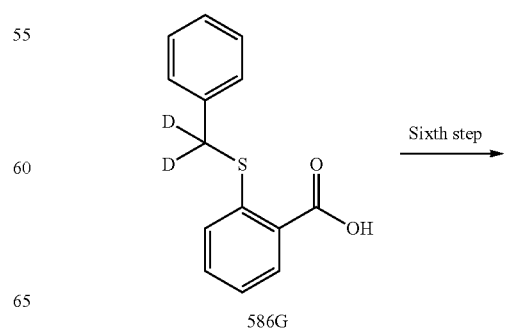
586G

487

-continued

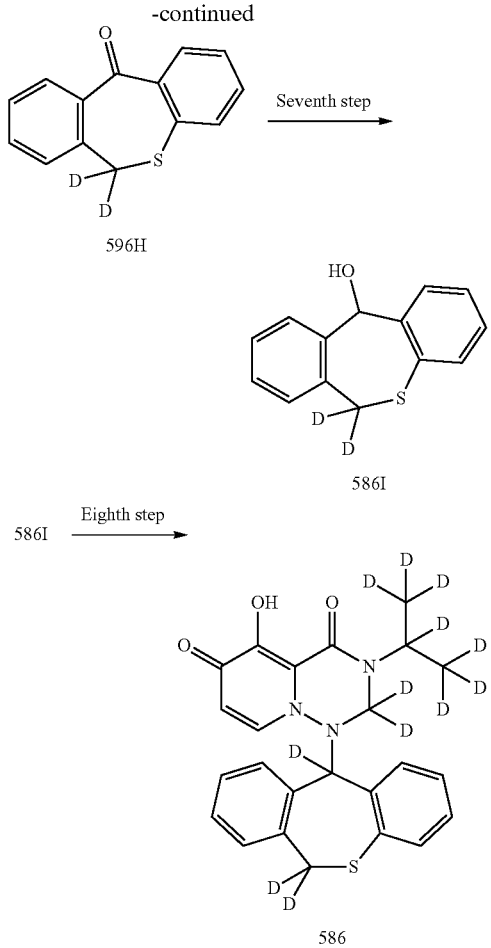

First Step
Compound 95B (2.29 g, 8.12 mmol) was dissolved in pyridine (10 ml), iso-propyl-D$_7$-amine hydrochloride (1.00 g, 9.75 mmol), 1H-benzo[d][1,2,3]triazol-1-ol (1.10 g, 8.12 mmol) and N1-((ethylimino)methylene)-N3,N3-dimethyl-propane-1,3-diamine hydrochloride (3.11 g, 16.2 mmol) were added, and the mixture was stirred at room temperature for 20 hours. The reaction solution was poured into water, the mixture was extracted with ethyl acetate, and the extract was dried with sodium sulfate. The solvent was distilled off under reduced pressure, and the resulting crude product was purified by silica gel column chromatography, and eluted with chloroform-methanol (97:3, v/v). To the resulting compound was added diethyl ether, and the precipitated residue was filtered to obtain 1.36 g of a white solid 586B.

Second Step
Compound 586B (1.36 g, 4.64 mmol) obtained in the first step was dissolved in dimethylformamide (20 ml), potassium carbonate (3.20 g, 23.2 mmol) was added, and the mixture was stirred at room temperature for 50 minutes. O-(2,4-dinitrophenyl)hydroxylamine (1.85 g, 9.27 mmol) was added, and the mixture was stirred at room temperature for 18 hours. To the reaction solution was added chloroform, the generated precipitate was removed by filtration, and the filtrate was concentrated under reduced pressure. The resulting crude product was purified by amino column chromatography, and eluted with chloroform-methanol (97:3, v/v) to obtain 835 mg of a colorless solid 586C.

$^1$H-NMR (CDCl$_3$) δ: 5.28 (2H, s), 5.63 (2H, s), 6.32 (1H, d, J=7.7 Hz), 7.10 (1H, brs), 7.42 (6H, m).

488

Third Step
Compound 586C (581 mg, 1.88 mmol) obtained in the second step and paraformaldehyde-D$_2$ (181 mg, 5.65 mmol) were added to ethanol (12 ml), and the mixture was stirred at 140° C. for 30 minutes under microwave irradiation. The reaction solution was concentrated under reduced pressure, and the resulting crude product was purified by amino column chromatography, and eluted with chloroform-methanol (97:3, v/v). To the resulting compound was added diethyl ether, and the precipitated residue was filtered to obtain 140 mg of white solid 586D.

$^1$H-NMR (CDCl$_3$) δ: 4.39 (2H, d, J=8.1 Hz), 5.36 (2H, s), 5.42 (1H, t, J=8.0 Hz), 6.37 (1H, d, J=7.6 Hz), 7.48 (6H, m).

Fourth Step
Compound 586E (972 mg, 5.78 mmol) was dissolved in tetrahydrofuran (10 ml), sodium hydride (60%, 231 mg, 5.78 mmol) and benzyl bromide-D$_2$ (1.00 g, 5.78 mmol) were added at 0° C., and the mixture was stirred at 60° C. for 30 minutes. The reaction solution was added to dilute hydrochloric acid, the mixture was extracted with ethyl acetate, and the organic layer was washed with an aqueous sodium bicarbonate solution. The solvent was distilled off under reduced pressure to obtain 1.48 g of a white solid 586F.

$^1$H-NMR (CDCl$_3$) δ: 3.95 (3H, s), 7.17-7.48 (8H, m), 8.00 (1H, dd, J=7.8, 1.3 Hz).

Fifth Step
Compound 586F (1.50 g, 5.76 mmol) obtained in the fourth step was dissolved in methanol (20 ml) and tetrahydrofuran (20 ml), a 2N aqueous sodium hydroxide solution (14.4 ml, 28.8 mmol) was added, and the mixture was stirred at room temperature for 3 hours. To the reaction solution was added dilute hydrochloric acid to make the solution acidic, the mixture was extracted with ethyl acetate, and the organic layer was washed with an aqueous saturated sodium chloride solution, and dried with sodium sulfate. The solvent was distilled off under reduced pressure, to the resulting compound were added n-hexane-ethyl acetate, and the precipitated residue was filtered to obtain 1.17 g of a white solid 586G.

$^1$H-NMR (CDCl$_3$) δ: 7.18-7.48 (8H, m), 8.11 (1H, dd, J=7.9, 1.6 Hz).

Sixth Step
To compound 586G (1.15 g, 4.67 mmol) obtained in the fifth step was added toluene (10 ml), dimethylformamide (0.100 ml, 1.29 mmol) and thionyl chloride (0.410 ml, 5.60 mmol) were added, and the mixture was stirred at 130° C. for 1.5 hours. After cooled to room temperature, the reaction solution was concentrated under reduced pressure. To the resulting compound was added n-hexane, and the precipitated residue was filtered to obtain 1.16 g of a white solid. To aluminum chloride (718 mg, 5.38 mmol) were added dichloromethane (10 ml) and nitromethane (0.5 ml), a dichloromethane solution (5 ml) of 500 mg of the compound obtained above was added at 0° C., and the mixture was stirred at room temperature for 5 hours. To the reaction solution was added an aqueous sodium hydroxide solution, the mixture was extracted with methylene chloride, and the organic layer was dried with sodium sulfate. The solvent was concentrated under reduced pressure, and the resulting crude product was purified by silica gel column chromatography, and eluted with n-hexane-ethyl acetate (4:1, v/v). To the resulting compound was added n-hexane, and the precipitated residue was filtered to obtain 155 mg of a pale yellow solid 586H.

$^1$H-NMR (CDCl$_3$) δ: 7.21-7.39 (6H, m), 7.46 (1H, td, J=7.5, 1.4 Hz), 7.59 (1H, dd, J=7.5, 1.4 Hz), 8.21 (1H, dd, J=8.0, 1.0 Hz).

Seventh Step

Compound 586H (150 mg, 0.657 mmol) obtained in the sixth step was dissolved in tetrahydrofuran (3 ml), lithium aluminum hydride-$D_4$ (13.8 mg, 0.329 mmol) was added at 0° C., and the mixture was stirred at room temperature for 2 hours. To the reaction solution was added dilute hydrochloric acid, the mixture was extracted with ethyl acetate, and dried with sodium sulfate, and the solvent was distilled off under reduced pressure. To the resulting compound were added n-hexane-dichloromethane, and the precipitated residue was filtered to obtain 114 mg of a white solid 586I.

$^1$H-NMR (CDCl$_3$) δ: 7.17 (6H, m), 7.40-7.52 (2H, m).

Eighth Step

Compound 586D (76.0 mg, 0.236 mmol) and 586I (54.5 mg, 0.236 mmmol) were dissolved in acetic acid (3.2 ml), and concentrated sulfuric acid (0.8 ml) was added dropwise under water-cooling. After the mixture was stirred at room temperature for 30 minutes, the mixture was poured into water, and extracted with ethyl acetate. The organic layer was dried with sodium sulfate, the solvent was distilled off under reduced pressure, to the resulting crude product were added ethyl acetate-diethyl ether, and the precipitated residue was filtered to obtain 32 mg of a white solid 586.

$^1$H-NMR (DMSO-d$_6$) δ: 5.57 (1H, d, J=7.3 Hz), 6.82-7.44 (9H, m).

MS: m/z=446 [M+H]$^+$

Using a commercially available heavy hydrogen reagent, and according to Reference example 586, compounds 587 to 591 were synthesized.

REFERENCE EXAMPLE 587

[Chemical formula 636]

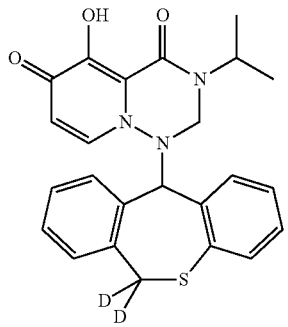

MS: m/z=436 [M+H]$^+$

REFERENCE EXAMPLE 588

[Chemical formula 637]

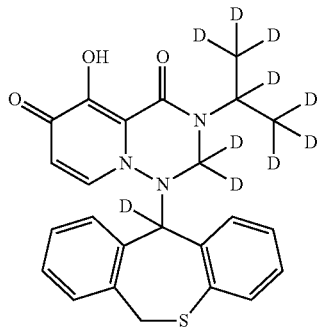

$^1$H-NMR (DMSO-d$_6$) δ: 3.87 (1H, d, J=13.4 Hz), 5.58 (1H, d, J=7.8 Hz), 5.60 (1H, d, J=12.6 Hz), 6.81-7.48 (9H, m).

REFERENCE EXAMPLE 589

[Chemical formula 638]

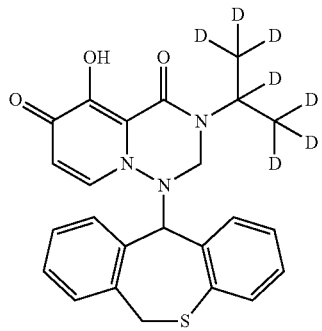

MS: m/z=441 [M+H]$^+$

REFERENCE EXAMPLE 590

[Chemical formula 639]

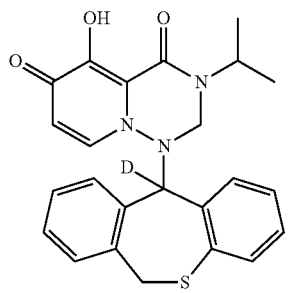

MS: m/z=435 [M+H]$^+$

REFERENCE EXAMPLE 591

[Chemical formula 640]

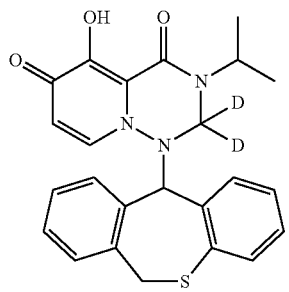

MS: m/z=436 [M+H]$^+$

REFERENCE EXAMPLE 592

[Chemical formula 641]

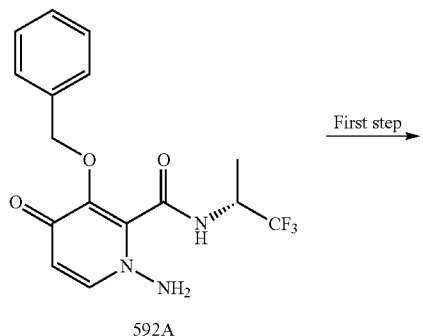

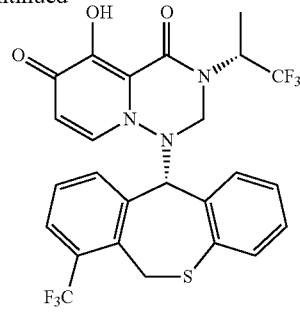

First Step

Compound 592A (22.8 g, 64.1 mmol) and 7-(trifluoromethyl)-6,11-dihydrodibenzo[b,e]thiepin-11-ol (19 g, 64.1 mmol) were suspended in 1,2-dichloroethane, dichloroacetic acid (13.2 mL, 160 mmol) was added, and the mixture was stirred for 2.5 hours under heat-refluxing. The mixture was cooled to room temperature and diluted with dichloromethane, then washed with an aqueous saturated sodium bicarbonate solution and an aqueous saturated sodium chloride solution, and dried. The solvent was distilled off, and the resulting solid was solidified by adding ethyl acetate-diisopropylether to obtain 32 g (containing 10% of 592A) of compound 592B.

MS: m/z=634 $[M+H]^+$.

Rf: 0.56 (AcOEt only).

Second Step

To an N,N-dimethylacetoamide (120 mL) solution of compound 592B (6.0 g, 9.47 mmol) were added 2-tert-butylimino2-diethylamino-1,3-dimethylperhydro-1,3,2-diazaphosphorine (16.5 mL, 56.8 mmol) and paraformaldehyde (569 mg, 18.9 mmol), and the mixture was stirred at room temperature for 3 hours. Subsequently, TsCl (3.61 g, 18.9 mmol) was slowly added, and the mixture was stirred for further 2 hours. To the reaction solution was added a 1N aqueous HCl solution, and the mixture was extracted with ethyl acetate two times. The organic layer was washed with water and an aqueous saturated sodium chloride solution, and dried. After the solvent was distilled off, the resulting solid was purified by silica gel column chromatography. The materials were eluted firstly with hexane-ethyl acetate (2:3, v/v) and, then eluted with hexane-ethyl acetate (1:9, v/v). Concentration of an objective fraction afforded 1.74 g of compound 592C as a pale yellow solid.

$^1$H-NMR (CDCl$_3$) δ: 1.14 (3H, d, J=7.2 Hz), 3.96 (1H, d, J=14.6 Hz), 4.34 (1H, d, J=13.2 Hz), 4.81 (1H, d, J=13.2 Hz), 5.17 (1H, s), 5.46 (1H, d, J=10.8 Hz), 5.56 (1H, d, J=10.8 Hz), 5.60 (1H, m), 5.82 (1H, d, J=14.6 Hz), 5.87 (1H, d, J=7.7 Hz), 6.56 (1H, d, J=7.2 Hz), 6.73 (1H, m), 7.04-7.11 (2H, m), 7.09 (1H, d, J=7.7 Hz), 7.29-7.38 (5H, m), 7.56 (2H, m), 7.78 (1H, m).

MS: m/z=646 $[M+H]^+$.

Rf: 0.65 (AcOEt only).

Third Step

To an N,N-dimethylacetoamide (34 mL) solution of compound 592C (1.7 g, 2.63 mmol) were added anhydrous LiCl (1.3 g, 31.6 mmol) and paraformaldehyde (569 mg, 18.9 mmol), and the mixture was stirred at 100° C. for 3 hours. To the reaction solution was added a 1N aqueous HCl solution, and the mixture was extracted with ethyl acetate two times. The organic layer was washed with water and an aqueous saturated sodium chloride solution, and dried. After the solvent was distilled off, the resulting solid was purified by silica gel column chromatography. The materials were eluted firstly with chloroform-methanol (99:1, v/v) and, then, with chloroform-methanol (96:4, v/v). An objective fraction was concentrated, and the resulting solid was solidified by adding ethyl acetate-diisopropylether to obtain 1.33 g of compound 592 as a colorless solid.

$^1$H-NMR (CDCl$_3$) δ: 1.21 (3H, d, J=7.2 Hz), 2.90 (1H, brs), 3.99 (1H, d, J=14.5 Hz), 4.45 (1H, d, J=13.2 Hz), 4.92 (1H, d, J=13.2 Hz), 5.24 (1H, s), 5.54 (1H, m), 5.83 (1H, d, J=7.72 Hz), 5.87 (1H, d, J=14.5 Hz), 6.70 (1H, d, J=7.1 Hz), 6.84 (1H, m), 7.07-7.16 (2H, m), 7.13 (1H, d, J=7.7 Hz), 7.36-7.42 (2H, m), 7.80 (1H, m).

MS: m/z=556 [M+H]$^+$.

Rf: 0.46 (CHCl3:MeOH=9:1).

REFERENCE EXAMPLE 593

[Chemical formula 642]

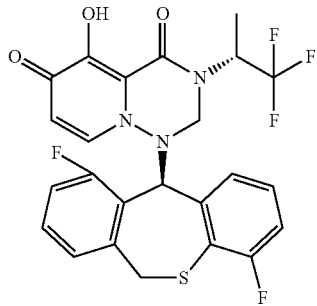

$^1$H-NMR (DMSO-d$_6$) δ: 1.35 (3H, d, J=7.0 Hz), 4.12 (1H, d, J=13.7 Hz), 4.49 (1H, d, J=13.1 Hz), 5.14 (1H, d, J=13.0 Hz), 5.20 (1H, m), 5.68 (3H, m), 6.74 (1H, d, J=7.5 Hz), 6.93 (1H, m), 7.12-7.46 (5H, m).

REFERENCE EXAMPLE 594

[Chemical formula 643]

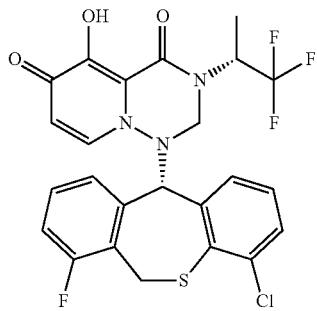

$^1$H-NMR (DMSO-d$_6$) δ: 1.21 (3H, d, J=7.2 Hz), 4.27 (1H, d, J=14.1 Hz), 4.61 (1H, d, J=13.4 Hz), 5.08 (1H, d, J=13.4 Hz), 5.47 (1H, m), 5.55 (1H, d, J=15.8 Hz), 5.75 (1H, d, J=7.6 Hz), 5.83 (1H, s), 6.97 (1H, t, J=7.8 Hz), 7.06 (1H, dd, J=7.8, 1.6 Hz), 7.21 (1H, d, J=7.7 Hz), 7.41 (4H, m).

MS: m/z=540 [M+H]$^+$.

REFERENCE EXAMPLE 595

[Chemical formula 644]

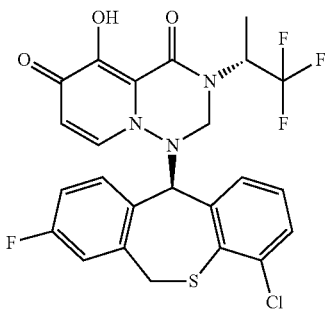

$^1$H-NMR (DMSO-d$_6$) δ: 1.42 (3H, d, J=7.2 Hz), 4.08 (1H, d, J=13.3 Hz), 4.49 (1H, d, J=13.1 Hz), 5.12 (1H, m), 5.16 (1H, d, J=13.1 Hz), 5.51 (1H, s), 5.70 (2H, m), 6.93 (1H, t, J=7.8 Hz), 7.05 (1H, dd, J=7.9, 1.3 Hz), 7.18 (2H, m), 7.37-7.43 (3H, m).

MS: m/z=540 [M+H]$^+$.

REFERENCE EXAMPLE 596

[Chemical formula 645]

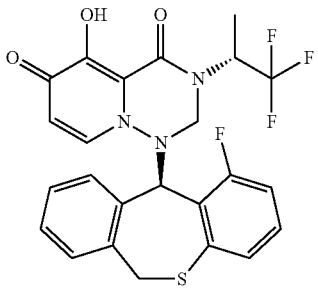

$^1$H-NMR (DMSO-d$_6$) δ: 1.35 (3H, d, J=7.2 Hz), 3.90 (1H, d, J=12.8 Hz), 4.42 (1H, d, J=13.1 Hz), 5.12 (1H, m), 5.14 (1H, d, J=12.5 Hz), 5.36 (1H, s), 5.58 (1H, d, J=13.4 Hz), 5.71 (1H, d, J=7.5 Hz), 6.70 (1H, td, J=8.3, 2.6 Hz), 6.96-7.06 (2H, m), 7.21 (1H, d, J=7.6 Hz), 7.26 (2H, d, J=3.5 Hz), 7.42 (2H, m).

MS: m/z=506 [M+H]$^+$.

REFERENCE EXAMPLE 597

[Chemical formula 646]

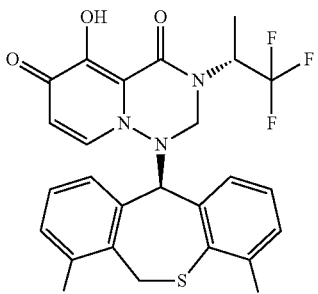

$^1$H-NMR (DMSO-d$_6$) δ: 1.38 (3H, d, J=7.2 Hz), 4.23 (1H, d, J=13.9 Hz), 4.52 (1H, d, J=13.1 Hz), 5.10 (1H, m), 5.12

(1H, d, J=12.8 Hz), 5.44 (1H, d, J=14.2 Hz), 5.52 (1H, s), 5.69 (1H, d, J=7.6 Hz), 6.91 (1H, t, J=7.8 Hz), 7.04 (1H, d, J=7.2 Hz), 7.15 (2H, m), 7.28-7.40 (3H, m).

MS: m/z=540 [M+H]⁺.

REFERENCE EXAMPLE 598

[Chemical formula 647]

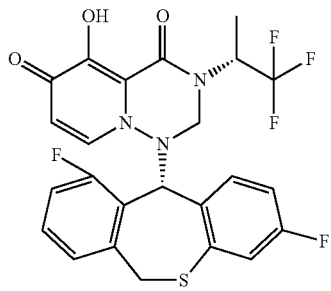

¹H-NMR (DMSO-d₆) δ: 1.12 (3H, d, J=7.3 Hz), 4.02 (1H, d, J=13.1 Hz), 4.50 (1H, d, J=13.4 Hz), 5.07 (1H, d, J=13.4 Hz), 5.50 (1H, m), 5.64 (1H, d, J=13.4 Hz), 5.69 (1H, s), 5.75 (1H, d, J=7.5 Hz), 6.73 (1H, td, J=8.5, 2.6 Hz), 7.02 (2H, m), 7.21 (2H,m), 7.35 (1H, d, J=7.0 Hz), 7.47 (1H, t, J=6.8 Hz).

MS: m/z=524 [M+H]⁺.

REFERENCE EXAMPLE 599

[Chemical formula 648]

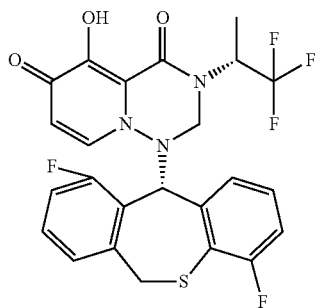

¹H-NMR (DMSO-d₆) δ: 1.10 (3H, d, J=7.5 Hz), 4.11 (1H, d, J=13.6 Hz), 4.51 (1H, d, J=13.4 Hz), 5.05 (1H, d, J=13.3 Hz), 5.49 (1H, m), 5.67 (3H, m), 6.80 (1H, d, J=7.8 Hz), 6.92 (1H, dd, J=13.6, 7.7 Hz), 7.11-7.24 (3H, m), 7.36 (1H, d, J=7.5 Hz), 7.47 (1H, t, J=6.9 Hz).

MS: m/z=524 [M+H]⁺.

REFERENCE EXAMPLE 600

[Chemical formula 649]

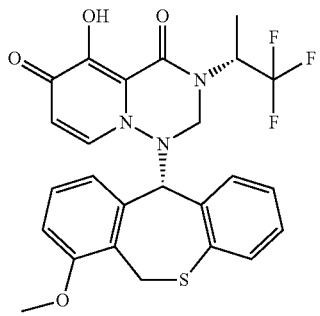

¹H-NMR (DMSO-d₆) δ: 1.19 (3H, d, J=7.2 Hz), 3.86 (3H, s), 4.22 (1H, d, J=13.3 Hz), 4.49 (1H, d, J=13.1 Hz), 5.06 (1H, d, J=13.3 Hz), 5.34 (1H, d, J=13.3 Hz), 5.46 (1H, m), 5.55 (1H, s), 5.65 (1H, d, J=7.8 Hz), 6.84 (1H, t, J=7.2 Hz), 6.94 (1H, d, J=7.8 Hz), 7.14 (6H, m).

MS: m/z=518 [M+H]⁺.

REFERENCE EXAMPLE 601

[Chemical formula 650]

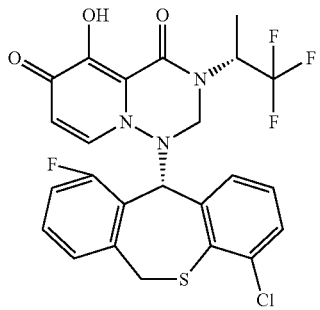

¹H-NMR (DMSO-d₆) δ: 1.09 (3H, d, J=7.1 Hz), 4.15 (1H, d, J=13.6 Hz), 4.53 (1H, d, J=13.6 Hz), 5.07 (1H, d, J=14.0 Hz), 5.48 (1H, m), 5.70 (3H, m), 6.93 (2H, m), 7.14-7.26 (2H, m), 7.35-7.51 (3H, m).

MS: m/z=540 [M+H]⁺.

REFERENCE EXAMPLE 602

[Chemical formula 651]

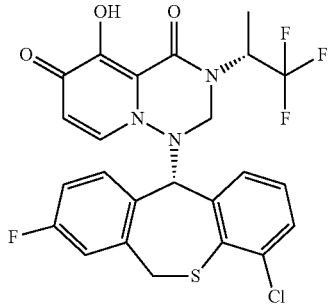

¹H-NMR (DMSO-d₆) δ: 1.18 (3H, d, J=7.0 Hz), 4.03 (1H, d, J=14.5 Hz), 4.47 (1H, d, J=13.6 Hz), 5.03 (1H, d, J=13.1 Hz), 5.46 (1H, m), 5.68-5.74 (3H, m), 6.94 (2H, m), 7.10-7.17 (2H, m), 7.34-7.40 (2H, m), 7.63 (1H, m).

MS: m/z=540 [M+H]⁺.

REFERENCE EXAMPLE 603

[Chemical formula 652]

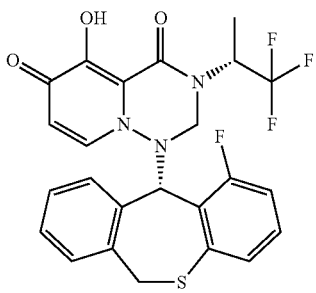

¹H-NMR (DMSO-d₆) δ: 1.14 (3H, t, J=6.3 Hz), 3.90 (1H, d, J=13.6 Hz), 4.39 (1H, d, J=13.4 Hz), 5.06 (1H, d, J=13.0 Hz), 5.46 (1H, m), 5.63 (1H, s), 5.64 (1H, d, J=13.2 Hz), 5.73 (1H, d, J=7.6 Hz), 6.73 (1H, td, J=8.3, 2.7 Hz), 6.96-7.04 (2H, m), 7.21 (1H, d, J=7.6 Hz), 7.27 (1H, dt, J=10.3, 3.7 Hz), 7.43 (2H, m), 7.53 (1H, d, J=7.3 Hz).
MS: m/z=506 [M+H]⁺.

REFERENCE EXAMPLE 604

[Chemical formula 653]

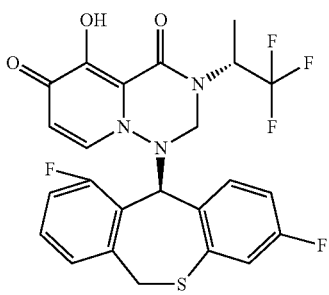

¹H-NMR (DMSO-d₆) δ: 1.35 (3H, d, J=7.2 Hz), 4.01 (1H, d, J=13.4 Hz), 4.47 (1H, d, J=13.1 Hz), 5.17 (1H, d, J=12.7 Hz), 5.20 (1H, m), 5.63 (1H, d, J=13.7 Hz), 5.66 (1H, s), 5.72 (1H, d, J=7.6 Hz), 6.72 (1H, td, J=8.3, 2.8 Hz), 6.92 (1H, dd, J=8.6, 6.0 Hz), 7.04 (1H, dd, J=10.0, 2.5 Hz), 7.19 (2H, d, J=7.0 Hz), 7.30 (1H, d, J=7.0 Hz), 7.43 (1H, m).
MS: m/z=524 [M+H]⁺.

REFERENCE EXAMPLE 605

[Chemical formula 654]

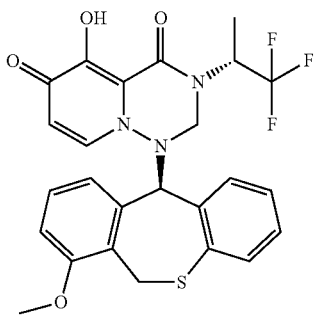

¹H-NMR (DMSO-d₆) δ: 1.37 (3H, d, J=7.3 Hz), 3.85 (3H, s), 4.23 (1H, d, J=13.6 Hz), 4.50 (1H, d, J=12.8 Hz), 5.13 (1H, d, J=12.8 Hz), 5.14 (1H, m), 5.28 (1H, s), 5.30 (1H, d, J=12.4 Hz), 5.63 (1H, d, J=7.8 Hz), 6.80-7.25 (8H, m).
MS: m/z=518 [M+H]⁺.

REFERENCE EXAMPLE 606

[Chemical formula 655]

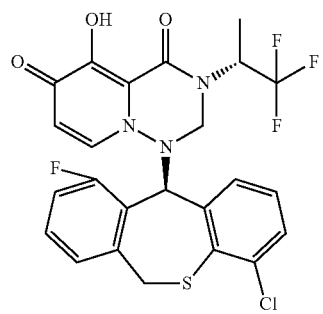

¹H-NMR (DMSO-d₆) δ: 1.35 (3H, d, J=7.5 Hz), 4.13 (1H, d, J=13.9 Hz), 4.48 (1H, d, J=13.1 Hz), 5.14 (1H, d, J=12.5 Hz), 5.20 (1H, m), 5.69 (3H, m), 6.90 (2H, m), 7.18 (2H, m), 7.32 (1H, d, J=8.1 Hz), 7.43 (2H, m).
MS: m/z=540 [M+H]⁺.

REFERENCE EXAMPLE 607

[Chemical formula 656]

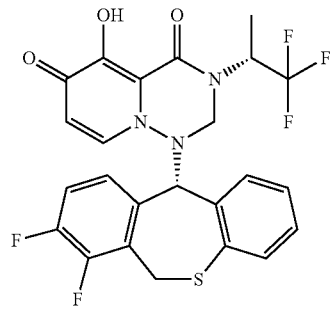

MS: m/z=524 [M+H]⁺.

REFERENCE EXAMPLE 608

[Chemical formula 657]

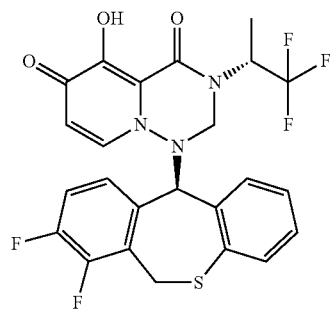

MS: m/z=524 [M+H]⁺.

REFERENCE EXAMPLE 609
[Chemical formula 658]
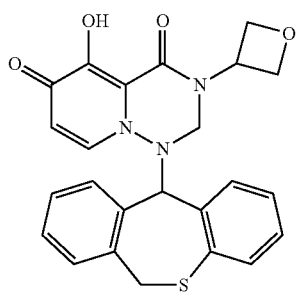
MS: m/z=448 [M+H]⁺. RT=1.54 min.
REFERENCE EXAMPLE 610
[Chemical formula 659]
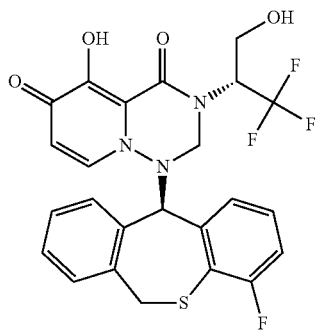
MS: m/z=522 [M+H]⁺. RT=1.84 min.
REFERENCE EXAMPLE 611
[Chemical formula 660]
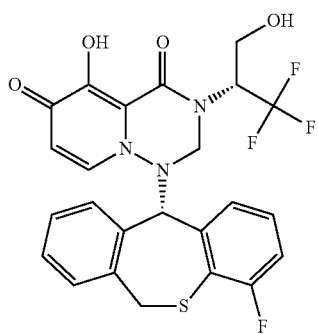
MS: m/z=522 [M+H]⁺. RT=1.76 min.
REFERENCE EXAMPLE 612
[Chemical formula 661]
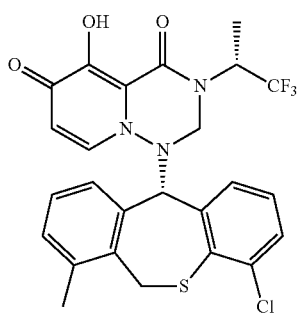
MS: m/z=536 [M+H]⁺
REFERENCE EXAMPLE 613
[Chemical formula 662]
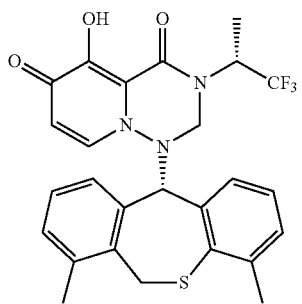
MS: m/z=516 [M+H]⁺
REFERENCE EXAMPLE 614
[Chemical formula 663]
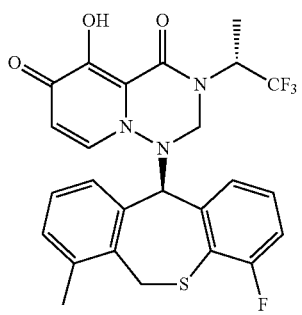
MS: m/z=520 [M+H]⁺

REFERENCE EXAMPLE 615

[Chemical formula 664]

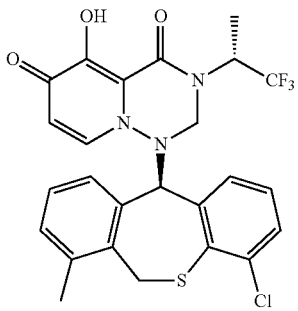

MS: m/z=536 [M+H]+

REFERENCE EXAMPLE 616

[Chemical formula 665]

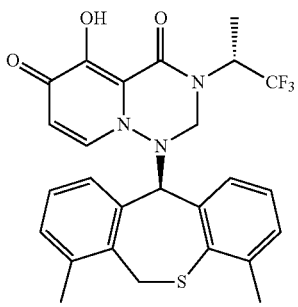

MS: m/z=516 [M+H]+

REFERENCE EXAMPLE 617

[Chemical formula 666]

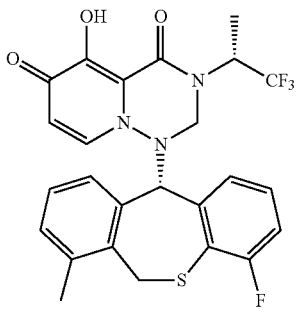

MS: m/z=520 [M+H]+

REFERENCE EXAMPLE 618

[Chemical formula 667]

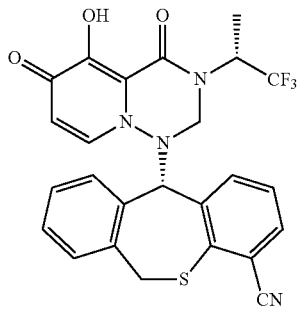

$^1$H-NMR (CDCl$_3$) δ: 1.15 (3H, d, J=7.5 Hz), 3.82 (1H, d, J=13.7 Hz), 4.49 (1H, d, J=13.1 Hz), 4.91 (1H, d, J=13.7 Hz), 5.18 (1H, s), 5.51 (1H, m), 5.71 (1H, d, J=13.1 Hz), 5.88 (1H, d, J=7.5 Hz), 6.94 (2H, m), 7.14-7.52 (6H, m).
MS: m/z=513.20 [M+H]+.

REFERENCE EXAMPLE 619

[Chemical formula 668]

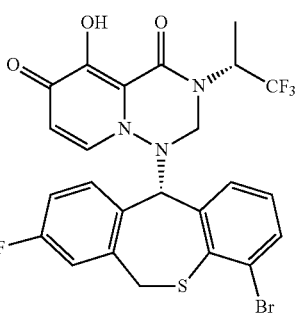

$^1$H-NMR (CDCl$_3$) δ: 1.19 (3H, d, J=7.3 Hz), 2.00 (1H, brs), 3.65 (1H, d, J=13.6 Hz), 4.46 (1H, d, J=13.3 Hz), 4.87 (1H, d, J=13.3 Hz), 5.17 (1H, s), 5.51 (1H, m), 5.74 (1H, d, J=13.6 Hz), 5.86 (1H, d, J=7.7 Hz), 6.68-6.75 (2H, m), 6.98 (1H, dt, J=2.6, 8.3 Hz), 7.10 (1H, d, J=7.7 Hz), 7.11 (1H, dd, J=2.6, 8.3 Hz), 7.17 (1H, dd, J=5.3, 8.3 Hz), 7.45 (1H, dd, J=2.6, 6.9 Hz).
MS: m/z=585 [M+H]+.

REFERENCE EXAMPLE 620

[Chemical formula 669]

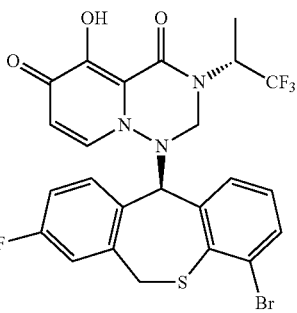

¹H-NMR (CDCl₃) δ: 1.42 (3H, d, J=7.3 Hz), 2.00 (1H, brs), 3.63 (1H, d, J=13.6 Hz), 4.54 (1H, d, J=12.6 Hz), 5.05 (1H, d, J=12.6 Hz), 5.24 (1H, s), 5.37 (1H, m), 5.77 (1H, d, J=13.6 Hz), 5.79 (1H, d, J=7.6 Hz), 6.68 (1H, d, J=7.3 Hz), 6.73 (1H, dd, J=2.1, 7.3 Hz), 6.97 (1H, dt, J=2.6, 8.4 Hz), 7.04 (1H, dd, J=2.6, 8.4 Hz), 7.16 (1H, d, J=7.6 Hz), 7.16 (1H, m), 7.42 (1H, dd, J=2.1, 7.3 Hz).

MS: m/z=585 [M+H]⁺.

REFERENCE EXAMPLE 621

[Chemical formula 670]

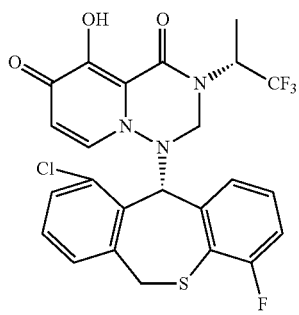

MS: m/z=540 [M+H]⁺.

REFERENCE EXAMPLE 622

[Chemical formula 671]

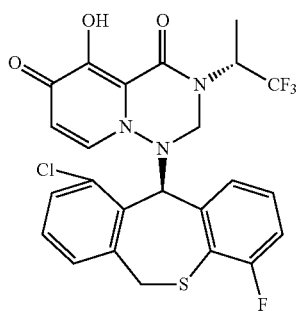

MS: m/z=540 [M+H]⁺.

REFERENCE EXAMPLE 623

[Chemical formula 672]

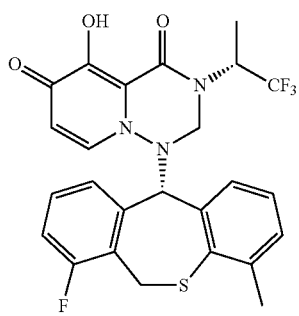

¹H-NMR (CDCl₃) δ: 1.19 (3H, d, J=7.3 Hz), 2.10 (1H, brs), 2.25 (3H, s), 4.21 (1H, d, J=13.6 Hz), 4.48 (1H, d, 13.3 Hz), 4.89 (1H, d, J=13.3 Hz), 5.18 (1H, s), 5.37 (1H, dd, J=2.0, 13.6 Hz), 5.52 (1H, s), 5.80 (1H, d, J=7.8 Hz), 6.57 (1H, d, J=7.2 Hz), 6.75 (1H, t, J=7.6 Hz), 6.97-7.04 (2H, m), 7.12 (1H, d, J=7.8 Hz), 7.17-7.24 (2H, m).

MS: m/z=520 [M+H]⁺.

REFERENCE EXAMPLE 624

[Chemical formula 673]

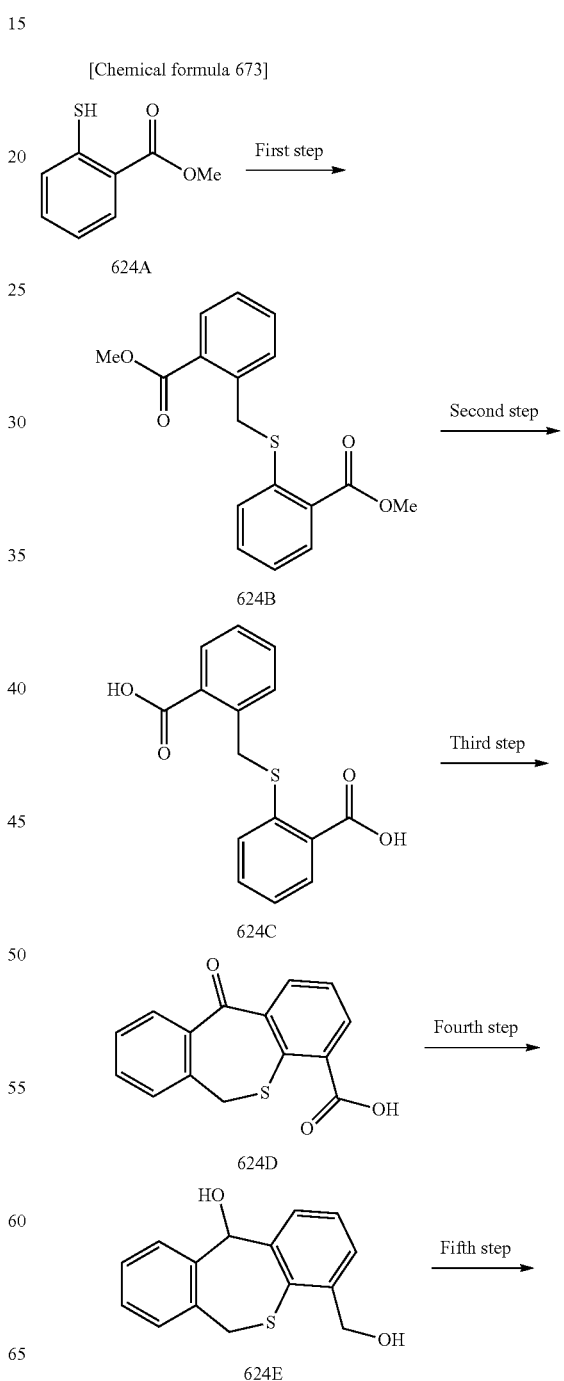

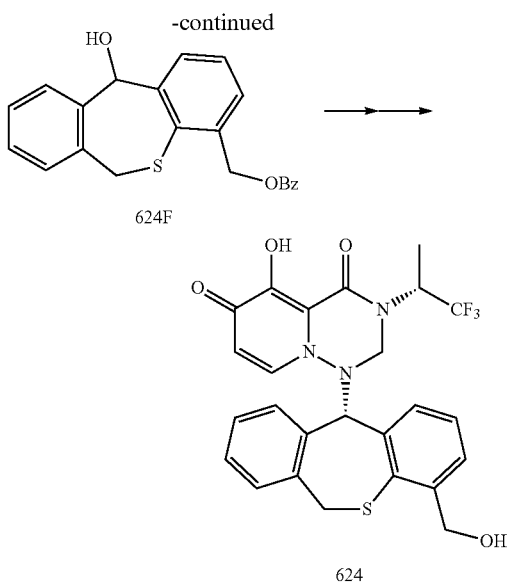

First Step

Compound 624A (14.7 g, 87.0 mmol) and methyl 2-(bromomethyl)benzoate (20.0 g, 87.0 mmol) were dissolved in DMF (200 ml), cesium carbonate (42.7 g, 131 mmol) was added, and the mixture was stirred at room temperature for 2 hours. The reaction solution was filtered, ethyl acetate was added to the filtrate, and the mixture was washed with water and an aqueous saturated sodium bicarbonate solution. After the organic layer was dried with sodium sulfate, the solvent was distilled off under reduced pressure. The resulting solid was crushed by adding hexane, and filtered out to obtain 26.2 g of a white solid 624B.

$^1$H-NMR (CDCl$_3$) δ: 3.89 (6H, s), 4.64 (2H, s), 7.14-7.52 (6H, m), 7.94 (2H, t, J=7.1 Hz).

Second Step

Compound 624B (26.2 g, 83.0 mmol) was dissolved in methanol (200 ml) and THF (200 ml), a 2N aqueous sodium hydroxide solution (207 ml, 414 mmol) was added at room temperature, and the mixture was stirred at room temperature for 3 days. To the reaction solution was added dilute hydrochloric acid to make the solution acidic, and the generated white precipitate was filtered and dried to obtain 23.1 g of a white solid 624C.

$^1$H-NMR (DMSO-d$_6$) δ: 4.58 (2H, s), 7.20 (1H, td, J=7.2, 1.3 Hz), 7.35-7.54 (5H, m), 7.85 (2H, t, J=6.9 Hz).

Third Step

To compound 624C (2.66 g, 9.23 mmol) was added polyphosphoric acid (30 g), and the mixture was stirred at 120° C. for 3 hours. After the reaction solution was cooled to room temperature, water was added, the mixture was extracted with ethyl acetate, and the organic layer was dried with sodium sulfate. The solvent was distilled off under reduced pressure to obtain 2.37 g of a pale brown solid 624D.

$^1$H-NMR (CDCl$_3$) δ: 4.05 (2H, s), 7.27 (1H, d, J=7.4 Hz), 7.36-7.42 (2H, m), 7.52 (1H, td, J=7.6, 1.3 Hz), 7.62 (1H, dd, J=7.5, 1.1 Hz), 8.23 (1H, dd, J=7.6, 1.7 Hz), 8.52 (1H, dd, J=8.1, 1.7 Hz).

Fourth Step

To compound 624D (96.0 mg, 0.355 mmol) was added toluene (2 ml), DMF (0.028 mmol) and thionyl chloride (0.131 ml, 1.80 mmol) were added, and the mixture was stirred at 130° C. for 1 hour. After the solvent was distilled off under reduced pressure, the substance was dissolved in methanol (1 ml) and THF (1 ml), sodium borohydride (100 mg, 2.64 mmol) was added, and the mixture was stirred at room temperature for 1 hour. To the reaction solution was added an aqueous ammonium chloride solution, the mixture was extracted with ethyl acetate, and the organic layer was dried with sodium sulfate. The solvent was distilled off under reduced pressure, and the resulting crude product was purified by silica gel column chromatography and eluted with n-hexane-ethyl acetate (1:1, v/v) to obtain 41 mg of a white solid 624E.

$^1$H-NMR (CDCl$_3$) δ: 2.09 (1H, t, J=6.3 Hz), 2.79 (1H, d, J=3.7 Hz), 4.43 (2H, d, J=1.3 Hz), 4.76 (2H, m), 6.33 (1H, d, J=3.0 Hz), 7.18-7.34 (5H, m), 7.52-7.56 (2H, m).

Fifth Step

Compound 624E (40.0 mg, 0.155 mmol) was dissolved in dichloromethane (2 ml), pyridine (61.2 mg, 0.774 mmol) and benzoyl chloride (21.8 mg, 0.155 mmol) were added, and the mixture was stirred at room temperature for 2 hours. To the reaction solution was added water, the mixture was extracted with ethyl acetate, and the organic layer was dried with sodium sulfate. The solvent was distilled off under reduced pressure, and the resulting crude product was purified by silica gel column chromatography and eluted with n-hexane-ethyl acetate (1:1, v/v) to obtain 30 mg of a white solid 624F.

$^1$H-NMR (CDCl$_3$) δ: 2.83 (1H, d, J=3.4 Hz), 4.27 (1H, d, J=13.9 Hz), 4.41 (1H, d, J=14.0 Hz), 5.42 (2H, s), 6.35 (1H, d, J=2.9 Hz), 7.12-7.58 (5H, m), 8.06 (2H, dd, J=8.2, 1.4 Hz).

Hereinbelow, according to Reference example 592, compound 624 was synthesized by the same procedure.

MS: m/z=518 [M+H]$^+$.

REFERENCE EXAMPLE 625

[Chemical formula 674]

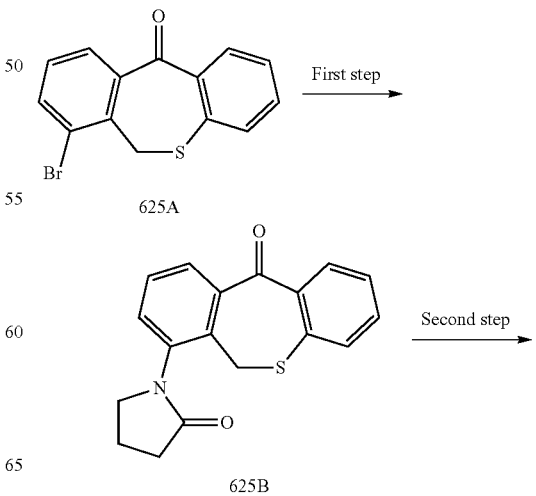

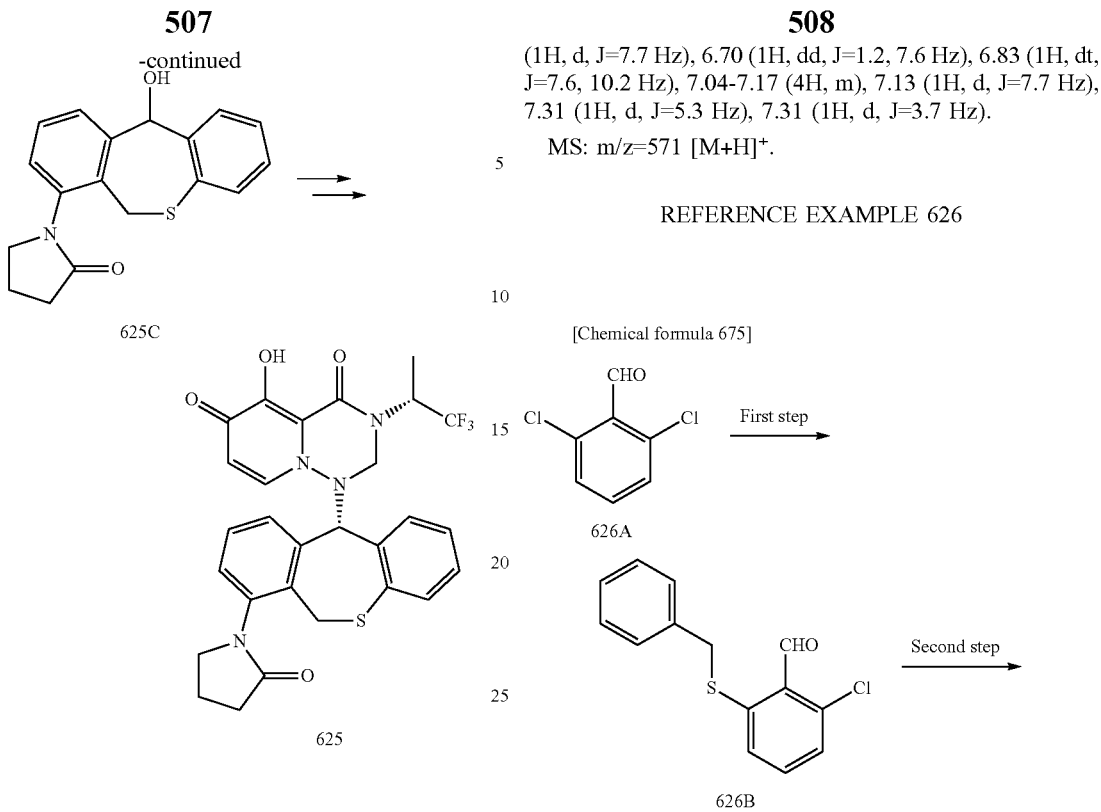

(1H, d, J=7.7 Hz), 6.70 (1H, dd, J=1.2, 7.6 Hz), 6.83 (1H, dt, J=7.6, 10.2 Hz), 7.04-7.17 (4H, m), 7.13 (1H, d, J=7.7 Hz), 7.31 (1H, d, J=5.3 Hz), 7.31 (1H, d, J=3.7 Hz).

MS: m/z=571 [M+H]$^+$.

REFERENCE EXAMPLE 626

[Chemical formula 675]

First Step

To a toluene (3.3 ml) solution of compound 625A (700 mg, 2.29 mmol) were added 2-pyrrolidone (264 μL, 3.44 mmol), N,N'-dimethylethylene diamine (49 μL, 0.46 mmol), copper iodide (87 mg, 0.46 mmol), and potassium carbonate (634 mg, 4.59 mmol) under nitrogen stream, and the mixture was stirred at 110° C. for 8 hours. After cooled to room temperature, the reaction solution was directly purified by silica gel column chromatography. Elution with chloroform-methanol (19:1, v/v) and concentration of an objective fraction afforded 620 mg of compound 625B as a gray white solid.

MS: m/z=310 [M+H]$^+$.

Rf: 0.50 (CHCl3:MeOH=19:1).

Second Step

A THF (8 mL) solution of compound 625B (620 mg, 2.0 mmol) was added to an ice-cooled MeOH (4 ml) solution of NaBH4 (227 mg, 6.0 mmol), and the mixture was stirred for 1 hour. After water was added, followed by extraction with ethyl acetate two times, the organic layer was washed with an aqueous saturated sodium chloride solution, and dried. The solvent was distilled off, and the resulting solid was purified by silica gel column chromatography. Elution with chloroform-methanol (19:1, v/v) and concentration of an objective fraction afforded 621 mg of compound 625C as a colorless solid.

$^1$H-NMR (CDCl$_3$) δ: 2.26 (2H, m, J=6.9, 7.2, 8.0 Hz), 2.61 (2H, t, J=8.0 Hz), 2.89 (1H, d, J=2.9 Hz), 3.77 (2H, m, J=6.9, 7.2, 9.7 Hz), 4.24 (1H, brs), 6.13 (1H, s), 7.02-7.14 (4H, m), 7.29 (1H, t, J=7.8 Hz), 7.46 (1H, d, J=7.2 Hz), 7.56 (1H, d, J=6.0 Hz).

Rf: 0.30 (CHCl3:MeOH=19:1).

Hereinbelow, according to Reference example 592, compound 625 was synthesized by the same procedure.

$^1$H-NMR (CDCl$_3$) δ: 1.18 (3H, d, J=7.32), 2.33 (2H, m), 2.65 (2H, t, J=8.1 Hz), 3.65 (1H, d, J=14.2 Hz), 3.77-3.95 (2H, m), 4.60 (1H, d, J=13.4 Hz), 4.87 (1H, d, J=13.4 Hz), 5.16 (1H, s), 5.48 (1H, m), 5.50 (1H, d, J=14.2 Hz), 5.82

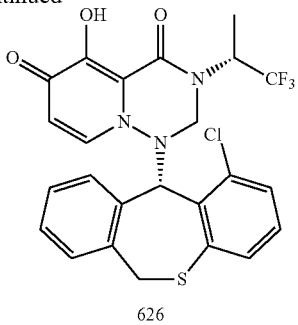

626

First Step

A N,N-dimethylformamide (200 mL) solution of compound 626A (20.0 g, 114 mmol) and phenylmethanethiol (14.19 g, 114 mmol) was cooled to 1 to 3° C., and t-butoxypotassium (14.11 g, 126 mmol) was put over 20 minutes while the same temperature was retained. After the reaction solution was stirred at the same temperature for 30 minutes, temperature was gradually raised to room temperature, and the mixture was stirred at the same temperature for 2 hours. Ice water was added, and the mixture was extracted with ethyl acetate. The extract was washed with water three times, washed with an aqueous saturated sodium chloride solution, and dried. The solvent was distilled off, and the resulting oil was solidified by adding diisopropyl ether to obtain 15.0 g of compound 626B.

$^1$H-NMR (CDCl$_3$) δ: 4.16 (2H, s), 7.19-7.41 (8H, m), 10.61 (1H, s).

MS: m/z=263 [M+H]$^+$.

Second Step

Compound 626B (6.9 g, 26.3 mmol) was suspended in 1,4-dioxane (60 mL), SULFAMIC ACID (5.61 g, 57.8 mmol) was added, and the mixture was cooled to 1 to 3° C. To the reaction solution was added dropwise an aqueous solution (20 ml) of sodium hypochlorite (5.23 g, 57.8 mmol) over 10 minutes while temperature was retained at the same temperature. After the reaction solution was stirred at the same temperature for 30 minutes, temperature was gradually raised to room temperature, and the mixture was stirred at the same temperature for 2 hours. To the reaction solution was added ice water, and the mixture was extracted with ethyl acetate. The extract was washed with an aqueous saturated sodium chloride solution, and dried. The solvent was distilled off, and the resulting oil was solidified by adding diisopropyl ether to obtain 7.1 g of compound 626C.

$^1$H-NMR (DMSO-d6) δ: 3.99 (1H, d, J=11.2 Hz), 4.41 (1H, d, J=11.2 Hz), 7.11 (2H, brs), 7.33 (3H, brs), 7.49 (1H, d, J=7.2 Hz), 7.60 (1H, t, J=7.2 Hz), 7.73 (1H, d, J=7.2 Hz), 10.4 (1H, brs).

MS: m/z=295 [M+H]$^+$.

Third Step

Compound 626C (8.0 g, 27.1 mmol) was suspended in acetonitrile (40 mL), and sodium iodide (12.1 g, 81.0 mmol) was added. Into the reaction solution was put BF3 etherate (5.16 ml, 40.7 mmol) at once, and the mixture was stirred at the same temperature for 30 minutes. To the reaction solution was added ice water and a 10% aqueous sodium sulfite solution, and the mixture was extracted with ethyl acetate. The extract was washed with an aqueous saturated sodium chloride solution, and dried. The solvent was distilled off, and the resulting oil was solidified by adding diisopropyl ether to obtain 5.0 g of compound 626D.

$^1$H-NMR (CDCl$_3$) δ: 4.11 (2H, s), 7.22-7.34 (8H, m).

MS: m/z=277 [M−H]$^+$.

Fourth Step

Compound 626D (2.5 g, 9.0 mmol) was put into 20 g of polyphosphoric acid heated to 120° C. over 60 minutes. Thereafter, the mixture was stirred at the same temperature for 6 hours. After the reaction solution was cooled to room temperature, and the mixture was put into ice water and extracted with ethyl acetate. The extract was washed with an aqueous saturated sodium chloride solution, and dried. The solvent was distilled off, and the resulting oil was purified by silica gel column chromatography. The materials were eluted firstly with n-hexane and, then, with n-hexane-ethyl acetate (1:1, v/v). An objective fraction was concentrated, and solidified by adding hexane to obtain 710 mg of compound 626E as a white solid.

$^1$H-NMR (CDCl$_3$) δ: 4.05 (2H, s), 7.20-7.25 (2H, m), 7.32-7.37 (2H, m), 7.46 (1H, d, J=7.2 Hz), 7.59 (1H, d, J=7.2 Hz), 8.16 (1H, d, J=7.2 Hz).

MS: m/z=261 [M−H]$^+$.

Fifth Step

A tetrahydrofuran (10 mL) solution of compound 626E (730 mg, 2.80 mmol) was cooled to 1 to 3° C., and lithium borohydride (61 mg, 2.80 mmol) was put while the same temperature was retained. The mixture was stirred at the same temperature for 30 minutes. To the reaction solution was added ice water and a 10% aqueous ammonium chloride solution, and the mixture was extracted with ethyl acetate. The extract was washed with an aqueous saturated sodium chloride solution, and dried. The solvent was distilled off, and the resulting oil was solidified by adding diisopropyl ether to obtain 530 mg of compound 626F.

$^1$H-NMR (CDCl$_3$) δ: 2.48 (1H, d, J=5.3 Hz), 4.31 (1H, d, J=11.2 Hz), 4.48 (1H, d, J=11.2 Hz), 6.14 (1H, d, J=5.3 Hz), 7.03-7.46 (7H, m).

Hereinbelow, according to Reference example 592, compound 626 was synthesized by the same procedure.

$^1$H-NMR (CDCl$_3$) δ: 1.14 (3H, d, J=6.9 Hz), 3.92 (1H, d, J=7.8 Hz), 4.40 (1H, d, J=7.8 Hz), 5.08 (1H, d, J=7.8 Hz), 5.39-5.52 (1H, m), 5.60-5.65 (2H, m), 5.76 (1H, d, J=6.9 Hz), 6.96-7.01 (1H, m), 7.17-7.55 (7H, m), 8.31 (1H, s).

REFERENCE EXAMPLE 627

[Chemical formula 676]

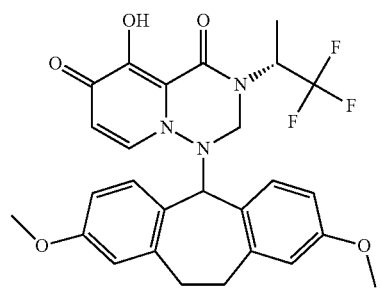

MS: m/z=530 [M+H]$^+$. RT=2.08 min.

REFERENCE EXAMPLE 628
[Chemical formula 677]
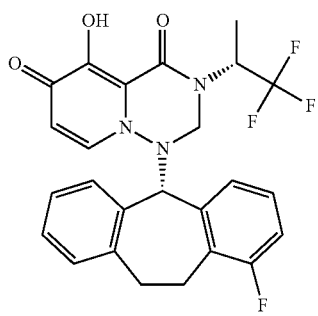
MS: m/z=530 [M+H]+. RT=2.21 min.
REFERENCE EXAMPLE 629
[Chemical formula 678]
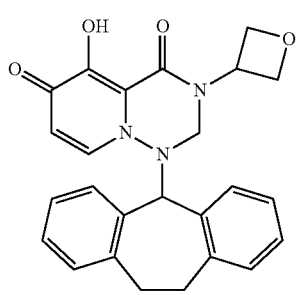
MS: m/z=430 [M+H]+. RT=1.64 min.
REFERENCE EXAMPLE 630
[Chemical formula 679]
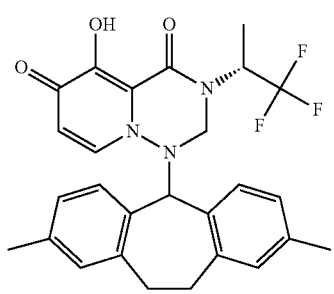
MS: m/z=498 [M+H]+. RT=2.43 min.
REFERENCE EXAMPLE 631
[Chemical formula 680]
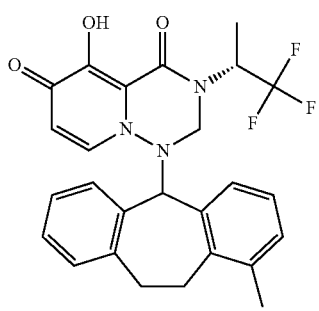
MS: m/z=484 [M+H]+. RT=2.24 min.
REFERENCE EXAMPLE 632
[Chemical formula 681]
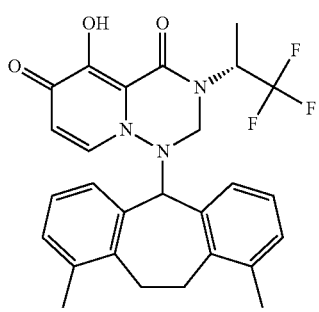
MS: m/z=498 [M+H]+. RT=2.35 min.
REFERENCE EXAMPLE 633
[Chemical formula 682]
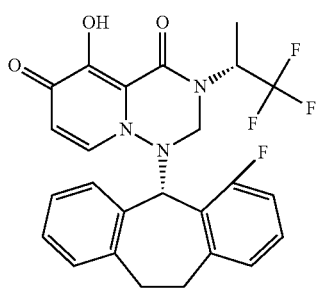
MS: m/z=488 [M+H]+. RT=2.12 min.

REFERENCE EXAMPLE 634
[Chemical formula 683]
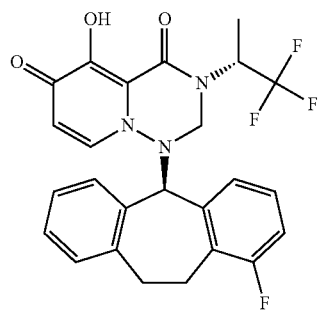
MS: m/z=488 [M+H]+. RT=2.17 min.
REFERENCE EXAMPLE 635
[Chemical formula 684]
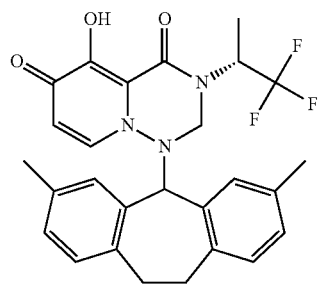
MS: m/z=498 [M+H]+. RT=2.40 min.
REFERENCE EXAMPLE 636
[Chemical formula 685]
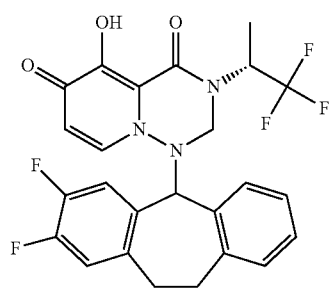
MS: m/z=506 [M+H]+. RT=2.17 min.
REFERENCE EXAMPLE 637
[Chemical formula 686]
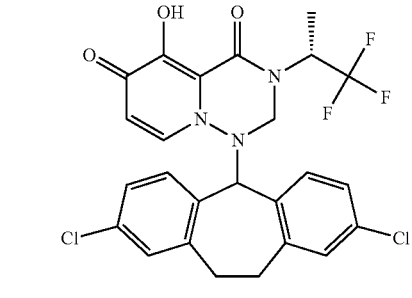
MS: m/z=538 [M+H]+ RT=2.46 min.
REFERENCE EXAMPLE 638
[Chemical formula 687]
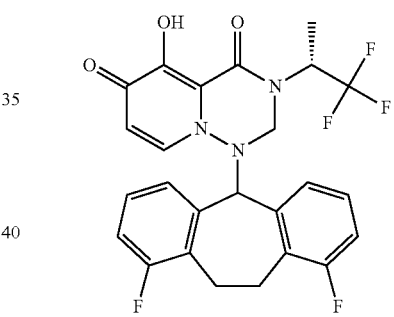
MS: m/z=506 [M+H]+ RT=2.21 min.
REFERENCE EXAMPLE 639
[Chemical formula 688]
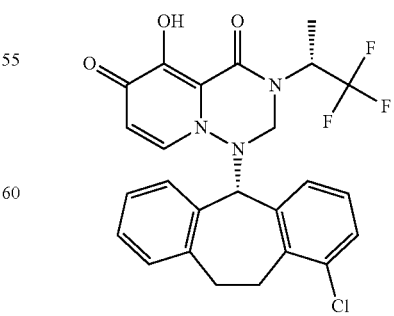
MS: m/z=504 [M+H]+ RT=2.36 min.

REFERENCE EXAMPLE 640
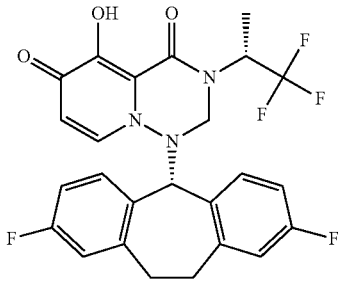
MS: m/z=506 [M+H]+ RT=2.17 min.
REFERENCE EXAMPLE 641
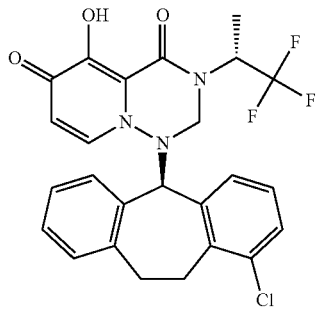
MS: m/z=504 [M+H]+ RT=2.36 min.
REFERENCE EXAMPLE 642
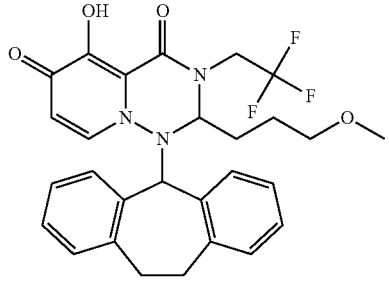
¹H-NMR (CDCl₃) δ: 1.47-1.58 (1H, m), 1.62-1.75 (2H, m), 1.82-1.92 (1H, m), 2.83-2.91 (1H, m), 3.00-3.11 (1H, m), 3.15 (3H, s), 3.18-3.24 (1H, m), 3.47-3.72 (2H, m), 4.08-4.23 (2H, m), 4.36-4.54 (2H, m), 4.92 (1H, s), 5.79 (1H, d, J=7.5 Hz), 6.60-6.68 (2H, m), 6.93 (1H, t, J=7.2 Hz), 7.10-7.39 (6H, m).
REFERENCE EXAMPLE 643
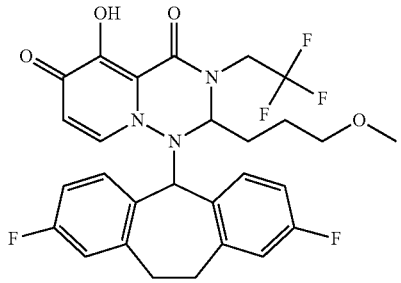
¹H-NMR (CDCl₃) δ: 1.47-1.56 (1H, m), 1.59-1.72 (2H, m), 1.81-1.91 (1H, m), 2.83 (1H, ddd, J=4.2 Hz, 4.2 Hz, 14.7 Hz), 3.00-3.11 (1H, m), 3.16 (3H, s), 3.19-3.26 (2H, m), 3.47-3.57 (1H, m), 3.77-3.91 (1H, m), 4.16-4.34 (2H, m), 4.40-4.45 (1H, m), 4.96 (1H, s), 5.86 (1H, d, J=7.8 Hz), 6.63-6.71 (2H, m), 6.82-6.85 (1H, m), 6.91-6.98 (1H, m), 7.00-7.04 (1H, m), 7.11-7.15 (1H, m).
REFERENCE EXAMPLE 644
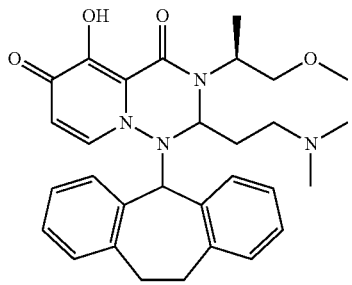
MS: m/z=517 [M+H]+.
REFERENCE EXAMPLE 645
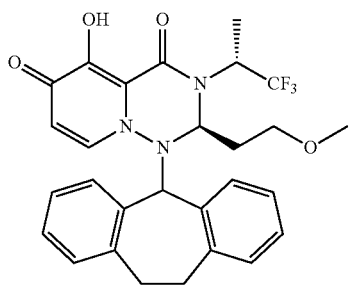
MS: m/z=528 [M+H]+

REFERENCE EXAMPLE 646

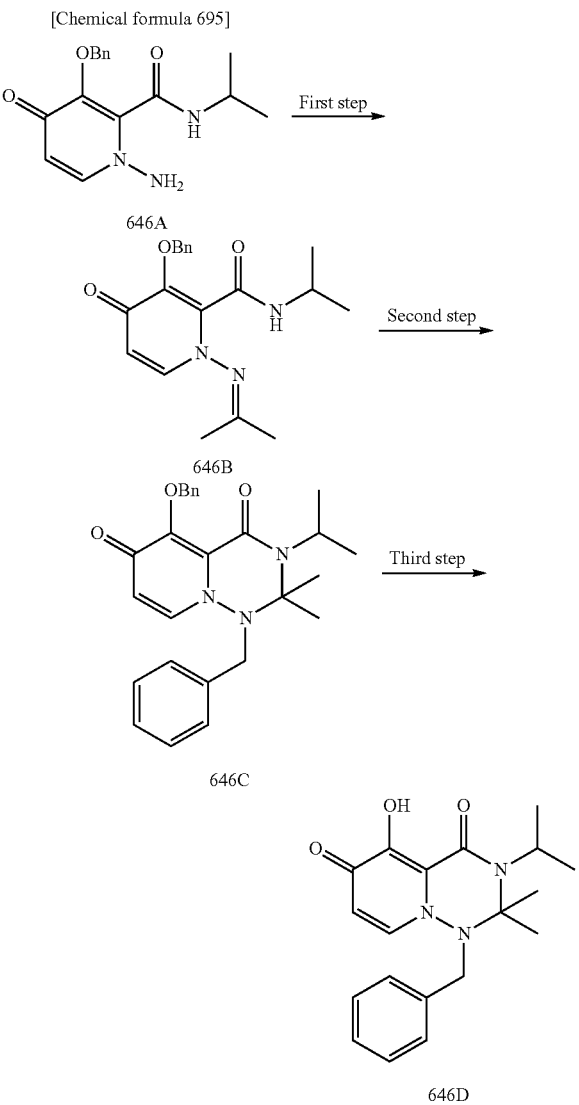

First Step

Compound 646A (100 mg, 0.33 mmol) was dissolved in acetone (1 mL)-toluene (1 mL), acetic acid (0.02 mL, 0.33 mmol) was added, and the mixture was heated to reflux for 2 hours. The reaction solution was concentrated under reduced pressure, and the residue was purified by silica gel column chromatography. The materials were eluted firstly with chloroform and, then, with chloroform-methanol (10:1, v/v). Concentration of an objective fraction afforded 117 mg of compound 646B as an oil.

$^1$H-NMR (CDCl$_3$) δ: 1.10 (6H, d, J=6.6 Hz), 1.95 (3H, s), 2.17 (3H, s), 4.01 (1H, q, J=14.3 Hz), 5.30 (2H, s), 6.36 (1H, brs), 6.45 (1H, d, J=7.6 Hz), 6.92 (1H, d, J=7.6 Hz), 7.29-7.40 (5H, m).

Second Step

A DMF (170 mL) solution of compound 646B was ice-cooled to 1 to 3° C., and benzyl bromide (0.11 mL, 0.92 mmol) and cesium carbonate (301 mg, 0.92 mmol) were added. After the reaction solution was stirred at room temperature for 3 hours, the mixture was distributed between ethyl acetate and water. The ethyl acetate layer was separated, and the aqueous layer was extracted with ethyl acetate once. The combined extracts were sequentially washed with water two times and an aqueous saturated sodium chloride solution, and dried. The solvent was distilled off, and the resulting oil was purified by silica gel column chromatography. The materials were eluted firstly with chloroform and, then, with chloroform-methanol (10:1, v/v). Concentration of an objective fraction afforded 10 mg of compound 646C as an oil.

MS: m/z=432 [M+H]$^+$

Third Step

Compound 646C (10 mg, 0.023 mmol) was dissolved in MeOH (0.5 mL), 10% Pd—C (2.5 mg) was added, and the mixture was subjected to a catalytic reduction reaction under hydrogen stream. The catalyst was removed by filtration, and the filtrate was concentrated. The resulting residue was purified by diol silica gel column chromatography. The materials were eluted firstly with chloroform and, then, with chloroform-methanol (10:1, v/v). Concentration of an objective fraction afforded 3.4 mg of compound 646 as an oil.

MS: m/z=342 [M+H]$^+$.

REFERENCE EXAMPLE 647

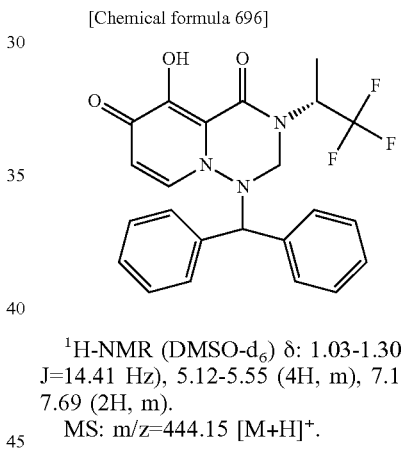

$^1$H-NMR (DMSO-d$_6$) δ: 1.03-1.30 (3H, m), 4.51 (1H, t, J=14.41 Hz), 5.12-5.55 (4H, m), 7.18-7.46 (9H, m), 7.58-7.69 (2H, m).

MS: m/z=444.15 [M+H]$^+$.

REFERENCE EXAMPLE 648

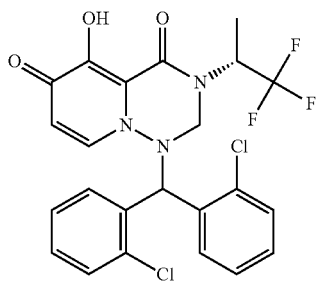

$^1$H-NMR (DMSO-d$_6$) δ: 1.12-1.35 (2H, m), 4.46-4.55 (1H, m), 5.24-5.61 (3H, m), 6.33-6.42 (1H, m), 7.23-7.67 (8H, m), 8.22-8.29 (1H, m).

MS: m/z=512.15 [M+H]$^+$.

REFERENCE EXAMPLE 649

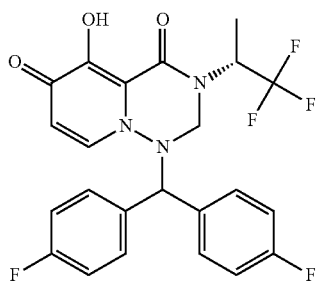

MS: m/z=480.15 [M+H]⁺.

REFERENCE EXAMPLE 650

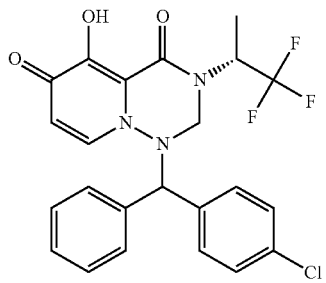

MS: m/z=520 [M+H]⁺. RT=2.21 min.

REFERENCE EXAMPLE 651

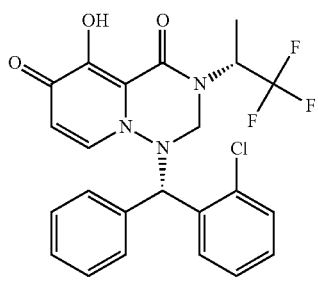

MS: m/z=487 [M+H]⁺. RT=2.04 min.

REFERENCE EXAMPLE 652

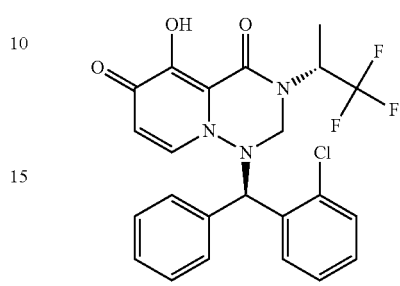

MS: m/z=478 [M+H]⁺. RT=2.04 min.

LCMS Method

Column: ACQUITY UPLC registered trademark BEH C18 (1.7 μm i.d. 2.1×50 mm) (Waters)

Flow rate: 0.8 mL/min.

UV detection wavelength: 254 nm

Mobile phase: an aqueous solution containing 0.1% formic acid for [A], an acetonitrile solution containing 0.1% formic acid for [B]

Gradient: a linear gradient of 10% to 100% solvent [B] over 3.5 minutes was performed, and 100% solvent [B] was retained for 0.5 minutes.

REFERENCE EXAMPLE 653

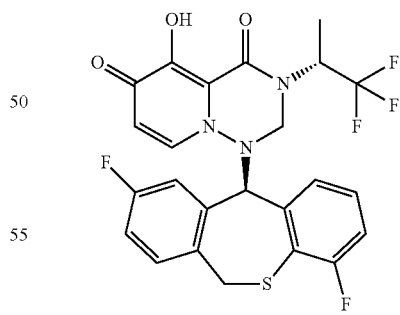

$^1$H-NMR (CDCl$_3$) δ: 1.45 (3H, d, J=7.4 Hz), 3.69 (1H, d, J=13.7 Hz), 4.52 (1H, d, J=12.6 Hz), 5.14-5.20 (2H, m), 5.32-5.45 (1H, m), 5.64 (1H, d, J=13.5 Hz), 5.74 (1H, d, J=7.7 Hz), 6.56 (1H, d, J=7.7 Hz), 6.81 (1H, ddd, J=7.8, 7.8, 3.9 Hz), 6.87-6.96 (2H, m), 7.11 (1H, ddd, J=8.2, 8.2, 2.6 Hz), 7.17 (1H, d, J=7.7 Hz), 7.32 (1H, dd, J=8.4, 5.4 Hz).

MS: m/z=524 [M+H]⁺.

REFERENCE EXAMPLE 654

[Chemical formula 703]

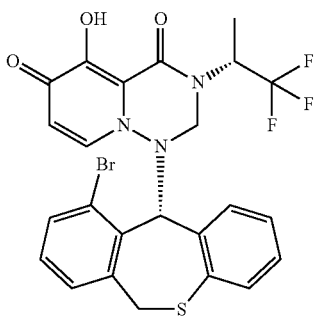

$^1$H-NMR (CDCl$_3$) δ: 1.15 (3H, d, J=7.4 Hz), 3.62 (1H, d, J=13.5 Hz), 4.44 (1H, d, J=12.9 Hz), 4.86 (1H, d, J=13.2 Hz), 5.43-5.56 (1H, m), 5.68 (1H, d, J=13.5 Hz), 5.83 (1H, d, J=7.7 Hz), 5.94 (1H, s), 6.81-6.91 (2H, m), 7.07-7.18 (3H, m), 7.26 (1H, t, J=7.7 Hz), 7.34 (1H, d, J=7.4 Hz), 7.55 (1H, d, J=8.0 Hz).

MS: m/z=566, 568 [M+H]$^+$.

REFERENCE EXAMPLE 655

[Chemical formula 704]

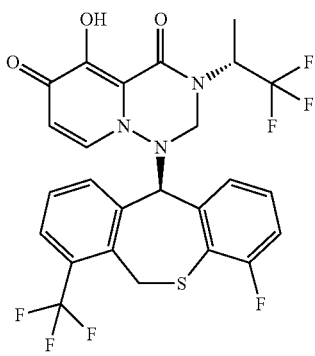

$^1$H-NMR (CDCl$_3$) δ: 1.44 (3H, d, J=7.4 Hz), 4.07 (1H, d, J=14.6 Hz), 4.52 (1H, d, J=12.6 Hz), 5.13 (1H, d, J=12.6 Hz), 5.34-5.47 (2H, m), 5.79 (1H, d, J=7.7 Hz), 5.93 (1H, d, J=14.6 Hz), 6.58 (1H, d, J=7.7 Hz), 6.82 (1H, ddd, J=7.9, 7.9, 5.6 Hz), 6.89-6.97 (1H, m), 7.14 (1H, d, J=7.7 Hz), 7.40 (2H, d, J=5.2 Hz), 7.76-7.83 (1H, m).

MS: m/z=573 [M+H]$^+$.

REFERENCE EXAMPLE 656

[Chemical formula 705]

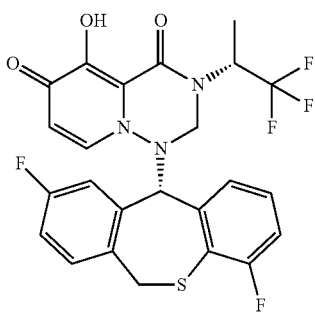

$^1$H-NMR (CDCl$_3$) δ: 1.22 (3H, d, J=7.4 Hz), 3.72 (1H, d, J=13.7 Hz), 4.48 (1H, d, J=13.2 Hz), 4.90 (1H, d, J=13.2 Hz), 5.13 (1H, s), 5.50-5.58 (1H, m), 5.61 (1H, d, J=14.0 Hz), 5.86 (1H, d, J=7.7 Hz), 6.56 (1H, d, J=7.7 Hz), 6.84 (1H, ddd, J=7.9, 7.9, 5.6 Hz), 6.91-7.00 (2H, m), 7.11-7.19 (2H, m), 7.40 (1H, dd, J=8.4, 5.4 Hz).

MS: m/z=524 [M+H]$^+$.

REFERENCE EXAMPLE 657

[Chemical formula 706]

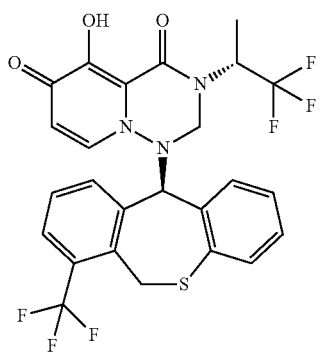

$^1$H-NMR (CDCl$_3$) δ: 1.45 (3H, d, J=7.3 Hz), 3.97 (1H, d, J=14.5 Hz), 4.53 (1H, d, J=12.7 Hz), 5.12 (1H, d, J=12.7 Hz), 5.32 (1H, s), 5.35-5.49 (1H, m), 5.76 (1H, d, J=7.6 Hz), 5.90 (1H, d, J=14.5 Hz), 6.73 (1H, d, J=7.6 Hz), 6.78-6.86 (1H, m), 7.03-7.14 (2H, m), 7.19 (1H, dd, J=7.7, 0.8 Hz), 7.36-7.43 (2H, m), 7.77 (1H, dd, J=6.3, 2.9 Hz).

MS: m/z=556 [M+H]$^+$.

REFERENCE EXAMPLE 658

[Chemical formula 707]

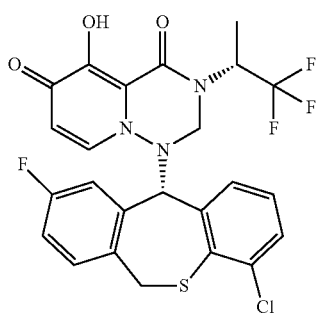

$^1$H-NMR (CDCl$_3$) δ: 1.21 (3H, d, J=7.1 Hz), 3.74 (1H, d, J=13.7 Hz), 4.47 (1H, d, J=12.9 Hz), 4.90 (1H, d, J=13.2 Hz), 5.13 (1H, s), 5.47-5.60 (1H, m), 5.65 (1H, d, J=13.7 Hz), 5.86 (1H, d, J=7.7 Hz), 6.68 (1H, d, J=7.7 Hz), 6.81 (1H, dd, J=7.8, 7.8 Hz), 6.94 (1H, dd, J=8.5, 2.5 Hz), 7.10-7.20 (2H, m), 7.27-7.31 (1H, m), 7.39 (1H, dd, J=8.4, 5.4 Hz).

MS: m/z=540 [M+H]$^+$.

REFERENCE EXAMPLE 659

[Chemical formula 708]

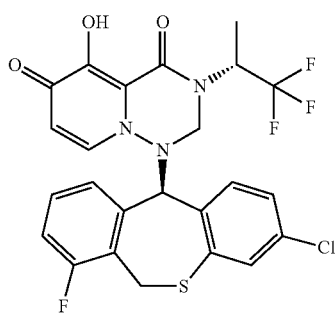

$^1$H-NMR (CDCl$_3$) δ: 1.45 (3H, d, J=7.1 Hz), 4.31 (1H, d, J=14.0 Hz), 4.53 (1H, d, J=12.6 Hz), 5.15 (1H, d, J=12.6 Hz), 5.21 (1H, s), 5.31-5.45 (1H, m), 5.64 (1H, d, J=14.0 Hz), 5.80 (1H, d, J=7.7 Hz), 6.51 (1H, ddd, J=8.0, 8.0, 2.6 Hz), 6.70 (1H, dd, J=8.4, 5.6 Hz), 6.80 (1H, dd, J=9.3, 2.5 Hz), 7.10 (1H, d, J=7.7 Hz), 7.15-7.25 (2H, m), 7.51 (1H, d, J=8.0 Hz).

MS: m/z=540 [M+H]$^+$.

REFERENCE EXAMPLE 660

[Chemical formula 709]

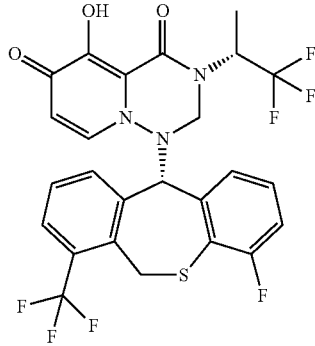

$^1$H-NMR (CDCl$_3$) δ: 1.20 (3H, d, J=7.4 Hz), 4.09 (1H, d, J=14.6 Hz), 4.44 (1H, d, J=13.2 Hz), 4.92 (1H, d, J=13.5 Hz), 5.32 (1H, s), 5.48-5.60 (1H, m), 5.85-5.95 (2H, m), 6.56 (1H, d, J=7.7 Hz), 6.85 (1H, ddd, J=8.0, 8.0, 5.6 Hz), 6.92-7.00 (1H, m), 7.11 (1H, d, J=7.7 Hz), 7.39-7.44 (2H, m), 7.80-7.87 (1H, m).

MS: m/z=574 [M+H]$^+$.

REFERENCE EXAMPLE 661

[Chemical formula 710]

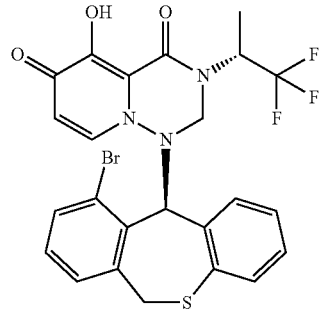

MS: m/z=566, 568 [M+H]$^+$.

REFERENCE EXAMPLE 662

[Chemical formula 711]

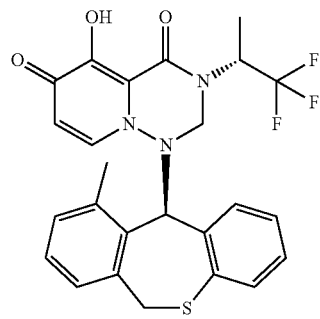

MS: m/z=502 [M+H]$^+$.

REFERENCE EXAMPLE 663

[Chemical formula 712]

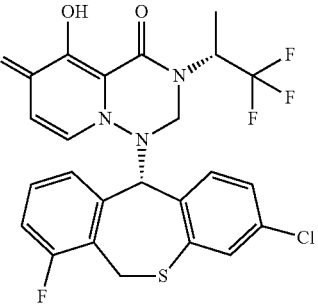

$^1$H-NMR (CDCl$_3$) δ: 1.21 (3H, d, J=7.1 Hz), 4.33 (1H, d, J=14.0 Hz), 4.48 (1H, d, J=13.2 Hz), 4.90 (1H, d, J=12.6 Hz), 5.16 (1H, s), 5.46-5.59 (1H, m), 5.62 (1H, d, J=13.7 Hz), 5.90 (1H, d, J=7.7 Hz), 6.54 (1H, ddd, J=7.7, 7.7, 2.5 Hz), 6.69 (1H, dd, J=8.7, 5.6 Hz), 6.84 (1H, dd, J=9.3, 2.5 Hz), 7.11 (1H, d, J=7.7 Hz), 7.15 (1H, d, J=7.7 Hz), 7.23 (1H, dd, J=7.8, 7.8 Hz), 7.55 (1H, d, J=8.0 Hz).

MS: m/z=540 [M+H]$^+$.

REFERENCE EXAMPLE 664

[Chemical formula 713]

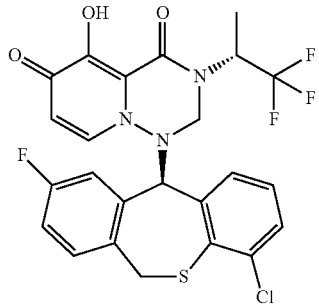

$^1$H-NMR (CDCl$_3$) δ: 1.45 (3H, d, J=7.1 Hz), 3.71 (1H, d, J=13.7 Hz), 4.52 (1H, d, J=12.6 Hz), 5.13-5.19 (2H, m), 5.32-5.45 (1H, m), 5.68 (1H, d, J=13.7 Hz), 5.74 (1H, d, J=7.7 Hz), 6.68 (1H, dd, J=7.7, 1.4 Hz), 6.78 (1H, dd, J=7.8, 7.8 Hz), 6.92 (1H, d, J=9.1 Hz), 7.07-7.18 (2H, m), 7.24 (1H, dd, J=8.0, 1.4 Hz), 7.32 (1H, dd, J=8.2, 5.5 Hz).
MS: m/z=540 [M+H]$^+$.

REFERENCE EXAMPLE 665

[Chemical formula 714]

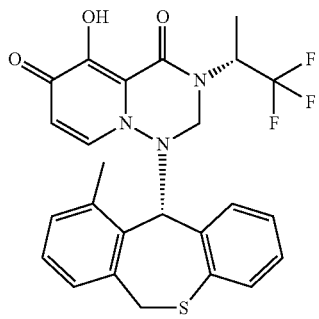

$^1$H-NMR (CDCl$_3$) δ: 0.92 (3H, d, J=7.1 Hz), 2.35 (3H, s), 3.60 (1H, d, J=13.5 Hz), 4.49 (1H, d, J=12.9 Hz), 4.82 (1H, d, J=12.4 Hz), 5.39-5.51 (2H, m), 5.60 (1H, d, J=13.5 Hz), 5.85 (1H, d, J=7.7 Hz), 6.69 (1H, d, J=7.4 Hz), 6.79-6.87 (1H, m), 7.05 (1H, d, J=7.7 Hz), 7.10-7.15 (3H, m), 7.22 (1H, d, J=7.1 Hz), 7.27-7.33 (1H, m).
MS: m/z=502 [M+H]$^+$.

Methods for synthesizing intermediate compounds i-1 to i-72 for synthesizing parent compounds are shown below.

SYNTHESIS OF INTERMEDIATE COMPOUND i-3

[Chemical formula 715]

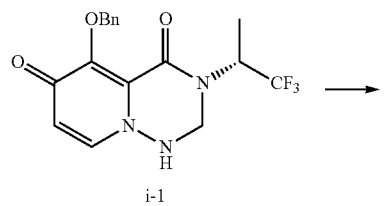

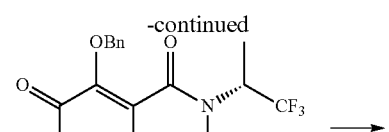

Step 1

Compound i-1 (50.0 g, 136 mmol) was dissolved in dichloromethane (500 mL), Boc$_2$O (34.8 mL, 150 mmol) and DMAP (831 mg, 6.81 mmol) were added, and the mixture was stirred at room temperature for 2 hours. Thereafter, NBS (29.1 g, 163 mmol) was added, and the mixture was further stirred at room temperature overnight.

The organic layer was washed with water and aqueous saturated sodium chloride solution, and then dried with anhydrous magnesium sulfate. The solvent was distilled off under reduced pressure, and the resulting residue was purified by silica gel column chromatography (hexane-ethyl acetate) to obtain compound i-2 (64.0 g, yield 86%).

$^1$H-NMR (DMSO-d$_6$) δ: 8.62 (s, 1H), 7.58 (t, J=8.6 Hz, 2H), 7.38 (brs, 3H), 5.44 (brs, 1H), 5.23 (d, J=10.6 Hz, 2H), 5.14 (d, J=11.9 Hz, 1H), 3.40 (s, 1H), 1.47-1.43 (m, 12H).

Step 2

A methanol (600 mL) solution of compound i-2 (64.0 g, 117 mmol) was cooled to 0° C. with ice water. A 2 mol/L aqueous sodium hydroxide solution (76 mL, 152 mmol) was added thereto, and the mixture was stirred at 0° C. for 1 hour. Under an ice bath, the mixture was neutralized with 2 mol/L hydrochloric acid, and the precipitated solid was separated by filtration. The solid was washed with water, and dried to obtain compound i-3 (40.5 g, yield 78%).

$^1$H-NMR (DMSO-d$_6$) δ: 8.38 (s, 1H), 7.62 (t, J=6.6 Hz, 1H), 7.53 (d, J=7.1 Hz, 2H), 7.35-7.33 (m, 3H), 5.29 (brs, 1H), 5.11 (q, J=12.5 Hz, 2H), 4.75 (t, J=6.9 Hz, 1H), 4.65 (t, J=11.1 Hz, 1H), 1.45 (d, J=7.1 Hz, 3H).

SYNTHESIS OF INTERMEDIATE COMPOUND i-5

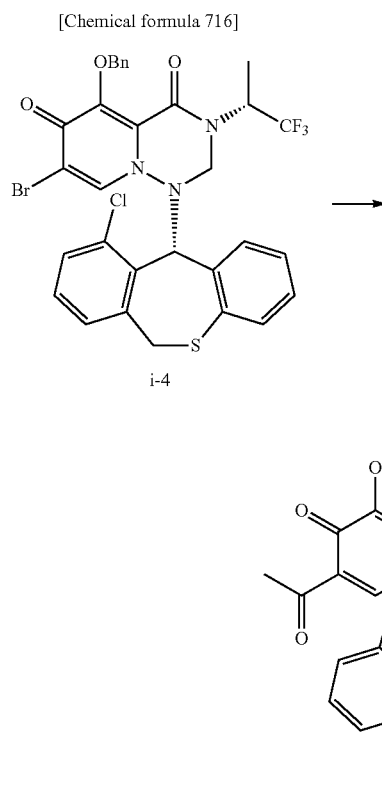

Step 1

To compound i-4 (6.60 g, 9.55 mmol), dioxane (66 mL), Pd$_2$(PPh$_3$)$_2$ (670 mg, 0.955 mmol), and tributyl(1-ethoxyvinyl)tin (4.84 mL, 14.3 mmol) were added under nitrogen atmosphere, and the mixture was heated to reflux for 2 hours and 30 minutes. After cooling the mixture to room temperature, 1 mol/L hydrochloric acid (20 mL) was added, and the mixture was stirred at room temperature for 20 minutes. Water was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel column chromatography (hexane-ethyl acetate) to obtain compound i-5 (5.50 g, yield 88%).

$^1$H-NMR (DMSO-d$_6$) δ: 7.75 (s, 1H), 7.59 (d, J=6.6 Hz, 2H), 7.50 (s, 1H), 7.42-7.39 (m, 5H), 7.11 (s, 2H), 6.80 (s, 1H), 6.54 (d, J=7.1 Hz, 1H), 5.74 (s, 1H), 5.64 (d, J=13.4 Hz, 1H), 5.57 (brs, 1H), 5.45 (d, J=10.6 Hz, 1H), 5.25 (d, J=10.6 Hz, 1H), 5.12 (d, J=13.6 Hz, 1H), 4.52 (d, J=13.6 Hz, 1H), 3.96 (d, J=13.6 Hz, 1H), 2.37 (s, 3H), 1.02 (d, J=6.3 Hz, 3H).

SYNTHESIS OF INTERMEDIATE COMPOUND i-7

[Chemical formula 717]

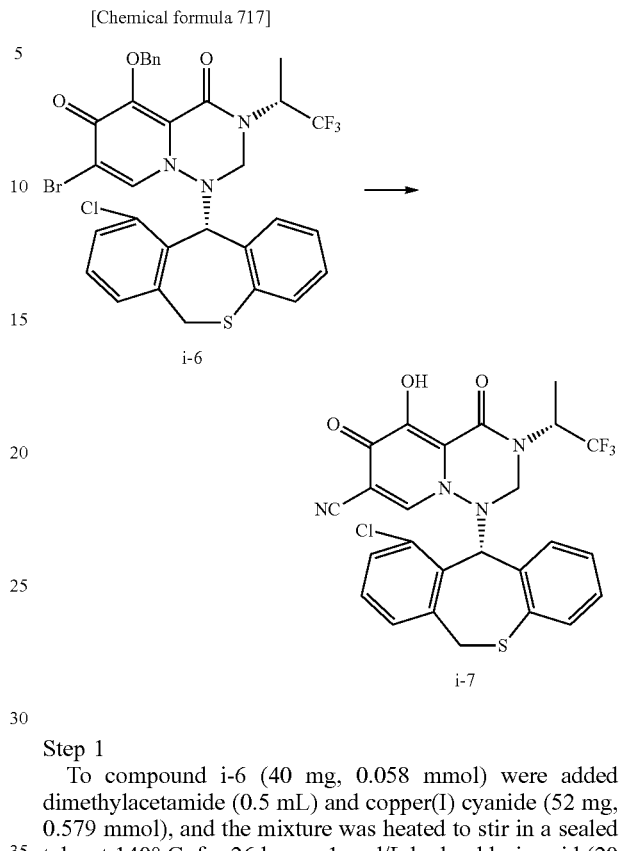

Step 1

To compound i-6 (40 mg, 0.058 mmol) were added dimethylacetamide (0.5 mL) and copper(I) cyanide (52 mg, 0.579 mmol), and the mixture was heated to stir in a sealed tube at 140° C. for 26 hours. 1 mol/L hydrochloric acid (20 mL) was added, and the mixture was extracted with ethyl acetate. The organic layer was washed with aqueous saturated sodium chloride solution, and then dried with anhydrous sodium sulfate. The solvent was distilled off under reduced pressure, and the resulting residue was purified by preparative LCMS (method 14) to obtain compound i-7 (8.0 mg, yield 25%).

$^1$H-NMR (DMSO-d$_6$) δ: 7.58 (s, 1H), 7.51 (s, 1H), 7.46 (s, 2H), 7.21 (brs, 2H), 6.92-6.88 (m, 2H), 5.86 (s, 1H), 5.65 (d, J=12.6 Hz, 1H), 5.48 (brs, 1H), 4.95 (brs, 1H), 4.49 (brs, 1H), 3.97 (d, J=13.4 Hz, 2H), 1.02 (s, 3H).

SYNTHESIS OF INTERMEDIATE COMPOUND i-10

[Chemical formula 718]

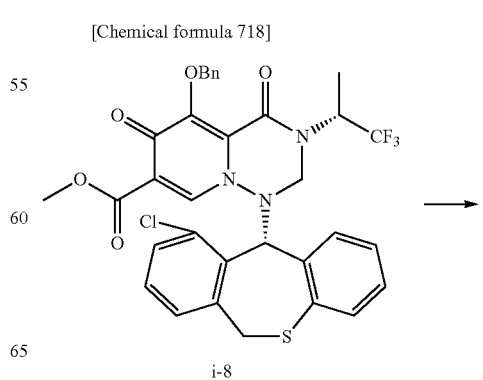

-continued

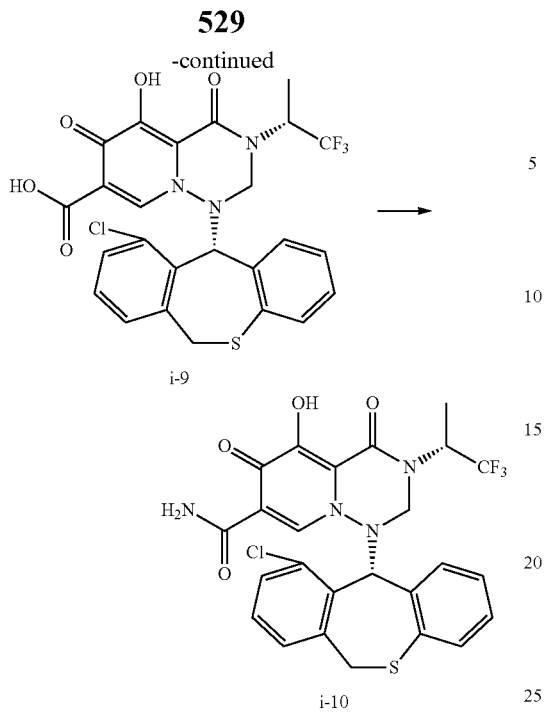

i-9 i-10

Step 1

To compound i-8 (110 mg, 0.164 mmol) were added methanol (1 mL), tetrahydrofuran (1 mL), and 2 mol/L aqueous sodium hydroxide solution (0.246 mL, 0.492 mmol), and the mixture was stirred at 60° C. for 3 hours, then 2 mol/L aqueous sodium hydroxide solution (0.164 mL, 0.328 mmol) was further stirred at 60° C. for 4 hours. The mixture was neutralized with 2 mol/L hydrochloric acid, and then extracted with chloroform. The organic layer was washed with aqueous saturated sodium chloride solution, and then dried with anhydrous sodium sulfate. The solvent was distilled off under reduced pressure to obtain compound i-9 (91 mg, 98%).

MS: m/z=566 [M+H]$^+$. RT=2.30 min.

Step 2

To compound i-9 (20 mg, 0.035 mmol) were added dimethylformamide (0.5 mL), 2 mol/L ammonia-methanol solution (0.053 mL, 0.106 mmol), [4-(4,6-dimethoxy-1,3,5-triazin-2-yl)-4-methylmorpholinium chloride] (29.3 mg, 0.106 mmol), and the mixture was stirred at room temperature overnight. Thereafter, a 28% sodium methoxide-methanol solution (34.1 mg, 0.177 mmol) was added, and the mixture was further stirred at room temperature for 1 hour. After adding 0.5 mol/L hydrochloric acid, the mixture was extracted with ethyl acetate. The organic layer was washed with aqueous saturated sodium chloride solution, and then dried with anhydrous sodium sulfate. The solvent was distilled off under reduced pressure, and the resulting residue was purified by preparative LCMS (method 14) to obtain compound i-10 (4.0 mg, yield 20%).

MS: m/z=565 [M+H]$^+$. RT=2.03 min.

SYNTHESIS OF INTERMEDIATE COMPOUND
i-12

[Chemical formula 719]

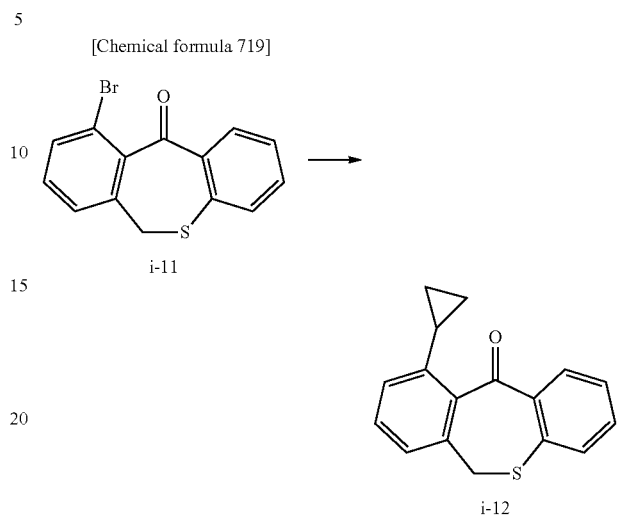

i-11 i-12

Step 1

To compound i-11 (1.00 g, 3.28 mmol) were added tetrahydrofuran (25 mL), [1,1'-bis(di-tert-butylphosphino)ferrocene]palladium(II)dichloride (214 mg, 4.91 mmol), potassium cyclopropyltrifluoroborate (727 mg, 4.91 mmol), and a 2 mol/L aqueous sodium carbonate solution (4.91 mL, 9.83 mmol) under nitrogen atmosphere, and the mixture was heated to reflux for 20 hours. After adding water, the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel column chromatography (hexane-chloroform) to obtain compound i-12 (350 mg, yield 24%).

MS: m/z=267 [M+H]$^+$. RT=2.46 min.

SYNTHESIS OF INTERMEDIATE COMPOUND
i-14

[Chemical formula 720]

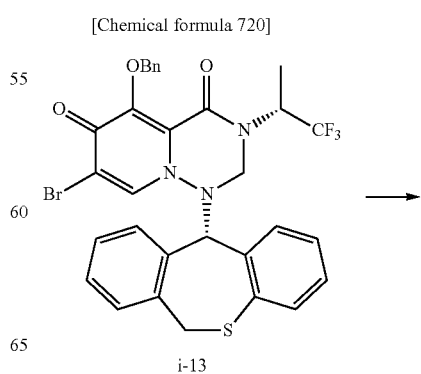

i-13

531
-continued

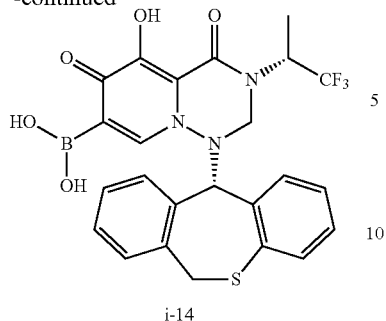

i-14

Step 1

To compound i-13 (200 mg, 0.305 mmol) were added tetrahydrofuran (3 mL), bis(pinacolato)diboron (232 mg, 0.914 mmol), $PdCl_2(dppf) \cdot CH_2Cl_2$ (24.9 mg, 0.030 mmol), and potassium acetate (90 mg, 0.914 mmol), and the mixture was stirred at 80° C. for 3 hours and 30 minutes. After cooled to room temperature, the mixture was filtered with celite, and the solvent was distilled off under reduced pressure. After adding 1 mol/L hydrochloric acid, the mixture was extracted with ethyl acetate. The organic layer was washed with aqueous saturated sodium chloride solution, and then dried with anhydrous sodium sulfate. To the obtained brown substance were added dimethylacetamide (2 mL) and lithium chloride (64.5 mg, 1.53 mmol), and the mixture was stirred at 100° C. for 4 hours. After cooled to room temperature, 1 mol/L hydrochloric acid was added, and the mixture was extracted with ethyl acetate. The organic layer was washed with aqueous saturated sodium chloride solution, and then dried with anhydrous sodium sulfate. The solvent was distilled off under reduced pressure, and the resulting residue was purified by preparative LCMS (method 14) to obtain compound i-14 (59 mg, yield 37%).

MS: m/z=532 [M+H]$^+$. RT=2.02 min.

SYNTHESIS OF INTERMEDIATE COMPOUND i-16

532
-continued i-16

Step 1

To compound i-15 (20 mg, 0.030 mmol) were added tetrahydrofuran (0.5 mL), PEPPSI-IPr (2.07 mg, 3.05 μmol), and 2 mol/L methyl zinc chloride-tetrahydrofuran solution (0.076 mL, 0.152 mmol), and the mixture was heated to stir in a sealed tube at 100° C. for 3 hours under nitrogen stream. After cooled to room temperature, 2 mol/L hydrochloric acid was added, and the mixture was extracted with ethyl acetate. The organic layer was washed with aqueous saturated sodium chloride solution, and then dried with anhydrous sodium sulfate. The solvent was distilled off under reduced pressure, and the resulting residue was purified by silica gel column chromatography (DIOL, hexane-ethyl acetate) to obtain compound i-16 (4.0 mg, yield 26%).

$^1$H-NMR (DMSO-d$_6$) δ: 7.54 (s, 1H), 7.46 (s, 1H), 7.41 (s, 1H), 7.25 (s, 2H), 7.08 (s, 2H), 6.91 (s, 1H), 6.81 (s, 1H), 5.68 (d, J=13.1 Hz, 1H), 5.56 (s, 1H), 5.48 (s, 1H), 5.05 (d, J=13.6 Hz, 1H), 4.41 (d, J=12.6 Hz, 1H), 3.87 (d, J=12.9 Hz, 1H), 1.52 (s, 3H), 1.18 (d, J=6.3 Hz, 3H).

SYNTHESIS OF INTERMEDIATE COMPOUND i-18

[Chemical formula 721]

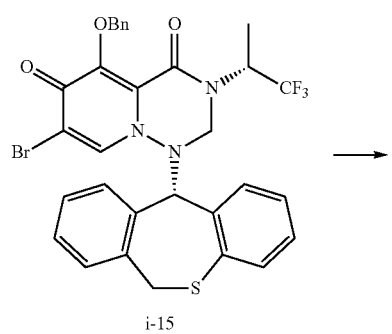

i-15

[Chemical formula 722]

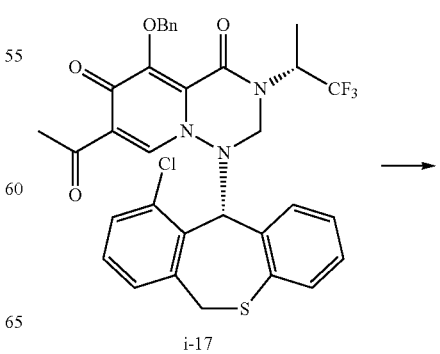

i-17

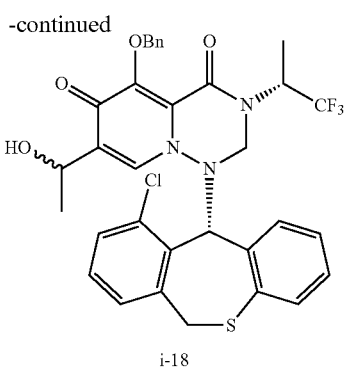

i-18

Step 1

Compound i-17 (50 mg, 0.076 mmol) was dissolved in tetrahydrofuran (1 mL), and the mixture was cooled to −78° C. with dry ice-acetone. A 1.06 mol/L diisobutylaluminum hydride-hexane solution (0.108 mL, 0.115 mmol) was added thereto, and the mixture was stirred at −78° C. for 1 hour. A saturated Rochelle salt solution was added, and the mixture was stirred at room temperature for 20 minutes and then extracted with ethyl acetate. The organic layer was washed with aqueous saturated sodium chloride solution, and then dried with anhydrous sodium sulfate. The solvent was distilled off under reduced pressure, and the resulting residue was purified by silica gel column chromatography (hexane-ethyl acetate) to obtain compound i-18 (35 mg, yield 70%).

$^1$H-NMR (DMSO-$d_6$) δ: 7.53 (s, 3H), 7.46 (s, 2H), 7.36 (d, J=7.3 Hz, 3H), 7.29 (s, 1H), 7.15 (s, 2H), 6.80 (brs, 1H), 6.47 (d, J=7.1 Hz, 1H), 5.70 (s, 1H), 5.61 (d, J=14.4 Hz, 1H), 5.53 (brs, 1H), 5.33 (d, J=11.1 Hz, 1H), 5.13 (d, J=11.4 Hz, 1H), 5.01 (d, J=12.9 Hz, 1H), 4.92 (s, 1H), 4.57 (s, 1H), 4.47 (d, J=13.9 Hz, 1H), 3.98 (d, J=13.9 Hz, 1H), 0.98 (d, J=6.8 Hz, 3H), 0.71 (d, J=5.3 Hz, 3H).

SYNTHESIS OF INTERMEDIATE COMPOUND i-20

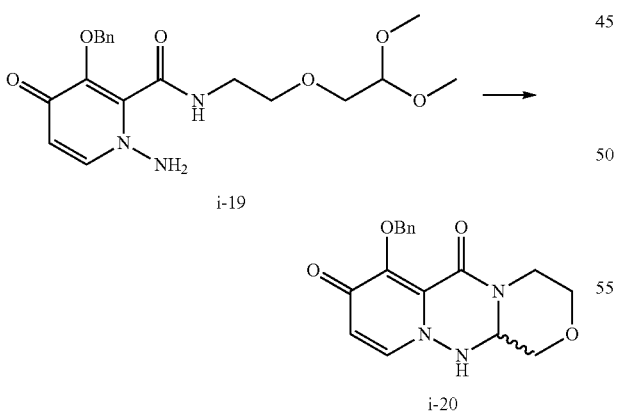

[Chemical formula 723]

i-19 i-20

Step 1

To compound i-19 (560 mg, 1.43 mmol) were added toluene (250 mL), acetic acid (25 mL), and tosyl acid monohydrate (54.4 mg, 0.286 mmol), and the mixture was heated to reflux for 16 hours. The solvent was distilled off under reduced pressure, and the resulting residue was purified by silica gel column chromatography (hexane-ethyl acetate) to obtain compound i-20 (210 mg, yield 45%).

$^1$H-NMR (DMSO-$d_6$) δ: 7.56 (d, J=6.8 Hz, 2H), 7.36-7.27 (m, 5H), 6.23 (d, J=7.3 Hz, 1H), 5.06 (s, 2H), 4.79 (t, J=11.7 Hz, 1H), 4.14 (d, J=13.4 Hz, 1H), 4.02 (brs, 2H), 3.43 (t, J=13.0 Hz, 1H), 3.13 (t, J=10.5 Hz, 1H), 2.95 (t, J=11.1 Hz, 1H).

SYNTHESIS OF INTERMEDIATE COMPOUND i-25

[Chemical formula 724]

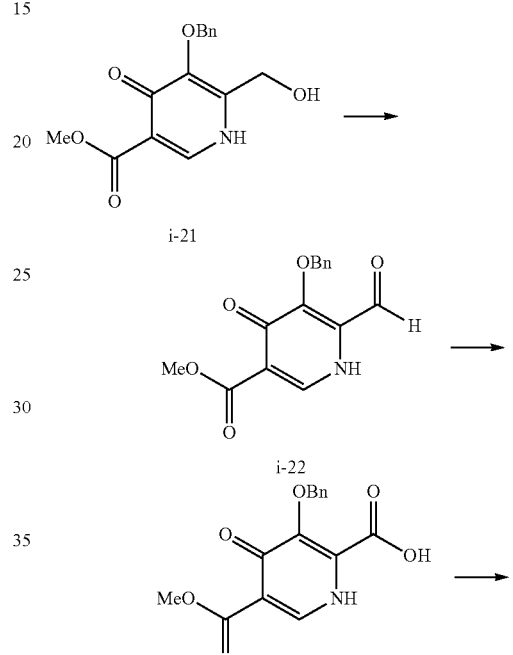

i-21 i-22 i-23 i-24 i-25

Step 1

Compound i-21 (30.0 g, 104 mmol) was suspended in methanol (450 mL), and dissolved by heating to 65° C. Manganese dioxide (75 g, 863 mmol) was added, and the mixture was stirred at 65° C. for 2 hours. The solid was removed by filtration, and the filtrate was distilled off under reduced pressure. To the resulting residue were added tet-

535 rahydrofuran-diisopropyl ether to precipitate a solid, then the solid was filtered to obtain compound i-22 (27.55 g, yield 93%).

$^1$H-NMR (CDCl$_3$) δ: 3.99 (s, 3H), 5.43 (s, 2H), 7.27-7.45 (m, 6H), 8.62 (s, 1H), 10.05 (s, 1H).

Step 2

Sodium chlorite (34.6 g, 383 mmol) was dissolved in water (150 mL), and the mixture was cooled to 0° C. with ice water. Amidosulfuric acid (37.2 mg, 383 mmol) was added thereto, and the mixture was stirred for 40 minutes. Compound i-22 (27.5 g, 96 mmol) was dissolved in tetrahydrofuran (450 mL) and DMF (45 mL) in another flask, and the mixture was cooled to 0° C. with ice water. The aqueous solution prepared as above was added dropwise thereto, and the mixture was stirred at 0° C. for 1 hour. The solvent was concentrated under reduced pressure, water and diisopropyl ether were added, and the solid was filtered to obtain compound i-23 (19.49 g, yield 67%).

$^1$H-NMR (DMSO-d$_6$) δ: 3.74 (s, 3H), 5.11 (s, 2H), 7.27-7.40 (m, 4H), 7.44-7.50 (m, 2H), 8.11 (s, 1H).

Step 3

Compound i-23 (14.0 g, 46.2 mmol) was dissolved in DMF (140 mL), and the solution was ice-cooled. (R)-1,1,1-trifluoroisopropylamine hydrochloride (10.36 g, 69.2 mmol), EDC (11.50 g, 60.0 mmol), HOBt (8.11 g, 60.0 mmol), and triethylamine (19.2 mL, 138 mmol) were added, and the mixture was stirred at room temperature for 4 hours. Water was added to the reaction solution to stop the reaction. The solution was extracted with ethyl acetate, and the organic layer was washed with water and aqueous saturated sodium chloride solution, and then dried with anhydrous magnesium sulfate. The solvent was distilled off under reduced pressure, and the resulting residue was purified by silica gel chromatography (chloroform-methanol) to obtain compound i-24 (12.87 g, yield 70%).

MS: m/z=399.1 [M+H]$^+$.

Step 4

Compound i-24 (12.55 g, 31.5 mmol) was dissolved in DMF (130 mL). Potassium carbonate (21.77 g, 158 mmol) was added, and the mixture was stirred for 15 minutes. 2,4-dinitrophenylhydroxylamine (9.41 g, 47.3 mmol) was added, and the mixture was stirred for 3 hours. To the reaction solution was added chloroform, the precipitated solid was removed by filtration, and the filtrate was distilled off under reduced pressure. To the resulting DMF solution were added paraformaldehyde (851 mg, 28.3 mmol) and acetic acid (0.09 mL, 1.58 mmol), and the mixture was stirred at 110° C. for 3 hours and 30 minutes. The reaction solution was allowed to cool, the solvent was distilled off under reduced pressure, and the resulting residue was purified by silica gel chromatography (chloroform-methanol) to obtain compound i-25 (8.15 g, yield 61%).

$^1$H-NMR (CDCl$_3$) δ: 1.32 (d, J=7.2 Hz, 3H), 3.79 (s, 3H), 4.39-4.54 (m, 2H), 5.14 (d, J=10.2 Hz, 1H), 5.24 (m, 1H), 5.28 (d, J=10.2 Hz, 1H), 6.54 (m, 1H), 7.25-7.33 (m, 3H), 7.45-7.52 (m, 2H), 8.18 (s, 1H).

536

SYNTHESIS OF INTERMEDIATE COMPOUND i-29

[Chemical formula 725]

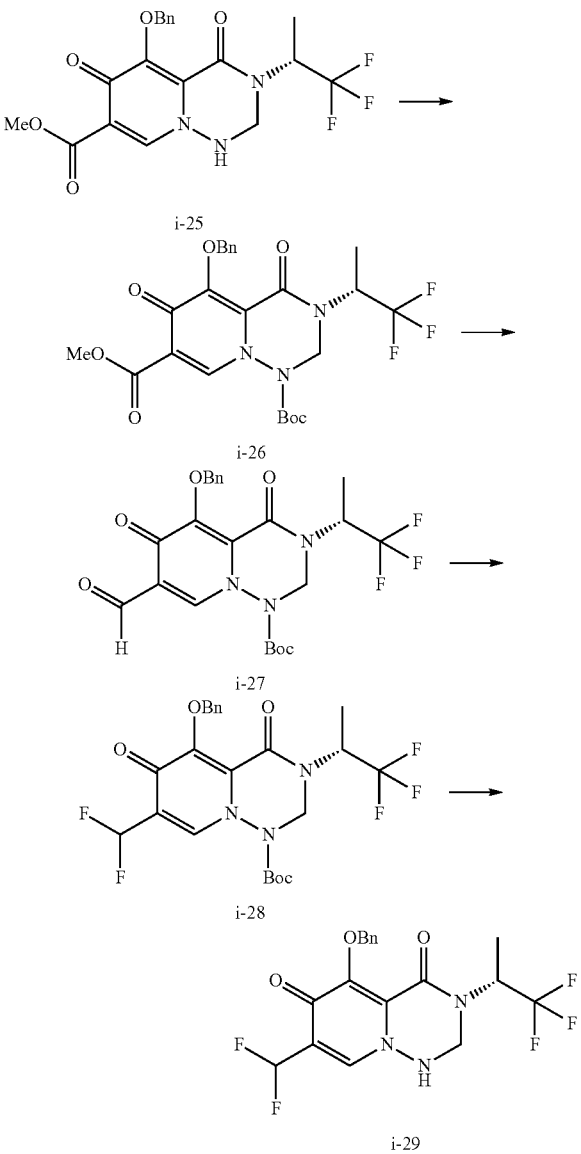

Step 1

Compound i-25 (1.5 g, 3.5 mmol) was suspended in dichloromethane. Boc$_2$O (0.86 mL, 3.7 mmol) and DMAP (43 mg, 0.35 mmol) were added, and the mixture was stirred at room temperature for 1 hour. Water was added, and the mixture was extracted with chloroform. The organic layer was washed with water and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-26 (1.59 g, yield 86%).

$^1$H-NMR (CDCl$_3$) δ: 1.33-1.50 (m, 12H), 3.91 (s, 3H), 4.71 (m, 0.6H), 4.88 (m, 0.4H), 5.13-5.60 (m, 4H), 7.27-7.37 (m, 3H), 7.49-7.66 (m, 2H), 8.16 (s, 1H).

Step 2

Compound i-26 (1.5 g, 2.9 mmol) was suspended in toluene (30 mL) under nitrogen atmosphere, and the mixture was cooled to −78° C. with dry ice-acetone. A DIBAL-hexane solution (3.0 mL, 3.1 mmol) was added dropwise thereto, and the mixture was stirred at −78° C. for 1 hour. To the reaction solution was added ethyl acetate to stop the reaction, and the mixture was heated to room temperature. An aqueous potassium sodium tartrate solution was added, and the mixture was stirred vigorously at room temperature for 1 hour. Two layers were separated, and the organic layer was washed with water and aqueous saturated sodium chloride solution, and then dried with anhydrous sodium sulfate. The solvent was distilled off under reduced pressure, and the resulting residue was purified by silica gel chromatography (hexane-ethyl acetate) to obtain compound i-27 (568 mg, yield 40%).

$^1$H-NMR (CDCl$_3$) δ: 1.38-1.49 (m, 12H), 4.58-4.81 (m, 1H), 5.23-5.70 (m, 4H), 7.27-7.40 (m, 3H), 7.47-7.65 (m, 2H), 7.95 (s, 1H), 10.32 (s, 1H).

Step 3

Compound i-27 (550 mg, 1.1 mmol) was dissolved in dichloromethane (11 mL). The solution was ice-cooled, bis(2-methoxyethyl)aminosulfur trifluoride (0.72 mL, 3.9 mmol) was added, and the mixture was heated to room temperature and stirred for 2 hours. Water was added to the reaction solution to stop the reaction, and the mixture was extracted with ethyl acetate. The organic layer was washed with saturated sodium bicarbonate water, water, and aqueous saturated sodium chloride solution, and then dried with anhydrous sodium sulfate. The solvent was distilled off under reduced pressure, and the resulting residue was purified by silica gel chromatography (hexane-ethyl acetate) to obtain compound i-28 (408 mg, yield 71%).

$^1$H-NMR (CDCl$_3$) δ: 1.36-1.52 (m, 12H), 4.68 (m, 0.7H), 4.78 (m, 0.3H), 5.18-5.59 (m, 4H), 6.89 (t, J=54.9 Hz, 1H), 7.27-7.38 (m, 3H), 7.47-7.63 (m, 2H), 7.64 (s, 1H).

Step 4

Compound i-28 (400 mg, 0.77 mmol) was dissolved in methanol (6 mL). The solution was ice-cooled, a 2 mol/L aqueous sodium hydroxide solution (0.5 mL, 1.0 mmol) was added, and the mixture was stirred at 0° C. for 1 hour. The reaction solution was diluted by adding water, and the mixture was extracted with chloroform. The organic layer was washed with water and aqueous saturated sodium chloride solution, and then dried with anhydrous sodium sulfate. The solvent was distilled off under reduced pressure to obtain compound i-29 (286 mg, yield 89%).

$^1$H-NMR (CDCl$_3$) δ: 1.38 (d, J=7.2 Hz, 3H), 4.47 (d, J=7.8 Hz, 2H), 5.22 (d, J=10.2 Hz, 1H), 5.29 (m, 1H), 5.34 (d, J=10.2 Hz, 1H), 5.82 (m, 1H), 6.80 (t, J=55.2 Hz, 1H), 7.28-7.37 (m, 3H), 7.48-7.55 (m, 2H), 7.71 (s, 1H).

SYNTHESIS OF INTERMEDIATE COMPOUND i-32

[Chemical formula 726]

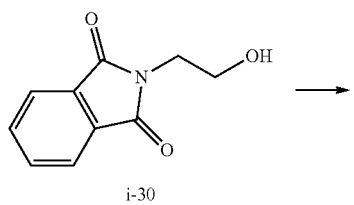

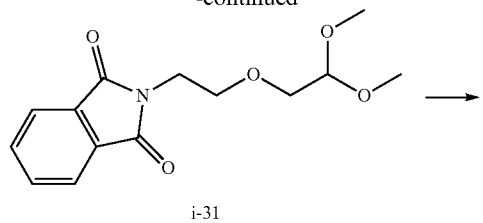

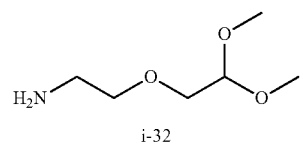

Step 1

Compound i-30 (13.3 g, 69.9 mmol) was dissolved in DMF (60 mL). The solution was ice-cooled, sodium hydride (3.3 g, 83 mmol) was added, and the mixture was stirred at 0° C. for 15 minutes. Bromoacetaldehyde dimethyl acetal (12.3 mL, 104 mmol) and potassium iodide (1.16 g, 7.0 mmol) were added thereto, and the mixture was stirred at room temperature for 3 hours. Water was added to the reaction solution to stop the reaction, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-31 (8.8 g, yield 45%).

$^1$H-NMR (CDCl$_3$) δ: 3.34 (s, 6H), 3.53 (d, J=5.1 Hz, 2H), 3.76 (t, J=5.7 Hz, 2H), 3.91 (t, J=5.7 Hz, 2H), 4.44 (t, J=5.1 Hz, 1H), 7.72 (m, 2H), 7.85 (m, 2H).

Step 2

Compound i-31 (8.79 g, 31.5 mmol) was dissolved in ethanol (100 mL). Hydrazine monohydrate (3.0 mL, 62.9 mmol) was added, and the mixture was stirred at 60° C. for 2 hours. After cooling, the precipitated solid was removed by filtration, and the filtrate was distilled off under reduced pressure. The reprecipitated solid was removed by filtration, and the filtrate was distilled off under reduced pressure to obtain compound i-32 (4.37 g, yield 93%).

$^1$H-NMR (CDCl$_3$) δ: 2.87 (m, 2H), 3.40 (s, 6H), 3.49-3.57 (m, 4H), 4.53 (m, 1H).

SYNTHESIS OF INTERMEDIATE COMPOUNDs i-36 AND i-37

[Chemical formula 727]

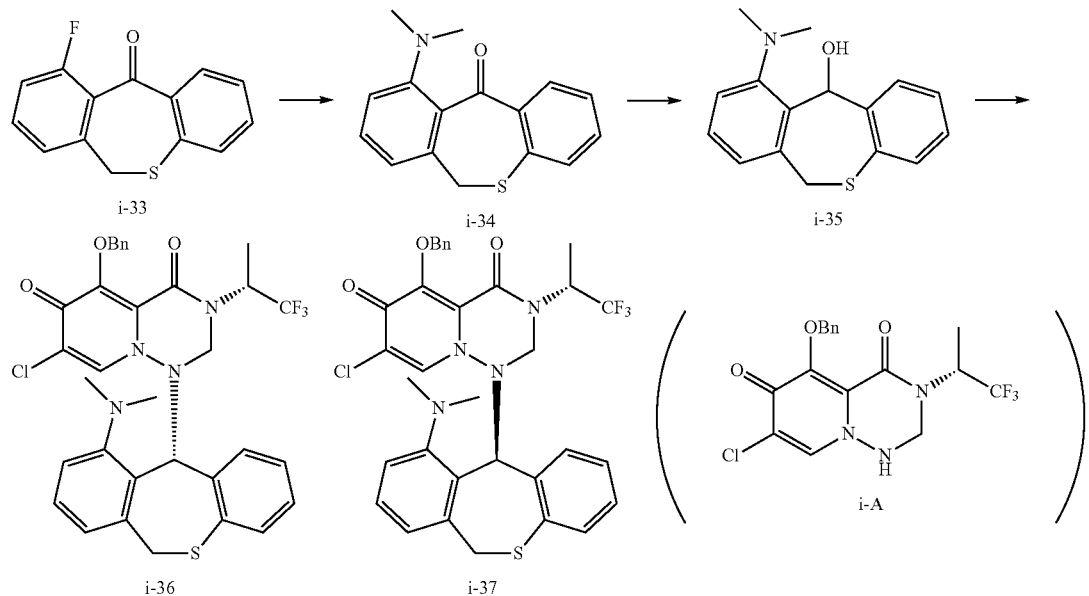

Step 1

Compound i-33 (1.00 g, 4.09 mmol) was dissolved in DMF (5 mL), dimethylamine hydrochloride (384 mg, 4.71 mmol), potassium carbonate (651 mg, 4.71 mmol), and triethylamine (0.653 mL, 4.71 mmol) were added, and the mixture was stirred in a sealed tube at 160° C. for 17.5 hours. Water was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-34 (587 mg, yield 53%).

$^1$H-NMR (CDCl$_3$) δ: 2.71 (s, 6H), 3.96 (s, 2H), 6.68 (d, J=7.3 Hz, 1H), 6.84 (d, J=8.5 Hz, 1H), 7.18-7.36 (m, 4H), 7.99 (dd, J=7.9, 1.5 Hz, 1H).

Step 2

Compound i-34 (587 mg, 2.18 mmol) was dissolved in tetrahydrofuran (20 mL), sodium bis(2-methoxyethoxy)aluminiumhydride-toluene solution (3.39 mL, 10.9 mmol) was added dropwise under ice-cooling, and the mixture was stirred at room temperature for 3.5 hours. Under ice-cooling, an aqueous Rochelle salt (7.06 g, 25.0 mmol) solution (50 mL) was added, and the mixture was heated to room temperature. The solution was extracted with ethyl acetate, and the organic layer was washed with aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-35 (460 mg, yield 78%).

$^1$H-NMR (CDCl$_3$) δ: 2.61 (s, 6H), 3.67 (d, J=13.7 Hz, 1H), 4.95 (d, J=13.7 Hz, 1H), 6.61 (d, J=7.1 Hz, 1H), 6.96-7.18 (m, 4H), 7.24-7.28 (m, 2H), 7.79 (d, J=7.7 Hz, 1H), 9.88 (d, J=6.6 Hz, 1H).

Step 3

Compound i-35 (100 mg, 0.368 mmol) was dissolved in ethyl acetate (3 mL), compound i-A (222 mg, 0.553 mmol) and chloroacetic acid (104 mg, 1.11 mmol) were added, and the mixture was stirred in a sealed tube at 120° C. for 4 hours. The mixture was diluted with ethyl acetate, washed with an aqueous saturated sodium bicarbonate solution and water, and then dried with anhydrous sodium sulfate. The solvent was distilled off under reduced pressure, and the resulting residue was purified by silica gel chromatography (hexane-ethyl acetate) to obtain compound i-36 (107 mg, yield 44%) and compound i-37 (42.7 mg, yield 18%).

4: $^1$H-NMR (CDCl$_3$) δ: 0.96 (d, J=7.1 Hz, 3H), 2.48 (s, 6H), 3.49 (d, J=14.0 Hz, 1H), 4.18 (d, J=13.2 Hz, 1H), 4.66 (d, J=13.2 Hz, 1H), 5.35-5.52 (m, 2H), 5.59 (d, J=10.4 Hz, 1H), 5.79 (d, J=14.0 Hz, 1H), 5.99 (s, 1H), 6.57 (d, J=7.7 Hz, 1H), 6.72 (t, J=7.1 Hz, 1H), 7.03-7.15 (m, 4H), 7.26-7.38 (m, 5H), 7.58-7.64 (m, 2H). 5: MS: m/z=655.15 [M+H]$^+$.

SYNTHESIS OF INTERMEDIATE COMPOUND i-42

[Chemical formula 728]

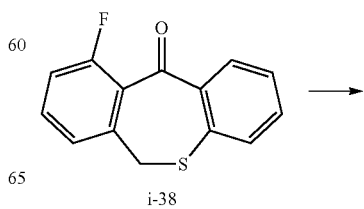

i-38

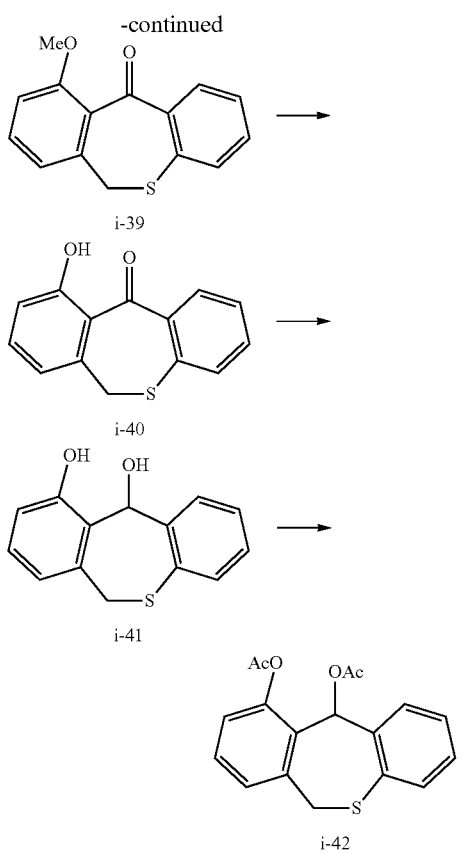

¹H-NMR (CDCl₃) δ: 4.05 (s, 2H), 6.72 (d, J=6.9 Hz, 1H), 6.98 (dd, J=8.2, 1.1 Hz, 1H), 7.32-7.48 (m, 4H), 8.29 (dd, J=7.6, 2.1 Hz, 1H), 12.35 (s, 1H).

Step 3

Compound i-40 (500 mg, 2.06 mmol) was dissolved in tetrahydrofuran (10 mL), sodium bis(2-methoxyethoxy)aluminiumhydride-toluene solution (3.21 mL, 10.3 mmol) was added dropwise under ice-cooling, and the mixture was stirred for 1 hour under ice-cooling. Under ice-cooling, an aqueous Rochelle salt (2.82 g, 10.0 mmol) solution (20 mL) was added, and the mixture was heated to room temperature. The solution was extracted with ethyl acetate, and the organic layer was washed with water and aqueous saturated sodium chloride solution, and then dried with anhydrous magnesium sulfate. The solvent was distilled off under reduced pressure, and to the resulting residue were added dichloromethane-hexane to precipitate a solid, then the solid was filtered to obtain compound i-41 (389 mg, yield 77%).

¹H-NMR (CDCl₃) δ: 3.28 (s, 1H), 3.77 (d, J=13.2 Hz, 1H), 4.73 (d, J=13.2 Hz, 1H), 6.69 (s, 1H), 6.73-6.78 (m, 2H), 7.06-7.17 (m, 4H), 7.60-7.65 (m, 1H), 8.45 (s, 1H).

Step 4

Compound i-41 (150 mg, 0.614 mmol) was suspended in acetonitrile (1.5 mL), triethylamine (0.426 mL, 3.07 mmol), acetic acid anhydride (0.290 mL, 3.07 mmol) and DMAP (37.5 mg, 0.307 mmol) were added, and the mixture was stirred at room temperature for 1.5 hours. Water was added, and the mixture was extracted with ethyl acetate. The organic layer was washed with an aqueous hydrochloric acid solution and aqueous saturated sodium chloride solution, and then dried with anhydrous sodium sulfate. The solvent was distilled off under reduced pressure, and the resulting residue was purified by silica gel chromatography (hexane-ethyl acetate) to obtain compound i-42 (171 mg, yield 85%).

¹H-NMR (CDCl₃) δ: 2.03 (s, 3H), 2.41 (s, 3H), 3.55 (d, J=14.0 Hz, 1H), 5.38 (d, J=13.9 Hz, 1H), 6.97-7.16 (m, 5H), 7.24 (s, 1H), 7.29 (t, J=7.9 Hz, 1H), 7.40 (d, J=7.8 Hz, 1H).

SYNTHESIS OF INTERMEDIATE COMPOUND i-49

Step 1

Compound i-38 (12.0 g, 49.1 mmol) was dissolved in tetrahydrofuran (20 mL), a sodium methoxide-methanol solution (60.0 mL, 311 mmol) was added, and the mixture was refluxed for 4 hours. An aqueous hydrochloric acid solution was added, and the mixture was extracted with ethyl acetate. The organic layer was washed with water and aqueous saturated sodium chloride solution, and then dried with anhydrous sodium sulfate. The solvent was distilled off under reduced pressure, and to the resulting residue were added dichloromethane-hexane to precipitate a solid, then the solid was filtered to obtain compound i-39 (10.5 g, yield 84%).

¹H-NMR (CDCl₃) δ: 3.79 (s, 3H), 3.99 (s, 2H), 6.85 (dd, J=7.8, 6.2 Hz, 2H), 7.19-7.26 (m, 2H), 7.30-7.39 (m, 2H), 7.95 (dd, J=8.2, 1.4 Hz, 1H).

Step 2

Compound i-39 was suspended in dichloromethane (100 mL) under nitrogen atmosphere, and a 1 mol/L tribromoborane-dichloromethane solution (82.0 mL, 82.0 mmol) was added dropwise under ice-cooling, then the mixture was stirred at room temperature for 2 hours. An aqueous sodium bicarbonate solution was added under ice-cooling, and then the mixture was heated to room temperature. An aqueous saturated sodium chloride solution was added, and the mixture was extracted with dichloromethane. The organic layer was washed with aqueous saturated sodium chloride solution and dried with anhydrous sodium sulfate. The solvent was distilled off under reduced pressure, and to the resulting residue were added dichloromethane-hexane to precipitate a solid, then the solid was filtered to obtain compound i-40 (8.42 g, yield 85%).

[Chemical formula 729]

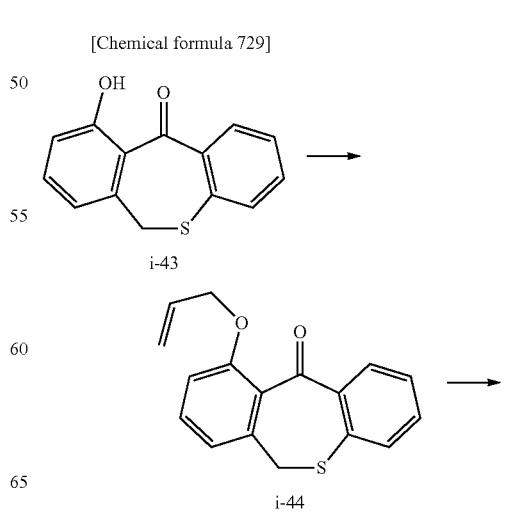

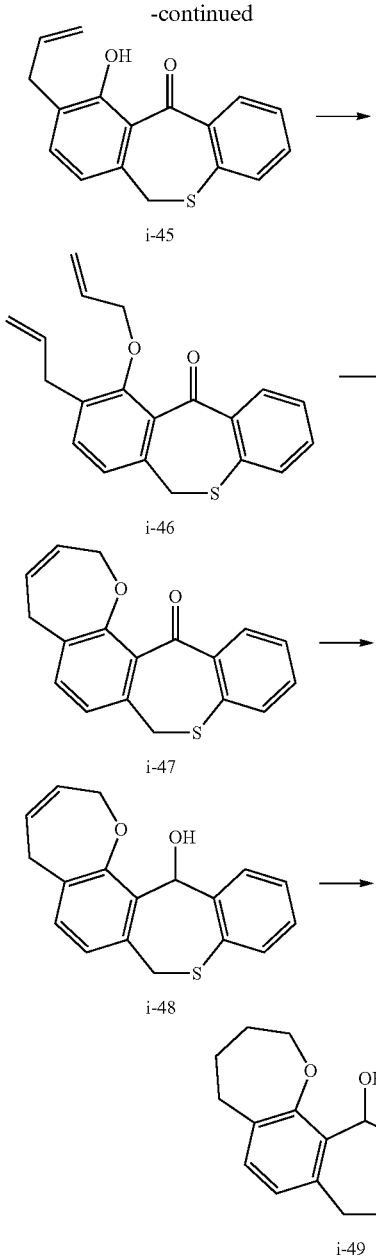

i-45 i-46 i-47 i-48 i-49

Step 1

Compound i-43 (4.06 g, 16.7 mmol) was dissolved in DMSO (40 mL), potassium phosphate (7.11 g, 33.5 mmol) and allyl bromide (2.18 mL, 25.1 mmol) were added, and the mixture was stirred at room temperature for 6 hours. Water was added, and the mixture was extracted with ethyl acetate. The organic layer was washed with water and aqueous saturated sodium chloride solution, and then dried with anhydrous magnesium sulfate. The solvent was distilled off under reduced pressure, and to the resulting residue was added hexane to precipitate a solid, then the solid was filtered to obtain compound i-44 (4.28 g, yield 91%).

$^1$H-NMR (CDCl$_3$) δ: 4.00 (s, 2H), 4.50-4.55 (m, 2H), 5.20-5.26 (m, 1H), 5.32-5.41 (m, 1H), 5.89-6.03 (m, 1H), 6.84 (d, J=8.0 Hz, 2H), 7.19-7.26 (m, 2H), 7.29-7.37 (m, 2H), 7.92 (dd, J=8.2, 1.4 Hz, 1H).

Step 2

Compound i-44 (50.0 mg, 0.177 mmol) was dissolved in DMA (1 mL), and the solution was stirred in a sealed tube at 230° C. for 6 hours. An aqueous hydrochloric acid solution was added, and the mixture was extracted with ethyl acetate. The organic layer was washed with an aqueous hydrochloric acid solution and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-45 (37.1 mg, yield 74%).

$^1$H-NMR (CDCl$_3$) δ: 3.43 (d, J=6.6 Hz, 2H), 4.01 (s, 2H), 5.05-5.15 (m, 2H), 6.01 (ddt, J=17.3, 10.1, 6.8 Hz, 1H), 6.65 (d, J=7.4 Hz, 1H), 7.24 (d, J=7.7 Hz, 1H), 7.29-7.46 (m, 3H), 8.27 (dd, J=8.0, 1.6 Hz, 1H), 12.69 (s, 1H).

Step 3

Compound i-45 (600 mg, 2.13 mmol) was dissolved in DMSO (6 mL), potassium phosphate (902 mg, 4.25 mmol) and allyl bromide (0.276 mL, 3.19 mmol) were added, and the mixture was stirred at room temperature for 2 hours. Water was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-46 (642 mg, yield 88%).

$^1$H-NMR (CDCl$_3$) δ: 3.40 (d, J=6.3 Hz, 2H), 3.99 (s, 2H), 4.27-4.32 (m, 2H), 5.03-5.07 (m, 1H), 5.08-5.12 (m, 1H), 5.15-5.21 (m, 1H), 5.25-5.33 (m, 1H), 5.85-6.04 (m, 2H), 6.95 (d, J=8.0 Hz, 1H), 7.18-7.27 (m, 4H), 7.30-7.37 (m, 1H), 7.88-7.94 (m, 1H).

Step 4

Compound i-46 (560 mg, 1.74 mmol) was dissolved in dichloromethane (56 mL) under nitrogen atmosphere, a second generation Grubbs catalyst (147 mg, 0.174 mmol) was added, and the mixture was stirred at room temperature for 14 hours. The solvent was distilled off under reduced pressure, and the resulting residue was purified by silica gel chromatography (hexane-ethyl acetate) to obtain compound i-47 (366 mg, yield 72%).

$^1$H-NMR (CDCl$_3$) δ: 3.22-3.28 (m, 2H), 3.82 (s, 2H), 4.42-4.47 (m, 2H), 5.23-5.31 (m, 1H), 5.57-5.67 (m, 1H), 6.72 (d, J=7.7 Hz, 1H), 6.95 (d, J=7.7 Hz, 1H), 7.00-7.07 (m, 2H), 7.11-7.19 (m, 1H), 7.74-7.79 (m, 1H).

Step 5

Compound i-47 (362 mg, 1.23 mmol) was dissolved in tetrahydrofuran (7 mL), sodium bis(2-methoxyethoxy)aluminiumhydride-toluene solution (1.15 mL, 3.69 mmol) was added dropwise under ice-cooling, and the mixture was stirred for 45 minutes under ice-cooling. Under ice-cooling, an aqueous Rochelle salt (2.11 g, 7.50 mmol) solution (30 mL) was added, and the mixture was heated to room temperature. The solution was extracted with ethyl acetate, and the organic layer was washed with aqueous saturated sodium chloride solution, then dried with anhydrous magnesium sulfate. The solvent was distilled off under reduced pressure, and the resulting residue was purified by silica gel chromatography (hexane-ethyl acetate) to obtain compound i-48 (352 mg, yield 97%).

$^1$H-NMR (CDCl$_3$) δ: 3.29-3.40 (m, 1H), 3.43-3.55 (m, 1H), 3.95 (d, J=5.5 Hz, 1H), 4.06 (d, J=13.7 Hz, 1H), 4.47-4.52 (m, 2H), 4.82 (d, J=13.7 Hz, 1H), 5.33-5.41 (m, 1H), 5.74-5.84 (m, 1H), 6.43 (d, J=5.8 Hz, 1H), 6.92 (d, J=7.7 Hz, 1H), 6.99 (d, J=7.7 Hz, 1H), 7.06-7.14 (m, 3H), 7.46-7.52 (m, 1H).

Step 6

To a tetrahydrofuran-methanol (1:1, 3 mL) solution of compound i-48 (215 mg, 0.725 mmol) was added 10% palladium carbon (77.0 mg, 0.073 mmol), and the mixture was stirred at room temperature for 1.5 hours under hydrogen atmosphere. The solid was removed by filtration, and the filtrate was distilled off under reduced pressure. The resulting residue was purified by silica gel column chromatography (hexane-ethyl acetate) to obtain compound i-49 (139 mg, yield 64%).

$^1$H-NMR (CDCl$_3$) δ: 1.45-1.55 (m, 1H), 1.67-1.80 (m, 1H), 1.85-2.01 (m, 2H), 2.65-2.85 (m, 2H), 3.63-3.74 (m, 1H), 4.06-4.16 (m, 1H), 4.29 (d, J=13.5 Hz, 1H), 4.49 (d, J=13.5 Hz, 1H), 4.58-4.70 (m, 1H), 6.44 (d, J=6.9 Hz, 1H), 6.88 (d, J=7.4 Hz, 1H), 7.02 (d, J=7.7 Hz, 1H), 7.07-7.11 (m, 3H), 7.49-7.55 (m, 1H).

SYNTHESIS OF INTERMEDIATE COMPOUNDs i-51 AND i-54

[Chemical formula 730]

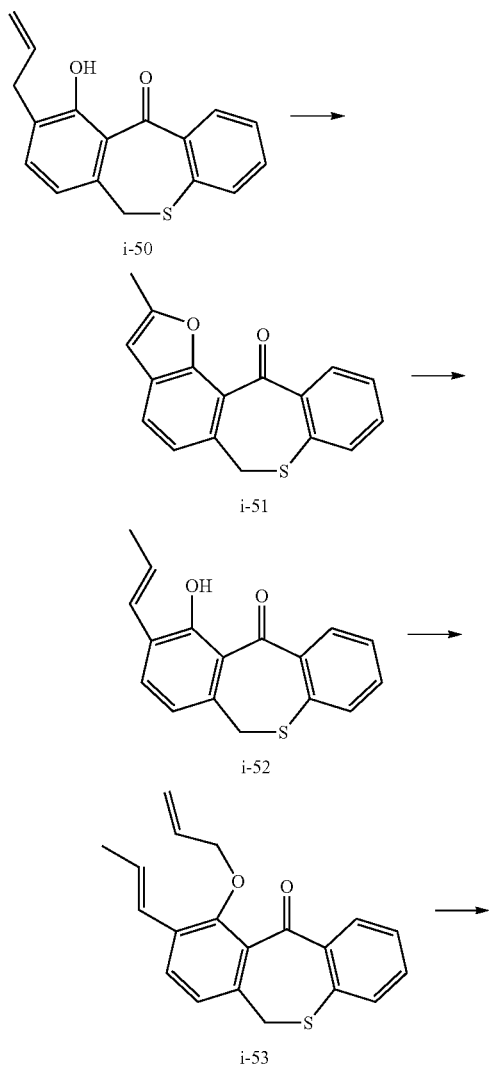

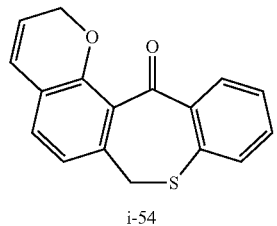

i-54

Step 1

Compound i-51 (676 mg, 2.39 mmol) was dissolved in dioxane (10 mL), dichlorobis(acetonitrile)palladium (155 mg, 0.599 mmol), sodium carbonate (254 mg, 2.39 mmol) and benzoquinone (259 mg, 2.39 mmol) were added, and the mixture was stirred in a sealed tube at 100° C. for 27 hours. The mixture was diluted with ethyl acetate, and the solid was removed by filtration. The filtrate was washed with water and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-51 (166 mg, yield 25%) and compound i-52 (280 mg, yield 41%).

16: MS: m/z=280.95 [M+H]$^+$.

17: $^1$H-NMR (CDCl$_3$) δ: 1.92 (dd, J=6.6, 1.6 Hz, 3H), 4.01 (s, 2H), 6.25 (dq, J=15.8, 6.6 Hz, 1H), 6.66 (d, J=7.7 Hz, 1H), 6.77 (d, J=15.8 Hz, 1H), 7.30-7.51 (m, 4H), 8.26-8.31 (m, 1H), 12.67 (s, 1H).

Step 2

Compound i-52 (250 mg, 0.885 mmol) was dissolved in DMSO (2.5 mL), potassium phosphate (376 mg, 1.77 mmol) and allyl bromide (0.115 mL, 1.33 mmol) were added, and the mixture was stirred at room temperature for 2 hours. Water was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-53 (285 mg, yield 100%).

$^1$H-NMR (CDCl$_3$) δ: 1.88 (dd, J=6.6, 1.5 Hz, 3H), 3.98 (s, 2H), 4.31 (dt, J=5.5, 1.3 Hz, 2H), 5.17 (dd, J=10.5, 1.2 Hz, 1H), 5.29 (dq, J=17.9, 1.5 Hz, 1H), 5.90-6.02 (m, 1H), 6.21 (dq, J=17.9, 6.6 Hz, 1H), 6.57 (dd, J=15.9, 1.2 Hz, 1H), 6.94 (d, J=7.9 Hz, 1H), 7.17-7.24 (m, 2H), 7.28-7.36 (m, 1H), 7.45 (d, J=7.9 Hz, 1H), 7.88 (dd, J=8.2, 1.4 Hz, 1H).

Step 3

Compound i-53 (310 mg, 0.961 mmol) was dissolved in dichloromethane (31 mL) under nitrogen atmosphere, a second generation Grubbs catalyst (82.0 mg, 0.096 mmol) was added, and the mixture was stirred at room temperature for 14 hours. The solvent was distilled off under reduced pressure, and the resulting residue was purified by silica gel chromatography (hexane-ethyl acetate) to obtain compound i-54 (170 mg, yield 63%).

$^1$H-NMR (CDCl$_3$) δ: 3.95 (s, 2H), 4.82 (dd, J=3.4, 1.8 Hz, 2H), 5.75 (dt, J=9.9, 3.4 Hz, 1H), 6.38 (d, J=9.9 Hz, 1H), 6.72 (d, J=7.4 Hz, 1H), 7.4 Hz, 1H), 6.97 (d, J=7.4 Hz, 1H), 7.19-7.26 (m, 2H), 7.30-7.38 (m, 1H), 7.95-8.00 (m, 1H).

SYNTHESIS OF INTERMEDIATE COMPOUND i-56

[Chemical formula 731]

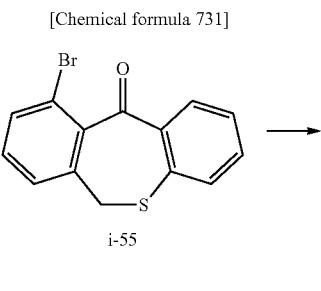

i-55

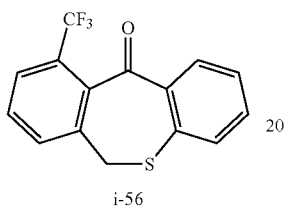

i-56

Step 1

Compound i-55 (100 mg, 0.328 mmol) was suspended in DMF (1 mL), methyl 2,2-difluoro-2-(fluorosulfonyl)acetate (0.124 mL, 0.983 mmol) and copper iodide (68.6 mg, 0.360 mmol) were added, and the mixture was stirred at 130° C. for 4 hours. Water was added, and the mixture was extracted with ethyl acetate. The organic layer was washed with aqueous saturated sodium chloride solution, and then dried with anhydrous magnesium sulfate. The solvent was distilled off under reduced pressure to obtain compound i-56 (96 mg, yield 100%).

$^1$H-NMR (CDCl$_3$) δ: 4.04 (s, 2H), 7.17-7.26 (m, 2H), 7.29-7.36 (m, 1H), 7.41-7.53 (m, 2H), 7.57-7.62 (m, 1H), 7.78 (d, J=7.8 Hz, 1H).

SYNTHESIS OF INTERMEDIATE COMPOUND i-60

[Chemical formula 732]

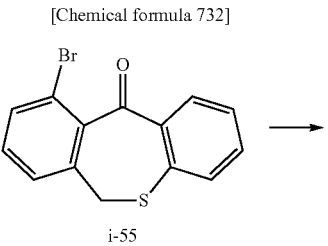

i-55

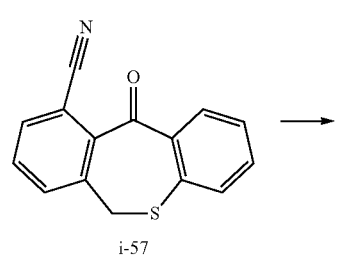

i-57

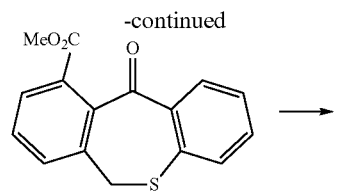

i-58

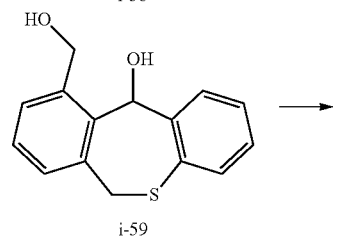

i-59

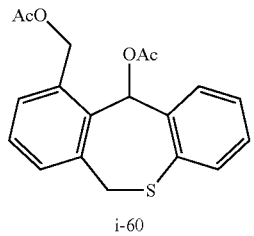

i-60

Step 1

Compound i-55 (3.00 g, 9.83 mmol) was suspended in DMF (30 mL), copper cyanide (2.64 g, 29.5 mmol) was added, and the mixture was refluxed for 8 hours. Water was added, and the mixture was extracted with chloroform. The organic layer was washed with water, and then dried with anhydrous magnesium sulfate. The solvent was distilled off under reduced pressure, and to the resulting residue were added dichloromethane-diethyl ether-hexane to precipitate a solid, then the solid was filtered to obtain compound i-57 (1.72 g, yield 70%).

$^1$H-NMR (CDCl$_3$) δ: 4.06 (s, 2H), 7.27-7.35 (m, 2H), 7.40-7.57 (m, 3H), 7.68 (dd, J=7.4, 1.4 Hz, 1H), 8.16-8.21 (m, 1H).

Step 2

Compound i-57 (25.0 mg, 0.099 mmol) was suspended in methanol (0.5 mL), trimethylsilyl chloride (0.051 mL, 0.398 mmol) was added, and the mixture was stirred at 50° C. for 4.5 hours. An aqueous sodium bicarbonate solution was added, the mixture was extracted with chloroform, and the organic layer was dried with anhydrous sodium sulfate. The solvent was distilled off under reduced pressure, and the resulting residue was purified by silica gel chromatography (hexane-ethyl acetate) to obtain compound i-58 (11.4 mg, yield 40%).

$^1$H-NMR (CDCl$_3$) δ: 3.87 (s, 3H), 4.09 (s, 2H), 7.25-7.53 (m, 5H), 7.86-7.91 (m, 1H), 7.98 (dd, J=7.8, 1.6 Hz, 1H).

Step 3

Compound i-58 (600 mg, 2.11 mmol) was added to tetrahydrofuran (8 mL) under nitrogen atmosphere, lithium aluminum hydride (481 mg, 12.66 mmol) was added under ice-cooling, and the mixture was stirred for 45 minutes under ice-cooling. Under ice-cooling, an aqueous saturated ammonium chloride solution (1.5 mL) was added dropwise, and the mixture was heated to room temperature. The solution was extracted with ethyl acetate, and the organic layer was washed with an aqueous hydrochloric acid solution and aqueous saturated sodium chloride solution, then dried with anhydrous magnesium sulfate. The solvent was distilled off under reduced pressure, and the resulting residue was purified by silica gel chromatography (hexane-ethyl acetate) to obtain compound i-59 (415 mg, yield 76%).

$^1$H-NMR (DMSO-$d_6$) δ: 3.48-3.70 (m, 1H), 4.34-4.49 (m, 2H), 4.95 (t, J=5.4 Hz, 1H), 5.18-5.47 (m, 1H), 5.79-5.88 (m, 2H), 6.78-6.95 (m, 3H), 6.99-7.11 (m, 3H), 7.22 (d, J=6.0 Hz, 1H).

Step 4

Compound i-59 (70.0 mg, 0.271 mmol) was suspended in acetonitrile (1 mL), triethylamine (0.188 mL, 1.36 mmol), acetic acid anhydride (0.128 mL, 1.36 mmol) and DMAP (16.6 mg, 0.135 mmol) were added, and the mixture was stirred at room temperature for 30 minutes. Water was added, and the mixture was extracted with ethyl acetate. The organic layer was washed with an aqueous hydrochloric acid solution and aqueous saturated sodium chloride solution, and then dried with anhydrous sodium sulfate. The solvent was distilled off under reduced pressure to obtain compound i-60 (93.0 mg, yield 100%).

$^1$H-NMR (CDCl$_3$) δ: 1.92 (s, 3H), 2.08 (s, 3H), 3.53 (d, J=14.0 Hz, 1H), 5.38 (d, J=1.4 Hz, 2H), 5.47 (d, J=14.0 Hz, 1H), 7.03-7.20 (m, 4H), 7.24-7.31 (m, 2H), 7.48 (dd, J=7.6, 1.2 Hz, 1H).

SYNTHESIS OF INTERMEDIATE COMPOUND i-61

[Chemical formula 733]

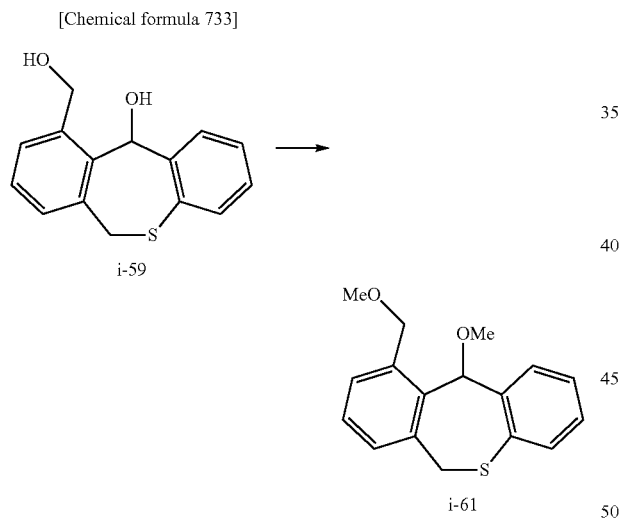

Step 1

Compound i-59 (100 mg, 0.387 mmol) was added to tetrahydrofuran under nitrogen atmosphere, sodium hydride (37.2 mg, 0.929 mmol) was added under ice-cooling, and the mixture was stirred for 5 minutes under ice-cooling. Thereafter, methyl iodide (0.145 mL, 2.32 mmol) was added, and the mixture was stirred at room temperature for 2 hours. Water was added, and the mixture was extracted with ethyl acetate. The organic layer was washed with an aqueous hydrochloric acid solution and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-61 (106 mg, yield 96%).

$^1$H-NMR (CDCl$_3$) δ: 3.29 (s, 3H), 3.34 (s, 3H), 3.40 (d, J=13.1 Hz, 1H), 4.45-4.58 (m, 2H), 5.63 (s, 1H), 5.70 (d, J=13.1 Hz, 1H), 7.00-7.24 (m, 6H), 7.35 (d, J=7.4 Hz, 1H).

SYNTHESIS OF INTERMEDIATE COMPOUND i-65

[Chemical formula 734]

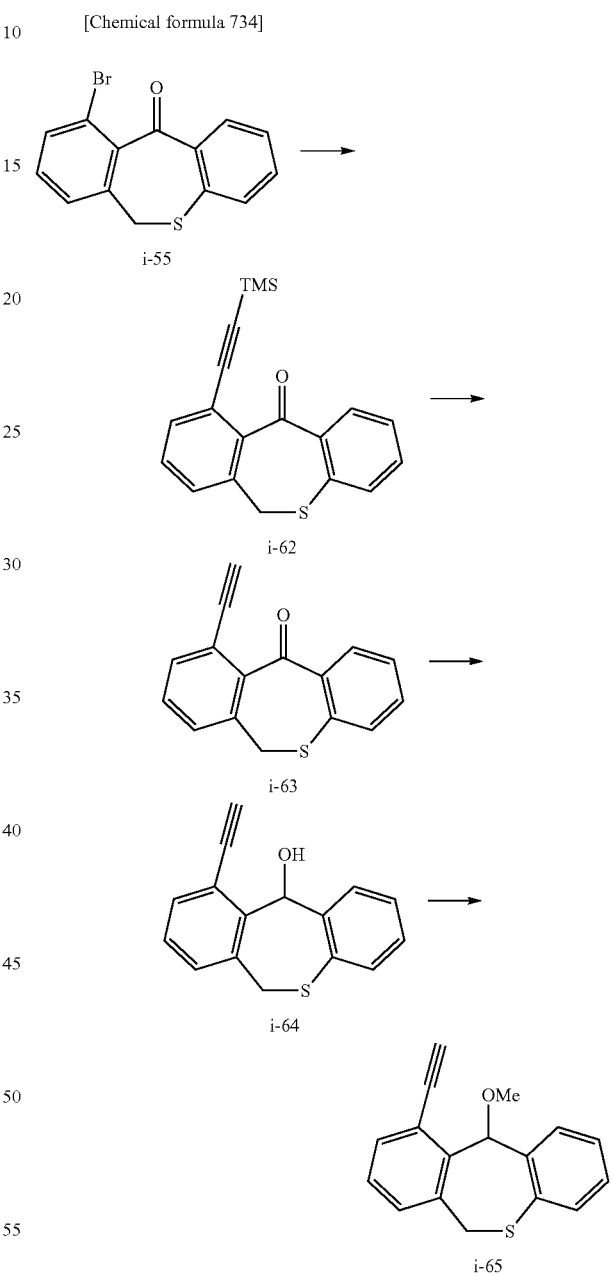

Step 1

Compound i-55 (2.10 g, 6.88 mmol) was suspended in DMF (10.5 mL), copper iodide (262 mg, 1.38 mmol), dichlorobis(triphenylphosphine)palladium (966 mg, 1.38 mmol), trimethylsilylacetylene (4.86 mL, 34.4 mmol), and triethylamine (14.0 mL, 101 mmol) were added, and the mixture was stirred in a sealed tube at 140° C. for 11 hours. The mixture was diluted with ethyl acetate, and the solid was removed by filtration. The filtrate was washed with an aqueous hydrochloric acid solution and aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-62 (1.34 g, yield 60%).

MS: m/z=323.05 [M+H]$^+$.

Step 2

Compound i-62 (1.34 g, 4.16 mmol) was dissolved in methanol (40 mL), potassium carbonate (1.72 g, 12.5 mmol) was added, and the mixture was stirred at room temperature for 1.5 hours. Water was added, and the mixture was extracted with ethyl acetate. The organic layer was washed with aqueous saturated sodium chloride solution, and then dried with anhydrous magnesium sulfate. The solvent was distilled off under reduced pressure, and the resulting residue was purified by silica gel chromatography (hexane-ethyl acetate) to obtain compound i-63 (967 mg, yield 93%).

$^1$H-NMR (CDCl$_3$) δ: 3.20 (s, 1H), 4.05 (s, 2H), 7.14-7.30 (m, 4H), 7.40 (t, J=7.8 Hz, 1H), 7.51 (d, J=7.6 Hz, 1H), 7.79 (dt, J=7.7, 0.8 Hz, 1H).

Step 3

Compound i-63 (619 mg, 2.47 mmol) was added to tetrahydrofuran (12 mL) under nitrogen atmosphere, lithium aluminum hydride (282 mg, 7.42 mmol) was added under ice-cooling, and the mixture was stirred for 1 hour under ice-cooling. Under ice-cooling, an aqueous saturated ammonium chloride solution (15 mL) was added dropwise, and the mixture was heated to room temperature. The solution was extracted with ethyl acetate, and the organic layer was washed with an aqueous hydrochloric acid solution and aqueous saturated sodium chloride solution, then dried with anhydrous magnesium sulfate. The solvent was distilled off under reduced pressure, and the resulting residue was purified by silica gel chromatography (hexane-ethyl acetate) to obtain compound i-64 (554 mg, yield 89%).

$^1$H-NMR (CDCl$_3$) δ: 2.73 (d, J=3.4 Hz, 1H), 3.41 (s, 1H), 3.57 (d, J=13.6 Hz, 1H), 5.63 (d, J=13.6 Hz, 1H), 6.55 (d, J=3.4 Hz, 1H), 7.04-7.26 (m, 5H), 7.37-7.44 (m, 2H).

Step 4

A tetrahydrofuran (2 mL) solution of compound i-64 (50.0 mg, 0.198 mmol) was cooled to −78° C. with dry ice-acetone under nitrogen atmosphere. A 1.65 mol/L n-butyllithium-hexane solution (0.312 mL, 0.515 mmol) was added dropwise thereto, and the mixture was stirred at room temperature for 20 minutes. The mixture was again cooled to −78° C. with dry ice-acetone, then methyl iodide (0.248 mL, 3.96 mmol) was added dropwise, and the mixture was stirred for 1.5 hours while the mixture was heated to room temperature. An aqueous saturated ammonium chloride solution (1.5 mL) was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel column chromatography (hexane-ethyl acetate) to obtain compound i-65 (44.9 mg, yield 81%).

$^1$H-NMR (CDCl$_3$) δ: 2.14 (s, 3H), 3.34 (s, 3H), 3.38 (d, J=13.5 Hz, 1H), 5.62 (d, J=13.5 Hz, 1H), 5.97 (s, 1H), 7.01-7.23 (m, 5H), 7.29 (dd, J=7.3, 1.8 Hz, 1H), 7.36 (d, J=7.4 Hz, 1H).

SYNTHESIS OF INTERMEDIATE COMPOUND i-67

[Chemical formula 735]

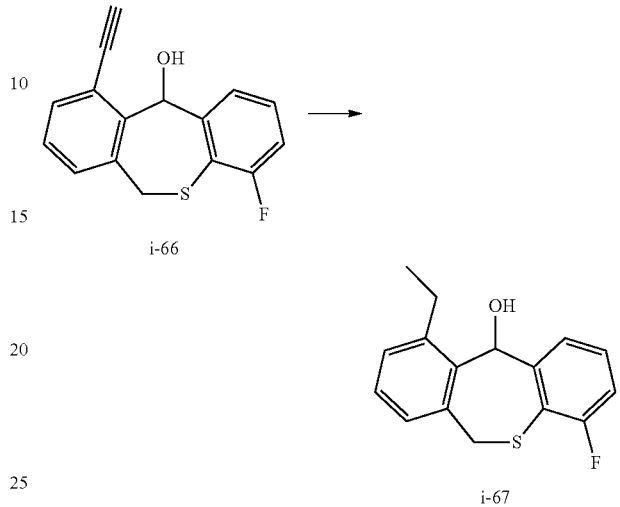

Step 1

To a tetrahydrofuran-methanol (1:1, 6 mL) solution of compound i-66 (520 mg, 1.92 mmol) was added 10% palladium carbon (205 mg, 0.192 mmol), and the mixture was stirred at room temperature for 1 hour under hydrogen atmosphere. The solid was removed by filtration, and the filtrate was distilled off under reduced pressure. The resulting residue was purified by silica gel column chromatography (hexane-ethyl acetate) to obtain compound i-67 (370 mg, yield 70%).

$^1$H-NMR (CDCl$_3$) δ: 1.25 (t, J=7.5 Hz, 3H), 2.48 (d, J=1.7 Hz, 1H), 2.82 (dq, J=2.7, 7.5 Hz, 2H), 3.63 (d, J=13.6 Hz, 1H), 5.79 (d, J=13.6 Hz, 1H), 6.25 (s, 1H), 6.97-7.32 (m, 7H).

SYNTHESIS OF INTERMEDIATE COMPOUND i-69

[Chemical formula 736]

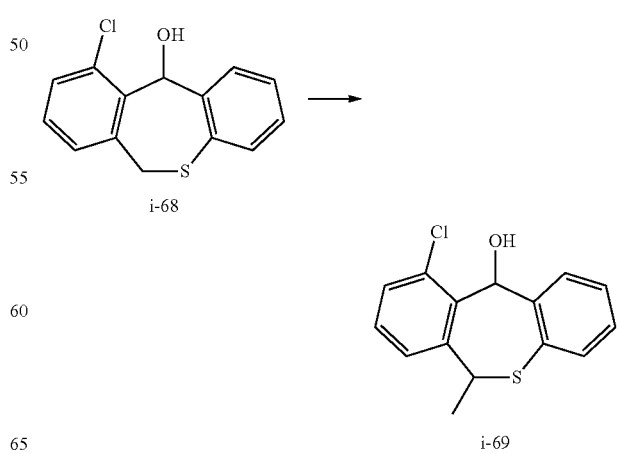

Step 1

A tetrahydrofuran (40 mL) solution of compound i-68 (1.00 g, 3.81 mmol) was cooled to −78° C. with dry ice-acetone under nitrogen atmosphere. A 1.65 mol/L n-butyllithium-hexane solution (6.92 mL, 11.4 mmol) was added dropwise thereto, and the mixture was stirred at room temperature for 30 minutes. The mixture was again cooled to −78° C. with dry ice-acetone, then methyl iodide (2.38 mL, 38.1 mmol) was added dropwise, and the mixture was stirred for 2.5 hours while the mixture was heated to room temperature. After the reaction solution was concentrated, water was added, and the mixture was extracted with ethyl acetate. The organic layer was washed with aqueous saturated sodium chloride solution, and then dried with anhydrous magnesium sulfate. The solvent was distilled off under reduced pressure, and the resulting residue was purified by silica gel column chromatography (hexane-ethyl acetate) to obtain compound i-69 (522 mg, yield 50%).

$^1$H-NMR (CDCl$_3$) δ: 1.74 (d, J=6.9 Hz, 3H), 4.96-5.09 (m, 2H), 6.65 (d, J=10.7 Hz, 1H), 7.10-7.28 (m, 6H), 7.49-7.52 (m, 1H).

SYNTHESIS OF INTERMEDIATE COMPOUND i-72

[Chemical formula 737]

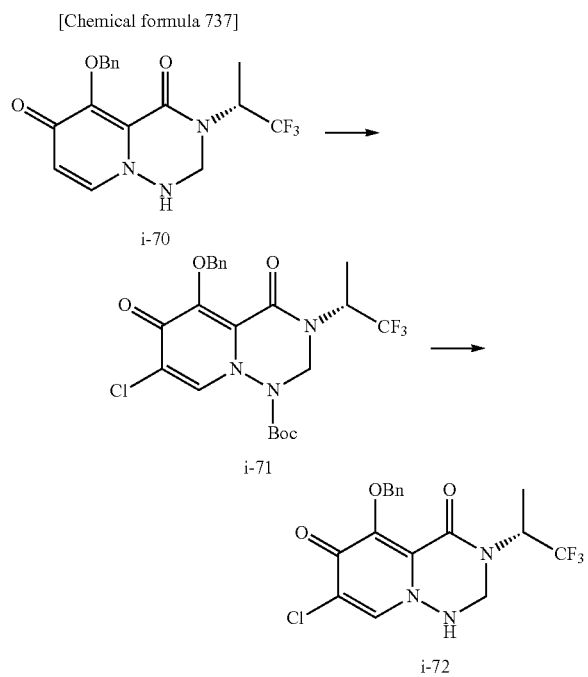

Step 1

Compound i-70 (500 mg, 1.36 mmol) was dissolved in dichloromethane (10 mL), Boc$_2$O (0.348 mL, 1.50 mmol) and DMAP (16 mg, 0.136 mmol) were added, and the mixture was stirred at room temperature for 1 hour. Thereafter, NCS (273 mg, 2.04 mmol) was added, and the mixture was heated to reflux for 7 hours, and then stirred at room temperature for 4 days.

The reaction solution was concentrated, and the resulting residue was purified by silica gel column chromatography (chloroform-methanol) to obtain compound i-71 (670 mg, yield 98%).

MS: m/z=502.12 [M+H]$^+$

Step 2

To an ethanol solution of compound i-71 (670 mg, 1.34 mmol) was added a 2M aqueous hydrochloric acid solution (3.34 mL, 6.67 mmol), and the mixture was stirred at 60° C. for 3 hours. Saturated sodium bicarbonate water was added, the mixture was extracted with chloroform. The organic layer was washed with water and aqueous saturated sodium chloride solution, and then dried with anhydrous magnesium sulfate. The solvent was distilled off under reduced pressure to obtain compound i-72 (452 mg, 1.13 mmol).

MS: m/z=402.08 [M+H]$^+$

Hereinbelow, Reference examples 666 to 775 were synthesized using the above intermediate compounds.

SYNTHESIS OF REFERENCE EXAMPLE 666

[Chemical formula 738]

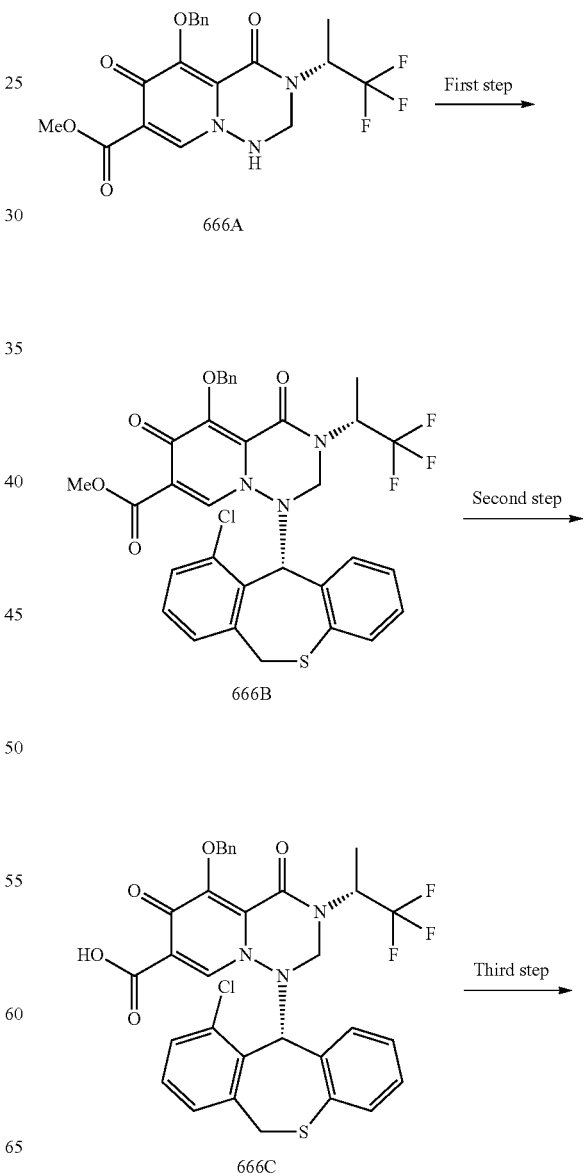

-continued

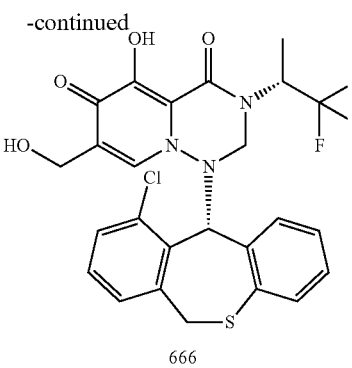

666

First Step

Compound 666A (1.0 g, 2.4 mmol), 10-chloro-6,11-dihydrodibenzo[b,e]thiepin-11-ol (741 mg, 2.8 mmol), and a propanephosphonic acid anhydride-50% ethyl acetate solution (10 mL, 16.8 mmol) were mixed, and the mixture was stirred at 100° C. for 5 hours. To the reaction solution was added ethyl acetate, the solution was diluted, and the solution was washed with water and aqueous saturated sodium chloride solution, and then dried with anhydrous sodium sulfate. The solvent was distilled off under reduced pressure, and the resulting residue was purified by silica gel chromatography (hexane-ethyl acetate) to obtain compound 666B (451 mg, yield 29%).

$^1$H-NMR (CDCl$_3$) δ: 1.09 (d, J=7.5 Hz, 3H), 3.62 (d, J=13.5 Hz, 1H), 3.76 (s, 3H), 4.37 (d, J=13.2 Hz, 1H), 4.80 (d, J=13.2 Hz, 1H), 5.43 (d, 10.5 Hz, 1H), 5.53-5.66 (m, 3H), 5.86 (s, 1H), 6.58 (m, 1H), 6.76 (m, 1H), 7.04-7.13 (m, 2H), 7.26-7.38 (m, 6H), 7.58-7.63 (m, 2H), 7.99 (s, 1H).

Second Step

Compound 666B (570 mg, 0.85 mmol) was dissolved in tetrahydrofuran (6 mL) and methanol (1.5 mL). The solution was ice-cooled, a 2 mol/L aqueous sodium hydroxide solution (0.64 mL, 1.28 mmol) was added thereto, and the mixture was stirred at 0° C. for 30 minutes. Hydrochloric acid was added to the reaction solution to stop the reaction, and the mixture was extracted with ethyl acetate. The organic layer was washed with water and aqueous saturated sodium chloride solution, and then dried with anhydrous sodium sulfate. The solvent was distilled off under reduced pressure, and the resulting residue was purified by silica gel chromatography (hexane-ethyl acetate) to obtain compound 666C (433 mg, yield 78%).

$^1$H-NMR (CDCl$_3$) δ: 1.09 (d, J=7.2 Hz, 3H), 3.62 (d, J=13.8 Hz, 1H), 4.42 (d, J=13.2 Hz, 1H), 4.82 (d, J=13.2 Hz, 1H), 5.50-5.62 (m, 3H), 5.66 (d, J=10.8 Hz, 1H), 5.82 (s, 1H), 6.38 (m, 1H), 6.70 (m, 1H), 7.05-7.16 (m, 2H), 7.26-7.39 (m, 6H), 7.51-7.56 (m, 2H), 8.12 (s, 1H), 14.31 (s, 1H).

Third Step

Compound 666C (289 mg, 0.44 mmol) was dissolved in tetrahydrofuran (5 mL). The solution was ice-cooled, triethylamine (0.18 mL, 1.3 mmol) and ethyl chloroformate (0.11 mL, 1.1 mmol) were added, and the mixture was stirred for 15 minutes. The mixture was cooled to −78° C. with dry ice-acetone, a DIBAL-hexane solution (2.1 mL, 2.2 mmol) was added, and the mixture was stirred at −78° C. for 40 minutes. To the reaction solution was added ethyl acetate to stop the reaction, and the mixture was heated to room temperature. An aqueous potassium sodium tartrate solution was added, and the mixture was stirred vigorously at room temperature for 2 hours. The organic layer was dried with anhydrous sodium sulfate. The solvent was distilled off under reduced pressure, and the resulting residue was dissolved in DMF (2 ml). Lithium chloride (70 mg, 1.7 mmol) was added, and the mixture was stirred at 100° C. for 2 hours. The mixture was allowed to cool, diluted with ethyl acetate, and washed with 2 mol/L hydrochloric acid, water, and aqueous saturated sodium chloride solution. The solvent was distilled off under reduced pressure, and to the resulting residue were added ethyl acetate-diisopropyl ether to precipitate a solid, then the solid was filtered to obtain compound 666 (40.5 mg, yield 17%).

$^1$H-NMR (CDCl$_3$) δ: 1.16 (d, J=7.2 Hz, 3H), 3.63 (d, J=13.5 Hz, 1H), 4.06 (d, J=13.2 Hz, 1H), 4.24 (d, J=13.2 Hz, 1H), 4.44 (d, J=12.9 Hz, 1H), 4.87 (d, J=12.9 Hz, 1H), 5.50 (m, 1H), 5.72 (d, J=13.5 Hz, 1H), 5.93 (s, 1H), 6.75 (m, 1H), 6.83 (m, 1H), 7.09-7.14 (m, 2H), 7.22 (s, 1H), 7.27-7.39 (m, 1H).

MS: m/z=552.2 [M+H]$^+$.

REFERENCE EXAMPLE 667

[Chemical formula 739]

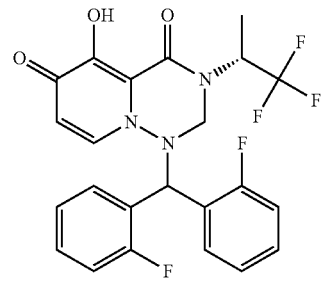

MS: m/z=480.15 [M+H]$^+$.

REFERENCE EXAMPLE 668

[Chemical formula 740]

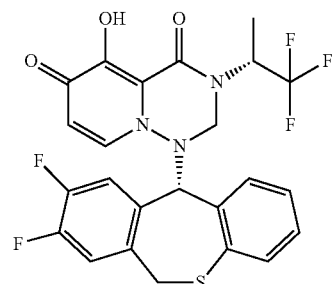

MS: m/z=524 [M+H]$^+$.

REFERENCE EXAMPLE 669
[Chemical formula 741]
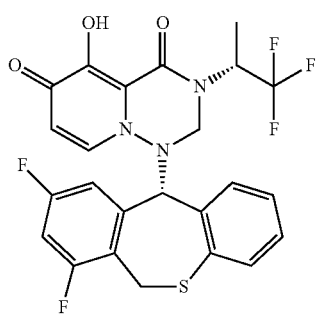
MS: m/z=524 [M+H]$^+$.
REFERENCE EXAMPLE 670
[Chemical formula 742]
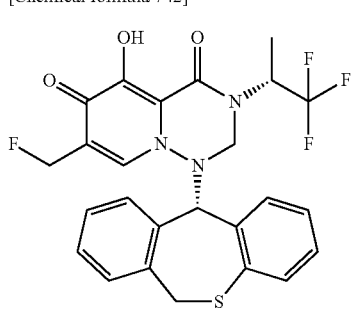
MS: m/z=520 [M+H]$^+$.
REFERENCE EXAMPLE 671
[Chemical formula 743]
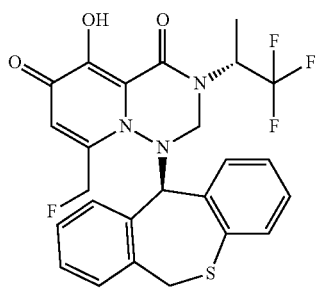
MS: m/z=520 [M+H]$^+$.
REFERENCE EXAMPLE 672
[Chemical formula 744]
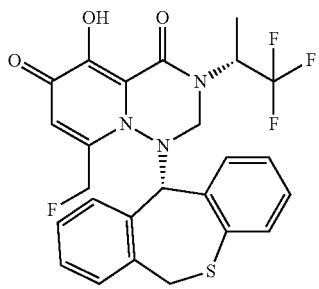
MS: m/z=520 [M+H]$^+$.
REFERENCE EXAMPLE 673
[Chemical formula 745]
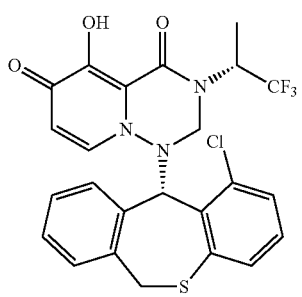
MS: m/z=522.19 [M+H]$^+$.
REFERENCE EXAMPLE 674
[Chemical formula 746]
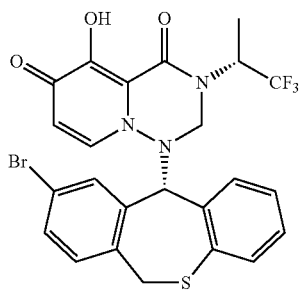
MS: m/z=566.98 [M+H]$^+$.

REFERENCE EXAMPLE 675
[Chemical formula 747]
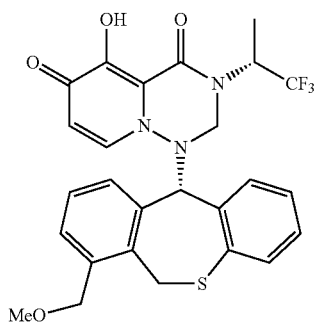
MS: m/z=532.22 [M+H]⁺.
REFERENCE EXAMPLE 676
[Chemical formula 748]
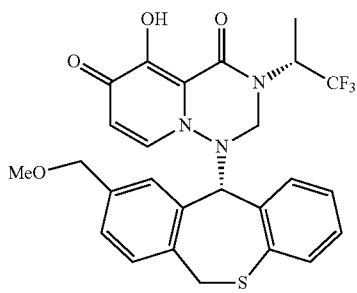
MS: m/z=532.22 [M+H]⁺.
REFERENCE EXAMPLE 677
[Chemical formula 749]
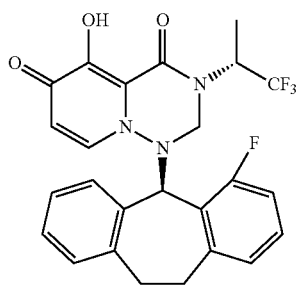
MS: m/z=488 [M+H]⁺. RT=2.11 min.
REFERENCE EXAMPLE 678
[Chemical formula 750]
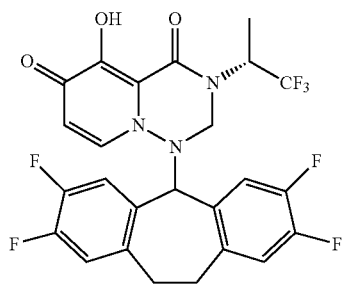
MS: m/z=542 [M+H]⁺. RT=2.23 min.
REFERENCE EXAMPLE 679
[Chemical formula 751]
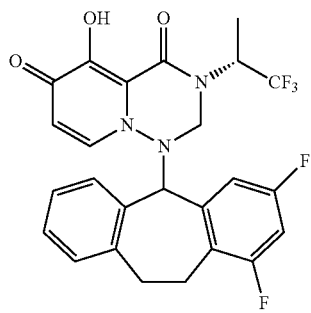
MS: m/z=506 [M+H]⁺. RT=2.21 min.
REFERENCE EXAMPLE 680
[Chemical formula 752]
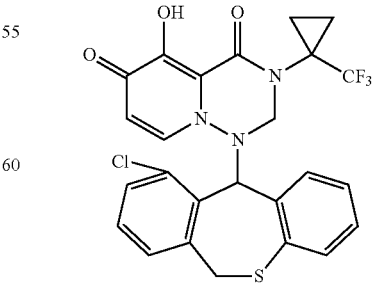
MS: m/z=534 [M+H]⁺. RT=2.06 min.

REFERENCE EXAMPLE 681

[Chemical formula 753]

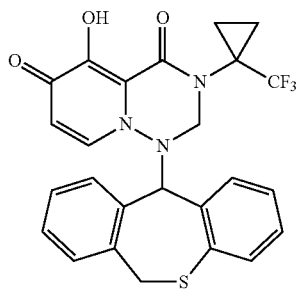

MS: m/z=500 [M+H]$^+$. RT=2.05 min.

REFERENCE EXAMPLE 682

[Chemical formula 754]

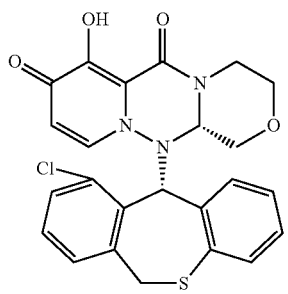

MS: m/z=482 [M+H]$^+$. RT=1.76 min.

REFERENCE EXAMPLE 683

[Chemical formula 755]

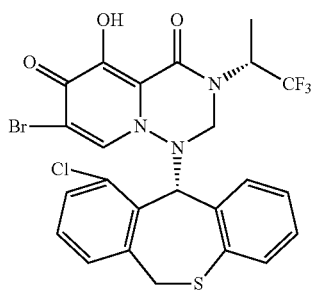

MS: m/z=600 [M+H]$^+$. RT=2.32 min. (メソッド 6 で測定)

REFERENCE EXAMPLE 684

[Chemical formula 756]

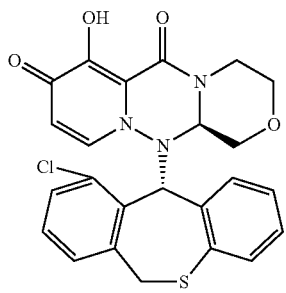

MS: m/z=482 [M+H]$^+$. RT=1.82 min.

REFERENCE EXAMPLE 685

[Chemical formula 757]

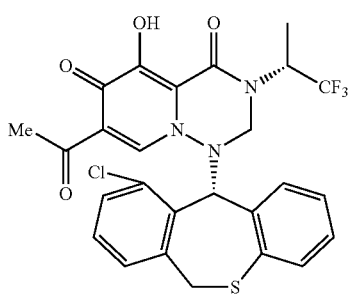

MS: m/z=564 [M+H]$^+$. RT=2.23 min.

REFERENCE EXAMPLE 686

[Chemical formula 758]

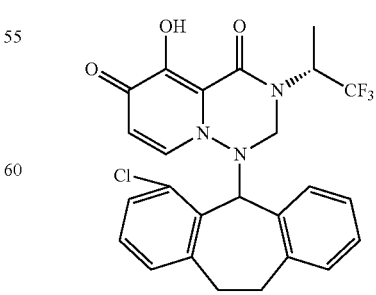

MS: m/z=[M+H]$^+$. RT=. min.

REFERENCE EXAMPLE 687
[Chemical formula 759]
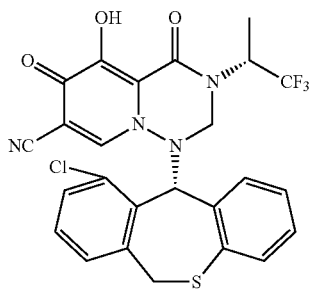
MS: m/z=547 [M+H]⁺. RT=2.20 min.
REFERENCE EXAMPLE 688
[Chemical formula 760]
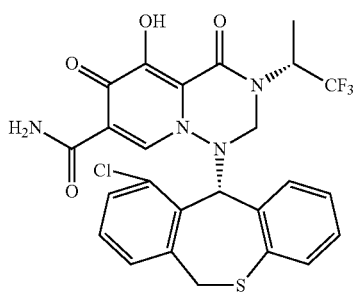
MS: m/z=565 [M+H]⁺. RT=2.03 min.
REFERENCE EXAMPLE 689
[Chemical formula 761]
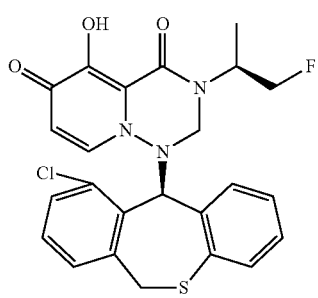
MS: m/z=486 [M+H]⁺. RT=1.96 min.
REFERENCE EXAMPLE 690
[Chemical formula 762]
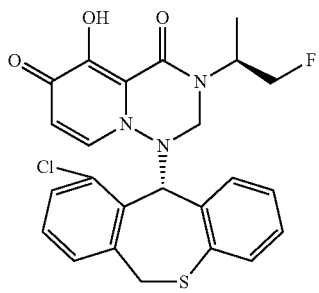
MS: m/z=486 [M+H]⁺. RT=1.96 min.
REFERENCE EXAMPLE 691
[Chemical formula 763]
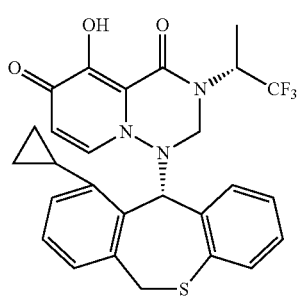
MS: m/z=529 [M+H]⁺. RT=2.21 min.
REFERENCE EXAMPLE 692
[Chemical formula 764]
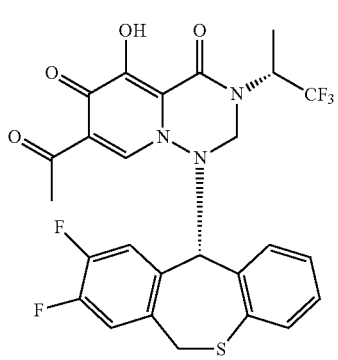
MS: m/z=566 [M+H]⁺. RT=2.23 min.

REFERENCE EXAMPLE 693
[Chemical formula 765]
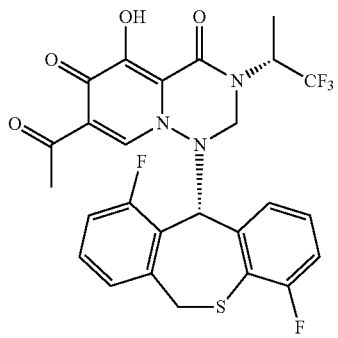
MS: m/z=566 [M+H]⁺. RT=2.16 min.
REFERENCE EXAMPLE 694
[Chemical formula 766]
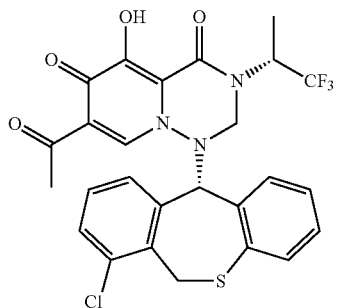
MS: m/z=564 [M+H]⁺. RT=2.33 min.
REFERENCE EXAMPLE 695
[Chemical formula 767]
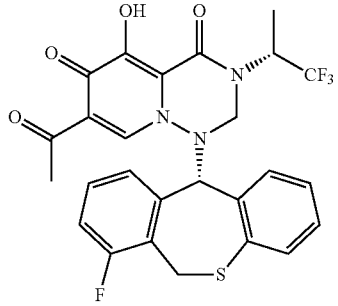
MS: m/z=548 [M+H]⁺. RT=2.20 min.
REFERENCE EXAMPLE 696
[Chemical formula 768]
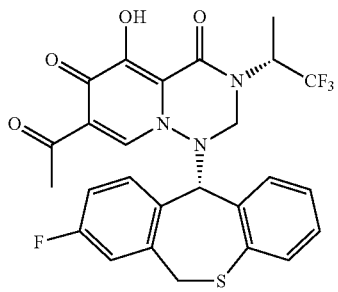
MS: m/z=548 [M+H]⁺. RT=2.17 min.
REFERENCE EXAMPLE 697
[Chemical formula 769]
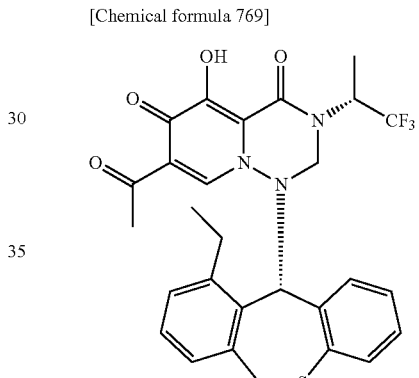
S
MS: m/z=558 [M+H]⁺. RT=2.31 min.
REFERENCE EXAMPLE 698
[Chemical formula 770]
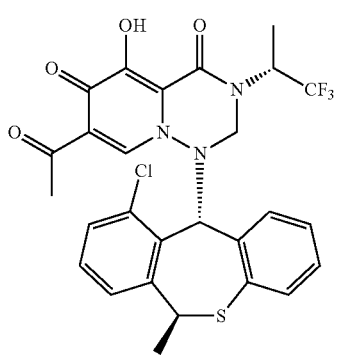
MS: m/z=578 [M+H]⁺. RT=2.35 min.

REFERENCE EXAMPLE 699
[Chemical formula 771]
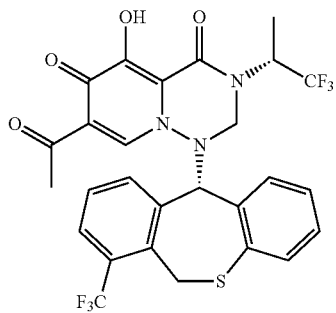
MS: m/z=598 [M+H]+. RT=2.37 min.
REFERENCE EXAMPLE 700
[Chemical formula 772]
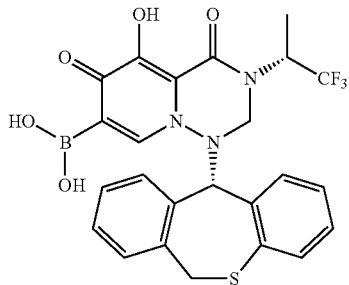
MS: m/z=532 [M+H]+. RT=2.02 min.
REFERENCE EXAMPLE 701
[Chemical formula 773]
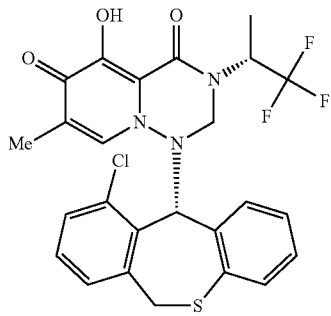
MS: m/z=536 [M+H]+. RT=2.14 min.
REFERENCE EXAMPLE 702
[Chemical formula 774]
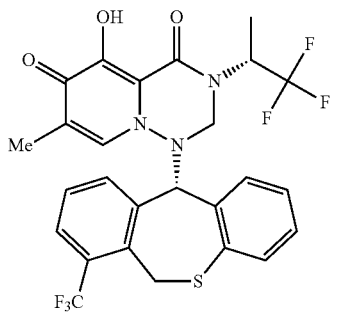
MS: m/z=570 [M+H]+. RT=2.35 min.
REFERENCE EXAMPLE 703
[Chemical formula 775]
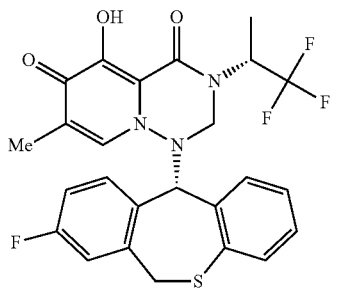
MS: m/z=520 [M+H]+. RT=2.13 min.
REFERENCE EXAMPLE 704
[Chemical formula 776]
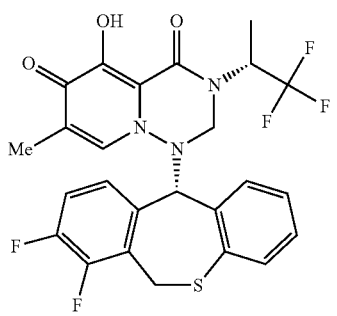
MS: m/z=538 [M+H]+. RT=2.24 min.

REFERENCE EXAMPLE 705
[Chemical formula 777]
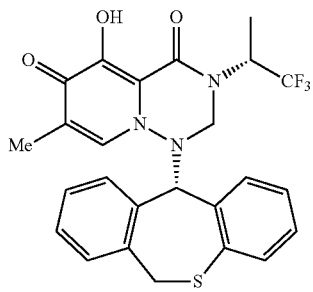
MS: m/z=502 [M+H]+. RT=2.13 min.
REFERENCE EXAMPLE 706
[Chemical formula 778]
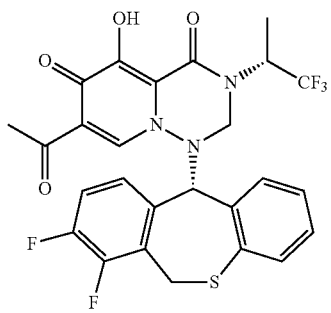
MS: m/z=566 [M+H]+. RT=2.27 min.
REFERENCE EXAMPLE 707
[Chemical formula 779]
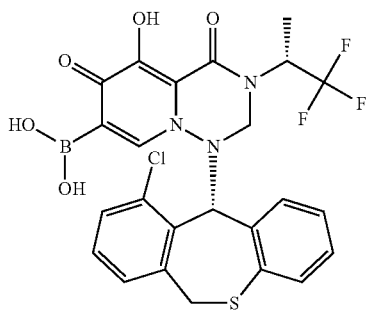
MS: m/z=566 [M+H]+. RT=2.11 min.
REFERENCE EXAMPLE 708
[Chemical formula 780]
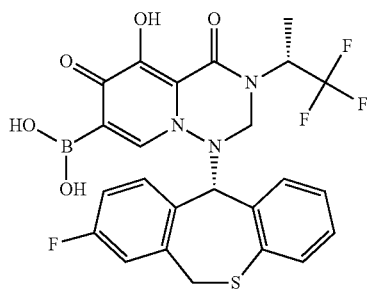
MS: m/z=550 [M+H]+. RT=2.06 min.
REFERENCE EXAMPLE 709
[Chemical formula 781]
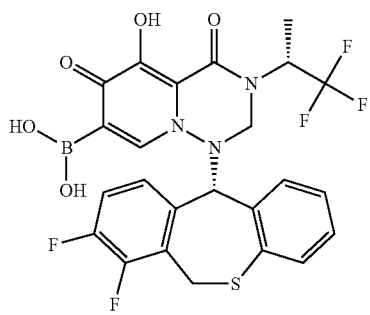
MS: m/z=568 [M+H]+. RT=2.14 min.
REFERENCE EXAMPLE 710
[Chemical formula 782]
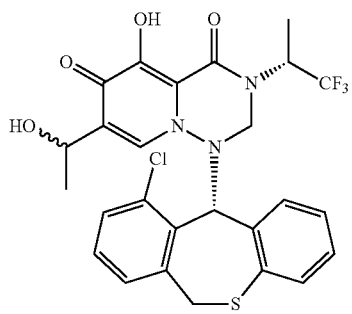
MS: m/z=566 [M+H]+. RT=2.00 min.

REFERENCE EXAMPLE 711

[Chemical formula 783]

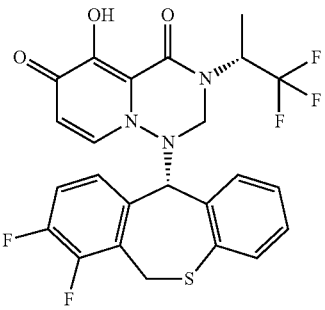

¹H-NMR (CDCl₃) δ: 1.23 (d, J=7.5 Hz, 3H), 4.11 (d, J=13.8 Hz, 1H), 4.48 (d, J=12.9 Hz, 1H), 4.90 (d, J=12.9 Hz, 1H), 5.13 (s, 1H), 5.41 (dd, J=13.8, 3.0 Hz, 1H), 5.54 (m, 1H), 5.82 (d, J=7.8 Hz, 1H), 6.69 (d, J=7.2 Hz, 1H), 6.85 (m, 1H), 6.96 (m, 1H), 7.03-7.14 (m, 3H), 7.16 (d, J=7.2 Hz, 1H).

REFERENCE EXAMPLE 712

[Chemical formula 784]

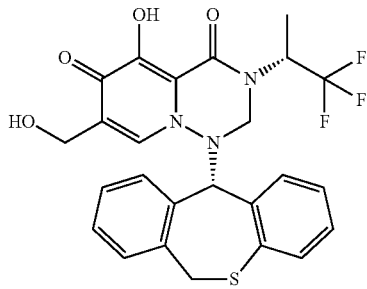

¹H-NMR (CDCl₃) δ: 1.19 (d, J=6.9 Hz, 3H), 3.61 (d, J=13.5 Hz, 1H), 4.07 (d, J=13.2 Hz, 1H), 4.24 (d, J=13.2 Hz, 1H), 4.50 (d, J=13.2 Hz, 1H), 4.88 (d, J=13.2 Hz, 1H), 5.09 (s, 1H), 5.51 (m, 1H), 5.67 (d, J=13.5 Hz, 1H), 6.66 (m, 1H), 6.79 (m, 1H), 7.04-7.12 (m, 2H), 7.18 (m, 1H), 7.24-7.30 (m, 2H), 7.35-7.46 (m, 2H).
MS: m/z=518.3 [M+H]⁺.

REFERENCE EXAMPLE 713

[Chemical formula 785]

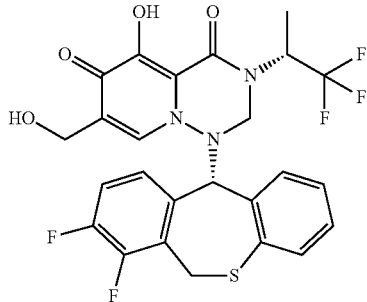

¹H-NMR (CDCl₃) δ: 1.25 (d, J=7.2 Hz, 3H), 4.07 (d, J=13.2 Hz, 1H), 4.10 (d, J=13.8 Hz, 1H), 4.29 (d, J=13.2 Hz, 1H), 4.48 (d, J=13.2 Hz, 1H), 4.90 (d, J=13.2 Hz, 1H), 5.12 (s, 1H), 5.44 (dd, J=13.8, 3.0 Hz, 1H), 5.52 (m, 1H), 6.64 (m, 1H), 6.82 (m, 1H), 6.95 (m, 1H), 7.02-7.13 (m, 3H), 7.25 (s, 1H).
MS: m/z=554.2 [M+H]⁺.

REFERENCE EXAMPLE 714

[Chemical formula 786]

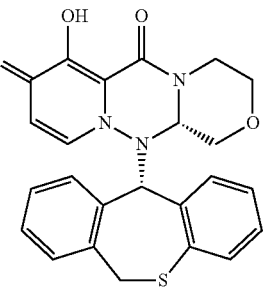

¹H-NMR (CDCl₃) δ: 2.98 (m, 1H), 3.46 (m, 1H), 3.57 (t, J=10.5 Hz, 1H), 3.58 (d, J=13.5 Hz, 1H), 3.79 (dd, J=12.3, 3.0 Hz, 1H), 3.96 (dd, J=11.4, 3.0 Hz, 1H), 4.63 (m, 2H), 5.25 (s, 1H), 5.52 (d, J=13.5 Hz, 1H), 5.75 (d, J=7.8 Hz, 1H), 6.70 (m, 1H), 6.81 (m, 1H), 7.04-7.10 (m, 3H), 7.19-7.37 (m, 3H), 7.43 (m, 1H).
MS: m/z=448.1 [M+H]⁺.

REFERENCE EXAMPLE 715

[Chemical formula 787]

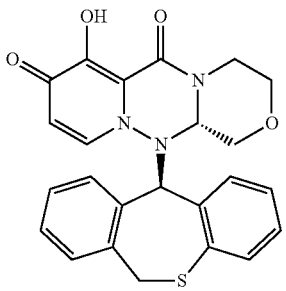

¹H-NMR (CDCl₃) δ: 2.83 (m, 1H), 3.43 (m, 1H), 3.55 (t, J=10.5 Hz, 1H), 3.61 (d, J=13.8 Hz, 1H), 3.78 (dd, J=12.0, 3.0 Hz, 1H), 4.04 (dd, J=11.1, 3.0 Hz, 1H), 4.50 (m, 1H), 4.60 (m, 1H), 5.13 (s, 1H), 5.64 (d, J=13.8 Hz, 1H), 5.73 (d, J=7.8 Hz, 1H), 6.59 (d, J=7.8 Hz, 1H), 6.81 (m, 1H), 7.07-7.15 (m, 2H), 7.20-7.37 (m, 5H).
MS: m/z=448.1 [M+H]⁺.

REFERENCE EXAMPLE 716

[Chemical formula 788]

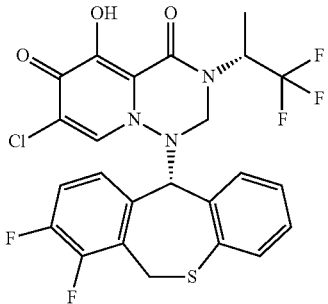

¹H-NMR (CDCl₃) δ: 1.26 (d, J=7.2 Hz, 3H), 4.13 (d, J=13.8 Hz, 1H), 4.49 (d, J=13.2 Hz, 1H), 4.94 (d, J=13.2 Hz, 1H), 5.13 (s, 1H), 5.38 (dd, J=13.8, 2.4 Hz, 1H), 5.52 (m, 1H), 6.68 (m, 1H), 6.86 (m, 1H), 6.97 (m, 1H), 7.03-7.20 (m, 3H), 7.50 (s, 1H).
MS: m/z=558.0 [M+H]⁺.

REFERENCE EXAMPLE 717

[Chemical formula 789]

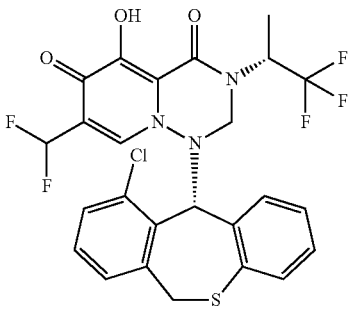

¹H-NMR (CDCl₃) δ: 1.18 (d, J=7.2 Hz, 3H), 3.65 (d, J=13.5 Hz, 1H), 4.47 (d, J=12.9 Hz, 1H), 4.90 (d, J=12.9 Hz, 1H), 5.49 (m, 1H), 5.66 (d, J=13.5 Hz, 1H), 5.93 (s, 1H), 6.60 (t, J=54.9 Hz, 1H), 6.77 (m, 1H), 6.86 (m, 1H), 7.11-7.16 (m, 2H), 7.28-7.37 (m, 3H), 7.49 (s, 1H).

REFERENCE EXAMPLE 718

[Chemical formula 790]

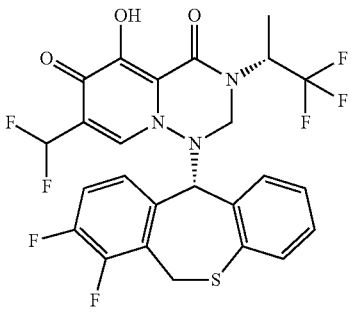

¹H-NMR (CDCl₃) δ: 1.25 (d, J=7.2 Hz, 3H), 4.11 (d, J=13.8 Hz, 1H), 4.51 (d, J=13.2 Hz, 1H), 4.93 (d, J=13.2 Hz, 1H), 5.11 (s, 1H), 5.38 (dd, J=13.8, 3.0 Hz, 1H), 5.52 (m, 1H), 6.58 (t, J=54.6 Hz, 1H), 6.65 (m, 1H), 6.84 (m, 1H), 6.95 (m, 1H), 7.02-7.15 (m, 3H), 7.52 (s, 1H).

REFERENCE EXAMPLE 719

[Chemical formula 791]

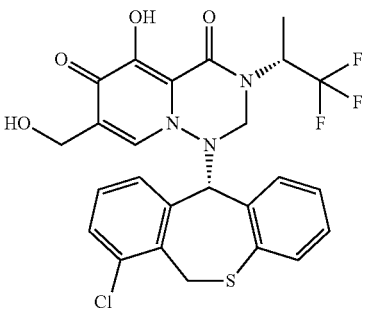

¹H-NMR (CDCl₃) δ: 1.23 (d, J=7.2 Hz, 3H), 4.08 (d, J=12.9 Hz, 1H), 4.24 (d, J=13.5 Hz, 1H), 4.32 (d, J=14.1 Hz, 1H), 4.50 (d, J=12.9 Hz, 1H), 4.90 (d, J=13.5 Hz, 1H), 5.13 (s, 1H), 5.53 (m, 1H), 5.64 (d, J=14.1 Hz, 1H), 6.64 (m, 1H), 6.80 (m, 1H), 7.06-7.12 (m, 3H), 7.20 (m, 1H), 7.24 (s, 1H), 7.53 (m, 1H).
MS: m/z=552.2 [M+H]⁺.

REFERENCE EXAMPLE 720

[Chemical formula 792]

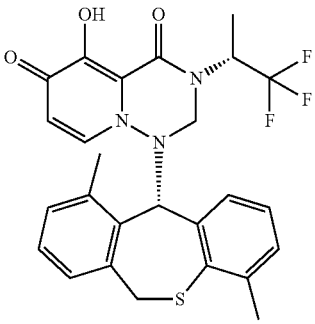

¹H-NMR (CDCl₃) δ: 0.90 (d, J=7.4 Hz, 3H), 2.25 (s, 3H), 2.34 (s, 3H), 3.70 (d, J=13.5 Hz, 1H), 4.49 (d, J=12.9 Hz, 1H), 4.81 (d, J=12.9 Hz, 1H), 5.38-5.50 (m, 2H), 5.62 (d, J=13.5 Hz, 1H), 5.84 (d, J=7.7 Hz, 1H), 6.56 (d, J=7.7 Hz, 1H), 6.75 (t, J=7.6 Hz, 1H), 6.98 (d, J=7.7 Hz, 1H), 7.05 (d, J=7.7 Hz, 1H), 7.12 (d, J=7.1 Hz, 1H), 7.21 (d, J=6.6 Hz, 1H), 7.26-7.32 (m, 1H).

REFERENCE EXAMPLE 721

[Chemical formula 793]

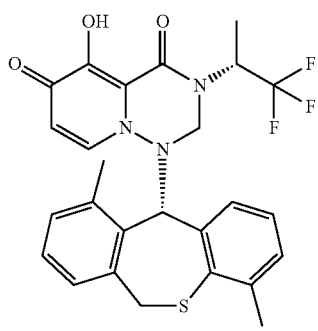

$^1$H-NMR (CDCl$_3$) δ: 0.93 (d, J=7.2 Hz, 3H), 2.38 (s, 3H), 3.75 (d, J=13.6 Hz, 1H), 4.52 (d, J=12.9 Hz, 1H), 4.85 (d, J=12.9 Hz, 1H), 5.41-5.54 (m, 2H), 5.69 (d, J=13.6 Hz, 1H), 5.93 (d, J=7.7 Hz, 1H), 6.68 (d, J=7.6 Hz, 1H), 6.84 (t, J=7.8 Hz, 1H), 7.04 (d, J=7.7 Hz, 1H), 7.18 (d, J=7.6 Hz, 1H), 7.25-7.40 (m, 3H).

REFERENCE EXAMPLE 722

[Chemical formula 794]

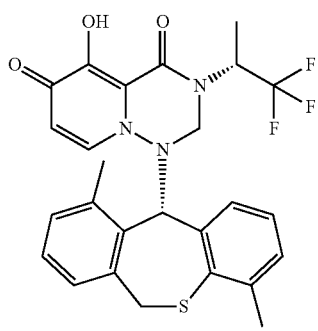

$^1$H-NMR (CDCl$_3$) δ: 0.90 (d, J=7.4 Hz, 3H), 2.34 (s, 3H), 3.69 (d, J=13.5 Hz, 1H), 4.48 (d, J=12.6 Hz, 1H), 4.82 (d, J=12.6 Hz, 1H), 5.38-5.50 (m, 2H), 5.62 (d, J=13.5 Hz, 1H), 5.88 (d, J=7.7 Hz, 1H), 6.53 (d, J=7.7 Hz, 1H), 6.83 (td, J=8.0, 5.5 Hz, 1H), 6.92-7.00 (m, 1H), 7.03 (d, J=7.7 Hz, 1H), 7.15 (d, J=7.4 Hz, 1H), 7.23 (d, J=7.1 Hz, 1H), 7.32 (t, J=7.6 Hz, 1H).

REFERENCE EXAMPLE 723

[Chemical formula 795]

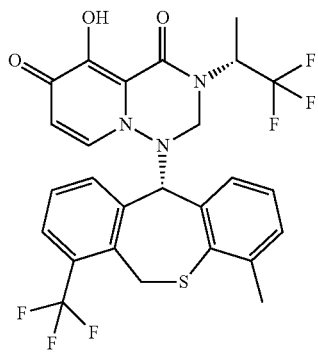

$^1$H-NMR (CDCl$_3$) δ: 1.19 (d, J=7.4 Hz, 3H), 2.24 (s, 3H), 4.09 (d, J=14.3 Hz, 1H), 4.44 (d, J=12.9 Hz, 1H), 4.91 (d, J=12.9 Hz, 1H), 5.27 (s, 1H), 5.49-5.59 (m, 1H), 5.81 (d, J=7.7 Hz, 1H), 5.91 (d, J=14.3 Hz, 1H), 6.58 (d, J=7.7 Hz, 1H), 6.76 (t, J=7.6 Hz, 1H), 7.02-7.10 (m, 2H), 7.34-7.43 (m, 2H), 7.70-7.83 (m, 1H).

REFERENCE EXAMPLE 724

[Chemical formula 796]

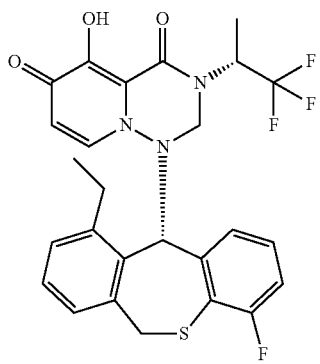

$^1$H-NMR (CDCl$_3$) δ: 0.89 (d, J=7.2 Hz, 3H), 1.08 (t, J=7.5 Hz, 3H), 2.62-2.77 (m, 2H), 3.68 (d, J=13.6 Hz, 1H), 4.44 (d, J=12.7 Hz, 1H), 4.79 (d, J=12.7 Hz, 1H), 5.37-5.47 (m, 1H), 5.58 (s, 1H), 5.69 (d, J=13.6 Hz, 1H), 5.87 (d, J=7.6 Hz, 1H), 6.53 (d, J=7.3 Hz, 1H), 6.82 (td, J=7.8, 5.8 Hz, 1H), 6.90-6.98 (m, 1H), 7.00 (d, J=7.6 Hz, 1H), 7.17-7.23 (m, 2H), 7.36 (t, J=7.5 Hz, 1H).

REFERENCE EXAMPLE 725

[Chemical formula 797]

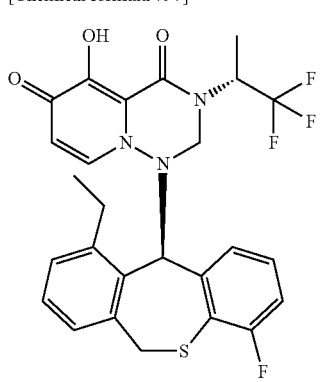

MS: m/z=534.20 [M+H]$^+$.

REFERENCE EXAMPLE 726

[Chemical formula 798]

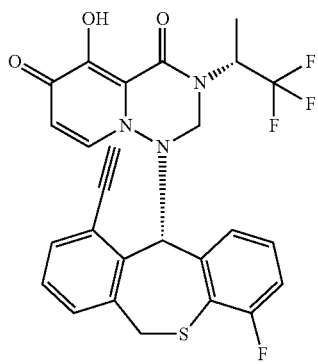

¹H-NMR (CDCl₃) δ: 1.15 (d, J=7.4 Hz, 3H), 3.55 (s, 1H), 3.71 (d, J=13.5 Hz, 1H), 4.44 (d, J=12.9 Hz, 1H), 4.87 (d, J=12.9 Hz, 1H), 5.43-5.54 (m, 1H), 5.65 (d, J=13.5 Hz, 1H), 5.87 (d, J=7.7 Hz, 1H), 6.14 (s, 1H), 6.63 (d, J=7.4 Hz, 1H), 6.84 (td, J=8.0, 5.7 Hz, 1H), 6.91-7.00 (m, 1H), 7.10 (d, J=7.7 Hz, 1H), 7.37-7.42 (m, 2H), 7.46-7.52 (m, 1H).

REFERENCE EXAMPLE 727

[Chemical formula 799]

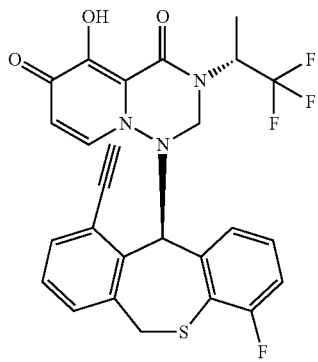

MS: m/z=530.10 [M+H]⁺.

REFERENCE EXAMPLE 728

[Chemical formula 800]

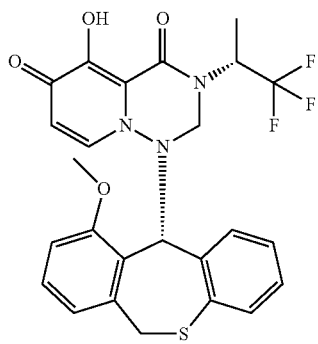

¹H-NMR (CDCl₃) δ: 1.09 (d, J=7.1 Hz, 3H), 3.59 (d, J=13.5 Hz, 1H), 3.79 (s, 3H), 4.51 (d, J=12.9 Hz, 1H), 4.84 (d, J=12.9 Hz, 1H), 5.43-5.56 (m, 1H), 5.67 (d, J=13.5 Hz, 1H), 5.83 (d, J=7.7 Hz, 1H), 5.92 (s, 1H), 6.74 (d, J=7.7 Hz, 1H), 6.77-6.86 (m, 2H), 6.95 (d, J=7.7 Hz, 1H), 7.05-7.10 (m, 2H), 7.19 (d, J=7.7 Hz, 1H), 7.35 (t, J=8.1 Hz, 1H).

REFERENCE EXAMPLE 729

[Chemical formula 801]

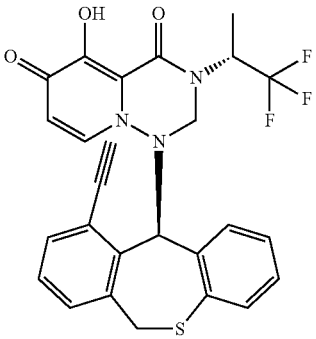

MS: m/z=512.10 [M+H]⁺.

REFERENCE EXAMPLE 730

[Chemical formula 802]

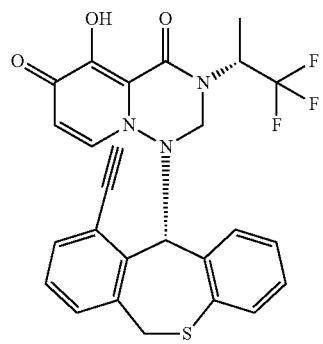

¹H-NMR (CDCl₃) δ: 1.18 (d, J=7.1 Hz, 3H), 3.55 (s, 1H), 3.63 (d, J=13.2 Hz, 1H), 4.46 (d, J=11.5 Hz, 1H), 4.94 (d, J=11.5 Hz, 1H), 5.44-5.54 (m, 1H), 5.63 (d, J=13.2 Hz, 1H), 6.01 (d, J=4.4 Hz, 1H), 6.07 (s, 1H), 6.77 (d, J=7.4 Hz, 1H), 6.83-6.85 (m, 1H), 7.07-7.16 (m, 2H), 7.17-7.24 (m, 1H), 7.36-7.40 (m, 2H), 7.44-7.50 (m, 1H).

REFERENCE EXAMPLE 731

[Chemical formula 803]

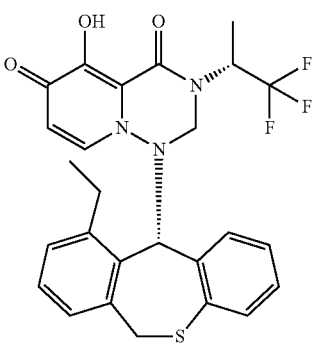

¹H-NMR (CDCl₃) δ: 0.91 (d, J=7.4 Hz, 3H), 1.08 (t, J=7.4 Hz, 3H), 2.62-2.79 (m, 2H), 3.59 (d, J=13.2 Hz, 1H), 4.46 (d, J=12.6 Hz, 1H), 4.82 (d, J=12.6 Hz, 1H), 5.38-5.48 (m, 1H), 5.51 (s, 1H), 5.68 (d, J=13.2 Hz, 1H), 5.92 (d, J=6.9 Hz, 1H), 6.68 (d, J=8.0 Hz, 1H), 6.78-6.87 (m, 1H), 7.05 (d, J=7.1 Hz, 1H), 7.09-7.14 (m, 2H), 7.19 (d, J=7.7 Hz, 1H), 7.23 (d, J=7.4 Hz, 1H), 7.36 (t, J=7.7 Hz, 1H).

REFERENCE EXAMPLE 732

[Chemical formula 804]

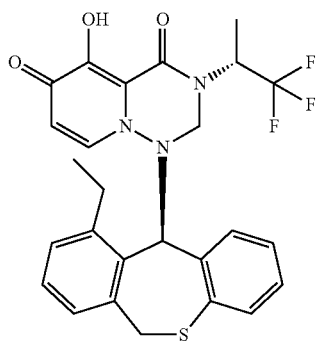

MS: m/z=516.75 [M+H]⁺.

REFERENCE EXAMPLE 733

[Chemical formula 805]

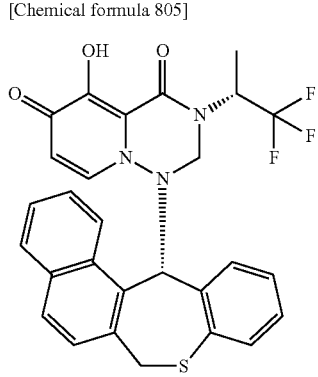 [SMILES: C[C@@H](N1CN([C@@H]2c3ccccc3SCc3ccc4ccccc4c32)n2ccc(=O)c(O)c2C1=O)C(F)(F)F]

¹H-NMR (CDCl₃) δ: 0.23 (d, J=7.1 Hz, 3H), 3.75 (d, J=13.5 Hz, 1H), 4.47 (d, J=12.9 Hz, 1H), 4.84 (d, J=12.9 Hz, 1H), 5.23-5.33 (m, 1H), 5.91 (d, J=7.7 Hz, 1H), 5.97 (d, J=13.5 Hz, 1H), 6.19 (s, 1H), 6.81-6.93 (m, 2H), 7.07-7.12 (m, 2H), 7.21 (d, J=7.7 Hz, 1H), 7.48 (d, J=8.2 Hz, 1H), 7.52 (d, J=7.4 Hz, 1H), 7.57-7.64 (m, 1H), 7.87 (d, J=8.2 Hz, 1H), 7.92 (d, J=8.5 Hz, 1H), 8.07 (d, J=8.8 Hz, 1H).

REFERENCE EXAMPLE 734

[Chemical formula 806]

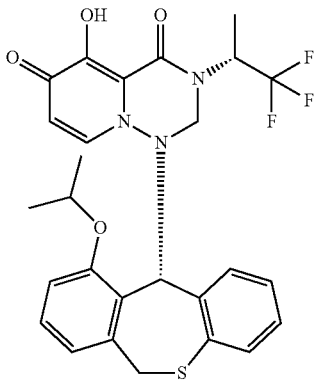

¹H-NMR (CDCl₃) δ: 1.12 (d, J=5.8 Hz, 6H), 1.43 (d, J=6.0 Hz, 3H), 3.58 (d, J=13.5 Hz, 1H), 4.43-4.57 (m, 2H), 4.84 (d, J=12.9 Hz, 1H), 5.41-5.52 (m, 1H), 5.61 (d, J=13.5 Hz, 1H), 5.88 (d, J=7.7 Hz, 1H), 5.94 (s, 1H), 6.67 (d, J=7.7 Hz, 1H), 6.77-6.87 (m, 2H), 6.91 (d, J=7.1 Hz, 1H), 7.09 (d, J=3.6 Hz, 2H), 7.16 (d, J=7.7 Hz, 1H), 7.31 (t, J=8.0 Hz, 1H).

REFERENCE EXAMPLE 735

[Chemical formula 807]

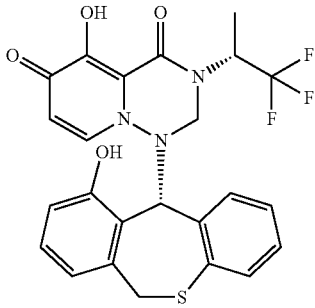

¹H-NMR (DMSO-d₆) δ: 0.93 (d, J=7.4 Hz, 3H), 3.59 (d, J=13.5 Hz, 1H), 4.27 (d, J=12.9 Hz, 1H), 4.84 (d, J=12.9 Hz, 1H), 5.24-5.35 (m, 1H), 5.38 (d, J=13.5 Hz, 1H), 5.48 (d, J=7.4 Hz, 1H), 5.59 (s, 1H), 6.50 (d, J=7.4 Hz, 1H), 6.57-6.71 (m, 4H), 6.86-7.03 (m, 5H), 9.98 (s, 1H).

REFERENCE EXAMPLE 736

[Chemical formula 808]

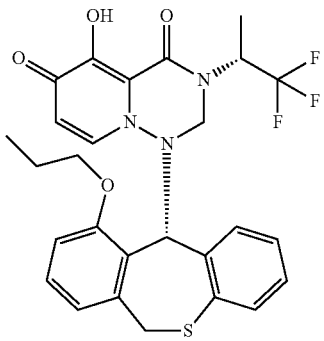

¹H-NMR (CDCl₃) δ: 1.00-1.10 (m, 6H), 1.74-1.87 (m, 2H), 3.59 (d, J=13.2 Hz, 1H), 3.78-3.95 (m, 2H), 4.55 (d, J=12.4 Hz, 1H), 4.92 (d, J=12.4 Hz, 1H), 5.39-5.52 (m, 1H), 5.65 (d, J=13.2 Hz, 1H), 5.97 (s, 1H), 6.01-6.11 (m, 1H), 6.66 (d, J=7.4 Hz, 1H), 6.81 (d, J=8.2 Hz, 2H), 6.93 (d, J=7.4 Hz, 1H), 7.07-7.11 (m, 2H), 7.21-7.25 (m, 1H), 7.32 (t, J=8.0 Hz, 1H).

REFERENCE EXAMPLE 737

[Chemical formula 809]

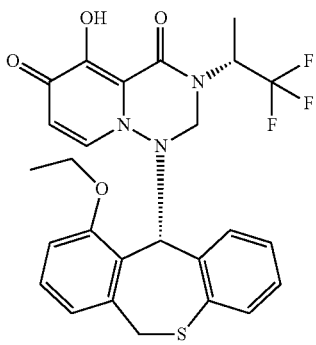

¹H-NMR (CDCl₃) δ: 1.09 (d, J=7.1 Hz, 3H), 1.40 (t, J=6.9 Hz, 3H), 3.59 (d, J=13.2 Hz, 1H), 3.87-4.07 (m, 2H), 4.53 (d, J=13.2 Hz, 1H), 4.86 (d, J=13.2 Hz, 1H), 5.43-5.53 (m, 1H), 5.64 (d, J=13.2 Hz, 1H), 5.91 (d, J=7.4 Hz, 1H), 5.96 (s, 1H), 6.70 (d, J=7.7 Hz, 1H), 6.78-6.84 (m, 2H), 6.93 (d, J=7.4 Hz, 1H), 7.06-7.10 (m, 2H), 7.20 (d, J=7.7 Hz, 1H), 7.32 (t, J=8.0 Hz, 1H).

REFERENCE EXAMPLE 738

[Chemical formula 810]

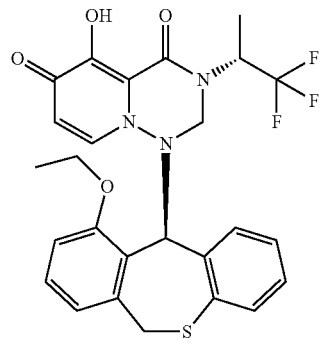

MS: m/z=532.5 [M+H]⁺.

REFERENCE EXAMPLE 739

[Chemical formula 811]

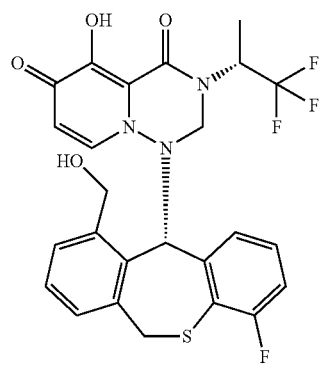

¹H-NMR (CDCl₃) δ: 0.93 (d, J=6.9 Hz, 3H), 3.73 (d, J=13.7 Hz, 1H), 4.58 (d, J=12.9 Hz, 1H), 4.64 (d, J=11.8 Hz, 1H), 4.82-4.90 (m, 2H), 5.31-5.43 (m, 1H), 5.62 (d, J=13.7 Hz, 1H), 5.90 (d, J=7.7 Hz, 1H), 6.09 (s, 1H), 6.65 (d, J=6.6 Hz, 1H), 6.69-6.78 (m, 1H), 6.90-6.98 (m, 1H), 7.00 (d, J=7.7 Hz, 1H), 7.27-7.41 (m, 3H).

REFERENCE EXAMPLE 740

[Chemical formula 812]

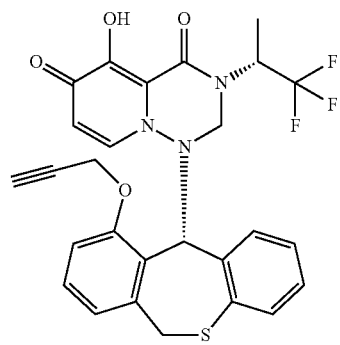

¹H-NMR (CDCl₃) δ: 1.16 (d, J=7.1 Hz, 3H), 3.49 (s, 1H), 3.60 (d, J=13.2 Hz, 1H), 4.49-4.62 (m, 2H), 4.74 (dd, J=15.9, 2.2 Hz, 1H), 4.85 (d, J=13.5 Hz, 1H), 5.44-5.57 (m, 1H), 5.67 (d, J=13.2 Hz, 1H), 5.82 (d, J=7.7 Hz, 1H), 5.89 (s, 1H), 6.74 (d, J=8.0 Hz, 1H), 6.78-6.85 (m, 1H), 7.01 (dd, J=8.1, 3.7 Hz, 2H), 7.05-7.12 (m, 2H), 7.20 (d, J=7.7 Hz, 1H), 7.36 (t, J=8.1 Hz, 1H).

REFERENCE EXAMPLE 741

[Chemical formula 813]

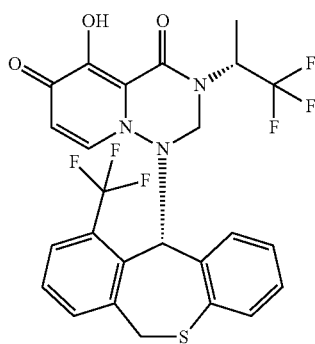

MS: m/z=556.15 [M+H]⁺.

REFERENCE EXAMPLE 742

[Chemical formula 814]

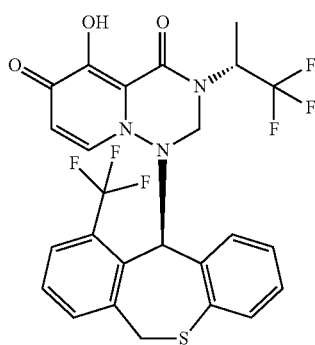

MS: m/z=556.15 [M+H]⁺.

REFERENCE EXAMPLE 743

[Chemical formula 815]

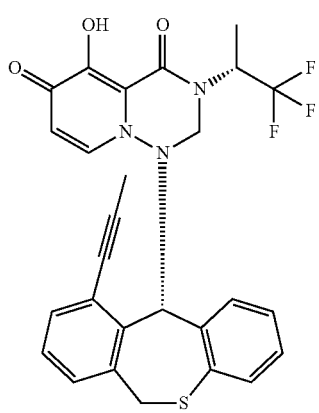

¹H-NMR (CDCl₃) δ: 1.15 (d, J=7.4 Hz, 3H), 2.14 (s, 3H), 3.59 (d, J=13.5 Hz, 1H), 4.45 (d, J=12.9 Hz, 1H), 4.85 (d, J=12.9 Hz, 1H), 5.43-5.53 (m, 1H), 5.58 (d, J=13.5 Hz, 1H), 5.83 (d, J=7.7 Hz, 1H), 6.08 (s, 1H), 6.71 (d, J=7.4 Hz, 1H), 6.80-6.87 (m, 1H), 7.07-7.14 (m, 3H), 7.26-7.38 (m, 3H).

REFERENCE EXAMPLE 744

[Chemical formula 816]

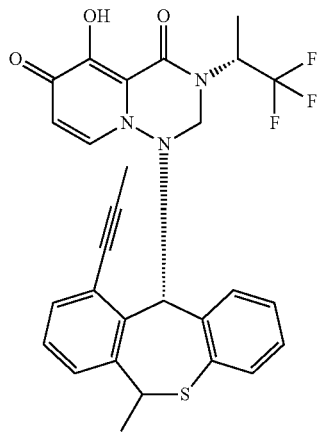

¹H-NMR (CDCl₃) δ: 1.16 (d, J=7.1 Hz, 3H), 1.78 (d, J=6.9 Hz, 3H), 2.14 (s, 3H), 4.43 (d, J=12.9 Hz, 1H), 4.83 (d, J=12.9 Hz, 1H), 5.42-5.54 (m, 1H), 5.84 (d, J=7.7 Hz, 1H), 5.99 (q, J=7.1 Hz, 1H), 6.22 (s, 1H), 6.69 (d, J=7.1 Hz, 1H), 6.79-6.86 (m, 1H), 7.03-7.14 (m, 3H), 7.31-7.42 (m, 3H).

REFERENCE EXAMPLE 745

[Chemical formula 817]

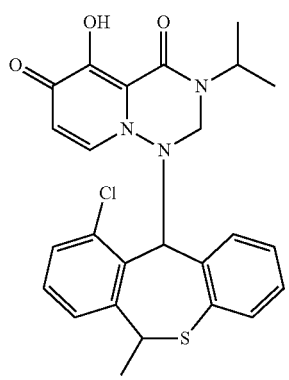

¹H-NMR (CDCl₃) δ: 1.03 (d, J=6.7 Hz, 3H), 1.21 (d, J=6.4 Hz, 3H), 1.78 (d, J=6.4 Hz, 3H), 4.34 (d, J=12.3 Hz, 1H), 4.70-4.84 (m, 1H), 5.03 (d, J=12.3 Hz, 1H), 6.08-6.27 (m, 3H), 6.70-6.86 (m, 2H), 7.01-7.22 (m, 3H), 7.30-7.42 (m, 3H).

REFERENCE EXAMPLE 746

[Chemical formula 818]

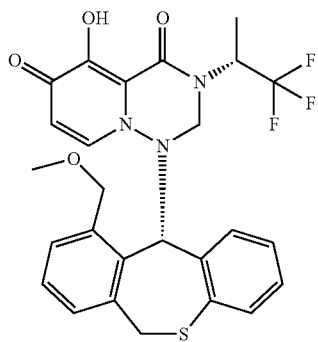

¹H-NMR (CDCl₃) δ: 0.88 (d, J=7.1 Hz, 3H), 3.43 (s, 3H), 3.62 (d, J=13.5 Hz, 1H), 4.27 (d, J=11.0 Hz, 1H), 4.38 (d, J=11.0 Hz, 1H), 4.52 (d, J=13.2 Hz, 1H), 4.84 (d, J=13.2 Hz, 1H), 5.25-5.35 (m, 1H), 5.60 (d, J=13.5 Hz, 1H), 5.70 (s, 1H), 5.91 (d, J=7.1 Hz, 1H), 6.64 (d, J=7.4 Hz, 1H), 6.80-6.88 (m, 1H), 6.96 (d, J=7.7 Hz, 1H), 7.10-7.16 (m, 2H), 7.22 (dd, J=6.3, 2.5 Hz, 1H), 7.32-7.39 (m, 2H).

REFERENCE EXAMPLE 747

[Chemical formula 819]

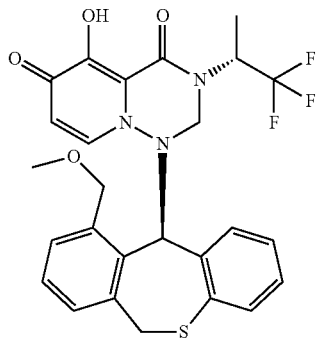

MS: m/z=532.20 [M+H]⁺.

REFERENCE EXAMPLE 748

[Chemical formula 820]

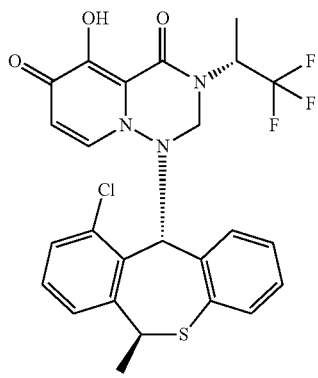

¹H-NMR (CDCl₃) δ: 1.15 (d, J=7.4 Hz, 3H), 1.80 (d, J=6.9 Hz, 3H), 4.42 (d, J=13.2 Hz, 1H), 4.86 (d, J=13.2 Hz, 1H), 5.46-5.57 (m, 1H), 5.83 (d, J=7.7 Hz, 1H), 6.07 (s, 1H), 6.12 (q, J=7.1 Hz, 1H), 6.77-6.89 (m, 2H), 7.04-7.17 (m, 3H), 7.33-7.45 (m, 3H).

REFERENCE EXAMPLE 749

[Chemical formula 821]

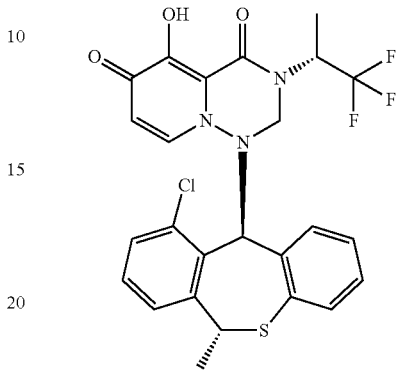

MS: m/z=536.05 [M+H]⁺.

REFERENCE EXAMPLE 750

[Chemical formula 822]

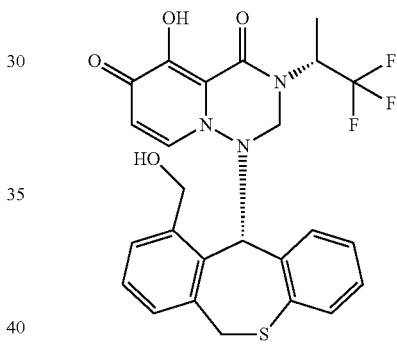

¹H-NMR (CDCl₃) δ: 0.96 (d, J=7.4 Hz, 3H), 3.64 (d, J=13.7 Hz, 1H), 4.58 (d, J=13.2 Hz, 1H), 4.64 (d, J=11.8 Hz, 1H), 4.82-4.91 (m, 2H), 5.33-5.43 (m, 1H), 5.60 (d, J=13.7 Hz, 1H), 5.86 (d, J=7.4 Hz, 1H), 6.01 (s, 1H), 6.71-6.83 (m, 2H), 7.02 (d, J=7.7 Hz, 1H), 7.11 (d, J=3.6 Hz, 2H), 7.27-7.39 (m, 3H).

REFERENCE EXAMPLE 751

[Chemical formula 823]

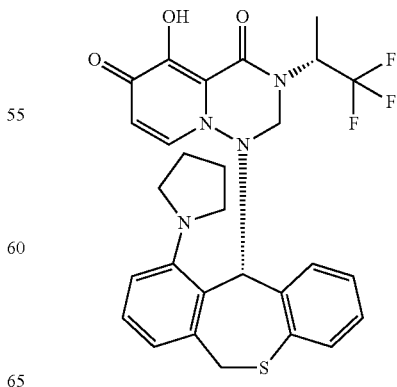

MS: m/z=557.20 [M+H]⁺.

REFERENCE EXAMPLE 752

[Chemical formula 824]

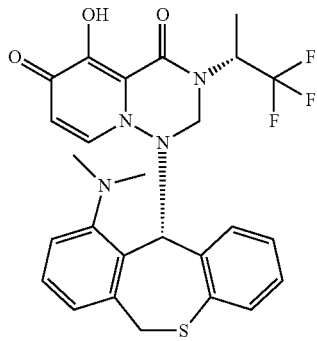

¹H-NMR (CDCl₃) δ: 1.05 (d, J=7.1 Hz, 3H), 2.49 (s, 6H), 3.50 (d, J=13.7 Hz, 1H), 4.24 (d, J=13.2 Hz, 1H), 4.72 (d, J=13.2 Hz, 1H), 5.35-5.48 (m, 1H), 5.80 (d, J=8.0 Hz, 1H), 5.91 (d, J=13.7 Hz, 1H), 6.05 (s, 1H), 6.75-6.86 (m, 2H), 7.02-7.15 (m, 5H), 7.36 (t, J=7.8 Hz, 1H).

REFERENCE EXAMPLE 753

[Chemical formula 825]

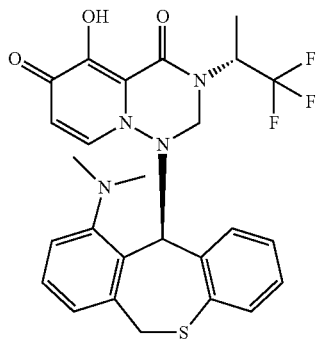

MS: m/z=531.25 [M+H]⁺.

REFERENCE EXAMPLE 754

[Chemical formula 826]

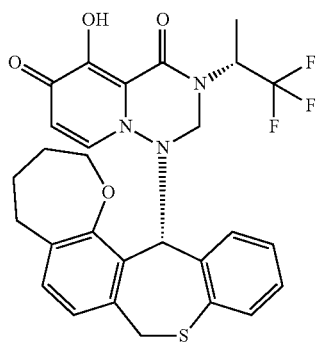

¹H-NMR (CDCl₃) δ: 1.14 (d, J=7.4 Hz, 3H), 1.24-1.34 (m, 1H), 1.80 (d, J=14.8 Hz, 1H), 1.88-2.04 (m, 2H), 2.60-2.70 (m, 1H), 2.70-2.82 (m, 1H), 3.09 (t, J=11.8 Hz, 1H), 3.59 (d, J=13.5 Hz, 1H), 4.37 (d, J=11.5 Hz, 1H), 4.45 (d, J=13.2 Hz, 1H), 4.81 (d, J=13.2 Hz, 1H), 5.44-5.54 (m, 1H), 5.58 (d, J=13.5 Hz, 1H), 5.83 (d, J=7.7 Hz, 1H), 6.00 (s, 1H), 6.73 (d, J=7.7 Hz, 1H), 6.78-6.85 (m, 1H), 6.95 (d, J=7.7 Hz, 1H), 7.07-7.21 (m, 4H).

REFERENCE EXAMPLE 755

[Chemical formula 827]

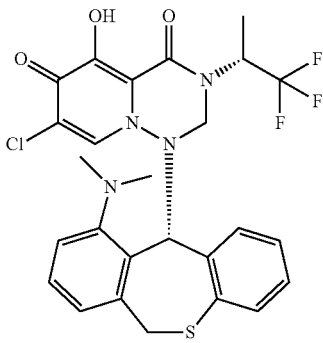

¹H-NMR (CDCl₃) δ: 1.08 (d, J=7.4 Hz, 3H), 2.50 (s, 6H), 3.53 (d, J=14.0 Hz, 1H), 4.26 (d, J=13.2 Hz, 1H), 4.74 (d, J=13.2 Hz, 1H), 5.35-5.45 (m, 1H), 5.87 (d, J=14.0 Hz, 1H), 6.05 (s, 1H), 6.75 (d, J=7.7 Hz, 1H), 6.84 (t, J=6.5 Hz, 1H), 7.07-7.18 (m, 4H), 7.33-7.40 (m, 2H).

REFERENCE EXAMPLE 756

[Chemical formula 828]

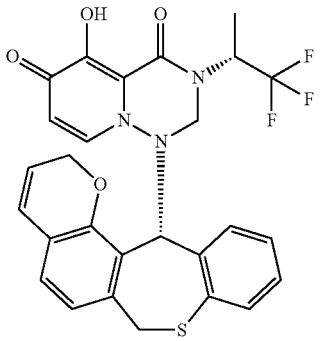

¹H-NMR (CDCl₃) δ: 1.22 (d, J=6.7 Hz, 3H), 3.49-3.60 (m, 1H), 4.50-4.61 (m, 1H), 4.71 (d, J=14.8 Hz, 1H), 4.90 (d, J=11.6 Hz, 1H), 5.40-5.65 (m, 2H), 5.75-5.82 (m, 2H), 6.03-6.16 (m, 1H), 6.37 (d, J=9.8 Hz, 1H), 6.69 (d, J=7.3 Hz, 1H), 6.78-6.87 (m, 2H), 6.97 (d, J=7.3 Hz, 1H), 7.07-7.14 (m, 2H).

REFERENCE EXAMPLE 757

[Chemical formula 829]

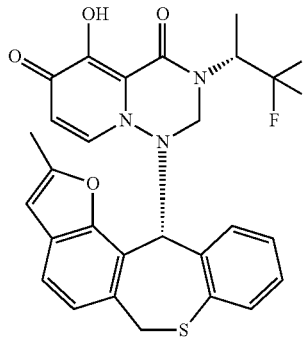

¹H-NMR (CDCl₃) δ: 0.70 (d, J=7.1 Hz, 3H), 2.46 (s, 3H), 3.73 (d, J=13.5 Hz, 1H), 4.51 (d, J=13.2 Hz, 1H), 4.87 (d, J=13.2 Hz, 1H), 5.41-5.52 (m, 1H), 5.70 (d, J=13.5 Hz, 1H), 5.85 (d, J=7.7 Hz, 1H), 5.92 (s, 1H), 6.38 (s, 1H), 6.79-6.90 (m, 2H), 7.07-7.11 (m, 2H), 7.17 (d, J=8.0 Hz, 1H), 7.22 (d, J=7.7 Hz, 1H), 7.45 (d, J=8.0 Hz, 1H).

REFERENCE EXAMPLE 758

[Chemical formula 830]

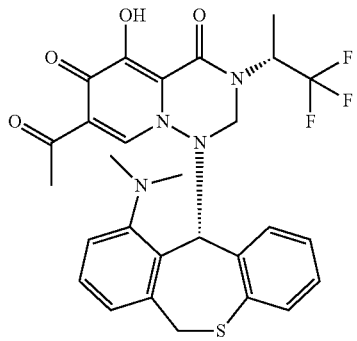

¹H-NMR (CDCl₃) δ: 1.09 (d, J=7.1 Hz, 3H), 2.50 (s, 6H), 2.52 (s, 3H), 3.51 (d, J=13.7 Hz, 1H), 4.27 (d, J=13.2 Hz, 1H), 4.73 (d, J=13.2 Hz, 1H), 5.35-5.48 (m, 1H), 5.93 (d, J=13.7 Hz, 1H), 6.04 (s, 1H), 6.70-6.83 (m, 2H), 7.00-7.16 (m, 4H), 7.36 (t, J=7.7 Hz, 1H), 7.84 (s, 1H).

REFERENCE EXAMPLE 759

[Chemical formula 831]

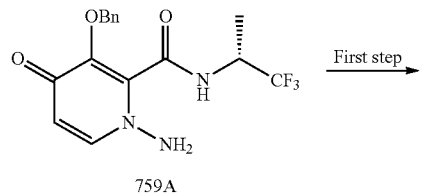

759A

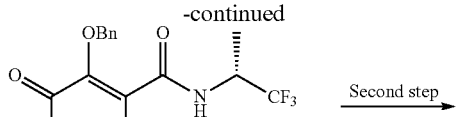

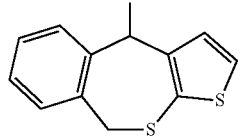

759B

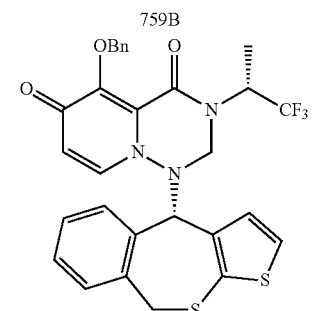

759C

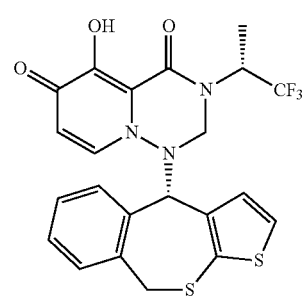

759

First Step

Compound 759A (124 mg, 0.35 mmol) was suspended in dichloromethane. 4,9-dihydrobenzo[e]thieno[2,3-b]thiepin-ol (82 mg, 0.35 mmol) and dichloroacetic acid (87 μL, 1.05 mmol) were added, and the mixture was stirred at room temperature for 1 hour. Water was added, and the mixture was extracted with chloroform. The organic layer was washed with water and aqueous saturated sodium chloride solution, and then dried with anhydrous magnesium sulfate. The solvent was distilled off under reduced pressure, and the resulting residue was purified by silica gel chromatography (chloroform-methanol) to obtain compound 759B (180 mg, yield 90%).

MS: m/z=572.29 [M+H]⁺.

Second Step

Compound 759B (108 mg, 0.18 mmol) was suspended in DMA.

Paraformaldehyde (113 mg, 0.38 mmol) and BEMP (0.33 mL, 1.13 mmol), and the mixture was stirred for 5 minutes under ice-cooling, and then stirred at room temperature for 2 days. Thereafter, tosyl chloride (72 mg, 0.38 mmol) was added, and the mixture was stirred for 3 days. A saturated ammonia chloride water was added, and the precipitated solid was filtered. The resulting residue was purified by silica gel column chromatography (chloroform-methanol) to obtain compound 759C (16 mg, yield 15%).

MS: m/z=584.25 [M+H]⁺

Third Step

Compound 759C (16 mg, 0.03 mmol) was suspended in DMF. Lithium chloride (17 mg, 0.41 mmol) was added, and the mixture was stirred at 90° C. for 7 hours. A 1M aqueous hydrochloric acid solution was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by diol silica gel chromatography (chloroform-methanol) to obtain compound 759 (9 mg, 0.02 mmol).

MS: m/z=494.18 [M+H]$^+$

REFERENCE EXAMPLE 760

[Chemical formula 832]

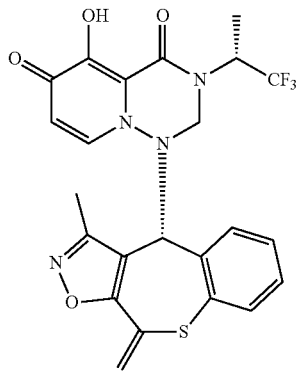

MS: m/z=505.11 [M+H]$^+$

REFERENCE EXAMPLE 761

[Chemical formula 833]

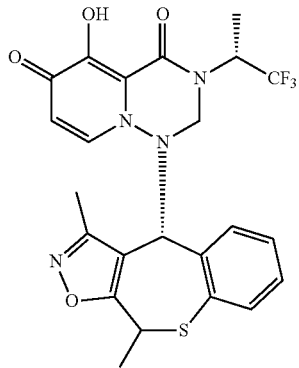

MS: m/z=507.09 [M+H]

REFERENCE EXAMPLE 762

[Chemical formula 834]

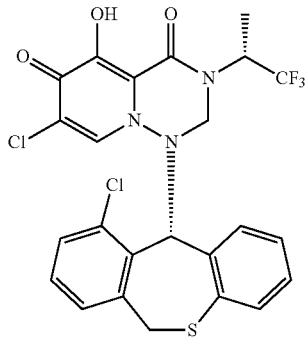

MS: m/z=556.18 [M+H]$^+$

REFERENCE EXAMPLE 763

[Chemical formula 835]

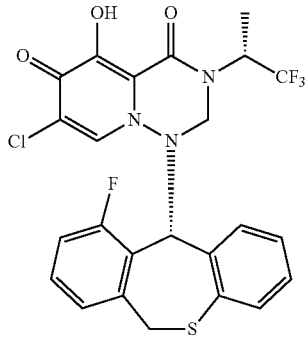

MS: m/z=540.12 [M+H]$^+$

REFERENCE EXAMPLE 764

[Chemical formula 836]

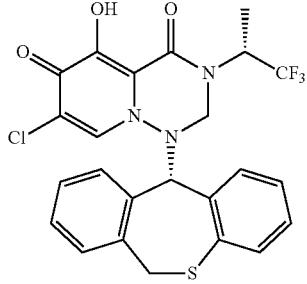

MS: m/z=522.05 [M+H]$^+$

REFERENCE EXAMPLE 765

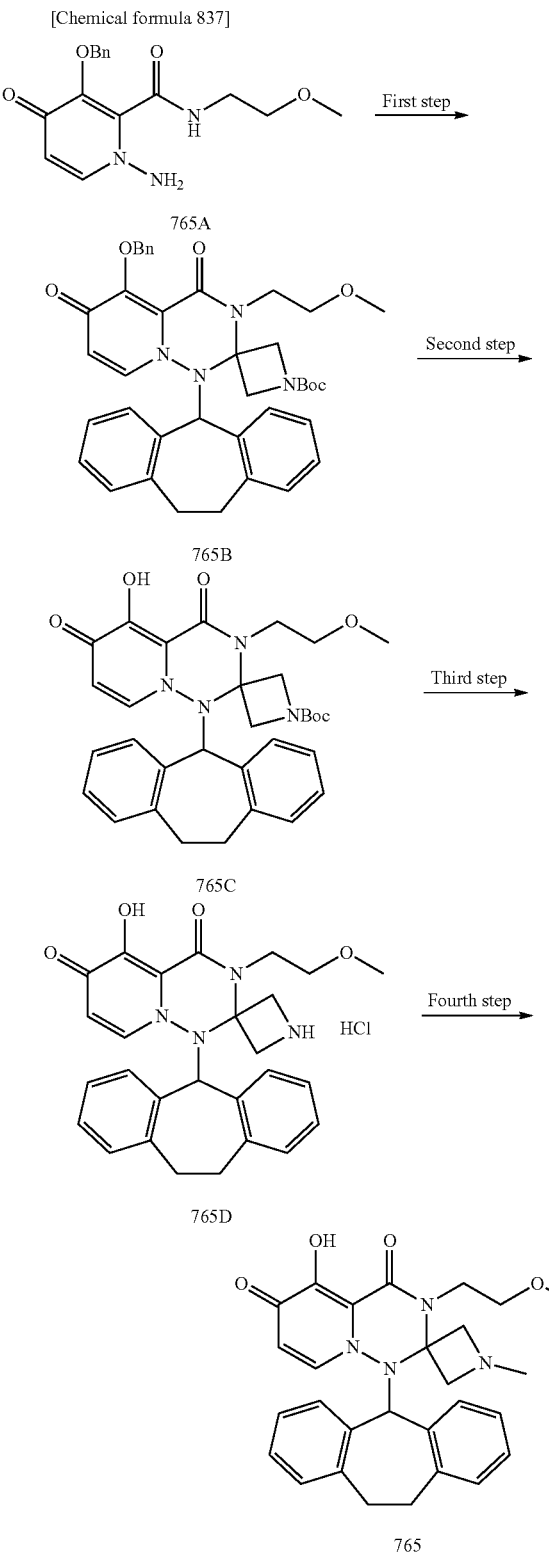

First Step

Compound 765A (722 mg, 2.43 mmol) was suspended in DMF. N-Boc azetidinone (1.25 g, 7.30 mmol) and cesium carbonate (2.96 g, 12.16 mmol) were added, and the mixture was stirred for 30 minutes under ice-cooling, and then stirred at room temperature for 30 minutes. Thereafter, 5-chlorodibenzosuberane (1.67 g, 7.30 mmol) was added, and the mixture was stirred for 3 hours. Insolubles were separated by filtration, then a 0.5M aqueous hydrochloric acid solution was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel chromatography (chloroform-methanol) to obtain compound 765B (176 mg, yield 11%).

MS: m/z=663.33 [M+H]$^+$.

Second Step

Compound 765B (176 mg, 0.27 mmol) was suspended in DMA. Lithium chloride (113 mg, 2.66 mmol) was added, and the mixture was stirred at 100° C. for 2 hours. A 0.5M aqueous hydrochloric acid solution was added, and the precipitated solid was filtered to obtain compound 765C (92 mg, 0.16 mmol).

MS: m/z=573.29 [M+H]$^+$

Third Step

To compound 765C (45 mg, 0.08 mmol) was added 4N HCl/dioxane (0.68 mL, 2.75 mmol), and the mixture was stirred for 3 hours under ice-cooling. The reaction solution was diluted with diisopropyl ether, and the generated solid was filtered to obtain compound 765D (29 mg, 0.057 mmol).

MS: m/z=474.19 [M+H]$^+$

Fourth Step

Compound 765D (31 mg, 0.06 mmol) was suspended in dichloromethane. 37% formaldehyde (25 μL, 0.91 mmol), triethylamine (10 μL, 0.07 mmol), acetic acid (5 μL, 0.09 mmol), and NaBH(OAc)$_3$ (25 mg, 0.12 mmol) were added, and the mixture was stirred at room temperature for 1 hour. Saturated sodium bicarbonate water was added, the mixture was extracted with chloroform. The organic layer was washed with water and aqueous saturated sodium chloride solution, and then dried with anhydrous magnesium sulfate. The solvent was distilled off under reduced pressure, then the residue was solidified with hexane to obtain compound 765 (15 mg, 0.03 mmol).

MS: m/z=487.25 [M+H]$^+$

REFERENCE EXAMPLE 766

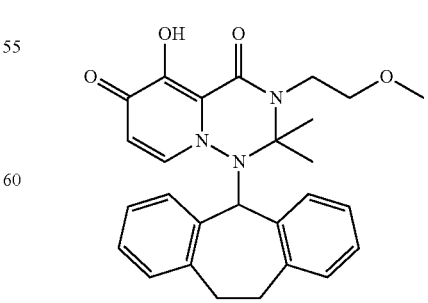

MS: m/z=461.23 [M+H]$^+$

REFERENCE EXAMPLE 767

[Chemical formula 838]

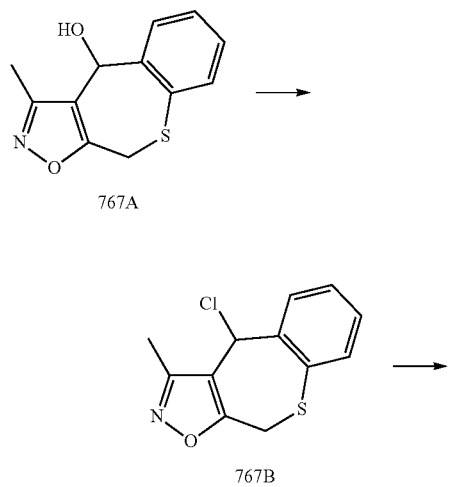

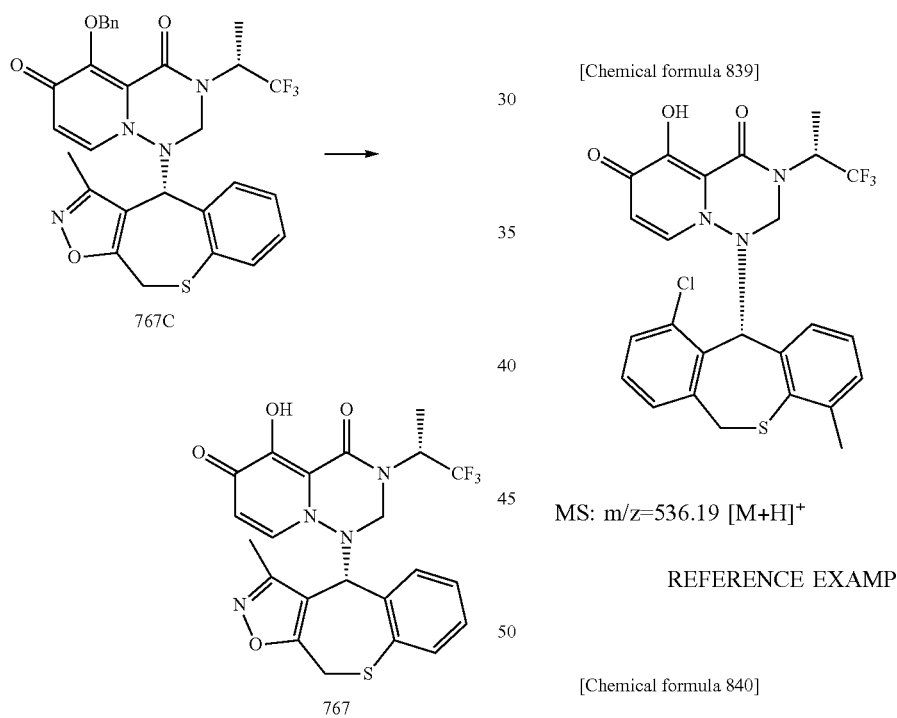

First Step

Compound 767A (87 mg, 0.37 mmol) was suspended in dichloromethane. Thionyl chloride (54 μL, 0.75 mmol) was added, and the mixture was heated to reflux for 2 hours. After concentration of the reaction solution, the resulting residue was solidified with hexane to obtain compound 767B (48 mg, yield 51%).

Second Step

Compound 767B (70 mg, 0.19 mmol) was suspended in DMF. Compound 12 (48 mg, 0.19 mmol) and cesium carbonate (186 mg, 0.57 mmol) were added, and the mixture was stirred at room temperature for 2 hours. Insolubles were separated by filtration, then water was added to the filtrate, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was purified by silica gel chromatography (chloroform-methanol) to obtain compound 767C (32 mg, 0.06 mmol).

MS: m/z=583.16 [M+H]$^+$

Third Step

Compound 767C (31 mg, 0.05 mmol) was suspended in THF-methanol. 10% palladium carbon (15 mg) was added, and the mixture was stirred at room temperature for 24 hours under hydrogen atmosphere. Insolubles were separated by filtration, then the filtrate was concentrated, and the resulting residue was purified by diol silica gel chromatography (chloroform-methanol) to obtain compound 767 (6 mg, 0.01 mmol).

MS: m/z=493.16 [M+H]$^+$

REFERENCE EXAMPLE 768

[Chemical formula 839]

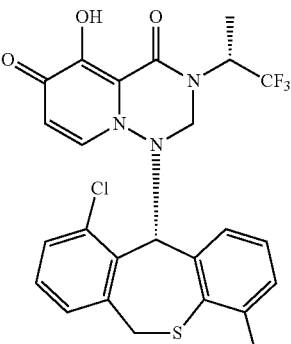

MS: m/z=536.19 [M+H]$^+$

REFERENCE EXAMPLE 769

[Chemical formula 840]

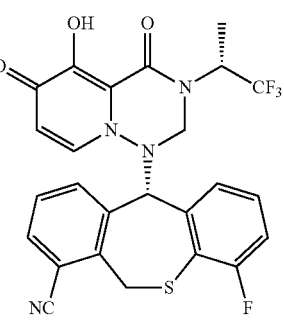

MS: m/z=531.49 [M+H]$^+$

REFERENCE EXAMPLE 770
[Chemical formula 841]
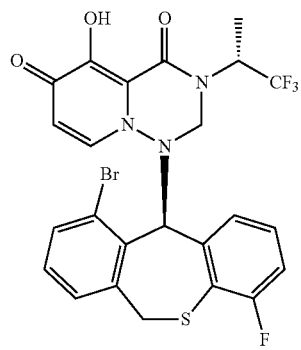
MS: m/z=584.09 [M+H]+
REFERENCE EXAMPLE 771
[Chemical formula 842]
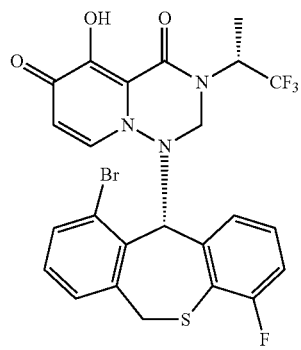
MS: m/z=586.07 [M+H]+
REFERENCE EXAMPLE 772
[Chemical formula 843]
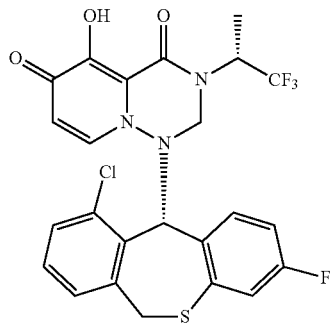
MS: m/z=540.14 [M+H]+
REFERENCE EXAMPLE 773
[Chemical formula 844]
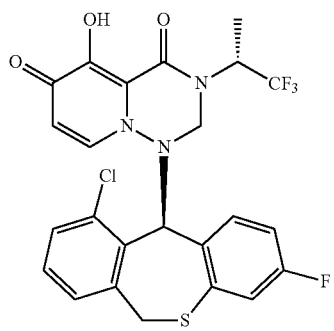
MS: m/z=540.14 [M+H]+
Reference Examples 774 and 775
[Chemical formula 845]
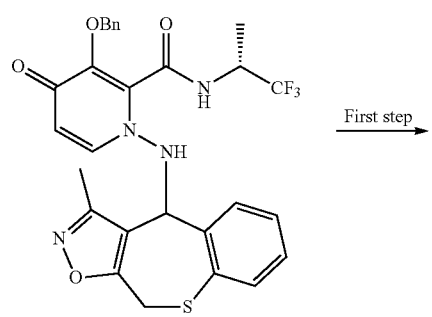
774A

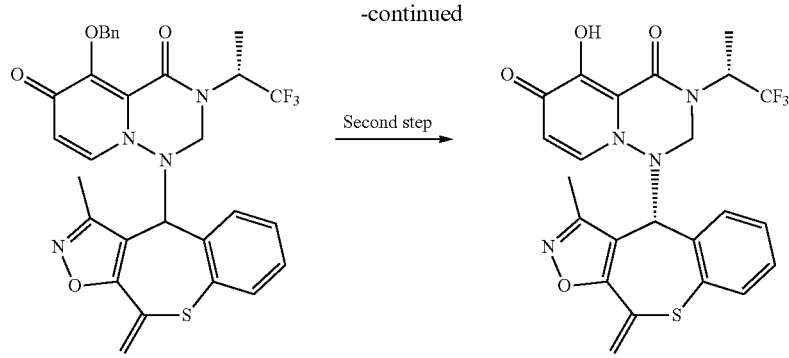

774B → Second step → 774

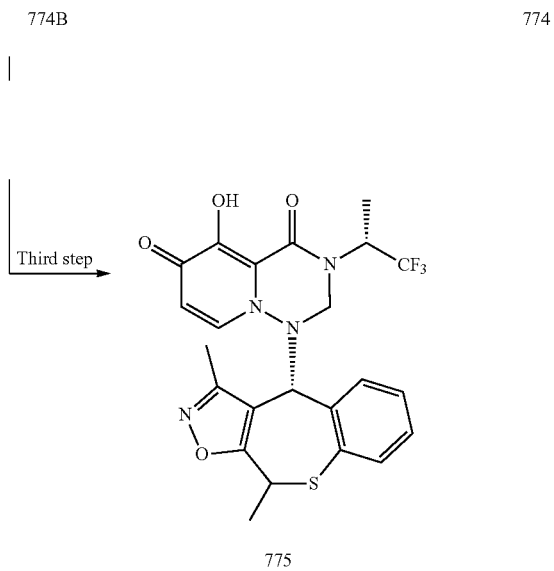

Third step

775

First Step

Compound 774A (111 mg, 0.20 mmol) was suspended in DMA. Paraformaldehyde (11 mg, 0.39 mmol) and BEMP (0.34 mL, 1.17 mmol), and the mixture was stirred at room temperature for 1.5 hours. Thereafter, tosyl chloride (74 mg, 0.39 mmol) was added, and the mixture was stirred for 2 hours. A saturated chloride ammonia water was added, and the precipitated solid was filtered. The resulting solid was purified by silica gel chromatography (hexane-ethyl acetate) to obtain compound 774B (16 mg, yield 14%).

MS: m/z=595.18 [M+H]$^+$

Second Step

Compound 774B (16 mg, 0.03 mmol) was suspended in DMA. Lithium chloride (11 mg, 0.27 mmol) was added, and the mixture was stirred at 100° C. for 3 hours. A 0.5M aqueous hydrochloric acid solution was added, and the generated solid was filtered to obtain compound 774 (3 mg, 0.006 mmol).

MS: m/z=505.11 [M+H]$^+$

Third Step

Compound 774B (21 mg, 0.04 mmol) was suspended in methanol. 10% palladium carbon (15 mg) was added, and the mixture was stirred at room temperature for 20 hours under hydrogen atmosphere. Insolubles were separated by filtration, then the filtrate was concentrated, and the resulting residue was suspended in DMA. Lithium chloride (12 mg, 0.28 mmol) was added, and the mixture was stirred at 100° C. for 3 hours. A 0.5M aqueous hydrochloric acid solution was added, and the mixture was extracted with ethyl acetate. The organic layer was washed with water and aqueous saturated sodium chloride solution, and then dried with anhydrous magnesium sulfate. The solvent was distilled off under reduced pressure, and the resulting residue was solidified with diisopropyl ether to obtain compound 775 (9 mg, 0.02 mmol).

MS: m/z=507.13 [M+H]$^+$

The following EX-1 to EX-29 can be also synthesized like the Reference examples, and are a preferable embodiment of the parent compound.

[Chemical formula 846]

EX-1

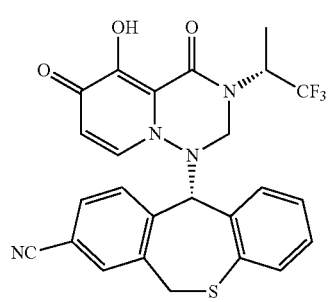

601
-continued
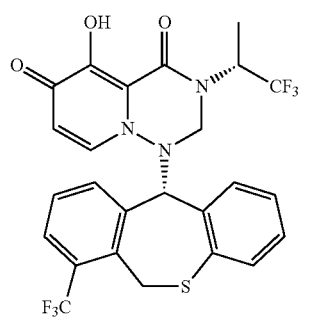
EX-2
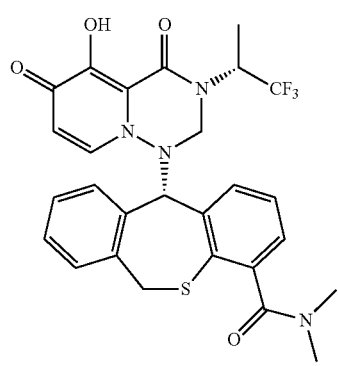
EX-3
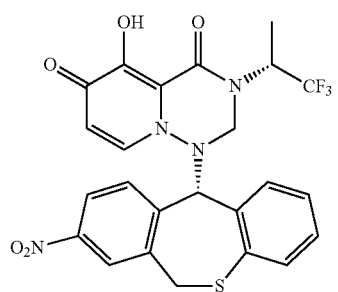
EX-4
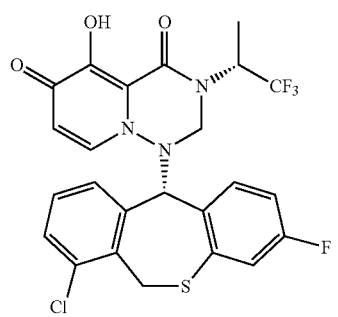
EX-5
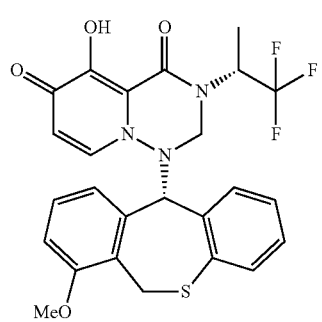
EX-6
602
-continued
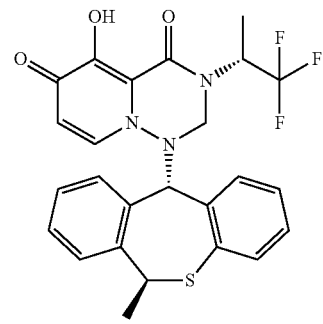
EX-7
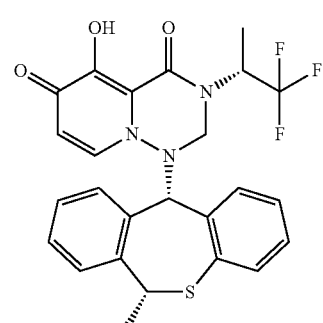
EX-8
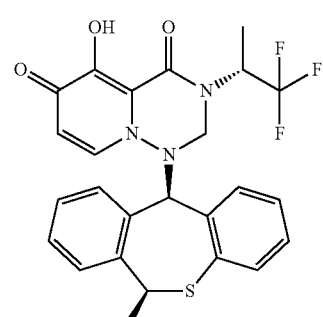
EX-9
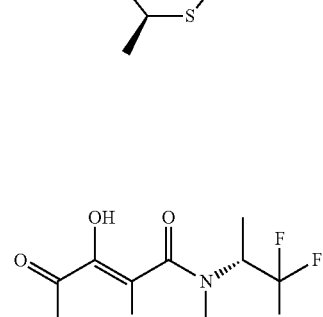
EX-10
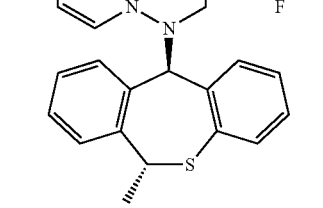

603
-continued
EX-11
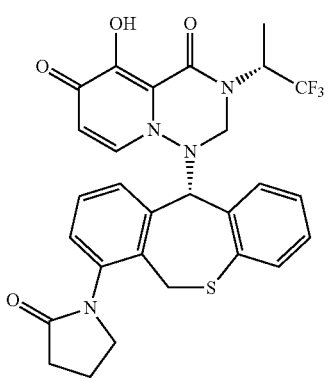
EX-12
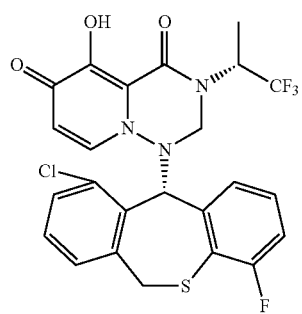
[Chemical formula 847]
EX-13
EX-14
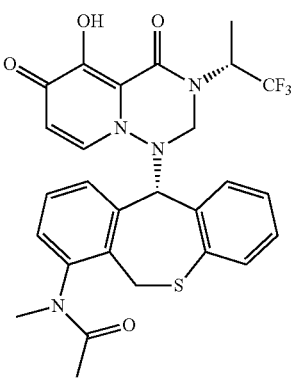
604
-continued
EX-15
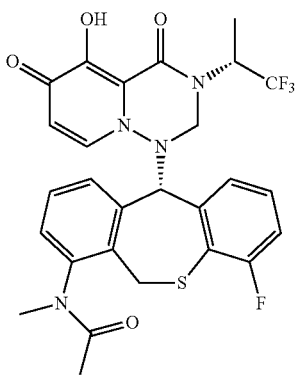
EX-16
EX-17
EX-18

EX-19 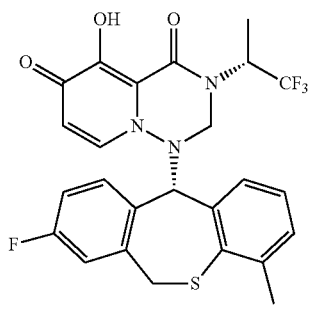
EX-20 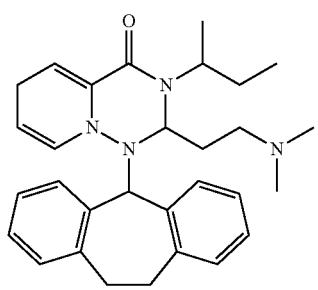
EX-21 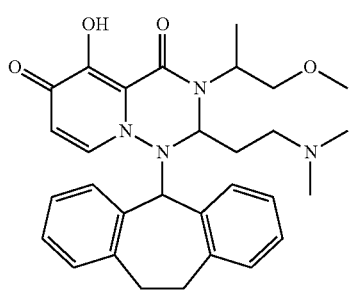
EX-22 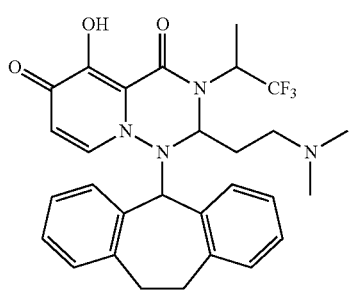
EX-23 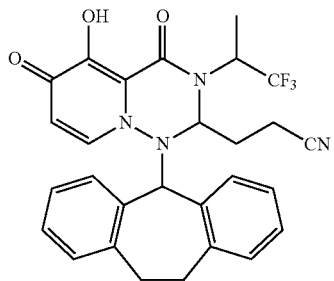
EX-24 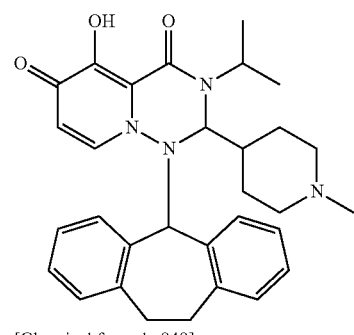
[Chemical formula 848]
EX-25 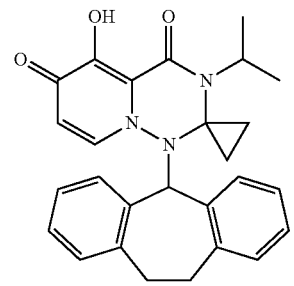
EX-26 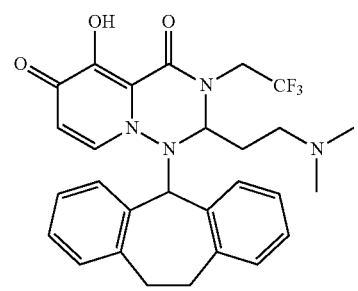 [SMILES: COCCN1C(=O)c2c(O)c(=O)ccn2N(C2c3ccccc3CCc3ccccc32)C1(C)C]
EX-27 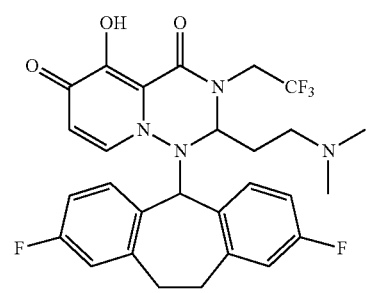
EX-28 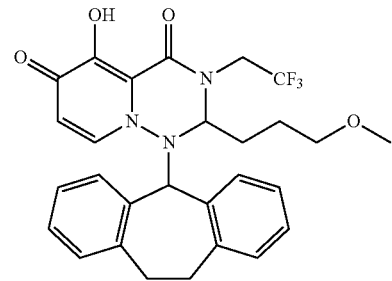

-continued

EX-29

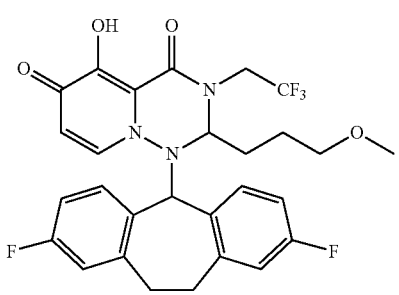

Hereinbelow, compounds of Examples 1 to 241 in connection with the present invention are shown.

EXAMPLE 1

[Chemical formula 849]

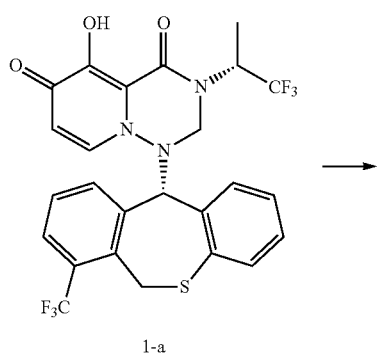

1-a

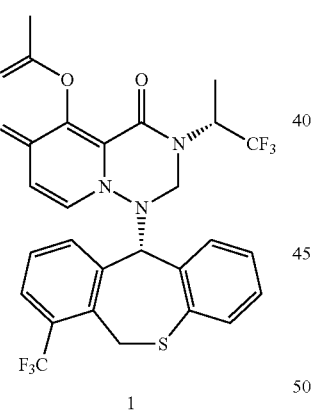

1

First Step

To a dichloromethane (1 ml) solution of compound 1-a (50 mg, 0.0900 mmol) and triethylamine (46 mg, 0.45 mmol) were added acetic acid anhydride (28 mg, 0.27 mmol) and DMAP (11 mg, 0.0090 mmol) at room temperature, and the mixture was stirred for 3 hours while the same temperature was retained. The reaction solution was diluted with dichloromethane (10 ml), and then water was added. The dichloromethane layer was separated, and the aqueous layer was extracted with dichloromethane once. After the combined extracts were dried with sodium sulfate, the solvent was distilled off, and the resulting solid was washed with ethyl acetate-diisopropyl ether to obtain 27 mg of compound of Example 1.

$^1$H-NMR (CDCl$_3$) δ: 1.18 (3H, d, J=7.5 Hz), 2.44 (3H, s), 3.98 (1H, d, J=14.7 Hz), 4.41 (1H, d, J=13.5 Hz), 4.95 (1H, d, J=13.2 Hz), 5.25 (1H, s), 5.46-5.57 (1H, m), 5.86 (1H, d, J=14.7 Hz), 5.97 (1H, d, J=7.8 Hz), 6.89-6.94 (2H, m), 7.06-7.21 (3H, m), 7.39 (2H, d, J=3.9 Hz), 7.78-7.82 (1H, m).

EXAMPLE 2

[Chemical formula 850]

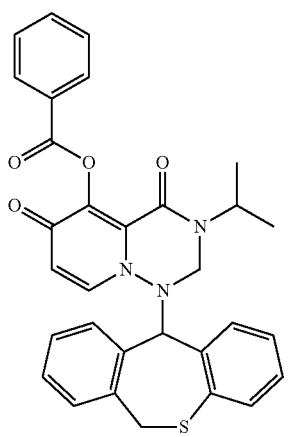

$^1$H-NMR (CDCl$_3$) δ: 1.02 (3H, d, J=6.6 Hz), 1.06 (3H, d, J=6.9 Hz), 3.58-3.62 (1H, m), 4.36 (1H, d, J=13.2 Hz), 4.70 (1H, brs), 4.82-4.91 (1H, m), 5.19 (1H, d, J=8.4 Hz), 5.67-5.75 (1H, m), 6.02 (1H, brs), 6.86 (1H, brs), 7.00-7.08 (3H, m), 7.13-7.51 (4H, m), 7.55-7.63 (2H, m), 8.07 (1H, d, J=7.5 Hz), 8.26 (2H, d, J=7.5 Hz).

EXAMPLE 3

[Chemical formula 851]

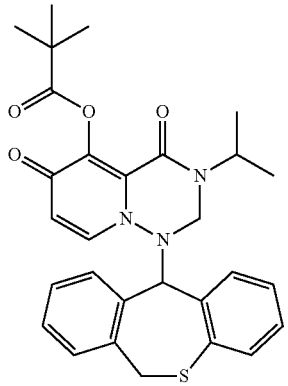

$^1$H-NMR (CDCl$_3$) δ: 1.03 (3H, d, J=6.6 Hz), 1.08 (3H, d, J=8.4 Hz), 1.45 (9H, s), 3.56-3.60 (1H, m), 4.33 (1H, d, J=13.2 Hz), 4.79 (2H, brs), 5.15 (1H, brs), 5.68 (1H, brs), 5.90 (1H, brs), 6.84 (1H, brs), 6.94 (1H, brs), 7.05-7.06 (2H, m), 7.15-7.27 (3H, m), 7.33-7.43 (2H, m).

EXAMPLE 4
[Chemical formula 852]
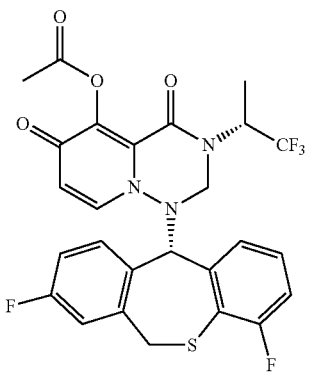
MS: m/z=566 [M+H]$^+$,
Rf: 0.56 (CHCl3:MeOH=9:1).
EXAMPLE 5
[Chemical formula 853]
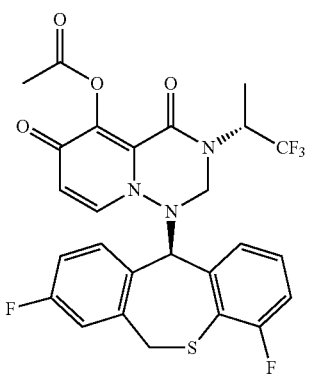
MS: m/z=566 [M+H]$^+$,
Rf: 0.52 (CHCl3:MeOH=9:1).
EXAMPLE 6
[Chemical formula 854]
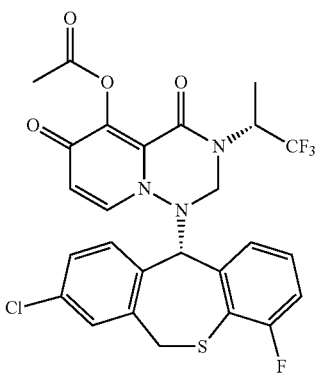
MS: m/z=582 [M+H]$^+$,
Rf: 0.56 (CHCl3:MeOH=9:1).
EXAMPLE 7
[Chemical formula 855]
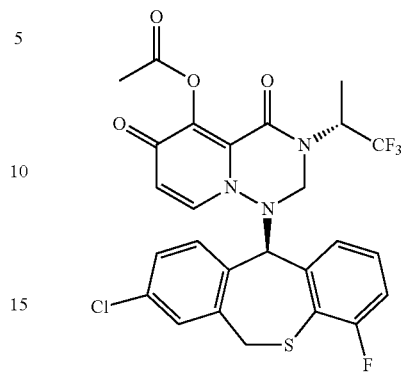
MS: m/z=582 [M+H]$^+$,
Rf: 0.52 (CHCl3:MeOH=9:1).
EXAMPLE 8
[Chemical formula 856]
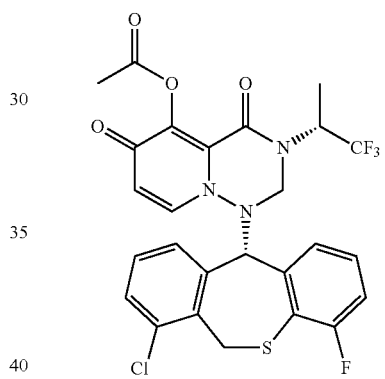
MS: m/z=582 [M+H]$^+$,
Rf: 0.56 (CHCl3:MeOH=9:1).
EXAMPLE 9
[Chemical formula 857]
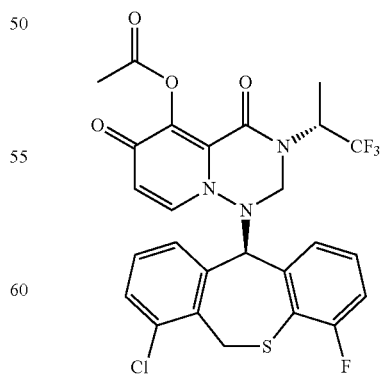
MS: m/z=582 [M+H]$^+$,
Rf: 0.52 (CHCl3:MeOH=9:1).

EXAMPLE 10

[Chemical formula 858]

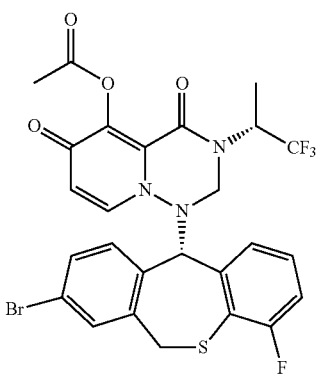

$^1$H-NMR (CDCl$_3$) δ: 1.16 (3H, d, J=7.3 Hz), 2.43 (3H, s), 3.64 (1H, d, J=13.6 Hz), 4.42 (1H, d, J=12.9 Hz), 4.91 (1H, d, J=12.9 Hz), 5.18 (1H, s), 5.49 (1H, m), 5.74 (1H, d, J=13.6 Hz), 6.00 (1H, d, J=7.7 Hz), 6.79 (1H, t, J=7.7 Hz), 6.87 (1H, m), 6.97 (1H, dt, J=2.6, 8.0 Hz), 7.08-7.18 (3H, m), 7.45 (1H, dd, J=1.5, 8.0 Hz).

MS: m/z=627 [M+H]$^+$.

Rf: 0.53 (CHCl$_3$:MeOH=9:1).

EXAMPLE 11

[Chemical formula 859]

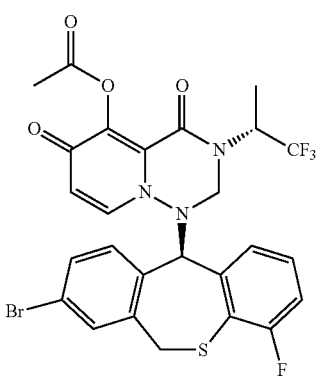

MS: m/z=627 [M+H]$^+$,

Rf: 0.46 (CHCl$_3$:MeOH=9:1).

EXAMPLE 12

[Chemical formula 860]

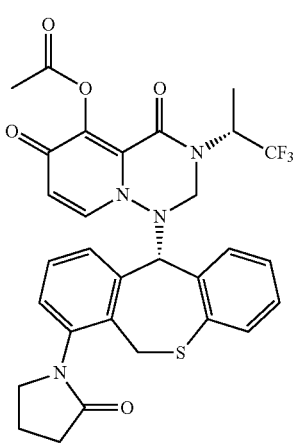

$^1$H-NMR (CDCl$_3$) δ: 1.14 (3H, d, J=7.2 Hz), 2.32 (2H, m), 2.43 (3H, s), 2.65 (2H, t, J=8.1 Hz), 3.64 (1H, d, J=14.2 Hz), 3.86 (2H, m), 4.56 (1H, d, J=13.5 Hz), 4.91 (1H, d, J=13.5 Hz), 5.17 (1H, s), 5.44 (1H, m), 5.50 (1H, d, J=14.2 Hz), 5.96 (1H, d, J=7.8 Hz), 6.88 (1H, m), 7.03-7.16 (3H, m), 7.20 (1H, d, J=7.8 Hz), 7.30 (3H, m).

MS: m/z=613 [M+H]$^+$.

Rf: 0.5 (CHCl$_3$:MeOH=9:1).

EXAMPLE 13

[Chemical formula 861]

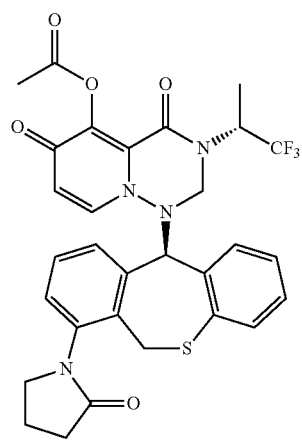

MS: m/z=613 [M+H]$^+$,

Rf: 0.4 (CHCl$_3$:MeOH=9:1).

EXAMPLE 14

[Chemical formula 862]

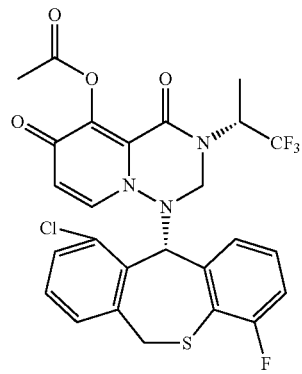

MS: m/z=582 [M+H]$^+$,

Rf: 0.56 (CHCl$_3$:MeOH=9:1).

EXAMPLE 15

[Chemical formula 863]

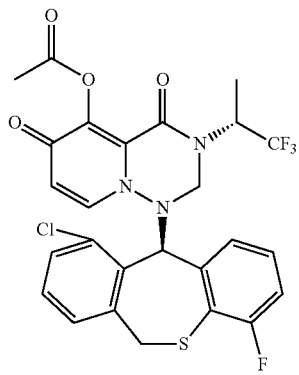

MS: m/z=582 [M+H]+,
Rf: 0.46 (CHCl₃:MeOH=9:1).

EXAMPLE 16

[Chemical formula 864]

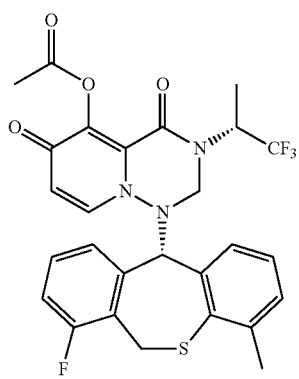

MS: m/z=562 [M+H]+,
Rf: 0.53 (CHCl₃:MeOH=9:1).

EXAMPLE 17

[Chemical formula 865]

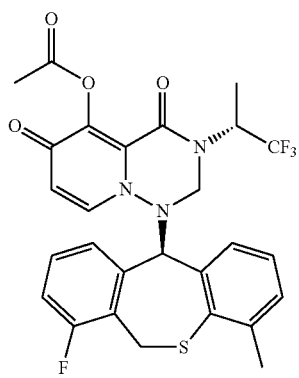

MS: m/z=562 [M+H]+,
Rf: 0.46 (CHCl₃:MeOH=9:1).

EXAMPLE 18

[Chemical formula 866]

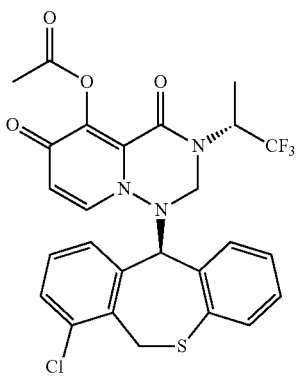

$^1$H-NMR (CDCl₃) δ: 1.13 (3H, d, J=6.1 Hz), 2.42 (3H, s), 4.31 (1H, d, J=13.9 Hz), 4.57 (1H, d, J=12.6 Hz), 4.97 (1H, d, J=12.6 Hz), 5.26 (1H, s), 5.28 (1H, m), 5.62 (1H, d, J=13.9 Hz), 5.96 (1H, d, J=7.8 Hz), 6.87 (1H, m), 7.04-7.12 (3H, m), 7.19 (1H, t, J=7.9 Hz), 7.32 (1H, d, J=7.5 Hz), 7.49 (1H, dd, J=1.2, 7.9 Hz).
MS: m/z=564 [M+H]+.

EXAMPLE 19

[Chemical formula 867]

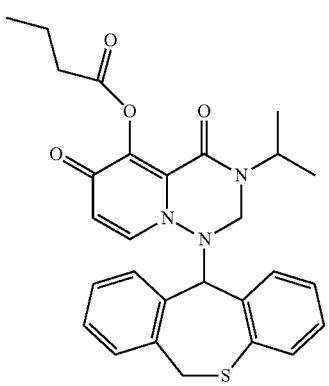

$^1$H-NMR (DMSO-d₆) δ: 0.97-1.09 (9H, m), 1.68 (2H, m), 2.55 (2H, t, J=7.2 Hz), 3.88 (1H, d, J=13.3 Hz), 4.27 (1H, d, J=13.7 Hz), 4.59 (1H, m), 4.99 (1H, d, J=13.6 Hz), 5.33 (1H, s), 5.73 (2H, dd, J=53.9, 10.8 Hz), 6.83-7.48 (9H, m).
MS: m/z=504 [M+H]+.

EXAMPLE 20

[Chemical formula 868]

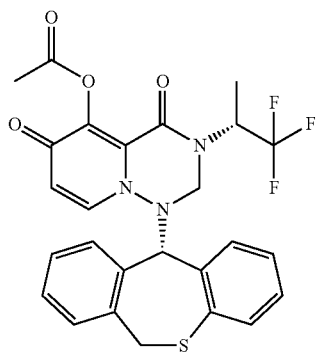

$^1$H-NMR (CDCl$_3$) δ: 1.15 (3H, d, J=7.3 Hz), 2.44 (3H, s), 3.61 (1H, d, J=13.4 Hz), 4.46 (1H, d, J=13.1 Hz), 4.91 (1H, d, J=13.3 Hz), 5.12 (1H, s), 5.42-5.57 (1H, m), 5.64 (1H, d, J=13.4 Hz), 5.98 (1H, d, J=7.8 Hz), 6.87 (2H, s), 6.99-7.61 (7H, m).
MS: m/z=530 [M+H]$^+$.

EXAMPLE 21

[Chemical formula 869]

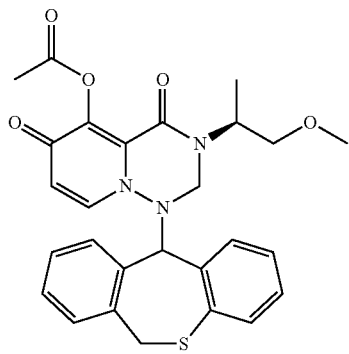

EXAMPLE 22

[Chemical formula 870]

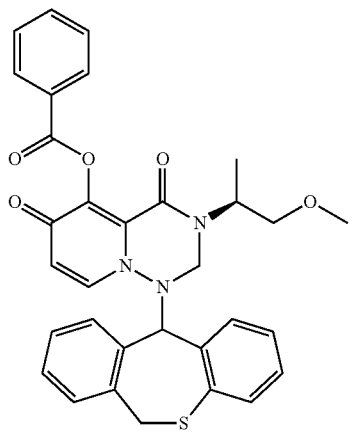

EXAMPLE 23

[Chemical formula 871]

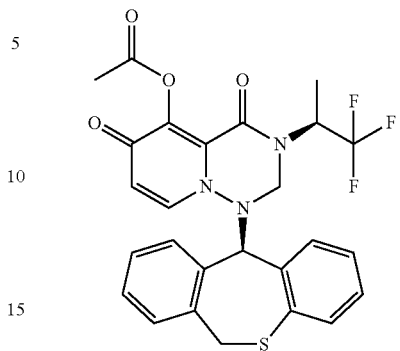

$^1$H-NMR (CDCl$_3$) δ: 1.15 (3H, d, J=7.3 Hz), 2.44 (3H, s), 3.61 (1H, d, J=13.4 Hz), 4.46 (1H, d, J=13.1 Hz), 4.91 (1H, d, J=13.3 Hz), 5.12 (1H, s), 5.42-5.57 (1H, m), 5.64 (1H, d, J=13.4 Hz), 5.98 (1H, d, J=7.8 Hz), 6.87 (2H, s), 6.99-7.61 (7H, m).

EXAMPLE 24

[Chemical formula 872]

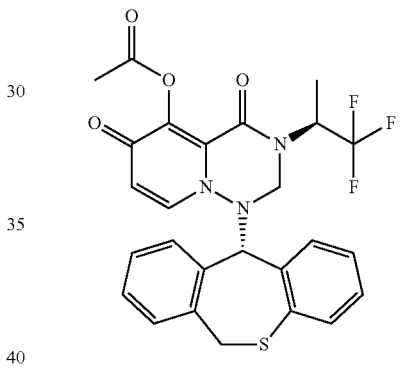

$^1$H-NMR (CDCl$_3$) δ: 1.34 (3H, d, J=7.3 Hz), 2.43 (3H, s), 3.60 (1H, d, J=13.3 Hz), 4.57 (1H, d, J=12.5 Hz), 4.97 (1H, d, J=12.5 Hz), 5.23 (1H, s), 5.29 (1H, m), 5.66 (1H, d, J=13.1 Hz), 5.97 (1H, d, J=7.9 Hz), 6.87 (2H, s), 7.05-7.42 (8H, m).

EXAMPLE 25

[Chemical formula 873]

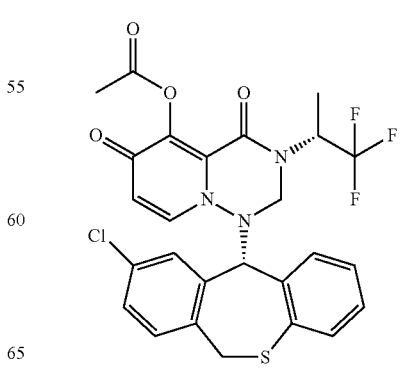

EXAMPLE 26

[Chemical formula 874]

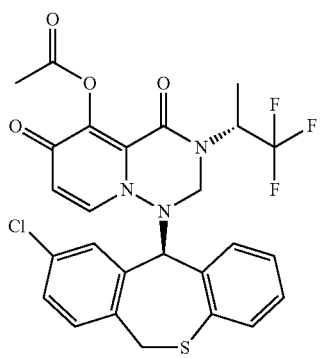

EXAMPLE 27

[Chemical formula 875]

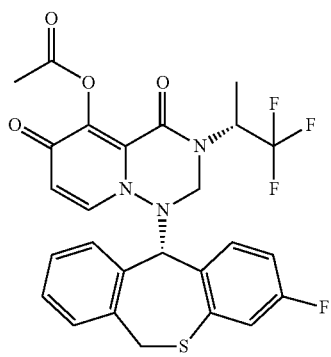

$^1$H-NMR (CDCl$_3$) δ: 1.16 (3H, d, J=7.4 Hz), 2.46 (3H, s), 3.63 (1H, d, J=13.5 Hz), 4.46 (1H, d, J=13.2 Hz), 4.93 (1H, d, J=13.2 Hz), 5.14 (1H, s), 5.51 (1H, m), 5.68 (1H, d, J=13.5 Hz), 6.07 (1H, d, J=8.0 Hz), 6.63 (1H, t, J=8.0 Hz), 6.84 (2H, m), 7.18-7.49 (6H, m).
MS: m/z=541 [M+H]$^+$.

EXAMPLE 28

[Chemical formula 876]

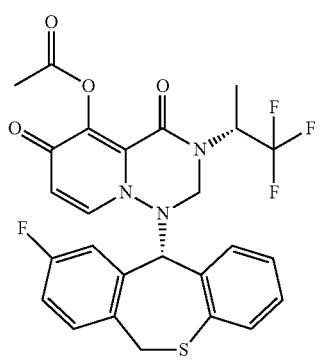

$^1$H-NMR (CDCl$_3$) δ: 1.21 (3H, d, J=7.2 Hz), 2.41 (3H, d, J=15.1 Hz), 3.62 (1H, d, J=13.6 Hz), 4.44 (1H, d, J=13.3 Hz), 4.93 (1H, d, J=13.1 Hz), 5.06 (1H, s), 5.50 (1H, m), 5.58 (1H, d, J=13.4 Hz), 5.98 (1H, d, J=7.8 Hz), 6.88-7.39 (8H, m).

EXAMPLE 29

[Chemical formula 877]

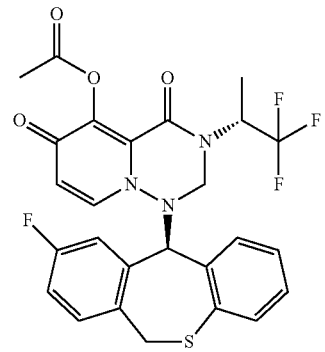

$^1$H-NMR (CDCl$_3$) δ: 1.35 (3H, d, J=7.5 Hz), 2.42 (3H, s), 3.61 (1H, d, J=13.4 Hz), 4.56 (1H, d, J=12.8 Hz), 4.99 (1H, d, J=12.8 Hz), 5.16 (1H, s), 5.23-5.38 (1H, m), 5.59 (1H, d, J=13.6 Hz), 5.97 (1H, d, J=7.8 Hz), 6.91-7.38 (8H, m).

EXAMPLE 30

[Chemical formula 878]

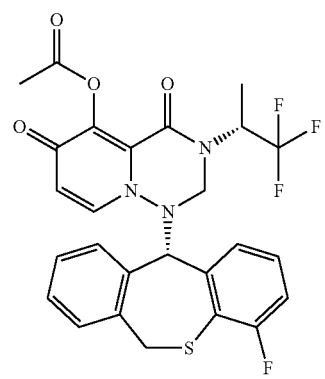

EXAMPLE 31

[Chemical formula 879]

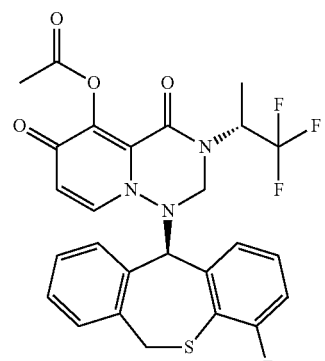

EXAMPLE 32
[Chemical formula 880]
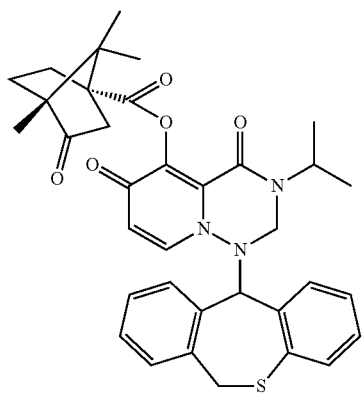
EXAMPLE 33
[Chemical formula 881]
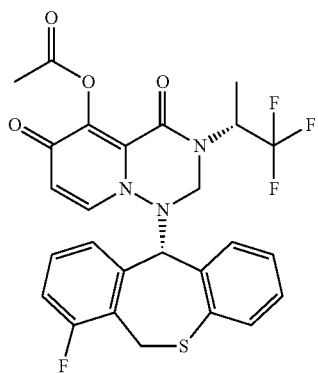
EXAMPLE 34
[Chemical formula 882]
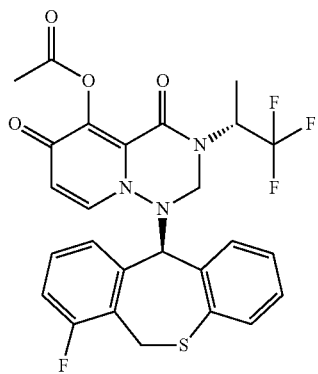
EXAMPLE 35
[Chemical formula 883]
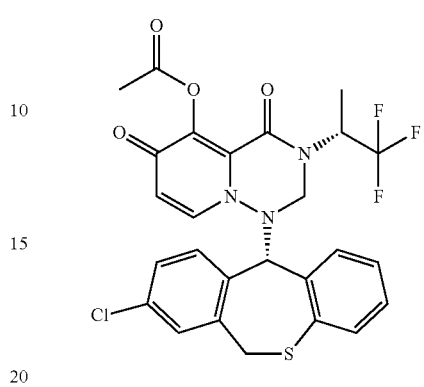
EXAMPLE 36
[Chemical formula 884]
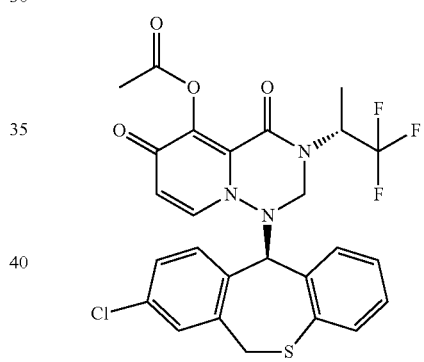
EXAMPLE 37
[Chemical formula 885]
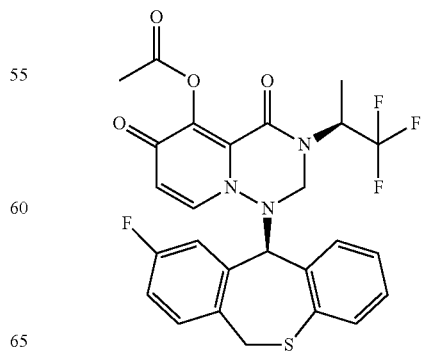

EXAMPLE 38
[Chemical formula 886]
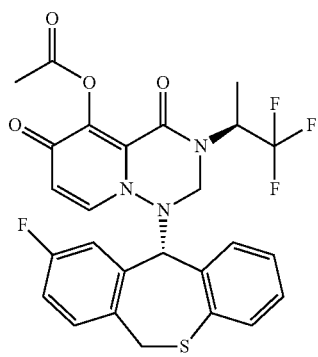
EXAMPLE 39
[Chemical formula 887]
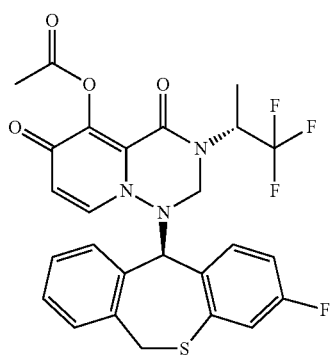
¹H-NMR (CDCl₃) δ: 1.35 (3H, d, J=7.5 Hz), 2.42 (3H, s), 3.61 (1H, d, J=13.4 Hz), 4.56 (1H, d, J=12.8 Hz), 4.99 (1H, d, J=12.8 Hz), 5.16 (1H, s), 5.23-5.38 (1H, m), 5.59 (1H, d, J=13.6 Hz), 5.97 (1H, d, J=7.8 Hz), 6.91-7.38 (8H, m).
EXAMPLE 40
[Chemical formula 888]
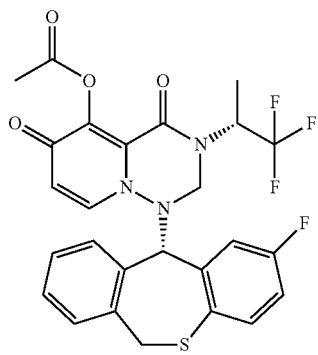
EXAMPLE 41
[Chemical formula 889]
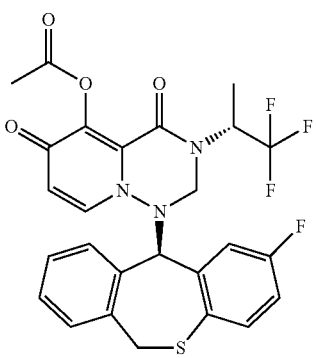
EXAMPLE 42
[Chemical formula 890]
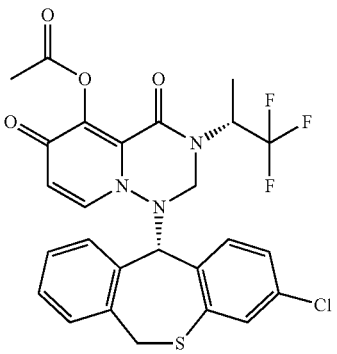
EXAMPLE 43
[Chemical formula 891]
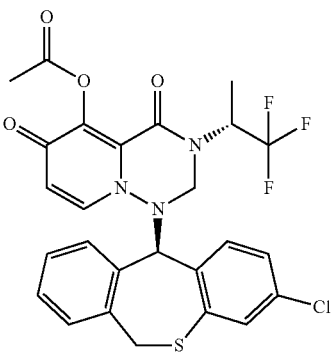

EXAMPLE 44
[Chemical formula 892]
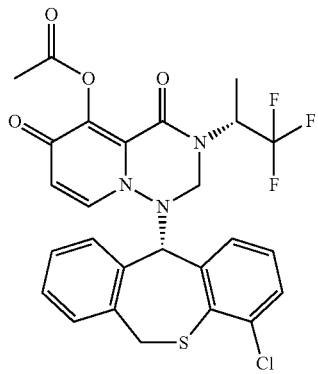
EXAMPLE 45
[Chemical formula 893]
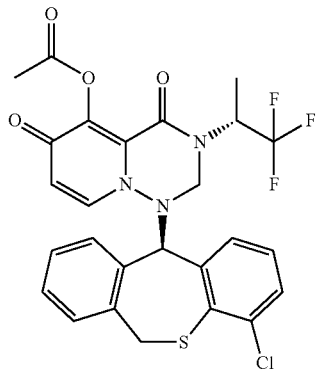
EXAMPLE 46
[Chemical formula 894]
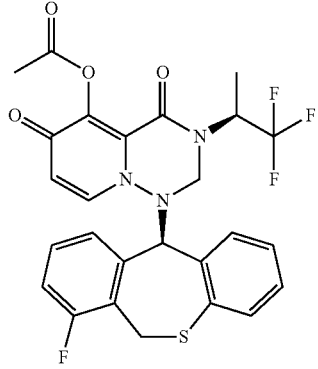
EXAMPLE 47
[Chemical formula 895]
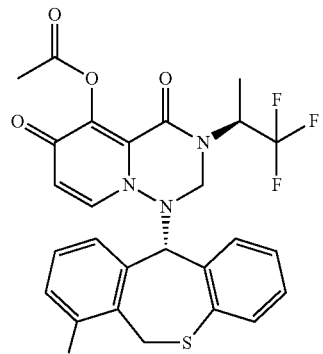
EXAMPLE 48
[Chemical formula 896]
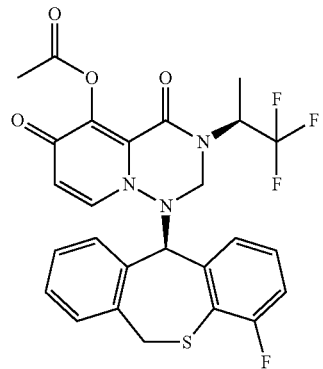
EXAMPLE 49
[Chemical formula 897]
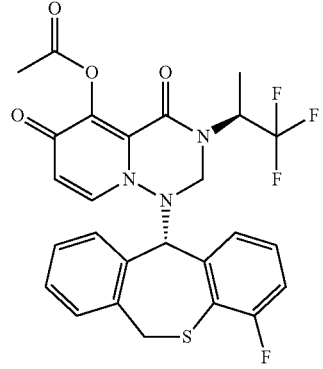

EXAMPLE 50
[Chemical formula 898]
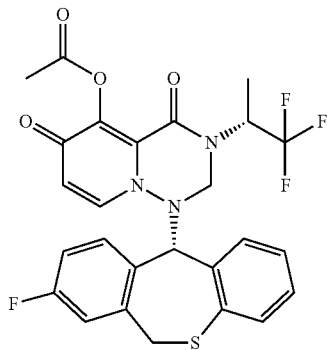
MS: m/z=548 [M+H]+.
EXAMPLE 51
[Chemical formula 899]
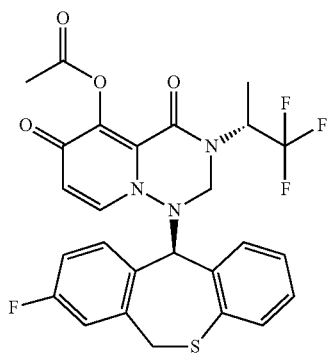
EXAMPLE 52
[Chemical formula 900]
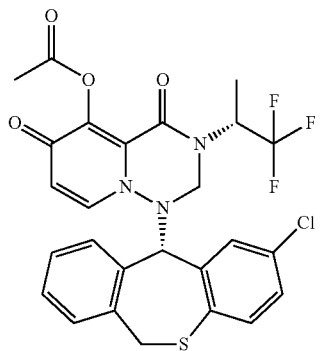
EXAMPLE 53
[Chemical formula 901]
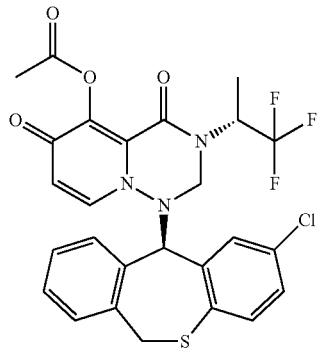
EXAMPLE 54
[Chemical formula 902]
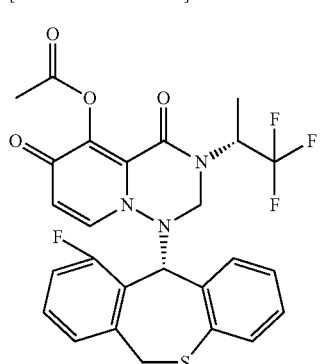
EXAMPLE 55
[Chemical formula 903]
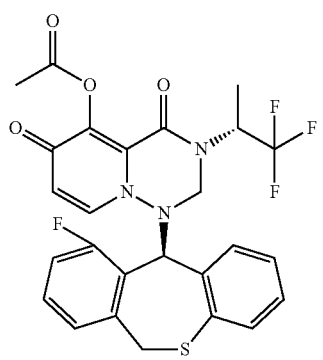

EXAMPLE 56
[Chemical formula 904]
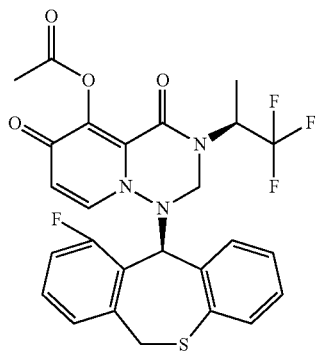
EXAMPLE 57
[Chemical formula 905]
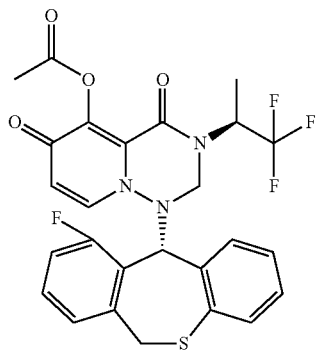
EXAMPLE 58
[Chemical formula 906]
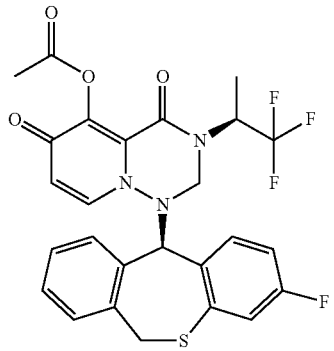
EXAMPLE 59
[Chemical formula 907]
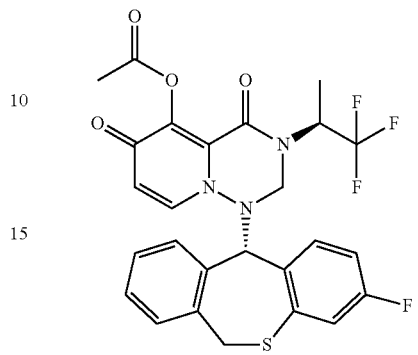
EXAMPLE 60
[Chemical formula 908]
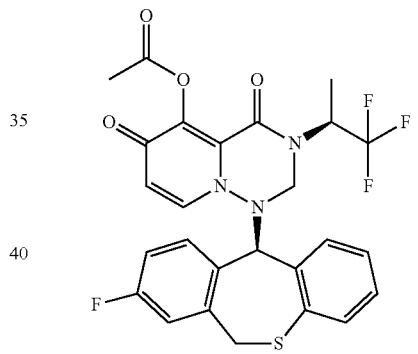
EXAMPLE 61
[Chemical formula 909]
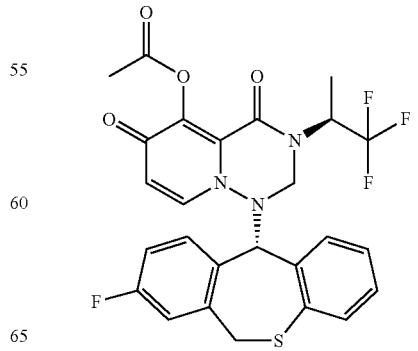

EXAMPLE 62
[Chemical formula 910]
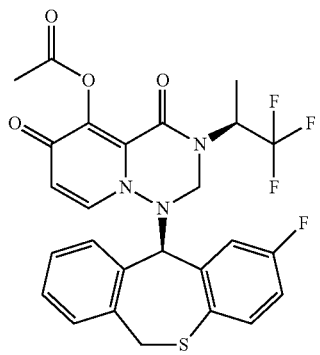
EXAMPLE 63
[Chemical formula 911]
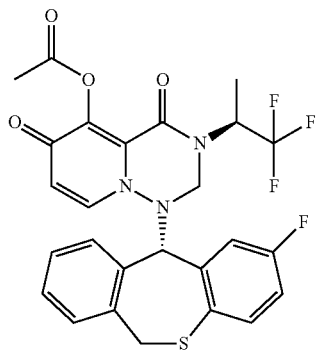
EXAMPLE 64
[Chemical formula 912]
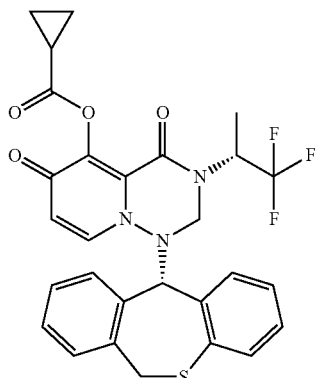
¹H-NMR (DMSO-d$_6$) δ: 1.07 (4H, m), 1.17 (3H, d, J=6.9 Hz), 1.88 (1H, m), 3.88 (1H, d, J=13.6 Hz), 4.38 (1H, d, J=13.6 Hz), 5.11 (1H, d, J=13.4 Hz), 5.46 (1H, m), 5.51 (1H, s), 5.63 (1H, d, J=13.3 Hz), 5.87 (1H, d, J=7.8 Hz), 6.84-7.60 (9H, m).
MS: m/z=556 [M+H]⁺.
EXAMPLE 65
[Chemical formula 913]
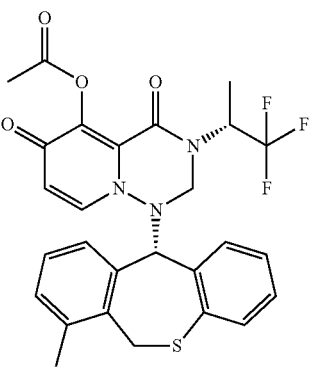
EXAMPLE 66
[Chemical formula 914]
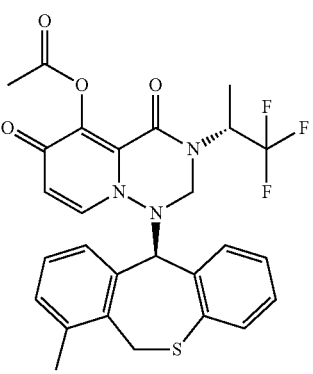
EXAMPLE 67
[Chemical formula 915]
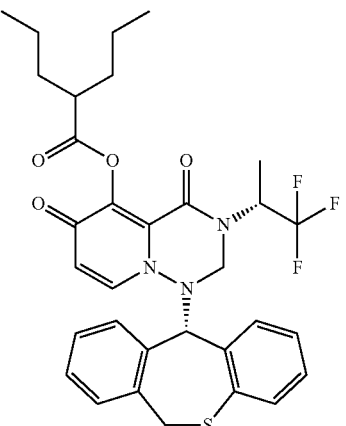
MS: m/z=614 [M+H]⁺.

EXAMPLE 68
[Chemical formula 916]
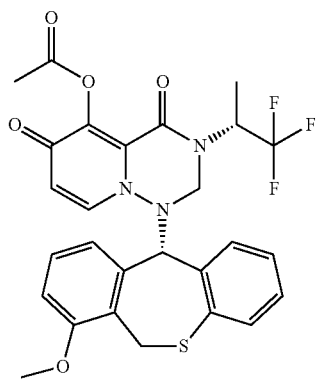
EXAMPLE 69
[Chemical formula 917]
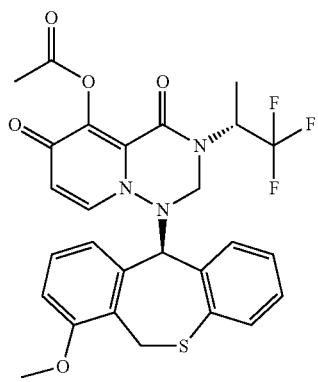
EXAMPLE 70
[Chemical formula 918]
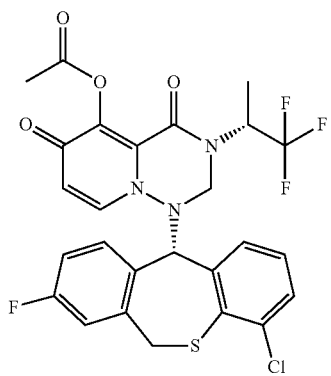
EXAMPLE 71
[Chemical formula 919]
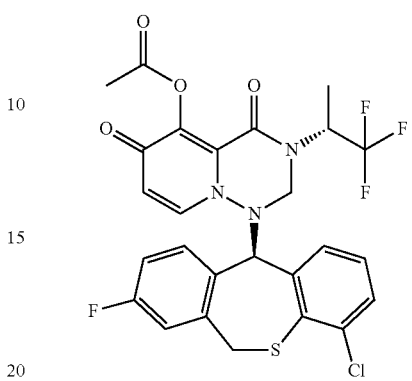
EXAMPLE 72
[Chemical formula 920]
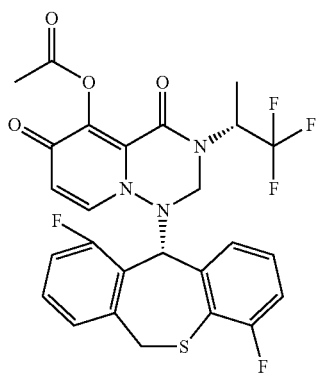
EXAMPLE 73
[Chemical formula 921]
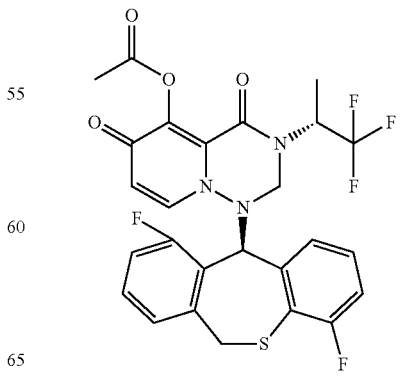

EXAMPLE 74
[Chemical formula 922]
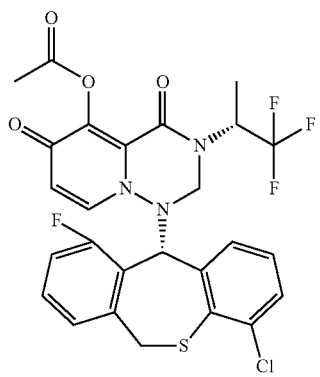
EXAMPLE 75
[Chemical formula 923]
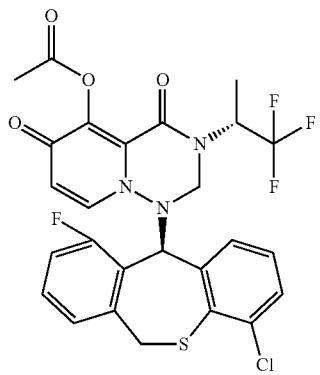
EXAMPLE 76
[Chemical formula 924]
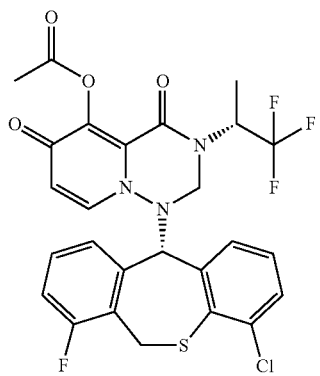
$^1$H-NMR (CDCl$_3$) δ: 1.17 (3H, d, J=7.2 Hz), 2.44 (3H, s), 4.22 (1H, d, J=13.7 Hz), 4.44 (1H, d, J=13.3 Hz), 4.93 (1H, d, J=13.6 Hz), 5.23 (1H, s), 5.42 (1H, d, J=15.7 Hz), 5.50 (1H, m), 6.00 (1H, d, J=7.9 Hz), 6.85-7.29 (7H, m).
MS: m/z=582 [M+H]$^+$.
EXAMPLE 77
[Chemical formula 925]
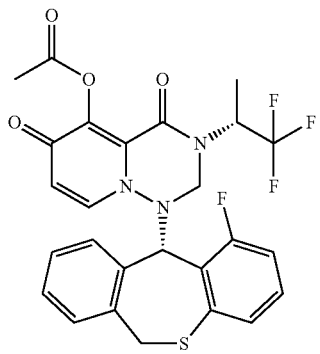
EXAMPLE 78
[Chemical formula 926]
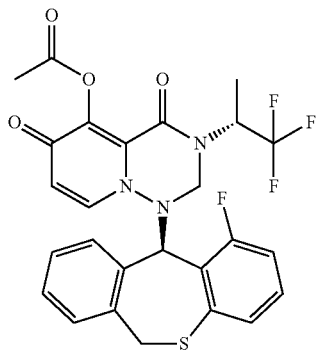
EXAMPLE 79
[Chemical formula 927]
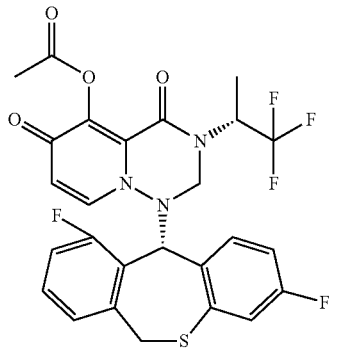

EXAMPLE 80
[Chemical formula 928]
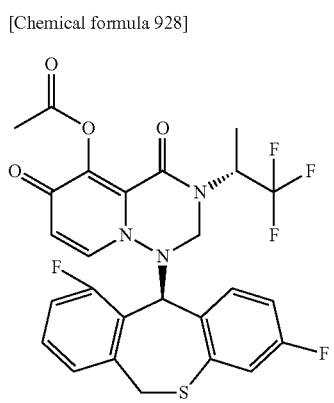 [SMILES: CC(=O)Oc1c2n(ccc1=O)N([C@H]1c3ccc(F)cc3SCc3cccc(F)c31)CN([C@H](C)C(F)(F)F)C2=O]
EXAMPLE 81
[Chemical formula 929]
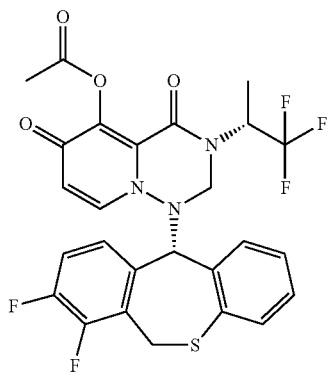
EXAMPLE 82
[Chemical formula 930]
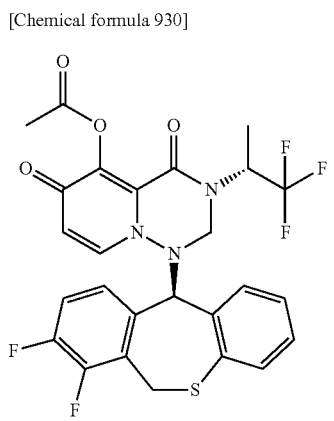 [SMILES: CC(=O)Oc1c2n(ccc1=O)N([C@H]1c3ccccc3SCc3c1ccc(F)c3F)CN([C@H](C)C(F)(F)F)C2=O]
EXAMPLE 83
[Chemical formula 931]
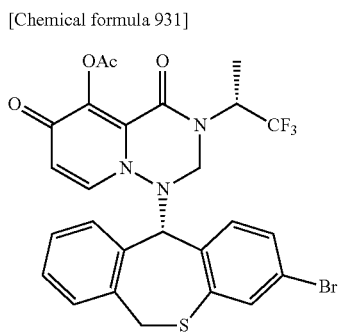
MS: m/z=609.90 [M+H]$^+$.
EXAMPLE 84
[Chemical formula 932]
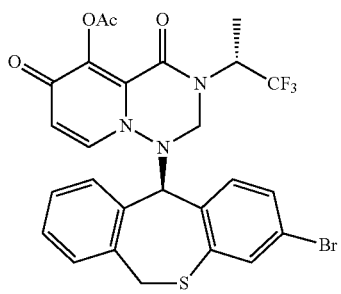
MS: m/z=609.90 [M+H]$^+$.
EXAMPLE 85
[Chemical formula 933]
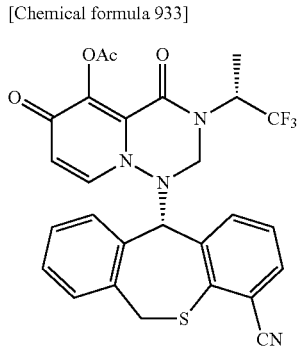 [SMILES: CC(=O)Oc1c2n(ccc1=O)N([C@H]1c3ccccc3CSc3c(C#N)cccc31)CN([C@H](C)C(F)(F)F)C2=O]
MS: m/z=555.20 [M+H]$^+$.

EXAMPLE 86

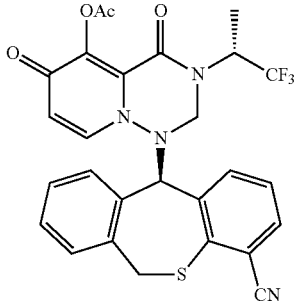

[Chemical formula 934]

MS: m/z=555.20 [M+H]⁺.

EXAMPLE 87

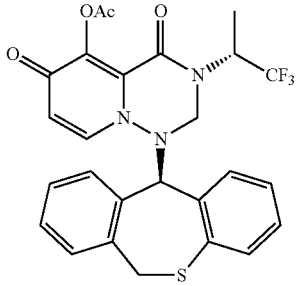

[Chemical formula 935]

$^1$H-NMR (CDCl$_3$) δ: 1.34 (3H, d, J=7.4 Hz), 2.42 (3H, s), 3.60 (1H, d, J=13.3 Hz), 4.56 (1H, d, J=12.7 Hz), 4.96 (1H, d, J=12.4 Hz), 5.20-5.34 (2H, m), 5.65 (1H, d, J=13.5 Hz), 5.97 (1H, d, J=7.9 Hz), 6.76-7.41 (9H, m).
MS: m/z=530 [M+H]⁺.

EXAMPLE 88

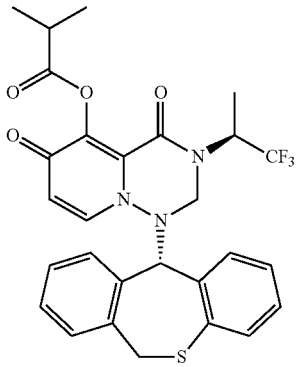

[Chemical formula 936]

$^1$H-NMR (CDCl$_3$) δ: 1.34 (3H, d, J=7.5 Hz), 1.39 (6H, d, J=6.8 Hz), 2.92-3.00 (1H, m), 3.59 (1H, d, J=13.1 Hz), 4.56 (1H, d, J=12.7 Hz), 4.97 (1H, d, J=12.2 Hz), 5.22-5.30 (2H, m), 5.65 (1H, d, J=13.7 Hz), 6.00 (1H, d, 7.9 Hz), 6.90-7.39 (9H, m).
MS: m/z=558 [M+H]⁺.

EXAMPLE 89

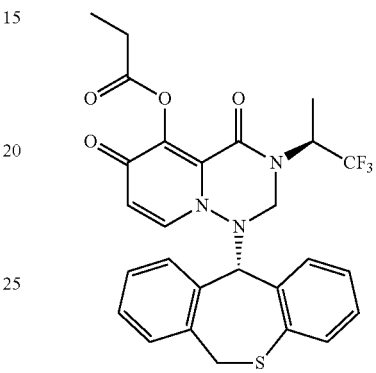

[Chemical formula 937]

$^1$H-NMR (CDCl$_3$) δ: 1.26-1.35 (6H, m), 2.76 (2H, q, J=7.3 Hz), 3.59 (1H, d, J=13.2 Hz), 4.56 (1H, d, J=12.6 Hz), 4.96 (1H, d, J=12.8 Hz), 5.22-5.30 (2H, m), 5.66 (1H, d, J=13.4 Hz), 5.95 (1H, d, J=7.7 Hz), 6.89-7.42 (9H, m).
MS: m/z=544 [M+H]⁺.

EXAMPLE 90

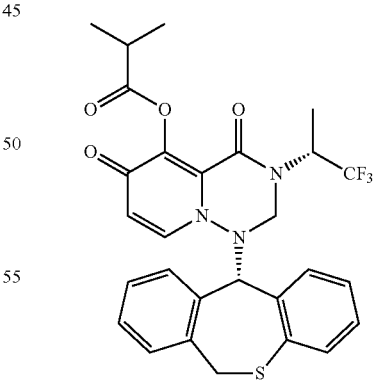

[Chemical formula 938]

$^1$H-NMR (CDCl$_3$) δ: 1.12 (3H, d, J=7.2 Hz), 1.40 (6H, d, J=6.9 Hz), 2.93-3.02 (1H, m), 3.60 (1H, d, J=13.1 Hz), 4.44 (1H, d, J=13.1 Hz), 4.90 (1H, d, J=12.9 Hz), 5.12 (1H, s), 5.46-5.66 (2H, m), 5.93 (1H, d, J=7.7 Hz), 6.89 (2H, brs), 7.06-7.28 (5H, m), 7.35-7.44 (2H, m).
MS: m/z=558 [M+H]⁺.

EXAMPLE 91

[Chemical formula 939]

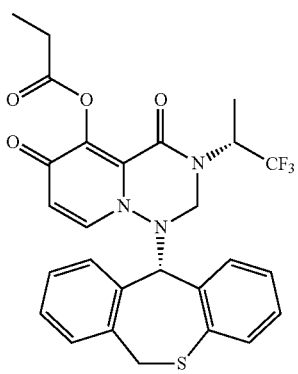

$^1$H-NMR (CDCl$_3$) δ: 1.13 (3H, d, J=6.1 Hz), 1.31 (3H, t, J=7.5 Hz), 2.77 (2H, q, J=7.6 Hz), 3.60 (1H, d, J=13.4 Hz), 4.45 (1H, d, J=13.2 Hz), 4.90 (1H, d, J=13.3 Hz), 5.12 (1H, s), 5.44-5.66 (2H, m), 5.95 (1H, d, J=7.9 Hz), 6.89 (2H, brs), 7.06-7.45 (7H, m).

MS: m/z=544 [M+H]$^+$.

EXAMPLE 92

[Chemical formula 940]

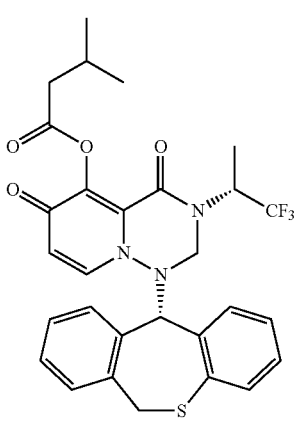

$^1$H-NMR (CDCl$_3$) δ: 1.09-1.14 (9H, m), 2.26-2.35 (1H, m), 2.60 (2H, d, J=6.6 Hz), 3.60 (1H, d, J=13.5 Hz), 4.44 (1H, d, J=13.0 Hz), 4.90 (1H, d, J=12.7 Hz), 5.11 (1H, s), 5.46-5.65 (2H, m), 5.94 (1H, d, J=8.1 Hz), 6.88 (2H, brs), 7.07-7.44 (7H, m).

MS: m/z=572 [M+H]$^+$.

EXAMPLE 93

[Chemical formula 941]

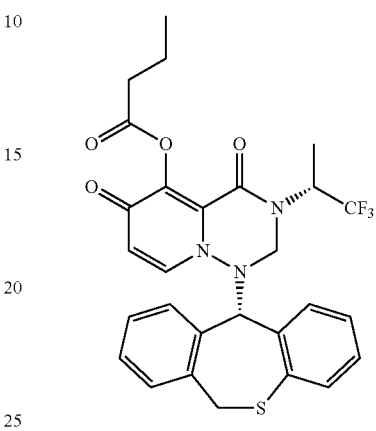

$^1$H-NMR (CDCl$_3$) δ: 1.05-1.14 (6H, m), 1.81-1.88 (2H, m), 2.71 (2H, t, J=7.4 Hz), 3.61 (1H, d, J=13.4 Hz), 4.45 (1H, d, J=13.4 Hz), 4.91 (1H, d, J=13.3 Hz), 5.12 (1H, s), 5.47-5.66 (2H, m), 5.95 (1H, d, J=8.0 Hz), 6.89 (2H, brs), 7.07-7.45 (7H, m).

MS: m/z=558 [M+H]$^+$.

EXAMPLE 94

[Chemical formula 942]

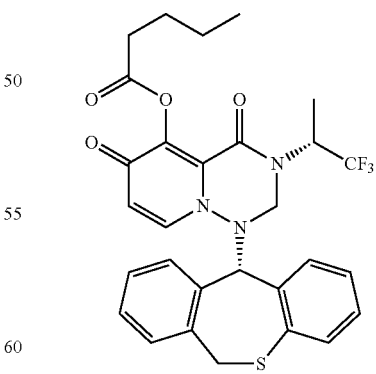

MS: m/z=572 [M+H]$^+$.

EXAMPLE 95

[Chemical formula 943]

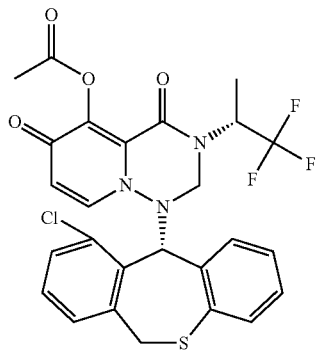

$^1$H-NMR (DMSO-$d_6$) δ: 1.03 (3H, d, J=8.0 Hz), 2.29 (3H, s), 3.98 (1H, d, J=12.0 Hz), 4.53 (1H, d, 12.0 Hz), 5.13 (1H, d, 12.0 Hz), 5.47 (1H, m), 5.66 (1H, d, J=12.0 Hz), 5.79 (1H, s), 5.92 (1H, d, J=8.0 Hz), 6.81 (1H, d, 8.0 Hz), 6.91 (1H, m), 7.13-7.22 (2H, m), 7.27 (1H, d, J=8.0 Hz), 7.45 (2H, m), 7.51 (1H, m).

MS: m/z=564 [M+H]$^+$. RT=2.10 min.

EXAMPLE 96

[Chemical formula 944]

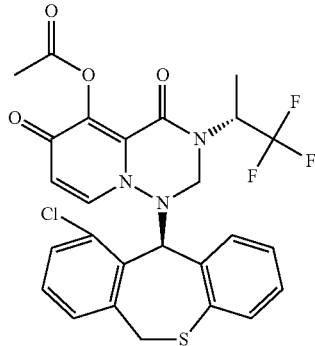

$^1$H-NMR (DMSO-$d_6$) δ: 1.40 (3H, d, J=8.0 Hz), 2.42 (3H, s), 3.62 (1H, d, J=12.0 Hz), 4.48 (1H, d, 12.0 Hz), 5.02 (2H, m), 5.64 (1H, m), 5.97 (1H, d, J=8.0 Hz), 6.05 (1H, s), 6.91 (1H, m), 7.05-7.15 (2H, m), 7.20-7.35 (5H, m)

MS: m/z=564 [M+H]$^+$. RT=2.11 min.

EXAMPLE 97

[Chemical formula 945]

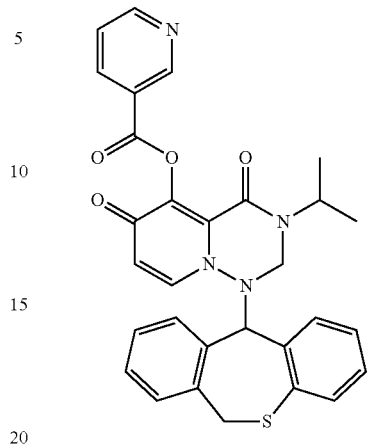

$^1$H-NMR (DMSO-$d_6$) δ: 0.94-1.02 (6H, m), 3.89 (1H, d, J=13.42 Hz), 4.29 (1H, d, J=13.57 Hz), 4.54 (1H, t, J=6.79 Hz), 5.04 (1H, d, J=13.42 Hz), 5.50 (2H, t, J=51.02 Hz), 5.91 (1H, d, J=7.78 Hz), 6.87-7.26 (5H, m), 7.42 (4H, dt, J=21.66, 7.66 Hz), 7.64-7.68 (1H, m), 8.40-8.43 (1H, m), 8.90 (1H, dd, J=4.73, 1.68 Hz), 9.20 (1H, d, J=1.68 Hz).

MS: m/z=539.00 [M+H]$^+$.

EXAMPLE 98

[Chemical formula 946]

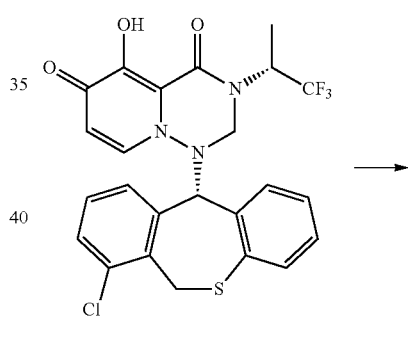

98-a

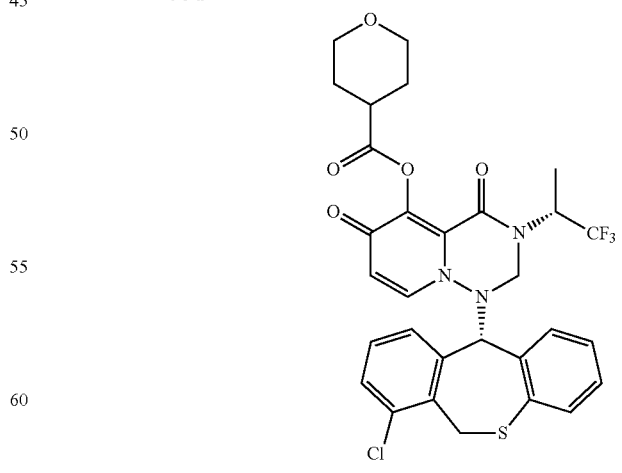

98

To a DMF (1 ml) solution of Tetrahydro-2H-pyran-4-carboxylic acid (125 mg, 0.958 mmol) and triethylamine (194 mg, 1.92 mmol) was added dropwise ethyl chloroformate (94 mg, 0.862 mmol) at room temperature. After the reaction solution was stirred at the same temperature for 5 minutes, compound 98-a (50 mg, 0.0958 mmol) was added, and the mixture was stirred for 5 hours. The reaction solution was diluted by ethyl acetate (10 ml), and water was added. The organic layer was separated, and the aqueous layer was extracted with ethyl acetate once. The extract was washed with water three times, and dried with sodium sulfate, and the solvent was distilled off. the resulting solid was washed with ethyl acetate-diisopropyl ether to obtain 30 mg of compound of Example 98.

$^1$H-NMR (CDCl$_3$) δ:1.18 (3H, d, J=7.5 Hz), 1.98-2.13 (4H, m), 2.95-3.03 (1H, m), 3.40-3.57 (2H, m), 3.95-4.14 (2H, m), 4.31 (1H, d, J=14.1 Hz), 4.45 (1H, d, J=13.2 Hz), 4.92 (1H, d, J=13.5 Hz), 5.16 (1H, s), 5.45-5.57 (1H, m), 5.60 (1H, d, J=14.1 Hz), 5.95 (1H, d, J=7.8 Hz), 6.91 (2H, brs), 7.09-7.26 (5H, m), 7.53 (1H, d, J=8.1 hz).

EXAMPLE 99

[Chemical formula 947]

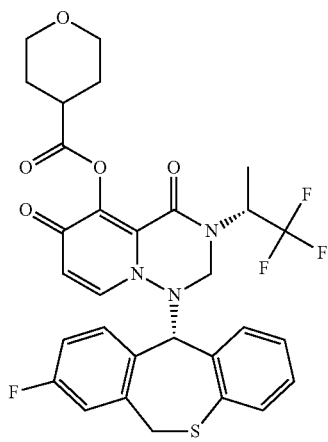

$^1$H-NMR (CDCl$_3$) δ:1.16 (3H, d, J=7.2 Hz), 1.98-2.14 (4H, m), 2.95-3.05 (1H, m), 3.49-3.57 (3H, m), 4.03-4.09 (2H, m), 4.44 (1H, d, J=13.2 Hz), 4.91 (1H, d, J=12.9 Hz), 5.13 (1H, s), 5.44-5.54 (1H, m), 5.66 (1H, d, J=13.5 Hz), 5.94 (1H, d, J=8.1 Hz), 6.91-6.99 (3H, m), 7.07-7.22 (5H, m).

EXAMPLE 100

[Chemical formula 948]

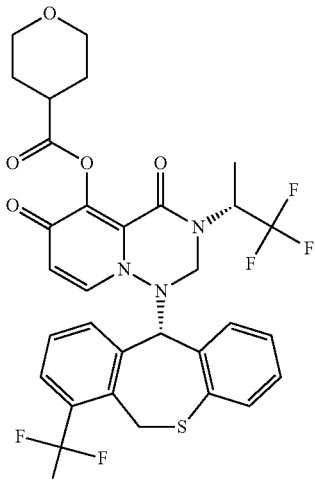

$^1$H-NMR (CDCl$_3$) δ:1.16 (3H, d, J=7.2 Hz), 2.01-2.13 (4H, m), 2.95-3.04 (1H, m), 3.49-3.57 (2H, m), 3.96-4.08 (3H, m), 4.41 (1H, d, J=13.5 Hz), 4.94 (1H, d, J=13.5 Hz), 5.26 (1H, s), 5.45-5.55 (1H, m), 5.86 (1H, d, J=14.7 Hz), 5.95 (1H, d, J=7.5 Hz), 6.91-6.93 (2H, m), 7.07-7.19 (3H, m), 7.38-7.39 (2H, m), 7.79-7.82 (1H, m).

EXAMPLE 101

[Chemical formula 949]

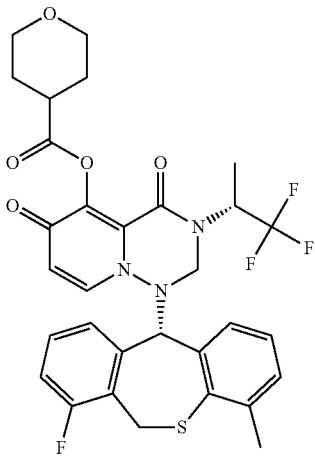

$^1$H-NMR (CDCl$_3$) δ:1.15 (3H, d, J=7.2 Hz), 1.98-2.12 (4H, m), 2.94-3.04 (1H, m), 3.48-3.56 (2H, m), 4.04-4.07 (2H, m), 4.21 (1H, d, J=13.8 Hz), 4.45 (1H, d, J=13.2 Hz), 4.92 (1H, d, J=13.2 Hz), 5.20 (1H, s), 5.37 (1H, d, J=13.5 Hz), 5.43-5.54 (1H, m), 5.93 (1H, d, J=7.8 Hz), 6.77 (1H, brs), 6.82-6.86 (1H, m), 6.97-6.99 (1H, m), 7.04 (2H, d, J=7.5 Hz), 7.17-7.25 (3H, m).

EXAMPLE 102

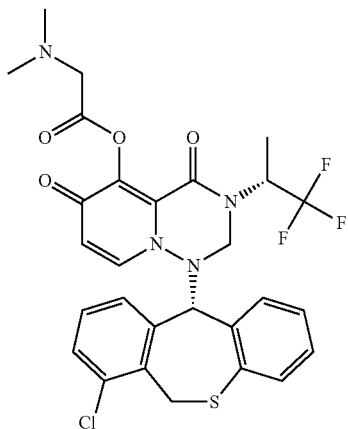

[Chemical formula 950]

$^1$H-NMR (CDCl$_3$) δ:1.19 (3H, d, J=7.2 Hz), 2.50 (6H, s), 3.55-3.68 (2H, m), 4.31 (1H, d, J=13.8 Hz), 4.44 (1H, d, J=13.2 Hz), 4.92 (1H, d, J=13.2 Hz), 5.45-5.58 (1H, m), 5.61 (1H, d, J=13.8 Hz), 5.95 (1H, d, J=7.8 Hz), 6.90 (2H, brs), 7.07-7.11 (3H, m), 7.16-7.25 (2H, m), 7.52 (2H, d, J=6.9 Hz).

EXAMPLE 103

[Chemical formula 951]

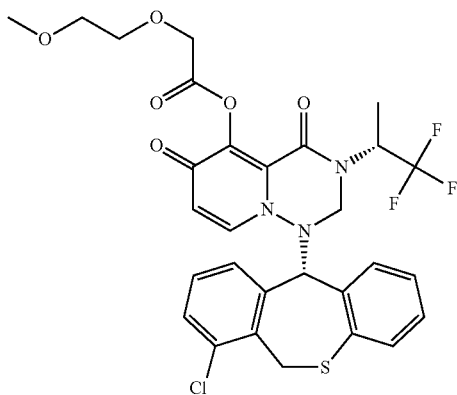

$^1$H-NMR (CDCl$_3$) δ:1.18 (3H, d, J=7.2 Hz), 2.17 (2H, s), 3.32 (3H, s), 3.63-3.66 (2H, m), 3.87-3.90 (2H, m), 4.31 (1H, d, J=13.8 Hz), 4.45 (1H, d, J=13.5 Hz), 6.60 (2H, d, J=2.1 Hz), 4.92 (1H, d, J=12.6 Hz), 5.15 (1H, s), 5.44-5.54 (1H, m), 5.60 (1H, d, J=13.8 Hz), 5.95 (1H, d, J=7.8 Hz), 6.89-6.90 (2H, m), 7.07-7.14 (3H, m), 7.16-7.25 (2H, m), 7.52 (1H, d, J=6.9 Hz).

EXAMPLE 104

[Chemical formula 952]

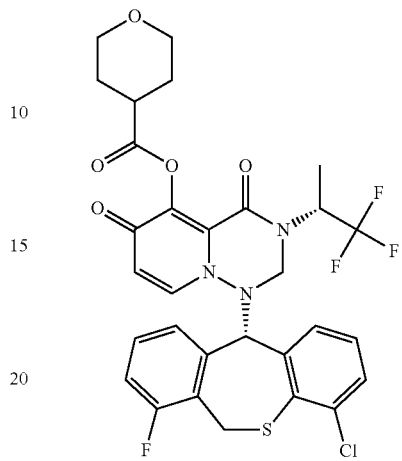

$^1$H-NMR (CDCl$_3$) δ: 1.19 (3H, d, J=7.2 Hz), 2.09 (4H, m), 3.03 (1H, dm), 3.55 (2H, m), 4.10 (2H, m), 4.26 (1H, d, J=13.6 Hz), 4.48 (1H, d, J=13.1 Hz), 4.96 (1H, d, J=12.8 Hz), 5.28 (1H, s), 5.46 (1H, d, J=13.4 Hz), 5.54 (1H, d, J=8.1 Hz), 6.03 (1H, d, J=7.9 Hz), 6.94-7.34 (7H, m).
MS: m/z=652 [M+H]$^+$.

EXAMPLE 105

[Chemical formula 953]

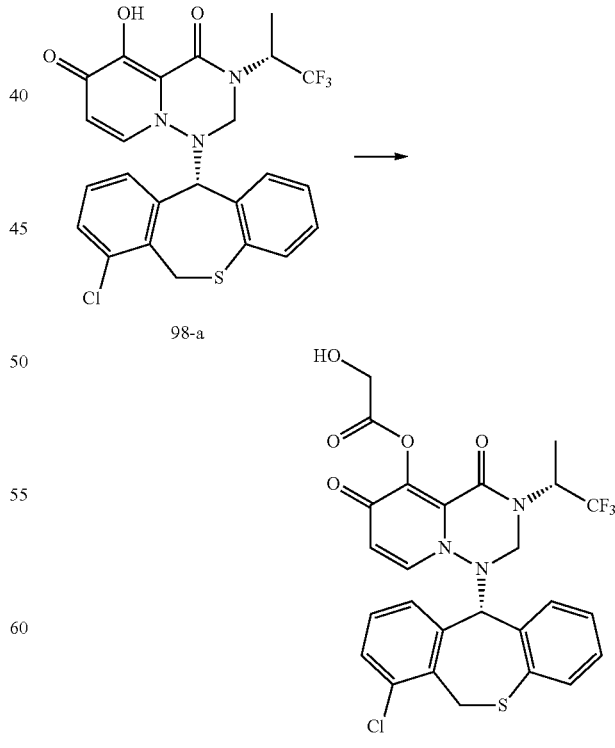

According to the method shown in Bioorganic & Medicinal Chemistry Letters; English; 14; 12; 2004; 3231-3234, ethyl chloroformate (93 mg, 0.862 mmol) was added to a DMF (1 ml) solution of 2-(tert-butyldimethylsilyloxy)acetic acid (82 mg, 0.958 mmol) and triethylamine (194 mg, 1.92 mmol) at room temperature, and the mixture was stirred at the same temperature for 3 minutes. Compound 98-a (50 mg, 0.0958 mmol) was added to the reaction solution, and the mixture was further stirred for 1 hour. The reaction solution was diluted with ethyl acetate (10 ml), and water was added. The organic layer was separated, and the aqueous layer was extracted with ethyl acetate once. The extract was washed with water three times, and dried with sodium sulfate, and the solvent was distilled off. The resulting crude product was dissolved in THF (2 ml), a 1M THF solution (0.287 ml, 0.287 mmol) of TBAF was added at room temperature, and the mixture was stirred at the same temperature for 30 minutes. Water was added to the reaction solution, followed by extraction with ethyl acetate two times. The extract was dried with sodium sulfate, and the solvent was distilled off, then the resulting solid was washed with ethyl acetate-diisopropyl ether to obtain 30 mg of compound of Example 105.

$^1$H-NMR (CDCl$_3$) δ: 1.24 (3H, d, J=7.2 Hz), 4.36 (1H, d, J=14.1 Hz), 4.52 (1H, d, J=13.2 Hz), 4.62 (1H, d, J=16.5 Hz), 4.90-4.97 (2H, m), 5.14 (1H, s), 5.51-5.62 (2H, m), 6.12 (1H, d, J=7.8 Hz), 6.68 (1H, d, J=7.2 Hz), 6.84-6.90 (1H, m), 7.10-7.18 (3H, m), 7.20-7.24 (1H, m), 7.37 (1H, d, J=7.8 Hz), 7.55 (1H, d, J=6.9 Hz).

EXAMPLE 106

[Chemical formula 954]

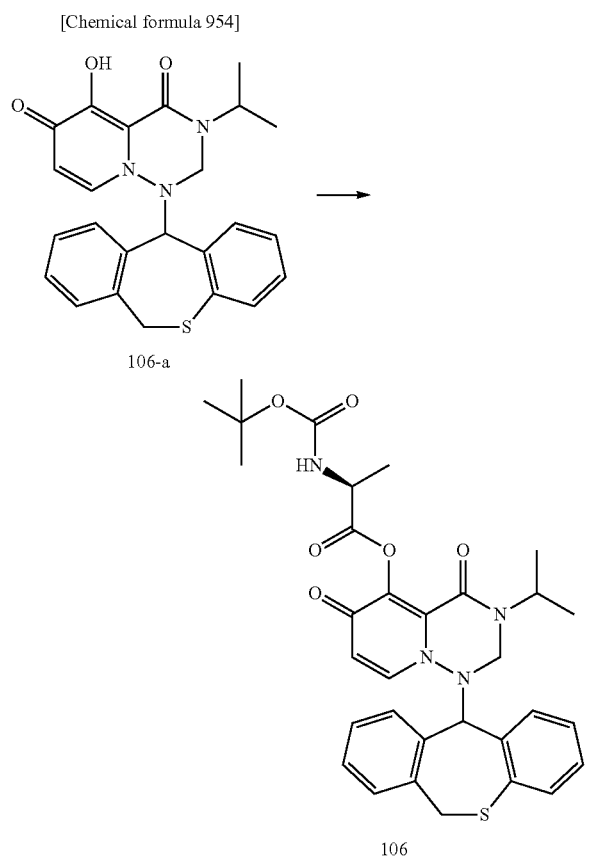

(S)-2-(tert-butoxycarbonylamino)propanoic acid (301 mg, 1.59 mmol) was dissolved in THF (2 ml), N-methylmorpholine (0.175 ml, 1.59 mmol) and isobutyl chloroformate (0.209 ml, 1.59 mmol) were added at 0° C., and the mixture was stirred for 15 minutes. A dichloromethane solution (1 ml) of 106-a (69.0 mg, 0.159 mmol) synthesized according to Example was added at 0° C., and the mixture was stirred at room temperature for 4 hours. To the reaction solution was added water, the mixture was extracted with ethyl acetate, and the organic layer was dried with sodium sulfate. The solvent was distilled off under reduced pressure, and the resulting crude product was purified by silica gel column chromatography, and eluted with chloroform-methanol (97:3, v/v). The resulting product was solidified by adding dichloromethane-diisopropyl ether-diethyl ether to obtain 40 mg of compound of Example 106 as a white solid.

EXAMPLE 107

[Chemical formula 955]

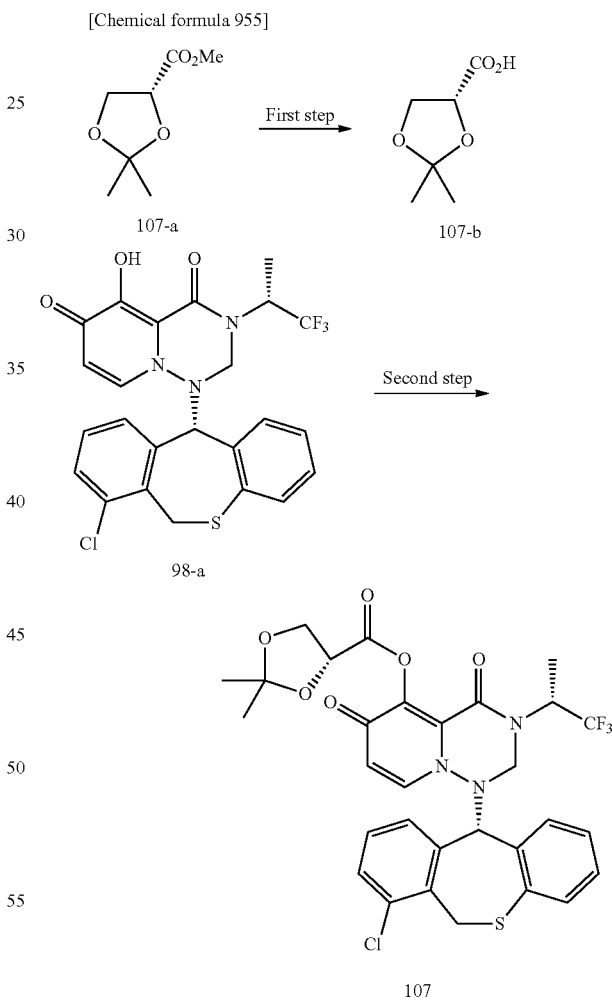

First Step

To a methanol (80 mL) solution of (R)-methyl 2,2-dimethyl-1,3-dioxolane-4-carboxylate (107-a, 11.22 g, 70.1 mmol) was added sodium hydroxide monohydrate (2.94 g, 70.1 mmol) at room temperature, and the mixture was stirred for 3 hours. The solvent was distilled off under reduced pressure, to the resulting residue was added 2N hydrochloric acid (35 mL) under ice-cooling, and the mixture was extracted with chloromethane (100 mL×2). The organic layer was washed with water (50 mL), and dried with magnesium sulfate. The solvent was distilled off under reduced pressure, and the resulting crude product of compound 107-b was used in a next reaction without purification.

Second Step

To a dichloromethane (2 mL) solution of compound 98-a (41.7 mg, 0.285 mmol), triethylamine (0.106 mL, 0.765 mmol) and 4-dimethylaminopyridine (5.7 mg, 0.047 mmol) was added 2-methyl-6-nitrobenzoic anhydride (100 mg, 0.290 mmol) at room temperature, and the mixture was stirred for 10 minutes. Compound 5C (51.7 mg, 0.099 mmol) was added to the reaction solution, and the mixture was stirred for 1.5 hours. To the reaction solution was added water (2 mL), then the mixture was extracted with dichloromethane, and the organic layer was dried with sodium sulfate. The solvent was distilled off under reduced pressure, and the resulting residue was purified by silica gel column chromatography (ethyl acetate/n-hexane=60%→100%) to obtain compound of Example 107 (40.4 mg, 63%) as a white solid.

MS: m/z=650.35 [M+H]$^+$.

EXAMPLE 108

[Chemical formula 956]

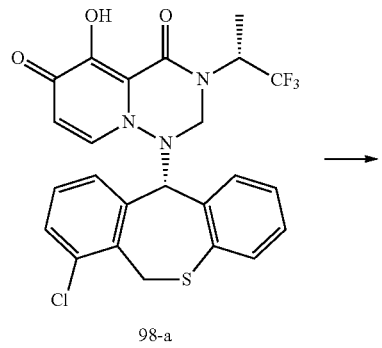

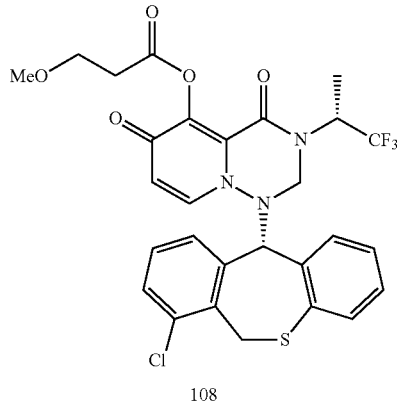

First Step

To a dichloromethane (1 mL) solution of compound 98-a (50.0 mg, 0.096 mmol), triethylamine (0.0660 mL, 0.476 mmol) and N-methylimidazole (0.0038 mL, 0.048 mmol) was added 3-methoxypropionyl chloride (33.0 mg, 0.269 mmol) at room temperature, and the mixture was stirred for 16 hours. To the reaction solution were added water (1 mL) and hydrochloric acid (2M, 1 mL), the mixture was extracted with dichloromethane, and the organic layer was dried with sodium sulfate. The solvent was distilled off under reduced pressure, the resulting residue was purified by silica gel column chromatography (ethyl acetate/n-hexane=60%→100%), and the resulting product was converted into a powder with ethyl acetate-isopropyl ether to obtain compound of Example 108 (47.0 mg, 81%) as a white solid.

$^1$H-NMR (CDCl$_3$) δ: 1.18 (3H, d, J=7.2 Hz), 3.03 (2H, t, J=6.9 Hz), 3.43 (3H, s), 3.85 (2H, m), 4.31 (1H, d, J=13.7 Hz), 4.45 (1H, d, J=13.2 Hz), 4.92 (1H, d, J=13.2 Hz), 5.16 (1H, s), 5.52 (1H, m), 5.60 (1H, d, J=13.7 Hz), 5.96 (1H, d, J=8.1 Hz), 6.90 (2H, m), 7.10-7.23 (5H, m), 7.53 (1H, d, J=8.1 Hz).

MS: m/z=608.20 [M]$^+$.

EXAMPLE 109

[Chemical formula 957]

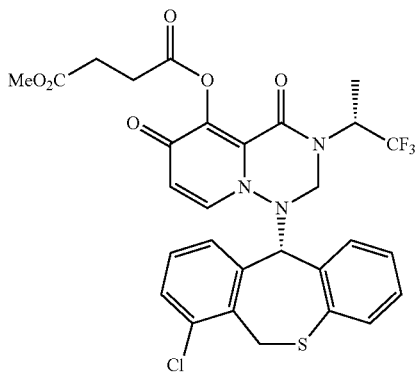

According to Example 108, compound of Example 109 was synthesized by the same procedure.

$^1$H-NMR (CDCl$_3$) δ: 1.18 (3H, d, J=7.5 Hz), 2.83 (2H, t, J=7.4 Hz), 3.10 (2H, t, J=7.4 Hz), 3.74 (3H, s), 4.31 (1H, d, J=13.8 Hz), 4.45 (1H, d, J=13.2 Hz), 4.92 (1H, d, J=13.2 Hz), 5.15 (1H, s), 5.50 (1H, m), 5.60 (1H, d, J=13.8 Hz), 5.96 (1H, d, J=8.1 Hz), 6.91 (2H, m), 7.10-7.23 (5H, m), 7.53 (1H, d, J=8.1 Hz).

MS: m/z=636.15 [M]$^+$.

EXAMPLE 110

[Chemical formula 958]

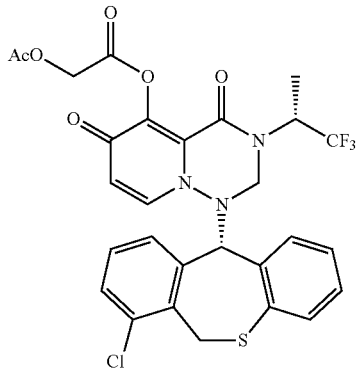

According to Example 108, compound of Example 110 was synthesized by the same procedure.

¹H-NMR (CDCl₃) δ: 1.18 (3H, d, J=7.2 Hz), 2.22 (3H, s), 4.31 (1H, d, J=13.8 Hz), 4.46 (1H, d, J=13.4 Hz), 4.92 (1H, d, J=13.4 Hz), 5.05 (1H, d, J=16.5 Hz), 5.15 (1H, d, J=16.5 Hz), 5.15 (1H, s), 5.54 (1H, m), 5.60 (1H, d, J=13.8 Hz), 5.97 (1H, d, J=8.1 Hz), 6.82-6.94 (2H, m), 7.09-7.23 (5H, m), 7.54 (1H, d, J=8.1 Hz).

MS: m/z=622.15 [M]⁺.

EXAMPLE 111

[Chemical formula 959]

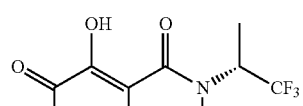

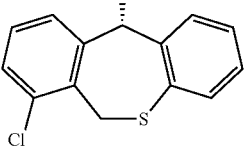

98-a

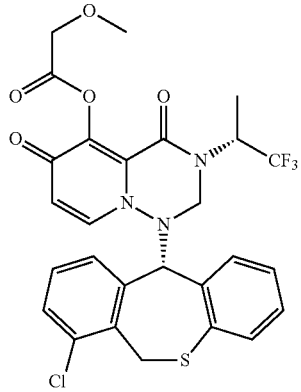

111

A dichloromethane (1.0 mL) solution of compound 98-a (50 mg, 0.10 mmol) was ice-cooled, triethylamine (0.040 ml, 0.29 mmol) and 2-methoxyacetyl chloride (11 mg, 0.11 mmol) were added, and the mixture was stirred for 1 hour under ice-cooling, then stirred at room temperature for 2 hours. Thereafter, to the reaction solution was added ethyl acetate, the mixture was washed with water, and sodium sulfide was added to dry it. The solvent was distilled off, and a solid of the resulting oil was precipitated by using ethyl acetate to obtain 31 mg of compound of Example 111 as a white solid.

¹H-NMR (CDCl₃) δ: 1.19 (3H, d, 7.1 Hz), 3.59 (3H, s), 4.31 (1H, d, J=13.9 Hz), 4.41-4.54 (3H, m), 4.93 (1H, d, J=13.3 Hz), 5.16 (1H, s), 5.46-5.63 (2H, m), 5.97 (1H, d, J=7.9 Hz), 6.90 (2H, brs), 7.09-7.24 (5H, m), 7.53 (1H, d, J=7.4 Hz).

MS: m/z=594 [M+H]⁺.

EXAMPLE 112

[Chemical formula 960]

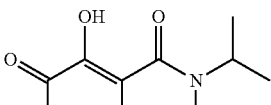

106-a

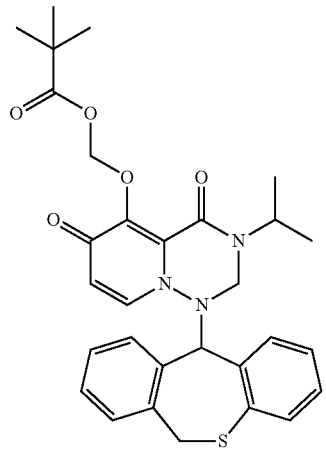

112

First Step

An acetonitrile (2 ml) solution of compound 106-a (100 mg, 0.231 mmol), chloromethyl pivalate (482 mg, 3.20 mmol) and sodium iodide (480 mg, 3.20 mmol) was stirred at 80° C. for 6 hours. After cooled to room temperature, water was added, and the mixture was extracted with ethyl acetate three times. The combined extracts were dried with sodium sulfate, and the solvent was distilled off. The resulting oil was purified by silica gel column chromatography. The materials were eluted firstly with ethyl acetate and, then, with ethyl acetate-methanol (7:3, v/v). Concentration of an objective fraction afforded 35 mg of compound of Example 112 as a solid.

¹H-NMR (CDCl₃) δ: 1.06 (3H, d, J=16.2 Hz), 10.9 (3H, d, J=9.3 Hz), 1.26 (9H, s), 3.58 (1H, d, J=13.2 Hz), 4.29 (1H, d, J=13.2 Hz), 4.73-4.82 (1H, m), 4.77 (1H, d, J=12.9 Hz), 5.10 (1H, s), 5.68 (2H, d, J=13.2 Hz), 5.88-5.93 (3H, m), 6.86-6.88 (2H, m), 7.04-7.10 (2H, m), 7.15-7.27 (3H, m), 7.32-7.42 (2H, m).

EXAMPLE 113

[Chemical formula 961]

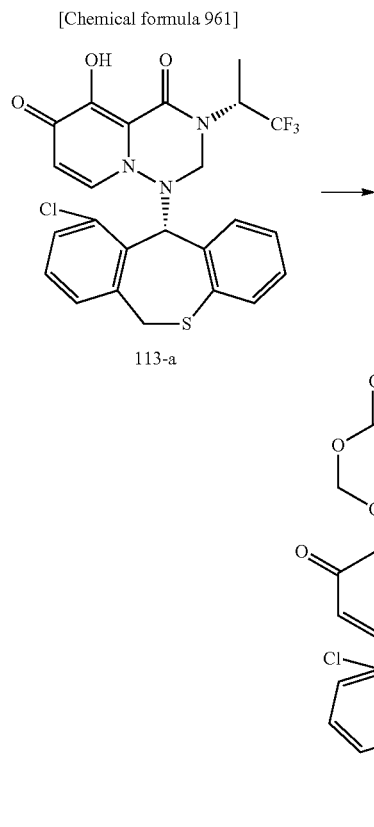

To an aqueous (0.5 mL) suspension of compound 113-a (50 mg, 0.10 mmol) and potassium carbonate (40 mg, 0.29 mmol) were added tetrabutylammonium hydrogen sulfate (33 mg, 0.10 mmol) and dichloromethane (1.0 ml), and the mixture was stirred at room temperature for 10 minutes. To the reaction solution was added a dichloromethane (1.0 ml) solution of iodomethyl acetate (56 mg, 0.19 mmol), and the mixture was further stirred for 2 hours. Thereafter, to the reaction solution was added water, the dichloromethane layer was separated, and the aqueous layer was extracted with dichloromethane once. The combined extracts were washed with an aqueous saturated sodium chloride solution and brine, and then sodium sulfide was added to dry them. The solvent was distilled off, and the resulting oil was purified by silica gel column chromatography. The materials were eluted firstly with chloroform and, then, with chloroform-methanol (94:6, v/v). An objective fraction was concentrated, and solidified by adding diisopropyl ether to obtain 41 mg of compound of Example 113 as a white solid.

$^1$H-NMR (DMSO-d6) δ: 0.98 (3H, d, J=7.2 Hz), 2.02 (3H, s), 3.98 (1H, d, J=7.2 Hz), 4.48 (1H, d, J=7.2 Hz), 5.05 (1H, d, J=7.2 Hz), 5.42-5.49 (1H, m), 5.61 (1H, d, J=7.2 Hz), 5.66-5.77 (3H, m), 5.87 (1H, d, J=7.2 Hz), 6.86-6.95 (2H, m), 7.16-7.20 (3H, m), 7.45-7.52 (3H, m).

MS: m/z=594 [M+H]$^+$.

According to Example 113, the following compounds were synthesized by the same procedure.

EXAMPLE 114

[Chemical formula 962]

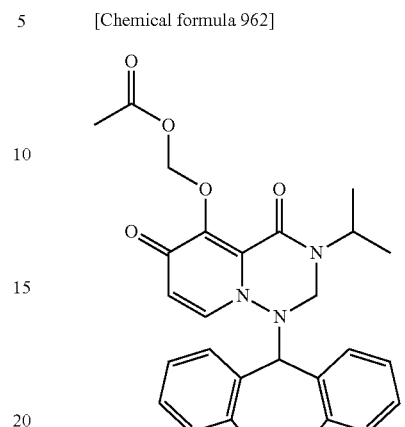

$^1$H-NMR (CDCl$_3$) δ: 1.07 (3H, d, J=6.6 Hz), 1.09 (3H, d, J=6.6 Hz), 2.15 (3H, s), 7.58 (1H, d, J=13.5 Hz), 4.30 (1H, d, J=12.9 Hz), 4.75-4.83 (1H, m), 4.77 (1H, d, J=12.9 Hz), 5.12 (1H, s), 5.69 (d, J=13.5 Hz), 5.82-5.92 (3H, m), 6.84-6.91 (2H, m), 7.04-7.08 (2H, m), 7.20-7.28 (3H, m), 7.32-7.42 (2H, m).

EXAMPLE 115

[Chemical formula 963]

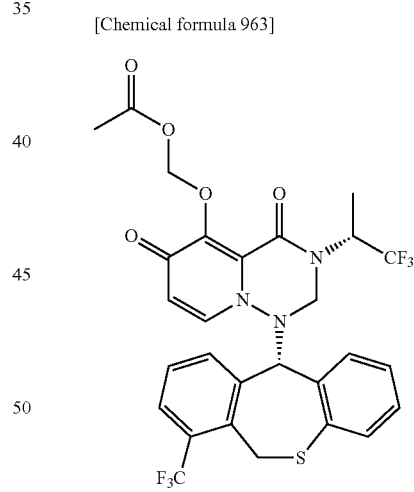

$^1$H-NMR (CDCl$_3$) δ: 1.17 (3H, d, J=7.3 Hz), 2.12 (3H, s), 3.90 (1H, d, J=14.7 Hz), 4.38 (1H, d, J=13.3 Hz), 4.91 (1H, d, J=13.3 Hz), 5.23 (1H, s), 5.57 (1H, m), 5.86 (1H, d, J=6.4 Hz), 5.86 (1H, d, J=14.7 Hz), 5.94 (1H, d, J=7.8 Hz), 6.84 (1H, dd, J=1.2, 7.9 Hz), 6.91 (1H, dt, J=1.7, 6.8 Hz), 7.09 (1H, dd, J=1.4, 7.6 Hz), 7.12 (1H, dd, J=1.4, 6.6 Hz), 7.16 (1H, d, J=7.8 Hz), 7.6-7.42 (2H, m), 7.81 (1H, dd, J=2.1, 6.8 Hz).

MS: m/z=628 [M+H]$^+$.

EXAMPLE 116
[Chemical formula 964]
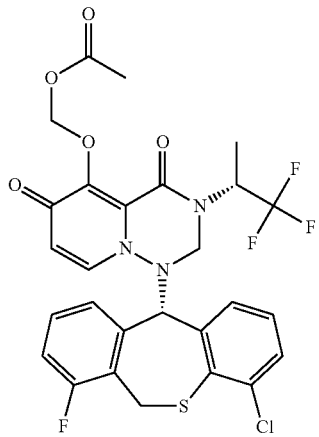
¹H-NMR (CDCl₃) δ: 1.19 (3H, d, J=7.2 Hz), 2.15 (3H, s), 4.26 (1H, d, J=13.9 Hz), 4.45 (1H, d, J=12.9 Hz), 4.92 (1H, d, J=13.3 Hz), 5.24 (1H, s), 5.45 (1H, dd, J=13.8, 1.9 Hz), 5.53-5.63 (1H, m), 5.89 (1H, d, J=6.4 Hz), 5.95 (1H, d, J=6.4 Hz), 6.01 (1H, d, J=7.7 Hz), 6.84-7.34 (7H, m).
MS: m/z=612 [M+H]⁺.
EXAMPLE 117
[Chemical formula 965]
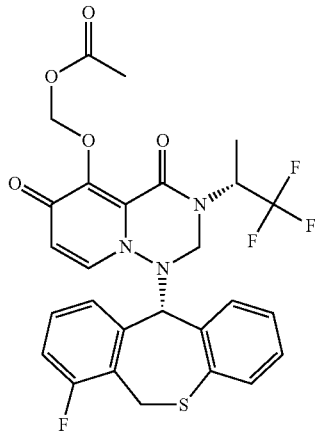
¹H-NMR (CDCl₃) δ: 1.17 (3H, d, J=7.2 Hz), 2.10 (3H, s), 4.11 (1H, d, J=13.6 Hz), 4.42 (1H, d, J=13.1 Hz), 4.89 (1H, d, J=13.0 Hz), 5.13 (1H, s), 5.33 (1H, dd, J=13.6, 2.2 Hz), 5.55 (1H, m), 5.84-5.94 (3H, m), 6.81-7.25 (8H, m).
EXAMPLE 118
[Chemical formula 966]
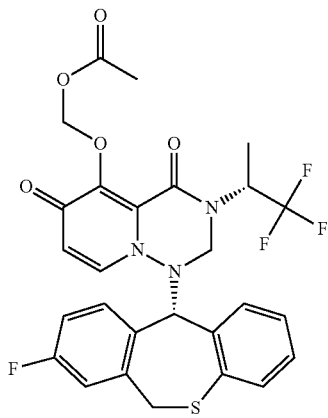
¹H-NMR (CDCl₃) δ: 1.18 (3H, d, J=7.3 Hz), 2.11 (3H, s), 3.56 (1H, d, J=13.6 Hz), 4.42 (1H, d, J=13.0 Hz), 4.88 (1H, d, J=13.4 Hz), 5.10 (1H, s), 5.55 (1H, m), 5.67 (1H, d, J=13.4 Hz), 5.85-5.94 (3H, m), 6.81-7.26 (8H, m).
MS: m/z=578 [M+H]⁺.
EXAMPLE 119
[Chemical formula 967]
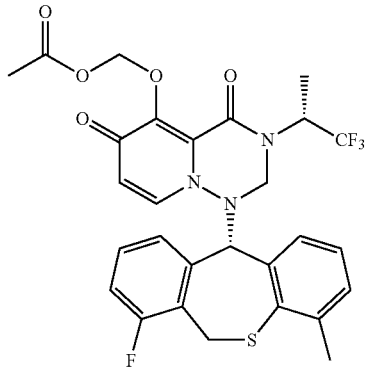
MS: m/z=592 [M+H]⁺.

EXAMPLE 120

[Chemical formula 968]

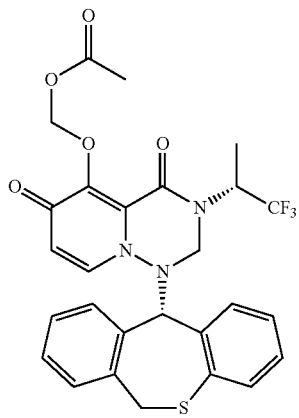

$^1$H-NMR (CDCl$_3$) δ: 1.13 (3H, d, 6.1 Hz), 2.10 (3H, s), 3.60 (1H, d, 13.4 Hz), 4.42 (1H, d, J=13.0 Hz), 4.87 (1H, d, J=13.1 Hz), 5.07 (1H, s), 5.48-5.64 (2H, m), 5.85-5.97 (3H, m), 6.80-6.89 (2H, m), 7.05-7.44 (7H, m).

MS: m/z=560 [M+H]$^+$.

EXAMPLE 121

[Chemical formula 969]

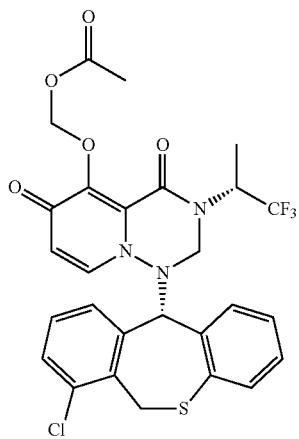

$^1$H-NMR (CDCl$_3$) δ: 1.18 (3H, d, 7.3 Hz), 2.10 (3H, s), 4.31 (1H, d, 13.9 Hz), 4.42 (1H, d, J=13.3 Hz), 4.88 (1H, d, J=12.8 Hz), 5.12 (1H, s), 5.50-5.62 (2H, m), 5.84-5.94 (3H, m), 6.80-6.91 (2H, m), 7.07-7.22 (5H, m), 7.52 (1H, d, J=7.6 Hz).

MS: m/z=594 [M+H]$^+$.

EXAMPLE 122

[Chemical formula 970]

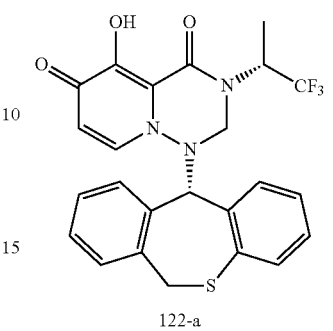

122-a

→

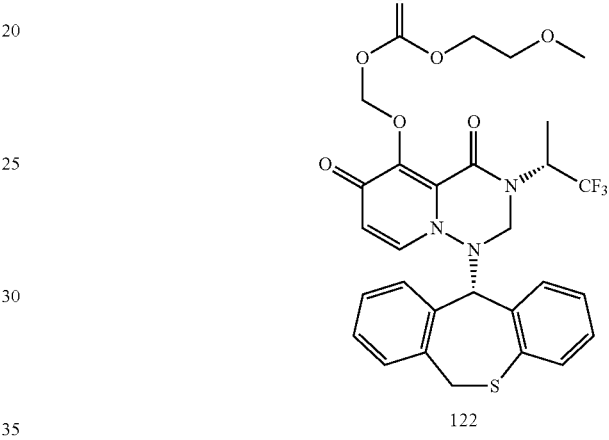

122

To an aqueous (1.0 mL) suspension of compound 122-a (50 mg, 0.10 mmol) and potassium carbonate (138 mg, 0.22 mmol) were added tetrabutylammonium hydrogen sulfate (34 mg, 0.10 mmol) and dichloromethane (0.5 ml), and the mixture was stirred at room temperature for 10 minutes. To the reaction solution was added a dichloromethane (0.5 ml) solution of iodomethyl 2-methoxyethyl carbonate (57 mg, 0.22 mmol), and the mixture was further stirred for 2 hours. Thereafter, to the reaction solution was added water, the dichloromethane layer was separated, and the aqueous layer was extracted with dichloromethane once. The combined extracts were washed with an aqueous saturated sodium chloride solution and brine, and then sodium sulfide was added to dry them. The solvent was distilled off, and the resulting oil was purified by silica gel column chromatography. The materials were eluted firstly with chloroform and, then, with chloroform-methanol (94:6, v/v). An objective fraction was concentrated, and washed using hexane-diethyl ether to obtain 39 mg of compound of Example 122 as a white solid.

$^1$H-NMR (CDCl$_3$) δ: 1.15 (3H, d, J=7.2 Hz), 3.38 (3H, s), 3.58-3.69 (3H, m), 4.28-4.44 (3H, m), 4.87 (1H, d, J=13.0 Hz), 5.09 (1H, s), 5.51-5.66 (2H, m), 5.90-5.96 (3H, m), 6.84-7.44 (9H, m).

MS: m/z=620 [M+H]$^+$.

EXAMPLE 123

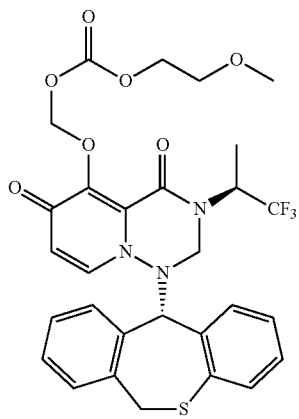

According to Example 122, compound of Example 123 was synthesized by the same procedure.

$^1$H-NMR (CDCl$_3$) δ: 1.32 (3H, d, J=7.3 Hz), 3.39 (3H, s), 3.59 (1H, d, J=13.3 Hz), 3.68-3.71 (2H, m), 4.39 (2H, dt, J=7.22, 2.14 Hz), 4.53 (1H, d, J=12.7 Hz), 4.92 (1H, d, J=12.7 Hz), 5.23-5.36 (2H, m), 5.67 (1H, d, J=13.2 Hz), 5.84 (1H, d, J=6.4 Hz), 5.92 (1H, d, J=6.5 Hz), 5.95 (1H, d, J=7.8 Hz), 6.83-7.41 (9H, m).

MS: m/z=620 [M+H]$^+$.

EXAMPLE 124

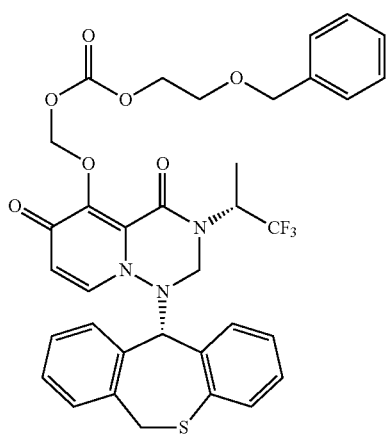

According to Example 122, compound of Example 124 was synthesized by the same procedure.

$^1$H-NMR (CDCl$_3$) δ: 1.10 (3H, d, J=7.3 Hz), 3.60 (1H, d, J=13.4 Hz), 3.75 (2H, t, J=4.4 Hz), 4.33-4.42 (3H, m), 4.57 (2H, s), 4.85 (1H, d, J=13.6 Hz), 5.07 (1H, s), 5.46-5.64 (2H, m), 5.90-5.96 (3H, m), 6.82-6.88 (2H, m), 7.06-7.43 (12H, m).

MS: m/z=696 [M+H]$^+$.

EXAMPLE 125

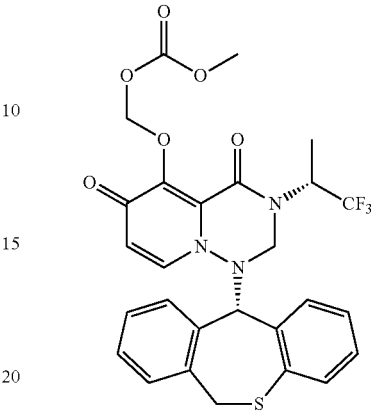

According to Example 122, compound of Example 125 was synthesized by the same procedure.

$^1$H-NMR (CDCl$_3$) δ: 1.14 (3H, d, J=7.2 Hz), 3.61 (1H, d, J=13.4 Hz), 3.83 (3H, s), 4.42 (1H, d, J=13.2 Hz), 4.87 (1H, d, J=13.0 Hz), 5.08 (1H, s), 5.48-5.65 (2H, m), 5.87 (1H, d, J=6.5 Hz), 5.94 (1H, d, J=6.2 Hz), 5.96 (1H, d, J=4.8 Hz), 6.79-6.85 (2H, m), 7.05-7.44 (7H, m).

MS: m/z=576 [M+H]$^+$.

EXAMPLE 126

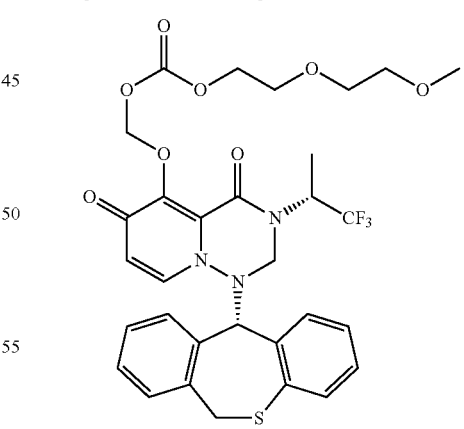

According to Example 122, compound of Example 126 was synthesized by the same procedure.

$^1$H-NMR (CDCl$_3$) δ: 1.13 (3H, d, 6.0 Hz), 3.36 (3H, s), 3.52-3.79 (7H, m), 4.31-4.44 (3H, m), 4.87 (1H, d, J=13.0 Hz), 5.09 (1H, s), 5.50-5.73 (2H, m), 5.89-5.98 (3H, m), 6.81-6.88 (2H, m), 7.05-7.45 (7H, m).

MS: m/z=664 [M+H]$^+$.

EXAMPLE 127

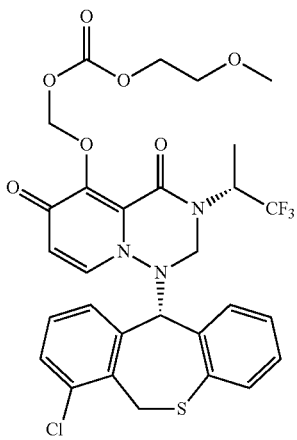

According to Example 122, compound of Example 127 was synthesized by the same procedure.

$^1$H-NMR (CDCl$_3$) δ: 1.19 (3H, d, 7.2 Hz), 3.37 (1H, s), 3.62-3.69 (2H, m), 4.29-4.43 (4H, m), 4.88 (1H, d, J=13.6 Hz), 5.14 (1H, s), 5.50-5.63 (2H, m), 5.90-5.96 (3H, m), 6.82-6.89 (2H, m), 7.05-7.24 (5H, m), 7.52 (1H, d, J=7.9 Hz).

MS: m/z=654 [M+H]$^+$.

EXAMPLE 128

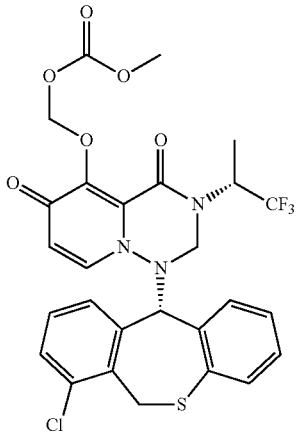

According to Example 122, compound of Example 128 was synthesized by the same procedure.

$^1$H-NMR (CDCl$_3$) δ: 1.19 (3H, d, 7.2 Hz), 3.83 (3H, s), 4.31 (1H, d, J=13.9 Hz), 4.42 (1H, d, J=13.1 Hz), 4.89 (1H, d, J=13.4 Hz), 5.12 (1H, s), 5.49-5.61 (2H, m), 5.87 (1H, d, J=6.5 Hz), 5.93-5.97 (2H, m), 6.77-6.89 (2H, m), 7.09-7.24 (5H, m), 7.52 (1H, d, J=8.2 Hz).

MS: m/z=610 [M+H]$^+$.

EXAMPLE 129

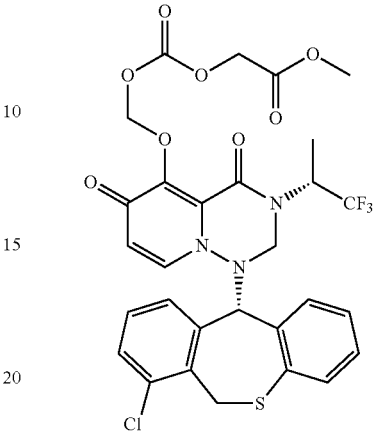

According to Example 122, compound of Example 129 was synthesized by the same procedure.

$^1$H-NMR (CDCl$_3$) δ: 1.21 (3H, d, 7.3 Hz), 3.77 (3H, s), 4.31 (1H, d, J=14.0 Hz), 4.43 (1H, d, J=13.3 Hz), 4.60-4.70 (2H, m), 4.85-4.93 (2H, m), 5.31 (1H, s), 5.56-5.66 (2H, m), 5.93-6.01 (3H, m), 6.86-6.92 (2H, m), 7.08-7.51 (5H, m), 7.52 (1H, d, J=7.8 Hz).

MS: m/z=668 [M+H]$^+$.

EXAMPLE 130

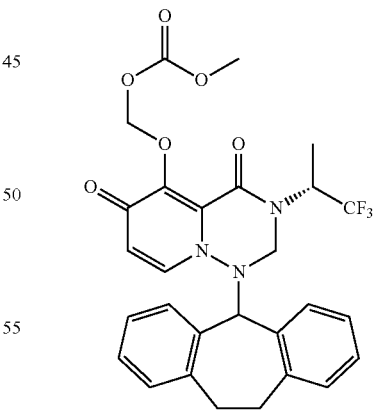

According to Example 122, compound of Example 130 was synthesized by the same procedure.

$^1$H-NMR (CDCl$_3$) δ: 1.16-1.37 (3H, m), 2.77-2.87 (1H, m), 3.04-3.15 (1H, m), 3.41-3.53 (1H, m), 3.83-3.89 (3H, m), 4.24-4.42 (2H, m), 4.70-4.82 (1H, m), 5.02-5.45 (2H, m), 5.82-5.99 (3H, m), 6.72-7.35 (9H, m).

MS: m/z=558 [M+H]$^+$.

EXAMPLE 131

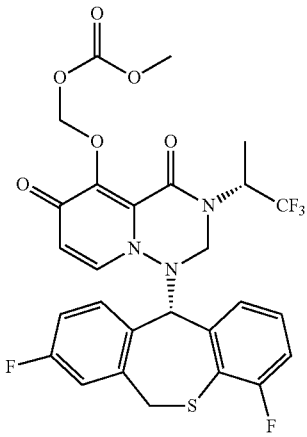

[Chemical formula 979]

According to Example 122, compound of Example 131 was synthesized by the same procedure.

$^1$H-NMR (CDCl$_3$) δ: 1.17 (3H, d, 7.2 Hz), 3.65 (1H, d, J=13.4 Hz), 3.83 (3H, s), 4.41 (1H, d, 13.3 Hz), 4.88 (1H, d, J=13.4 Hz), 5.17 (1H, s), 5.47-5.57 (1H, m), 5.68 (1H, d, J=13.4 Hz), 5.87 (1H, d, J=6.6 Hz), 5.95-6.00 (2H, m), 6.65 (1H, d, J=7.3 Hz), 6.83-6.99 (3H, m), 7.01-7.20 (3H, m).

MS: m/z=612 [M+H]$^+$.

EXAMPLE 132

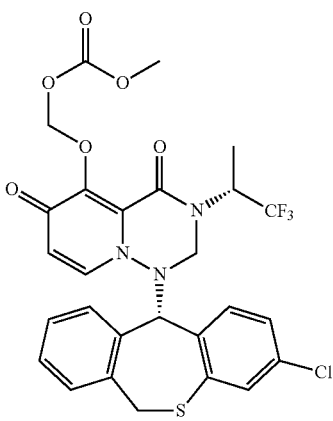

[Chemical formula 980]

According to Example 122, compound of Example 132 was synthesized by the same procedure.

$^1$H-NMR (CDCl$_3$) δ: 1.12 (3H, d, 7.2 Hz), 3.62 (1H, d, J=13.3 Hz), 3.83 (3H, s), 4.40 (1H, d, 12.9 Hz), 4.86 (1H, d, J=12.7 Hz), 5.06 (1H, s), 5.48-5.62 (2H, m), 5.88 (1H, d, J=6.5 Hz), 5.97 (1H, d, J=6.6 Hz), 6.02 (1H, d, J=7.8 Hz), 6.75-6.85 (2H, m), 7.08-7.43 (6H, m).

MS: m/z=610 [M+H]$^+$.

EXAMPLE 133

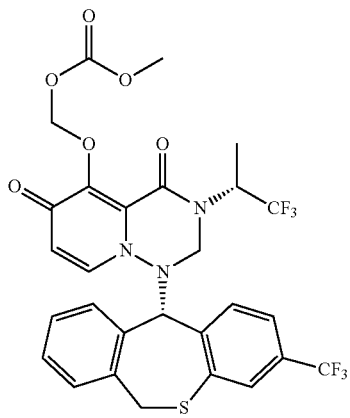

[Chemical formula 981]

According to Example 122, compound of Example 133 was synthesized by the same procedure.

$^1$H-NMR (CDCl$_3$) δ: 1.11 (3H, d, 7.1 Hz), 3.68 (1H, d, J=13.4 Hz), 3.84 (3H, s), 4.43 (1H, d, 13.5 Hz), 4.88 (1H, d, J=12.8 Hz), 5.16 (1H, s), 5.47-5.64 (2H, m), 5.90 (1H, d, J=6.4 Hz), 5.95-5.99 (2H, m), 7.00 (1H, d, J=7.7 Hz), 7.11-7.49 (8H, m).

MS: m/z=644 [M+H]$^+$.

EXAMPLE 134

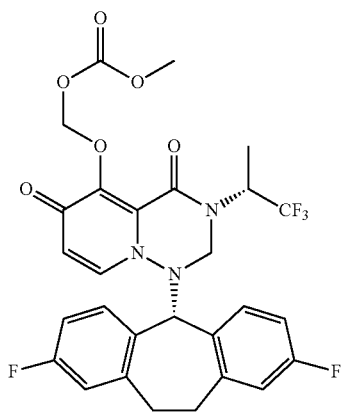

[Chemical formula 982]

According to Example 122, compound of Example 134 was synthesized by the same procedure.

$^1$H-NMR (CDCl$_3$) δ: 1.19-1.35 (3H, m), 2.77-2.89 (1H, m), 3.04-3.14 (1H, m), 3.37-3.51 (1H, m), 3.83-3.89 (3H, m), 4.27-4.41 (2H, m), 4.71-4.82 (1H, m), 5.03-5.52 (2H, m), 5.89-6.00 (3H, m), 6.68-7.19 (7H, m).

MS: m/z=594 [M+H]$^+$.

EXAMPLE 135

[Chemical formula 983]

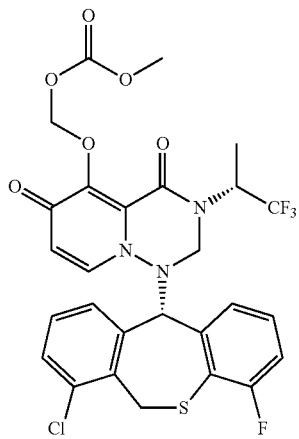

According to Example 122, compound of Example 135 was synthesized by the same procedure.

$^1$H-NMR (CDCl$_3$) δ: 1.18 (3H, d, 7.4 Hz), 3.83 (3H, s), 4.37-4.43 (2H, m), 4.89 (1H, d, J=12.9 Hz), 5.19 (1H, s), 5.49-5.64 (2H, m), 5.87 (1H, d, J=6.5 Hz), 5.95-6.00 (2H, m), 6.65 (1H, d, J=7.3 Hz), 7.07-7.25 (4H, m), 7.54 (1H, d, J=7.0 Hz).

MS: m/z=628 [M+H]$^+$.

EXAMPLE 136

[Chemical formula 984]

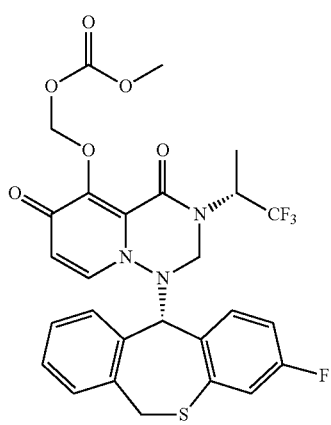

According to Example 122, compound of Example 136 was synthesized by the same procedure.

$^1$H-NMR (CDCl$_3$) δ: 1.13 (3H, d, 7.0 Hz), 3.61 (1H, d, J=13.7 Hz), 3.83 (3H, s), 4.40 (1H, d, J=13.0 Hz), 4.86 (1H, d, J=13.5 Hz), 5.08 (1H, s), 5.49-5.65 (2H, m), 5.88 (1H, d, J=6.5 Hz), 5.95-6.02 (2H, m), 6.53-6.60 (1H, m), 6.79-6.84 (2H, m), 7.14-7.43 (5H, m).

MS: m/z=594 [M+H]$^+$.

EXAMPLE 137

[Chemical formula 985]

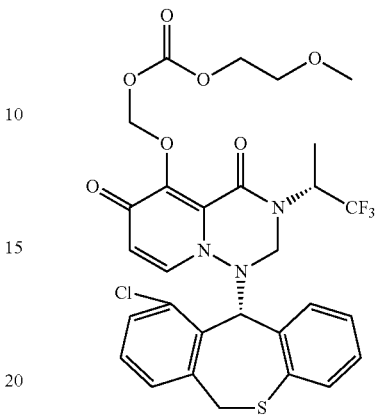

According to Example 122, compound of Example 137 was synthesized by the same procedure.

$^1$H-NMR (CDCl$_3$) δ: 1.08 (3H, d, 7.2 Hz), 3.38 (3H, s), 3.60-3.68 (3H, m), 4.28-4.39 (3H, m), 4.85 (1H, d, J=13.0 Hz), 5.48-5.57 (1H, m), 5.65 (1H, d, J=13.6 Hz), 5.87-5.98 (4H, m), 6.87-6.96 (2H, m), 7.07-7.17 (3H, m), 7.25-7.34 (3H, m).

MS: m/z=654 [M+H]$^+$.

EXAMPLE 138

[Chemical formula 986]

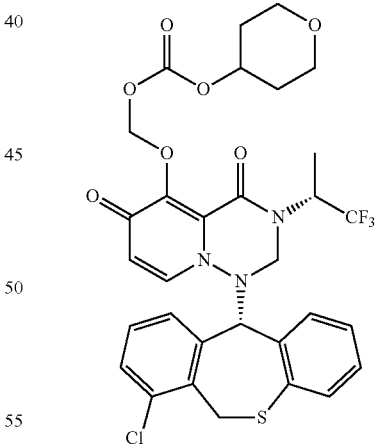

According to Example 122, compound of Example 138 was synthesized by the same procedure.

$^1$H-NMR (CDCl$_3$) δ: 1.18 (3H, d, 7.4 Hz), 1.81 (2H, brs), 2.02 (2H, brs), 3.54-3.62 (2H, m), 3.91-3.99 (3H, m), 4.31 (1H, d, J=13.7 Hz), 4.42 (1H, d, J=12.9 Hz), 4.86-4.92 (2H, m), 5.11 (1H, s), 5.45-5.61 (2H, m), 5.90-5.95 (3H, m), 6.71-6.87 (2H, m), 7.03-7.25 (5H, m), 7.52 (1H, d, J=6.9 Hz).

MS: m/z=680 [M+H]$^+$.

EXAMPLE 139

[Chemical formula 987]

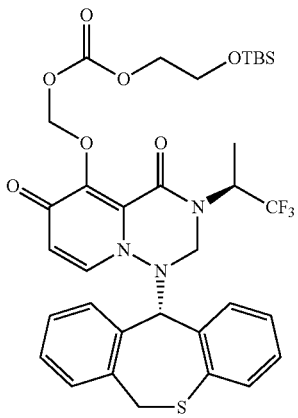

According to Example 122, compound of Example 139 was synthesized by the same procedure.
MS: m/z=720 [M+H]⁺.

EXAMPLE 140

[Chemical formula 988]

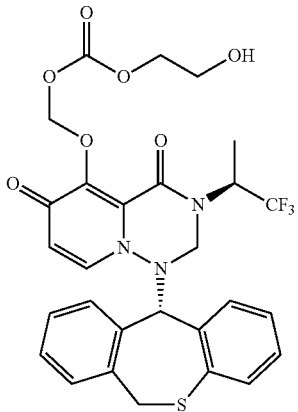

Compound of Example 140 was obtained as a by-product of Example 139.
MS: m/z=606 [M+H]⁺.

EXAMPLE 141

[Chemical formula 989]

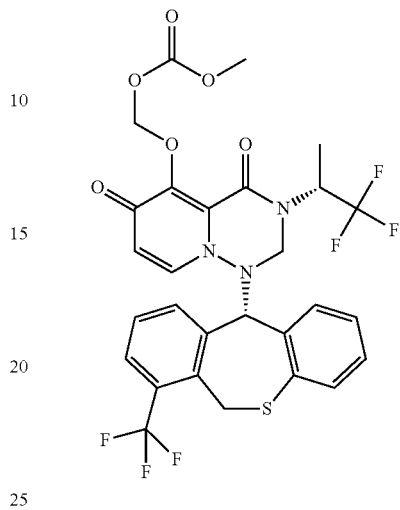

$^1$H-NMR (CDCl$_3$) δ: 1.18 (3H, d, J=7.2 Hz), 3.84 (3H, s), 3.99 (1H, d, J=14.7 Hz), 4.39 (1H, d, J=13.2 Hz), 4.92 (1H, d, J=13.2 Hz), 5.23 (1H, s), 5.55 (1H, m), 5.8-6.0 (4H, m), 6.7-7.0 (2H, m), 7.0-7.3 (3H, m), 7.3-7.5 (2H, m), 7.81 (1H, dd, J=6.3 Hz, J=2.7 Hz)
MS: m/z=644 [M+H]⁺.

EXAMPLE 142

[Chemical formula 990]

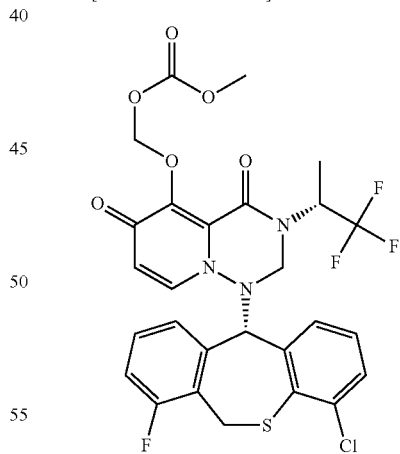

$^1$H-NMR (CDCl$_3$) δ: 1.18 (3H, d, J=7.5 Hz), 3.85 (3H, s), 4.24 (1H, d, J=13.8 Hz), 4.43 (1H, d, J=13.2 Hz), 4.91 (1H, d, J=13.2 Hz), 5.23 (1H, s), 5.43 (1H, d, J=13.8 Hz), 5.54 (1H, m), 5.8-6.1 (3H, m), 6.7-7.1 (3H, m), 7.1-7.4 (4H, m)
MS: m/z=628 [M+H]⁺.

EXAMPLE 143

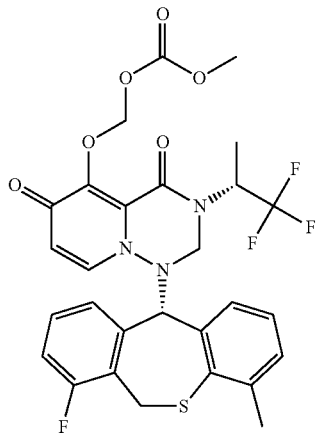

[Chemical formula 991]

$^1$H-NMR (CDCl$_3$) δ: 1.17 (3H, d, J=7.5 Hz), 2.25 (3H, s), 3.83 (3H, s), 4.21 (1H, d, J=13.8 Hz), 4.43 (1H, d, J=13.5 Hz), 4.90 (1H, d, J=13.5 Hz), 5.17 (1H, s), 5.37 (1H, d, J=15.6 Hz), 5.53 (1H, m), 5.8-6.0 (3H, m), 6.6-6.8 (2H, m), 6.9-7.1 (2H, m), 7.1-7.3 (3H, m)
MS: m/z=608 [M+H]$^+$.

EXAMPLE 144

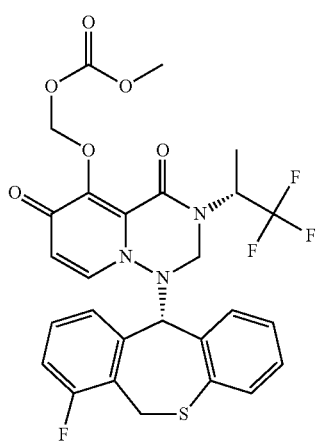

[Chemical formula 992]

$^1$H-NMR (CDCl$_3$) δ: 1.18 (3H, d, J=6.9 Hz), 3.84 (3H, s), 4.12 (1H, d, J=13.8 Hz), 4.42 (1H, d, J=13.2 Hz), 4.90 (1H, d, J=13.2 Hz), 5.14 (1H, s), 5.34 (1H, d, J=13.8 Hz), 5.54 (1H, m), 5.8-6.0 (3H, m), 6.7-6.9 (2H, m), 6.9-7.1 (3H, m), 7.1-7.3 (3H, m)
MS: m/z=594 [M+H]$^+$.

EXAMPLE 145

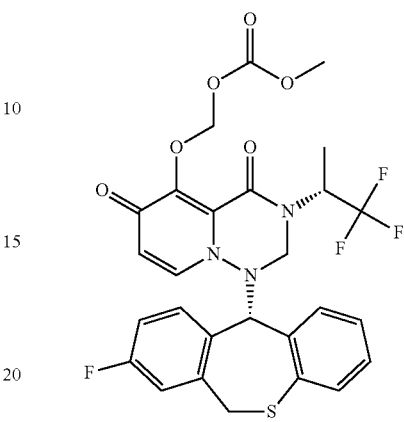

[Chemical formula 993]

$^1$H-NMR (CDCl$_3$) δ: 1.18 (3H, d, J=7.5 Hz), 3.56 (1H, d, J=13.5 Hz), 3.84 (3H, s), 4.42 (1H, d, J=13.2 Hz), 4.89 (1H, d, J=13.2 Hz), 5.10 (1H, s), 5.53 (1H, m), 5.66 (1H, d, J=13.5 Hz), 5.8-6.0 (3H, m), 6.7-7.0 (3H, m), 7.0-7.3 (5H, m)
MS: m/z=594 [M+H]$^+$.

EXAMPLE 146

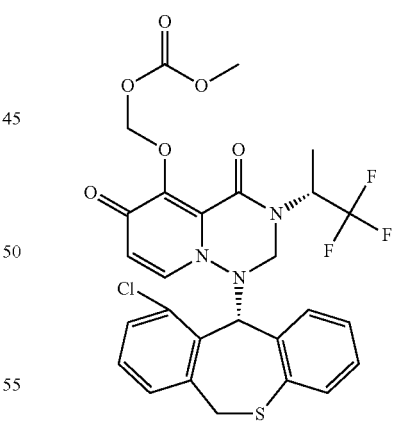

[Chemical formula 994]

$^1$H-NMR (CDCl$_3$) δ: 1.08 (3H, d, J=7.2 Hz), 3.63 (1H, d, J=12.6 Hz), 3.83 (3H, s), 4.39 (1H, d, J=13.2 Hz), 4.86 (1H, d, J=13.2 Hz), 5.23 (1H, m), 5.65 (1H, d, J=13.5 Hz), 5.8-6.0 (4H, m), 6.8-7.0 (2H, m), 7.0-7.2 (3H, m), 7.2-7.4 (3H, m)
MS: m/z=610 [M+H]$^+$.

EXAMPLE 147
[Chemical formula 995]
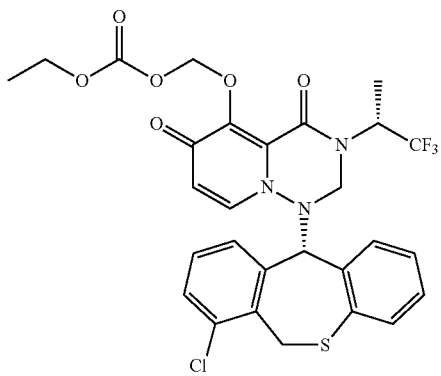
¹H-NMR (CDCl₃) δ: 1.13 (3H, d, J=6.0 Hz), 1.34 (3H, t, J=7.1 Hz), 3.65 (1H, m), 4.29 (3H, m), 4.42 (1H, d, J=13.5 Hz), 4.90 (1H, d, J=13.5 Hz), 5.13 (1H, s), 5.58 (2H, m), 5.92 (3H, m), 6.82 (2H, m), 7.00-7.26 (5H, m), 7.53 (1H, d, J=8.4 Hz).
MS: m/z=624.15 [M]⁺.
EXAMPLE 148
[Chemical formula 996]
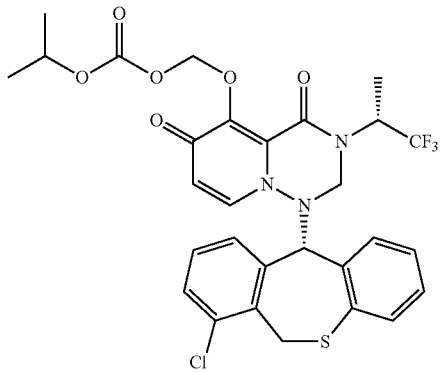
¹H-NMR (CDCl₃) δ: 1.18 (3H, d, J=7.2 Hz), 1.34 (3H, t, J=6.3 Hz), 1.35 (3H, t, J=6.3 Hz), 4.32 (1H, d, J=13.7 Hz), 4.42 (1H, d, J=13.1 Hz), 4.89 (1H, d, J=13.1 Hz), 4.96 (1H, m), 5.13 (1H, s), 5.54 (1H, m), 5.60 (1H, d, J=13.7 Hz), 5.87 (1H, d, J=6.8 Hz), 5.95 (2H, d, J=6.9 Hz), 6.85 (2H, m), 7.06-7.26 (5H, m), 7.53 (1H, d, J=6.8 Hz).
MS: m/z=638.15 [M]⁺.
EXAMPLE 149
[Chemical formula 997]
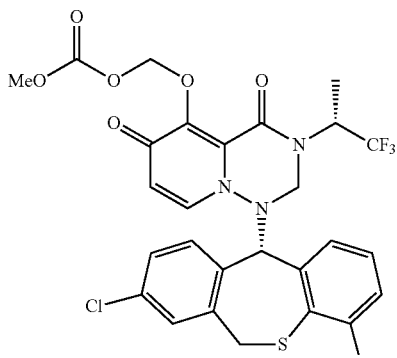
MS: m/z=628.35 [M]⁺.
EXAMPLE 150
[Chemical formula 998]
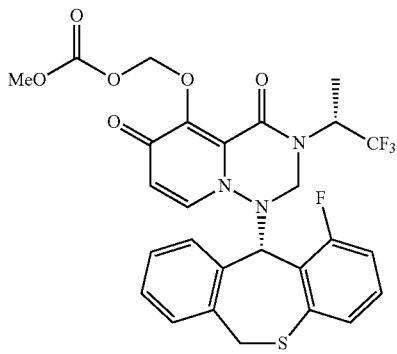
MS: m/z=594.15 [M]⁺.
EXAMPLE 151
[Chemical formula 999]
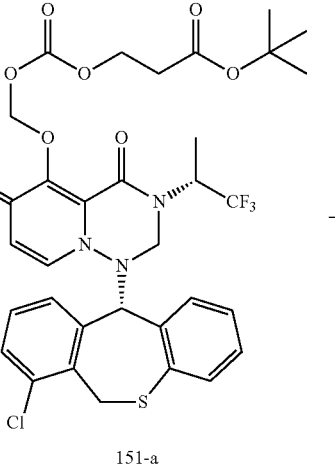
151-a -continued

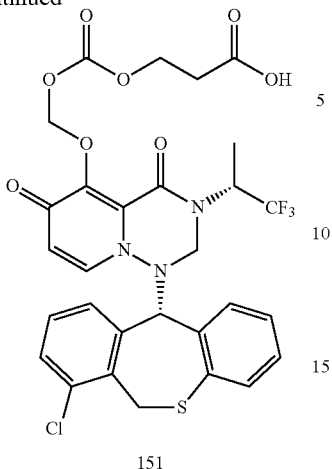

151

According to Example 122, compound 151-a was synthesized by the same procedure.

To an ethyl acetate (2.0 mL) solution of compound 151-a (67 mg, 0.093 mmol) was added a 4N HCl ethyl acetate solution (2.0 ml), and the mixture was stirred at room temperature overnight. Thereafter, to the reaction solution were added ethyl acetate and water, the ethyl acetate layer was separated, and the aqueous layer was extracted with ethyl acetate two times. To the combined extracts was added sodium sulfide, and the mixture was dried, then the solvent was distilled off. To the resulting oil was added diisopropyl ether, and the precipitated solid was filtered to obtain 12 mg of compound of Example 151 as a white solid.

$^1$H-NMR (CDCl$_3$) δ: 1.24 (3H, d, 6.8 Hz), 2.80 (2H, brs), 4.31 (1H, d, J=13.7 Hz), 4.40-4.51 (3H, m), 4.86 (2H, m), 4.86 (1H, d, 13.1 Hz), 5.21 (1H, s), 5.53-5.62 (2H, m), 5.83-5.93 (3H, m), 6.75-6.86 (2H, m), 7.09-7.25 (5H, m), 7.48 (1H, d, J=9.0 Hz).

MS: m/z=668 [M+H]$^+$.

EXAMPLE 152

[Chemical formula 1000]

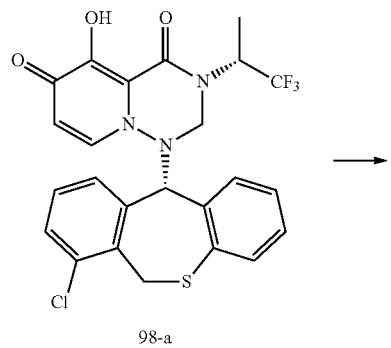

98-a

-continued

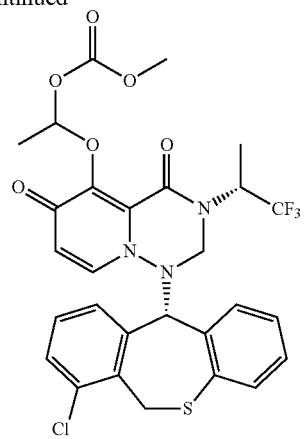

152

Compound 98-a (43 mg, 0.29 mmol) and silver(I) oxide (44 mg, 0.10 mmol) were added to an acetonitrile (1.5 mL) solution of 1-chloroethyl methyl carbonate (166 mg, 0.96 mmol), and the mixture was stirred at 50° C. for 4 hours, and then allowed to stand at room temperature overnight. Thereafter, the reaction solution was filtered with celite, the solvent was distilled off, and the resulting oil was purified by silica gel column chromatography. The materials were eluted firstly with chloroform and, then, with chloroform-methanol (95:5, v/v). An objective fraction was concentrated, and washed using hexane-diisopropyl ether to obtain 54 mg of compound of Example 152 as a white solid.

$^1$H-NMR (CDCl$_3$) δ: 1.14-1.16 (3H, m), 1.82-1.85 (3H, m), 3.66-3.83 (3H, m), 4.27-4.43 (2H, m), 4.82-4.91 (1H, m), 5.10-5.12 (1H, m), 5.54-5.62 (2H, m), 5.89-5.93 (1H, m), 6.52-6.56 (1H, m), 6.75-6.98 (2H, m), 7.07-7.21 (5H, m), 7.52 (1H, d, J=8.1 Hz).

MS: m/z=624 [M+H]$^+$.

EXAMPLE 153

[Chemical formula 1001]

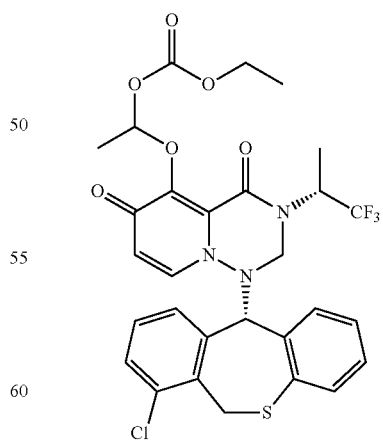

According to Example 152, compound of Example 153 was synthesized by the same procedure.

$^1$H-NMR (CDCl$_3$) δ: 1.14-1.16 (3H, m), 1.21-1.41 (3H, m), 1.84 (3H, d, J=5.1 Hz), 4.02-4.43 (4H, m), 4.83-4.89

(1H, m), 5.09-5.11 (1H, m), 5.54-5.61 (2H, m), 5.88-5.92 (1H, m), 6.48-6.55 (1H, m), 6.75-7.21 (7H, m), 7.51 (1H, d, J=8.2 Hz).

MS: m/z=638 [M+H]⁺.

EXAMPLE 154

[Chemical formula 1002]

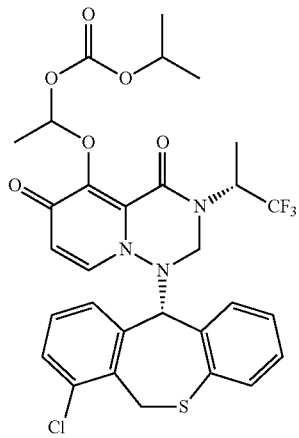

According to Example 152, compound of Example 154 was synthesized by the same procedure.

¹H-NMR (CDCl₃) δ: 1.10-1.43 (9H, m), 1.83 (3H, d, J=5.3 Hz), 4.27-4.43 (2H, m), 4.67-4.90 (2H, m), 5.08-5.12 (1H, m), 5.54-5.60 (2H, m), 5.86-5.91 (1H, m), 6.43-6.57 (1H, m), 6.71-7.20 (7H, m), 7.51 (1H, d, J=8.1 Hz).

MS: m/z=652 [M+H]⁺.

EXAMPLE 155

[Chemical formula 1003]

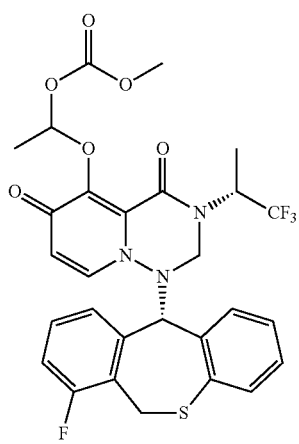

According to Example 152, compound of Example 155 was synthesized by the same procedure.

¹H-NMR (CDCl₃) δ: 1.12-1.15 (3H, m), 1.82-1.85 (3H, m), 3.66-3.84 (3H, m), 4.08-4.14 (1H, m), 4.37-4.44 (1H, m), 4.82-4.92 (1H, m), 5.12-5.14 (1H, m), 5.28-5.32 (1H, m), 5.52-5.60 (1H, m), 5.89-5.93 (1H, m), 6.51-6.55 (1H, m), 6.77-7.24 (8H, m).

MS: m/z=608 [M+H]⁺.

EXAMPLE 156

[Chemical formula 1004]

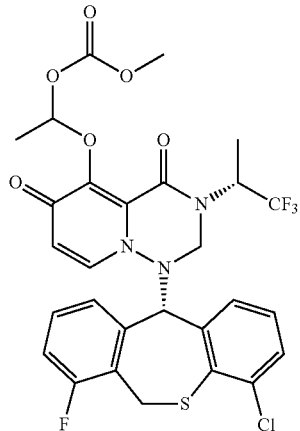

According to Example 152, compound of Example 156 was synthesized by the same procedure.

¹H-NMR (CDCl₃) δ: 1.10-1.14 (3H, m), 1.82-1.84 (3H, m), 3.65-3.83 (3H, m), 4.17-4.23 (1H, m), 4.36-4.42 (1H, m), 4.82-4.90 (1H, m), 5.17-5.19 (1H, m), 5.35-5.58 (2H, m), 5.92-5.96 (1H, m), 6.49-6.53 (1H, m), 6.71-7.14 (4H, m), 7.21-7.29 (3H, m).

MS: m/z=642 [M+H]⁺.

EXAMPLE 157

[Chemical formula 1005]

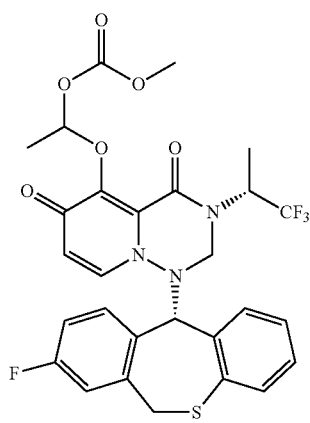

According to Example 152, compound of Example 157 was synthesized by the same procedure.

¹H-NMR (CDCl₃) δ: 1.12-1.15 (3H, m), 1.82-1.85 (3H, m), 3.51-3.55 (1H, m), 3.66-3.83 (3H, m), 4.37-4.43 (1H, m), 4.81-4.89 (1H, m), 5.07-5.09 (1H, m), 5.53-5.68 (2H, m), 5.88-5.91 (1H, m), 6.51-6.56 (1H, m), 6.76-7.00 (3H, m), 7.06-7.18 (5H, m).

MS: m/z=608 [M+H]⁺.

EXAMPLE 158

[Chemical formula 1006]

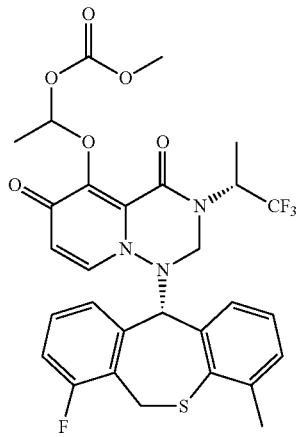

According to Example 152, compound of Example 158 was synthesized by the same procedure.

¹H-NMR (CDCl₃) δ: 1.10-1.14 (3H, m), 1.81-1.84 (3H, m), 2.24-2.25 (3H, m), 3.65-3.83 (3H, m), 4.17-4.23 (1H, m), 4.38-4.43 (1H, m), 4.82-4.90 (1H, m), 5.14-5.16 (1H, m), 5.31-5.38 (1H, m), 5.51-5.60 (1H, m), 5.86-5.90 (1H, m), 6.51-6.56 (1H, m), 6.65-7.23 (7H, m).

MS: m/z=622 [M+H]⁺.

EXAMPLE 159

[Chemical formula 1007]

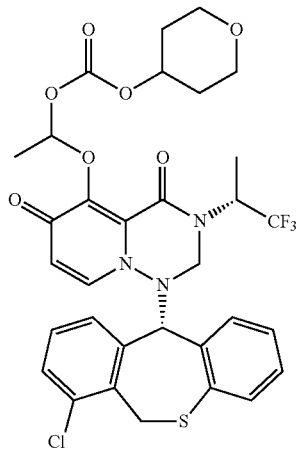

According to Example 152, compound of Example 159 was synthesized by the same procedure.

¹H-NMR (CDCl₃) δ: 1.10-1.16 (3H, m), 1.63-2.02 (7H, m), 3.44-4.04 (4H, m), 4.27-4.44 (2H, m), 4.62-4.90 (2H, m), 5.05-5.13 (1H, m), 5.49-5.61 (2H, m), 5.87-5.91 (1H, m), 6.44-6.58 (1H, m), 6.78-7.26 (7H, m), 7.53 (1H, d, J=7.8 Hz).

MS: m/z=694 [M+H]⁺.

EXAMPLE 160

[Chemical formula 1008]

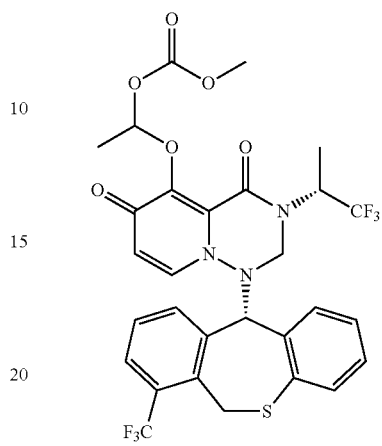

According to Example 152, compound of Example 160 was synthesized by the same procedure.

¹H-NMR (CDCl₃) δ: 1.12-1.15 (3H, m), 1.82-1.85 (3H, m), 3.66-3.84 (3H, m), 3.94-4.00 (1H, m), 4.33-4.39 (1H, m), 4.84-4.92 (1H, m), 5.20-5.21 (1H, m), 5.52-5.62 (1H, m), 5.80-5.93 (2H, m), 6.51-6.56 (1H, m), 6.71-7.14 (5H, m), 7.36-7.38 (2H, m), 7.78-7.81 (1H, m).

MS: m/z=658 [M+H]⁺.

EXAMPLE 161

[Chemical formula 1009]

¹H-NMR (CDCl₃) δ: 1.05 (6H, m), 1.19-1.27 (3H, m), 1.34-1.45 (3H, m), 1.82-1.87 (3H, m), 2.80 (1H, ddd, J=4.2 Hz, 4.2 Hz, 13.8 Hz), 4.02-3.14 (1H, m), 3.43-3.52 (1H, m), 4.15-4.21 (1H, m), 4.25-4.38 (1H, m), 4.59-4.77 (2H, m), 5.05 (1H, d, J=11.7 Hz), 5.76-5.81 (1H, m), 6.45-6.51 (1H, m), 6.64-6.67 (1H, m), 6.79 (0.5H, d, J=7.5 Hz), 6.90-7.35 (6.5H, m).

EXAMPLE 162

[Chemical formula 1010]

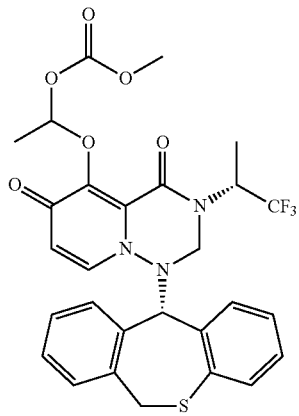

According to Example 152, compound of Example 162 was synthesized by the same procedure.

$^1$H-NMR (CDCl$_3$) δ: 1.10 (3H, d, 7.3 Hz), 1.84 (3H, d, 5.2 Hz), 3.60 (1H, d, 13.5 Hz), 3.65 (3H, s), 4.41 (1H, d, J=13.0 Hz), 4.87 (1H, d, J=12.7 Hz), 5.06 (1H, s), 5.52-5.62 (2H, m), 5.91 (1H, d, J=7.8 Hz), 6.53 (1H, q, J=5.3), 6.76-6.84 (2H, m), 7.06-7.43 (7H, m).

MS: m/z=590 [M+H]$^+$.

EXAMPLE 163

[Chemical formula 1011]

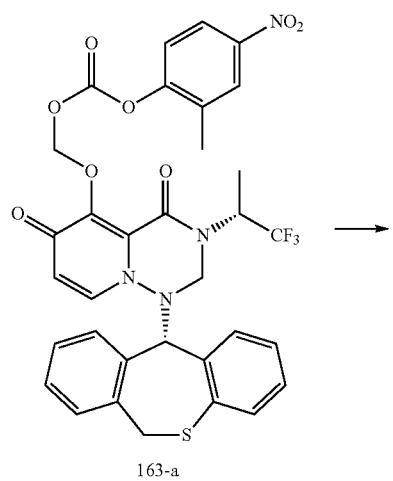

163-a

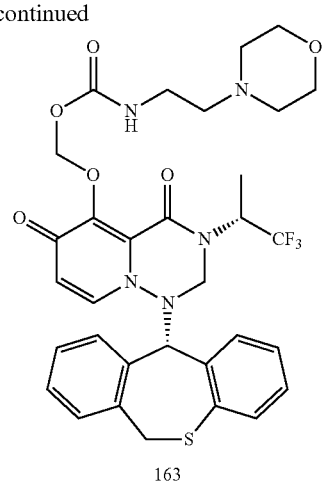

163

According to Example 122, compound 163-a was synthesized by the same procedure.

To an acetonitrile (1.0 mL) solution of compound 163-a (70 mg, 0.10 mmol) and potassium carbonate (138 mg, 0.22 mmol) were added 2-morpholinoethanamine (31 mg, 0.24 mmol), DMAP (13 mg, 0.10 mmol) and triethylamine (0.042 ml, 0.30 mmol), and the mixture was stirred at room temperature overnight. Thereafter, to the reaction solution was added water, the dichloromethane layer was separated, and the aqueous layer was extracted with dichloromethane once. The combined extracts were washed with an aqueous saturated sodium chloride solution and brine, and then sodium sulfide was added to dry them. The solvent was distilled off, and the resulting oil was purified by silica gel column chromatography. The materials were eluted firstly with chloroform and, then, with chloroform-methanol (94:6, v/v). An objective fraction was concentrated, and washed using diisopropyl ether to obtain 26 mg of compound of Example 163 as a yellowish-white solid.

MS: m/z=674 [M+H]$^+$.

EXAMPLE 164

[Chemical formula 1012]

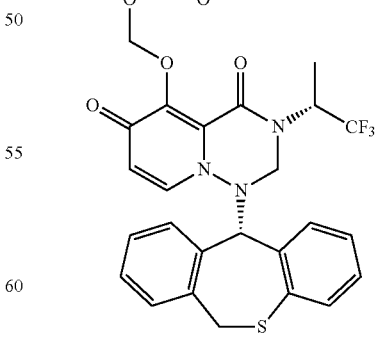

According to Example 163, compound of Example 164 was synthesized by the same procedure.

$^1$H-NMR (CDCl$_3$) δ: 1.13 (3H, d, 7.0 Hz), 1.33-1.36 (6H, m), 3.61 (1H, d, J=13.4 Hz), 4.42 (1H, d, J=13.3 Hz), 4.85-4.99 (2H, m), 5.08 (1H, s), 5.49-5.64 (2H, m), 5.86 (1H, d, J=6.4 Hz), 5.93-5.97 (2H, m), 6.82-6.88 (2H, m), 7.05-7.44 (7H, m).

MS: m/z=604 [M+H]⁺.

EXAMPLE 165

[Chemical formula 1013]

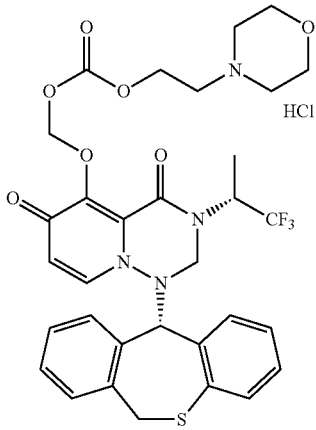

According to Example 163, compound of Example 165 was synthesized by the same procedure.

MS: m/z=675 [M+H]⁺.

EXAMPLE 166

[Chemical formula 1014]

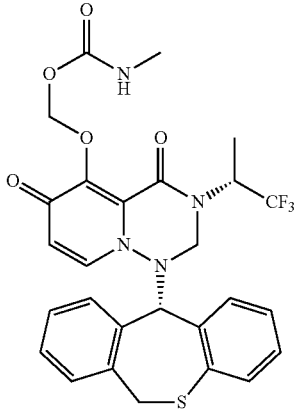

According to Example 163, compound of Example 166 was synthesized by the same procedure.

$^1$H-NMR (CDCl$_3$) δ: 1.12 (3H, d, 7.3 Hz), 2.78 (3H, d, J=5.0), 3.60 (1H, d, J=13.1 Hz), 4.42 (1H, d, J=13.3 Hz), 4.78 (1H, brs), 4.87 (1H, d, J=12.9 Hz), 5.09 (1H, s), 5.54-5.64 (2H, m), 5.84-5.94 (3H, m), 6.83-6.89 (2H, m), 7.07-7.44 (7H, m).

MS: m/z=575 [M+H]⁺.

EXAMPLE 167

[Chemical formula 1015]

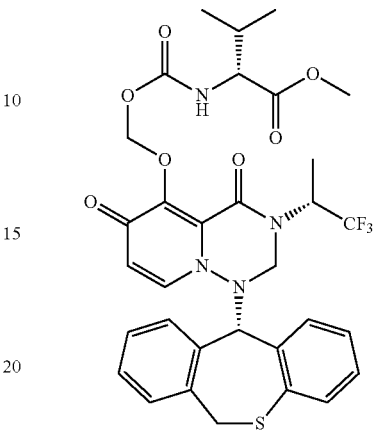

According to Example 163, compound of Example 167 was synthesized by the same procedure.

MS: m/z=675 [M+H]⁺.

EXAMPLE 168

[Chemical formula 1016]

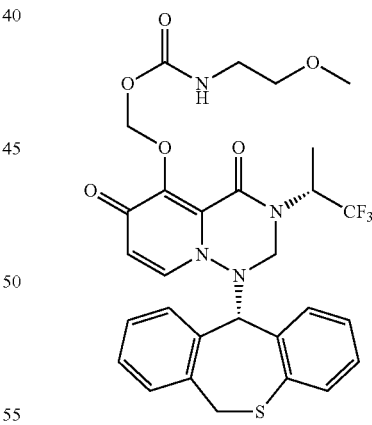

According to Example 163, compound of Example 168 was synthesized by the same procedure.

$^1$H-NMR (CDCl$_3$) δ: 1.12 (3H, d, 7.4 Hz), 3.35-3.38 (5H, m), 3.46 (2H, t, J=5.1 Hz), 3.60 (1H, d, J=13.4 Hz), 4.42 (1H, d, J=13.1), 4.87 (1H, d, J=12.4 Hz), 5.09-5.16 (2H, m), 5.87-5.94 (3H, m), 6.81-6.89 (2H, m), 7.05-7.45 (7H, m).

MS: m/z=619 [M+H]⁺.

EXAMPLE 169

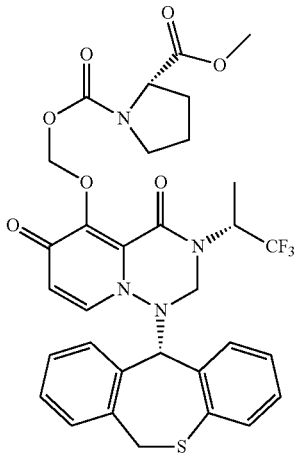

According to Example 163, compound of Example 169 was synthesized by the same procedure.

MS: m/z=673 [M+H]$^+$.

EXAMPLE 170

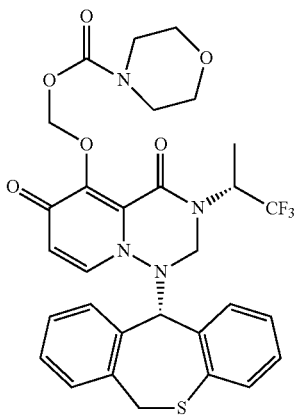

According to Example 163, compound of Example 170 was synthesized by the same procedure.

$^1$H-NMR (CDCl$_3$) δ: 1.12 (3H, d, 7.3 Hz), 3.48-3.77 (9H, m), 4.42 (1H, d, J=13.4 Hz), 4.87 (1H, d, J=13.4), 5.07 (1H, s), 5.49-5.63 (2H, m), 5.91-5.94 (3H, m), 6.84-6.86 (2H, m), 7.06-7.45 (7H, m).

MS: m/z=631 [M+H]$^+$.

EXAMPLE 171

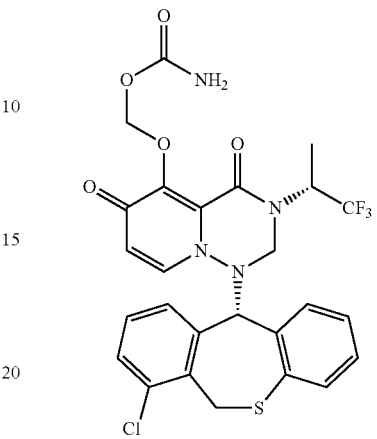

According to Example 163, compound of Example 171 was synthesized by the same procedure.

$^1$H-NMR (CDCl$_3$) δ: 1.17 (3H, d, 7.3 Hz), 4.31 (1H, d, J=13.9 Hz), 4.42 (1H, d, J=13.2 Hz), 4.72 (2H, brs), 4.89 (1H, d, J=12.8 Hz), 5.14 (1H, s), 5.55-5.62 (2H, m), 5.87 (2H, s), 5.94 (1H, d, J=7.8 Hz), 6.81-6.89 (2H, m), 7.07-7.21 (5H, m), 7.52 (1H, d, J=7.1 Hz).

MS: m/z=595 [M+H]$^+$.

EXAMPLE 172

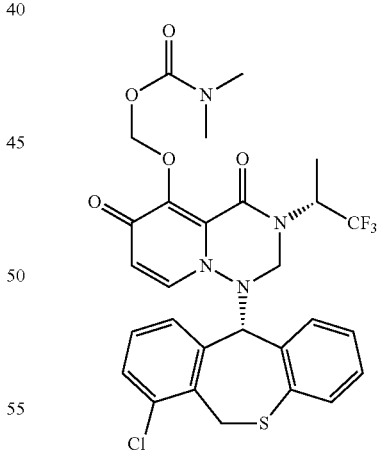

According to Example 163, compound of Example 172 was synthesized by the same procedure.

$^1$H-NMR (CDCl$_3$) δ: 1.16 (3H, d, 7.8 Hz), 2.89 (3H, s), 2.95 (3H, s), 4.31 (1H, d, J=14.0 Hz), 4.41 (1H, d, J=13.5 Hz), 4.89 (1H, d, J=13.3 Hz), 5.13 (1H, s), 5.52-5.61 (2H, m), 5.85-5.96 (3H, m), 6.83-6.88 (2H, m), 7.07-7.22 (5H, m), 7.52 (1H, d, J=7.0 Hz).

MS: m/z=623 [M+H]$^+$.

EXAMPLE 173

[Chemical formula 1021]

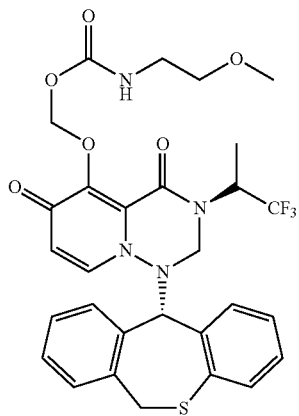

According to Example 163, compound of Example 173 was synthesized by the same procedure.

$^1$H-NMR (CDCl$_3$) δ: 1.33 (3H, d, 7.4 Hz), 3.37-3.62 (8H, m), 4.52 (1H, d, J=12.4 Hz), 4.92 (1H, d, J=12.4 Hz), 5.23-5.30 (3H, m), 5.65 (1H, d, 13.0 Hz), 5.80-5.95 (3H, m), 6.84-6.91 (2H, m), 7.03-7.09 (2H, m), 7.18-7.41 (5H, m).

MS: m/z=619 [M+H]$^+$.

EXAMPLE 174

[Chemical formula 1022]

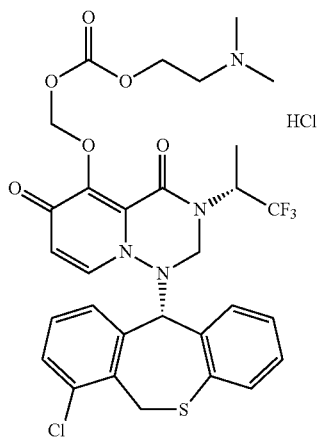

According to Example 163, compound of Example 174 was synthesized by the same procedure.

$^1$H-NMR (CDCl$_3$) δ: 1.38 (3H, d, 7.2 Hz), 2.92 (1H, d, 4.5 Hz), 3.10 (1H, d, 4.5 Hz), 3.45 (2H, brs), 4.34 (1H, d, J=14.3 Hz), 4.52-4.57 (2H, m), 4.90 (1H, d, J=13.8 Hz), 5.10 (1H, brs), 5.52-5.60 (3H, m), 5.75 (1H, d, J=6.9 Hz), 6.02 (1H, d, J=6.8 Hz), 6.85-6.96 (3H, m), 7.07-7.28 (3H, m), 7.50-7.57 (2H, m), 7.73 (1H, d, J=7.4 Hz).

MS: m/z=667 [M+H]$^+$.

EXAMPLE 175

[Chemical formula 1023]

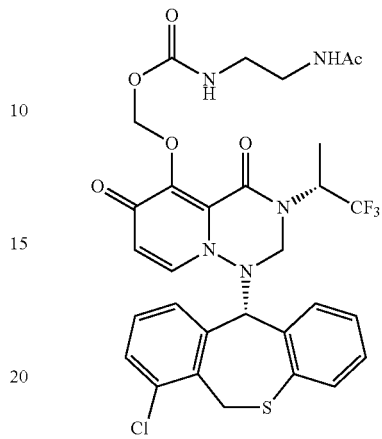

According to Example 163, compound of Example 175 was synthesized by the same procedure.

$^1$H-NMR (CDCl$_3$) δ: 1.16 (3H, d, 7.3 Hz), 2.01 (3H, s), 3.19-3.45 (4H, m), 4.32 (1H, d, 14.0 Hz), 4.46 (1H, d, J=13.2 Hz), 4.90 (1H, d, J=13.1 Hz), 5.17-5.19 (2H, m), 5.53-5.68 (3H, m), 5.89-5.97 (2H, m), 6.87-6.95 (2H, m), 7.08-7.26 (5H, m), 7.54 (1H, d, J=7.8 Hz).

MS: m/z=680 [M+H]$^+$.

EXAMPLE 176

[Chemical formula 1024]

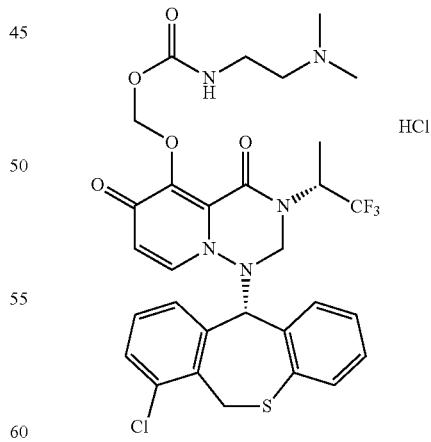

According to Example 163, compound of Example 176 was synthesized by the same procedure.

MS: m/z=666 [M+H]$^+$.

EXAMPLE 177

[Chemical formula 1025]

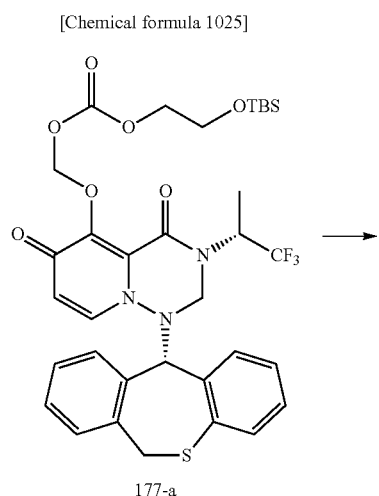

177-a

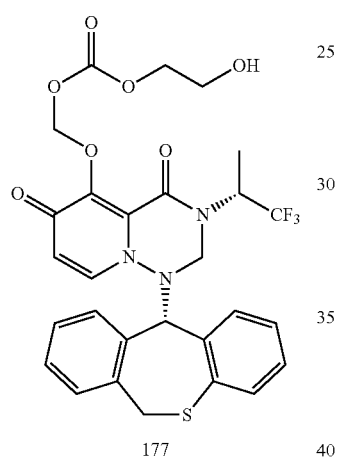

177

According to Example 163, compound 177-a was synthesized by the same procedure.

To an ethyl acetate solution (2.0 mL) solution of compound 177-a (129 mg, 0.17 mmol) was added a 4N HCl ethyl acetate solution (2.0 ml), and the mixture was stirred at room temperature for 30 minutes. Thereafter, to the reaction solution was added water, the ethyl acetate layer was separated, and the aqueous layer was extracted with ethyl acetate two times. The combined extracts were washed with an aqueous saturated sodium chloride solution and brine, and then sodium sulfide was added to dry them. The solvent was distilled off, and the resulting oil was purified by silica gel column chromatography. The materials were eluted firstly with chloroform and, then, with chloroform-methanol (94:6, v/v). An objective fraction was concentrated, and washed using diisopropyl ether to obtain 10 mg of compound of Example 177 as a pale pink solid.

$^1$H-NMR (CDCl$_3$) δ: 1.15 (3H, d, 7.2 Hz), 3.61 (1H, d, 13.4 Hz), 3.92 (2H, brs), 4.30-4.51 (3H, m), 4.86 (1H, d, J=12.8), 5.09 (1H, s), 5.44-5.62 (2H, m), 5.86 (1H, d, J=6.6 Hz), 5.94-5.97 (2H, m), 6.88-6.90 (2H, m), 7.08-7.44 (7H, m).

MS: m/z=606 [M+H]$^+$.

EXAMPLE 178

[Chemical formula 1026]

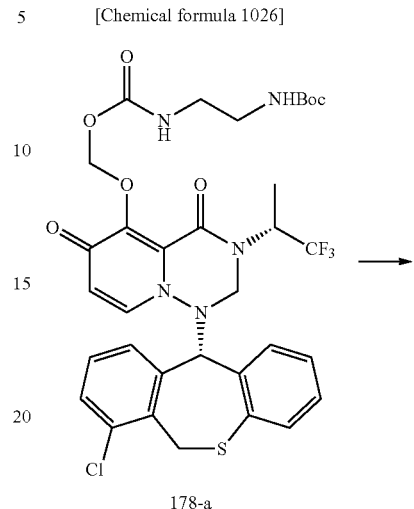

178-a

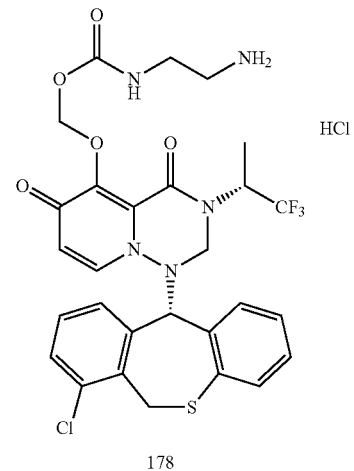

178

According to Example 163, compound 178-a was synthesized by the same procedure.

To an ethyl acetate solution (1.0 mL) solution of compound 178-a (81 mg, 0.11 mmol) was added a 4N HCl ethyl acetate solution (1.0 ml), and the mixture was stirred at room temperature for 1 hour and 30 minutes. A solid precipitated from the reaction solution was filtered, and washed with diisopropyl ether to obtain 54 mg of compound of Example 178 as a white solid.

MS: m/z=638 [M+H]$^+$.

EXAMPLE 179

[Chemical formula 1027]

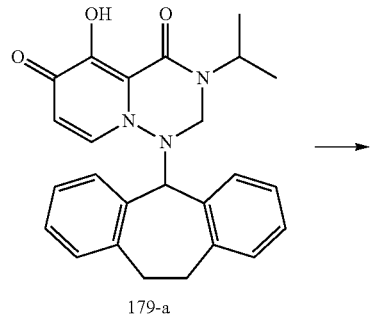

179-a

↓

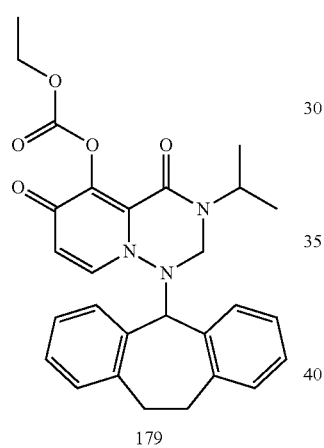

179

A DMF (1 ml) solution of compound 179-a (50 mg, 0.120 mmol) and triethylamine (61 mg, 0.60 mmol) was cooled to 1 to 3° C., and ethyl chloroformate (26 mg, 0.24 mmol) was added dropwise while the same temperature was retained. After the reaction solution was stirred at room temperature for 30 minutes, water was added, and the mixture was extracted with ethyl acetate three times. The extract was washed with water three times, and dried with sodium sulfate, then the solvent was distilled off. The resulting solid was washed with ethyl-diisopropyl ether to obtain 24 mg of compound of Example 179.

$^1$H-NMR (CDCl$_3$) δ: 1.11 (3H, d, J=6.9 Hz), 1.12 (3H, d, J=6.9 Hz), 1.44 (3H, t, J=6.9 Hz), 2.82 (1H, ddd, J=4.5 Hz, 4.5 Hz, 14.1 Hz), 3.09 (1H, ddd, J=3.9H, 13.5 Hz, 13.5 Hz), 3.49 (1H, ddd, J=4.2 Hz, 4.2 Hz, 17.4 Hz), 4.24 (1H, d, 13.2 Hz), 4.29-4.43 (2H, m), 4.40 (1H, d, J=7.2 Hz), 4.66-4.77 (1H, m), 4.69 (1H, d, J=12.9 Hz), 5.10 (1H, s), 5.87 (1H, d, J=8.1 Hz), 6.77 (1H, d, J=7.8 Hz), 6.79-6.82 (1H, m), 6.98 (1H, t, J=7.2 Hz), 7.07-7.37 (6H, m).

According to Example 179, the following compounds of Examples were synthesized by the same procedure.

EXAMPLE 180

[Chemical formula 1028]

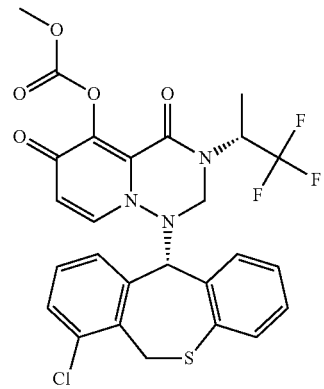

$^1$H-NMR (CDCl$_3$) δ: 1.20 (3H, d, J=7.2 Hz), 3.98 (3H, s), 4.31 (1H, d, J=13.8 Hz), 4.46 (1H, d, J=13.2 Hz), 4.93 (1H, d, J=13.2 Hz), 5.16 (1H, s), 5.48-5.57 (1H, m), 5.60 (1H, d, J=14.1 Hz), 5.99 (1H, d, J=7.8 Hz), 6.23-6.93 (2H, m), 7.07-7.25 (6H, m), 7.51-7.54 (1H, m).

EXAMPLE 181

[Chemical formula 1029]

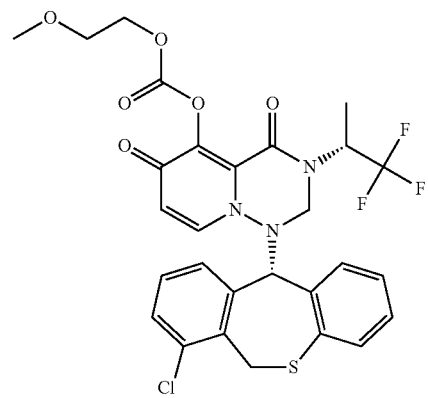

$^1$H-NMR (CDCl$_3$) δ: 1.20 (3H, d, J=7.2 Hz), 3.45 (3H, s), 3.74 (2H, t, J=5.1 Hz), 4.31 (1H, d, J=13.8 Hz), 4.43-4.48 (3H, m), 4.93 (1H, d, J=13.2 Hz), 5.16 (1H, s), 5.48-5.57 (1H, m), 5.60 (1H, d, J=14.1 Hz), 5.98 (1H, d, J=7.8 Hz), 6.82-6.92 (2H, m), 7.06-7.12 (3H, m), 7.14-7.25 (2H, m), 7.52 (1H, d, J=8.1 Hz).

EXAMPLE 182

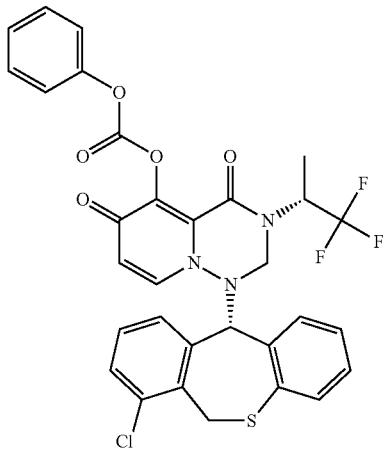

[Chemical formula 1030]

¹H-NMR (CDCl₃) δ: 1.22 (3H, d, J=7.2 Hz), 4.31 (1H, d, J=13.8 Hz), 4.48 (1H, d, J=13.2 Hz), 4.95 (1H, d, J=13.2 Hz), 5.17 (1H, s), 5.53-5.63 (2H, m), 6.02 (1H, d, J=7.8 Hz), 6.83-6.88 (2H, m), 7.06-7.13 (3H, m), 7.17-7.39 (3H, m), 7.41-7.51 (4H, m), 7.51-7.55 (1H, m).

EXAMPLE 183

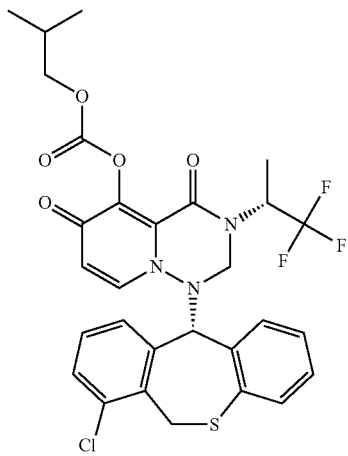

[Chemical formula 1031]

¹H-NMR (CDCl₃) δ: 1.04 (6H, d, J=6.6 Hz), 1.19 (3H, d, J=7.2 Hz), 2.08-2.17 (1H, m), 4.11 (2H, d, J=6.6 Hz), 4.31 (1H, d, J=13.8 Hz), 4.46 (1H, d, J=13.5 Hz), 4.93 (1H, d, J=12.9 Hz), 5.16 (1H, s), 5.48-5.62 (2H, m), 5.98 (1H, d, J=8.1 Hz), 6.82-6.92 (2H, m), 7.07-7.26 (5H, m), 7.51-7.55 (1H, m).

EXAMPLE 184

[Chemical formula 1032]

¹H-NMR (CDCl₃) δ: 1.19 (3H, d, J=7.2 Hz), 1.60 (9 H, s), 4.31 (1H, d, J=13.8 Hz), 4.45 (1H, d, J=13.2 Hz), 4.92 (1H, d, J=13.2 Hz), 5.17 (1H, s), 5.48-5.63 (2H, m), 5.97 (1H, d, J=7.5 Hz), 6.81-6.92 (2H, m), 7.07-7.14 (3H, m), 7.17-7.22 (2H, m), 7.12-7.54 (1H, m).

EXAMPLE 185

[Chemical formula 1033]

¹H-NMR (DMSO-d₆) δ: 1.01 (6H, t, J=7.17 Hz), 1.31 (3H, t, J=7.09 Hz), 3.88 (1H, d, J=13.27 Hz), 4.20-4.30 (3H, m), 4.61 (1H, t, J=6.71 Hz), 5.00 (1H, d, J=13.42 Hz), 5.32 (1H, s), 5.65 (1H, d, J=13.27 Hz), 5.87 (1H, d, J=7.78 Hz), 6.82-6.93 (2H, m), 7.06-7.15 (2H, m), 7.22-7.50 (5H, m).

MS: m/z=505.95 [M+H]⁺.

EXAMPLE 186

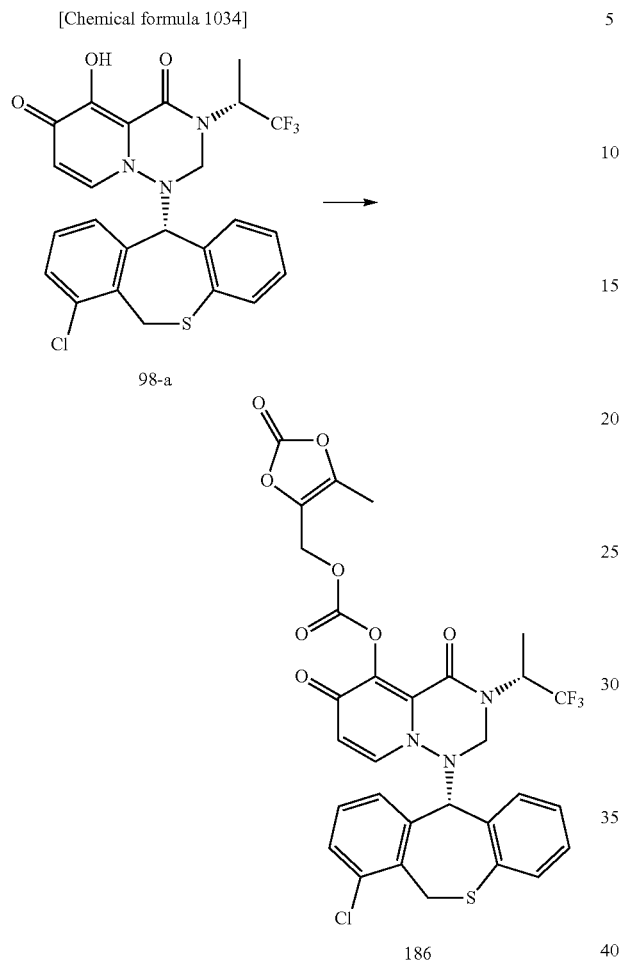

According to the method shown in Journal of Medicinal Chemistry; English; 39; 2; 1996; 480-486, to a DMF (1 ml) solution of compound 98-a (50 mg, 0.0958 mmol) and triethylamine (48 mg, 0.48 mmol) were added (5-methyl-2-oxo-1,3-dioxol-4-yl)methyl 4-nitrophenyl carbonate (85 mg, 0.29 mmol) and DMAP (1.2 mg, 0.096 mmol) at room temperature, and the mixture was stirred at the same temperature for 6 hours. The reaction solution was diluted with ethyl acetate (10 ml), and water was added. The organic layer was separated, and the aqueous layer was extracted with ethyl acetate once. The extract was washed with water three times, and dried with sodium sulfate, and the solvent was distilled off. The resulting crude product was purified by silica gel column chromatography. The materials were eluted firstly with ethyl acetate and, then, with ethyl acetate-methanol (4:1, v/v). Concentration of an objective fraction afforded 31 mg of compound of Example 186 as a solid.

$^1$H-NMR (CDCl$_3$) δ: 1.21 (3H, d, J=7.2 Hz), 2.27 (3H, s), 4.33 (1H, d, J=14.1 Hz), 4.47 (1H, d, J=13.5 Hz), 4.91 (2H, d, J=13.2 Hz), 5.18 (1H, d, J=17.7 Hz), 5.21 (1H, s), 5.38-5.49 (1H, m), 5.58 (1H, d, J=13.8 Hz), 6.01 (1H, d, J=7.8 Hz), 6.83-6.89 (2H, m), 7.08-7.15 (2H, m), 7.18-7.27 (3H, m), 7.51-7.54 (1H, m).

According to Example 186, the following compounds were synthesized by the same procedure.

EXAMPLE 187

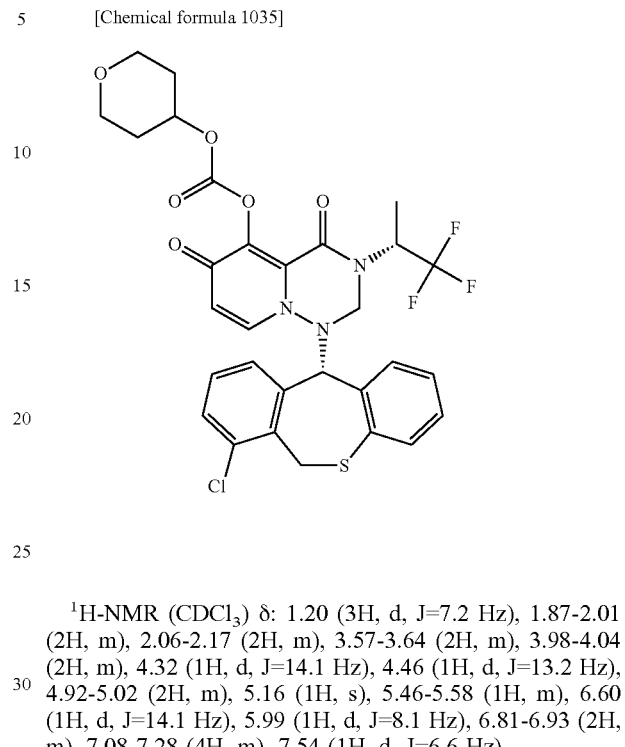

$^1$H-NMR (CDCl$_3$) δ: 1.20 (3H, d, J=7.2 Hz), 1.87-2.01 (2H, m), 2.06-2.17 (2H, m), 3.57-3.64 (2H, m), 3.98-4.04 (2H, m), 4.32 (1H, d, J=14.1 Hz), 4.46 (1H, d, J=13.2 Hz), 4.92-5.02 (2H, m), 5.16 (1H, s), 5.46-5.58 (1H, m), 6.60 (1H, d, J=14.1 Hz), 5.99 (1H, d, J=8.1 Hz), 6.81-6.93 (2H, m), 7.08-7.28 (4H, m), 7.54 (1H, d, J=6.6 Hz).

EXAMPLE 188

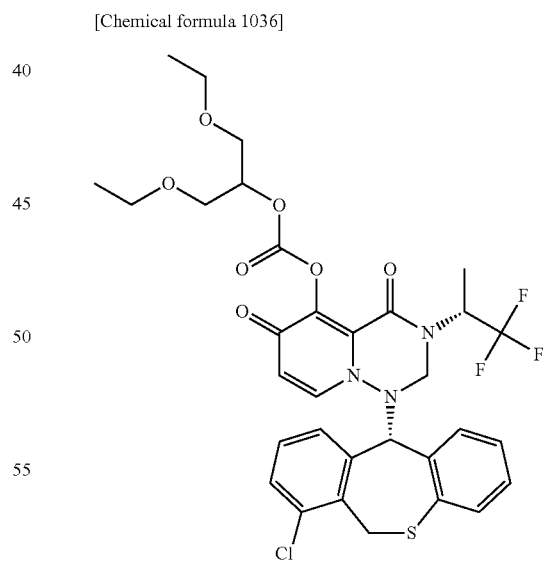

$^1$H-NMR (CDCl$_3$) δ: 1.12-1.27 (12H, m), 3.55-3.66 (5H, m), 3.73-3.79 (4H, m), 4.31 (1H, d, J=13.8 Hz), 4.45 (1H, d, J=13.2 Hz), 4.93 (1H, d, J=13.2 Hz), 5.03-5.06 (1H, m), 5.16 (1H, s), 5.46-5.62 (2H, m), 5.95-6.00 (1H, m), 6.85-6.92 (2H, m), 7.07-7.26 (5H, m), 7.53 (1H, d, J=7.8 Hz).

EXAMPLE 189

[Chemical formula 1037]

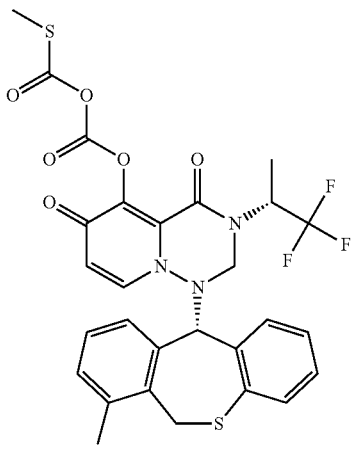

$^1$H-NMR (CDCl$_3$) δ: 1.19 (3H, d, J=7.2 Hz), 2.94 (3H, s), 4.32 (1H, d, J=13.8 Hz), 4.46 (1H, d, J=13.2 Hz), 4.93 (1H, d, J=13.8 Hz), 5.16 (1H, s), 5.51-5.62 (2H, m), 5.98 (1H, d, J=7.8 Hz), 6.82-6.84 (1H, m), 6.88-6.93 (1H, m), 7.07-7.12 (3H, m), 7.14-7.26 (3H, m), 7.51-7.54 (1H, m).

EXAMPLE 190

[Chemical formula 1038]

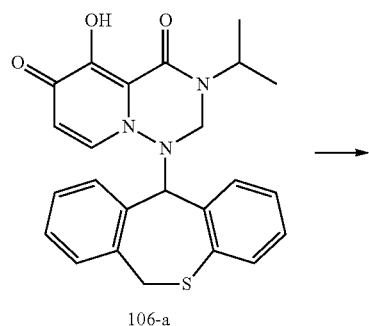

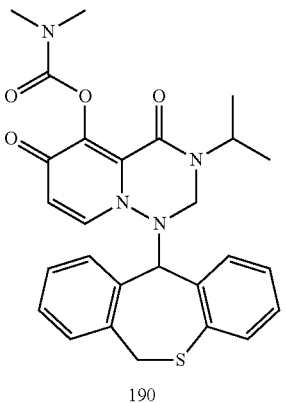

Compound 106-a (80.0 mg, 0.185 mmol) was dissolved in dichloromethane (1 ml), triethylamine (0.051 ml, 0.37 mmol), dimethylcarbamic chloride (39.7 mg, 0.369 mmol), and DMAP (cat.) were added, and the mixture was stirred at 50° C. for 3 hours. To the reaction solution was added water, the mixture was extracted with ethyl acetate, and the organic layer was washed with water, and dried with sodium sulfate. The solvent was distilled off under reduced pressure, and the resulting crude product was purified by silica gel column chromatography, and eluted with chloroform-methanol (97:3, v/v). Dichloromethane-ethyl acetate-diethyl ether were added, and the mixture was solidified to obtain 47 mg of compound of Example 190 as a white solid.

MS: m/z=505 [M+H]$^+$.

EXAMPLE 191

[Chemical formula 1039]

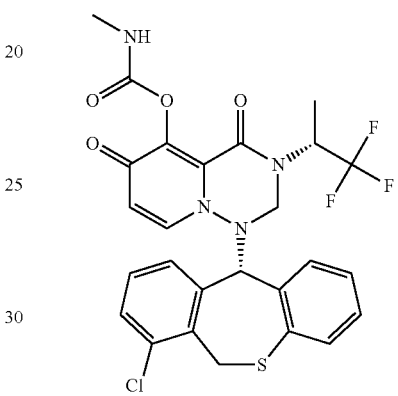

$^1$H-NMR (CDCl$_3$) δ: 1.17 (3H, d, J=7.2 Hz), 2.96 (3H, d, J=5.1 Hz), 4.30 (1H, d, J=13.8 Hz), 4.45 (1H, d, J=13.2 Hz), 4.92 (1H, d, J=12.9 Hz), 5.20 (1H s), 5.29-5.30 (1H, m), 5.48-5.58 (1H, m), 5.60 (1H, d, J=13.8 Hz), 5.96 (1H, d, J=13.8 Hz), 6.91-6.92 (2H, m), 7.06-7.21 (5H, m), 7.50-7.53 (1H, m).

EXAMPLE 192

[Chemical formula 1040]

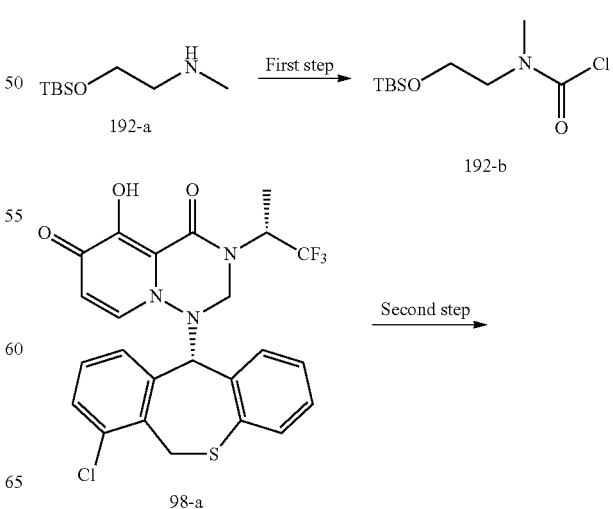

-continued

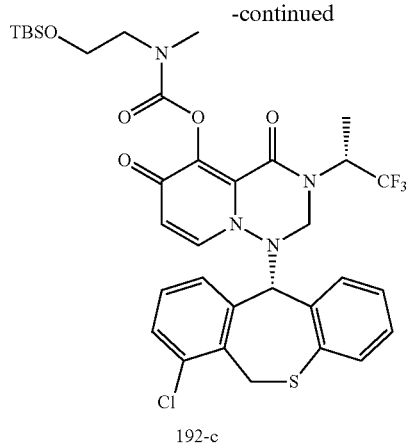

192-c

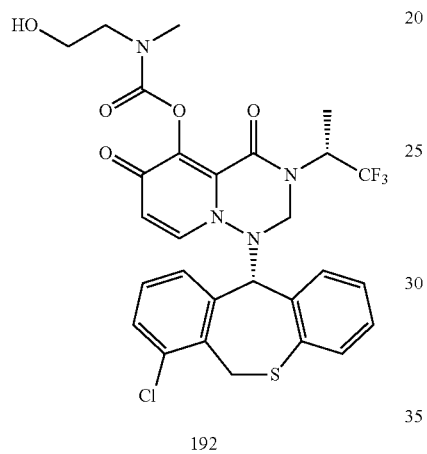

192

First Step
According to the method described in Chem. Pharm. Bull. 55, 328-333 (2007), compound 192-b was synthesized.

Second Step
To a pyridine (1 mL) solution of compound 192-b (78.0 mg, 0.273 mmol) was added compound 98-a (51.0 mg, 0.098 mmol), and the mixture was stirred at room temperature for 1.5 hours, at 50° C. for 3 hours, and 70° C. for 7 hours. The reaction solution was diluted with ethyl acetate (10 mL), the mixture was washed with water (5 mL) and hydrochloric acid (2M, 5 mL), and the organic layer was dried with sodium sulfate. The solvent was distilled off under reduced pressure, and the resulting crude product of compound 192-c was used in a next reaction without purification.

Third Step
To an ethanol (0.5 mL) solution of the crude product of compound 192-c obtained in the second step was added concentrated hydrochloric acid (0.050 ml) at room temperature, and the mixture was stirred for 2 hours. To the reaction solution was added water (20 mL), and the mixture was extracted with chloroform, then the organic layer was dried with sodium sulfate. The solvent was distilled off under reduced pressure, and the resulting residue was purified by silica gel column chromatography (ethyl acetate/n-hexane=80%→100%), and the resulting product was converted into a powder with ethyl acetate-ethyl ether to obtain compound of Example 192 (39.7 mg, 65%) as a white solid.

$^1$H-NMR (CDCl$_3$) δ: 1.17 (3H, d, J=6.9 Hz), 3.02-3.70 (5H, m), 3.80-4.25 (4H, m), 4.32 (1H, m), 4.47 (1H, d, J=13.2 Hz), 4.94 (1H, m), 5.18 (1H, m), 5.30 (1H, m), 5.60 (1H, d, J=13.8 Hz), 5.97 (1H, m), 6.75-7.25 (5H, m), 7.52 (1H, d, J=7.8 Hz).

MS: m/z=623.15 [M]$^+$.

EXAMPLE 193

[Chemical formula 1041]

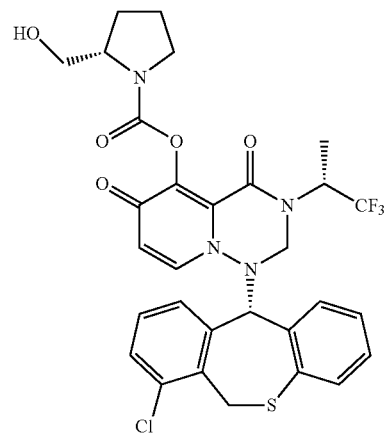

According to Example 192, compound of Example 193 was synthesized by the same procedure.

$^1$H-NMR (CDCl$_3$) δ: 1.17 (3H, d, J=8.1 Hz), 1.80-2.20 (4H, m), 3.50-4.20 (6H, m), 4.20-4.80 (3H, m), 4.92 (1H, m), 5.19 (1H, m), 5.56 (1H, m), 5.61 (1H, d, J=14.1 Hz), 5.97 (1H, d, J=8.4 Hz), 6.60-7.26 (5H, m), 7.53 (1H, d, J=8.4 Hz).

MS: m/z=649.20 [M]$^+$.

EXAMPLE 194

[Chemical formula 1042]

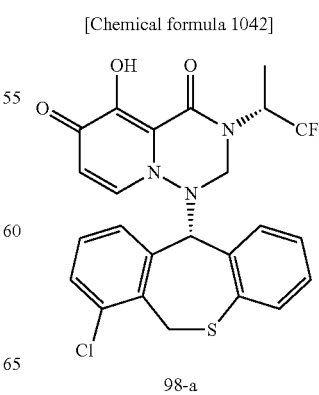

98-a (1H, d, J=13.5 Hz), 5.21 (1H, brs), 5.47-5.62 (2H, m), 5.94 (1H, brs), 6.97-7.24 (7H, m), 7.51 (1H, d, J=7.9 Hz).
MS: m/z=593 [M+H]⁺.

EXAMPLE 196, Example 196-b

[Chemical formula 1044]

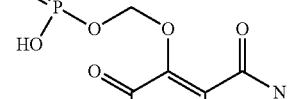

First Step

Compound 106-a (140 mg, 0.323 mmol) was dissolved in DMF (2 mL), and a DMF (1.0 ml) solution of potassium carbonate (89 mg, 0.646 mmol) and dibenzyl chloromethyl phosphate (158 mg, 0.484 mmol) were added at 0° C. under nitrogen stream. The reaction mixed solution was stirred at room temperature for 1 week, and water was added. The mixture was extracted with ethyl acetate (2×20 mL), and the combined organic layers were washed with water and an

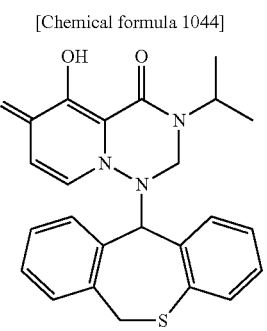

194

To a pyridine (1.0 mL) solution of compound 98-a (50 mg, 0.10 mmol) was added morpholine-4-carbonyl chloride (43 mg, 0.29 mmol), and the mixture was stirred at 50° C. for 10 hours. Thereafter, to the reaction solution were added an aqueous 2N HCl solution and ethyl acetate, the ethyl acetate layer was separated, and the aqueous layer was extracted with ethyl acetate. To the combined extracts was added sodium sulfide to dry them, then the solvent was distilled off, and the resulting oil was purified by silica gel column chromatography. The materials were eluted firstly with chloroform and, then, with chloroform-methanol (97:3, v/v). An objective fraction was concentrated, and washed using diisopropyl ether to obtain 49 mg of compound of Example 194 as a white solid.
¹H-NMR (CDCl₃) δ: 1.19 (3H, d, 7.1 Hz), 3.60-3.81 (8H, m), 4.30 (1H, d, J=14.3 Hz), 4.44 (1H, d, J=13.3 Hz), 4.89 (1H, d, J=14.8 Hz), 5.19 (1H, s), 5.48-5.62 (2H, m), 5.93 (1H, d, J=7.4 Hz), 6.95-7.24 (7H, m), 7.52 (1H, d, J=7.5 Hz).
MS: m/z=635 [M+H]⁺.

EXAMPLE 195

[Chemical formula 1043]

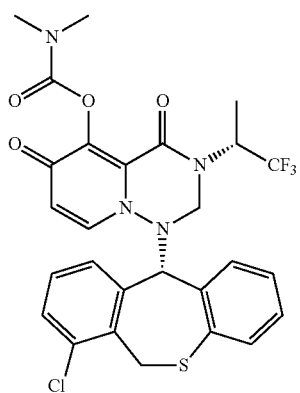

According to Example 194, compound of Example 195 was synthesized by the same procedure.
¹H-NMR (CDCl₃) δ: 1.15 (3H, d, J=6.5 Hz), 2.97-3.18 (6H, m), 4.29 (1H, d, J=13.73 Hz), 4.44 (1H, d, J=13.3 Hz), 4.89 aqueous saturated sodium chloride solution, and dried with sodium sulfate, then filtered, and concentrated under reduced pressure. The residue was purified by silica gel column chromatography (chloroform-methanol=50:1) to obtain compound of Example 196-b.

¹H-NMR (CDCl₃) δ: 1.01 (6H, dd, J=8.90, 6.88 Hz), 3.58 (1H, d, J=13.09 Hz), 4.21 (1H, d, J=13.09 Hz), 4.61-4.73 (2H, m), 5.01-5.10 (5H, m), 5.63 (1H, d, J=13.26 Hz), 5.77 (1H, dd, J=13.26, 5.37 Hz), 5.87-5.95 (2H, m), 6.81-6.85 (2H, m), 7.02-7.08 (2H, m), 7.13-7.42 (15H, m).

Second Step

Compound 196-b (60 mg, 0.083 mmol) was dissolved in a mixed solvent of THF (2 mL) and methanol (2 mL), and 10%-palladium-carbon (10 mg) was added. Under hydrogen stream, the mixture was stirred at room temperature for 2 hours, and filtered with celite. The filtrate was purified by preparative HPLC to obtain objective compound of Example 196. (18 mg, 40%)

¹H-NMR (DMSO-d₆) δ: 1.01 (6H, dd, J=14.64, 6.86 Hz), 3.90 (1H, d, J=13.27 Hz), 4.32 (1H, d, J=13.57 Hz), 4.59-4.71 (1H, m), 5.01 (1H, d, J=13.42 Hz), 5.43-5.62 (4H, m), 6.17 (1H, d, J=7.63 Hz), 6.80-6.89 (1H, m), 6.91-6.99 (1H, m), 7.07-7.14 (2H, m), 7.27 (1H, t, J=6.63 Hz), 7.38-7.52 (4H, m).

EXAMPLE 197, Example 197-b

[Chemical formula 1045]

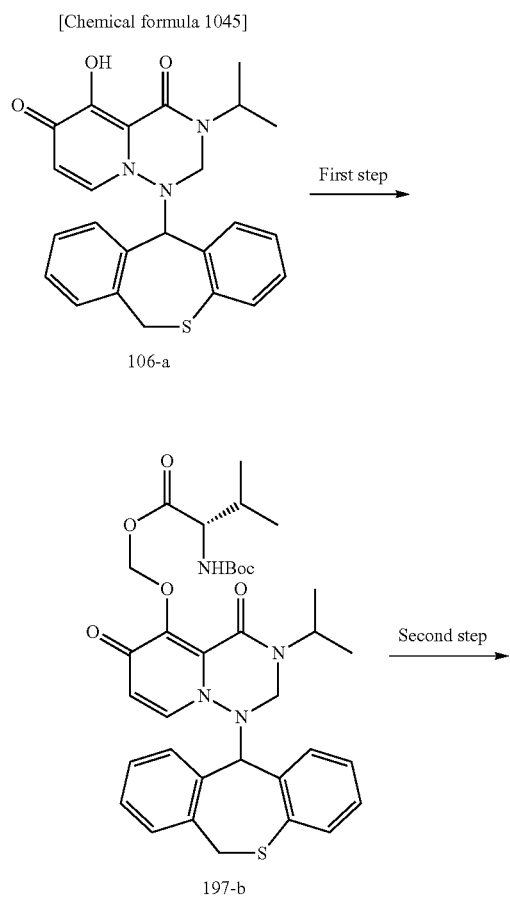

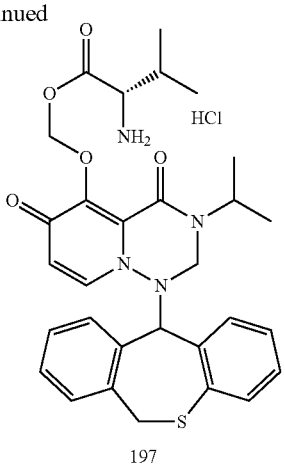

First Step

To an acetone (3 ml) solution of (S)-chloromethyl 2-(tert-butoxycarbonylamino)-3-d cesium carbonate (138 mg, 0.519 mmol) was added sodium iodide (390 mg, 2.6 mmol) at room temperature under nitrogen stream, and the mixture was stirred for 20 hours. After filtration, the filtrate was concentrated under reduced pressure, a 10%-aqueous sodium thiosulfate solution was added to the residue, and the mixture was extracted with ethyl acetate (30 mL). The organic layer was washed with water, dried with sodium sulfate, and filtered, then concentrated under reduced pressure. The residue was dissolved in acetone (0.5 mL), compound 106-a (100 mg, 0.231 mmol) and cesium carbonate (169 mg, 0.52 mmol) were added to the mixture stirred for 30 minutes in acetone (2.5 ml) under nitrogen stream under ice-cooling. This reaction mixture was stirred at room temperature for 4 hours, and concentrated under reduced pressure, and then water was added. The mixture was extracted with ethyl acetate (2×30 mL), and the combined organic layers were washed with water and an aqueous saturated sodium chloride solution, and dried with sodium sulfate, then filtered, and concentrated under reduced pressure. The residue was purified by silica gel column chromatography (chloroform-methanol=50:1) to obtain compound of Example 197-b. (130 mg, 85%)

¹H-NMR (CDCl₃) δ: 0.90-1.11 (12H, m), 1.44 (9H, d, J=9.00 Hz), 2.20-2.41 (1H, m), 3.59 (1H, d, J=13.27 Hz), 4.27-4.43 (2H, m), 4.76-4.86 (2H, m), 5.10-5.29 (2H, m), 5.68 (1H, dd, J=13.27, 2.44 Hz), 5.81-6.17 (3H, m), 6.80-6.94 (2H, m), 7.03-7.15 (2H, m), 7.20-7.44 (5H, m).

MS: m/z=668.05 [M+H]⁺.

Second Step

Compound 197-b (130 mg, 0.196 mmol) was dissolved in ethyl acetate (4 ml), a 4N hydrochloric acid ethyl acetate solution (4 ml, 16.00 mmol) was added at room temperature, and the mixture was stirred for 3 hours. After concentration under reduced pressure, the residue was diluted with ether, and the solid was filtered to obtain hydrochloride of compound of Example 197. (85 mg, 72.3%)

¹H-NMR (DMSO-d₆) δ: 0.96-1.05 (11H, m), 2.22-2.28 (1H, m), 3.90 (2H, d, J=12.36 Hz), 4.28 (1H, d, J=13.73 Hz), 4.55-4.65 (1H, m), 4.90-4.99 (1H, m), 5.30 (1H, d, J=7.42 Hz), 5.63 (1H, d, J=13.46 Hz), 5.86-5.89 (4H, m), 6.87-6.96 (2H, m), 7.07-7.16 (2H, m), 7.27-7.32 (2H, m), 7.44-7.49 (3H, m), 8.42 (3H, s).

MS: m/z=563.25 [M+H]⁺.

EXAMPLE 198

[Chemical formula 1046]

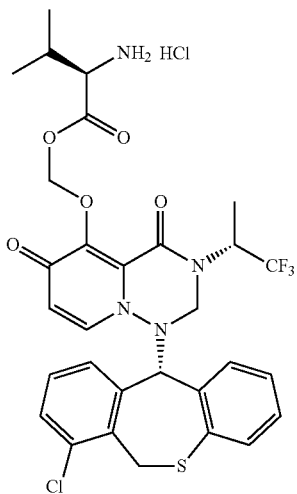

According to Example 197, compound of Example 198 was synthesized by the same procedure.
MS: m/z=651 [M+H]⁺.

EXAMPLE 199

[Chemical formula 1047]

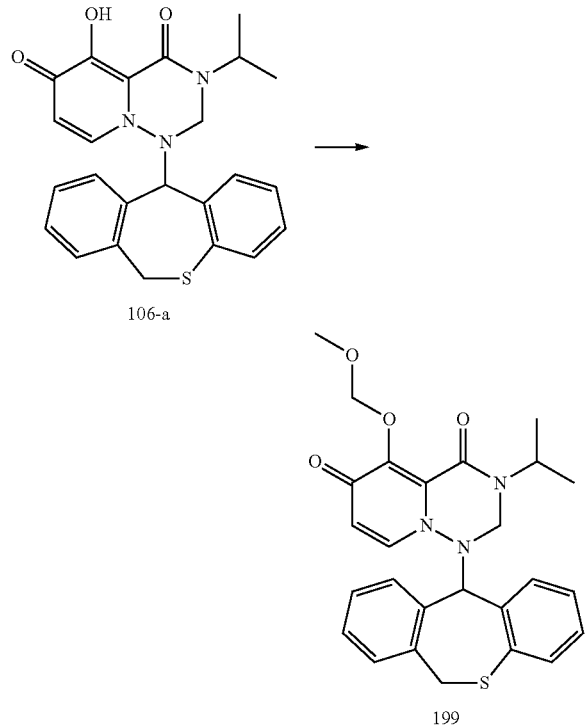

A DMF (1 ml) solution of compound 106-a (33 mg, 0.076 mmol) and triethylamine (24 mg, 0.235 mmol) was cooled to 1 to 3° C., and chloromethyl methyl ether (12.6 mg, 0.157 mmol) was added dropwise while the same temperature was retained. After the reaction solution was stirred at the same temperature for 30 minutes, water was added, and the mixture was extracted with ethyl acetate three times. The extract was washed with water three times, and dried with sodium sulfate, then the solvent was distilled off. The resulting solid was washed with ethyl-diisopropyl ether to obtain 22 mg of compound of Example 199.

$^1$H-NMR (CDCl$_3$) δ: 1.08 (3H, d, J=7.2 Hz), 1.11 (3H, d, J=7.2 Hz), 3.59 (1H, d, J=13.2 Hz), 3.64 (3H, s), 4.32 (1H, d, J=12.9 Hz), 4.77-4.85 (2H, m), 5.14 (1H, s), 5.32 (1H, d, J=6.0 Hz), 5.50 (1H, d, J=6.0 Hz), 5.70 (1H, d, J=13.2 Hz), 5.90 (1H, d, J=6.9 Hz), 6.77-6.84 (2H, m), 7.05-7.07 (2H, m), 7.18-7.28 (3H, m), 7.33-7.43 (2H, m).

EXAMPLE 200

[Chemical formula 1048]

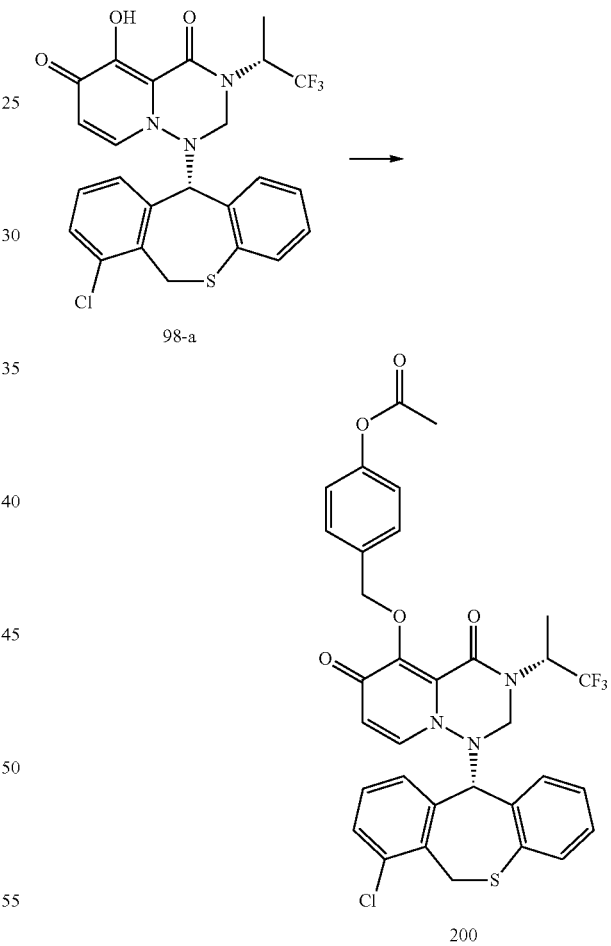

A DMF (1 ml) solution of 4-(hydroxymethyl)phenyl acetate (53 mg, 0.287 mmol) and sodium iodide (72 mg, 0.48 mmol) was stirred at room temperature for 30 minutes. To the reaction solution were added potassium carbonate (66 mg, 0.48 mmol) and compound 98-a (50 mg, 0.0958 mmol), and the mixture was further stirred at the same temperature for 5 hours. The reaction solution was diluted with ethyl acetate (10 ml), and water was added. The organic layer was separated, and the aqueous layer was extracted with ethyl acetate once. The extract was washed with water three times, and dried with sodium sulfate, and the solvent was distilled off. The resulting crude product was purified by silica gel column chromatography. The materials were eluted firstly with ethyl acetate and, then, with ethyl acetate-methanol (7:3, v/v). Concentration of an objective fraction afforded 34 mg of compound of Example 200 as a solid.

¹H-NMR (CDCl₃) δ: 1.16 (3H, d, J=7.2 Hz), 2.28 (3H, s), 4.29 (1H, d, J=13.8 Hz), 4.38 (1H, d, J=13.2 Hz), 4.81 (1H, d, J=12.9 Hz), 5.08 (1H, s), 5.45 (1H, d, J=10.8 Hz), 5.52-5.61 (2H, m), 5.87 (1H, d, J=7.5 Hz), 6.57 (1H, d, J=7.5 Hz), 6.73-6.79 (1H, m), 7.04-7.20 (7H, m), 7.51 (1H, d, J=7.2 Hz), 7.57 (2H, d, J=8.4 Hz).

EXAMPLE 201

[Chemical formula 1049]

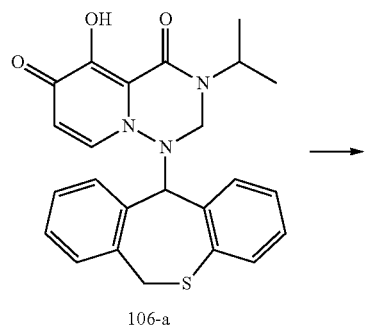

106-a

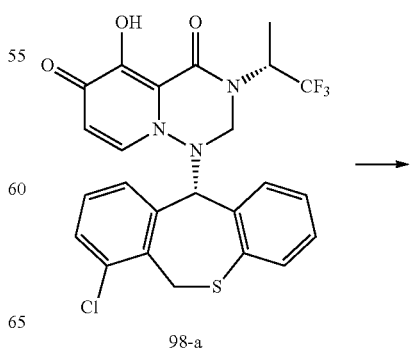

201

First Step

Compound 106-a (80.0 mg, 0.185 mmol) synthesized according to Example and 4-(chloromethyl)-5-methyl-1,3-dioxol-2-one (41.1 mg, 0.277 mmol) were dissolved in DMF (1 ml), potassium carbonate (93.0 mg, 0.673 mmol) was added, and the mixture was stirred at 50° C. for 2 hours. To the reaction solution was added water, the mixture was extracted with ethyl acetate, and the organic layer was washed with water, and dried with sodium sulfate. The solvent was distilled off under reduced pressure, and the resulting crude product was purified by silica gel column chromatography, and eluted with chloroform-methanol (95:5, v/v). Dichloromethane-diethyl ether were added, and the mixture was solidified to obtain 60 mg of compound of Example 201 as a white solid.

¹H-NMR (DMSO-d₆) δ: 1.00 (6H, s), 2.10 (3H, s), 3.89 (1H, d, J=13.1 Hz), 4.25 (1H, d, J=12.7 Hz), 4.59 (1H, m), 4.90-5.04 (3H, m), 5.27 (1H, s), 5.62 (1H, d, J=13.3 Hz), 5.83 (1H, d, J=4.9 Hz), 6.91-7.44 (9H, m).

MS: m/z=546 [M+H]⁺.

EXAMPLE 202

[Chemical formula 1050]

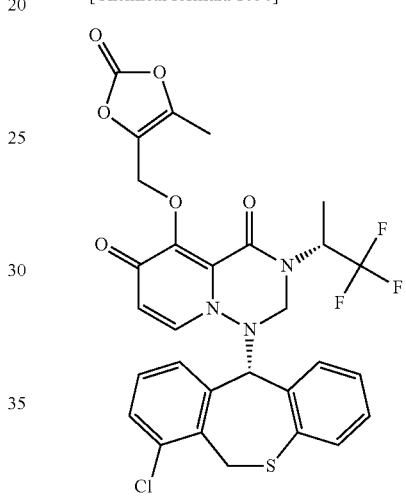

¹H-NMR (CDCl₃) δ: 1.18 (3H, d, J=7.2 Hz), 2.18 (3H, s), 4.33 (1H, d, J=13.8 Hz), 4.43 (1H, d, J=13.2 Hz), 4.86 (1H, d, J=13.5 Hz), 5.15 (1H, d, J=13.5 Hz), 5.17 (1H, s), 5.35 (1H, d, J=13.8 Hz), 5.48-5.59 (2H, m), 5.94 (1H, d, J=13.8 Hz), 6.77 (1H, d, J=7.5 Hz), 6.86-6.91 (1H, m), 7.07-7.26 (5H, m), 7.50-7.53 (1H, m).

EXAMPLE 203

[Chemical formula 1051]

98-a

-continued

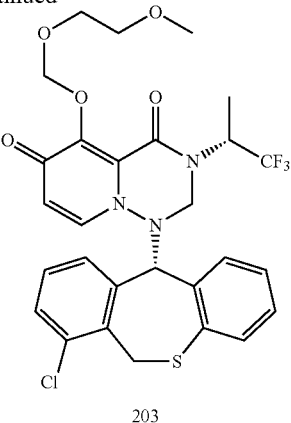

203

A DMF (1.0 mL) solution of compound 98-a (50 mg, 0.10 mmol) was ice-cooled, and triethylamine (0.040 ml, 0.29 mmol) and 1-(chloromethoxy)-2-methoxyethane (24 mg, 0.19 mmol) were added, and the mixture was stirred for 1 hour under ice-cooling, then stirred at room temperature overnight. Thereafter, to the reaction solution were added water and ethyl acetate, the ethyl acetate layer was separated, and the aqueous layer was extracted with ethyl acetate. The combined extracts were washed with water and brine, and then sodium sulfide was added to dry them. The solvent was distilled off, and the resulting oil was purified by silica gel column chromatography. The materials were eluted firstly with chloroform and, then, with chloroform-methanol (97:3, v/v). An objective fraction was concentrated, and washed using diisopropyl ether to obtain 18 mg of compound of Example 203 as a white solid.

$^1$H-NMR (CDCl$_3$) δ: 1.19 (3H, d, 7.6 Hz), 3.36 (3H, s), 3.51-3.55 (2H, m), 3.93-4.00 (2H, m), 4.32 (1H, d, 14.2 Hz), 4.43 (1H, d, J=13.3 Hz), 4.88 (1H, d, J=12.8 Hz), 5.14 (1H, s), 5.55-5.66 (3H, m), 5.90 (1H, d, J=7.8 Hz), 6.73-6.85 (2H, m), 7.09-7.22 (5H, m), 7.53 (1H, d, J=8.9 Hz).

MS: m/z=610 [M+H]$^+$.

EXAMPLE 204

[Chemical formula 1052]

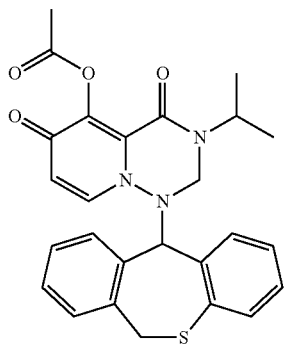

$^1$H-NMR (CDCl$_3$) δ: 1.06 (3H, d, J=7.1 Hz), 1.09 (3H, d, J=7.1 Hz), 2.43 (3H, s), 3.59 (1H, d, J=13.5 Hz), 4.34 (1H, d, J=13.2 Hz), 4.70-4.86 (2H, m), 5.14 (1H, s), 5.70 (1H, d, J=13.5 Hz), 5.94 (1H, d, J=7.7 Hz), 6.81-6.92 (2H, m), 7.03-7.08 (2H, m), 7.15-7.26 (3H, m), 7.32-7.44 (2H, m).

MS: m/z=476 [M+H]$^+$.

EXAMPLE 205

[Chemical formula 1053]

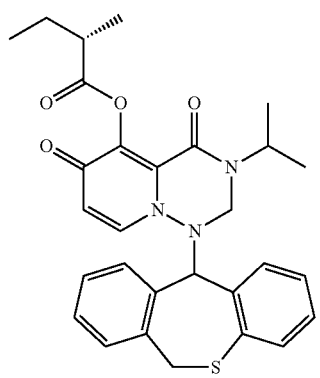

$^1$H-NMR (CDCl$_3$) δ: 1.02-1.15 (9H, m), 1.39 (3H, d, J=6.9 Hz), 1.58-1.72 (1H, m), 1.90-2.05 (1H, m), 2.71-2.84 (1H, m), 3.59 (1H, d, J=13.2 Hz), 4.34 (1H, d, J=12.9 Hz), 4.69-4.90 (2H, m), 5.15 (1H, s), 5.70 (1H, d, J=12.9 Hz), 5.86-5.98 (1H, m), 6.76-6.99 (2H, m), 7.04-7.10 (2H, m), 7.15-7.29 (3H, m), 7.32-7.44 (2H, m).

MS: m/z=518 [M+H]$^+$.

EXAMPLE 206

[Chemical formula 1054]

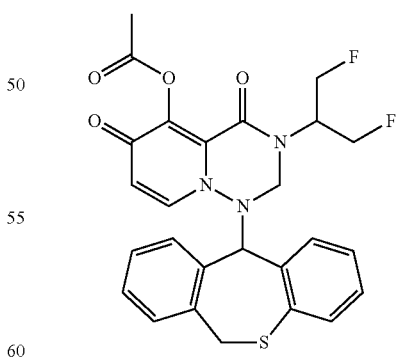

$^1$H-NMR (CDCl$_3$) δ: 2.41 (3H, s), 3.58 (1H, d, J=13.5 Hz), 4.41-4.87 (6H, m), 5.07 (1H, d, J=13.2 Hz), 5.26 (1H, s), 5.65 (1H, d, J=13.5 Hz), 5.97 (1H, d, J=7.7 Hz), 6.80-6.92 (2H, m), 7.04-7.10 (2H, m), 7.25-7.45 (5H, m).

MS: m/z=512 [M+H]$^+$.

EXAMPLE 207

[Chemical formula 1055]

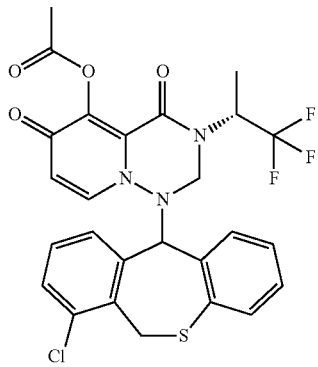

¹H-NMR (CDCl₃) δ: 1.20 (3H, d, J=7.3 Hz), 2.44 (3H, s), 4.32 (1H, d, J=13.9 Hz), 4.46 (1H, d, J=13.3 Hz), 4.93 (1H, d, J=13.3 Hz), 5.16 (1H, s), 5.45-5.58 (1H, m), 5.61 (1H, d, J=13.9 Hz), 5.97 (1H, d, J=7.9 Hz), 6.80-6.94 (2H, m), 7.05-7.13 (3H, m), 7.15-7.24 (2H, m), 7.53 (1H, d, J=7.8 Hz).
MS: m/z=564 [M+H]⁺.

EXAMPLE 208

[Chemical formula 1056]

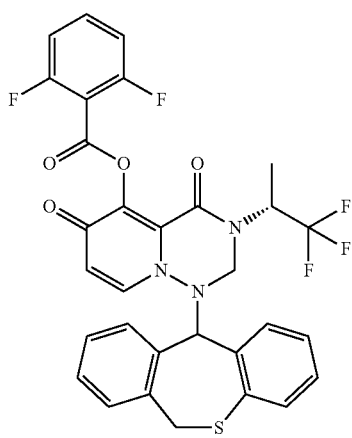

¹H-NMR (CDCl₃) δ: 1.13 (3H, d, J=7.3 Hz), 3.63 (1H, d, J=13.4 Hz), 4.48 (1H, d, J =13.1 Hz), 4.95 (1H, d, J=13.0 Hz), 5.17 (1H, s), 5.44-5.58 (1H, m), 5.65 (1H, d, J=13.0 Hz), 6.02 (1H, d, J=7.9 Hz), 6.90-7.61 (12H, m).
MS: m/z=628 [M+H]⁺.

EXAMPLE 209

[Chemical formula 1057]

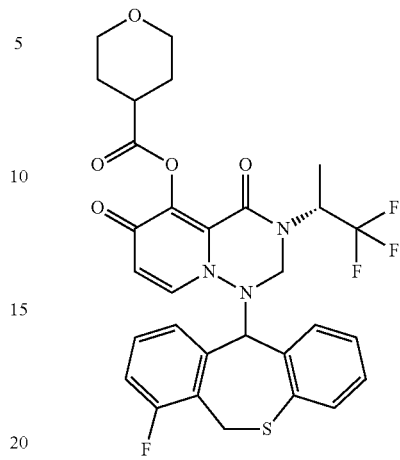

¹H-NMR (CDCl₃) δ: 1.16 (3H, d, J=7.4 Hz), 1.99-2.15 (4H, m), 2.93-3.06 (1H, m), 3.47-3.58 (2H, m), 4.01-4.16 (3H, m), 4.45 (1H, d, J=13.2 Hz), 4.93 (1H, d, J=13.5 Hz), 5.18 (1H, s), 5.35 (1H, d, J=14.0 Hz), 5.43-5.56 (1H, m), 5.95 (1H, d, J=7.7 Hz), 6.82-7.02 (3H, m), 7.06-7.15 (2H, m), 7.19-7.26 (3H, m).
MS: m/z=618 [M+H]⁺.

EXAMPLE 210

[Chemical formula 1058]

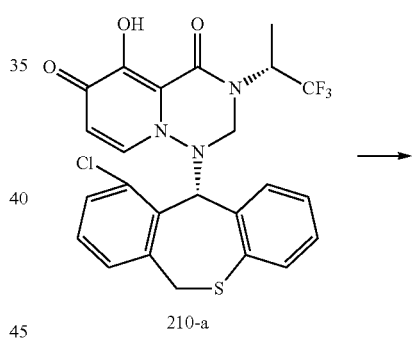

210-a

→

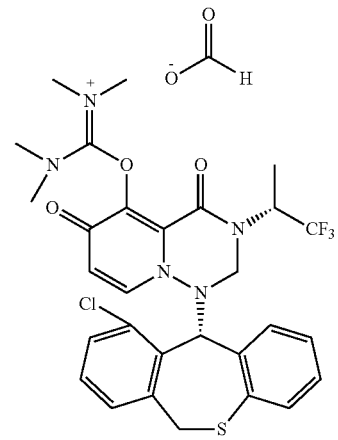

210

Step

To compound 210-a (101 mg, 0.193 mmol) were added dimethylformamide (1 mL), HATU (50 mg, 0.148 mmol)

and N-methylmorpholine (0.041 mL, 0.370 mmol), and the mixture was stirred at room temperature for 6 hours. The reaction solution was purified by preparative LCMS (method 14) to obtain compound of Example 210 (50 mg, yield 51%).

$^1$H-NMR (DMSO-$d_6$) δ: 7.53 (s, 1H), 7.47 (s, 3H), 7.20 (s, 2H), 6.99 (s, 1H), 6.87 (s, 1H), 6.17 (s, 1H), 5.83 (s, 1H), 5.61 (d, J=13.0 Hz, 1H), 5.50 (s, 1H), 5.24 (d, J=13.0 Hz, 1H), 4.67 (d, J=13.0 Hz, 1H), 4.04 (d, J=11.0 Hz, 1H), 3.10 (s, 6H), 3.05 (s, 6H), 1.09 (s, 3H).

MS: m/z=620 [M+H]$^+$. RT=1.73 min.

EXAMPLE 211

[Chemical formula 1059]

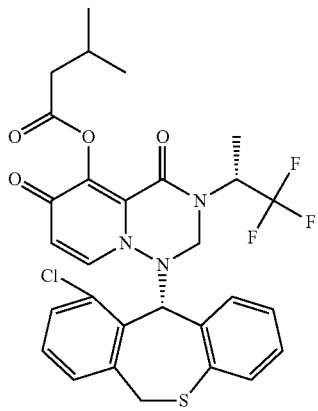

MS: m/z=645 [M+H]$^+$. RT=2.53 min.

EXAMPLE 212

[Chemical formula 1060]

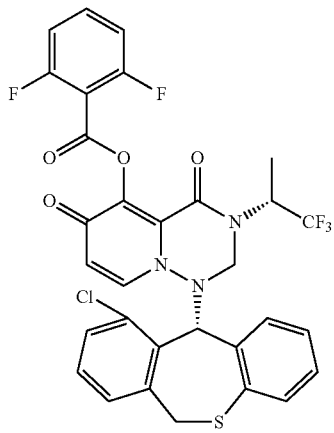

MS: m/z=662 [M+H]$^+$. RT=2.35 min.

EXAMPLE 213

[Chemical formula 1061]

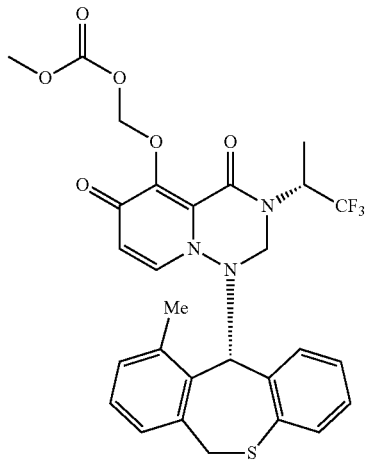

MS: m/z=590 [M+H]$^+$. RT=2.17 min.

EXAMPLE 214

[Chemical formula 1062]

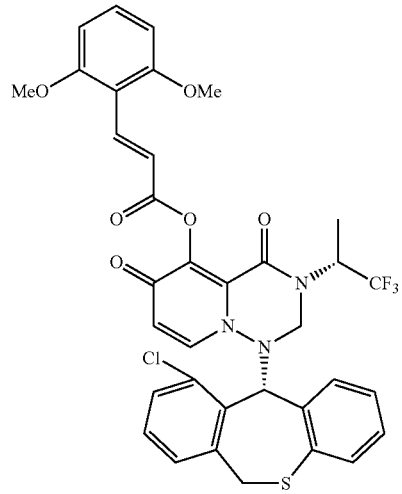

MS: m/z=712 [M+H]$^+$. RT=2.52 min.

EXAMPLE 215
[Chemical formula 1063]
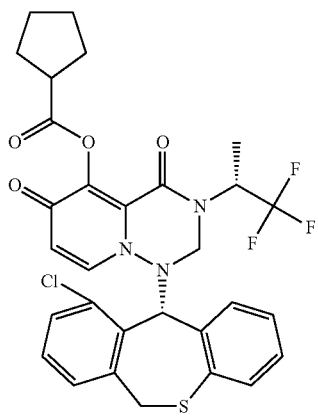
MS: m/z=618 [M+H]⁺. RT=2.56 min.
EXAMPLE 216
[Chemical formula 1064]
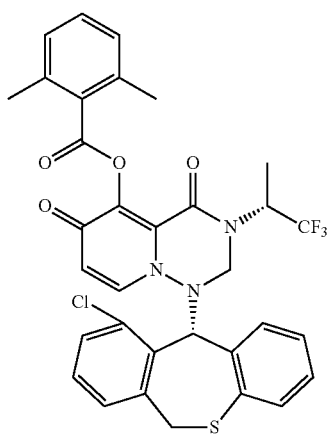
MS: m/z=654 [M+H]⁺. RT=2.71 min.
EXAMPLE 217
[Chemical formula 1065]
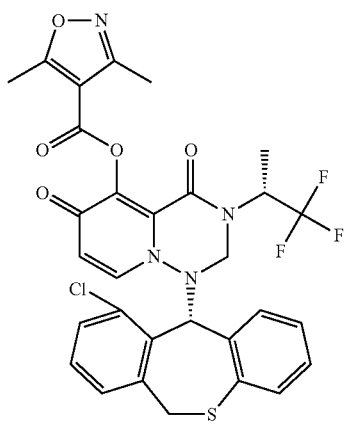
MS: m/z=645 [M+H]⁺. RT=2.35 min.
EXAMPLE 218
[Chemical formula 1066]
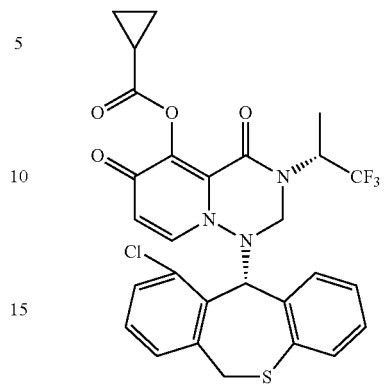
MS: m/z=590 [M+H]⁺. RT=2.19 min.
EXAMPLE 219
[Chemical formula 1067]
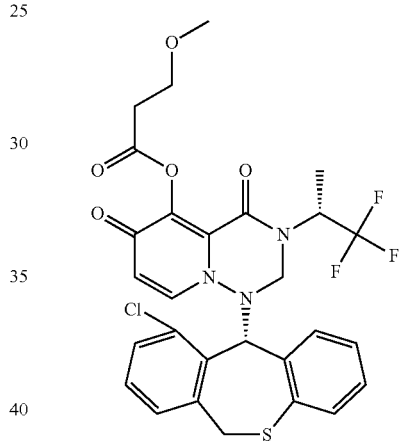
MS: m/z=608 [M+H]⁺. RT=2.17 min.
EXAMPLE 220
[Chemical formula 1068]
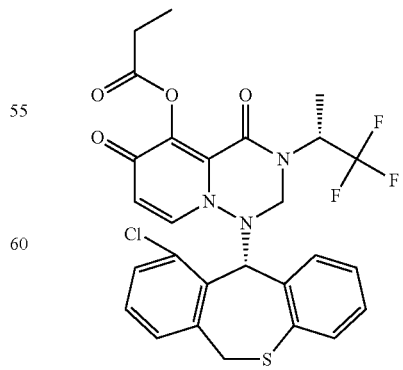
MS: m/z=578 [M+H]⁺. RT=2.23 min.

EXAMPLE 221
[Chemical formula 1069]
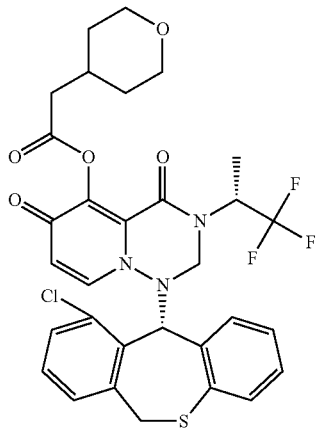
MS: m/z=648 [M+H]⁺. RT=2.24 min.
EXAMPLE 222
[Chemical formula 1070]
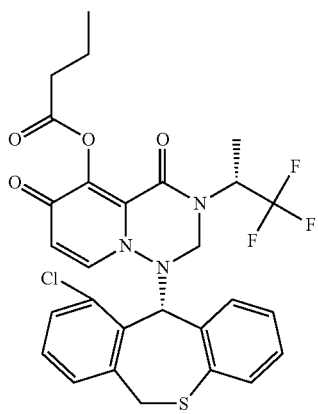
MS: m/z=592 [M+H]⁺. RT=2.38 min.
EXAMPLE 223
[Chemical formula 1071]
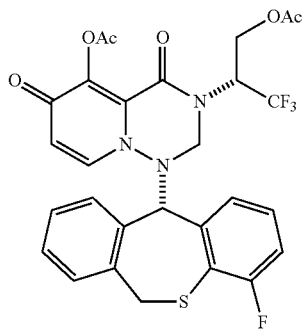
MS: m/z=606 [M+H]⁺. RT=2.10 min.
EXAMPLE 224
[Chemical formula 1072]
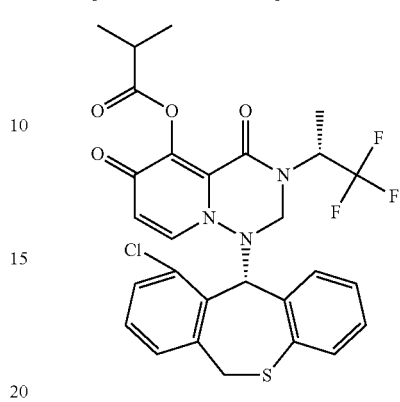
MS: m/z=592 [M+H]⁺. RT=2.38 min.
EXAMPLE 225
[Chemical formula 1073]
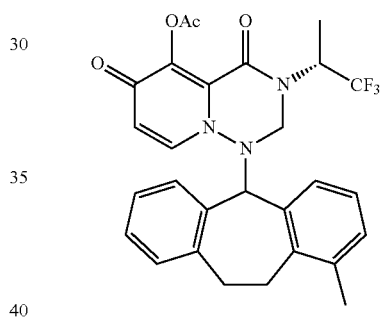
MS: m/z=526 [M+H]⁺. RT=2.27 min.
EXAMPLE 226
[Chemical formula 1074]
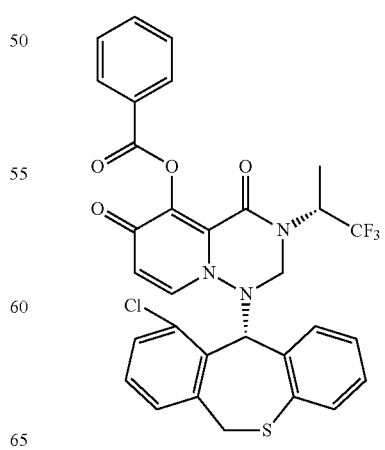
MS: m/z=626 [M+H]⁺. RT=2.38 min.

EXAMPLE 227
[Chemical formula 1075]
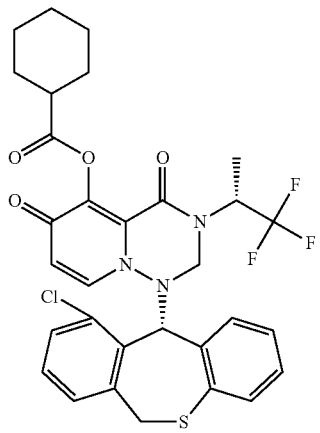
MS: m/z=632 [M+H]⁺. RT=2.69 min.
EXAMPLE 228
[Chemical formula 1076]
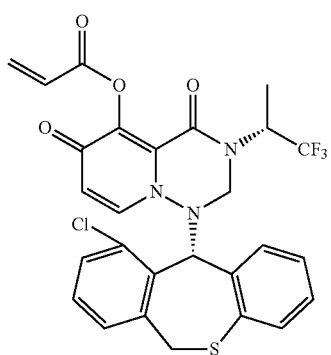
MS: m/z=576.11 [M+H]⁺.
EXAMPLE 229
[Chemical formula 1077]
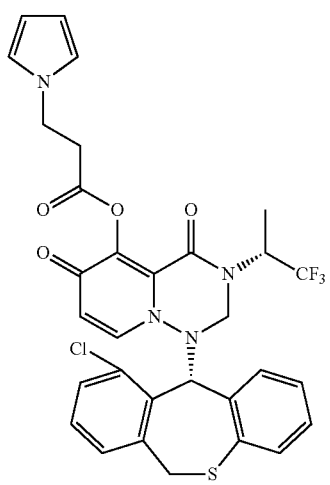
MS: m/z=643.88 [M+H]⁺.
EXAMPLE 230
[Chemical formula 1078]
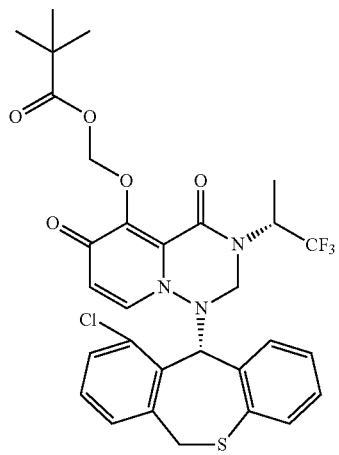
MS: m/z=636.88 [M+H]⁺.
EXAMPLE 231
[Chemical formula 1079]
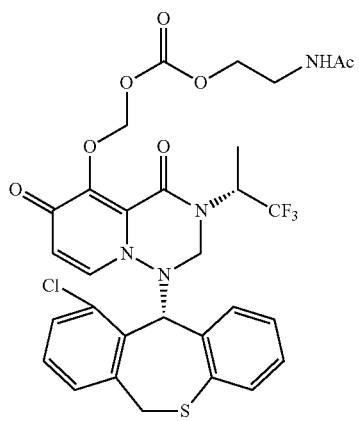
MS: m/z=681.26 [M+H]⁺.
EXAMPLE 232
[Chemical formula 1080]
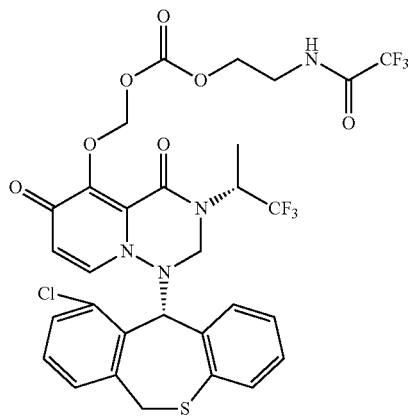
MS: m/z=735.19 [M+H]⁺.

EXAMPLE 233
[Chemical formula 1081]
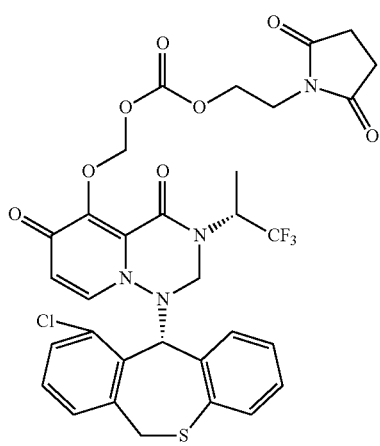
MS: m/z=721.22 [M+H]+.
EXAMPLE 234
[Chemical formula 1082]
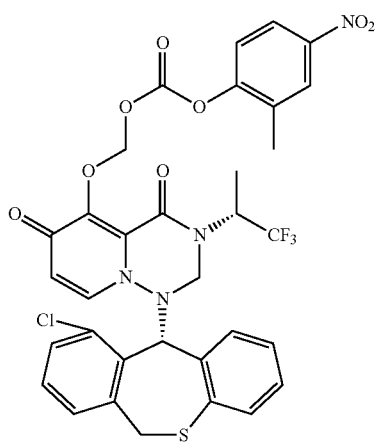
MS: m/z=731.19 [M+H]+.
EXAMPLE 235
[Chemical formula 1083]
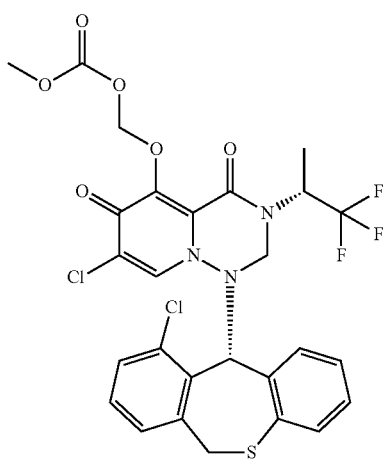
1H-NMR (CDCl3) δ: 1.09 (d, J=7.2 Hz, 3H), 3.65 (d, J=13.8 Hz, 1H), 3.82 (s, 3H), 4.39 (d, J=13.2 Hz, 1H), 4.87 (d, J=13.2 Hz, 1H), 5.52 (m, 1H), 5.63 (d, J=13.8 Hz, 1H), 5.88 (d, J=6.6 Hz, 1H), 5.94 (s, 1H), 6.00 (d, J=6.6 Hz, 1H), 6.88-6.98 (m, 2H), 7.14-7.19 (m, 2H), 7.27-7.38 (m, 3H), 7.52 (s, 1H).
MS: m/z=644.2 [M+H]+.
EXAMPLE 236
[Chemical formula 1084]
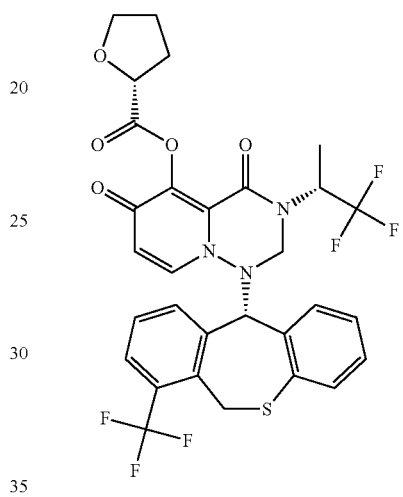
MS: m/z=654 [M+H]+.
EXAMPLE 237
[Chemical formula 1085]
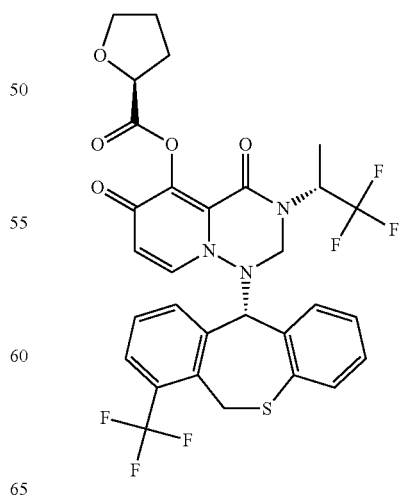
MS: m/z=654 [M+H]+.

EXAMPLE 238

[Chemical formula 1086]

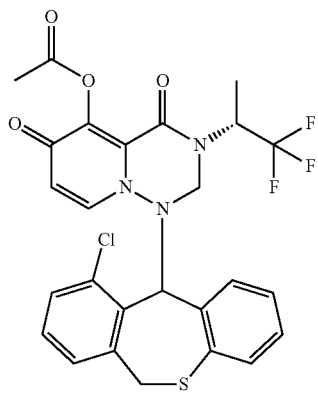

MS: m/z=564.15 [M+H]+.

EXAMPLE 239

[Chemical formula 1087]

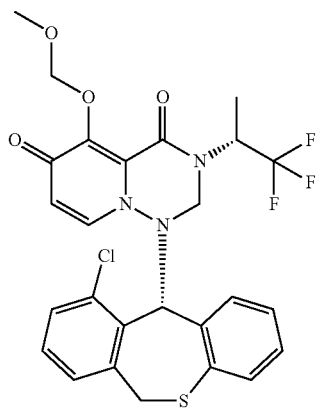

$^1$H-NMR (CDCl$_3$) δ: 1.09 (d, J=7.1 Hz, 3H), 3.55 (s, 3H), 3.63 (d, J=13.5 Hz, 1H), 4.40 (d, J=13.2 Hz, 1H), 4.87 (d, J=13.2 Hz, 1H), 5.26 (d, J=6.0 Hz, 1H), 5.51-5.70 (m, 3H), 5.89-5.95 (m, 2H), 6.84-6.89 (m, 2H), 7.07-7.20 (m, 3H), 7.26-7.37 (m, 3H).

EXAMPLE 240

[Chemical formula 1088]

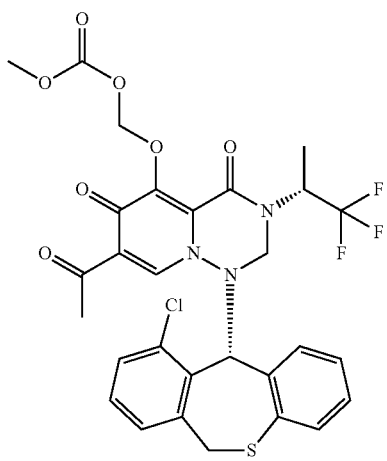

$^1$H-NMR (CDCl$_3$) δ: 1.10 (d, J=7.1 Hz, 3H), 2.48 (s, 3H), 3.63 (d, J=13.5 Hz, 1H), 3.83 (s, 3H), 4.41 (d, J=13.2 Hz, 1H), 4.87 (d, J=13.2 Hz, 1H), 5.47-5.58 (m, 1H), 5.68 (d, J=13.5 Hz, 1H), 5.87 (d, J=6.6 Hz, 1H), 5.93 (s, 1H), 6.01 (d, J=6.6 Hz, 1H), 6.84-6.91 (m, 1H), 6.95 (d, J=7.4 Hz, 1H), 7.05-7.15 (m, 2H), 7.25-7.38 (m, 3H), 7.93 (s, 1H).

EXAMPLE 241

[Chemical formula 1089]

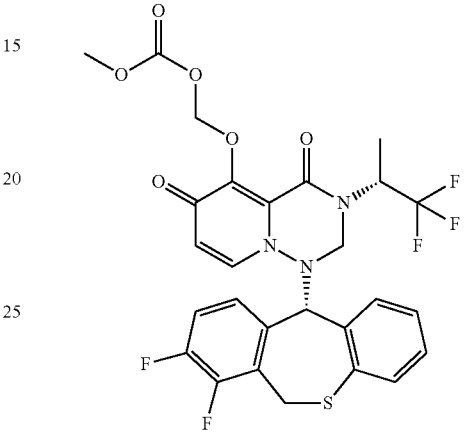

$^1$H-NMR (CDCl$_3$) δ: 1.21 (d, J=7.1 Hz, 3H), 3.83 (s, 3H), 4.11 (d, J=13.7 Hz, 1H), 4.42 (d, J=13.2 Hz, 1H), 4.91 (d, J=13.2 Hz, 1H), 5.13 (s, 1H), 5.40 (dd, J=13.7, 2.6 Hz, 1H), 5.49-5.59 (m, 1H), 5.87 (d, J=6.6 Hz, 1H), 5.93-5.96 (m, 2H), 6.79 (d, J=7.4 Hz, 1H), 6.84-6.91 (m, 1H), 6.97 (dd, J=8.7, 4.3 Hz, 1H), 7.04-7.15 (m, 3H), 7.26 (d, J=4.7 Hz, 1H).

LCMS measurement conditions of compounds of Reference examples and Examples are described below.

1) Conditions for the case where not specifically stated;
Column: ACQUITY UPLC(R)BEH C18 (1.7 μm i.d. 2.1×50 mm) (Waters)
Flow rate: 0.8 mL/min.
UV detection wavelength: 254 nm
Mobile phase: an aqueous solution containing 0.1% formic acid for [A], an acetonitrile solution containing 0.1% formic acid for [B]
Gradient: a linear gradient of 10% to 100% solvent [B] was performed over 3.5 minutes, and 100% solvent [B] was retained for 0.5 minutes.

2) Method 6;
Column: Gemini-NX (5 μm, i.d. 4.6×50 mm) (Phenomenex)
Flow rate: 3 mL/min.
UV detection wavelength: 254 nm
Mobile phase: an aqueous solution containing 0.1% formic acid for [A], an acetonitrile solution containing 0.1% formic acid for [B]
Gradient: a linear gradient of 5% to 100% solvent [B] was performed over 3.5 minutes, and 100% solvent [B] was retained for 0.5 minutes.

3) Method 14;
Column: Gemini-NX (C18, 5 μm, AXIA Packed, i.d. 21.2×50 mm) (Phenomenex)
Flow rate: 25 mL/min.
UV detection wavelength: 254 nm Mobile phase: an aqueous solution containing 0.1% formic acid for [A], an acetonitrile solution containing 0.1% formic acid for [B]
Gradient:
Narrow Gradient (6 min): a linear gradient of X % to Y % solvent [B] was performed over 4 minutes, and 100% solvent [B] was retained for 1 minute.
  Intermediate compound i-7: X=35, Y=55
  Intermediate compound i-10: X=30, Y=50
  Intermediate compound i-14: X=30, Y=50
  Example 210: X=20, Y=40
Standard Gradient (7 min): a linear gradient of 10% to 100% solvent [B] was performed over 5 minutes, and 100% solvent [B] was retained for 1 minute.

Further, the following combinations of substituents can be also synthesized by the method described in the above Reference examples and Examples, and are a preferable embodiment of the present invention.

Compounds in which, in the following formula (I):

[Chemical formula 1090]

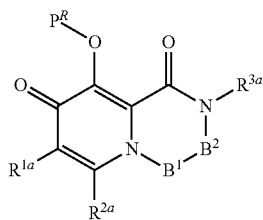

(I)

combinations of $R^{3a}$ and $R^{7a}$ of the following formulae (I-A) and (I-B):

[Chemical formula 1091]

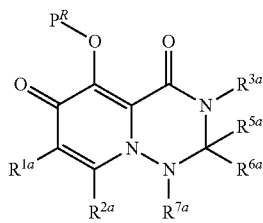

(I-A)

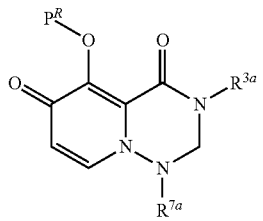

(I-B)

(wherein $P^R$ is same as that of item 1)
are selected from the following Tables 15 to 20, respectively.
Combinations of ($R^{3a}$, $R^{7a}$)
(R3-1, R7-1), (R3-1, R7-2), (R3-1, R7-3), (R3-1, R7-4), (R3-1, R7-5), (R3-1, R7-6), (R3-1, R7-7), (R3-1, R7-8), (R3-1, R7-9), (R3-1, R7-10), (R3-1, R7-11), (R3-1, R7-12), (R3-1, R7-13), (R3-1, R7-14), (R3-1, R7-15), (R3-1, R7-16), (R3-1, R7-17), (R3-1, R7-18), (R3-1, R7-19), (R3-1, R7-20), (R3-1, R7-21), (R3-1, R7-22), (R3-1, R7-23), (R3-1, R7-24), (R3-1, R7-25), (R3-1, R7-26), (R3-1, R7-27), (R3-1, R7-28), (R3-1, R7-29), (R3-1, R7-30), (R3-1, R7-31), (R3-1, R7-32), (R3-1, R7-33), (R3-1, R7-34), (R3-1, R7-35), (R3-1, R7-36), (R3-1, R7-37), (R3-1, R7-38), (R3-1, R7-39), (R3-1, R7-40), (R3-1, R7-41), (R3-1, R7-42), (R3-1, R7-43), (R3-1, R7-44), (R3-1, R7-45), (R3-1, R7-46), (R3-1, R7-47), (R3-1, R7-48), (R3-1, R7-49), (R3-1, R7-50), (R3-1, R7-51), (R3-1, R7-52), (R3-1, R7-53), (R3-1, R7-54), (R3-1, R7-55), (R3-1, R7-56), (R3-1, R7-57), (R3-1, R7-58), (R3-1, R7-59), (R3-1, R7-60), (R3-1, R7-61), (R3-1, R7-62), (R3-1, R7-63), (R3-1, R7-64), (R3-1, R7-65), (R3-1, R7-66), (R3-1, R7-67), (R3-1, R7-68), (R3-1, R7-69), (R3-1, R7-70), (R3-1, R7-71), (R3-1, R7-72), (R3-1, R7-73), (R3-1, R7-74), (R3-1, R7-75), (R3-1, R7-76), (R3-1, R7-77),
(R3-2, R7-1), (R3-2, R7-2), (R3-2, R7-3), (R3-2, R7-4), (R3-2, R7-5), (R3-2, R7-6), (R3-2, R7-7), (R3-2, R7-8), (R3-2, R7-9), (R3-2, R7-10), (R3-2, R7-11), (R3-2, R7-12), (R3-2, R7-13), (R3-2, R7-14), (R3-2, R7-15), (R3-2, R7-16), (R3-2, R7-17), (R3-2, R7-18), (R3-2, R7-19), (R3-2, R7-20), (R3-2, R7-21), (R3-2, R7-22), (R3-2, R7-23), (R3-2, R7-24), (R3-2, R7-25), (R3-2, R7-26), (R3-2, R7-27), (R3-2, R7-28), (R3-2, R7-29), (R3-2, R7-30), (R3-2, R7-31), (R3-2, R7-32), (R3-2, R7-33), (R3-2, R7-34), (R3-2, R7-35), (R3-2, R7-36), (R3-2, R7-37), (R3-2, R7-38), (R3-2, R7-39), (R3-2, R7-40), (R3-2, R7-41), (R3-2, R7-42), (R3-2, R7-43), (R3-2, R7-44), (R3-2, R7-45), (R3-2, R7-46), (R3-2, R7-47), (R3-2, R7-48), (R3-2, R7-49), (R3-2, R7-50), (R3-2, R7-51), (3-2, R7-52), (R3-2, R7-53), (R3-2, R7-54), (R3-2, R7-55), (R3-2, R7-56), (R3-2, R7-57), (R3-2, R7-58), (R3-2, R7-59), (R3-2, R7-60), (R3-2, R7-61), (R3-2, R7-62), (R3-2, R7-63), (R3-2, R7-64), (R3-2, R7-65), (R3-2, R7-66), (R3-2, R7-67), (R3-2, R7-68), (R3-2, R7-69), (R3-2, R7-70), (R3-2, R7-71), (R3-2, R7-72), (R3-2, R7-73), (R3-2, R7-74), (R3-2, R7-75), (R3-2, R7-76), (R3-2, R7-77),
(R3-3, R7-1), (R3-3, R7-2), (R3-3, R7-3), (R3-3, R7-4), (R3-3, R7-5), (R3-3, R7-6), (R3-3, R7-7), (R3-3, R7-8), (R3-3, R7-9), (R3-3, R7-10), (R3-3, R7-11), (R3-3, R7-12), (R3-3, R7-13), (R3-3, R7-14), (R3-3, R7-15), (R3-3, R7-16), (R3-3, R7-17), (R3-3, R7-18), (R3-3, R7-19), (R3-3, R7-20), (R3-3, R7-21), (R3-3, R7-22), (R3-3, R7-23), (R3-3, R7-24), (R3-3, R7-25), (R3-3, R7-26), (R3-3, R7-27), (R3-3, R7-28), (R3-3, R7-29), (R3-3, R7-30), (R3-3, R7-31), (R3-3, R7-32), (R3-3, R7-33), (R3-3, R7-34), (R3-3, R7-35), (R3-3, R7-36), (R3-3, R7-37), (R3-3, R7-38), (R3-3, R7-39), (R3-3, R7-40), (R3-3, R7-41), (R3-3, R7-42), (R3-3, R7-43), (R3-3, R7-44), (R3-3, R7-45), (R3-3, R7-46), (R3-3, R7-47), (R3-3, R7-48), (R3-3, R7-49), (R3-3, R7-50), (R3-3, R7-51), (3-3, R7-52), (R3-3, R7-53), (R3-3, R7-54), (R3-3, R7-55), (R3-3, R7-56), (R3-3, R7-57), (R3-3, R7-58), (R3-3, R7-59), (R3-3, R7-60), (R3-3, R7-61), (R3-3, R7-62), (R3-3, R7-63), (R3-3, R7-64), (R3-3, R7-65), (R3-3, R7-66), (R3-3, R7-67), (R3-3, R7-68), (R3-3, R7-69), (R3-3, R7-70), (R3-3, R7-71), (R3-3, R7-72), (R3-3, R7-73), (R3-3, R7-74), (R3-3, R7-75), (R3-3, R7-76), (R3-3, R7-77).

TABLE 15
| | $R^{3a}$ |
|---|---|
| R3-1 | 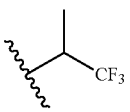 |
| R3-2 | 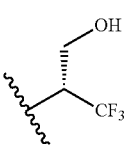 |
| R3-3 | 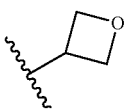 [SMILES: *C1COC1] |
TABLE 16
| | $R^{7a}$ |
|---|---|
| R7-1 | 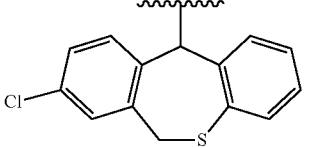 [SMILES: *C1c2ccc(Cl)cc2CSc2ccccc21] |
| R7-2 | 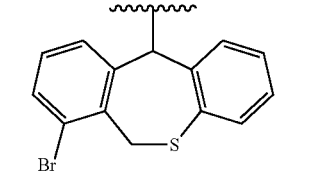 [SMILES: *C1c2ccccc2SCc2c(Br)cccc21] |
| R7-3 | 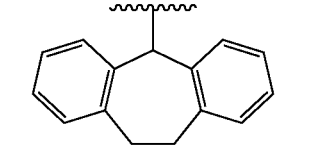 [SMILES: *C1c2ccccc2CCc2ccccc21] |
| R7-4 | 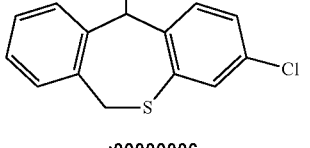 |
| R7-5 | 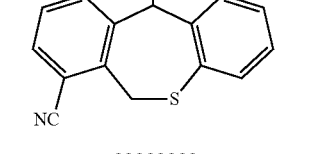 |
| R7-6 | 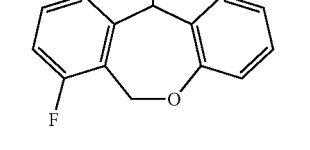 |
TABLE 16-continued
| | $R^{7a}$ |
|---|---|
| R7-7 | 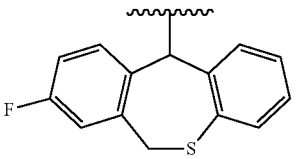 [SMILES: *C1c2ccc(F)cc2CSc2ccccc21] |
| R7-8 | 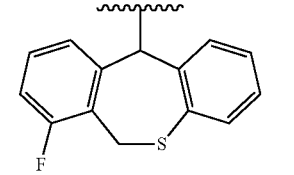 [SMILES: *C1c2ccccc2SCc2c(F)cccc21] |
| R7-9 | 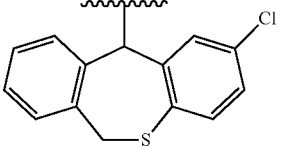 |
| R7-10 | 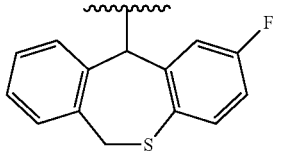 [SMILES: *C1c2ccccc2CSc2ccc(F)cc21] |
| R7-11 | 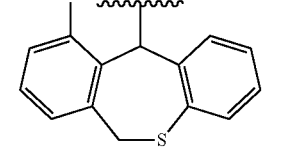 [SMILES: *C1c2ccccc2CSc2ccccc21] |
| R7-12 | 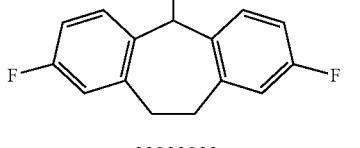 |
| R7-13 | 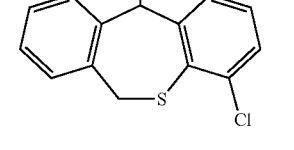 |
| R7-14 | 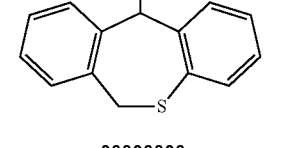 |
| R7-15 | 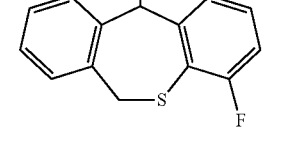 |

TABLE 16-continued
| | $R^{7a}$ |
|---|---|
| R7-16 | 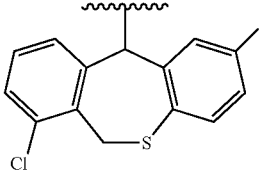 |
| R7-17 | 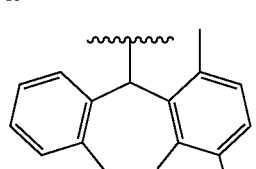 |
| R7-18 | 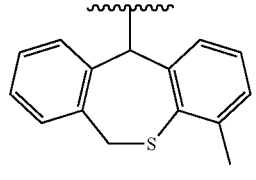 [SMILES: *C1c2ccccc2CSc2c(C)cccc21] |
TABLE 17
| | $R^{7a}$ |
|---|---|
| R7-19 | 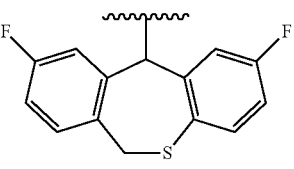 [SMILES: *C1c2cc(F)ccc2CSc2ccc(F)cc21] |
| R7-20 | 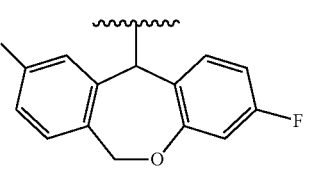 |
| R7-21 | 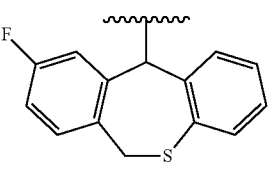 [SMILES: *C1c2cc(F)ccc2CSc2ccccc21] |
| R7-22 | 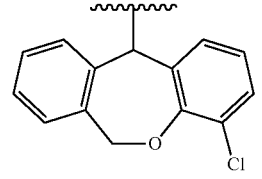 [SMILES: *C1c2ccccc2COc2c(Cl)cccc21] |
| R7-23 | 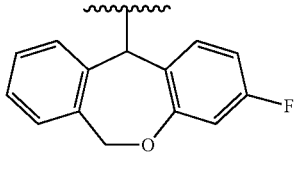 [SMILES: *C1c2ccccc2COc2cc(F)ccc21] |
TABLE 17-continued
| | $R^{7a}$ |
|---|---|
| R7-24 | 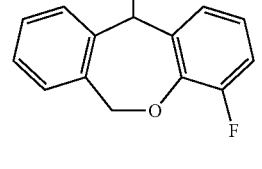 |
| R7-25 | 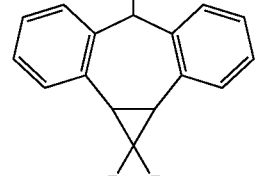 |
| R7-26 | 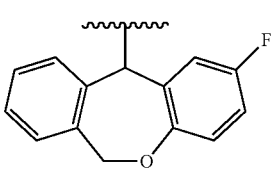 [SMILES: *C1c2ccccc2COc2ccc(F)cc21] |
| R7-27 | 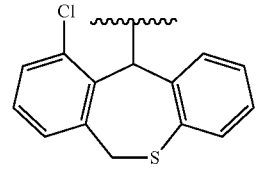 |
| R7-28 | 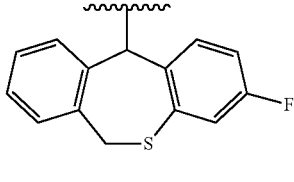 [SMILES: *C1c2ccccc2CSc2cc(F)ccc21] |
| R7-29 | 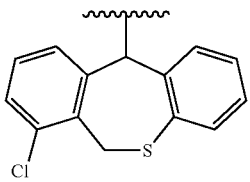 |
| R7-30 | 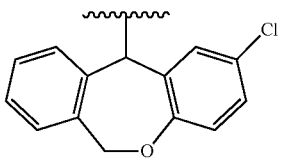 |
| R7-31 | 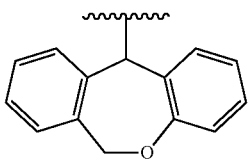 |

TABLE 17-continued

| | $R^{7a}$ |
|---|---|
| R7-32 | (structure: dibenzosuberane with two F substituents) |
| R7-33 | (structure: dibenzosuberane with two Cl substituents) |
| R7-34 | (structure: dibenzoxepine with F substituent) |
| R7-35 | (structure: dibenzoxepine with Cl substituent) |
| R7-36 | (structure: benzothienothiepine) |

TABLE 18

| | $R^{7a}$ |
|---|---|
| R7-37 | (structure: dibenzothiepine with Cl substituent) |
| R7-38 | (structure: dibenzothiepine with F$_3$C substituent) |
| R7-39 | (structure: dibenzazepinone with NH-C(=O)) |

TABLE 18-continued

| | $R^{7a}$ |
|---|---|
| R7-40 | (structure: dibenzosuberane) |
| R7-41 | (structure: dibenzothiepine with CN substituent) |
| R7-42 | (structure: dibenzothiepine with Br and F substituents) |
| R7-43 | (structure: dibenzothiepine with methyl substituent) |
| R7-44 | (structure: dibenzosuberane with OMe substituent) |
| R7-45 | (structure: dibenzothiepine with OCF$_3$ substituent) |
| R7-46 | (structure: dibenzothiepine S-oxide) |
| R7-47 | (structure: dibenzothiepine with Br substituent) |

TABLE 18-continued

| | $R^{7a}$ |
|---|---|
| R7-48 | (dibenzosulfur-containing tricyclic with NC and F substituents) |
| R7-49 | (tricyclic with F and CH2OH substituents) |
| R7-50 | (dibenzoxepine with isopropyl substituent) |
| R7-51 | (dibenzothiepine sulfone) |
| R7-52 | (tricyclic with COOH) |
| R7-53 | (dibenzothiepine with CN) |
| R7-54 | (dibenzothiepine with Br and Cl) |

TABLE 19

| | $R^{7a}$ |
|---|---|
| R7-55 | (dibenzothiepine with Br and F) |
| R7-56 | (dibenzothiepine with F and Br) |
| R7-57 | (dibenzothiepine with Br and F) |
| R7-58 | (dibenzothiepine with NC and Cl) |
| R7-59 | (dibenzothiepine with F and Br) |
| R7-60 | (dibenzothiepine with F and Br) |
| R7-61 | (dibenzothiepine with NC and F) |
| R7-62 | (dibenzothiepine with F and CN) |

TABLE 19-continued

| | $R^{7a}$ |
|---|---|
| R7-63 | dibenzothiepine with CN, F substituents |
| R7-64 | dibenzothiepine with NC, Cl substituents |
| R7-65 | dibenzothiepine with F, CN substituents |
| R7-66 | dibenzothiepine with F, NC substituents |
| R7-67 | dibenzothiepine with Br, Cl substituents |
| R7-68 | dibenzothiepine with Cl, Br substituents |
| R7-69 | dibenzothiepine with Br, Cl substituents |
| R7-70 | dibenzothiepine with NC substituent |

TABLE 19-continued

| | $R^{7a}$ |
|---|---|
| R7-71 | dibenzothiepine with Cl, Br substituents |
| R7-72 | dibenzothiepine with Cl, Br substituents |

TABLE 20

| | $R^{7a}$ |
|---|---|
| R7-73 | dibenzothiepine with Cl, CN substituents |
| R7-74 | dibenzothiepine with NC, Cl substituents |
| R7-75 | dibenzothiepine with Cl, CN substituents |
| R7-76 | dibenzoxepine |
| R7-77 | dibenzothiepine with Cl, NC substituents |

In addition, the following combinations of substituents can be also synthesized by the method described in the above Reference examples and Examples, and are a preferable embodiment of the present invention.

Compounds in which,
combinations of $P^R$ and $R^{7a}$ of the following formula (I-C):

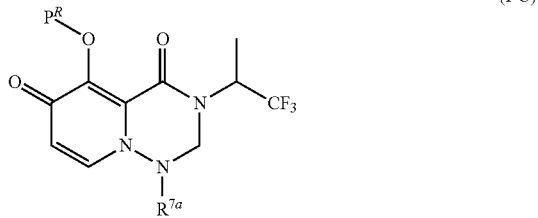

[Chemical formula 1092]

are selected from the following Table 21 and the above Tables 15 to 20, respectively.

Combinations of ($P^R$, $R^{7a}$)

(PR-1, R7-1), (PR-1, R7-2), (PR-1, R7-3), (PR-1, R7-4), (PR-1, R7-5), (PR-1, R7-6), (PR-1, R7-7), (PR-1, R7-8), (PR-1, R7-9), (PR-1, R7-10), (PR-1, R7-11), (PR-1, R7-12), (PR-1, R7-13), (PR-1, R7-14), (PR-1, R7-15), (PR-1, R7-16), (PR-1, R7-17), (PR-1, R7-18), (PR-1, R7-19), (PR-1, R7-20), (PR-1, R7-21), (PR-1, R7-22), (PR-1, R7-23), (PR-1, R7-24), (PR-1, R7-25), (PR-1, R7-26), (PR-1, R7-27), (PR-1, R7-28), (PR-1, R7-29), (PR-1, R7-30), (PR-1, R7-31), (PR-1, R7-32), (PR-1, R7-33), (PR-1, R7-34), (PR-1, R7-35), (PR-1, R7-36), (PR-1, R7-37), (PR-1, R7-38), (PR-1, R7-39), (PR-1, R7-40), (PR-1, R7-41), (PR-1, R7-42), (PR-1, R7-43), (PR-1, R7-44), (PR-1, R7-45), (PR-1, R7-46), (PR-1, R7-47), (PR-1, R7-48), (PR-1, R7-49), (PR-1, R7-50), (PR-1, R7-51), (PR-1, R7-52), (PR-1, R7-53), (PR-1, R7-54), (PR-1, R7-55), (PR-1, R7-56), (PR-1, R7-57), (PR-1, R7-58), (PR-1, R7-59), (PR-1, R7-60), (PR-1, R7-61), (PR-1, R7-62), (PR-1, R7-63), (PR-1, R7-64), (PR-1, R7-65), (PR-1, R7-66), (PR-1, R7-67), (PR-1, R7-68), (PR-1, R7-69), (PR-1, R7-70), (PR-1, R7-71), (PR-1, R7-72), (PR-1, R7-73), (PR-1, R7-74), (PR-1, R7-75), (PR-1, R7-76), (PR-1, R7-77), (PR-2, R7-1), (PR-2, R7-2), (PR-2, R7-3), (PR-2, R7-4), (PR-2, R7-5), (PR-2, R7-6), (PR-2, R7-7), (PR-2, R7-8), (PR-2, R7-9), (PR-2, R7-10), (PR-2, R7-11), (PR-2, R7-12), (PR-2, R7-13), (PR-2, R7-14), (PR-2, R7-15), (PR-2, R7-16), (PR-2, R7-17), (PR-2, R7-18), (PR-2, R7-19), (PR-2, R7-20), (PR-2, R7-21), (PR-2, R7-22), (PR-2, R7-23), (PR-2, R7-24), (PR-2, R7-25), (PR-2, R7-26), (PR-2, R7-27), (PR-2, R7-28), (PR-2, R7-29), (PR-2, R7-30), (PR-2, R7-31), (PR-2, R7-32), (PR-2, R7-33), (PR-2, R7-34), (PR-2, R7-35), (PR-2, R7-36), (PR-2, R7-37), (PR-2, R7-38), (PR-2, R7-39), (PR-2, R7-40), (PR-2, R7-41), (PR-2, R7-42), (PR-2, R7-43), (PR-2, R7-44), (PR-2, R7-45), (PR-2, R7-46), (PR-2, R7-47), (PR-2, R7-48), (PR-2, R7-49), (PR-2, R7-50), (PR-2, R7-51), (PR-2, R7-52), (PR-2, R7-53), (PR-2, R7-54), (PR-2, R7-55), (PR-2, R7-56), (PR-2, R7-57), (PR-2, R7-58), (PR-2, R7-59), (PR-2, R7-60), (PR-2, R7-61), (PR-2, R7-62), (PR-2, R7-63), (PR-2, R7-64), (PR-2, R7-65), (PR-2, R7-66), (PR-2, R7-67), (PR-2, R7-68), (PR-2, R7-69), (PR-2, R7-70), (PR-2, R7-71), (PR-2, R7-72), (PR-2, R7-73), (PR-2, R7-74), (PR-2, R7-75), (PR-2, R7-76), (PR-2, R7-77), (PR-3, R7-1), (PR-3, R7-2), (PR-3, R7-3), (PR-3, R7-4), (PR-3, R7-5), (PR-3, R7-6), (PR-3, R7-7), (PR-3, R7-8), (PR-3, R7-9), (PR-3, R7-10), (PR-3, R7-11), (PR-3, R7-12), (PR-3, R7-13), (PR-3, R7-14), (PR-3, R7-15), (PR-3, R7-16), (PR-3, R7-17), (PR-3, R7-18), (PR-3, R7-19), (PR-3, R7-20), (PR-3, R7-21), (PR-3, R7-22), (PR-3, R7-23), (PR-3, R7-24), (PR-3, R7-25), (PR-3, R7-26), (PR-3, R7-27), (PR-3, R7-28), (PR-3, R7-29), (PR-3, R7-30), (PR-3, R7-31), (PR-3, R7-32), (PR-3, R7-33), (PR-3, R7-34), (PR-3, R7-35), (PR-3, R7-36), (PR-3, R7-37), (PR-3, R7-38), (PR-3, R7-39), (PR-3, R7-40), (PR-3, R7-41), (PR-3, R7-42), (PR-3, R7-43), (PR-3, R7-44), (PR-3, R7-45), (PR-3, R7-46), (PR-3, R7-47), (PR-3, R7-48), (PR-3, R7-49), (PR-3, R7-50), (PR-3, R7-51), (PR-3, R7-52), (PR-3, R7-53), (PR-3, R7-54), (PR-3, R7-55), (PR-3, R7-56), (PR-3, R7-57), (PR-3, R7-58), (PR-3, R7-59), (PR-3, R7-60), (PR-3, R7-61), (PR-3, R7-62), (PR-3, R7-63), (PR-3, R7-64), (PR-3, R7-65), (PR-3, R7-66), (PR-3, R7-67), (PR-3, R7-68), (PR-3, R7-69), (PR-3, R7-70), (PR-3, R7-71), (PR-3, R7-72), (PR-3, R7-73), (PR-3, R7-74), (PR-3, R7-75), (PR-3, R7-76), (PR-3, R7-77), (PR-4, R7-1), (PR-4, R7-2), (PR-4, R7-3), (PR-4, R7-4), (PR-4, R7-5), (PR-4, R7-6), (PR-4, R7-7), (PR-4, R7-8), (PR-4, R7-9), (PR-4, R7-10), (PR-4, R7-11), (PR-4, R7-12), (PR-4, R7-13), (PR-4, R7-14), (PR-4, R7-15), (PR-4, R7-16), (PR-4, R7-17), (PR-4, R7-18), (PR-4, R7-19), (PR-4, R7-20), (PR-4, R7-21), (PR-4, R7-22), (PR-4, R7-23), (PR-4, R7-24), (PR-4, R7-25), (PR-4, R7-26), (PR-4, R7-27), (PR-4, R7-28), (PR-4, R7-29), (PR-4, R7-30), (PR-4, R7-31), (PR-4, R7-32), (PR-4, R7-33), (PR-4, R7-34), (PR-4, R7-35), (PR-4, R7-36), (PR-4, R7-37), (PR-4, R7-38), (PR-4, R7-39), (PR-4, R7-40), (PR-4, R7-41), (PR-4, R7-42), (PR-4, R7-43), (PR-4, R7-44), (PR-4, R7-45), (PR-4, R7-46), (PR-4, R7-47), (PR-4, R7-48), (PR-4, R7-49), (PR-4, R7-50), (PR-4, R7-51), (PR-4, R7-52), (PR-4, R7-53), (PR-4, R7-54), (PR-4, R7-55), (PR-4, R7-56), (PR-4, R7-57), (PR-4, R7-58), (PR-4, R7-59), (PR-4, R7-60), (PR-4, R7-61), (PR-4, R7-62), (PR-4, R7-63), (PR-4, R7-64), (PR-4, R7-65), (PR-4, R7-66), (PR-4, R7-67), (PR-4, R7-68), (PR-4, R7-69), (PR-4, R7-70), (PR-4, R7-71), (PR-4, R7-72), (PR-4, R7-73), (PR-4, R7-74), (PR-4, R7-75), (PR-4, R7-76), (PR-4, R7-77), (PR-5, R7-1), (PR-5, R7-2), (PR-5, R7-3), (PR-5, R7-4), (PR-5, R7-5), (PR-5, R7-6), (PR-5, R7-7), (PR-5, R7-8), (PR-5, R7-9), (PR-5, R7-10), (PR-5, R7-11), (PR-5, R7-12), (PR-5, R7-13), (PR-5, R7-14), (PR-5, R7-15), (PR-5, R7-16), (PR-5, R7-17), (PR-5, R7-18), (PR-5, R7-19), (PR-5, R7-20), (PR-5, R7-21), (PR-5, R7-22), (PR-5, R7-23), (PR-5, R7-24), (PR-5, R7-25), (PR-5, R7-26), (PR-5, R7-27), (PR-5, R7-28), (PR-5, R7-29), (PR-5, R7-30), (PR-5, R7-31), (PR-5, R7-32), (PR-5, R7-33), (PR-5, R7-34), (PR-5, R7-35), (PR-5, R7-36), (PR-5, R7-37), (PR-5, R7-38), (PR-5, R7-39), (PR-5, R7-40), (PR-5, R7-41), (PR-5, R7-42), (PR-5, R7-43), (PR-5, R7-44), (PR-5, R7-45), (PR-5, R7-46), (PR-5, R7-47), (PR-5, R7-48), (PR-5, R7-49), (PR-5, R7-50), (PR-5, R7-51), (PR-5, R7-52), (PR-5, R7-53), (PR-5, R7-54), (PR-5, R7-55), (PR-5, R7-56), (PR-5, R7-57), (PR-5, R7-58), (PR-5, R7-59), (PR-5, R7-60), (PR-5, R7-61), (PR-5, R7-62), (PR-5, R7-63), (PR-5, R7-64), (PR-5, R7-65), (PR-5, R7-66), (PR-5, R7-67), (PR-5, R7-68), (PR-5, R7-69), (PR-5, R7-70), (PR-5, R7-71), (PR-5, R7-72), (PR-5, R7-73), (PR-5, R7-74), (PR-5, R7-75), (PR-5, R7-76), (PR-5, R7-77).

TABLE 21

| | |
|---|---|
| | P^R ⤳ |
| PR-1 | tetrahydropyran-4-yl-C(=O)- ⤳ |
| PR-2 | CH₃-C(=O)-O-CH₂- ⤳ |
| PR-3 | (iPr)-O-C(=O)-O-CH- ⤳ (with methyl) |
| PR-4 | CH₃-O-C(=O)-O-CH₂- ⤳ |
| PR-5 | CH₃-O-CH₂CH₂-O-C(=O)-O-CH₂- ⤳ |

Further, in the above compounds of Reference examples 1 to 775, the following combinations in which a part corresponding to —OH group of the following formula (II):

[Chemical formula 1093]

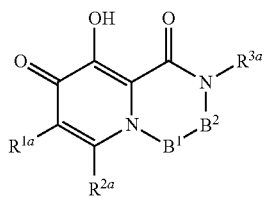

(II)

(wherein each substituent is same meaning as that of item 1)
are converted into a prodrug by PR-1 to PR-5 in the above Table 21 are also a preferable embodiment of the present invention. These compounds can be also synthesized by a general method known to a person skilled in the art or the method described in Examples, using the above compound of Reference example as a raw material.

Combinations of (Number of compound of Reference example, $P^R$)

(Reference example 1, PR-1), (Reference example 1, PR-2), (Reference example 1, PR-3), (Reference example 1, PR-4), (Reference example 1, PR-5), (Reference example 2, PR-1), (Reference example 2, PR-2), (Reference example 2, PR-3), (Reference example 2, PR-4), (Reference example 2, PR-5), (Reference example 3, PR-1), (Reference example 3, PR-2), (Reference example 3, PR-3), (Reference example 3, PR-4), (Reference example 3, PR-5), (Reference example 4, PR-1), (Reference example 4, PR-2), (Reference example 4, PR-3), (Reference example 4, PR-4), (Reference example 4, PR-5), (Reference example 5, PR-1), (Reference example 5, PR-2), (Reference example 5, PR-3), (Reference example 5, PR-4), (Reference example 5, PR-5), (Reference example 6, PR-1), (Reference example 6, PR-2), (Reference example 6, PR-3), (Reference example 6, PR-4), (Reference example 6, PR-5), (Reference example 7, PR-1), (Reference example 7, PR-2), (Reference example 7, PR-3), (Reference example 7, PR-4), (Reference example 7, PR-5), (Reference example 8, PR-1), (Reference example 8, PR-2), (Reference example 8, PR-3), (Reference example 8, PR-4), (Reference example 8, PR-5), (Reference example 9, PR-1), (Reference example 9, PR-2), (Reference example 9, PR-3), (Reference example 9, PR-4), (Reference example 9, PR-5), (Reference example 10, PR-1), (Reference example 10, PR-2), (Reference example 10, PR-3), (Reference example 10, PR-4), (Reference example 10, PR-5), (Reference example 11, PR-1), (Reference example 11, PR-2), (Reference example 11, PR-3), (Reference example 11, PR-4), (Reference example 11, PR-5), (Reference example 12, PR-1), (Reference example 12, PR-2), (Reference example 12, PR-3), (Reference example 12, PR-4), (Reference example 12, PR-5), (Reference example 13, PR-1), (Reference example 13, PR-2), (Reference example 13, PR-3), (Reference example 13, PR-4), (Reference example 13, PR-5), (Reference example 14, PR-1), (Reference example 14, PR-2), (Reference example 14, PR-3), (Reference example 14, PR-4), (Reference example 14, PR-5), (Reference example 15, PR-1), (Reference example 15, PR-2), (Reference example 15, PR-3), (Reference example 15, PR-4), (Reference example 15, PR-5), (Reference example 16, PR-1), (Reference example 16, PR-2), (Reference example 16, PR-3), (Reference example 16, PR-4), (Reference example 16, PR-5), (Reference example 17, PR-1), (Reference example 17, PR-2), (Reference example 17, PR-3), (Reference example 17, PR-4), (Reference example 17, PR-5), (Reference example 18, PR-1), (Reference example 18, PR-2), (Reference example 18, PR-3), (Reference example 18, PR-4), (Reference example 18, PR-5), (Reference example 19, PR-1), (Reference example 19, PR-2), (Reference example 19, PR-3), (Reference example 19, PR-4), (Reference example 19, PR-5), (Reference example 20, PR-1), (Reference example 20, PR-2), (Reference example 20, PR-3), (Reference example 20, PR-4), (Reference example 20, PR-5), (Reference example 21, PR-1), (Reference example 21, PR-2), (Reference example 21, PR-3), (Reference example 21, PR-4), (Reference example 21, PR-5), (Reference example 22, PR-1), (Reference example 22, PR-2), (Reference example 22, PR-3), (Reference example 22, PR-4), (Reference example 22, PR-5), (Reference example 23, PR-1), (Reference example 23, PR-2), (Reference example 23, PR-3), (Reference example 23, PR-4), (Reference example 23, PR-5), (Reference example 24, PR-1), (Reference example 24, PR-2), (Reference example 24, PR-3), (Reference example 24, PR-4), (Reference example 24, PR-5), (Reference example 25, PR-1), (Reference example 25, PR-2), (Reference example 25, PR-3), (Reference example 25, PR-4), (Reference example 25, PR-5), (Reference example 26, PR-1), (Reference example 26, PR-2), (Reference example 26, PR-3), (Reference example 26, PR-4), (Reference example 26, PR-5), (Reference example 27, PR-1), (Reference example 27, PR-2), (Reference example 27, PR-3), (Reference example 27, PR-4), (Reference example 27, PR-5), (Reference example 28, PR-1), (Reference example 28, PR-2), (Reference example 28, PR-3), (Reference example 28, PR-4), (Reference example 28, PR-5), (Reference example 29, PR-1), (Reference example 29, PR-2), (Reference example 29, PR-3), (Reference example 29, PR-4), (Reference example 29, PR-5), (Reference example 30, PR-1), (Reference example 30, PR-2), (Reference example 30, PR-3), (Reference example 30, PR-4), (Reference example 30, PR-5), (Reference example 31, PR-1), (Reference example 31, PR-2), (Reference example 31, PR-3), (Reference example 31, PR-4), (Reference example 31, PR-5), (Reference example 32, PR-1), (Reference example 32, PR-2), (Reference example 32, PR-3), (Reference example 32, PR-4), (Reference example 32, PR-5), (Reference example 33, PR-1), (Reference example 33, PR-2), (Reference example 33, PR-3), (Reference example 33, PR-4), (Reference example 33, PR-5), (Reference example 34, PR-1), (Reference example 34, PR-2), (Reference example 34, PR-3), (Reference example 34, PR-4), (Reference example 34, PR-5), (Reference example 35, PR-1), (Reference example 35, PR-2), (Reference example 35, PR-3), (Reference example 35, PR-4), (Reference example 35, PR-5), (Reference example 36, PR-1), (Reference example 36, PR-2), (Reference example 36, PR-3), (Reference example 36, PR-4), (Reference example 36, PR-5), (Reference example 37, PR-1), (Reference example 37, PR-2), (Reference example 37, PR-3), (Reference example 37, PR-4), (Reference example 37, PR-5), (Reference example 38, PR-1), (Reference example 38, PR-2), (Reference example 38, PR-3), (Reference example 38, PR-4), (Reference example 38, PR-5), (Reference example 39, PR-1), (Reference example 39, PR-2), (Reference example 39, PR-3), (Reference example 39, PR-4), (Reference example 39, PR-5), (Reference example 40, PR-1), (Reference example 40, PR-2), (Reference example 40, PR-3), (Reference example 40, PR-4), (Reference example 40, PR-5), (Reference example 41, PR-1), (Reference example 41, PR-2), (Reference example 41, PR-3), (Reference example 41, PR-4), (Reference example 41, PR-5), (Reference example 42, PR-1), (Reference example 42, PR-2), (Reference example 42, PR-3), (Reference example 42, PR-4), (Reference example 42, PR-5), (Reference example 43, PR-1), (Reference example 43, PR-2), (Reference example 43, PR-3), (Reference example 43, PR-4), (Reference example 43, PR-5), (Reference example 44, PR-1), (Reference example 44, PR-2), (Reference example 44, PR-3), (Reference example 44, PR-4), (Reference example 44, PR-5), (Reference example 45, PR-1), (Reference example 45, PR-2), (Reference example 45, PR-3), (Reference example 45, PR-4), (Reference example 45, PR-5), (Reference example 46, PR-1), (Reference example 46, PR-2), (Reference example 46, PR-3), (Reference example 46, PR-4), (Reference example 46, PR-5), (Reference example 47, PR-1), (Reference example 47, PR-2), (Reference example 47, PR-3), (Reference example 47, PR-4), (Reference example 47, PR-5), (Reference example 48, PR-1), (Reference example 48, PR-2), (Reference example 48, PR-3), (Reference example 48, PR-4), (Reference example 48, PR-5), (Reference example 49, PR-1), (Reference example 49, PR-2), (Reference example 49, PR-3), (Reference example 49, PR-4), (Reference example 49, PR-5), (Reference example 50, PR-1), (Reference example 50, PR-2), (Reference example 50, PR-3), (Reference example 50, PR-4), (Reference example 50, PR-5), (Reference example 51, PR-1), (Reference example 51, PR-2), (Reference example 51, PR-3), (Reference example 51, PR-4), (Reference example 51, PR-5), (Reference example 52, PR-1), (Reference example 52, PR-2), (Reference example 52, PR-3), (Reference example 52, PR-4), (Reference example 52, PR-5), (Reference example 53, PR-1), (Reference example 53, PR-2), (Reference example 53, PR-3), (Reference example 53, PR-4), (Reference example 53, PR-5), (Reference example 54, PR-1), (Reference example 54, PR-2), (Reference example 54, PR-3), (Reference example 54, PR-4), (Reference example 54, PR-5), (Reference example 55, PR-1), (Reference example 55, PR-2), (Reference example 55, PR-3), (Reference example 55, PR-4), (Reference example 55, PR-5), (Reference example 56, PR-1), (Reference example 56, PR-2), (Reference example 56, PR-3), (Reference example 56, PR-4), (Reference example 56, PR-5), (Reference example 57, PR-1), (Reference example 57, PR-2), (Reference example 57, PR-3), (Reference example 57, PR-4), (Reference example 57, PR-5), (Reference example 58, PR-1), (Reference example 58, PR-2), (Reference example 58, PR-3), (Reference example 58, PR-4), (Reference example 58, PR-5), (Reference example 59, PR-1), (Reference example 59, PR-2), (Reference example 59, PR-3), (Reference example 59, PR-4), (Reference example 59, PR-5), (Reference example 60, PR-1), (Reference example 60, PR-2), (Reference example 60, PR-3), (Reference example 60, PR-4), (Reference example 60, PR-5), (Reference example 61, PR-1), (Reference example 61, PR-2), (Reference example 61, PR-3), (Reference example 61, PR-4), (Reference example 61, PR-5), (Reference example 62, PR-1), (Reference example 62, PR-2), (Reference example 62, PR-3), (Reference example 62, PR-4), (Reference example 62, PR-5), (Reference example 63, PR-1), (Reference example 63, PR-2), (Reference example 63, PR-3), (Reference example 63, PR-4), (Reference example 63, PR-5), (Reference example 64, PR-1), (Reference example 64, PR-2), (Reference example 64, PR-3), (Reference example 64, PR-4), (Reference example 64, PR-5), (Reference example 65, PR-1), (Reference example 65, PR-2), (Reference example 65, PR-3), (Reference example 65, PR-4), (Reference example 65, PR-5), (Reference example 66, PR-1), (Reference example 66, PR-2), (Reference example 66, PR-3), (Reference example 66, PR-4), (Reference example 66, PR-5), (Reference example 67, PR-1), (Reference example 67, PR-2), (Reference example 67, PR-3), (Reference example 67, PR-4), (Reference example 67, PR-5), (Reference example 68, PR-1), (Reference example 68, PR-2), (Reference example 68, PR-3), (Reference example 68, PR-4), (Reference example 68, PR-5), (Reference example 69, PR-1), (Reference example 69, PR-2), (Reference example 69, PR-3), (Reference example 69, PR-4), (Reference example 69, PR-5), (Reference example 70, PR-1), (Reference example 70, PR-2), (Reference example 70, PR-3), (Reference example 70, PR-4), (Reference example 70, PR-5), (Reference example 71, PR-1), (Reference example 71, PR-2), (Reference example 71, PR-3), (Reference example 71, PR-4), (Reference example 71, PR-5), (Reference example 72, PR-1), (Reference example 72, PR-2), (Reference example 72, PR-3), (Reference example 72, PR-4), (Reference example 72, PR-5), (Reference example 73, PR-1), (Reference example 73, PR-2), (Reference example 73, PR-3), (Reference example 73, PR-4), (Reference example 73, PR-5), (Reference example 74, PR-1), (Reference example 74, PR-2), (Reference example 74, PR-3), (Reference example 74, PR-4), (Reference example 74, PR-5), (Reference example 75, PR-1), (Reference example 75, PR-2), (Reference example 75, PR-3), (Reference example 75, PR-4), (Reference example 75, PR-5), (Reference example 76, PR-1), (Reference example 76, PR-2), (Reference example 76, PR-3), (Reference example 76, PR-4), (Reference example 76, PR-5), (Reference example 77, PR-1), (Reference example 77, PR-2), (Reference example 77, PR-3), (Reference example 77, PR-4), (Reference example 77, PR-5), (Reference example 78, PR-1), (Reference example 78, PR-2), (Reference example 78, PR-3), (Reference example 78, PR-4), (Reference example 78, PR-5), (Reference example 79, PR-1), (Reference example 79, PR-2), (Reference example 79, PR-3), (Reference example 79, PR-4), (Reference example 79, PR-5), (Reference example 80, PR-1), (Reference example 80, PR-2), (Reference example 80, PR-3), (Reference example 80, PR-4), (Reference example 80, PR-5), (Reference example 81, PR-1), (Reference example 81, PR-2), (Reference example 81, PR-3), (Reference example 81, PR-4), (Reference example 81, PR-5), (Reference example 82, PR-1), (Reference example 82, PR-2), (Reference example 82, PR-3), (Reference example 82, PR-4), (Reference example 82, PR-5), (Reference example 83, PR-1), (Reference example 83, PR-2), (Reference example 83, PR-3), (Reference example 83, PR-4), (Reference example 83, PR-5), (Reference example 84, PR-1), (Reference example 84, PR-2), (Reference example 84, PR-3), (Reference example 84, PR-4), (Reference example 84, PR-5), (Reference example 85, PR-1), (Reference example 85, PR-2), (Reference example 85, PR-3), (Reference example 85, PR-4), (Reference example 85, PR-5), (Reference example 86, PR-1), (Reference example 86, PR-2), (Reference example 86, PR-3), (Reference example 86, PR-4), (Reference example 86, PR-5), (Reference example 87, PR-1), (Reference example 87, PR-2), (Reference example 87, PR-3), (Reference example 87, PR-4), (Reference example 87, PR-5), (Reference example 88, PR-1), (Reference example 88, PR-2), (Reference example 88, PR-3), (Reference example 88, PR-4), (Reference example 88, PR-5), (Reference example 89, PR-1), (Reference example 89, PR-2), (Reference example 89, PR-3), (Reference example 89, PR-4), (Reference example 89, PR-5), (Reference example 90, PR-1), (Reference example 90, PR-2), (Reference example 90, PR-3), (Reference example 90, PR-4), (Reference example 90, PR-5), (Reference example 91, PR-1), (Reference example 91, PR-2), (Reference example 91, PR-3), (Reference example 91, PR-4), (Reference example 91, PR-5), (Reference example 92, PR-1), (Reference example 92, PR-2), (Reference example 92, PR-3), (Reference example 92, PR-4), (Reference example 92, PR-5), (Reference example 93, PR-1), (Reference example 93, PR-2), (Reference example 93, PR-3), (Reference example 93, PR-4), (Reference example 93, PR-5), (Reference example 94, PR-1), (Reference example 94, PR-2), (Reference example 94, PR-3), (Reference example 94, PR-4), (Reference example 94, PR-5), (Reference example 95, PR-1), (Reference example 95, PR-2), (Reference example 95, PR-3), (Reference example 95, PR-4), (Reference example 95, PR-5), (Reference example 96, PR-1), (Reference example 96, PR-2), (Reference example 96, PR-3), (Reference example 96, PR-4), (Reference example 96, PR-5), (Reference example 97, PR-1), (Reference example 97, PR-2), (Reference example 97, PR-3), (Reference example 97, PR-4), (Reference example 97, PR-5), (Reference example 98, PR-1), (Reference example 98, PR-2), (Reference example 98, PR-3), (Reference example 98, PR-4), (Reference example 98, PR-5), (Reference example 99, PR-1), (Reference example 99, PR-2), (Reference example 99, PR-3), (Reference example 99, PR-4), (Reference example 99, PR-5), (Reference example 100, PR-1), (Reference example 100, PR-2), (Reference example 100, PR-3), (Reference example 100, PR-4), (Reference example 100, PR-5), (Reference example 101, PR-1), (Reference example 101, PR-2), (Reference example 101, PR-3), (Reference example 101, PR-4), (Reference example 101, PR-5), (Reference example 102, PR-1), (Reference example 102, PR-2), (Reference example 102, PR-3), (Reference example 102, PR-4), (Reference example 102, PR-5), (Reference example 103, PR-1), (Reference example 103, PR-2), (Reference example 103, PR-3), (Reference example 103, PR-4), (Reference example 103, PR-5), (Reference example 104, PR-1), (Reference example 104, PR-2), (Reference example 104, PR-3), (Reference example 104, PR-4), (Reference example 104, PR-5), (Reference example 105, PR-1), (Reference example 105, PR-2), (Reference example 105, PR-3), (Reference example 105, PR-4), (Reference example 105, PR-5), (Reference example 106, PR-1), (Reference example 106, PR-2), (Reference example 106, PR-3), (Reference example 106, PR-4), (Reference example 106, PR-5), (Reference example 107, PR-1), (Reference example 107, PR-2), (Reference example 107, PR-3), (Reference example 107, PR-4), (Reference example 107, PR-5), (Reference example 108, PR-1), (Reference example 108, PR-2), (Reference example 108, PR-3), (Reference example 108, PR-4), (Reference example 108, PR-5), (Reference example 109, PR-1), (Reference example 109, PR-2), (Reference example 109, PR-3), (Reference example 109, PR-4), (Reference example 109, PR-5), (Reference example 110, PR-1), (Reference example 110, PR-2), (Reference example 110, PR-3), (Reference example 110, PR-4), (Reference example 110, PR-5), (Reference example 111, PR-1), (Reference example 111, PR-2), (Reference example 111, PR-3), (Reference example 111, PR-4), (Reference example 111, PR-5), (Reference example 112, PR-1), (Reference example 112, PR-2), (Reference example 112, PR-3), (Reference example 112, PR-4), (Reference example 112, PR-5), (Reference example 113, PR-1), (Reference example 113, PR-2), (Reference example 113, PR-3), (Reference example 113, PR-4), (Reference example 113, PR-5), (Reference example 114, PR-1), (Reference example 114, PR-2), (Reference example 114, PR-3), (Reference example 114, PR-4), (Reference example 114, PR-5), (Reference example 115, PR-1), (Reference example 115, PR-2), (Reference example 115, PR-3), (Reference example 115, PR-4), (Reference example 115, PR-5), (Reference example 116, PR-1), (Reference example 116, PR-2), (Reference example 116, PR-3), (Reference example 116, PR-4), (Reference example 116, PR-5), (Reference example 117, PR-1), (Reference example 117, PR-2), (Reference example 117, PR-3), (Reference example 117, PR-4), (Reference example 117, PR-5), (Reference example 118, PR-1), (Reference example 118, PR-2), (Reference example 118, PR-3), (Reference example 118, PR-4), (Reference example 118, PR-5), (Reference example 119, PR-1), (Reference example 119, PR-2), (Reference example 119, PR-3), (Reference example 119, PR-4), (Reference example 119, PR-5), (Reference example 120, PR-1), (Reference example 120, PR-2), (Reference example 120, PR-3), (Reference example 120, PR-4), (Reference example 120, PR-5), (Reference example 121, PR-1), (Reference example 121, PR-2), (Reference example 121, PR-3), (Reference example 121, PR-4), (Reference example 121, PR-5), (Reference example 122, PR-1), (Reference example 122, PR-2), (Reference example 122, PR-3), (Reference example 122, PR-4), (Reference example 122, PR-5), (Reference example 123, PR-1), (Reference example 123, PR-2), (Reference example 123, PR-3), (Reference example 123, PR-4), (Reference example 123, PR-5), (Reference example 124, PR-1), (Reference example 124, PR-2), (Reference example 124, PR-3), (Reference example 124, PR-4), (Reference example 124, PR-5), (Reference example 125, PR-1), (Reference example 125, PR-2), (Reference example 125, PR-3), (Reference example 125, PR-4), (Reference example 125, PR-5), (Reference example 126, PR-1), (Reference example 126, PR-2), (Reference example 126, PR-3), (Reference example 126, PR-4), (Reference example 126, PR-5), (Reference example 127, PR-1), (Reference example 127, PR-2), (Reference example 127, PR-3), (Reference example 127, PR-4), (Reference example 127, PR-5), (Reference example 128, PR-1), (Reference example 128, PR-2), (Reference example 128, PR-3), (Reference example 128, PR-4), (Reference example 128, PR-5), (Reference example 129, PR-1), (Reference example 129, PR-2), (Reference example 129, PR-3), (Reference example 129, PR-4), (Reference example 129, PR-5), (Reference example 130, PR-1), (Reference example 130, PR-2), (Reference example 130, PR-3), (Reference example 130, PR-4), (Reference example 130, PR-5), (Reference example 131, PR-1), (Reference example 131, PR-2), (Reference example 131, PR-3), (Reference example 131, PR-4), (Reference example 131, PR-5), (Reference example 132, PR-1), (Reference example 132, PR-2), (Reference example 132, PR-3), (Reference example 132, PR-4), (Reference example 132, PR-5), (Reference example 133, PR-1), (Reference example 133, PR-2), (Reference example 133, PR-3), (Reference example 133, PR-4), (Reference example 133, PR-5), (Reference example 134, PR-1), (Reference example 134, PR-2), (Reference example 134, PR-3), (Reference example 134, PR-4), (Reference example 134, PR-5), (Reference example 135, PR-1), (Reference example 135, PR-2), (Reference example 135, PR-3), (Reference example 135, PR-4), (Reference example 135, PR-5), (Reference example 136, PR-1), (Reference example 136, PR-2), (Reference example 136, PR-3), (Reference example 136, PR-4), (Reference example 136, PR-5), (Reference example 137, PR-1), (Reference example 137, PR-2), (Reference example 137, PR-3), (Reference example 137, PR-4), (Reference example 137, PR-5), (Reference example 138, PR-1), (Reference example 138, PR-2), (Reference example 138, PR-3), (Reference example 138, PR-4), (Reference example 138, PR-5), (Reference example 139, PR-1), (Reference example 139, PR-2), (Reference example 139, PR-3), (Reference example 139, PR-4), (Reference example 139, PR-5), (Reference example 140, PR-1), (Reference example 140, PR-2), (Reference example 140, PR-3), (Reference example 140, PR-4), (Reference example 140, PR-5), (Reference example 141, PR-1), (Reference example 141, PR-2), (Reference example 141, PR-3), (Reference example 141, PR-4), (Reference example 141, PR-5), (Reference example 142, PR-1), (Reference example 142, PR-2), (Reference example 142, PR-3), (Reference example 142, PR-4), (Reference example 142, PR-5), (Reference example 143, PR-1), (Reference example 143, PR-2), (Reference example 143, PR-3), (Reference example 143, PR-4), (Reference example 143, PR-5), (Reference example 144, PR-1), (Reference example 144, PR-2), (Reference example 144, PR-3), (Reference example 144, PR-4), (Reference example 144, PR-5), (Reference example 145, PR-1), (Reference example 145, PR-2), (Reference example 145, PR-3), (Reference example 145, PR-4), (Reference example 145, PR-5), (Reference example 146, PR-1), (Reference example 146, PR-2), (Reference example 146, PR-3), (Reference example 146, PR-4), (Reference example 146, PR-5), (Reference example 147, PR-1), (Reference example 147, PR-2), (Reference example 147, PR-3), (Reference example 147, PR-4), (Reference example 147, PR-5), (Reference example 148, PR-1), (Reference example 148, PR-2), (Reference example 148, PR-3), (Reference example 148, PR-4), (Reference example 148, PR-5), (Reference example 149, PR-1), (Reference example 149, PR-2), (Reference example 149, PR-3), (Reference example 149, PR-4), (Reference example 149, PR-5), (Reference example 150, PR-1), (Reference example 150, PR-2), (Reference example 150, PR-3), (Reference example 150, PR-4), (Reference example 150, PR-5), (Reference example 151, PR-1), (Reference example 151, PR-2), (Reference example 151, PR-3), (Reference example 151, PR-4), (Reference example 151, PR-5), (Reference example 152, PR-1), (Reference example 152, PR-2), (Reference example 152, PR-3), (Reference example 152, PR-4), (Reference example 152, PR-5), (Reference example 153, PR-1), (Reference example 153, PR-2), (Reference example 153, PR-3), (Reference example 153, PR-4), (Reference example 153, PR-5), (Reference example 154, PR-1), (Reference example 154, PR-2), (Reference example 154, PR-3), (Reference example 154, PR-4), (Reference example 154, PR-5), (Reference example 155, PR-1), (Reference example 155, PR-2), (Reference example 155, PR-3), (Reference example 155, PR-4), (Reference example 155, PR-5), (Reference example 156, PR-1), (Reference example 156, PR-2), (Reference example 156, PR-3), (Reference example 156, PR-4), (Reference example 156, PR-5), (Reference example 157, PR-1), (Reference example 157, PR-2), (Reference example 157, PR-3), (Reference example 157, PR-4), (Reference example 157, PR-5), (Reference example 158, PR-1), (Reference example 158, PR-2), (Reference example 158, PR-3), (Reference example 158, PR-4), (Reference example 158, PR-5), (Reference example 159, PR-1), (Reference example 159, PR-2), (Reference example 159, PR-3), (Reference example 159, PR-4), (Reference example 159, PR-5), (Reference example 160, PR-1), (Reference example 160, PR-2), (Reference example 160, PR-3), (Reference example 160, PR-4), (Reference example 160, PR-5), (Reference example 161, PR-1), (Reference example 161, PR-2), (Reference example 161, PR-3), (Reference example 161, PR-4), (Reference example 161, PR-5), (Reference example 162, PR-1), (Reference example 162, PR-2), (Reference example 162, PR-3), (Reference example 162, PR-4), (Reference example 162, PR-5), (Reference example 163, PR-1), (Reference example 163, PR-2), (Reference example 163, PR-3), (Reference example 163, PR-4), (Reference example 163, PR-5), (Reference example 164, PR-1), (Reference example 164, PR-2), (Reference example 164, PR-3), (Reference example 164, PR-4), (Reference example 164, PR-5), (Reference example 165, PR-1), (Reference example 165, PR-2), (Reference example 165, PR-3), (Reference example 165, PR-4), (Reference example 165, PR-5), (Reference example 166, PR-1), (Reference example 166, PR-2), (Reference example 166, PR-3), (Reference example 166, PR-4), (Reference example 166, PR-5), (Reference example 167, PR-1), (Reference example 167, PR-2), (Reference example 167, PR-3), (Reference example 167, PR-4), (Reference example 167, PR-5), (Reference example 168, PR-1), (Reference example 168, PR-2), (Reference example 168, PR-3), (Reference example 168, PR-4), (Reference example 168, PR-5), (Reference example 169, PR-1), (Reference example 169, PR-2), (Reference example 169, PR-3), (Reference example 169, PR-4), (Reference example 169, PR-5), (Reference example 170, PR-1), (Reference example 170, PR-2), (Reference example 170, PR-3), (Reference example 170, PR-4), (Reference example 170, PR-5), (Reference example 171, PR-1), (Reference example 171, PR-2), (Reference example 171, PR-3), (Reference example 171, PR-4), (Reference example 171, PR-5), (Reference example 172, PR-1), (Reference example 172, PR-2), (Reference example 172, PR-3), (Reference example 172, PR-4), (Reference example 172, PR-5), (Reference example 173, PR-1), (Reference example 173, PR-2), (Reference example 173, PR-3), (Reference example 173, PR-4), (Reference example 173, PR-5), (Reference example 174, PR-1), (Reference example 174, PR-2), (Reference example 174, PR-3), (Reference example 174, PR-4), (Reference example 174, PR-5), (Reference example 175, PR-1), (Reference example 175, PR-2), (Reference example 175, PR-3), (Reference example 175, PR-4), (Reference example 175, PR-5), (Reference example 176, PR-1), (Reference example 176, PR-2), (Reference example 176, PR-3), (Reference example 176, PR-4), (Reference example 176, PR-5), (Reference example 177, PR-1), (Reference example 177, PR-2), (Reference example 177, PR-3), (Reference example 177, PR-4), (Reference example 177, PR-5), (Reference example 178, PR-1), (Reference example 178, PR-2), (Reference example 178, PR-3), (Reference example 178, PR-4), (Reference example 178, PR-5), (Reference example 179, PR-1), (Reference example 179, PR-2), (Reference example 179, PR-3), (Reference example 179, PR-4), (Reference example 179, PR-5), (Reference example 180, PR-1), (Reference example 180, PR-2), (Reference example 180, PR-3), (Reference example 180, PR-4), (Reference example 180, PR-5), (Reference example 181, PR-1), (Reference example 181, PR-2), (Reference example 181, PR-3), (Reference example 181, PR-4), (Reference example 181, PR-5), (Reference example 182, PR-1), (Reference example 182, PR-2), (Reference example 182, PR-3), (Reference example 182, PR-4), (Reference example 182, PR-5), (Reference example 183, PR-1), (Reference example 183, PR-2), (Reference example 183, PR-3), (Reference example 183, PR-4), (Reference example 183, PR-5), (Reference example 184, PR-1), (Reference example 184, PR-2), (Reference example 184, PR-3), (Reference example 184, PR-4), (Reference example 184, PR-5), (Reference example 185, PR-1), (Reference example 185, PR-2), (Reference example 185, PR-3), (Reference example 185, PR-4), (Reference example 185, PR-5), (Reference example 186, PR-1), (Reference example 186, PR-2), (Reference example 186, PR-3), (Reference example 186, PR-4), (Reference example 186, PR-5), (Reference example 187, PR-1), (Reference example 187, PR-2), (Reference example 187, PR-3), (Reference example 187, PR-4), (Reference example 187, PR-5), (Reference example 188, PR-1), (Reference example 188, PR-2), (Reference example 188, PR-3), (Reference example 188, PR-4), (Reference example 188, PR-5), (Reference example 189, PR-1), (Reference example 189, PR-2), (Reference example 189, PR-3), (Reference example 189, PR-4), (Reference example 189, PR-5), (Reference example 190, PR-1), (Reference example 190, PR-2), (Reference example 190, PR-3), (Reference example 190, PR-4), (Reference example 190, PR-5), (Reference example 191, PR-1), (Reference example 191, PR-2), (Reference example 191, PR-3), (Reference example 191, PR-4), (Reference example 191, PR-5), (Reference example 192, PR-1), (Reference example 192, PR-2), (Reference example 192, PR-3), (Reference example 192, PR-4), (Reference example 192, PR-5), (Reference example 193, PR-1), (Reference example 193, PR-2), (Reference example 193, PR-3), (Reference example 193, PR-4), (Reference example 193, PR-5), (Reference example 194, PR-1), (Reference example 194, PR-2), (Reference example 194, PR-3), (Reference example 194, PR-4), (Reference example 194, PR-5), (Reference example 195, PR-1), (Reference example 195, PR-2), (Reference example 195, PR-3), (Reference example 195, PR-4), (Reference example 195, PR-5), (Reference example 196, PR-1), (Reference example 196, PR-2), (Reference example 196, PR-3), (Reference example 196, PR-4), (Reference example 196, PR-5), (Reference example 197, PR-1), (Reference example 197, PR-2), (Reference example 197, PR-3), (Reference example 197, PR-4), (Reference example 197, PR-5), (Reference example 198, PR-1), (Reference example 198, PR-2), (Reference example 198, PR-3), (Reference example 198, PR-4), (Reference example 198, PR-5), (Reference example 199, PR-1), (Reference example 199, PR-2), (Reference example 199, PR-3), (Reference example 199, PR-4), (Reference example 199, PR-5), (Reference example 200, PR-1), (Reference example 200, PR-2), (Reference example 200, PR-3), (Reference example 200, PR-4), (Reference example 200, PR-5), (Reference example 201, PR-1), (Reference example 201, PR-2), (Reference example 201, PR-3), (Reference example 201, PR-4), (Reference example 201, PR-5), (Reference example 202, PR-1), (Reference example 202, PR-2), (Reference example 202, PR-3), (Reference example 202, PR-4), (Reference example 202, PR-5), (Reference example 203, PR-1), (Reference example 203, PR-2), (Reference example 203, PR-3), (Reference example 203, PR-4), (Reference example 203, PR-5), (Reference example 204, PR-1), (Reference example 204, PR-2), (Reference example 204, PR-3), (Reference example 204, PR-4), (Reference example 204, PR-5), (Reference example 205, PR-1), (Reference example 205, PR-2), (Reference example 205, PR-3), (Reference example 205, PR-4), (Reference example 205, PR-5), (Reference example 206, PR-1), (Reference example 206, PR-2), (Reference example 206, PR-3), (Reference example 206, PR-4), (Reference example 206, PR-5), (Reference example 207, PR-1), (Reference example 207, PR-2), (Reference example 207, PR-3), (Reference example 207, PR-4), (Reference example 207, PR-5), (Reference example 208, PR-1), (Reference example 208, PR-2), (Reference example 208, PR-3), (Reference example 208, PR-4), (Reference example 208, PR-5), (Reference example 209, PR-1), (Reference example 209, PR-2), (Reference example 209, PR-3), (Reference example 209, PR-4), (Reference example 209, PR-5), (Reference example 210, PR-1), (Reference example 210, PR-2), (Reference example 210, PR-3), (Reference example 210, PR-4), (Reference example 210, PR-5), (Reference example 211, PR-1), (Reference example 211, PR-2), (Reference example 211, PR-3), (Reference example 211, PR-4), (Reference example 211, PR-5), (Reference example 212, PR-1), (Reference example 212, PR-2), (Reference example 212, PR-3), (Reference example 212, PR-4), (Reference example 212, PR-5), (Reference example 213, PR-1), (Reference example 213, PR-2), (Reference example 213, PR-3), (Reference example 213, PR-4), (Reference example 213, PR-5), (Reference example 214, PR-1), (Reference example 214, PR-2), (Reference example 214, PR-3), (Reference example 214, PR-4), (Reference example 214, PR-5), (Reference example 215, PR-1), (Reference example 215, PR-2), (Reference example 215, PR-3), (Reference example 215, PR-4), (Reference example 215, PR-5), (Reference example 216, PR-1), (Reference example 216, PR-2), (Reference example 216, PR-3), (Reference example 216, PR-4), (Reference example 216, PR-5), (Reference example 217, PR-1), (Reference example 217, PR-2), (Reference example 217, PR-3), (Reference example 217, PR-4), (Reference example 217, PR-5), (Reference example 218, PR-1), (Reference example 218, PR-2), (Reference example 218, PR-3), (Reference example 218, PR-4), (Reference example 218, PR-5), (Reference example 219, PR-1), (Reference example 219, PR-2), (Reference example 219, PR-3), (Reference example 219, PR-4), (Reference example 219, PR-5), (Reference example 220, PR-1), (Reference example 220, PR-2), (Reference example 220, PR-3), (Reference example 220, PR-4), (Reference example 220, PR-5), (Reference example 221, PR-1), (Reference example 221, PR-2), (Reference example 221, PR-3), (Reference example 221, PR-4), (Reference example 221, PR-5), (Reference example 222, PR-1), (Reference example 222, PR-2), (Reference example 222, PR-3), (Reference example 222, PR-4), (Reference example 222, PR-5), (Reference example 223, PR-1), (Reference example 223, PR-2), (Reference example 223, PR-3), (Reference example 223, PR-4), (Reference example 223, PR-5), (Reference example 224, PR-1), (Reference example 224, PR-2), (Reference example 224, PR-3), (Reference example 224, PR-4), (Reference example 224, PR-5), (Reference example 225, PR-1), (Reference example 225, PR-2), (Reference example 225, PR-3), (Reference example 225, PR-4), (Reference example 225, PR-5), (Reference example 226, PR-1), (Reference example 226, PR-2), (Reference example 226, PR-3), (Reference example 226, PR-4), (Reference example 226, PR-5), (Reference example 227, PR-1), (Reference example 227, PR-2), (Reference example 227, PR-3), (Reference example 227, PR-4), (Reference example 227, PR-5), (Reference example 228, PR-1), (Reference example 228, PR-2), (Reference example 228, PR-3), (Reference example 228, PR-4), (Reference example 228, PR-5), (Reference example 229, PR-1), (Reference example 229, PR-2), (Reference example 229, PR-3), (Reference example 229, PR-4), (Reference example 229, PR-5), (Reference example 230, PR-1), (Reference example 230, PR-2), (Reference example 230, PR-3), (Reference example 230, PR-4), (Reference example 230, PR-5), (Reference example 231, PR-1), (Reference example 231, PR-2), (Reference example 231, PR-3), (Reference example 231, PR-4), (Reference example 231, PR-5), (Reference example 232, PR-1), (Reference example 232, PR-2), (Reference example 232, PR-3), (Reference example 232, PR-4), (Reference example 232, PR-5), (Reference example 233, PR-1), (Reference example 233, PR-2), (Reference example 233, PR-3), (Reference example 233, PR-4), (Reference example 233, PR-5), (Reference example 234, PR-1), (Reference example 234, PR-2), (Reference example 234, PR-3), (Reference example 234, PR-4), (Reference example 234, PR-5), (Reference example 235, PR-1), (Reference example 235, PR-2), (Reference example 235, PR-3), (Reference example 235, PR-4), (Reference example 235, PR-5), (Reference example 236, PR-1), (Reference example 236, PR-2), (Reference example 236, PR-3), (Reference example 236, PR-4), (Reference example 236, PR-5), (Reference example 237, PR-1), (Reference example 237, PR-2), (Reference example 237, PR-3), (Reference example 237, PR-4), (Reference example 237, PR-5), (Reference example 238, PR-1), (Reference example 238, PR-2), (Reference example 238, PR-3), (Reference example 238, PR-4), (Reference example 238, PR-5), (Reference example 239, PR-1), (Reference example 239, PR-2), (Reference example 239, PR-3), (Reference example 239, PR-4), (Reference example 239, PR-5), (Reference example 240, PR-1), (Reference example 240, PR-2), (Reference example 240, PR-3), (Reference example 240, PR-4), (Reference example 240, PR-5), (Reference example 241, PR-1), (Reference example 241, PR-2), (Reference example 241, PR-3), (Reference example 241, PR-4), (Reference example 241, PR-5), (Reference example 242, PR-1), (Reference example 242, PR-2), (Reference example 242, PR-3), (Reference example 242, PR-4), (Reference example 242, PR-5), (Reference example 243, PR-1), (Reference example 243, PR-2), (Reference example 243, PR-3), (Reference example 243, PR-4), (Reference example 243, PR-5), (Reference example 244, PR-1), (Reference example 244, PR-2), (Reference example 244, PR-3), (Reference example 244, PR-4), (Reference example 244, PR-5), (Reference example 245, PR-1), (Reference example 245, PR-2), (Reference example 245, PR-3), (Reference example 245, PR-4), (Reference example 245, PR-5), (Reference example 246, PR-1), (Reference example 246, PR-2), (Reference example 246, PR-3), (Reference example 246, PR-4), (Reference example 246, PR-5), (Reference example 247, PR-1), (Reference example 247, PR-2), (Reference example 247, PR-3), (Reference example 247, PR-4), (Reference example 247, PR-5), (Reference example 248, PR-1), (Reference example 248, PR-2), (Reference example 248, PR-3), (Reference example 248, PR-4), (Reference example 248, PR-5), (Reference example 249, PR-1), (Reference example 249, PR-2), (Reference example 249, PR-3), (Reference example 249, PR-4), (Reference example 249, PR-5), (Reference example 250, PR-1), (Reference example 250, PR-2), (Reference example 250, PR-3), (Reference example 250, PR-4), (Reference example 250, PR-5), (Reference example 251, PR-1), (Reference example 251, PR-2), (Reference example 251, PR-3), (Reference example 251, PR-4), (Reference example 251, PR-5), (Reference example 252, PR-1), (Reference example 252, PR-2), (Reference example 252, PR-3), (Reference example 252, PR-4), (Reference example 252, PR-5), (Reference example 253, PR-1), (Reference example 253, PR-2), (Reference example 253, PR-3), (Reference example 253, PR-4), (Reference example 253, PR-5), (Reference example 254, PR-1), (Reference example 254, PR-2), (Reference example 254, PR-3), (Reference example 254, PR-4), (Reference example 254, PR-5), (Reference example 255, PR-1), (Reference example 255, PR-2), (Reference example 255, PR-3), (Reference example 255, PR-4), (Reference example 255, PR-5), (Reference example 256, PR-1), (Reference example 256, PR-2), (Reference example 256, PR-3), (Reference example 256, PR-4), (Reference example 256, PR-5), (Reference example 257, PR-1), (Reference example 257, PR-2), (Reference example 257, PR-3), (Reference example 257, PR-4), (Reference example 257, PR-5), (Reference example 258, PR-1), (Reference example 258, PR-2), (Reference example 258, PR-3), (Reference example 258, PR-4), (Reference example 258, PR-5), (Reference example 259, PR-1), (Reference example 259, PR-2), (Reference example 259, PR-3), (Reference example 259, PR-4), (Reference example 259, PR-5), (Reference example 260, PR-1), (Reference example 260, PR-2), (Reference example 260, PR-3), (Reference example 260, PR-4), (Reference example 260, PR-5), (Reference example 261, PR-1), (Reference example 261, PR-2), (Reference example 261, PR-3), (Reference example 261, PR-4), (Reference example 261, PR-5), (Reference example 262, PR-1), (Reference example 262, PR-2), (Reference example 262, PR-3), (Reference example 262, PR-4), (Reference example 262, PR-5), (Reference example 263, PR-1), (Reference example 263, PR-2), (Reference example 263, PR-3), (Reference example 263, PR-4), (Reference example 263, PR-5), (Reference example 264, PR-1), (Reference example 264, PR-2), (Reference example 264, PR-3), (Reference example 264, PR-4), (Reference example 264, PR-5), (Reference example 265, PR-1), (Reference example 265, PR-2), (Reference example 265, PR-3), (Reference example 265, PR-4), (Reference example 265, PR-5), (Reference example 266, PR-1), (Reference example 266, PR-2), (Reference example 266, PR-3), (Reference example 266, PR-4), (Reference example 266, PR-5), (Reference example 267, PR-1), (Reference example 267, PR-2), (Reference example 267, PR-3), (Reference example 267, PR-4), (Reference example 267, PR-5), (Reference example 268, PR-1), (Reference example 268, PR-2), (Reference example 268, PR-3), (Reference example 268, PR-4), (Reference example 268, PR-5), (Reference example 269, PR-1), (Reference example 269, PR-2), (Reference example 269, PR-3), (Reference example 269, PR-4), (Reference example 269, PR-5), (Reference example 270, PR-1), (Reference example 270, PR-2), (Reference example 270, PR-3), (Reference example 270, PR-4), (Reference example 270, PR-5), (Reference example 271, PR-1), (Reference example 271, PR-2), (Reference example 271, PR-3), (Reference example 271, PR-4), (Reference example 271, PR-5), (Reference example 272, PR-1), (Reference example 272, PR-2), (Reference example 272, PR-3), (Reference example 272, PR-4), (Reference example 272, PR-5), (Reference example 273, PR-1), (Reference example 273, PR-2), (Reference example 273, PR-3), (Reference example 273, PR-4), (Reference example 273, PR-5), (Reference example 274, PR-1), (Reference example 274, PR-2), (Reference example 274, PR-3), (Reference example 274, PR-4), (Reference example 274, PR-5), (Reference example 275, PR-1), (Reference example 275, PR-2), (Reference example 275, PR-3), (Reference example 275, PR-4), (Reference example 275, PR-5), (Reference example 276, PR-1), (Reference example 276, PR-2), (Reference example 276, PR-3), (Reference example 276, PR-4), (Reference example 276, PR-5), (Reference example 277, PR-1), (Reference example 277, PR-2), (Reference example 277, PR-3), (Reference example 277, PR-4), (Reference example 277, PR-5), (Reference example 278, PR-1), (Reference example 278, PR-2), (Reference example 278, PR-3), (Reference example 278, PR-4), (Reference example 278, PR-5), (Reference example 279, PR-1), (Reference example 279, PR-2), (Reference example 279, PR-3), (Reference example 279, PR-4), (Reference example 279, PR-5), (Reference example 280, PR-1), (Reference example 280, PR-2), (Reference example 280, PR-3), (Reference example 280, PR-4), (Reference example 280, PR-5), (Reference example 281, PR-1), (Reference example 281, PR-2), (Reference example 281, PR-3), (Reference example 281, PR-4), (Reference example 281, PR-5), (Reference example 282, PR-1), (Reference example 282, PR-2), (Reference example 282, PR-3), (Reference example 282, PR-4), (Reference example 282, PR-5), (Reference example 283, PR-1), (Reference example 283, PR-2), (Reference example 283, PR-3), (Reference example 283, PR-4), (Reference example 283, PR-5), (Reference example 284, PR-1), (Reference example 284, PR-2), (Reference example 284, PR-3), (Reference example 284, PR-4), (Reference example 284, PR-5), (Reference example 285, PR-1), (Reference example 285, PR-2), (Reference example 285, PR-3), (Reference example 285, PR-4), (Reference example 285, PR-5), (Reference example 286, PR-1), (Reference example 286, PR-2), (Reference example 286, PR-3), (Reference example 286, PR-4), (Reference example 286, PR-5), (Reference example 287, PR-1), (Reference example 287, PR-2), (Reference example 287, PR-3), (Reference example 287, PR-4), (Reference example 287, PR-5), (Reference example 288, PR-1), (Reference example 288, PR-2), (Reference example 288, PR-3), (Reference example 288, PR-4), (Reference example 288, PR-5), (Reference example 289, PR-1), (Reference example 289, PR-2), (Reference example 289, PR-3), (Reference example 289, PR-4), (Reference example 289, PR-5), (Reference example 290, PR-1), (Reference example 290, PR-2), (Reference example 290, PR-3), (Reference example 290, PR-4), (Reference example 290, PR-5), (Reference example 291, PR-1), (Reference example 291, PR-2), (Reference example 291, PR-3), (Reference example 291, PR-4), (Reference example 291, PR-5), (Reference example 292, PR-1), (Reference example 292, PR-2), (Reference example 292, PR-3), (Reference example 292, PR-4), (Reference example 292, PR-5), (Reference example 293, PR-1), (Reference example 293, PR-2), (Reference example 293, PR-3), (Reference example 293, PR-4), (Reference example 293, PR-5), (Reference example 294, PR-1), (Reference example 294, PR-2), (Reference example 294, PR-3), (Reference example 294, PR-4), (Reference example 294, PR-5), (Reference example 295, PR-1), (Reference example 295, PR-2), (Reference example 295, PR-3), (Reference example 295, PR-4), (Reference example 295, PR-5), (Reference example 296, PR-1), (Reference example 296, PR-2), (Reference example 296, PR-3), (Reference example 296, PR-4), (Reference example 296, PR-5), (Reference example 297, PR-1), (Reference example 297, PR-2), (Reference example 297, PR-3), (Reference example 297, PR-4), (Reference example 297, PR-5), (Reference example 298, PR-1), (Reference example 298, PR-2), (Reference example 298, PR-3), (Reference example 298, PR-4), (Reference example 298, PR-5), (Reference example 299, PR-1), (Reference example 299, PR-2), (Reference example 299, PR-3), (Reference example 299, PR-4), (Reference example 299, PR-5), (Reference example 300, PR-1), (Reference example 300, PR-2), (Reference example 300, PR-3), (Reference example 300, PR-4), (Reference example 300, PR-5), (Reference example 301, PR-1), (Reference example 301, PR-2), (Reference example 301, PR-3), (Reference example 301, PR-4), (Reference example 301, PR-5), (Reference example 302, PR-1), (Reference example 302, PR-2), (Reference example 302, PR-3), (Reference example 302, PR-4), (Reference example 302, PR-5), (Reference example 303, PR-1), (Reference example 303, PR-2), (Reference example 303, PR-3), (Reference example 303, PR-4), (Reference example 303, PR-5), (Reference example 304, PR-1), (Reference example 304, PR-2), (Reference example 304, PR-3), (Reference example 304, PR-4), (Reference example 304, PR-5), (Reference example 305, PR-1), (Reference example 305, PR-2), (Reference example 305, PR-3), (Reference example 305, PR-4), (Reference example 305, PR-5), (Reference example 306, PR-1), (Reference example 306, PR-2), (Reference example 306, PR-3), (Reference example 306, PR-4), (Reference example 306, PR-5), (Reference example 307, PR-1), (Reference example 307, PR-2), (Reference example 307, PR-3), (Reference example 307, PR-4), (Reference example 307, PR-5), (Reference example 308, PR-1), (Reference example 308, PR-2), (Reference example 308, PR-3), (Reference example 308, PR-4), (Reference example 308, PR-5), (Reference example 309, PR-1), (Reference example 309, PR-2), (Reference example 309, PR-3), (Reference example 309, PR-4), (Reference example 309, PR-5), (Reference example 310, PR-1), (Reference example 310, PR-2), (Reference example 310, PR-3), (Reference example 310, PR-4), (Reference example 310, PR-5), (Reference example 311, PR-1), (Reference example 311, PR-2), (Reference example 311, PR-3), (Reference example 311, PR-4), (Reference example 311, PR-5), (Reference example 312, PR-1), (Reference example 312, PR-2), (Reference example 312, PR-3), (Reference example 312, PR-4), (Reference example 312, PR-5), (Reference example 313, PR-1), (Reference example 313, PR-2), (Reference example 313, PR-3), (Reference example 313, PR-4), (Reference example 313, PR-5), (Reference example 314, PR-1), (Reference example 314, PR-2), (Reference example 314, PR-3), (Reference example 314, PR-4), (Reference example 314, PR-5), (Reference example 315, PR-1), (Reference example 315, PR-2), (Reference example 315, PR-3), (Reference example 315, PR-4), (Reference example 315, PR-5), (Reference example 316, PR-1), (Reference example 316, PR-2), (Reference example 316, PR-3), (Reference example 316, PR-4), (Reference example 316, PR-5), (Reference example 317, PR-1), (Reference example 317, PR-2), (Reference example 317, PR-3), (Reference example 317, PR-4), (Reference example 317, PR-5), (Reference example 318, PR-1), (Reference example 318, PR-2), (Reference example 318, PR-3), (Reference example 318, PR-4), (Reference example 318, PR-5), (Reference example 319, PR-1), (Reference example 319, PR-2), (Reference example 319, PR-3), (Reference example 319, PR-4), (Reference example 319, PR-5), (Reference example 320, PR-1), (Reference example 320, PR-2), (Reference example 320, PR-3), (Reference example 320, PR-4), (Reference example 320, PR-5), (Reference example 321, PR-1), (Reference example 321, PR-2), (Reference example 321, PR-3), (Reference example 321, PR-4), (Reference example 321, PR-5), (Reference example 322, PR-1), (Reference example 322, PR-2), (Reference example 322, PR-3), (Reference example 322, PR-4), (Reference example 322, PR-5), (Reference example 323, PR-1), (Reference example 323, PR-2), (Reference example 323, PR-3), (Reference example 323, PR-4), (Reference example 323, PR-5), (Reference example 324, PR-1), (Reference example 324, PR-2), (Reference example 324, PR-3), (Reference example 324, PR-4), (Reference example 324, PR-5), (Reference example 325, PR-1), (Reference example 325, PR-2), (Reference example 325, PR-3), (Reference example 325, PR-4), (Reference example 325, PR-5), (Reference example 326, PR-1), (Reference example 326, PR-2), (Reference example 326, PR-3), (Reference example 326, PR-4), (Reference example 326, PR-5), (Reference example 327, PR-1), (Reference example 327, PR-2), (Reference example 327, PR-3), (Reference example 327, PR-4), (Reference example 327, PR-5), (Reference example 328, PR-1), (Reference example 328, PR-2), (Reference example 328, PR-3), (Reference example 328, PR-4), (Reference example 328, PR-5), (Reference example 329, PR-1), (Reference example 329, PR-2), (Reference example 329, PR-3), (Reference example 329, PR-4), (Reference example 329, PR-5), (Reference example 330, PR-1), (Reference example 330, PR-2), (Reference example 330, PR-3), (Reference example 330, PR-4), (Reference example 330, PR-5), (Reference example 331, PR-1), (Reference example 331, PR-2), (Reference example 331, PR-3), (Reference example 331, PR-4), (Reference example 331, PR-5), (Reference example 332, PR-1), (Reference example 332, PR-2), (Reference example 332, PR-3), (Reference example 332, PR-4), (Reference example 332, PR-5), (Reference example 333, PR-1), (Reference example 333, PR-2), (Reference example 333, PR-3), (Reference example 333, PR-4), (Reference example 333, PR-5), (Reference example 334, PR-1), (Reference example 334, PR-2), (Reference example 334, PR-3), (Reference example 334, PR-4), (Reference example 334, PR-5), (Reference example 335, PR-1), (Reference example 335, PR-2), (Reference example 335, PR-3), (Reference example 335, PR-4), (Reference example 335, PR-5), (Reference example 336, PR-1), (Reference example 336, PR-2), (Reference example 336, PR-3), (Reference example 336, PR-4), (Reference example 336, PR-5), (Reference example 337, PR-1), (Reference example 337, PR-2), (Reference example 337, PR-3), (Reference example 337, PR-4), (Reference example 337, PR-5), (Reference example 338, PR-1), (Reference example 338, PR-2), (Reference example 338, PR-3), (Reference example 338, PR-4), (Reference example 338, PR-5), (Reference example 339, PR-1), (Reference example 339, PR-2), (Reference example 339, PR-3), (Reference example 339, PR-4), (Reference example 339, PR-5), (Reference example 340, PR-1), (Reference example 340, PR-2), (Reference example 340, PR-3), (Reference example 340, PR-4), (Reference example 340, PR-5), (Reference example 341, PR-1), (Reference example 341, PR-2), (Reference example 341, PR-3), (Reference example 341, PR-4), (Reference example 341, PR-5), (Reference example 342, PR-1), (Reference example 342, PR-2), (Reference example 342, PR-3), (Reference example 342, PR-4), (Reference example 342, PR-5), (Reference example 343, PR-1), (Reference example 343, PR-2), (Reference example 343, PR-3), (Reference example 343, PR-4), (Reference example 343, PR-5), (Reference example 344, PR-1), (Reference example 344, PR-2), (Reference example 344, PR-3), (Reference example 344, PR-4), (Reference example 344, PR-5), (Reference example 345, PR-1), (Reference example 345, PR-2), (Reference example 345, PR-3), (Reference example 345, PR-4), (Reference example 345, PR-5), (Reference example 346, PR-1), (Reference example 346, PR-2), (Reference example 346, PR-3), (Reference example 346, PR-4), (Reference example 346, PR-5), (Reference example 347, PR-1), (Reference example 347, PR-2), (Reference example 347, PR-3), (Reference example 347, PR-4), (Reference example 347, PR-5), (Reference example 348, PR-1), (Reference example 348, PR-2), (Reference example 348, PR-3), (Reference example 348, PR-4), (Reference example 348, PR-5), (Reference example 349, PR-1), (Reference example 349, PR-2), (Reference example 349, PR-3), (Reference example 349, PR-4), (Reference example 349, PR-5), (Reference example 350, PR-1), (Reference example 350, PR-2), (Reference example 350, PR-3), (Reference example 350, PR-4), (Reference example 350, PR-5), (Reference example 351, PR-1), (Reference example 351, PR-2), (Reference example 351, PR-3), (Reference example 351, PR-4), (Reference example 351, PR-5), (Reference example 352, PR-1), (Reference example 352, PR-2), (Reference example 352, PR-3), (Reference example 352, PR-4), (Reference example 352, PR-5), (Reference example 353, PR-1), (Reference example 353, PR-2), (Reference example 353, PR-3), (Reference example 353, PR-4), (Reference example 353, PR-5), (Reference example 354, PR-1), (Reference example 354, PR-2), (Reference example 354, PR-3), (Reference example 354, PR-4), (Reference example 354, PR-5), (Reference example 355, PR-1), (Reference example 355, PR-2), (Reference example 355, PR-3), (Reference example 355, PR-4), (Reference example 355, PR-5), (Reference example 356, PR-1), (Reference example 356, PR-2), (Reference example 356, PR-3), (Reference example 356, PR-4), (Reference example 356, PR-5), (Reference example 357, PR-1), (Reference example 357, PR-2), (Reference example 357, PR-3), (Reference example 357, PR-4), (Reference example 357, PR-5), (Reference example 358, PR-1), (Reference example 358, PR-2), (Reference example 358, PR-3), (Reference example 358, PR-4), (Reference example 358, PR-5), (Reference example 359, PR-1), (Reference example 359, PR-2), (Reference example 359, PR-3), (Reference example 359, PR-4), (Reference example 359, PR-5), (Reference example 360, PR-1), (Reference example 360, PR-2), (Reference example 360, PR-3), (Reference example 360, PR-4), (Reference example 360, PR-5), (Reference example 361, PR-1), (Reference example 361, PR-2), (Reference example 361, PR-3), (Reference example 361, PR-4), (Reference example 361, PR-5), (Reference example 362, PR-1), (Reference example 362, PR-2), (Reference example 362, PR-3), (Reference example 362, PR-4), (Reference example 362, PR-5), (Reference example 363, PR-1), (Reference example 363, PR-2), (Reference example 363, PR-3), (Reference example 363, PR-4), (Reference example 363, PR-5), (Reference example 364, PR-1), (Reference example 364, PR-2), (Reference example 364, PR-3), (Reference example 364, PR-4), (Reference example 364, PR-5), (Reference example 365, PR-1), (Reference example 365, PR-2), (Reference example 365, PR-3), (Reference example 365, PR-4), (Reference example 365, PR-5), (Reference example 366, PR-1), (Reference example 366, PR-2), (Reference example 366, PR-3), (Reference example 366, PR-4), (Reference example 366, PR-5), (Reference example 367, PR-1), (Reference example 367, PR-2), (Reference example 367, PR-3), (Reference example 367, PR-4), (Reference example 367, PR-5), (Reference example 368, PR-1), (Reference example 368, PR-2), (Reference example 368, PR-3), (Reference example 368, PR-4), (Reference example 368, PR-5), (Reference example 369, PR-1), (Reference example 369, PR-2), (Reference example 369, PR-3), (Reference example 369, PR-4), (Reference example 369, PR-5), (Reference example 370, PR-1), (Reference example 370, PR-2), (Reference example 370, PR-3), (Reference example 370, PR-4), (Reference example 370, PR-5), (Reference example 371, PR-1), (Reference example 371, PR-2), (Reference example 371, PR-3), (Reference example 371, PR-4), (Reference example 371, PR-5), (Reference example 372, PR-1), (Reference example 372, PR-2), (Reference example 372, PR-3), (Reference example 372, PR-4), (Reference example 372, PR-5), (Reference example 373, PR-1), (Reference example 373, PR-2), (Reference example 373, PR-3), (Reference example 373, PR-4), (Reference example 373, PR-5), (Reference example 374, PR-1), (Reference example 374, PR-2), (Reference example 374, PR-3), (Reference example 374, PR-4), (Reference example 374, PR-5), (Reference example 375, PR-1), (Reference example 375, PR-2), (Reference example 375, PR-3), (Reference example 375, PR-4), (Reference example 375, PR-5), (Reference example 376, PR-1), (Reference example 376, PR-2), (Reference example 376, PR-3), (Reference example 376, PR-4), (Reference example 376, PR-5), (Reference example 377, PR-1), (Reference example 377, PR-2), (Reference example 377, PR-3), (Reference example 377, PR-4), (Reference example 377, PR-5), (Reference example 378, PR-1), (Reference example 378, PR-2), (Reference example 378, PR-3), (Reference example 378, PR-4), (Reference example 378, PR-5), (Reference example 379, PR-1), (Reference example 379, PR-2), (Reference example 379, PR-3), (Reference example 379, PR-4), (Reference example 379, PR-5), (Reference example 380, PR-1), (Reference example 380, PR-2), (Reference example 380, PR-3), (Reference example 380, PR-4), (Reference example 380, PR-5), (Reference example 381, PR-1), (Reference example 381, PR-2), (Reference example 381, PR-3), (Reference example 381, PR-4), (Reference example 381, PR-5), (Reference example 382, PR-1), (Reference example 382, PR-2), (Reference example 382, PR-3), (Reference example 382, PR-4), (Reference example 382, PR-5), (Reference example 383, PR-1), (Reference example 383, PR-2), (Reference example 383, PR-3), (Reference example 383, PR-4), (Reference example 383, PR-5). (Reference example 384, PR-1), (Reference example 384, PR-2), (Reference example 384, PR-3), (Reference example 384, PR-4), (Reference example 384, PR-5), (Reference example 385, PR-1), (Reference example 385, PR-2), (Reference example 385, PR-3), (Reference example 385, PR-4), (Reference example 385, PR-5), (Reference example 386, PR-1), (Reference example 386, PR-2), (Reference example 386, PR-3), (Reference example 386, PR-4), (Reference example 386, PR-5), (Reference example 387, PR-1), (Reference example 387, PR-2), (Reference example 387, PR-3), (Reference example 387, PR-4), (Reference example 387, PR-5), (Reference example 388, PR-1), (Reference example 388, PR-2), (Reference example 388, PR-3), (Reference example 388, PR-4), (Reference example 388, PR-5), (Reference example 389, PR-1), (Reference example 389, PR-2), (Reference example 389, PR-3), (Reference example 389, PR-4), (Reference example 389, PR-5), (Reference example 390, PR-1), (Reference example 390, PR-2), (Reference example 390, PR-3), (Reference example 390, PR-4), (Reference example 390, PR-5), (Reference example 391, PR-1), (Reference example 391, PR-2), (Reference example 391, PR-3), (Reference example 391, PR-4), (Reference example 391, PR-5), (Reference example 392, PR-1), (Reference example 392, PR-2), (Reference example 392, PR-3), (Reference example 392, PR-4), (Reference example 392, PR-5), (Reference example 393, PR-1), (Reference example 393, PR-2), (Reference example 393, PR-3), (Reference example 393, PR-4), (Reference example 393, PR-5), (Reference example 394, PR-1), (Reference example 394, PR-2), (Reference example 394, PR-3), (Reference example 394, PR-4), (Reference example 394, PR-5), (Reference example 395, PR-1), (Reference example 395, PR-2), (Reference example 395, PR-3), (Reference example 395, PR-4), (Reference example 395, PR-5), (Reference example 396, PR-1), (Reference example 396, PR-2), (Reference example 396, PR-3), (Reference example 396, PR-4), (Reference example 396, PR-5), (Reference example 397, PR-1), (Reference example 397, PR-2), (Reference example 397, PR-3), (Reference example 397, PR-4), (Reference example 397, PR-5), (Reference example 398, PR-1), (Reference example 398, PR-2), (Reference example 398, PR-3), (Reference example 398, PR-4), (Reference example 398, PR-5), (Reference example 399, PR-1), (Reference example 399, PR-2), (Reference example 399, PR-3), (Reference example 399, PR-4), (Reference example 399, PR-5), (Reference example 400, PR-1), (Reference example 400, PR-2), (Reference example 400, PR-3), (Reference example 400, PR-4), (Reference example 400, PR-5), (Reference example 401, PR-1), (Reference example 401, PR-2), (Reference example 401, PR-3), (Reference example 401, PR-4), (Reference example 401, PR-5), (Reference example 402, PR-1), (Reference example 402, PR-2), (Reference example 402, PR-3), (Reference example 402, PR-4), (Reference example 402, PR-5), (Reference example 403, PR-1), (Reference example 403, PR-2), (Reference example 403, PR-3), (Reference example 403, PR-4), (Reference example 403, PR-5), (Reference example 404, PR-1), (Reference example 404, PR-2), (Reference example 404, PR-3), (Reference example 404, PR-4), (Reference example 404, PR-5), (Reference example 405, PR-1), (Reference example 405, PR-2), (Reference example 405, PR-3), (Reference example 405, PR-4), (Reference example 405, PR-5), (Reference example 406, PR-1), (Reference example 406, PR-2), (Reference example 406, PR-3), (Reference example 406, PR-4), (Reference example 406, PR-5), (Reference example 407, PR-1), (Reference example 407, PR-2), (Reference example 407, PR-3), (Reference example 407, PR-4), (Reference example 407, PR-5), (Reference example 408, PR-1), (Reference example 408, PR-2), (Reference example 408, PR-3), (Reference example 408, PR-4), (Reference example 408, PR-5), (Reference example 409, PR-1), (Reference example 409, PR-2), (Reference example 409, PR-3), (Reference example 409, PR-4), (Reference example 409, PR-5), (Reference example 410, PR-1), (Reference example 410, PR-2), (Reference example 410, PR-3), (Reference example 410, PR-4), (Reference example 410, PR-5), (Reference example 411, PR-1), (Reference example 411, PR-2), (Reference example 411, PR-3), (Reference example 411, PR-4), (Reference example 411, PR-5), (Reference example 412, PR-1), (Reference example 412, PR-2), (Reference example 412, PR-3), (Reference example 412, PR-4), (Reference example 412, PR-5), (Reference example 413, PR-1), (Reference example 413, PR-2), (Reference example 413, PR-3), (Reference example 413, PR-4), (Reference example 413, PR-5), (Reference example 414, PR-1), (Reference example 414, PR-2), (Reference example 414, PR-3), (Reference example 414, PR-4), (Reference example 414, PR-5), (Reference example 415, PR-1), (Reference example 415, PR-2), (Reference example 415, PR-3), (Reference example 415, PR-4), (Reference example 415, PR-5), (Reference example 416, PR-1), (Reference example 416, PR-2), (Reference example 416, PR-3), (Reference example 416, PR-4), (Reference example 416, PR-5), (Reference example 417, PR-1), (Reference example 417, PR-2), (Reference example 417, PR-3), (Reference example 417, PR-4), (Reference example 417, PR-5), (Reference example 418, PR-1), (Reference example 418, PR-2), (Reference example 418, PR-3), (Reference example 418, PR-4), (Reference example 418, PR-5), (Reference example 419, PR-1), (Reference example 419, PR-2), (Reference example 419, PR-3), (Reference example 419, PR-4), (Reference example 419, PR-5), (Reference example 420, PR-1), (Reference example 420, PR-2), (Reference example 420, PR-3), (Reference example 420, PR-4), (Reference example 420, PR-5), (Reference example 421, PR-1), (Reference example 421, PR-2), (Reference example 421, PR-3), (Reference example 421, PR-4), (Reference example 421, PR-5), (Reference example 422, PR-1), (Reference example 422, PR-2), (Reference example 422, PR-3), (Reference example 422, PR-4), (Reference example 422, PR-5), (Reference example 423, PR-1), (Reference example 423, PR-2), (Reference example 423, PR-3), (Reference example 423, PR-4), (Reference example 423, PR-5), (Reference example 424, PR-1), (Reference example 424, PR-2), (Reference example 424, PR-3), (Reference example 424, PR-4), (Reference example 424, PR-5), (Reference example 425, PR-1), (Reference example 425, PR-2), (Reference example 425, PR-3), (Reference example 425, PR-4), (Reference example 425, PR-5), (Reference example 426, PR-1), (Reference example 426, PR-2), (Reference example 426, PR-3), (Reference example 426, PR-4), (Reference example 426, PR-5), (Reference example 427, PR-1), (Reference example 427, PR-2), (Reference example 427, PR-3), (Reference example 427, PR-4), (Reference example 427, PR-5), (Reference example 428, PR-1), (Reference example 428, PR-2), (Reference example 428, PR-3), (Reference example 428, PR-4), (Reference example 428, PR-5), (Reference example 429, PR-1), (Reference example 429, PR-2), (Reference example 429, PR-3), (Reference example 429, PR-4), (Reference example 429, PR-5), (Reference example 430, PR-1), (Reference example 430, PR-2), (Reference example 430, PR-3), (Reference example 430, PR-4), (Reference example 430, PR-5), (Reference example 431, PR-1), (Reference example 431, PR-2), (Reference example 431, PR-3), (Reference example 431, PR-4), (Reference example 431, PR-5), (Reference example 432, PR-1), (Reference example 432, PR-2), (Reference example 432, PR-3), (Reference example 432, PR-4), (Reference example 432, PR-5), (Reference example 433, PR-1), (Reference example 433, PR-2), (Reference example 433, PR-3), (Reference example 433, PR-4), (Reference example 433, PR-5), (Reference example 434, PR-1), (Reference example 434, PR-2), (Reference example 434, PR-3), (Reference example 434, PR-4), (Reference example 434, PR-5), (Reference example 435, PR-1), (Reference example 435, PR-2), (Reference example 435, PR-3), (Reference example 435, PR-4), (Reference example 435, PR-5), (Reference example 436, PR-1), (Reference example 436, PR-2), (Reference example 436, PR-3), (Reference example 436, PR-4), (Reference example 436, PR-5), (Reference example 437, PR-1), (Reference example 437, PR-2), (Reference example 437, PR-3), (Reference example 437, PR-4), (Reference example 437, PR-5), (Reference example 438, PR-1), (Reference example 438, PR-2), (Reference example 438, PR-3), (Reference example 438, PR-4), (Reference example 438, PR-5), (Reference example 439, PR-1), (Reference example 439, PR-2), (Reference example 439, PR-3), (Reference example 439, PR-4), (Reference example 439, PR-5), (Reference example 440, PR-1), (Reference example 440, PR-2), (Reference example 440, PR-3), (Reference example 440, PR-4), (Reference example 440, PR-5), (Reference example 441, PR-1), (Reference example 441, PR-2), (Reference example 441, PR-3), (Reference example 441, PR-4), (Reference example 441, PR-5), (Reference example 442, PR-1), (Reference example 442, PR-2), (Reference example 442, PR-3), (Reference example 442, PR-4), (Reference example 442, PR-5), (Reference example 443, PR-1), (Reference example 443, PR-2), (Reference example 443, PR-3), (Reference example 443, PR-4), (Reference example 443, PR-5), (Reference example 444, PR-1), (Reference example 444, PR-2), (Reference example 444, PR-3), (Reference example 444, PR-4), (Reference example 444, PR-5), (Reference example 445, PR-1), (Reference example 445, PR-2), (Reference example 445, PR-3), (Reference example 445, PR-4), (Reference example 445, PR-5), (Reference example 446, PR-1), (Reference example 446, PR-2), (Reference example 446, PR-3), (Reference example 446, PR-4), (Reference example 446, PR-5), (Reference example 447, PR-1), (Reference example 447, PR-2), (Reference example 447, PR-3), (Reference example 447, PR-4), (Reference example 447, PR-5), (Reference example 448, PR-1), (Reference example 448, PR-2), (Reference example 448, PR-3), (Reference example 448, PR-4), (Reference example 448, PR-5), (Reference example 449, PR-1), (Reference example 449, PR-2), (Reference example 449, PR-3), (Reference example 449, PR-4), (Reference example 449, PR-5), (Reference example 450, PR-1), (Reference example 450, PR-2), (Reference example 450, PR-3), (Reference example 450, PR-4), (Reference example 450, PR-5), (Reference example 451, PR-1), (Reference example 451, PR-2), (Reference example 451, PR-3), (Reference example 451, PR-4), (Reference example 451, PR-5), (Reference example 452, PR-1), (Reference example 452, PR-2), (Reference example 452, PR-3), (Reference example 452, PR-4), (Reference example 452, PR-5), (Reference example 453, PR-1), (Reference example 453, PR-2), (Reference example 453, PR-3), (Reference example 453, PR-4), (Reference example 453, PR-5), (Reference example 454, PR-1), (Reference example 454, PR-2), (Reference example 454, PR-3), (Reference example 454, PR-4), (Reference example 454, PR-5), (Reference example 455, PR-1), (Reference example 455, PR-2), (Reference example 455, PR-3), (Reference example 455, PR-4), (Reference example 455, PR-5), (Reference example 456, PR-1), (Reference example 456, PR-2), (Reference example 456, PR-3), (Reference example 456, PR-4), (Reference example 456, PR-5), (Reference example 457, PR-1), (Reference example 457, PR-2), (Reference example 457, PR-3), (Reference example 457, PR-4), (Reference example 457, PR-5), (Reference example 458, PR-1), (Reference example 458, PR-2), (Reference example 458, PR-3), (Reference example 458, PR-4), (Reference example 458, PR-5), (Reference example 459, PR-1), (Reference example 459, PR-2), (Reference example 459, PR-3), (Reference example 459, PR-4), (Reference example 459, PR-5), (Reference example 460, PR-1), (Reference example 460, PR-2), (Reference example 460, PR-3), (Reference example 460, PR-4), (Reference example 460, PR-5), (Reference example 461, PR-1), (Reference example 461, PR-2), (Reference example 461, PR-3), (Reference example 461, PR-4), (Reference example 461, PR-5), (Reference example 462, PR-1), (Reference example 462, PR-2), (Reference example 462, PR-3), (Reference example 462, PR-4), (Reference example 462, PR-5), (Reference example 463, PR-1), (Reference example 463, PR-2), (Reference example 463, PR-3), (Reference example 463, PR-4), (Reference example 463, PR-5), (Reference example 464, PR-1), (Reference example 464, PR-2), (Reference example 464, PR-3), (Reference example 464, PR-4), (Reference example 464, PR-5), (Reference example 465, PR-1), (Reference example 465, PR-2), (Reference example 465, PR-3), (Reference example 465, PR-4), (Reference example 465, PR-5), (Reference example 466, PR-1), (Reference example 466, PR-2), (Reference example 466, PR-3), (Reference example 466, PR-4), (Reference example 466, PR-5), (Reference example 467, PR-1), (Reference example 467, PR-2), (Reference example 467, PR-3), (Reference example 467, PR-4), (Reference example 467, PR-5), (Reference example 468, PR-1), (Reference example 468, PR-2), (Reference example 468, PR-3), (Reference example 468, PR-4), (Reference example 468, PR-5), (Reference example 469, PR-1), (Reference example 469, PR-2), (Reference example 469, PR-3), (Reference example 469, PR-4), (Reference example 469, PR-5), (Reference example 470, PR-1), (Reference example 470, PR-2), (Reference example 470, PR-3), (Reference example 470, PR-4), (Reference example 470, PR-5), (Reference example 471, PR-1), (Reference example 471, PR-2), (Reference example 471, PR-3), (Reference example 471, PR-4), (Reference example 471, PR-5), (Reference example 472, PR-1), (Reference example 472, PR-2), (Reference example 472, PR-3), (Reference example 472, PR-4), (Reference example 472, PR-5), (Reference example 473, PR-1), (Reference example 473, PR-2), (Reference example 473, PR-3), (Reference example 473, PR-4), (Reference example 473, PR-5), (Reference example 474, PR-1), (Reference example 474, PR-2), (Reference example 474, PR-3), (Reference example 474, PR-4), (Reference example 474, PR-5), (Reference example 475, PR-1), (Reference example 475, PR-2), (Reference example 475, PR-3), (Reference example 475, PR-4), (Reference example 475, PR-5), (Reference example 476, PR-1), (Reference example 476, PR-2), (Reference example 476, PR-3), (Reference example 476, PR-4), (Reference example 476, PR-5), (Reference example 477, PR-1), (Reference example 477, PR-2), (Reference example 477, PR-3), (Reference example 477, PR-4), (Reference example 477, PR-5), (Reference example 478, PR-1), (Reference example 478, PR-2), (Reference example 478, PR-3), (Reference example 478, PR-4), (Reference example 478, PR-5), (Reference example 479, PR-1), (Reference example 479, PR-2), (Reference example 479, PR-3), (Reference example 479, PR-4), (Reference example 479, PR-5), (Reference example 480, PR-1), (Reference example 480, PR-2), (Reference example 480, PR-3), (Reference example 480, PR-4), (Reference example 480, PR-5), (Reference example 481, PR-1), (Reference example 481, PR-2), (Reference example 481, PR-3), (Reference example 481, PR-4), (Reference example 481, PR-5), (Reference example 482, PR-1), (Reference example 482, PR-2), (Reference example 482, PR-3), (Reference example 482, PR-4), (Reference example 482, PR-5), (Reference example 483, PR-1), (Reference example 483, PR-2), (Reference example 483, PR-3), (Reference example 483, PR-4), (Reference example 483, PR-5), (Reference example 484, PR-1), (Reference example 484, PR-2), (Reference example 484, PR-3), (Reference example 484, PR-4), (Reference example 484, PR-5), (Reference example 485, PR-1), (Reference example 485, PR-2), (Reference example 485, PR-3), (Reference example 485, PR-4), (Reference example 485, PR-5), (Reference example 486, PR-1), (Reference example 486, PR-2), (Reference example 486, PR-3), (Reference example 486, PR-4), (Reference example 486, PR-5), (Reference example 487, PR-1), (Reference example 487, PR-2), (Reference example 487, PR-3), (Reference example 487, PR-4), (Reference example 487, PR-5), (Reference example 488, PR-1), (Reference example 488, PR-2), (Reference example 488, PR-3), (Reference example 488, PR-4), (Reference example 488, PR-5), (Reference example 489, PR-1), (Reference example 489, PR-2), (Reference example 489, PR-3), (Reference example 489, PR-4), (Reference example 489, PR-5), (Reference example 490, PR-1), (Reference example 490, PR-2), (Reference example 490, PR-3), (Reference example 490, PR-4), (Reference example 490, PR-5), (Reference example 491, PR-1), (Reference example 491, PR-2), (Reference example 491, PR-3), (Reference example 491, PR-4), (Reference example 491, PR-5), (Reference example 492, PR-1), (Reference example 492, PR-2), (Reference example 492, PR-3), (Reference example 492, PR-4), (Reference example 492, PR-5), (Reference example 493, PR-1), (Reference example 493, PR-2), (Reference example 493, PR-3), (Reference example 493, PR-4), (Reference example 493, PR-5), (Reference example 494, PR-1), (Reference example 494, PR-2), (Reference example 494, PR-3), (Reference example 494, PR-4), (Reference example 494, PR-5), (Reference example 495, PR-1), (Reference example 495, PR-2), (Reference example 495, PR-3), (Reference example 495, PR-4), (Reference example 495, PR-5), (Reference example 496, PR-1), (Reference example 496, PR-2), (Reference example 496, PR-3), (Reference example 496, PR-4), (Reference example 496, PR-5), (Reference example 497, PR-1), (Reference example 497, PR-2), (Reference example 497, PR-3), (Reference example 497, PR-4), (Reference example 497, PR-5), (Reference example 498, PR-1), (Reference example 498, PR-2), (Reference example 498, PR-3), (Reference example 498, PR-4), (Reference example 498, PR-5), (Reference example 499, PR-1), (Reference example 499, PR-2), (Reference example 499, PR-3), (Reference example 499, PR-4), (Reference example 499, PR-5), (Reference example 500, PR-1), (Reference example 500, PR-2), (Reference example 500, PR-3), (Reference example 500, PR-4), (Reference example 500, PR-5), (Reference example 501, PR-1), (Reference example 501, PR-2), (Reference example 501, PR-3), (Reference example 501, PR-4), (Reference example 501, PR-5), (Reference example 502, PR-1), (Reference example 502, PR-2), (Reference example 502, PR-3), (Reference example 502, PR-4), (Reference example 502, PR-5), (Reference example 503, PR-1), (Reference example 503, PR-2), (Reference example 503, PR-3), (Reference example 503, PR-4), (Reference example 503, PR-5), (Reference example 504, PR-1), (Reference example 504, PR-2), (Reference example 504, PR-3), (Reference example 504, PR-4), (Reference example 504, PR-5), (Reference example 505, PR-1), (Reference example 505, PR-2), (Reference example 505, PR-3), (Reference example 505, PR-4), (Reference example 505, PR-5), (Reference example 506, PR-1), (Reference example 506, PR-2), (Reference example 506, PR-3), (Reference example 506, PR-4), (Reference example 506, PR-5), (Reference example 507, PR-1), (Reference example 507, PR-2), (Reference example 507, PR-3), (Reference example 507, PR-4), (Reference example 507, PR-5), (Reference example 508, PR-1), (Reference example 508, PR-2), (Reference example 508, PR-3), (Reference example 508, PR-4), (Reference example 508, PR-5), (Reference example 509, PR-1), (Reference example 509, PR-2), (Reference example 509, PR-3), (Reference example 509, PR-4), (Reference example 509, PR-5), (Reference example 510, PR-1), (Reference example 510, PR-2), (Reference example 510, PR-3), (Reference example 510, PR-4), (Reference example 510, PR-5), (Reference example 511, PR-1), (Reference example 511, PR-2), (Reference example 511, PR-3), (Reference example 511, PR-4), (Reference example 511, PR-5), (Reference example 512, PR-1), (Reference example 512, PR-2), (Reference example 512, PR-3), (Reference example 512, PR-4), (Reference example 512, PR-5), (Reference example 513, PR-1), (Reference example 513, PR-2), (Reference example 513, PR-3), (Reference example 513, PR-4), (Reference example 513, PR-5), (Reference example 514, PR-1), (Reference example 514, PR-2), (Reference example 514, PR-3), (Reference example 514, PR-4), (Reference example 514, PR-5), (Reference example 515, PR-1), (Reference example 515, PR-2), (Reference example 515, PR-3), (Reference example 515, PR-4), (Reference example 515, PR-5), (Reference example 516, PR-1), (Reference example 516, PR-2), (Reference example 516, PR-3), (Reference example 516, PR-4), (Reference example 516, PR-5), (Reference example 517, PR-1), (Reference example 517, PR-2), (Reference example 517, PR-3), (Reference example 517, PR-4), (Reference example 517, PR-5), (Reference example 518, PR-1), (Reference example 518, PR-2), (Reference example 518, PR-3), (Reference example 518, PR-4), (Reference example 518, PR-5), (Reference example 519, PR-1), (Reference example 519, PR-2), (Reference example 519, PR-3), (Reference example 519, PR-4), (Reference example 519, PR-5), (Reference example 520, PR-1), (Reference example 520, PR-2), (Reference example 520, PR-3), (Reference example 520, PR-4), (Reference example 520, PR-5), (Reference example 521, PR-1), (Reference example 521, PR-2), (Reference example 521, PR-3), (Reference example 521, PR-4), (Reference example 521, PR-5), (Reference example 522, PR-1), (Reference example 522, PR-2), (Reference example 522, PR-3), (Reference example 522, PR-4), (Reference example 522, PR-5), (Reference example 523, PR-1), (Reference example 523, PR-2), (Reference example 523, PR-3), (Reference example 523, PR-4), (Reference example 523, PR-5), (Reference example 524, PR-1), (Reference example 524, PR-2), (Reference example 524, PR-3), (Reference example 524, PR-4), (Reference example 524, PR-5), (Reference example 525, PR-1), (Reference example 525, PR-2), (Reference example 525, PR-3), (Reference example 525, PR-4), (Reference example 525, PR-5), (Reference example 526, PR-1), (Reference example 526, PR-2), (Reference example 526, PR-3), (Reference example 526, PR-4), (Reference example 526, PR-5), (Reference example 527, PR-1), (Reference example 527, PR-2), (Reference example 527, PR-3), (Reference example 527, PR-4), (Reference example 527, PR-5), (Reference example 528, PR-1), (Reference example 528, PR-2), (Reference example 528, PR-3), (Reference example 528, PR-4), (Reference example 528, PR-5), (Reference example 529, PR-1), (Reference example 529, PR-2), (Reference example 529, PR-3), (Reference example 529, PR-4), (Reference example 529, PR-5), (Reference example 530, PR-1), (Reference example 530, PR-2), (Reference example 530, PR-3), (Reference example 530, PR-4), (Reference example 530, PR-5), (Reference example 531, PR-1), (Reference example 531, PR-2), (Reference example 531, PR-3), (Reference example 531, PR-4), (Reference example 531, PR-5), (Reference example 532, PR-1), (Reference example 532, PR-2), (Reference example 532, PR-3), (Reference example 532, PR-4), (Reference example 532, PR-5), (Reference example 533, PR-1), (Reference example 533, PR-2), (Reference example 533, PR-3), (Reference example 533, PR-4), (Reference example 533, PR-5), (Reference example 534, PR-1), (Reference example 534, PR-2), (Reference example 534, PR-3), (Reference example 534, PR-4), (Reference example 534, PR-5), (Reference example 535, PR-1), (Reference example 535, PR-2), (Reference example 535, PR-3), (Reference example 535, PR-4), (Reference example 535, PR-5), (Reference example 536, PR-1), (Reference example 536, PR-2), (Reference example 536, PR-3), (Reference example 536, PR-4), (Reference example 536, PR-5), (Reference example 537, PR-1), (Reference example 537, PR-2), (Reference example 537, PR-3), (Reference example 537, PR-4), (Reference example 537, PR-5), (Reference example 538, PR-1), (Reference example 538, PR-2), (Reference example 538, PR-3), (Reference example 538, PR-4), (Reference example 538, PR-5), (Reference example 539, PR-1), (Reference example 539, PR-2), (Reference example 539, PR-3), (Reference example 539, PR-4), (Reference example 539, PR-5), (Reference example 540, PR-1), (Reference example 540, PR-2), (Reference example 540, PR-3), (Reference example 540, PR-4), (Reference example 540, PR-5), (Reference example 541, PR-1), (Reference example 541, PR-2), (Reference example 541, PR-3), (Reference example 541, PR-4), (Reference example 541, PR-5), (Reference example 542, PR-1), (Reference example 542, PR-2), (Reference example 542, PR-3), (Reference example 542, PR-4), (Reference example 542, PR-5), (Reference example 543, PR-1), (Reference example 543, PR-2), (Reference example 543, PR-3), (Reference example 543, PR-4), (Reference example 543, PR-5), (Reference example 544, PR-1), (Reference example 544, PR-2), (Reference example 544, PR-3), (Reference example 544, PR-4), (Reference example 544, PR-5), (Reference example 545, PR-1), (Reference example 545, PR-2), (Reference example 545, PR-3), (Reference example 545, PR-4), (Reference example 545, PR-5), (Reference example 546, PR-1), (Reference example 546, PR-2), (Reference example 546, PR-3), (Reference example 546, PR-4), (Reference example 546, PR-5), (Reference example 547, PR-1), (Reference example 547, PR-2), (Reference example 547, PR-3), (Reference example 547, PR-4), (Reference example 547, PR-5), (Reference example 548, PR-1), (Reference example 548, PR-2), (Reference example 548, PR-3), (Reference example 548, PR-4), (Reference example 548, PR-5), (Reference example 549, PR-1), (Reference example 549, PR-2), (Reference example 549, PR-3), (Reference example 549, PR-4), (Reference example 549, PR-5), (Reference example 550, PR-1), (Reference example 550, PR-2), (Reference example 550, PR-3), (Reference example 550, PR-4), (Reference example 550, PR-5), (Reference example 551, PR-1), (Reference example 551, PR-2), (Reference example 551, PR-3), (Reference example 551, PR-4), (Reference example 551, PR-5), (Reference example 552, PR-1), (Reference example 552, PR-2), (Reference example 552, PR-3), (Reference example 552, PR-4), (Reference example 552, PR-5), (Reference example 553, PR-1), (Reference example 553, PR-2), (Reference example 553, PR-3), (Reference example 553, PR-4), (Reference example 553, PR-5), (Reference example 554, PR-1), (Reference example 554, PR-2), (Reference example 554, PR-3), (Reference example 554, PR-4), (Reference example 554, PR-5), (Reference example 555, PR-1), (Reference example 555, PR-2), (Reference example 555, PR-3), (Reference example 555, PR-4), (Reference example 555, PR-5), (Reference example 556, PR-1), (Reference example 556, PR-2), (Reference example 556, PR-3), (Reference example 556, PR-4), (Reference example 556, PR-5), (Reference example 557, PR-1), (Reference example 557, PR-2), (Reference example 557, PR-3), (Reference example 557, PR-4), (Reference example 557, PR-5), (Reference example 558, PR-1), (Reference example 558, PR-2), (Reference example 558, PR-3), (Reference example 558, PR-4), (Reference example 558, PR-5), (Reference example 559, PR-1), (Reference example 559, PR-2), (Reference example 559, PR-3), (Reference example 559, PR-4), (Reference example 559, PR-5), (Reference example 560, PR-1), (Reference example 560, PR-2), (Reference example 560, PR-3), (Reference example 560, PR-4), (Reference example 560, PR-5), (Reference example 561, PR-1), (Reference example 561, PR-2), (Reference example 561, PR-3), (Reference example 561, PR-4), (Reference example 561, PR-5), (Reference example 562, PR-1), (Reference example 562, PR-2), (Reference example 562, PR-3), (Reference example 562, PR-4), (Reference example 562, PR-5), (Reference example 563, PR-1), (Reference example 563, PR-2), (Reference example 563, PR-3), (Reference example 563, PR-4), (Reference example 563, PR-5), (Reference example 564, PR-1), (Reference example 564, PR-2), (Reference example 564, PR-3), (Reference example 564, PR-4), (Reference example 564, PR-5), (Reference example 565, PR-1), (Reference example 565, PR-2), (Reference example 565, PR-3), (Reference example 565, PR-4), (Reference example 565, PR-5), (Reference example 566, PR-1), (Reference example 566, PR-2), (Reference example 566, PR-3), (Reference example 566, PR-4), (Reference example 566, PR-5), (Reference example 567, PR-1), (Reference example 567, PR-2), (Reference example 567, PR-3), (Reference example 567, PR-4), (Reference example 567, PR-5), (Reference example 568, PR-1), (Reference example 568, PR-2), (Reference example 568, PR-3), (Reference example 568, PR-4), (Reference example 568, PR-5), (Reference example 569, PR-1), (Reference example 569, PR-2), (Reference example 569, PR-3), (Reference example 569, PR-4), (Reference example 569, PR-5), (Reference example 570, PR-1), (Reference example 570, PR-2), (Reference example 570, PR-3), (Reference example 570, PR-4), (Reference example 570, PR-5), (Reference example 571, PR-1), (Reference example 571, PR-2), (Reference example 571, PR-3), (Reference example 571, PR-4), (Reference example 571, PR-5), (Reference example 572, PR-1), (Reference example 572, PR-2), (Reference example 572, PR-3), (Reference example 572, PR-4), (Reference example 572, PR-5), (Reference example 573, PR-1), (Reference example 573, PR-2), (Reference example 573, PR-3), (Reference example 573, PR-4), (Reference example 573, PR-5), (Reference example 574, PR-1), (Reference example 574, PR-2), (Reference example 574, PR-3), (Reference example 574, PR-4), (Reference example 574, PR-5), (Reference example 575, PR-1), (Reference example 575, PR-2), (Reference example 575, PR-3), (Reference example 575, PR-4), (Reference example 575, PR-5), (Reference example 576, PR-1), (Reference example 576, PR-2), (Reference example 576, PR-3), (Reference example 576, PR-4), (Reference example 576, PR-5), (Reference example 577, PR-1), (Reference example 577, PR-2), (Reference example 577, PR-3), (Reference example 577, PR-4), (Reference example 577, PR-5), (Reference example 578, PR-1), (Reference example 578, PR-2), (Reference example 578, PR-3), (Reference example 578, PR-4), (Reference example 578, PR-5), (Reference example 579, PR-1), (Reference example 579, PR-2), (Reference example 579, PR-3), (Reference example 579, PR-4), (Reference example 579, PR-5), (Reference example 580, PR-1), (Reference example 580, PR-2), (Reference example 580, PR-3), (Reference example 580, PR-4), (Reference example 580, PR-5), (Reference example 581, PR-1), (Reference example 581, PR-2), (Reference example 581, PR-3), (Reference example 581, PR-4), (Reference example 581, PR-5), (Reference example 582, PR-1), (Reference example 582, PR-2), (Reference example 582, PR-3), (Reference example 582, PR-4), (Reference example 582, PR-5). (Reference example 583, PR-1), (Reference example 583, PR-2), (Reference example 583, PR-3), (Reference example 583, PR-4), (Reference example 583, PR-5), (Reference example 584, PR-1), (Reference example 584, PR-2), (Reference example 584, PR-3), (Reference example 584, PR-4), (Reference example 584, PR-5), (Reference example 585, PR-1), (Reference example 585, PR-2), (Reference example 585, PR-3), (Reference example 585, PR-4), (Reference example 585, PR-5), (Reference example 586, PR-1), (Reference example 586, PR-2), (Reference example 586, PR-3), (Reference example 586, PR-4), (Reference example 586, PR-5), (Reference example 587, PR-1), (Reference example 587, PR-2), (Reference example 587, PR-3), (Reference example 587, PR-4), (Reference example 587, PR-5), (Reference example 588, PR-1), (Reference example 588, PR-2), (Reference example 588, PR-3), (Reference example 588, PR-4), (Reference example 588, PR-5), (Reference example 589, PR-1), (Reference example 589, PR-2), (Reference example 589, PR-3), (Reference example 589, PR-4), (Reference example 589, PR-5), (Reference example 590, PR-1), (Reference example 590, PR-2), (Reference example 590, PR-3), (Reference example 590, PR-4), (Reference example 590, PR-5), (Reference example 591, PR-1), (Reference example 591, PR-2), (Reference example 591, PR-3), (Reference example 591, PR-4), (Reference example 591, PR-5), (Reference example 592, PR-1), (Reference example 592, PR-2), (Reference example 592, PR-3), (Reference example 592, PR-4), (Reference example 592, PR-5), (Reference example 593, PR-1), (Reference example 593, PR-2), (Reference example 593, PR-3), (Reference example 593, PR-4), (Reference example 593, PR-5), (Reference example 594, PR-1), (Reference example 594, PR-2), (Reference example 594, PR-3), (Reference example 594, PR-4), (Reference example 594, PR-5), (Reference example 595, PR-1), (Reference example 595, PR-2), (Reference example 595, PR-3), (Reference example 595, PR-4), (Reference example 595, PR-5), (Reference example 596, PR-1), (Reference example 596, PR-2), (Reference example 596, PR-3), (Reference example 596, PR-4), (Reference example 596, PR-5), (Reference example 597, PR-1), (Reference example 597, PR-2), (Reference example 597, PR-3), (Reference example 597, PR-4), (Reference example 597, PR-5), (Reference example 598, PR-1), (Reference example 598, PR-2), (Reference example 598, PR-3), (Reference example 598, PR-4), (Reference example 598, PR-5), (Reference example 599, PR-1), (Reference example 599, PR-2), (Reference example 599, PR-3), (Reference example 599, PR-4), (Reference example 599, PR-5), (Reference example 600, PR-1), (Reference example 600, PR-2), (Reference example 600, PR-3), (Reference example 600, PR-4), (Reference example 600, PR-5), (Reference example 601, PR-1), (Reference example 601, PR-2), (Reference example 601, PR-3), (Reference example 601, PR-4), (Reference example 601, PR-5), (Reference example 602, PR-1), (Reference example 602, PR-2), (Reference example 602, PR-3), (Reference example 602, PR-4), (Reference example 602, PR-5), (Reference example 603, PR-1), (Reference example 603, PR-2), (Reference example 603, PR-3), (Reference example 603, PR-4), (Reference example 603, PR-5), (Reference example 604, PR-1), (Reference example 604, PR-2), (Reference example 604, PR-3), (Reference example 604, PR-4), (Reference example 604, PR-5), (Reference example 605, PR-1), (Reference example 605, PR-2), (Reference example 605, PR-3), (Reference example 605, PR-4), (Reference example 605, PR-5), (Reference example 606, PR-1), (Reference example 606, PR-2), (Reference example 606, PR-3), (Reference example 606, PR-4), (Reference example 606, PR-5), (Reference example 607, PR-1), (Reference example 607, PR-2), (Reference example 607, PR-3), (Reference example 607, PR-4), (Reference example 607, PR-5), (Reference example 608, PR-1), (Reference example 608, PR-2), (Reference example 608, PR-3), (Reference example 608, PR-4), (Reference example 608, PR-5), (Reference example 609, PR-1), (Reference example 609, PR-2), (Reference example 609, PR-3), (Reference example 609, PR-4), (Reference example 609, PR-5), (Reference example 610, PR-1), (Reference example 610, PR-2), (Reference example 610, PR-3), (Reference example 610, PR-4), (Reference example 610, PR-5), (Reference example 611, PR-1), (Reference example 611, PR-2), (Reference example 611, PR-3), (Reference example 611, PR-4), (Reference example 611, PR-5), (Reference example 612, PR-1), (Reference example 612, PR-2), (Reference example 612, PR-3), (Reference example 612, PR-4), (Reference example 612, PR-5), (Reference example 613, PR-1), (Reference example 613, PR-2), (Reference example 613, PR-3), (Reference example 613, PR-4), (Reference example 613, PR-5), (Reference example 614, PR-1), (Reference example 614, PR-2), (Reference example 614, PR-3), (Reference example 614, PR-4), (Reference example 614, PR-5), (Reference example 615, PR-1), (Reference example 615, PR-2), (Reference example 615, PR-3), (Reference example 615, PR-4), (Reference example 615, PR-5), (Reference example 616, PR-1), (Reference example 616, PR-2), (Reference example 616, PR-3), (Reference example 616, PR-4), (Reference example 616, PR-5), (Reference example 617, PR-1), (Reference example 617, PR-2), (Reference example 617, PR-3), (Reference example 617, PR-4), (Reference example 617, PR-5), (Reference example 618, PR-1), (Reference example 618, PR-2), (Reference example 618, PR-3), (Reference example 618, PR-4), (Reference example 618, PR-5), (Reference example 619, PR-1), (Reference example 619, PR-2), (Reference example 619, PR-3), (Reference example 619, PR-4), (Reference example 619, PR-5), (Reference example 620, PR-1), (Reference example 620, PR-2), (Reference example 620, PR-3), (Reference example 620, PR-4), (Reference example 620, PR-5), (Reference example 621, PR-1), (Reference example 621, PR-2), (Reference example 621, PR-3), (Reference example 621, PR-4), (Reference example 621, PR-5), (Reference example 622, PR-1), (Reference example 622, PR-2), (Reference example 622, PR-3), (Reference example 622, PR-4), (Reference example 622, PR-5), (Reference example 623, PR-1), (Reference example 623, PR-2), (Reference example 623, PR-3), (Reference example 623, PR-4), (Reference example 623, PR-5), (Reference example 624, PR-1), (Reference example 624, PR-2), (Reference example 624, PR-3), (Reference example 624, PR-4), (Reference example 624, PR-5), (Reference example 625, PR-1), (Reference example 625, PR-2), (Reference example 625, PR-3), (Reference example 625, PR-4), (Reference example 625, PR-5), (Reference example 626, PR-1), (Reference example 626, PR-2), (Reference example 626, PR-3), (Reference example 626, PR-4), (Reference example 626, PR-5), (Reference example 627, PR-1), (Reference example 627, PR-2), (Reference example 627, PR-3), (Reference example 627, PR-4), (Reference example 627, PR-5), (Reference example 628, PR-1), (Reference example 628, PR-2), (Reference example 628, PR-3), (Reference example 628, PR-4), (Reference example 628, PR-5), (Reference example 629, PR-1), (Reference example 629, PR-2), (Reference example 629, PR-3), (Reference example 629, PR-4), (Reference example 629, PR-5), (Reference example 630, PR-1), (Reference example 630, PR-2), (Reference example 630, PR-3), (Reference example 630, PR-4), (Reference example 630, PR-5), (Reference example 631, PR-1), (Reference example 631, PR-2), (Reference example 631, PR-3), (Reference example 631, PR-4), (Reference example 631, PR-5), (Reference example 632, PR-1), (Reference example 632, PR-2), (Reference example 632, PR-3), (Reference example 632, PR-4), (Reference example 632, PR-5), (Reference example 633, PR-1), (Reference example 633, PR-2), (Reference example 633, PR-3), (Reference example 633, PR-4), (Reference example 633, PR-5), (Reference example 634, PR-1), (Reference example 634, PR-2), (Reference example 634, PR-3), (Reference example 634, PR-4), (Reference example 634, PR-5), (Reference example 635, PR-1), (Reference example 635, PR-2), (Reference example 635, PR-3), (Reference example 635, PR-4), (Reference example 635, PR-5), (Reference example 636, PR-1), (Reference example 636, PR-2), (Reference example 636, PR-3), (Reference example 636, PR-4), (Reference example 636, PR-5), (Reference example 637, PR-1), (Reference example 637, PR-2), (Reference example 637, PR-3), (Reference example 637, PR-4), (Reference example 637, PR-5), (Reference example 638, PR-1), (Reference example 638, PR-2), (Reference example 638, PR-3), (Reference example 638, PR-4), (Reference example 638, PR-5), (Reference example 639, PR-1), (Reference example 639, PR-2), (Reference example 639, PR-3), (Reference example 639, PR-4), (Reference example 639, PR-5), (Reference example 640, PR-1), (Reference example 640, PR-2), (Reference example 640, PR-3), (Reference example 640, PR-4), (Reference example 640, PR-5), (Reference example 641, PR-1), (Reference example 641, PR-2), (Reference example 641, PR-3), (Reference example 641, PR-4), (Reference example 641, PR-5), (Reference example 642, PR-1), (Reference example 642, PR-2), (Reference example 642, PR-3), (Reference example 642, PR-4), (Reference example 642, PR-5), (Reference example 643, PR-1), (Reference example 643, PR-2), (Reference example 643, PR-3), (Reference example 643, PR-4), (Reference example 643, PR-5), (Reference example 644, PR-1), (Reference example 644, PR-2), (Reference example 644, PR-3), (Reference example 644, PR-4), (Reference example 644, PR-5), (Reference example 645, PR-1), (Reference example 645, PR-2), (Reference example 645, PR-3), (Reference example 645, PR-4), (Reference example 645, PR-5), (Reference example 646, PR-1), (Reference example 646, PR-2), (Reference example 646, PR-3), (Reference example 646, PR-4), (Reference example 646, PR-5), (Reference example 647, PR-1), (Reference example 647, PR-2), (Reference example 647, PR-3), (Reference example 647, PR-4), (Reference example 647, PR-5), (Reference example 648, PR-1), (Reference example 648, PR-2), (Reference example 648, PR-3), (Reference example 648, PR-4), (Reference example 648, PR-5), (Reference example 649, PR-1), (Reference example 649, PR-2), (Reference example 649, PR-3), (Reference example 649, PR-4), (Reference example 649, PR-5), (Reference example 650, PR-1), (Reference example 650, PR-2), (Reference example 650, PR-3), (Reference example 650, PR-4), (Reference example 650, PR-5), (Reference example 651, PR-1), (Reference example 651, PR-2), (Reference example 651, PR-3), (Reference example 651, PR-4), (Reference example 651, PR-5), (Reference example 652, PR-1), (Reference example 652, PR-2), (Reference example 652, PR-3), (Reference example 652, PR-4), (Reference example 652, PR-5), (Reference example 653, PR-1), (Reference example 653, PR-2), (Reference example 653, PR-3), (Reference example 653, PR-4), (Reference example 653, PR-5), (Reference example 654, PR-1), (Reference example 654, PR-2), (Reference example 654, PR-3), (Reference example 654, PR-4), (Reference example 654, PR-5), (Reference example 655, PR-1), (Reference example 655, PR-2), (Reference example 655, PR-3), (Reference example 655, PR-4), (Reference example 655, PR-5), (Reference example 656, PR-1), (Reference example 656, PR-2), (Reference example 656, PR-3), (Reference example 656, PR-4), (Reference example 656, PR-5), (Reference example 657, PR-1), (Reference example 657, PR-2), (Reference example 657, PR-3), (Reference example 657, PR-4), (Reference example 657, PR-5), (Reference example 658, PR-1), (Reference example 658, PR-2), (Reference example 658, PR-3), (Reference example 658, PR-4), (Reference example 658, PR-5), (Reference example 659, PR-1), (Reference example 659, PR-2), (Reference example 659, PR-3), (Reference example 659, PR-4), (Reference example 659, PR-5), (Reference example 660, PR-1), (Reference example 660, PR-2), (Reference example 660, PR-3), (Reference example 660, PR-4), (Reference example 660, PR-5), (Reference example 661, PR-1), (Reference example 661, PR-2), (Reference example 661, PR-3), (Reference example 661, PR-4), (Reference example 661, PR-5), (Reference example 662, PR-1), (Reference example 662, PR-2), (Reference example 662, PR-3), (Reference example 662, PR-4), (Reference example 662, PR-5), (Reference example 663, PR-1), (Reference example 663, PR-2), (Reference example 663, PR-3), (Reference example 663, PR-4), (Reference example 663, PR-5), (Reference example 664, PR-1), (Reference example 664, PR-2), (Reference example 664, PR-3), (Reference example 664, PR-4), (Reference example 664, PR-5), (Reference example 665, PR-1), (Reference example 665, PR-2), (Reference example 665, PR-3), (Reference example 665, PR-4), (Reference example 665, PR-5).

For example, the above (Reference example 1, PR-1) means a compound shown by the following structural formula:

[Chemical formula 1094]

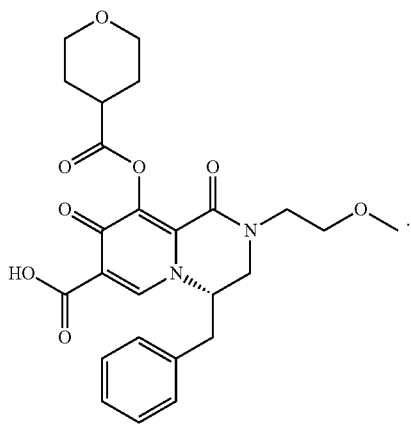

As intermediate synthesis examples, methods for synthesizing intermediates useful for carrying out the present application are shown below.

INTERMEDIATE SYNTHESIS EXAMPLE 1

[Chemical formula 1095]

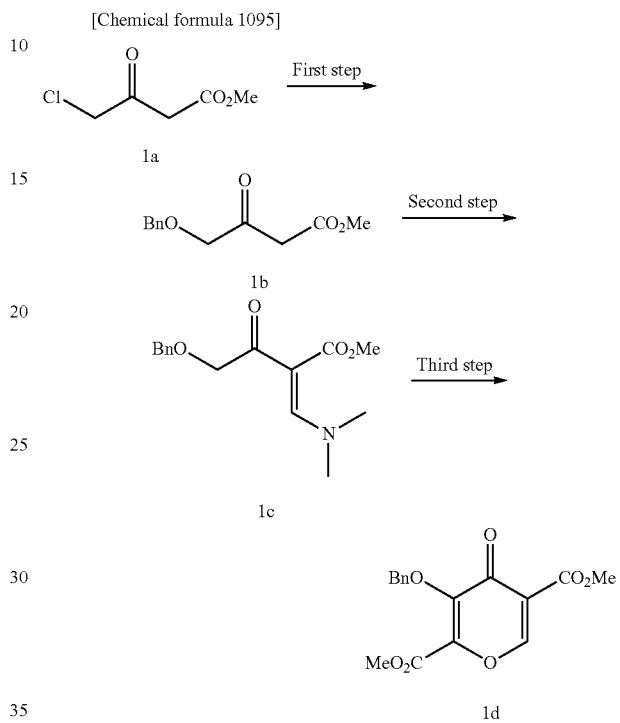

First Step

A solution of benzyl alcohol (1.00 g, 9.25 mmol) in THF (3 ml) was added to a suspension of sodium tert-pentoxide (2.55 g, 23.2 mmol) in THF (4 ml) at room temperature under nitrogen atmosphere, and the mixture was stirred at 40° C. for 2 hours. This reaction solution was cooled in an ice bath, and a THF (3 ml) solution of compound 1a (1.53 g, 10.2 mmol) was added dropwise at 0 to 10° C. After the reaction solution was stirred at room temperature for 2 hours, 2N hydrochloric acid (15 ml) was added, followed by extraction with ethyl acetate two times. The combined extracts were washed sequentially with water, saturated sodium bicarbonate water, water and aqueous saturated sodium chloride solution, and then dried with anhydrous sodium sulfate. The solvent was distilled off, and the resulting oil was purified by silica gel column chromatography (n-hexane-ethyl acetate 4:1, v/v) to obtain 1.89 g (yield 92%) of compound 1b as an oil product.

$^1$H-NMR (CDCl$_3$) δ: 3.56 (2H, s), 3.71 (3H, s), 4.14 (2H, s), 4.59 (2H, s), 7.27-7.42 (5H, m).

Second Step

Compound 1b (1.80 g, 8.1 mmol) was dissolved in 1,4-dioxane (18 mL), N,N-dimethylformamide dimethyl acetal (1.45 g, 12.2 mmol) was added, and the mixture was stirred at room temperature for 6 hours. The reaction solution was concentrated under reduced pressure, and the residue was purified by silica gel column chromatography (n-hexane-ethyl acetate 1:4, v/v) to obtain 1.77 g (yield 79%) of compound 1c as an oil product.

¹H-NMR (CDCl₃) δ: 2.90 (3H, br), 3.25 (3H, br), 3.69 (3H, s), 4.45 (2H, s), 4.59 (2H, s), 7.24-7.40 (5H, m), 7.73 (s, 1H).

Third Step

Sodium tert-butoxide (2.55 g, 23.2 mmol), dimethyl oxalate (639 mg, 5.41 mmol) and DMI (3 ml) were added to a three-neck flask under nitrogen atmosphere, and a DMI (2 ml) solution of compound 1c (0.50 g, 1.80 mmol) was added dropwise thereto at 25 to 30° C. After stirring at room temperature for 7 hours, 2N hydrochloric acid (10 ml) was added, and the mixture was stirred at room temperature for 15 hours. The reaction solution was extracted with ethyl acetate two times, and the combined extracts were washed sequentially with water, saturated sodium bicarbonate water, water and aqueous saturated sodium chloride solution, and then dried with anhydrous sodium sulfate. The solvent was distilled off, and the resulting residue was purified by silica gel column chromatography (n-hexane-ethyl acetate 2:1 to 1:1, v/v) to obtain 488 mg (yield 85%) of compound 1d as a white solid.

¹H-NMR (CDCl₃) δ: 3.89 (3H, s), 3.93 (3H, s), 5.34 (2H, s), 7.32-7.40 (3H, m), 7.45-7.49 (2H, m), 8.50 (1H, s).

INTERMEDIATE SYNTHESIS EXAMPLE 2

[Chemical formula 1096]

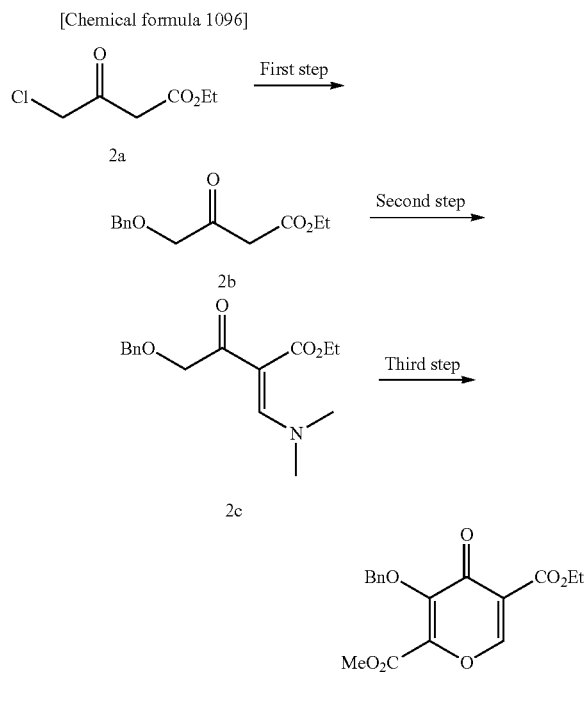

First Step

A DMI (3 ml) solution of benzyl alcohol (0.66 g, 6.1 mmol) was added to a DMI (4 ml) suspension of sodium tert-pentoxide (1.67 g, 15.2 mmol) at room temperature under nitrogen atmosphere, and the mixture was stirred at 40° C. for 2 hours. This reaction solution was cooled in an ice bath, and a DMI (3 ml) solution of compound 2a (1.10 g, 6.68 mmol) was added dropwise at 0 to 10° C. The reaction solution was stirred at 0 to 5° C. for 2 hours, and at room temperature for 3 hours, and 2N hydrochloric acid (15 ml) was added, followed by extraction with ethyl acetate two times. The combined extracts were washed sequentially with water, saturated sodium bicarbonate water, water and aqueous saturated sodium chloride solution, and then dried with anhydrous sodium sulfate. The solvent was distilled off, and the resulting oil product was purified by silica gel column chromatography (n-hexane-ethyl acetate 4:1, v/v) to obtain 1.29 g (yield 90%) of compound 2b as an oil product.

¹H-NMR (CDCl₃) δ: 1.25 (3H, t, J=7.2 Hz), 3.54 (2H, s), 4.14 (2H, s), 4.17 (2H, q, J=7.2 Hz), 4.59 (2H, s), 7.28-7.40 (5H, m).

Second Step

Compound 2b (9.73 g, 41.2 mmol) was dissolved in toluene (45 ml), N,N-dimethylformamide dimethyl acetal (7.36 g, 61.8 mmol) was added, and the mixture was stirred at room temperature for 5 hours. Water was added to the reaction solution, followed by extraction with ethyl acetate two times. The combined extracts were washed sequentially with water, and aqueous saturated sodium chloride solution, and then dried with anhydrous magnesium sulfate. The solvent was distilled off, and the resulting oil product was purified by silica gel column chromatography (n-hexane-ethyl acetate 1:1 to 3:7, v/v) to obtain 7.90 g (yield 66%) of compound 2c as an oil product.

¹H-NMR (CDCl₃) δ: 1.25 (3H, t, J=7.2 Hz), 2.95 (3H, br), 3.22 (3H, br), 4.15 (2H, q, J=7.2 Hz), 4.45 (2H, s), 4.59 (2H, s), 7.22-7.40 (5H, m), 7.73 (1H, s).

Third Step

Sodium tert-butoxide (495 mg, 5.15 mmol) and DMI (2 ml) were added to a three-neck flask under nitrogen atmosphere, and dimethyl oxalate (608 mg, 5.15 mmol) and a DMI (3 ml) solution of compound 2c (0.50 g, 1.72 mmol) were added dropwise thereto at 25 to 30° C. After stirring at room temperature for 4 hours, 2N hydrochloric acid (10 ml) was added, and the mixture was stirred at room temperature for 15 hours. The reaction solution was extracted with toluene two times, and the combined extracts were washed sequentially with water, saturated sodium bicarbonate water, water and aqueous saturated sodium chloride solution, and then dried with anhydrous sodium sulfate. The solvent was distilled off, and the resulting residue was purified by silica gel column chromatography (n-hexane-ethyl acetate 2:1, v/v) to obtain 420 mg (yield 74%) of compound 2d as a white solid.

¹H-NMR (CDCl₃) δ: 1.39 (3H, t, J=7.2 Hz), 3.88 (3H, s), 4.39 (2H, q, J=7.2 Hz), 5.34 (2H, s), 7.30-7.41 (3H, m), 7.45-7.50 (2H, m), 8.48 (1H, s).

INTERMEDIATE SYNTHESIS EXAMPLE 3

[Chemical formula 1097]

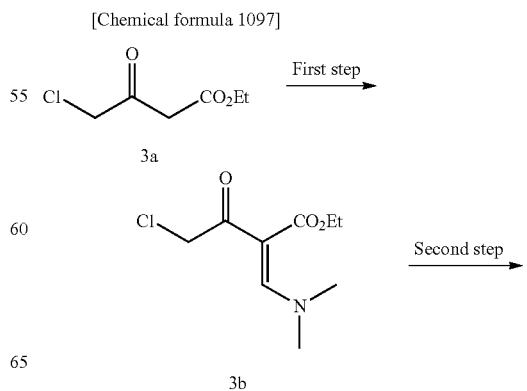

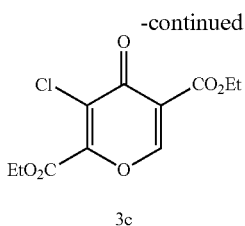

3c

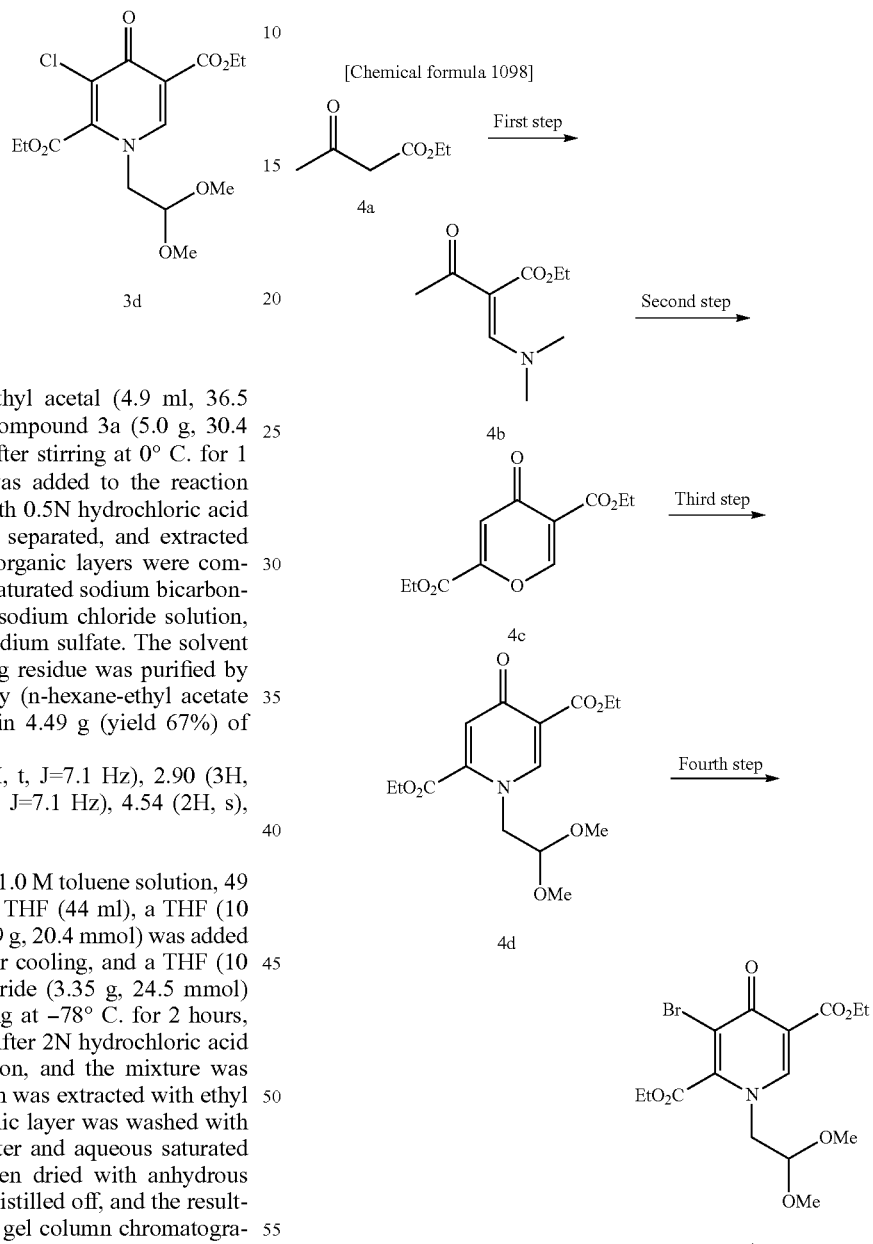

First Step

N,N-dimethylformamide dimethyl acetal (4.9 ml, 36.5 mmol) was added dropwise to compound 3a (5.0 g, 30.4 mmol) at 0° C. under cooling. After stirring at 0° C. for 1 hour, 100 ml of ethyl acetate was added to the reaction solution, followed by washing with 0.5N hydrochloric acid (50 ml). The aqueous layer was separated, and extracted with ethyl acetate (50 ml). The organic layers were combined, washed sequentially with saturated sodium bicarbonate water and aqueous saturated sodium chloride solution, and then dried with anhydrous sodium sulfate. The solvent was distilled off, and the resulting residue was purified by silica gel column chromatography (n-hexane-ethyl acetate 1:1 (v/v)→ethyl acetate) to obtain 4.49 g (yield 67%) of compound 3b as an oil product.

$^1$H-NMR (CDCl$_3$) δ: 1.32 (3H, t, J=7.1 Hz), 2.90 (3H, brs), 3.29 (3H, brs), 4.23 (2H, q, J=7.1 Hz), 4.54 (2H, s), 7.81 (1H, s).

Second Step

Lithium hexamethyldisilazide (1.0 M toluene solution, 49 ml, 49.0 mmol) was diluted with THF (44 ml), a THF (10 ml) solution of compound 3b (4.49 g, 20.4 mmol) was added dropwise thereto at −78° C. under cooling, and a THF (10 ml) solution of ethyl oxalyl chloride (3.35 g, 24.5 mmol) was added dropwise. After stirring at −78° C. for 2 hours, temperature was raised to 0° C. After 2N hydrochloric acid was added to the reaction solution, and the mixture was stirred for 20 minutes, the solution was extracted with ethyl acetate (200 ml×2), and the organic layer was washed with saturated sodium bicarbonate water and aqueous saturated sodium chloride solution and then dried with anhydrous sodium sulfate. The solvent was distilled off, and the resulting residue was purified by silica gel column chromatography (n-hexane-ethyl acetate 7:3-5:5→0:10 (v/v)) to obtain 1.77 g (yield 31%) of compound 3c as a white solid.

$^1$H-NMR (CDCl$_3$) δ: 1.36-1.46 (6H, m), 4.35-4.52 (8H, m), 8.53 (1H, s).

Third Step

Aminoacetaldehyde dimethyl acetal (0.13 ml, 1.20 mmol) was added to an ethanol (6 ml) solution of compound 3c (300 mg, 1.09 mmol) at 0° C., and the mixture was stirred at 0° C. for 1 hour and 30 minutes, at room temperature for 18 hours and, then, at 60° C. for 4 hours. After the solvent was distilled off from the reaction solvent under reduced pressure, the resulting residue was purified by silica gel column chromatography (n-hexane-ethyl acetate 5:5→0:10 (v/v)) to obtain 252 mg (yield 64%) of compound 3d as an oil product.

$^1$H-NMR (CDCl$_3$) δ: 1.36-1.47 (6H, m), 3.42 (6H, s), 3.90 (2H, d, J=5.2 Hz), 4.37 (3H, q, J=7.2 Hz), 4.50 (2H, q, J=7.2 Hz), 8.16 (1H, s).

INTERMEDIATE SYNTHESIS EXAMPLE 4

[Chemical formula 1098]

First Step

N,N-dimethylformamide dimethyl acetal (12.2 ml, 92.2 mmol) was added dropwise to compound 4a (10.0 g, 76.8 mmol) at 0° C. under cooling. After stirring at 0° C. for 1 hour and 30 minutes and, then, at room temperature for 2 hours and 30 minutes, 100 ml of ethyl acetate was added to the reaction solution, and the solvent was distilled off. The resulting residue was purified by silica gel column chromatography (n-hexane-ethyl acetate 5:5→0:10 (v/v)) to obtain 12.45 g (yield 88%) of compound 4b as an oil product.

$^1$H-NMR (CDCl$_3$) δ: 1.32 (3H, t, J=7.1 Hz), 2.33 (3H, s), 3.04 (6H, brs), 4.23 (2H, q, J=7.2 Hz), 7.68 (1H, s).

Second Step

Lithium hexamethyldisilazide (1.0M toluene solution, 24 ml, 24.0 mmol) was diluted with THF (20 ml), a THF (5 ml) solution of compound 4b (1.85 g, 10.0 mmol) was added dropwise thereto at −78° C. under cooling, and a THF (5 ml) solution of ethyl oxalyl chloride (1.34 ml, 12.0 mmol) was added dropwise. After stirring at −78° C. for 2 hours, 2N-hydrochloric acid was added to the reaction solution, and the mixture was stirred at room temperature for 20 minutes. The solution was extracted with ethyl acetate, and the organic layer was washed sequentially with saturated sodium bicarbonate water and aqueous saturated sodium chloride solution, and then dried with anhydrous sodium sulfate. The solvent was distilled off, and the resulting residue was purified by silica gel column chromatography (n-hexane-ethyl acetate 75:25→455:5 (v/v)) to obtain 1.03 g (yield 43%) of compound 4c as a brown oil product.

$^1$H-NMR (CDCl$_3$) δ: 1.38 (3H, t, J=7.1 Hz), 1.42 (3H, t, J=7.4 Hz), 4.33-4.47 (4H, m), 7.19 (1H, s), 8.54 (1H, s).

Third Step

Aminoacetaldehyde dimethyl acetal (0.34 ml, 3.11 mmol) was added to an ethanol (6.8 ml) solution of compound 4c (680 mg, 2.83 mmol) at 0° C., and the mixture was allowed to stand at room temperature for 16 hours. After the solvent was distilled off from the reaction solution under reduced pressure, the resulting residue was purified by silica gel column chromatography (n-hexane-ethyl acetate 90:10 (v/v)) to obtain 875 mg (yield 94%) of compound 4d as an oil product.

$^1$H-NMR (CDCl$_3$) δ: 1.38 (3H, t, J=7.1 Hz), 1.39 (3H, t, J=7.1 Hz), 3.40 (6H, s), 4.33 (2H, d, J=4.7 Hz), 4.37 (4H, q, J=7.1 Hz), 4.49 (1H, t, J=4.7 Hz), 7.06 (1H, s), 8.17 (1H, s).

Fourth Step

N-bromosuccinimide (1.46 g, 8.18 mmol) was added to a DMF (10 ml) solution of compound 4d (2.68 g, 8.18 mmol), and the mixture was stirred at room temperature for 48 hours. After saturated sodium bicarbonate water was added to the reaction solution, the solution was extracted with ethyl acetate, and the organic layer was washed sequentially with water and aqueous saturated sodium chloride solution, and then dried with anhydrous sodium sulfate. The solvent was distilled off, and the resulting residue was purified by silica gel column chromatography (n-hexane-ethyl acetate 90:10 (v/v)) to obtain 2.83 g (yield 85%) of compound 4e as an oil product.

$^1$H-NMR (CDCl$_3$) δ: 1.38 (3H, t, J=7.1 Hz), 1.46 (3H, t, J=7.1 Hz), 3.42 (6H, s), 3.88 (3H, d, J=5.0 Hz), 4.37 (3H, q, J=7.1 Hz), 4.51 (2H, q, J=7.1 Hz), 4.54 (2H, t, J=5.2 Hz), 8.17 (1H, s).

INTERMEDIATE SYNTHESIS EXAMPLE 5

[Chemical formula 1099]

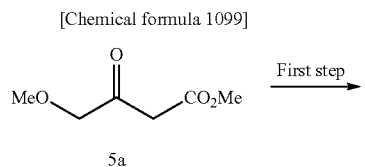

5a

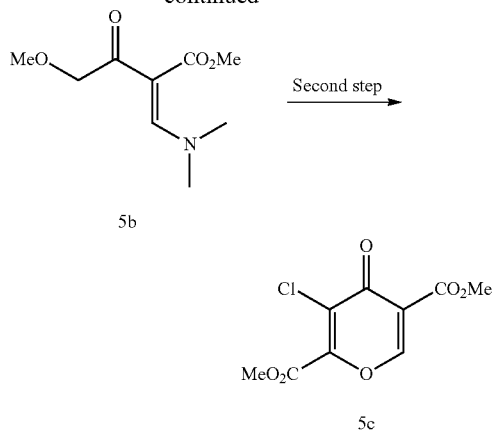

First Step

Compound 5a (598 mg, 4.09 mmol) and N,N-dimethylformamide dimethyl acetal (488 mg, 4.09 mmol) were dissolved in toluene (1 ml), and the solution was stirred at room temperature for 11 hours. The solvent was distilled off from the reaction solution under reduced pressure, and the resulting residue (containing compound 5b) was used in Second step without purification.

Second Step

Sodium tert-butoxide (400 mg, 4.16 mmol) was suspended in DMI (5 ml), a DMI (5 ml) solution of the crude product obtained in First step was added thereto, then, a THF (10 ml) solution of dimethyl oxalate (983 mg, 8.32 mmol) was added dropwise, and the mixture was stirred at room temperature for 45 minutes. The reaction solution was poured into 2N hydrochloric acid-methanol (20 ml), and the mixture was stirred at 0° C. for 20 minutes. Water was added, the solution was extracted with ethyl acetate, and the organic layer was washed sequentially with water, saturated sodium bicarbonate water, and aqueous saturated sodium chloride solution, and dried with anhydrous sodium sulfate. After the solvent was distilled off, the resulting residue was purified by silica gel column chromatography to obtain 222 mg (yield: 22% from 5a) of compound 3C.

$^1$H-NMR (CDCl$_3$) δ: 3.91 (3H, s), 3.97 (3H, s), 4.05 (3H, s), 8.50 (1H, s).

INTERMEDIATE SYNTHESIS EXAMPLE 6

[Chemical formula 1100]

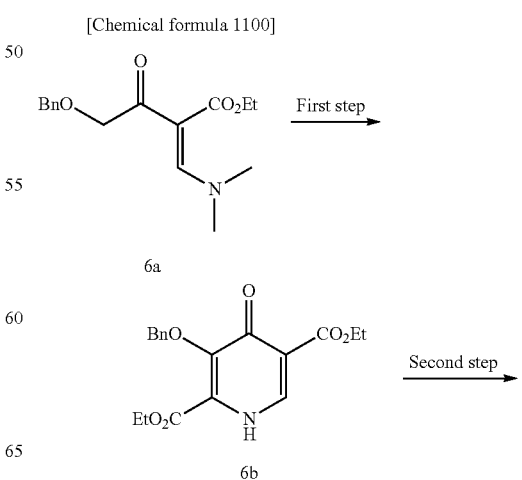

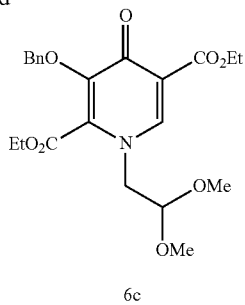

6c

First Step

Lithium hexamethyldisilazide (1.0M toluene solution, 12 ml, 12.0 mmol) was diluted with THF (11 ml), a THF (2 ml) solution of compound 6a (1.46 g, 5.0 mmol) was added dropwise thereto at −78° C. under cooling, and a THF (2 ml) solution of ethyl oxalyl chloride (0.67 ml, 6.0 mmol) was added dropwise. After stirring at −78° C. for 2 hours, ammonium acetate (500 mg) and acetic acid (10 ml) were added to the reaction solution, and the mixture was stirred at 65° C. for 1 hour and 30 minutes. Water was added to the reaction solution, the solvent was extracted with ethyl acetate, and the organic layer was washed sequentially with water, and saturated sodium bicarbonate water, and dried with anhydrous sodium sulfate. The solvent was distilled off, and the resulting residue was purified by silica gel column chromatography (n-hexane-ethyl acetate 55:45→45:55 (v/v)) to obtain 505.1 mg of compound 6b as a yellow solid. It was washed with isopropyl ether-hexane (1:2), and dried under reduced pressure to obtain 416.8 mg (yield 24%) of compound 6b as a yellow crystal.

$^1$H-NMR (CDCl$_3$) δ: 1.35 (3H, t, J=7.1 Hz), 1.46 (3H, t, J=7.1 Hz), 4.40 (2H, q, J=7.2 Hz), 4.50 (2H, q, J=7.1 Hz), 5.20 (2H, s), 7.33-7.41 (3H, m), 7.49-7.52 (2H, m), 8.76 (1H, s), 11.61 (1H, brs).

Second Step

Cesium carbonate (73.3 mg, 0.23 mmol) and bromoacetaldehyde dimethyl acetal (38.0 mg, 0.23 mmol) were added to a DMF (1 ml) solution of compound 6b (51.8 mg, 0.15 mmol), and the mixture was stirred at room temperature overnight. Cesium carbonate (73.3 mg, 0.23 mmol) and bromoacetaldehyde dimethyl acetal (38.0 mg, 0.23 mmol) were further added, and the mixture was further stirred at 100° C. for 20 minutes. After water was added to the reaction solution, the solution was extracted with ethyl acetate, and the organic layer was washed sequentially with water and aqueous saturated sodium chloride solution, and dried with anhydrous sodium sulfate. The solvent was distilled off, and the resulting residue was purified by silica gel column chromatography (n-hexane-ethyl acetate 50:50→30:70 (v/v)) to obtain 35.3 mg (yield 54%) of compound 6c as a colorless oil product.

$^1$H-NMR (CDCl$_3$) δ: 1.26 (3H, t, J=7.1 Hz), 1.40 (3H, t, J=7.1 Hz), 3.39 (6H, s), 3.91 (2H, d, J=5.0 Hz), 4.29 (2H, q, J=7.1 Hz), 4.40 (2H, q, J=7.2 Hz), 4.50 (1H, t, J=5.0 Hz), 5.30 (2H, s), 7.31-7.37 (3H, m), 7.43-7.46 (2H, m), 8.12 (1H, s).

INTERMEDIATE SYNTHESIS EXAMPLE 7

[Chemical formula 1101]

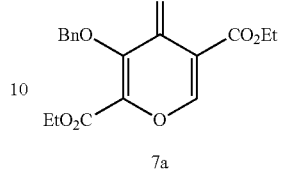

7a

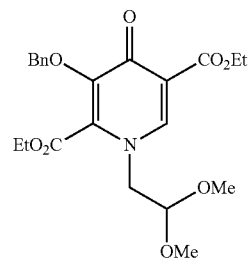

7b

First Step

Aminoacetaldehyde dimethyl acetal (7.80 mmol) was added to an ethanol (5 ml) solution of compound 7a (900 mg, 2.60 mmol), and the mixture was stirred at room temperature for 22 hours. Ethyl acetate (5 ml) and water (5 ml) were added to the reaction solution, followed by extraction with ethyl acetate (5 ml). After the organic layer was washed with water (10 ml), the solvent was distilled off, and the resulting residue was purified by silica gel column chromatography (n-hexane-ethyl acetate 2:1) to obtain 0.37 g (yield 33%) of compound 7b as a colorless oil product.

$^1$H-NMR (CDCl$_3$) δ: 7.90 (1H, s), 7.45-7.43 (5H, m), 5.30 (2H, s), 4.51 (1H, t, J=5.1 Hz), 4.40 (2H, q, J=7.1 Hz), 4.30 (2H, q, J=7.1 Hz), 3.91 (2H, d, J=5.1 Hz), 3.46 (6H, s), 1.40 (3H, t, J=7.1 Hz), 1.26 (3H, t, J=7.1 Hz).

The compounds in connection with the present invention and/or the parent compounds of the compounds in connection with the present invention are useful for symptoms and/or diseases which are induced by influenza virus. For example, they are useful for treating and/or preventing, or improving symptoms of, cold-like symptoms accompanying fever, algor, headache, muscular pain, general malaise etc., airway inflammation symptoms such as pharyngalgia, nasal secretion, nasal congestion, cough, sputum etc., gastrointestinal symptoms such as abdominal pain, vomitus, diarrhea etc. and, further, complications accompanying secondary infection such as acute encephalopathy and pneumonia.

Since the compounds in connection with the present invention are a prodrug and thus have advantages that oral absorbability is high, good bioavailability is exhibited, good clearance is exhibited, and pulmonary transitivity is high, they can be excellent medicaments.

Since the parent compounds of the compounds in connection with the present invention have the effects such as high inhibitory activity on cap structure-dependent endonuclease, and high selectivity due to a virus-specific enzyme, they can be medicaments having reduced side effects.

Further, since the compounds in connection with the present invention and/or the parent compounds of the compounds in connection with the present invention also have advantages that metabolism stability is high, solubility is high, oral absorbability is high, good bioavailability is exhibited, good clearance is exhibited, pulmonary transitivity is high, a half life is long, a non-protein binding rate is high, hERG channel inhibition is low, CYP inhibition is low, CPE (CytoPathic Effect) inhibiting effect is recognized, and/or negativity is exhibited in a phototoxicity test, an Ames test and a gene toxicity test, or toxicity such as liver damage is not caused. Therefore, the compounds in connection with the present invention can be excellent medicaments.

The compounds in connection with the present invention and/or the parent compounds of the compounds in connection with the present invention can be administered orally or parenterally. In the case of oral administration, the present compounds can be also used as a normal preparation, for example, as any dosage form of solid preparations such as tablets, powders, granules, capsules etc.; solutions; oleaginous suspensions; or liquid preparations such as syrups or elixirs etc. In the case of parenteral administration, the compounds in connection with the present invention can be used as aqueous or oleaginous suspension injectables, or nose drops. Upon preparation of them, conventional excipients, binders, lubricants, aqueous solvents, oleaginous solvents, emulsifiers, suspending agents, preservatives, stabilizers etc. can be arbitrarily used. The pharmaceutical composition of the present invention can be produced by combining (for example, mixing) a therapeutically effective amount of the present compound with pharmaceutically acceptable carriers or diluents.

A dose of the compounds in connection with the present invention is different depending on an administration method, an age, a weight and the state of a patient, and a kind of a disease and, usually, in the case of oral administration, about 0.05 mg to 3000 mg, preferably about 0.1 mg to 1000 mg for adult per day may be administered, if necessary, by division. In addition, in the case of parenteral administration, about 0.01 mg to 1000 mg, preferably about 0.05 mg to 500 mg for adult per day is administered.

TEST EXAMPLE 1

Measurement of Cap-dependant Endonuclease (CEN) Inhibitory Activity

1) Preparation of Substrate
30merRNA(5'-pp-[m2'-O]GAA UAU(-Cy3) GCA UCA CUA GUA AGC UUU GCU CUA-BHQ2-3': manufactured by Japan Bio Services Co., LTD.) in which G at a 5' end is diphosphate-modified, a hydroxy group at 2' position is methoxylation-modified, U sixth from a 5' end is labelled with Cy3, and a 3' end is labelled with BHQ2 was purchased, and a cap structure was added using ScriptCap system manufactured by EPICENTRE (a product was m7G [5']-ppp-[5'] [m2'-O]GAA UAU(-Cy3) GCA UCA CUA GUA AGC UUU GCU CUA(-BHQ2)-3'). This was separated and purified by denatured polyacrylamide gel electrophoresis, and used as a substrate.

2) Preparation of Enzyme
RNP was prepared from a virus particle using standard method (Reference Document: VIROLOGY (1976) 73, p 327-338 OLGA M. ROCHOVANSKY). Specifically, A/WSN/33 virus (1×10$^3$ PFU/mL, 200 µL) was inoculated in a 10 days old embryonated chicken egg. After incubation at 37° C. for 2 days, the allantoic fluid of the chicken egg was recovered. A virus particle was purified by ultracentrifugation using 20% sucrose, solubilized using TritonX-100 and lysolecithin, and an RNP fraction (50-70% glycerol fraction) was collected by ultracentrifugation using a 30-70% glycerol density gradient, and was used as an enzyme solution (containing approximately 1 nM PB1-PB2-PA complex).

3) Enzymatic Reaction
An enzymatic reaction solution (2.5 µL) (composition: 53 mM Tris-hydrochloride (pH 7.8), 1 mM MgCl$_2$, 1.25 mM dithiothreitol, 80 mM NaCl, 12.5% glycerol, enzyme solution 0.15 µL) was dispensed into a 384-well plate made of polypropylene. Then, 0.5 µL of a test compound solution which had been serially diluted with dimethyl sulfoxide (DMSO) was added to the plate. As a positive control (PC) or a negative control (NC), 0.5 µL of DMSO was added to the plate respectively. Each plate was mixed well. Then, 2 µL of a substrate solution (1.4 nM substrate RNA, 0.05% Tween20) was added to initiate a reaction. After room temperature incubation for 60 minutes, 1 µL of the reaction solution was collected and added to 10 µL of a Hi-Di formamide solution (containing GeneScan 120 Liz Size Standard as a sizing marker: manufactured by Applied Biosystems (ABI)) in order to stop the reaction. For NC, the reaction was stopped in advance by adding EDTA (4.5 mM) before initiation of the reaction (all concentrations described above are final concentrations).

3) Measurement of Inhibition Ratio (IC$_{50}$ Value)
The solution for which the reaction was stopped was heated at 85° C. for 5 minutes, rapidly cooled on ice for 2 minutes, and analyzed with an ABI PRIZM 3730 genetic analyzer. A peak of the cap-dependent endonuclease product was quantitated by analysis software ABI Genemapper, a CEN reaction inhibition ratio (%) of a test compound was obtained by setting fluorescent intensities of PC and NC to be 0% inhibition and 100% inhibition, respectively, an IC$_{50}$ value was obtained using curve fitting software (XLfit2.0: Model 205 (manufactured by IDBS) etc.). The IC$_{50}$ values of test substances being a parent compound, are shown in Tables 22 to 34.

TEST EXAMPLE 2

CYP Inhibition Test

Using commercially available pooled human liver microsomes, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenytoin (CYP2C19), 5 µmol/L dextromethorphan (CYP2D6), 1 µmol/L terfenadine (CYP3A4); reaction time, 15 minutes; reaction temperature, 37° C.; enzyme, pooled human liver microsomes 0.2 mg protein/mL; test drug concentration, 1, 5, 10, 20 µmol/L (four points).

Each five kinds of substrates, human liver microsomes, or a test drug in 50 mM Hepes buffer as a reaction solution was added to a 96-well plate at the composition as described above, NADPH, as a cofactor was added to initiate metabolism reactions as markers and, after the reaction at 37° C. for 15 minutes, a methanol/acetonitrile=1/1 (v/v) solution was added to stop the reaction. After the centrifugation at 3000 rpm for 15 minutes, resorufin (CYP1A2 metabolite) in the centrifugal supernatant was quantified by a fluorescent multilabel counter and tolubtamide hydroxide (CYP2C9 metabolite), mephenytoin 4' hydroxide (CYP2C19 metabolite), dextrorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

TEST EXAMPLE 3

Solubility Test

The solubility of each compound was determined under 1% DMSO addition conditions. A 10 mM solution of the compound was prepared with DMSO, and 6 µL of the compound solution was added to 594 µL of an artificial intestinal juice (water and 118 mL of 0.2 mol/L NaOH reagent were added to 250 mL of 0.2 mol/L potassium dihydrogen phosphate reagent to reach 1000 mL) with pH of 6.8. The mixture was left standing for 16 hours at 25° C., and the mixture was vacuum-filtered. The filtrate was two-fold diluted with methanol/water=1/1, and the compound concentration in the filtrate was measured with HPLC or LC/MS/MS by the absolute calibration method.

TEST EXAMPLE 4

Metabolism Stability Test

A reaction was performed (oxidative reaction) at 37° C. for 0 minute or 30 minutes in the presence of 1 mmol/L NADPH in 0.2 mL of a buffer (50 mmol/L tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

TEST EXAMPLE 5 hERG Test

For the purpose of assessing risk of an electrocardiogram QT interval prolongation, effects on delayed rectifier $K^+$ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +50 mV for 2 seconds and, further, repolarization pulse stimulation at −50 mV for 2 seconds was recorded. After the generated current was stabilized, extracellular solution (NaCl: 137 mmol/L, KCl: 4 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test substance had been dissolved at an objective concentration was applied to the cell under the room temperature condition for 10 minutes. From the resulting $I_{Kr}$, an absolute value of the tail peak current was measured based on the current value at the resting membrane potential using an analysis software (DataXpress ver. 1, Molecular Devices Corporation). Further, the inhibition rate relative to the tail peak current before application of the test substance was calculated, and compared with the vehicle-applied group (0.1% dimethyl sulfoxide solution) to assess influence of the test substance on $I_{Kr}$.

TEST EXAMPLE 6

CPE Inhibitory Effect Confirming Assay

<Material>
2% FCS E-MEM (prepared by adding kanamycin and FCS to MEM (Minimum Essential Medium) (Invitrogen))
0.5% BSA E-MEM (prepared by adding kanamycin and BSA to MEM (Minimum Essential Medium) (Invitrogen))
HBSS (Hanks' Balanced Salt Solution)
MDBK cell
Cells were adjusted to the appropriate cell number ($3\times10^5$/mL) with 2% FCS E-MEM.
MDCK cell
After washing with HBSS two times, cells were adjusted to the appropriate cell number ($5\times10^5$/mL) with 0.5% BSA E-MEM.
Trypsin solution
Trypsin from porcine pancreas (SIGMA) was dissolved in PBS(−), and filtrated with a 0.45 µm filter.
EnVision (PerkinElmer)
WST-8 Kit (Kishida Chemical Co., Ltd.)
10% SDS solution
<Operation Procedure>
Dilution and Dispensation of Test Sample As a culture medium, 2% FCS E-MEM was used at the use of MDBK cells, and 0.5% BSA E-MEM was used at the use of MDCK cells. Hereinafter, for diluting virus, cells and a test sample, the same culture medium was used.

A test sample was diluted with a culture medium to an appropriate concentration in advance, and then 2 to 5-fold serial dilution on a 96 well plate (50 µL/well) was prepared. Two plates, one for measuring anti-Flu activity and the another for measuring cytotoxicity, were prepared. Each assay was performed triplicate for each drug.

At the use of MDCK cells, Trypsin was added to the cells to be a final concentration of 3 µg/mL only for measuring anti-Flu activity.
Dilution and Dispensation of Influenza Virus An influenza virus was diluted with a culture medium to an appropriate concentration in advance, and each 50 µL/well was dispensed on a 96-well plate containing a test substance. Each 50 µL/well of a culture medium was dispensed on a plate containing a test substance for measuring cytotoxicity.

Dilution and Dispensation of Cell

Each 100 μL/well of cells which had been adjusted to the appropriate cell number was dispensed on a 96 well plate containing a test sample.

This was mixed with a plate mixer, and incubated in a $CO_2$ incubator for 3 days for measuring anti-Flu activity and measuring cytotoxity.

Dispensation of WST-8

The cells in the 96-well plate which had been incubated for 3 days was observed visually under a microscope, and appearance of the cells, the presence or absence of a crystal of test substance were checked. The supernatant was removed so that the cells were not absorbed from the plate.

WST-8 Kit was diluted 10-fold with a culture medium, and each 100 μL was dispensed into each well. After mixing with a plate mixer, cells were incubated in a $CO_2$ incubator for 1 to 3 hours.

After incubation, regarding the plate for measuring anti-Flu activity, each 10 μL/well of a 10% SDS solution was dispensed in order to inactivate a virus.

Measurement of Absorbance

After the 96-well plate was mixed, absorbance was measured with EnVision at two wavelengths of 450 nm/620 nm.

<Calculation of Each Measurement Item Value>

The value was calculated using Microsoft Excel or a program having the equivalent calculation and processing ability, based on the following calculation equation.

Calculation of effective inhibition concentration to achieve 50% influenza infected cell death (EC50)

$$EC50 = 10^Z$$

$$Z = (50\% - \text{High \%})/(\text{High \%} - \text{Low \%}) \times \{\log(\text{High conc.}) - \log(\text{Low conc.})\} + \log(\text{High conc.})$$

For test substances (compounds of Reference examples) being a parent compound, measurement results of Test Example 1 and Test Example 6 are shown in Tables 22 to 34.

TABLE 22

| Reference example No. | CEN $IC_{50}$ (μM) | CPE $EC_{50}$ (μM) |
|---|---|---|
| 2 | 0.048 | 0.293 |
| 14 | 0.043 | 0.313 |
| 16 | 0.065 | 0.632 |
| 26 | 0.108 | 0.547 |
| 37 | 0.101 | 0.318 |
| 43 | 0.078 | 1.410 |
| 48 | 0.087 | 10.90 |
| 56 | 0.358 | 3.860 |
| 62 | 0.110 | 1.680 |
| 63 | 0.170 | 2.000 |
| 94 | 0.096 | 1.470 |
| 99 | 0.341 | 2.000 |
| 108 | 0.037 | 0.019 |
| 128 | 0.063 | 0.416 |
| 138 | 0.166 | 0.100 |
| 139 | 0.189 | 0.741 |
| 143 | 0.224 | 0.333 |
| 150 | 0.193 | 0.553 |
| 175 | 0.132 | 0.102 |
| 178 | 0.061 | 0.075 |

TABLE 23

| Reference example No. | CEN $IC_{50}$ (μM) | CPE $EC_{50}$ (μM) |
|---|---|---|
| 181 | 0.049 | 0.349 |
| 182 | 0.099 | 0.562 |
| 183 | 0.074 | 2.370 |
| 184 | 0.055 | 0.403 |
| 185 | 0.132 | 1.920 |
| 186 | 0.085 | 0.159 |
| 187 | 0.085 | 0.282 |
| 190 | 0.143 | 2.640 |
| 191 | 0.238 | 2.820 |
| 199 | 0.236 | 2.720 |
| 204 | 0.299 | 2.360 |
| 224 | 0.276 | 0.119 |
| 225 | 0.283 | 0.663 |
| 228 | 0.243 | 0.141 |
| 230 | 0.282 | 0.525 |
| 233 | 0.228 | 2.240 |
| 238 | 0.101 | 0.440 |
| 240 | 0.037 | 0.048 |
| 241 | 0.197 | 0.063 |
| 242 | 0.114 | 0.059 |
| 243 | 0.076 | 0.020 |
| 244 | 0.249 | 0.108 |
| 246 | 0.082 | 0.026 |
| 247 | 0.282 | 2.260 |
| 248 | 0.103 | 0.489 |
| 249 | 0.151 | 1.890 |
| 250 | 0.113 | 0.476 |
| 251 | 0.058 | 0.157 |
| 252 | 0.107 | 0.454 |
| 253 | 0.235 | 0.280 |
| 254 | 0.135 | 0.564 |
| 255 | 0.052 | 0.319 |
| 256 | 0.038 | 0.400 |

TABLE 24

| Reference example No. | CEN $IC_{50}$ (μM) | CPE $EC_{50}$ (μM) |
|---|---|---|
| 257 | 0.041 | 0.055 |
| 258 | 0.042 | 0.028 |
| 259 | 0.066 | 0.026 |
| 260 | 0.091 | 0.065 |
| 261 | 0.058 | 0.047 |
| 262 | 0.032 | 0.038 |
| 263 | 0.085 | 0.075 |
| 264 | 0.064 | 0.128 |
| 265 | 0.172 | 0.036 |
| 266 | 0.043 | 0.085 |
| 267 | 0.029 | 0.063 |
| 268 | 0.018 | 0.074 |
| 269 | 0.073 | 0.417 |
| 270 | 0.058 | 0.129 |
| 271 | 0.073 | 0.102 |
| 272 | 0.082 | 0.030 |
| 273 | 0.016 | 0.084 |
| 274 | 0.038 | 0.016 |
| 274 | 0.157 | 0.056 |
| 276 | 0.053 | 0.089 |
| 277 | 0.039 | 0.071 |
| 278 | 0.205 | 0.074 |
| 279 | 0.056 | 0.119 |
| 280 | 0.068 | 0.145 |
| 281 | 0.026 | 0.018 |
| 282 | 0.036 | 0.029 |
| 283 | 0.028 | 0.021 |
| 284 | 0.042 | 0.019 |
| 285 | 0.044 | 0.017 |
| 286 | 0.161 | 0.121 |
| 287 | 0.154 | 0.268 |
| 288 | 0.299 | 0.085 |
| 289 | 0.031 | 0.419 |

TABLE 25

| Reference example No. | CEN IC$_{50}$ (μM) | CPE EC$_{50}$ (μM) |
|---|---|---|
| 290 | 0.067 | 0.492 |
| 292 | 0.155 | 2.230 |
| 293 | 0.290 | 0.437 |
| 294 | 0.035 | 0.018 |
| 295 | 0.052 | 0.334 |
| 296 | 0.130 | 0.397 |
| 297 | 0.045 | 0.033 |
| 298 | 0.044 | 0.012 |
| 299 | 0.050 | 0.015 |
| 300 | 0.058 | 0.021 |
| 301 | 0.062 | 0.017 |
| 302 | 0.035 | 0.014 |
| 304 | 0.018 | 0.015 |
| 305 | 0.059 | 0.103 |
| 306 | 0.076 | 0.021 |
| 307 | 0.052 | 0.095 |
| 308 | 0.072 | 0.019 |
| 309 | 0.040 | 0.013 |
| 310 | 0.108 | 0.522 |
| 311 | 0.040 | 0.026 |
| 312 | 0.019 | 0.029 |
| 313 | 0.189 | 0.050 |
| 314 | 0.149 | 0.026 |
| 315 | 0.057 | 0.115 |
| 316 | 0.069 | 0.083 |
| 317 | 0.048 | 0.017 |
| 318 | 0.130 | 0.015 |
| 320 | 0.045 | 0.011 |
| 321 | 0.019 | 0.019 |
| 322 | 0.113 | 0.028 |
| 323 | 0.077 | 0.019 |
| 324 | 0.107 | 0.035 |
| 325 | 0.032 | 0.025 |

TABLE 26

| Reference example No. | CEN IC$_{50}$ (μM) | CPE EC$_{50}$ (μM) |
|---|---|---|
| 326 | 0.043 | 0.005 |
| 327 | 0.092 | 0.024 |
| 328 | 0.029 | 0.168 |
| 329 | 0.058 | 0.023 |
| 330 | 0.026 | 0.019 |
| 331 | 0.045 | 0.335 |
| 332 | 0.048 | 0.020 |
| 333 | 0.021 | 0.425 |
| 334 | 0.075 | 0.032 |
| 335 | 0.019 | 0.016 |
| 336 | 0.051 | 0.070 |
| 337 | 0.058 | 0.028 |
| 338 | 0.074 | 0.085 |
| 339 | 0.183 | 0.040 |
| 340 | 0.101 | 0.027 |
| 341 | 0.016 | 0.027 |
| 342 | 0.099 | 0.026 |
| 343 | 0.122 | 0.018 |
| 344 | 0.050 | 0.009 |
| 345 | 0.097 | 0.008 |
| 346 | 0.028 | 0.018 |
| 347 | 0.014 | 0.017 |
| 348 | 0.054 | 0.080 |
| 349 | 0.053 | 0.075 |
| 351 | 0.091 | 0.019 |
| 352 | 0.067 | 0.020 |
| 354 | 0.025 | 0.083 |
| 355 | 0.040 | 0.075 |
| 356 | 0.066 | 0.020 |
| 357 | 0.138 | 0.386 |
| 358 | 0.051 | 0.069 |
| 359 | 0.037 | 0.080 |
| 360 | 0.042 | 0.087 |

TABLE 27

| Reference example No. | CEN IC$_{50}$ (μM) | CPE EC$_{50}$ (μM) |
|---|---|---|
| 361 | 0.039 | 0.145 |
| 362 | 0.084 | 0.067 |
| 363 | 0.058 | 0.067 |
| 364 | 0.112 | 0.515 |
| 365 | 0.041 | 2.250 |
| 366 | 0.090 | 0.838 |
| 368 | 0.140 | 0.470 |
| 369 | 0.294 | 0.434 |
| 370 | 0.113 | 0.061 |
| 371 | 0.161 | 0.074 |
| 372 | 0.164 | 0.146 |
| 373 | 0.065 | 0.050 |
| 374 | 0.137 | 0.154 |
| 375 | 0.037 | 0.073 |
| 376 | 0.063 | 0.092 |
| 377 | 0.024 | 0.022 |
| 378 | 0.047 | 0.022 |
| 380 | 0.123 | 0.018 |
| 381 | 0.200 | 0.034 |
| 382 | 0.032 | 0.094 |
| 384 | 0.153 | 0.293 |
| 386 | 0.075 | 0.096 |
| 387 | 0.300 | 1.150 |
| 388 | 0.133 | 0.063 |
| 390 | 0.095 | 0.029 |
| 391 | 0.264 | 0.071 |
| 392 | 0.153 | 0.025 |
| 394 | 0.087 | 0.064 |
| 395 | 0.043 | 0.089 |
| 396 | 0.056 | 0.060 |
| 397 | 0.055 | 0.077 |
| 398 | 0.034 | 0.118 |
| 399 | 0.105 | 0.061 |

TABLE 28

| Reference example No. | CEN IC$_{50}$ (μM) | CPE EC$_{50}$ (μM) |
|---|---|---|
| 400 | 0.067 | 0.079 |
| 401 | 0.089 | 0.133 |
| 402 | 0.085 | 0.081 |
| 403 | 0.090 | 0.070 |
| 404 | 0.084 | 0.063 |
| 405 | 0.074 | 0.051 |
| 406 | 0.119 | 0.022 |
| 407 | 0.035 | 0.017 |
| 408 | 0.135 | 0.061 |
| 409 | 0.093 | 0.029 |
| 410 | 0.265 | 0.014 |
| 411 | 0.046 | 0.014 |
| 412 | 0.292 | 0.203 |
| 413 | 0.050 | 0.005 |
| 414 | 1.890 | 0.131 |
| 415 | 0.285 | 0.022 |
| 416 | 0.112 | 0.019 |
| 417 | 0.030 | 0.003 |
| 418 | 0.121 | 0.072 |
| 419 | 0.124 | 0.019 |
| 420 | 0.058 | 0.021 |
| 423 | 0.280 | 0.019 |
| 425 | 0.183 | 0.047 |
| 429 | 0.016 | 0.004 |
| 430 | 0.168 | 0.029 |
| 431 | 0.097 | 0.011 |
| 432 | 0.155 | 0.062 |
| 433 | 0.014 | 0.017 |
| 441 | 0.044 | 0.005 |
| 443 | 0.166 | 0.004 |
| 444 | 0.066 | 0.003 |
| 445 | 0.013 | 0.004 |
| 446 | 0.007 | 0.011 |

TABLE 29

| Reference example No. | CEN IC$_{50}$ (μM) | CPE EC$_{50}$ (μM) |
|---|---|---|
| 447 | 0.096 | 0.018 |
| 448 | 0.039 | 0.008 |
| 449 | 0.062 | 0.021 |
| 450 | 0.023 | 0.014 |
| 452 | 0.177 | 0.016 |
| 453 | 0.186 | 0.049 |
| 454 | 0.012 | 0.004 |
| 455 | 0.025 | 0.071 |
| 456 | 0.032 | 0.004 |
| 457 | 0.242 | 0.014 |
| 458 | 0.048 | 0.014 |
| 459 | 0.287 | 0.048 |
| 460 | 0.085 | 0.009 |
| 461 | 0.255 | 0.074 |
| 462 | 0.069 | 0.011 |
| 463 | 0.012 | 0.005 |
| 464 | 0.024 | 0.014 |
| 469 | 0.016 | 0.004 |
| 470 | 0.008 | 0.003 |
| 475 | 0.164 | 0.441 |
| 476 | 0.031 | 0.014 |
| 478 | 0.088 | 0.129 |
| 479 | 0.117 | 0.064 |
| 480 | 0.151 | 0.084 |
| 481 | 0.114 | 0.086 |
| 482 | 0.103 | 0.031 |
| 483 | 0.101 | 0.027 |
| 485 | 0.221 | 0.424 |
| 486 | 0.140 | 0.072 |
| 487 | 0.091 | 0.026 |
| 488 | 0.151 | 0.027 |
| 489 | 0.133 | 0.014 |
| 490 | 0.212 | 0.468 |

TABLE 30

| Reference example No. | CEN IC$_{50}$ (μM) | CPE EC$_{50}$ (μM) |
|---|---|---|
| 491 | 0.069 | 0.099 |
| 492 | 0.121 | 0.160 |
| 493 | 0.112 | 0.101 |
| 495 | 0.277 | 0.310 |
| 496 | 0.170 | 0.177 |
| 497 | 0.215 | 0.511 |
| 498 | 0.161 | 0.351 |
| 502 | 0.042 | 0.142 |
| 506 | 0.247 | 1.620 |
| 507 | 0.063 | 0.197 |
| 508 | 0.036 | 0.056 |
| 509 | 0.015 | 0.014 |
| 511 | 0.175 | 0.015 |
| 514 | 0.049 | 0.018 |
| 515 | 0.197 | 0.019 |
| 516 | 0.039 | 0.017 |
| 518 | 0.049 | 0.024 |
| 520 | 0.212 | 0.017 |
| 521 | 0.191 | 0.015 |
| 522 | 0.039 | 0.014 |
| 523 | 0.035 | 0.014 |
| 524 | 0.057 | 0.026 |
| 525 | 0.141 | 0.090 |
| 526 | 0.044 | 0.019 |
| 527 | 0.127 | 0.088 |
| 532 | 0.098 | 0.075 |
| 533 | 0.065 | 0.391 |
| 534 | 0.165 | 1.200 |
| 536 | 0.071 | 0.027 |
| 537 | 0.152 | 0.022 |
| 538 | 0.196 | 0.030 |
| 544 | 0.168 | 0.051 |
| 546 | 0.202 | 0.124 |

TABLE 31

| Reference example No. | CEN IC$_{50}$ (μM) | CPE EC$_{50}$ (μM) |
|---|---|---|
| 547 | 0.032 | 0.027 |
| 548 | 0.086 | 0.038 |
| 549 | 0.076 | 2.100 |
| 550 | 0.042 | 0.042 |
| 551 | 0.041 | 0.107 |
| 552 | 0.230 | 0.085 |
| 553 | 0.028 | 0.030 |
| 554 | 0.065 | 0.465 |
| 555 | 0.023 | 0.012 |
| 556 | 0.023 | 0.412 |
| 557 | 0.281 | 2.470 |
| 558 | 0.114 | 0.541 |
| 560 | 0.027 | 0.173 |
| 561 | 0.073 | 0.008 |
| 562 | 0.022 | 0.062 |
| 563 | 0.049 | 0.464 |
| 564 | 0.088 | 0.136 |
| 565 | 0.154 | 0.726 |
| 568 | 0.264 | 2.810 |
| 569 | 0.138 | 1.010 |
| 570 | 0.081 | 2.050 |
| 571 | 0.065 | 0.320 |
| 573 | 0.055 | 0.158 |
| 574 | 0.165 | 0.442 |
| 575 | 0.058 | 0.087 |
| 576 | 0.063 | 0.027 |
| 577 | 0.233 | 0.337 |
| 581 | 0.083 | 0.480 |

TABLE 32

| Reference example No | CEN IC$_{50}$ (μM) | CPE EC$_{50}$ (μM) |
|---|---|---|
| 592 | 0.029 | 0.012 |
| 594 | 0.011 | 0.004 |
| 597 | 0.339 | 0.049 |
| 598 | 0.016 | 0.005 |
| 599 | 0.025 | 0.008 |
| 600 | 0.059 | 0.036 |
| 601 | 0.025 | 0.008 |
| 602 | 0.005 | 0.004 |
| 603 | 0.037 | 0.015 |
| 609 | 0.053 | 0.025 |
| 611 | 0.055 | 0.043 |
| 612 | 0.055 | 0.013 |
| 613 | 0.173 | 0.018 |
| 617 | 0.053 | 0.017 |
| 618 | 0.029 | 0.018 |
| 619 | 0.005 | 0.006 |
| 621 | 0.006 | 0.002 |
| 622 | 0.089 | 0.012 |
| 623 | 0.021 | 0.003 |
| 624 | 0.065 | 0.057 |
| 628 | 0.043 | 0.013 |
| 629 | 0.089 | 0.064 |
| 631 | 0.075 | 0.041 |
| 632 | 0.132 | 0.038 |

TABLE 33

| Reference example No | CEN IC$_{50}$ (μM) | CPE EC$_{50}$ (μM) |
|---|---|---|
| 633 | 0.053 | 0.022 |
| 634 | 0.103 | 0.017 |
| 636 | 0.074 | 0.015 |
| 638 | 0.130 | 0.021 |
| 639 | 0.055 | 0.017 |
| 640 | 0.057 | 0.006 |
| 641 | 0.046 | 0.023 |
| 642 | 0.256 | 0.094 |

TABLE 33-continued

| Reference example No | CEN IC$_{50}$ (μM) | CPE EC$_{50}$ (μM) |
|---|---|---|
| 643 | 0.163 | 0.132 |
| 644 | 0.238 | 0.060 |
| 645 | 0.105 | 0.016 |
| 648 | 0.132 | 0.059 |
| 649 | 0.182 | 0.051 |
| 650 | 0.219 | 0.103 |
| 651 | 0.056 | 0.013 |
| 652 | 0.330 | 0.079 |
| 654 | 0.008 | 0.001 |
| 656 | 0.070 | 0.019 |
| 658 | 0.053 | 0.019 |
| 660 | 0.036 | 0.011 |
| 661 | 0.135 | 0.014 |
| 662 | 0.316 | 0.022 |
| 663 | 0.031 | 0.018 |
| 665 | 0.018 | 0.005 |

TABLE 34

| Reference example No. | CEN IC$_{50}$ (μM) | CPE EC$_{50}$ (μM) |
|---|---|---|
| 666 | 0.00336 | 0.00391 |
| 668 | 0.0126 | 0.00384 |
| 682 | 0.0197 | 0.0035 |
| 686 | 0.0151 | 0.00786 |
| 691 | 0.00367 | 0.00405 |
| 692 | 0.0369 | 0.00964 |
| 704 | 0.0111 | 0.0035 |
| 706 | 0.0186 | 0.00719 |
| 707 | 0.0402 | 0.00305 |
| 708 | 0.0465 | 0.00849 |
| 709 | 0.0343 | 0.00709 |
| 710 | 0.0206 | 0.00981 |
| 711 | 0.00557 | 0.00428 |
| 712 | 0.0164 | 0.00645 |
| 716 | 0.00554 | 0.0056 |
| 719 | 0.0026 | 0.00836 |
| 720 | 0.0191 | 0.00624 |
| 721 | 0.00696 | 0.00395 |
| 722 | 0.0192 | 0.00378 |
| 724 | 0.00507 | 0.00633 |
| 726 | 0.00374 | 0.00393 |
| 728 | 0.0747 | 0.00432 |
| 730 | 0.00252 | 0.000799 |
| 731 | 0.00576 | 0.00208 |
| 741 | 0.021 | 0.00351 |
| 748 | 0.0242 | 0.00914 |
| 752 | 0.0142 | 0.00312 |
| 753 | 0.109 | 0.0185 |
| 762 | 0.0315 | 0.0059 |
| 768 | 0.0153 | 0.00364 |
| 771 | 0.00589 | 0.00405 |
| 772 | 0.00522 | 0.00368 |

Based on the above results, the parent compounds exhibit high cap-dependent endonuclease (CEN) inhibitory activity and/or high CPE inhibitory effect and thus can be a useful agent for treatment and/or prevention of symptom and/or disease induced by infection with influenza virus.

TEST EXAMPLE 7

Influenza Virus-infected Mouse Lethality Inhibitory Test

<Mouse>

BALB/cAnNCrlCrlj (female, 5-week-old; CHARLES RIVER LABORATORIES JAPAN, INC.) was purchased, and 6- to 7-week-old mice were used in the test.

<Preparation of Virus Solution>

A/WS/33, A/Victoria/3/75 or B/Maryland/1/59 (ATCC) was passaged in mouse lung to make a mouse-acclimatized virus. A freezing-stored mouse-acclimatized virus solution was rapidly thawed, and diluted with DPBS to an infectivity titer to be used (in the case of A/WS/33: 800-4000TCID$_{50}$/mouse, in the case of A/Victoria/3/75: 750 TCID$_{50}$/mouse, in the case of B/Maryland/1/59: 100 TCID$_{50}$/mouse).

<Infection>

Under anesthesia with ketamine•xylazine mixture, 100 ul of the prepared virus solution was nasally inoculated to directly infect mouse lung.

<Preparation of Test Sample>

A test sample was suspended in a 0.5% methylcellulose solution to a suitable concentration.

<Administration of Test Sample to Infected Mouse>

A suitably diluted test sample was orally administered at 200 ul to a mouse immediately after virus infection or after the elapse of a certain period of time.

<Drug Efficacy Assessment>

The mouse was reared for 14 days after virus infection, and a necessary dose per day for 50% lethality inhibition, ED$_{50}$ (mg/kg/day), a lethality inhibition rate at a maximum dose (% survival), or days during which the mouse survives 50% as compared with a control at a maximum dose (50% life extension days) was calculated. Alternatively, the amount of virus in the lung for several days after virus infection was measured, and compared with the amount of virus of control to evaluate virus inhibitory effect.

<Euthanasia>

The mouse after completion of the test was euthanized by carbon dioxide or halothane excessive administration.

<Result>

The ED$_{50}$ values of single dose are shown.

Number of compound of Reference example 413: 12.3

Number of compound of Example 20: 4.4

Based on the above results, it was revealed that compound of Example 20 obtained by converting compound of Reference example 413 being a parent compound into a prodrug exhibits lethality inhibitory effect at lower concentration.

TEST EXAMPLE 8

BA Test

Experimental Material and Method for Studying Oral Absorbability (1) Animal to be used: A mouse or rat was used.

(2) Rearing conditions: Mouse and rat ingested a solid feed and sterilized tap water ad-libitum.

(3) Dose and setting of grouping: A predetermined dose was administered orally or intravenously. A group was set as follows. (a dose varied for every compound)

Oral administration 1 to 30 mg/kg (n=2 to 3)

Intravenous administration 0.5 to 10 mg/kg (n=2 to 3)

(4) Preparation of administration solution: For oral administration, a solution or suspension was administered. For intravenous administration, a compound which was solubilized was administered.

(5) Administration method: For oral administration, the administration solution was forcibly administered to the stomach by oral sonde. For intravenous administration, the administration solution was administered with a syringe equipped with an injection needle through a tail vein.

(6) Assessment item: Blood was collected with time, and a plasma drug concentration was measured using LC/MS/MS.

(7) Statistical analysis: Regarding plasma concentration transition, an area under a plasma concentration-time curve (AUC) was calculated using a non-linear minimum square method program WinNonlin (registered trademark), and bioavailability (BA) was calculated from AUC of an oral-administered group and an intervenous-administered group.
<Result>

The measurement results measured using a rat are shown in the following Table 35.

TABLE 35

| Reference example No (Parent compound) | Parent compound BA(%) | Example No. (Prodrug) | Prodrug BA(%) |
|---|---|---|---|
| 301 | 2.3 | 114 | 6.8 |
| 301 | 2.3 | 204 | 13.0 |
| 413 | 4.3 | 20 | 13.2 |
| 429 | 13.3 | 137 | 19.8 |
| 429 | 13.3 | 146 | 30.5 |
| 445 | 12.1 | 117 | 23.3 |
| 445 | 12.1 | 155 | 26.9 |
| 445 | 12.1 | 209 | 18.6 |
| 592 | 4.2 | 100 | 10.7 |
| 592 | 4.2 | 141 | 17.9 |
| 592 | 4.2 | 160 | 15.8 |
| 594 | 5.0 | 104 | 14.8 |
| 594 | 5.0 | 116 | 21.3 |
| 594 | 5.0 | 142 | 10.3 |
| 594 | 5.0 | 156 | 17.8 |

Based on the above results, the prodrug had improved bioavailability other than the parent compound.

Therefore, the compound of the present invention has excellent oral absorbability and can be a useful agent for treatment and/or prevention of symptom and/or disease induced by infection with influenza virus.

Figures 3, 4:
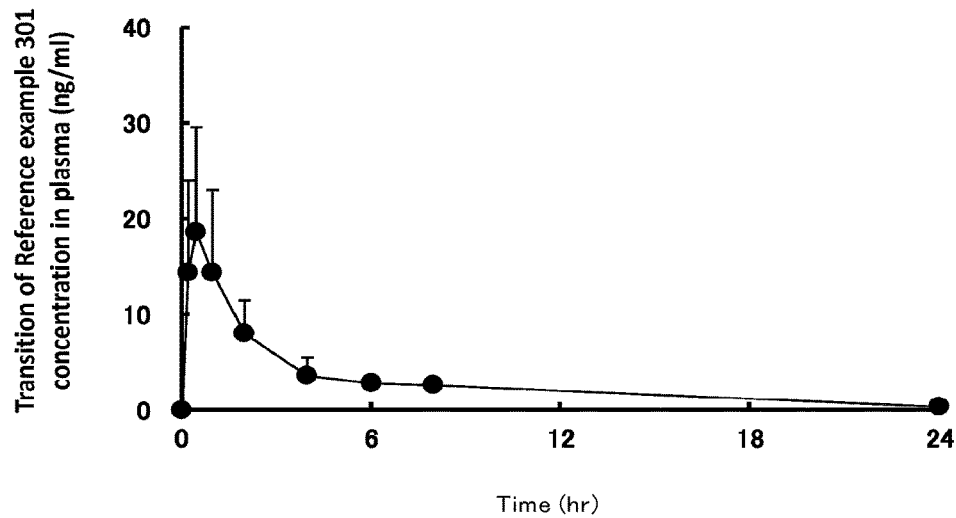
FIG. 3 is a result of measuring changes in the plasma concentration of Reference example 301, for compound of Example 204 obtained by converting into a prodrug compound of Reference example 301 that is a parent compound, after oral administration to rat under non-fasting conditions.
FIG. 4 is a graph showing an average of the changes in the plasma concentration when the measurement shown in FIG. 3 is performed three times.

FIGS. 1 to 4 show a result of determining changes in the plasma concentration of Reference example 301, for compounds of Examples 114 and 204 prepared by converting compound of Reference example 301 being a parent compound into a prodrug, after oral administration to rat under non-fasting conditions.

BA after oral administrating Examples 114 and 204 was 6.8% and 13.0%, respectively. Improvement of bioavailability was found when compared to the case of orally administrating compound of Reference example 301 being a parent compound (BA=2.3%). The Tmax values of both compounds were 1 hr or less, and it was shown that oral absorbability was high. In addition, in compounds of Examples 114 and 204, the concentration in all plasma samples was a determination limit or less.

Based on the above test results, it was revealed that the compound of Example converted into a prodrug was absorbed into the body after oral administration, and rapidly converted into a parent compound in the blood. Therefore, the compound of the present invention can be a useful agent for treatment and/or prevention of symptom and/or disease induced by infection with influenza virus.

FORMULATION EXAMPLE 1

A granule containing the following ingredients is manufactured.

| Ingredients | A compound represented by formula (I) | 10 mg |
| | Lactose | 700 mg |
| | Cornstarch | 274 mg |
| | HPC-L | 16 mg |
| | | 1000 mg |

A compound represented by formula (I) and lactose are passed through a 60 mesh sieve. Cornstarch is passed through a 120 mesh sieve. These are mixed with a V-type blender. To the mixed powder is added an aqueous HPC-L (low viscosity hydroxypropylcellulose) solution, and the mixture is kneaded together, granulated (extrusion granulation, pore diameter 0.5-1 mm), and dried. The obtained dried granule is passed through a vibrating sieve (12/60 mesh) to obtain a granule.

FORMULATION EXAMPLE 2

A granule for encapsulation containing the following ingredients is manufactured.

| Ingredients | A compound represented by formula (I) | 15 mg |
| | Lactose | 90 mg |
| | Cornstarch | 42 mg |
| | HP C-L | 3 mg |
| | | 150 mg |

A compound represented by formula (I) and lactose are passed through a 60 mesh sieve. Cornstarch is passed through a 120 mesh sieve. These are mixed, a HPC-L solution is added to the mixed powder, then the mixture is kneaded together, granulated, and dried. The obtained dried granule is trimmed, and then 150 mg thereof is filled into a No. 4 hard gelatin capsule.

FORMULATION EXAMPLE 3

A tablet containing the following ingredients is manufactured.

| Ingredients | A compound represented by formula (I) | 10 mg |
| | Lactose | 90 mg |
| | microcrystalline cellulose | 30 mg |
| | CMC-Na | 15 mg |
| | Magnesium stearate | 5 mg |
| | | 150 mg |

A compound represented by formula (I), lactose, microcrystalline cellulose, and CMC-Na (carboxymethylcellulose sodium salt) are passed through a 60 mesh sieve and mixed. Magnesium stearate is added to the mixed powder to obtain a mixed powder for tablet. The mixed powder is compressed directly to obtain a 150 mg tablet.

FORMULATION EXAMPLE 4

The following ingredients were mixed under heat, and then sterilized to obtain an injectable solution.

| Ingredients | A compound shown by formula (I) | 3 mg |
| | Nonionic surfactant | 15 mg |
| | Purified water for injection | 1 ml |

INDUSTRIAL APPLICABILITY

The compound of the present invention has cap-dependent endonuclease (CEN) inhibitory activity after absorption into the body. The compound of the present invention can be a useful agent for treatment and/or prevention of symptom and/or disease induced by infection with influenza virus.

The invention claimed is:
1. A compound represented by formula:

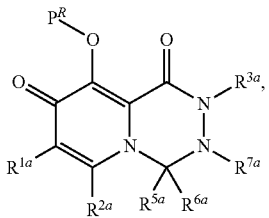

a pharmaceutically acceptable salt, or a solvate thereof:
wherein:
$P^R$ is a group to form a prodrug;
$R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy optionally substituted by substituent group C, heterocycleoxycarbonyl optionally substituted by substituent group C,
—Z—N($R^{41}$)($R^{42}$),
—Z—N($R^{43}$)—SO$_2$—($R^{44}$),
—Z—C(=O)—N($R^{45}$)—SO$_2$—($R^{46}$),
—Z—N($R^{47}$)—C(=O)—$R^{48}$,
—Z—S—$R^{49}$,
—Z—SO$_2$—$R^{410}$,
—Z—S(=O)—$R^{411}$,
—Z—N($R^{412}$)—C(=O)—O—$R^{413}$,
—Z—N($R^{414}$)—C(=O)—N($R^{415}$)($R^{416}$),
—Z—C(=O)—N($R^{417}$)—C(=O)—N($R^{418}$)($R^{419}$),
—Z—N($R^{420}$)—C(=O)—C(=O)—$R^{421}$, or
—Z—B(—O$R^{422}$)(—O$R^{423}$)
wherein $R^{41}$, $R^{42}$, $R^{43}$, $R^{45}$, $R^{47}$, $R^{48}$, $R^{49}$, $R^{412}$, $R^{413}$, $R^{414}$, $R^{415}$, $R^{416}$, $R^{417}$, $R^{418}$, $R^{19}$, $R^{420}$, and $R^{421}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
$R^{44}$, $R^{46}$, $R^{410}$, $R^{411}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
$R^{41}$ and $R^{42}$, $R^{415}$ and $R^{416}$, and $R^{418}$ and $R^{419}$, each may be taken together with an adjacent atom to form heterocycle,
$R^{422}$ and $R^{423}$ are each independently an hydrogen atom, lower alkyl optionally substituted by substituent group C, or $R^{422}$ and $R^{423}$ may be taken together with an adjacent atom to form heterocycle, and
Z is a single bond or straight or branched lower alkylene;
$R^{2a}$ is hydrogen, halogen, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—N($R^{B1}$)—SO$_2$—$R^{B2}$,
—Z—N($R^{B3}$)—C(=O)—$R^{B4}$,
—Z—N($R^{B5}$)—C(=O)—O—$R^{B6}$,
—Z—C(=O)—N($R^{B7}$)($R^{B8}$),
—Z—N($R^{B9}$)($R^{B10}$), or
—Z—SO$_2$—$R^{B11}$
wherein $R^{B1}$, $R^{B3}$, $R^{B4}$, $R^{B5}$, $R^{B6}$, $R^{B7}$, $R^{B8}$, $R^{B9}$, and $R^{B10}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
$R^{B2}$ and $R^{B11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B7}$ and $R^{B8}$, and $R^{B9}$ and $R^{B10}$ may be taken together with an adjacent atom to form heterocycle, and Z is a single bond or straight or branched lower alkylene;

$R^{3a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$),
—Z—N($R^{C9}$)($R^{C10}$),
—Z—SO$_2$—$R^{C11}$, or
—Z—N($R^{C12}$)—O—C(=O)—$R^{C13}$ wherein $R^{C1}$, $R^{C3}$, $R^{C4}$, $R^{C5}$, $R^{C6}$, $R^{C7}$, $R^{C8}$, $R^{C9}$, $R^{C10}$, $R^{C12}$, $R^{C13}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C2}$ and $R^{C11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C7}$ and $R^{C8}$, and $R^{C9}$ and $R^{C10}$ each may be taken together with an adjacent atom to form heterocycle, and Z is a single bond or straight or branched lower alkylene;

$R^{5a}$, $R^{6a}$, and $R^{7a}$ are each independently selected from a substituent group consisting of hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C, —Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$),
—Z—C($R^{D7}$)($R^{D8}$)($R^{D9}$),
—Z—CH$_2$—$R^{D10}$,
—Z—N($R^{D11}$)—C(=O)—O—$R^{D12}$, and
—Z—($R^{D13}$)—C(=O)—$R^{D14}$, or $R^{5a}$ and $R^{6a}$ may be taken together to form heterocyclic group optionally substituted by substituent group C, wherein $R^{D1}$, $R^{D4}$, $R^{D5}$, $R^{D6}$, $R^{D9}$, $R^{D11}$, $R^{D12}$, $R^{D13}$, and $R^{D14}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D2}$ and $R^{D3}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D7}$, $R^{D8}$, and $R^{D10}$ are each independently carbocyclic group optionally substituted by substituent group C, or heterocyclic group optionally substituted by substituent group C, $R^{D5}$ and $R^{D6}$ may be taken together with an adjacent atom to form heterocycle, Y is straight or branched lower alkylene, and Z is a single bond or straight or branched lower alkylene; and $R^{3a}$ and $R^{7a}$ may be taken together with an adjacent atom to form heterocycle optionally substituted by substituent group D, with a proviso that the following c) are excluded:

c) $R^{5a}$, $R^{6a}$, and $R^{7a}$ are all hydrogens;

wherein the substituent group C is selected from the group consisting of halogen, cyano, hydroxy, carboxy, formyl, amino, oxo, nitro, lower alkyl, lower alkenyl, lower alkynyl, halogeno lower alkyl, lower alkyloxy, lower alkynyloxy, lower alkylthio, hydroxy lower alkyl, carbocyclic group, heterocyclic group, heterocyclic group substituted by oxo, carbocycle lower alkyloxy, carbocycleoxy lower alkyl, carbocycle lower alkyloxy lower alkyl, heterocycle lower alkyloxy, heterocycleoxy lower alkyl, heterocycle lower alkyloxy lower alkyl, halogeno lower alkyloxy, lower alkyloxy lower alkyl, lower alkyloxy lower alkyloxy, lower alkylcarbonyl, lower alkylcarbonyloxy, lower alkyloxycarbonyl, lower alkylamino, lower alkylcarbonylamino, halogeno lower alkyl carbonylamino, lower alkylaminocarbonyl, lower alkylsulfonyl, lower alkylsulfinyl, and lower alkyl sulfonylamino; and the substituent group D is selected from the group consisting of halogen, cyano, hydroxy, carboxy, formyl, amino, oxo, nitro, lower alkyl, halogeno lower alkyl, lower alkyloxy, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkyl aminocarbonyl, lower alkylsulfonyl, lower alkylsulfonylamino, carbocyclic group optionally substituted by substituent group C, heterocyclic group optionally substituted by substituent group C, carbocycle lower alkyl optionally substituted by substituent group C, and heterocycle lower alkyl optionally substituted by substituent group C.

2. The compound according to claim 1, or the pharmaceutically acceptable salt thereof or the solvate thereof, wherein $R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy optionally substituted by substituent group C, heterocycleoxycarbonyl optionally substituted by substituent group C, —Z—N($R^{41}$)($R^{42}$),
—Z—N($R^{43}$)—SO$_2$—($R^{44}$),
—Z—N($R^{47}$)—C(=O)—$R^{48}$,
—Z—S—$R^{49}$,
—Z—SO$_2$—$R^{410}$,
—Z—N($R^{412}$)—C(=O)—O—$R^{413}$,
—Z—N($R^{420}$)—C(=O)—C(=O)—$R^{421}$, or
—Z—B(—O$R^{422}$)(—O$R^{423}$), wherein substituent group C, $R^{41}$, $R^{42}$, $R^{43}$, $R^{44}$, $R^{47}$, $R^{48}$, $R^{49}$, $R^{410}$, $R^{412}$, $R^{413}$, $R^{420}$, $R^{421}$, $R^{422}$, $R^{423}$, and Z are as defined in claim 1.

3. The compound according to claim 1, or the pharmaceutically acceptable salt thereof or the solvate thereof, wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, —Z—N($R^{41}$)($R^{42}$),
—Z—N($R^{47}$)—C(=O)—$R^{48}$,
—Z—N($R^{412}$)—C(=O)—O—$R^{413}$, or
—Z—B(—O$R^{422}$)(—$R^{423}$), wherein substituent group C, $R^{41}$, $R^{42}$, $R^{47}$, $R^{48}$, $R^{412}$, $R^{413}$, $R^{422}$, $R^{423}$, and Z are as defined in claim 1.

4. The compound according to claim 1, or the pharmaceutically acceptable salt thereof or the solvate thereof, wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, or

—Z—N($R^{41}$)($R^{42}$), wherein substituent group C, $R^{41}$, $R^{42}$, and Z are as defined in claim 1.

5. The compound according to claim 1, or the pharmaceutically acceptable salt thereof or the solvate thereof, wherein $R^{1a}$ is hydrogen, or carboxy.

6. The compound according to claim 1, or the pharmaceutically acceptable salt thereof or the solvate thereof, wherein $R^{2a}$ is hydrogen, lower alkyl optionally substituted by substituent group C, carbocycle lower alkyl optionally substituted by substituent group C, heterocycle lower alkyl optionally substituted by substituent group C, or

—Z—N($R^{B9}$)($R^{B10}$), wherein substituent group C, $R^{B9}$, $R^{B10}$, and Z are as defined in claim 1.

7. The compound according to claim 1, or the pharmaceutically acceptable salt thereof or the solvate thereof, wherein $R^{2a}$ is hydrogen or lower alkyl optionally substituted by substituent group C and substituent group C is as defined in claim 1.

8. The compound according to claim 1, or the pharmaceutically acceptable salt thereof or the solvate thereof, wherein $R^{3a}$ is hydrogen, lower alkyl optionally substituted by substituent group C, lower alkenyl optionally substituted by substituent group C, lower alkynyl optionally substituted by substituent group C, carbocyclic group optionally substituted by substituent group C, carbocycle lower alkyl optionally substituted by substituent group C, carbocycleoxy lower alkyl optionally substituted by substituent group C, heterocycle lower alkyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$), or
—Z—N($R^{C9}$)($R^{C10}$), wherein substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, and Z are as defined in claim 1.

9. The compound according to claim 1, or the pharmaceutically acceptable salt thereof or the solvate thereof,
wherein $R^{3a}$ is hydrogen, lower alkyl optionally substituted by substituent group C, carbocyclic group optionally substituted by substituent group C, heterocyclic group optionally substituted by substituent group C, carbocycle lower alkyl optionally substituted by substituent group C, and
substituent group C is as defined in claim 1.

10. The compound according to claim 1, or the pharmaceutically acceptable salt thereof or the solvate thereof,
wherein $R^{5a}$ is hydrogen,
$R^{6a}$ is hydrogen, or lower alkyl optionally substituted by substituent group C, and
$R^{7a}$ is lower alkyl optionally substituted by substituent group C, carbocyclic group optionally substituted by substituent group C, carbocycleoxy lower alkyl optionally substituted by substituent group C, heterocyclic group optionally substituted by substituent group C, carbocycle lower alkyl optionally substituted by substituent group C, heterocycle lower alkyl optionally substituted by substituent group C, or
—Z—C($R^{D7}$)($R^{D8}$)($R^{D9}$),
wherein substituent group C, $R^{D7}$, $R^{D8}$, $R^{D9}$, and Z are as defined in claim 1.

11. The compound according to claim 10, or the pharmaceutically acceptable salt thereof or the solvate thereof,
wherein $R^{7a}$ is a group shown below:

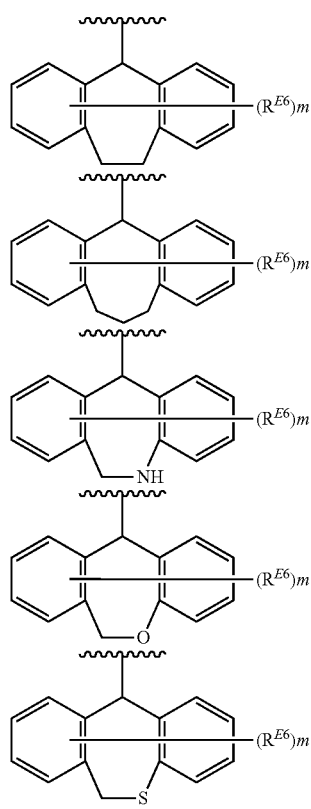

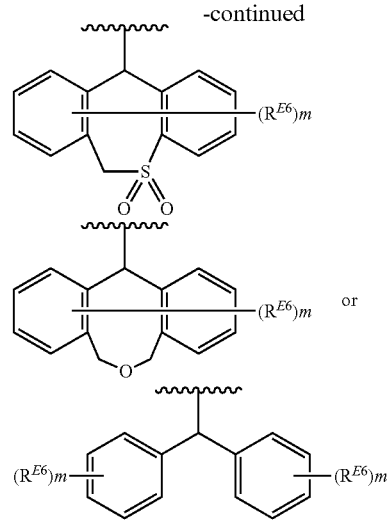

wherein $R^{E6}$ is selected from a substitute group C, m is an of 0 or 1 or more, provided that m of $R^{E6}$s is same or different groups selected from substituent group C; and substituent group C is same as those of as defined in claim 1.

12. The compound according to claim 1, or the pharmaceutically acceptable salt thereof or the solvate thereof,
wherein $R^{6a}$ is hydrogen,
$R^{3a}$ and $R^{7a}$ are taken together with an adjacent atom to form heterocycle optionally substituted by substituent group D, and
$R^{5a}$ is hydrogen, lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C,
—Y—S—$R^{D1}$,
—C(=O)—C(=O)—$R^{D2}$, or
—C(=O)—N($R^{D3}$)($R^{D4}$),
wherein $R^{D1}$, $R^{D2}$, $R^{D3}$, $R^{D4}$, Y substituent group C and substituent group D are as defined in claim 1.

13. The compound according to claim 12, or the pharmaceutically acceptable salt thereof or the solvate thereof,
wherein $R^{5a}$ is hydrogen, carbocyclic group optionally substituted by substituent group C, carbocycle lower alkyl optionally substituted by substituent group C, heterocyclic group optionally substituted by substituent group C, or heterocycle lower alkyl optionally substituted by substituent group C, and
wherein substituent group C is as defined in claim 1.

14. The compound according to claim 12, or the pharmaceutically acceptable salt thereof or the solvate thereof,
wherein substituent group D is carbocyclic group optionally substituted by substituent group C, heterocyclic group optionally substituted by substituent group C, carbocycle lower alkyl optionally substituted by substituent group C, or heterocycle lower alkyl optionally substituted by substituent group C.

15. The compound according to claim 1, or the pharmaceutically acceptable salt thereof or the solvate thereof, wherein $P^R$ is a group selected from the group consisting of:
a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N($P^{R2}$)$_2$,
i) —C(=O)—O-L-O—$P^{R2}$,
j) —CH$_2$—O—$P^{R3}$,
k) —CH$_2$—O-L-O—$P^{R3}$,
l) —CH$_2$—O—C(=O)—$P^{R3}$,
m) —CH$_2$—O—C(=O)—O—$P^{R3}$,
n) —CH(—CH$_3$)—O—C(=O)—O—$P^{R3}$,
o) —CH$_2$—O—C(=O)—N(—K)—$P^{R3}$,
p) —CH$_2$—O—C(=O)—O-L-O—$P^{R3}$,
q) —CH$_2$—O—C(=O)—O-L-N($P^{R3}$)$_2$,
r) —CH$_2$—O—C(=O)—N(—K)-L-O—$P^{R3}$,
s) —CH$_2$—O—C(=O)—N(—K)-L-N($P^{R3}$)$_2$,
t) —CH$_2$—O—C(=O)—O-L-O-L-O—$P^{R3}$,
u) —CH$_2$—O—C(=O)—O-L-N(—K)—C(=O)—$P^{R3}$,
v) —CH$_2$—O—P(=O)(—OH)$_2$,
w) —CH$_2$—O—P(=O)(—OBn)$_2$, and
x) —C(=N$^+P^{R5}$$_2$)(—N$P^{R5}$$_2$)

wherein L is straight or branched lower alkylene, or straight or branched lower alkenylene, K is hydrogen, or straight or branched lower alkyl, $P^{R0}$ is lower alkyl optionally substituted by substituent group F, or lower alkenyl optionally substituted by substituent group F, $P^{R1}$ is carbocyclic group optionally substituted by substituent group F, heterocyclic group optionally substituted by substituent group F, lower alkyl amino optionally substituted by substituent group F, or lower alkylthio optionally substituted by substituent group F, $P^{R2}$ is lower alkyl optionally substituted by substituent group F, carbocyclic group optionally substituted by substituent group F, or heterocyclic group optionally substituted by substituent group F, $P^{R3}$ is lower alkyl optionally substituted by substituent group F, carbocyclic group optionally substituted by substituent group F, heterocyclic group optionally substituted by substituent group F, lower alkyl amino optionally substituted by substituent group F, carbocycle lower alkyl optionally substituted by substituent group F, heterocycle lower alkyl optionally substituted by substituent group F, or lower alkylsilyl, and $P^{R5}$ is lower alkyl optionally substituted by substituent group F, wherein substituent group F is selected from the group consisting of oxo, lower alkyl, hydroxy lower alkyl, amino, lower alkylamino, carbocycle lower alkyl, lower alkylcarbonyl, halogen, hydroxy, carboxy, lower alkylcarbonylamino, lower alkylcarbonyloxy, lower alkyloxycarbonyl, lower alkyloxy, cyano, and nitro.

16. A pharmaceutical composition containing a compound according to claim 1, or a pharmaceutically acceptable salt thereof or a solvate thereof, and at least one pharmaceutically acceptable excipient.

17. A method for treating influenza characterized in administering a compound according to claim 1, or a pharmaceutically acceptable salt thereof or a solvate thereof, to a subject in need thereof.

* * * * *

UNITED STATES PATENT AND TRADEMARK OFFICE
CERTIFICATE OF CORRECTION

| | |
|---|---|
| PATENT NO. | : 10,202,379 B2 |
| APPLICATION NO. | : 15/676540 |
| DATED | : February 12, 2019 |
| INVENTOR(S) | : Chika Takahashi |

Page 1 of 1

It is certified that error appears in the above-identified patent and that said Letters Patent is hereby corrected as shown below:

On the Title Page

Item (72), after "Masayoshi MIYAGAWA, Osaka (JP)", please add --; Naoyuki SUZUKI, Osaka (JP)--.

Signed and Sealed this
Sixteenth Day of April, 2019

Andrei Iancu
*Director of the United States Patent and Trademark Office*